(12) United States Patent
Salvati et al.

(10) Patent No.: US 8,642,576 B2
(45) Date of Patent: *Feb. 4, 2014

(54) HETEROCYCLIC CETP INHIBITORS

(75) Inventors: Mark E. Salvati, Lawrenceville, NJ (US); Heather Finlay, Skillman, NJ (US); Bang-Chi Chen, Plainsboro, NJ (US); Lalgudi S. Harikrishnan, Princeton, NJ (US); Ji Jiang, West Windsor, NJ (US); James A. Johnson, Pennington, NJ (US); Muthoni G. Kamau, Lawrenceville, NJ (US); R. Michael Lawrence, Yardley, PA (US); Jianqing Li, Guilford, CT (US); John Lloyd, Yardley, PA (US); Michael M. Miller, Pennington, NJ (US); Zulan Pi, Pennington, NJ (US); Jennifer X. Qiao, Princeton, NJ (US); Richard A. Rampulla, Flemington, NJ (US); Jacques Y. Roberge, Princeton, NJ (US); Tammy C. Wang, Lawrenceville, NJ (US); Yufeng Wang, North Brunswick, NJ (US); Wu Yang, Princeton Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/597,364

(22) Filed: Aug. 29, 2012

(65) Prior Publication Data

US 2012/0322761 A1 Dec. 20, 2012

Related U.S. Application Data

(62) Division of application No. 12/797,760, filed on Jun. 10, 2010, now Pat. No. 8,304,403, which is a division of application No. 11/558,979, filed on Nov. 13, 2006, now Pat. No. 7,790,770.

(60) Provisional application No. 60/739,374, filed on Nov. 23, 2005.

(51) Int. Cl.
| | |
|---|---|
| A61K 31/166 | (2006.01) |
| A61K 31/137 | (2006.01) |
| A61K 31/426 | (2006.01) |
| A61K 31/4468 | (2006.01) |
| A61K 31/505 | (2006.01) |
| A61K 31/695 | (2006.01) |
| A61K 31/5375 | (2006.01) |
| A61K 31/17 | (2006.01) |
| C07C 275/26 | (2006.01) |
| C07C 233/73 | (2006.01) |
| C07C 37/02 | (2006.01) |
| C07C 41/01 | (2006.01) |

(52) U.S. Cl.
USPC ............ 514/63; 514/595; 514/617; 514/648; 514/371; 514/329; 514/256; 514/239.5; 514/423; 564/56; 564/185; 568/775; 568/656; 548/196; 548/538; 546/224; 544/335; 544/165

(58) Field of Classification Search
None
See application file for complete search history.

(56) References Cited

U.S. PATENT DOCUMENTS

| | | | |
|---|---|---|---|
| 5,041,458 A | 8/1991 | Basarab | |
| 5,936,102 A | 8/1999 | Popkova et al. | |
| 6,528,687 B2 * | 3/2003 | Cobley et al. | 564/415 |
| 6,723,752 B2 | 4/2004 | Sikorski et al. | |
| 6,982,348 B2 | 1/2006 | Kori et al. | |
| 7,790,770 B2 * | 9/2010 | Salvati et al. | 514/617 |
| 8,304,403 B2 * | 11/2012 | Salvati et al. | 514/63 |
| 2002/0103217 A1 | 8/2002 | Scott et al. | |
| 2003/0066984 A1 | 4/2003 | Prechtl et al. | |
| 2004/0034076 A1 | 2/2004 | Amberg et al. | |
| 2005/0154025 A1 | 7/2005 | Sato et al. | |
| 2007/0135631 A1 * | 6/2007 | Salvati et al. | 544/162 |

FOREIGN PATENT DOCUMENTS

| | | |
|---|---|---|
| AU | 752165 | 6/1999 |
| CA | 2 294 150 | 12/1998 |
| CA | 2 355 251 | 6/2000 |
| JP | 2003-48875 | 2/2003 |
| WO | WO 94/14833 | 7/1994 |
| WO | WO 00/34437 | 6/2000 |
| WO | WO 02/074747 | 9/2002 |

(Continued)

OTHER PUBLICATIONS

R. Gust, Archiv der Pharmazie, (1994), 327(1), p. 49-54.*
Wu and Farrelly, Toxicology 236:1-6, 2007.
Cited ref-STN-search-11558979, (2008).
Hudlicky, Milos, "Reductions in organic chemistry," Ellis Horwood Limited, 1984, pp. 28-29, 62-65.

(Continued)

Primary Examiner — Yong Chu
(74) Attorney, Agent, or Firm — Terence J. Bogie

(57) ABSTRACT

Compounds of formula Ia and Ib

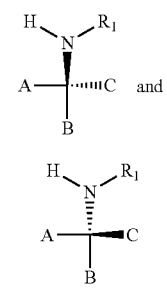

wherein A, B, C and $R_1$ are described herein.

14 Claims, No Drawings

(56) References Cited

FOREIGN PATENT DOCUMENTS

| WO | WO 2004/017908 | 3/2004 |
|----|----------------|--------|
| WO | WO 2005/030185 | 4/2005 |
| WO | WO 2005/037796 | 4/2005 |
| WO | WO 2005/092833 | 10/2005 |
| WO | WO 2005/092845 | 10/2005 |
| WO | WO 2005/095395 | 10/2005 |
| WO | WO 2005/095409 | 10/2005 |
| WO | WO 2005/097805 | 10/2005 |
| WO | WO 2005/097806 | 10/2005 |
| WO | WO 2005/100298 | 10/2005 |
| WO | WO 2006/042150 | 4/2006 |
| WO | WO 2006/065659 | 6/2006 |
| WO | WO 2007/062314 | 5/2007 |
| WO | WO 2007/062342 | 5/2007 |

OTHER PUBLICATIONS

Peytob, O.A., Reaction of Nucleophilic Aromatic Replacement, 1999, pp. 570-609. (Original article and English translation).

Alcaide, B. et al., "The reaction of alpha-diketones with primary heteroaromatic amines. Synthesis and reactions of imidazo[1,2-a]pyridine-3(2H0-ones and N-heteroaryl alpha-iminoketones", Tetrahedron, vol. 45, No. 21, pp. 6841-6856 (1989).

Lau, C. K. et al., "Structure based design of a series of potent and selective non peptidic PTP-1B inhibitors", Bioorganic & Medicinal Chemistry Letters, vol. 14, pp. 1043-1048 (2004).

Scapin, G. et al., "The structural basis for the selectivity of benzotriazole inhibitors of PTP1B", Biochemistry, vol. 42, pp. 11451-11459 (2003).

Shaw, A.W. et al., "Asymmetric synthesis of α,α-diaryl and α-aryl-α-heteroaryl alkylamines by organometallic additions to N-tert-butanesulfinyl ketimines", Tetrahedron Letters, vol. 42, pp. 7173-7176 (2001).

Skerrett, E.J. et al., "Insecticidal Activity and Chemical Constitution. Part V. Synthesis of Some Di-$p$-chlorophenylalkanes", Journal of the Chemical Society, Part III, pp. 3308-3312 (1952).

Khr Ivanov, Izvest. Khim. Inst., Bulgar. Akad. Nauk. (1 957), vol. 5, p. 93-102 (Abstract from STN search report).

Google search under HPLC chiral separation (201 1).

Wikipedia under Chiral Resolution (201 1).

Brunner, H. et al., "Synthesis and Antitumor Activity of Pt(II) Complexes of Benzyl-1,2-diaminoethane Ligands", Chem. Ber., vol. 123, pp. 1029-1038 (1990).

Gust, R., Aqua[1,1-bis(4-hydroxyphenyl)-1,2-diamino-2-phenylethane]-sulfatoplatinum(II), a New Compound for the Treatment of the Mammary Carcinoma, Arch. Pharm. (Weinheim), vol. 327, pp. 49-54 (1994).

* cited by examiner

HETEROCYCLIC CETP INHIBITORS

RELATED APPLICATION

This application is a divisional of prior U.S. patent application Ser. No. 12/797,760, filed on Jun. 10, 2010, issued as U.S. Pat. No. 8,304,403, which is a divisional of U.S. patent application Ser. No. 11/558,979 filed on Nov. 13, 2006, issued as U.S. Pat. No. 7,790,770 B2, which claims the benefit of U.S. Provisional Application No. 60/739,374, filed on Nov. 23, 2005, the entirety of each of these applications being incorporated herein by reference.

FIELD OF THE INVENTION

This present invention provides for cholesteryl ester transfer protein (CETP) inhibitors, pharmaceutical compositions containing such inhibitors and the use of such inhibitors to elevate certain plasma lipid levels, including high density lipoprotein (HDL)-cholesterol and to lower certain other plasma lipid levels, such as low density lipoprotein (LDL)-cholesterol and triglycerides and accordingly to treat diseases which are affected by low levels of HDL cholesterol and/or high levels of LDL-cholesterol and triglycerides, such as atherosclerosis and cardiovascular diseases in certain mammals (i.e., those which have CETP in their plasma), including humans.

BACKGROUND OF THE INVENTION

Atherosclerosis and its associated coronary artery disease (CAD) is the leading cause of mortality in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S., where cardiovascular disease accounts for 44% of all deaths, with 53% of these associated with atherosclerotic coronary heart disease.

Risk for development of atherosclerosis has been shown to be strongly correlated with certain plasma lipid levels. While elevated LDL-C may be the most recognized form of dyslipidemia, it is by no means the only significant lipid associated contributor to CHD. Low HDL-C is also a known risk factor for CHD (Gordon, D J. et al., "High-density Lipoprotein Cholesterol and Cardiovascular Disease", Circulation, (1989), 79:8-15).

High LDL-cholesterol and triglyceride levels are positively correlated, while high levels of HDL-cholesterol are negatively correlated with the risk for developing cardiovascular diseases. Thus, dyslipidemia is not a unitary risk profile for CHD but may be comprised of one or more lipid aberrations.

Among the many factors controlling plasma levels of these disease dependent principles, cholesteryl ester transfer protein (CETP) activity affects all three. The role of this 70,000 dalton plasma glycoprotein found in a number of animal species, including humans, is to transfer cholesteryl ester and triglyceride between lipoprotein particles, including high density lipoproteins (HDL), low density lipoproteins (LDL), very low density lipoproteins (VLDL), and chylomicrons. The net result of CETP activity is a lowering of HDL cholesterol and an increase in LDL cholesterol. This effect on lipoprotein profile is believed to be pro-atherogenic, especially in subjects whose lipid profile constitutes an increased risk for CHD.

No wholly satisfactory HDL-elevating therapies exist. Niacin can significantly increase HDL, but has serious toleration issues which reduce compliance. Fibrates and the HMG CoA reductase inhibitors raise HDL-C only modestly (about 10-12%). As a result, there is a significant unmet medical need for a well-tolerated agent which can significantly elevate plasma HDL levels, thereby reversing or slowing the progression of atherosclerosis.

Thus, although there are a variety of anti-atherosclerosis therapies, there is a continuing need and a continuing search in this field of art for alternative therapies.

SUMMARY OF THE INVENTION

In accordance with the present invention, heterocyclic compounds and related compounds are provided that have the general structures:

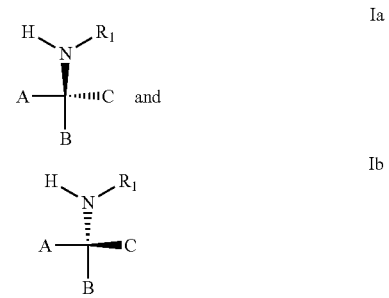

wherein A, B, C and $R_1$ are defined below.

By use of a respective effective amount of at least one compound described herein, provided are methods of treating, preventing or slowing the progression of a disease requiring cholesteryl ester transfer protein inhibition, or inhibiting the cholesteryl ester transfer protein.

Also provided are pharmaceutical compositions comprising a therapeutically effective amount of at least one compound described herein and a pharmaceutically acceptable vehicle or carrier thereof. Such compositions can further comprise one or more additional therapeutic agents.

DEFINITIONS

The terms "alk" or "alkyl" refer to straight or branched chain hydrocarbon groups having 1 to 12 carbon atoms, or 1 to 8 carbon atoms, such as methyl, ethyl, n-propyl, i-propyl, n-butyl, i-butyl, t-butyl, pentyl, hexyl, heptyl, octyl, or any subset of the foregoing. The term "substituted alkyl" refers to alkyl groups substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkenyl" refers to straight or branched chain hydrocarbon groups having 2 to 12 carbon atoms, or 2 to 4 carbon atoms, and at least one double carbon to carbon bond (either cis or trans), such as ethenyl. The term "substituted alkenyl" refers to alkenyl groups substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkynyl" refers to straight or branched chain hydrocarbon groups having 2 to 12 carbon atoms, or 2 to 4 carbon atoms, and at least one triple carbon to carbon bond, such as ethynyl. The term "substituted alkynyl" refers to alkynyl groups substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "aryl" refers to aromatic homocyclic (i.e., hydrocarbon) mono-, bi- or tricyclic ring-containing groups such as having 6 to 12 members such as phenyl, naphthyl and biphenyl. Phenyl is an example of an aryl group. The term "substituted aryl" refers to aryl groups substituted with one or more groups (such as by groups described above in the definition of $R^{10}$), such as selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane and sulfonyl, or any subset of the foregoing, where optionally one or more pair of substituents together with the atoms to which they are bonded form a 3 to 7 member ring.

The term "cycloalkyl" refers to mono-, bi- or tri homocyclic ring groups of 3 to 15 carbon atoms which are, respectively, fully saturated and partially unsaturated. The rings of multi-ring cycloalkyl groups may be either fused, bridged and/or joined through one or more spiro unions. The term "substituted cycloalkyl" refers to a cycloalkyl group substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The terms "halogen" and "halo" refer to fluorine, chlorine, bromine and iodine.

The terms "heterocycle", "heterocyclic", "heterocyclic group" or "heterocyclyl" refer to fully saturated or partially or completely unsaturated, including aromatic ("heteroaryl") or nonaromatic cyclic groups (for example, 3 to 13 ring member monocyclic, 7 to 17 ring member bicyclic, or 10 to 20 ring member tricyclic ring systems, such as, in certain embodiments, a monocyclic or bicyclic ring containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions.

Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl,

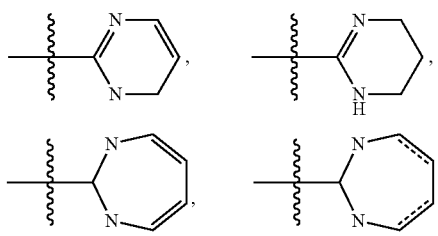

and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranyl, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4 dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl),

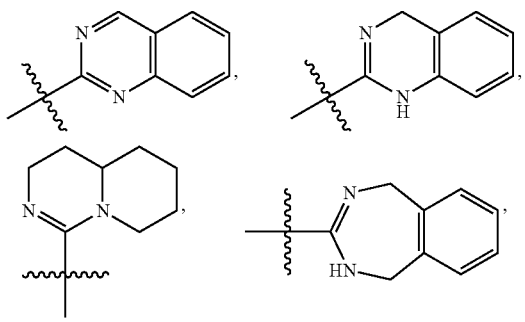

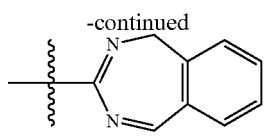

and the like.

Exemplary tricyclic heterocyclic groups include carbazolyl, benzidolyl, phenanthrolinyl, acridinyl, phenanthridinyl, xanthenyl and the like.

The terms "substituted heterocycle", "substituted heterocyclic", "substituted heterocyclic group" and "substituted heterocyclyl" refer to heterocycle, heterocyclic and heterocyclo groups substituted with one or more groups (such as by groups described above in the definition of $R^{10}$), such as selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, or any subset of the foregoing, where optionally one or more pair of substituents together with the atoms to which they are bonded form a 3 to 7 member ring.

Throughout the specification, groups and substituents thereof may be chosen to provide stable moieties and compounds.

The compounds of formulas Ia and Ib form salts or solvates which are also within the scope of this invention. Reference to a compound of the formula Ia or Ib herein is understood to include reference to salts thereof, unless otherwise indicated. The term "salt(s)", as employed herein, denotes acidic and/or basic salts formed with inorganic and/or organic acids and bases. In addition, when a compound of formula Ia or Ib contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula Ia and Ib may be formed, for example, by reacting a compound of formula Ia or Ib with an amount of acid or base, such as an equivalent amount, in a medium such as one in which the salt precipitates or in an aqueous medium followed by lyophilization.

The compounds of formula Ia and Ib which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula Ia and Ib which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Any compound that can be converted in vivo to provide the bioactive agent (i.e., a compound of formula Ia or Ib) is a prodrug within the scope and spirit of the invention.

The term "prodrugs" as employed herein includes esters and carbonates formed by reacting one or more hydroxyls of compounds of formula Ia and Ib with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) *The Practice of Medicinal Chemistry*, Camille G. Wermuth et al., Ch 31 (Academic Press, 1996);

b) *Design of Prodrugs*, edited by H. Bundgaard (Elsevier, 1985);

c) *A Textbook of Drug Design and Development*, P. Krogsgaard-Larson and H. Bundgaard, eds., Ch. 5, pp. 113-191 (Harwood Academic Publishers, 1991); and d) *Hydrolysis in Drug and Prodrug Metabolism*, Bernard Testa and Joachim M. Mayer, (Wiley-VCH, 2003).

Said references are incorporated herein by reference.

In addition, compounds of the present invention are, subsequent to their preparation, preferably isolated and purified to obtain a composition containing an amount by weight equal to or greater than 99% formula Ia or Ib compound ("substantially pure" compound Ia or Ib), which may be used or formulated as described herein. Such "substantially pure" compounds of formula Ia and Ib are also contemplated herein as part of the present invention.

To the extent that compounds of the formula Ia and Ib, and salts thereof, may exist in their tautomeric form, all such tautomeric forms are contemplated herein as part of the present invention.

All stereoisomers of the present compounds, such as those which may exist due to asymmetric carbons on the various substituents, including enantiomeric forms (which may exist even in the absence of asymmetric carbons) and diastereomeric forms, are contemplated within the scope of this invention. Individual stereoisomers of the compounds of the invention may, for example, be substantially free of other isomers, or may be admixed, for example, as racemates or with all other, or other selected, stereoisomers.

The terms "including", "such as", "for example" and the like are intended to refer to exemplary embodiments and not to limit the scope of the present invention.

DETAILED DESCRIPTION OF THE INVENTION

It will be understood that any given exemplary embodiment can be combined with one or more additional exemplary embodiments.

In accordance with the present invention, compounds of formula Ia and Ib are provided

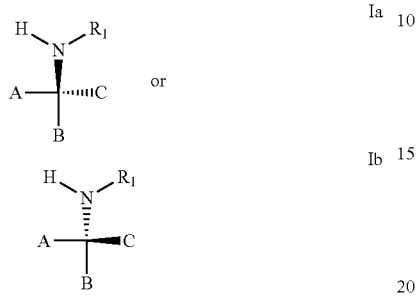

or stereoisomers or prodrugs or pharmaceutically acceptable salt forms thereof, wherein:

A is phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$S(O)_pR_6$, 18) $SO_2NHR_6$, 19) —$COOR_6$, 20) —NHC(CN)$NHR_6$, 21) —$CONR_6R_6$, 22) ($C_2$-$C_6$)-alkynyl, which may be optionally substituted with one or more $R_{20}$'s, 23) ($C_2$-$C_6$)-alkenyl, which may be optionally substituted with one or more $R_{20}$'s, 24) —$OCOR_6$, 25) —$OCOOR_6$, 26) —$OCONR_6R_6$, or 27) cycloalkyl, which may be optionally substituted with one or more $R_{20}$'s; or any two adjacent substituents may join together to form a 4- to 8-membered ring, which optionally may contain 1-4 heteroatoms selected from N, O, and S and be optionally substituted with one or more $R_{20}$'s;

B is:
(a) phenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) —$S(O)_pR_6$, 17) —$SO_2NHR_6$, 18) —$COOR_6$, 19) —NHC(CN)$NHR_6$, 20) —$CONR_6R_6$; and 21) cycloalkyl, which may be optionally substituted with one or more $R_{20}$'s; or
(b) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) —$S(O)_pR_6$, 17) —$SO_2NHR_6$, 18) —$COOR_6$, 19) —NHC(CN)$NHR_6$, 20) —$CONR_6R_6$; and 21) cycloalkyl, which may be optionally substituted with one or more $R_{20}$'s;

C is:
(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) —$S(O)_pR_6$, 15) —$SO_2NHR_6$, 16) —$COR_6$, 17) —NHC(CN)$NHR_6$; and 18) cycloalkyl, which may be optionally substituted with one or more $R_{20}$'s;
(b) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl; and 15) cycloalkyl, which may be optionally substituted with one or more $R_{20}$'s;
(c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) —$S(O)_pR_6$, 15) —$SO_2NHR_6$, 16) —$COOR_6$, 17) —NHC(CN)$NHR_6$; and 18) cycloalkyl, which may be optionally substituted with one or more $R_{20}$'s; or
(d) heterocyclo, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) —$S(O)_6R_6$, 15) —$SO_2NHR_6$, 16) —$COR_6$, 17) —NHC(CN)$NHR_6$; and 18) cycloalkyl, which may be optionally substituted with one or more $R_{20}$'s;

$R_1$ is H, —$C(O)R_3$, —$C(O)NR_2R_3$, —$C(O)OR_4$, —$SO_2R_5$, —$C(S)NHR_7$, —$CR_8R_8R_5$, or —$C(S)R_3$;

$R_2$ is:
- (a) H;
- (b) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) ($C_2$-$C_6$)-alkenyl, 15) ($C_2$-$C_6$)-alkynyl, 16) —$S(O)_pR_6$, 17) —$SO_2NHR_6$, 18) —$COR_6$, 19) —NHC(CN)$NHR_6$; and 20) cycloalkyl, which may be optionally substituted with one or more $R_{20}$'s;
- (c) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ($C_2$-$C_6$)-alkynyl, 18) —$COR_6$, 19) —$S(O)_pR_6$, 20) —$SO_2NHR_6$, 21) —$COOR_6$, 22) —NHC(CN)$NHR_6$; and 23) cycloalkyl, which may be optionally substituted with one or more $R_{20}$'s; or
- (d) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CO($C_1$-$C_6$)-alkyl, 16) —COOH, 17) —$CO_2$($C_1$-$C_6$)-alkyl, 18) —$CONR_6R_6$, 19) ($C_2$-$C_6$)-alkenyl, 20) ($C_2$-$C_6$)-alkynyl; and 21) cycloalkyl, which may be optionally substituted with one or more $R_{20}$'s;

$R_3$ is:
- (a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$CONR_6R_6$, 13) ($C_2$-$C_6$)-alkenyl, 14) ($C_2$-$C_6$)-alkynyl, 15) —$COR_6$, 16) —$S(O)_pR_6$, 17) —$SO_2NHR_6$, 18) —$COR_6$, 19) —NHC(CN)$NHR_6$; and 20) cycloalkyl, which may be optionally substituted with one or more $R_{20}$'s;
- (b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, 23) —NHC(CN)$NHR_6$; and 24) cycloalkyl, which may be optionally substituted with one or more $R_{20}$'s;
- (c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, 23) —NHC(CN)$NHR_6$; and 24) cycloalkyl, which may be optionally substituted with one or more $R_{20}$'s;
- (d) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, 23) —NHC(CN)$NHR_6$; and 24) cycloalkyl, which may be optionally substituted with one or more $R_{20}$'s;
- (e) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, 23) NHC(CN)$NHR_6$; and 24) cycloalkyl, which may be optionally substituted with one or more $R_{20}$'s; or (f) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ($C_2$-$C_6$)-alkynyl, 18) —$COR_6$, 19) —$S(O)_pR_6$, 20) —$SO_2NHR_6$, 21) —$COOR_6$, 22) —NHC(CN)$NHR_6$; and 23) cycloalkyl, which may be optionally substituted with one or more $R_{20}$'s;

or $R_2$ and $R_3$ are taken together to form a 3- to 9-membered ring, which optionally may contain 1-4 heteroatoms selected from N, O, and S and be optionally substituted with one or more $R_{20}$'s;

$R_4$ is:

(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, 23) —NHC(CN)$NHR_6$; and 24) cycloalkyl, which may be optionally substituted with one or more $R_{20}$'s;

(b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, 23) —NHC(CN)$NHR_6$; and 24) cycloalkyl, which may be optionally substituted with one or more $R_{20}$'s;

(c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, 23) —NHC(CN)$NHR_6$; and 24) cycloalkyl, which may be optionally substituted with one or more $R_{20}$'s;

(d) ($C_2$-$C_6$)-alkenyl; or (e) ($C_2$-$C_6$)-alkynyl;

$R_5$ is arylalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, 23) —NHC(CN)$NHR_6$; and 24) cycloalkyl, which may be optionally substituted with one or more $R_{20}$'s;

$R_6$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, 22) —NHC(CN)$NHR_{36}$, or 23) cycloalkyl, which may be optionally substituted with one or more $R_{20}$'s;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, 24) —NHC(CN)$NHR_{36}$; and 25) cycloalkyl, which may be optionally substituted with one or more $R_{20}$'s;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —NHC(CN)$NHR_{36}$; and 26) cycloalkyl, which may be optionally substituted with one or more $R_{20}$'s;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —NHC(CN)$NHR_{36}$; and 26) cycloalkyl, which may be optionally substituted with one or more $R_{20}$'s;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —NHC(CN)$NHR_{36}$; and 26) cycloalkyl, which may be optionally substituted with one or more $R_{20}$'s;

(f) hydrogen;

(g) alkynyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, 22) —NHC(CN)$NHR_{36}$, or 23) cycloalkyl, which may be optionally substituted with one or more $R_{20}$'s; or (h) alkenyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, 22) —NHC(CN)$NHR_{36}$, or 23) cycloalkyl, which may be optionally substituted with one or more $R_{20}$'s;

or two $R_6$'s are taken together to form a 3- to 9-membered ring, which optionally may contain 1-4 heteroatoms selected from N, O, and S and be optionally substituted with one or more $R_{20}$'s;

$R_7$ is aryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_6$, 20) —$S(O)_pR_{26}$, 21) —$SO_2NHR_{26}$, 22) —$COOR_{26}$, 23) —NHC(CN)$NHR_{26}$; and 24) cycloalkyl, which may be optionally substituted with one or more $R_{20}$'s;

$R_8$ can independently be:

(a) H;

(b) alkyl, which may be optionally substituted with one or more substituents selected from the group consisting of:

1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) ($C_2$-$C_6$)-alkenyl, 13) aryl($C_2$-$C_6$)-alkynyl, 14) —$CONR_{26}R_{26}$, 15) =O, 16) ($C_2$-$C_6$)-alkynyl, 17) —$COR_{26}$, 18) —$S(O)_pR_{26}$, 19) —$SO_2NHR_{26}$, 20) —$COOR_{26}$, 21) —NHC(CN)$NHR_{26}$; and 22) cycloalkyl, which may be optionally substituted with one or more $R_{20}$'s;

(c) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_{26}$, 20) —$S(O)_pR_{26}$, 21) —$SO_2NHR_{26}$, 22) —$COOR_{26}$, 23) —NHC(CN)$NHR_{26}$; and 24) cycloalkyl, which may be optionally substituted with one or more $R_{20}$'s;

(d) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_{26}$, 20) —$S(O)_pR_{26}$, 21) —$SO_2NHR_{26}$, 22) —$COOR_{26}$, 23) —NHC(CN)$NHR_{26}$; and 24) cycloalkyl, which may be optionally substituted with one or more $R_{20}$'s;

(e) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_{26}$, 20) —$S(O)_pR_{26}$, 21) —$SO_2NHR_{26}$, 22) —$COOR_{26}$, 23) —NHC(CN)$NHR_{26}$; and 24) cycloalkyl, which may be optionally substituted with one or more $R_{20}$'s; or (f) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_{26}$, 20) —$S(O)_pR_{26}$, 21) —$SO_2NHR_{26}$, 22) —$COOR_{26}$, 23) —NHC(CN)$NHR_{26}$; and 24) cycloalkyl, which may be optionally substituted with one or more $R_{20}$'s;

or two $R_8$'s are taken together to form a 3- to 9-membered ring, which may optionally contain 1-4 heteroatoms selected from N, O, and S and be optionally substituted with one or more $R_{20}$'s;

$R_9$ and $R_{10}$ are independently: (a) hydrogen; (b) —[(C=O)$O_r]_s$aryl, wherein the aryl may be optionally substituted with one or more $R_{20}$'s; (c) —[(C=O)$O_r]_s$($C_2$-$C_8$)-alkenyl, wherein the alkenyl may be optionally substituted with one or more $R_{20}$'s; (d) [(C=O)$O_r]_s$($C_1$-$C_8$)alkyl, wherein the alkyl may be optionally substituted with one or more $R_{20}$'s; (e) heterocyclyl optionally substituted with one or more $R_{20}$'s; (f) —$CONR_{26}R_{26}$; (g) —($C_2$-$C_6$)-alkynyl; (h) —$COR_{26}$; (i) —$S(O)_pR_{26}$; (j) —$SO_2NHR_{26}$; (k) —$COOR_{26}$; (l) —NHC(CN)$NHR_{26}$; or m) —[(C=O)$O_r]_s$cycloalkyl, which may be optionally substituted with one or more $R_{20}$'s;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p)=O; (q) —($C_2$-$C_6$)-alkynyl; (r) —$COR_{26}$; (s) —$S(O)_pR_{26}$; (t) —$SO_2NHR_{26}$; (u) —$COOR_{26}$; (v) —NHC(CN)$NHR_{26}$; (w) cycloalkyl, which may be optionally substituted with one or more $R_{21}$'s; (x) cycloalkylalkyl, which may be optionally substituted with one or more $R_{21}$'s; or (y) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) =O; (r) ($C_2$-$C_6$)- alkynyl; (s) cycloalkyl; (t) cycloalkylalkyl; (u) —COR$_{26}$; (v) —S(O)$_p$R$_{26}$; (w) —SO$_2$NHR$_{26}$; (x) —COOR$_{26}$; or (y) —NHC(CN)NHR$_{26}$;

R$_{26}$, at each occurrence, is independently:

(a) alkyl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) heteroaryl, which may be optionally substituted with one or more R$_{40}$'s, 11) heterocyclyl, which may be optionally substituted with one or more R$_{40}$'s, 12) halo(C$_1$-C$_6$)alkyl, 13) (C$_2$-C$_6$)-alkenyl, 14) —COOH, 15) —CONR$_{36}$R$_{36}$, 16) =O, 17) (C$_2$-C$_6$)-alkynyl, 18) —COR$_{36}$, 19) —S(O)$_p$R$_{36}$, 20) —SO$_2$NHR$_{36}$, 21) —COOR$_{36}$, 22) —NHC(CN)NHR$_{36}$; and 23) cycloalkyl, which may be optionally substituted with one or more R$_{40}$'s;

(b) aryl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) arylalkyl, which may be optionally substituted with one or more R$_{40}$'s, 11) heteroaryl, which may be optionally substituted with one or more R$_{40}$'s, 12) heteroarylalkyl, which may be optionally substituted with one or more R$_{40}$'s, 13) heterocyclyl, which may be optionally substituted with one or more R$_{40}$'s, 14) heterocyclylalkyl, which may be optionally substituted with one or more R$_{40}$'s, 15) halo(C$_1$-C$_6$)alkyl, 16) —COOH, 17) —CONR$_{36}$R$_{36}$, 18) =O, 19) (C$_2$-C$_6$)-alkynyl, 20) —COR$_{36}$, 21) —S(O)$_p$R$_{36}$, 22) —SO$_2$NHR$_{36}$, 23) —COOR$_{36}$, 24) —NHC(CN)NHR$_{36}$; and 25) cycloalkyl, which may be optionally substituted with one or more R$_{40}$'s;

(c) cycloalkyl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) arylalkyl, which may be optionally substituted with one or more R$_{40}$'s, 11) heteroaryl, which may be optionally substituted with one or more R$_{40}$'s, 12) heteroarylalkyl, which may be optionally substituted with one or more R$_{40}$'s, 13) heterocyclyl, which may be optionally substituted with one or more R$_{40}$'s, 14) heterocyclylalkyl, which may be optionally substituted with one or more R$_{40}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, 25) —NHC(CN)NHR$_{36}$; and 26) cycloalkyl, which may be optionally substituted with one or more R$_{40}$'s;

(d) heteroaryl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) arylalkyl, which may be optionally substituted with one or more R$_{40}$'s, 11) heteroaryl, which may be optionally substituted with one or more R$_{40}$'s, 12) heteroarylalkyl, which may be optionally substituted with one or more R$_{40}$'s, 13) heterocyclyl, which may be optionally substituted with one or more R$_{40}$'s, 14) heterocyclylalkyl, which may be optionally substituted with one or more R$_{40}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, 25) —NHC(CN)NHR$_{36}$; and 26) cycloalkyl, which may be optionally substituted with one or more R$_{40}$'s;

(e) heterocyclyl, other than heteroaryl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) arylalkyl, which may be optionally substituted with one or more R$_{40}$'s, 11) heteroaryl, which may be optionally substituted with one or more R$_{40}$'s, 12) heteroarylalkyl, which may be optionally substituted with one or more R$_{40}$'s, 13) heterocyclyl, which may be optionally substituted with one or more R$_{40}$'s, 14) heterocyclylalkyl, which may be optionally substituted with one or more R$_{40}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, 25) —NHC(CN)NHR$_{36}$; and 26) cycloalkyl, which may be optionally substituted with one or more R$_{40}$'s;

(f) hydrogen;

(g) alkynyl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) heteroaryl, which may be optionally substituted with one or more R$_{40}$'s, 11) heterocyclyl, which may be optionally substituted with one or more R$_{40}$'s, 12) halo(C$_1$-C$_6$)alkyl, 13) (C$_2$-C$_6$)-alkenyl, 14) —COOH, 15) —CONR$_{36}$R$_{36}$, 16) =O, 17) (C$_2$-C$_6$)-alkynyl, 18) —COR$_{36}$, 19) —S(O)$_p$R$_{36}$, 20) —SO$_2$NHR$_{36}$, 21) —COOR$_{36}$, 22) —NHC(CN)NHR$_{36}$, or 23) cycloalkyl, which may be optionally substituted with one or more R$_{20}$'s; or (h) alkenyl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) heteroaryl, which may be optionally substituted with one or more R$_{40}$'s, 11) heterocyclyl, which may be optionally substituted with one or more R$_{40}$'s, 12) halo(C$_1$-C$_6$)alkyl, 13) (C$_2$-C$_6$)-alkenyl, 14) —COOH, 15) —CONR$_{36}$R$_{36}$, 16) =O, 17) (C$_2$-C$_6$)-alkynyl, 18) —COR$_{36}$, 19) —S(O)$_p$R$_{36}$, 20) —SO$_2$NHR$_{36}$, 21) —COOR$_{36}$, 22) —NHC(CN)NHR$_{36}$, or 23) cycloalkyl, which may be optionally substituted with one or more R$_{40}$'s;

or two R$_{26}$'s are taken together to form a 3- to 9-membered ring, which optionally may contain 1-4 heteroatoms selected from N, O, and S and be optionally substituted with one or more R$_{40}$'s;

$R_{29}$ and $R_{30}$ are independently hydrogen, —[(C=O)O$_r$]$_s$aryl, [(C=O)O$_r$]$_s$alkenyl, —[(C=O)O$_r$]$_s$alkyl, heterocyclyl, —CONR$_{46}$R$_{46}$, alkynyl, —COR$_{36}$, S(O)$_p$R$_{36}$, —SO$_2$NHR$_{36}$, —COOR$_{36}$, —C(CN)NHR$_{36}$, or cycloalkyl, wherein the aryl, alkyl, alkenyl, cycloalkyl or heterocyclyl may be optionally substituted with one or more $R_4$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —NR$_{49}$R$_{50}$, aryl, arylalkyl, heteroaryl, heteroarylalkyl, heterocyclyl, heterocyclylalkyl, haloalkyl, haloalkyloxy, —CONR$_{49}$R$_{50}$, alkenyl, arylalkyloxy, =O, alkynyl, cycloalkyl, cycloalkylalkyl, —COR$_{49}$, —S(O)$_p$R$_{49}$, —SO$_2$NHR$_{49}$, COOR$_{49}$, or —NHC(CN)NHR$_{49}$;

$R_{49}$ and $R_{50}$, at each occurrence, are independently hydrogen, alkyl, aryl, cycloalkyl, heteroaryl or heterocyclyl, other than heteroaryl;

r is 0 to 5;
s is 0 to 4; and
p is 1 or 2.

In one embodiment, compounds of the present invention are provided wherein the compounds are compounds of formula Ia

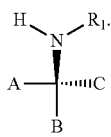

Ia

In another embodiment, compounds of the present invention are provided wherein:

A is phenyl, which is substituted with one or more substituents selected from the group consisting of: 1) halo, 2) (C$_1$-C$_6$)-alkyl, which may be optionally substituted with one or more $R_{20}$'s, 3) —OR$_6$, 4) (C$_1$-C$_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo(C$_1$-C$_6$)alkyl, 15) —COR$_6$, 16) =O, 17) —S(O)$_p$R$_6$, 18) —SO$_2$NHR$_6$, 19) —COOR$_6$, 20) —NHC(CN)NHR$_6$, 21) —CONR$_6$R$_6$, 22) (C$_2$-C$_6$)-alkynyl, which may be optionally substituted with one or more $R_{20}$'s, 23) (C$_2$-C$_6$)-alkenyl, which may be optionally substituted with one or more $R_{20}$'s, 24) —OCOR$_6$, 25) —OCOOR$_6$, or 26) —OCONR$_6$R$_6$; or any two adjacent substituents may join together to form a 4- to 8-membered ring, which optionally may contain 1-4 heteroatoms selected from N, O, and S and be optionally substituted with one or more $R_{20}$'s;

B is:
(a) phenyl, which is substituted with one or more substituents selected from the group consisting of: 1) halo, 2) (C$_1$-C$_6$)-alkyl, which may be optionally substituted with one or more $R_{20}$'s, 3) —OR$_6$, 4) (C$_1$-C$_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo(C$_1$-C$_6$)alkyl, 15) —COR$_6$, 16) —S(O)$_p$R$_6$, 17) —SO$_2$NHR$_6$, 18) —COOR$_6$, 19) —NHC(CN)NHR$_6$, and 20) —CONR$_6$R$_6$; or (b) heteroaryl, which is substituted with one or more substituents selected from the group consisting of: 1) halo, 2) (C$_1$-C$_6$)-alkyl, which may be optionally substituted with one or more $R_{20}$'s, 3) —OR$_6$, 4) (C$_1$-C$_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo(C$_1$-C$_6$)alkyl, 15) —COR$_6$, 16) —S(O)$_p$R$_6$, 17) —SO$_2$NHR$_6$, 18) —COOR$_6$, 19) —NHC(CN)NHR$_6$, and 20) —CONR$_6$R$_6$;

C is:
(a) alkyl, which may be optionally substituted with one or more substituents selected from the group consisting of: 1) halo, 2) (C$_1$-C$_6$)-alkyl, which may be optionally substituted with one or more $R_{20}$'s, 3) —OR$_6$, 4) (C$_1$-C$_6$)-alkylthio, 5) cyano, 6) nitro, 7) —NR$_9$R$_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo(C$_1$-C$_6$)alkyl, 12) —COR$_6$, 13) —CONR$_6$R$_6$, 14) —S(O)$_6$R$_6$, 15) —SO$_2$NHR$_6$, 16) —COOR$_6$, and 17) —NHC(CN)NHR$_6$;

(b) alkenyl, which may be optionally substituted with one or more substituents selected from the group consisting of: 1) halo, 2) (C$_1$-C$_6$)-alkyl, which may be optionally substituted with one or more $R_{20}$'s, 3) —OR$_6$, 4) (C$_1$-C$_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo(C$_1$-C$_6$)alkyl; or (c) cycloalkyl, which may be optionally substituted with one or more substituents selected from the group consisting of: 1) halo, 2) (C$_1$-C$_6$)-alkyl, which may be optionally substituted with one or more $R_{20}$'s, 3) —OR$_6$, 4) (C$_1$-C$_6$)-alkylthio, 5) cyano, 6) nitro, 7) —NR$_9$R$_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo(C$_1$-C$_6$)alkyl, 12) —COR$_6$, 13) —CONR$_6$R$_6$, 14) —S(O)$_6$R$_6$, 15) —SO$_2$NHR$_6$, 16) —COOR$_6$, and 17) —NHC(CN)NHR$_6$;

$R_1$ is H, —C(O)$R_3$, —C(O)N$R_2R_3$, —C(O)O$R_4$, —SO$_2R_5$, —C(S)NH$R_7$, —C$R_8R_8R_8$, or —C(S)$R_3$;

$R_2$ is:
(a) H;
(b) alkyl, which may be optionally substituted with one or more substituents selected from the group consisting of: 1) halo, 2) ($C_1$-$C_6$)-alkyl, which may be optionally substituted with one or more $R_{20}$'s, 3) —O$R_6$, 4) ($C_1$-$C_6$)-alkylthio, 5) cyano, 6) nitro, 7) —N$R_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —CO$R_6$, 13) —CON$R_6R_6$, 14) ($C_2$-$C_6$)-alkenyl, 15) ($C_2$-$C_6$)-alkynyl, 16) —S(O)$_pR_6$, 17) —SO$_2$NH$R_6$, 18) —CO$R_6$, and 19) —NHC(CN)NH$R_6$;
(c) alkenyl, which may be optionally substituted with one or more substituents selected from the group consisting of: 1) halo, 2) ($C_1$-$C_6$)-alkyl, which may be optionally substituted with one or more $R_{20}$'s, 3) —O$R_6$, 4) ($C_1$-$C_6$)-alkylthio, 5) cyano, 6) nitro, 7) —N$R_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CON$R_6R_6$, 16) ($C_2$-$C_6$)-alkenyl, 17) ($C_2$-$C_6$)-alkynyl, 18) —CO$R_6$, 19) —S(O)$_pR_6$, 20) —SO$_2$NH$R_6$, 21) —COO$R_6$, and 22) —NHC(CN)NH$R_6$; or
(d) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —O$R_6$, 4) ($C_1$-$C_6$)-alkylthio, 5) cyano, 6) nitro, 7) —N$R_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CO($C_1$-$C_6$)-alkyl, 16) —COOH, 17) —CO$_2$($C_1$-$C_6$)-alkyl, 18) —CON$R_6R_6$, 19) ($C_2$-$C_6$)-alkenyl, and 20) ($C_2$-$C_6$)-alkynyl;

$R_3$ is:
(a) alkyl, which may be optionally substituted with one or more substituents selected from the group consisting of: 1) halo, 2) ($C_1$-$C_6$)-alkyl, which may be optionally substituted with one or more $R_{20}$'s, 3) —O$R_6$, 4) ($C_1$-$C_6$)-alkylthio, 5) cyano, 6) nitro, 7) —N$R_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —CON$R_6R_6$, 13) ($C_2$-$C_6$)-alkenyl, 14) ($C_2$-$C_6$)-alkynyl, 15) —CO$R_6$, 16) —S(O)$_pR_6$, 17) —SO$_2$NH$R_6$, 18) —COO$R_6$, and 19) —NHC(CN)NH$R_6$;
(b) aryl, which may be optionally substituted with one or more substituents selected from the group consisting of: 1) halo, 2) ($C_1$-$C_6$)-alkyl, which may be optionally substituted with one or more $R_{20}$'s, 3) —O$R_6$, 4) ($C_1$-$C_6$)-alkylthio, 5) cyano, 6) nitro, 7) —N$R_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CON$R_6R_6$, 16) ($C_2$-$C_6$)-alkenyl, 17) =O, 18) ($C_2$-$C_6$)-alkynyl, 19) —CO$R_6$, 20) —S(O)$_pR_6$, 21) —SO$_2$NH$R_6$, 22) —COO$R_6$, and 23) —NHC(CN)NH$R_6$;
(c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —O$R_6$, 4) ($C_1$-$C_6$)-alkylthio, 5) cyano, 6) nitro, 7) —N$R_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CON$R_6R_6$, 16) ($C_2$-$C_6$)-alkenyl, 17) =O, 18) ($C_2$-$C_6$)-alkynyl, 19) —CO$R_6$, 20) —S(O)$_pR_6$, 21) —SO$_2$NH$R_6$, 22) —COO$R_6$, and 23) —NHC(CN)NH$R_6$;
(d) heteroaryl, which may be optionally substituted with one or more substituents selected from the group consisting of: 1) halo, 2) ($C_1$-$C_6$)-alkyl, which may be optionally substituted with one or more $R_{20}$'s, 3) —O$R_6$, 4) ($C_1$-$C_6$)-alkylthio, 5) cyano, 6) nitro, 7) —N$R_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CON$R_6R_6$, 16) ($C_2$-$C_6$)-alkenyl, 17) =O, 18) ($C_2$-$C_6$)-alkynyl, 19) —CO$R_6$, 20) —S(O)$_pR_6$, 21) —SO$_2$NH$R_6$, 22) —COO$R_6$, and 23) —NHC(CN)NH$R_6$;
(e) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —O$R_6$, 4) ($C_1$-$C_6$)-alkylthio, 5) cyano, 6) nitro, 7) —N$R_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CON$R_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, and 23) —$NHC(CN)NHR_6$; or (f) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ($C_2$-$C_6$)-alkynyl, 18) —$COR_6$, 19) —$S(O)_pR_6$, 20) —$SO_2NHR_6$, 21) —$COOR_6$, and 22) —$NHC(CN)NHR_6$;

or $R_2$ and $R_3$ are taken together to form a 3- to 9-membered ring, which optionally may contain 1-4 heteroatoms selected from N, O, and S and be optionally substituted with one or more $R_{20}$'s;

$R_4$ is:
(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, and 23) —$NHC(CN)NHR_6$;

(b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, and 23) —$NHC(CN)NHR_6$;

(c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, and 23) —$NHC(CN)NHR_6$;

(d) ($C_2$-$C_6$)-alkenyl; or
(e) ($C_2$-$C_6$)-alkynyl;

$R_5$ is arylalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, and 23) —$NHC(CN)NHR_6$;

$R_6$, at each occurrence, is independently:
(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, 22) —$NHC(CN)NHR_{36}$, or 23) cycloalkyl, which may be optionally substituted with one or more $R_{20}$'s;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —$NHC(CN)NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8)

—NR$_9$R$_{10}$, 9) aryl, which may be optionally substituted with one or more R$_{20}$'s, 10) arylalkyl, which may be optionally substituted with one or more R$_{20}$'s, 11) heteroaryl, which may be optionally substituted with one or more R$_{20}$'s, 12) heteroarylalkyl, which may be optionally substituted with one or more R$_{20}$'s, 13) heterocyclyl, which may be optionally substituted with one or more R$_{20}$'s, 14) heterocyclylalkyl, which may be optionally substituted with one or more R$_{20}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(d) heteroaryl, which may be optionally substituted with one or more substituents selected from the group consisting of: 1) halo, 2) —OH, 3) (C$_1$-C$_6$)-alkyl, which may be optionally substituted with one or more R$_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more R$_{20}$'s, 10) arylalkyl, which may be optionally substituted with one or more R$_{20}$'s, 11) heteroaryl, which may be optionally substituted with one or more R$_{20}$'s, 12) heteroarylalkyl, which may be optionally substituted with one or more R$_{20}$'s, 13) heterocyclyl, which may be optionally substituted with one or more R$_{20}$'s, 14) heterocyclylalkyl, which may be optionally substituted with one or more R$_{20}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(e) heterocyclyl, other than heteroaryl, which may be optionally substituted with one or more substituents selected from the group consisting of: 1) halo, 2) —OH, 3) (C$_1$-C$_6$)-alkyl, which may be optionally substituted with one or more R$_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more R$_{20}$'s, 10) arylalkyl, which may be optionally substituted with one or more R$_{20}$'s, 11) heteroaryl, which may be optionally substituted with one or more R$_{20}$'s, 12) heteroarylalkyl, which may be optionally substituted with one or more R$_{20}$'s, 13) heterocyclyl, which may be optionally substituted with one or more R$_{20}$'s, 14) heterocyclylalkyl, which may be optionally substituted with one or more R$_{20}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(f) hydrogen;

(g) alkynyl, which may be optionally substituted with one or more substituents selected from the group consisting of: 1) halo, 2) —OH, 3) (C$_1$-C$_6$)-alkyl, which may be optionally substituted with one or more R$_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more R$_{20}$'s, 10) heteroaryl, which may be optionally substituted with one or more R$_{20}$'s, 11) heterocyclyl, which may be optionally substituted with one or more R$_{20}$'s, 12) halo(C$_1$-C$_6$)alkyl, 13) (C$_2$-C$_6$)-alkenyl, 14) —COOH, 15) —CONR$_{36}$R$_{36}$, 16) =O, 17) (C$_2$-C$_6$)-alkynyl, 18) —COR$_{36}$, 19) —S(O)$_p$R$_{36}$, 20) —SO$_2$NHR$_{36}$, 21) —COOR$_{36}$, 22) —NHC(CN)NHR$_{36}$, or 23) cycloalkyl, which may be optionally substituted with one or more R$_{20}$'s; or (h) alkenyl, which may be optionally substituted with one or more substituents selected from the group consisting of: 1) halo, 2) —OH, 3) (C$_1$-C$_6$)-alkyl, which may be optionally substituted with one or more R$_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more R$_{20}$'s, 10) heteroaryl, which may be optionally substituted with one or more R$_{20}$'s, 11) heterocyclyl, which may be optionally substituted with one or more R$_{20}$'s, 12) halo(C$_1$-C$_6$)alkyl, 13) (C$_2$-C$_6$)-alkenyl, 14) —COOH, 15) —CONR$_{36}$R$_{36}$, 16) =O, 17) (C$_2$-C$_6$)-alkynyl, 18) —COR$_{36}$, 19) —S(O)$_p$R$_{36}$, 20) —SO$_2$NHR$_{36}$, 21) —COOR$_{36}$, 22) —NHC(CN)NHR$_{36}$, or 23) cycloalkyl, which may be optionally substituted with one or more R$_{20}$'s;

or two R$_6$'s are taken together to form a 3- to 9-membered ring, which optionally may contain 1-4 heteroatoms selected from N, O, and S and be optionally substituted with one or more R$_{20}$'s;

R$_7$ is aryl, which may be optionally substituted with one or more substituents selected from the group consisting of: 1) halo, 2) (C$_1$-C$_6$)-alkyl, which may be optionally substituted with one or more R$_{20}$'s, 3) —OR$_{26}$, 4) (C$_1$-C$_6$)-alkylthio, 5) cyano, 6) nitro, 7) —NR$_9$R$_{10}$, 8) aryl, which may be optionally substituted with one or more R$_{20}$'s, 9) arylalkyl, which may be optionally substituted with one or more R$_{20}$'s, 10) heteroaryl, which may be optionally substituted with one or more R$_{20}$'s, 11) heteroarylalkyl, which may be optionally substituted with one or more R$_{20}$'s, 12) heterocyclyl, which may be optionally substituted with one or more R$_{20}$'s, 13) heterocyclylalkyl, which may be optionally substituted with one or more R$_{20}$'s, 14) halo(C$_1$-C$_6$)alkyl, 15) (C$_2$-C$_6$)-alkenyl, 16) —CONR$_{26}$R$_{26}$, 17) =O, 18) (C$_2$-C$_6$)-alkynyl, 19) —COR$_6$, 20) —S(O)$_p$R$_{26}$, 21) —SO$_2$NHR$_{26}$, 22) —COOR$_{26}$, and 23) —NHC(CN)NHR$_{26}$;

R$_8$ can independently be:

(a) H;

(b) alkyl, which may be optionally substituted with one or more substituents selected from the group consisting of: 1) halo, 2) (C$_1$-C$_6$)-alkyl, which may be optionally substituted with one or more R$_{20}$'s, 3) —OR$_{26}$, 4) (C$_1$-C$_6$)-alkylthio, 5) cyano, 6) nitro, 7) —NR$_9$R$_{10}$, 8) aryl, which may be optionally substituted with one or more R$_{20}$'s, 9) heteroaryl, which may be optionally substituted with one or more R$_{20}$'s, 10) heterocyclyl, which may be optionally substituted with one or more R$_{20}$'s, 11) halo(C$_1$-C$_6$)alkyl, 12) (C$_2$-C$_6$)-alkenyl, 13) aryl(C$_2$-C$_6$)-alkynyl, 14) —CONR$_{26}$R$_{26}$, 15) =O, 16) (C$_2$-C$_6$)-alkynyl, 17) —COR$_{26}$, 18) —S(O)$_p$R$_{26}$, 19) —SO$_2$NHR$_{26}$, 20) —COOR$_{26}$, and 21) —NHC(CN)NHR$_{26}$;

(c) aryl, which may be optionally substituted with one or more substituents selected from the group consisting of: 1) halo, 2) (C$_1$-C$_6$)-alkyl, which may be optionally substituted with one or more R$_{20}$'s, 3) —OR$_{26}$, 4) (C$_1$-C$_6$)-alkylthio, 5) cyano, 6) nitro, 7) —NR$_9$R$_{10}$, 8) aryl, which may be optionally substituted with one or more R$_{20}$'s, 9) arylalkyl, which may be optionally substituted with one or more R$_{20}$'s, 10) heteroaryl, which may be optionally substituted with one or more R$_{20}$'s, 11) heteroarylalkyl, which may be optionally substituted with one or more R$_{20}$'s, 12) heterocyclyl, which may be optionally substituted with one or more R$_{20}$'s, 13) heterocyclylalkyl, which may be optionally substituted with one or more R$_{20}$'s, 14) halo(C$_1$-C$_6$)alkyl, 15) (C$_2$-C$_6$)-alkenyl, 16) —CONR$_{26}$R$_{26}$, 17) =O, 18) (C$_2$-C$_6$)-alkynyl, 19) —COR$_{26}$, 20) —S(O)$_p$R$_{26}$, 21) —SO$_2$NHR$_{26}$, 22) —COOR$_{26}$, and 23) —NHC(CN)NHR$_{26}$;

(d) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_{26}$, 20) —$S(O)_pR_{26}$, 21) —$SO_2NHR_{26}$, 22) —$COOR_{26}$, and 23) —$NHC(CN)NHR_{26}$;

(e) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_{26}$, 20) —$S(O)_pR_{26}$, 21) —$SO_2NHR_{26}$, 22) —$COOR_{26}$, and 23) —$NHC(CN)NHR_{26}$; or (f) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_{26}$, 20) —$S(O)_pR_{26}$, 21) —$SO_2NHR_{26}$, 22) —$COOR_{26}$, and 23) —$NHC(CN)NHR_{26}$;

or two $R_8$'s are taken together to form a 3- to 9-membered ring, which may optionally contain 1-4 heteroatoms selected from N, O, and S and be optionally substituted with one or more $R_{20}$'s;

$R_9$ and $R_{10}$ are independently: (a) hydrogen; (b) —[(C=O)$O_r$]$_s$aryl, wherein the aryl may be optionally substituted with one or more $R_{20}$'s; (c) —[(C=O)$O_r$]$_s$($C_2$-$C_8$)-alkenyl, wherein the alkenyl may be optionally substituted with one or more $R_{20}$'s; (d) —[(C=O)$O_r$]$_s$($C_1$-$C_8$)alkyl, wherein the alkyl may be optionally substituted with one or more $R_{20}$'s; (e) heterocyclyl optionally substituted with one or more $R_{20}$'s;

(f) —$CONR_{26}R_{26}$; (g) —($C_2$-$C_6$)-alkynyl; (h) —$COR_{26}$; (i) —$S(O)_pR_{26}$; (j) —$SO_2NHR_{26}$; (k) —$COOR_{26}$; or (l) —$NHC(CN)NHR_{26}$;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is: (a) halo; (b) ($C_1$-$C_6$)-alkyl, which may be optionally substituted with one or more $R_{21}$'s; c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) =O; (q) —($C_2$-$C_6$)-alkynyl; (r) —$COR_{26}$; (s) —$S(O)_pR_{26}$; (t) —$SO_2NHR_{26}$; (u) —$COOR_{26}$; (v) —$NHC(CN)NHR_{26}$; (w) cycloalkyl, which may be optionally substituted with one or more $R_{21}$'s; (x) cycloalkylalkyl, which may be optionally substituted with one or more $R_{21}$'s; or (y) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) =O; (r) ($C_2$-$C_6$)-alkynyl; (s) cycloalkyl; (t) cycloalkylalkyl; (u) —$COR_{26}$; (v) —$S(O)_pR_{26}$; (w) —$SO_2NHR_{26}$; (x) —$COOR_{26}$; or (y) —$NHC(CN)NHR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) NHC(CN)NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —$NHC(CN)NHR_{36}$;

(c) cycloalkyl, which may be optionally substituted with one or more substituents selected from the group consisting of: 1) halo, 2) —OH, 3) $(C_1$-$C_6)$-alkyl, which may be optionally substituted with one or more $R_{40}$'s, 4) —$OR_{36}$, 5) $(C_1$-$C_6)$-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo$(C_1$-$C_6)$alkyl, 16) $(C_2$-$C_6)$-alkenyl, 17) —COOH, 18) —$CONR_{36}R_{36}$, 19) =O, 20) $(C_2$-$C_6)$-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(d) heteroaryl, which may be optionally substituted with one or more substituents selected from the group consisting of: 1) halo, 2) —OH, 3) $(C_1$-$C_6)$-alkyl, which may be optionally substituted with one or more $R_{40}$'s, 4) —$OR_{36}$, 5) $(C_1$-$C_6)$-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo$(C_1$-$C_6)$alkyl, 16) $(C_2$-$C_6)$-alkenyl, 17) —COOH, 18) —$CONR_{36}R_{36}$, 19) =O, 20) $(C_2$-$C_6)$-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(e) heterocyclyl, other than heteroaryl, which may be optionally substituted with one or more substituents selected from the group consisting of: 1) halo, 2) —OH, 3) $(C_1$-$C_6)$-alkyl, which may be optionally substituted with one or more $R_{40}$'s, 4) —$OR_{36}$, 5) $(C_1$-$C_6)$-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo$(C_1$-$C_6)$alkyl, 16) $(C_2$-$C_6)$-alkenyl, 17) —COOH, 18) —$CONR_{36}R_{36}$, 19) =O, 20) $(C_2$-$C_6)$-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(f) hydrogen;

(g) alkynyl, which may be optionally substituted with one or more substituents selected from the group consisting of: 1) halo, 2) —OH, 3) $(C_1$-$C_6)$-alkyl, which may be optionally substituted with one or more $R_{40}$'s, 4) —$OR_{36}$, 5) $(C_1$-$C_6)$-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo$(C_1$-$C_6)$alkyl, 13) $(C_2$-$C_6)$-alkenyl, 14) —COOH, 15) —$CONR_{36}R_{36}$, 16) =O, 17) $(C_2$-$C_6)$-alkynyl, 18) —$COR_{36}$, 19) —$S(O)_pR_{36}$, 20) —$SO_2NHR_{36}$, 21) —$COOR_{36}$, 22) —$NHC(CN)NHR_{36}$, or 23) cycloalkyl, which may be optionally substituted with one or more $R_{20}$'s; or (h) alkenyl, which may be optionally substituted with one or more substituents selected from the group consisting of: 1) halo, 2) —OH, 3) $(C_1$-$C_6)$-alkyl, which may be optionally substituted with one or more $R_{40}$'s, 4) —$OR_{36}$, 5) $(C_1$-$C_6)$-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo$(C_1$-$C_6)$alkyl, 13) $(C_2$-$C_6)$-alkenyl, 14) —COOH, 15) —$CONR_{36}R_{36}$, 16) =O, 17) $(C_2$-$C_6)$-alkynyl, 18) —$COR_{36}$, 19) —$S(O)_pR_{36}$, 20) —$SO_2NHR_{36}$, 21) —$COOR_{36}$, 22) —$NHC(CN)NHR_{36}$, or 23) cycloalkyl, which may be optionally substituted with one or more $R_{40}$'s;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —$[(C=O)O_r]_s$aryl, $[(C=O)O_r]_s$alkenyl, —$[(C=O)O_r]_s$alkyl, heterocyclyl, —$CONR_{46}R_{46}$, alkynyl, —$COR_{36}$, $S(O)_pR_{36}$, —$SO_2NHR_{36}$, —$COOR_{36}$, or —$C(CN)NHR_{36}$, wherein the aryl, alkyl, alkenyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, =O, alkynyl, cycloalkyl, cycloalkylalkyl, —$COR_{49}$, —$S(O)_pR_{49}$, —$SO_2NHR_{49}$, $COOR_{49}$, or —$NHC(CN)NHR_{49}$;

$R_{49}$ and $R_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2.

In yet another embodiment, compounds of the present invention are provided wherein:

A is phenyl, which is substituted with one or more substituents selected from the group consisting of: 1) halo, 2) $(C_1$-$C_6)$-alkyl, which may be optionally substituted with one or more $R_{20}$'s, 3) —$OR_6$, 4) $(C_1$-$C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1$-$C_6)$alkyl, 15) —$COR_6$, 16) =O, 17) —$COR_6$, 18) —$CONR_6R_6$, 19) $(C_2$-$C_6)$-alkynyl, which may be optionally substituted with one or more $R_{20}$'s, 20) $(C_2$-$C_6)$-alkenyl, which may be optionally substituted with one or more $R_{20}$'s, 21) —$OCOR_6$, 22) —$OCOOR_6$, or 23) —$OCONR_6R_6$; or any two adjacent substituents may join together to form a 4- to 8-membered ring, which optionally may contain 1-4 heteroatoms selected from N, O, and S and be optionally substituted with one or more $R_{20}$'s;

B is:
(a) phenyl, which is substituted with one or more substituents selected from the group consisting of: 1) halo, 2) $(C_1$-$C_6)$-alkyl, which may be optionally substituted with one or more $R_{20}$'s, 3) —$OR_6$, 4) $(C_1$-$C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1$-$C_6)$alkyl, 15) —$COR_6$, 16) —$COOR_6$, and 17) —$CONR_6R_6$; or
(b) a nitrogen containing heteroaryl, which is substituted with one or more substituents selected from the group consisting of: 1) halo, 2) $(C_1$-$C_6)$-alkyl, which may be optionally substituted with one or more $R_{20}$'s, 3) —$OR_6$, 4) $(C_1$-$C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1$-$C_6)$alkyl, 15) —$COR_6$, 16) —$COOR_6$, and 17) —$CONR_6R_6$;

C is alkyl, which is substituted with one or more substituents selected from the group consisting of: 1) halo, 2) —$OR_6$, 3) —$NR_9R_{10}$, 4) aryl, which may be optionally substituted with one or more $R_{20}$'s, 5) heteroaryl, which may be optionally substituted with one or more $R_{20}$'s, 6) heterocyclyl, which may be optionally substituted with one or more $R_{20}$'s, 7) —$CONR_6R_6$, and 8) —$COOR_6$;

$R_1$ is —$C(O)R_3$, —$C(O)NR_2R_3$, —$C(O)OR_4$ or $CH_2R_5$;

$R_2$ is:
(a) H;
(b) alkyl, which may be optionally substituted with one or more substituents selected from the group consisting of: 1) halo, 2) $(C_1$-$C_6)$-alkyl, which may be optionally substituted with one or more $R_{20}$'s, 3) —$OR_6$, 4) $(C_1$-$C_6)$-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo $(C_1$-$C_6)$alkyl, 12) —$OR_6$, 13) —$CONR_6R_6$, 14) $(C_2$-$C_6)$-alkenyl, 15) $(C_2$-$C_6)$-alkynyl, and 16) $COOR_6$;
(c) alkenyl, which may be optionally substituted with one or more substituents selected from the group consisting of: 1) halo, 2) $(C_1$-$C_6)$-alkyl, which may be optionally substituted with one or more $R_{20}$'s, 3) —$OR_6$, 4) $(C_1$-$C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1$-$C_6)$alkyl, 15) —$CONR_6R_6$, 16) $(C_2$-$C_6)$-alkenyl, 17) $(C_2$-$C_6)$-alkynyl, 18) —$OR_6$, and 19) —$COOR_6$; or
(d) cycloalkyl, which may be optionally substituted with one or more substituents selected from the group consisting of: 1) halo, 2) $(C_1$-$C_6)$-alkyl, which may be optionally substituted with one or more $R_{20}$'s, 3) —$OR_6$, 4) $(C_1$-$C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1$-$C_6)$alkyl, 15) —$CO(C_1$-$C_6)$-alkyl, 16) —$COOH$, 17) —$CO_2$ $(C_1$-$C_6)$-alkyl, 18) —$CONR_6R_6$, 19) $(C_2$-$C_6)$-alkenyl, and 20) $(C_2$-$C_6)$-alkynyl;

$R_3$ is:
(a) alkyl, which may be optionally substituted with one or more substituents selected from the group consisting of: 1) halo, 2) $(C_1$-$C_6)$-alkyl, which may be optionally substituted with one or more $R_{20}$'s, 3) —$OR_6$, 4) $(C_1$-$C_6)$-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo $(C_1$-$C_6)$alkyl, 12) —$CONR_6R_6$, 13) $(C_2$-$C_6)$-alkenyl, 14) $(C_2$-$C_6)$-alkynyl, 15) —$COR_6$, and 16) —$COOR_6$;
(b) aryl, which may be optionally substituted with one or more substituents selected from the group consisting of: 1) halo, 2) $(C_1$-$C_6)$-alkyl, which may be optionally substituted with one or more $R_{20}$'s, 3) —$OR_6$, 4) $(C_1$-$C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1$-$C_6)$alkyl, 15) —$CONR_6R_6$, 16) $(C_2$-$C_6)$-alkenyl, 17) =O, 18) $(C_2$-$C_6)$-alkynyl, 19) —$COR_6$, and 20) —$COOR_6$;
(c) cycloalkyl, which may be optionally substituted with one or more substituents selected from the group consisting of: 1) halo, 2) $(C_1$-$C_6)$-alkyl, which may be optionally substituted with one or more $R_{20}$'s, 3) —$OR_6$, 4) $(C_1$-$C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1$-$C_6)$alkyl, 15) —$CONR_6R_6$, 16) $(C_2$-$C_6)$-alkenyl, 17) =O, 18) $(C_2$-$C_6)$-alkynyl, 19) —$COR_6$, and 20) —$COOR_6$;
(d) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;

(e) heterocyclyl, other than heteroaryl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$OR_6$, and 20) —$COOR_6$; or (f) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ($C_2$-$C_6$)-alkynyl, 18) —$OR_6$, and 19) —$COOR_6$;

or $R_2$ and $R_3$ are taken together to form a 3- to 9-membered ring, which optionally may contain 1-4 heteroatoms selected from N, O, and S and may be optionally substituted with one or more $R_{20}$'s;

$R_4$ is:
(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;

(b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$; or (c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;

$R_6$, at each occurrence, is independently:
(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —$NHC(CN)NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —$NHC(CN)NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —S(O)$_p$$R_{36}$, 23) —$SO_2NHR_{36}$, 24) —$COOR_{36}$, and 25) NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —S(O)$_p$$R_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —S(O)$_p$$R_{36}$, 23) —$SO_2NHR_{36}$, 24) —$COOR_{36}$, and 25) —NHC(CN)$NHR_{36}$; or (f) hydrogen;

or two $R_6$'s are taken together to form a 3- to 9-membered ring, which optionally may contain 1-4 heteroatoms selected from N, O, and S and may be optionally substituted with one or more $R_{20}$'s;

$R_8$ can independently be:

(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) heterocyclyl, which may be optionally substituted with one or more $R_{20}$'s, 10) heterocyclyl, which may be optionally substituted with one or more $R_{20}$'s, 11) halo($C_1$-$C_6$)alkyl, 12) ($C_2$-$C_6$)-alkenyl, 13) aryl($C_2$-$C_6$)-alkynyl, 14) —$CONR_{26}R_{26}$, 15) =O, 16) ($C_2$-$C_6$)-alkynyl, 17) —$COR_{26}$, and 18) —$COOR_{26}$;

(b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_{26}$, and 20) —$COOR_{26}$;

(c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_{26}$, and 20) —$COOR_{26}$;

(d) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_{26}$, and 20) —$COOR_{26}$; or (e) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_{26}$, and 20) —$COOR_{26}$;

or two $R_8$'s are taken together to form a 3- to 9-membered ring, which may optionally contain 1-4 heteroatoms selected from N, O, and S and may be optionally substituted with one or more $R_{20}$'s;

$R_9$ and $R_{10}$ are independently: (a) hydrogen; (b) —[(C=O)$O_r]_s$aryl, wherein the aryl may be optionally substituted with one or more $R_{20}$'s; (c) —[(C=O)$O_r]_s$($C_1$-$C_8$)alkyl, wherein the alkyl may be optionally substituted with one or more $R_{20}$'s; or (d) heterocyclyl optionally substituted with one or more $R_{20}$'s;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano, (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) —($C_2$-$C_6$)-alkynyl; (q) —$COR_{26}$; (r) —$COOR_{26}$; (s) cycloalkyl, which may be optionally substituted with one or more $R_{21}$'s; (t) cycloalkylalkyl, which may be optionally substituted with one or more $R_{21}$'s; or (u) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) ($C_2$-$C_6$)-alkynyl; (r) cycloalkyl; (s) cycloalkylalkyl; (t) —$OR_{26}$; or (u) —$COOR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) $SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$; or (f) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —[(C=O)O$_r$]$_s$aryl, —[(C=O)O$_r$]$_s$alkyl, or heterocyclyl, wherein the aryl, alkyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —NR$_{49}$R$_{50}$, aryl, arylalkyl, heteroaryl, heteroarylalkyl, heterocyclyl, heterocyclylalkyl, haloalkyl, haloalkyloxy, —CONR$_{49}$R$_{50}$, alkenyl, arylalkyloxy, =O, alkynyl, cycloalkyl, cycloalkylalkyl, —COR$_{49}$ or —COOR$_{49}$;

$R_{49}$ and $R_{50}$, at each occurrence, are independently hydrogen, alkyl, aryl, heteroaryl or heterocyclyl, other than heteroaryl;

r is 0 to 3;

s is 0 to 2; and p is 1 or 2.

In still yet another embodiment, compounds of the present invention are provided wherein:

A is phenyl, which is substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —COR$_6$, 16) =O, 17) —COR$_6$, 18) —CONR$_6$R$_6$, 19) ($C_2$-$C_6$)-alkynyl, which may be optionally substituted with one or more $R_{20}$'s, 20) —OCOR$_6$, 21) —OCOOR$_6$, or 22) —OCONR$_6$R$_6$; or any two adjacent substituents may join together to form a 4- to 8-membered ring, which optionally may contain 1-4 heteroatoms selected from N, O, and S and be optionally substituted with one or more $R_{20}$'s;

B is:
(a) phenyl, which is substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —COOR$_6$, and 16) —CONR$_6$R$_6$; or
(b) a 6- to 10-membered nitrogen containing heteroaryl, which is substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —COR$_6$, and 16) —CONR$_6$R$_6$;

C is alkyl, which is substituted with one or more substituents selected from the group consisting of: 1) halo, 2) —OR$_6$, 3) —NR$_9$R$_{10}$, 4) aryl, which may be optionally substituted with one or more $R_{20}$'s, 5) a nitrogen containing heteroaryl, which may be optionally substituted with one or more $R_{20}$'s, 6) —CONR$_6$R$_6$, and 7) —COOR$_6$;

$R_1$ is —C(O)R$_3$, —C(O)NR$_2$R$_3$ or —CH$_2$R$_8$;

$R_2$ is:
(a) H;
(b) alkyl, which may be optionally substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo ($C_1$-$C_6$)alkyl, 12) —COR$_6$, 13) —CONR$_6$R$_6$, 14) ($C_2$-$C_6$)-alkenyl, 15) ($C_2$-$C_6$)-alkynyl, and 16) —COOR$_6$; or
(c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CO($C_1$-$C_6$)-alkyl, 16) —COOH, 17) —CO$_2$ ($C_1$-$C_6$)-alkyl, 18) —CONR$_6$R$_6$, 19) ($C_2$-$C_6$)-alkenyl, and 20) ($C_2$-$C_6$)-alkynyl;

$R_3$ is:
(a) alkyl, which may be optionally substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo ($C_1$-$C_6$)alkyl, 12) —CONR$_6$R$_6$, 13) ($C_2$-$C_6$)-alkenyl, 14) ($C_2$-$C_6$)-alkynyl, 15) —COR$_6$, and 16) —COOR$_6$;
(b) aryl, which may be optionally substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CONR$_6$R$_6$, 16) ($C_2$-$C_6$)-alkenyl, 17) =O, 18) ($C_2$-$C_6$)-alkynyl, 19) —COR$_6$, and 20) —COOR$_6$;

(c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CONR$_6$R$_6$, 16) ($C_2$-$C_6$)-alkenyl, 17) =O, 18) ($C_2$-$C_6$)-alkynyl, 19) —COR$_6$, and 20) —COOR$_6$;

(d) heteroaryl, which may be optionally substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CONR$_6$R$_6$, 16) ($C_2$-$C_6$)-alkenyl, 17) =O, 18) ($C_2$-$C_6$)-alkynyl, 19) —COR$_6$, and 20) —COOR$_6$;

(e) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CONR$_6$R$_6$, 16) ($C_2$-$C_6$)-alkenyl, 17) =O, 18) ($C_2$-$C_6$)-alkynyl, 19) —COR$_6$, and 20) —COOR$_6$; or (f) alkenyl, which may be optionally substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CONR$_6$R$_6$, 16) ($C_2$-$C_6$)-alkenyl, 17) ($C_2$-$C_6$)-alkynyl, 18) —OR$_6$, and 19) —COOR$_6$;

or $R_2$ and $R_3$ are taken together to form a 3- to 9-membered ring, which optionally may contain 1-4 heteroatoms selected from N, O, and S and may be optionally substituted with one or more $R_{20}$'s;

$R_6$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —CONR$_{36}$R$_{36}$, 16) =O, 17) ($C_2$-$C_6$)-alkynyl, 18) —COR$_{36}$, 19) —S(O)$_p$R$_{36}$, 20) —SO$_2$NHR$_{36}$, 21) —COOR$_{36}$, and 22) —NHC(CN)NHR$_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —CONR$_{36}$R$_{36}$, 18) =O, 19) ($C_2$-$C_6$)-alkynyl, 20) —COR$_{36}$, 21) —S(O)$_p$R$_{36}$, 22) —SO$_2$NHR$_{36}$, 23) —COOR$_{36}$, and 24) —NHC(CN)NHR$_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$; or (f) hydrogen;

or two $R_6$'s are taken together to form a 3- to 9-membered ring, which optionally may contain 1-4 heteroatoms selected from N, O, and S and may be optionally substituted with one or more $R_{20}$'s;

$R_8$ can independently be:

(a) alkyl, which may be optionally substituted with one or more substituents selected from the group consisting of: 1) halo, 2) ($C_1$-$C_6$)-alkyl, which may be optionally substituted with one or more $R_{20}$'s, 3) —OR$_{26}$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) ($C_2$-$C_6$)-alkenyl, 13) aryl($C_2$-$C_6$)-alkynyl, 14) —CONR$_{26}$R$_{26}$, 15) =O, 16) ($C_2$-$C_6$)-alkynyl, 17) —COR$_{26}$, and 18) —COOR$_{26}$;

(b) aryl, which may be optionally substituted with one or more substituents selected from the group consisting of: 1) halo, 2) ($C_1$-$C_6$)-alkyl, which may be optionally substituted with one or more $R_{20}$'s, 3) —OR$_{26}$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —CONR$_{26}$R$_{26}$, 17) =O, 18) ($C_2$-$C_6$)-alkynyl, 19) —COR$_{26}$, and 20) —COOR$_{26}$;

(c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —OR$_{26}$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —CONR$_{26}$R$_{26}$, 17) =O, 18) ($C_2$-$C_6$)-alkynyl, 19) —COR$_{26}$, and 20) —COOR$_{26}$;

(d) heteroaryl, which may be optionally substituted with one or more substituents selected from the group consisting of: 1) halo, 2) ($C_1$-$C_6$)-alkyl, which may be optionally substituted with one or more $R_{20}$'s, 3) —OR$_{26}$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —CONR$_{26}$R$_{26}$, 17) =O, 18) ($C_2$-$C_6$)-alkynyl, 19) —COR$_{26}$, and 20) —COOR$_{26}$; or (e) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —OR$_{26}$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —CONR$_{26}$R$_{26}$, 17) =O, 18) ($C_2$-$C_6$)-alkynyl, 19) —COR$_{26}$, and 20) —COOR$_{26}$;

or two $R_8$'s are taken together to form a 3- to 9-membered ring, which may optionally contain 1-4 heteroatoms selected from N, O, and S and may be optionally substituted with one or more $R_{20}$'s;

$R_9$ and $R_{10}$ are independently: (a) hydrogen, (b) —[(C=O)O$_r$]$_s$aryl, wherein the aryl may be optionally substituted with one or more $R_{20}$'s, or (c) —[(C=O)O$_r$]$_s$($C_1$-$C_8$)alkyl, wherein the alkyl may be optionally substituted with one or more $R_{20}$'s;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is: (a) halo; (b) ($C_1$-$C_6$)-alkyl, which may be optionally substituted with one or more $R_{21}$'s; (c) —OR$_{26}$; (d) ($C_1$-$C_6$)-alkylthio; (e) cyano; (f) nitro; (g) —NR$_{29}$R$_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) —($C_2$-$C_6$)-alkynyl; (q) —$COR_{26}$; (r) —$COOR_{26}$; (s) cycloalkyl, which may be optionally substituted with one or more $R_{21}$'s; (t) cycloalkylalkyl, which may be optionally substituted with one or more $R_{21}$'s; or (u) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) ($C_2$-$C_6$)-alkynyl; (r) cycloalkyl; (s) cycloalkylalkyl; (t) —$COR_{26}$; or (u) —$COOR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —$NHC(CN)NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —$NHC(CN)NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo ($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$; or (f) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —[(C=O)$O_r$]$_s$aryl, or [(C=O)$O_r$]$_s$alkyl, wherein the aryl or alkyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, =O, alkynyl, cycloalkyl, cycloalkylalkyl, —$COR_{49}$ or —$COR_{49}$;

$R_{49}$ and $R_{50}$, at each occurrence, are independently hydrogen, alkyl, aryl or heteroaryl;

r is 0 to 2;

s is 0 to 1; and p is 1 or 2.

In one embodiment, compounds of the present invention are provided wherein:

A is phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$COOR_6$, 18) ($C_2$-$C_6$)-alkynyl, which may be optionally substituted with one or more $R_{20}$'s, 19) —$OCOR_6$, and 20) —$OCOOR_6$; or any two adjacent substituents may join together to form a 4- to 8-membered ring, which optionally may contain 1-4 heteroatoms selected from N, O, and S and be optionally substituted with one or more $R_{20}$'s;

B is:
- (a) phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, and 15) —$COOR_6$; or
- (b) a 6-membered nitrogen containing heteroaryl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, and 15) —$COOR_6$;

C is alkyl, which is substituted with one or more substituents selected from the group consisting of: 1) halo, 2) phenyl, which may be optionally substituted with one or more $R_{20}$'s, or 3) a 5- or 6-membered nitrogen containing heteroaryl, which may be optionally substituted with one or more $R_{20}$'s;

$R_1$ is —C(O)$R_3$, —C(O)$NR_2R_3$ or $CH_2R_8$;

$R_2$ is:
- (a) H; or
- (b) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) ($C_2$-$C_6$)-alkenyl, 15) ($C_2$-$C_6$)-alkynyl, and 16) $COOR_6$;

$R_3$ is:
- (a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$CONR_6R_6$, 13) ($C_2$-$C_6$)-alkenyl, 14) ($C_2$-$C_6$)-alkynyl, 15) —$COR_6$, and 16) $COOR_6$;
- (b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;
- (c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;
- (d) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$; or
- (e) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —NR$_9$R$_{10}$, 8) aryl, which may be optionally substituted with one or more R$_{20}$'s, 9) arylalkyl, which may be optionally substituted with one or more R$_{20}$'s, 10) heteroaryl, which may be optionally substituted with one or more R$_{20}$'s, 11) heteroarylalkyl, which may be optionally substituted with one or more R$_{20}$'s, 12) heterocyclyl, which may be optionally substituted with one or more R$_{20}$'s, 13) heterocyclylalkyl, which may be optionally substituted with one or more R$_{20}$'s, 14) halo (C$_1$-C$_6$)alkyl, 15) —CONR$_6$R$_6$, 16) (C$_2$-C$_6$)-alkenyl, 17) =O, 18) (C$_2$-C$_6$)-alkynyl, 19) —COR$_6$, and 20) —COOR$_6$;

R$_6$, at each occurrence, is independently:

(a) alkyl, which may be optionally substituted with one or more substituents selected from the group consisting of: 1) halo, 2) —OH, 3) (C$_1$-C$_6$)-alkyl, which may be optionally substituted with one or more R$_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more R$_{20}$'s, 10) heteroaryl, which may be optionally substituted with one or more R$_{20}$'s, 11) heterocyclyl, which may be optionally substituted with one or more R$_{20}$'s, 12) halo(C$_1$-C$_6$)alkyl, 13) (C$_2$-C$_6$)-alkenyl, 14) —COOH, 15) —CONR$_{36}$R$_{36}$, 16) =O, 17) (C$_2$-C$_6$)-alkynyl, 18) —COR$_{36}$, 19) —S(O)$_p$R$_{36}$, 20) —SO$_2$NHR$_{36}$, 21) —COOR$_{36}$, and 22) —NHC(CN)NHR$_{36}$;

(b) aryl, which may be optionally substituted with one or more substituents selected from the group consisting of: 1) halo, 2) —OH, 3) (C$_1$-C$_6$)-alkyl, which may be optionally substituted with one or more R$_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more R$_{20}$'s, 10) arylalkyl, which may be optionally substituted with one or more R$_{20}$'s, 11) heteroaryl, which may be optionally substituted with one or more R$_{20}$'s, 12) heteroarylalkyl, which may be optionally substituted with one or more R$_{20}$'s, 13) heterocyclyl, which may be optionally substituted with one or more R$_{20}$'s, 14) heterocyclylalkyl, which may be optionally substituted with one or more R$_{20}$'s, 15) halo(C$_1$-C$_6$)alkyl, 16) —COOH, 17) —CONR$_{36}$R$_{36}$, 18) =O, 19) (C$_2$-C$_6$)-alkynyl, 20) —COR$_{36}$, 21) —S(O)$_p$R$_{36}$, 22) —SO$_2$NHR$_{36}$, 23) —COOR$_{36}$, and 24) —NHC(CN)NHR$_{36}$;

(c) cycloalkyl, which may be optionally substituted with one or more substituents selected from the group consisting of: 1) halo, 2) —OH, 3) (C$_1$-C$_6$)-alkyl, which may be optionally substituted with one or more R$_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more R$_{20}$'s, 10) arylalkyl, which may be optionally substituted with one or more R$_{20}$'s, 11) heteroaryl, which may be optionally substituted with one or more R$_{20}$'s, 12) heteroarylalkyl, which may be optionally substituted with one or more R$_{20}$'s, 13) heterocyclyl, which may be optionally substituted with one or more R$_{20}$'s, 14) heterocyclylalkyl, which may be optionally substituted with one or more R$_{20}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(d) heteroaryl, which may be optionally substituted with one or more substituents selected from the group consisting of: 1) halo, 2) —OH, 3) (C$_1$-C$_6$)-alkyl, which may be optionally substituted with one or more R$_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more R$_{20}$'s, 10) arylalkyl, which may be optionally substituted with one or more R$_{20}$'s, 11) heteroaryl, which may be optionally substituted with one or more R$_{20}$'s, 12) heteroarylalkyl, which may be optionally substituted with one or more R$_{20}$'s, 13) heterocyclyl, which may be optionally substituted with one or more R$_{20}$'s, 14) heterocyclylalkyl, which may be optionally substituted with one or more R$_{20}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(e) heterocyclyl, other than heteroaryl, which may be optionally substituted with one or more substituents selected from the group consisting of: 1) halo, 2) —OH, 3) (C$_1$-C$_6$)-alkyl, which may be optionally substituted with one or more R$_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more R$_{20}$'s, 10) arylalkyl, which may be optionally substituted with one or more R$_{20}$'s, 11) heteroaryl, which may be optionally substituted with one or more R$_{20}$'s, 12) heteroarylalkyl, which may be optionally substituted with one or more R$_{20}$'s, 13) heterocyclyl, which may be optionally substituted with one or more R$_{20}$'s, 14) heterocyclylalkyl, which may be optionally substituted with one or more R$_{20}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$; or (f) hydrogen;

R$_8$ can independently be:

(a) alkyl, which may be optionally substituted with one or more substituents selected from the group consisting of: 1) halo, 2) (C$_1$-C$_6$)-alkyl, which may be optionally substituted with one or more R$_{20}$'s, 3) —OR$_{26}$, 4) (C$_1$-C$_6$)-alkylthio, 5) cyano, 6) nitro, 7) —NR$_9$R$_{10}$, 8) aryl, which may be optionally substituted with one or more R$_{20}$'s, 9) heteroaryl, which may be optionally substituted with one or more R$_{20}$'s, 10) heterocyclyl, which may be optionally substituted with one or more R$_{20}$'s, 11) halo (C$_1$-C$_6$)alkyl, 12) (C$_2$-C$_6$)-alkenyl, 13) aryl(C$_2$-C$_6$)-alkynyl, 14) —CONR$_{26}$R$_{26}$, 15) =O, 16) (C$_2$-C$_6$)-alkynyl, 17) —COR$_{26}$, and 18) —COOR$_{26}$;

(b) aryl, which may be optionally substituted with one or more substituents selected from the group consisting of: 1) halo, 2) (C$_1$-C$_6$)-alkyl, which may be optionally substituted with one or more R$_{20}$'s, 3) —OR$_{26}$, 4) (C$_1$-C$_6$)-alkylthio, 5) cyano, 6) nitro, 7) —NR$_9$R$_{10}$, 8) aryl, which may be optionally substituted with one or more R$_{20}$'s, 9) arylalkyl, which may be optionally substituted with one or more R$_{20}$'s, 10) heteroaryl, which may be optionally substituted with one or more R$_{20}$'s, 11) heteroarylalkyl, which may be optionally substituted with one or more R$_{20}$'s, 12) heterocyclyl, which may be optionally substituted with one or more R$_{20}$'s, 13) heterocyclylalkyl, which may be optionally substituted with one or more R$_{20}$'s, 14) halo(C$_1$-C$_6$)alkyl, 15) (C$_2$-C$_6$)-alkenyl, 16) —CONR$_{26}$R$_{26}$, 17) =O, 18) (C$_2$-C$_6$)-alkynyl, 19) —COR$_{26}$, and 20) —COOR$_{26}$;

(c) cycloalkyl, which may be optionally substituted with one or more substituents selected from the group consisting of: 1) halo, 2) (C$_1$-C$_6$)-alkyl, which may be optionally substituted with one or more R$_{20}$'s, 3)

—OR$_{26}$, 4) (C$_1$-C$_6$)-alkylthio, 5) cyano, 6) nitro, 7) —NR$_9$R$_{10}$, 8) aryl, which may be optionally substituted with one or more R$_{20}$'s, 9) arylalkyl, which may be optionally substituted with one or more R$_{20}$'s, 10) heteroaryl, which may be optionally substituted with one or more R$_{20}$'s, 11) heteroarylalkyl, which may be optionally substituted with one or more R$_{20}$'s, 12) heterocyclyl, which may be optionally substituted with one or more R$_{20}$'s, 13) heterocyclylalkyl, which may be optionally substituted with one or more R$_{20}$'s, 14) halo(C$_1$-C$_6$)alkyl, 15) (C$_2$-C$_6$)-alkenyl, 16) —CONR$_{26}$R$_{26}$, 17) =O, 18) (C$_2$-C$_6$)-alkynyl, 19) —COR$_{26}$, and 20) —COOR$_{26}$;

(d) heteroaryl, which may be optionally substituted with one or more substituents selected from the group consisting of: 1) halo, 2) (C$_1$-C$_6$)-alkyl, which may be optionally substituted with one or more R$_{20}$'s, 3) —OR$_{26}$, 4) (C$_1$-C$_6$)-alkylthio, 5) cyano, 6) nitro, 7) —NR$_9$R$_{10}$, 8) aryl, which may be optionally substituted with one or more R$_{20}$'s, 9) arylalkyl, which may be optionally substituted with one or more R$_{20}$'s, 10) heteroaryl, which may be optionally substituted with one or more R$_{20}$'s, 11) heteroarylalkyl, which may be optionally substituted with one or more R$_{20}$'s, 12) heterocyclyl, which may be optionally substituted with one or more R$_{20}$'s, 13) heterocyclylalkyl, which may be optionally substituted with one or more R$_{20}$'s, 14) halo(C$_1$-C$_6$)alkyl, 15) (C$_2$-C$_6$)-alkenyl, 16) —CONR$_{26}$R$_{26}$, 17) =O, 18) (C$_2$-C$_6$)-alkynyl, 19) —COR$_{26}$, and 20) —COOR$_{26}$; or (e) heterocyclyl, other than heteroaryl, which may be optionally substituted with one or more substituents selected from the group consisting of: 1) halo, 2) (C$_1$-C$_6$)-alkyl, which may be optionally substituted with one or more R$_{20}$'s, 3) —OR$_{26}$, 4) (C$_1$-C$_6$)-alkylthio, 5) cyano, 6) nitro, 7) —NR$_9$R$_{10}$, 8) aryl, which may be optionally substituted with one or more R$_{20}$'s, 9) arylalkyl, which may be optionally substituted with one or more R$_{20}$'s, 10) heteroaryl, which may be optionally substituted with one or more R$_{20}$'s, 11) heteroarylalkyl, which may be optionally substituted with one or more R$_{20}$'s, 12) heterocyclyl, which may be optionally substituted with one or more R$_{20}$'s, 13) heterocyclylalkyl, which may be optionally substituted with one or more R$_{20}$'s, 14) halo(C$_1$-C$_6$)alkyl, 15) (C$_2$-C$_6$)-alkenyl, 16) —CONR$_{26}$R$_{26}$, 17) =O, 18) (C$_2$-C$_6$)-alkynyl, 19) —COR$_{26}$, and 20) —COOR$_{26}$;

or two R$_8$'s are taken together to form a 3- to 9-membered ring, which may optionally contain 1-4 heteroatoms selected from N, O, and S and may be optionally substituted with one or more R$_{20}$'s;

R$_9$ and R$_{10}$ are independently: (a) hydrogen, or (b) —[(C=O)O$_r$]$_s$(C$_1$-C$_8$)alkyl, wherein the alkyl may be optionally substituted with one or more R$_{20}$'s;

or R$_9$ and R$_{10}$ are taken together with the nitrogen to which both are attached to form a 3- to 8-membered ring, which may optionally contain 1-4 heteroatoms selected from N, O, and S and be optionally substituted with one or more R$_{20}$'s;

R$_{20}$ is: (a) halo; (b) (C$_1$-C$_6$)-alkyl, which may be optionally substituted with one or more R$_{21}$'s; (c) —OR$_{26}$; (d) (C$_1$-C$_6$)-alkylthio; (e) cyano; (f) nitro; (g) —NR$_{29}$R$_{30}$; (h) aryl, which may be optionally substituted with one or more R$_{21}$'s; (i) arylalkyl, which may be optionally substituted with one or more R$_{21}$'s; (j) heteroaryl, which may be optionally substituted with one or more R$_{21}$'s; (k) heteroarylalkyl, which may be optionally substituted with one or more R$_{21}$'s; (l) heterocyclyl, which may be optionally substituted with one or more R$_{21}$'s; (m) heterocyclylalkyl, which may be optionally substituted with one or more R$_{21}$'s; (n) halo(C$_1$-C$_6$)alkyl; (o) (C$_2$-C$_6$)-alkenyl; (p) —(C$_2$-C$_6$)-alkynyl; (q) —COR$_{26}$; (r) —COOR$_{26}$; (s) cycloalkyl, which may be optionally substituted with one or more R$_{21}$'s; (t) cycloalkylalkyl, which may be optionally substituted with one or more R$_{21}$'s; or (u) —CONR$_{26}$R$_{26}$;

R$_{21}$ is: (a) halo; (b) (C$_1$-C$_6$)-alkyl; (c) —OR$_{26}$; (d) (C$_1$-C$_6$)-alkylthio; (e) cyano; (f) nitro; (g) —NR$_{29}$R$_{30}$; (h) aryl; (i) arylalkyl; (j) heteroaryl; (k) heteroarylalkyl; (l) heterocyclyl; (m) heterocyclylalkyl; (n) halo(C$_1$-C$_6$)alkyl; (o) —CONR$_{26}$R$_{26}$; (p) (C$_2$-C$_6$)-alkenyl; (q) (C$_2$-C$_6$)-alkynyl; (r) cycloalkyl; (s) cycloalkylalkyl; (t) —OR$_{26}$; or (u) —COOR$_{26}$;

R$_{26}$, at each occurrence, is independently:
(a) alkyl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) heteroaryl, which may be optionally substituted with one or more R$_{40}$'s, 11) heterocyclyl, which may be optionally substituted with one or more R$_{40}$'s, 12) halo(C$_1$-C$_6$)alkyl, 13) (C$_2$-C$_6$)-alkenyl, 14) —COOH, 15) —CONR$_{36}$R$_{36}$, 16) =O, 17) (C$_2$-C$_6$)-alkynyl, 18) —COR$_{36}$, 19) —S(O)$_p$R$_{36}$, 20) —SO$_2$NHR$_{36}$, 21) —COOR$_{36}$, and 22) —NHC(CN)NHR$_{36}$;

(b) aryl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) arylalkyl, which may be optionally substituted with one or more R$_{40}$'s, 11) heteroaryl, which may be optionally substituted with one or more R$_{40}$'s, 12) heteroarylalkyl, which may be optionally substituted with one or more R$_{40}$'s, 13) heterocyclyl, which may be optionally substituted with one or more R$_{40}$'s, 14) heterocyclylalkyl, which may be optionally substituted with one or more R$_{40}$'s, 15) halo(C$_1$-C$_6$)alkyl, 16) —COOH, 17) —CONR$_{36}$R$_{36}$, 18) =O, 19) (C$_2$-C$_6$)-alkynyl, 20) —COR$_{36}$, 21) —S(O)$_p$R$_{36}$, 22) —SO$_2$NHR$_{36}$, 23) —COR$_{36}$, and 24) —NHC(CN)NHR$_{36}$;

(c) cycloalkyl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) arylalkyl, which may be optionally substituted with one or more R$_{40}$'s, 11) heteroaryl, which may be optionally substituted with one or more R$_{40}$'s, 12) heteroarylalkyl, which may be optionally substituted with one or more R$_{40}$'s, 13) heterocyclyl, which may be optionally substituted with one or more R$_{40}$'s, 14) heterocyclylalkyl, which may be optionally substituted with one or more R$_{40}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) $SO_2NHR_{36}$, 24) —$COOR_{36}$, and 25) —$NHC(CN)NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$; or (f) hydrogen;

$R_{29}$ and $R_{30}$ are independently hydrogen or —[(C=O)$O_r]_s$alkyl, wherein the alkyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, =O, alkynyl, cycloalkyl, cycloalkylalkyl, —$COR_{49}$, or —$COOR_{49}$;

$R_{49}$ and $R_{50}$, at each occurrence, are independently hydrogen, alkyl, aryl, or heteroaryl;

r is 0 to 2;

s is 0 to 1; and p is 1 or 2.

In another embodiment, compounds of the present invention are provided wherein:

A is phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) ($C_2$-$C_6$)-alkynyl, which may be optionally substituted with one or more $R_{20}$'s, and 18) —$OCOR_6$; or any two adjacent substituents may join together to form a 4- to 8-membered ring, which optionally may contain 1-4 heteroatoms selected from N, O, and S and be optionally substituted with one or more $R_{20}$'s;

B is phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl;

C is alkyl, which is substituted with one or more substituents selected from the group consisting of: 1) phenyl, which may be optionally substituted with one or more $R_{20}$'s, or 2) a 5- or 6-membered nitrogen containing heteroaryl, which may be optionally substituted with one or more $R_{20}$'s;

$R_1$ is —$C(O)R_3$, —$C(O)NHR_3$ or —$CH_2R_8$;

$R_3$ is:

(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo ($C_1$-$C_6$)alkyl, 12) —$CONR_6R_6$, 13) ($C_2$-$C_6$)-alkenyl, 14) ($C_2$-$C_6$)-alkynyl, 15) —$COR_6$, and 16) $COOR_6$;

(b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;

(c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;

(d) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$; or (e) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) —($C_2$-$C_6$)-alkynyl, 19) —$COR_6$, and 20) —$COOR_6$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)NHR_{36}$; or (f) hydrogen;

$R_8$ can independently be:

(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) ($C_2$-$C_6$)-alkenyl, 13) aryl($C_2$-$C_6$)-alkynyl, 14) —$CONR_{26}R_{26}$, 15) =O, 16) ($C_2$-$C_6$)-alkynyl, 17) —$COR_{26}$, and 18) —$COOR_{26}$;

(b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_{26}$, and 20) —$COOR_{26}$;

(c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_{26}$, and 20) —$COOR_{26}$;

(d) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_{26}$, and 20) —$COOR_{26}$; or (e) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_{26}$, and 20) —$COOR_{26}$;

$R_9$ and $R_{10}$ are independently: (a) hydrogen; or (b) —[(C=O)$O_r$]$_s$($C_1$-$C_8$)alkyl, wherein the alkyl may be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) —($C_2$-$C_6$)-alkynyl; (q) —$COR_{26}$; (r) —$COOR_{26}$; (s) cycloalkyl, which may be optionally substituted with one or more $R_{21}$'s; (t) cycloalkylalkyl, which may be optionally substituted with one or more $R_{21}$'s; or (u) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) ($C_2$-$C_6$)-alkynyl; (r) cycloalkyl; (s) cycloalkylalkyl; (t) —$COR_{26}$; or (u) —$COOR_{26}$;

$R_{26}$, at each occurrence, is independently:
(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)NHR$_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)NHR$_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$; or (f) hydrogen;

$R_{29}$ and $R_{30}$ are independently hydrogen or —$[(C=O)O_r]_s$alkyl, wherein the alkyl may be optionally substituted with one or more $R_{40}$'s;

$R_{36}$, at each occurrence, is independently alkyl, aryl, heteroaryl or heterocyclyl, other than heteroaryl, wherein the alkyl, aryl, heteroaryl or heterocyclyl may be optionally substituted with one or more $R_{40}$'s;

$R_{40}$ is halo, —OH, alkyl, alkyloxy, alkylthio, cyano, nitro, aryl, arylalkyl, heteroaryl, heteroarylalkyl, heterocyclyl, heterocyclylalkyl, haloalkyl, haloalkyloxy, alkenyl, arylalkyloxy, =O, alkynyl, cycloalkyl or cycloalkylalkyl;

r is 0 to 2;

s is 0 to 1; and p is 1 or 2.

In yet another embodiment, compounds of the present invention are provided wherein:

A is phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, and 17) —$OCOR_6$; or any two adjacent substituents may join together to form a 4- to 8-membered ring, which optionally may contain 1-4 heteroatoms selected from N, O, and S and be optionally substituted with one or more $R_{20}$'s;

B is phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl;

C is methyl, which is substituted with one or more substituents selected from the group consisting of: 1) phenyl, which may be optionally substituted with one or more $R_{20}$'s, or 2) a 5- or 6-membered nitrogen containing heteroaryl, which may be optionally substituted with one or more $R_{20}$'s;

$R_1$ is —$C(O)R_3$, —$C(O)NHR_3$ or $CH_2R_8$;

$R_3$ is:

(a) alkyl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo ($C_1$-$C_6$)alkyl, 12) —$CONR_6R_6$, 13) ($C_2$-$C_6$)-alkenyl, 14) ($C_2$-$C_6$)-alkynyl, 15) —$COR_6$, and 16) —$COOR_6$;

(b) aryl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;

(c) cycloalkyl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COR_6$;

(d) heteroaryl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$; or (e) heterocyclyl, other than heteroaryl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$SO_2NHR_{36}$, 20) —$COOR_{36}$, and 21) —NHC(CN)$NHR_{36}$;

(b) aryl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$SO_2NHR_{36}$, 22) —$COOR_{36}$, and 23) —NHC(CN)$NHR_{36}$;

(c) heteroaryl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$SO_2NHR_{36}$, 23) —$COOR_{36}$, and 24) —NHC(CN)$NHR_{36}$; or (d) hydrogen;

$R_8$ can independently be:

(a) alkyl, which may be optionally substituted with one or more substituents selected from the group consisting of: 1) halo, 2) ($C_1$-$C_6$)-alkyl, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) ($C_2$-$C_6$)-alkenyl, 13) aryl($C_2$-$C_6$)-alkynyl, 14) —$CONR_{26}R_{26}$, 15) =O, 16) ($C_2$-$C_6$)-alkynyl, 17) —$COR_{26}$, and 18) —$COOR_{26}$;

(b) aryl, which may be optionally substituted with one or more substituents selected from the group consisting of: 1) halo, 2) ($C_1$-$C_6$)-alkyl, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_{26}$, and 20) —$COOR_{26}$;

(c) cycloalkyl, which may be optionally substituted with one or more substituents selected from the group consisting of: 1) halo, 2) ($C_1$-$C_6$)-alkyl, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-

$C_6$)-alkenyl, 16) —$CONR_{26}R_{26}$, 17) =O, 18) ($C_2$-$C_6$)-alkynyl, 19) —$COR_{26}$, and 20) —$COOR_{26}$;

(d) heteroaryl, which may be optionally substituted with one or more substituents selected from the group consisting of: 1) halo, 2) ($C_1$-$C_6$)-alkyl, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_{26}$, and 20) —$COOR_{26}$; or (e) heterocyclyl, other than heteroaryl, which may be optionally substituted with one or more substituents selected from the group consisting of: 1) halo, 2) ($C_1$-$C_6$)-alkyl, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_{26}$, and 20) —$COOR_{26}$;

$R_9$ and $R_{10}$ are independently: (a) hydrogen; or (b) —$[(C=O)O_r]_s(C_1$-$C_8)$alkyl, wherein the alkyl may be optionally substituted with one or more $R_{20}$'s;

$R_{20}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) —($C_2$-$C_6$)-alkynyl; (q) —$COR_{26}$; (r) —$COR_{26}$; (s) cycloalkyl, which may be optionally substituted with one or more $R_{21}$'s; (t) cycloalkylalkyl, which may be optionally substituted with one or more $R_{21}$'s; or (u) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) ($C_2$-$C_6$)-alkynyl; (r) cycloalkyl; (s) cycloalkylalkyl; (t) —$COR_{26}$; or (u) —$COOR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$SO_2NHR_{36}$, 20) —$COOR_{36}$, and 21) —$NHC(CN)NHR_{36}$;

(b) aryl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =, 19) ($C_2$-$C_6$)-alkynyl, 20) —$COR_{36}$, 21) —$SO_2NHR_{36}$, 22) —$COOR_{36}$, and 23) —$NHC(CN)NHR_{36}$;

(c) heteroaryl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$SO_2NHR_{36}$, 23) —$COOR_{36}$, and 24) —$NHC(CN)NHR_{36}$; or (d) hydrogen;

$R_{29}$ and $R_{30}$ are independently hydrogen or —$[(C=O)O_r]_s$alkyl, wherein the alkyl may be optionally substituted with one or more $R_{40}$'s;

$R_{36}$, at each occurrence, is independently alkyl, aryl or heteroaryl, wherein the alkyl, aryl or heteroaryl may be optionally substituted with one or more $R_{40}$'s;

$R_{40}$ is halo, —OH, alkyl, alkyloxy, alkylthio, cyano, nitro, aryl, arylalkyl, heteroaryl, heteroarylalkyl, heterocyclyl, heterocyclylalkyl, haloalkyl, haloalkyloxy, alkenyl, arylalkyloxy, =O, alkynyl, cycloalkyl, or cycloalkylalkyl;

r is 0 to 2; and s is 0 to 1.

In still yet another embodiment, compounds of the present invention are provided wherein:

A is phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, and 15) —$COR_6$;

B is phenyl, which is substituted with one or more substituents selected from the group consisting of: 1) halo, 2) ($C_1$-

$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl;

C is methyl, which is substituted with a 5- or 6-membered nitrogen containing heteroaryl, which may be optionally substituted with one or more $R_{20}$'s;

$R_1$ is —$C(O)R_3$, —$C(O)NHR_3$ or $CH_2R_8$;

$R_3$ is:

(a) alkyl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) aryl, which may be optionally substituted with one or more $R_{20}$'s, 8) heteroaryl, which may be optionally substituted with one or more $R_{20}$'s, 9) heterocyclyl, which may be optionally substituted with one or more $R_{20}$'s, 10) halo($C_1$-$C_6$)alkyl, 11) ($C_2$-$C_6$)-alkenyl, 12) ($C_2$-$C_6$)-alkynyl, 13) —$COR_6$, and 14) —$COR_6$;

(b) aryl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, 13) halo($C_1$-$C_6$)alkyl, 14) ($C_2$-$C_6$)-alkenyl, 15) ($C_2$-$C_6$)-alkynyl, 16) —$OR_6$, and 17) —$COOR_6$;

(c) cycloalkyl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, 13) halo($C_1$-$C_6$)alkyl, 14) ($C_2$-$C_6$)-alkenyl, 15) ($C_2$-$C_6$)-alkynyl, 16) —$OR_6$, and 17) —$COOR_6$;

(d) heteroaryl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, 13) halo($C_1$-$C_6$)alkyl, 14) ($C_2$-$C_6$)-alkenyl, 15) ($C_2$-$C_6$)-alkynyl, 16) —$COR_6$, and 17) —$COOR_6$; or (e) heterocyclyl, other than heteroaryl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, 13) halo($C_1$-$C_6$)alkyl, 14) ($C_2$-$C_6$)-alkenyl, 15) ($C_2$-$C_6$)-alkynyl, 16) —$COR_6$, and 17) —$COOR_6$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) ($C_2$-$C_6$)-alkenyl, 13) —COOH, 14) ($C_2$-$C_6$)-alkynyl, 15) —$COR_{36}$, and 16) —$COOR_{36}$; or (b) hydrogen;

$R_8$ can independently be:

(a) alkyl, which may be optionally substituted with one or more substituents selected from the group consisting of: 1) halo, 2) ($C_1$-$C_6$)-alkyl, 3) —$OR_{26}$, 4) ($C_1$-$C_6$)-alkylthio, 5) cyano, 6) nitro, 7) aryl, which may be optionally substituted with one or more $R_{20}$'s, 8) heteroaryl, which may be optionally substituted with one or more $R_{20}$'s, 9) heterocyclyl, which may be optionally substituted with one or more $R_{20}$'s, 10) halo($C_1$-$C_6$)alkyl, 11) ($C_2$-$C_6$)-alkenyl, 12) ($C_2$-$C_6$)-alkynyl, 13) —$COR_{26}$, and 14) —$COOR_{26}$;

(b) aryl, which may be optionally substituted with one or more substituents selected from the group consisting of: 1) halo, 2) ($C_1$-$C_6$)-alkyl, 3) —$OR_{26}$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, 13) halo($C_1$-$C_6$)alkyl, 14) ($C_2$-$C_6$)-alkenyl, 15) ($C_2$-$C_6$)-alkynyl, 16) —$COR_{26}$, and 17) —$COOR_{26}$;

(c) cycloalkyl, which may be optionally substituted with one or more substituents selected from the group consisting of: 1) halo, 2) ($C_1$-$C_6$)-alkyl, 3) —$OR_{26}$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, 13) halo($C_1$-$C_6$)alkyl, 14) ($C_2$-$C_6$)-alkenyl, 15) ($C_2$-$C_6$)-alkynyl, 16) —$COR_{26}$, and 17) —$COOR_{26}$;

(d) heteroaryl, which may be optionally substituted with one or more substituents selected from the group consisting of: 1) halo, 2) ($C_1$-$C_6$)-alkyl, 3) —$OR_{26}$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, 13) halo($C_1$-$C_6$)alkyl, 14) ($C_2$-$C_6$)-alkenyl, 15) ($C_2$-$C_6$)-alkynyl, 16) —$COR_{26}$, and 17) —$COOR_{26}$; or (e) heterocyclyl, other than heteroaryl, which may be optionally substituted with one or more substituents selected from the group consisting of: 1) halo, 2) ($C_1$-$C_6$)-alkyl, 3) —$OR_{26}$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, 13) halo($C_1$-$C_6$)alkyl, 14) ($C_2$-$C_6$)-alkenyl, 15) ($C_2$-$C_6$)-alkynyl, 16) —$COR_{26}$, and 17) —$COOR_{26}$;

$R_{20}$ is: (a) halo; (b) ($C_1$-$C_6$)-alkyl; (c) —$OR_{26}$; (d) ($C_1$-$C_6$)-alkylthio; (e) cyano; (f) nitro; (g) aryl, which may be optionally substituted with one or more $R_{21}$'s; (h) arylalkyl, which may be optionally substituted with one or more $R_{21}$'s; (i) heteroaryl, which may be optionally substituted with one or more $R_{21}$'s; (j) heteroarylalkyl, which may be optionally substituted with one or more $R_{21}$'s; (k) heterocyclyl, which may be optionally substituted with one or more $R_{21}$'s; (l) heterocyclylalkyl, which may be optionally substituted with one or more $R_{21}$'s; (m) halo($C_1$-$C_6$)alkyl; (n) ($C_2$-$C_6$)-alkenyl; (o) —($C_2$-$C_6$)-alkynyl; (p) —$COR_{26}$; (q) —$COOR_{26}$; (r) cycloalkyl, which may be optionally substituted with one or more $R_{21}$'s; or (s) cycloalkylalkyl, which may be optionally substituted with one or more $R_{21}$'s;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) aryl; (h) arylalkyl; (i) heteroaryl; (j) heteroarylalkyl; (k) heterocyclyl; (l) heterocyclylalkyl; (m) halo($C_1$-$C_6$)alkyl; (n) ($C_2$-$C_6$)-alkenyl; (o) ($C_2$-$C_6$)-alkynyl; (p) cycloalkyl; (q) cycloalkylalkyl; (r) —$COR_{26}$; or (s) —$COOR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) aryl, which may be optionally substituted with one or more $R_{40}$'s, 9) heteroaryl, which may be optionally substituted with one or more $R_{40}$'s, 10) heterocyclyl, which may be optionally substituted with one or more $R_{40}$'s, 11) halo($C_1$-$C_6$)alkyl, 12) ($C_2$-$C_6$)-alkenyl, 13) —COOH, 14) ($C_2$-$C_6$)-alkynyl, 15) —$COR_{36}$, or 16) —$COOR_{36}$; or (b) hydrogen;

$R_{36}$, at each occurrence, is independently alkyl, aryl or heteroaryl, wherein the alkyl, aryl or heteroaryl may be optionally substituted with one or more $R_{40}$'s; and $R_{40}$ is halo, —OH, alkyl, alkyloxy, alkylthio, cyano, nitro, aryl, arylalkyl, heteroaryl, heteroarylalkyl, heterocyclyl, heterocyclylalkyl, haloalkyl, haloalkyloxy, alkenyl, arylalkyloxy, alkynyl, cycloalkyl or cycloalkylalkyl.

Also in accordance with the present invention, compounds of the present invention are those wherein:

A is:

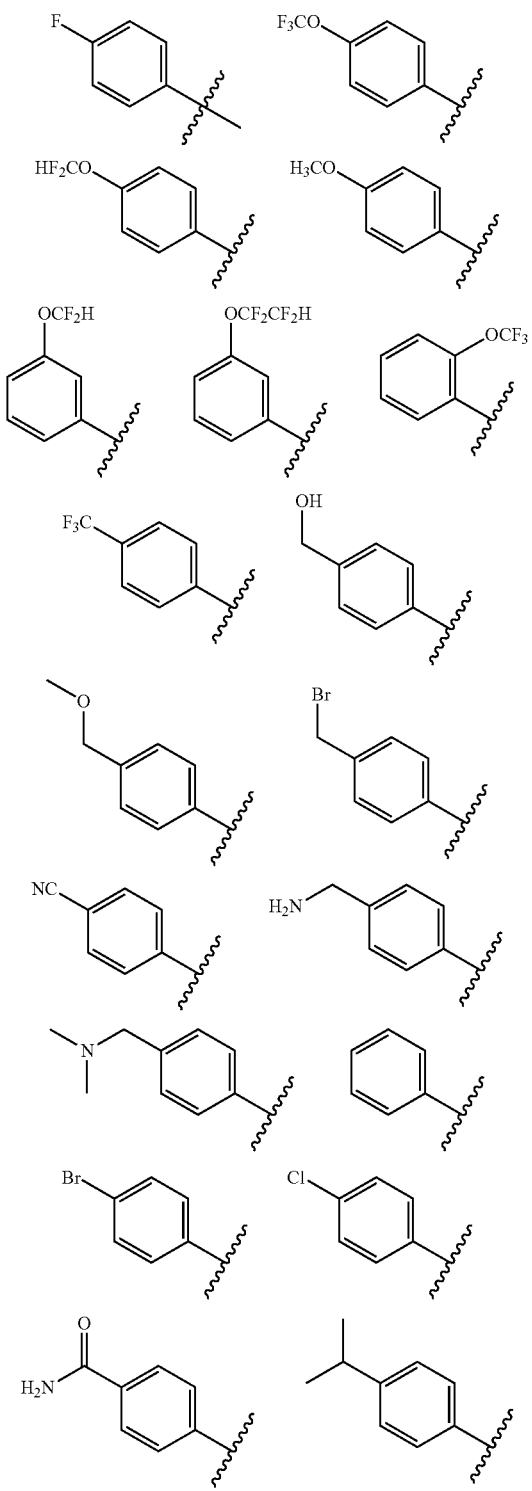

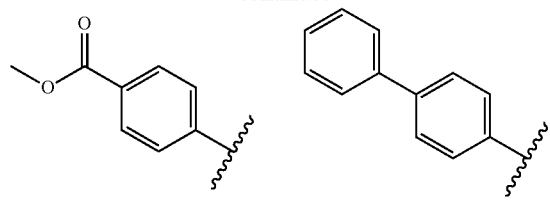
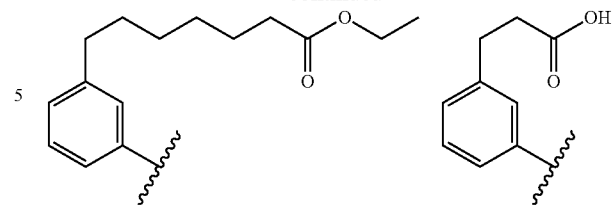
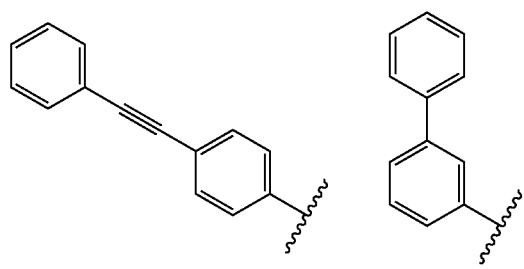
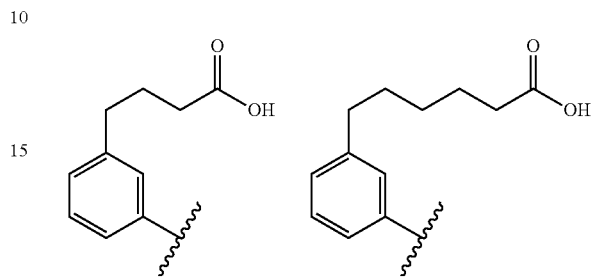
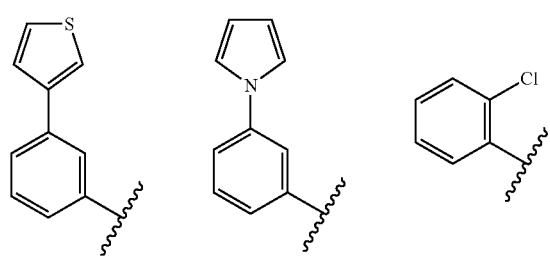
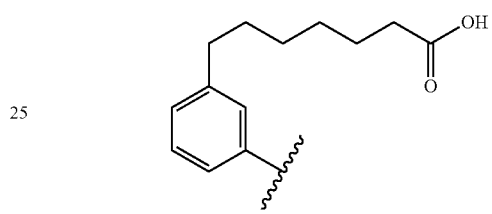
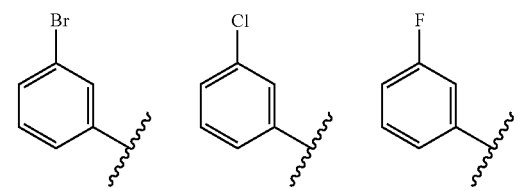
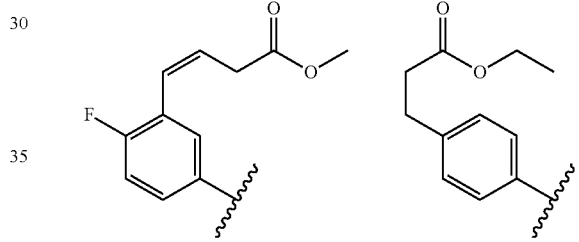
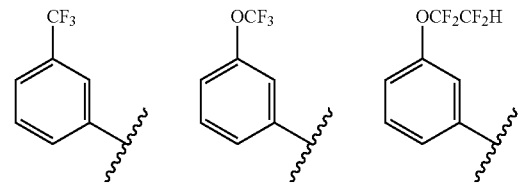
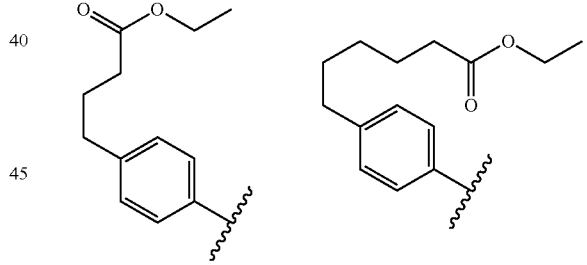
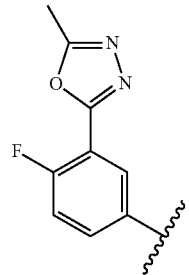
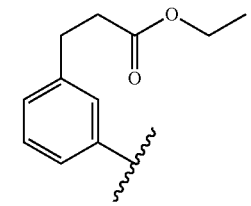
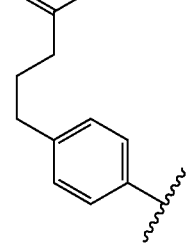
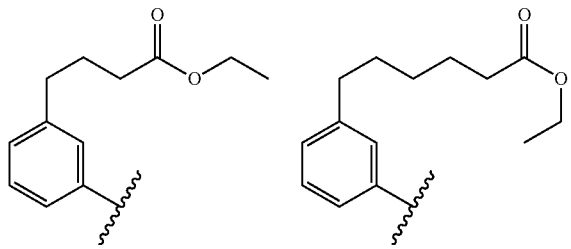
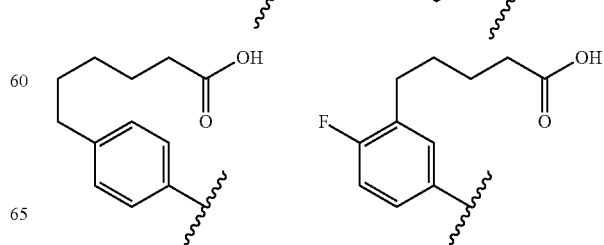

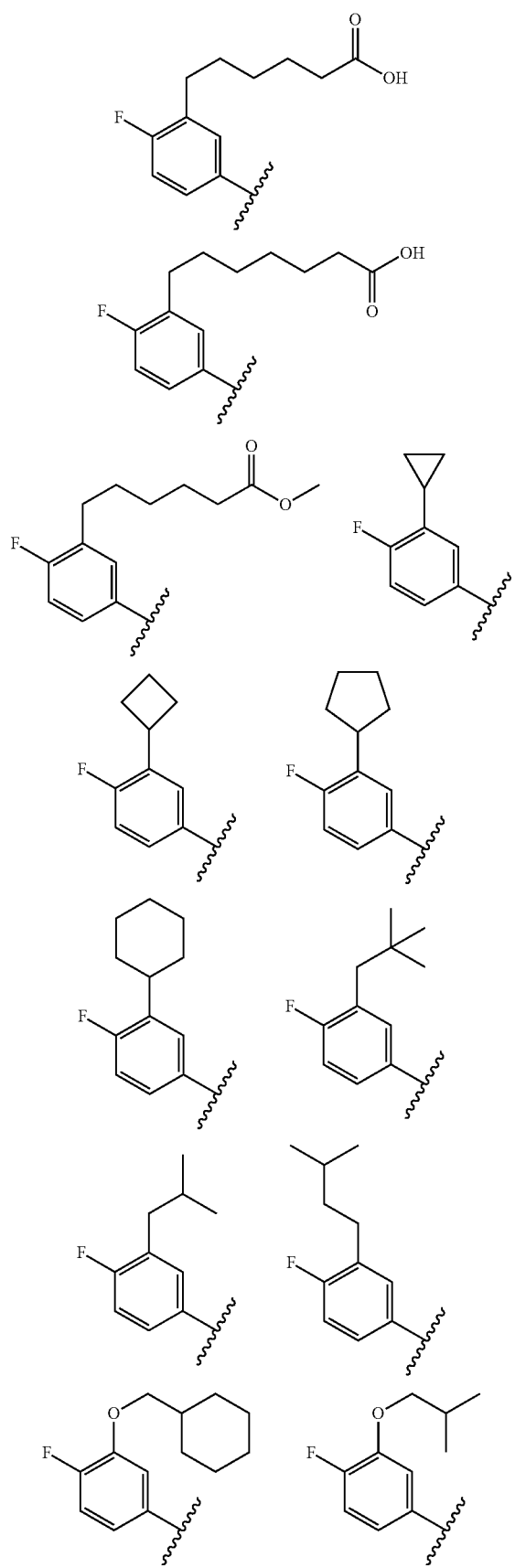
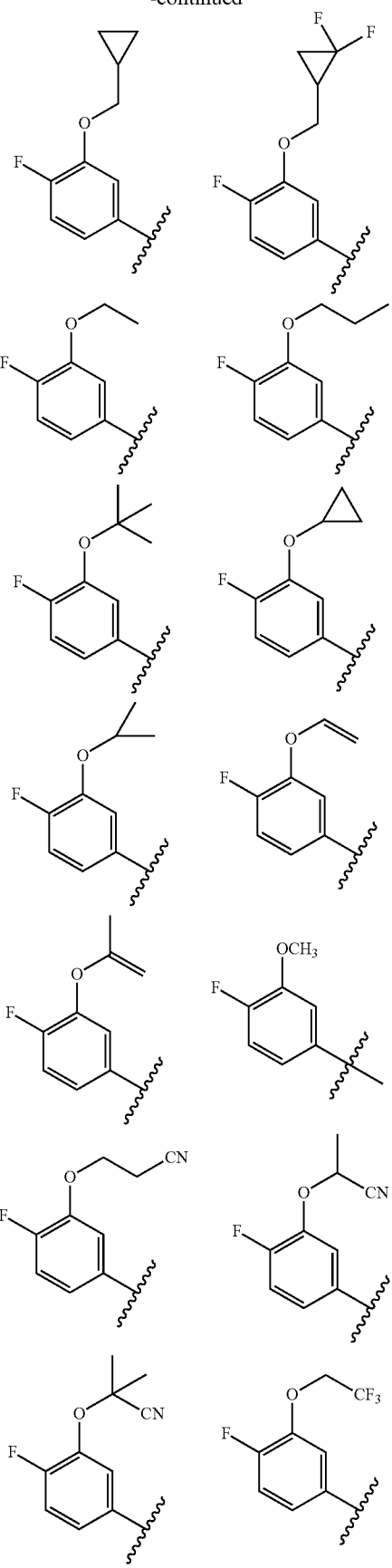

73
-continued
74
-continued
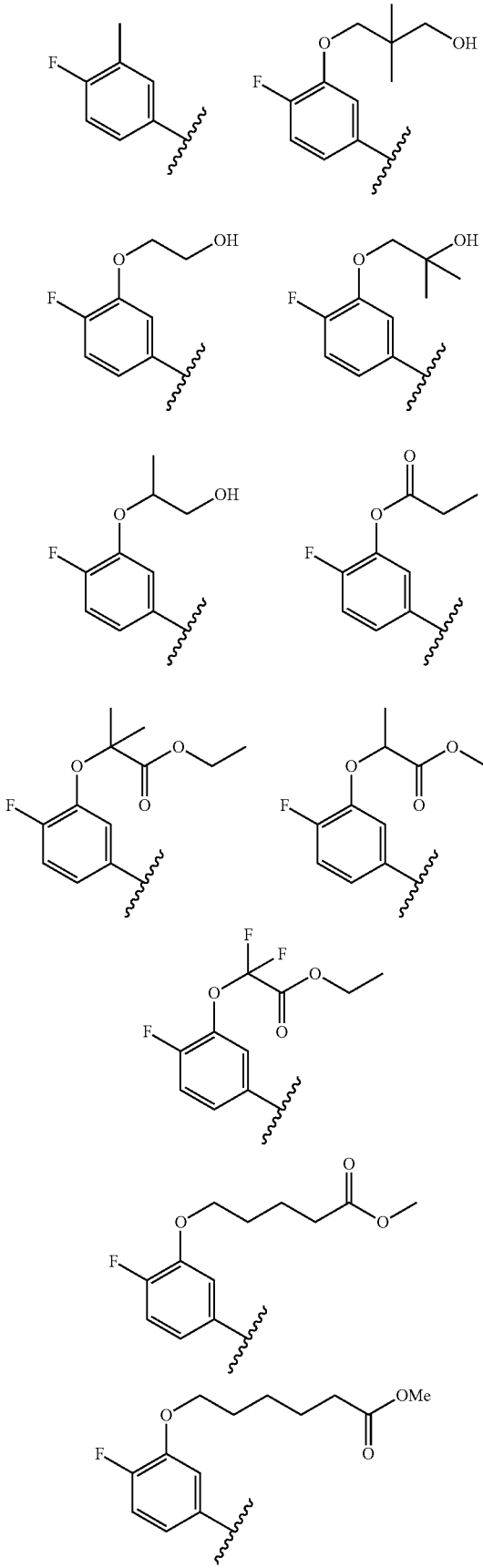
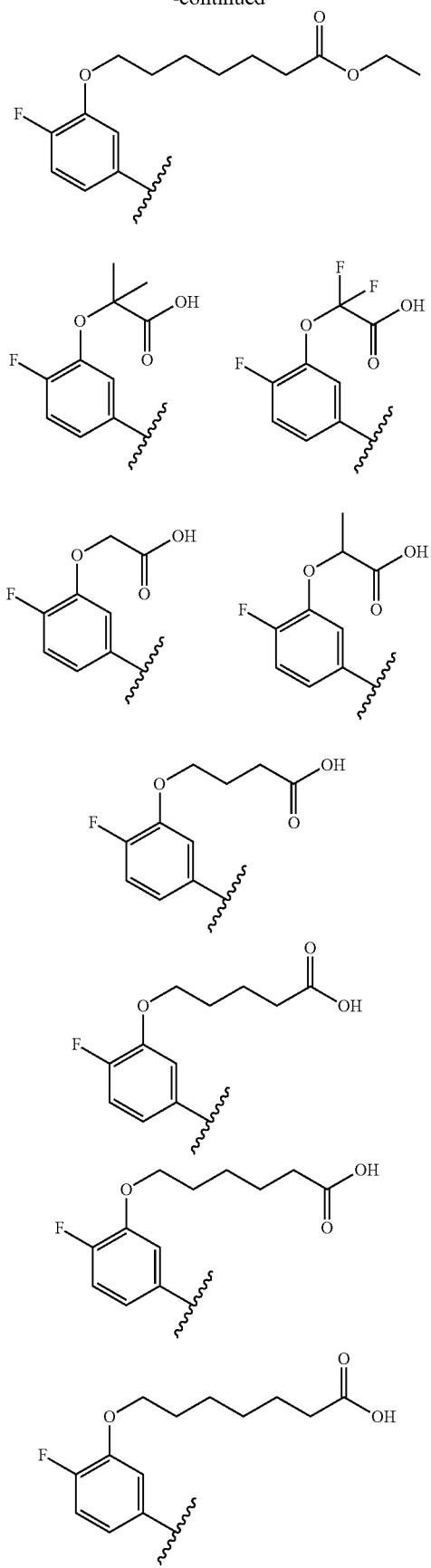

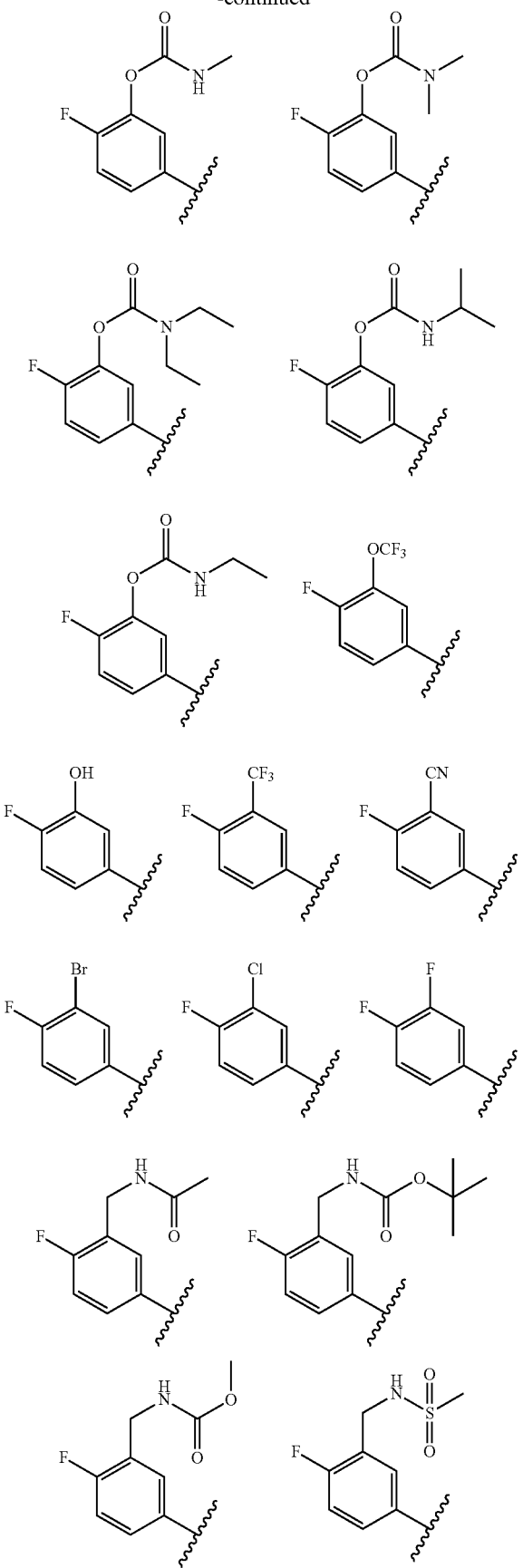
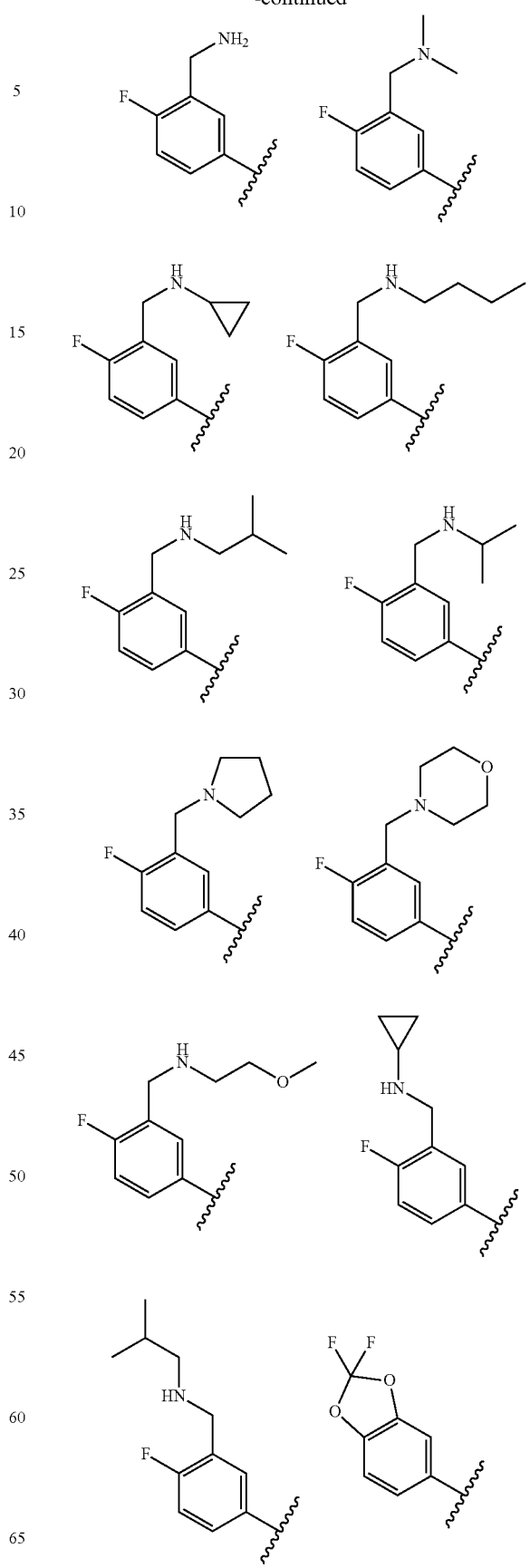

77
-continued
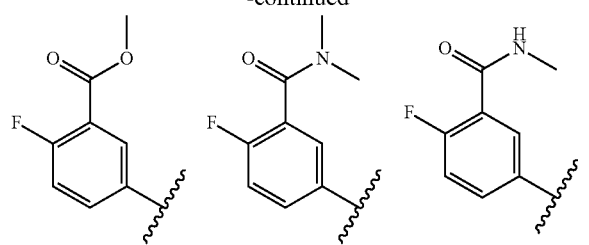
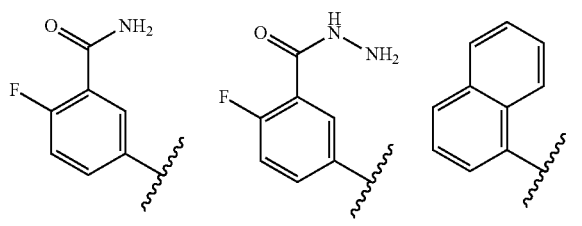
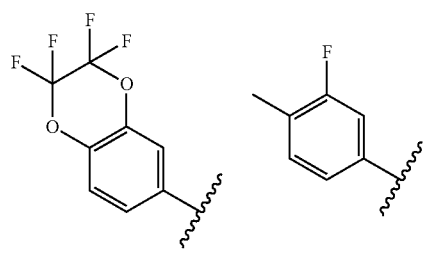
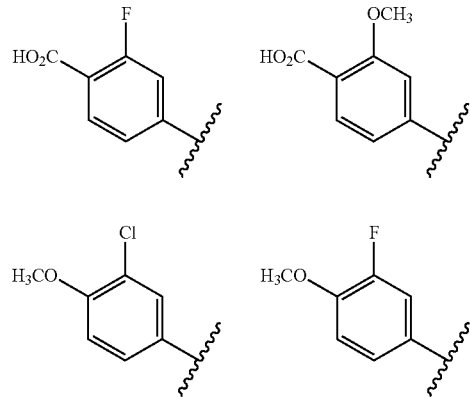
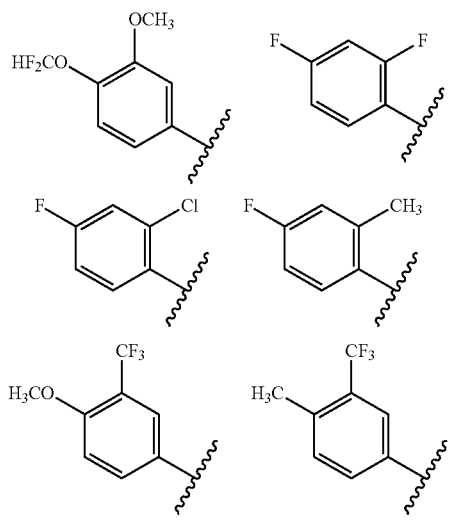
78
-continued
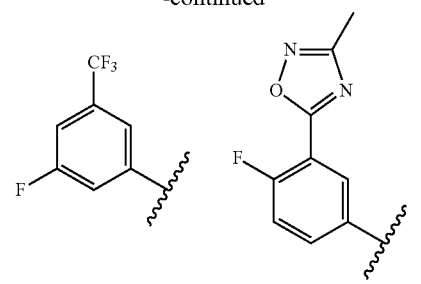
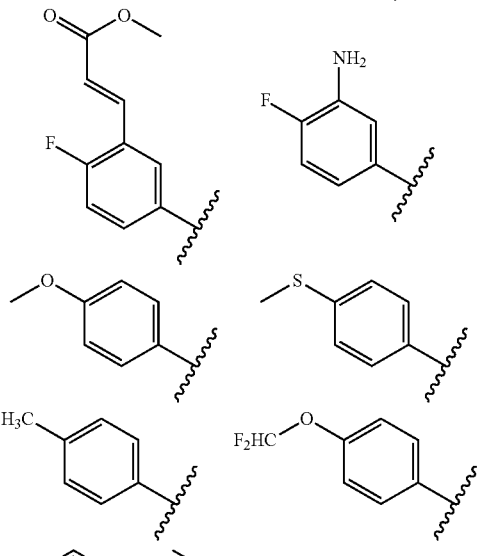
or -continued
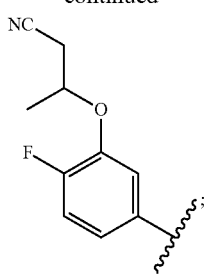
B is:
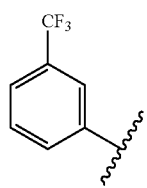 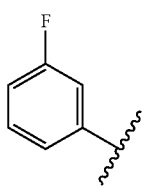 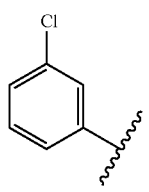
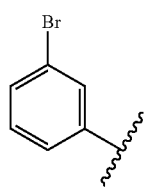 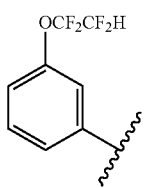 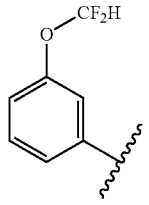
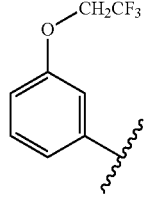 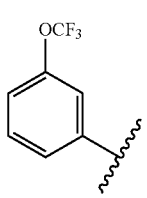
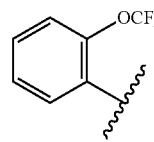 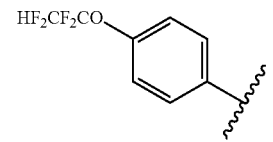
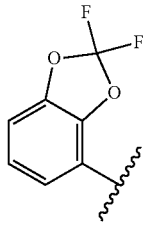 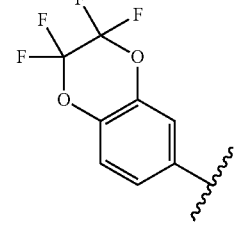
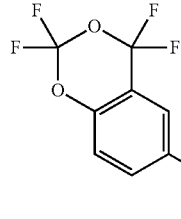 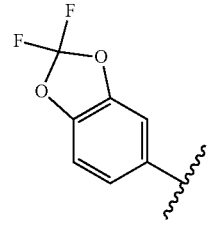
-continued
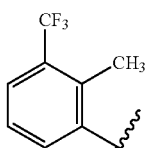 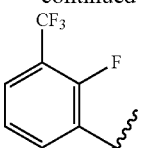 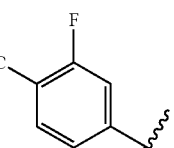
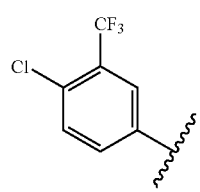 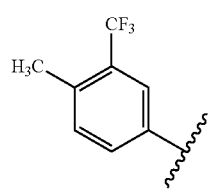
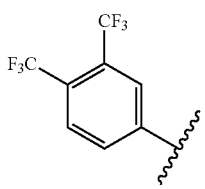 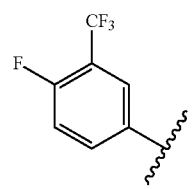
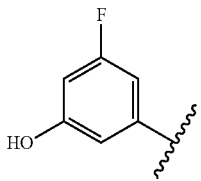 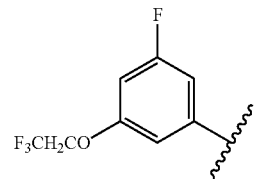
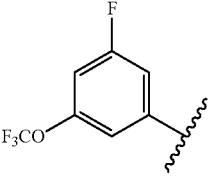 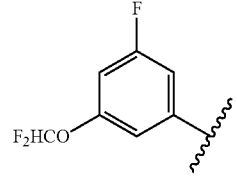
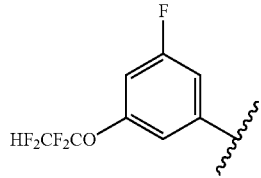 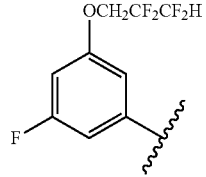
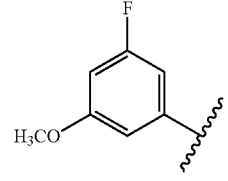 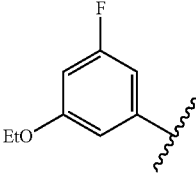
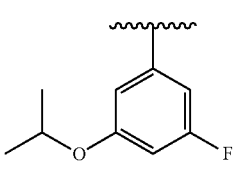 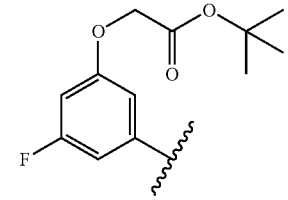
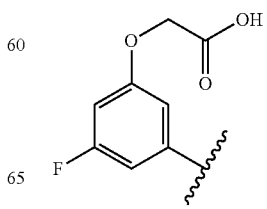 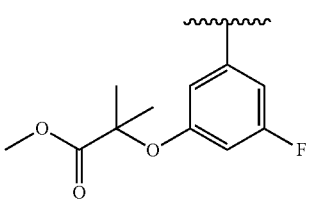

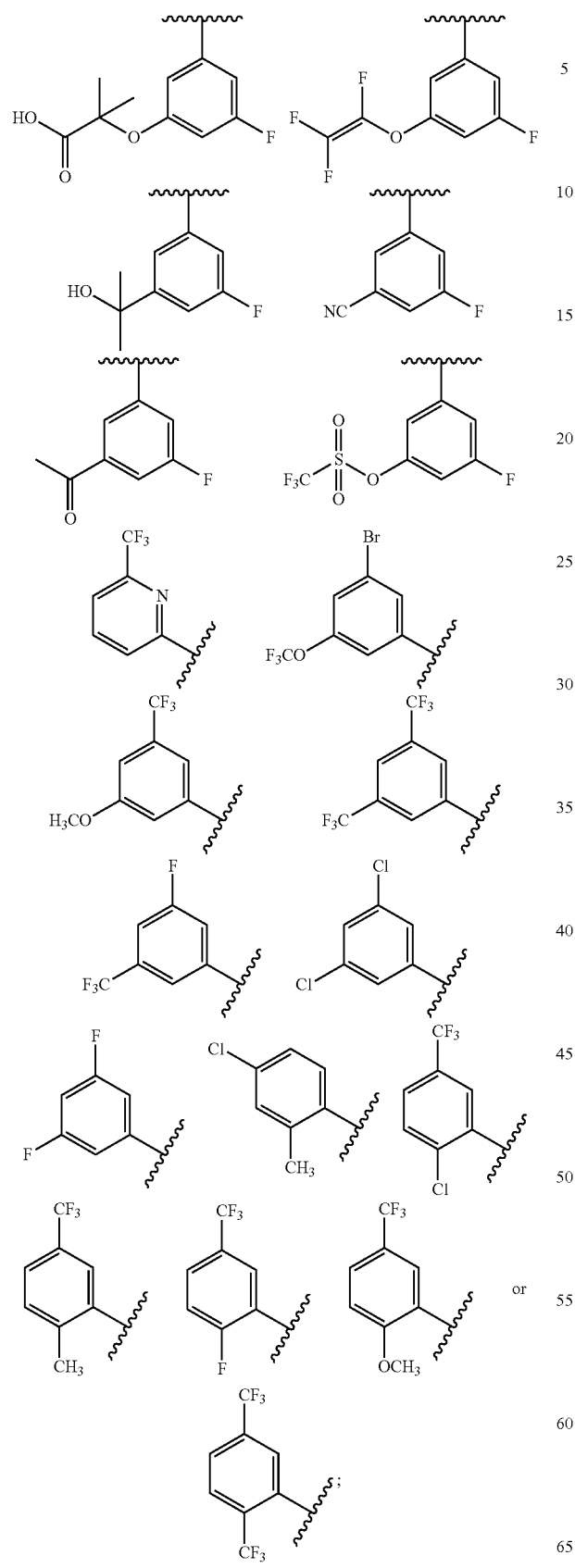

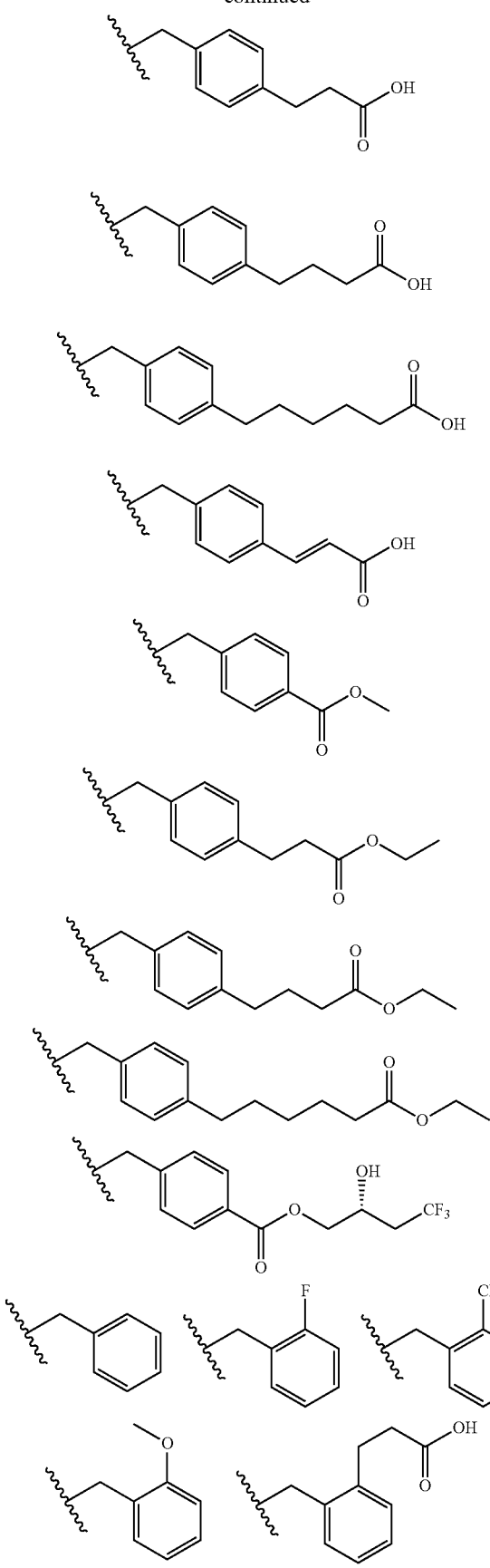
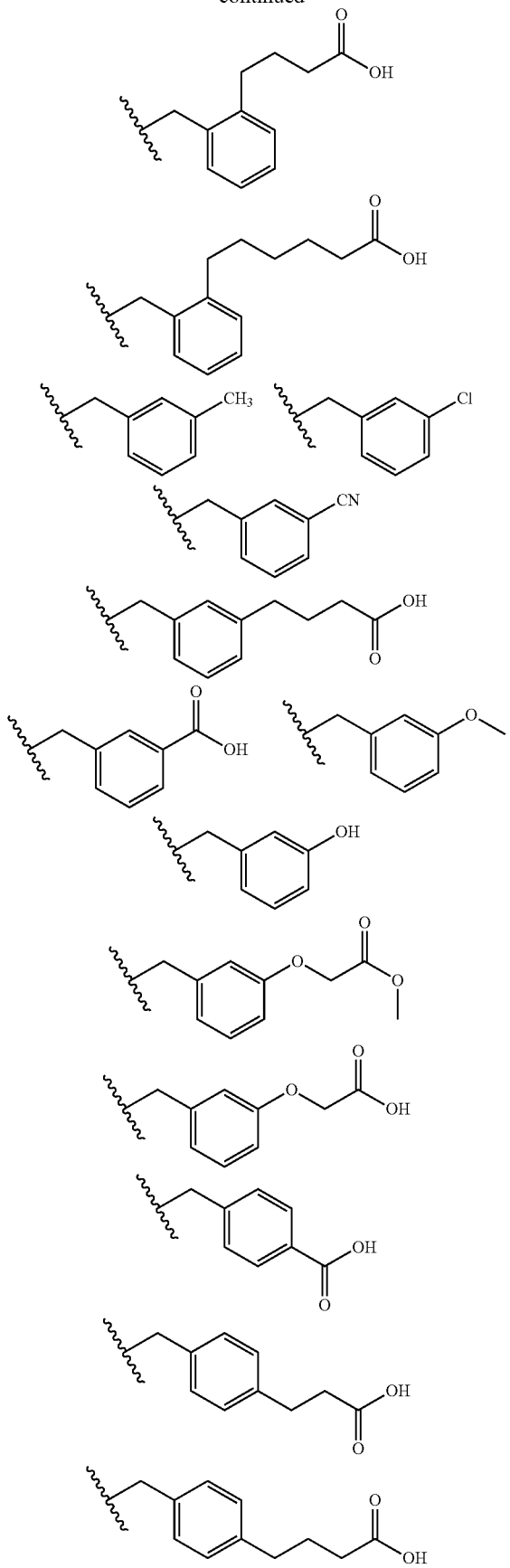

85
-continued
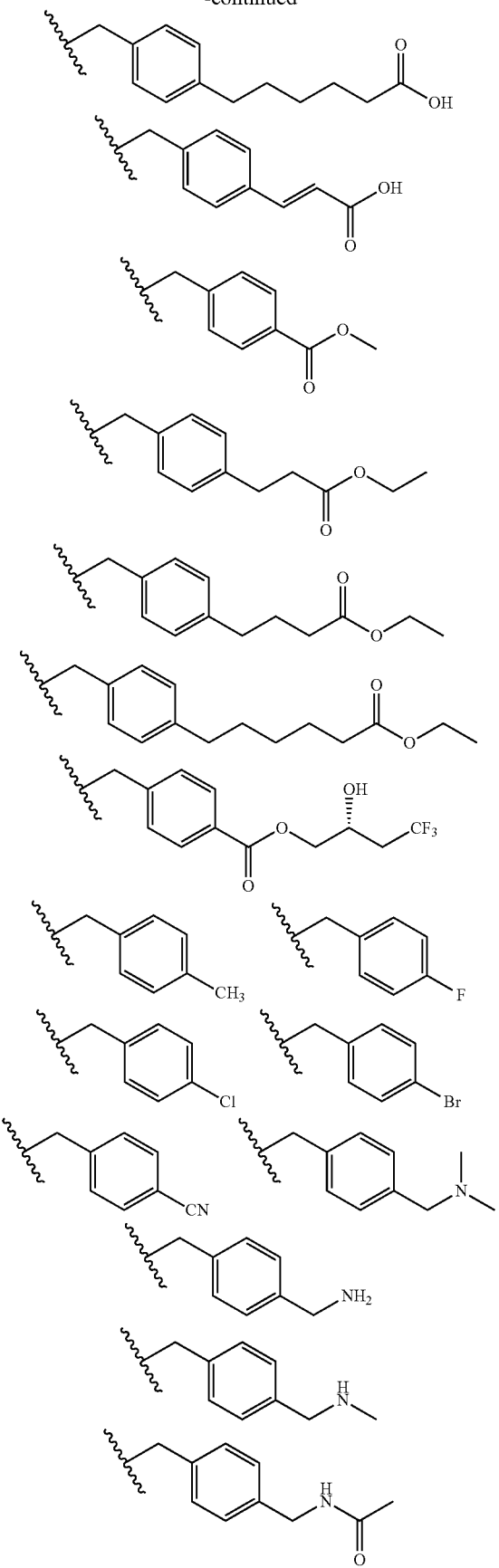
86
-continued
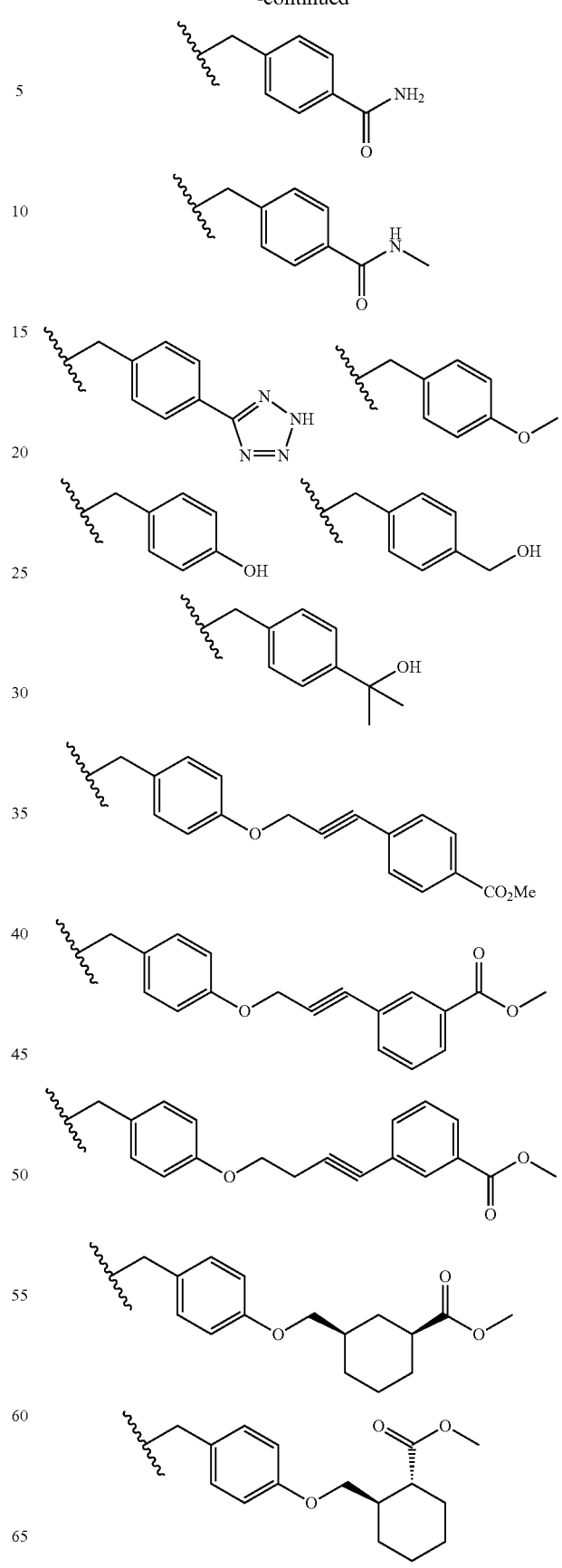

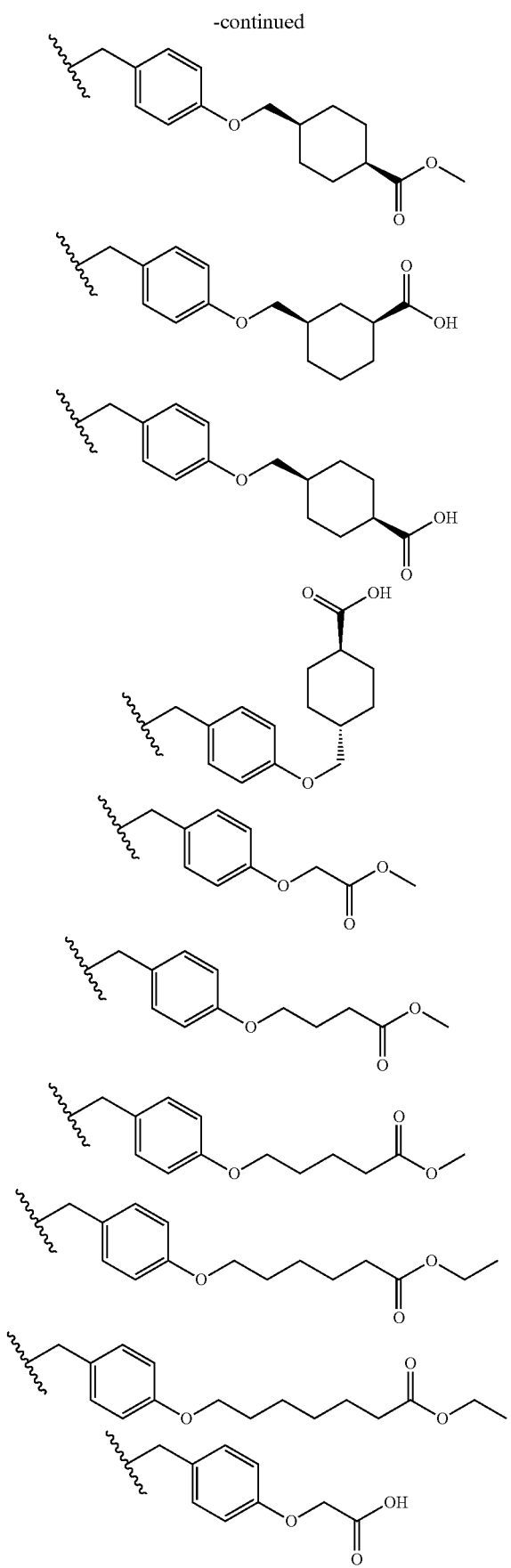
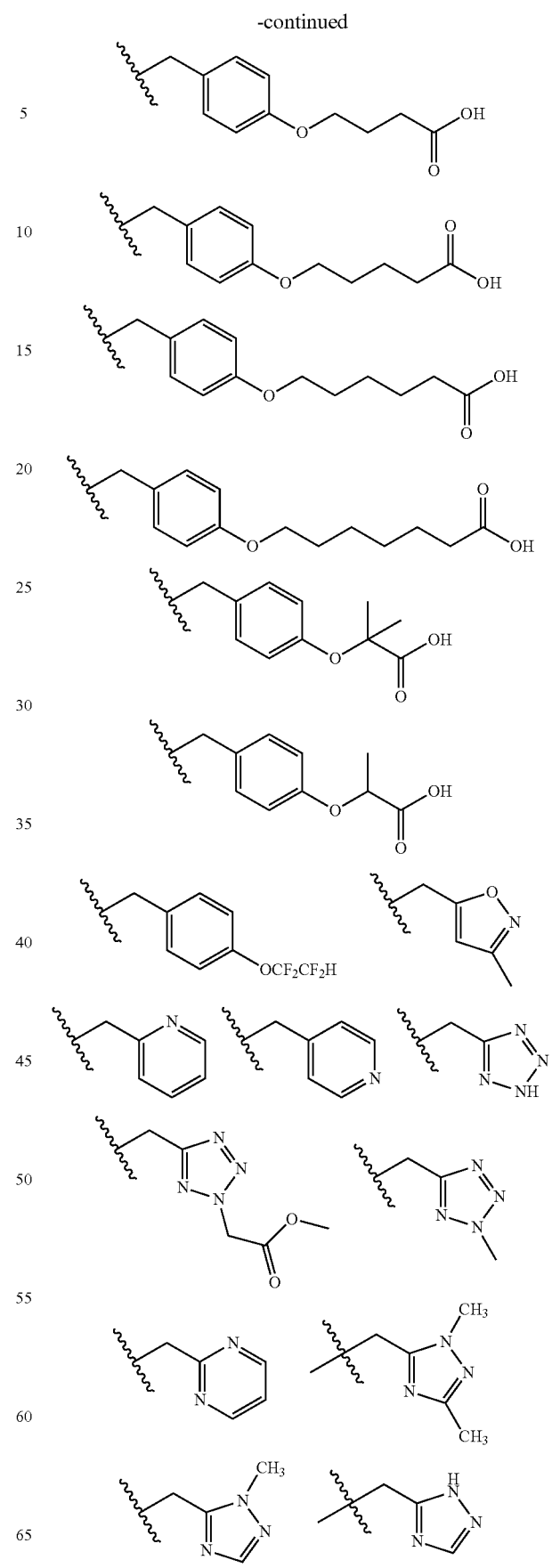

-continued $R_1$ is:

(a) —C(O)$R_3$, wherein $R_3$:

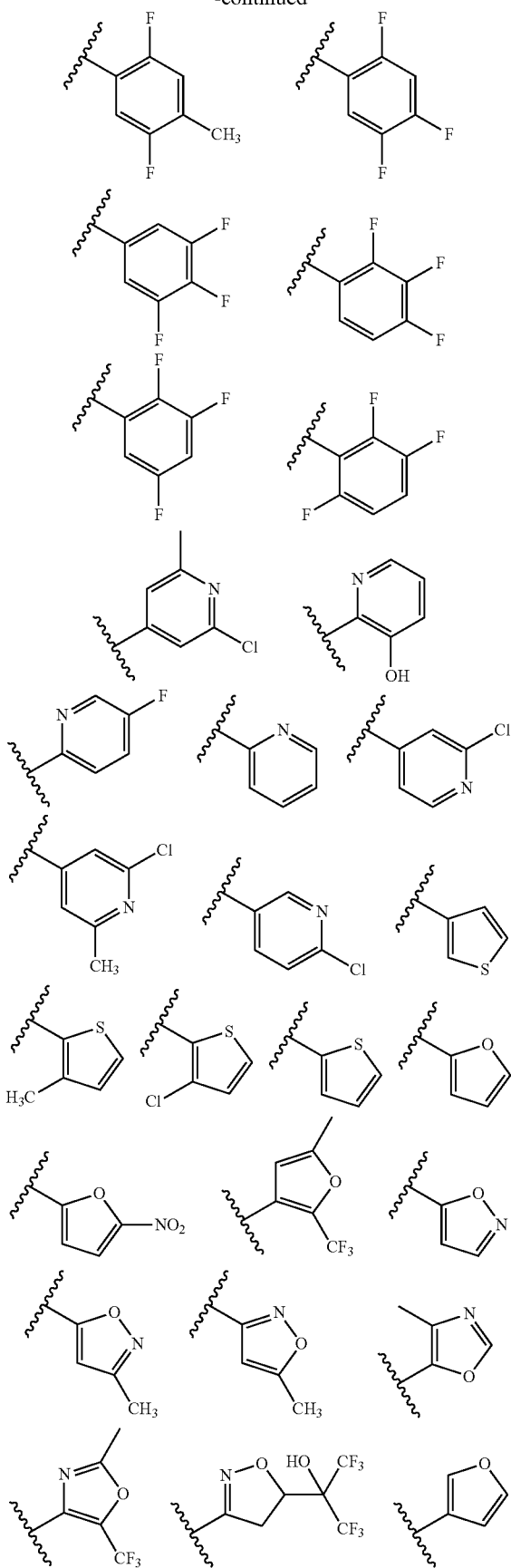
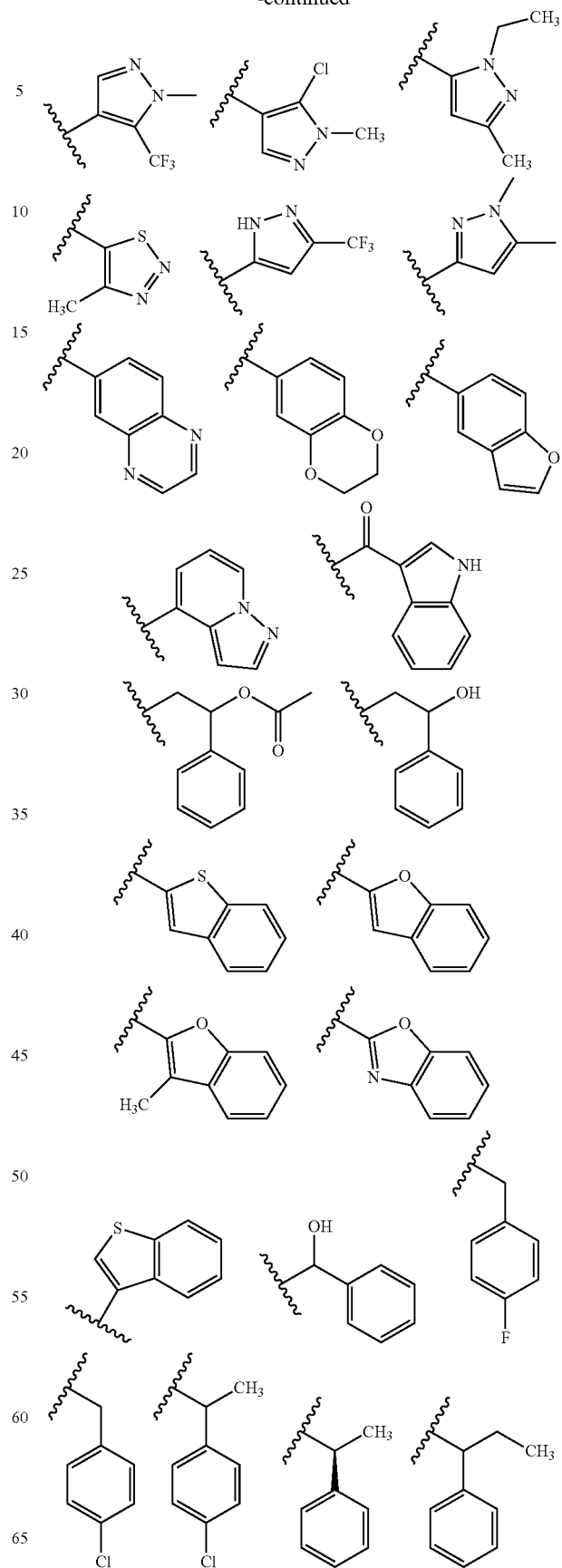

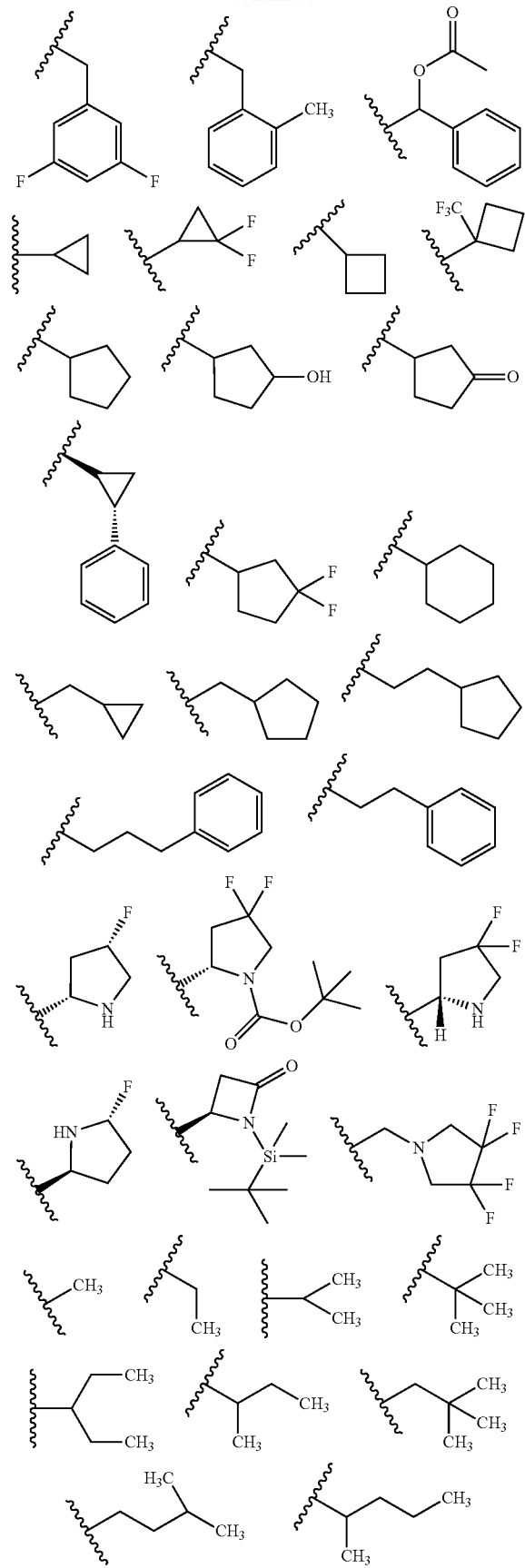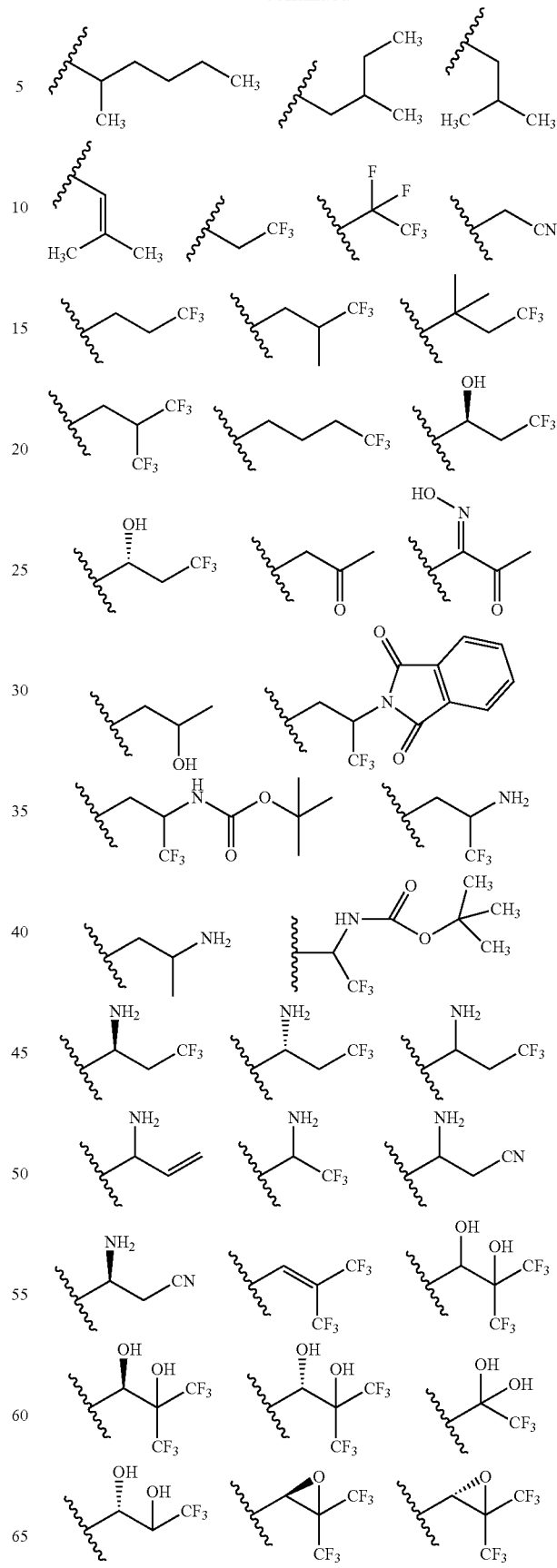

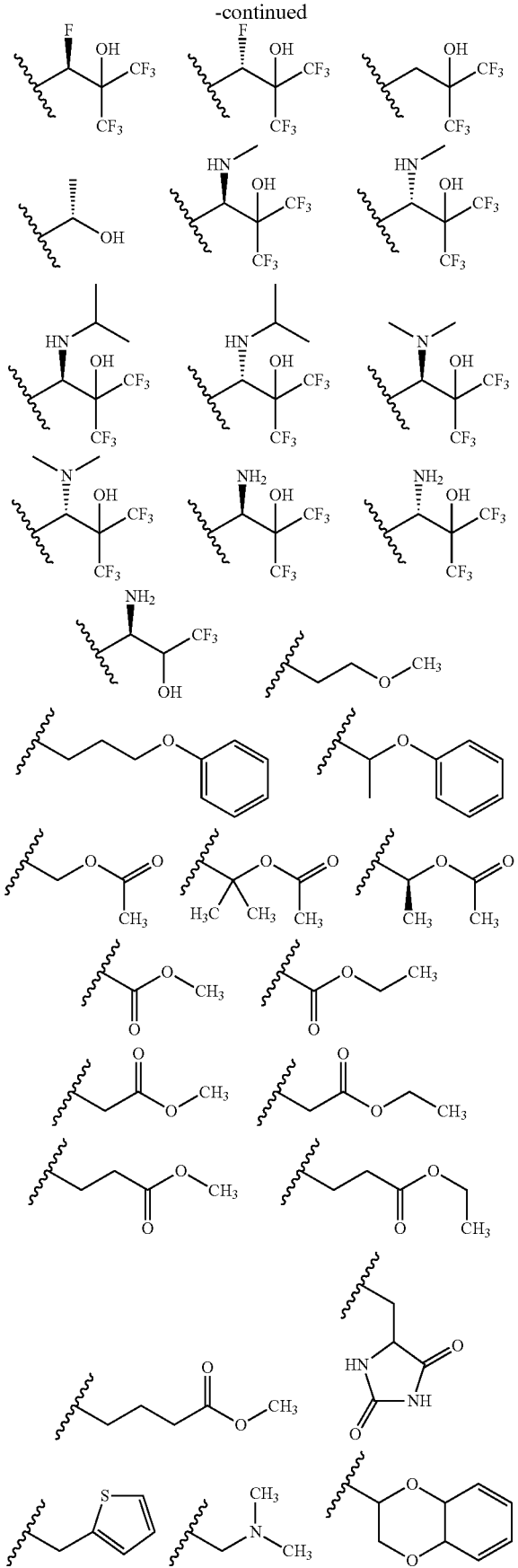
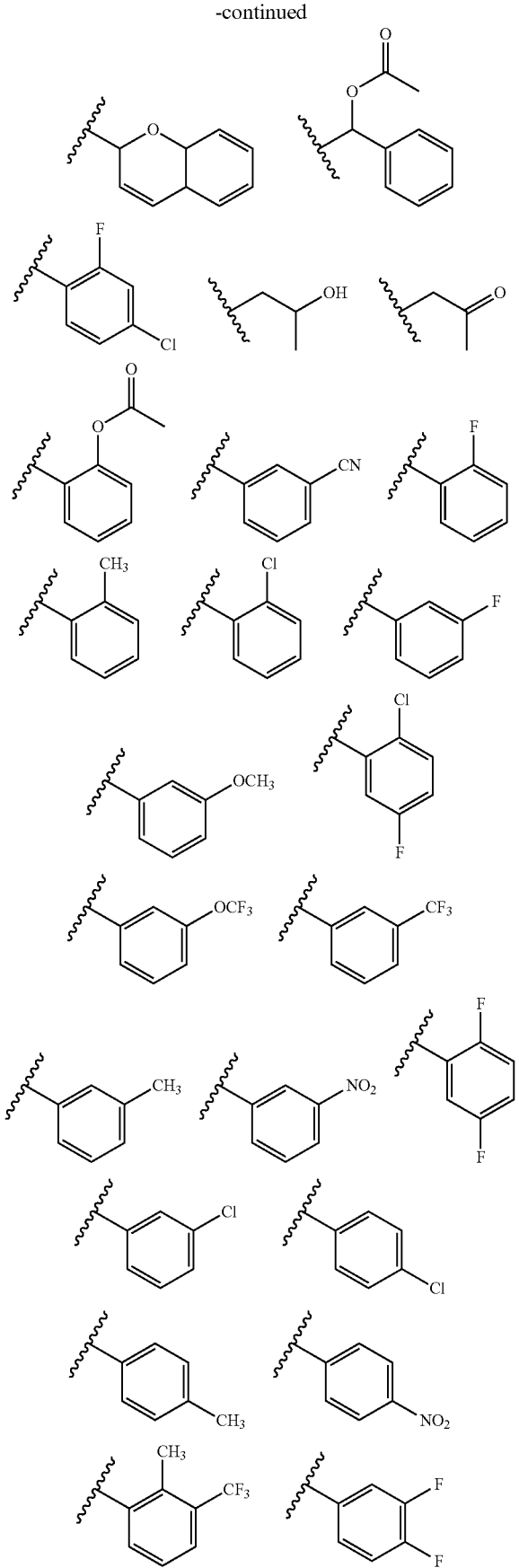

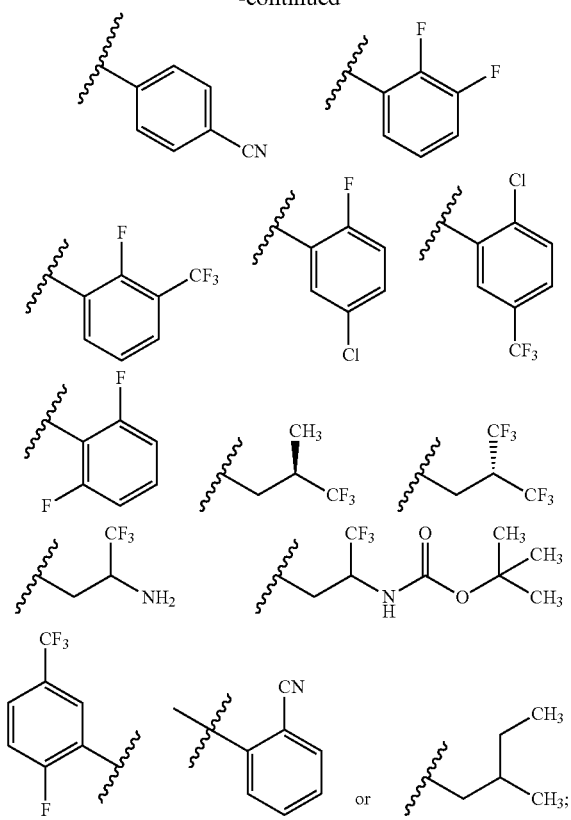
(b) —C(O)NHR$_3$, wherein the R$_3$ is:
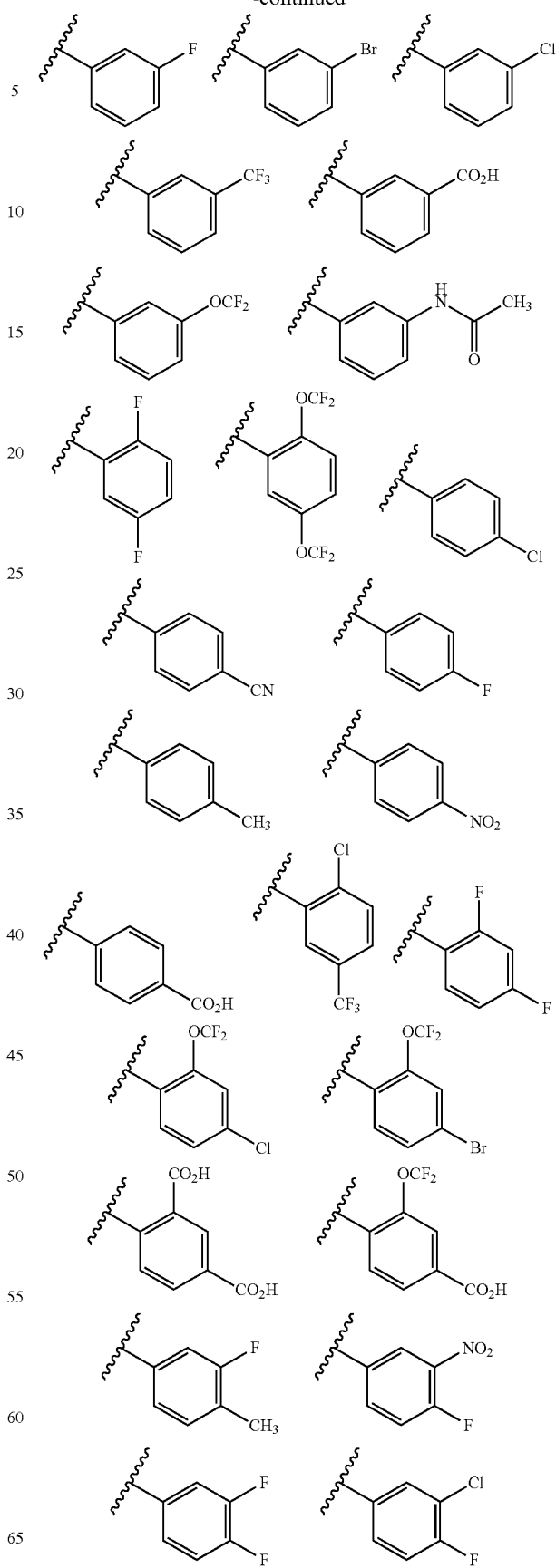

99
-continued
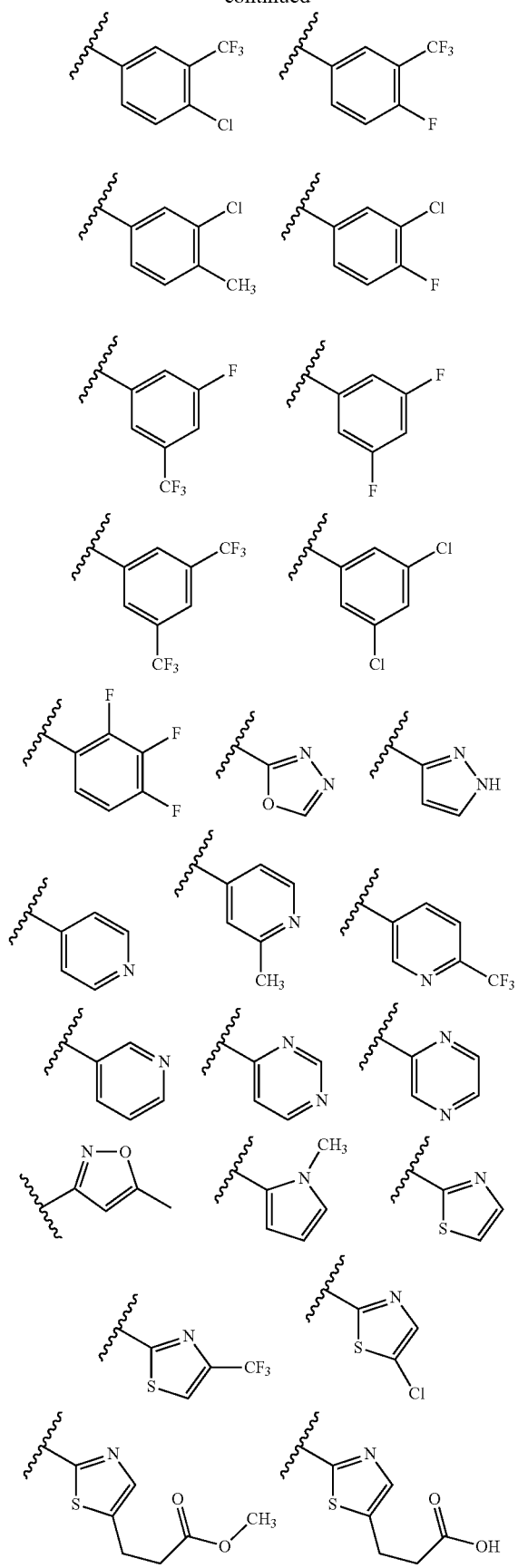
100
-continued
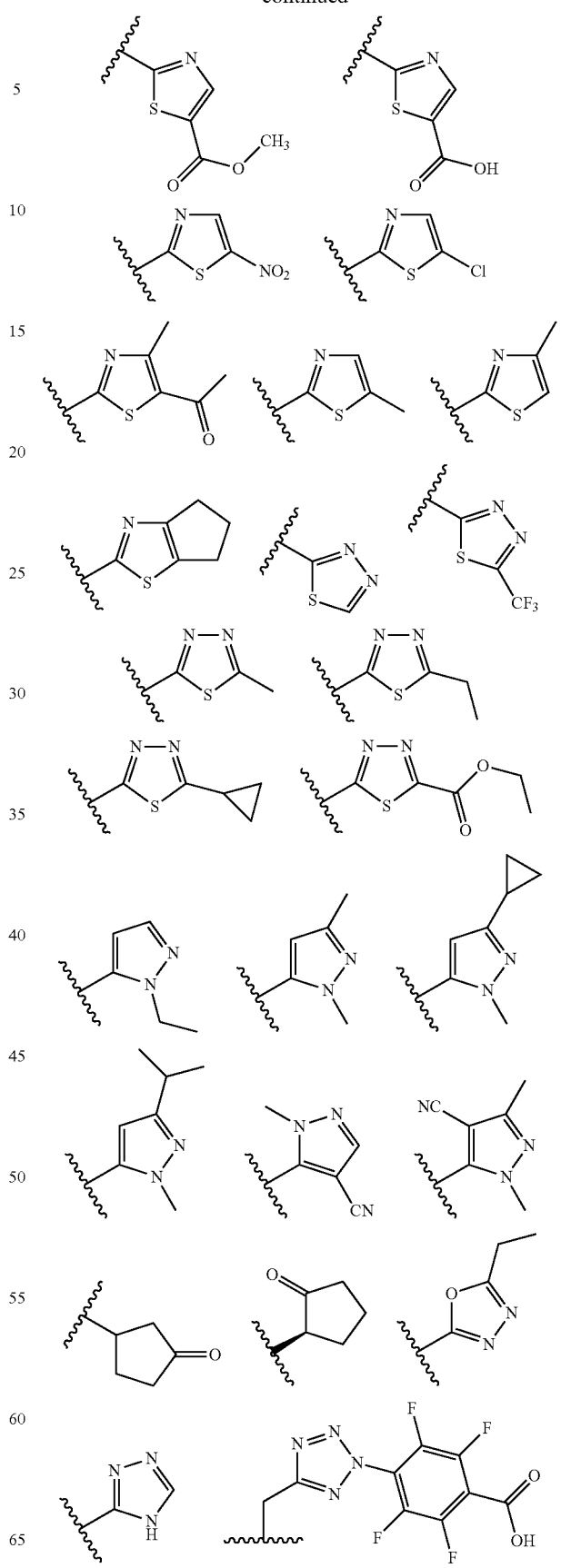

101
-continued
102
-continued
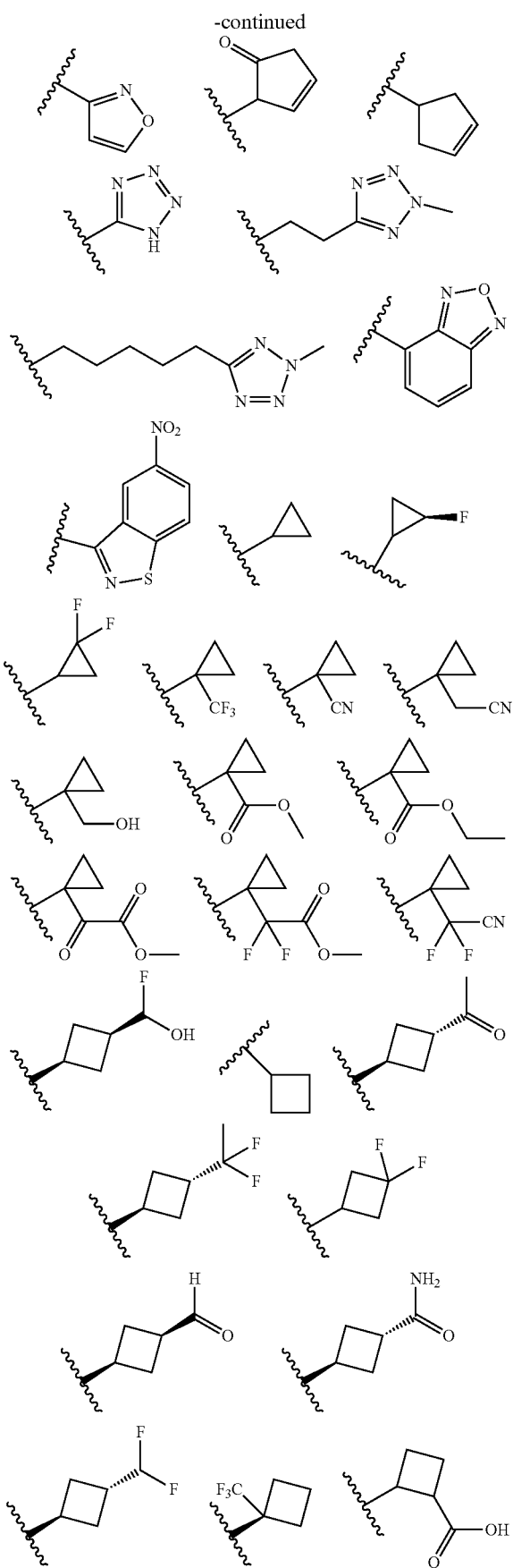
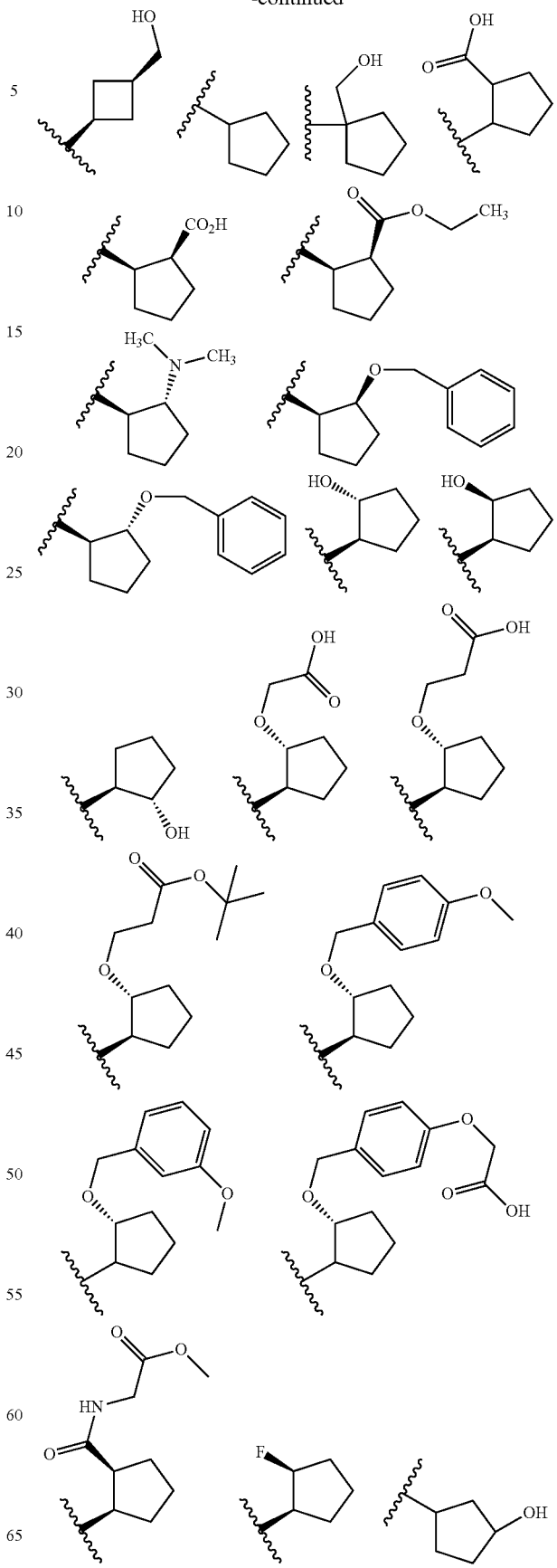

103
-continued
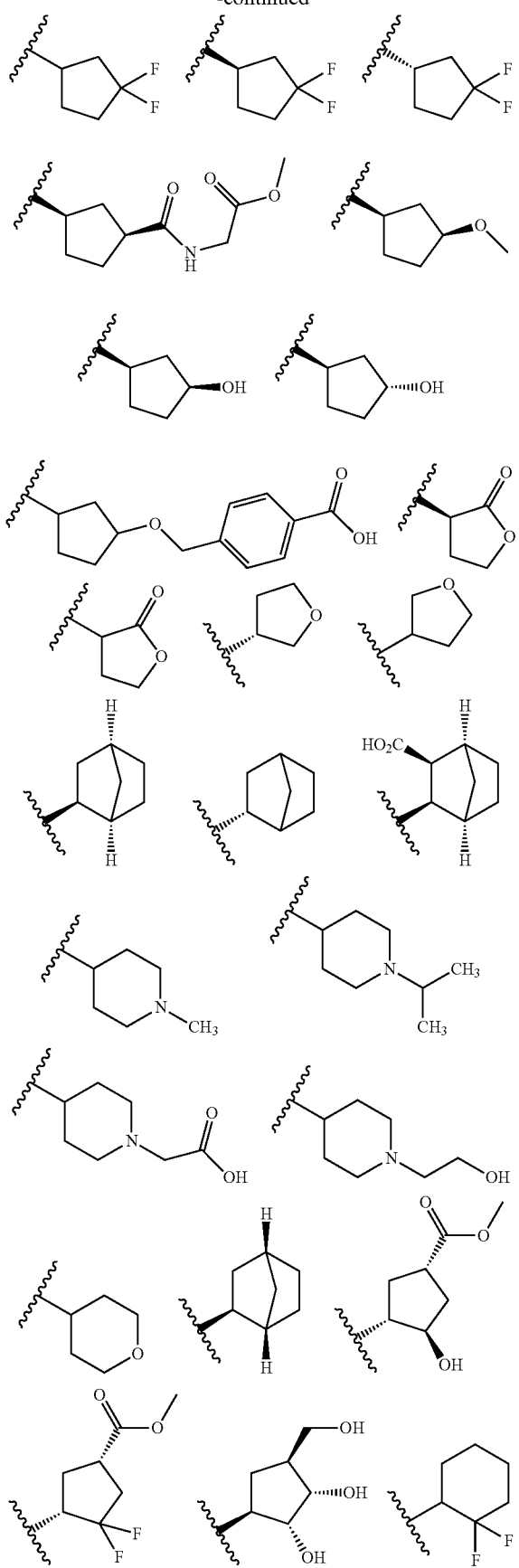
104
-continued
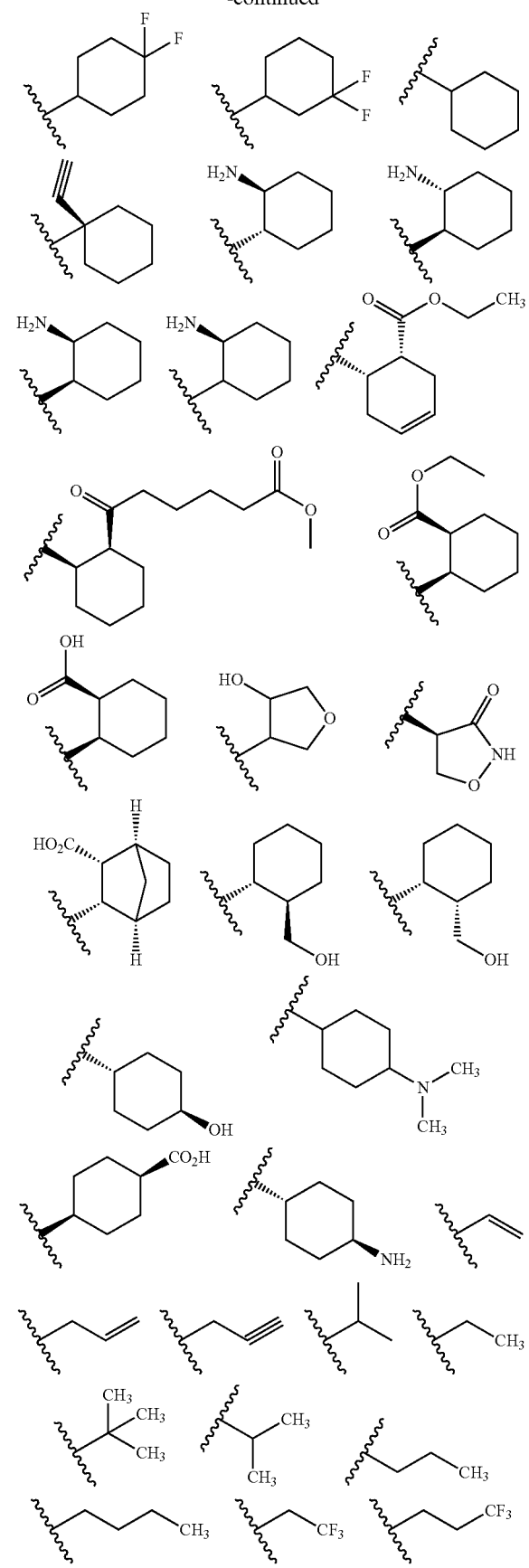

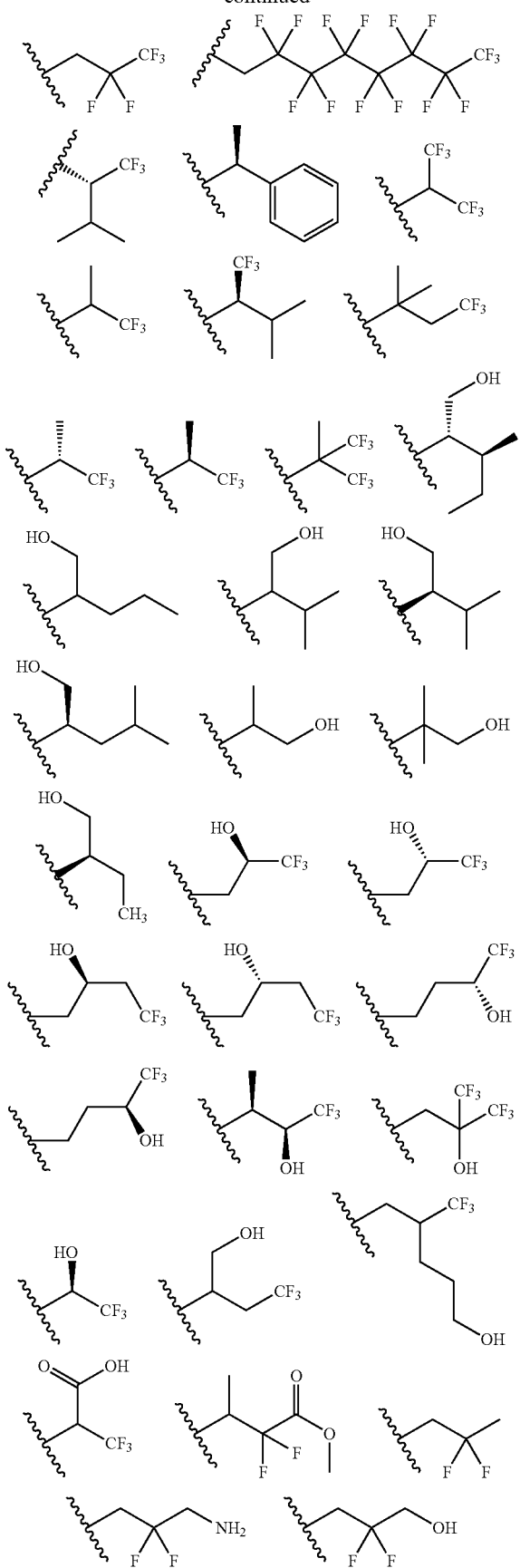
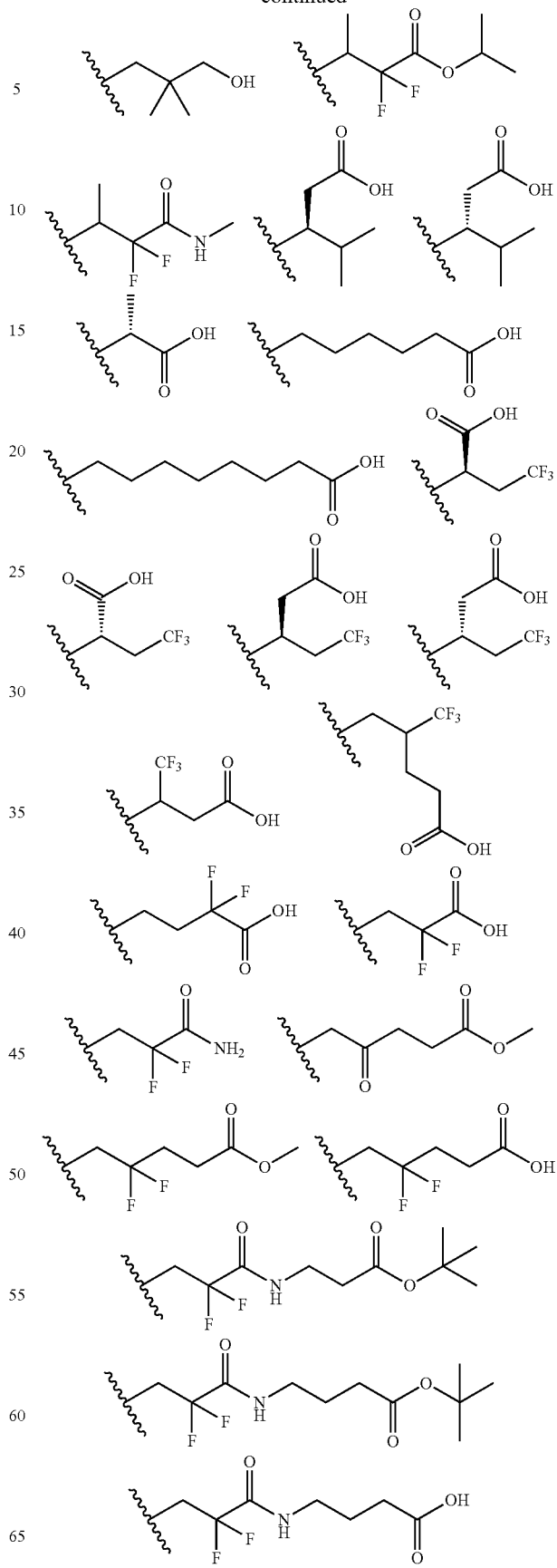

107
-continued
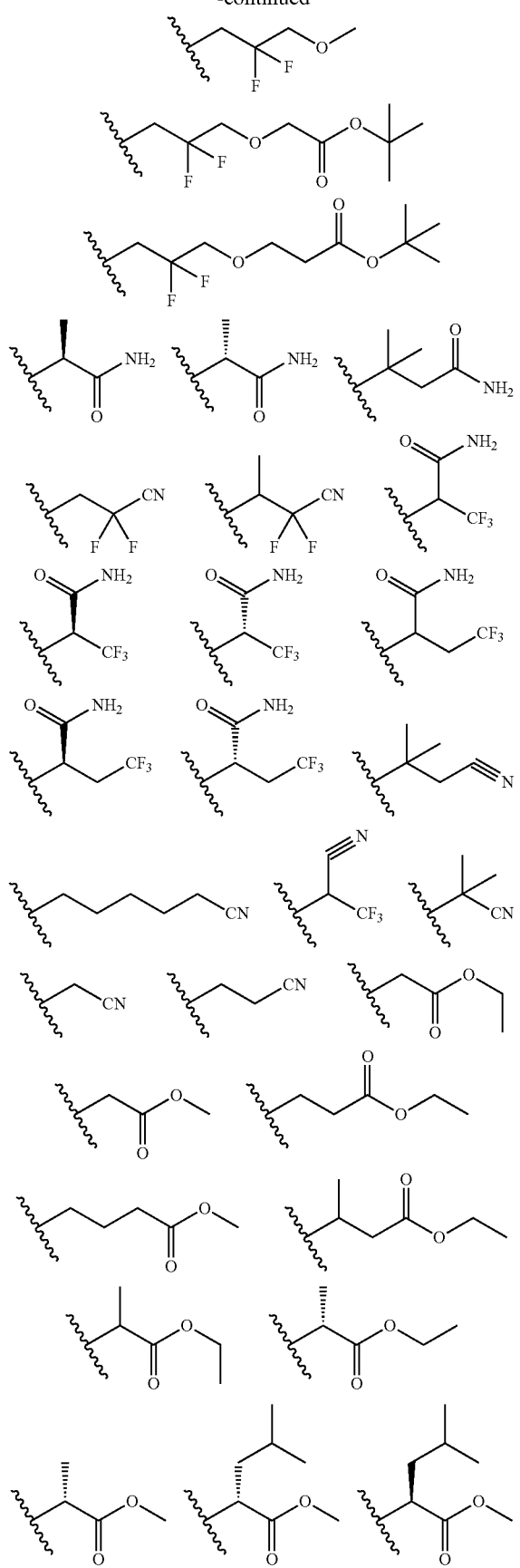
108
-continued
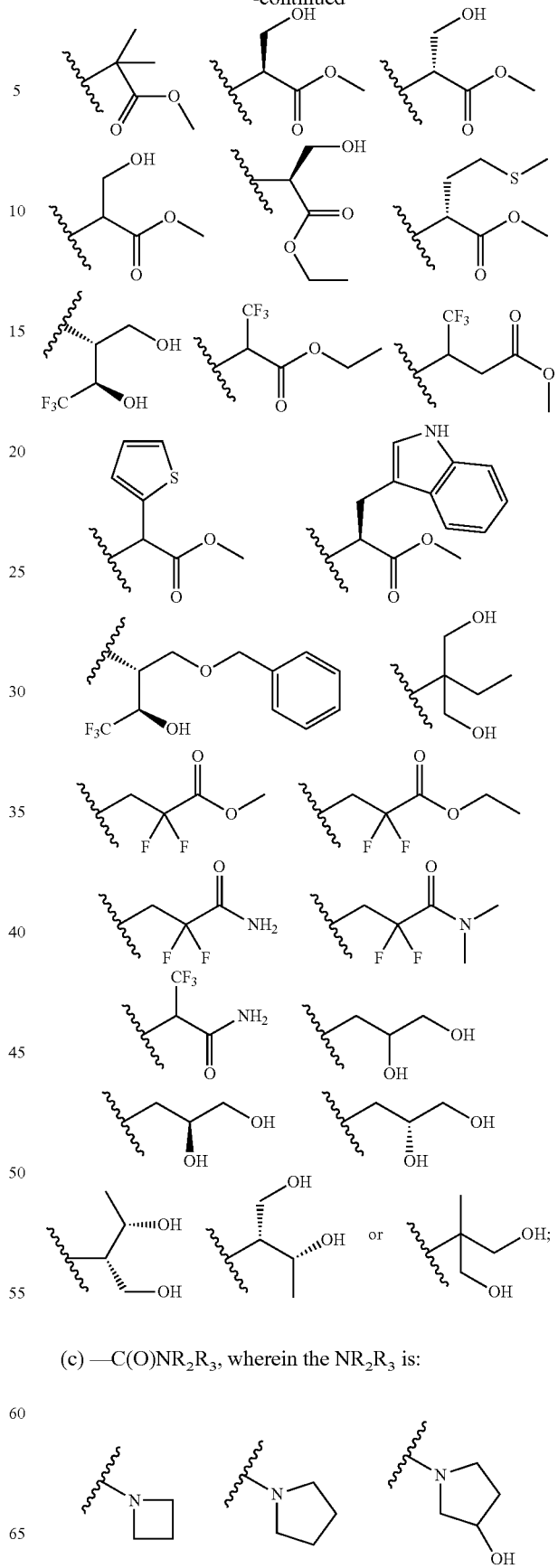
(c) —C(O)NR$_2$R$_3$, wherein the NR$_2$R$_3$ is:
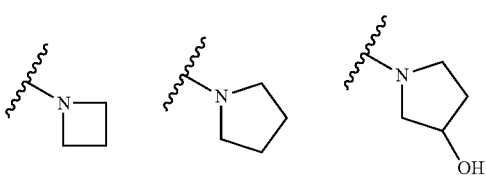

109
-continued
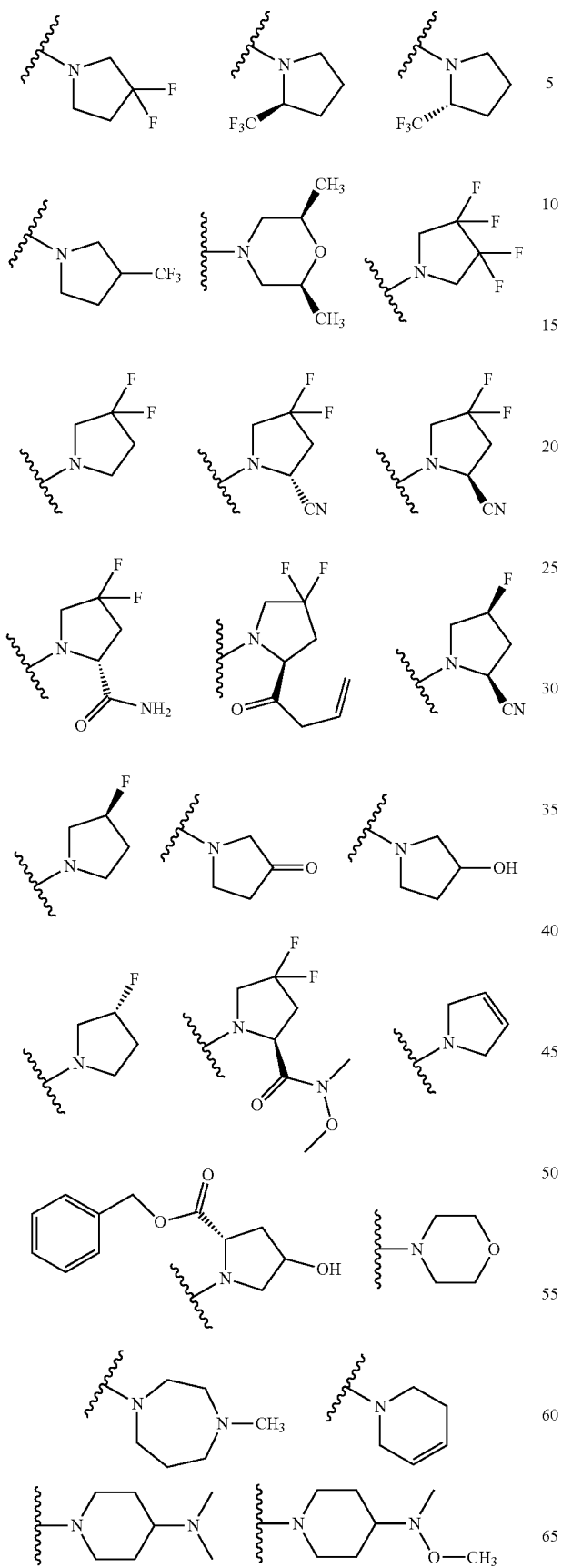
110
-continued
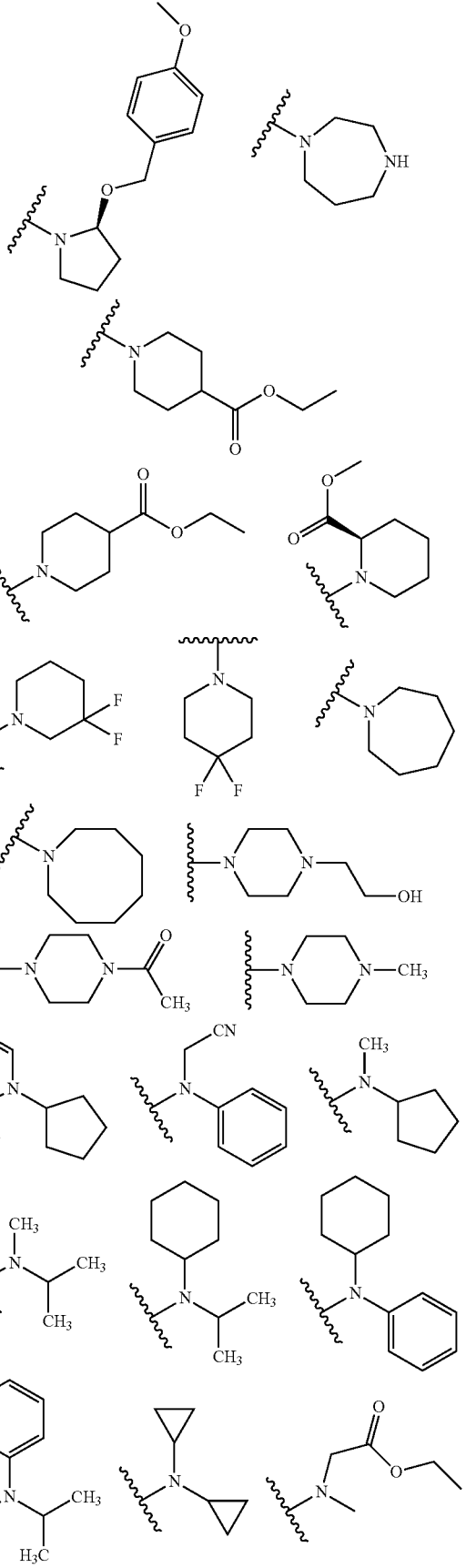

-continued
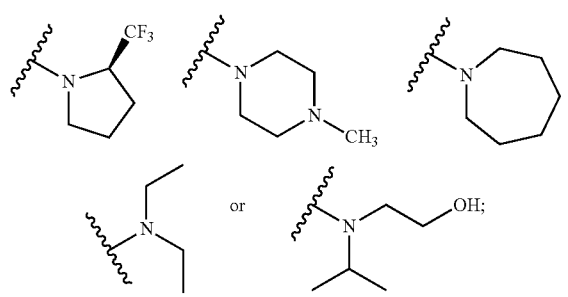
(d) —C(O)OR₄ wherein the R₄ is:
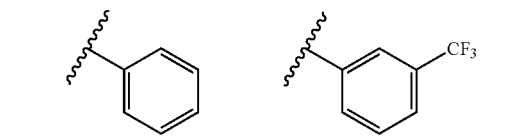
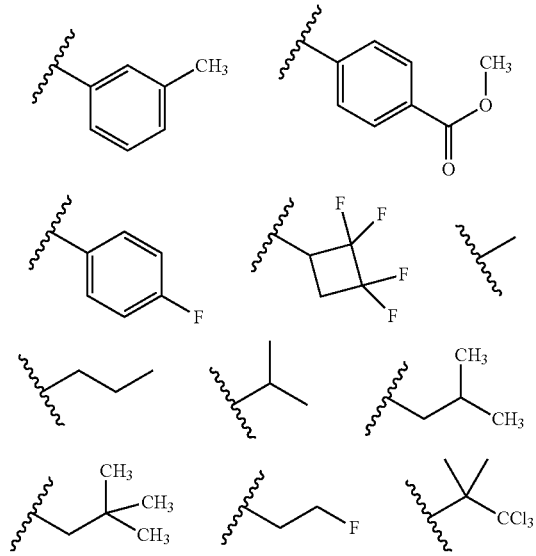
(e) —SO₂R₅ wherein the R₅ is:
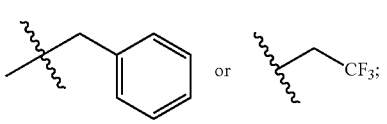 [SMILES: *Cc1ccccc1 ; *CC(F)(F)F]
(f) —CSNHR₇ wherein the R₇ is:
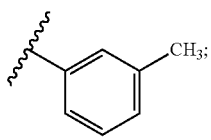
(g) —CH₂R₈ wherein the R₈ is:
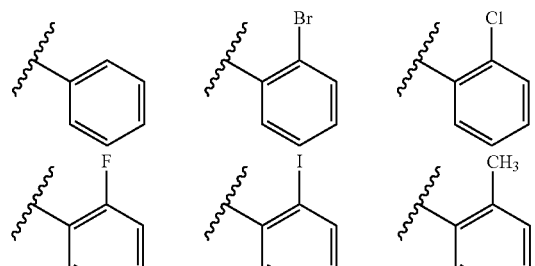
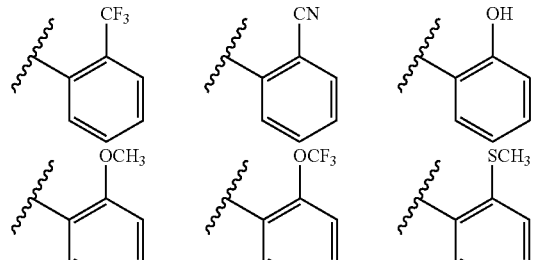
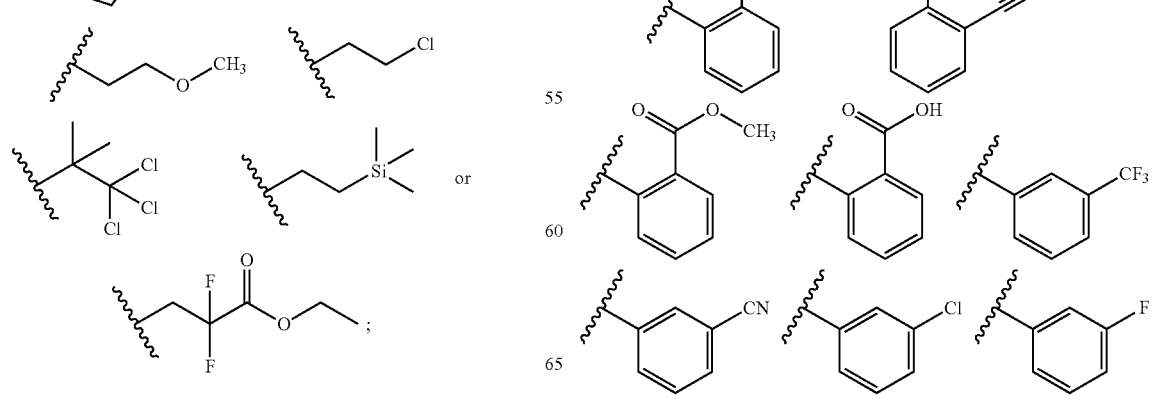

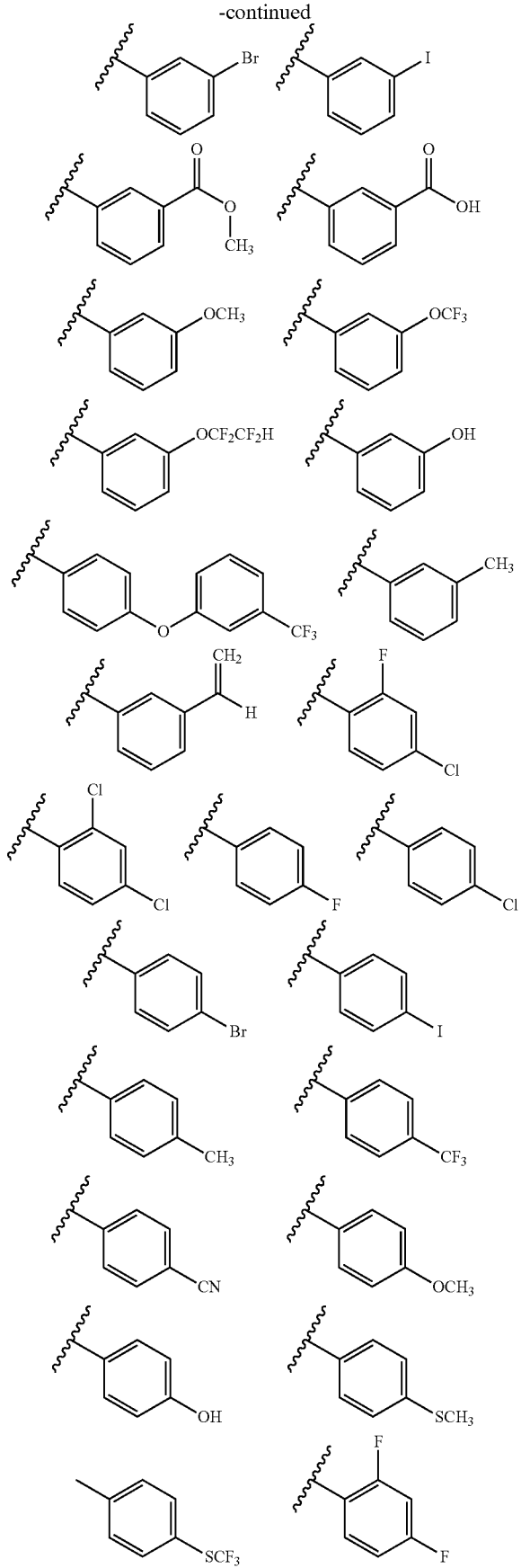
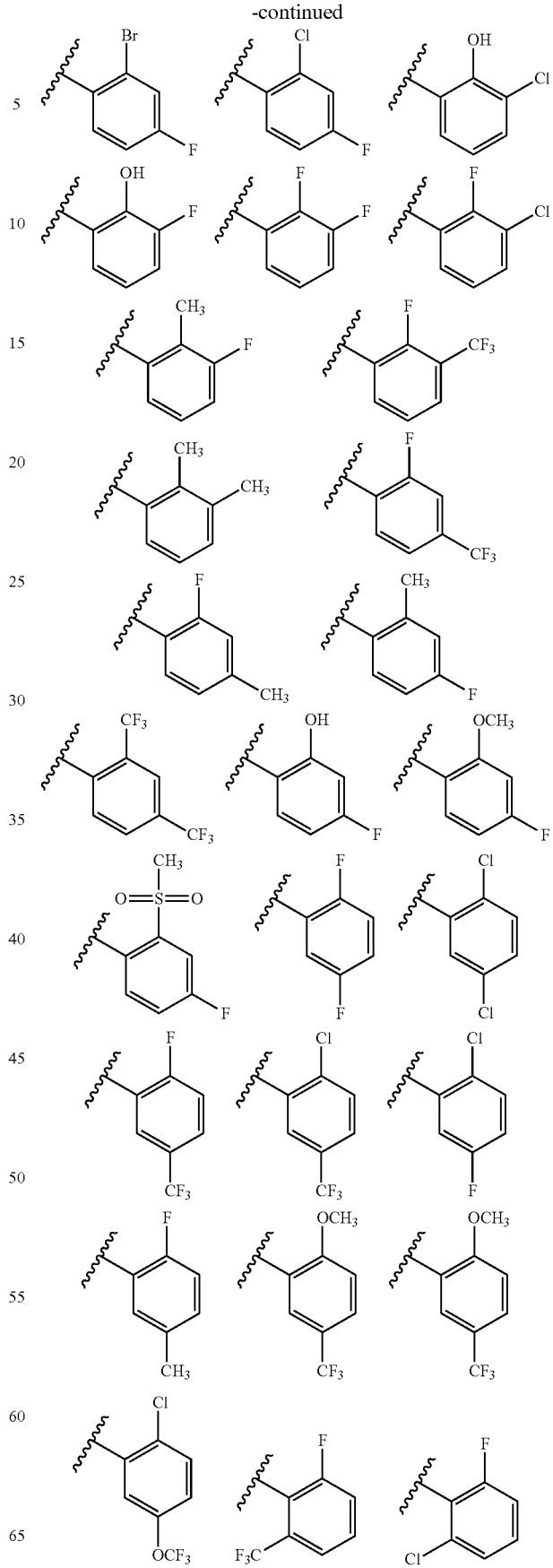

115
-continued
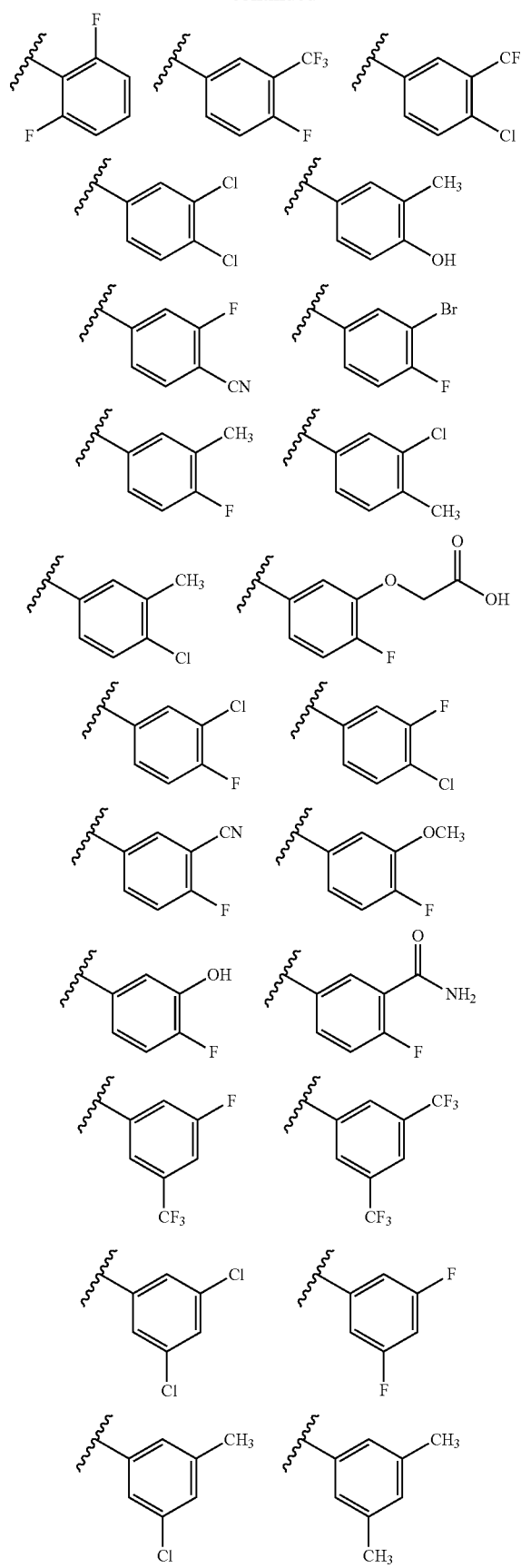
116
-continued
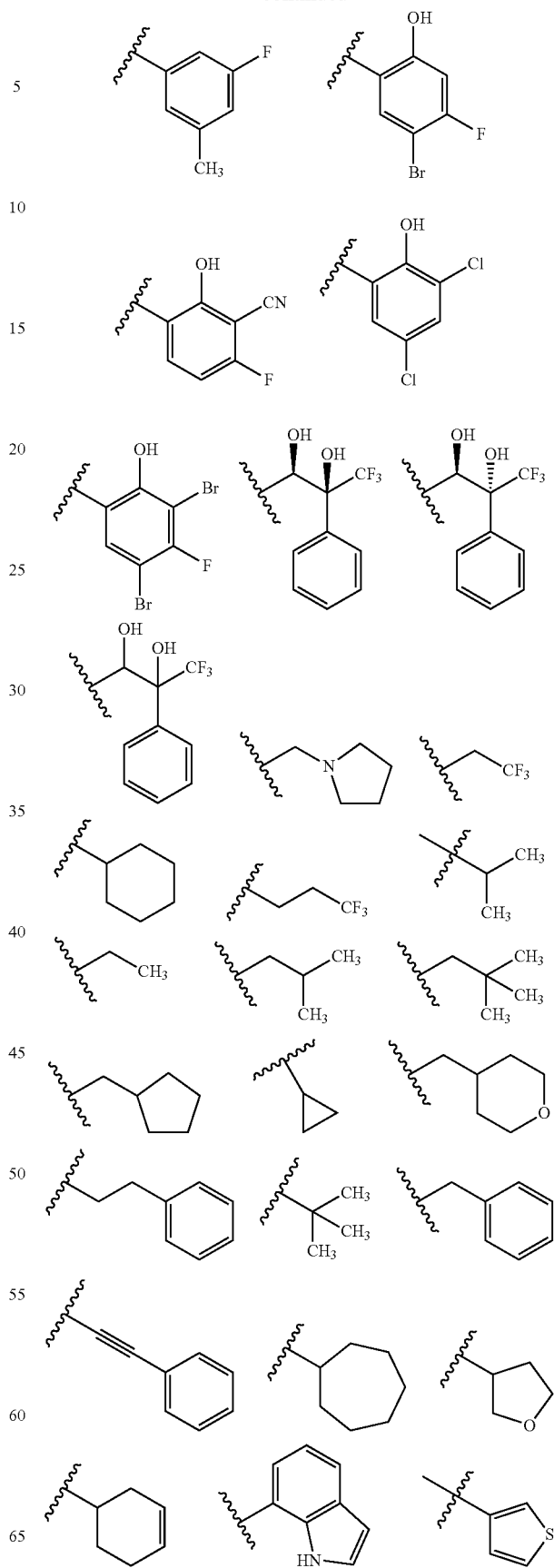

117
-continued
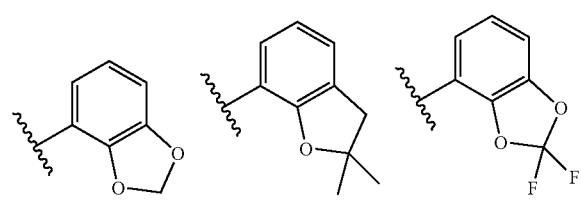
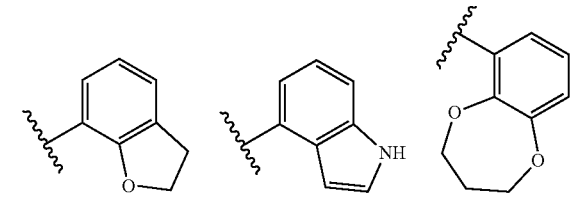
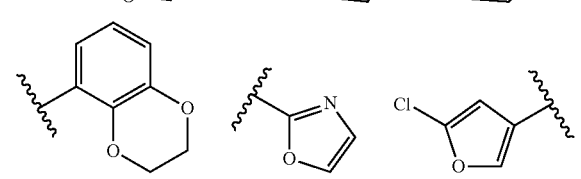
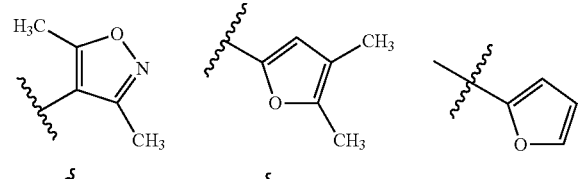
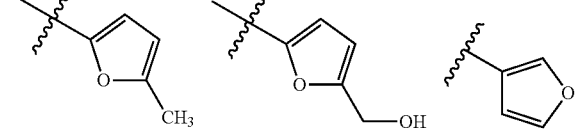
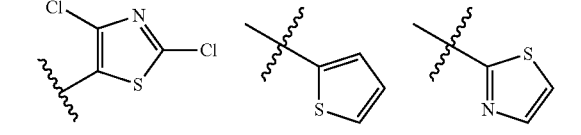
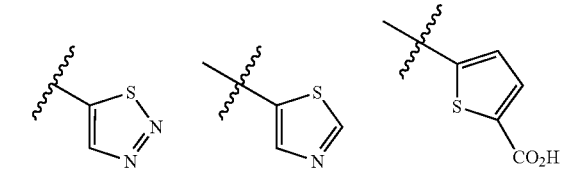
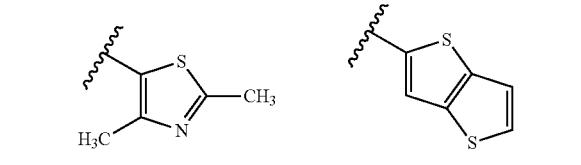
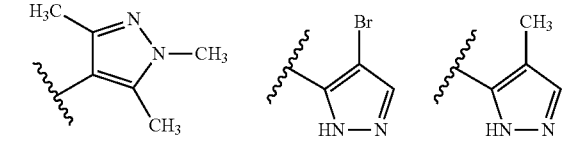
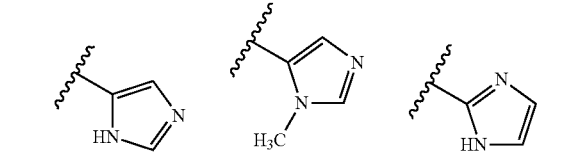
118
-continued
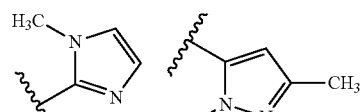
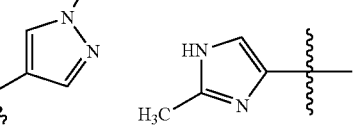
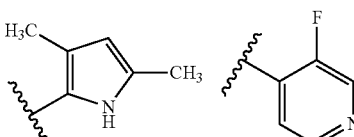
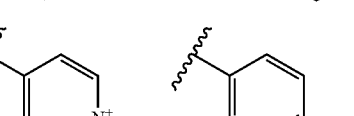
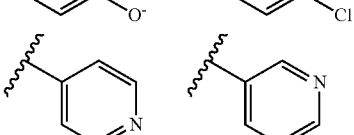
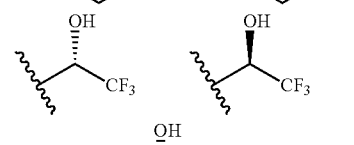
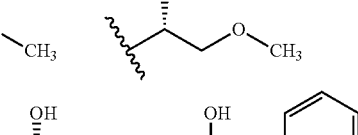
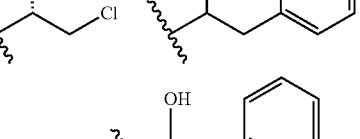
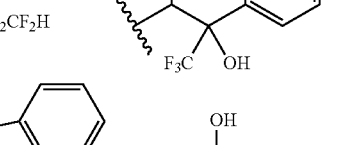
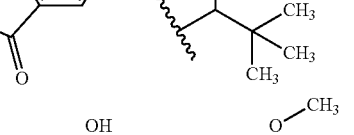
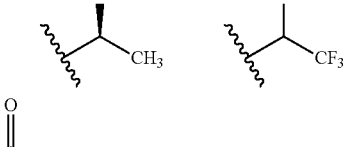
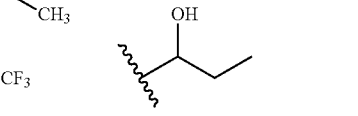

-continued
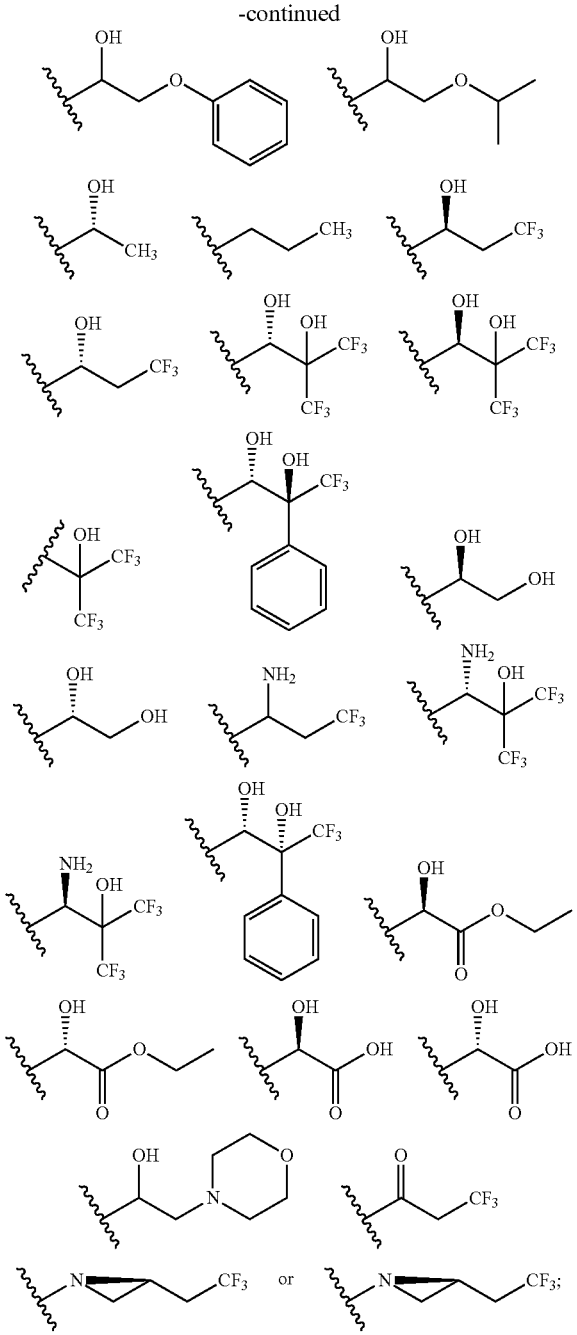
(h) —C(S)R₃ wherein the R₃ is:
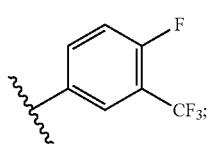 [SMILES: *c1ccc(F)c(C(F)(F)F)c1]
(i) —C(=NR₃)Oalkyl wherein the R₃ is:
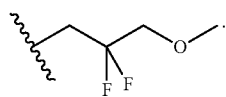 [SMILES: *CC(F)(F)COC]
Also in accordance with the present invention, compounds of the present invention are those wherein:
A is:
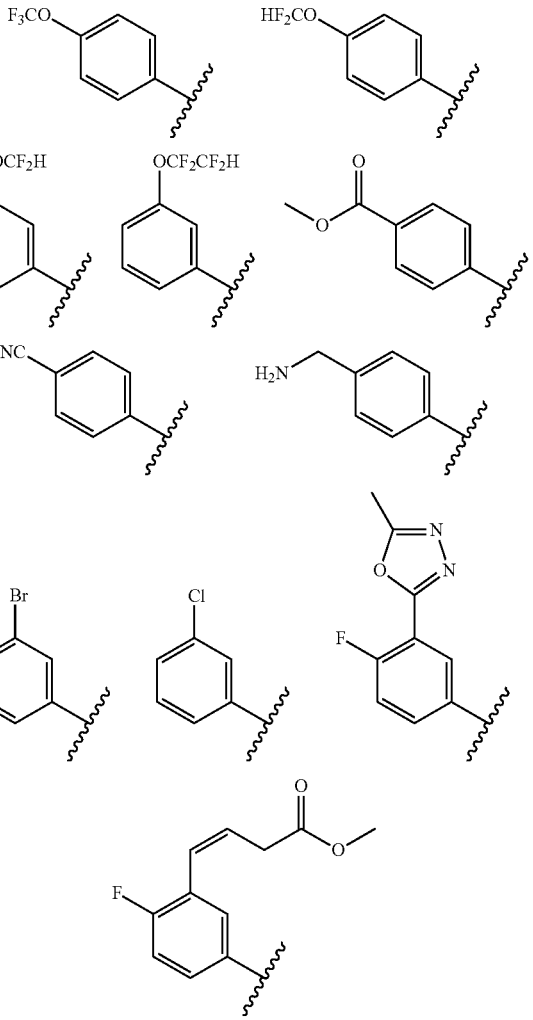

121
-continued
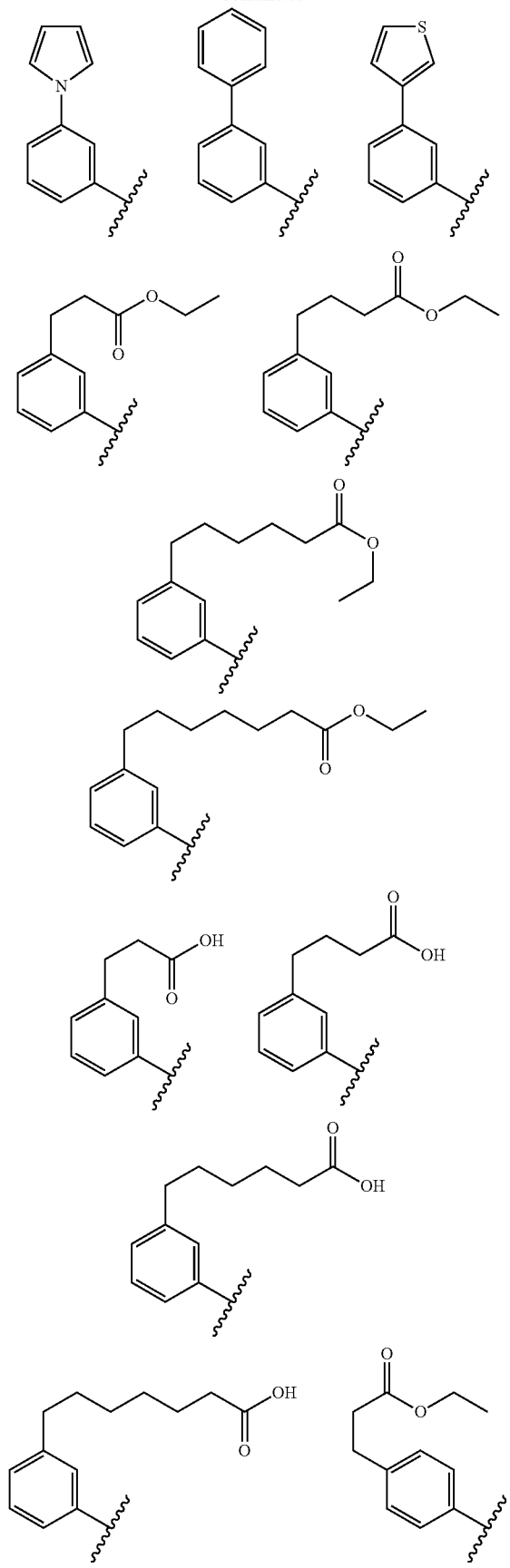
122
-continued
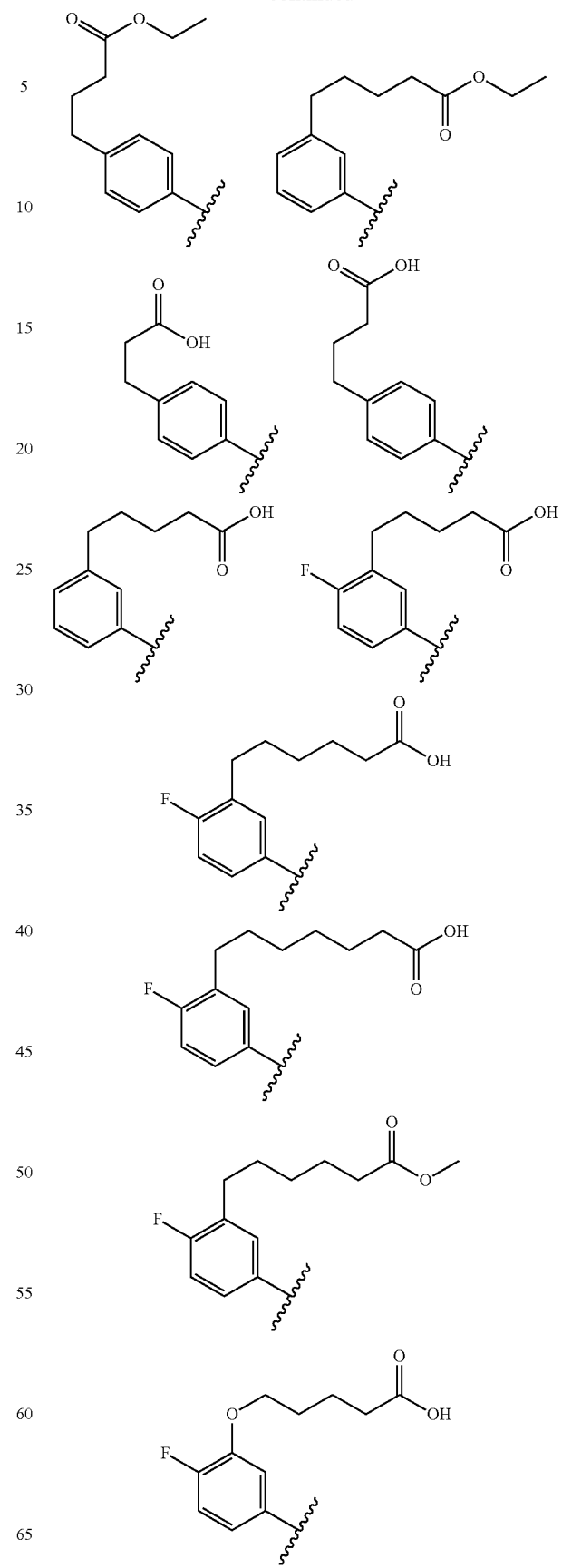

123
-continued
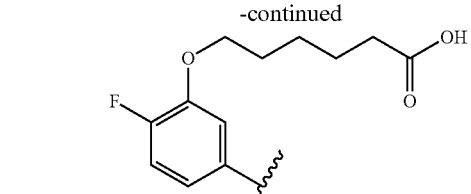
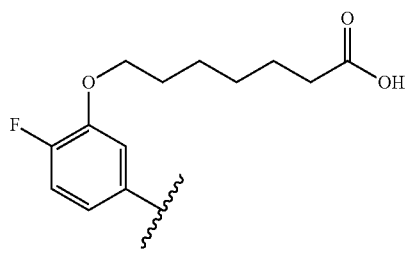
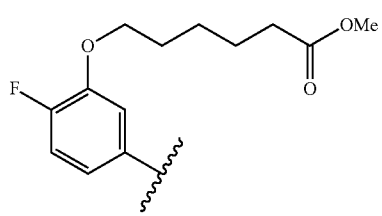
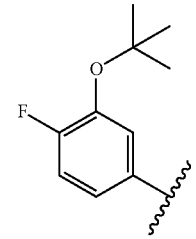
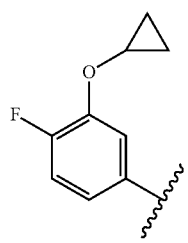 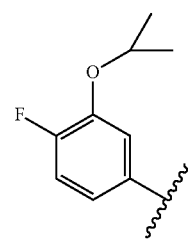
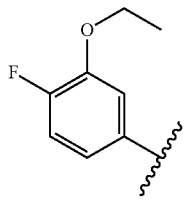 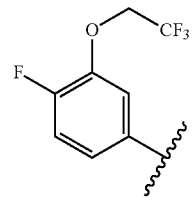 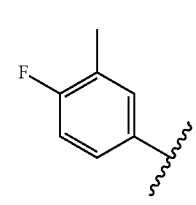
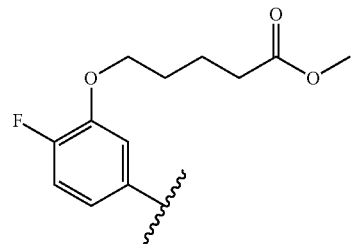 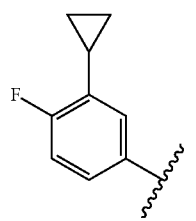
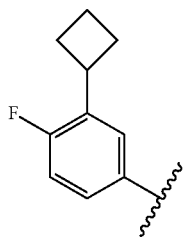 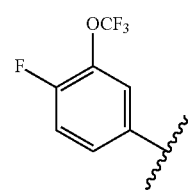 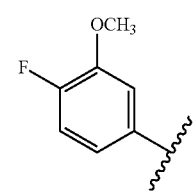
124
-continued
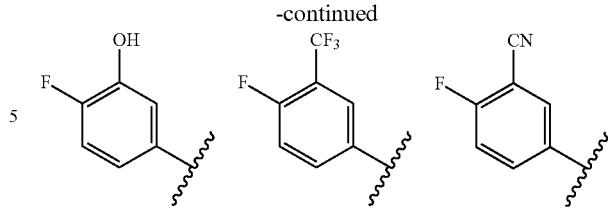
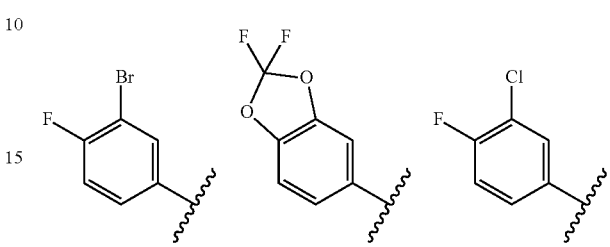
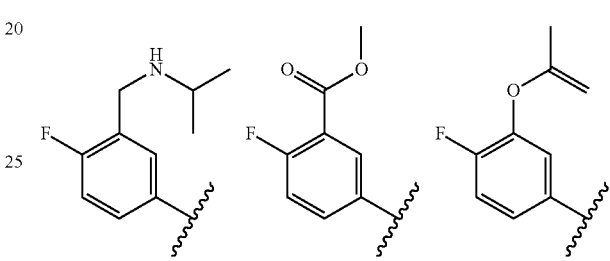
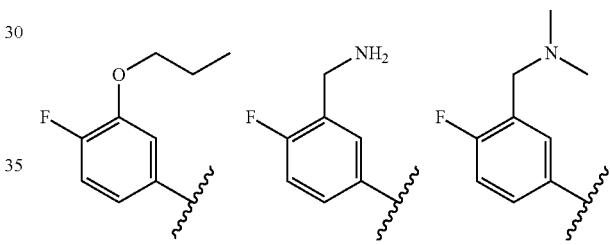
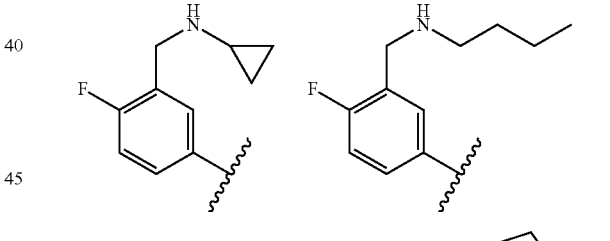
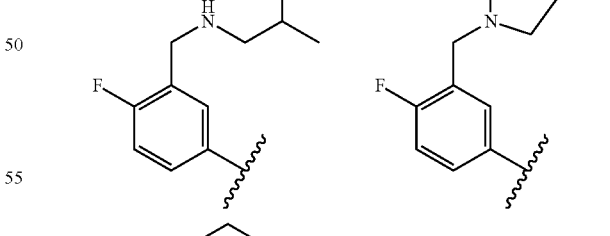
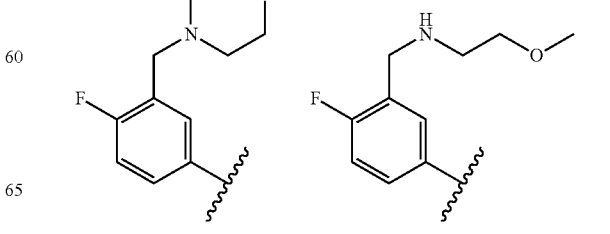

125
-continued
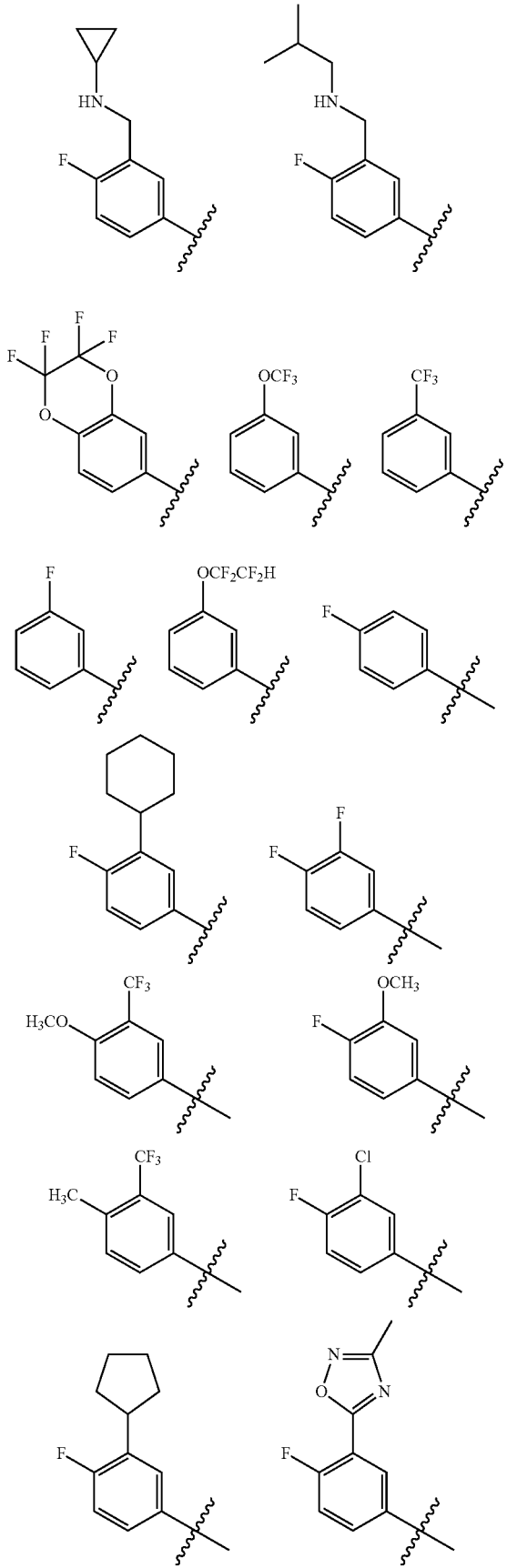
126
-continued
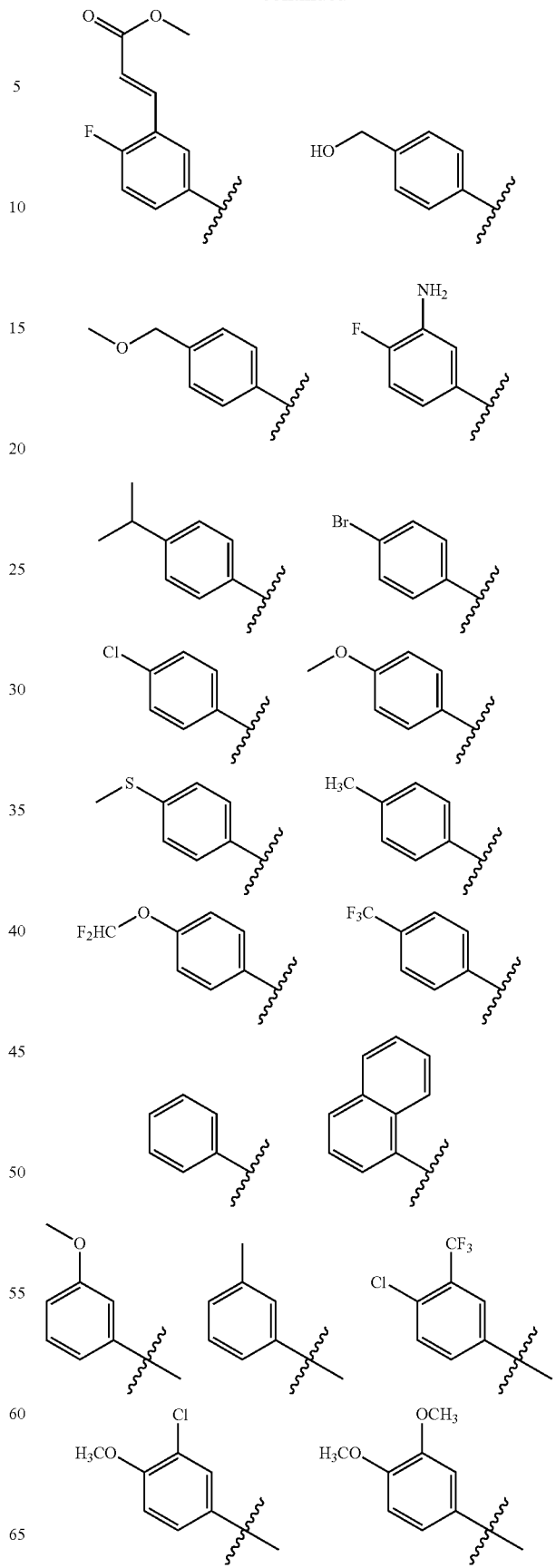

127
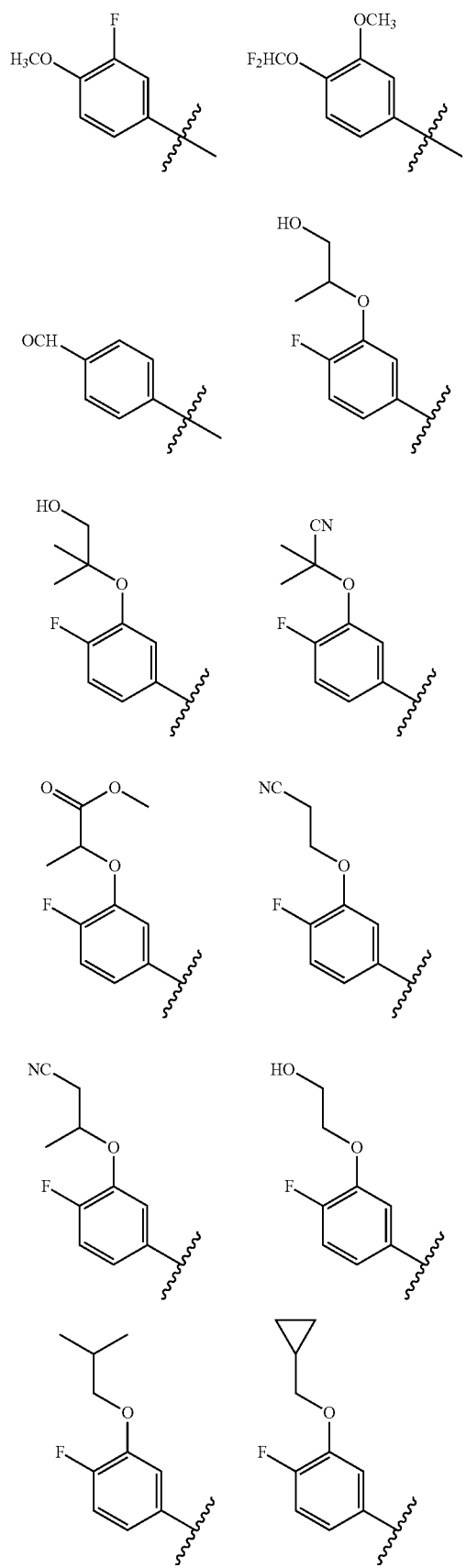
128
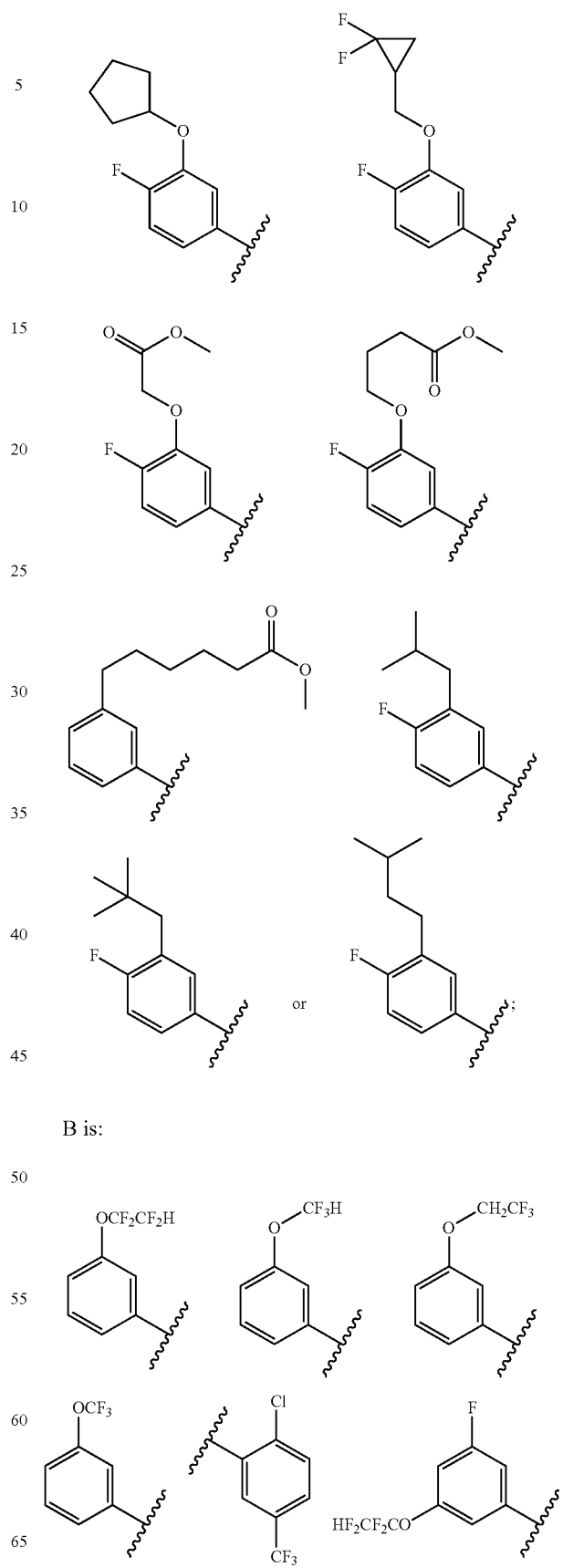
B is:

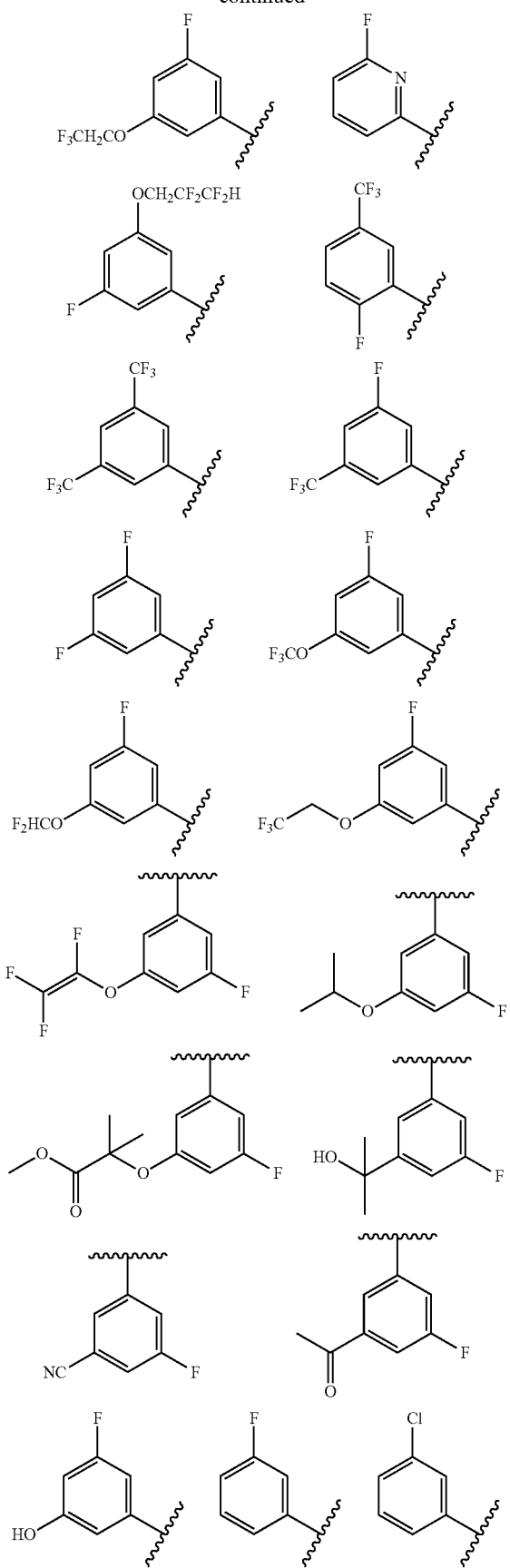
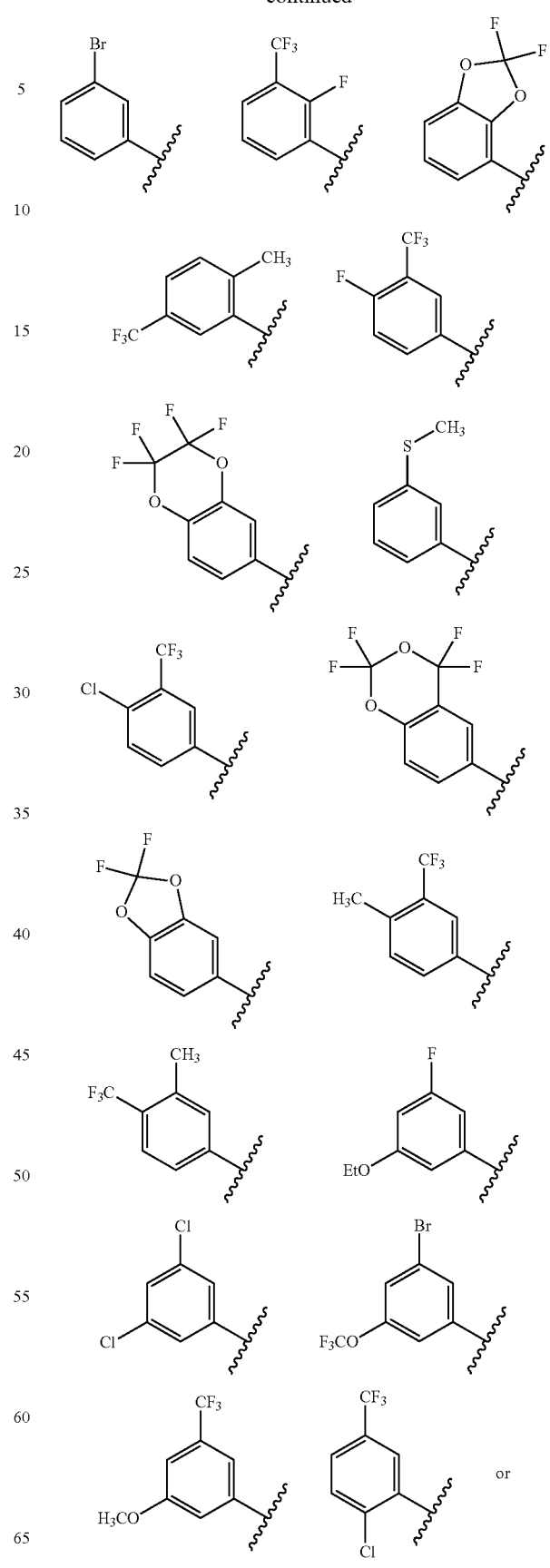

-continued
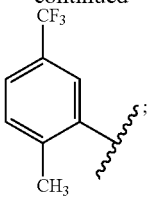
C is:
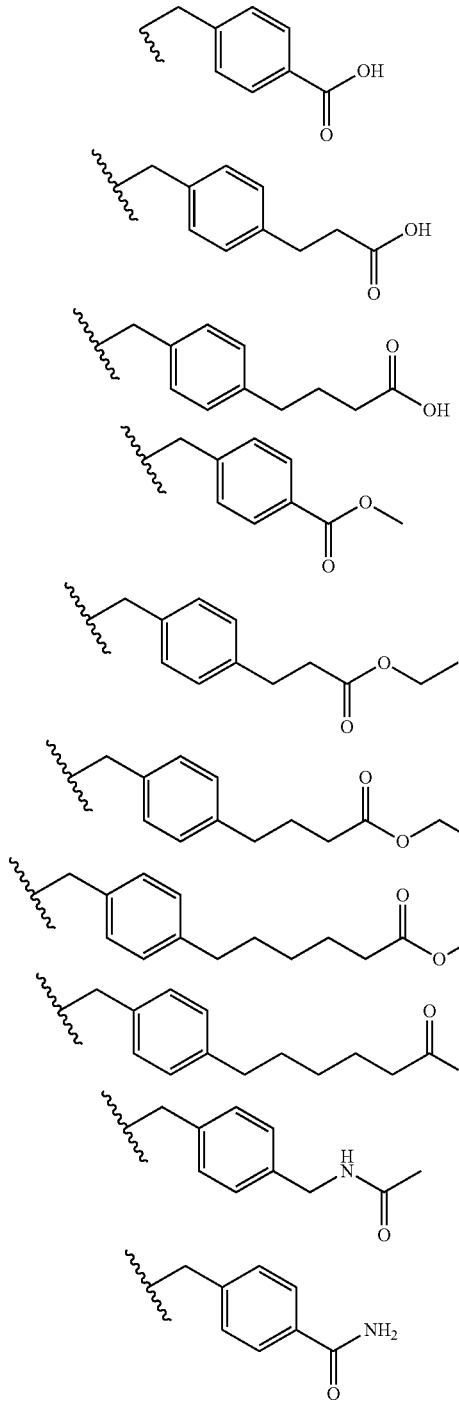
-continued
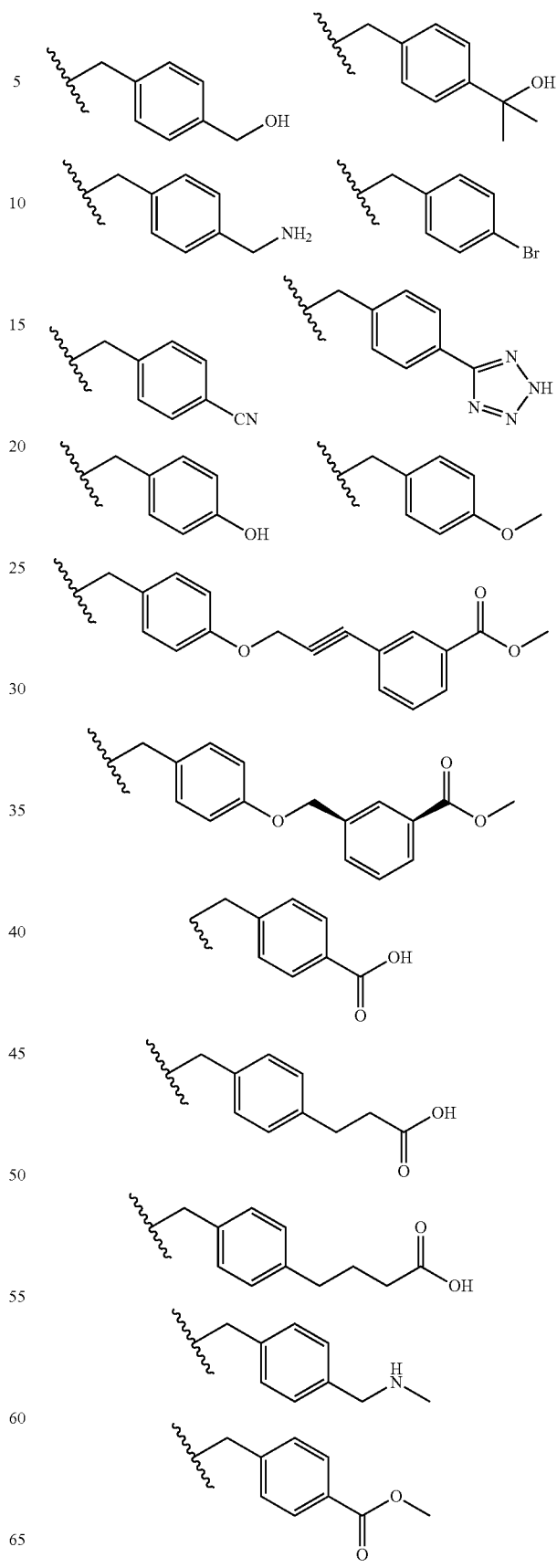

133
-continued
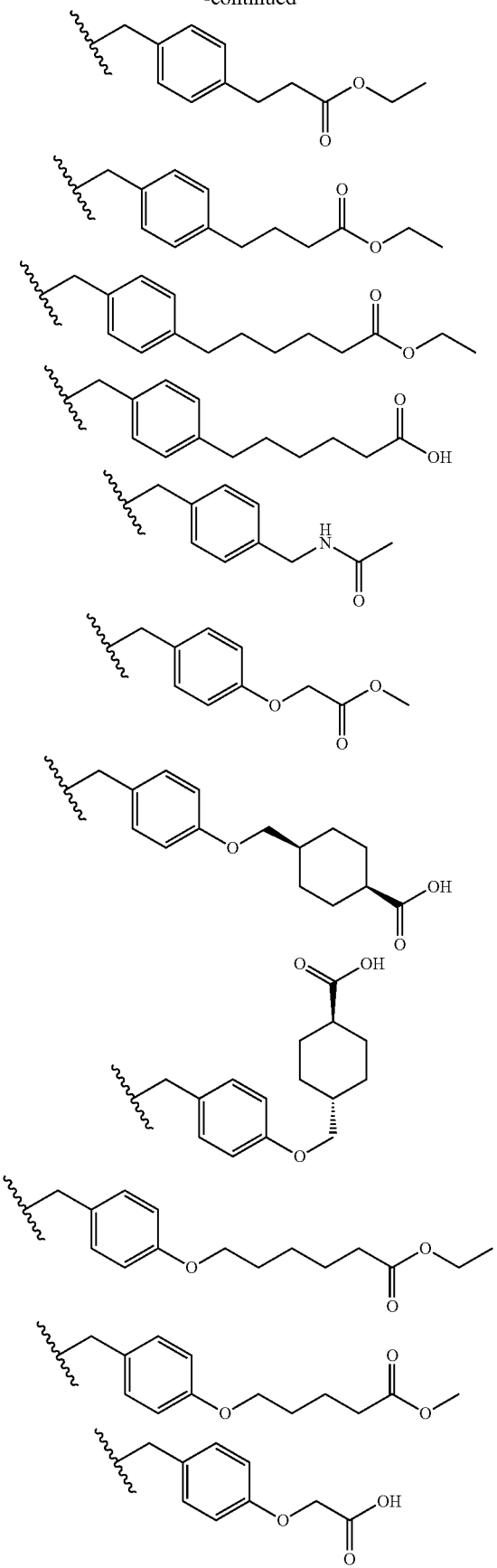
134
-continued
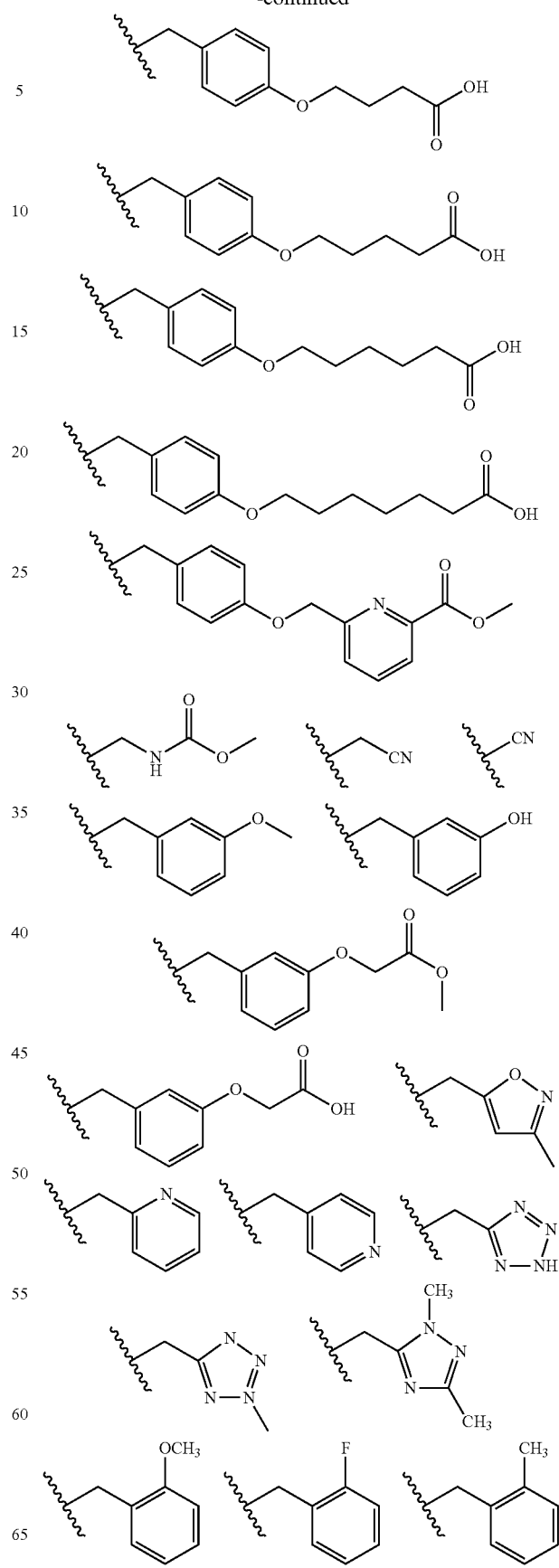

135
-continued
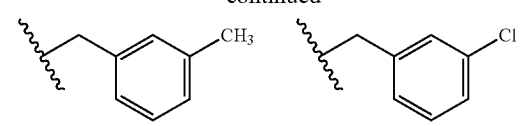
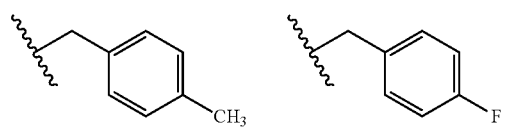
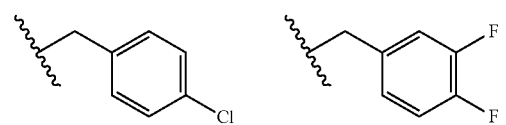
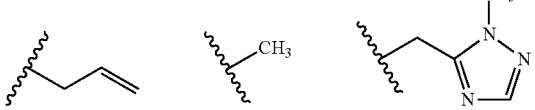
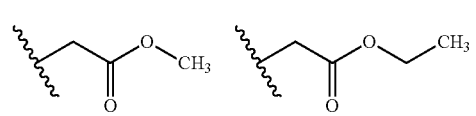
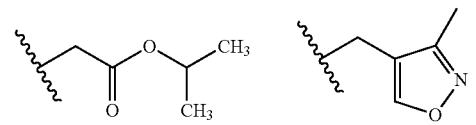
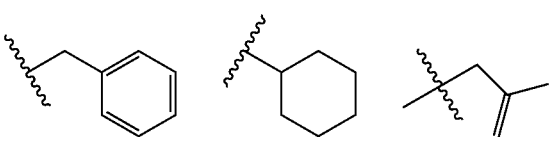
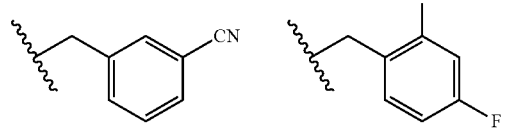
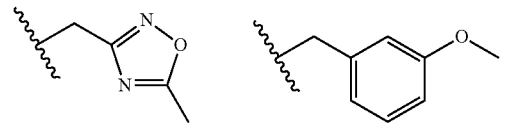
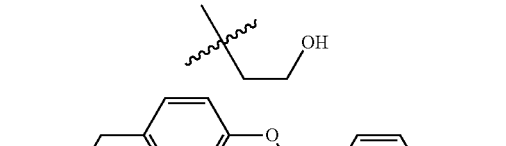
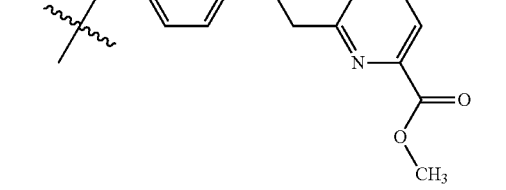
136
-continued
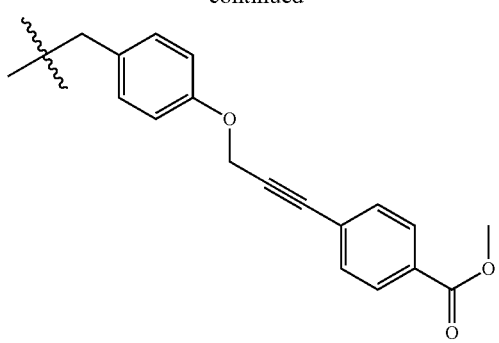
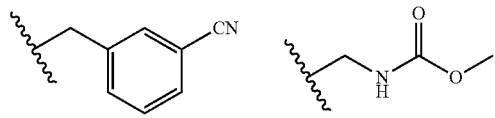
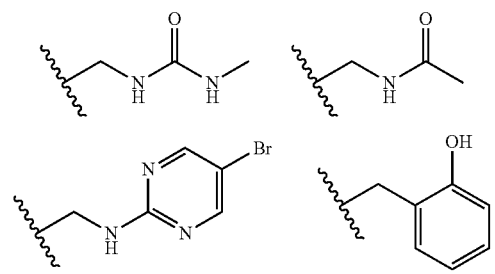
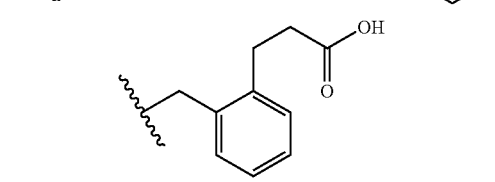
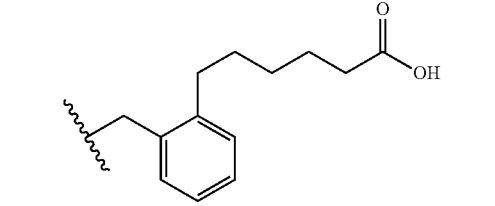
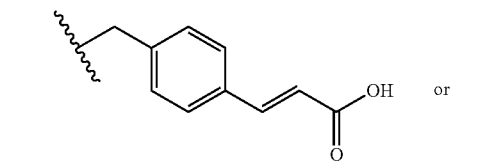
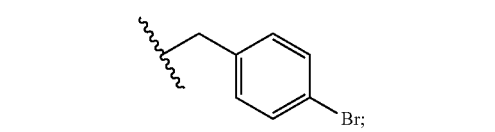
$R_1$ is H or:
(a) —C(O)$R_3$, wherein $R_3$:
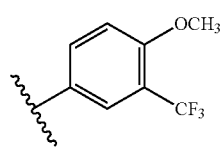
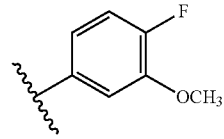

137
-continued
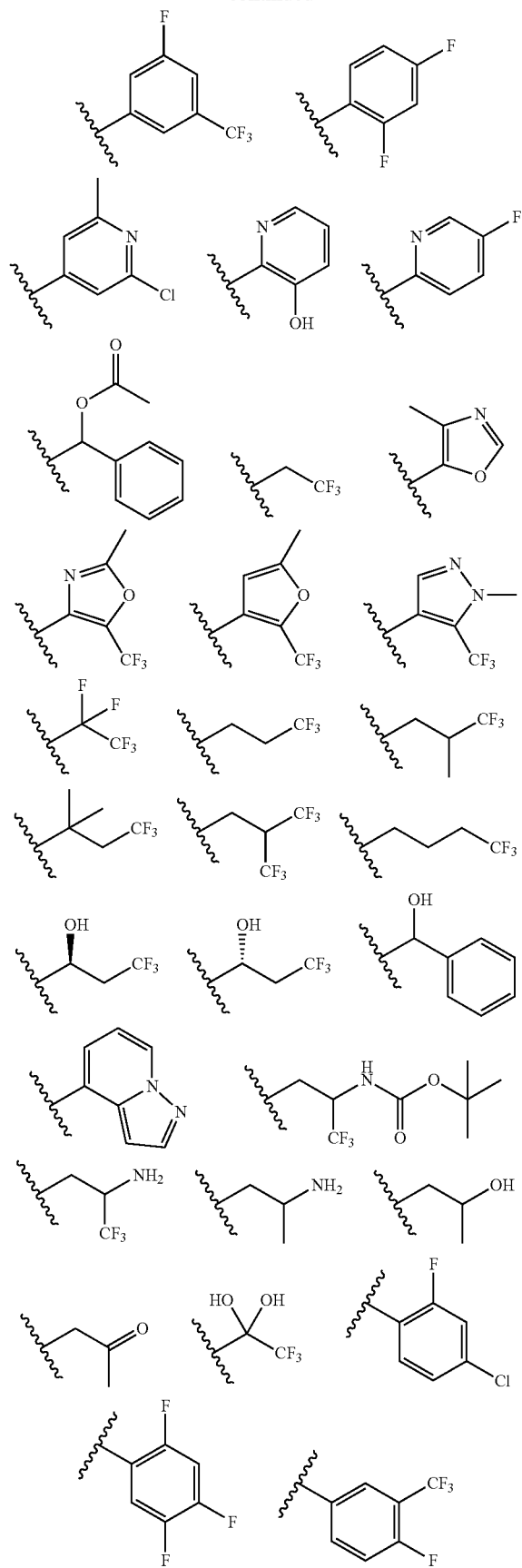
138
-continued
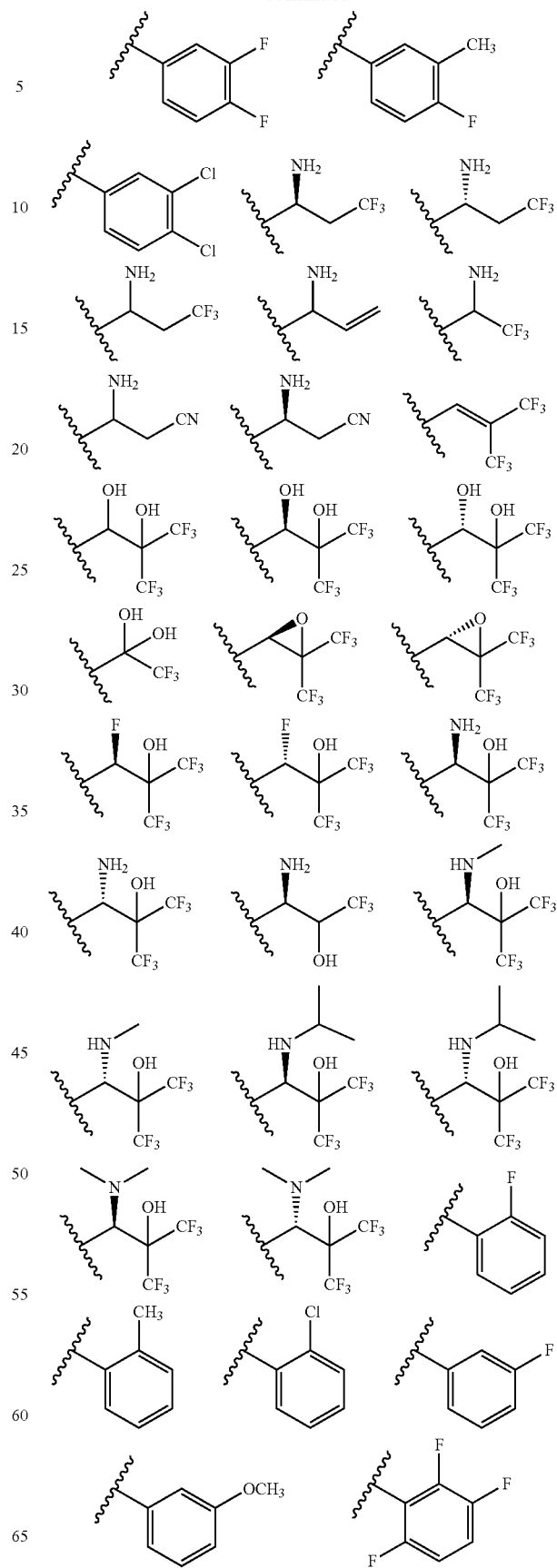

139
-continued
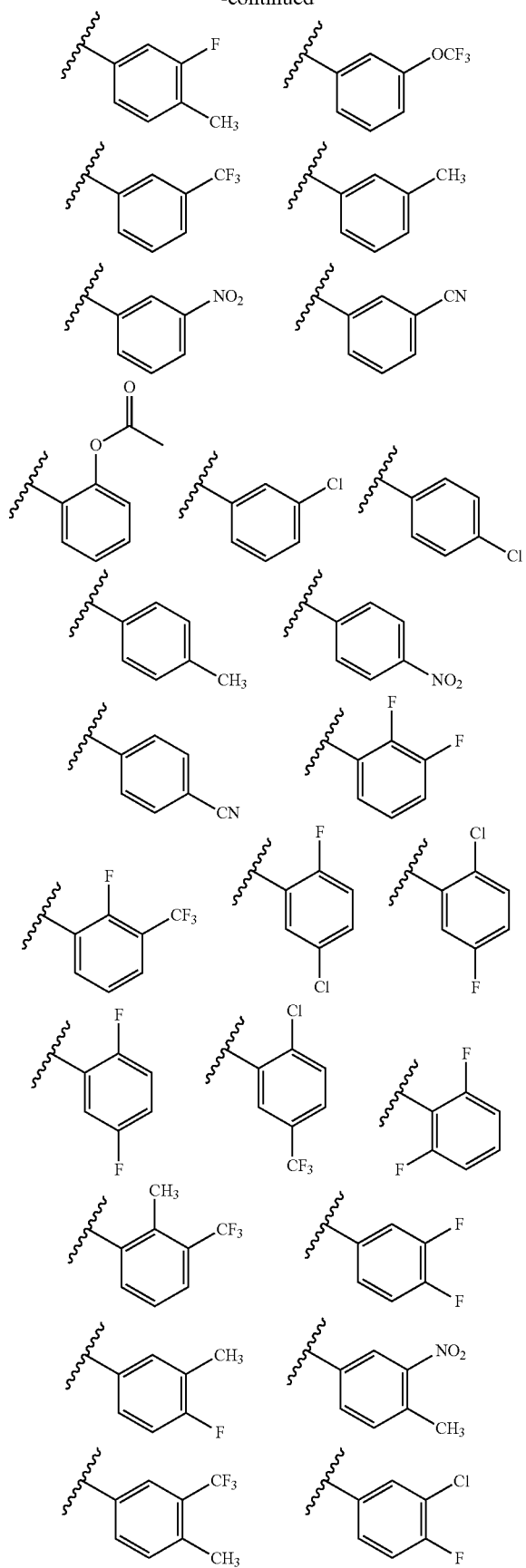
140
-continued
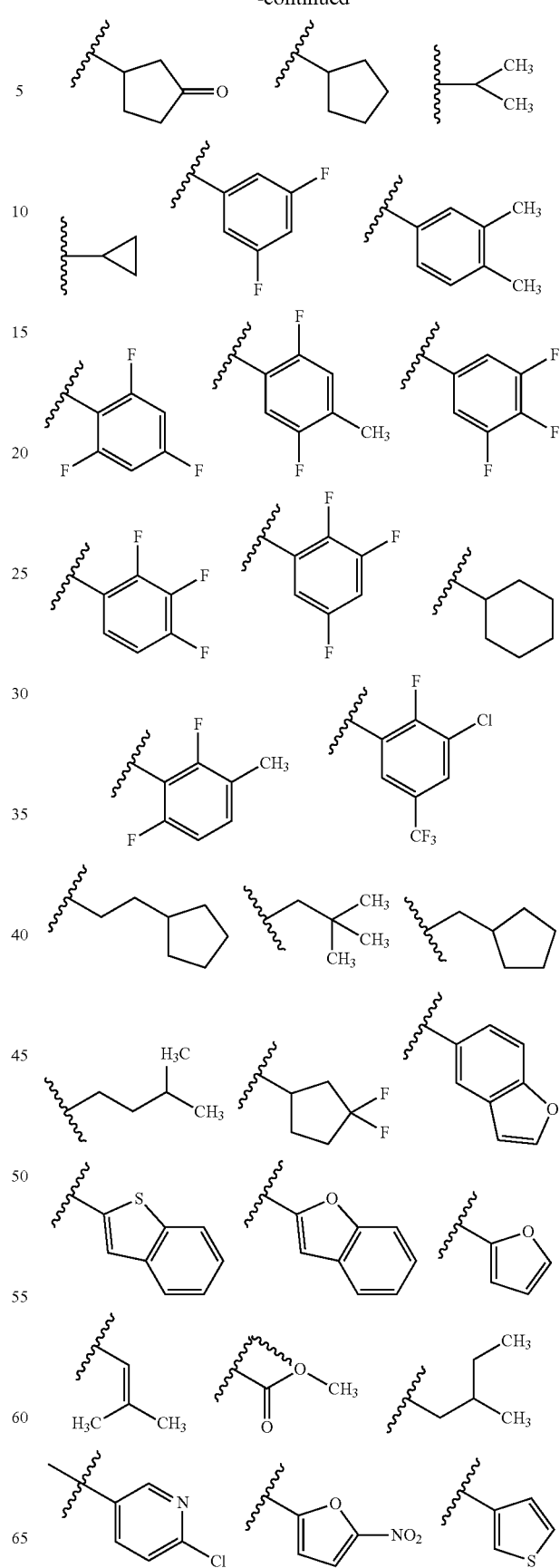

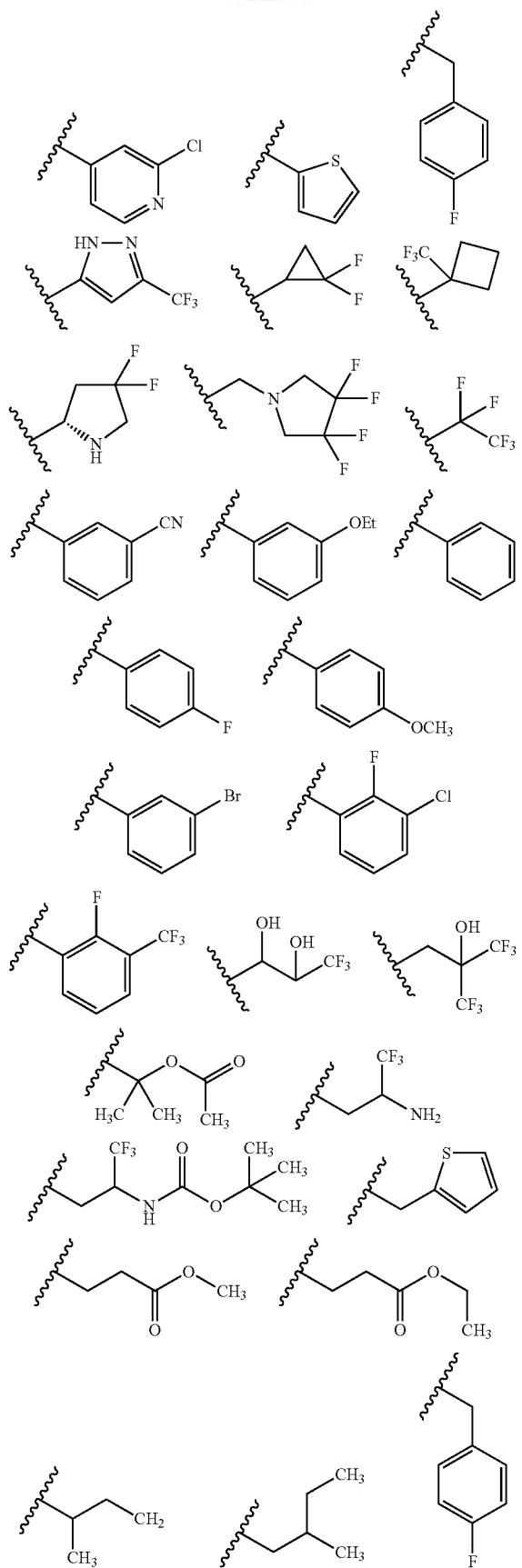
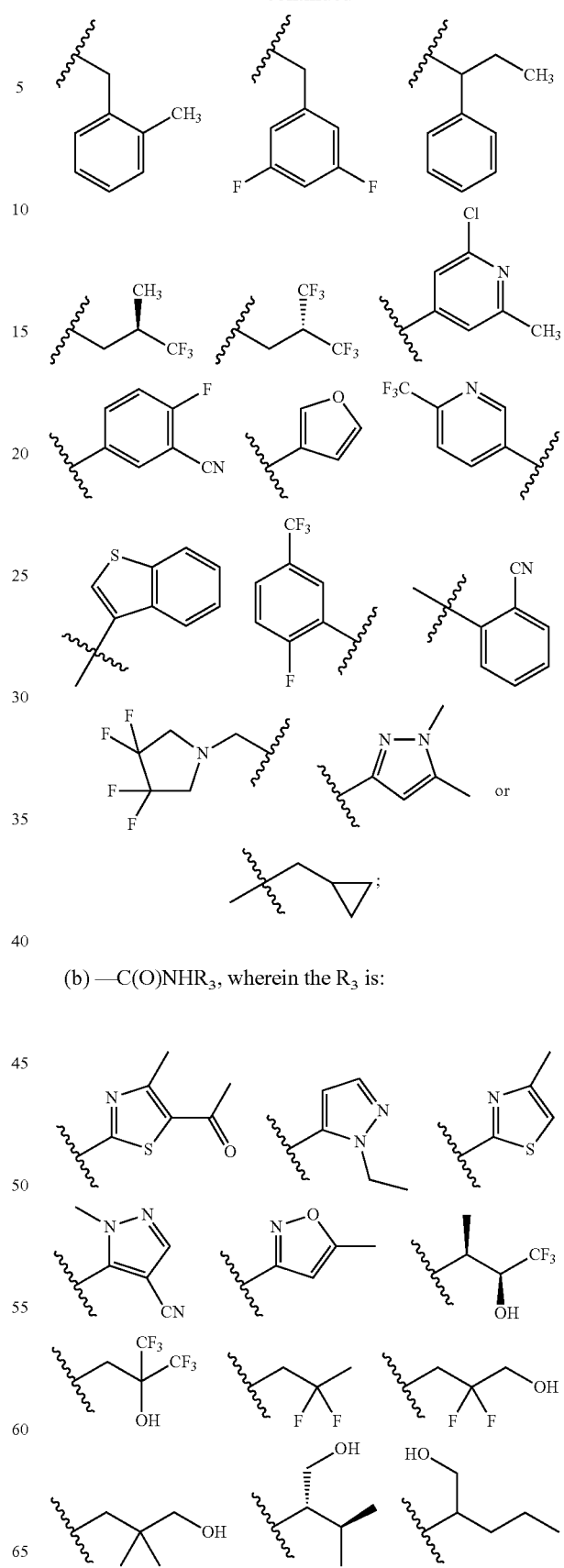
(b) —C(O)NHR$_3$, wherein the R$_3$ is:

143
-continued
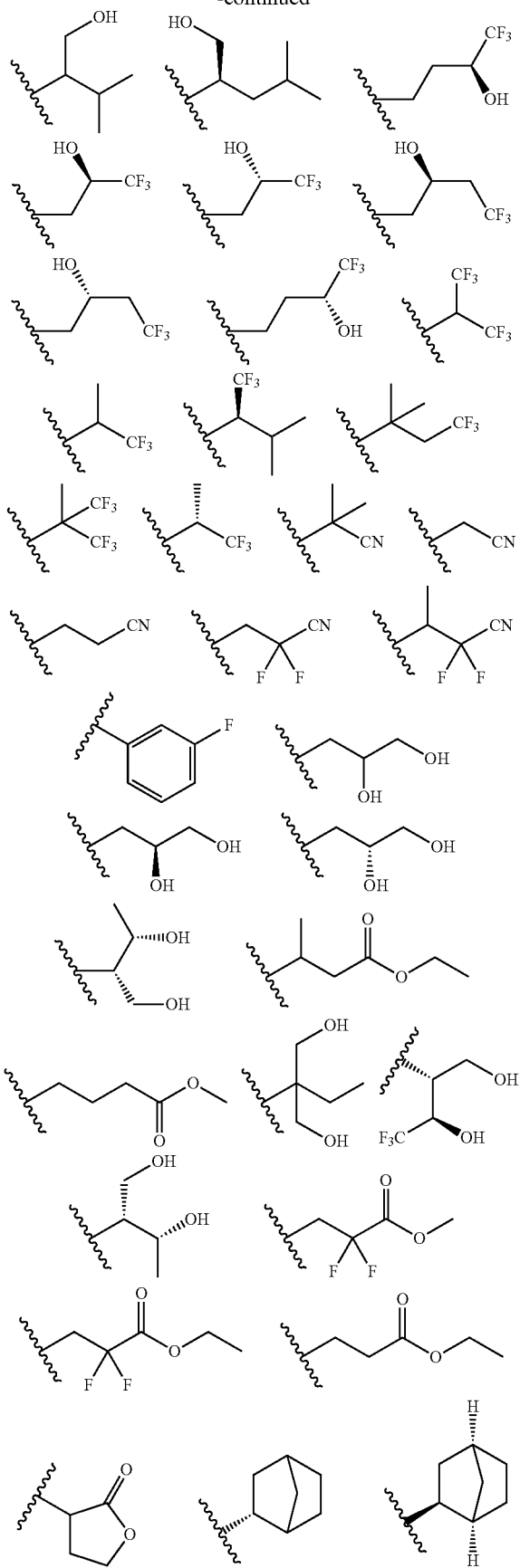
144
-continued
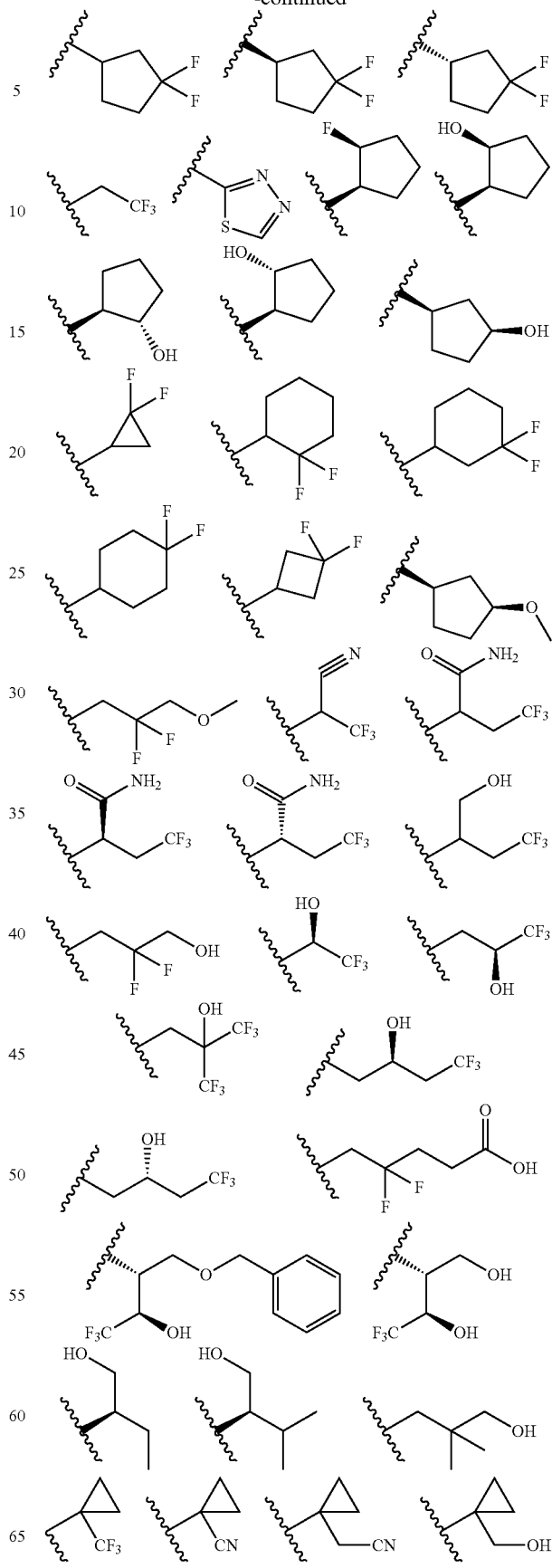

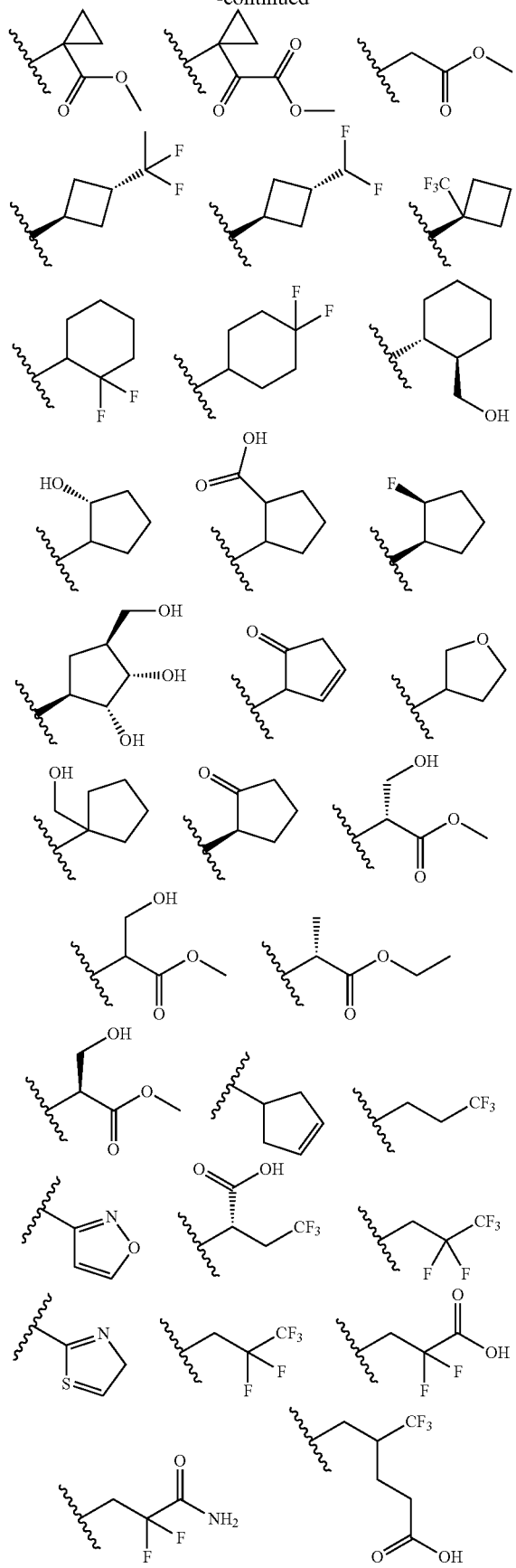
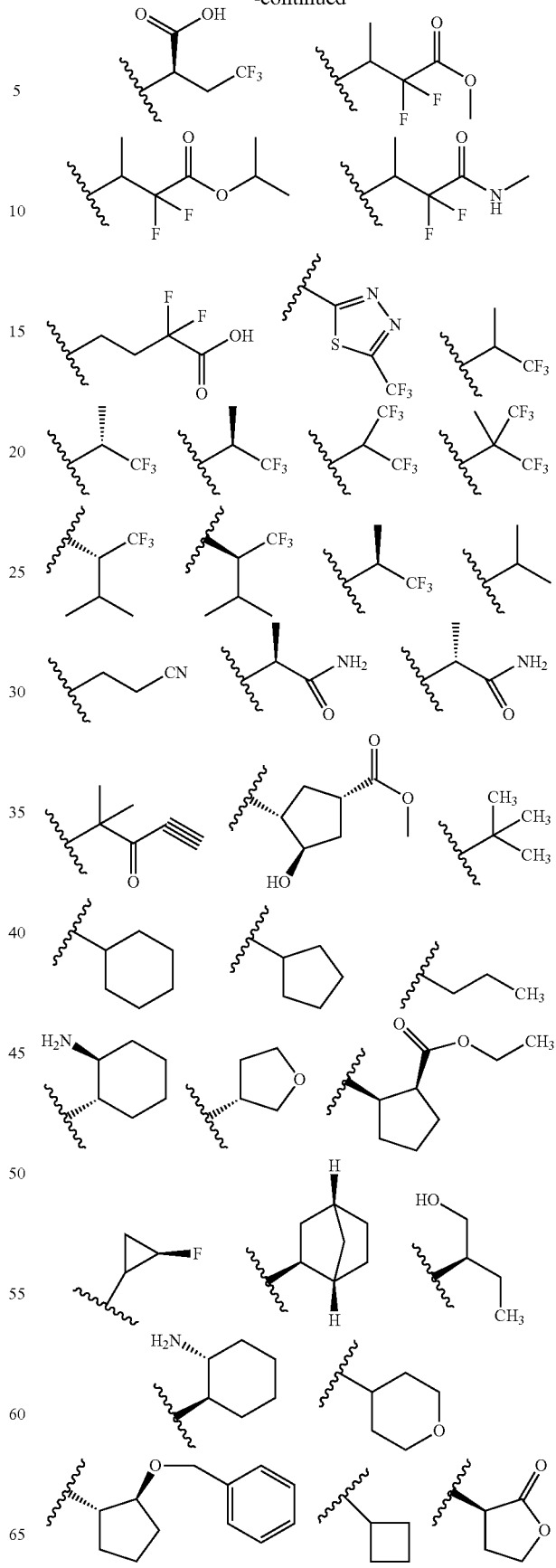

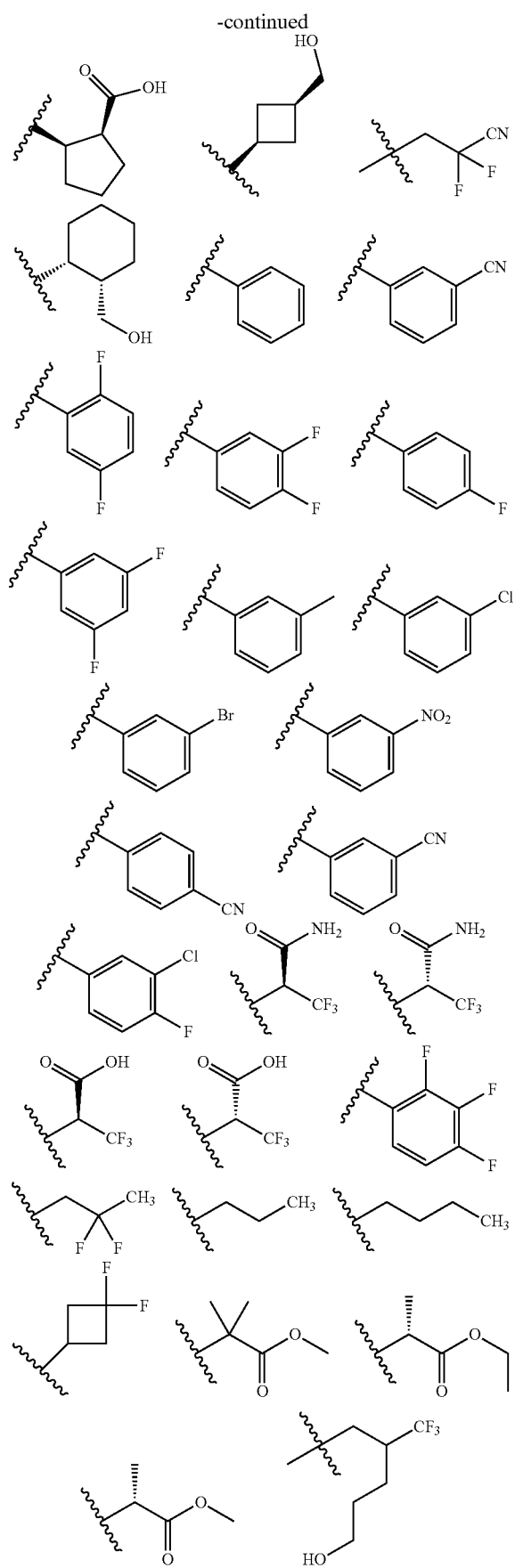
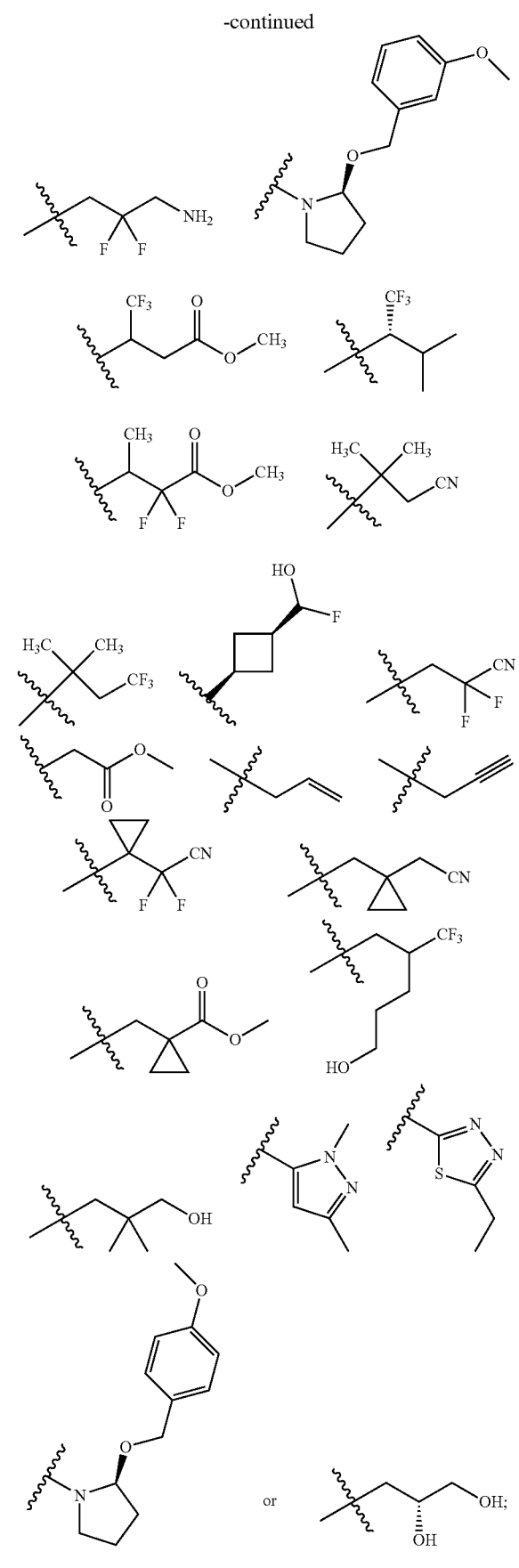

(c) —C(O)NR$_2$R$_3$, wherein the NR$_2$R$_3$ is:
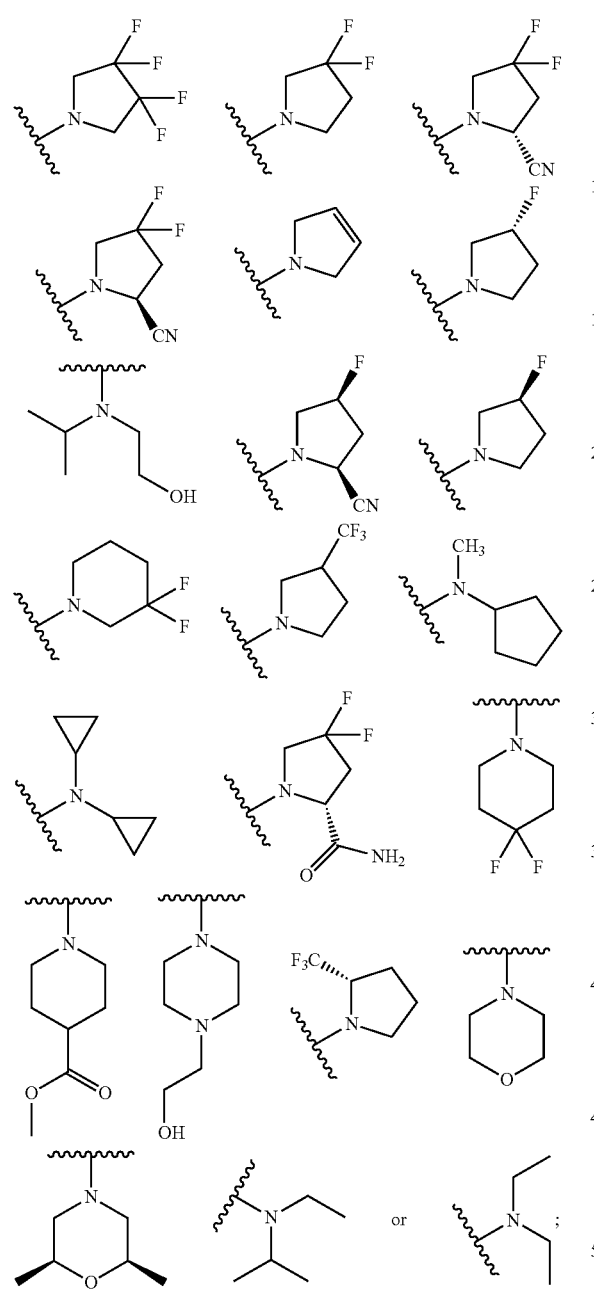
(d) —C(O)OR$_4$ wherein the R$_4$ is:
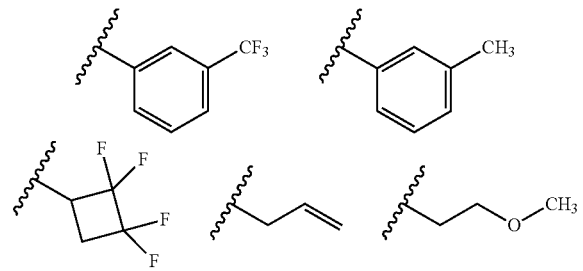
-continued
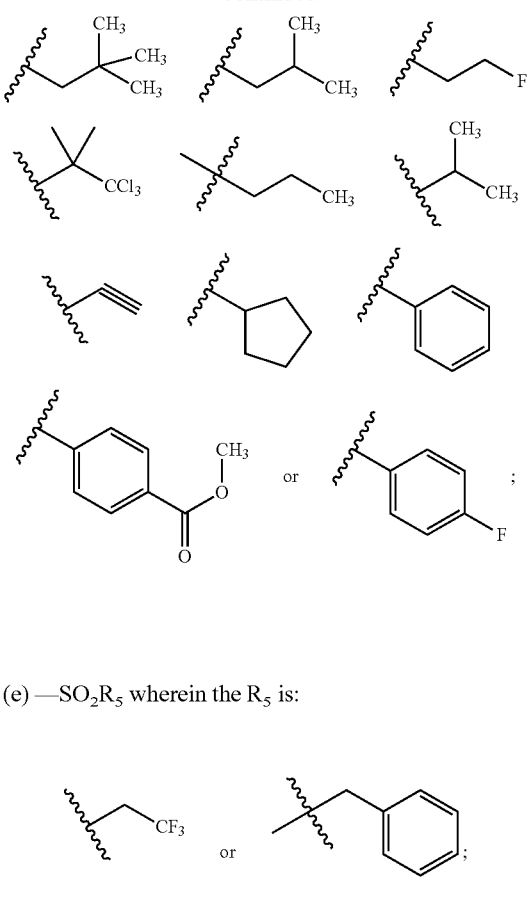
(e) —SO$_2$R$_5$ wherein the R$_5$ is:
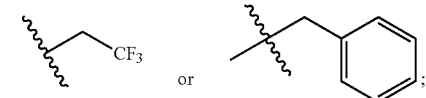
(f) —CSNHR$_7$ wherein the R$_7$ is:
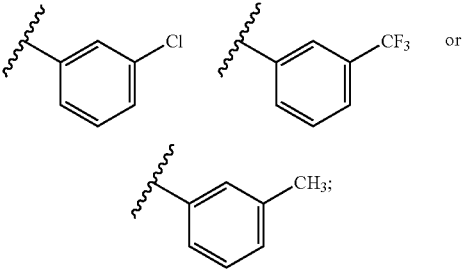
(g) —CH$_2$R$_8$ wherein the R$_8$ is:
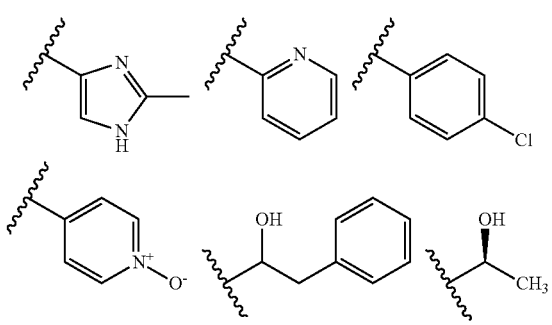

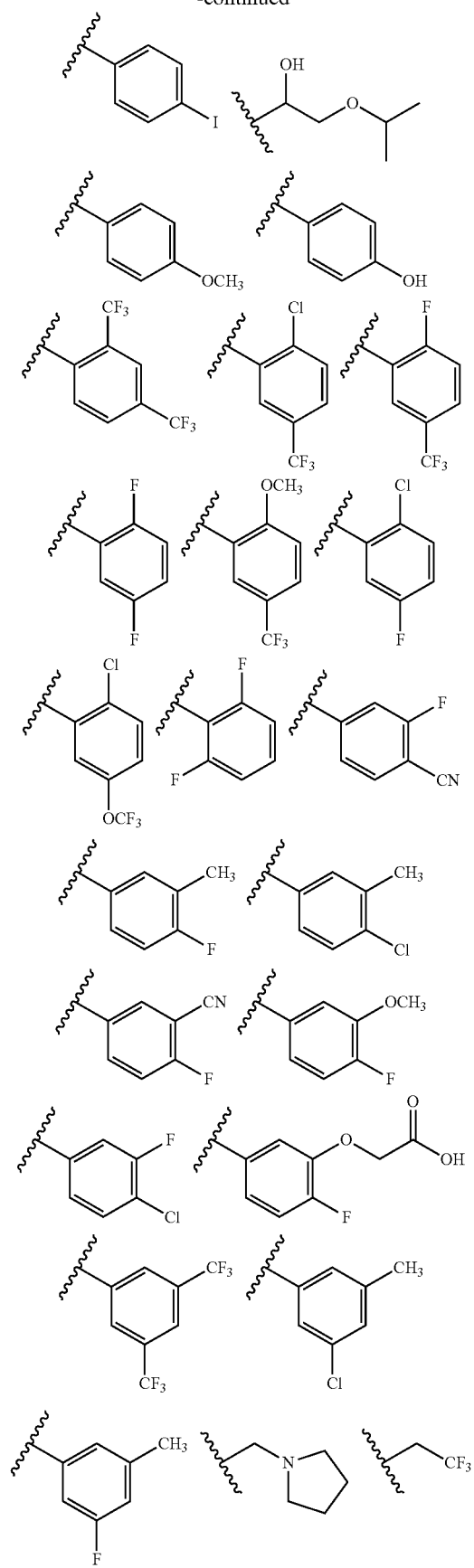
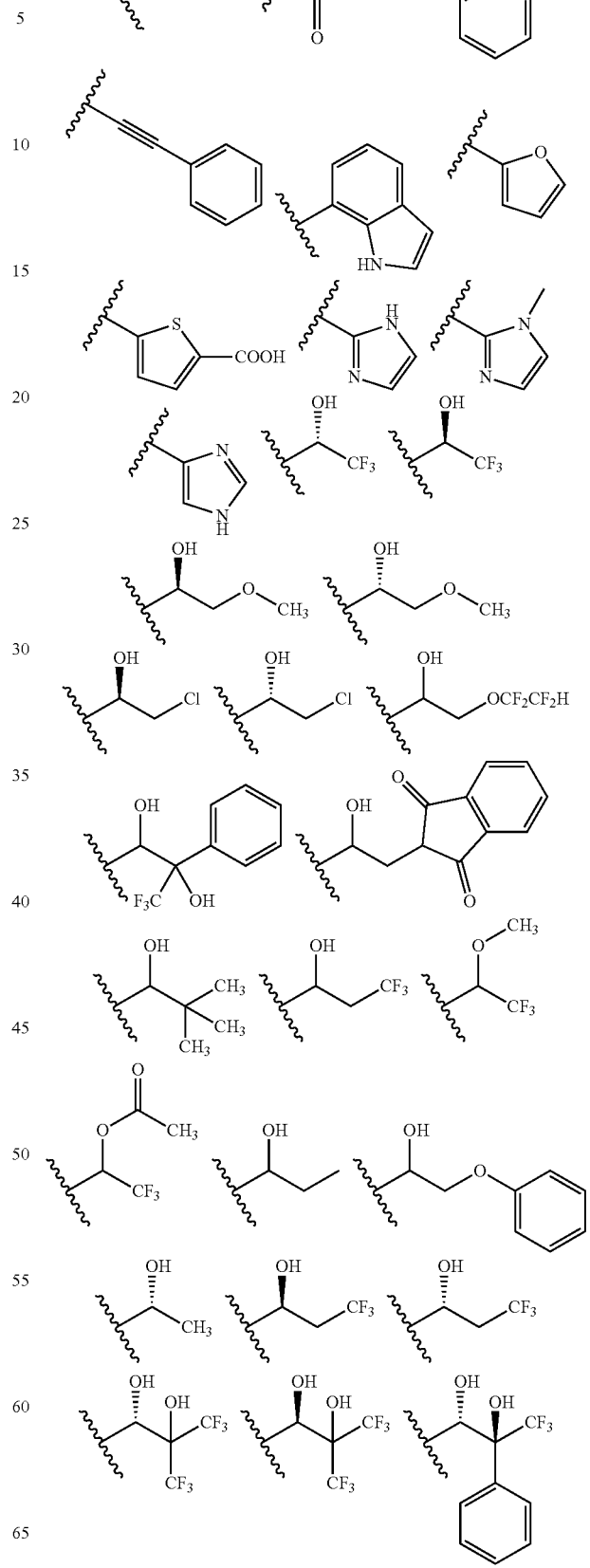

153
-continued
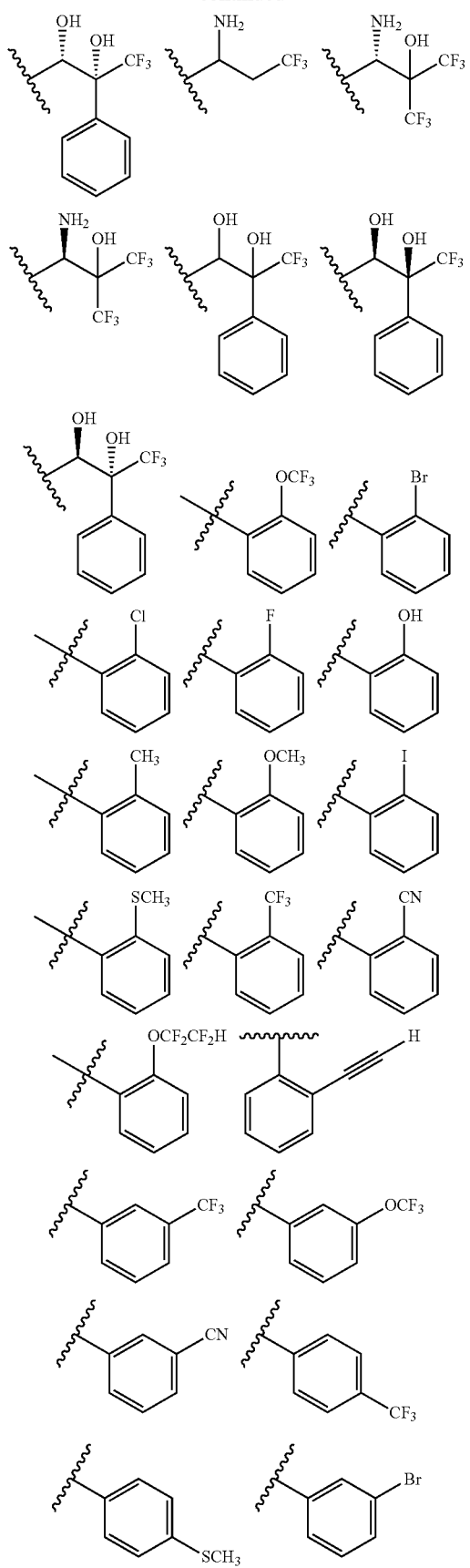
154
-continued
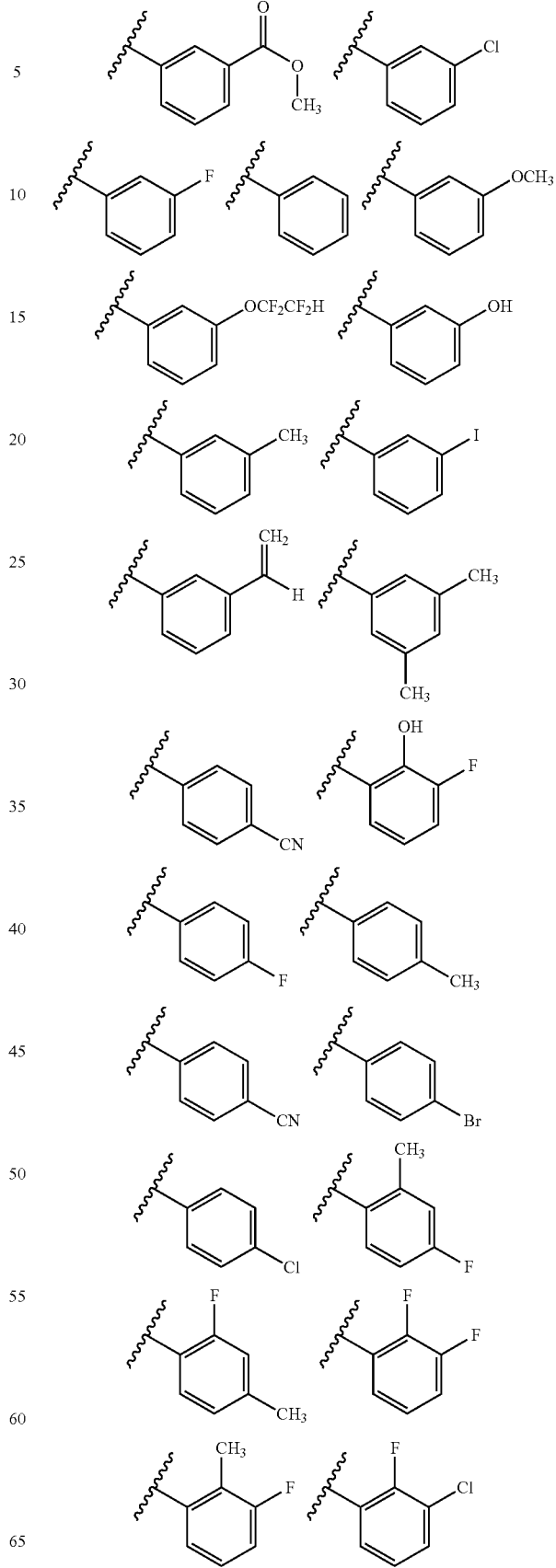

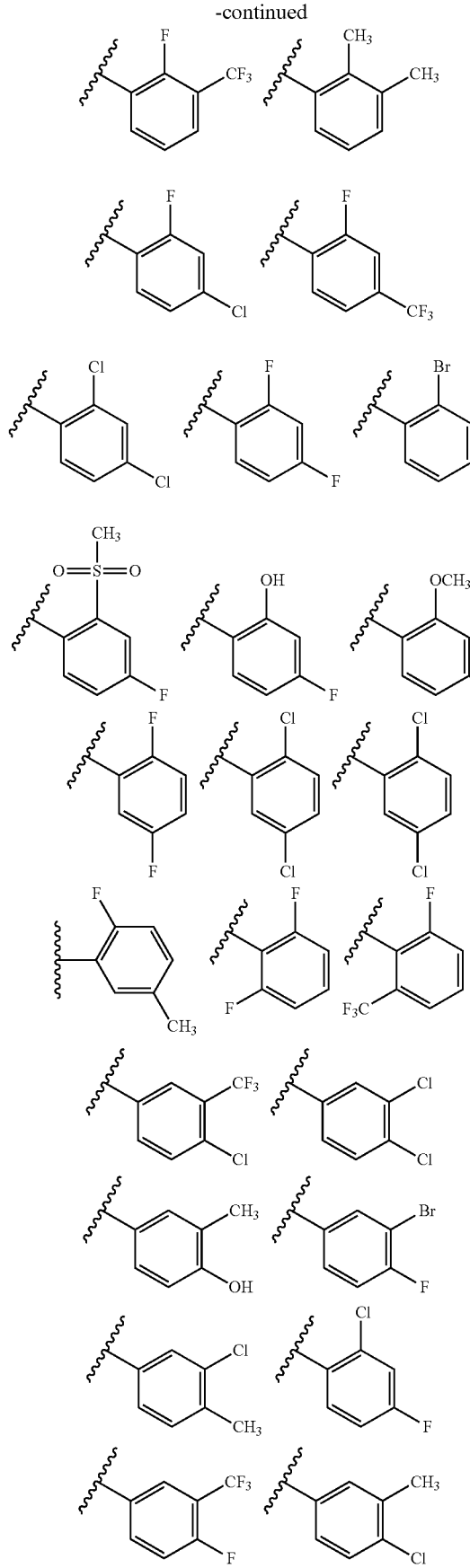
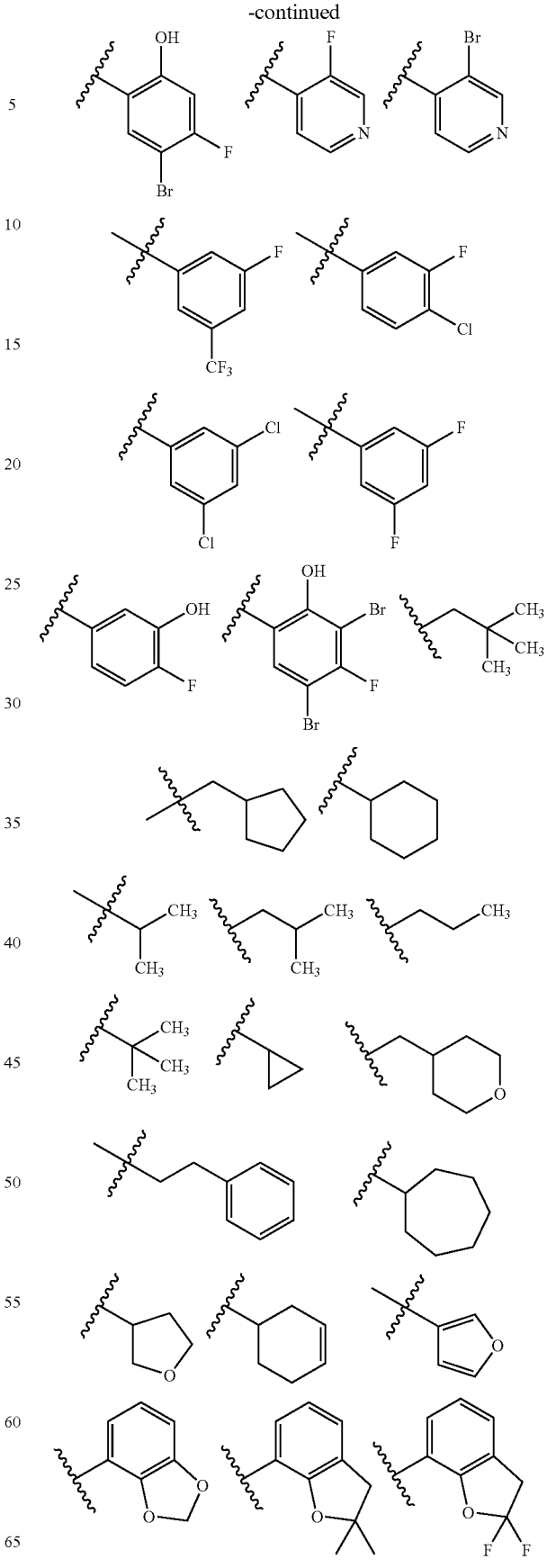

-continued

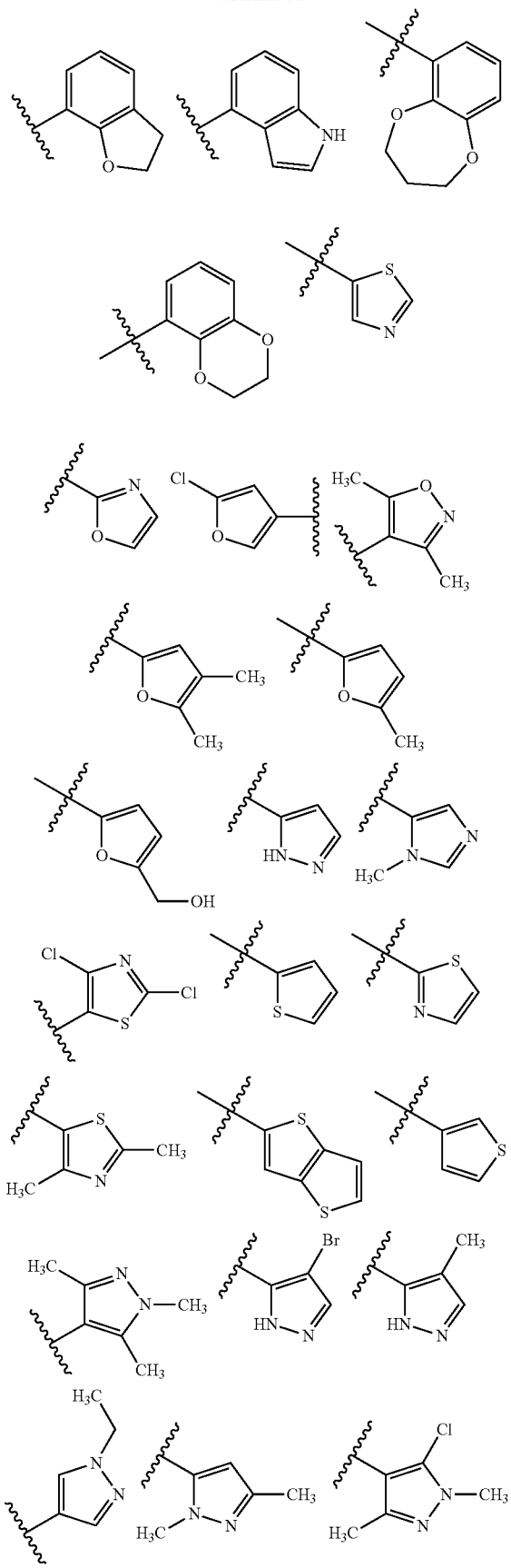

-continued

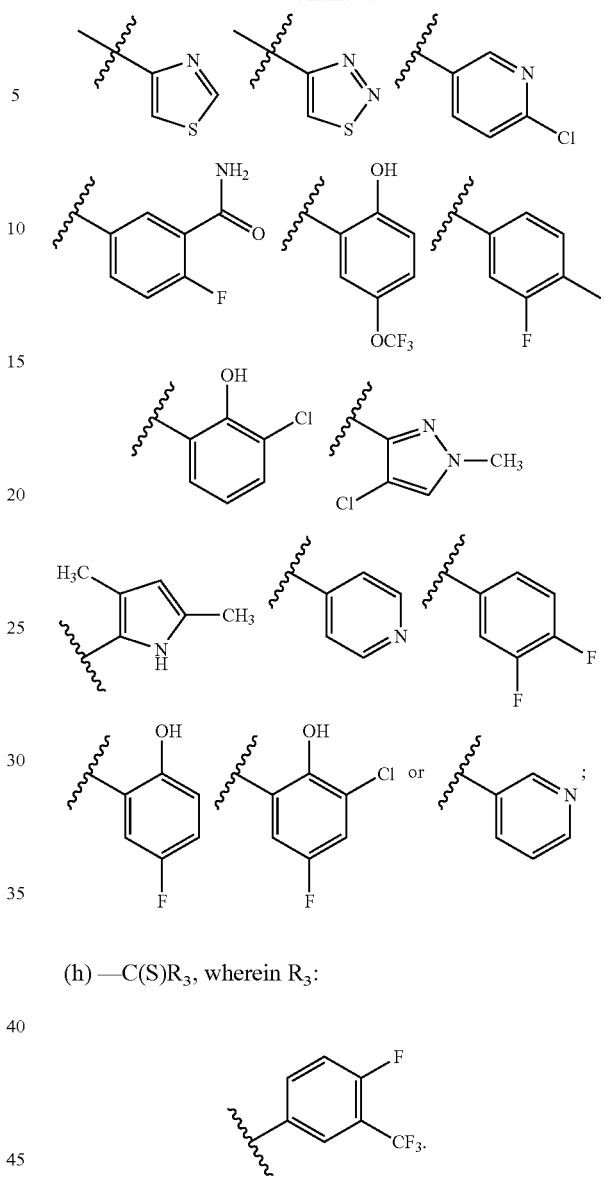

(h) —C(S)R$_3$, wherein R$_3$:

In another embodiment, compounds of the present invention are selected from the compounds exemplified in the examples, for example, Examples 273, 293, 305, and 337.

In yet another embodiment, pharmaceutical compositions comprised of compounds of the present invention alone or in combination with a pharmaceutically acceptable carrier and/or at least one additional therapeutic agent.

In still yet another embodiment, methods of inhibiting the cholesteryl ester transfer protein comprising administering to a mammal in need of treatment a compound and/or pharmaceutical composition of the present invention are provided.

In one embodiment, methods for treating, preventing or slowing the progression of Alzheimer's, atherosclerosis, venous thrombosis, coronary artery disease, coronary heart disease, coronary vascular disease, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia in a mammal (including a human being either male or female) by administering to a mammal in need of such treatment an atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia treating, preventing or slowing amount of a compound and/or pharmaceutical composition of the present invention are provided.

In another embodiment, methods for treating, preventing or slowing the progression of atherosclerosis in a mammal by administering to a mammal in need of such treatment an atherosclerotic treating, preventing or slowing amount of a compound and/or pharmaceutical composition of the present invention are provided.

In another embodiment, methods for treating, preventing or slowing the progression of peripheral vascular disease in a mammal by administering to a mammal in need of such treatment a peripheral vascular disease treating, preventing or slowing amount of a compound and/or pharmaceutical composition of the present invention are provided.

In yet another embodiment, methods for treating, preventing or slowing the progression of dyslipidemia in a mammal by administering to a mammal in need of such treatment a dyslipidemia treating, preventing or slowing amount of a compound and/or pharmaceutical composition of the present invention are provided.

In still yet another embodiment, methods for treating, preventing or slowing the progression of hyperbetalipoproteinemia in a mammal by administering to a mammal in need of such treatment a hyperbetalipoproteinemia treating, preventing or slowing amount of a compound and/or pharmaceutical composition of the present invention are provided.

In one embodiment, methods for treating, preventing or slowing the progression of hypoalphalipoproteinemia in a mammal by administering to a mammal in need of such treatment a hypoalphalipoproteinemia treating, preventing or slowing amount of a compound and/or pharmaceutical composition of the present invention are provided.

In another embodiment, methods for treating, preventing or slowing the progression of hypercholesterolemia in a mammal by administering to a mammal in need of such treatment a hypercholesterolemia treating, preventing or slowing amount of a compound and/or pharmaceutical composition of the present invention are provided.

In yet another embodiment, methods for treating, preventing or slowing the progression of hypertriglyceridemia in a mammal by administering to a mammal in need of such treatment a hypertriglyceridemia treating, preventing or slowing amount of a compound and/or pharmaceutical composition of the present invention are provided.

In still yet another embodiment, methods for treating, preventing or slowing the progression of familial-hypercholesterolemia in a mammal by administering to a mammal in need of such treatment a familial-hypercholesterolemia treating, preventing or slowing amount of a compound and/or pharmaceutical composition of the present invention are provided.

In one embodiment, methods for treating, preventing or slowing the progression of cardiovascular disorders in a mammal by administering to a mammal in need of such treatment a cardiovascular disorder treating, preventing or slowing amount of a compound and/or pharmaceutical composition of the present invention are provided.

In another embodiment, methods for treating, preventing or slowing the progression of angina in a mammal by administering to a mammal in need of such treatment an angina treating, preventing or slowing amount of a compound and/or pharmaceutical composition of the present invention are provided.

In yet another embodiment, methods for treating, preventing or slowing the progression of ischemia in a mammal by administering to a mammal in need of such treatment an ischemic disease treating, preventing or slowing amount of a compound and/or pharmaceutical composition of the present invention are provided.

In still yet another embodiment, methods for treating, preventing or slowing the progression of cardiac ischemia in a mammal by administering to a mammal in need of such treatment a cardiac ischemic treating, preventing or slowing amount of a compound and/or pharmaceutical composition of the present invention are provided.

In one embodiment, methods for treating, preventing or slowing the progression of stroke in a mammal by administering to a mammal in need of such treatment a stroke treating, preventing or slowing amount of a compound and/or pharmaceutical composition of the present invention are provided.

In one embodiment, methods for treating, preventing or slowing the progression of a myocardial infarction in a mammal by administering to a mammal in need of such treatment a myocardial infarction treating, preventing or slowing amount of a compound and/or pharmaceutical composition of the present invention are provided.

In another embodiment, methods for treating, preventing or slowing the progression of reperfusion injury in a mammal by administering to a mammal in need of such treatment a reperfusion injury treating, preventing or slowing amount of a compound and/or pharmaceutical composition of the present invention are provided.

In another embodiment, methods for treating, preventing or slowing the progression of angioplastic restenosis in a mammal by administering to a mammal in need of such treatment an angioplastic restenosis treating, preventing or slowing amount of a compound and/or pharmaceutical composition of the present invention are provided.

In yet another embodiment, methods for treating, preventing or slowing the progression of hypertension in a mammal by administering to a mammal in need of such treatment a hypertension treating, preventing or slowing amount of a compound and/or pharmaceutical composition of the present invention are provided.

In yet another embodiment, methods for treating, preventing or slowing the progression of the ascular complications of diabetes in a mammal by administering to a mammal in need of such treatment a vascular complications of diabetes treating, preventing or slowing amount of a compound and/or pharmaceutical composition of the present invention are provided.

In still yet another embodiment, methods for treating, preventing or slowing the progression of obesity in a mammal by administering to a mammal in need of such treatment an obesity treating, preventing or slowing amount of a compound and/or pharmaceutical composition of the present invention are provided.

In one embodiment, methods for treating, preventing or slowing the progression of endotoxemia in a mammal by administering to a mammal in need of such treatment an endotoxemia treating, preventing or slowing amount of a compound and/or pharmaceutical composition of the present invention are provided.

In another embodiment, methods for treating, preventing or slowing the progression of a disease requiring cholesteryl ester transfer protein inhibitor therapy comprising administering, concurrently or sequentially, to a mammal in need of treatment, prevention or slowing a therapeutically effective amount of a compound of the present invention and at least one additional therapeutic agent.

In yet another embodiment, methods of inhibiting remnant lipoprotein production comprising administering to a mammal a compound and/or pharmaceutical composition of the present invention are provided.

In still yet another embodiment, methods of raising HDL cholesterol in a mammal comprising administering to a mammal in need of treatment a compound and/or pharmaceutical composition of the present invention are provided.

Mono fluorinated phenols have been widely used as synthetic blocks for many bioactive compounds. To date, there have been several methods reported in the literature for the synthesis of such phenols. For example, such phenols may be prepared by: (i) electrophilic fluorination of phenols using a range of $F^+$ reagents; (ii) hydrolysis of bromofluorobenzene or chlorofluorobenzene catalysized by a copper reagent; (iii) diazotization of a corresponding fluoroaniline; (iv) selective hydroxy substitution of difluorobenzoic acid with solid sodium hydroxide in 1,3-dimethyl-2-imidazolidinone (see, Journal of Fluorine Chemistry, 121:97-99 (2003) and Bioorganic & Medicinal Chemistry, 12:5661-5675 (2004)); and (iv) the replacement of fluoroatom of activated arylfluorides such as fluoroanthracene-9,10-diones, fluorobenz[g]isoquinoline-5,10-diones and fluoronitrobenzenes with sodium trimethylsilanoate in specific solvent THF (see Synthetic Communications, 28(18):3415-3422). However, most of these methods use reagents that unsafe, highly hazardous and/or not readily available. In addition, these methods may only be suitable for the synthesis of 2- or 4-fluorophenols, and/or produce the desired compounds in low yields.

Thus, although there are a variety of methods used to produce mono fluorinated phenols, there is a continuing need and a continuing search in this field of art for alternative methods to produce mono fluorinated phenols under safe conditions and in greater yields.

In one embodiment, processes for the preparation of mainly a compound of formula WW, B—$OCF_2CF_2H$, comprising reducing a mixture comprised of a compound of formula WW and a compound of formula YY, B—$OCF_2CF_2Br$, with zinc dust under acidic conditions, wherein B is phenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl, 15) —$COR_6$, 16) —$S(O)_6R_6$, 17) —$SO_2NHR_6$, 18) —$COOR_6$, 19) —$NHC(CN)NHR_6$, and 20) —$CONR_6R_6$ and $R_6$, $R_9$ and $R_{10}$ are defined as set forth above, are provided.

In one embodiment, processes for the preparation of a mixture comprised of a compound of formula WW and a compound of formula YY, B—$OCF_2CF_2Br$, comprising reacting a compound of formula ZZ, B—OH, with 1,2-dibromotetrafluoroethane under basic conditions, wherein B is phenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl, 15) —$COR_6$, 16) —$S(O)_pR_6$, 17) —$SO_2NHR_6$, 18) —$COOR_6$, 19) —$NHC(CN)NHR_6$, and 20) —$CONR_6R_6$ and $R_6$, $R_9$ and $R_{10}$ are defined as set forth above, are provided.

In one embodiment, processes for the preparation of a compound of formula ZZ comprising reacting a compound of formula AAA, B—F, with potassium trimethylsilanoate in a solvent other than THF, wherein B is phenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl, 15) —$COR_6$, 16) —$S(O)_pR_6$, 17) —$SO_2NHR_6$, 18) —$COOR_6$, 19) —$NHC(CN)NHR_6$, and 20) —$CONR_6R_6$ and $R_6$, $R_9$ and $R_{10}$ are defined as set forth above, are provided.

In another embodiment, processes for the preparation of compound of formula WW, wherein B is phenyl, which may be optionally substituted with one or more substituents selected from the group consisting of: 1) halo, 2) ($C_1$-$C_6$)-alkyl, which may be optionally substituted with one or more $R_{20}$'s, 3)-Oalkyl, and 4) cyano, are provided. The present inventions provides such methods.

In one embodiment, processes for the preparation of mainly a compound of formula WW, wherein the acid is trifluoroacetic acid, acetic acid, formic acid and other acidic solvents known in the art, preferably acetic acid, are provided.

In another embodiment, processes for the preparation of mainly a compound of formula WW, wherein the step of reducing the mixture of a compound of formula WW and a compound of formula YY to form mainly a compound of formula WW comprises heating the reaction mixture at about 50° C. for about one to about 15 hours, preferably for about five (5) hours, are provided.

In yet another one embodiment, processes for the preparation of a mixture of a compound of formula WW and a compound of formula YY, wherein the base is sodium hydride, sodium methoxide, potassium methoxide, potassium carbonate, sodium carbonate, cesium carbonate, lithium carbonate, and ammonium carbonate, preferably cesium carbonate, are provided.

In still yet another embodiment, processes for the preparation of a mixture of a compound of formula WW and a compound of formula YY, wherein the step of reacting a compound of formula ZZ with 1,2-dibromotetrafluoroethane is carried out in a solvent, are provided.

In another embodiment, processes for the preparation of a mixture of a compound of formula WW and a compound of formula YY, wherein the solvent is diglyme, DMSO, DMF or NMP, preferably, DMSO, are provided.

In one embodiment, processes for the preparation of a mixture of a compound of formula WW and a compound of formula YY, wherein the step of reacting a compound of formula ZZ with 1,2-dibromotetrafluoroethane comprises heating the reaction mixture at about 50° to about 140° C., preferably at about 50° C., for about ten (10) minutes to about 15 hours, preferably about five (5) hours, are provided.

In another embodiment, processes for the preparation of a compound of formula ZZ, wherein the solvent is diglyme, dioxane, DMF or diethoxyethane, preferably diglyme or diethoxyethan, are provided.

In yet another embodiment, processes for the preparation of a compound of formula ZZ, wherein the step of reacting a compound of formula AAA with potassium trimethylsilanoate in a solvent other than THF comprises heating the reaction mixture at about 100° to about 140° C., preferably at about 120° C., for about three (3) hours to about three (3) days, preferably, for about five (5) hours, are provided.

Synthesis

Generally, compounds of the present invention may be prepared by methods such as those illustrated in the following Schemes A to W. Exemplary compounds of the present invention were prepared by the methods illustrated in the examples set forth below. Solvents, temperatures, pressures, and other reaction conditions may readily be selected by one of ordinary skill in the art. Starting materials are commercially available or readily prepared by one of ordinary skill in the art. Combinatorial techniques may be employed in the preparation of compounds, for example, where the intermediates possess groups suitable for these techniques.

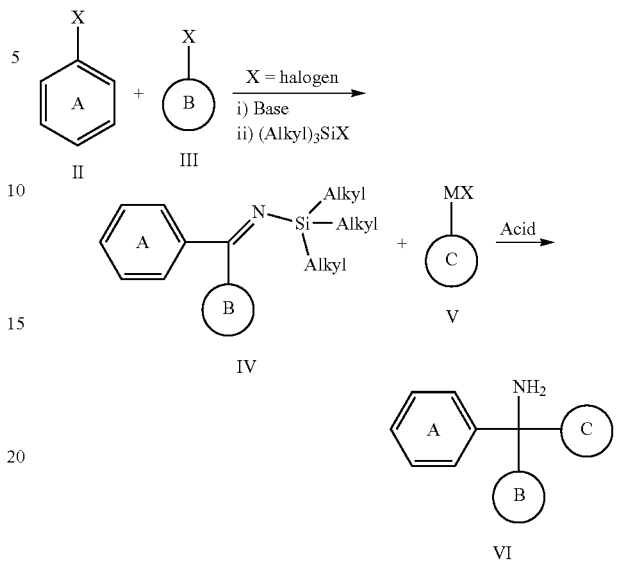

Scheme A

As illustrated in Scheme A, a substituted phenyl reagent of Formula II, wherein the composition of A is as described under Formula Ia & Ib, with the requirement that at least one of the substituents (X) attached to the reagent of Formula II is a nitrile group or a halogen group, such as bromine, can be combined with a reagent of Formula III, wherein the composition of B is as described under Formula Ia & Ib, with the requirement that at least one of the substituents (X) attached to the reagent of Formula III is a halide group, such as bromine, or a nitrile group, followed by treatment with a base, such as nBuLi. Alternatively, a substituted phenyl reagent of Formula II, wherein the composition of A is as described under Formula Ia & Ib, with the requirement that at least one of the substituents (X) attached to the reagent of Formula II is an aldehyde group or a halogen group, such as bromine, can be combined with a reagent of Formula III, wherein the composition of B is as described under Formula Ia & Ib, with the requirement that at least one of the substituents (X) attached to the reagent of Formula III is a halide group, such as bromine, or an aldehyde group, followed by treatment with a base, such as nBuLi, followed by treatment with an oxidizing agent such as, MnO$_4$ or Jone's Reagent. The resulting mixture can then be treated with a tri-alkyl silyl halide reagent, such as trimethylsilyl chloride, to yield a trimethylsilyl imide intermediate of Formula IV. To the imide intermediate of Formula IV can be added a metal halide (MX) reagent, such as an alkyl lithium complex, a magnesium bromide complex or a magnesium chloride complex, or a zinc bromide or zinc chloride complex, of Formula V, where the metal halide complex is made from a reagent wherein the composition of C is as described under Formula Ia & Ib, followed by treatment with acid, such as HCl, to remove the silyl group, to yield the racemic intermediate of Formula VI. As will be described in the proceeding schemes, the racemic intermediate of Formula VI will allow for the generation of compounds of Formula Ia or Ib via the routes to be described.

Scheme B

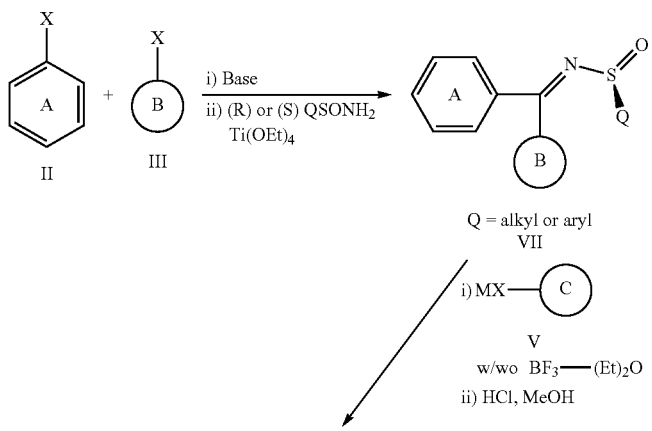

Q = alkyl or aryl
VII

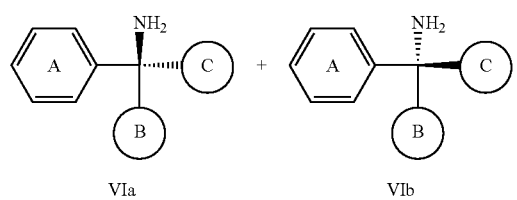

As illustrated in Scheme B, a substituted phenyl reagent of Formula II, wherein the composition of A is as described under Formula Ia & Ib, with the requirement that at least one of the substituents (X) attached to the reagent of Formula II is a nitrile group or a halogen group, such as bromine, can be combined with a reagent of Formula III, wherein the composition of B is as described under Formula Ia & Ib, with the requirement that at least one of the substituents (X) attached to the reagent of Formula III is a halide group, such as bromine, or a nitrile group, followed by treatment with a base, such as nBuLi. Alternatively, a substituted phenyl reagent of Formula II, wherein the composition of A is as described under Formula Ia & Ib, with the requirement that at least one of the substituents (X) attached to the reagent of Formula II is an aldehyde group or a halogen group, such as bromine, can be combined with a reagent of Formula III, wherein the composition of B is as described under Formula Ia & Ib, with the requirement that at least one of the substituents (X) attached to the reagent of Formula III is a halide group, such as bromine, or an aldehyde group, followed by treatment with a base, such as nBuLi, followed by treatment with an oxidizing agent such as, $MnO_4$ or Jone's Reagent. The resulting mixture can then be treated with a substituted sulfinamide reagent, such as (R)-4-methylbenzenesulfinamide or (R)-4-methylbenzenesulfinamide or (S)-2-methylpropane-2-sulfinamide or (R)-2-methylpropane-2-sulfinamide, along with $Ti(OEt)_4$, to yield a the sulfinyl imide intermediate of Formula VII. To the sulfinyl imide intermediate of Formula VII can be added a metal halide reagent (MX), such as a magnesium bromide complex or a magnesium chloride complex, or a zinc bromide or zinc chloride complex, of Formula V, where the metal halide complex is made from a reagent wherein the composition of C is as described under Formula Ia & Ib, with or without a Lewis acid, such as $BF_3.(Et)_2O$, followed by treatment with acid, such as HCl, to hydrolyze the sulfinamide, to yield the intermediates of Formula VIa and VIb. By application of substituted sulfinamide reagent, such as (R)-4-methylbenzenesulfinamide or (R)-4-methylbenzenesulfinamide or (S)-2-methylpropane-2-sulfinamide or (R)-2-methylpropane-2-sulfinamide one skilled in the art can enrich the formation of the (R) antipode (Formula VIa) versus the (S) antipode (Formula VIb) or the (S) antipode (Formula VIb) versus the (R) antipode (Formula VIa), respectively. As will be described in the proceeding schemes, the intermediate of Formula VIa and VIb will allow for the generation of compounds of Formula Ia or Ib via the routes to be described.

Scheme C

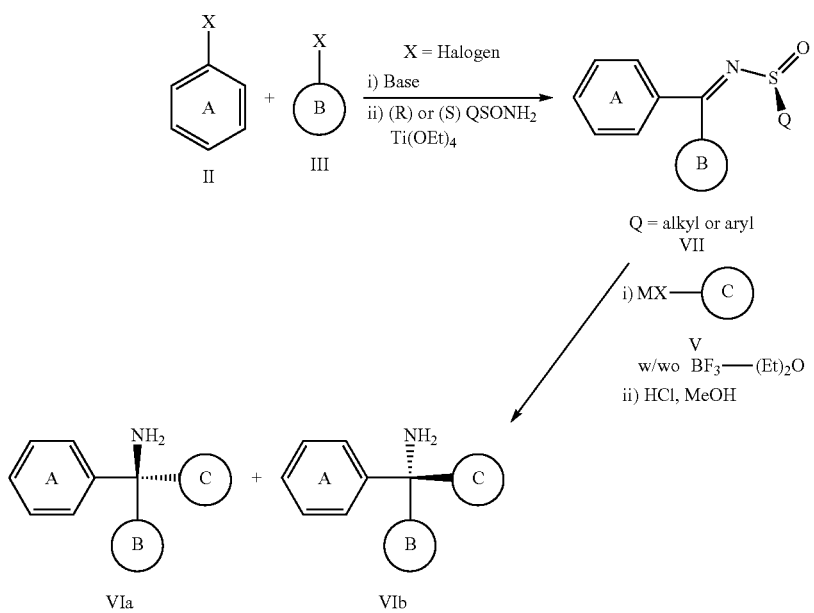

As illustrated in Scheme C, a substituted phenyl reagent of Formula II, wherein the composition of A is as described under Formula Ia & Ib, with the requirement that at least one of the substituents (X) attached to the reagent of Formula III is an alkyl ester group, such as a methyl or an ethyl ester, can be combined with a reagent of Formula III, wherein the composition of B is as described under Formula Ia & Ib, with the requirement that at least one of the substituents (X) attached to the reagent of Formula III is a halide group, such as bromine, followed by treatment with a base, such as nBuLi. The resulting mixture can then be treated with a substituted sulfinamide reagent, such as (R)-4-methylbenzenesulfinamide or (R)-4-methylbenzenesulfinamide or (S)-2-methylpropane-2-sulfinamide or (R)-2-methylpropane-2-sulfinamide, along with Ti(OEt)$_4$, to yield a the sulfonylimide intermediate of Formula VII. In addition, as illustrated in Scheme C, a substituted phenyl reagent of Formula II, wherein the composition of A is as described under Formula Ia & Ib, with the requirement that at least one of the substituents (X) attached to the reagent of Formula II is a halide group, such as bromine, can be combined with a reagent of Formula III, wherein the composition of B is as described under Formula Ia & Ib, with the requirement that at least one of the substituents (X) attached to the reagent of Formula III is an alkyl ester group, such as a methyl or an ethyl ester, followed by treatment with a base, such as nBuLi. The resulting mixture can then be treated with a substituted sulfinamide reagent, such as (R)-4-methylbenzenesulfinamide or (R)-4-methylbenzenesulfinamide or (S)-2-methylpropane-2-sulfinamide or (R)-2-methylpropane-2-sulfinamide, along with Ti(OEt)$_4$, to yield a the sulfinyl imide intermediate of Formula VII. To the sulfinyl imide intermediate of Formula VII can be added a metal halide reagent, such as an alkyl lithium complex, a magnesium bromide or a magnesium chloride complex, or a zinc bromide or zinc chloride complex, of Formula V, where the metal halide complex is made from a reagent wherein the composition of C is as described under Formula Ia & Ib, with or without a Lewis acid, such as BF$_3$.(Et)$_2$O, followed by treatment with acid, such as HCl, to hydrolyze the sulfinamide, to yield the intermediates of Formula VIa and VIb. By application of substituted sulfinamide reagent, such as (R)-4-methylbenzenesulfinamide or (R)-4-methylbenzenesulfinamide or (S)-2-methylpropane-2-sulfinamide or (R)-2-methylpropane-2-sulfinamide one skilled in the art can enrich the formation of the (R) antipode (Formula VIa) versus the (S) antipode (Formula VIb) or the (S) antipode (Formula VIb) versus the (R) antipode (Formula VIa), respectively. As will be described in the proceeding schemes, the intermediate of Formula VIa and VIb will allow for the generation of compounds of Formula Ia or Ib via the routes to be described.

Scheme D

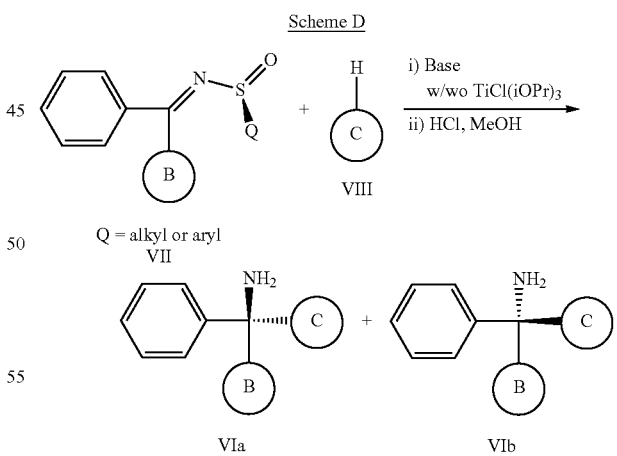

As illustrated in Scheme D, to the sulfinyl imide intermediate of Formula VII can be added a base, such as LDA or nBuLi, with or with out the addition of TiCl(iOPr)$_3$, and a reagent of Formula VIII, wherein the composition of C is as described under Formula Ia & Ib, with the requirement that at least one of the substituents attached to the reagent of Formula VIII is a hydrogen that can be deprotonated to yield a reactive anion species, followed by treatment with acid, such as HCl, to hydrolyze the sulfinamide, to yield the intermediates of Formula VIa and VIb. By application of substituted sulfinamide reagent, such as (R)-4-methylbenzenesulfinamide or (R)-4-methylbenzenesulfinamide or (S)-2-methylpropane-2-sulfinamide or (R)-2-methylpropane-2-sulfinamide one skilled in the art can enrich the formation of the (R) antipode (Formula VIa) versus the (S) antipode (Formula VIb) or the (S) antipode (Formula VIb) versus the (R) antipode (Formula VIa), respectively. As will be described in the proceeding schemes, the intermediate of Formula VIa and VIb will allow for the generation of compounds of Formula Ia or Ib via the routes to be described.

Scheme E

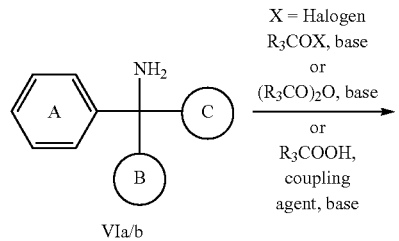

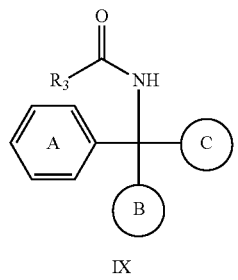

As illustrated in Scheme E, an advanced intermediate of Formula VIa/b can be treated with an acylating agent, such as an acid halide of Formula R₃COX, where X=a halogen, such as chlorine or bromine, or an anhydride of Formula (R₃CO)₂O, with or without the presence of a base, such as triethylamine, pyridine or N-ethyl-N-isopropylpropan-2-amine, to generate an amide derivative of Formula IX, where R₃ is derived from the afore mentioned acylating agent or anhydride and is as described for Formula Ia and Ib. Alternatively, one can treat an advanced intermediate of Formula VIa/b with a carboxylate intermediate of Formula R₃COOH, along with a coupling agent, such as EDCI, DCC or other agents known to one skilled in the art for facilitating amide bond formation, along with or without a base, such as triethylamine, pyridine or N-ethyl-N-isopropylpropan-2-amine, to generate an amide derivative of Formula IX, which is a compound of Formula Ia and Ib, where R₃ is as described for Formula Ia and Ib.

Scheme F

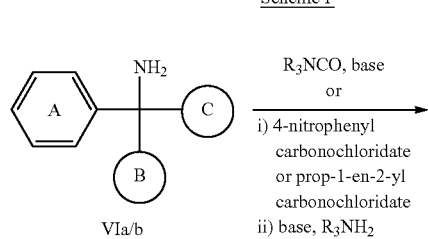

-continued

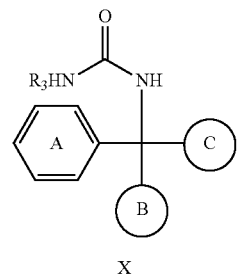

As illustrated in Scheme F, an advanced intermediate of Formula VIa/b can be treated with an isocyanate of Formula R₃NCO, with or without the presence of a base, such as triethylamine, pyridine or N-ethyl-N-isopropylpropan-2-amine, to generate an urea derivative of Formula X, where R₃ is derived from the afore mentioned isocyanate reagents and is as described for Formula Ia and Ib. Alternatively, one can react an advanced intermediate of Formula VIa/b with an agent such as 4-nitrophenyl carbonochloridate or prop-1-en-2-yl carbonochloridate, to create a reactive carbamate intermediate which can then be reacted with an amine or amine salt intermediate of Formula R₃NH₂, with or without the presence of a base, such as triethylamine, pyridine or N-ethyl-N-isopropylpropan-2-amine, to generate an urea derivative of Formula X, which is a compound of Formula Ia and Ib, where R₃ is as described for Formula Ia and Ib.

Scheme G

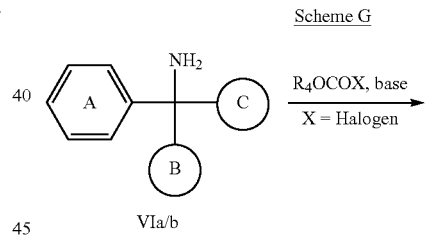

As illustrated in Scheme G, an advanced intermediate of Formula VIa/b can be treated with a carbonochloridate of Formula R₄OCOCl, in the presence of a base, such as potassium carbonate, to generate a carbamate derivative of Formula XI, which is a compound of Formula Ia and Ib, where R₄ is derived from the afore mentioned carbonochloridate reagents and is as described for Formula Ia and Ib.

Scheme H

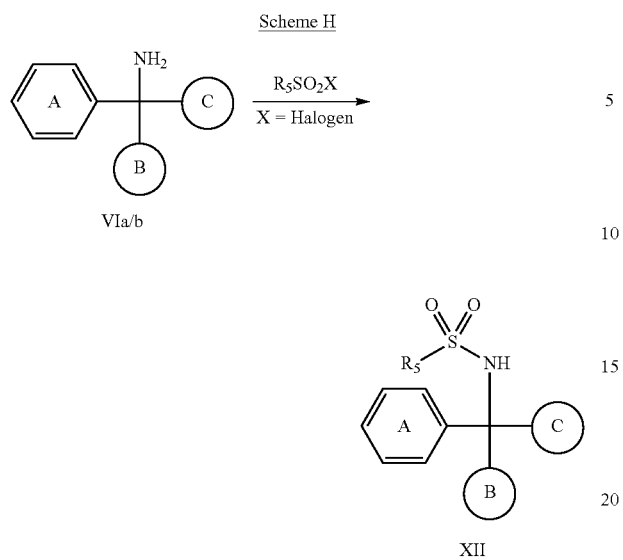

As illustrated in Scheme H, an advanced intermediate of Formula VIa/b can be treated with a sulfonyl chloride of Formula $R_5SO_2Cl$, in the presence of a base, such as triethylamine, pyridine or N-ethyl-N-isopropylpropan-2-amine, to generate a sulfonamide derivative of Formula XII, which is a compound of Formula Ia and Ib, where $R_5$ is derived from the afore mentioned sulfonyl chloride reagents and is as described for Formula Ia and Ib.

Scheme I

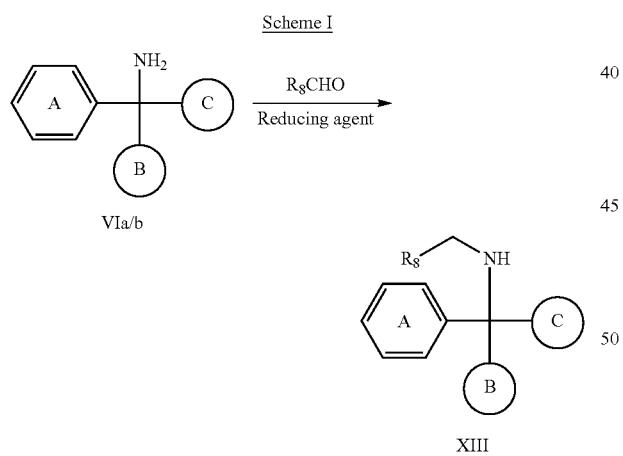

As illustrated in Scheme I, an advanced intermediate of Formula VIa/b can be treated with an aldehyde of Formula $R_8CHO$, with or without a catalytic amount of an acid, such as acetic acid, followed by treatment with a reducing agent, such as $NaBH(OAc)_3$, to generate an alkyl amine derivative of Formula XIII, which is a compound of Formula Ia and Ib, where $R_8$ is derived from the afore mentioned aldehyde reagents and is as described for Formula Ia and Ib.

Scheme J

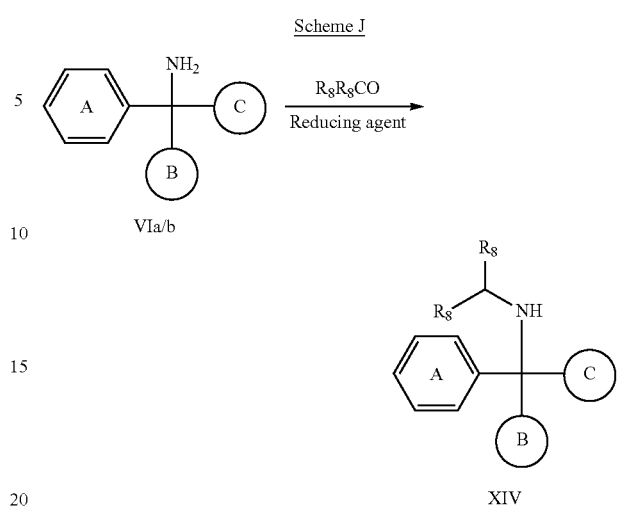

As illustrated in Scheme J, an advanced intermediate of Formula VIa/b can be treated with ketone of Formula $R_8R_8CO$, with or without a catalytic amount of an acid, such as acetic acid, followed by treatment with a reducing agent, such as $NaBH(OAc)_3$, to generate an alkyl amine derivative of Formula XIV, which is a compound of Formula Ia and Ib, where $R_8$ is derived from the afore mentioned ketone reagents and is as described for Formula Ia and Ib.

Scheme K

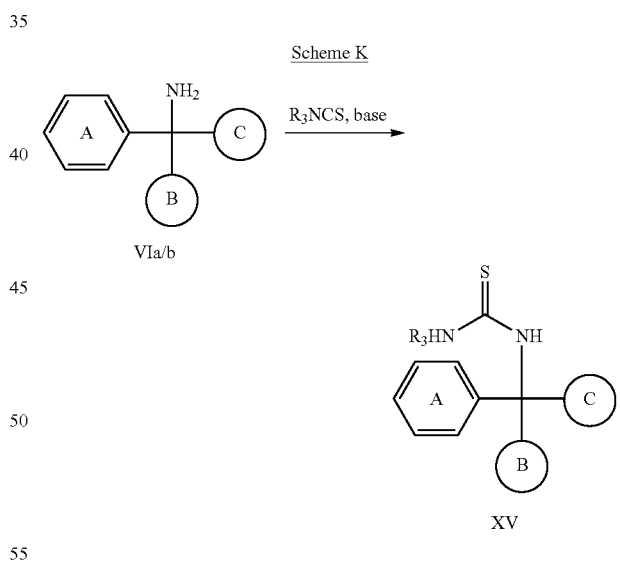

As illustrated in Scheme K, an advanced intermediate of Formula VIa/b can be treated with an isothiocyanate of Formula $R_3NCS$, with or without a base, such as triethylamine, pyridine or N-ethyl-N-isopropylpropan-2-amine, to generate a thiourea derivative of Formula XV, which is a compound of Formula Ia and Ib, where $R_3$ is derived from the afore mentioned isothiocyanate reagents and is as described for Formula Ia and Ib.

Scheme L

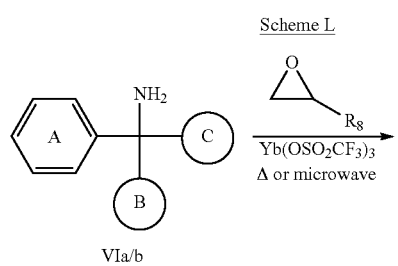

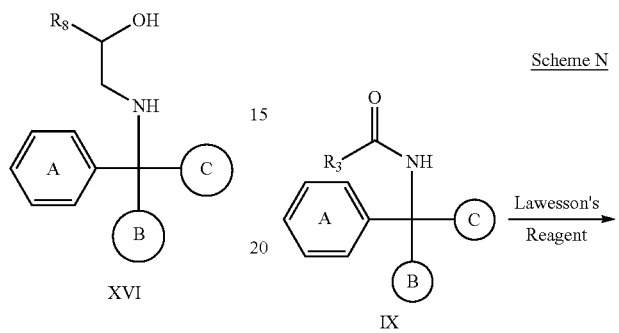

As illustrated in Scheme L, an advanced intermediate of Formula VIa/b can be treated with an oxirane reagent, of Formula CH₂OCHR₈, in the presence of a catalyst, such as Sc(OSO₂CF₃)₃ or Yb(OSO₂CF₃)₃, with standard heating or via irradiation in a microwave, to generate an alkyl hydroxy amine derivative of Formula XVI, which is a compound of Formula Ia and Ib, where $R_8$ is derived from the afore mentioned oxirane reagents and is as described for Formula Ia and Ib.

Scheme M

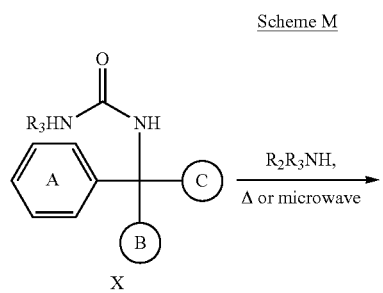

As illustrated in Scheme M, a reagent of Formula X, which is a compound of Formula Ia and Ib, can be treated with a disubstituted amine reagent of Formula $R_2R_3NH$, with heating or via irradiation in a microwave, to obtained a disubstituted urea derivative of Formula XVII, which is a compound of Formula Ia and Ib, where $R_2$ and $R_3$ is derived from the afore mentioned disubstituted amine reagent and is as described for Formula Ia and Ib.

Scheme N

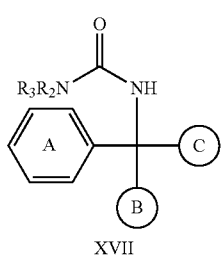

As illustrated in Scheme N, a reagent of Formula IX, which is a compound of Formula Ia and Ib, can be treated with an agent, such as Lawesson's reagent or any other reagent known to one skilled in the art for conversion of an amide functional group to a thioamide functional group, to obtained a thioamide derivative of Formula XVIII, which is a compound of Formula Ia and Ib, where $R_3$ is derived as described for Formula Ia and Ib.

Scheme O

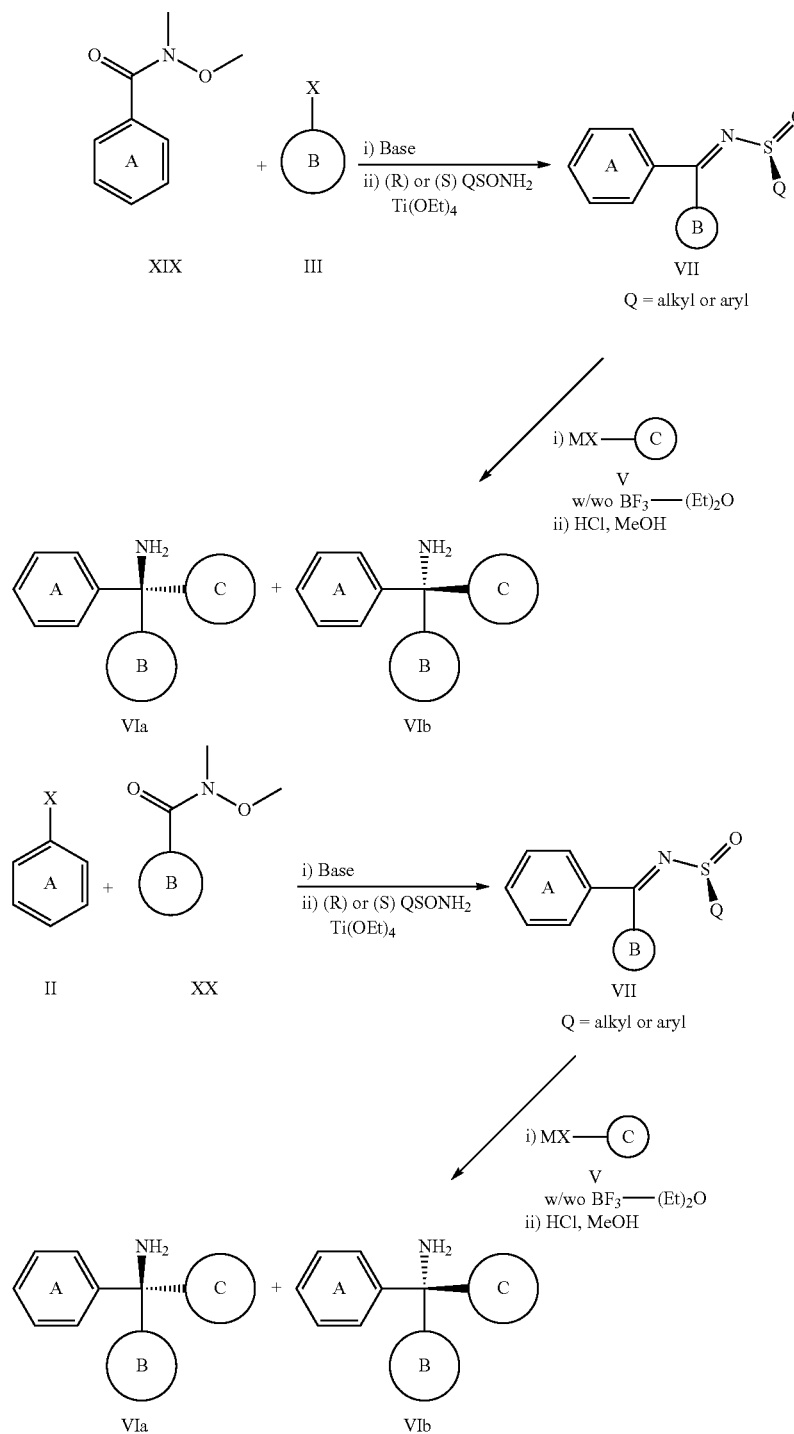

As illustrated in Scheme O, a substituted phenyl reagent of Formula XIX, wherein the composition of A is as described under Formula Ia & Ib, with the requirement that at least one of the substituents attached to the reagent of Formula XIX is a N-methoxy-N-methylacetamide group, can be combined with a reagent of Formula III, wherein the composition of B is as described under Formula Ia & Ib, with the requirement that at least one of the substituents (X) attached to the reagent of Formula III is a halide group, such as bromine, followed by treatment with a base, such as nBuLi. The resulting mixture can then be treated with a substituted sulfinamide reagent, such as (R)-4-methylbenzenesulfinamide or (R)-4-methyl-benzenesulfinamide or (S)-2-methylpropane-2-sulfinamide or (R)-2-methylpropane-2-sulfinamide, along with Ti(OEt)$_4$, to yield a the sulfinyl imide intermediate of Formula VII. To the sulfinyl imide intermediate of Formula VII can be added a Scheme P

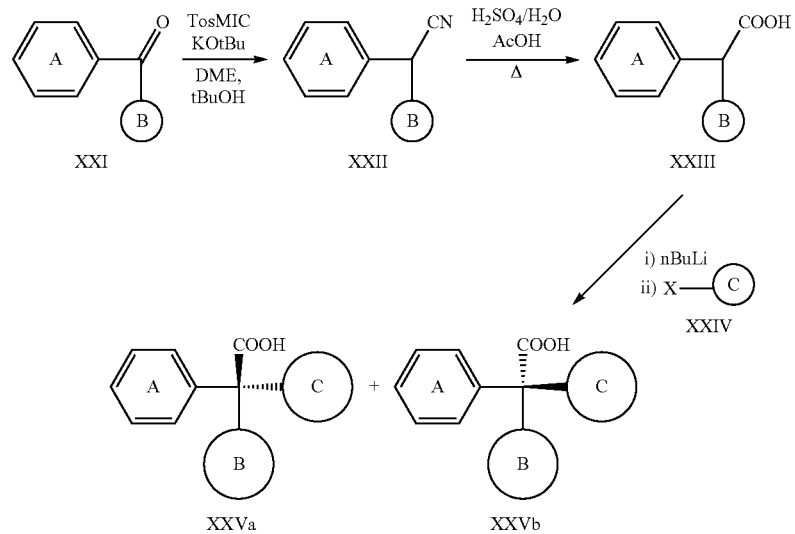

metal halide reagent (MX), such as a magnesium bromide complex or a magnesium chloride complex, or a zinc bromide or zinc chloride complex, of Formula V, where the metal halide complex is made from a reagent wherein the composition of C is as described under Formula Ia & Ib, with or without a Lewis acid, such as BF$_3$.(Et)$_2$O, followed by treatment with acid, such as HCl, to hydrolyze the sulfinamide, to yield the penultimate intermediates of Formula VIa and VIb. In addition, a substituted phenyl reagent of Formula II, wherein the composition of A is as described under Formula Ia & Ib, with the requirement that at least one of the substituents attached to the reagent of Formula II is a halide group, such as bromine, can be combined with a reagent of Formula XX, wherein the composition of B is as described under Formula Ia & Ib, with the requirement that at least one of the substituents (X) attached to the reagent of Formula XX, is a N-methoxy-N-methylacetamide group, followed by treatment with a base, such as nBuLi. The resulting mixture can then be treated with a substituted sulfinamide reagent, such as (R)-4-methylbenzenesulfinamide or (R)-4-methylbenzenesulfinamide or (S)-2-methylpropane-2-sulfinamide or (R)-2-methylpropane-2-sulfinamide, along with Ti(OEt)$_4$, to yield a the sulfinyl imide intermediate of Formula VII. To the sulfinyl imide intermediate of Formula VII can be added a metal halide reagent (MX), such as a magnesium bromide complex or a magnesium chloride complex, or a zinc bromide or zinc chloride complex, of Formula V, where the metal halide complex is made from a reagent wherein the composition of C is as described under Formula Ia & Ib, with or without a Lewis acid, such as BF$_3$.(Et)$_2$O, followed by treatment with acid, such as HCl, to hydrolyze the sulfinamide, to yield the penultimate intermediates of Formula VIa and VIb. By application of substituted sulfinamide reagent, such as (R)-4-methylbenzenesulfinamide or (R)-4-methylbenzenesulfinamide or (S)-2-methylpropane-2-sulfinamide or (R)-2-methylpropane-2-sulfinamide one skilled in the art can enrich the formation of the (R) antipode (Formula VIa) versus the (S) antipode (Formula VIb) or the (S) antipode (Formula VIb) versus the (R) antipode (Formula VIa), respectively. As will be described in the proceeding schemes, the penultimate intermediate of Formula VIa and VIb will allow for the generation of compounds of Formula Ia or Ib via the routes to be described.

As illustrated in Scheme A and Scheme P, a substituted phenyl reagent of Formula II, wherein the composition of A is as described under Formula Ia & Ib, with the requirement that at least one of the substituents (X) attached to the reagent of Formula II is a nitrile group or a halogen group, such as bromine, can be combined with a reagent of Formula III, wherein the composition of B is as described under Formula Ia & Ib, with the requirement that at least one of the substituents (X) attached to the reagent of Formula III is a halide group, such as bromine, or a nitrile group, followed by treatment with a base, such as nBuLi, followed by treatment with aqueous acid, such as 1N HCl, to form a benzophenone intermediate of Formula XXI. Alternatively, a substituted phenyl reagent of Formula II, wherein the composition of A is as described under Formula Ia & Ib, with the requirement that at least one of the substituents (X) attached to the reagent of Formula II is an aldehyde group or a halogen group, such as bromine, can be combined with a reagent of Formula III, wherein the composition of B is as described under Formula Ia & Ib, with the requirement that at least one of the substituents (X) attached to the reagent of Formula III is a halide group, such as bromine, or an aldehyde group, followed by treatment with a base, such as nBuLi, followed by treatment with aqueous acid, such as 1N HCl, to form a benzophenone intermediate of Formula XXI. Alternately, as illustrated in Scheme C and Scheme P, a substituted phenyl reagent of Formula II, wherein the composition of A is as described under Formula Ia & Ib, with the requirement that at least one of the substituents (X) attached to the reagent of Formula II is an alkyl ester group, such as a methyl or an ethyl ester, can be combined with a reagent of Formula III, wherein the composition of B is as described under Formula Ia & Ib, with the requirement that at least one of the substituents (X) attached to the reagent of Formula III is a halide group, such as bromine, followed by treatment with a base, such as nBuLi, followed by treatment with aqueous acid, to yield a benzophenone intermediate of Formula XXI. In addition, as illustrated in Scheme C and Scheme P, a substituted phenyl reagent of Formula II, wherein the composition of A is as described under Formula Ia & Ib, with the requirement that at least one of the substituents (X) attached to the reagent of Formula II is a halide group, such as bromine, can be combined with a reagent of Formula III, wherein the composition of B is as described under Formula Ia & Ib, with the requirement that at least one of the substituents (X) attached to the reagent of Formula III is an alkyl ester group, such as a methyl or an ethyl ester, followed by treatment with a base, such as nBuLi, followed by treatment with aqueous acid, to yield a benzophenone intermediate of Formula XXI. As illustrated in Scheme O and Scheme P, a substituted phenyl reagent of Formula XIX, wherein the composition of A is as described under Formula Ia & Ib, with the requirement that at least one of the substituents attached to the reagent of Formula XIX is a N-methoxy-N-methylacetamide group, can be combined with a reagent of Formula III, wherein the composition of B is as described under Formula Ia & Ib, with the requirement that at least one of the substituents (X) attached to the reagent of Formula III is a halide group, followed by treatment with a base, such as nBuLi, followed by treatment with aqueous acid, to yield a benzophenone intermediate of Formula XXI, or a substituted phenyl reagent of Formula II, wherein the composition of A is as described under Formula Ia & Ib, with the requirement that at least one of the substituents attached to the reagent of Formula II is a halide group, such as bromine, can be combined with a reagent of Formula XX, wherein the composition of B is as described under Formula Ia & Ib, with the requirement that at least one of the substituents (X) attached to the reagent of Formula XX, is a N-methoxy-N-methylacetamide group, followed by treatment with a base, such as nBuLi, followed by treatment with aqueous acid, to yield a benzophenone intermediate of Formula XXI. Numerous alternate approaches well known to one skilled in the art can also be employed to generate a benzophenone intermediate of Formula XXI.

As illustrated in Scheme P, an intermediate benzophenone of Formula XXI can be treated with an agent such as 1-(isocyanomethylsulfonyl)-4-methylbenzene (TosMIC) and a base, such as potassium tert-butoxide, to yield an intermediate of Formula XXII. Hydrolysis of an intermediate of Formula XXII can be accomplished by treatment with an acid, such as aqueous $H_2SO_4$ and acetic acid, to yield an intermediate of Formula XXIII. An intermediate of Formula XXIII can be treated with a base, such as n-butyl lithium, followed by an alkyl halide reagent of Formula XXIV, where X is a halide, such as chlorine, bromine or iodine and the composition of C is as described under Formula Ia and Ib, to yield an intermediate of Formula XXVa and XXVb, which are key intermediates for the synthesis of compounds of Formula Ia and Ib.

Scheme Q

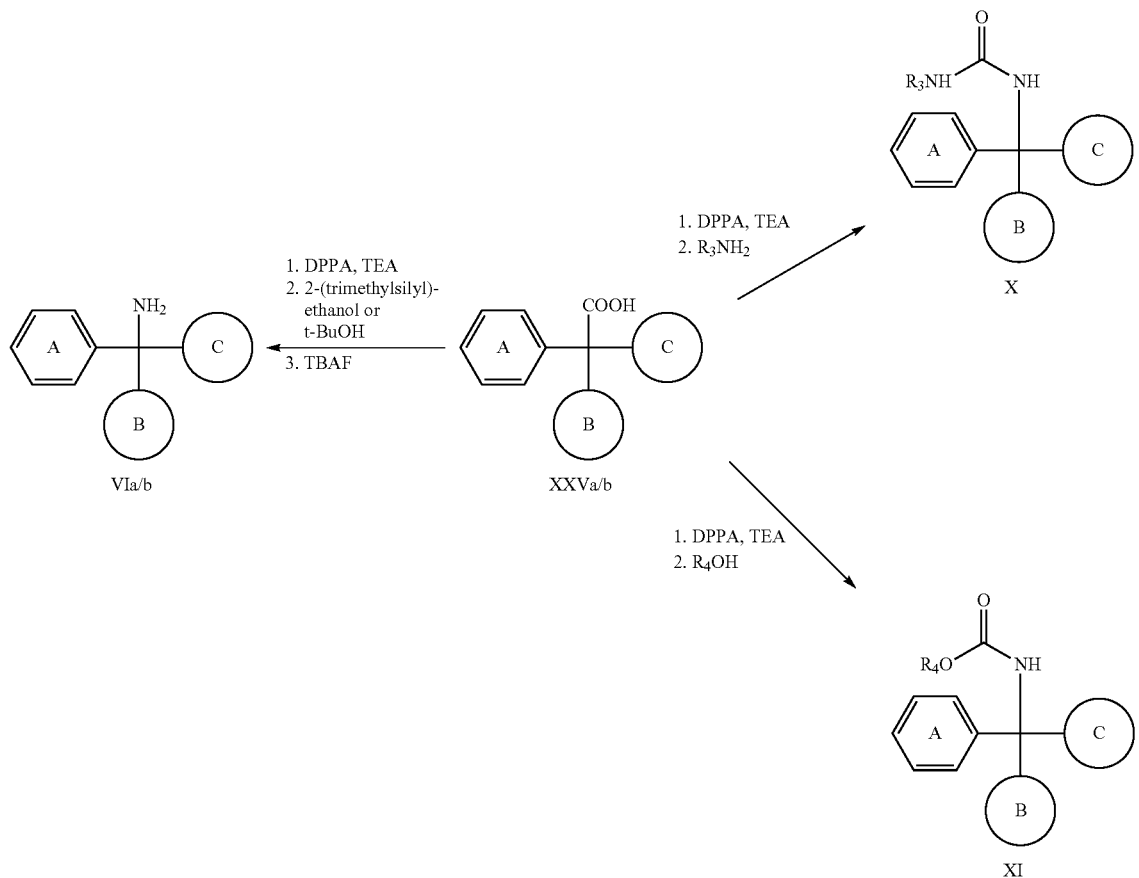

As illustrated in Scheme Q, an intermediate of Formula XXVa/b can be treated with an agent such as diphenylphosphoryl azide (DPPA) in the presence of a base, such as triethyl amine (TEA), followed by treatment with an agent, such as 2-(trimethylsilyl)ethanol or tert-butyl alcohol and eventual cleavage of the resulting intermediate carbamate by treatment with agents such as tetrabutylammonium fluoride (TBAF) or trifluoroacetic acid, to yield the advanced intermediate of Formula VIa/b, which is a key intermediate for the synthesis of compounds of Formula Ia and Ib. An intermediate of Formula XXVa/b can be treated with an agent such as diphenylphosphoryl azide (DPPA) in the presence of a base, such as triethyl amine (TEA), followed by treatment with an agent of formula $R_3NH_2$, were $R_3$ is defined as described under Formula Ia and Ib, to give compounds of Formula X, which are compounds of Formula Ia and Ib. In addition, an intermediate of Formula XXVa/b can be treated with an agent such as diphenylphosphoryl azide (DPPA) in the presence of a base, such as triethyl amine (TEA), followed by treatment with an agent of formula $R_4OH$, were $R_4$ is defined as described under Formula Ia and Ib, to give compounds of Formula XI, which are compounds of Formula Ia and Ib.

zinc, along with $NH_4OAc$ and $NH_4OH$, to yield an intermediate of Formula XXVII. An intermediate of Formula XXVII can be treated with a formylating agent, such as acetic formic anhydride, followed by dehydration through treatment with an agent such as $POCl_3$, to yield the isonitrile intermediate of Formula XXVIII. The isonitrile intermediate of Formula XXVIII can be treated with a base, such as aqueous KOH, along with tetrabutylammonium bromide, followed by an alkyl halide reagent of Formula XXIV where the composition of C is as described under Formula Ia and Ib, and the X can be a halide, such as chlorine, bromine or iodine, to yield intermediates of Formula XXIXa and XXIXb, which are key intermediates for the synthesis of compounds of Formula Ia and Ib. The formation of an intermediate of Formula XXIXa or XXIXb from an intermediate of Formula XXVIII, as described above, can also be performed in the presence of a chiral catalyst such as, but not limited to, N-benzylcincho- Scheme R

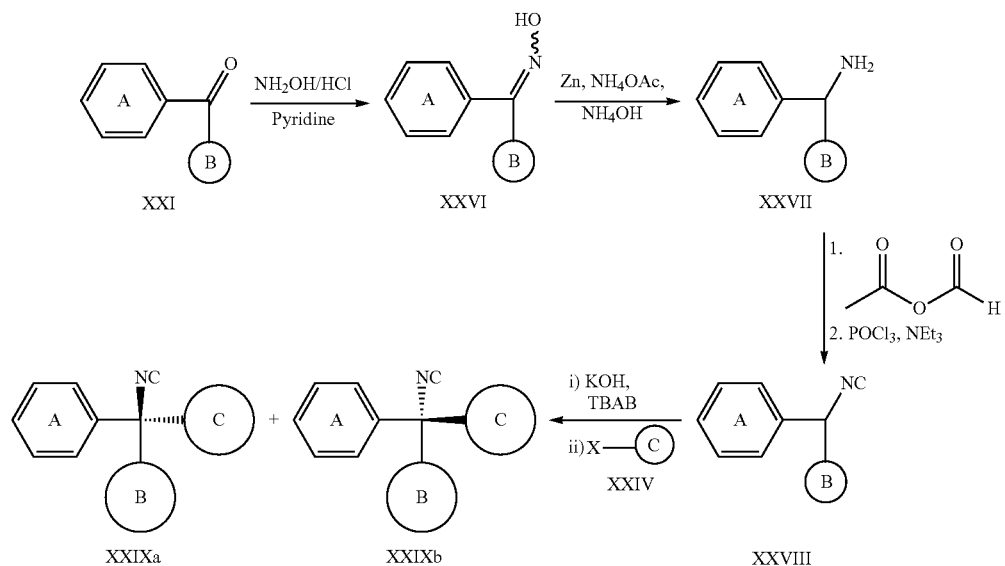

As illustrated in Scheme R, an intermediate of Formula XXI, made as described in Schemes P, can be treated with a reagent such as $NH_2OH$, in the presence of an acid such as HCl, followed by treatment with a base such as pyridine, to yield an intermediate of Formula XXVI. An intermediate of Formula XXVI can be treated with a reducing agent such as ninium chloride or N-benzylcinchonidinium chloride, to enrich the formation of the intermediate of Formula XXIXa over the intermediate of Formula XXIXb or to enrich the formation of the intermediate of Formula XXIXb over the intermediate of Formula XXIXa as needed to make compounds of Formula Ia and Ib.

Scheme S

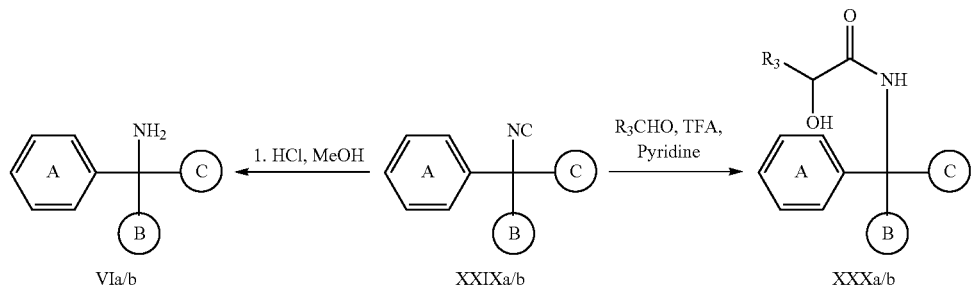

As illustrated in Scheme S, an intermediate of Formula XXIXa/b can be converted to an intermediate of Formula VIa/b by treatment with an acid such as HCl in methanol. As described in earlier schemes, and intermediate of Formula VIa/b is a key intermediate for the synthesis of compounds of Formula Ia and Ib. In addition, an intermediate of Formula XXIXa/b can be treated directly with an aldehyde of Formula R₃CHO, where the definition of R₃ is as described under Formula Ia and Ib, and an acid, such as trifluoroacetic acid, in the presence of a base, such as pyridine, to yield compounds of Formula XXXa/b, which are a compounds of Formula Ia and Ib.

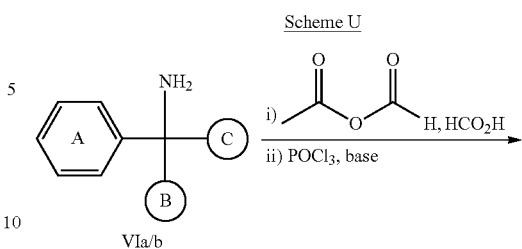

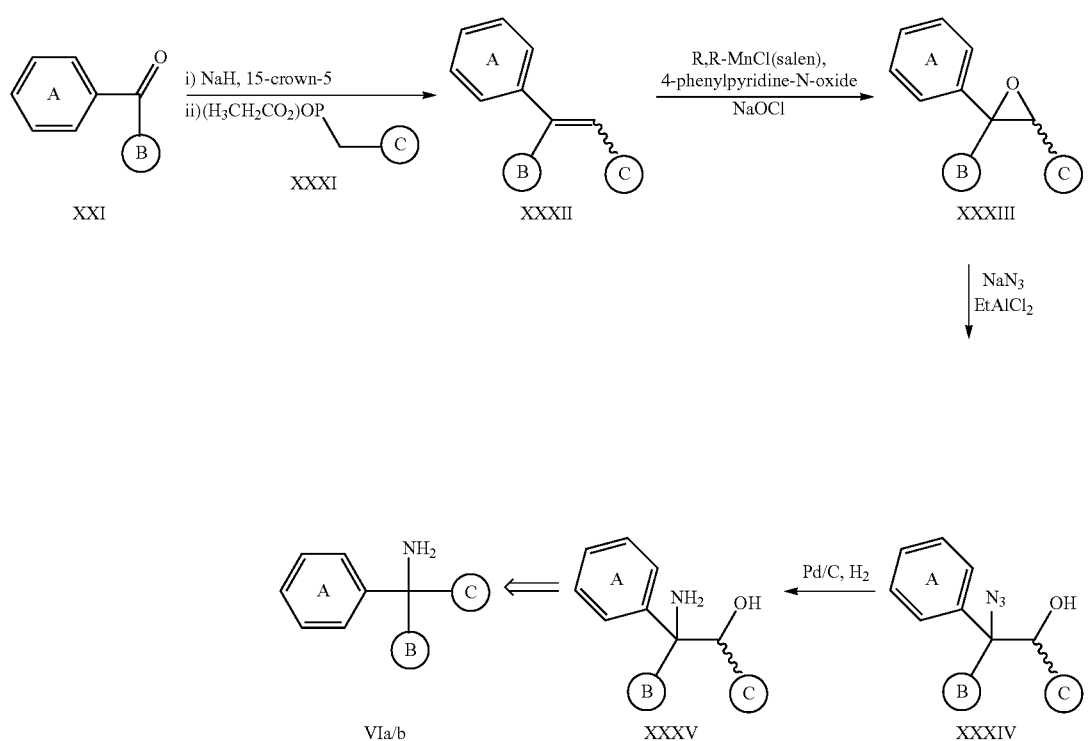

As illustrated in Scheme T, an intermediate of Formula XXI, made as described in Schemes P, can be reacted with a reagent of Formula XXXI, where the composition of C is as described under Formula Ia and Ib, to yield a styrene intermediate of Formula XXXII. A reagent of Formula XXXII can be derived from a variety of commercially available intermediates or can readily be made by one skilled in the art. A styrene intermediate of Formula XXXII can be treated with an expoxidizing agent, such as sodium chlorite in the presence of 4-phenylpyridine-N-oxide, with or without a chiral catalyst such as, (1R,2R)-(−)-[1,2-cyclo-hexanediamino-N, N'-bis(3,5-di-t-butyl-salicylidene)]manganese (III) chloride, (R,R—MnCl (salen)), to obtain an oxirane intermediate of Formula XXXIII. Treatment of the oxirane intermediate of Formula XXXIII with an agent such as NaN₃, in the presence of a Lewis acid such as ethylaluminum dichloride, yields the azide intermediate of Formula XXXIV. Reduction of the azide intermediate of Formula XXXIV can be achieved over palladium on charcoal in the presence of H₂ gas to generate the advanced intermediate of Formula XXXIV. An intermediate of Formula XXXV is embodied by the intermediate of Formula VIa/b which is a key intermediate on route to the synthesis of compounds of Formula Ia and Ib.

-continued

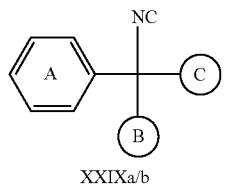

As illustrated in Scheme U, an intermediate of Formula VIa/b, can be converted to an intermediate of compound XXXIIIa/b by treatment with a formylating agent, such as, acetic formic anhydride, followed by a dehydrating agent, such as phosphorous oxychloride, along with a base, such as triethylamine. As described in Scheme S, an intermediate of Formula XXIXa/b can be utilized to make compounds of Formula Ia and Ib.

Scheme V

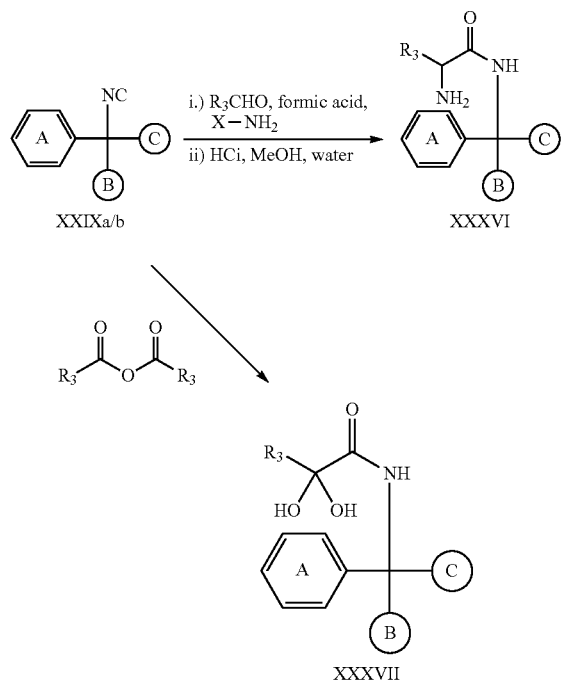

As illustrated in Scheme V, an intermediate of Formula XXIXa/b, can be treated with an aldehyde reagent of Formula $R_3$CHO, where $R_3$ is as described for Formula Ia and Ib, along with an acid, such as formic acid, and an amine reagent, of general formula X—$NH_2$, where X represents a cleavable protection group selected readily by one skilled in the art, followed by treatment with and acid, such as HCl, in the presence of an alcohol and water, to yield a compound of Formula XXXVI, which is a compound of Formula Ia and Ib. Alternately a reagent of Formula XXIXa/b can be treated with an anhydride reagent of Formula $(R_3CO)_2O$, where $R_3$ is as described for Formula Ia and Ib, to yield a compound of Formula XXXVII, which is a compound of Formula Ia and Ib.

Scheme W

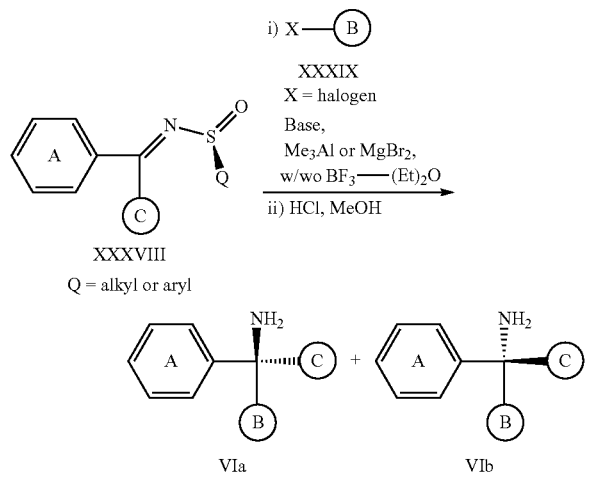

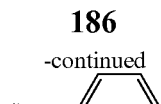

As illustrated in Scheme W, by applications of routes described in Schemes A, B, C and O for the synthesis of an intermediate of Formula VII, one skilled in the art can make intermediates of Formula XXXVII and XXXX, where the definition of A, B and C are as defined for Formula Ia and Ib. An intermediate of Formula XXXVIII can be reacted with an intermediate of Formula XXXIX, where X is a halogen, such as bromine, iodine or chlorine, and the definition of C is as described for Formula Ia and Ib, in the presence of a base, such as n-butyl lithium or tert-butyl lithium, along with a metalating agent such as, $CH_3Al$ or $MgBr_2$, followed by hydrolysis of the sulfinamide, to yield the intermediate of Formula VIa and VIb, which is a key intermediate on route to compounds of Formula Ia and Ib. An intermediate of Formula XXXX can be reacted with an intermediate of Formula XXXXI, where X is a halogen, such as bromine, iodine or chlorine, and the definition of A is as described for Formula Ia and Ib, in the presence of a base, such as n-butyl lithium or tert-butyl lithium, along with a metalating agent such as, $CH_3Al$, followed by hydrolysis of the sulfinamide, to yield the intermediate of Formula VIa and VIb, which is a key intermediate on route to compounds of Formula Ia and Ib.

The above schemes give an overview of several general processes for the synthesis of compounds of Formula Ia and Ib. Additional compounds of Formula Ia and Ib can readily be made by one of ordinary skill in the art by further modification of functional groups at positions A, B, C or $R_1$ of compounds of Formula Ia and Ib made by the processes illustrated in the included schemes. The Examples that follow described numerous applications of the routes described in Schemes A-W as well as additional routes to compounds of Formula Ia and Ib achieved through modification of functional groups at positions A, B, C or $R_1$ of compounds of Formula Ia and Ib.

Utility

Compounds of the present invention have been shown to inhibit cholesterol ester transfer protein (CETP) by greater than 30% at two different concentrations of less than 100 uM, preferably with a potency less than 5 uM, more preferably with a potency less than 500 nM. Compounds of the invention were also found to inhibit cholesterol ester transfer activity using in vitro assays that contained up to 96% plasma, and to inhibit plasma cholesterol ester transfer activity in animals. Accordingly, compounds within the scope of the present invention inhibit the CETP protein, and as such are expected to be useful in the treatment, prevention, and/or slowing of the progression of various disorders.

For example, the compounds of the present invention, their prodrugs and the salts of such compounds and prodrugs can be adapted to therapeutic use as agents that inhibit cholesterol ester transfer protein activity in mammals, particularly humans. Thus, the compounds of the present invention are expected to be useful in elevating plasma HDL cholesterol, its associated components, and the functions performed by them in mammals, particularly humans. By virtue of their expected activity, these agents are also expected to reduce VLDL cholesterol, LDL cholesterol and their associated components in mammals, particularly humans. Hence, these compounds are expected to be useful for the treatment and correction of the various dyslipidemias observed to be associated with the development and incidence of atherosclerosis and cardiovascular disease, including hypoalphalipoproteinemia, hyperbetalipoproteinemia, hypertriglyceridemia, and familial-hypercholesterolemia (see U.S. Pat. No. 6,489,478, incorporated herein by reference).

Further, introduction of a functional CETP gene into an animal lacking CETP (mouse) results in reduced HDL levels (Agellon, L. B. et al., J. Biol. Chem., 266:10796-10801 (1991)) and, increased susceptibility to atherosclerosis. (Marotti, K. R. et al., Nature, 364:73-75 (1993)). Also, inhibition of CETP activity with an inhibitory antibody raises HDL-cholesterol in hamster (Evans, G. F. et al., J. Lipid Research, 35:1634-1645 (1994)) and rabbit (Whitlock, M. E. et al, J. Clin. Invest., 84:129-137 (1989)). Suppression of increased plasma CETP by intravenous injection with antisense oligodeoxynucleotides against CETP mRNA reduced atherosclerosis in cholesterol-fed rabbits (Sugano, M. et al., J. Biol. Chem., 273:5033-5036 (1998)). Importantly, human subjects deficient in plasma CETP, due to a genetic mutation possess markedly elevated plasma HDL-cholesterol levels and apolipoprotein A-I, the major apoprotein component of HDL. In addition, most demonstrate markedly decreased plasma LDL cholesterol and apolipoprotein B (the major apolipoprotein component of LDL. (Inazu, A. et al., N. Engl. J. Med., 323: 1234-1238 (1990)).

Given the negative correlation between the levels of HDL cholesterol and HDL associated lipoproteins, and the positive correlation between triglycerides, LDL cholesterol, and their associated apolipoproteins in blood with the development of cardiovascular, cerebral vascular and peripheral vascular diseases, the compounds of the present invention, their prodrugs and the salts of such compounds and prodrugs, by virtue of their pharmacologic action, are expected to be useful for the treatment, prevention, the arrestment and/or regression of atherosclerosis and its associated disease states. These include cardiovascular disorders (e.g., angina, cardiac ischemia and myocardial infarction), complications due to cardiovascular disease therapies (e.g., reperfusion injury and angioplastic restenosis), hypertension, stroke, and atherosclerosis associated with organ transplantation.

Because of the beneficial effects widely associated with elevated HDL levels, an agent which inhibits CETP activity in humans, by virtue of its HDL increasing ability, also provides valuable avenues for therapy in a number of other disease areas as well.

Accordingly, given the ability of the compounds of the present invention, their prodrugs and the salts of such compounds and prodrugs to alter lipoprotein composition via inhibition of cholesterol ester transfer, they are expected to be useful in the treatment, prevention and/or slowing of the progression of vascular complications associated with diabetes. Hyperlipidemia is present in most subjects with diabetes mellitus (Howard, B. V., J. Lipid Res. 28:613 (1987)). Even in the presence of normal lipid levels, diabetic subjects experience a greater risk of cardiovascular disease (Kannel, W. B. et al., Diabetes Care, 2:120 (1979)). CETP-mediated cholesteryl ester transfer is known to be abnormally increased in both insulin-dependent (Bagdade, J. D. et al., Eur. J. Clin. Invest., 21:161 (1991)) and non-insulin dependent diabetes (Bagdade, J. D. et al., Atherosclerosis, 104:69 (1993)). It has been suggested that the abnormal increase in cholesterol transfer results in changes in lipoprotein composition, particularly for VLDL and LDL, that are more atherogenic (Bagdade, J. D. et al., J. Lipid Res., 36:759 (1995)). These changes would not necessarily be observed during routine lipid screening. Thus, it is expected that the present invention will be useful in reducing the risk of vascular complications as a result of the diabetic condition.

In addition, the compounds of the present invention are expected to be useful in the treatment of obesity. In both humans (Radeau, T. et al., J. Lipid Res., 36(12):2552-2561 (1995)) and nonhuman primates (Quinet, E. et al., J. Clin. Invest., 87(5):1559-1566 (1991)) mRNA for CETP is expressed at high levels in adipose tissue. The adipose message increases with fat feeding (Martin, L. J. et al., J. Lipid Res., 34(3):437-446 (1993)), and is translated into functional transfer protein and through secretion contributes significantly to plasma CETP levels. In human adipocytes the bulk of cholesterol is provided by plasma LDL and HDL (Fong, B. S. et al., Biochimica et Biophysica Acta, 1004(1):53-60 (1989)). The uptake of HDL cholesteryl ester is dependent in large part on CETP (Benoist, F. et al., J. Biol. Chem., 272 (38):23572-23577 (1997)). This ability of CETP to stimulate HDL cholesteryl uptake, coupled with the enhanced binding of HDL to adipocytes in obese subjects (Jimenez, J. G. et al., Int. J. Obesity, 13(5):699-709 (1989)), suggests a role for CETP, not only in generating the low HDL phenotype for these subjects, but in the development of obesity itself by promoting cholesterol accumulation. Inhibitors of CETP activity that block this process therefore serve as useful adjuvants to dietary therapy in causing weight reduction.

CETP inhibitors are useful in the treatment of inflammation due to Gram-negative sepsis and septic shock. For example, the systemic toxicity of Gram-negative sepsis is in large part due to endotoxin, a lipopolysaccharide (LPS) released from the outer surface of the bacteria, which causes an extensive inflammatory response. Lipopolysaccharide can form complexes with lipoproteins (Ulevitch, R. J. et al., J. Clin. Invest. 67:827-837 (1981)). In vitro studies have demonstrated that binding of LPS to HDL substantially reduces the production and release of mediators of inflammation (Ulevitch, R. J. et al., J. Clin. Invest. 62:1313-1324 (1978)). In vivo studies show that transgenic mice expressing human apo-Al and elevated HDL levels are protected from septic shock (Levine, D. M. et al., Proc. Natl. Acad. Sci., 90:12040-12044 (1993)). Importantly, administration of reconstituted HDL to humans challenged with endotoxin resulted in a decreased inflammatory response (Pajkrt, D. et al., J. Exp. Med., 184:1601-1608 (1996)). The CETP inhibitors, by virtue of the fact that they raise HDL levels, attenuate the development of inflammation and septic shock.

Thus, the present invention provides methods for the prevention or treatment of one or more of the aforementioned disorders, comprising the step of administering to a subject in need thereof an effective amount of at least one compound of the present invention, its prodrug and the salt of such compound and prodrugs. Other therapeutic agents such as those described below may be employed with the inventive compounds in the present methods. In the methods of the present invention, such other therapeutic agent(s) may be administered prior to, simultaneously with or following the administration of the compound(s) of the present invention.

In addition, the compounds of the present invention are expected to be useful in the inhibition of remnant lipoprotein production (Okamoto et al., WO 2005/030185).

CETP Assay

CETP inhibition can be determined at a specific concentration of test compound in any of the assays described herein. Potencies are more generally calculated by determining $IC_{50}$ values using these assays.

CETP Scintillation Proximity Assay

Compounds of the present invention inhibit CETP-dependent cholesterol ester transfer from HDL to LDL as described here. Dilutions of compounds in DMSO (1 μl) are added to BD plates (#353232). To this is added 20 μl of a mixture containing $^3$H-CE/HDL (0.15 μl), biotinylated LDL (~5 μg protein/ml final concentration) and unlabeled HDL (16 μg/ml final concentration) in a buffer containing 50 mM HEPES, pH 7.4, 150 mM NaCl and 0.05% sodium azide. Reactions are initiated by the addition of 10 μl of buffer containing purified human recombinant CETP, and incubated at 37° C. At the end of the reaction, 60 μl of LEADseeker beads (#RPNQ0261, 2 mg/ml in buffer containing 1 mg/ml BSA and 0.05 mg protein/ml HDL) are added, the plates are covered and subsequently read. Background activity is determined in a set of wells that receive buffer but no CETP. The level of inhibition is determined by comparing the readings in wells that contain compound to the readings in control wells containing DMSO.

Plasma Cholesterol Ester Transfer Assay

Compounds of the present invention were also tested for the ability to inhibit cholesterol ester transfer activity in plasma as described here. Dilutions of compounds in DMSO (1 μl) are added to 384-well polypropylene plates. To each well is added 29 ul of human plasma containing 0.15 ul $^3$H-CE/HDL. The reaction is incubated at 37° C. and terminated by the addition of 6 ul of precipitation reagent (2:1:1 of water:1M $MgCl_2$:2% Dextralip 50), to precipitate LDL and VLDL. After 10 minutes at room temperature, 15 μl of the reaction is transferred to filter plates (Millipore, #MHVBN45) pre-wetted with 100 ul phosphate buffered saline. The plates are centrifuged (1800 rpm) at room temperature for 10 minutes, and 50 ul Microscint-20 is added. The plates are then sealed and read. Background activity is determined with plasma samples incubated at 4° C. The level of inhibition is determined by comparing the readings in wells that contain compound to the readings in control wells containing DMSO.

In Vivo Cholesterol Ester Transfer Activity

Compounds of the present invention have further been shown to inhibit plasma cholesterol ester transfer activity in mice that are dually transgenic for human CETP and apoB-100 (hCETP/apoB-100) as described here.

Mice (commercially available from Taconic) are fasted for two hours and plasma obtained before dosing. The animals are then dosed with vehicle or compound (p.o.). The vehicle may vary as needed to dissolve the compound, while at the same time having no, or minimal, activity on plasma cholesterol ester transfer activity. Plasma samples are collected again at various times after dosing and assayed for cholesterol ester transfer activity.

To measure CETP activity in plasma samples obtained from animals treated with compounds, the following methodology is employed. To a sample of plasma (typically between 9 and 30 ul), 1 μl of diluted $^3$H-CE/HDL is added (0.15 μl $^3$H-CE/HDL and 0.85 ul assay buffer) to label endogenous HDL. Assay buffer contains 50 mM HEPES, pH 7.4, and 150 mM NaCl. The reaction is incubated at 37° C., and LDL/VLDL precipitated with 3 μl of precipitation reagent (4:1:1 of water:0.5M $MgCl_2$:1% Dextralip 50). The tubes are centrifuged for 15-30 minutes at 10,000×g (10° C.), the supernatants discarded, and the pellets dissolved in 140 μl of 2% SDS. Half of the SDS solution (70 μl) is transferred to scintillation tubes, scintillation fluid is added, and radioactivity measured in a scintillation counter. Background activity is determined for each sample with an aliquot incubated at 4° C. Plasma cholesterol ester transfer inhibition is calculated by comparing the transfer activity in a plasma sample obtained after dosing to the transfer activity in the plasma sample obtained from the same animal before dosing. All data are background subtracted.

The in vivo assay described above (with appropriate modifications within the skill in the art) may be used to determine the activity of other lipid or triglyceride controlling agents as well as the compounds of this invention. The assays set forth above also provide a means whereby the activities of the compounds of the present invention, their prodrugs and the salts of such compounds and prodrugs (or the other agents described herein) can be compared to each other and with the activities of other known compounds. The results of these comparisons are useful for determining dosage levels in mammals, including humans, for the treatment of the above described disease/conditions.

HDL Cholesterol Protocol

The ability of CETP inhibitors to increase HDL cholesterol (HDL-C) can be shown in mammalian subjects via methods known to one of ordinary skill in the art (see Evans, G. F. et al., J. Lipid Research, 35:1634-1645 (1994)). For example, compounds of the present invention have been shown to be efficacious in the elevation of HDL-C in golden syrian hamsters. The hamsters are fed a moderate fat diet containing variable amounts of coconut oil and cholesterol to alter their HDL-C and LDL-C levels. The moderately fat-fed hamsters are fasted and bled to determine baseline HDL-C levels, then dosed orally with compound for three days in an appropriate vehicle. The animals are fasted and bled again on the third day of dosing, and the results are compared to the baseline HDL-C levels. The compounds increase HDL-C in this model in a dose-dependent manner, demonstrating their usefulness to alter plasma lipids.

Antiobesity Protocol

The ability of CETP inhibitors to cause weight loss can be assessed in obese human subjects with body mass index (BMI)≥30 $kg/m^2$. Doses of inhibitor are administered sufficient to result in an increase of ≥25% in HDL cholesterol levels. BMI and body fat distribution, defined as waist (W) to hip (H) ratio (WHR), are monitored during the course of the 3-6 month studies, and the results for treatment groups compared to those receiving placebo.

The above assays can of course be varied by those skilled in the art.

The present invention also provides pharmaceutical compositions comprising at least one of the compounds of the present invention, their prodrugs and the salts of such compounds and prodrugs capable of preventing, treating, and/or slowing the progression of one or more of the aforementioned disorders in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the present invention may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non aqueous solutions or suspensions); nasally such as by inhalation spray; topically, such as in the form of a cream or ointment; or rectally such as in the form of suppositories; in dosage unit formulations containing non toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of present invention may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non toxic, parenterally acceptable diluents or solvents, such as mannitol, 1,3 butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.001 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The compounds of the present invention may be employed alone or in combination with each other and/or other suitable therapeutic agents useful in the treatment of the aforementioned disorders or other disorders.

For example, they may be used in combination with a HMG-CoA reductase inhibitor, a cholesterol synthesis inhibitor, a cholesterol absorption inhibitor, another CETP inhibitor, a MTP/Apo B secretion inhibitor, a PPAR modulator and other cholesterol lowering agents such as a fibrate, niacin, an ion-exchange resin, an antioxidant, an ACAT inhibitor, and a bile acid sequestrant. Other pharmaceutical agents would also include the following: a bile acid reuptake inhibitor, an ileal bile acid transporter inhibitor, an ACC inhibitor, an antihypertensive (such as NORVASC®), a selective estrogen receptor modulator, a selective androgen receptor modulator, an antibiotic, an antidiabetic (such as metformin, a PPARγ activator, a sulfonylurea, insulin, an aldose reductase inhibitor (ARI) and a sorbitol dehydrogenase inhibitor (SDI)), aspirin (acetylsalicylic acid) and niacin and combinations thereof.

Any HMG-CoA reductase inhibitor may be used in the combination aspect of this invention. The term HMG-CoA reductase inhibitor refers to compounds which inhibit the bioconversion of hydroxymethylglutaryl-coenzyme A to mevalonic acid catalyzed by the enzyme HMG-CoA reductase. Such inhibition is readily determined by those skilled in the art according to standard assays (e.g., Meth. Enzymol., 71:455-509 (1981) and references cited therein). A variety of these compounds are described and referenced below however other HMG-CoA reductase inhibitors will be known to those skilled in the art. U.S. Pat. No. 4,231,938 (the disclosure of which is hereby incorporated by reference) discloses certain compounds isolated after cultivation of a microorganism belonging to the genus *Aspergillus*, such as lovastatin. Also, U.S. Pat. No. 4,444,784 (the disclosure of which is hereby incorporated by reference) discloses synthetic derivatives of the aforementioned compounds, such as simvastatin. Also, U.S. Pat. No. 4,739,073 (the disclosure of which is incorporated by reference) discloses certain substituted indoles, such as fluvastatin. Also, U.S. Pat. No. 4,346,227 (the disclosure of which is incorporated by reference) discloses ML-236B derivatives, such as pravastatin. Also, EP-491226A (the disclosure of which is incorporated by reference) discloses certain pyridyldihydroxyheptenoic acids, such as cerivastatin. In addition, U.S. Pat. No. 5,273,995 (the disclosure of which is incorporated by reference) discloses certain 6-[2-(substituted-pyrrol-1-yl)alkyl]pyran-2-ones such as atorvastatin and any pharmaceutically acceptable form thereof (i.e. LIPITOR®). Additional HMG-CoA reductase inhibitors include rosuvastatin and pitavastatin. Statins also include such compounds as rosuvastatin disclosed in U.S. Pat. No. RE37,314 E, pitavastatin disclosed in EP 304063 B1 and U.S. Pat. No. 5,011,930; mevastatin, disclosed in U.S. Pat. No. 3,983,140; velostatin, disclosed in U.S. Pat. No. 4,448,784 and U.S. Pat. No. 4,450,171; compactin, disclosed in U.S. Pat. No. 4,804,770; dalvastatin, disclosed in European Patent Application Publication No. 738510 A2; fluindostatin, disclosed in European Patent Application Publication No. 363934 A1; and dihydrocompactin, disclosed in U.S. Pat. No. 4,450,171.

Any PPAR modulator may be used in the combination aspect of this invention. The term PPAR modulator refers to compounds which modulate peroxisome proliferator activator receptor (PPAR) activity in mammals, particularly humans. Such modulation is readily determined by those skilled in the art according to standard assays known in the literature. It is believed that such compounds, by modulating the PPAR receptor, regulate transcription of key genes involved in lipid and glucose metabolism such as those in fatty acid oxidation and also those involved in high density lipoprotein (HDL) assembly (for example, apolipoprotein AI gene transcription), accordingly reducing whole body fat and increasing HDL cholesterol. By virtue of their activity, these compounds also reduce plasma levels of triglycerides, VLDL cholesterol, LDL cholesterol and their associated components such as apolipoprotein B in mammals, particularly humans, as welt as increasing HDL cholesterol and apolipoprotein AI. Hence, these compounds are useful for the treatment and correction of the various dyslipidemias observed to be associated with the development and incidence of atherosclerosis and cardiovascular disease, including hypoalphalipoproteinemia and hypertriglyceridemia. A variety of these compounds are described and referenced below, however, others will be known to those skilled in the art. International Publication Nos. WO 02/064549 and WO 02/064130, U.S. patent application Ser. No. 10/720,942, and U.S. patent application 60/552,114 disclose certain compounds which are PPARα activators.

Any other PPAR modulator may be used in the combination aspect of this invention. In particular, modulators of PPARβ and/or PPARγ may be useful in combination with compounds of the present invention. An example PPAR inhibitor is described in US 2003/0225158 as {5-Methoxy-2-methyl-4-[4-(4-trifluoromethyl-benzy]oxy)-benzylsulfany]-phenoxy}-acetic acid.

Any MTP/Apo B (microsomal triglyceride transfer protein and or apolipoprotein B) secretion inhibitor may be used in the combination aspect of this invention. The term MTP/Apo B secretion inhibitor refers to compounds which inhibit the secretion of triglycerides, cholesteryl ester, and phospholipids. Such inhibition is readily determined by those skilled in the art according to standard assays (e.g., Wetterau, J. R., Science, 258:999 (1992)). A variety of these compounds are described and referenced below however other MTP/Apo B secretion inhibitors will be known to those skilled in the art, including implitapride (Bayer) and additional compounds such as those disclosed in WO 96/40640 and WO 98/23593, (two exemplary publications). For example, the following MTP/Apo B secretion inhibitors are particularly useful: 4'-trifluoromethyl-biphenyl-2-carboxylic acid [2-(1H-[1,2,4,]triazol-3-ylmethyl)-1,2,3,4-tetrahydro-isoquinolin-6-yl]-amide; 4'-trifluoromethyl-biphenyl-2-carboxylic acid [2-(2-acetylamino-ethyl)-1,2,3,4-tetrahydro-isoquinolin-6-yl]-amide; (2-{6-[(4'-trifluoromethyl-biphenyl-2-carbonyl)-amino]-3, 4-dihydro-1H-isoquinolin-2-yl}-ethyl)-carbamic acid methyl ester; 4'-trifluoromethyl-biphenyl-2-carboxylic acid [2-(1H-imidazol-2-ylmethyl)-1,2,3,4-tetrahydro-isoquinolin-6-yl]-amide; 4'-trifluoromethyl-biphenyl-2-carboxylic acid [2-(2,2-diphenyl-ethyl)-1,2,3,4-tetrahydro-isoquinolin-6-yl]-amide; 4'-trifluoromethyl-biphenyl-2-carboxylic acid [2-(2-ethoxy-ethyl)-1,2,3,4-tetrahydro-isoquinolin-6-yl]-amide; (S)—N-{2-[benzyl(methyl)amino]-2-oxo-1-phenylethyl}-1-methyl-5-[4'-(trifluoromethyl)[1,1'-biphenyl]-2-carboxamido]-2-carboxamide; (S)-2-[(4'-trifluoromethyl-biphenyl-2-carbonyl)-amino]-quinoline-6-carboxylic acid (pentylcarbamoyl-phenyl-methyl)-amide; 1H-indole-2-carboxamide, 1-methyl-N-[(1S)-2-[methyl(phenylmethyl)amino]-2-oxo-1-phenylethyl]-5-[[[4'-(trifluoromethyl)[1,1'-biphenyl]-2-yl]carbonyl]amino]; and N-[(1S)-2-(benzylmethylamino)-2-oxo-1-phenylethyl]-1-methyl-5-[[[4'-(thfluoromethyl)[1,1'-biphenyl]-2-yl]carbonyl]amino]-1H-indole-2-carboxamide.

Any HMG-CoA synthase inhibitor may be used in the combination aspect of this invention. The term HMG-CoA synthase inhibitor refers to compounds which inhibit the biosynthesis of hydroxymethylglutaryl-coenzyme A from acetyl-coenzyme A and acetoacetyl-coenzyme A, catalyzed by the enzyme HMG-CoA synthase. Such inhibition is readily determined by those skilled in the art according to standard assays (Meth. Enzymol., 35:155-160 (1975); Meth. Enzymol., 110:19-26 (1985) and references cited therein). A variety of these compounds are described and referenced below, however other HMG-CoA synthase inhibitors will be known to those skilled in the art. U.S. Pat. No. 5,120,729 discloses certain beta-lactam derivatives. U.S. Pat. No. 5,064,856 discloses certain spiro-lactone derivatives prepared by culturing a microorganism (MF5253). U.S. Pat. No. 4,847,271 discloses certain oxetane compounds such as 11-(3-hydroxymethyl-4-oxo-2-oxetayl)-3,5,7-trimethyl-2,4-undecadienoic acid derivatives.

Any compound that decreases HMG-CoA reductase gene expression may be used in the combination aspect of this invention. These agents may be HMG-CoA reductase transcription inhibitors that block the transcription of DNA or translation inhibitors that prevent or decrease translation of mRNA coding for HMG-CoA reductase into protein. Such compounds may either affect transcription or translation directly, or may be biotransformed to compounds that have the aforementioned activities by one or more enzymes in the cholesterol biosynthetic cascade or may lead to the accumulation of an isoprene metabolite that has the aforementioned activities. Such compounds may cause this effect by decreasing levels of SREBP (sterol receptor binding protein) by inhibiting the activity of site-1 protease (SIP) or agonizing the oxysterol receptor or SCAP. Such regulation is readily determined by those skilled in the art according to standard assays (Meth. Enzymol., 110:9-19 (1985)). Several compounds are described and referenced below, however other inhibitors of HMG-CoA reductase gene expression will be known to those skilled in the art. U.S. Pat. No. 5,041,432 discloses certain 15-substituted lanosterol derivatives. Other oxygenated sterols that suppress synthesis of HMG-CoA reductase are discussed by E. I. Mercer (Prog. Lip. Res., 32:357-416 (1993)).

Any compound having activity as a CETP inhibitor can serve as the second compound in the combination therapy aspect of the present invention. The term CETP inhibitor refers to compounds that inhibit the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat.

No. 6,140,343). A variety of CETP inhibitors will be known to those skilled in the art, for example, those disclosed in U.S. Pat. Nos. 6,140,343 and 6,197,786. CETP inhibitors disclosed in these patents include compounds, such as [2R,4S]-4-[(3,5-bis-trifluoromethylbenzyl)methoxycarbonylamino]-2-ethyl-6-trifluoromethyl-3,4-dihydro-2H-quinoline-1-carboxylic acid ethyl ester (torcetrapib). CETP inhibitors are also described in U.S. Pat. No. 6,723,752, which includes a number of CETP inhibitors including (2R)-3-{[3-(4-chloro-3-ethyl-phenoxy)-phenyl]-[[3-(1,1,2,2-tetrafluoroethoxy)phenyl]methyl]amino}-1,1,1-trifluoro-2-propanol. Moreover, CETP inhibitors included herein are also described in U.S. patent application Ser. No. 10/807,838 and PCT Publication No. WO 2006/090250. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in J. Antibiot., 49(8):815-816 (1996), and Bioorg. Med. Chem. Lett., 6:1951-1954 (1996), respectively.

Any squalene synthetase inhibitor may be used in the combination aspect of this invention. The term squalene synthetase inhibitor refers to compounds which inhibit the condensation of 2 molecules of farnesylpyrophosphate to form squalene, catalyzed by the enzyme squalene synthetase. Such inhibition is readily determined by those skilled in the art according to standard assays (Meth. Enzymol., 15:393-454 (1969) and Meth. Enzymol., 110:359-373 (1985) and references contained therein). A variety of these compounds are described in and referenced below however other squalene synthetase inhibitors will be known to those skilled in the art. U.S. Pat. No. 5,026,554 discloses fermentation products of the microorganism MF5465 (ATCC 74011) including zaragozic acid. A summary of other patented squalene synthetase inhibitors has been compiled (Curr. Op. Ther. Patents, 861-864 (1993)).

Any squalene epoxidase inhibitor may be used in the combination aspect of this invention. The term squalene epoxidase inhibitor refers to compounds which inhibit the bioconversion of squalene and molecular oxygen into squalene-2,3-epoxide, catalyzed by the enzyme squalene epoxidase. Such inhibition is readily determined by those skilled in the art according to standard assays (Biochim. Biophys. Acta, 794:466-471 (1984)). A variety of these compounds are described and referenced below, however other squalene epoxidase inhibitors will be known to those skilled in the art. U.S. Pat. Nos. 5,011,859 and 5,064,864 disclose certain fluoro analogs of squalene. EP publication 395,768 A discloses certain substituted allylamine derivatives. PCT publication WO 93/12069 A discloses certain amino alcohol derivatives. U.S. Pat. No. 5,051,534 discloses certain cyclopropyloxy-squalene derivatives.

Any squalene cyclase inhibitor may be used as the second component in the combination aspect of this invention. The term squalene cyclase inhibiter refers to compounds which inhibit the bioconversion of squalene-2,3-epoxide to lanosterol, catalyzed by the enzyme squalene cyclase. Such inhibition is readily determined by those skilled in the art according to standard assays (FEBS Lett., 244:347-350 (1989)). In addition, the compounds described and referenced below are squalene cyclase inhibitors, however other squalene cyclase inhibitors will also be known to those skilled in the art. PCT publication WO 94/10150 discloses certain 1,2,3,5,6,7,8,8a-octahydro-5,5,8(beta)-trimethyl-6-isoquinolineamine derivatives, such as N-trifluoroacetyl-1,2,3,5,6,7,8,8a-octahydro-2-allyl-5,5,8(beta)-trimethyl-6(beta)-isoquinolineamine. French patent publication 2697250 discloses certain beta, beta-dimethyl-4-piperidine ethanol derivatives such as 1-(1,5,9-trimethyldecyl)-beta,beta-dimethyl-4-piperidineethanol.

Any combined squalene epoxidase/squalene cyclase inhibitor may be used as the second component in the combination aspect of this invention. The term combined squalene epoxidase/squalene cyclase inhibitor refers to compounds that inhibit the bioconversion of squalene to lanosterol via a squalene-2,3-epoxide intermediate. In some assays it is not possible to distinguish between squalene epoxidase inhibitors and squalene cyclase inhibitors, however, these assays are recognized by those skilled in the art. Thus, inhibition by combined squalene epoxidase/squalene cyclase inhibitors is readily determined by those skilled in art according to the aforementioned standard assays for squalene cyclase or squalene epoxidase inhibitors. A variety of these compounds are described and referenced below, however other squalene epoxidase/squalene cyclase inhibitors will be known to those skilled in the art. U.S. Pat. Nos. 5,084,461 and 5,278,171 disclose certain azadecalin derivatives. EP publication 468,434 discloses certain piperidyl ether and thioether derivatives such as 2-(1-piperidyl)pentyl isopentyl sulfoxide and 2-(1-piperidyl)ethyl ethyl sulfide. PCT publication WO 94/01404 discloses certain acyl-piperidines such as 1-(1-oxopentyl-5-phenylthio)-4-(2-hydroxy-1-methyl)-ethyl)piperidine. U.S. Pat. No. 5,102,915 discloses certain cyclopropyloxy-squalene derivatives.

The compounds of the present invention may also be administered in combination with naturally occurring compounds that act to lower plasma LDL cholesterol levels or raise plasma HDL levels via a pathway distinct from CETP inhibitors. These naturally occurring compounds are commonly called nutraceuticals and include, for example, garlic extract and niacin. Niacin is a particularly attractive secondary agent for combination with a CETP inhibitor as it also raises HDL cholesterol levels. Furthermore, niacin lowers LDL cholesterol and triglycerides. Therefore, a combination of niacin and a CETP inhibitor would not only provide the potential for enhanced HDL-raising efficacy, it would yield a very favorable shift in the overall cardiovascular risk profile by decreasing LDL cholesterol and triglycerides. Niacin is commercially available in various dosage forms. Immediate release niacin may be purchase over-the-counter in pharmacies or health-food stores. A slow-release form of niacin is available and is known as Niaspan. Niacin may also be combined with other therapeutic agents such as iovastatin, an HMG-CoA reductase inhibitor. This combination therapy with iovastatin is known as ADVICOR™ (Kos Pharmaceuticals Inc.). In long term clinical trials, niacin either as monotherapy or in combination with HMG-CoA reductase inhibitors has been shown to reduce cardiovascular events, cardiovascular deaths and all cause mortality.

Any cholesterol absorption inhibitor can be used as an additional component in the combination aspect of the present invention. The term cholesterol absorption inhibition refers to the ability of a compound to prevent cholesterol contained within the lumen of the intestine from entering into the intestinal cells and/or passing from within the intestinal cells into the lymph system and/or into the blood stream. Such cholesterol absorption inhibition activity is readily determined by those skilled in the art according to standard assays (e.g., J. Lipid Res., 34:377-395 (1993)). Cholesterol absorption inhibitors are known to those skilled in the art and are described, for example, in PCT WO 94/00480. An example of a recently approved cholesterol absorption inhibitor is ZETIA™ (ezetimibe) (Schering-Plough/Merck).

Any ACAT inhibitor may be used in the combination therapy aspect of the present invention. The term ACAT inhibitor refers to compounds that inhibit the intracellular esterification of dietary cholesterol by the enzyme acyl CoA: cholesterol acyltransferase. Such inhibition may be determined readily by one of skill in the art according to standard assays, such as the method of Heider et al. described in J. Lipid Res., 24:1127 (1983). A variety of these compounds are known to those skilled in the art, for example, U.S. Pat. No. 5,510,379 discloses certain carboxysulfonates, while WO 96/26948 and WO 96/10559 both disclose urea derivatives having ACAT inhibitory activity. Examples of ACAT inhibitors include compounds such as Avasimibe (Pfizer), CS-505 (Sankyo) and Eflucimibe (Ell Lilly and Pierre Fabre).

A lipase inhibitor may be used in the combination therapy aspect of the present invention. A lipase inhibitor is a compound that inhibits the metabolic cleavage of dietary triglycerides or plasma phospholipids into free fatty acids and the corresponding glycerides (e.g. EL, HL, etc.). Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a glyceride and fatty acid. In the intestine, the resultant free fatty acids and monoglycerides are incorporated into bile acid-phospholipid micelles, which are subsequently absorbed at the level of the brush border of the small intestine. The micelles eventually enter the peripheral circulation as chylomicrons. Such lipase inhibition activity is readily determined by those skilled in the art according to standard assays (e.g., Meth. Enzymol. 286:190-231). Pancreatic lipase mediates the metabolic cleavage of fatty acids from triglycerides at the 1- and 3-carbon positions. The primary site of the metabolism of ingested fats is in the duodenum and proximal jejunum by pancreatic tipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions. Such pancreatic lipase inhibition activity is readily determined by those skilled in the art according to standard assays (e.g., Meth. Enzymol. 286:190-231).

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, Abrams, C. K. et al., Gastroenterology, 92:125 (1987). Such gastric lipase inhibition activity is readily determined by those skilled in the art according to standard assays (e.g., Meth. Enzymol., 286:190-231).

A variety of gastric and/or pancreatic lipase inhibitors are known to one of ordinary skill in the art. Preferred lipase inhibitors are those inhibitors that are selected from the group consisting of lipstatin, tetrahydrolipstatin (orlistat), valilactone, esterastin, ebelactone A, and ebelactone B. The compound tetrahydrolipstatin is especially preferred. The lipase inhibitor, N-3-trifluoromethylphenyl-N'-3-chloro-4'-trifluoromethylphenylurea, and the various urea derivatives related thereto, are disclosed in U.S. Pat. No. 4,405,644. The lipase inhibitor, esteracin, is disclosed in U.S. Pat. Nos. 4,189,438 and 4,242,453. The lipase inhibitor, cyclo-O,O'-[(1,6-hexanediyl)-bis-(iminocarbonyl)]dioxime, and the various bis (iminocarbonyl)dioximes related thereto may be prepared as described in Petersen et al., Liebig's Annalen, 562:205-229 (1949).

A variety of pancreatic lipase inhibitors are described herein below. The pancreatic lipase inhibitors lipstatin, (2S, 3S,5S,7Z,10Z)-5-[(S)-2-formamido-4-methyl-valeryloxy]-2-hexyl-3-hydroxy-7,10-hexadecanoic acid lactone, and tetrahydrolipstatin (orlistat), (2S,3S,5S)-5-[(S)-2-formamido-4-methyl-valeryloxy]-2-hexyl-3-hydroxy-hexadecanoic 1,3 acid lactone, and the variously substituted N-formylleucine derivatives and stereoisomers thereof, are disclosed In U.S. Pat. No. 4,598,089. For example, tetrahydrolipstatin is prepared as described in, e.g., U.S. Pat. Nos. 5,274,143; 5,420, 305; 5,540,917; and 5,643,874. The pancreatic lipase inhibitor, FL-386, 1-[4-(2-methylpropyl)cyclohexyl]-2-[(phenylsulfonyl)oxy]ethanone, and the variously substituted sulfonate derivatives related thereto, are disclosed in U.S. Pat. No. 4,452,813. The pancreatic lipase inhibitor, WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512, 565; 5,391,571 and 5,602,151. The pancreatic lipase inhibitor, valilactone, and a process for the preparation thereof by the microbial cultivation of *Actinomycetes* strain MG147-CF2, are disclosed in Kitahara, et al., J. Antibiotics, 40(11): 1647-1650 (1987). The pancreatic lipase inhibitors, ebelactone A and ebelactone B, and a process for the preparation thereof by the microbial cultivation of *Actinomycetes* strain MG7-G1, are disclosed in Umezawa et al., J. Antibiotics, 33:1594-1596 (1980). The use of ebelactones A and B in the suppression of monoglyceride formation is disclosed in Japanese Kokai 08-143457, published Jun. 4, 1996.

Other compounds that are marketed for hyperlipidemia, including hypercholesterolemia and which are intended to help prevent or treat atherosclerosis include bile acid sequestrants, such as Welchol®, Colestid®, LoCholest® and Questran®; and fibric acid derivatives, such as Atromid®, Lopid® and Tricot®.

Diabetes can be treated by administering to a patient having diabetes (especially Type II), insulin resistance, impaired glucose tolerance, metabolic syndrome, or the like, or any of the diabetic complications such as neuropathy, nephropathy, retinopathy or cataracts, a therapeutically effective amount of a compound of the present invention in combination with other agents (e.g., insulin) that can be used to treat diabetes. This includes the classes of anti-diabetic agents (and specific agents) described herein.

Any glycogen phosphorylase inhibitor can be used as the second agent in combination with a compound of the present invention. The term glycogen phosphorylase inhibitor refers to compounds that inhibit the bioconversion of glycogen to glucose-1-phosphate which is catalyzed by the enzyme glycogen phosphorylase. Such glycogen phosphorylase inhibition activity is readily determined by those skilled in the art according to standard assays (e.g., J. Med. Chem. 41:2934-2938 (1998)). A variety of glycogen phosphorylase inhibitors are known to those skilled in the art including those described in WO 96/39384 and WO 96/39385.

Any aldose reductase inhibitor can be used in combination with a compound of the present invention. The term aldose reductase inhibitor refers to compounds that inhibit the bioconversion of glucose to sorbitol, which is catalyzed by the enzyme aldose reductase. Aldose reductase inhibition is readily determined by those skilled in the art according to standard assays (e.g., J. Malone, "Red Celt Sorbitol, an Indicator of Diabetic Control", Diabetes, 29:861-864 (1980)). A variety of aldose reductase inhibitors are known to those skilled in the art, such as those described in U.S. Pat. No. 6,579,879, which includes 6-(5-chloro-3-methylbenzo furan-2-sulfonyl)-2H-pyridazin-3-one.

Any sorbitol dehydrogenase inhibitor can be used in combination with a compound of the present invention. The term sorbitol dehydrogenase inhibitor refers to compounds that inhibit the bioconversion of sorbitol to fructose which is catalyzed by the enzyme sorbitol dehydrogenase. Such sorbitol dehydrogenase inhibitor activity is readily determined by those skilled in the art according to standard assays (e.g., Analyt. Biochem., 280:329-331 (2000)). A variety of sorbitol dehydrogenase inhibitors are known, for example, U.S. Pat. Nos. 5,728,704 and 5,866,578 disclose compounds and a method for treating or preventing diabetic complications by inhibiting the enzyme sorbitol dehydrogenase.

Any glucosidase inhibitor can be used in combination with a compound of the present invention. A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom. Such glucosidase inhibition activity is readily determined by those skilled in the art according to standard assays (e.g., Biochemistry, 8:4214 (1969)). A generally preferred glucosidase inhibitor includes an amylase inhibitor. An amylase inhibitor is a glucosidase inhibitor that inhibits the enzymatic degradation of starch or glycogen into maltose. Such amylase inhibition activity is readily determined by those skilled in the art according to standard assays (e.g., Meth. Enzymol., 1:149 (1955)). The inhibition of such enzymatic degradation is beneficial in reducing amounts of bioavailable sugars, including glucose and maltose, and the concomitant deleterious conditions resulting therefrom.

A variety of glucosidase inhibitors are known to one of ordinary skill in the art and examples are provided below. Preferred glucosidase inhibitors are those inhibitors that are selected from the group consisting of acarbose, adiposine, voglibose, miglitol, emiglitate, camiglibose, tendamistate, trestatin, pradimicin-Q and salbostatin. The glucosidase inhibitor, acarbose, and the various amino sugar derivatives related thereto are disclosed in U.S. Pat. Nos. 4,062,950 and 4,174,439 respectively. The glucosidase inhibitor, adiposine, is disclosed in U.S. Pat. No. 4,254,256. The glucosidase inhibitor, voglibose, 3,4-dideoxy-4-[[2-hydroxy-1-(hydroxymethyl)ethyl]amino]-2-C-(hydroxymethyl)-D-epi-inositol and the various N-substituted pseudo-aminosugars related thereto, are disclosed in U.S. Pat. No. 4,701,559. The glucosidase inhibitor, miglitol, (2R,3R,4R,5S)-1-(2-hydroxyethyl)-2-(hydroxymethyl)-3,4,5-piperidinetriol, and the various 3,4,5-trihydroxypiperidines related thereto, are disclosed in U.S. Pat. No. 4,639,436. The glucosidase inhibitor, emiglitate, ethyl p-[2-[(2R,3R,4R,5S)-3,4,5-trihydroxy-2-(hydroxymethyl)piperidino]ethoxy]-benzoate, the various derivatives related thereto and pharmaceutically acceptable acid addition salts thereof, are disclosed in U.S. Pat. No. 5,192,772. The glucosidase inhibitor, MDL-25637, 2,6-dideoxy-7-O-β-D-glucopyrano-syl-2,6-imino-D-glycero-L-gluco-heptitol, the various homodisaccharides related thereto and the pharmaceutically acceptable acid addition salts thereof, are disclosed in U.S. Pat. No. 4,634,765. The glucosidase inhibitor, camiglibose, methyl 6-deoxy-6-[(2R,3R,4R,5S)-3,4,5-trihydroxy-2-(hydroxymethyl)piperidino]-(α-D-glucopyranoside sesquihydrate, the deoxy-nojirimycin derivatives related thereto, the various pharmaceutically acceptable salts thereof and synthetic methods for the preparation thereof, are disclosed in U.S. Pat. Nos. 5,157,116 and 5,504,078. The glycosidase inhibitor, salbostatin and the various pseudosaccharides related thereto, are disclosed In U.S. Pat. No. 5,091,524.

A variety of amylase inhibitors are known to one of ordinary skill in the art. The amylase inhibitor, tendamistat and the various cyclic peptides related thereto, are disclosed in U.S. Pat. No. 4,451,455. The amylase inhibitor AI-3688 and the various cyclic polypeptides related thereto are disclosed in U.S. Pat. No. 4,623,714. The amylase inhibitor, trestatin, consisting of a mixture of trestatin A, trestatin B and trestatin C and the various trehalose-containing aminosugars related thereto are disclosed in U.S. Pat. No. 4,273,765.

Additional anti-diabetic compounds, which can be used as the second agent in combination with a compound of the present invention, include, for example, the following: biguanides (e.g., metformin), insulin secretagogues (e.g., sulfonylureas and glinides), glitazones, non-glitazone PPARγ agonists, PPARβ agonists, inhibitors of DPP-IV, inhibitors of PDES5, inhibitors of GSK-3, glucagon antagonists, inhibitors of f-1,6-BPase(Metabasis/Sankyo), GLP-1/analogs (AC 2993, also known as exendin-4), insulin and insulin mimetics (Merck natural products). Other examples would include PKC-β inhibitors and AGE breakers.

The compounds of the present invention can be used in combination with anti-obesity agents. Any anti-obesity agent can be used as the second agent in such combinations and examples are provided herein. Such anti-obesity activity is readily determined by those skilled in the art according to standard assays known in the art.

Suitable anti-obesity agents include phenylpropanolamine, ephedrine, pseudoephedrine, phentermine, β$_3$ adrenergic receptor agonists, apolipoprotein-B secretion/microsomal triglyceride transfer protein (apo-B/MTP) inhibitors, MCR-4-agonists, cholecystokinin-A (CCK-A) agonists, monoamine reuptake inhibitors (e.g., sibutramine), sympathomimetic agents, serotoninergic agents, cannabinoid receptor (CB-1) antagonists (e.g., rimonabant described in U.S. Pat. No. 5,624,941 (SR-141,716A), purine compounds, such as those described in US Patent Publication No. 2004/0092520; pyrazolo[1,5-a][1,3,5]triazine compounds, such as those described in U.S. Non-Provisional patent application Ser. No. 10/763,105; and bicyclic pyrazolyl and imidazolyl compounds, such as those described in U.S. Provisional Application No. 60/518,280, dopamine agonists (e.g., bromocriptine), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (e.g., tetrahydrolipstatin, i.e. orlistat), bombesin agonists, anorectic agents (e.g., a bombesin agonist), Neuropeptide-Y antagonists, thyroxine, thyromimetic agents, dehydroepiandrosterones or analogs thereof, glucocorticoid receptor agonists or antagonists, orexin receptor antagonists, urocortin binding protein antagonists, glucagon-like peptide-1 receptor agonists, ciliary neurotrophic factors (e.g., Axokine™), human agouti-related proteins (AGRP), ghrelin receptor antagonists, histamine 3 receptor antagonists or inverse agonists, neuromedin U receptor agonists, and the like. Rimonabant (SR-141,716A also known under the trade name Acomplia™ available from Sanofi-Aventis) can be prepared as described in U.S. Pat. No. 5,624,941. Other suitable CB-1 antagonists include those described in U.S. Pat. Nos. 5,747,524, 6,432, 984 and 6,518,264; U.S. Patent Publication Nos. US2004/0092520, US2004/0157839, US2004/0214855, and US2004/0214838; U.S. patent application Ser. No. 10/971,599; and PCT Patent Publication Nos. WO 02/076949, WO 031075660, WO 04/048317, WO 04/013120, and WO 04/012671.

Preferred apolipoprotein-B secretion/microsomal triglyceride transfer protein (apo-B/MTP) inhibitors for use as antiobesity agents are gut-selective MTP inhibitors, such as dirlotapide described in U.S. Pat. No. 6,720,351; 4-(4-(4-(4-((2-((4-methyl-4H-1,2,4-triazol-3-ylthio)methyl)-2-(4-chlorophenyl)-1,3-dioxolan-4-yl)methoxy)phenyl) piperazin-1-yl)phenyl)-2-sec-butyl-2H-1,2,4-triazol-3(4H)-one (R103757) described in U.S. Pat. Nos. 5,521,186 and 5,929,075; and implitapide (BAY 13-9952) described in U.S. Pat. No. 6,265,431. As used herein, the term "gut-selective" means that the MTP Inhibitor has a higher exposure to the gastro-intestinal tissues versus systemic exposure.

Any thyromimetic can be used as the second agent in combination with a compound of the present Invention. Such thyromimetic activity is readily determined by those skilled in the art according to standard assays (e.g., Atherosclerosis, 126: 53-63 (1996)). A variety of thyromimetic agents are known to those skilled in the art, for example those disclosed in U.S. Pat. Nos. 4,766,121; 4,826,876; 4,910,305; 5,061, 798; 5,284,971; 5,401,772; 5,654,468; and 5,569,674. Other antiobesity agents include sibutramine which can be prepared as described in U.S. Pat. No. 4,929,629 and bromocriptine which can be prepared as described in U.S. Pat. Nos. 3,752, 814 and 3,752,888.

The compounds of the present invention can also be used in combination with other antihypertensive agents. Any antihypertensive agent can be used as the second agent in such combinations and examples are provided herein. Such antihypertensive activity is readily determined by those skilled in the art according to standard assays (e.g., blood pressure measurements).

Examples of presently marketed products containing antihypertensive agents include calcium channel blockers, such as Cardizem®, Adalat®, Calan®, Cardene®, Covera®, Dilacor®, DynaCirc®, Procardia XL®, Sular®, Tiazac®, Vascor®, Verelan®, Isoptin®, Nimotop®, Norvasc®, and Plendile; angiotensin converting enzyme (ACE) inhibitors, such as Accupril®, Altace®, Captopril®, Lotensin®, Mavik®, Monopril®, Prinivil®, Univasc®, Vasotec® and Zestril®.

Amlodipine and related dihydropyridine compounds are disclosed in U.S. Pat. No. 4,572,909, as potent anti-ischemic and antihypertensive agents. U.S. Pat. No. 4,879,303 discloses amlodipine benzenesulfonate salt (also termed amlodipine besylate). Amlodipine and amlodipine besylate are potent and long lasting calcium channel blockers. As such, amlodipine, amlodipine besylate, amlodipine maleate and other pharmaceutically acceptable acid addition salts of amlodipine have utility as antihypertensive agents and as antiischemic agents. Amlodipine besylate is currently sold as Norvasc®.

Calcium channel blockers which are within the scope of this invention include, but are not limited to: bepridil, which may be prepared as disclosed in U.S. Pat. No. 3,962,238 or U.S. Reissue No. 30,577; clentiazem, which may be prepared as disclosed in U.S. Pat. No. 4,567,175; diltiazem, fendiline, which may be prepared as disclosed in U.S. Pat. No. 3,262, 977; gallopamil, which may be prepared as disclosed in U.S. Pat. No. 3,261,859; mibefradil, which may be prepared as disclosed in U.S. Pat. No. 4,808,605; prenylamine, which may be prepared as disclosed in U.S. Pat. No. 3,152,173; semotiadil, which may be prepared as disclosed in U.S. Pat. No. 4,786,635; terodiline, which may be prepared as disclosed in U.S. Pat. No. 3,371,014; verapamil, which may be prepared as disclosed in U.S. Pat. No. 3,261,859; aranipine, which may be prepared as disclosed in U.S. Pat. No. 4,572, 909; barnidipine, which may be prepared as disclosed in U.S. Pat. No. 4,220,649; benidipine, which may be prepared as disclosed in European Patent Application Publication No. 106,275; cilnidipine, which may be prepared as disclosed in U.S. Pat. No. 4,672,068; efonidipine, which may be prepared as disclosed in U.S. Pat. No. 4,885,284; elgodipine, which may be prepared as disclosed in U.S. Pat. No. 4,952,592; felodipine, which may be prepared as disclosed in U.S. Pat. No. 4,264,611; isradipine, which may be prepared as disclosed in U.S. Pat. No. 4,466,972; lacidipine, which may be prepared as disclosed in U.S. Pat. No. 4,801,599; lercanidipine, which may be prepared as disclosed in U.S. Pat. No. 4,705,797; manidipine, which may be prepared as disclosed in U.S. Pat. No. 4,892,875; nicardipine, which may be prepared as disclosed in U.S. Pat. No. 3,985,758; nifedipine, which may be prepared as disclosed in U.S. Pat. No. 3,485, 847; nilvadipine, which may be prepared as disclosed in U.S. Pat. No. 4,338,322; nimodipine, which may be prepared as disclosed in U.S. Pat. No. 3,799,934; nisoldipine, which may be prepared as disclosed in U.S. Pat. No. 4,154,839; nitrendipine, which may be prepared as disclosed in U.S. Pat. No. 3,799,934; cinnarizine, which may be prepared as disclosed in U.S. Pat. No. 2,882,271; flunarizine, which may be prepared as disclosed in U.S. Pat. No. 3,773,939; lidoflazine, which may be prepared as disclosed in U.S. Pat. No. 3,267, 104; lomerizine, which may be prepared as disclosed in U.S. Pat. No. 4,663,325; bencyclane, which may be prepared as disclosed in Hungarian Patent No. 151,865; etafenone, which may be prepared as disclosed in German Patent No. 1,265, 758; and perhexyline, which may be prepared as disclosed in British Patent No. 1,025,578.

Angiotensin Converting Enzyme Inhibitors (ACE-Inhibitors) which are within the scope of this invention include, but are not limited to: alacepril, which may be prepared as disclosed in U.S. Pat. No. 4,248,883; benazepril, which may be prepared as disclosed in U.S. Pat. No. 4,410,520; captopril, which may be prepared as disclosed in U.S. Pat. Nos. 4,046, 889 and 4,105,776; ceronapril, which may be prepared as disclosed in U.S. Pat. No. 4,462,790; delapril, which may be prepared as disclosed in U.S. Pat. No. 4,385,051; enalapril, which may be prepared as disclosed in U.S. Pat. No. 4,374, 829; fosinopril, which may be prepared as disclosed in U.S. Pat. No. 4,337,201; imadapril, which may be prepared as disclosed in U.S. Pat. No. 4,508,727; lisinopril, which may be prepared as disclosed in U.S. Pat. No. 4,555,502; moveltopril, which may be prepared as disclosed in Belgian Patent No. 893,553; perindopril, which may be prepared as disclosed in U.S. Pat. No. 4,508,729; quinapril, which may be prepared as disclosed in U.S. Pat. No. 4,344,949; ramipril, which may be prepared as disclosed in U.S. Pat. No. 4,587,258; spirapril, which may be prepared as disclosed in U.S. Pat. No. 4,470,972; temocapril, which may be prepared as disclosed in U.S. Pat. No. 4,699,905; and trandolapril, which may be prepared as disclosed in U.S. Pat. No. 4,933,361.

Angiotensin-II receptor antagonists (A-II antagonists) which are within the scope of this invention include, but are not limited to: candesartan, which may be prepared as disclosed in U.S. Pat. No. 5,196,444; eprosartan, which may be prepared as disclosed in U.S. Pat. No. 5,185,351; irbesartan, which may be prepared as disclosed in U.S. Pat. No. 5,270,317; losartan, which may be prepared as disclosed in U.S. Pat. No. 5,138,069; and valsartan, which may be prepared as disclosed in U.S. Pat. No. 5,399,578.

Beta-adrenergic receptor blockers (beta- or β-blockers) which are within the scope of this invention include, but are not limited to: acebutolol, which may be prepared as disclosed in U.S. Pat. No. 3,857,952; alprenolol, which may be prepared as disclosed in Netherlands Patent Application No. 6,605,692; amosulalol, which may be prepared as disclosed in U.S. Pat. No. 4,217,305; arotinolol, which may be prepared as disclosed in U.S. Pat. No. 3,932,400; atenolol, which may be prepared as disclosed in U.S. Pat. No. 3,663,607 or 3,836,671; befunolol, which may be prepared as disclosed in U.S. Pat. No. 3,853,923; betaxolol, which may be prepared as disclosed in U.S. Pat. No. 4,252,984; bevantolol, which may be prepared as disclosed in U.S. Pat. No. 3,857,981; bisoprolol, which may be prepared as disclosed in U.S. Pat. No. 4,171,370; bopindolol, which may be prepared as disclosed in U.S. Pat. No. 4,340,541; bucumolol, which may be prepared as disclosed in U.S. Pat. No. 3,663,570; bufetolol, which may be prepared as disclosed in U.S. Pat. No. 3,723,476; bufuralol, which may be prepared as disclosed in U.S. Pat. No. 3,929,836; bunitrolol, which may be prepared as disclosed in U.S. Pat. Nos. 3,940,489 and 3,961,071; buprandolol, which may be prepared as disclosed in U.S. Pat. No. 3,309,406; butiridine hydrochloride, which may be prepared as disclosed in French Patent No. 1,390,056; butofilolol, which may be prepared as disclosed in U.S. Pat. No. 4,252,825; carazolol, which may be prepared as disclosed in German Patent No. 2,240,599; carteolol, which may be prepared as disclosed in U.S. Pat. No. 3,910,924; carvedilol, which may be prepared as disclosed in U.S. Pat. No. 4,503,067; celiprolol, which may be prepared as disclosed in U.S. Pat. No. 4,034,009; cetamolol, which may be prepared as disclosed in U.S. Pat. No. 4,059,622; cloranolol, which may be prepared as disclosed in German Patent No. 2,213,044; dilevalol, which may be prepared as disclosed in Clifton et al., J. Med. Chem., 25:670 (1982); epanolol, which may be prepared as disclosed in European Patent Publication Application No. 41,491; indenolol, which may be prepared as disclosed in U.S. Pat. No. 4,045,482; labetalol, which may be prepared as disclosed in U.S. Pat. No. 4,012,444; levobunolol, which may be prepared as disclosed in U.S. Pat. No. 4,463,176; mepindolol, which may be prepared as disclosed in Seeman et al., Heir. Chim. Acta, 54:241 (1971); metipranolol, which may be prepared as disclosed in Czechoslovakian Patent Application No. 128,471; metoprolol, which may be prepared as disclosed in U.S. Pat. No. 3,873,600; moprolol, which may be prepared as disclosed in U.S. Pat. No. 3,501,7691; nadolol, which may be prepared as disclosed in U.S. Pat. No. 3,935,267; nadoxolol, which may be prepared as disclosed in U.S. Pat. No. 3,819,702; nebivalol, which may be prepared as disclosed in U.S. Pat. No. 4,654,362; nipradilol, which may be prepared as disclosed in U.S. Pat. No. 4,394,382; oxprenolol, which may be prepared as disclosed in British Patent No. 1,077,603; perbutolol, which may be prepared as disclosed in U.S. Pat. No. 3,551,493; pindolol, which may be prepared as disclosed in Swiss Patent Nos. 469,002 and 472,404; practolol, which may be prepared as disclosed in U.S. Pat. No. 3,408,387; pronethalol, which may be prepared as disclosed in British Patent No. 909,357; propranolol, which may be prepared as disclosed in U.S. Pat. Nos. 3,337,628 and 3,520,919; sotalol, which may be prepared as disclosed in Uloth et al., J. Med. Chem., 9:88 (1966); sufinalol, which may be prepared as disclosed in German Patent No. 2,728,641; talindol, which may be prepared as disclosed in U.S. Pat. Nos. 3,935,259 and 4,038,313; tertatolol, which may be prepared as disclosed in U.S. Pat. No. 3,960,891; tilisolol, which may be prepared as disclosed in U.S. Pat. No. 4,129,565; timolol, which may be prepared as disclosed in U.S. Pat. No. 3,655,663; toliprolol, which may be prepared as disclosed in U.S. Pat. No. 3,432,545; and xibenolol, which may be prepared as disclosed in U.S. Pat. No. 4,018,824.

Alpha-adrenergic receptor blockers (alpha- or α-blockers) which are within the scope of this invention include, but are not limited to: amosulalol, which may be prepared as disclosed in U.S. Pat. No. 4,217,307; arotinolol, which may be prepared as disclosed in U.S. Pat. No. 3,932,400; dapiprazole, which may be prepared as disclosed in U.S. Pat. No. 4,252,721; doxazosin, which may be prepared as disclosed in U.S. Pat. No. 4,188,390; fenspiride, which may be prepared as disclosed in U.S. Pat. No. 3,399,192; indoramin, which may be prepared as disclosed in U.S. Pat. No. 3,527,761; labetolol; naftopidil, which may be prepared as disclosed in U.S. Pat. No. 3,997,666; nicergoline, which may be prepared as disclosed in U.S. Pat. No. 3,228,943; prazosin, which may be prepared as disclosed in U.S. Pat. No. 3,511,836; tamsulosin, which may be prepared as disclosed in U.S. Pat. No. 4,703,063; tolazoline, which may be prepared as disclosed in U.S. Pat. No. 2,161,938; trimazosin, which may be prepared as disclosed in U.S. Pat. No. 3,669,968; and yohimbine, which may be isolated from natural sources according to methods well known to those skilled in the art.

The term "vasodilator," where used herein, is meant to include cerebral vasodilators, coronary vasodilators and peripheral vasodilators. Cerebral vasodilators within the scope of this invention include, but are not limited to: bencyclane; cinnarizine; citicoline, which may be isolated from natural sources as disclosed in Kennedy et al., J. Am. Chem. Soc., 77:250 (1955) or synthesized as disclosed in Kennedy, J. Biol. Chem., 222:185 (1956); cyclandelate, which may be prepared as disclosed in U.S. Pat. No. 3,663,597; ciclonicate, which may be prepared as disclosed in German Patent No, 1,910,481; diisopropylamine dichloroacetate, which may be prepared as disclosed in British Patent No. 862,248; eburnamonine, which may be prepared as disclosed in Hermann et al., J. Am. Chem. Soc., 101:1540 (1979); fasudil, which may be prepared as disclosed in U.S. Pat. No. 4,678,783; fenoxedil, which may be prepared as disclosed in U.S. Pat. No. 3,818,021; flunarizine, which may be prepared as disclosed in U.S. Pat. No. 3,773,939; ibudilast, which may be prepared as disclosed in U.S. Pat. No. 3,850,941; ifenprodil, which may be prepared as disclosed in U.S. Pat. No. 3,509,164; lomerizine, which may be prepared as disclosed in U.S. Pat. No. 4,663,325; nafronyl, which may be prepared as disclosed in U.S. Pat. No. 3,334,096; nicametate, which may be prepared as disclosed in Blicke et al., J. Am. Chem. Soc., 64:1722 (1942); nicergoline, which may be prepared as disclosed above; nimodipine, which may be prepared as disclosed in U.S. Pat. No. 3,799,934; papaverine, which may be prepared as reviewed in Goldberg, Chem. Prod. Chem. News, 17:371 (1954); pentifylline, which may be prepared as disclosed in German Patent No. 860,217; tinofedrine, which may be prepared as disclosed in U.S. Pat. No. 3,563,997; vincamine, which may be prepared as disclosed in U.S. Pat. No. 3,770,724; vinpocetine, which may be prepared as disclosed in U.S. Pat. No. 4,035,750; and viquidil, which may be prepared as disclosed in U.S. Pat. No. 2,500,444.

Coronary vasodilators within the scope of this invention include, but are not limited to: amotriphene, which may be prepared as disclosed in U.S. Pat. No. 3,010,965; bendazol, which may be prepared as disclosed in J. Chem. Soc., 2426 (1958); benfurodil hemisuccinate, which may be prepared as disclosed in U.S. Pat. No. 3,355,463; benziodarone, which may be prepared as disclosed in U.S. Pat. No. 3,012,042; chloracizine, which may be prepared as disclosed in British Patent No. 740,932; chromonar, which may be prepared as disclosed in U.S. Pat. No. 3,282,938; clobenfural, which may be prepared as disclosed in British Patent No. 1,160,925; clonitrate, which may be prepared from propanediol according to methods well known to those skilled in the art, e.g., see Annalen, 1870, 155, 165; cloricromen, which may be prepared as disclosed in U.S. Pat. No. 4,452,811; dilazep, which may be prepared as disclosed in U.S. Pat. No. 3,532,685; dipyridamole, which may be prepared as disclosed in British Patent No. 807,826; droprenilamine, which may be prepared as disclosed in German Patent No. 2,521,113; efloxate, which may be prepared as disclosed in British Patent Nos. 803,372 and 824,547; erythrityl tetranitrate, which may be prepared by nitration of erythritol according to methods well-known to those skilled in the art; etafenone, which may be prepared as disclosed in German Patent No. 1,265,758; fendiline, which may be prepared as disclosed in U.S. Pat. No. 3,262,977; floredil, which may be prepared as disclosed in German Patent No. 2,020,464; ganglefene, which may be prepared as disclosed in U.S.S.R. Patent No. 115,905; hexestrol, which may be prepared as disclosed in U.S. Pat. No. 2,357,985; hexobendine, which may be prepared as disclosed in U.S. Pat. No. 3,267,103; itramin tosylate, which may be prepared as disclosed in Swedish Patent No. 168,308; khellin, which may be prepared as disclosed in Baxter et al., J. Chem. Soc., 1949, S 30; lidoflazine, which may be prepared as disclosed in U.S. Pat. No. 3,267,104; mannitol hexanitrate, which may be prepared by the nitration of mannitol according to methods well-known to those skilled in the art; medibazine, which may be prepared as disclosed in U.S. Pat. No. 3,119,826; nitroglycerin; pentaerythritol tetranitrate, which may be prepared by the nitration of pentaerythritol according to methods well-known to those skilled in the art; pentrinitrol, which may be prepared as disclosed in German Patent No. 638, 422-3; perhexylline, which may be prepared as disclosed above; pimethylline, which may be prepared as disclosed in U.S. Pat. No. 3,350,400; prenylamine, which may be prepared as disclosed in U.S. Pat. No. 3,152,173; propatyl nitrate, which may be prepared as disclosed in French Patent No. 1,103,113; trapidil, which may be prepared as disclosed in East German Patent No. 55,956; tricromyl, which may be prepared as disclosed in U.S. Pat. No. 2,769,015; trimetazidine, which may be prepared as disclosed in U.S. Pat. No. 3,262,852; trolnitrate phosphate, which may be prepared by nitration of triethanolamine followed by precipitation with phosphoric acid according to methods well-known to those skilled in the art; visnadine, which may be prepared as disclosed in U.S. Pat. Nos. 2,816,118 and 2,980,699.

Peripheral vasodilators within the scope of this invention include, but are not limited to: aluminum nicotinate, which may be prepared as disclosed in U.S. Pat. No. 2,970,082; bamethan, which may be prepared as disclosed in Corrigan et al., J. Am. Chem. Soc., 67:1894 (1945); bencyclane, which may be prepared as disclosed above; betahistine, which may be prepared as disclosed in Walter et al., J. Am. Chem. Soc., 63:2771 (1941); bradykinin, which may be prepared as disclosed in Hamburg et al., Arch. Biochem. Biophys., 76:252 (1958); brovincamine, which may be prepared as disclosed in U.S. Pat. No. 4,146,643; bufeniode, which may be prepared as disclosed in U.S. Pat. No. 3,542,870; buflomedil, which may be prepared as disclosed in U.S. Pat. No. 3,895,030; butalamine, which may be prepared as disclosed in U.S. Pat. No. 3,338,899; cetiedil, which may be prepared as disclosed in French Patent No. 1,460,571; ciclonicate, which may be prepared as disclosed in German Patent No, 1,910,481; cinepazide, which may be prepared as disclosed in Belgian Patent No. 730,345; cinnarizine, which may be prepared as disclosed above; cyclandelate, which may be prepared as disclosed above; diisopropylamine dichloroacetate, which may be prepared as disclosed above; eledoisin, which may be prepared as disclosed in British Patent No. 984,810; fenoxedil, which may be prepared as disclosed above; flunarizine, which may be prepared as disclosed above; hepronicate, which may be prepared as disclosed in U.S. Pat. No. 3,384,642; ifenprodil, which may be prepared as disclosed above; iloprost, which may be prepared as disclosed in U.S. Pat. No. 4,692,464; inositol niacinate, which may be prepared as disclosed in Badgett et al., J. Am. Chem. Soc., 69:2907 (1947); isoxsuprine, which may be prepared as disclosed in U.S. Pat. No. 3,056,836; kallidin, which may be prepared as disclosed in Biochem. Biophys. Res. Commun., 6:210 (1961); kallikrein, which may be prepared as disclosed in German Patent No. 1,102,973; moxisylyte, which may be prepared as disclosed in German Patent No. 905,738; nafronyl, which may be prepared as disclosed above; nicametate, which may be prepared as disclosed above; nicergoline, which may be prepared as disclosed above; nicofuranose, which may be prepared as disclosed in Swiss Patent No. 366,523; nylidrin, which may be prepared as disclosed in U.S. Pat. Nos. 2,661,372 and 2,661,373; pentifylline, which may be prepared as disclosed above; pentoxifylline, which may be prepared as disclosed in U.S. Pat. No. 3,422,107; piribedil, which may be prepared as disclosed in U.S. Pat. No. 3,299,067; prostaglandin $E_1$, which may be prepared by any of the methods referenced in the Merck Index, Twelfth Edition, Budaveri, Ed., New Jersey, p. 1353 (1996); suloctidil, which may be prepared as disclosed in German Patent No. 2,334,404; tolazoline, which may be prepared as disclosed in U.S. Pat. No. 2,161,938; and xanthinol niacinate, which may be prepared as disclosed in German Patent No. 1,102,750.

The term "diuretic," within the scope of this invention, is meant to include diuretic benzothiadiazine derivatives, diuretic organomercurials, diuretic purines, diuretic steroids, diuretic sulfonamide derivatives, diuretic uracils and other diuretics such as amanozine, which may be prepared as disclosed in Austrian Patent No. 168,063; amiloride, which may be prepared as disclosed in Belgian Patent No. 639,386; arbutin, which may be prepared as disclosed in Tschitschibabin, Annalen, 1930, 479, 303; chlorazanil, which may be prepared as disclosed in Austrian Patent No. 168,063; ethacrynic acid, which may be prepared as disclosed in U.S. Pat. No. 3,255,241; etozolin, which may be prepared as disclosed in U.S. Pat. No. 3,072,653; hydracarbazine, which may be prepared as disclosed in British Patent No. 856,409; isosorbide, which may be prepared as disclosed in U.S. Pat. No. 3,160,641; mannitol; metochalcone, which may be prepared as disclosed in Freudenberg et al., Ber., 1957, 90, 957; muzolimine, which may be prepared as disclosed in U.S. Pat. No. 4,018,890;

perhexyline, which may be prepared as disclosed above; ticrynafen, which may be prepared as disclosed in U.S. Pat. No. 3,758,506; triamterene which may be prepared as disclosed in U.S. Pat. No. 3,051,230; and urea.

Diuretic benzothiadiazine derivatives within the scope of this invention include, but are not limited to: althiazide, which may be prepared as disclosed in British Patent No. 902,658; bendroflumethiazide, which may be prepared as disclosed in U.S. Pat. No. 3,265,573; benzthiazide, McManus et al., 136th Am. Soc. Meeting (Atlantic City, September 1959), Abstract of papers, pp 13-O; benzylhydrochlorothiazide, which may be prepared as disclosed in U.S. Pat. No. 3,108,097; buthiazide, which may be prepared as disclosed in British Patent Nos. 861,367 and 885,078; chlorothiazide, which may be prepared as disclosed in U.S. Pat. Nos. 2,809,194 and 2,937,169; chlorthalidone, which may be prepared as disclosed in U.S. Pat. No. 3,055,904; cyclopenthiazide, which may be prepared as disclosed in Belgian Patent No. 587,225; cyclothiazide, which may be prepared as disclosed in Whitehead et al., J. Org. Chem., 26:2814 (1961); epithiazide, which may be prepared as disclosed in U.S. Pat. No. 3,009,911; ethiazide, which may be prepared as disclosed in British Patent No. 861,367; fenquizone, which may be prepared as disclosed in U.S. Pat. No. 3,870,720; indapamide, which may be prepared as disclosed in U.S. Pat. No. 3,565,911; hydrochlorothiazide, which may be prepared as disclosed in U.S. Pat. No. 3,164,588; hydroflumethiazide, which may be prepared as disclosed in U.S. Pat. No. 3,254,076; methyclothiazide, which may be prepared as disclosed in Close et al, J. Am. Chem. Soc., 82:1132 (1960); meticrane, which may be prepared as disclosed in French Patent Nos. M2790 and 1,365,504; metolazone, which may be prepared as disclosed in U.S. Pat. No. 3,360,518; paraflutizide, which may be prepared as disclosed in Belgian Patent No. 620,829; polythiazide, which may be prepared as disclosed in U.S. Pat. No. 3,009,911; quinethazone, which may be prepared as disclosed in U.S. Pat. No. 2,976,289; teclothiazide, which may be prepared as disclosed in Close et al., J. Am. Chem. Soc., 82:1132 (1960); and trichlormethiazide, which may be prepared as disclosed in deStevens et al., Experientia, 16:113 (1960).

Diuretic sulfonamide derivatives within the scope of this invention include, but are not limited to: acetazolamide, which may be prepared as disclosed in U.S. Pat. No. 2,980,679; ambuside, which may be prepared as disclosed in U.S. Pat. No. 3,188,329; azosemide, which may be prepared as disclosed in U.S. Pat. No. 3,665,002; bumetanide, which may be prepared as disclosed in U.S. Pat. No. 3,634,583; butazolamide, which may be prepared as disclosed in British Patent No. 769,757; chloraminophenamide, which may be prepared as disclosed in U.S. Pat. Nos. 2,809,194, 2,965,655 and 2,965,656; clofenamide, which may be prepared as disclosed in Olivier, Rec. Trav. Chim., 1918, 37, 307; clopamide, which may be prepared as disclosed in U.S. Pat. No. 3,459,756; clorexolone, which may be prepared as disclosed in U.S. Pat. No. 3,183,243; disulfamide, which may be prepared as disclosed in British Patent No. 851,287; ethoxolamide, which may be prepared as disclosed in British Patent No. 795,174; furosemide, which may be prepared as disclosed in U.S. Pat. No. 3,058,882; mefruside, which may be prepared as disclosed in U.S. Pat. No. 3,356,692; methazolamide, which may be prepared as disclosed in U.S. Pat. No. 2,783,241; piretanide, which may be prepared as disclosed in U.S. Pat. No. 4,010,273; torasemide, which may be prepared as disclosed in U.S. Pat. No. 4,018,929; tripamide, which may be prepared as disclosed in Japanese Patent No. 73 05,585; and xipamide, which may be prepared as disclosed in U.S. Pat. No. 3,567,777.

Osteoporosis is a systemic skeletal disease, characterized by low bone mass and deterioration of bone tissue, with a consequent increase in bone fragility and susceptibility to fracture, in the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5-20% of patients dying within one year, and over 50% of survivors being incapacitated. The elderly are at greatest risk of osteoporosis, and the problem is therefore predicted to increase significantly within the aging of the population. Worldwide fracture incidence is forecasted to increase three-fold over the next 60 years, and one study has estimated that there will be 4.5 million hip fractures worldwide in 2050. Women are at greater risk of osteoporosis than men. Women experience a sharp acceleration of bone loss during the five years following menopause. Other factors that increase the risk include smoking, alcohol abuse, a sedentary lifestyle and low calcium intake.

Those skilled in the art will recognize that anti-resorptive agents (for example progestins, polyphosphonates, bisphosphonate(s), estrogen agonists/antagonists, estrogen, estrogen/progestin combinations, Premarin®, estrone, estriol or 17α- or 17β-ethynyl estradiol) may be used in conjunction with the compounds of the present invention.

Exemplary progestins are available from commercial sources and include: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, ethynodiol diacetate, etonogestrel, fluorogestone acetate, gestaclone, gestodene, gestonorone caproate, gestrinone, haloprogesterone, hydroxyprogesterone caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenproprionate, progesterone, quingestanol acetate, quingestrone, and tigestol. Preferred progestins are medroxyprogestrone, norethindrone and norethynedrel.

Exemplary bone resorption inhibiting polyphosphonates include polyphosphenates of the type disclosed in U.S. Pat. No. 3,683,080. Preferred polyphosphonates are geminal diphosphonates (also referred to as bis-phosphonates). Tiludronate disodium is an especially preferred polyphosphonata. Ibandronic acid is an especially preferred polyphosphonate. Alendronate and resindronate are especially preferred polyphosphonates. Zoledronic acid is an especially preferred polyphosphonate. Other preferred polyphosphonates are 6-amino-1-hydroxy-hexylidene-bisphosphonic acid and 1-hydroxy-3(methylpentylamino)-propylidene-bisphosphonic acid. The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid, N,N-dimethylamino methane diphosphonic acid, N-(2-hydroxyethyl)amino methane diphosphonic acid, butane-4-amino-1-hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

In particular, the compounds of this invention may be combined with a mammalian estrogen agonist/antagonist. Any estrogen agonist/antagonist may be used in the combination aspect of this invention. The term estrogen agonist/antagonist refers to compounds which bind with the estrogen receptor, inhibit bone turnover and/or prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue, and blocking the actions of estrogen in one or more tissues. Such activities are readily determined by those skilled in the art of standard assays including estrogen receptor binding assays, standard bone histomorphometric and densitometer methods (Eriksen E. F. et al., Bone Histomorphometry, Raven Press, New York, pp. 1-74 (1994); Grier, S. J. et al., "The Use of Dual-Energy X-Ray Absorptiometry In Animals", Inv. Radiol., 31(1):50-62 (1996); Wahner H. W. et al., The Evaluation of Osteoporosis: Dual Energy X-Ray Absorptiometry in Clinical Practice., Martin Dunitz Ltd., London, pp. 1-296 (1994)). A variety of these compounds are described and referenced below. Another preferred estrogen agonist/antagonist is 3-(4-{1,2-diphenyl-but-1-enyl)-phenyl)-acrylic acid, which is disclosed in Willson et al., Endocrinology, 138:3901-3911 (1997). Another preferred estrogen agonist/antagonist is tamoxifen: (ethanamine,2-(-4-(1,2-diphenyl-1-butenyl)phenoxy)-N,N-dimethyl, (Z)-2-, 2-hydroxy-1,2,3-propanetricarboxylate(1:1)) and related compounds which are disclosed in U.S. Pat. No. 4,536,516. Another related compound is 4-hydroxy tamoxifen, which is disclosed in U.S. Pat. No. 4,623,660. A preferred estrogen agonist/antagonist is raloxifene: (methanone, (6-hydroxy-2-(4-hydroxyphenyl)benzo[b]thien-3-yl)(4-(2-(1-piperidinyl)ethoxy)phenyl)hydrochloride) which is disclosed in U.S. Pat. No. 4,418,068. Another preferred estrogen agonist/antagonist is toremifene: (ethanamine, 2-(4-(4-chloro-1,2-diphenyl-1-butenyl)phenoxy)-N,N-dimethyl-, (Z)-, 2-hydroxy-1,2,3-propanetricarboxylate (1:1) which is disclosed in U.S. Pat. No. 4,996,225. Another preferred estrogen agonist/antagonist is centchroman: 1-(2-((4-(-methoxy-2,2, dimethyl-3-phenyl-chroman-4-yl)-phenoxy)-ethyl)-pyrrolidine, which is disclosed in U.S. Pat. No. 3,822,287. Also preferred is levormeloxifene.

Another preferred estrogen agonist/antagonist is idoxifene: (E)-1-(2-(4-(1-(4-iodo-phenyl)-2-phenyl-but-1-enyl)-phenoxy)-ethyl)-pyrrolidinone, which is disclosed in U.S. Pat. No. 4,839,155. Another preferred estrogen agonist/antagonist is 2-(4-methoxy-phenyl)-3-[4-(2-piperidin-1-yl-ethoxy)-phenoxy]-benzo[b]thiophen-6-ol which is disclosed in U.S. Pat. No. 5,488,058. Another preferred estrogen agonist/antagonist is 6-(4-hydroxy-phenyl)-5-(4-(2-piperidin-1-yl-ethoxy)-benzyl)-naphthalen-2-ol, which is disclosed in U.S. Pat. No. 5,484,795. Another preferred estrogen agonist/antagonist is (4-(2-(2-aza-bicyclo[2.2.1]hept-2-yl)-ethoxy)-phenyl)-(6-hydroxy-2-(4-hydroxyphenyl)-benzo[b]thiophen-3-yl)-methanone which is disclosed, along with methods of preparation, in PCT Publication No. WO 95/10513. Other preferred estrogen agonist/antagonists include the compounds, TSE-424 (Wyeth-Ayerst Laboratories) and arazoxifene.

Other preferred estrogen agonist/antagonists include compounds as described in U.S. Pat. No. 5,552,412. Especially preferred compounds described therein are: cis-6-('4-fluorophenyl)-5-(4-(2-piperidin-1-yl-ethoxy)-phenyl)-5,6,7,8-tetrahydronaphthalene-2-ol; (–)-cis-6-phenyl-5-(4-(2-pyrrolidin-1-yl-ethoxy)-phenyl)-5,6,7,8-tetrahydronaphthalene-2-ol (also known as lasofoxifene); cis-6-phenyl-5-(4-(2-pyrrolidin-1-yl-ethoxy)-phenyl)-5,6,7,8-tetrahydronaphthalene-2-ol; cis-1-(6'-pyrrolodinoethoxy-3'-pyridyl)-2-phenyl-6-hydroxy-1,2,3,4-tetrahydronaphthalene; 1-(4'-pyrrolidinoethoxyphenyl)-2-(4"-fluorophenyl)-6-hydroxy-1,2,3,44etrahydroisoquinoline; cis-6-(4-hydroxyphenyl)-5-(4-(2-piperidin-1-yl-ethoxy)-phenyl)-5,6,7,8-tetrahydronaphthalene-2-ol; and 1-(4'-pyrrolidinolethoxyphenyl)-2-phenyl-6-hydroxy-1,2,3,4-tetrahydroisoquinoline.

Other estrogen agonist/antagonists are described in U.S. Pat. No. 4,133,814, which discloses derivatives of 2-phenyl-3-aroyl-benzothiophene and 2-phenyl-3-aroylbenzothiophene-1-oxide.

Other anti-osteoporosis agents, which can be used as the second agent in combination with a compound of the present invention, include, for example, the following: parathyroid hormone (PTH) (a bone anabolic agent); parathyroid hormone (PTH) secretagogues (see, e.g., U.S. Pat. No. 6,132,774), particularly calcium receptor antagonists; calcitonin; vitamin D and vitamin D analogs.

Any selective androgen receptor modulator (SARM) can be used in combination with a compound of the present invention. A selective androgen receptor modulator (SARM) is a compound that possesses androgenic activity and which exerts tissue-selective effects. SARM compounds can function as androgen receptor agonists, partial agonists, partial antagonists or antagonists. Examples of suitable SARMs include compounds such as cyproterone acetate, chlormadinone, flutamide, hydroxyflutamide, bicalutamide, nilutamide, spironolactone, 4-(trifluoromethyl)-2(1H)-pyrrolidino [3,2-g]quinoline derivatives, 1,2-dihydropyridino[5,6-g]quinoline derivatives and piperidino[3,2-g]quinolinone derivatives.

Cypterone, also known as (1b,2b)-6-chloro-1,2-dihydro-17-hydroxy-3'H-cyclopropa[1,2]pregna-1,4,6-triene-3,20-dione is disclosed in U.S. Pat. No. 3,234,093. Chlormadinone, also known as 17-(acetyloxy)-6-chloropregna-4-,6-diene-3,20-dione, in its acetate form, acts as an anti-androgen and is disclosed in U.S. Pat. No. 3,485,852. Nilutamide, also known as 5,5-dimethyl-3-[4-nitro-3-(trifluoromethyl)phenyl]-2,4-imidazolidinedione and by the trade name Nilandron® is disclosed in U.S. Pat. No. 4,097,578. Flutamide, also known as 2-methyl-N-[4-nitro-3-(trifluoromethyl)phenyl]propanamide and the trade name Eulexin® is disclosed in U.S. Pat. No. 3,847,988. Bicalutamide, also known as 4'-cyano-a',a',a'-trifluoro-3-(4-fluorophenylsulfonyl)-2-hydroxy-2-methylpropiono-m-toluidide and the trade name Casodex® is disclosed in EP-100172. The enantiomers of biclutamide are discussed by Tucker et al., J. Med. Chem., 31:885-887 (1988). Hydroxyflutamide, a known androgen receptor antagonist in most tissues, has been suggested to function as a SARM for effects on IL-6 production by osteoblasts as disclosed in Hofbauer et al., J. Bone Miner. Res., 14:1330-1337 (1999). Additional SARMs have been disclosed in U.S. Pat. No. 6,017,924; WO 01/16108, WO 01/16133, WO 01/16139, WO 02/00617, WO 02/16310, U.S. Patent Application Publication No. US 2002/0099096, U.S. Patent Application Publication No. US 2003/0022868, WO 03/011302 and WO 03/011824.

Any compound having activity as an LXR modulator can serve as the second compound in the combination therapy aspect of the present invention. The term LXR modulator refers to compounds that modulate the liver X receptor (LXR), which has been identified as a regulator of cellular and whole body cholesterol metabolism. Such LXR modulation activity is readily determined by those skilled in the art according to standard assays (e.g., U.S. Pat. No. 6,140,343). A variety of LXR modulators will be known to those skilled in the art, for example, those disclosed in U.S. Patent Application Publication Nos. 2003/01814206, 2005/0080111, and 2005/0245515.

All of the above referenced patents and patent applications are hereby incorporated by reference herein.

The combinations can be co-formulated or in the form of kits packaged to provide appropriate dosages for co-administration.

The above other therapeutic agents, when employed in combination with the compounds of the present invention, may be used, for example, in those amounts indicated in the Physicians' Desk Reference (PDR) or as otherwise determined by one of ordinary skill in the art.

The following examples further illustrate the present invention, but of course, should not be construed as in any way limiting its scope.

The following abbreviations are used herein:
ee=enantiomeric excess
DMF=dimethylformamide
EtOAc=ethyl acetate
LDA=lithium diisopropylamide
Hünig's Base=DIEA=iPr$_2$NEt=N,N-diisopropylethylamine
Me=methyl
Et=ethyl
n-Bu=n-butyl
Bn=benzyl
iPr=isopropyl
Allyl=1-propenyl
RT=retention time
TFA=trifluoroacetic acid
THF=tetrahydrofuran
TLC=thin layer chromatography
TMS=trimethylsilyl
t-Bu=tert-butyl
MeI=methyl iodide
(BOC)$_2$O=di-tert-butyl dicarbonate
Ac$_2$O=acetic anhydride
TEA=NEt$_3$=Et$_3$N=triethylamine
n-BuLi=n-butyllithium
rt=room temperature
LC=liquid chromatography
Ph=phenyl
EtOH=ethanol
BuOH=butan-1-ol
DCE=dichloroethane
DMSO=dimethylsulfoxide
MS=molecular sieves
MS (ES)=Electro-Spray Mass Spectrometry
sat=saturated
AcOH=acetic acid
MeOH=methanol
Et$_2$O=diethyl ether
Ac=acetyl
h=hours
EDCI=water soluble dicarbonyl diimide, 1-(3-dimethylaminopropyl)-3-ethylcarbodiimide hydrochloride
HOBT=1-hydroxy-benzotriazole
TBAF=tetrabutylammonium fluoride
TBAF.3H$_2$O=tetrabutylammonium fluoride trihydrate
DMA=dimethylacetamide
DME=1,2-dimethoxyethane
HRMS=high resolution mass spectrometry
TBME=MTBE=methyl tert-butyl ether (i.e., 2-methoxy-2-methyl-propane)
PyBroP=bromo-tris-pyrrolidino-phosphonium hexafluorophosphate
PyBOP=benzotriazol-1-yl-oxytripyrrolidinophosphonium hexafluorophosphate
DEA=diethylamine
IPA=isopropylamine
TMSCl=trimethylsilylchloride
MS=mass spectrum
NMR=nuclear magnetic resonance
TMSI=trimethylsilyliodide
TMS=trimethylsilyl
PPA=polyphosphoric acid
LDA=lithium diisopropylamine
UV=ultraviolet
DCM=dichloromethane
DMAC=N,N-dimethylacetamide
DAST=diethylaminosulfurtrifluoride
HPLC=high performance liquid chromatography
SFC=super critical fluid chromatography
TBAB=tetrabutylammonium bromide
ACN=acetonitrile
IIDQ=polystyrene resin
TosMIC=tosylmethyl isocyanide
BINAP=2,2'-bis(diphenylphosphino)-1,1'-binaphthyl
Pd$_2$ (dba)$_3$=tris-(dibenzylideneacetone) dipalladium(0)
Pd(PPh$_3$)$_4$=tetrakis(triphenylphosphine) palladium(0)
[Ir(COD)Cl]$_2$=Chloro-1,5-cyclooctadiene iridium (I) dimer
Ar=argon
TBAB=tetrabutylammonium bromide
9-BBN=9-borabicyclo[3.3.1]nonane
DEAD=diethyl azodicarboxylate
DPPA=diphenyl phosphoryl azide
NBS=N-bromosuccinimide
DMAP=4-di(methylamino)pyridine
LAH=lithium aluminum hydride
NMP=1-methyl-2-pyrrolidone
NMM=1-methyl-2-morpholine
Super-hydride=lithium triethylborohydride
DIBAL-H=diisobutylaluminium hydride
Dess-Martin periodinane=1,1,1-tris(acetyloxy)-1,1-dihydro-1,2-benziodoxol-3-(1H)-one
Lawesson's reagent=2,4-bis(4-methoxyphenyl)-1,3,2,4-dithiadiphosphetane 2,4-disulfide
Jones[O] reagent=CrO$_3$/H$_2$SO$_4$/H$_2$O/acetone
PCy$_3$=tricyclohexylphosphine
Tf$_2$O=triflic anhydride=trifluoromethanesulfonic anhydride
Bu$_4$NBr=tetrabutylammonium bromide
TBDMSCl=tert-butylchlorodimethylsilane
TFFH=fluoro-N,N,N',N'-tetramethylformamidinium hexafluorophosphate
R,R—MnCl (Salen)=(1R,2R)-(−)-[1,2-cyclohexanediamino-N,N'-bis(3,5-di-t-butylsalicylidene)]manganese (III) chloride
LiOTf=lithium trifluoromethanesulfonate
Tf=trifluoromethanesulfonate
EtAlCl$_2$=ethyl aluminum dichloride
ZnEt$_2$=diethyl zinc
TsOH=4-methylbenzenesulfonic acid
Ts=4-methylbenzenesulfonate
n-Bu$_2$SnO$_2$=dibutyltin(IV) oxide
Boc=t-Boc=t-butoxycarbonyl
Pd(OH)$_2$/C=palladium (II) hydroxide on carbon
Pd/C=palladium on carbon
Fmoc=3,9-fluorenylmethoxycarbonyl
Cbz=carbobenzoxy allylMgBr=1-propenyl magnesium bromide
diglyme=diethylene glycol dimethyl ether=1-methoxy-2-(2-methoxyethoxy)ethane
TBME=tert-butyl methyl ether
L-proline =(S)-pyrrolidine-2-carboxylic acid
P(t-Bu)$_3$=tri-t-butyl phosphine
triphosgene=bis(trichloromethyl)carbonate Specifically exemplified compounds of Formula Ia and Ib are listed along with structure, name, HPLC retention time, molecular mass and the procedure employed to make such examples, in the proceeding text and in the tables set forth below. The absolute configuration of chiral examples was assigned by NMR comparison of the intermediate diastereomeric sulfinyl amides, but has not be confirmed by crystallographic assignment. Enantiomerically pure intermediate amines were obtained by separation of the racemic mixtures using SFC or by the chiral synthesis described in Procedures 4, 5 and 6.

The chromatography techniques used to determine the compound retention times in the tables are as follows:

(1) LCMS=Phenomenex Luna C18 column, 4.6×50 mm eluting with 10-90% MeOH/H$_2$O over 4 minutes containing 0.1% TFA; 4 mL/min, monitoring at 220 nm;

(2) LCMS=Phenomenex Luna C18 column, 4.6×30 mm eluting with 10-90% MeOH/H$_2$O over 2 minutes containing 0.1% TFA; 5 mL/min, monitoring at 220 nm;

(3) LCMS=Phenomenex Luna C18 column, 4.6×50 mm eluting with 10-90% MeOH/H$_2$O over 4 minutes containing 0.1% NH$_4$OAc; 4 mL/min, monitoring at 220 nm;

(4) LCMS=Waters Sunfire C18 column, 4.6×50 mm×5 m eluting with 10-90% MeOH/H$_2$O over 4 minutes containing 0.1% TFA; 4 mL/min, monitoring at 220 nm;

(5) LCMS=YMC ODS column 4.6×50 mm eluting with 10-90% MeOH/H$_2$O over 4 minutes containing 0.1% TFA, 4 mL/min, monitoring at 220 nm;

(6) LC=Chromolith SpeedROD column, 4.6×50 mm eluting with 10-90% MeOH/H$_2$O over 4 minutes containing 0.2% phosphoric acid, 4 mL/min, monitoring at 220 nm;

(7) LC=Phenomenex Synergi 4u POLAR-RP column, 21.2×100 mm eluting with 10-90% ACN/H$_2$O over 12 minutes containing 0.1% TFA; 4 mL/min, monitoring at 220 nm;

(8) LCMS=Phenomenex Luna C18 column, 4.6×50 mm eluting with 10-90% ACN/H$_2$O over 4 minutes containing 0.1% NH$_4$OAc; 4 mL/min, monitoring at 220 nm;

(9) LC=Chromolith SpeedROD column, 4.6×50 mm eluting with 10-90% ACN/H$_2$O over 2 minutes containing 0.2% phosphoric acid, 5 mL/min, monitoring at 220 nm;

(10) LCMS=Waters Sunfire C18 column, 4.6×50 mm eluting with 10-90% ACN/H$_2$O over 4 minutes containing 10 mM NH$_4$OAc; 4 mL/min, monitoring at 220 nm;

(11) LC=Phenomenex Luna C18 column, 4.6×50 mm eluting with 10-90% MeOH/H$_2$O over 4 minutes containing 0.2% phosphoric acid, 4 mL/min, monitoring at 220 nm;

(12) LCMS=Chromolith Performance RP-18e column, 4.6×100 mm eluting with 10-90% MeOH/H$_2$O over 2 minutes containing 0.1% trifluoroacetic acid, 5 mL/min, monitoring at 220 nm;

(13) LC=Chromolith Performance RP-18e column, 4.6×100 mm eluting with 10-90% acetonitrile/H$_2$O over 2 minutes containing 0.1% trifluoroacetic acid, 4 mL/min, monitoring at 220 nm;

(14) LCMS=Phenomenex Luna C18 column, 4.6×30 mm eluting with 10-90% ACN/H$_2$O over 2 minutes containing 0.1% TFA; 5 mL/min, monitoring at 220 nm;

(15) LCMS=Phenomenex Luna C18 column, 4.6×50 mm eluting with 10-90% ACN/H$_2$O over 4 minutes containing 0.1% TFA; 4 mL/min, monitoring at 220 nm;

(16) LCMS=Waters Sunfire C18 column, 4.6×50 mm eluting with 10-90% MeOH/H$_2$O over 8 minutes containing 0.1% TFA; 4 mL/min, monitoring at 220 nm.

The molecular mass of the compounds listed in the tables set forth below were determined by MS (ES) by the formula m/z.

Example 1

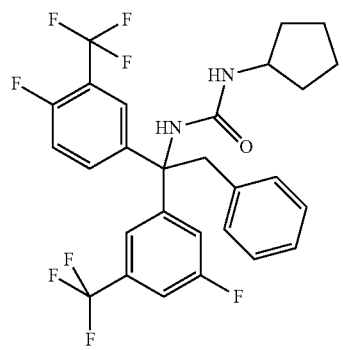 [SMILES: O=C(NC1CCCC1)NC(Cc1ccccc1)(c1cc(F)cc(C(F)(F)F)c1)c1ccc(F)c(C(F)(F)F)c1]

1-cyclopentyl-3-(1-(4-fluoro-3-(trifluoro methyl)phenyl)-1-(3-fluoro-5-(trifluoromethyl)phenyl)-2-phenylethyl)urea Procedure 1

1-(4-fluoro-3-(trifluoro methyl)phenyl)-1-(3-fluoro-5-(trifluoromethyl)phenyl)-2-phenylethanamine

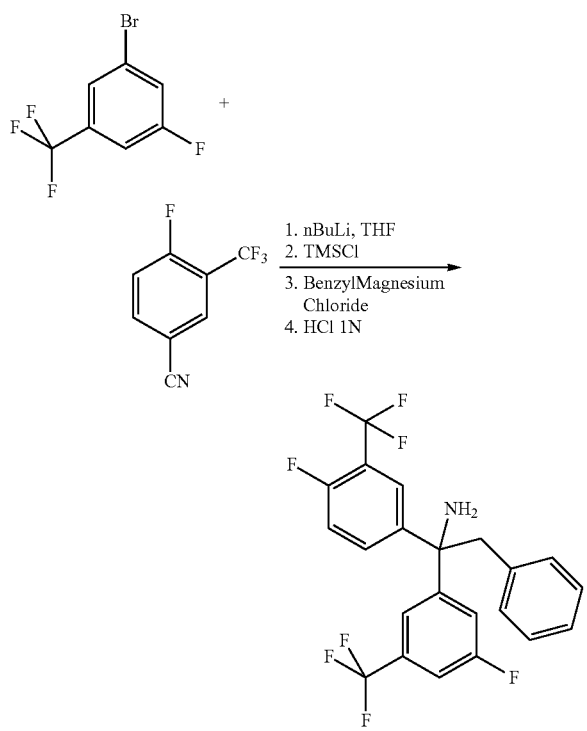

An ether solution (40 mL) of 1-bromo-3-fluoro-5-(trifluoromethyl)benzene (2.0 g, 8.23 mmol) was stirred in an oven-dried round bottom flask at −78° C. under Ar. n-BuLi (2.5 M in hexanes, 3.6 ml, 9.05 mmol, 1.1 eq) was added dropwise. The resulting solution was stirred at −78° C. for 30 min. A solution of 4-fluoro-3-(trifluoromethyl)benzonitrile (1.55 g, 8.23 mmol, 1.0 eq) in Et$_2$O (5 mL) was added dropwise. The resulting reddish mixture was stirred at −78° C. for 2 h. TMSCl (pretreated with Et$_3$N (TMSCl:Et$_3$N=10:1, v:v), 1.14 mL, 1.2 eq) was added dropwise. The dry ice bath was removed, and the resulting slurry was stirred at room temperature for 2 h. The reaction was cooled to −78° C. and a solution of benzyl magnesium chloride in THF (2.0 M, 8.4 m, 2 eq) was added dropwise. The resulting mixture was slowly warmed up to room temperature and stirred at room temperature overnight. (NHC5 (100 mL) was added. The mixture was stirred at room temperature for 30 min, extracted with Et$_2$O (2×), washed with 1N NaOH, H$_2$O and brine, dried over Na$_2$SO$_4$, filtered, and concentrated to dryness. The residue was purified by flash column chromatography (silica gel, hexanes:ethyl acetate) to give 1-(4-fluoro-3-(trifluoromethyl)phenyl)-1-(3-fluoro-5-(trifluoromethyl)phenyl)-2-phenylethanamine (1.6 g, yield: 44%). LC-MS ESI 3.42 min 429.2 (M-NH$_3$+H); $^1$H NMR (400 MHz, CHLOROFORM-D) δ ppm 7.66 (dd, J=6.7, 2.3 Hz, 1H), 7.49-7.59 (m, 1H), 7.45 (s, 1H), 7.18-7.30 (m, 6H), 6.74 (d, J=6.9 Hz, 2H), 3.57 (m, 2H).

Procedure 2

1-(4-Fluoro-3-(trimfluoromethyl)phenyl)-1-(3-fluoro-5-(trifluoromethyl)phenyl)-2-phenylethanamine (300 mg, 0.67 mmol) and cyclopentyl isocyanate (0.4 mL, 5.3 eq) were stirred in 1,4-dioxane (2 mL) at room temperature overnight. The reaction mixture was concentrated, and purified by flash chromatography (silica gel, hexanes/EtOAc) to give the racemic mixture of 1-cyclopentyl-3-(1-(4-fluoro-3-(trifluoromethyl)phenyl)-1-(3-fluoro-5-(trifluoromethyl)phenyl)-2-phenylethyl)urea (250 mg, yield: 67%). The racemate (250 mg) was dissolved in 10% isopropanol in heptane, and was resolved by chiral prep HPLC using an AD column (10% isopropanol heptane/0.1% DEA, isocratic) to give the fast eluting enantiomer 1 (110 mg) corresponding to (S)-1-cyclopentyl-3-(1-(4-fluoro-3-(trifluoromethyl)phenyl)-1-(3-fluoro-5-(trifluoromethyl)phenyl)-2-phenylethyl)urea, (analytical chiral HPLC (AD, 10% isopropanol/heptane/0.1% DEA, isocratic), retention time=4.85 min) and the slow eluting enantiomer 2 (105 mg) corresponding to (R)-1-cyclopentyl-3-(1-(4-fluoro-3-(trifluoromethyl)phenyl)-1-(3-fluoro-5-(trifluoromethyl)phenyl)-2-phenylethyl)urea, (analytical chiral HPLC (AD, 10% isopropanol/heptane/0.1% DEA, isocratic), retention time=14.11 min) LCMS (10-90% MeOH in H$_2$O with 0.1% TFA in a 4-min run), retention time=4.33 min, 557.32 (M+H); $^1$H NMR (400 MHz, CDCl$_3$) δ ppm 7.36-7.44 (m, 2H), 7.23-7.29 (m, 3H), 7.13-7.21 (m, 4H), 6.68-6.74 (m,

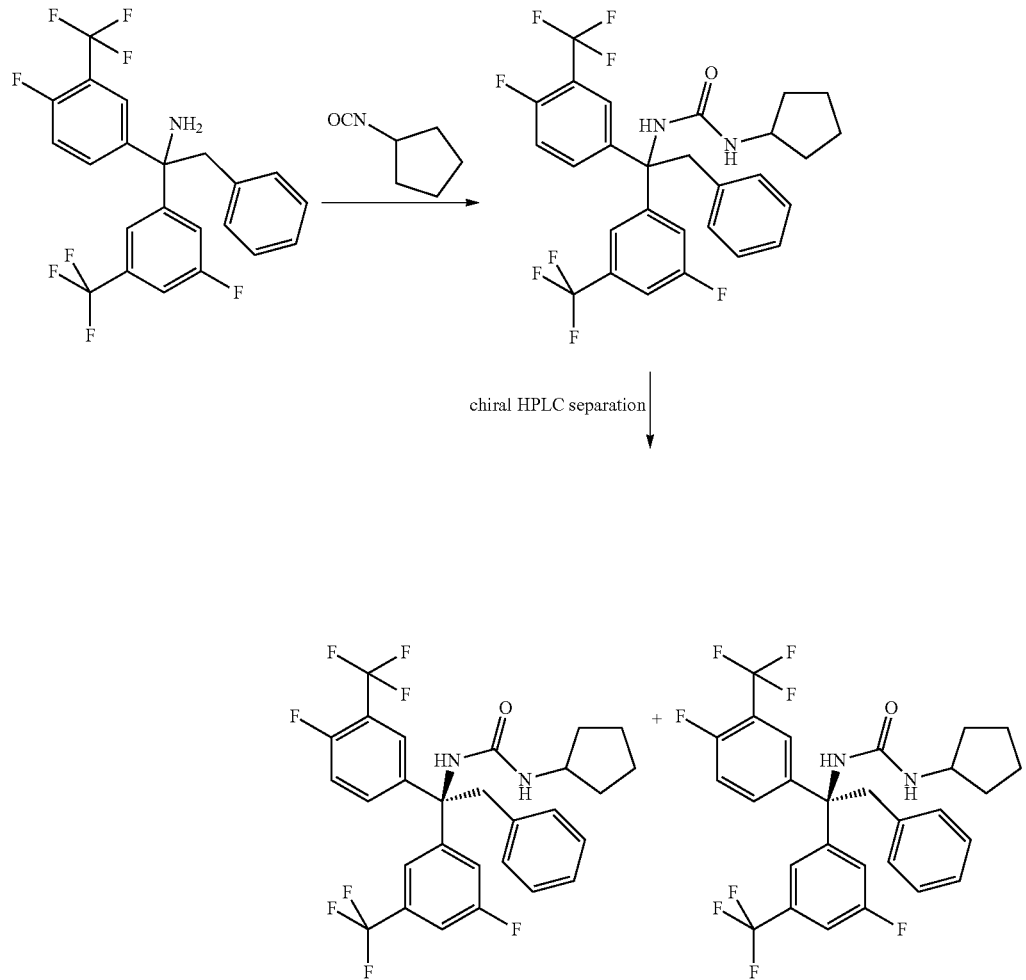

2H), 4.84 (s, 1H), 4.40 (s, br, 1H), 3.84-3.95 (m, 3H), 1.88-1.98 (m, 2H), 1.56-1.68 (m, 4H), 1.34 (d, J=6.36 Hz, 2H).

Example 2

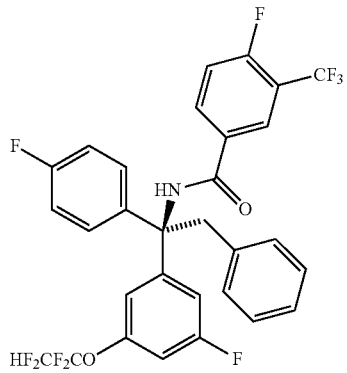

(R)-4-Fluoro-N-(1-(3-fluoro-5-(1,1,2,2-tetrafluoroethoxy)phenyl)-1-(4-fluorophenyl)-2-phenylethyl)-3-(trifluoromethyl)benzamide Procedure 3

Preparation of 1-bromo-3-fluoro-5-(1,1,2,2-tetrafluoroethoxy)benzene

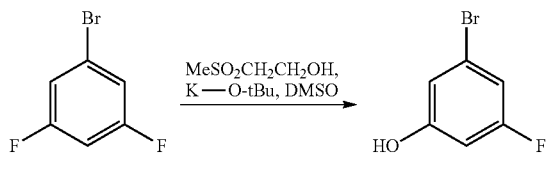

To a solution of 1-bromo-3,5-difluorobenzene (30.6 mL, 0.266 mole) and 2-(methylsulfonyl)ethanol (66 g, 0.531 mole) in DMSO (240 mL) was added potassium tert-butoxide (76.6 g, 0.682 mole) at 0° C. The resulting mixture was stirred at room temperature for 3 h and quench with 4N HCl slowly to pH≤1. The desired product was extracted with Et₂O (12 L) until no product was detected in the aqueous layer. The Et₂O was evaporated under reduced pressure to one third the amount of the solvent and washed with 1N NaOH (12 L). Then, the NaOH solution was adjusted to pH=3 and extracted with Et₂O until no desired product was detected in the aqueous layer. The Et₂O was evaporated under reduced pressure and passed through an Al₂O₃ column eluted with Et₂O to afford 3-bromo-5-fluorophenol as a colorless oil (48 g, 94% yield). LC-MS 190.33 (M+H); Analytical HPLC=2.26 minutes (0-100% CH₃CN in H₂O with 0.1% TFA in a 4-min run); ¹H NMR (400 MHz, CD₃OD) δ ppm 6.88-6.64 (m, 2H), 6.58-6.30 (m, 1H), 4.99 (s, 1H).

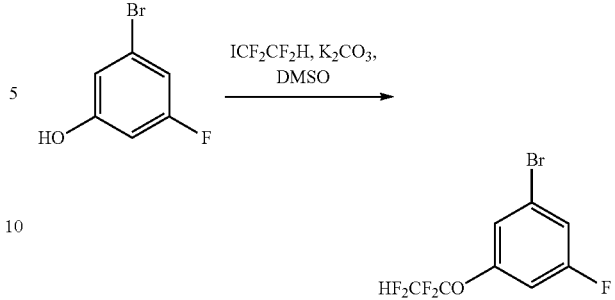

To a solution of 3-bromo-5-fluorophenol (47 g, 0.249 mole) and 2,2,3,3-tetrafluoroethyliodine (68 g, 0.298 mole) in DMSO (260 mL) was added potassium carbonate (137 g, 0.992 mole). The resulting mixture was stirred at 70° C. for 16 h. The inorganic salt was removed by filtration and the filter cake was washed with Et₂O (500 mL). The filtrate was diluted with 500 mL of H₂O and extracted with excess Et₂O (1.5 L). The Et₂O layer was washed with 0.5 N NaOH (250 mL), H₂O, brine, and dried over Na₂SO₄. The solvent was evaporated under reduced pressure and the crude product was passed through an Al₂O₃ column using Et₂O as the eluting solvent to afford 1-bromo-3-fluoro-5-(1,1,2,2-tetrafluoroethoxy)benzene (63 g, yield: 87%) as yellowish oil. LC-MS (ESI): 290.21 (M+H), retention time=3.66 minutes (0-100% MeOH in H₂O with 0.1% TFA in a 4-min run); ¹H NMR (400 MHz, CD₃OD) δ ppm 7.45-7.22 (m, 2H), 7.10 (d, J=9.23 Hz, 1H), 6.59-5.94 (m, 1H).

Procedure 4

(3-Fluoro-5-(1,1,2,2-tetrafluoroethoxy)phenyl)(4-fluorophenyl)methanone

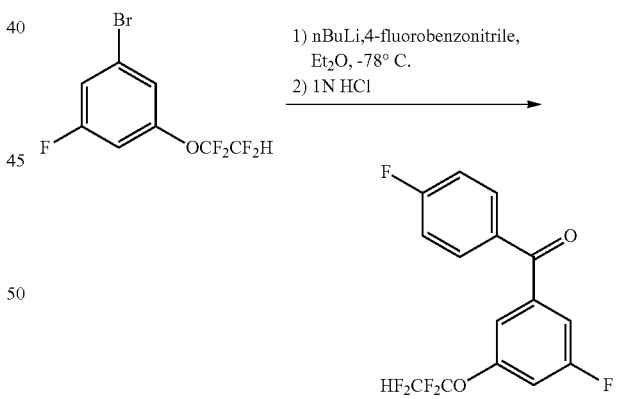

To an oven-dried round-bottomed flask cooled at −78° C., was added 1-bromo-3-fluoro-5-(1,1,2,2-tetrafluoroethoxy)benzene (7.20 g, 24.82 mmol) in anhydrous ether (300 mL) under Argon, and the mixture was stirred at −78° C. for 10 min. n-BuLi (2.5 M in hexanes, 11.5 mL, 28.75 mmol, 1.16 eq) was added dropwise at −78° C. The reaction mixture was stirred at −78° C. for 45 min. An Et₂O solution (20 mL) of 4-fluorobenzonitrile (3.06 g, 25.29 mmol, 1.02 eq) was added dropwise. The resulting reddish solution was stirred at −78° C. for 2 h. The reaction mixture was quenched by adding 1N HCl (200 mL), and the dry ice-acetone bath was removed. The resulting slurry was stirred at room temperature for 1 h followed by the addition of Et$_2$O (100 mL). The organic layer was separated, and then washed with sat'd NaHCO$_3$, H$_2$O, brine, dried over MgSO$_4$, filtered, and concentrated to dryness. The residue was purified by flash chromatography (EtOAc/hexanes=0 to 30%) to give (3-fluoro-5-(1,1,2,2-tetrafluoroethoxy)phenyl)(4-fluorophenyl)methanone as slightly tan oil (7.20 g, yield: 86.9%). $^1$H NMR (400 MHz, CDCl$_3$) δ ppm 7.85-7.80 (m, 2H), 7.40-7.37 (m, 2H), 7.20-7.14 (m, 3H), 5.92 (tt, J=52, 2.8 Hz, 1H); LC-MS (ESI) 335.31 (M+H), retention time=3.81 min (10-90% MeOH in H$_2$O with 0.1% TFA in a 4-min run).

Procedure 5

(R,E/Z)—N-((3-fluoro-5-(1,1,2,2-tetrafluoroethoxy)phenyl)(4-fluorophenyl)methylene)-2-methylpropane-2-sulfinamide

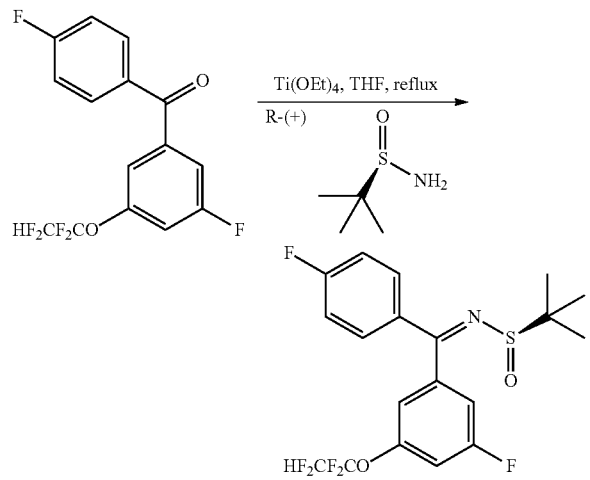

(3-Fluoro-5-(1,1,2,2-tetrafluoroethoxy)phenyl)(4-fluorophenyl)methanone (3.3 g, 9.88 mmol) was stirred in anhydrous THF (20 mL) at r.t. under N$_2$. (R)-(+)-2-Methylpropane-2-sulfinamide (1.21 g, 10 mmol, 1.01 eq) was added as one single portion, followed by addition of Ti(OEt)$_4$ (3.09 mL, 14.91 mmol, 1.51 eq). The resulting solution was heated at reflux for 48 hours. The cooled mixture was evaporated. H$_2$O (100 mL) was added, followed by the addition of EtOAc (100 mL). The mixture was filtered through celite, and washed with EtOAc (200 mL). The filtrate was washed with H$_2$O and brine, dried over Na$_2$SO$_4$, filtered, and concentrated to dryness. The residue was purified by silica gel flash chromatography and was eluted with hexanes and EtOAc (0-30% EtOAc in hexanes) to give (R)—N-((3-fluoro-5-(1,1,2,2-tetrafluoroethoxy)phenyl)(4-fluorophenyl)methylene)-2-methylpropane-2-sulfinamide as yellowish viscous oil which solidified after drying under vacuum as light yellow solids (3.50 g, yield: 81.0%). LC-MS ESI 437.88 (M+H), retention time=3.83 min (10-90% MeOH in H$_2$O with 0.1% TFA in a 4-min gradient); $^1$H NMR (400 MHz, CDCl$_3$) δ ppm 7.82-6.99 (br, m, 7H), 5.90 (tt, J=52, 4 Hz, 1H), 1.31 (s, 9H).

Procedure 6

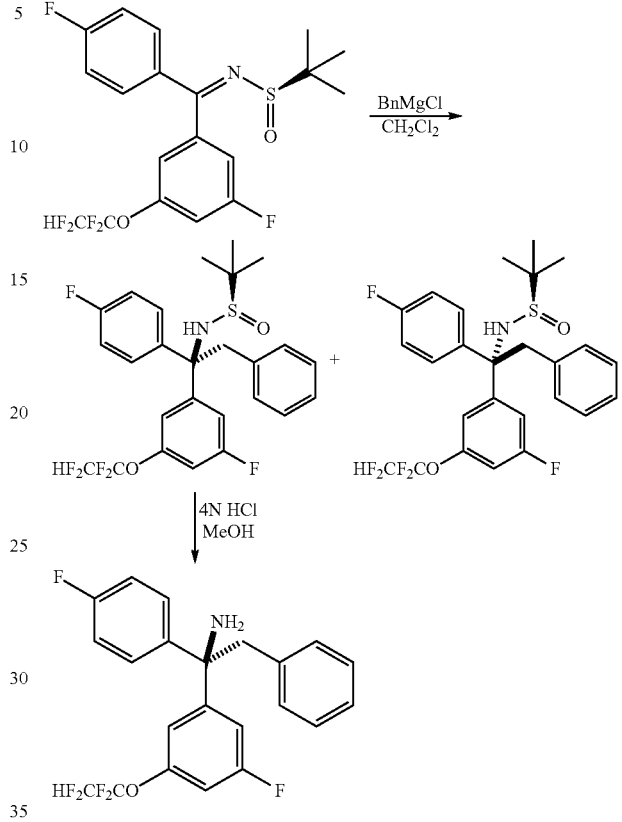

(R)—N-((3-Fluoro-5-(1,1,2,2-tetrafluoroethoxy)phenyl)(4-fluorophenyl)methylene)-2-methylpropane-2-sulfinamide (150 mg, 0.34 mmol) was stirred in anhydrous CH$_2$Cl$_2$ (7 mL) at −78° C. for 5 min under Argon. BF$_3$Et$_2$O (0.10 mL, 2.0 eq) was added dropwise. The mixture was stirred at −78° C. for 10 min. Benzylmagnesium chloride (1.0 M in Et$_2$O, 1.4 mL, 3.0 eq) was added slowly at −78° C., and the resulting mixture was stirred at −78° C. for 1.5 h. The reaction mixture was quenched with sat. NH$_4$Cl and then extracted with Et$_2$O (2×). The combined organic portion was washed with H$_2$O and brine, dried over Na$_2$SO$_4$, filtered, and concentrated to dryness. The residue was purified by flash chromatography (silica gel, EtOAc/hexanes=0-30%) to give the fast eluting fraction corresponding to (R)—N—((S)-1-(3-fluoro-5-(1,1,2,2-tetrafluoroethoxy)phenyl)-1-(4-fluorophenyl)-2-phenylethyl)-2-methylpropane-2-sulfinamide (29 mg): $^1$H NMR (400 MHz, CDCl$_3$) δ ppm 1.23 (s, 9H) 3.63 (d, J=12.4 Hz, 1H), 3.94 (d, J=12.4 Hz, 1H), 4.21 (s, 1H), 6.90 (m, 1H), 5.90 (m, 1H), 6.94-7.09 (m, 4H), 7.16-7.20 (m, 4H), 7.31-7.39 (m, 2H); LC-MS (ESI) 530.36 (M+H), retention time=4.11 min (10-90% MeOH in H$_2$O with 0.1% TFA in a 4-min run); and the slow eluting fraction corresponding to (R)—N—((R)-1-(3-fluoro-5-(1,1,2,2-tetrafluoroethoxy)phenyl)-1-(4-fluorophenyl)-2-phenylethyl)-2-methylpropane-2-sulfinamide (146 mg, total yield: 96.4%): $^1$H NMR (400 MHz, CDCl$_3$) δ ppm 7.35-7.43 (m, 2H), 7.13-7.20 (m, 3H), 7.07 (t, J=8.72 Hz, 2H), 6.93 (dd, J=7.58, 1.77 Hz, 2H), 6.84 (d, J=8.59 Hz, 1H), 6.70 (m, 2H), 5.85 (tt, J=52, 4 Hz, 1H), 4.25 (s, 1H), 4.02 (d, J=12.63 Hz, 1H), 3.58 (d, J=12.63 Hz, 1H), 1.20 (s, 9H); $^{13}$C NMR (CDCl$_3$) δ ppm 23.02, 46.99, 56.53, 65.70, 104.55, 104.96, 105.37, 107.06, 107.47, 107.92, 108.17, 109.56, 109.97, 112.32, 112.55, 115.37, 115.58, 116.13, 116.41, 116.69, 119.12, 127.21, 128.14, 130.91, 130.99, 132.07, 134.34, 137.48, 137.51, 149.09, 149.21, 150.52, 150.45, 161.20, 163.67; LC-MS (ESI) 530.36 (M+H), retention time=4.11 min (10-90% MeOH in H₂O with 0.1% TFA in a 4-min run).

(R)-1-(3-fluoro-5-(1,1,2,2-tetrafluoroethoxy)phenyl)-1-(4-fluorophenyl)-2-phenylethanamine

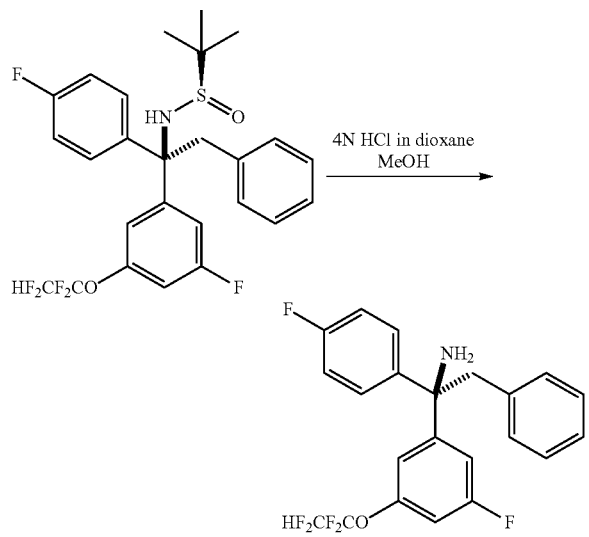

(R)—N—((R)-1-(3-fluoro-5-(1,1,2,2-tetrafluoroethoxy)phenyl)-1-(4-fluorophenyl)-2-phenylethyl)-2-methylpropane-2-sulfinamide (234 mg, 0.442 mmol) was stirred in 4N HCl in dioxane (1.5 mL) and MeOH (1.5 mL) at room temperature under Ar for 10 min. The reaction mixture was concentrated, and then purified by flash chromatography (silica gel, hexanes/EtOAc) to give (R)-1-(3-fluoro-5-(1,1,2,2-tetrafluoroethoxy)phenyl)-1-(4-fluorophenyl)-2-phenylethanamine (169 mg, 90%). LC-MS (ESI) 409.16 (M-NH₃+H), retention time=3.26 minutes (0-100% MeOH in H₂O with 0.1% TFA in 4-min run); Analytical HPLC: 2.52 minutes (0-100% CH₃CN in H₂O with 0.1% TFA in 4-min run); ¹H NMR (400 MHz, CD₃OD) δ ppm 7.29-7.50 (m, 2H), 6.87-7.22 (m, 8H), 6.77 (d, J=6.15 Hz, 2H), 6.04-6.48 (m, 1H), 3.57 (s, 2H).

Procedure 7

(R)-4-fluoro-N-(1-(3-fluoro-5-(1,1,2,2-tetrafluoroethoxy)phenyl)-1-(4-fluorophenyl)-2-phenylethyl)-3-(trifluoromethyl)benzamide

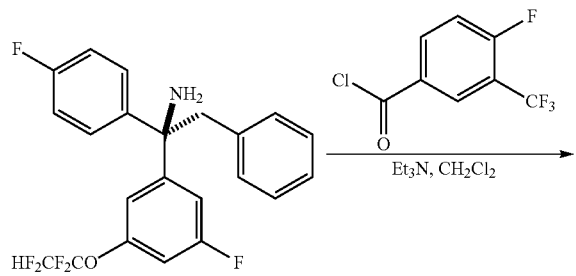

-continued

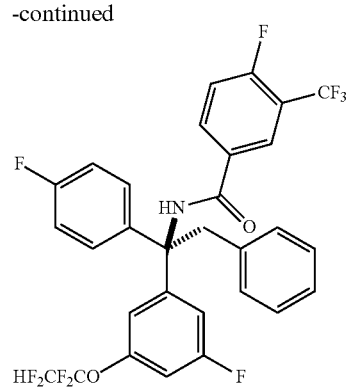

To a solution of (R)-1-(3-fluoro-5-(1,1,2,2-tetrafluoroethoxy)phenyl)-1-(4-fluorophenyl)-2-phenylethanamine (30 mg, 0.079 mmol) in CH₂Cl₂ (0.2 mL) was added 4-fluoro-3-(trifluoromethyl)benzoyl chloride (0.048 mL, 0.158 mmol), followed by Et₃N (0.04 mL, 0.158 mmol). The resulting mixture was stirred at room temperature for 5 h. The crude product was purified on a preparative HPLC column type using 30 to 100% CH₃CN in H₂O with 0.1% TFA for 10 minutes as mobile phase. The solvent was removed under reduced pressure to afford (R)-4-fluoro-N-(1-(3-fluoro-5-(1,1,2,2-tetrafluoroethoxy)phenyl)-1-(4-fluorophenyl)-2-phenylethyl)-3-(trifluoromethyl)benzamide (35 mg, 80% yield) as white powder. LC-MS (ESI) 568.30 (M+H), retention time=4.27 min (0-100% MeOH in H₂O with 0.1% TFA in a 4-min run); Analytical HPLC: 3.95 min (0-100% CH₃CN in H₂O with 0.1% TFA in a 4-min run, purity 100%); ¹H NMR (400 MHz, CD₃OD) δ ppm 3.88-4.01 (m, 1H), 4.10 (d, J=13.18 Hz, 1H), 6.69 (d, J=7.47 Hz, 2H), 6.97-7.51 (m, 11H), 7.99 (d, J=5.71 Hz, 2H), 8.90 (s, 1H).

Example 3

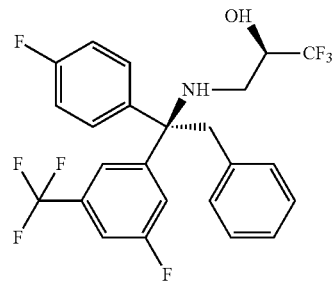 [SMILES: O[C@H](CN[C@](Cc1ccccc1)(c1ccc(F)cc1)c1cc(F)cc(C(F)(F)F)c1)C(F)(F)F]

(R)-1,1,1-trifluoro-3-((R)-1-(3-fluoro-5-(trifluoromethyl)phenyl)-1-(4-fluorophenyl)-2-phenylethylamino)propan-2-ol Procedure 8

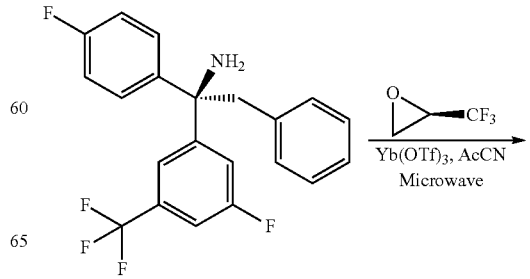

223
-continued

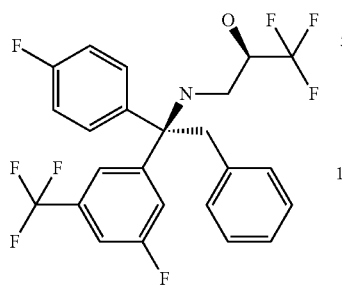

(R)-1-(3-fluoro-5-(trifluoromethyl)phenyl)-1-(4-fluorophenyl)-2-phenylethanamine was prepared as described in Procedures 4, 5 and 6. (R)-1-(3-fluoro-5-(trifluoromethyl)phenyl)-1-(4-fluorophenyl)-2-phenylethanamine (50 mg, 0.133 mmol) was dissolved in anhydrous acetonitrile (0.26 mL). (R)-2-(trifluoromethyl)oxirane (0.07 mL, 0.625 mmol), (approximate 85:15 ratio of R to S) was added to the solution in a microwave vial followed by $Yb(OSO_2CF_3)_3$ (0.005 g, 0.008 mmol). The sealed vial was heated to 160° C. for 30 minutes under microwave irradiation. The crude product was purified by preparative HPLC using 30-100% acetonitrile in $H_2O$ with 0.1% TFA as mobile phase to give (R)-1,1,1-trifluoro-3-((R)-1-(3-fluoro-5-(trifluoromethyl)phenyl)-1-(4-fluorophenyl)-2-phenylethylamino)propan-2-ol as a colorless oil (30 mg, 46% yield). LC-MS (ESI): 361.15 (M+H), retention time=4.10 min (0-100% MeOH in $H_2O$ with 0.1% TFA); Analytical HPLC: 3.49 min ($CH_3CN$ in $H_2O$ with 0.1% TFA in 4 min run, purity 100%); $^1H$ NMR (400 MHz, $CD_3OD$) δ ppm 2.59-2.73 (m, 1H), 2.72-2.84 (m, 1H), 3.69 (m, 2H), 4.09 (m, 1H), 6.61-6.82 (m, 2H), 7.00-7.19 (m, 5H), 7.20-7.48 (m, 5H).

Example 4

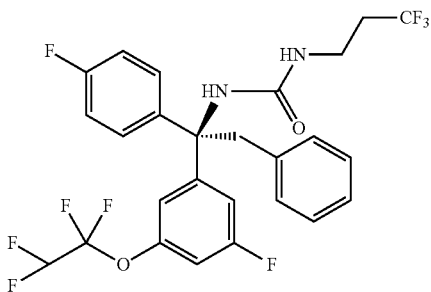 [SMILES: O=C(NCCC(F)(F)F)N[C@](Cc1ccccc1)(c1ccc(F)cc1)c1cc(F)cc(OC(F)(F)C(F)F)c1]

224
(R)-1-(1-(3-fluoro-5-(1,1,2,2-tetrafluoroethoxy)phenyl)-1-(4-fluorophenyl)-2-phenylethyl)-3-(3,3,3-trifluoropropyl)urea Procedure 9

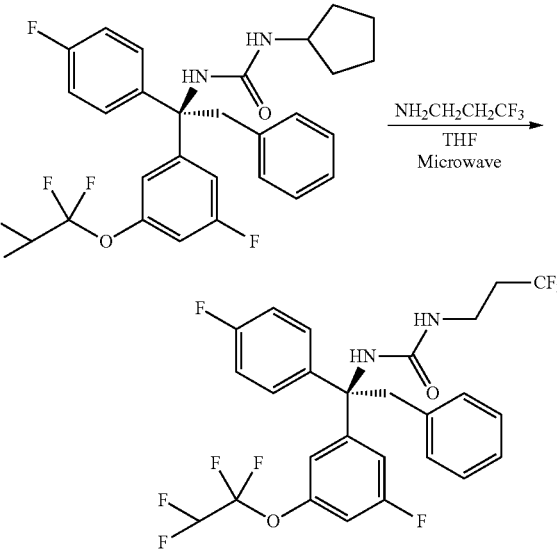

(R)-1-cyclopentyl-3-(1-(3-fluoro-5-(1,1,2,2-tetrafluoroethoxy)phenyl)-1-(4-fluorophenyl)-2-phenylethyl)urea was prepared as described in Procedure 2. To a microwave vial containing (R)-1-cyclopentyl-3-(1-(3-fluoro-5-(1,1,2,2-tetrafluoroethoxy)phenyl)-1-(4-fluorophenyl)-2-phenylethyl)urea (20 mg, 0.037 mmol) was added a pre-mixed solution of 3,3,3-trifluoromethylpropylamine (25 mg, 0.224 mmol) and $Et_3N$ (0.03 mL, 0.224 mmol) in THF (0.025 mL). The sealed vial was subjected to microwave irradiation at 150° C. for 1500 sec followed by dilution with MeOH. The crude product was isolated by preparative HPLC column type using 30-100% acetonitrile in $H_2O$ with 0.1% TFA as mobile phase to afford (R)-1-(1-(3-fluoro-5-(1,1,2,2-tetrafluoroethoxy)phenyl)-1-(4-fluorophenyl)-2-phenylethyl)-3-(3,3,3-trifluoropropyl)urea (76%) as white powder. LCMS (ESI): 565.36 (M+H), retention time=3.96 min (0-100% MeOH in $H_2O$ in a 4-min run); $^1H$ NMR (400 MHz, $CD_3OD$) δ ppm 2.18-2.41 (m, 2H), 3.34 (m, 2H), 3.75-3.87 (m, 1H), 3.88-4.00 (m, 1H), 6.07-6.45 (m, 1H), 6.71 (d, J=7.03 Hz, 2H), 6.85-7.05 (m, 5H), 7.05-7.22 (m, 5H).

Example 5

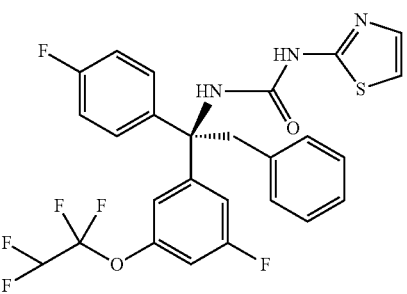 [SMILES: O=C(Nc1nccs1)N[C@](Cc1ccccc1)(c1ccc(F)cc1)c1cc(F)cc(OC(F)(F)C(F)F)c1]

225

(R)-1-(1-(3-fluoro-5-(1,1,2,2-tetrafluoroethoxy)phenyl)-1-(4-fluorophenyl)-2-phenylethyl)-3-(thiazol-2-yl)urea Procedure 10

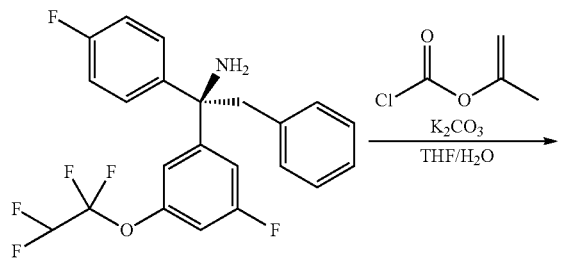

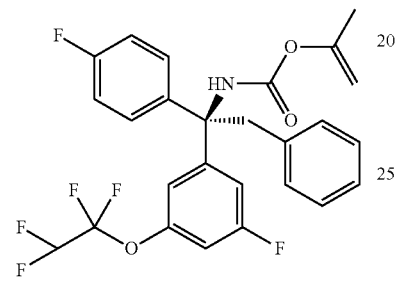

(R)-1-(3-fluoro-5-(1,1,2,2-tetrafluoroethoxy)phenyl)-1-(4-fluorophenyl)-2-phenylethanamine (48 mg, 0.11 mmol) was stirred in THF (0.5 mL) and H₂O (0.05 mL) at room temperature. K₂CO₃ (100 mg, 0.72 mmol, 6.6 eq) was added followed by the addition of isopropenyl chloroformate (0.030 mL, 0.275 mmol, 2.5 eq). The reaction mixture was stirred at room temperature overnight. The mixture was filtered, and the filtrate concentrated to dryness to give crude (R)-prop-1-en-2-yl 1-(3-fluoro-5-(1,1,2,2-tetrafluoroethoxy)phenyl)-1-(4-fluorophenyl)-2-phenylethylcarbamate as colorless film (60 mg, yield: quantative). LCMS: 4.18 min 409.27 (M-COOisopropenyl-NH₃+H) (4 min gradient, MeOH/H₂O 0.1% TFA).

226

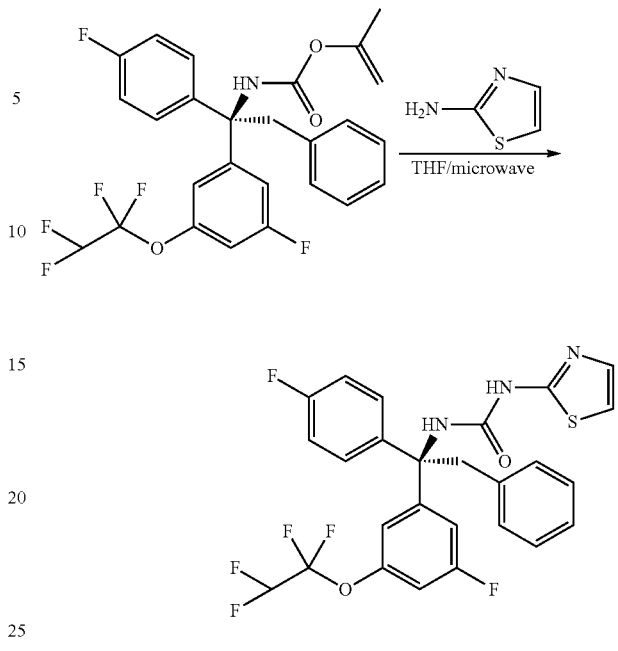

(R)-prop-1-en-2-yl 1-(3-fluoro-5-(1,1,2,2-tetrafluoroethoxy)phenyl)-1-(4-fluorophenyl)-2-phenylethylcarbamate (15 mg, 0.029 mmol) and 2-aminothiazole (8.2 mg, 0.082 mmol, 2.8 eq), and N-methylpyrrolidine (0.9 μl, 0.3 eq) were stirred in THF (0.3 mL) in a microwave vial. The reaction mixture was heated at 150° C. for 20 min under microwave irradiation. After cooling, the solvent was evaporated. The residue was purified by reverse phase HPLC (20-90% CH₃CN in H₂O with 0.1% TFA) to give pure (R)-1-(1-(3-fluoro-5-(1,1,2,2-tetrafluoroethoxy)phenyl)-1-(4-fluorophenyl)-2-phenylethyl)-3-(thiazol-2-yl)urea as white solids (6.5 mg, yield: 40.6%). $^1$H NMR (400 MHz, CDCl$_3$-D) δ ppm 7.29 (In, 1H), 7.23-7.18 (m, 3H), 7.16 (t, J=8.0 Hz, 2H), 7.02 (t, J=8.5 Hz, 2H), 6.94-6.89 (m, 4H), 6.71 (d, J=6.82 Hz, 2H), 5.86 (tt, J=47.1, 2.9 Hz, 1H), 3.84-3.75 (m, 2H); LC-MS (ESI) 552.28 (M+H), retention time=4.12 min (10-90% MeOH in H₂O with 0.1% TFA in a 4-min run).

TABLE 1

| Ex. No. | Structure | Name | Retention Time Min./ Molecular Mass | Prepared in the manner described in: |
|---|---|---|---|---|
| 6 | 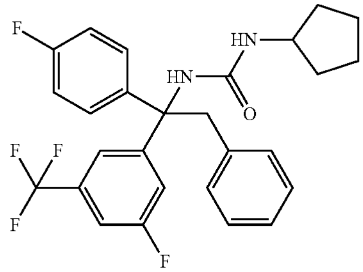 [SMILES: O=C(NC1CCCC1)NC(Cc1ccccc1)(c1ccc(F)cc1)c1cc(F)cc(C(F)(F)F)c1] | 1-cyclopentyl-3-(1-(3-fluoro-5-(trifluoromethyl)phenyl)-1-(4-fluorophenyl)-2-phenylethyl)urea | 3.61 LC 489.34 [M + H]⁺ | Procedure 1 and 2 |

TABLE 1-continued

| Ex. No. | Structure | Name | Retention Time Min./ Molecular Mass | Prepared in the manner described in: |
|---|---|---|---|---|
| 7 | 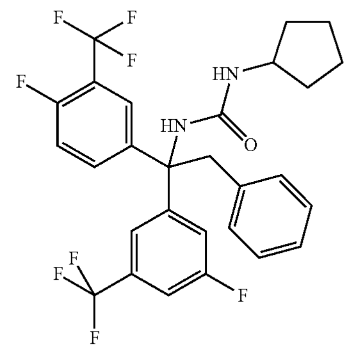 [SMILES: O=C(NC1CCCC1)NC(Cc1ccccc1)(c1cc(F)cc(C(F)(F)F)c1)c1ccc(F)c(C(F)(F)F)c1] | 1-cyclopentyl-3-(1-(4-fluoro-3-(trifluoromethyl)phenyl)-1-(3-fluoro-5-(trifluoromethyl)phenyl)-2-phenylethyl)urea | 4.30 LC 557.3 [M + H]⁺ | Procedure 1 and 2 |
| 8 | 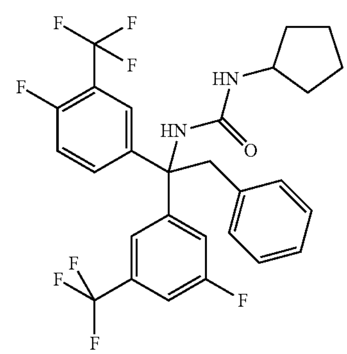 [SMILES: O=C(NC1CCCC1)NC(Cc1ccccc1)(c1cc(F)cc(C(F)(F)F)c1)c1ccc(F)c(C(F)(F)F)c1] | 1-cyclopentyl-3-(1-(4-fluoro-3-(trifluoromethyl)phenyl)-1-(3-fluoro-5-(trifluoromethyl)phenyl)-2-phenylethyl)urea | 4.30 LC 557.3 [M + H]⁺ | Procedure 1 and 2 |
| 9 | 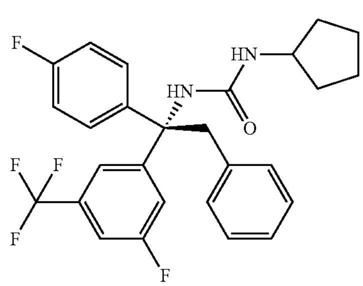 [SMILES: O=C(NC1CCCC1)N[C@@](Cc1ccccc1)(c1ccc(F)cc1)c1cc(F)cc(C(F)(F)F)c1] | (S)-1-cyclopentyl-3-(1-(3-fluoro-5-(trifluoromethyl)phenyl)-1-(4-fluorophenyl)-2-phenylethyl)urea | 3.60 LC 489.33 [M + H]⁺ | Procedure 4, 5, 6 and 2 |
| 10 | 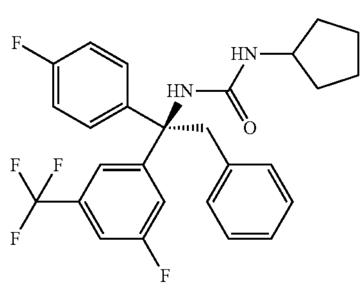 [SMILES: O=C(NC1CCCC1)N[C@](Cc1ccccc1)(c1ccc(F)cc1)c1cc(F)cc(C(F)(F)F)c1] | (R)-1-cyclopentyl-3-(1-(3-fluoro-5-(trifluoromethyl)phenyl)-1-(4-fluorophenyl)-2-phenylethyl)urea | 3.61 LC 489.33 [M + H]⁺ | Procedure 4, 5, 6 and 2 |

TABLE 1-continued

| Ex. No. | Structure | Name | Retention Time Min./ Molecular Mass | Prepared in the manner described in: |
| --- | --- | --- | --- | --- |
| 11 | 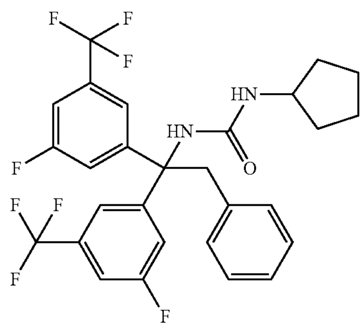 [SMILES: O=C(NC1CCCC1)NC(Cc1ccccc1)(c1cc(F)cc(C(F)(F)F)c1)c1cc(F)cc(C(F)(F)F)c1] | 1-(1,1-bis(3-fluoro-5-(trifluoromethyl)phenyl)-2-phenylethyl)-3-cyclopentylurea | 3.87 LC 557.34 [M + H]$^+$ | Procedure 14 and 2 |
| 12 | 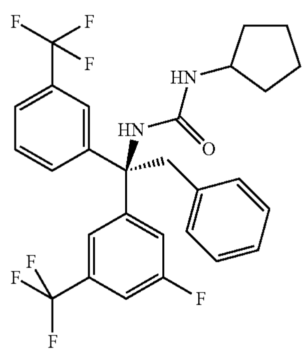 [SMILES: O=C(NC1CCCC1)N[C@](Cc1ccccc1)(c1cccc(C(F)(F)F)c1)c1cc(F)cc(C(F)(F)F)c1] | (R)-1-cyclopentyl-3-(1-(3-fluoro-5-(trifluoromethyl)phenyl)-2-phenyl-1-(3-(trifluoromethyl)phenyl)ethyl)urea | 4.30 LC 539.38 [M + H]$^+$ | Procedure 4, 5, 6 and 2 |
| 13 | 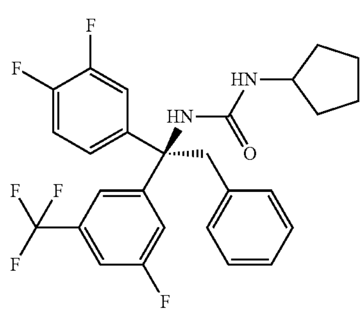 [SMILES: O=C(NC1CCCC1)N[C@@](Cc1ccccc1)(c1cc(F)cc(C(F)(F)F)c1)c1ccc(F)c(F)c1] | (R)-1-cyclopentyl-3-(1-(3,4-difluorophenyl)-1-(3-fluoro-5-(trifluoromethyl)phenyl)-2-phenylethyl)urea | 3.64 LC 507.34 [M + H]$^+$ | Procedure 4, 5, 6 and 2 |
| 14 | 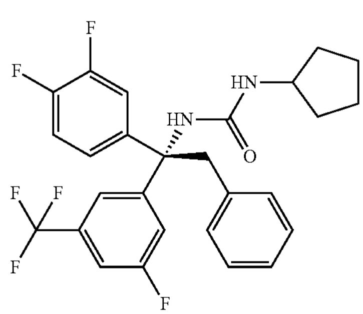 [SMILES: O=C(NC1CCCC1)N[C@](Cc1ccccc1)(c1cc(F)cc(C(F)(F)F)c1)c1ccc(F)c(F)c1] | (S)-1-cyclopentyl-3-(1-(3,4-difluorophenyl)-1-(3-fluoro-5-(trifluoromethyl)phenyl)-2-phenylethyl)urea | 3.64 LC 507.14 [M + H]$^+$ | Procedure 4, 5, 6 and 2 |

TABLE 1-continued

| Ex. No. | Structure | Name | Retention Time Min./ Molecular Mass | Prepared in the manner described in: |
|---|---|---|---|---|
| 15 | 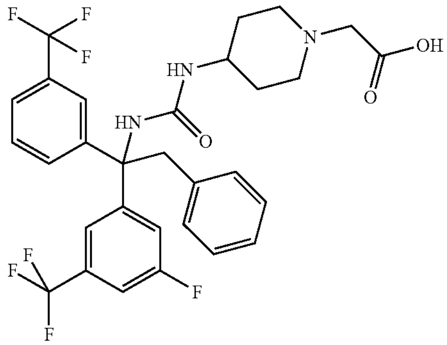 [SMILES: O=C(O)CN1CCC(NC(=O)NC(Cc2ccccc2)(c2cccc(C(F)(F)F)c2)c2cc(F)cc(C(F)(F)F)c2)CC1] | 2-(4-(3-(1-(3-fluoro-5-(trifluoromethyl)phenyl)-2-phenyl-1-(3-(trifluoromethyl)phenyl)ethyl)ureido)piperidin-1-yl)acetic acid | 3.75 LC 612.4 [M + H]+ | Procedure 1 and 2 |
| 16 | 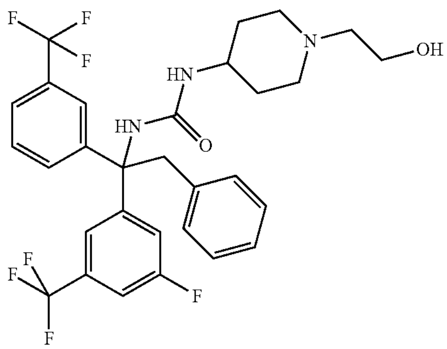 [SMILES: O=C(NC1CCN(CCO)CC1)NC(Cc1ccccc1)(c1cccc(C(F)(F)F)c1)c1cc(F)cc(C(F)(F)F)c1] | 1-(1-(3-fluoro-5-(trifluoromethyl)phenyl)-2-phenyl-1-(3-(trifluoromethyl)phenyl)ethyl)-3-(1-(2-hydroxyethyl)piperidin-4-yl)urea | 3.72 LC 598.45 [M + H]+ | Procedure 1 and 2 |
| 17 | 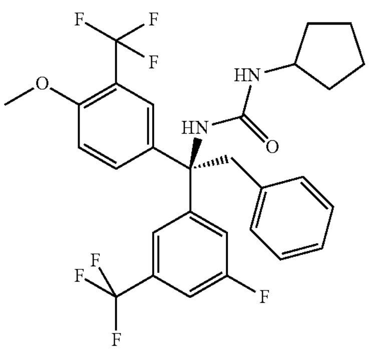 [SMILES: COc1ccc([C@@](Cc2ccccc2)(NC(=O)NC2CCCC2)c2cc(F)cc(C(F)(F)F)c2)cc1C(F)(F)F] | (R)-1-cyclopentyl-3-(1-(3-fluoro-5-(trifluoromethyl)phenyl)-1-(4-methoxy-3-(trifluoromethyl)phenyl)-2-phenylethyl)urea | 4.22 LC 569.39 [M + H]+ | Procedure 4, 5, 6 and 2 |
| 18 | 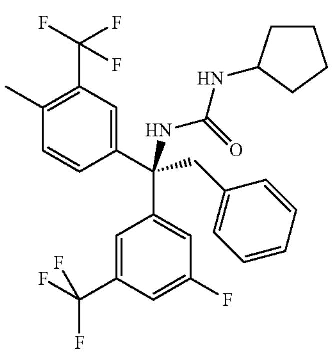 [SMILES: Cc1ccc([C@@](Cc2ccccc2)(NC(=O)NC2CCCC2)c2cc(F)cc(C(F)(F)F)c2)cc1C(F)(F)F] | (R)-1-cyclopentyl-3-(1-(3-fluoro-5-(trifluoromethyl)phenyl)-1-(4-methyl-3-(trifluoromethyl)phenyl)-2-phenylethyl)urea | 4.42 LC 553.38 [M + H]+ | Procedure 4, 5, 6 and 2 |

TABLE 1-continued

| Ex. No. | Structure | Name | Retention Time Min./ Molecular Mass | Prepared in the manner described in: |
|---|---|---|---|---|
| 19 | 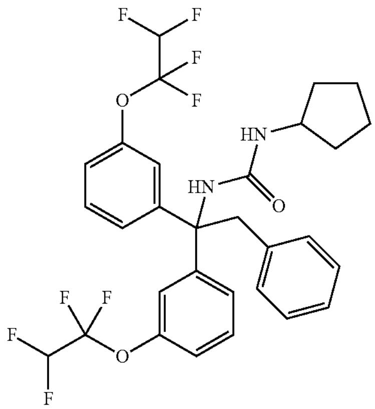 [SMILES: O=C(NC1CCCC1)NC(Cc1ccccc1)(c1cccc(OC(F)(F)C(F)F)c1)c1cccc(OC(F)(F)C(F)F)c1] | 1-cyclopentyl-3-(2-phenyl-1,1-bis(3-(1,1,2,2-tetrafluoro-ethoxy)phenyl)ethyl)urea | 4.13 LC 617.4 [M + H]+ | Procedure 1 and 2 |
| 20 | 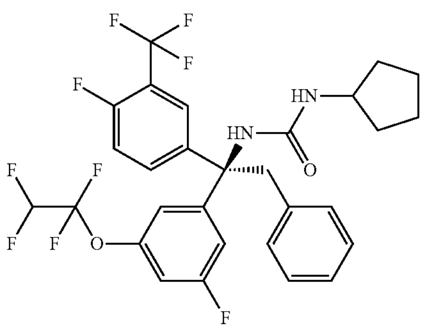 [SMILES: O=C(NC1CCCC1)N[C@@](Cc1ccccc1)(c1cc(F)cc(OC(F)(F)C(F)F)c1)c1ccc(F)c(C(F)(F)F)c1] | (R)-1-cyclopentyl-3-(1-(4-fluoro-3-(trifluoromethyl)phenyl)-1-(3-fluoro-5-(1,1,2,2-tetrafluoroethoxy)phenyl)-2-phenylethyl)urea | 3.74 LC 605.37 [M + H]+ | Procedure 1, 3 and 2 |
| 21 | 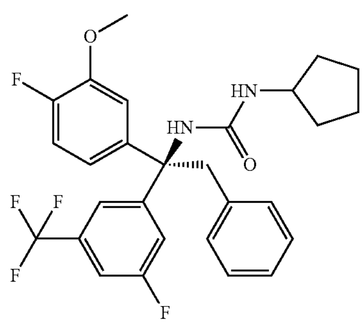 [SMILES: COc1cc([C@@](Cc2ccccc2)(NC(=O)NC2CCCC2)c2cc(F)cc(C(F)(F)F)c2)ccc1F] | (R)-1-cyclopentyl-3-(1-(4-fluoro-3-methoxyphenyl)-1-(3-fluoro-5-(trifluoromethyl)phenyl)-2-phenylethyl)urea | 4.17 LC 519.37 [M + H]+ | Procedure 4, 5, 6 and 2 |
| 22 | 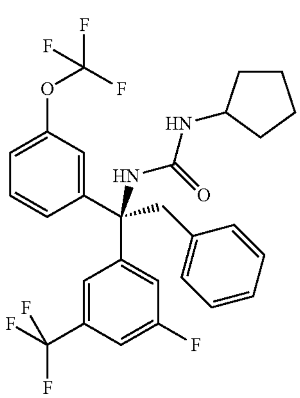 [SMILES: O=C(NC1CCCC1)N[C@](Cc1ccccc1)(c1cccc(OC(F)(F)F)c1)c1cc(F)cc(C(F)(F)F)c1] | (R)-1-cyclopentyl-3-(1-(3-fluoro-5-(trifluoromethyl)phenyl)-2-phenyl-1-(3-(trifluoromethoxy)phenyl)ethyl)urea | 4.30 LC 555.40 [M + H]+ | Procedure 4, 5, 6 and 2 |

TABLE 1-continued

| Ex. No. | Structure | Name | Retention Time Min./ Molecular Mass | Prepared in the manner described in: |
|---|---|---|---|---|
| 23 | 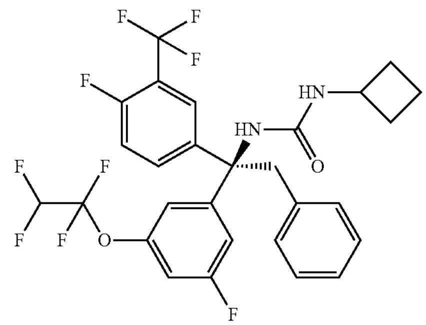 [SMILES: O=C(NC1CCC1)N[C@@](Cc1ccccc1)(c1cc(F)cc(OC(F)(F)C(F)F)c1)c1ccc(F)c(C(F)(F)F)c1] | (R)-1-cyclobutyl-3-(1-(4-fluoro-3-(trifluoromethyl)phenyl)-1-(3-fluoro-5-(1,1,2,2-tetrafluoroethoxy)phenyl)-2-phenylethyl)urea | 3.64 LC 591.39 [M + H]$^+$ | Procedure 3, 4, 5, 6 and 9 |
| 24 | 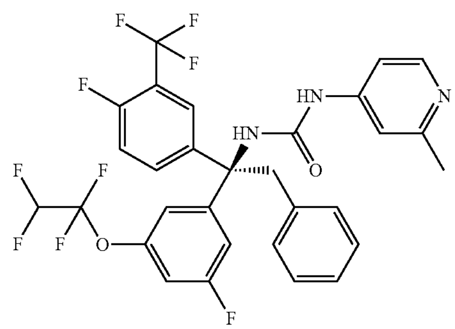 [SMILES: Cc1cc(NC(=O)N[C@@](Cc2ccccc2)(c2cc(F)cc(OC(F)(F)C(F)F)c2)c2ccc(F)c(C(F)(F)F)c2)ccn1] | (R)-1-(1-(4-fluoro-3-(trifluoromethyl)phenyl)-1-(3-fluoro-5-(1,1,2,2-tetrafluoroethoxy)phenyl)-2-phenylethyl)-3-(2-methylpyridin-4-yl)urea | 2.64 LC 648.49 [M + Na]$^+$ | Procedure 3, 4, 5, 6 and 9 |
| 25 | 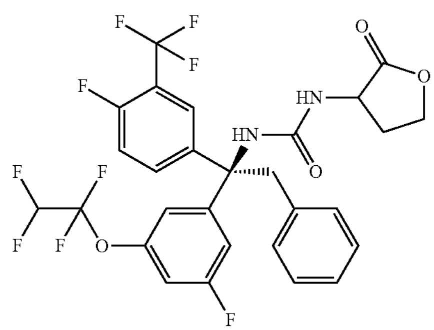 [SMILES: O=C(NC1CCOC1=O)N[C@@](Cc1ccccc1)(c1cc(F)cc(OC(F)(F)C(F)F)c1)c1ccc(F)c(C(F)(F)F)c1] | 1-((R)-1-(4-fluoro-3-(trifluoromethyl)phenyl)-1-(3-fluoro-5-(1,1,2,2-tetrafluoroethoxy)phenyl)-2-phenylethyl)-3-(2-oxo-tetrahydrofuran-3-yl)urea | 3.30 LC 621.39 [M + H]$^+$ | Procedure 3, 4, 5, 6 and 9 |
| 26 | 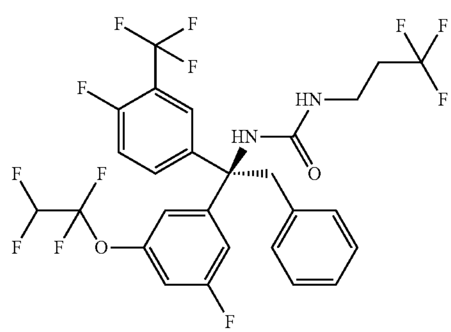 [SMILES: O=C(NCCC(F)(F)F)N[C@@](Cc1ccccc1)(c1cc(F)cc(OC(F)(F)C(F)F)c1)c1ccc(F)c(C(F)(F)F)c1] | (R)-1-(1-(4-fluoro-3-(trifluoromethyl)phenyl)-1-(3-fluoro-5-(1,1,2,2-tetrafluoroethoxy)phenyl)-2-phenylethyl)-3-(3,3,3-trifluoropropyl)urea | 3.59 LC 633.32 [M + H]$^+$ | Procedure 3, 4, 5, 6 and 9 |

TABLE 1-continued

| Ex. No. | Structure | Name | Retention Time Min./ Molecular Mass | Prepared in the manner described in: |
|---|---|---|---|---|
| 27 | 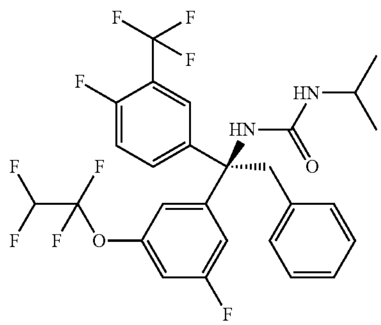 [SMILES: CC(C)NC(=O)N[C@@](Cc1ccccc1)(c1cc(F)cc(OC(F)(F)C(F)F)c1)c1ccc(F)c(C(F)(F)F)c1] | (R)-1-(1-(4-fluoro-3-(trifluoromethyl)phenyl)-1-(3-fluoro-5-(1,1,2,2-tetrafluoroethoxy)phenyl)-2-phenylethyl)-3-isopropylurea | 3.62 LC 579.34 [M + H]$^+$ | Procedure 3, 4, 5, 6 and 9 |
| 28 | 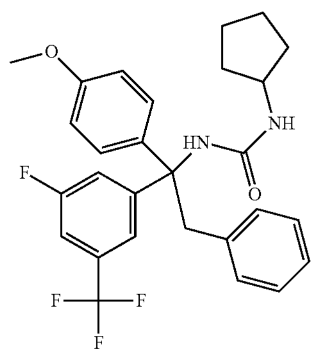 | 1-cyclopentyl-3-(1-(3-fluoro-5-(trifluoromethyl)phenyl)-1-(4-methoxyphenyl)-2-phenylethyl)urea | 4.13 LC 501.3 [M + H]$^+$ | Procedure 1 and 2 |
| 29 | 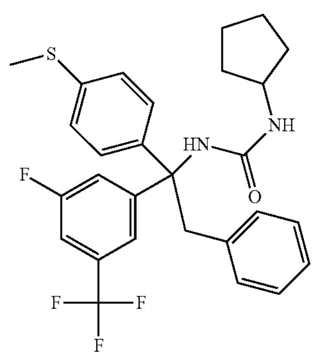 | 1-cyclopentyl-3-(1-(3-fluoro-5-(trifluoromethyl)phenyl)-1-(4-(methylthio)phenyl)-2-phenylethyl)urea | 4.24 LC 517.26 [M + H]$^+$ | Procedure 1 and 2 |
| 30 | 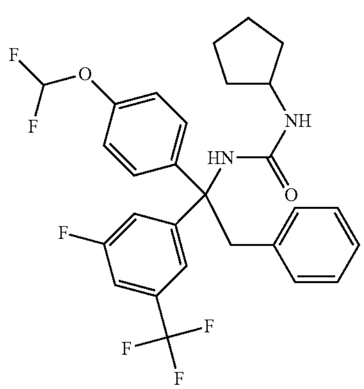 [SMILES: O=C(NC1CCCC1)NC(Cc1ccccc1)(c1ccc(OC(F)F)cc1)c1cc(F)cc(C(F)(F)F)c1] | 1-cyclopentyl-3-(1-(4-(difluoromethoxy)phenyl)-1-(3-fluoro-5-(trifluoromethyl)phenyl)-2-phenylethyl)urea | 4.12 LC 537.27 [M + H]$^+$ | Procedure 1 and 2 |

TABLE 1-continued

| Ex. No. | Structure | Name | Retention Time Min./ Molecular Mass | Prepared in the manner described in: |
|---|---|---|---|---|
| 31 | 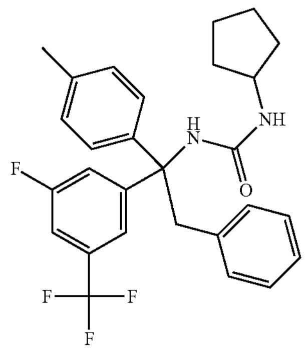 [SMILES: Cc1ccc(C(Cc2ccccc2)(NC(=O)NC2CCCC2)c2cc(F)cc(C(F)(F)F)c2)cc1] | 1-cyclopentyl-3-(1-(3-fluoro-5-(trifluoromethyl)phenyl)-2-phenyl-1-p-tolylethyl)urea | 4.24 LC 485.32 [M + H]+ | Procedure 1 and 2 |
| 32 | 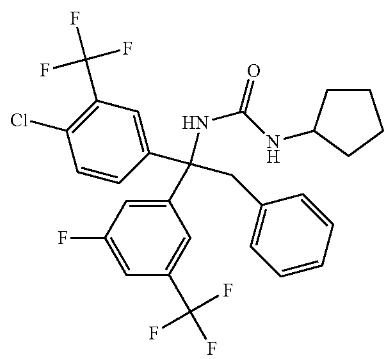 [SMILES: O=C(NC1CCCC1)NC(Cc1ccccc1)(c1cc(F)cc(C(F)(F)F)c1)c1ccc(Cl)c(C(F)(F)F)c1] | 1-(1-(4-chloro-3-(trifluoromethyl)phenyl)-1-(3-fluoro-5-(trifluoromethyl)phenyl)-2-phenylethyl)-3-cyclopentylurea | 4.30 LC 573.23 [M + H]+ | Procedure 1 and 2 |
| 33 | 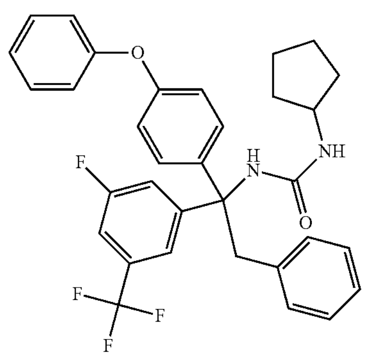 [SMILES: O=C(NC1CCCC1)NC(Cc1ccccc1)(c1ccc(Oc2ccccc2)cc1)c1cc(F)cc(C(F)(F)F)c1] | 1-cyclopentyl-3-(1-(3-fluoro-5-(trifluoromethyl)phenyl)-1-(4-phenoxyphenyl)-2-phenylethyl)urea | 4.38 LC 563.32 [M + H]+ | Procedure 1 and 2 |
| 34 | 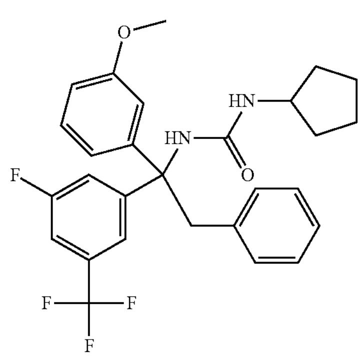 [SMILES: COc1cccc(C(Cc2ccccc2)(NC(=O)NC2CCCC2)c2cc(F)cc(C(F)(F)F)c2)c1] | 1-cyclopentyl-3-(1-(3-fluoro-5-(trifluoromethyl)phenyl)-1-(3-methoxyphenyl)-2-phenylethyl)urea | 4.14 LC 501.32 [M + H]+ | Procedure 1 and 2 |

TABLE 1-continued

| Ex. No. | Structure | Name | Retention Time Min./ Molecular Mass | Prepared in the manner described in: |
|---|---|---|---|---|
| 35 | 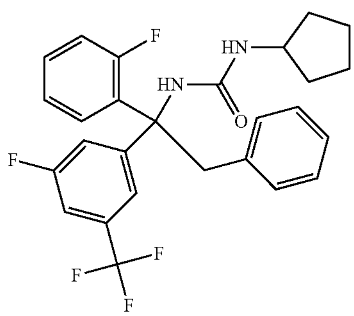 [SMILES: O=C(NC1CCCC1)NC(Cc1ccccc1)(c1cc(F)cc(C(F)(F)F)c1)c1ccccc1F] | 1-cyclopentyl-3-(1-(3-fluoro-5-(trifluoromethyl)phenyl)-1-(2-fluorophenyl)-2-phenylethyl)urea | 4.12 LC 489.26 [M + H]⁺ | Procedure 1 and 2 |
| 36 | 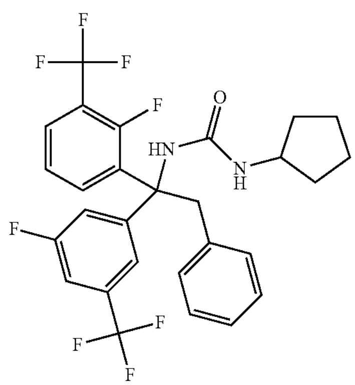 [SMILES: O=C(NC1CCCC1)NC(Cc1ccccc1)(c1cc(F)cc(C(F)(F)F)c1)c1cccc(C(F)(F)F)c1F] | 1-cyclopentyl-3-(1-(2-fluoro-3-(trifluoromethyl)phenyl)-1-(3-fluoro-5-(trifluoromethyl)phenyl)-2-phenylethyl)urea | 4.17 LC 557.26 [M + H]⁺ | Procedure 1 and 2 |
| 37 | 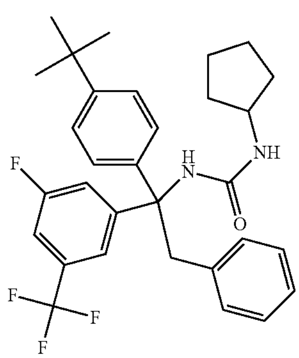 [SMILES: CC(C)(C)c1ccc(C(Cc2ccccc2)(NC(=O)NC2CCCC2)c2cc(F)cc(C(F)(F)F)c2)cc1] | 1-(1-(4-tert-butylphenyl)-1-(3-fluoro-5-(trifluoromethyl)phenyl)-2-phenylethyl)-3-cyclopentylurea | 4.47 LC 527.33 [M + H]⁺ | Procedure 1 and 2 |
| 38 | 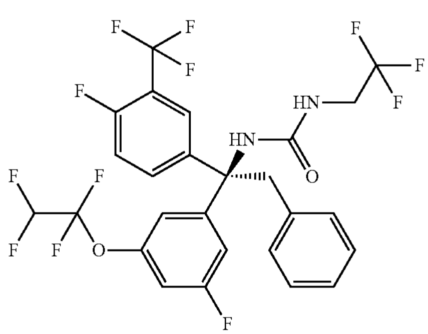 [SMILES: O=C(NCC(F)(F)F)N[C@@](Cc1ccccc1)(c1cc(F)cc(OC(F)(F)C(F)F)c1)c1ccc(F)c(C(F)(F)F)c1] | (R)-1-(1-(4-fluoro-3-(trifluoromethyl)phenyl)-1-(3-fluoro-5-(1,1,2,2-tetrafluoroethoxy)phenyl)-2-phenylethyl)-3-(2,2,2-trifluoroethyl)urea | 3.32 LC 619.31 [M + H]⁺ | Procedure 3, 4, 5, 6 and 9 |

TABLE 1-continued

| Ex. No. | Structure | Name | Retention Time Min./ Molecular Mass | Prepared in the manner described in: |
|---|---|---|---|---|
| 39 | 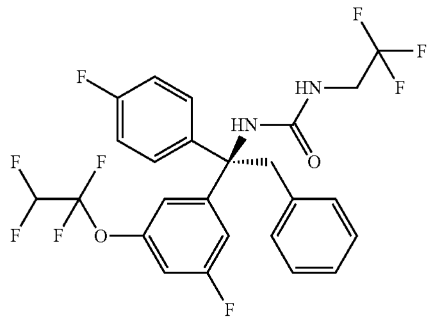 [SMILES: O=C(NCC(F)(F)F)N[C@](Cc1ccccc1)(c1ccc(F)cc1)c1cc(F)cc(OC(F)(F)C(F)F)c1] | (R)-1-(1-(3-fluoro-5-(1,1,2,2-tetrafluoroethoxy)phenyl)-1-(4-fluorophenyl)-2-phenylethyl)-3-(2,2,2-trifluoroethyl)urea | 3.14 LC 551.21 [M + H]+ | Procedure 3, 4, 5, 6 and 9 |
| 40 | 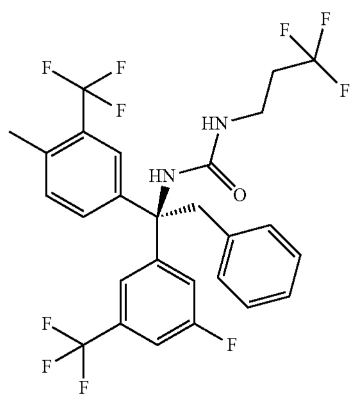 [SMILES: Cc1ccc([C@@](Cc2ccccc2)(NC(=O)NCCC(F)(F)F)c2cc(F)cc(C(F)(F)F)c2)cc1C(F)(F)F] | (R)-1-(1-(3-fluoro-5-(trifluoromethyl)phenyl)-1-(4-methyl-3-(trifluoromethyl)phenyl)-2-phenylethyl)-3-(3,3,3-trifluoropropyl)urea | 4.37 LC 580.98 [M + H]+ | Procedure 4, 5, 6 and 2 |
| 41 | 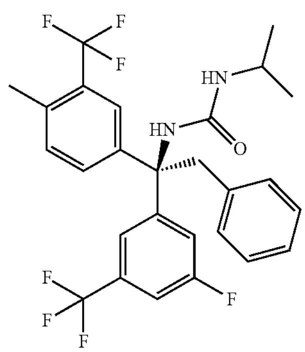 [SMILES: Cc1ccc([C@@](Cc2ccccc2)(NC(=O)NC(C)C)c2cc(F)cc(C(F)(F)F)c2)cc1C(F)(F)F] | (R)-1-(1-(3-fluoro-5-(trifluoromethyl)phenyl)-1-(4-methyl-3-(trifluoromethyl)phenyl)-2-phenylethyl)-3-isopropylurea | 4.36 LC 527.08 [M + H]+ | Procedure 4, 5, 6 and 2 |
| 42 | 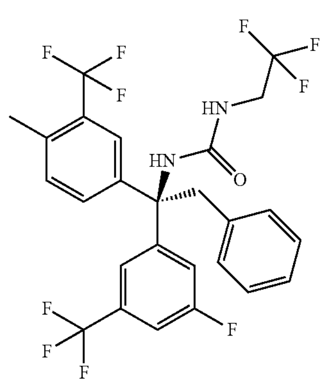 [SMILES: Cc1ccc([C@@](Cc2ccccc2)(NC(=O)NCC(F)(F)F)c2cc(F)cc(C(F)(F)F)c2)cc1C(F)(F)F] | (R)-1-(1-(3-fluoro-5-(trifluoromethyl)phenyl)-1-(4-methyl-3-(trifluoromethyl)phenyl)-2-phenylethyl)-3-(2,2,2-trifluoroethyl)urea | 4.32 LC 567.04 [M + H]+ | Procedure 4, 5, 6 and 2 |

TABLE 1-continued

| Ex. No. | Structure | Name | Retention Time Min./ Molecular Mass | Prepared in the manner described in: |
|---|---|---|---|---|
| 43 | 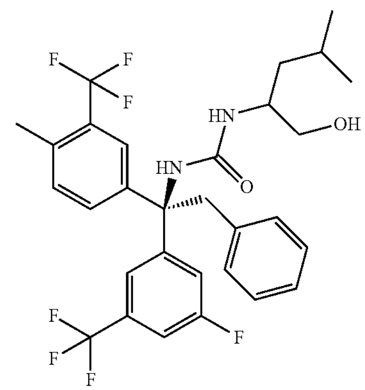 [SMILES: Cc1ccc([C@@](Cc2ccccc2)(NC(=O)NC(CO)CC(C)C)c2cc(F)cc(C(F)(F)F)c2)cc1C(F)(F)F] | 1-((R)-1-(3-fluoro-5-(trifluoromethyl)phenyl)-1-(4-methyl-3-(trifluoromethyl)phenyl)-2-phenylethyl)-3-(1-hydroxy-4-methylpentan-2-yl)urea | 4.40 LC 585.13 [M + H]$^+$ | Procedure 4, 5, 6 and 2 |
| 44 | 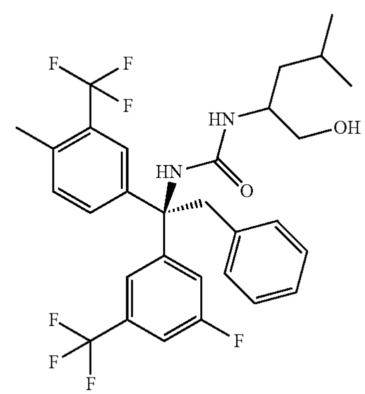 [SMILES: Cc1ccc([C@@](Cc2ccccc2)(NC(=O)NC(CO)CC(C)C)c2cc(F)cc(C(F)(F)F)c2)cc1C(F)(F)F] | 1-((R)-1-(3-fluoro-5-(trifluoromethyl)phenyl)-1-(4-methyl-3-(trifluoromethyl)phenyl)-2-phenylethyl)-3-(1-hydroxy-4-methylpentan-2-yl)urea | 4.41 LC 585.13 [M + H]$^+$ | Procedure 4, 5, 6 and 2 |
| 45 | 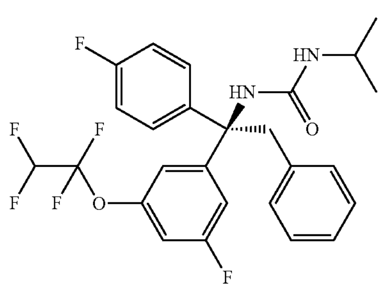 [SMILES: CC(C)NC(=O)N[C@](Cc1ccccc1)(c1ccc(F)cc1)c1cc(F)cc(OC(F)(F)C(F)F)c1] | (R)-1-(1-(3-fluoro-5-(1,1,2,2-tetrafluoroethoxy)phenyl)-1-(4-fluorophenyl)-2-phenylethyl)-3-isopropylurea | 3.95 LC 511.39 [M + H]$^+$ | Procedure 3 4, 5, 6 and 9 |
| 46 | 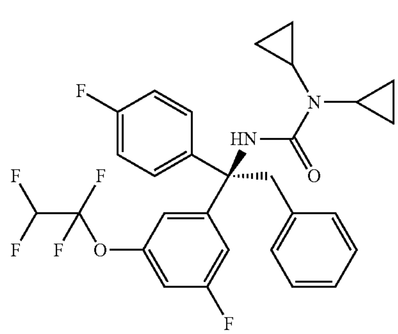 [SMILES: O=C(N[C@](Cc1ccccc1)(c1ccc(F)cc1)c1cc(F)cc(OC(F)(F)C(F)F)c1)N(C1CC1)C1CC1] | (R)-1,1-dicyclopropyl-3-(1-(3-fluoro-5-(1,1,2,2-tetrafluoroethoxy)phenyl)-1-(4-fluorophenyl)-2-phenylethyl)urea | 4.12 LC 549.32 [M + H]$^+$ | Procedure 3 4, 5, 6 and 9 |

TABLE 1-continued

| Ex. No. | Structure | Name | Retention Time Min./ Molecular Mass | Prepared in the manner described in: |
|---|---|---|---|---|
| 47 | 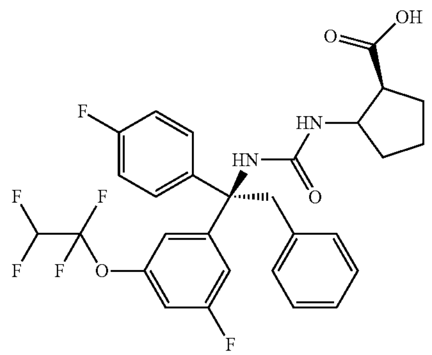 [SMILES: O=C(NC1CCC[C@@H]1C(=O)O)N[C@](Cc1ccccc1)(c1ccc(F)cc1)c1cc(F)cc(OC(F)(F)C(F)F)c1] | (1S)-2-(3-((R)-1-(3-fluoro-5-(1,1,2,2-tetrafluoroethoxy)phenyl)-1-(4-fluorophenyl)-2-phenylethyl)ureido)cyclopentanecarboxylic acid | 3.93 LC 581.04 [M + H]$^+$ | Procedure 3, 4, 5, 6 and 9 |
| 48 | 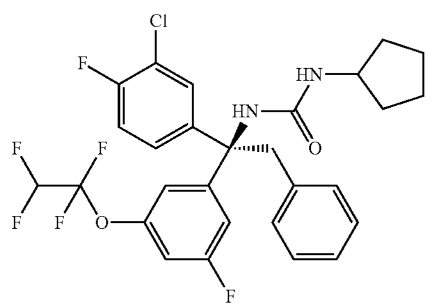 [SMILES: O=C(NC1CCCC1)N[C@@](Cc1ccccc1)(c1cc(F)cc(OC(F)(F)C(F)F)c1)c1ccc(F)c(Cl)c1] | (S)-1-(1-(3-chloro-4-fluorophenyl)-1-(3-fluoro-5-(1,1,2,2-tetrafluoroethoxy)phenyl)-2-phenylethyl)-3-cyclopentylurea | 3.72 LC 571.36 [M + H]$^+$ | Procedure 3, 4, 5, 6 and 2 |
| 49 | 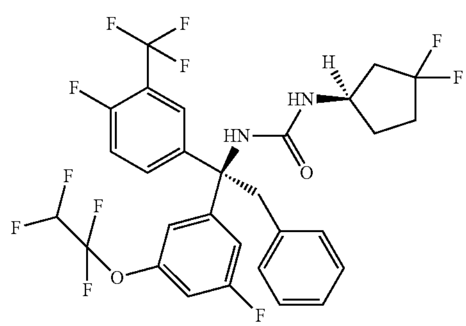 [SMILES: O=C(N[C@@H]1CCC(F)(F)C1)N[C@@](Cc1ccccc1)(c1cc(F)cc(OC(F)(F)C(F)F)c1)c1ccc(F)c(C(F)(F)F)c1] | 1-((R)-3,3-difluorocyclopentyl)-3-((R)-1-(4-fluoro-3-(trifluoromethyl)phenyl)-1-(3-fluoro-5-(1,1,2,2-tetrafluoroethoxy)phenyl)-2-phenylethyl)urea | 4.17 LC 641.3 [M + H]$^+$ | Procedure 3, 4, 5, 6 and 12 |
| 50 | 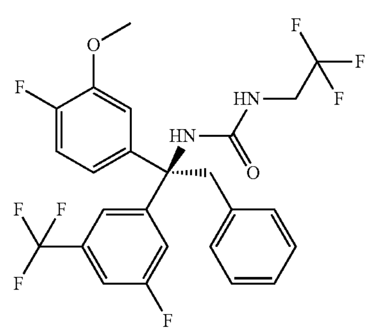 [SMILES: COc1cc([C@@](Cc2ccccc2)(NC(=O)NCC(F)(F)F)c2cc(F)cc(C(F)(F)F)c2)ccc1F] | (R)-1-(1-(4-fluoro-3-methoxyphenyl)-1-(3-fluoro-5-(trifluoromethyl)phenyl)-2-phenylethyl)-3-(2,2,2-trifluoroethyl)urea | 3.94 LC 532.98 [M + H]$^+$ | Procedure 4, 5, 6 and 9 |

TABLE 1-continued

| Ex. No. | Structure | Name | Retention Time Min./ Molecular Mass | Prepared in the manner described in: |
|---|---|---|---|---|
| 51 | 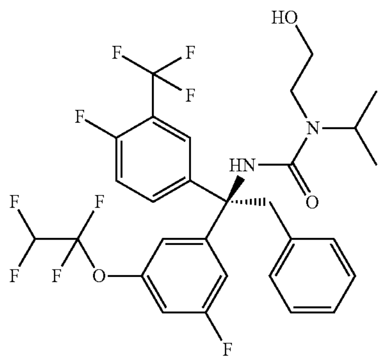 [SMILES: CC(C)N(CCO)C(=O)N[C@@](Cc1ccccc1)(c1cc(F)cc(OC(F)(F)C(F)F)c1)c1ccc(F)c(C(F)(F)F)c1] | (R)-3-(1-(4-fluoro-3-(trifluoromethyl)phenyl)-1-(3-fluoro-5-(1,1,2,2-tetrafluoroethoxy)phenyl)-2-phenylethyl)-1-(2-hydroxyethyl)-1-isopropylurea | 4.09 LC 623.02 [M + H]+ | Procedure 4, 5, 6 and 9 |
| 52 | 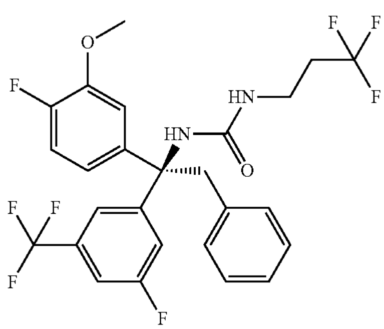 [SMILES: COc1cc([C@@](Cc2ccccc2)(NC(=O)NCCC(F)(F)F)c2cc(F)cc(C(F)(F)F)c2)ccc1F] | (R)-1-(1-(4-fluoro-3-methoxyphenyl)-1-(3-fluoro-5-(trifluoromethyl)phenyl)-2-phenylethyl)-3-(3,3,3-trifluoropropyl)urea | 3.49 LC 547.00 [M + H]+ | Procedure 4, 5, 6 and 9 |
| 53 | 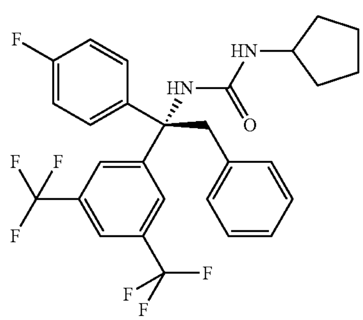 [SMILES: O=C(NC1CCCC1)N[C@@](Cc1ccccc1)(c1ccc(F)cc1)c1cc(C(F)(F)F)cc(C(F)(F)F)c1] | (S)-1-(1-(3,5-bis(trifluoromethyl)phenyl)-1-(4-fluorophenyl)-2-phenylethyl)-3-cyclopentylurea | 3.82 LC 539.03 [M + H]+ | Procedure 4, 5, 6 and 2 |
| 54 | 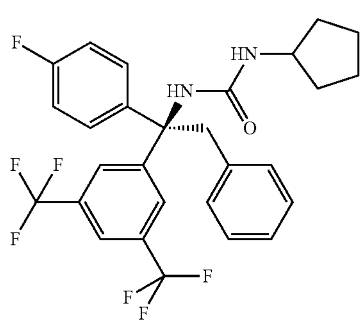 [SMILES: O=C(NC1CCCC1)N[C@](Cc1ccccc1)(c1ccc(F)cc1)c1cc(C(F)(F)F)cc(C(F)(F)F)c1] | (R)-1-(1-(3,5-bis(trifluoromethyl)phenyl)-1-(4-fluorophenyl)-2-phenylethyl)-3-cyclopentylurea | 3.80 LC 539.03 [M + H]+ | Procedure 4, 5, 6 and 2 |

TABLE 1-continued

| Ex. No. | Structure | Name | Retention Time Min./ Molecular Mass | Prepared in the manner described in: |
|---|---|---|---|---|
| 55 | 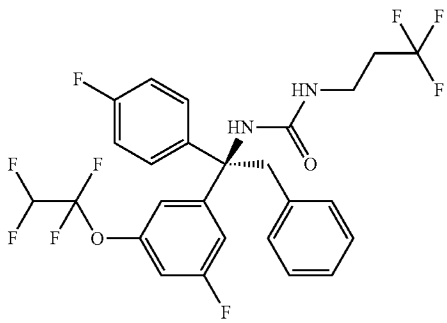 [SMILES: O=C(NCCC(F)(F)F)N[C@](Cc1ccccc1)(c1ccc(F)cc1)c1cc(F)cc(OC(F)(F)C(F)F)c1] | (R)-1-(1-(3-fluoro-5-(1,1,2,2-tetrafluoroethoxy)phenyl)-1-(4-fluorophenyl)-2-phenylethyl)-3-(3,3,3-trifluoropropyl)urea | 3.96 LC 565.36 [M + H]+ | Procedure 3, 4, 5, 6 and 9 |

TABLE 2

| Ex. No. | Structure | Name | Retention Time Min./ Molecular Mass | Prepared in the manner described in: |
|---|---|---|---|---|
| 56 | 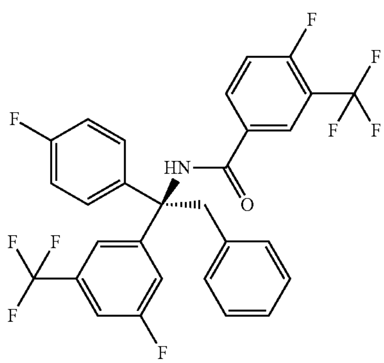 [SMILES: O=C(N[C@](Cc1ccccc1)(c1ccc(F)cc1)c1cc(F)cc(C(F)(F)F)c1)c1ccc(F)c(C(F)(F)F)c1] | (R)-4-fluoro-N-(1-(3-fluoro-5-(trifluoromethyl)phenyl)-1-(4-fluorophenyl)-2-phenylethyl)-3-(trifluoromethyl)benzamide | 3.95 LC 568.30 [M + H]+ | Procedure 4, 5, 6 and 7 |
| 57 | 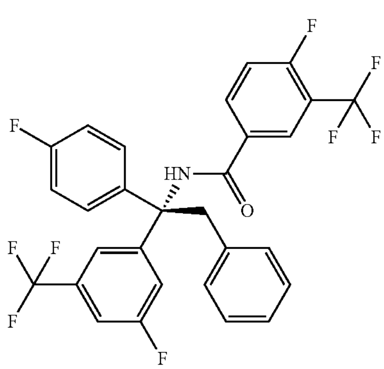 [SMILES: O=C(N[C@@](Cc1ccccc1)(c1ccc(F)cc1)c1cc(F)cc(C(F)(F)F)c1)c1ccc(F)c(C(F)(F)F)c1] | (S)-4-fluoro-N-(1-(3-fluoro-5-(trifluoromethyl)phenyl)-1-(4-fluorophenyl)-2-phenylethyl)-3-(trifluoromethyl)benzamide | 3.95 LC 568.24 [M + H]+ | Procedure 4, 5, 6 and 7 |

TABLE 2-continued

| Ex. No. | Structure | Name | Retention Time Min./ Molecular Mass | Prepared in the manner described in: |
|---|---|---|---|---|
| 58 | 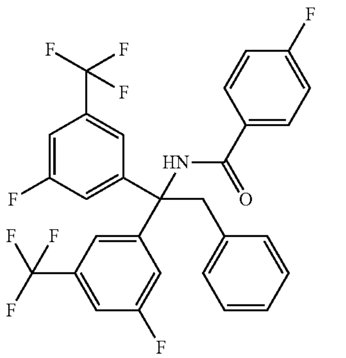 [SMILES: O=C(NC(Cc1ccccc1)(c1cc(F)cc(C(F)(F)F)c1)c1cc(F)cc(C(F)(F)F)c1)c1ccc(F)cc1] | N-(1,1-bis(3-fluoro-5-(trifluoromethyl)phenyl)-2-phenylethyl)-4-fluorobenzamide | 3.83 LC 568.3 [M + H]$^+$ | Procedure 1 and 7 |
| 59 | 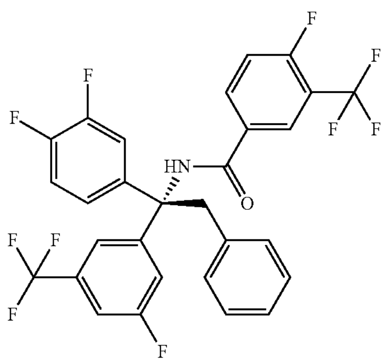 [SMILES: O=C(N[C@](Cc1ccccc1)(c1cc(F)cc(C(F)(F)F)c1)c1ccc(F)c(F)c1)c1ccc(F)c(C(F)(F)F)c1] | (S)-N-(1-(3,4-difluorophenyl)-1-(3-fluoro-5-(trifluoromethyl)phenyl)-2-phenylethyl)-4-fluoro-3-(trifluoromethyl)benzamide | 3.95 LC 586.26 [M + H]$^+$ | Procedure 4, 5, 6 and 7 |
| 60 | 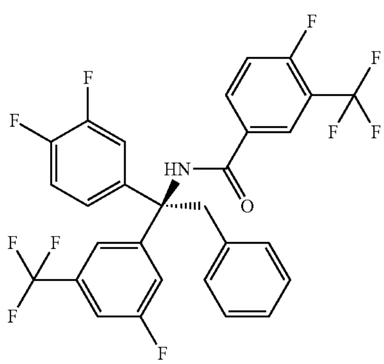 [SMILES: O=C(N[C@@](Cc1ccccc1)(c1cc(F)cc(C(F)(F)F)c1)c1ccc(F)c(F)c1)c1ccc(F)c(C(F)(F)F)c1] | (R)-N-(1-(3,4-difluorophenyl)-1-(3-fluoro-5-(trifluoromethyl)phenyl)-2-phenylethyl)-4-fluoro-3-(trifluoromethyl)benzamide | 3.93 LC 497.3 [M + H]$^+$ | Procedure 4, 5, 6 and 7 |
| 61 | 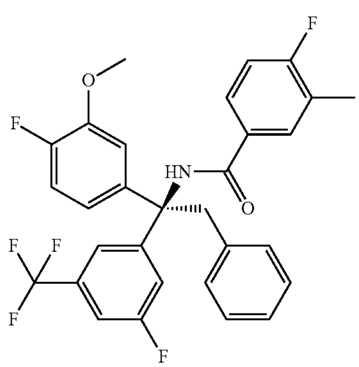 [SMILES: COc1cc([C@@](Cc2ccccc2)(NC(=O)c2ccc(F)c(C)c2)c2cc(F)cc(C(F)(F)F)c2)ccc1F] | (R)-4-fluoro-N-(1-(4-fluoro-3-methoxyphenyl)-1-(3-fluoro-5-(trifluoromethyl)phenyl)-2-phenylethyl)-3-methylbenzamide | 3.79 LC 544.35 [M + H]$^+$ | Procedure 4, 5, 6 and 7 |

TABLE 2-continued

| Ex. No. | Structure | Name | Retention Time Min./ Molecular Mass | Prepared in the manner described in: |
|---|---|---|---|---|
| 62 | 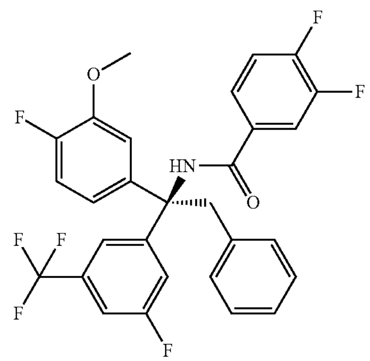 [SMILES: COc1cc([C@@](Cc2ccccc2)(NC(=O)c2ccc(F)c(F)c2)c2cc(F)cc(C(F)(F)F)c2)ccc1F] | (R)-3,4-difluoro-N-(1-(4-fluoro-3-methoxyphenyl)-1-(3-fluoro-5-(trifluoromethyl)phenyl)-2-phenylethyl)benzamide | 3.73 LC 570.32 [M + Na]+ | Procedure 4, 5, 6 and 7 |
| 63 | 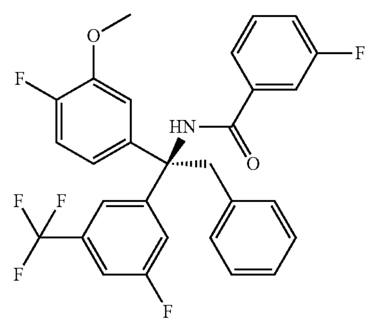 [SMILES: COc1cc([C@@](Cc2ccccc2)(NC(=O)c2cccc(F)c2)c2cc(F)cc(C(F)(F)F)c2)ccc1F] | (R)-3-fluoro-N-(1-(4-fluoro-3-methoxyphenyl)-1-(3-fluoro-5-(trifluoromethyl)phenyl)-2-phenylethyl)benzamide | 3.67 LC 530.33 [M + H]+ | Procedure 4, 5, 6 and 7 |
| 64 | 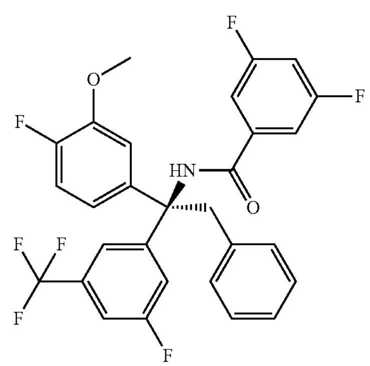 [SMILES: COc1cc([C@@](Cc2ccccc2)(NC(=O)c2cc(F)cc(F)c2)c2cc(F)cc(C(F)(F)F)c2)ccc1F] | (R)-3,5-difluoro-N-(1-(4-fluoro-3-methoxyphenyl)-1-(3-fluoro-5-(trifluoromethyl)phenyl)-2-phenylethyl)benzamide | 3.75 LC 548.33 [M + H]+ | Procedure 4, 5, 6 and 7 |
| 65 | 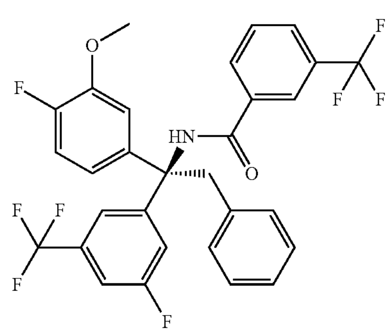 [SMILES: COc1cc([C@@](Cc2ccccc2)(NC(=O)c2cccc(C(F)(F)F)c2)c2cc(F)cc(C(F)(F)F)c2)ccc1F] | (R)-N-(1-(4-fluoro-3-methoxyphenyl)-1-(3-fluoro-5-(trifluoromethyl)phenyl)-2-phenylethyl)-3-(trifluoromethyl)benzamide | 3.86 LC 580.36 [M + H]+ | Procedure 4, 5, 6 and 7 |

TABLE 2-continued

| Ex. No. | Structure | Name | Retention Time Min./ Molecular Mass | Prepared in the manner described in: |
|---|---|---|---|---|
| 66 | 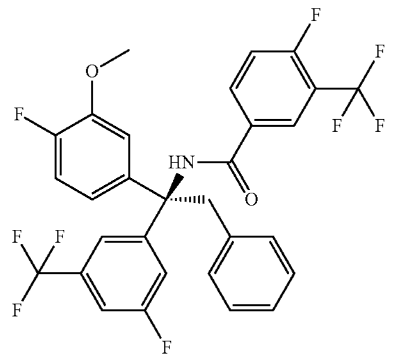 [SMILES: COc1cc([C@@](Cc2ccccc2)(NC(=O)c2ccc(F)c(C(F)(F)F)c2)c2cc(F)cc(C(F)(F)F)c2)ccc1F] | (R)-4-fluoro-N-(1-(4-fluoro-3-methoxyphenyl)-1-(3-fluoro-5-(trifluoromethyl)phenyl)-2-phenylethyl)-3-(trifluoromethyl)benzamide | 3.90 LC 598.36 [M + H]$^+$ | Procedure 4, 5, 6 and 7 |
| 67 | 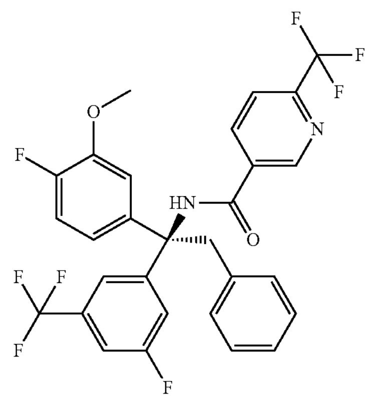 [SMILES: COc1cc([C@@](Cc2ccccc2)(NC(=O)c2ccc(C(F)(F)F)nc2)c2cc(F)cc(C(F)(F)F)c2)ccc1F] | (R)-N-(1-(4-fluoro-3-methoxyphenyl)-1-(3-fluoro-5-(trifluoromethyl)phenyl)-2-phenylethyl)-6-(trifluoromethyl) nicotinamide | 3.70 LC 581.34 [M + H]$^+$ | Procedure 4, 5, 6 and 7 |
| 68 | 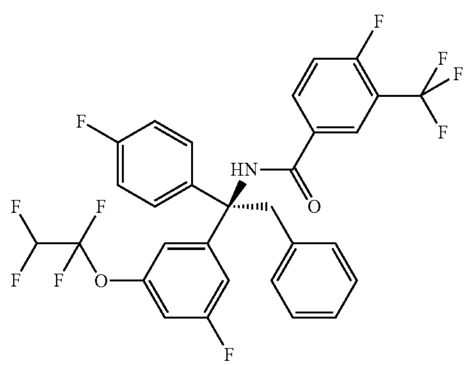 [SMILES: O=C(N[C@](Cc1ccccc1)(c1ccc(F)cc1)c1cc(F)cc(OC(F)(F)C(F)F)c1)c1ccc(F)c(C(F)(F)F)c1] | (R)-4-fluoro-N-(1-(3-fluoro-5-(1,1,2,2-tetrafluoroethoxy)phenyl)-1-(4-fluorophenyl)-2-phenylethyl)-3-(trifluoromethyl)benzamide | 3.95 LC 616.17 [M + H]$^+$ | Procedure 4, 5, 6 and 7 |
| 69 | 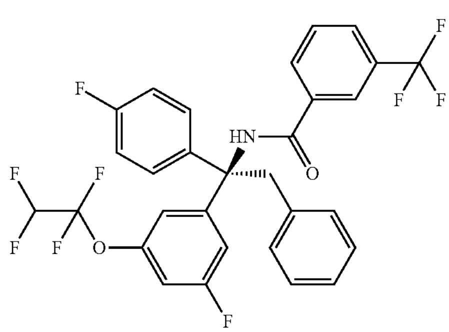 [SMILES: O=C(N[C@](Cc1ccccc1)(c1ccc(F)cc1)c1cc(F)cc(OC(F)(F)C(F)F)c1)c1cccc(C(F)(F)F)c1] | (R)-N-(1-(3-fluoro-5-(1,1,2,2-tetrafluoroethoxy)phenyl)-1-(4-fluorophenyl)-2-phenylethyl)-3-(trifluoromethyl)benzamide | 3.83 LC 598.37 [M + H]$^+$ | Procedure 4, 5, 6 and 7 |

TABLE 2-continued

| Ex. No. | Structure | Name | Retention Time Min./ Molecular Mass | Prepared in the manner described in: |
|---|---|---|---|---|
| 70 | 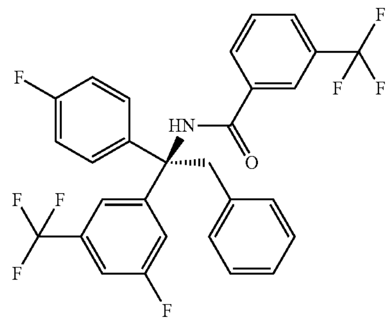 [SMILES: O=C(N[C@](Cc1ccccc1)(c1ccc(F)cc1)c1cc(F)cc(C(F)(F)F)c1)c1cccc(C(F)(F)F)c1] | (R)-N-(1-(3-fluoro-5-(trifluoromethyl)phenyl)-1-(4-fluorophenyl)-2-phenylethyl)-3-(trifluoromethyl)benzamide | 3.89 LC 550.36 [M + H]$^+$ | Procedure 4, 5, 6 and 7 |
| 71 | 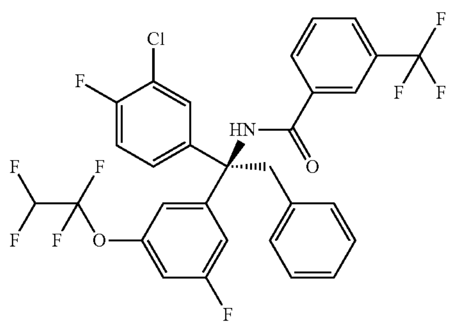 [SMILES: O=C(N[C@@](Cc1ccccc1)(c1cc(F)cc(OC(F)(F)C(F)F)c1)c1ccc(F)c(Cl)c1)c1cccc(C(F)(F)F)c1] | (S)-N-(1-(3-chloro-4-fluorophenyl)-1-(3-fluoro-5-(1,1,2,2-tetrafluoroethoxy)phenyl)-2-phenylethyl)-3-(trifluoromethyl)benzamide | 3.95 LC 632.32 [M + H]$^+$ | Procedure 4, 5, 6 and 7 |
| 72 | 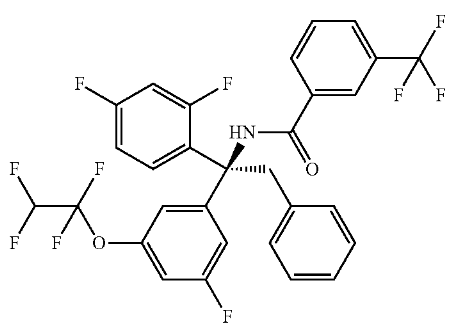 [SMILES: O=C(N[C@@](Cc1ccccc1)(c1cc(F)cc(OC(F)(F)C(F)F)c1)c1ccc(F)cc1F)c1cccc(C(F)(F)F)c1] | (S)-N-(1-(2,4-difluorophenyl)-1-(3-fluoro-5-(1,1,2,2-tetrafluoroethoxy)phenyl)-2-phenylethyl)-3-(trifluoromethyl)benzamide | 3.86 LC 616.34 [M + H]$^+$ | Procedure 4, 5, 6 and 7 |
| 73 | 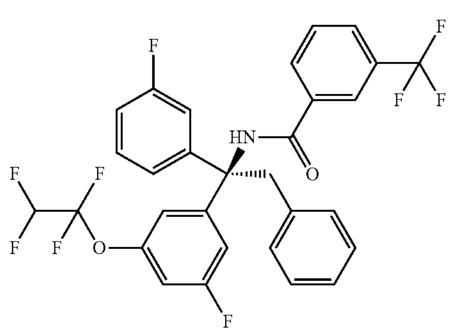 [SMILES: O=C(N[C@](Cc1ccccc1)(c1cccc(F)c1)c1cc(F)cc(OC(F)(F)C(F)F)c1)c1cccc(C(F)(F)F)c1] | (R)-N-(1-(3-fluoro-5-(1,1,2,2-tetrafluoroethoxy)phenyl)-1-(3-fluorophenyl)-2-phenylethyl)-3-(trifluoromethyl)benzamide | 3.81 LC N. Observed [M + H]$^+$ | Procedure 4, 5, 6 and 7 |

TABLE 2-continued

| Ex. No. | Structure | Name | Retention Time Min./ Molecular Mass | Prepared in the manner described in: |
|---|---|---|---|---|
| 74 | 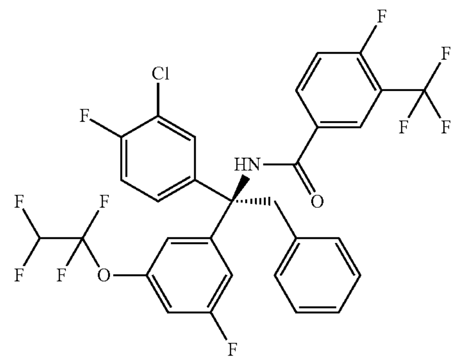 [SMILES: O=C(N[C@@](Cc1ccccc1)(c1cc(F)cc(OC(F)(F)C(F)F)c1)c1ccc(F)c(Cl)c1)c1ccc(F)c(C(F)(F)F)c1] | (S)-N-(1-(3-chloro-4-fluorophenyl)-1-(3-fluoro-5-(1,1,2,2-tetrafluoroethoxy)phenyl)-2-phenylethyl)-4-fluoro-3-(trifluoromethyl)benzamide | 4.03 LC 650.08 [M + H]$^+$ | Procedure 4, 5, 6 and 7 |

TABLE 3

| Ex. No. | Structure | Name | Retention Time Min./ Molecular Mass | Prepared in the manner described in: |
|---|---|---|---|---|
| 75 | 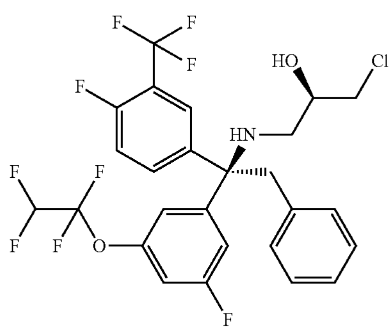 [SMILES: O[C@@H](CCl)CN[C@@](Cc1ccccc1)(c1cc(F)cc(OC(F)(F)C(F)F)c1)c1ccc(F)c(C(F)(F)F)c1] | (R)-1-chloro-3-((R)-1-(4-fluoro-3-(trifluoromethyl)phenyl)-1-(3-fluoro-5-(1,1,2,2-tetrafluoroethoxy)phenyl)-2-phenylethylamino)propan-2-ol | 3.24 LC 586.43 [M + H]$^+$ | Procedure 3, 4, 5, 6 and 8 |
| 76 | 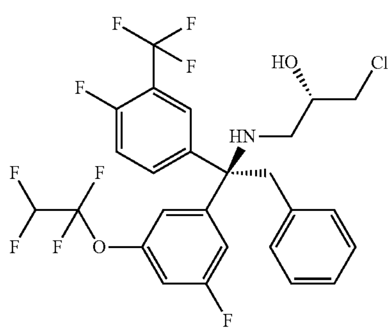 [SMILES: O[C@H](CCl)CN[C@@](Cc1ccccc1)(c1cc(F)cc(OC(F)(F)C(F)F)c1)c1ccc(F)c(C(F)(F)F)c1] | (S)-1-chloro-3-((R)-1-(4-fluoro-3-(trifluoromethyl)phenyl)-1-(3-fluoro-5-(1,1,2,2-tetrafluoroethoxy)phenyl)-2-phenylethylamino)propan-2-ol | 3.24 LC 586.43 [M + H]$^+$ | Procedure 3, 4, 5, 6 and 8 |

TABLE 3-continued

| Ex. No. | Structure | Name | Retention Time Min./ Molecular Mass | Prepared in the manner described in: |
|---|---|---|---|---|
| 77 | 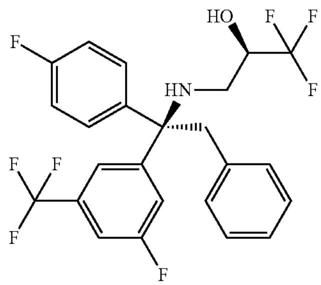 [SMILES: O[C@H](CN[C@](Cc1ccccc1)(c1ccc(F)cc1)c1cc(F)cc(C(F)(F)F)c1)C(F)(F)F] | (R)-1,1,1-trifluoro-3-((R)-1-(3-fluoro-5-(trifluoromethyl)phenyl)-1-(4-fluorophenyl)-2-phenylethylamino)propan-2-ol | 3.83 LC No obs [M + H]⁺ | Procedure 4, 5, 6 and 8 |
| 78 | 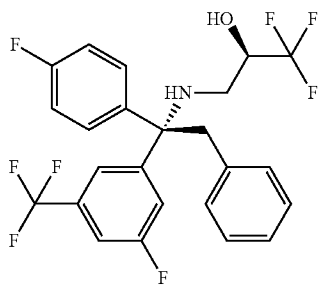 [SMILES: O[C@H](CN[C@@](Cc1ccccc1)(c1ccc(F)cc1)c1cc(F)cc(C(F)(F)F)c1)C(F)(F)F] | (R)-1,1,1-trifluoro-3-((S)-1-(3-fluoro-5-(trifluoromethyl)phenyl)-1-(4-fluorophenyl)-2-phenylethylamino)propan-2-ol | 3.48 LC No obs [M + H]⁺ | Procedure 4, 5, 6 and 8 |
| 79 | 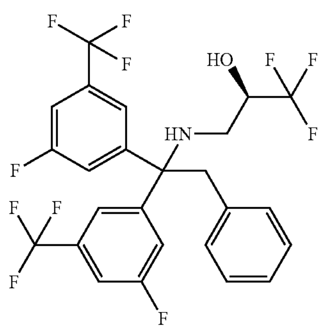 [SMILES: O[C@H](CNC(Cc1ccccc1)(c1cc(F)cc(C(F)(F)F)c1)c1cc(F)cc(C(F)(F)F)c1)C(F)(F)F] | (R)-3-(1,1-bis(3-fluoro-5-(trifluoromethyl)phenyl)-2-phenylethylamino)-1,1,1-trifluoropropan-2-ol | 3.88 LC No obs. [M + H]⁺ | Procedure 4, 5, 6 and 8 |
| 80 | 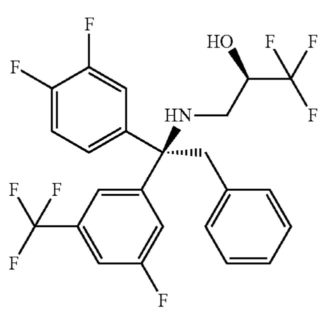 [SMILES: O[C@H](CN[C@@](Cc1ccccc1)(c1cc(F)cc(C(F)(F)F)c1)c1ccc(F)c(F)c1)C(F)(F)F] | (R)-3-((R)-1-(3,4-difluorophenyl)-1-(3-fluoro-5-(trifluoromethyl)phenyl)-2-phenylethylamino)-1,1,1-trifluoropropan-2-ol | 3.63 LC No obs. [M + H]⁺ | Procedure 4, 5, 6 and 8 |
| 81 | 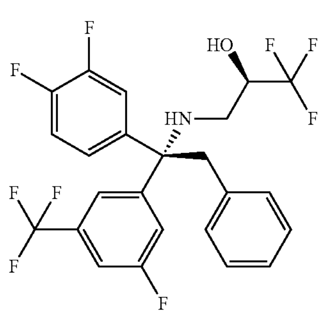 [SMILES: O[C@H](CN[C@](Cc1ccccc1)(c1cc(F)cc(C(F)(F)F)c1)c1ccc(F)c(F)c1)C(F)(F)F] | (R)-3-((S)-1-(3,4-difluorophenyl)-1-(3-fluoro-5-(trifluoromethyl)phenyl)-2-phenylethylamino)-1,1,1-trifluoropropan-2-ol | 3.64 LC No obs. [M + H]⁺ | Procedure 4, 5, 6 and 8 |

Additional compounds of the present invention were prepared by procedures analogous to those described above and to the additional procedures described below.

Example 82

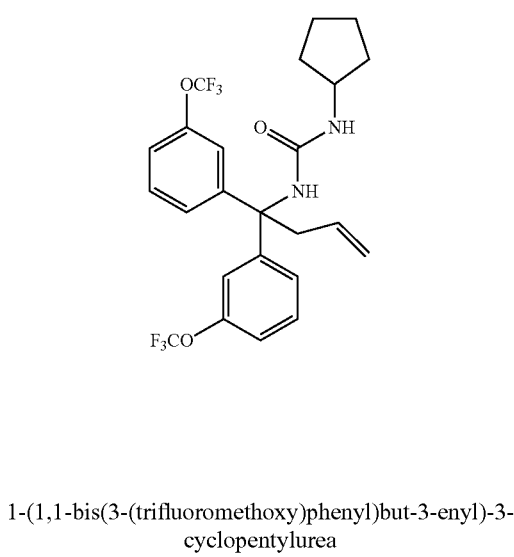

1-(1,1-bis(3-(trifluoromethoxy)phenyl)but-3-enyl)-3-cyclopentylurea

Procedure 11

Bis(3-(trifluoromethoxy)phenyl)methanone

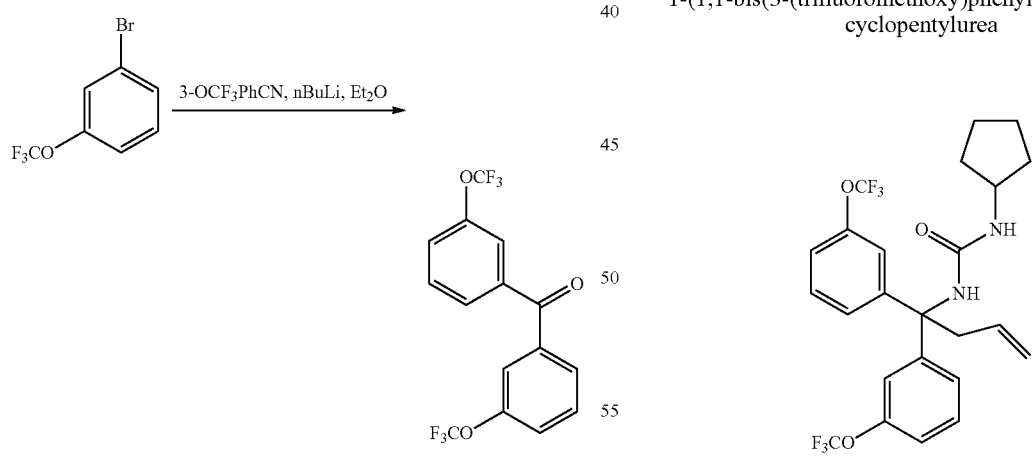

Using the same procedure as described in Example 2, Procedure 4, bis(3-(trifluoromethoxy)phenyl)methanone was obtained. $^1$H NMR (400 MHz, CDCl$_3$) δ ppm 7.39-7.45 (m, 1H),) 7.36 (m, 1H), 7.25 (d, J=15.92 Hz, 1H), 7.15-7.20 (m, 1H); $^{13}$C NMR (CDCl$_3$) δ ppm 193.27, 149.29, 138.66, 130.10, 128.27, 125.23, 124.26, 122.26, 121.69, 119.13, 116.56; LC-MS (ESI) 351.2 (M+H), retention time=4.0 min (10-90% MeOH in H$_2$O with 0.1% TFA in a 4-min run).

(R)—N-(bis(3-(trifluoromethoxy)phenyl)methylene)-2-methylpropane-2-sulfinamide

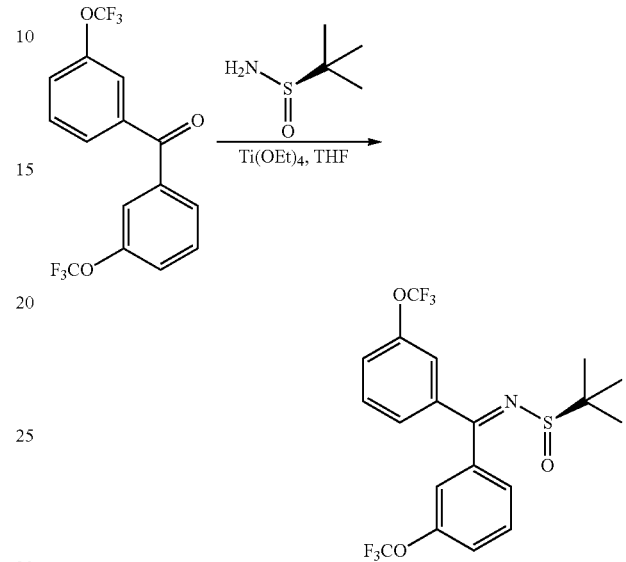

Using the same procedure as that of Procedure 5, (R)—N-(bis(3-(trifluoromethoxy)phenyl)methylene)-2-methylpropane-2-sulfinamide was obtained. $^1$H NMR (400 MHz, CDCl$_3$) δ ppm 7.62-7.28 (br, m, 8H),) 1.34 (s, 9H); LC-MS (ESI) 454.28 (M+H), retention time=4.12 min (10-90% MeOH in H$_2$O with 0.1% TFA in a 4-min run).

1-(1,1-bis(3-(trifluoromethoxy)phenyl)but-3-enyl)-3-cyclopentylurea

Using similar procedures as Procedure 6, and 2,1-(1,1-bis (3-(trifluoromethoxy)phenyl)but-3-enyl)-3-cyclopentylurea was obtained. $^1$H NMR (400 MHz, CDCl$_3$) δ ppm 7.41 (t, J=7.96 Hz, 2H), 7.37-7.31 (m, 2H) 7.27 (m, 2H), 7.18 (d, J=8.08 Hz, 2H), 5.48-5.36 (m, 1H), 5.25-5.15 (m, 3H), 4.10 (s, br, 1H), 3.86-3.96 (m, 1H), 3.17 (d, J=6.82 Hz, 2H), 1.86-1.76 (m, 2H), 1.53-1.42, (m, 4H) 1.18-1.07 (m, 2H); LC-MS (ESI) 503.33 (M+H), retention time=4.26 min (10-90% MeOH in H$_2$O with 0.1% TFA in a 4-min run).

Example 83

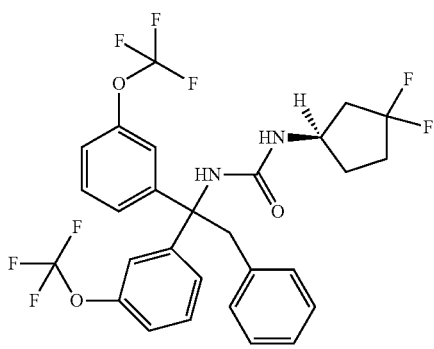 [SMILES: O=C(N[C@@H]1CCC(F)(F)C1)NC(Cc1ccccc1)(c1cccc(OC(F)(F)F)c1)c1cccc(OC(F)(F)F)c1]

(R)-1-(3,3-difluorocyclopentyl)-3-(2-phenyl-1,1-bis(3-(trifluoromethoxy)phenyl)ethyl)urea Procedure 12

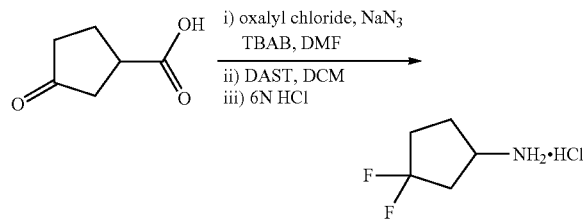

To the solution of 3-oxocyclopentanecarboxylic acid (2.85 g, 22.2 mmol) in dry $CH_2Cl_2$ (4 mL) was added oxalyl chloride (2.0M in dichloromethane, 13 mL) at 0° C. over 15 min followed by DMF (50 mL) After the addition was complete, the reaction mixture was stirred for 2 h (0° C. to rt). Tetrabutylammonium bromide (35 mg) was then added followed by a solution of sodium azide (2.17 g, 26.7 mmol, in the minimum amount of $H_2O$, 9 mL) at 0° C., and the resulting light brown reaction mixture was stirred for 1 h at rt. The reaction was monitored and upon completion, the organic phase was separated. The aqueous phase was extracted with $CH_2Cl_2$ (3×8 mL). The combined organic phases were washed with brine, dried with sodium sulfate, and filtered through a 2 cm plug of silica. The silica gel plug was washed with $CH_2Cl_2$, twice followed with 10% EtOAc in $CH_2Cl_2$. The resulting pale yellow filtrate was partially concentrated. Benzyl alcohol (25 mL) was added and the remainder of $CH_2Cl_2$ was removed under vacuum. The light brown solution was heated at 100° C. for 3 h. After it was cooled to room temperature, the brown solution was vacuum distilled. Benzyl alcohol was collected and the viscous brown oil residue was purified by flash chromatography (120 g $SiO_2$, 0-40% EtOAc/hexane) to provide benzyl 3-oxocyclopentylcarbamate as a pale yellow and colorless oil (2.39 g, 46% yield). $^1$H NMR ($CDCl_3$, 400 MHz): 7.35 (m, 5H), 5.09 (s, 2H), 4.87 (br, 1H), 4.28 (m, 1H), 2.63 (m, 1H), 2.39-2.15 (m, 4H), 1.86 (m, 1H). $^{13}$C NMR ($CDCl_3$, 400 MHz): 215.7, 155.8, 136.2, 128.6, 128.3, 128.2, 66.9, 49.3, 45.2, 37.0, 29.9. LC/MS: [M+H]=234.1.

To a solution of benzyl 3-oxocyclopentylcarbamate (2.32 g, 9.96 mmol) in $CH_2Cl_2$ (10 mL) was added DAST (4.3 mL, 28.9 mmol) at rt. The reaction mixture turned brown while shaken at rt overnight. When the transformation was complete by HPLC, brine was added at 0° C. slowly to quench the reaction [Caution: reacted violently]. $CH_2Cl_2$ was added and the solution was extracted with $CH_2Cl_2$ (3×10 mL). The combined organic phases were dried over $Na_2SO_4$, and concentrated. The residue was purified by flash chromatography (40 g $SiO_2$, 0-40% EtOAc/hexane) to furnish benzyl 3,3-difluorocyclopentylcarbamate as an off-white solid (1.5 g, 59%). $^1$H NMR ($CDCl_3$, 400 MHz): 7.35 (m, 5H), 5.09 (s, 2H), 4.90 (br, 1H), 4.23 (m, 1H), 2.50 (m, 1H), 2.25-1.98 (m, 4H), 1.70 (m, 1H). $^{13}$C NMR ($CDCl_3$, 400 MHz): 155.6, 136.2, 128.6, 128.3, 128.2, 66.9, 50.86, 49.3, 42.6 (t), 34.2 (t), 30.6. $^{19}$F NMR ($CDCl_3$, with $CFCl_3$ as standard, 400 MHz): −88.2 (m, 1F), −91.4 (m, 1F).

Benzyl 3,3-difluorocyclopentylcarbamate (1.5 g, 5.88 mmol) in 6N HCl (6 mL) was heated at 100° C. for 20 h. After the reaction mixture was cooled to rt, the brown solution was extracted with $Et_2O$ (2×2 mL) to remove unreacted starting material and toluene. The aqueous phase was dried in the speed vac with heating to give 3,3-difluorocyclopentanamine hydrochloride as a light brown solid (0.79 g, 85% yield). $^1$H NMR (MeOD-$d_4$, 400 MHz): 4.79 (m, 1H), 2.62 (m, 1H), 2.32 (m, 2H), 2.18 (m, 2H), 1.87 (m, 1H). $^{13}$C NMR (MeOD-$d_4$, 400 MHz): 131.4 (t), 41.0 (t), 34.8 (t), 28.9. $^{19}$F NMR (MeOD-$d_4$, with $CFCl_3$ as standard, 400 MHz): −93.0 (m, 2F). LC/MS: [M+H]=121.9.

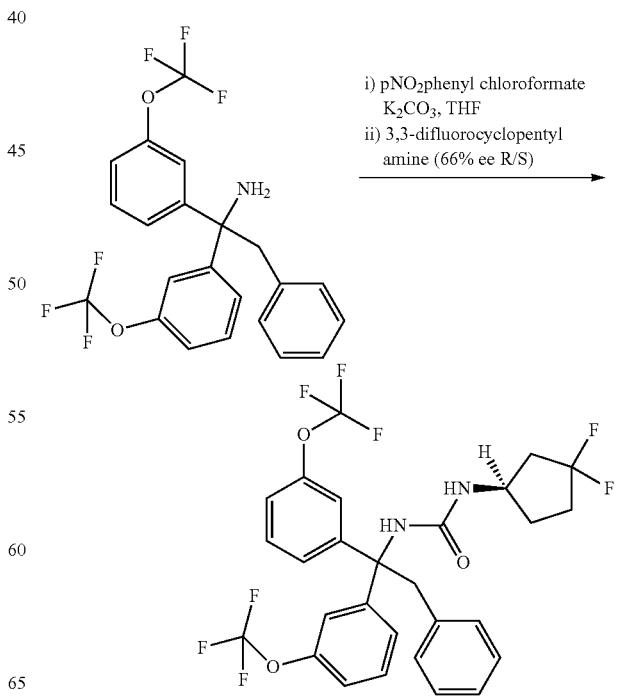

2-Phenyl-1,1-bis(3-(trifluoromethoxy)phenyl)ethanamine was prepared according as described for Procedure 6. To a solution of 2-phenyl-1,1-bis(3-(trifluoromethoxy)phenyl)ethanamine (77 mg, 0.17 mmol) in $CH_2Cl_2$ (1 mL), was added $K_2CO_3$ (241 mg, 1.7 mmol) followed by 4-nitrophenyl chloroformate (70 mg, 0.35 mmol). The reaction mixture was stirred at rt until the starting material was consumed. The solution was diluted with $CH_2Cl_2$ and washed with $NaHCO_3$. The organic layer were separated and the aqueous layer was extracted with $CH_2Cl_2$ (3×). The combined organic layer was dried over $Na_2SO_4$, filtered, and concentrated under reduced pressure. The residue was taken up in anhydrous $CH_2Cl_2$ (1.6 mL) and this mixture was used as a stock solution of the intermediate carbamate (0.11 M in $CH_2Cl_2$).

4-Nitrophenyl 2-phenyl-1,1-bis(3-(trifluoromethoxy)phenyl)ethylcarbamate (400 µL of the above stock solution, 0.044 mmol) was added to a vial followed by 3,3-difluorocyclopentanamine hydrochloride (14 mg, 0.087 mmol, 66.4% ee R) and Hunig's base (15 µL, 0.087 mmol). The reaction was monitored for the disappearance of the carbamate. Upon completion, the reaction mixture was diluted with $CH_2Cl_2$, washed with successively with $NaHCO_3$ and 1N NaOH, and extracted with $CH_2Cl_2$ (3×). The combined organics were dried over $Na_2SO_4$, filtered and concentrated under reduced pressure. Purification of the residue was accomplished by preparative HPLC (YMC Combiprep ODS-A 30×50 mm; mobile phase: 10% MeOH/90% $H_2O$/0.1% TFA) to provide the desired urea (9.1 mg) as a film. $^1$H NMR (500 MHz, $CDCl_3$, diastereomeric mixture, ca. 83:17) δ 7.36 (t, J=7.5 Hz, 2H), 7.22-7.10 (m, 7H), 7.06 (s, 2H), 6.65 (d, J=5.0 Hz, 2H), 4.89 (s, 1H), 4.33-4.24 (m, 1H), 4.23-4.14 (m, 1H), 3.76 (s, 2H), 2.42-2.30 (m, 1H), 2.13-1.93 (m, 3H), 1.77-1.67 (m, 1H), 1.48-1.41 (m, 1H); LC/MS (MeOH/$H_2O$/$NH_4OAc$ mobile phase) rt=4.26 min; [M+H]=589.3.

Example 84

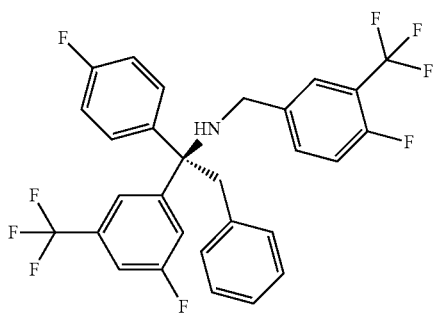 [SMILES: Fc1ccc([C@@](Cc2ccccc2)(NCc2ccc(F)c(C(F)(F)F)c2)c2cc(F)cc(C(F)(F)F)c2)cc1]

(R)—N-(4-fluoro-3-(trifluoromethyl)benzyl)-1-(3-fluoro-5-(trifluoromethyl)phenyl)-1-(4-fluorophenyl)-2-phenylethanamine Procedure 13

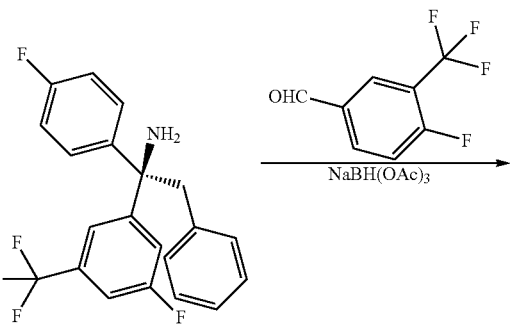

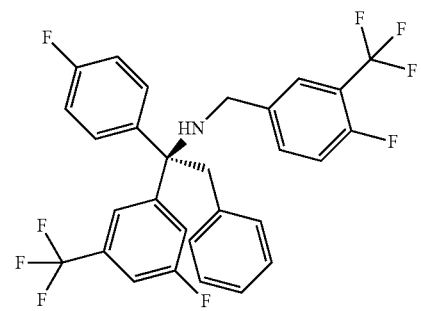

(R)-1-(3-fluoro-5-(trifluoromethyl)phenyl)-1-(4-fluorophenyl)-2-phenylethanamine (21.5 mg, 0.057 mmol) in dichloroethane (0.5 mL) in a two drum vial was added 4-fluoro-3-(trifluoromethyl)benzaldehyde (21.9 mg, 0.114 mmol) followed by a drop of acetic acid. The reaction mixture was shaken for 20 minutes at room temperature before NaBH(OAc)$_3$ (36.3 mg, 0.171 mmol) was added. The reaction was stirred at room temperature overnight. The solvents were removed and the residue was purified by preparative HPLC (phenominex C18 column, 21×100 mm, 5µ) using MeOH/$H_2O$ (with 0.1% TFA) to give (R)—N-(4-fluoro-3-(trifluoromethyl)benzyl)-1-(3-fluoro-5-(trifluoromethyl)phenyl)-1-(4-fluorophenyl)-2-phenylethanamine as a colorless oil (17.5 mg, 46% yield). LCMS: 4.32 min (4 min gradient, MeOH/$H_2O$ 0.1% TFA); $^1$H NMR (400 MHz, $CDCl_3$) δ ppm 3.78-3.91 (m, 4H), 6.60 (d, J=7.47 Hz, 2H), 7.14-7.27 (m, 7H), 7.35-7.48 (m, 6H).

TABLE 4

| Ex. No. | Structure | Name | Retention Time Min./ Molecular Mass | Prepared in the manner described in: |
|---|---|---|---|---|
| 85 | 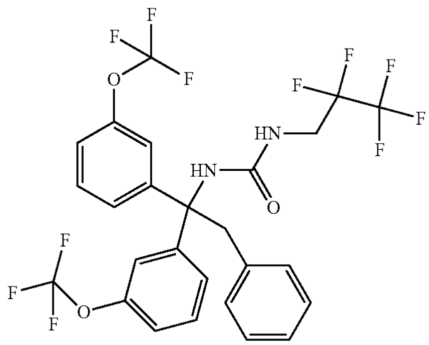 [SMILES: O=C(NCC(F)(F)C(F)(F)F)NC(Cc1ccccc1)(c1cccc(OC(F)(F)F)c1)c1cccc(OC(F)(F)F)c1] | 1-(2,2,3,3,3-pentafluoropropyl)-3-(2-phenyl-1,1-bis(3-(trifluoromethoxy)phenyl)ethyl)urea | 4.30 LC 617.3 $[M + H]^+$ | Procedure 11 and 12 |
| 86 | 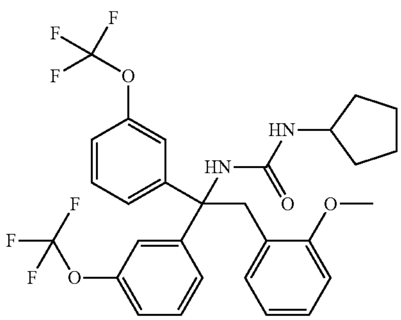 [SMILES: COc1ccccc1CC(NC(=O)NC1CCCC1)(c1cccc(OC(F)(F)F)c1)c1cccc(OC(F)(F)F)c1] | 1-cyclopentyl-3-(2-(2-methoxyphenyl)-1,1-bis(3-(trifluoromethoxy)phenyl)ethyl)urea | 3.92 LC 583.03 $[M + H]^+$ | Procedure 11 and 2 |

TABLE 5

| Ex. No. | Structure | Name | Retention Time Min./ Molecular Mass | Prepared in the manner described in: |
|---|---|---|---|---|
| 87 | 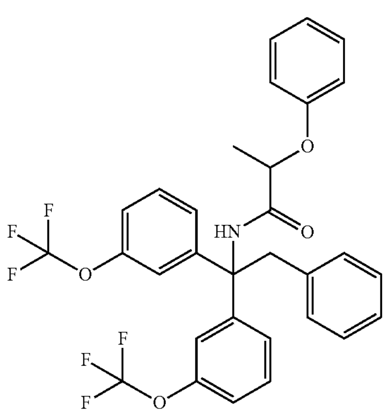 [SMILES: CC(Oc1ccccc1)C(=O)NC(Cc1ccccc1)(c1cccc(OC(F)(F)F)c1)c1cccc(OC(F)(F)F)c1] | 2-phenoxy-N-(2-phenyl-1,1-bis(3-(trifluoromethoxy)phenyl)ethyl)propanamide | 4.37 LC 590.16 $[M + H]^+$ | Procedure 11 and 7 |

TABLE 5-continued

| Ex. No. | Structure | Name | Retention Time Min./ Molecular Mass | Prepared in the manner described in: |
|---|---|---|---|---|
| 88 | 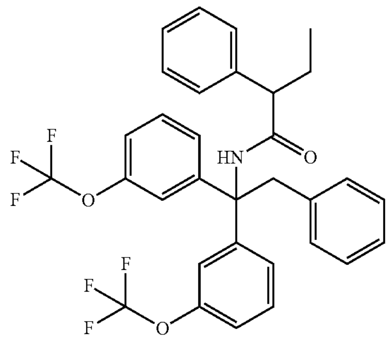 [SMILES: CCC(C(=O)NC(Cc1ccccc1)(c1cccc(OC(F)(F)F)c1)c1cccc(OC(F)(F)F)c1)c1ccccc1] | 2-phenyl-N-(2-phenyl-1,1-bis(3-(trifluoromethoxy)phenyl)ethyl)butanamide | 4.39 LC 588.22 [M + H]$^+$ | Procedure 11 and 7 |
| 89 | 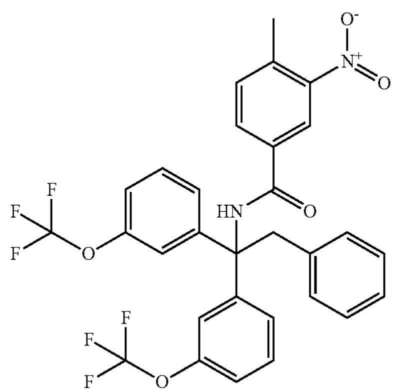 [SMILES: Cc1ccc(C(=O)NC(Cc2ccccc2)(c2cccc(OC(F)(F)F)c2)c2cccc(OC(F)(F)F)c2)cc1[N+](=O)[O-]] | 4-methyl-3-nitro-N-(2-phenyl-1,1-bis(3-(trifluoromethoxy)phenyl)ethyl)benzamide | 4.31 LC 605.15 [M + H]$^+$ | Procedure 11 and 7 |
| 90 | 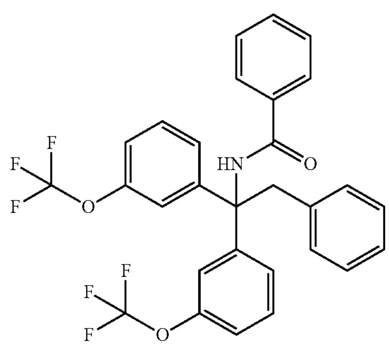 [SMILES: O=C(NC(Cc1ccccc1)(c1cccc(OC(F)(F)F)c1)c1cccc(OC(F)(F)F)c1)c1ccccc1] | N-(2-phenyl-1,1-bis(3-(trifluoromethoxy)phenyl)ethyl)benzamide | 4.24 LC 546.14 [M + H]$^+$ | Procedure 11 and 7 |
| 91 | 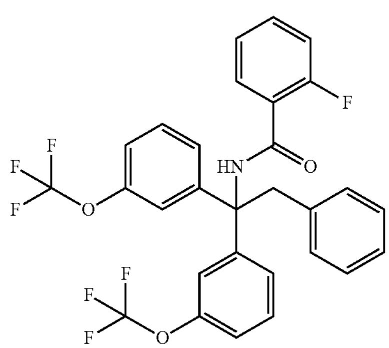 | 2-fluoro-N-(2-phenyl-1,1-bis(3-(trifluoromethoxy)phenyl)ethyl)benzamide | 4.27 LC 564.09 [M + H]$^+$ | Procedure 11 and 7 |

TABLE 5-continued

| Ex. No. | Structure | Name | Retention Time Min./ Molecular Mass | Prepared in the manner described in: |
|---|---|---|---|---|
| 92 | 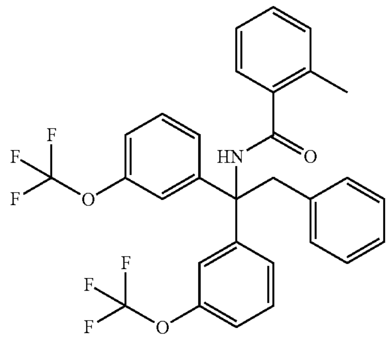 | 2-methyl-N-(2-phenyl-1,1-bis(3-(trifluoromethoxy)phenyl)ethyl)benzamide | 4.26 LC 560.14 [M + H]$^+$ | Procedure 11 and 7 |
| 93 | 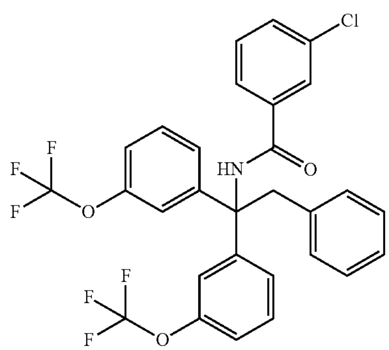 [SMILES: O=C(NC(Cc1ccccc1)(c1cccc(OC(F)(F)F)c1)c1cccc(OC(F)(F)F)c1)c1cccc(Cl)c1] | 3-chloro-N-(2-phenyl-1,1-bis(3-(trifluoromethoxy)phenyl)ethyl)benzamide | 4.36 LC 589.09 [M + H]$^+$ | Procedure 11 and 7 |
| 94 | 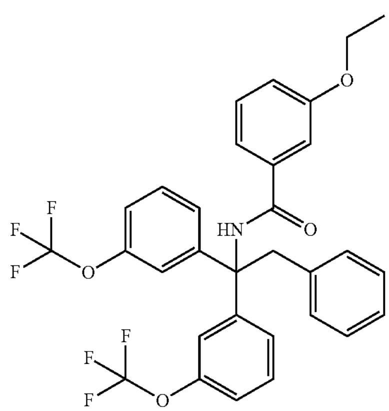 [SMILES: CCOc1cccc(C(=O)NC(Cc2ccccc2)(c2cccc(OC(F)(F)F)c2)c2cccc(OC(F)(F)F)c2)c1] | 3-ethoxy-N-(2-phenyl-1,1-bis(3-(trifluoromethoxy)phenyl)ethyl)benzamide | 4.32 LC 590.16 [M + H]$^+$ | Procedure 11 and 7 |
| 95 | 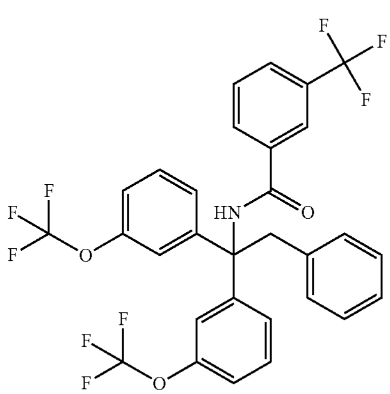 [SMILES: O=C(NC(Cc1ccccc1)(c1cccc(OC(F)(F)F)c1)c1cccc(OC(F)(F)F)c1)c1cccc(C(F)(F)F)c1] | N-(2-phenyl-1,1-bis(3-(trifluoromethoxy)phenyl)ethyl)-3-(trifluoromethyl)benzamide | 4.36 LC 614.1 [M + H]$^+$ | Procedure 11 and 7 |

TABLE 5-continued

| Ex. No. | Structure | Name | Retention Time Min./ Molecular Mass | Prepared in the manner described in: |
|---|---|---|---|---|
| 96 | 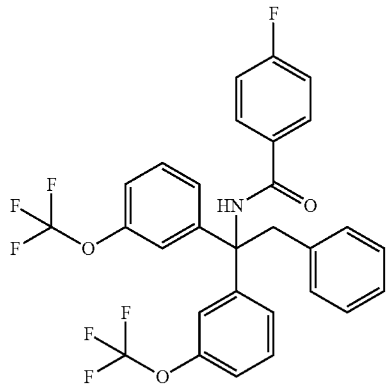 [SMILES: O=C(NC(Cc1ccccc1)(c1cccc(OC(F)(F)F)c1)c1cccc(OC(F)(F)F)c1)c1ccc(F)cc1] | 4-fluoro-N-(2-phenyl-1,1-bis(3-(trifluoromethoxy)phenyl)ethyl)benzamide | 4.28 LC 564.12 [M + H]$^+$ | Procedure 11 and 7 |
| 97 | 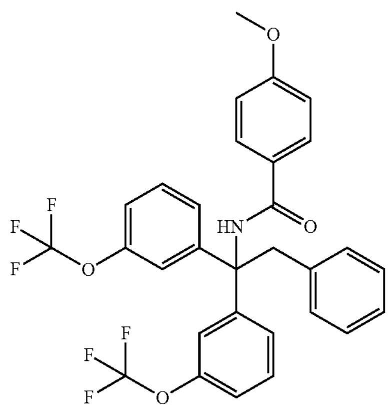 [SMILES: COc1ccc(C(=O)NC(Cc2ccccc2)(c2cccc(OC(F)(F)F)c2)c2cccc(OC(F)(F)F)c2)cc1] | 4-methoxy-N-(2-phenyl-1,1-bis(3-(trifluoromethoxy)phenyl)ethyl)benzamide | 4.26 LC 576.15 [M + H]$^+$ | Procedure 11 and 7 |
| 98 | 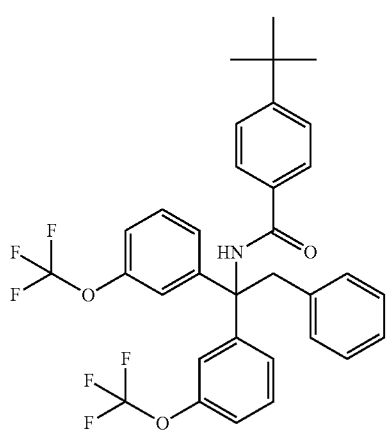 [SMILES: CC(C)(C)c1ccc(C(=O)NC(Cc2ccccc2)(c2cccc(OC(F)(F)F)c2)c2cccc(OC(F)(F)F)c2)cc1] | 4-tert-butyl-N-(2-phenyl-1,1-bis(3-(trifluoromethoxy)phenyl)ethyl)benzamide | 4.51 LC 602.16 [M + H]$^+$ | Procedure 11 and 7 |

TABLE 5-continued

| Ex. No. | Structure | Name | Retention Time Min./ Molecular Mass | Prepared in the manner described in: |
|---|---|---|---|---|
| 99 | 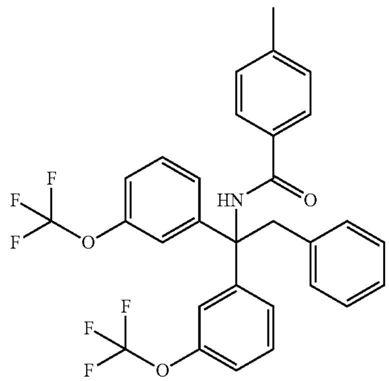 [SMILES: Cc1ccc(C(=O)NC(Cc2ccccc2)(c2cccc(OC(F)(F)F)c2)c2cccc(OC(F)(F)F)c2)cc1] | 4-methyl-N-(2-phenyl-1,1-bis(3-(trifluoromethoxy)phenyl)ethyl)benzamide | 4.30 LC 560.14 [M + H]$^+$ | Procedure 11 and 7 |
| 100 | 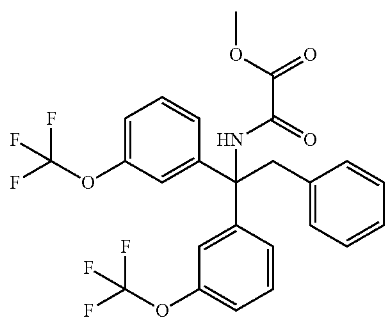 [SMILES: COC(=O)C(=O)NC(Cc1ccccc1)(c1cccc(OC(F)(F)F)c1)c1cccc(OC(F)(F)F)c1] | methyl 2-oxo-2-(2-phenyl-1,1-bis(3-(trifluoromethoxy)phenyl)ethylamino)acetate | 4.13 LC 528.08 [M + H]$^+$ | Procedure 11 and 7 |
| 101 | 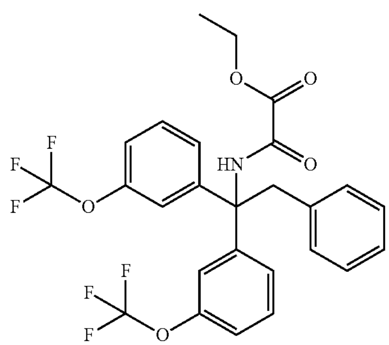 [SMILES: CCOC(=O)C(=O)NC(Cc1ccccc1)(c1cccc(OC(F)(F)F)c1)c1cccc(OC(F)(F)F)c1] | ethyl 2-oxo-2-(2-phenyl-1,1-bis(3-(trifluoromethoxy)phenyl)ethylamino)acetate | 4.18 LC 542.14 [M + H]$^+$ | Procedure 11 and 7 |
| 102 | 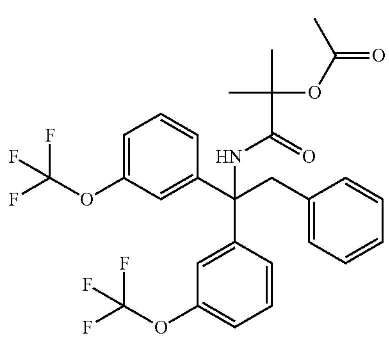 [SMILES: CC(=O)OC(C)(C)C(=O)NC(Cc1ccccc1)(c1cccc(OC(F)(F)F)c1)c1cccc(OC(F)(F)F)c1] | 2-methyl-1-oxo-1-(2-phenyl-1,1-bis(3-(trifluoromethoxy)phenyl)ethylamino)propan-2-yl acetate | 4.19 LC 570.15 [M + H]$^+$ | Procedure 11 and 7 |

TABLE 5-continued

| Ex. No. | Structure | Name | Retention Time Min./ Molecular Mass | Prepared in the manner described in: |
|---|---|---|---|---|
| 103 | 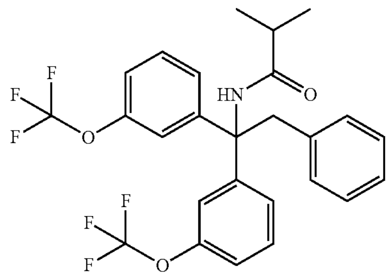 [SMILES: CC(C)C(=O)NC(Cc1ccccc1)(c1cccc(OC(F)(F)F)c1)c1cccc(OC(F)(F)F)c1] | N-(2-phenyl-1,1-bis(3-(trifluoromethoxy)phenyl)ethyl) isobutyramide | 4.22 LC 512.14 [M + H]+ | Procedure 11 and 7 |
| 104 | 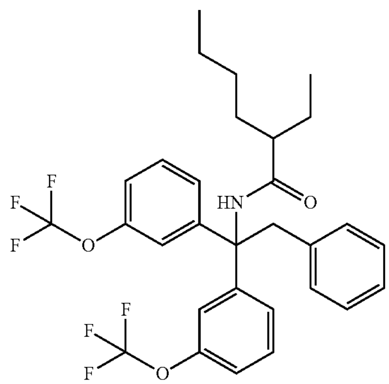 [SMILES: CCCCC(CC)C(=O)NC(Cc1ccccc1)(c1cccc(OC(F)(F)F)c1)c1cccc(OC(F)(F)F)c1] | 2-ethyl-N-(2-phenyl-1,1-bis(3-(trifluoromethoxy)phenyl)ethyl) hexanamide | 4.45 LC 568.21 [M + H]+ | Procedure 11 and 7 |
| 105 | 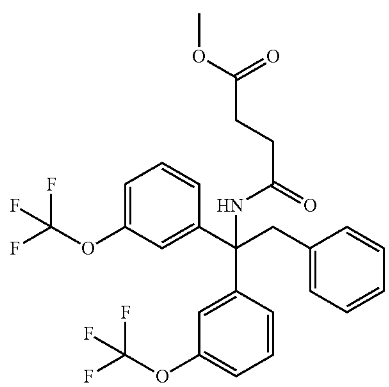 [SMILES: COC(=O)CCC(=O)NC(Cc1ccccc1)(c1cccc(OC(F)(F)F)c1)c1cccc(OC(F)(F)F)c1] | methyl 4-oxo-4-(2-phenyl-1,1-bis(3-(trifluoromethoxy)phenyl) ethylamino)butanoate | 4.17 LC 556.13 [M + H]+ | Procedure 11 and 7 |
| 106 | 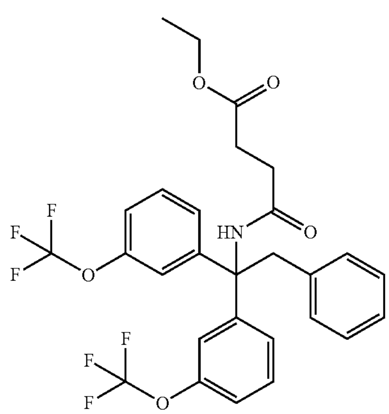 [SMILES: CCOC(=O)CCC(=O)NC(Cc1ccccc1)(c1cccc(OC(F)(F)F)c1)c1cccc(OC(F)(F)F)c1] | ethyl 4-oxo-4-(2-phenyl-1,1-bis(3-(trifluoromethoxy)phenyl) ethylamino)butanoate | 4.21 LC 570.15 [M + H]+ | Procedure 11 and 7 |

TABLE 5-continued

| Ex. No. | Structure | Name | Retention Time Min./ Molecular Mass | Prepared in the manner described in: |
|---|---|---|---|---|
| 107 | 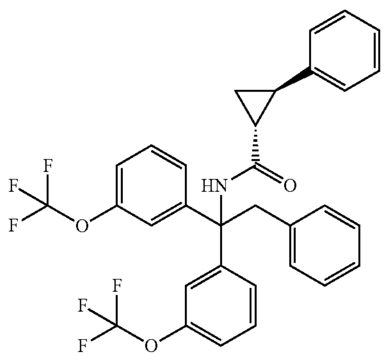 [SMILES: O=C(NC(Cc1ccccc1)(c1cccc(OC(F)(F)F)c1)c1cccc(OC(F)(F)F)c1)[C@@H]1C[C@H]1c1ccccc1] | (1R,2R)-2-phenyl-N-(2-phenyl-1,1-bis(3-(trifluoromethoxy)phenyl)ethyl)cyclopropanecarboxamide | 4.37 LC 586.15 [M + H]⁺ | Procedure 11 and 7 |
| 108 | 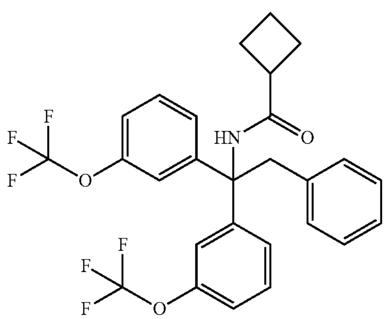 [SMILES: O=C(NC(Cc1ccccc1)(c1cccc(OC(F)(F)F)c1)c1cccc(OC(F)(F)F)c1)C1CCC1] | N-(2-phenyl-1,1-bis(3-(trifluoromethoxy)phenyl)ethyl)cyclobutanecarboxamide | 4.27 LC 524.13 [M + H]⁺ | Porcedure 11 and 7 |
| 109 | 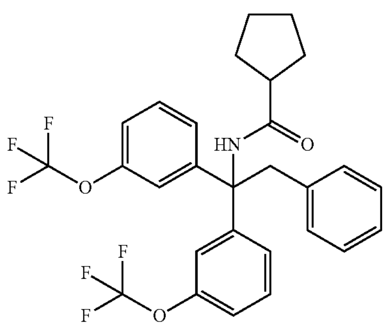 [SMILES: O=C(NC(Cc1ccccc1)(c1cccc(OC(F)(F)F)c1)c1cccc(OC(F)(F)F)c1)C1CCCC1] | N-(2-phenyl-1,1-bis(3-(trifluoromethoxy)phenyl)ethyl)cyclopentanecarboxamide | 4.32 LC 538.14 [M + H]⁺ | Procedure 11 and 7 |
| 110 | 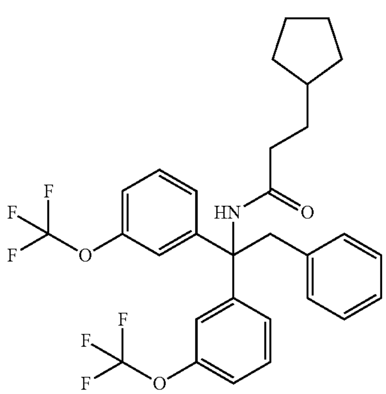 [SMILES: O=C(CCC1CCCC1)NC(Cc1ccccc1)(c1cccc(OC(F)(F)F)c1)c1cccc(OC(F)(F)F)c1] | 3-cyclopentyl-N-(2-phenyl-1,1-bis(3-(trifluoromethoxy)phenyl)ethyl)propanamide | 4.48 LC 566.17 [M + H]⁺ | Procedure 11 and 7 |

TABLE 5-continued

| Ex. No. | Structure | Name | Retention Time Min./ Molecular Mass | Prepared in the manner described in: |
|---|---|---|---|---|
| 111 | 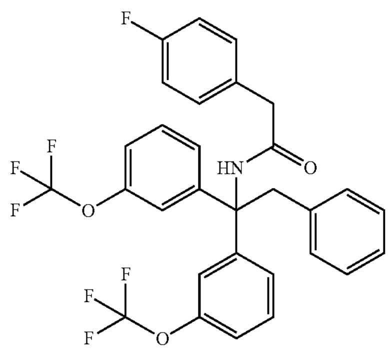 [SMILES: O=C(Cc1ccc(F)cc1)NC(Cc1ccccc1)(c1cccc(OC(F)(F)F)c1)c1cccc(OC(F)(F)F)c1] | 2-(4-fluorophenyl)-N-(2-phenyl-1,1-bis(3-(trifluoromethoxy)phenyl)ethyl)acetamide | 4.29 LC 578.1 [M + H]+ | Procedure 11 and 7 |
| 112 | 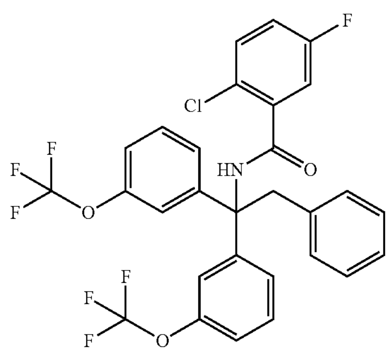 [SMILES: O=C(NC(Cc1ccccc1)(c1cccc(OC(F)(F)F)c1)c1cccc(OC(F)(F)F)c1)c1cc(F)ccc1Cl] | 2-chloro-5-fluoro-N-(2-phenyl-1,1-bis(3-(trifluoromethoxy)phenyl)ethyl)benzamide | 4.27 LC 598.06 [M + H]+ | Procedure 11 and 7 |
| 113 | 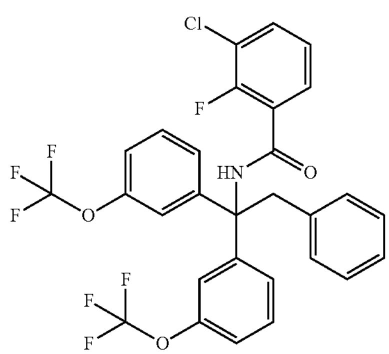 [SMILES: O=C(NC(Cc1ccccc1)(c1cccc(OC(F)(F)F)c1)c1cccc(OC(F)(F)F)c1)c1cccc(Cl)c1F] | 3-chloro-2-fluoro-N-(2-phenyl-1,1-bis(3-(trifluoromethoxy)phenyl)ethyl)benzamide | 4.35 LC 598.04 [M + H]+ | Procedure 11 and 7 |
| 114 | 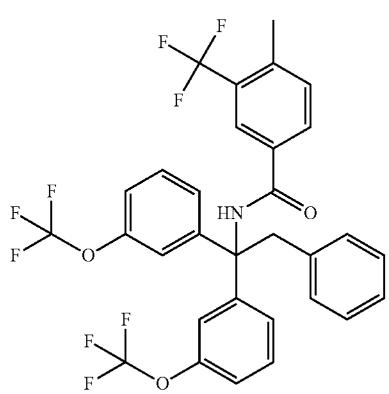 [SMILES: Cc1ccc(C(=O)NC(Cc2ccccc2)(c2cccc(OC(F)(F)F)c2)c2cccc(OC(F)(F)F)c2)cc1C(F)(F)F] | 4-methyl-N-(2-phenyl-1,1-bis(3-(trifluoromethoxy)phenyl)ethyl)-3-(trifluoromethyl)benzamide | 4.43 LC 628.11 [M + H]+ | Procedure 11 and 7 |

TABLE 5-continued

| Ex. No. | Structure | Name | Retention Time Min./ Molecular Mass | Prepared in the manner described in: |
|---|---|---|---|---|
| 115 | 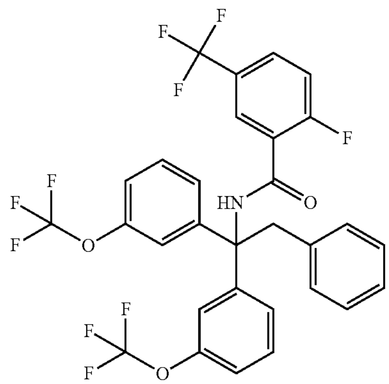 [SMILES: O=C(NC(Cc1ccccc1)(c1cccc(OC(F)(F)F)c1)c1cccc(OC(F)(F)F)c1)c1cc(C(F)(F)F)ccc1F] | 2-chloro-N-(2-phenyl-1,1-bis(3-(trifluoromethoxy)phenyl)ethyl)-5-(trifluoromethyl)benzamide | 4.36 LC 648.05 [M + H]$^+$ | Procedure 11 and 7 |
| 116 | 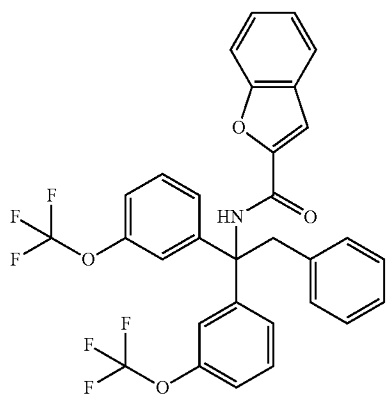 [SMILES: O=C(NC(Cc1ccccc1)(c1cccc(OC(F)(F)F)c1)c1cccc(OC(F)(F)F)c1)c1cc2ccccc2o1] | N-(2-phenyl-1,1-bis(3-(trifluoromethoxy)phenyl)ethyl) benzofuran-2-carboxamide | 4.39 LC 586.12 [M + H]$^+$ | Procedure 11 and 7 |
| 117 | 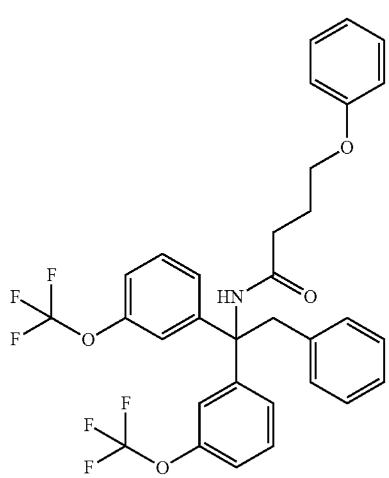 [SMILES: O=C(CCCOc1ccccc1)NC(Cc1ccccc1)(c1cccc(OC(F)(F)F)c1)c1cccc(OC(F)(F)F)c1] | 4-phenoxy-N-(2-phenyl-1,1-bis(3-(trifluoromethoxy)phenyl) ethyl)butanamide | 4.39 LC 604.16 [M + H]$^+$ | Procedure 11 and 7 |

TABLE 5-continued

| Ex. No. | Structure | Name | Retention Time Min./ Molecular Mass | Prepared in the manner described in: |
| --- | --- | --- | --- | --- |
| 118 | 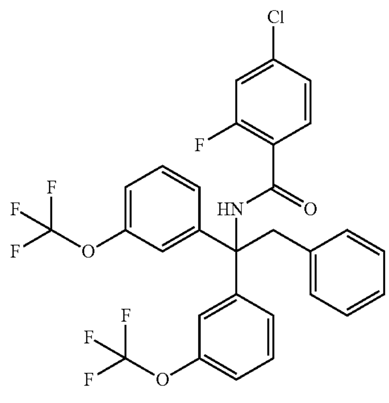 [SMILES: O=C(NC(Cc1ccccc1)(c1cccc(OC(F)(F)F)c1)c1cccc(OC(F)(F)F)c1)c1ccc(Cl)cc1F] | 4-chloro-2-fluoro-N-(2-phenyl-1,1-bis(3-(trifluoromethoxy)phenyl)ethyl)benzamide | 4.39 LC 598.1 [M + H]$^+$ | Procedure 11 and 7 |
| 119 | 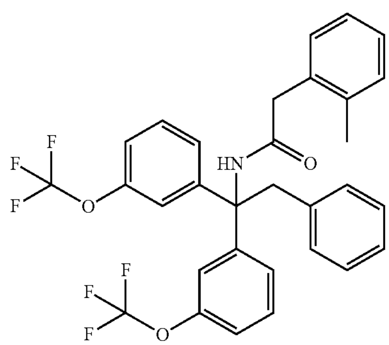 [SMILES: Cc1ccccc1CC(=O)NC(Cc1ccccc1)(c1cccc(OC(F)(F)F)c1)c1cccc(OC(F)(F)F)c1] | N-(2-phenyl-1,1-bis(3-(trifluoromethoxy)phenyl)ethyl)-2-o-tolylacetamide | 4.35 LC 574.15 [M + H]$^+$ | Procedure 11 and 7 |
| 120 | 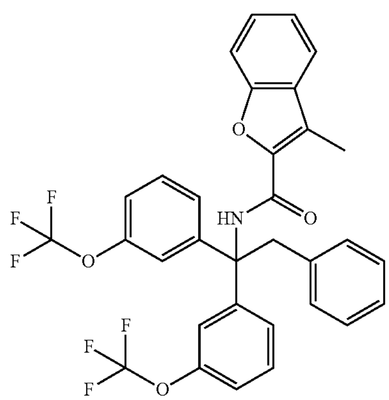 [SMILES: Cc1c(C(=O)NC(Cc2ccccc2)(c2cccc(OC(F)(F)F)c2)c2cccc(OC(F)(F)F)c2)oc2ccccc12] | 3-methyl-N-(2-phenyl-1,1-bis(3-(trifluoromethoxy)phenyl)ethyl)benzofuran-2-carboxamide | 4.57 LC 600.14 [M + H]$^+$ | Procedure 11 and 7 |
| 121 | 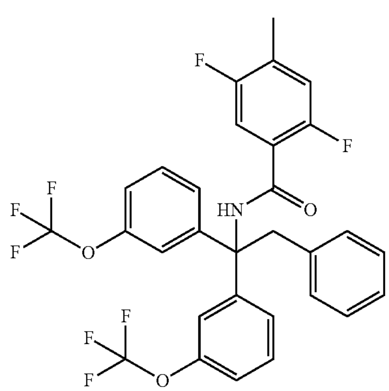 [SMILES: Cc1cc(F)c(C(=O)NC(Cc2ccccc2)(c2cccc(OC(F)(F)F)c2)c2cccc(OC(F)(F)F)c2)cc1F] | 2,5-difluoro-4-methyl-N-(2-phenyl-1,1-bis(3-(trifluoromethoxy)phenyl)ethyl)benzamide | 4.40 LC 596.1 [M + H]$^+$ | Procedure 11 and 7 |

TABLE 5-continued

| Ex. No. | Structure | Name | Retention Time Min./ Molecular Mass | Prepared in the manner described in: |
|---|---|---|---|---|
| 122 | 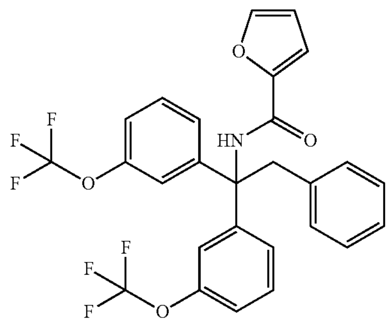 [SMILES: O=C(NC(Cc1ccccc1)(c1cccc(OC(F)(F)F)c1)c1cccc(OC(F)(F)F)c1)c1ccco1] | N-(2-phenyl-1,1-bis(3-(trifluoromethoxy)phenyl)ethyl) furan-2-carboxamide | 4.19 LC 536.13 [M + H]$^+$ | Procedure 11 and 7 |
| 127 | 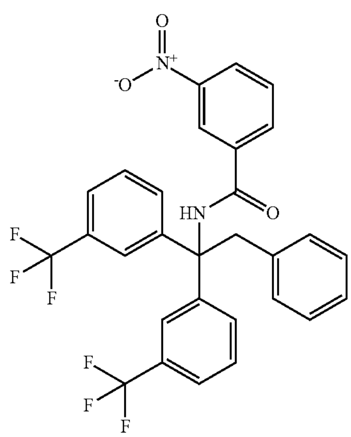 | 3-nitro-N-(2-phenyl-1,1-bis(3-(trilfuoromethyl)phenyl)ethyl) benzamide | 4.19 LC 559.22 [M + H]$^+$ | Procedure 11 and 7 |
| 128 | 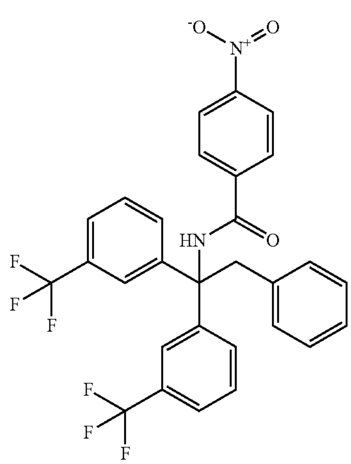 | 4-nitro-N-(2-phenyl-1,1-bis(3-(trifluoromethyl)phenyl)ethyl) benzamide | 4.19 LC 559.21 [M + H]$^+$ | Procedure 11 and 7 |

TABLE 5-continued

| Ex. No. | Structure | Name | Retention Time Min./ Molecular Mass | Prepared in the manner described in: |
|---|---|---|---|---|
| 129 | 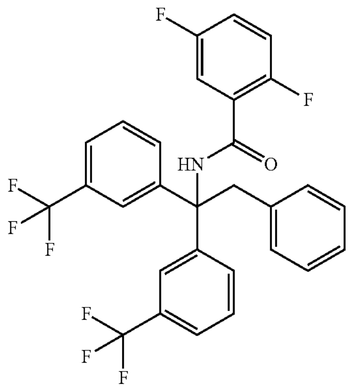 [SMILES: O=C(NC(Cc1ccccc1)(c1cccc(C(F)(F)F)c1)c1cccc(C(F)(F)F)c1)c1cc(F)ccc1F] | 2,5-difluoro-N-(2-phenyl-1,1-bis(3-(trifluoromethyl)phenyl)ethyl)benzamide | 4.19 LC 550.21 [M + H]$^+$ | Procedure 11 and 7 |
| 130 | 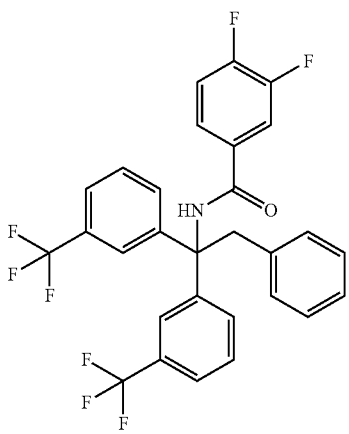 [SMILES: O=C(NC(Cc1ccccc1)(c1cccc(C(F)(F)F)c1)c1cccc(C(F)(F)F)c1)c1ccc(F)c(F)c1] | 3,4-difluoro-N-(2-phenyl-1,1-bis(3-(trifluoromethyl)phenyl)ethyl)benzamide | 4.22 LC 550.2 [M + H]$^+$ | Procedure 11 and 7 |
| 131 | 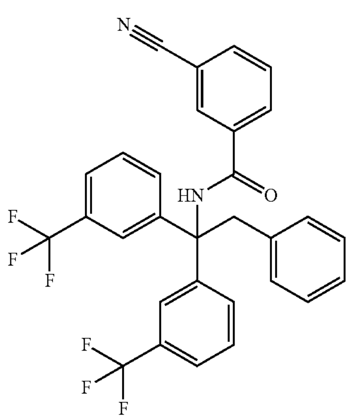 [SMILES: N#Cc1cccc(C(=O)NC(Cc2ccccc2)(c2cccc(C(F)(F)F)c2)c2cccc(C(F)(F)F)c2)c1] | 3-cyano-N-(2-phenyl-1,1-bis(3-(trifluoromethyl)phenyl)ethyl)benzamide | 4.10 LC 539.2 [M + H]$^+$ | Procedure 11 and 7 |

TABLE 5-continued

| Ex. No. | Structure | Name | Retention Time Min./ Molecular Mass | Prepared in the manner described in: |
|---|---|---|---|---|
| 132 | 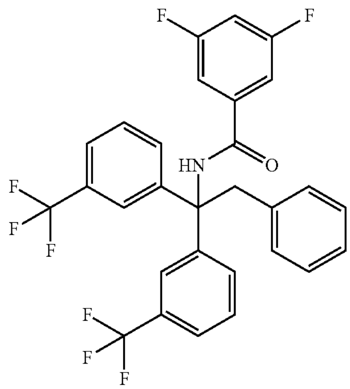 [SMILES: O=C(NC(Cc1ccccc1)(c1cccc(C(F)(F)F)c1)c1cccc(C(F)(F)F)c1)c1cc(F)cc(F)c1] | 3,5-difluoro-N-(2-phenyl-1,1-bis(3-(trifluoromethyl)phenyl)ethyl)benzamide | 4.24 LC 550.21 [M + H]$^+$ | Procedure 11 and 7 |
| 133 | 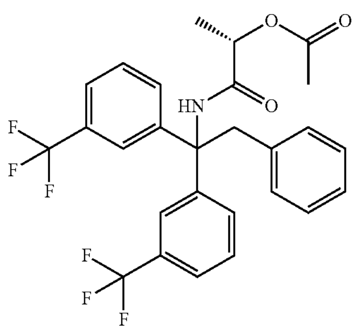 [SMILES: CC(=O)O[C@@H](C)C(=O)NC(Cc1ccccc1)(c1cccc(C(F)(F)F)c1)c1cccc(C(F)(F)F)c1] | (S)-1-oxo-1-(2-phenyl-1,1-bis(3-(trilfuoromethyl)phenyl)ethylamino)propan-2-yl acetate | 4.04 LC 524.23 [M + H]$^+$ | Procedure 11 and 7 |
| 134 | 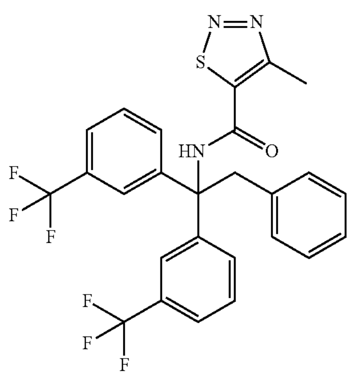 [SMILES: Cc1nnsc1C(=O)NC(Cc1ccccc1)(c1cccc(C(F)(F)F)c1)c1cccc(C(F)(F)F)c1] | 4-methyl-N-(2-phenyl-1,1-bis(3-(trifluoromethyl)phenyl)ethyl)-1,2,3-thiadiazole-5-carboxamide | 4.14 LC 536.2 [M + H]$^+$ | Procedure 11 and 7 |
| 135 | 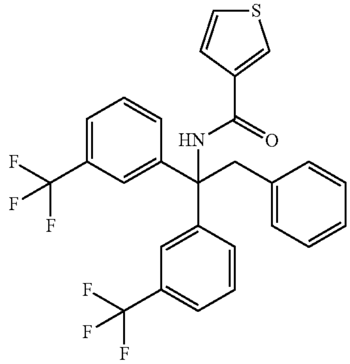 [SMILES: O=C(NC(Cc1ccccc1)(c1cccc(C(F)(F)F)c1)c1cccc(C(F)(F)F)c1)c1ccsc1] | N-(2-phenyl-1,1-bis(3-(trifluoromethyl)phenyl)ethyl)thiophene-3-carobxamide | 4.10 LC 520.17 [M + H]$^+$ | Procedure 11 and 7 |

TABLE 5-continued

| Ex. No. | Structure | Name | Retention Time Min./ Molecular Mass | Prepared in the manner described in: |
|---|---|---|---|---|
| 136 | 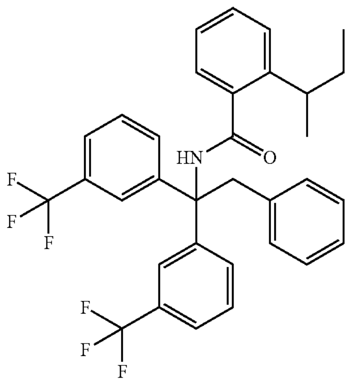 | 2-phenyl-N-(2-phenyl-1,1-bis(3-(trilfuoromethyl)phenyl)ethyl)butanamide | 4.29 LC 556.26 [M + H]$^+$ | Procedure 11 and 7 |
| 137 | 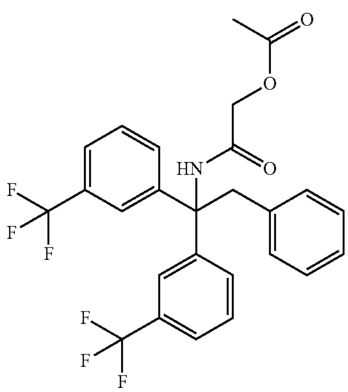 [SMILES: CC(=O)OCC(=O)NC(Cc1ccccc1)(c1cccc(C(F)(F)F)c1)c1cccc(C(F)(F)F)c1] | 2-oxo-2-(2-phenyl-1,1-bis(3-(trilfuoromethyl)phenyl)ethylamino)ethyl acetate | 4.00 LC 510.2 [M + H]$^+$ | Procedure 11 and 7 |
| 138 | 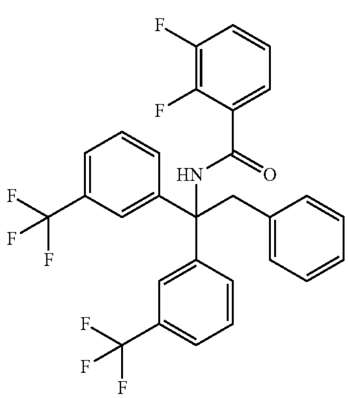 [SMILES: O=C(NC(Cc1ccccc1)(c1cccc(C(F)(F)F)c1)c1cccc(C(F)(F)F)c1)c1cccc(F)c1F] | 2,3-difluoro-N-(2-phenyl-1,1-bis(3-(trifluoromethyl)phenyl)ethyl)benzamide | 4.16 LC 550.14 [M + H]$^+$ | Procedure 11 and 7 |

TABLE 5-continued

| Ex. No. | Structure | Name | Retention Time Min./ Molecular Mass | Prepared in the manner described in: |
|---|---|---|---|---|
| 139 | 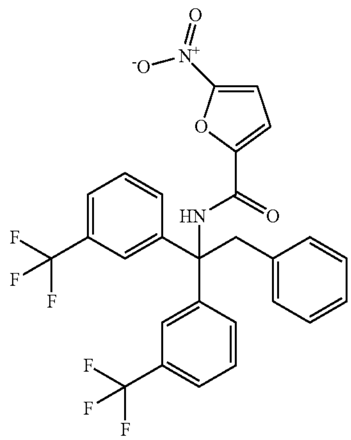 | 5-nitro-N-(2-phenyl-1,1-bis(3-(trifluoromethyl)phenyl)ethyl)furan-2-carobxamide | 4.11 LC 549.16 [M + H]$^+$ | Procedure 11 and 7 |
| 140 | 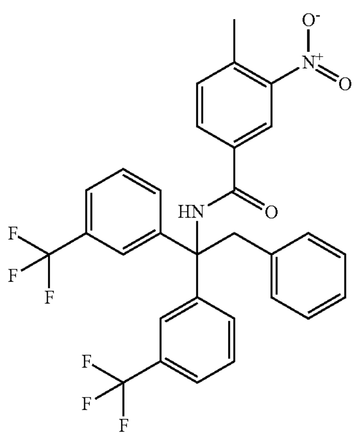 [SMILES: Cc1ccc(C(=O)NC(Cc2ccccc2)(c2cccc(C(F)(F)F)c2)c2cccc(C(F)(F)F)c2)cc1[N+](=O)[O-]] | 4-methyl-3-nitro-N-(2-phenyl-1,1-bis(3-(trifluoromethyl)phenyl)ethyl)benzamide | 4.23 LC 573.21 [M + H]$^+$ | Procedure 11 and 7 |
| 141 | 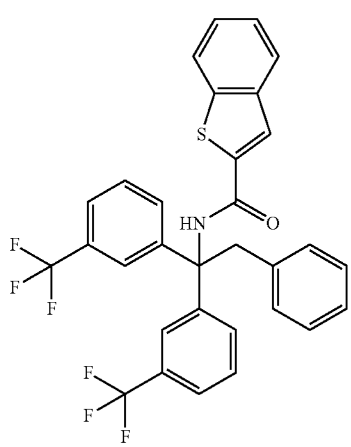 [SMILES: O=C(NC(Cc1ccccc1)(c1cccc(C(F)(F)F)c1)c1cccc(C(F)(F)F)c1)c1cc2ccccc2s1] | N-(2-phenyl-1,1-bis(3-(trifluoromethyl)phenyl)ethyl)benzo[b]thiophene-2-carboxamide | 4.29 LC 570.17 [M + H]$^+$ | Procedure 11 and 7 |

TABLE 5-continued

| Ex. No. | Structure | Name | Retention Time Min./ Molecular Mass | Prepared in the manner described in: |
|---|---|---|---|---|
| 142 | 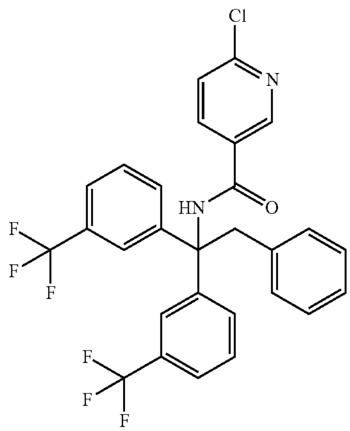 [SMILES: O=C(NC(Cc1ccccc1)(c1cccc(C(F)(F)F)c1)c1cccc(C(F)(F)F)c1)c1ccc(Cl)nc1] | 6-chloro-N-(2-phenyl-1,1-bis(3-(trifluoromethyl)phenyl)ethyl)nicotinamide | 4.15 LC 549.17 [M + H]$^+$ | Procedure 11 and 7 |
| 143 | 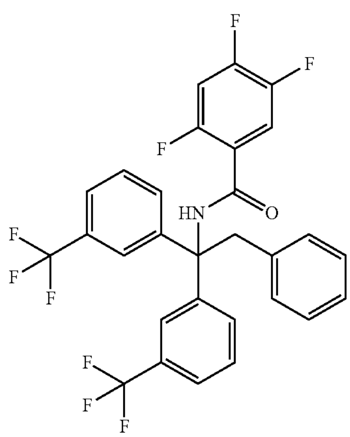 [SMILES: O=C(NC(Cc1ccccc1)(c1cccc(C(F)(F)F)c1)c1cccc(C(F)(F)F)c1)c1cc(F)c(F)cc1F] | 2,4,5-trifluoro-N-(2-phenyl-1,1-bis(3-(trifluoromethyl)phenyl)ethyl)benzamide | 4.24 LC 568.2 [M + H]$^+$ | Procedure 11 and 7 |
| 144 | 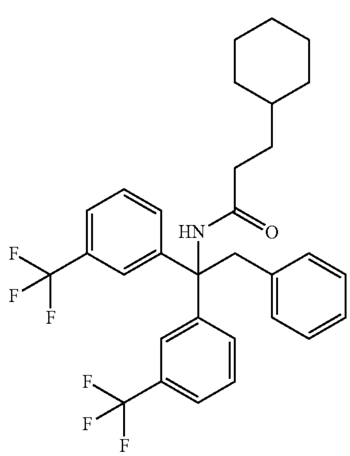 [SMILES: O=C(CCC1CCCCC1)NC(Cc1ccccc1)(c1cccc(C(F)(F)F)c1)c1cccc(C(F)(F)F)c1] | 3-cyclohexyl-N-(2-phenyl-1,1-bis(3-(trifluoromethyl)phenyl)ethyl)propanamide | 4.44 LC 548.27 [M + H]$^+$ | Procedure 11 and 7 |

TABLE 5-continued

| Ex. No. | Structure | Name | Retention Time Min./ Molecular Mass | Prepared in the manner described in: |
|---|---|---|---|---|
| 145 | 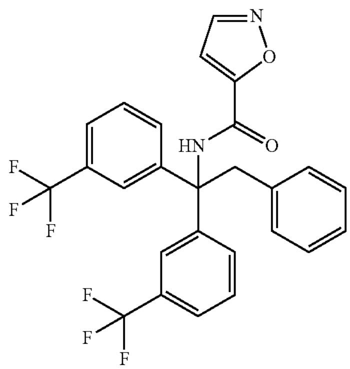 [SMILES: O=C(NC(Cc1ccccc1)(c1cccc(C(F)(F)F)c1)c1cccc(C(F)(F)F)c1)c1ccno1] | N-(2-phenyl-1,1-bis(3-(trifluoromethyl)phenyl)ethyl) isoxazole-5-carboxamide | 4.00 LC 505.18 [M + H]⁺ | Procedure 11 and 7 |
| 146 | 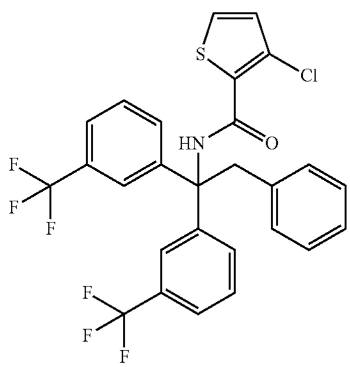 [SMILES: O=C(NC(Cc1ccccc1)(c1cccc(C(F)(F)F)c1)c1cccc(C(F)(F)F)c1)c1sccc1Cl] | 3-chloro-N-(2-phenyl-1,1-bis(3-(trifluoromethyl)phenyl)ethyl) thiophene-2-carboxamide | 4.22 LC 554.12 [M + H]⁺ | Procedure 11 and 7 |
| 147 | 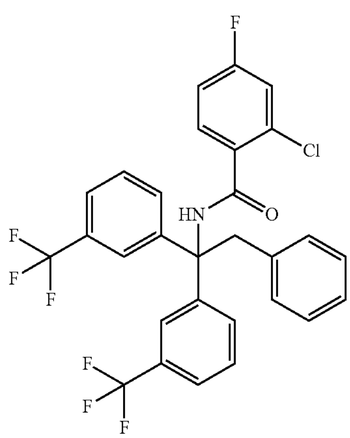 [SMILES: O=C(NC(Cc1ccccc1)(c1cccc(C(F)(F)F)c1)c1cccc(C(F)(F)F)c1)c1ccc(F)cc1Cl] | 2-chloro-4-fluoro-N-(2-phenyl-1,1-bis(3-(trifluoromethyl) phenyl)ethyl)benzamide | 4.18 LC 566.15 [M + H]⁺ | Procedure 11 and 7 |
| 148 | 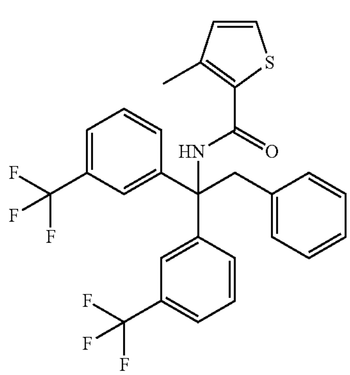 [SMILES: Cc1ccsc1C(=O)NC(Cc1ccccc1)(c1cccc(C(F)(F)F)c1)c1cccc(C(F)(F)F)c1] | 3-methyl-N-(2-phenyl-1,1-bis(3-(trifluoromethyl)phenyl)ethyl) thiophene-2-carboxamide | 4.15 LC 534.19 [M + H]⁺ | Procedure 11 and 7 |

TABLE 5-continued

| Ex. No. | Structure | Name | Retention Time Min./ Molecular Mass | Prepared in the manner described in: |
|---|---|---|---|---|
| 149 | 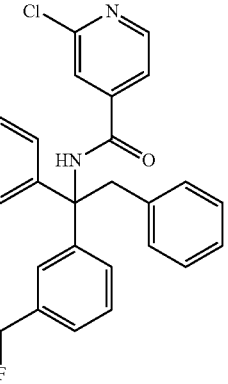 | 2-chloro-N-(2-phenyl-1,1-bis(3-(trifluoromethyl)phenyl)ethyl) isonicotinamide | 4.17 LC 549.17 [M + H]+ | Procedure 11 and 7 |
| 150 | 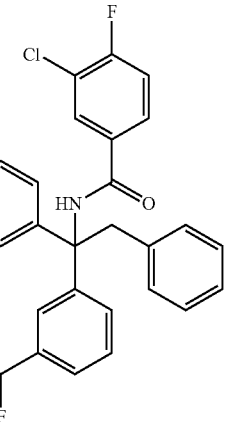 | 3-chloro-4-fluoro-N-(2-phenyl-1,1-bis(3-(trilfuoromethyl) phenyl)ethyl)benzamide | 4.30 LC 566.15 [M + H]+ | Procedure 11 and 7 |
| 151 | 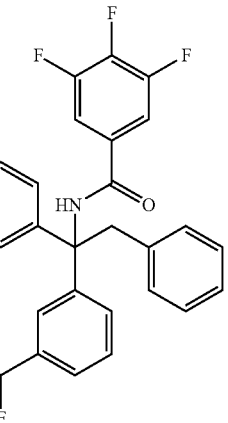 | 3,4,5-trifluoro-N-(2-phenyl-1,1-bis(3-(trifluoromethyl)phenyl) ethyl)benzamide | 4.33 LC 568.15 [M + H]+ | Procedure 11 and 7 |

TABLE 5-continued

| Ex. No. | Structure | Name | Retention Time Min./ Molecular Mass | Prepared in the manner described in: |
|---|---|---|---|---|
| 152 | 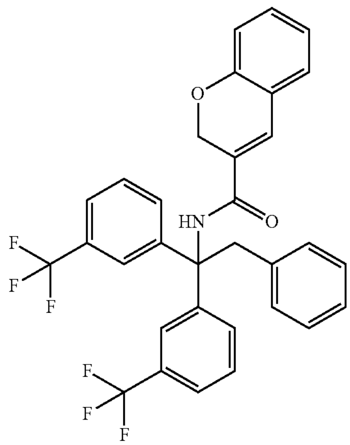 [SMILES: O=C(NC(Cc1ccccc1)(c1cccc(C(F)(F)F)c1)c1cccc(C(F)(F)F)c1)C1=Cc2ccccc2OC1] | N-(2-phenyl-1,1-bis(3-(trilfuoromethyl)phenyl)ethyl)-2H-chromene-3-carboxamide | 4.31 LC 568.17 [M + H]⁺ | Procedure 11 and 7 |
| 153 | 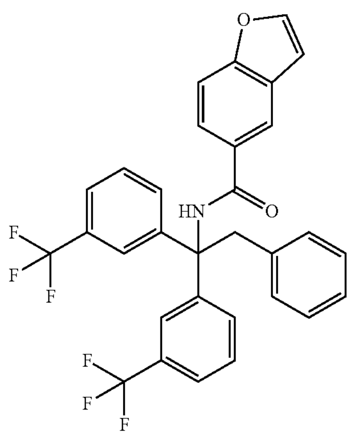 [SMILES: O=C(NC(Cc1ccccc1)(c1cccc(C(F)(F)F)c1)c1cccc(C(F)(F)F)c1)c1ccc2occc2c1] | N-(2-phenyl-1,1-bis(3-(trilfuoromethyl)phenyl)ethyl) benzofuran-5-carboxamide | 4.17 LC 554.16 [M + H]⁺ | Procedure 11 and 7 |
| 154 | 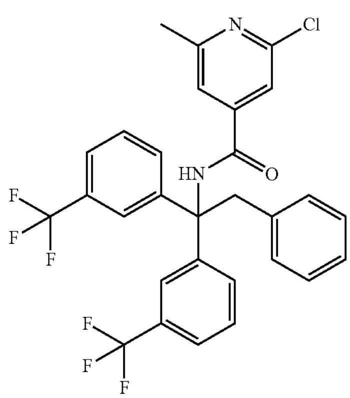 [SMILES: Cc1cc(C(=O)NC(Cc2ccccc2)(c2cccc(C(F)(F)F)c2)c2cccc(C(F)(F)F)c2)cc(Cl)n1] | 2-chloro-6-methyl-N-(2-phenyl-1,1-bis(3-(trilfuoromethyl) phenyl)ethyl)isonicotinamide | 4.23 LC 563.15 [M + H]⁺ | Procedure 11 and 7 |

TABLE 5-continued

| Ex. No. | Structure | Name | Retention Time Min./ Molecular Mass | Prepared in the manner described in: |
|---|---|---|---|---|
| 155 | 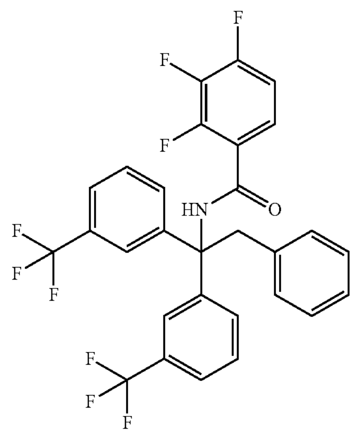 [SMILES: O=C(NC(Cc1ccccc1)(c1cccc(C(F)(F)F)c1)c1cccc(C(F)(F)F)c1)c1ccc(F)c(F)c1F] | 2,3,4-trifluoro-N-(2-phenyl-1,1-bis(3-(trifluoromethyl)phenyl)ethyl)benzamide | 4.23 LC 568.12 [M + H]$^+$ | Procedure 11 and 7 |
| 156 | 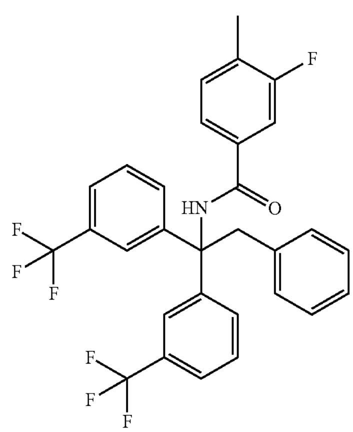 [SMILES: Cc1ccc(C(=O)NC(Cc2ccccc2)(c2cccc(C(F)(F)F)c2)c2cccc(C(F)(F)F)c2)cc1F] | 3-fluoro-4-methyl-N-(2-phenyl-1,1-bis(3-(trifluoromethyl)phenyl)ethyl)benzamide | 4.24 LC 546.15 [M + H]$^+$ | Procedure 11 and 7 |
| 157 | 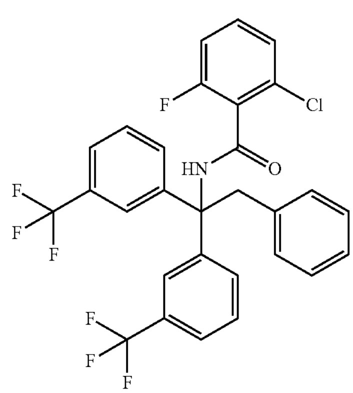 [SMILES: O=C(NC(Cc1ccccc1)(c1cccc(C(F)(F)F)c1)c1cccc(C(F)(F)F)c1)c1c(F)cccc1Cl] | 2-chloro-6-fluoro-N-(2-phenyl-1,1-bis(3-(trifluoromethyl)phenyl)ethyl)benzamide | 4.11 LC 566.13 [M + H]$^+$ | Procedure 11 and 7 |

TABLE 5-continued

| Ex. No. | Structure | Name | Retention Time Min./ Molecular Mass | Prepared in the manner described in: |
| --- | --- | --- | --- | --- |
| 158 | 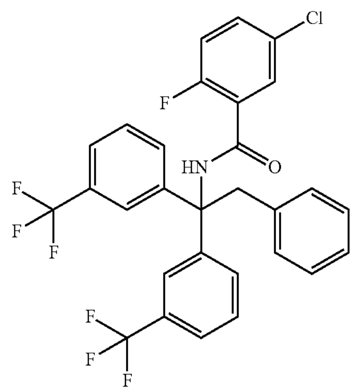 [SMILES: O=C(NC(Cc1ccccc1)(c1cccc(C(F)(F)F)c1)c1cccc(C(F)(F)F)c1)c1cc(Cl)ccc1F] | 5-chloro-2-fluoro-N-(2-phenyl-1,1-bis(3-(trifluoromethyl)phenyl)ethyl)benzamide | 4.27 LC 566.09 [M + H]⁺ | Procedure 11 and 7 |
| 159 | 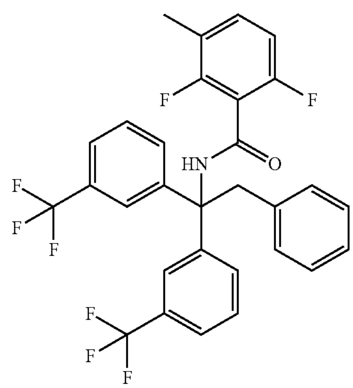 [SMILES: Cc1ccc(F)c(C(=O)NC(Cc2ccccc2)(c2cccc(C(F)(F)F)c2)c2cccc(C(F)(F)F)c2)c1F] | 2,6-difluoro-3-methyl-N-(2-phenyl-1,1-bis(3-(trifluoromethyl)phenyl)ethyl)benzamide | 4.13 LC 564.15 [M + H]⁺ | Procedure 11 and 7 |
| 160 | 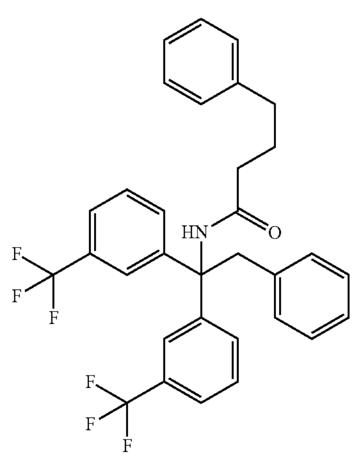 [SMILES: O=C(CCCc1ccccc1)NC(Cc1ccccc1)(c1cccc(C(F)(F)F)c1)c1cccc(C(F)(F)F)c1] | 4-phenyl-N-(2-phenyl-1,1-bis(3-(trifluoromethyl)phenyl)ethyl)butanamide | 4.30 LC 556.21 [M + H]⁺ | Procedure 11 and 7 |

TABLE 5-continued

| Ex. No. | Structure | Name | Retention Time Min./ Molecular Mass | Prepared in the manner described in: |
|---|---|---|---|---|
| 161 | 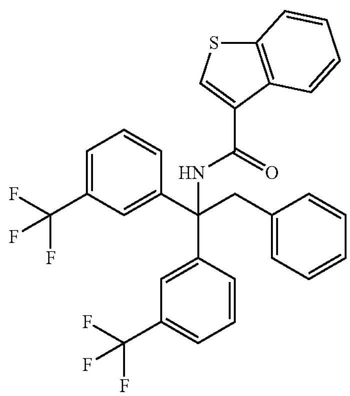 [SMILES: O=C(NC(Cc1ccccc1)(c1cccc(C(F)(F)F)c1)c1cccc(C(F)(F)F)c1)c1csc2ccccc12] | N-(2-phenyl-1,1-bis(3-(trifluoromethyl)phenyl)ethyl)benzo[b]thiophene-3-carboxamide | 4.28 LC 570.12 [M + H]$^+$ | Procedure 11 and 7 |
| 162 | 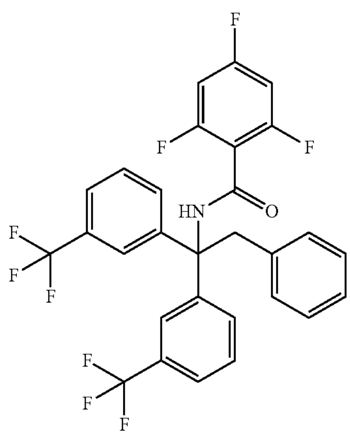 [SMILES: O=C(NC(Cc1ccccc1)(c1cccc(C(F)(F)F)c1)c1cccc(C(F)(F)F)c1)c1c(F)cc(F)cc1F] | 2,4,6-trifluroo-N-(2-phenyl-1,1-bis(3-(trifluoromethyl)phenyl)ethyl)benzamide | 4.12 LC 568.11 [M + H]$^+$ | Procedure 11 and 7 |
| 163 | 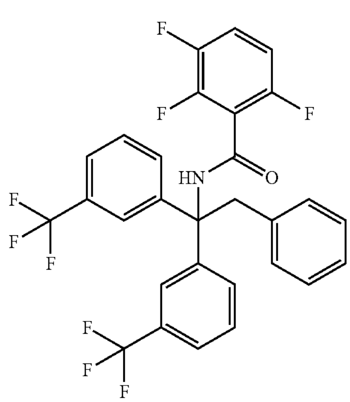 [SMILES: O=C(NC(Cc1ccccc1)(c1cccc(C(F)(F)F)c1)c1cccc(C(F)(F)F)c1)c1c(F)ccc(F)c1F] | 2,3,6-trifluoro-N-(2-phenyl-1,1-bis(3-(trifluoromethyl)phenyl)ethyl)benzamide | 4.11 LC 568.15 [M + H]$^+$ | Procedure 11 and 7 |

TABLE 5-continued

| Ex. No. | Structure | Name | Retention Time Min./ Molecular Mass | Prepared in the manner described in: |
|---|---|---|---|---|
| 164 | 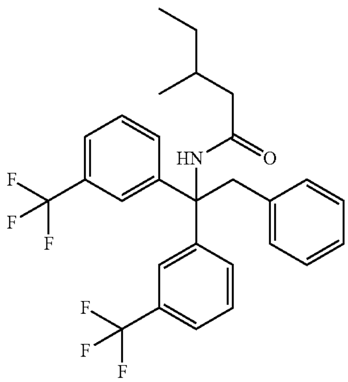 [SMILES: CCC(C)CC(=O)NC(Cc1ccccc1)(c1cccc(C(F)(F)F)c1)c1cccc(C(F)(F)F)c1] | 3-methyl-N-(2-phenyl-1,1-bis(3-(trifluoromethyl)phenyl)ethyl)pentanamide | 4.24 LC 508.26 [M + H]$^+$ | Procedure 11 and 7 |
| 165 | 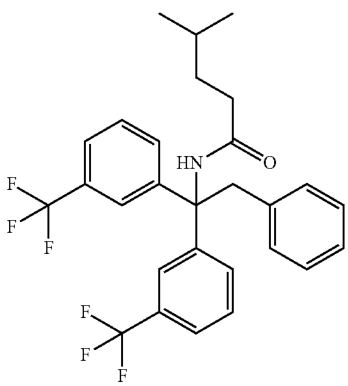 [SMILES: CC(C)CCC(=O)NC(Cc1ccccc1)(c1cccc(C(F)(F)F)c1)c1cccc(C(F)(F)F)c1] | 4-methyl-N-(2-phenyl-1,1-bis(3-(trifluoromethyl)phenyl)ethyl)pentanamide | 4.25 LC 508.19 [M + H]$^+$ | Procedure 11 and 7 |
| 166 | 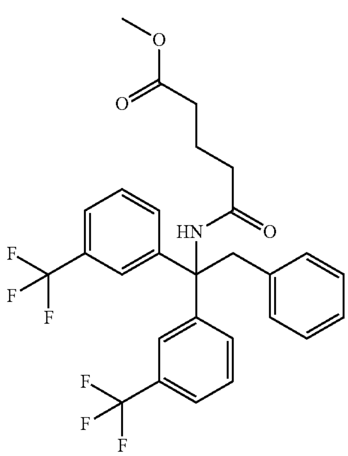 [SMILES: COC(=O)CCCC(=O)NC(Cc1ccccc1)(c1cccc(C(F)(F)F)c1)c1cccc(C(F)(F)F)c1] | methyl 5-oxo-5-(2-phenyl-1,1-bis(3-(trifluoromethyl)phenyl)ethylamino)pentanoate | 4.06 LC 538.2 [M + H]$^+$ | Procedure 11 and 7 |

TABLE 5-continued

| Ex. No. | Structure | Name | Retention Time Min./ Molecular Mass | Prepared in the manner described in: |
|---|---|---|---|---|
| 167 | 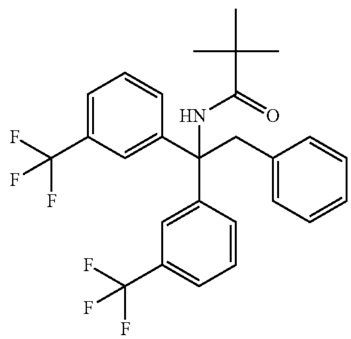 [SMILES: CC(C)(C)C(=O)NC(Cc1ccccc1)(c1cccc(C(F)(F)F)c1)c1cccc(C(F)(F)F)c1] | N-(2-phenyl-1,1-bis(3-(trifluoromethyl)phenyl)ethyl) pivalamide | 4.18 LC 494.19 [M + H]+ | Procedure 11 and 7 |
| 168 | 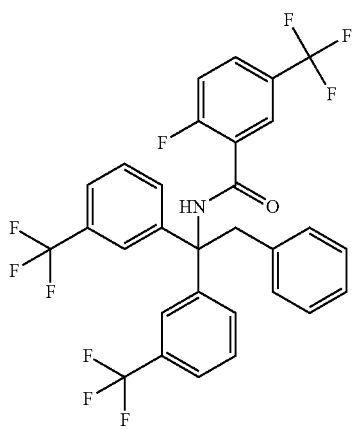 [SMILES: O=C(NC(Cc1ccccc1)(c1cccc(C(F)(F)F)c1)c1cccc(C(F)(F)F)c1)c1cc(C(F)(F)F)ccc1F] | 2-fluoro-N-(2-phenyl-1,1-bis(3-(trifluoromethyl)phenyl)ethyl)-5-(trifluoromethyl)benzamide | 4.26 LC 600.1 [M + H]+ | Procedure 11 and 7 |
| 169 | 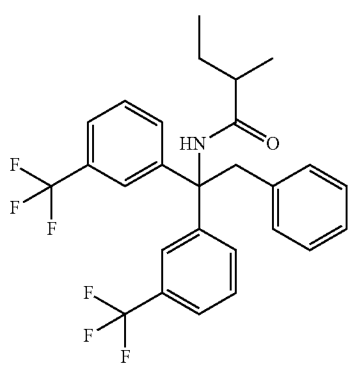 [SMILES: CCC(C)C(=O)NC(Cc1ccccc1)(c1cccc(C(F)(F)F)c1)c1cccc(C(F)(F)F)c1] | 2-methyl-N-(2-phenyl-1,1-bis(3-(trifluoromethyl)phenyl)ethyl) butanamide | 4.16 LC 494.19 [M + H]+ | Procedure 11 and 7 |

TABLE 5-continued

| Ex. No. | Structure | Name | Retention Time Min./ Molecular Mass | Prepared in the manner described in: |
|---|---|---|---|---|
| 170 | 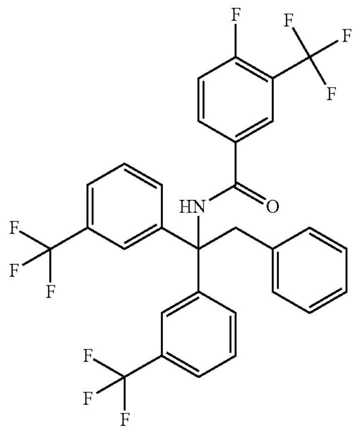 [SMILES: O=C(NC(Cc1ccccc1)(c1cccc(C(F)(F)F)c1)c1cccc(C(F)(F)F)c1)c1ccc(F)c(C(F)(F)F)c1] | 4-fluoro-N-(2-phenyl-1,1-bis(3-(trifluoromethyl)phenyl)ethyl)-3-(trifluoromethyl)benzamide | 4.30 LC 600.12 [M + H]$^+$ | Procedure 11 and 7 |
| 171 | 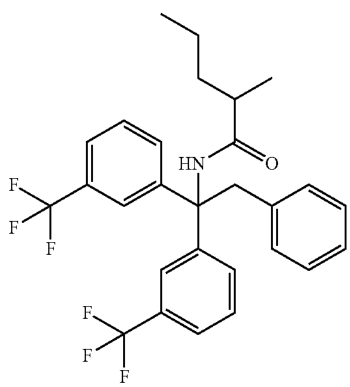 [SMILES: CCCC(C)C(=O)NC(Cc1ccccc1)(c1cccc(C(F)(F)F)c1)c1cccc(C(F)(F)F)c1] | 2-methyl-N-(2-phenyl-1,1-bis(3-(trifluoromethyl)phenyl)ethyl) pentanamide | 4.22 LC 508.26 [M + H]$^+$ | Procedure 11 and 7 |
| 172 | 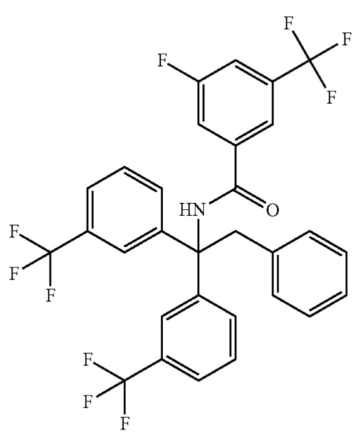 [SMILES: O=C(NC(Cc1ccccc1)(c1cccc(C(F)(F)F)c1)c1cccc(C(F)(F)F)c1)c1cc(F)cc(C(F)(F)F)c1] | 3-fluoro-N-(2-phenyl-1,1-bis(3-(trifluoromethyl)phenyl)ethyl)-5-(trifluoromethyl)benzamide | 4.35 LC 600.2 [M + H]$^+$ | Procedure 11 and 7 |

TABLE 5-continued

| Ex. No. | Structure | Name | Retention Time Min./ Molecular Mass | Prepared in the manner described in: |
|---|---|---|---|---|
| 173 | 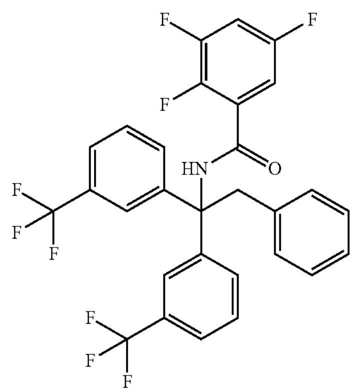 [SMILES: O=C(NC(Cc1ccccc1)(c1cccc(C(F)(F)F)c1)c1cccc(C(F)(F)F)c1)c1cc(F)cc(F)c1F] | 2,3,5-trifluoro-N-(2-phenyl-1,1-bis(3-(trifluoromethyl)phenyl)ethyl)benzamide | 4.22 LC 568.11 [M + H]+ | Procedure 11 and 7 |
| 174 | 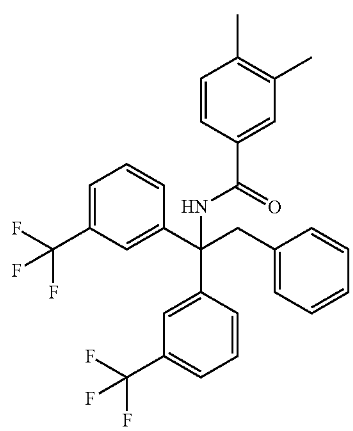 [SMILES: Cc1ccc(C(=O)NC(Cc2ccccc2)(c2cccc(C(F)(F)F)c2)c2cccc(C(F)(F)F)c2)cc1C] | 3,4-dimethyl-N-(2-phenyl-1,1-bis(3-(trifluoromethyl)phenyl)ethyl)benzamide | 4.26 LC 542.2 [M + H]+ | Procedure 11 and 7 |
| 175 | 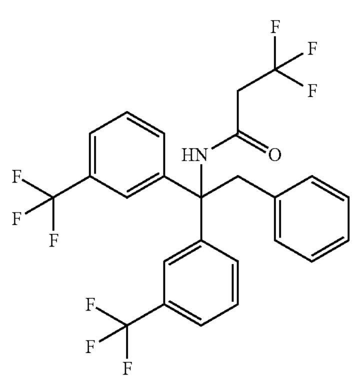 [SMILES: O=C(CC(F)(F)F)NC(Cc1ccccc1)(c1cccc(C(F)(F)F)c1)c1cccc(C(F)(F)F)c1] | 3,3,3-trifluoro-N-(2-phenyl-1,1-bis(3-(trifluoromethyl)phenyl)ethyl)propanamide | 4.07 LC 520.14 [M + H]+ | Procedure 11 and 7 |

TABLE 5-continued

| Ex. No. | Structure | Name | Retention Time Min./ Molecular Mass | Prepared in the manner described in: |
|---|---|---|---|---|
| 176 | 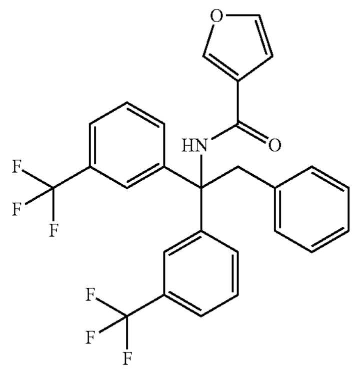 [SMILES: O=C(NC(Cc1ccccc1)(c1cccc(C(F)(F)F)c1)c1cccc(C(F)(F)F)c1)c1ccoc1] | N-(2-phenyl-1,1-bis(3-(trifluoromethyl)phenyl)ethyl)furan-3-carboxamide | 4.06 LC 504.15 [M + H]$^+$ | Procedure 11 and 7 |
| 177 | 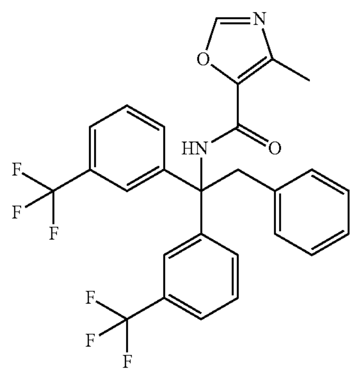 | 4-methyl-N-(2-phenyl-1,1-bis(3-(trifluoromethyl)phenyl)ethyl)oxazole-5-carboxamide | 4.06 LC 504.15 [M + H]$^+$ | Procedure 11 and 7 |
| 178 | 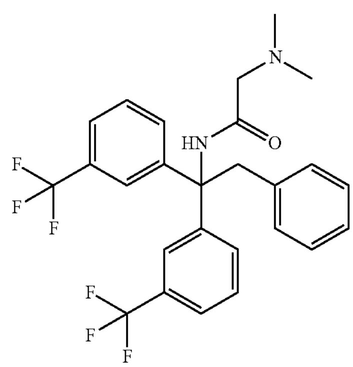 [SMILES: CN(C)CC(=O)NC(Cc1ccccc1)(c1cccc(C(F)(F)F)c1)c1cccc(C(F)(F)F)c1] | 2-(dimethylamino)-N-(2-phenyl-1,1-bis(3-(trilfuoromethyl)phenyl)ethyl)acetamide | 3.50 LC 495.22 [M + H]$^+$ | Procedure 11 and 7 |
| 179 | 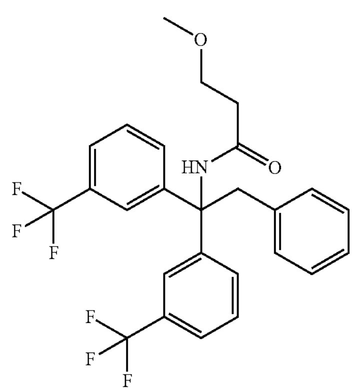 [SMILES: COCCC(=O)NC(Cc1ccccc1)(c1cccc(C(F)(F)F)c1)c1cccc(C(F)(F)F)c1] | 3-methoxy-N-(2-phenyl-1,1-bis(3-(trifluoromethyl)phenyl)ethyl)propanamide | 4.06 LC 496.19 [M + H]$^+$ | Procedure 11 and 7 |

TABLE 5-continued

| Ex. No. | Structure | Name | Retention Time Min./ Molecular Mass | Prepared in the manner described in: |
|---|---|---|---|---|
| 180 | 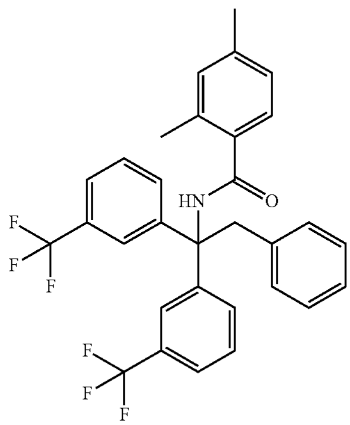 [SMILES: Cc1ccc(C(=O)NC(Cc2ccccc2)(c2cccc(C(F)(F)F)c2)c2cccc(C(F)(F)F)c2)c(C)c1] | 2,4-dimethyl-N-(2-phenyl-1,1-bis(3-(trifluoromethyl)phenyl)ethyl)benzamide | 4.23 LC 542.19 [M + H]$^+$ | Procedure 11 and 7 |
| 181 | 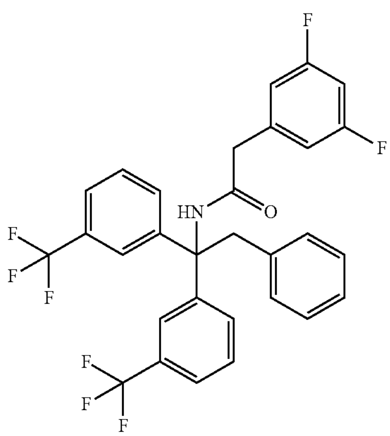 [SMILES: O=C(Cc1cc(F)cc(F)c1)NC(Cc1ccccc1)(c1cccc(C(F)(F)F)c1)c1cccc(C(F)(F)F)c1] | 2-(3,5-difluorophenyl)-N-(2-phenyl-1,1-bis(3-(trifluoromethyl)phenyl)ethyl)acetamide | 4.21 LC 564.15 [M + H]$^+$ | Procedure 11 and 7 |
| 182 | 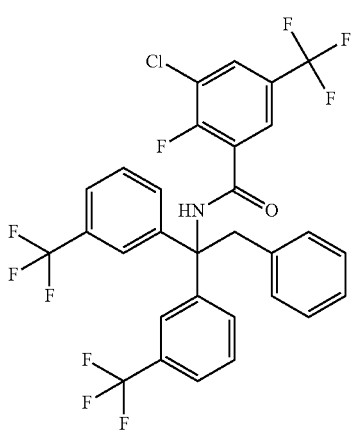 [SMILES: O=C(NC(Cc1ccccc1)(c1cccc(C(F)(F)F)c1)c1cccc(C(F)(F)F)c1)c1cc(C(F)(F)F)cc(Cl)c1F] | 3-chloro-2-fluoro-N-(2-phenyl-1,1-bis(3-(trifluoromethyl)phenyl)ethyl)-5-(trifluoromethyl)benzamide | 4.38 LC 634.17 [M + H]$^+$ | Procedure 11 and 7 |

TABLE 5-continued

| Ex. No. | Structure | Name | Retention Time Min./ Molecular Mass | Prepared in the manner described in: |
|---|---|---|---|---|
| 183 | 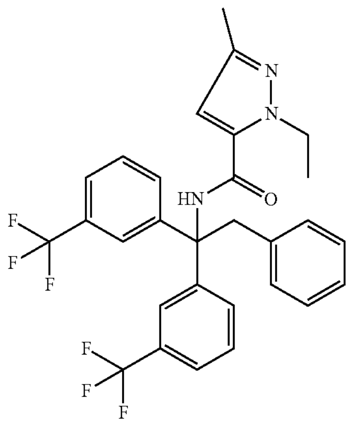 [SMILES: CCn1nc(C)cc1C(=O)NC(Cc1ccccc1)(c1cccc(C(F)(F)F)c1)c1cccc(C(F)(F)F)c1] | 1-ethyl-3-methyl-N-(2-phenyl-1,1-bis(3-(trifluoromethyl)phenyl)ethyl)-1H-pyrazole-5-carboxamide | 4.17 LC 546.27 [M + H]$^+$ | Procedure 11 and 7 |
| 184 | 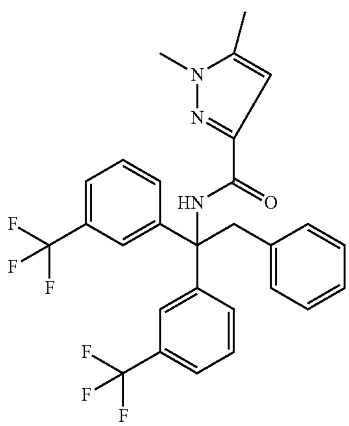 [SMILES: Cc1cc(C(=O)NC(Cc2ccccc2)(c2cccc(C(F)(F)F)c2)c2cccc(C(F)(F)F)c2)nn1C] | 1,5-dimethyl-N-(2-phenyl-1,1-bis(3-(trifluoromethyl)phenyl)ethyl)-1H-pyrazole-3-carboxamide | 4.09 LC 532.27 [M + H]$^+$ | Procedure 11 and 7 |
| 185 | 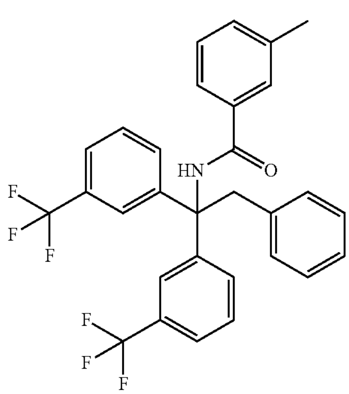 [SMILES: Cc1cccc(C(=O)NC(Cc2ccccc2)(c2cccc(C(F)(F)F)c2)c2cccc(C(F)(F)F)c2)c1] | 3-methyl-N-(2-phenyl-1,1-bis(3-(trifluoromethyl)phenyl)ethyl)benzamide | 4.20 LC 528.26 [M + H]$^+$ | Procedure 11 and 7 |

TABLE 5-continued

| Ex. No. | Structure | Name | Retention Time Min./ Molecular Mass | Prepared in the manner described in: |
|---|---|---|---|---|
| 186 | 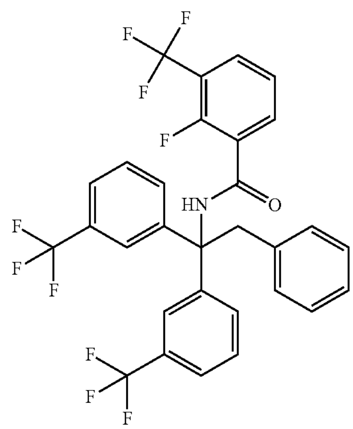 [SMILES: O=C(NC(Cc1ccccc1)(c1cccc(C(F)(F)F)c1)c1cccc(C(F)(F)F)c1)c1cccc(C(F)(F)F)c1F] | 2-fluoro-N-(2-phenyl-1,1-bis(3-(trifluoromethyl)phenyl)ethyl)-3-(trifluoromethyl)benzamide | 4.23 LC 600.17 [M + H]$^+$ | Procedure 11 and 7 |
| 187 | 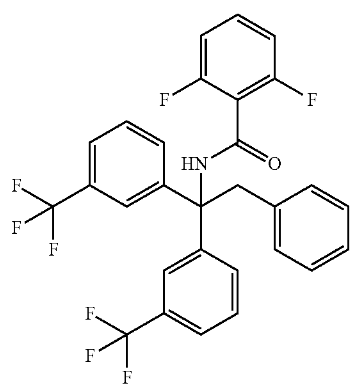 [SMILES: O=C(NC(Cc1ccccc1)(c1cccc(C(F)(F)F)c1)c1cccc(C(F)(F)F)c1)c1c(F)cccc1F] | 2,6-difluoro-N-(2-phenyl-1,1-bis(3-(trifluoromethyl)phenyl)ethyl)benzamide | 4.07 LC 550.17 [M + H]$^+$ | Procedure 11 and 7 |
| 188 | 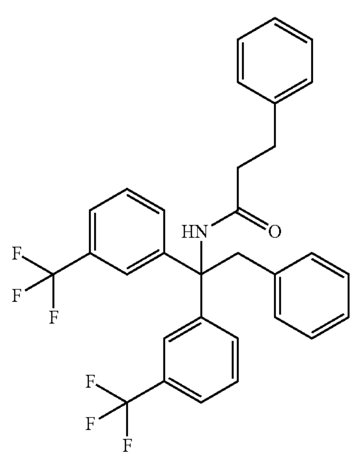 [SMILES: O=C(CCc1ccccc1)NC(Cc1ccccc1)(c1cccc(C(F)(F)F)c1)c1cccc(C(F)(F)F)c1] | 3-phenyl-N-(2-phenyl-1,1-bis(3-(trifluoromethyl)phenyl)ethyl)propanamide | 4.25 LC 542.26 [M + H]$^+$ | Procedure 11 and 7 |

TABLE 5-continued

| Ex. No. | Structure | Name | Retention Time Min./ Molecular Mass | Prepared in the manner described in: |
|---|---|---|---|---|
| 189 | 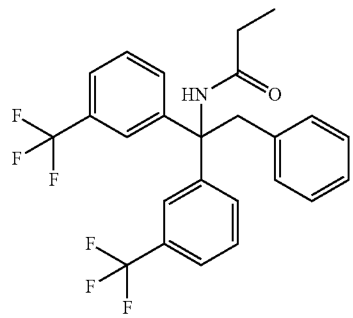 [SMILES: CCC(=O)NC(Cc1ccccc1)(c1cccc(C(F)(F)F)c1)c1cccc(C(F)(F)F)c1] | N-(2-phenyl-1,1-bis(3-(trifluoromethyl)phenyl)ethyl) propionamide | 4.06 LC 466.25 [M + H]+ | Procedure 11 and 7 |
| 190 | 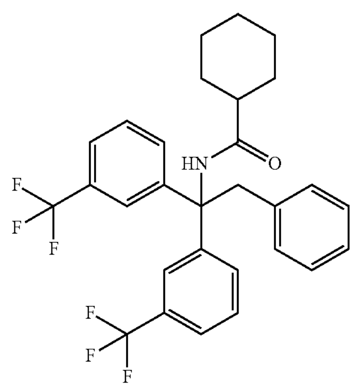 [SMILES: O=C(NC(Cc1ccccc1)(c1cccc(C(F)(F)F)c1)c1cccc(C(F)(F)F)c1)C1CCCCC1] | N-(2-phenyl-1,1-bis(3-(trifluoromethyl)phenyl)ethyl) cyclohexanecarboxamide | 4.26 LC 520.26 [M + H]+ | Procedure 11 and 7 |
| 191 | 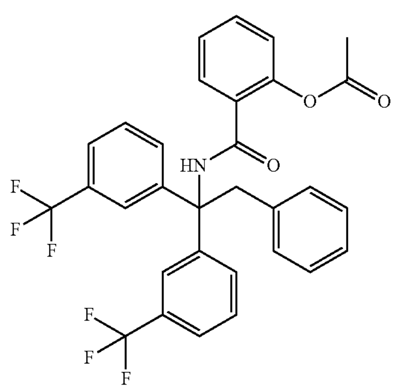 [SMILES: CC(=O)Oc1ccccc1C(=O)NC(Cc1ccccc1)(c1cccc(C(F)(F)F)c1)c1cccc(C(F)(F)F)c1] | 2-((2-phenyl-1,1-bis(3-(trifluoromethyl)phenyl)ethyl) carbamoyl)phenyl acetate | 4.07 LC 572.22 [M + H]+ | Procedure 11 and 7 |
| 192 | 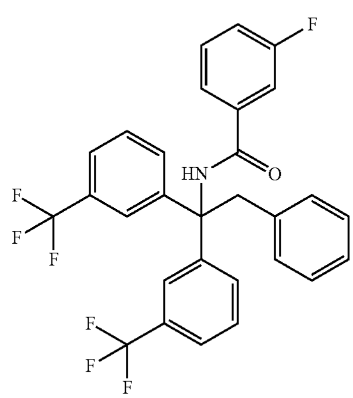 [SMILES: O=C(NC(Cc1ccccc1)(c1cccc(C(F)(F)F)c1)c1cccc(C(F)(F)F)c1)c1cccc(F)c1] | 3-fluoro-N-(2-phenyl-1,1-bis(3-(trifluoromethyl)phenyl)ethyl) benzamide | 4.17 LC 532.21 [M + H]+ | Procedure 11 and 7 |

TABLE 5-continued

| Ex. No. | Structure | Name | Retention Time Min./ Molecular Mass | Prepared in the manner described in: |
|---|---|---|---|---|
| 193 | 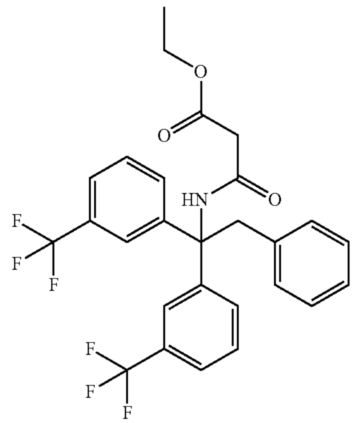 | ethyl 3-oxo-3-(2-phenyl-1,1-bis(3-(trifluoromethyl)phenyl)ethylamino)propanoate | 4.10 LC 539.2 [M + H]+ | Procedure 11 and 7 |
| 194 | 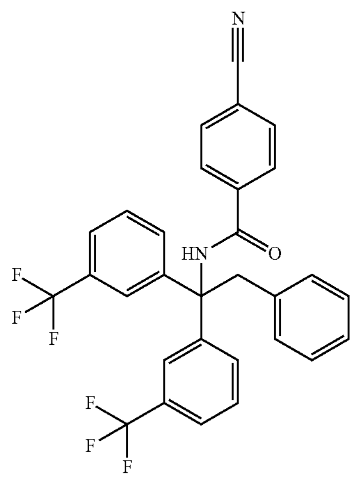 [SMILES: N#Cc1ccc(C(=O)NC(Cc2ccccc2)(c2cccc(C(F)(F)F)c2)c2cccc(C(F)(F)F)c2)cc1] | 4-cyano-N-(2-phenyl-1,1-bis(3-(trifluoromethyl)phenyl)ethyl)benzamide | 4.10 LC 539.2 [M + H]+ | Procedure 11 and 7 |
| 195 | 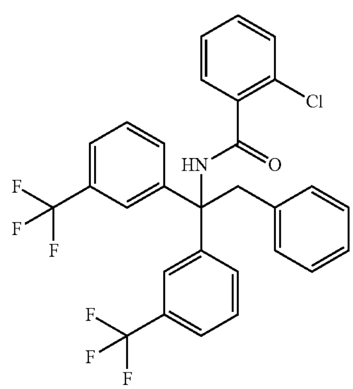 [SMILES: O=C(NC(Cc1ccccc1)(c1cccc(C(F)(F)F)c1)c1cccc(C(F)(F)F)c1)c1ccccc1Cl] | 2-chloro-N-(2-phenyl-1,1-bis(3-(trifluoromethyl)phenyl)ethyl)benzamide | 4.13 LC 548.17 [M + H]+ | Procedure 11 and 7 |

TABLE 5-continued

| Ex. No. | Structure | Name | Retention Time Min./ Molecular Mass | Prepared in the manner described in: |
|---|---|---|---|---|
| 196 | 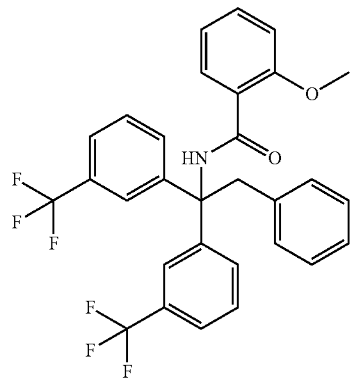 [SMILES: COc1ccccc1C(=O)NC(Cc1ccccc1)(c1cccc(C(F)(F)F)c1)c1cccc(C(F)(F)F)c1] | 2-methoxy-N-(2-phenyl-1,1-bis(3-(trifluoromethyl)phenyl)ethyl)benzamide | 4.21 LC 544.2 [M + H]$^+$ | Procedure 11 and 7 |
| 197 | 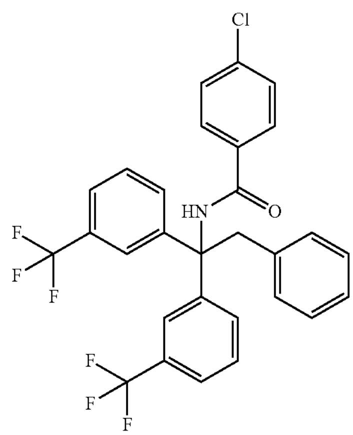 [SMILES: O=C(NC(Cc1ccccc1)(c1cccc(C(F)(F)F)c1)c1cccc(C(F)(F)F)c1)c1ccc(Cl)cc1] | 4-chloro-N-(2-phenyl-1,1-bis(3-(trifluoromethyl)phenyl)ethyl)benzamide | 4.25 LC 548.16 [M + H]$^+$ | Procedure 11 and 7 |
| 198 | 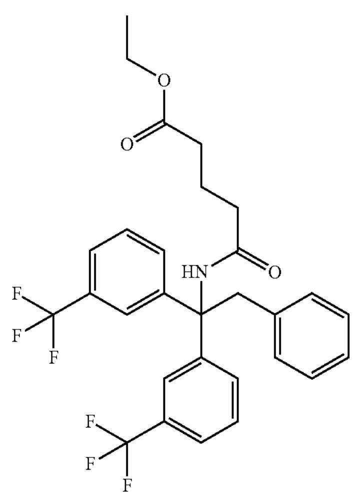 [SMILES: CCOC(=O)CCCC(=O)NC(Cc1ccccc1)(c1cccc(C(F)(F)F)c1)c1cccc(C(F)(F)F)c1] | ethyl 5-oxo-5-(2-phenyl-1,1-bis(3-(trifluoromethyl)phenyl)ethylamino)pentanoate | 4.11 LC 552.26 [M + H]$^+$ | Procedure 11 and 7 |

TABLE 5-continued

| Ex. No. | Structure | Name | Retention Time Min./ Molecular Mass | Prepared in the manner described in: |
|---|---|---|---|---|
| 199 | 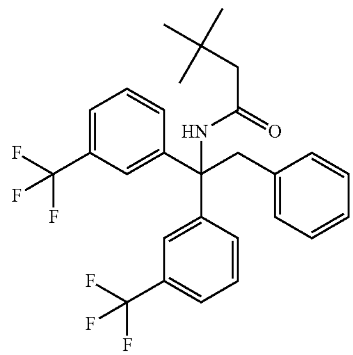 [SMILES: CC(C)(C)CC(=O)NC(Cc1ccccc1)(c1cccc(C(F)(F)F)c1)c1cccc(C(F)(F)F)c1] | 3,3-dimethyl-N-(2-phenyl-1,1-bis(3-(trifluoromethyl)phenyl)ethyl)butanamide | 4.23 LC 508.26 [M + H]$^+$ | Procedure 11 and 7 |
| 200 | 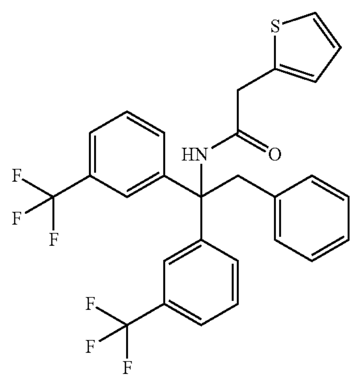 [SMILES: O=C(Cc1cccs1)NC(Cc1ccccc1)(c1cccc(C(F)(F)F)c1)c1cccc(C(F)(F)F)c1] | N-(2-phenyl-1,1-bis(3-(trifluoromethyl)phenyl)ethyl)-2-(thiophen-2-yl)acetamide | 4.14 LC 534.18 [M + H]$^+$ | Procedure 11 and 7 |
| 201 | 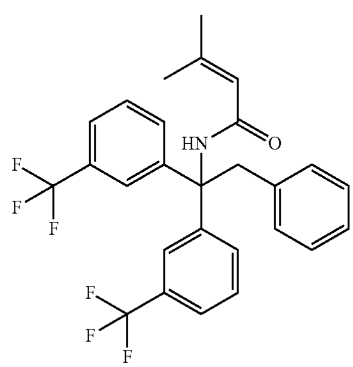 [SMILES: CC(C)=CC(=O)NC(Cc1ccccc1)(c1cccc(C(F)(F)F)c1)c1cccc(C(F)(F)F)c1] | 3-methyl-N-(2-phenyl-1,1-bis(3-(trifluoromethyl)phenyl)ethyl)but-2-enamide | 4.14 LC 492.26 [M + H]$^+$ | Procedure 11 and 7 |
| 202 | 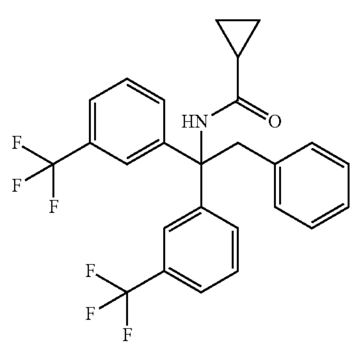 [SMILES: O=C(NC(Cc1ccccc1)(c1cccc(C(F)(F)F)c1)c1cccc(C(F)(F)F)c1)C1CC1] | N-(2-phenyl-1,1-bis(3-(trifluoromethyl)phenyl)ethyl)cyclopropanecarboxamide | 4.07 LC 478.23 [M + H]$^+$ | Procedure 11 and 7 |

TABLE 5-continued

| Ex. No. | Structure | Name | Retention Time Min./ Molecular Mass | Prepared in the manner described in: |
|---|---|---|---|---|
| 203 | 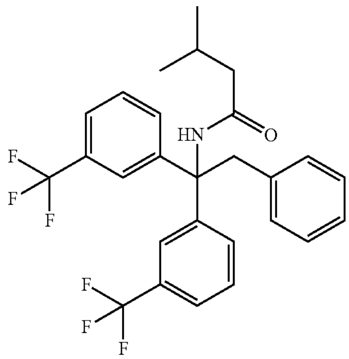 [SMILES: CC(C)CC(=O)NC(Cc1ccccc1)(c1cccc(C(F)(F)F)c1)c1cccc(C(F)(F)F)c1] | 3-methyl-N-(2-phenyl-1,1-bis(3-(trifluoromethyl)phenyl)ethyl) butanamide | 4.17 LC 494.26 [M + H]$^+$ | Procedure 11 and 7 |
| 204 | 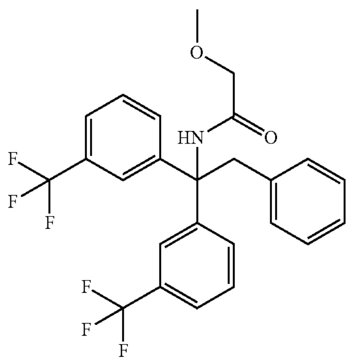 [SMILES: COCC(=O)NC(Cc1ccccc1)(c1cccc(C(F)(F)F)c1)c1cccc(C(F)(F)F)c1] | 2-methoxy-N-(2-phenyl-1,1-bis(3-(trifluoromethyl) phenyl)ethyl)acetamide | 4.03 LC 482.25 [M + H]$^+$ | Procedure 11 and 7 |
| 205 | 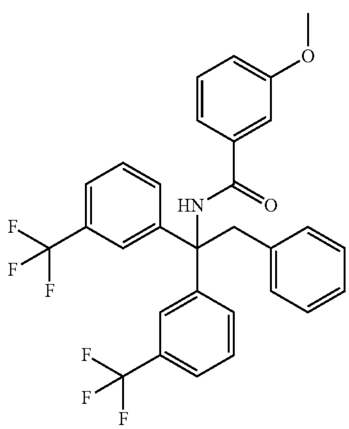 [SMILES: COc1cccc(C(=O)NC(Cc2ccccc2)(c2cccc(C(F)(F)F)c2)c2cccc(C(F)(F)F)c2)c1] | 3-methoxy-N-(2-phenyl-1,1-bis(3-(trifluoromethyl) phenyl)ethyl)benzamide | 4.15 LC 544.27 [M + H]$^+$ | Procedure 11 and 7 |
| 206 | 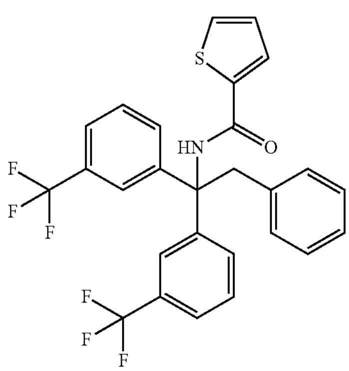 [SMILES: O=C(NC(Cc1ccccc1)(c1cccc(C(F)(F)F)c1)c1cccc(C(F)(F)F)c1)c1cccs1] | N-(2-phenyl-1,1-bis(3-(trifluoromethyl)phenyl)ethyl) thiophene-2-carboxamide | 4.09 LC 520.2 [M + H]$^+$ | Procedure 11 and 7 |

TABLE 6

| Ex. No | Compound Structure | Compound Name | Retention Time Min./ Molecular Mass | Procedure of Ex. |
|---|---|---|---|---|
| 207 | 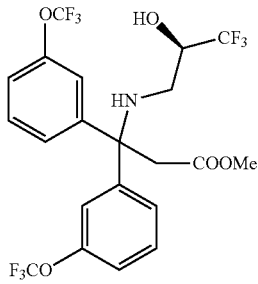 [SMILES: COC(=O)CC(NC[C@@H](O)C(F)(F)F)(c1cccc(OC(F)(F)F)c1)c1cccc(OC(F)(F)F)c1] | N-(4-fluoro-3-(trifluoromethyl)benzyl)-2-phenyl-1,1-bis(3-(trifluoromethoxy)phenyl) ethanamine | 4.51 LC No obs. [M + H]+ | Procedure 11 and 13 |

Additional compounds of the present invention were prepared by the general procedures analogous to those described above and to the additional general procedures described below.

Example 208

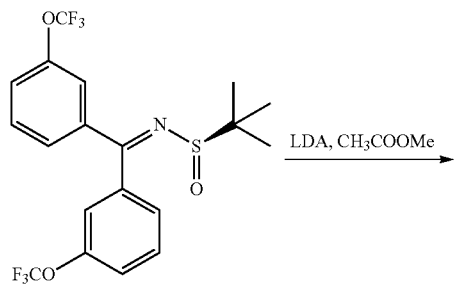

(R)-methyl 3-(3,3,3-trifluoro-2-hydroxypropylamino)-3,3-bis(3-(trifluoromethoxy)phenyl)propanoate

Procedure 14

(R)-methyl 3-(2-methylpropan-2-ylsulfinamido)-3,3-bis(3-(trifluoromethoxy)phenyl)propanoate -continued

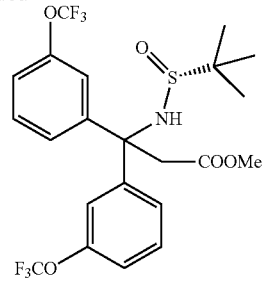

(R)—N-(bis(3-(trifluoromethoxy)phenyl)methylene)-2-methylpropane-2-sulfinamide was prepared as described for Procedure 11. Under an argon atmosphere, $CH_3COOMe$ (0.70 mL, 8.83 mmol, 2.0 eq) was stirred in anhydrous $Et_2O$ (50 mL) in an oven-dried round bottomed flask at −78° C. LDA (2.0 M, 4.4 mL, 8.8 mmol, 2.0 eq) was added dropwise. The resulting mixture was stirred at −78° C. for 30 min. (R)—N-(bis(3-(trifluoromethoxy)phenyl)methylene)-2-methylpropane-2-sulfinamide (2.0 g, 4.42 mmol) in $Et_2O$ (10 mL) was added dropwise to the above stirred solution. The reaction mixture was stirred at −78° C. for 1.5 h. Saturated $NH_4Cl$ was added, followed by the addition of EtOAc. The organic layer was washed with $H_2O$ and brine, dried over $Na_2SO_4$, filtered, and concentrated to dryness. The residue was purified by flash chromatography (silica gel, EtOAc/Hexanes=0 to 100%) to give N-(2-cyano-1,1-bis(3-(trifluoromethoxy)phenyl)-ethyl)-2-methylpropane-2-sulfinamide as light tan oil (1.96 g, yield: 84.1%). LC-MS (ESI) 528.34 (M+H), retention time=4.00 min (10-90% MeOH in $H_2O$ with 0.1% TFA in a 4-min run); $^1H$ NMR (400 MHz, $CDCl_3$) δ ppm 7.36 (d, J=8.0 Hz, 2H), 7.31 (t, J=8.0 Hz, 1H), 7.25-7.18 (m, 2H), 7.14-7.05 (m, 3H), 6.14 (s, 1H), 3.93 (d, J=16.1 Hz, 1H), 3.54 (d, J=15.9 Hz, 1H), 3.86 (m, 2H), 3.49 (s, 3H), 1.26 (s, 9H). $^{13}C$ NMR (400 MHz, $CDCl_3$) ppm 22.71, 43.84, 51.68, 56.41, 63.69, 118.63, 119.52, 120.49, 121.35, 124.27, 125.73, 129.81, 129.92, 143.83, 147.52, 149.33, 171.93.

Methyl 3-amino-3,3-bis(3-(trifluoromethoxy)phenyl)propanoate

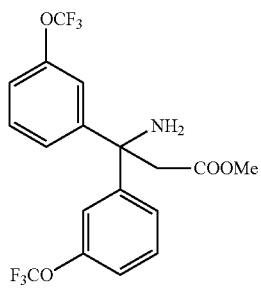 [SMILES: COC(=O)CC(N)(c1cccc(OC(F)(F)F)c1)c1cccc(OC(F)(F)F)c1]

Using the same procedure as that of Procedure 6, methyl 3-amino-3,3-bis(3-(trifluoromethoxy)phenyl)propanoate was obtained. LC-MS (ESI) 407.16 (M-NH$_3$+H), retention time=3.18 min (10-90% MeOH in H$_2$O with 0.1% TFA in a 4-min run); $^1$H NMR (400 MHz, CDC$_3$) δ ppm 7.18-7.27 (m, 6H), 7.02 (d, J=8.07 Hz, 2H), 3.47 (s, 3H), 3.17 (s, 2H).

(R)-methyl 3-(3,3,3-trifluoro-2-hydroxypropylamino)-3,3-bis(3-(trifluoromethoxy)phenyl)propanoate

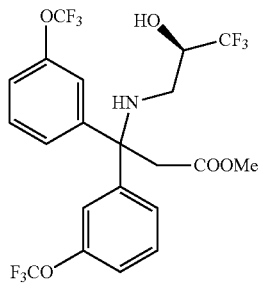 [SMILES: COC(=O)CC(NC[C@@H](O)C(F)(F)F)(c1cccc(OC(F)(F)F)c1)c1cccc(OC(F)(F)F)c1]

Using a similar procedure to that described in Procedure 8, (R)-methyl 3-(3,3,3-trifluoro-2-hydroxypropylamino)-3,3-bis(3-(trifluoromethoxy)phenyl)propanoate was obtained. LC-MS (ESI) 536.29 (M+H), retention time=3.93 min (10-90% MeOH in H$_2$O with 0.1% TFA in a 4-min run); $^1$H NMR (400 MHz, CDCl$_3$) δ ppm 7.38-7.35 (m, 2H), 7.24-7.19 (m, 2H), 7.13 (m, 4H), 3.44 (s, 3H), 3.22-3.35 (m, 2H), 2.57-2.74 (m, 2H).

Example 209

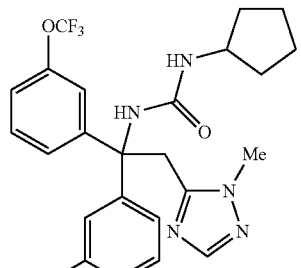

1-cyclopentyl-3-(2-(2-methyl-2H-1,2,4-triazol-3-yl)-1,1-bis(3-(trifluoromethoxy)phenyl)ethyl)urea Procedure 15

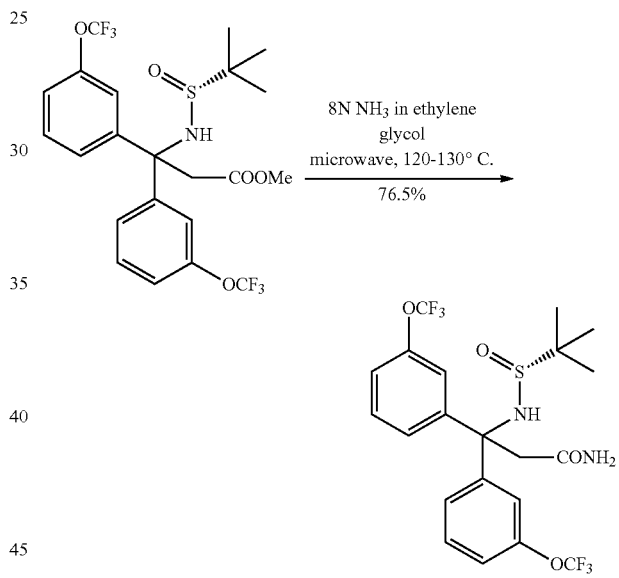

(R)-3-(2-methylpropan-2-ylsulfinamido)-3,3-bis(3-(trifluoromethoxy)phenyl)propanamide (prepared as described for Procedure 11, 0.70 g, 1.33 mmol) was dissolved in 8N NH$_3$ in ethylene glycol (6 mL) at room temperature in a microwave vial. The reaction mixture was heated at 120° C. for 1200 sec, and then at 130° C. for 1200 sec under microwave irradiation. After cooling, the cap was removed, and H$_2$O was added. The mixture was extracted with EtOAc (3×), washed with H$_2$O and brine, dried over Na$_2$SO$_4$, filtered and concentrated. The residue was purified by flash chromatography (silica gel, hexanes/EtOAc, then 10% MeOH in EtOAc) to give 3-(2-methylpropan-2-ylsulfinamido)-3,3-bis(3-(trifluoromethoxy)phenyl)-propanamide as white solid (0.52 g, yield: 76%) LCMS: 3.88 min [M+1]513.28 (4 min gradient, MeOH/H$_2$O 0.1% TFA); $^1$H NMR (400 MHz, CDCl$_3$) δ ppm 7.40-7.29 (m, 3H), 7.22-7.12 (m, 3H), 7.11-7.02 (m, 2H), 6.29 (m, 2H), 5.40 (s, br, 1H), 3.78 (d, J=14.50 Hz, 1H), 3.71 (s, 2H), 3.35 (d, J=14.50 Hz, 1H), 1.21-1.28 (m, 9H).

Procedure 16

(R)-2-methyl-N-(2-(2-methyl-2H-1,2,4-triazol-3-yl)-1,1-bis(3-(trifluoromethoxy)phenyl)ethyl)propane-2-sulfinamide

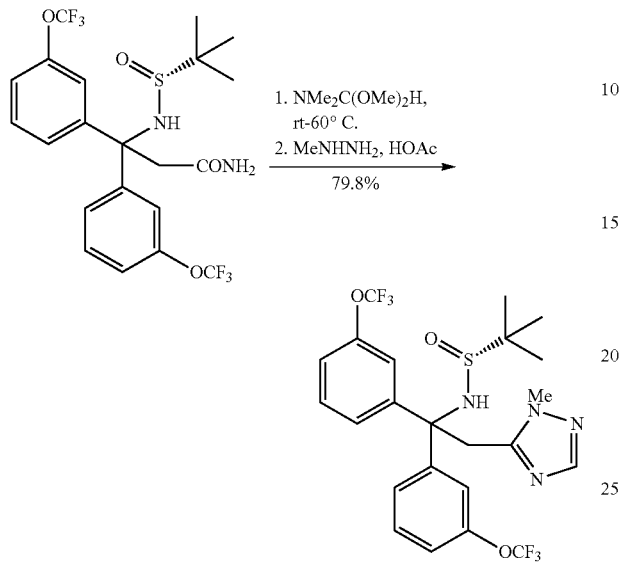

(R)-3-(2-methylpropan-2-ylsulfinamido)-3,3-bis(3-(trifluoromethoxy)phenyl)propanamide (Procedure 15, 0.21 g, 0.41 mmol) was stirred in N,N-dimethylformamide dimethylacetal (6 mL) at room temperature for 1.5 h, then 60° C. for 20 min. The solvent was evaporated to give crude N-(5-(dimethylamino)-3-oxo-1,1-bis(3-(trifluoromethoxy)phenyl)pent-4-enyl)-2-methylpropane-2-sulfinamide. LC-MS (ESI) 568.4 (M+H), retention time=3.60 min (10-90% MeOH in H$_2$O with 0.1% TFA in a 4-min run). This brownish residue was dissolved in HOAc (2 mL), and methyl hydrazine (0.4 mL) was added. The resulting reaction mixture was heated at 60° C. for 1.5 h. After cooling, H$_2$O was added. It was extracted with EtOAc (2×), washed with sat'd NaHCO$_3$, H$_2$O and brine, dried over Na$_2$SO$_4$, filtered and concentrated to dryness. The residue was purified by flash chromatography (silica gel, hexanes/EtOAc) to give 2-methyl-N-(2-(2-methyl-2H-1,2,4-triazol-3-yl)-1,1-bis(3-(trifluoromethoxy)phenyl)ethyl)propane-2-sulfinamide (0.18 g, yield: 79.8%). LC-MS (ESI) 551.35 (M+H), retention time=3.99 min (10-90% MeOH in H$_2$O with 0.1% TFA in a 4-min run);

2-(2-methyl-2H-1,2,4-triazol-3-yl)-1,1-bis(3-(trifluoromethoxy)phenyl)-ethanamine

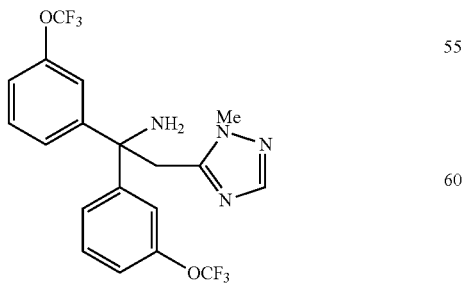

Using the same procedure as that described in Procedure 6, 2-(2-methyl-2H-1,2,4-triazol-3-yl)-1,1-bis(3-(trifluoromethoxy)phenyl)ethanamine was obtained. LC-MS (ESI) 447.24 (M+H), retention time=2.90 min (10-90% MeOH in H$_2$O with 0.1% TFA in a 4-min run);

1-cyclopentyl-3-(2-(2-methyl-2H-1,2,4-triazol-3-yl)-1,1-bis(3-(trifluoromethoxy)phenyl)ethyl)urea

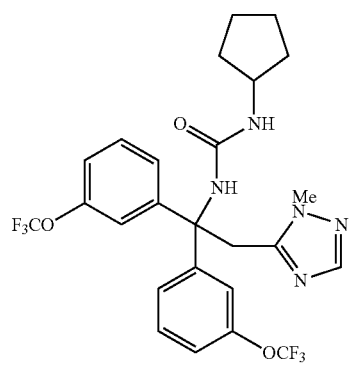 [SMILES: Cn1ncnc1CC(NC(=O)NC1CCCC1)(c1cccc(OC(F)(F)F)c1)c1cccc(OC(F)(F)F)c1]

Using the same procedure as described for Procedure 2, 1-cyclopentyl-3-(2-(2-methyl-2H-1,2,4-triazol-3-yl)-1,1-bis(3-(trifluoromethoxy)phenyl)ethyl)urea was obtained. LC-MS (ESI) 558.43 (M+H), retention time=3.81 min (10-90% MeOH in H$_2$O with 0.1% TFA in a 4-min run); $^1$H NMR (400 MHz, CDCl$_3$) δ ppm 7.44 (s, 1H), 7.32 (t, J=8.0 Hz, 2H), 7.26 (m, 2H), 7.18 (m, 2H), 7.11 (d, J=8.0 Hz, 2H), 6.96 (br, s, 1H), 4.56 (m, 1H), 3.87 (m, 1H), 3.73 (s, 2H), 3.35 (s, 3H), 1.92-1.85 (m, 2H), 1.61-1.49 (m, 4H), 1.29-1.22 (m, 2H).

Example 210

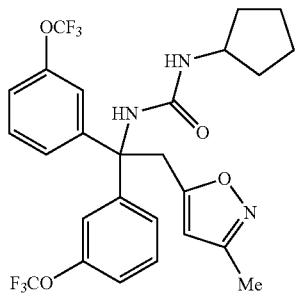 [SMILES: Cc1cc(CC(NC(=O)NC2CCCC2)(c2cccc(OC(F)(F)F)c2)c2cccc(OC(F)(F)F)c2)on1]

347

1-cyclopentyl-3-(2-(3-methylisoxazol-5-yl)-1,1-bis
(3-(trifluoromethoxy)phenyl)ethyl)urea Procedure 17

(R)-2-methyl-N-(2-(3-methylisoxazol-5-yl)-1,1-bis
(3-(trifluoromethoxy)phenyl)ethyl)propane-2-sulfi-
namide

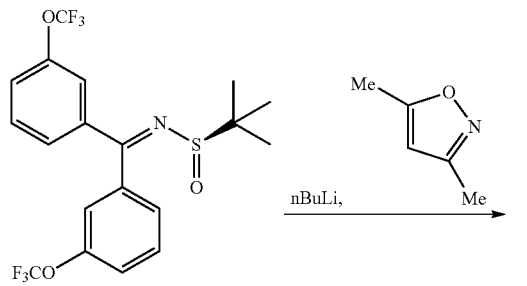

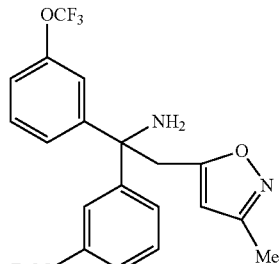

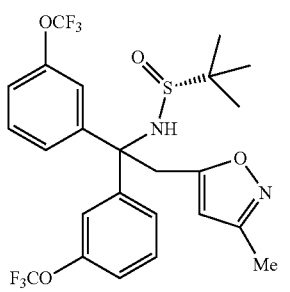

(R)—N-(bis(3-(trifluoromethoxy)phenyl)methylene)-2-methylpropane-2-sulfinamide was prepared as described for Procedure 11. Under an Argon atmosphere, 3,5-dimethylisoxazole (0.20 mL) was stirred in anhydrous THF in an oven-dried round bottomed flask at −78° C. nBuLi (2.5 M in hexanes, 0.84 mL, 2.1 mmol) was added dropwise. The resulting yellowish solution was stirred at −78° C. for 2 h. N-(bis(3-(trifluoromethoxy)phenyl)methylene)-2-methyl-propane-2-sulfinamide (0.81 g, 1.8 mmol) in THF (2 mL) was added dropwise to the above stirred solution. The reaction mixture was stirred at −78° C. for 5 h, then slowly warmed up to room temperature overnight. Saturated NH$_4$Cl was added, followed by the addition of EtOAc. The organic layer was washed with H$_2$O and brine, dried over Na$_2$SO$_4$, filtered, and concentrated to dryness. The residue was purified by flash chromatography (silica gel, EtOAc/Hexanes=0 to 100%, came out at 100% EtOAc) to give 2-methyl-N-(2-(3-methyl-isoxazol-5-yl)-1,1-bis(3-(trifluoromethoxy)phenyl)ethyl) propane-2-sulfinamide as light tan viscous oil (0.14 g, yield: 13.5% with 0.55 g recovery of the starting material). LC-MS (ESI) 551.38 (M+H), retention time=3.98 min (10-90% MeOH in H$_2$O with 0.1% TFA in a 4-min run); $^1$H NMR (400 MHz, CDCl$_3$) δ ppm 7.49-7.40 (m, 2H), 7.37-7.28 (m, 1H), 7.19 (d, J=6.57 Hz, 1H), 7.05-7.14 (m, 4H), 5.70 (s, 1H), 4.61 (s, 1H), 4.14 (d, J=14.40 Hz, 1H), 3.88 (d, J=14.40 Hz, 1H), 2.26 (s, 2H), 2.13 (s, 3H), 1.26 (s, 9H).

348

2-(3-methylisoxazol-5-yl)-1,1-bis(3-(trifluoromethoxy)phenyl)ethanamine

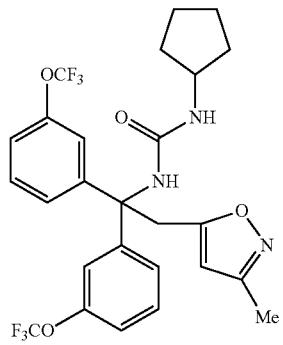 [SMILES: Cc1cc(CC(NC(=O)NC2CCCC2)(c2cccc(OC(F)(F)F)c2)c2cccc(OC(F)(F)F)c2)on1]

Using the same procedure as that described for Procedure 6, the titled compound was obtained. LC-MS (ESI) 447.35 (M+H), retention time=3.16 min (10-90% MeOH in H$_2$O with 0.1% TFA in a 4-min run).

1-cyclopentyl-3-(2-(3-methylisoxazol-5-yl)-1,1-bis
(3-(trifluoromethoxy)-phenyl)ethyl)urea

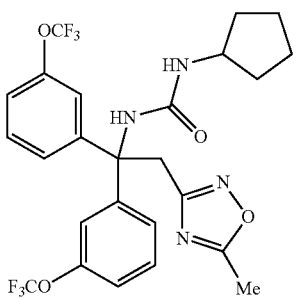 [SMILES: Cc1nc(CC(NC(=O)NC2CCCC2)(c2cccc(OC(F)(F)F)c2)c2cccc(OC(F)(F)F)c2)no1]

Using the same procedure as that described for Procedure 2, the titled compound was obtained. LC-MS (ESI) 558.41 (M+H), retention time=3.98 min (10-90% MeOH in H$_2$O with 0.1% TFA in a 4-min run); $^1$H NMR (400 MHz, CDCl$_3$) δ ppm 7.39-7.35 (m, 2H), 7.28-7.26 (m, 2H), 7.15-7.13 (m, 4H), 5.57 (s, 1H), 5.29 (m, 1H), 4.04 (s, 2H), 3.93 (m, 1H), 2.19 (s, 3H), 1.92-1.89 (m, 2H), 1.64-1.59 (m, 4H), 1.35-1.26 (m, 2H).

Example 211

349

1-cyclopentyl-3-(2-(5-methyl-1,2,4-oxadiazol-3-yl)-1,1-bis(3-(trifluoromethoxy)phenyl)ethyl)urea

Procedure 18

(R)—N-(2-cyano-1,1-bis(3-(trifluoromethoxy)phenyl)ethyl)-2-methylpropane-2-sulfinamide

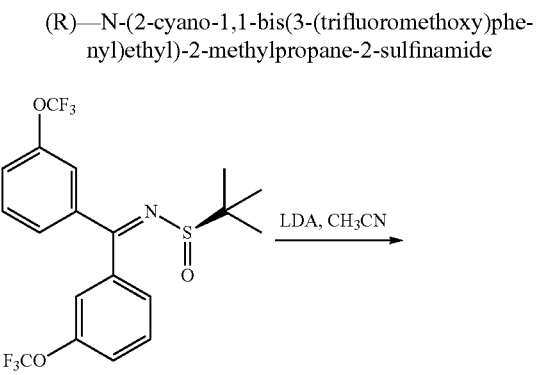

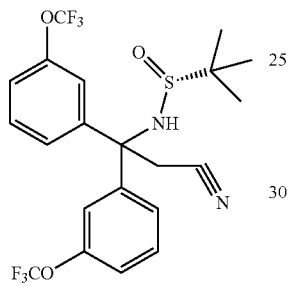

(R)—N-(bis(3-(trifluoromethoxy)phenyl)methylene)-2-methylpropane-2-sulfinamide was prepared as described for Procedure 11. Under an argon atmosphere, acetonitrile (0.46 mL, 8.84 mmol, 2.0 eq) was stirred in anhydrous Et$_2$O (40 mL) in an oven-dried round bottomed flask at −78° C. LDA (2.0 M, 4.42 mL, 8.84 mmol, 2.0 eq) was added dropwise. The resulting mixture was stirred at −78° C. for 30 min. (R)—N-(bis(3-(trifluoromethoxy)phenyl)methylene)-2-methylpropane-2-sulfinamide (2.0 g, 4.42 mmol) in Et$_2$O (10 mL) was added dropwise to the above stirred solution. The reaction mixture was stirred at −78° C. for 4 h. Sat'd NH$_4$Cl was added, followed by the addition of EtOAc. The organic layer was washed with H$_2$O and brine, dried over Na$_2$SO$_4$, filtered, and concentrated to dryness. The residue was purified by flash chromatography (silica gel, EtOAc/Hexanes=0 to 100%) to give (R)—N-(2-cyano-1,1-bis(3-(trifluoromethoxy)phenyl)ethyl)-2-methylpropane-2-sulfinamide as light tan oil (1.15 g, yield: 52.7% with 0.85 g recovery of the starting material). LC-MS (ESI) 495.26 (M+H), retention time=3.84 min (10-90% MeOH in H$_2$O with 0.1% TFA in a 4-min run); $^1$H NMR (400 MHz, CDCl$_3$) δ ppm 7.40-7.35 (m, 2H), 7.29 (d, J=8 Hz, 1H), 7.21-7.16 (m, 4H), 7.08 (m, 1H), 4.53 (s, 1H), 3.75 (d, J=16 Hz, 1H) 3.56 (d, J=16 Hz, 1H), 1.21 (s, 9H).

350

Procedure 19

2-methyl-N-(2-(3-methylisoxazol-5-yl)-1,1-bis(3-(trifluoromethoxy)phenyl)ethyl)propane-2-sulfinamide

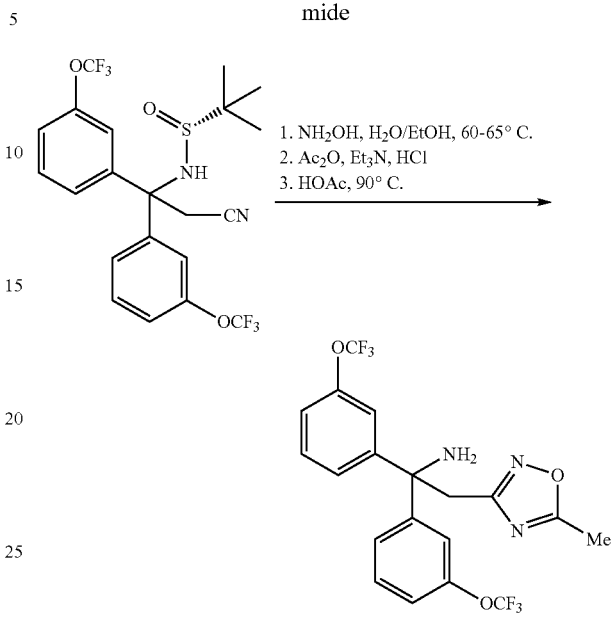

(R)—N-(2-Cyano-1,1-bis(3-(trifluoromethoxy)phenyl)ethyl)-2-methylpropane-2-sulfinamide (140 mg, 0.28 mmol) was stirred in EtOH (3 mL) and NH$_2$OH in H$_2$O (3 mL) in a capped microwave tube. The mixture was heated in an oil bath at 60-65° C. for 2 h. LC-MS (ESI) 528.42 (M+H), retention time=3.46 min (10-90% MeOH in H$_2$O with 0.1% TFA in a 4-min run). The cap was removed and the solvents were concentrated. The residue was dissolved in CH$_2$Cl$_2$, washed with H$_2$O, dried over MgSO$_4$, filtered, and concentrated to give crude N'-hydroxy-3-(2-methylpropan-2-ylsulfinamido)-3,3-bis(3-(trifluoromethoxy)phenyl)propanamidine. After drying under vacuum for 2 h, the residue was dissolved in CH$_2$Cl$_2$ (5 mL). Et$_3$N (0.25 mL, mmol, eq) was added followed by the addition of Ac$_2$O (0.1 mL). The resulting mixture was stirred at room temperature for 24 h. LC-MS (ESI) 570.49 (M+H), 592.49 (M+Na), retention time=3.92 min (10-90% MeOH in H$_2$O with 0.1% TFA in a 4-min run). CH$_2$Cl$_2$ (5 mL) was added. The organic layer was washed with H$_2$O, dried over MgSO$_4$, filtered, and concentrated to dryness to give colorless film (0.255 g). This residue was dissolved in HOAc (5 mL) and was heated at 90° C. for 4 h. After cooling, H$_2$O was added. The mixture was extracted with CH$_2$Cl$_2$ (2×) and the combined organic portion washed with sat'd NaHCO$_3$ (2×), H$_2$O and brine, dried over MgSO$_4$, filtered and concentrated. The residue was purified by flash chromatography (silica gel, EtOAc/Hexanes=0 to 100%) to give 2-methyl-N-(2-(3-methylisoxazol-5-yl)-1,1-bis(3-(trifluoromethoxy)phenyl)ethyl)propane-2-sulfinamide as colorless oil (52 mg, total yield for 3 steps: 41%). LC-MS (ESI) 441.29 (M-NH$_2$), retention time=3.14 min (10-90% MeOH in H$_2$O with 0.1% TFA in a 4-min run); $^1$H NMR (400 MHz, CDCl$_3$) δ ppm 7.26-7.19 (m, 5H), 7.00 (m, 3H), 3.57 (s, 2H), 2.39 (s, 3H).

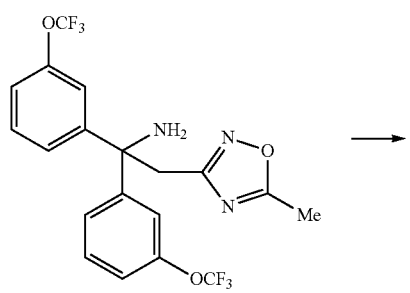

→

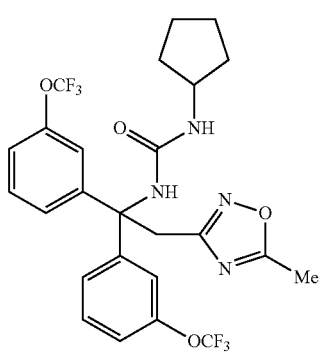

Using the same procedure described for Procedure 2,1-cyclopentyl-3-(2-(5-methyl-1,2,4-oxadiazol-3-yl)-1,1-bis(3-(trifluoromethoxy)phenyl)ethyl)urea was obtained after purification using reverse phase HPLC (30-90% MeOH in H₂O with 0.1% TFA in a 10 min gradient, came out 17.53-18.00 min). LC-MS (ESI) 559.25 (M+H), retention time=4.06 min (10-90% MeOH in H₂O with 0.1% TFA in a 4-min run); ¹H NMR (400 MHz, CDCl₃) δ ppm 7.36-7.28 (m, 4H), 7.20 (m, 2H), 7.10 (m, 2H), 3.93 (m, 1H), 3.84 (s, 2H), 2.46 (s, 3H), 1.89 (m, 2H), 1.56 (m, 4H), 1.28 (m, 2H).

Example 219

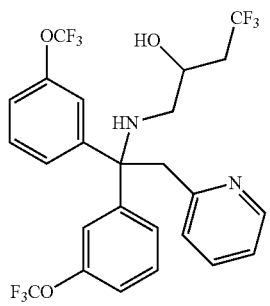 [SMILES: OC(CNC(Cc1ccccn1)(c1cccc(OC(F)(F)F)c1)c1cccc(OC(F)(F)F)c1)CC(F)(F)F]

4,4,4-trifluoro-1-(2-(pyridin-2-yl)-1,1-bis(3-(trifluoromethoxy)phenyl)ethylamino)butan-2-ol Procedure 20

(R)-2-methyl-N-(2-(pyridin-2-yl)-1,1-bis(3-(trifluoromethoxy)phenyl)ethyl)propane-2-sulfinamide

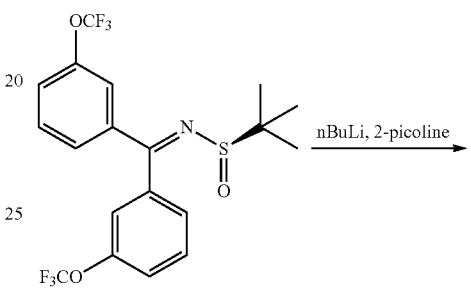

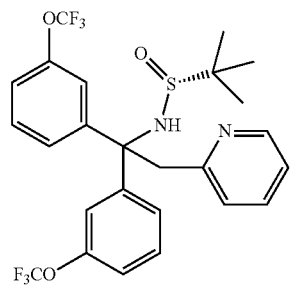

2-Picoline (0.20 mL, 2.0 mmol) was stirred in anhydrous Et₂O (20 mL) at 0° C. under Argon. nBuLi (2.5 M in hexanes, 0.84 mL, mmol) was added dropwise. The reaction mixture turned to dark brown, and stirred at 0° C. for 20 min, then at room temperature for 1 h. It was cooled back to 0° C., and (R)—N-(bis(3-(trifluoromethoxy)phenyl)-methylene)-2-methylpropane-2-sulfinamide (prepared as described in Example 82, Procedure 11) (0.906 g, 2.0 mmol) in Et₂O (4.0 mL) was added dropwise. The mixture was stirred at 0° C. for 1 h. then at room temperature for 1 h. The reaction was quenched by addition of sat'd NH₄Cl. EtOAc was added; the organic layer was washed with H₂O and brine, dried (Na₂SO₄), filtered, and concentrated to dryness. The residue was purified by flash chromatography (silica gel, EtOAc/

Hexanes=0 to 100%) to give 2-methyl-N-(2-(pyridin-2-yl)-1,1-bis(3-(trifluoromethoxy)phenyl)-ethyl)propane-2-sulfinamide as light tan solids (0.19 g with recovery of 0.59 g of starting material, yield: 48% based on recovery of the starting material). LC-MS (ESI) 547.38 (M+H), retention time=3.90 min (10-90% MeOH in H$_2$O with 0.1% TFA in a 4-min run); $^1$H NMR (400 MHz, CDCl$_3$) δ ppm 8.36-8.44 (m, 1H), 7.90 (m, 1H), 7.51 (d, J=8.59 Hz, 1H), 7.37 (td, J=7.83, 2.27 Hz, 2H), 7.19-7.24 (m, 2H), 7.11-7.17 (m, 3H), 6.98-7.07 (m, 2H), 6.75 (d, J=7.83 Hz, 1H), 4.15 (d, J=13.90 Hz, 1H), 3.81 (d, J=13.90 Hz, 1H), 1.25-1.33 (m, 9H)

2-(pyridin-2-yl)-1,1-bis(3-(trifluoromethoxy)phenyl)ethanamine

Using the same procedure described for Procedure 6, 2-(pyridin-2-yl)-1,1-bis(3-(trifluoromethoxy)phenyl)ethanamine was obtained. LC-MS (ESI) 444.38 (M+H), retention time=3.10 min (10-90% MeOH in H$_2$O with 0.1% TFA in a 4-min run);

4,4,4-trifluoro-1-(2-(pyridin-2-yl)-1,1-bis(3-(trifluoromethoxy)phenyl)ethylamino)butan-2-ol Using the procedure described for Procedure 8, 4,4,4-trifluoro-1-(2-(pyridin-2-yl)-1,1-bis(3-(trifluoromethoxy)phenyl)ethylamino)butan-2-ol was obtained after purification via reverse phase HPLC to give pure (+/−)-4,4,4-trifluoro-1-(2-(pyridin-2-yl)-1,1-bis(3-(trifluoromethoxy)phenyl)ethylamino)butan-2-ol as a TFA salt. LC-MS (ESI) 569.31 (M+H), retention time=3.21 min (10-90% MeOH in H$_2$O with 0.1% TFA in a 4-min run); $^1$H NMR (400 MHz, CDCl$_3$) δ ppm 8.65 (d, J=4.39 Hz, 1H), 7.63-7.70 (m, 1H), 7.41-7.47 (m, 1H), 7.34-7.38 (m, 2H), 7.30-7.14 (m, 5H), 6.98 (m, 1H), 6.81 (d, J=7.91 Hz, 1H), 4.47-4.53 (m, 1H), 3.86 (m, 2H), 2.84 (dd, J=12.08, 9.89 Hz, 1H), 2.67 (dd, J=11.86, 2.64 Hz, 1H), 2.46 (m, 1H), 2.22 (m, 1H).

TABLE 7

| Ex. No. | Structure | Name | Retention Time Min./ Molecular Mass | Prepared in the manner described in: |
|---|---|---|---|---|
| 220 | 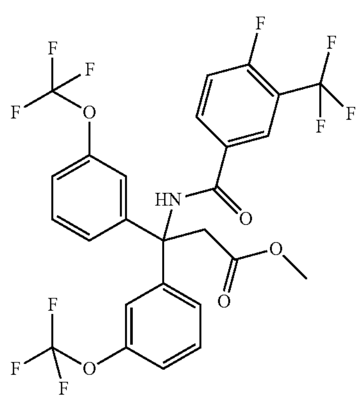 [SMILES: COC(=O)CC(NC(=O)c1ccc(F)c(C(F)(F)F)c1)(c1cccc(OC(F)(F)F)c1)c1cccc(OC(F)(F)F)c1] | methyl 3-(4-fluoro-3-(trifluoromethyl)benzamido)-3,3-bis(3-(trifluoromethoxy)phenyl) propanoate | 4.10 LC 614.36 [M + H]$^+$ | Procedures 11, 14 and 7 |

TABLE 7-continued

| Ex. No. | Structure | Name | Retention Time Min./ Molecular Mass | Prepared in the manner described in: |
|---|---|---|---|---|
| 221 | 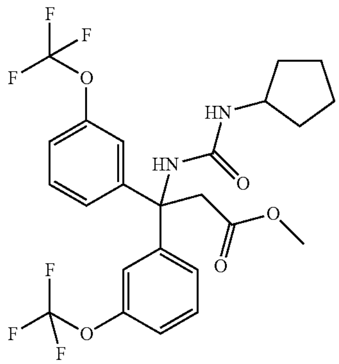 [SMILES: COC(=O)CC(NC(=O)NC1CCCC1)(c1cccc(OC(F)(F)F)c1)c1cccc(OC(F)(F)F)c1] | methyl 3-(3-cyclopentylureido)-3,3-bis(3-(trifluoromethoxy)phenyl)propanoate | 4.02 LC 535.38 [M + H]⁺ | Procedures 11, 14 and 2 |
| 222 | 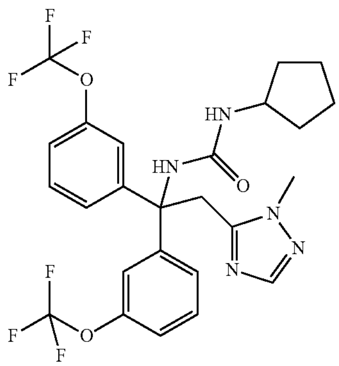 [SMILES: Cn1ncnc1CC(NC(=O)NC1CCCC1)(c1cccc(OC(F)(F)F)c1)c1cccc(OC(F)(F)F)c1] | 1-cyclopentyl-3-(2-(2-methyl-2H-1,2,4-triazol-3-yl)-1,1-bis(3-(trifluoromethoxy)phenyl)ethyl)urea | 3.81 LC 558.43 [M + H]⁺ | Procedures 15, 16 and 2 |
| 223 | 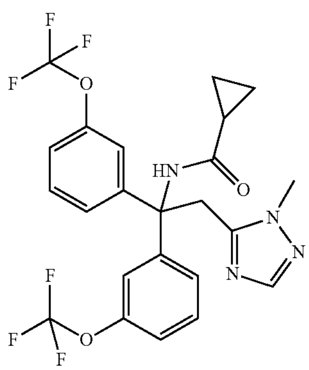 [SMILES: Cn1ncnc1CC(NC(=O)C1CC1)(c1cccc(OC(F)(F)F)c1)c1cccc(OC(F)(F)F)c1] | N-(2-(2-methyl-2H-1,2,4-triazol-3-yl)-1,1-bis(3-(trifluoromethoxy)phenyl)ethyl)cyclopropanecarboxamide | 3.61 LC 515.33 [M + H]⁺ | Procedures 15, 16 and 7 |
| 224 | 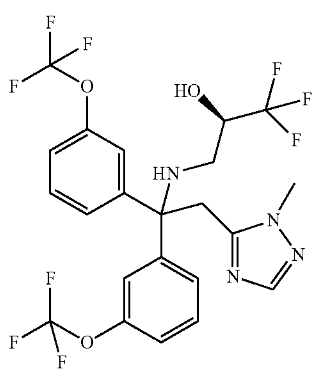 [SMILES: Cn1ncnc1CC(NC[C@@H](O)C(F)(F)F)(c1cccc(OC(F)(F)F)c1)c1cccc(OC(F)(F)F)c1] | (R)-1,1,1-trifluoro-3-(2-(2-methyl-2H-1,2,4-triazol-3-yl)-1,1-bis(3-(trifluoromethoxy)phenyl)ethylamino)propan-2-ol | 3.73 LC 559.4 [M + H]⁺ | Procedures 15, 16 and 8 |

TABLE 7-continued

| Ex. No. | Structure | Name | Retention Time Min./ Molecular Mass | Prepared in the manner described in: |
|---|---|---|---|---|
| 225 | 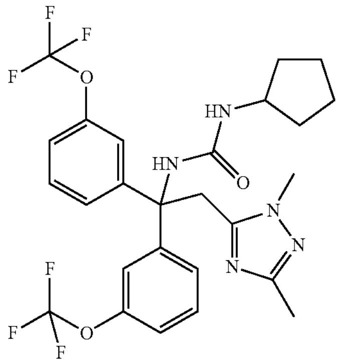 [SMILES: Cc1nc(CC(NC(=O)NC2CCCC2)(c2cccc(OC(F)(F)F)c2)c2cccc(OC(F)(F)F)c2)n(C)n1] | 1-cyclopentyl-3-(2-(2,5-dimethyl-2H-1,2,4-triazol-3-yl)-1,1-bis(3-(trifluoromethoxy)phenyl)ethyl)urea | 3.73 LC 572.48 [M + H]$^+$ | Procedures 15, 16 and 2 |
| 226 | 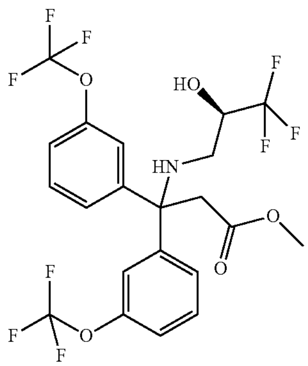 [SMILES: COC(=O)CC(NC[C@@H](O)C(F)(F)F)(c1cccc(OC(F)(F)F)c1)c1cccc(OC(F)(F)F)c1] | (R)-methyl-3-(3,3,3-trifluoro-2-hydroxypropylamino)-3,3-bis(3-(trifluoromethoxy)phenyl)propanoate | 3.93 LC 536.29 [M + H]$^+$ | Procedures 14 and 8 |
| 227 | 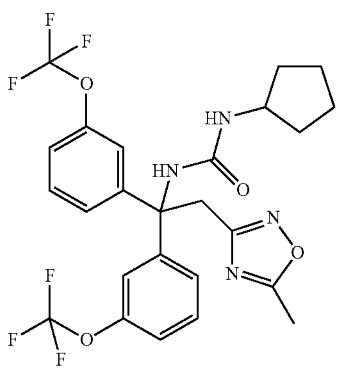 [SMILES: Cc1nc(CC(NC(=O)NC2CCCC2)(c2cccc(OC(F)(F)F)c2)c2cccc(OC(F)(F)F)c2)no1] | 1-cyclopentyl-3-(2-(5-methyl-1,2,4-oxadiazol-3-yl)-1,1-bis(3-(trifluoromethoxy)phenyl)ethyl)urea | 4.06 LC 559.25 [M + H]$^+$ | Procedures 18, 19 and 2 |
| 228 | 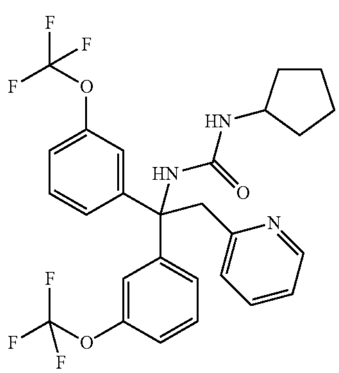 [SMILES: O=C(NC1CCCC1)NC(Cc1ccccn1)(c1cccc(OC(F)(F)F)c1)c1cccc(OC(F)(F)F)c1] | 1-cyclopentyl-3-(2-(pyridin-2-yl)-1,1-bis(3-(trifluoromethoxy)phenyl)ethyl)urea | 3.43 LC 554.4 [M + H]$^+$ | Procedures 20 and 2 |

TABLE 7-continued

| Ex. No. | Structure | Name | Retention Time Min./ Molecular Mass | Prepared in the manner described in: |
|---|---|---|---|---|
| 229 | 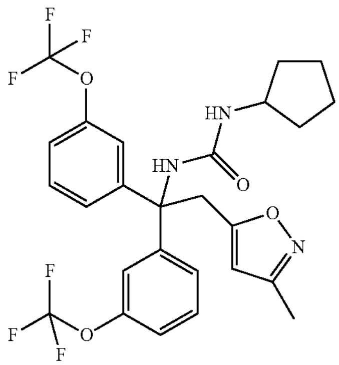 [SMILES: Cc1cc(CC(NC(=O)NC2CCCC2)(c2cccc(OC(F)(F)F)c2)c2cccc(OC(F)(F)F)c2)on1] | 1-cyclopentyl-3-(2-(3-methylisoxazol-5-yl)-1,1-bis(3-(trifluoromethoxy)phenyl)ethyl)urea | 3.98 LC 558.41 [M + H]$^+$ | Procedures 17 and 2 |
| 230 | 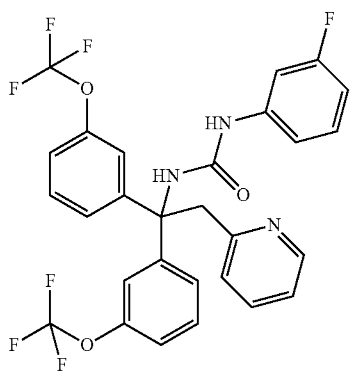 [SMILES: O=C(Nc1cccc(F)c1)NC(Cc1ccccn1)(c1cccc(OC(F)(F)F)c1)c1cccc(OC(F)(F)F)c1] | 1-(3-fluorophenyl)-3-(2-(pyridin-2-yl)-1,1-bis(3-(trifluoromethoxy)phenyl)ethyl)urea | 3.56 LC 580.33 [M + H]$^+$ | Procedures 20 and 2 |
| 231 | 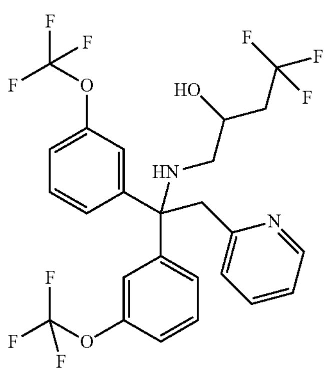 [SMILES: OC(CNC(Cc1ccccn1)(c1cccc(OC(F)(F)F)c1)c1cccc(OC(F)(F)F)c1)CC(F)(F)F] | 4,4,4-trifluoro-1-(2-(pyridin-2-yl)-1,1-bis(3-(trifluoromethoxy)phenyl)ethylamino)butan-2-ol | 3.21 LC 569.31 [M + H]$^+$ | Procedures 20 and 8 |
| 232 | 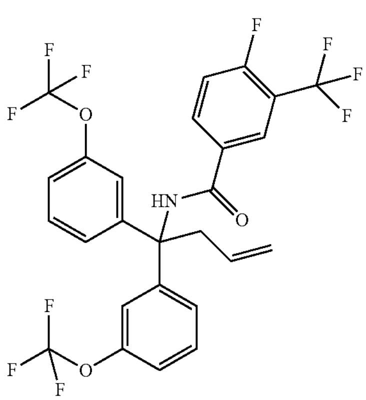 [SMILES: C=CCC(NC(=O)c1ccc(F)c(C(F)(F)F)c1)(c1cccc(OC(F)(F)F)c1)c1cccc(OC(F)(F)F)c1] | N-(1,1-bis(3-(trifluoromethoxy)phenyl)but-3-enyl)-4-fluoro-3-(trifluoromethyl)benzamide | 581.402 | Procedures 11 and 7 |

Example 233

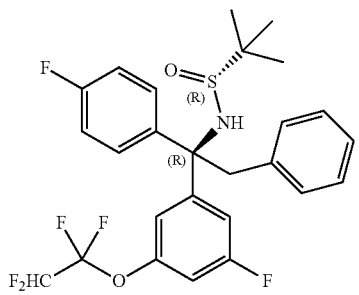

(R)—N—((R)-1-(3-fluoro-5-(1,1,2,2-tetrafluoroethoxy)phenyl)-1-(4-fluorophenyl)-2-phenylethyl)-2-methylpropane-2-sulfinamide

Procedure 21

(R)—N—((R)-1-(3-fluoro-5-(1,1,2,2-tetrafluoroethoxy)phenyl)-1-(4-fluorophenyl)-2-phenylethyl)-2-methylpropane-2-sulfinamide was prepared by analogous procedures described in Procedure 3, 4 and 5. The material was crystallized from CDCl₃ and an X-ray structure obtained.

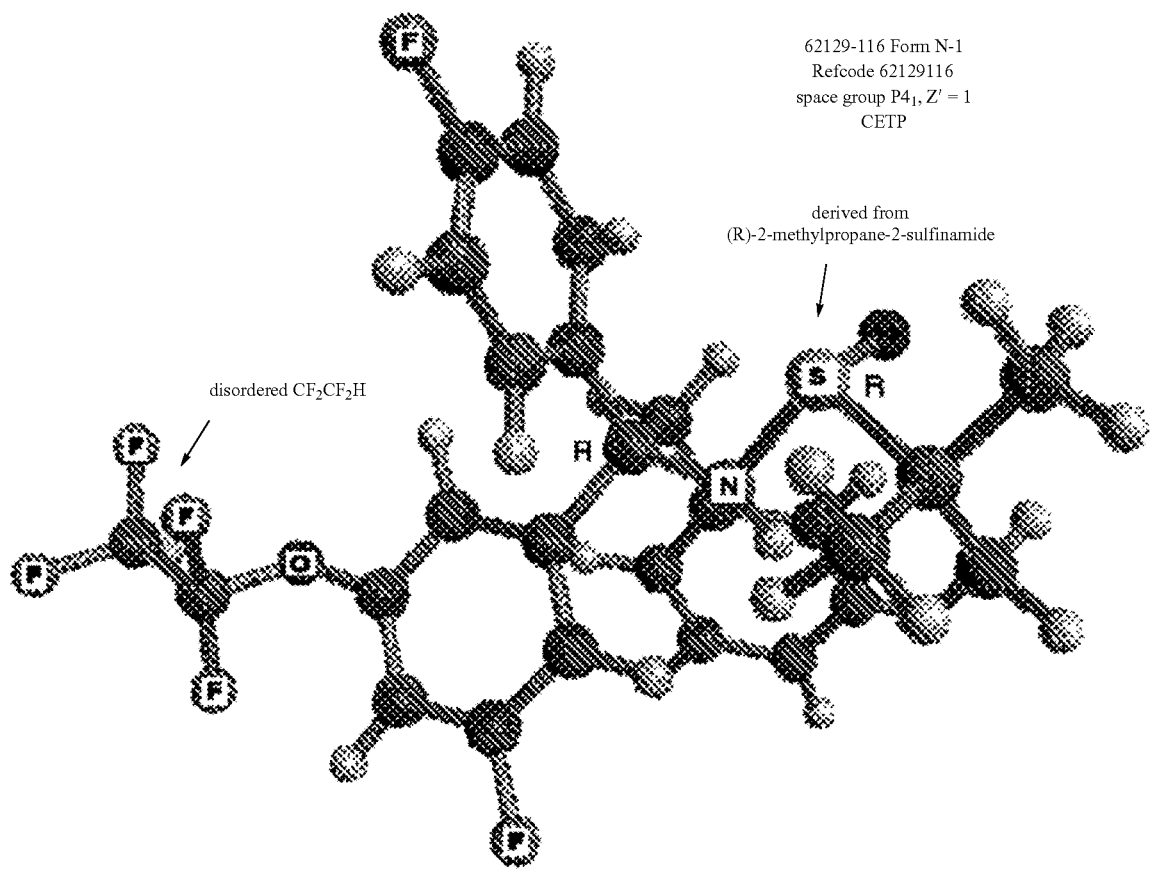

62129-116 Form N-1
Refcode 62129116
space group P4₁, Z' = 1
CETP derived from (R)-2-methylpropane-2-sulfinamide disordered CF₂CF₂H

TABLE 1

Properties of Crystal Forms

| CSD Refcode | FORM | Solvent Sites | % Solvent ideal (w/w) | HOT STAGE (° C.) | $D_{calc}$ (g/cc) | Z | V/Z | sg | T (° C.) |
|---|---|---|---|---|---|---|---|---|---|
| 62129116 | N-1 | None | — | 127-31 | 1.384 | 4 | 635 | P4₁ | −50 |

Example 234

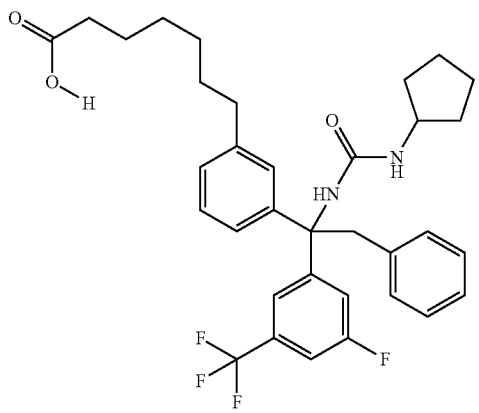 [SMILES: O=C(O)CCCCCCc1cccc(C(Cc2ccccc2)(NC(=O)NC2CCCC2)c2cc(F)cc(C(F)(F)F)c2)c1]

7-(3-(1-(3-cyclopentylureido)-1-(3-fluoro-5-(trifluoromethyl)phenyl)-2-phenylethyl)phenyl)heptanoic

Procedure 22

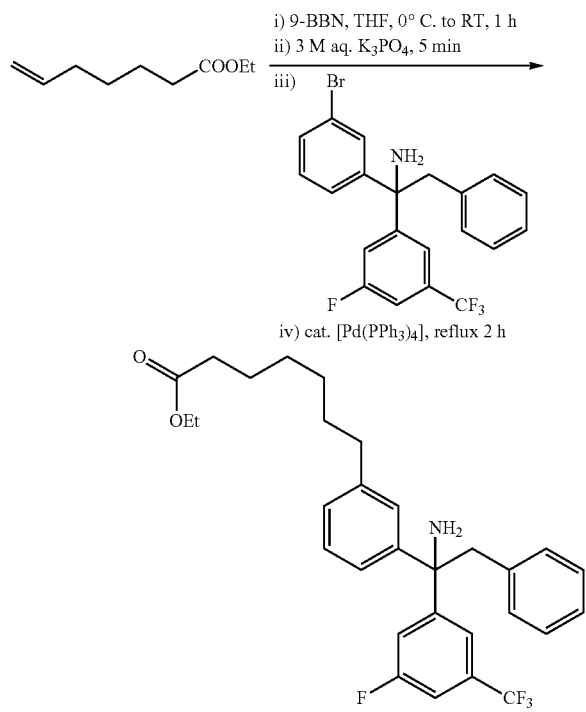

To a solution of ethyl hept-6-enoate (156 mg, 1 mmol) in dry THF (4 mL) cooled in an ice water bath was added a solution of 9-BBN (0.5 M in THF, 2.0 mL, 1 mmol). The cooling bath was removed and the reaction mixture was stirred for 1 h at room temperature. To the reaction mixture was added an aqueous solution of potassium phosphate (3 M, 0.66 mL, 2 mmol) and stirred for an additional 5 min. To the reaction mixture was added a solution of 1-(3-bromophenyl)-1-(3-fluoro-5-(trifluoromethyl)phenyl)-2-phenylethanamine, prepared as described in Procedure 1, (0.2 M in THF, 3 mL, 0.6 mmol), followed by tris-(dibenzylideneacetone)dipalladium(0) (45 mg, 0.04 mmol). The resulting yellow solution was heated under reflux for 20 h. The reaction mixture was cooled and concentrated under reduced pressure. The residue was extracted between water (10 mL) and ether (10 mL). The ether layer was washed twice with water, dried over $Na_2SO_4$ and concentrated under reduced pressure. The residue was purified by silica gel flash chromatography (2% to 10% EtOAc in Heptane) to yield ethyl 7-(3-(1-amino-1-(3-fluoro-5-(trifluoromethyl)phenyl)-2-phenylethyl)phenyl)heptanoate (169 mg, 54% yield). LCMS: RT=3.61 min, Purity 84% [M+H] 516.3 (Sunfire-S5-C18 column, 4.6×50 mm eluting with 10-90% MeOH/$H_2O$ over 4 minutes containing 0.1% TFA; 4 mL/min, monitoring at 220 nm).

Procedure 23

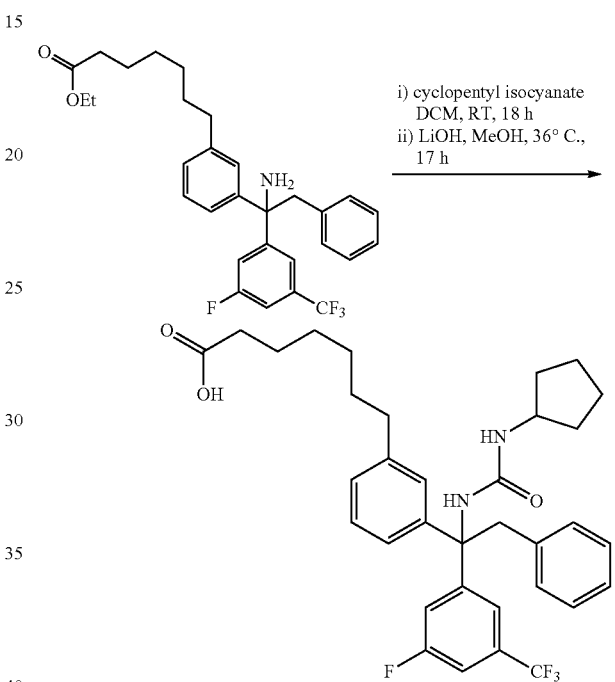

To a solution of ethyl 7-(3-(1-amino-1-(3-fluoro-5-(trifluoromethyl)phenyl)-2-phenylethyl)phenyl)heptanoate (169 mg, 0.33 mmol) in anhydrous DCM (1 mL) was added cyclopentyl isocyanate (22 mg, 0.2 mmol). The reaction mixture was stirred at rt for 18 h. To the reaction mixture was added anhydrous THF (1 mL) and the mixture was stirred at room temperature for additional 1 h. The solvents were evaporated on a rotary evaporator and the residue was dissolved in methanol and purified by preparative HPLC (RT=11.3 min, Waters Sunfire C18 OBD, 19×100 mm eluting with 26-90% MeCN/$H_2O$ containing 0.1% TFA over 9 min and hold at 90% for 7 more minutes; 40 mL/min, monitoring at 220 nm). The resulting solid was dissolved in methanol (1 mL) followed by the addition of aqueous lithium hydroxide (1 N, 0.25 mL, 0.25 mmol). The reaction mixture was heated at 36° C. for 18 h. The crude product was purified by preparative HPLC (RT=10.7 min, Waters Sunfire C18 OBD, 19×100 mm eluting with 18-90% MeCN/$H_2O$ over 10 min and hold at 90% for 6 additional minutes containing 0.1% TFA; 40 mL/min, monitoring at 220 nm) to yield 7-(3-(1-(3-cyclopentylureido)-1-(3-fluoro-5-(trifluoromethyl)phenyl)-2-phenylethyl)phenyl)heptanoic acid (Example 234, 32 mg, 53% yield for 2 steps). LCMS: RT=4.33 min, Purity>95%, [M+H] 599.4 (Sunfire-S5-C18 column, 4.6×50 mm eluting with 10-90% MeOH/$H_2O$ over 4 minutes containing 0.1% TFA; 4 mL/min, monitoring at 220 nm); NMR: 400 MHz $^1H$ ($CDCl_3$) 7.36 ppm, 1H, s; 7.16-7.24 ppm, 4H, m; 7.10-7.13 ppm, 3H, m; 6.97 ppm, 1H, d, J=7.7 Hz; 6.94 ppm, 1H, s; 6.67 ppm, 2H, d, J=7.1 Hz; 5.58 ppm, 1H, brd, s; 3.87 ppm, 1H, d, J=12.6 Hz; 3.83 ppm, 1H, m; 3.65 ppm, 1H, d, J=12.7 Hz; 2.54, 2H, t, J=7.5 Hz; 2.29 ppm, 2H, t, J=7.4 Hz; 1.73-1.84 ppm, 2H, m; 1.50-1.60 ppm, 8H, m; 1.15-1.36 ppm, 6H, m.

Example 235

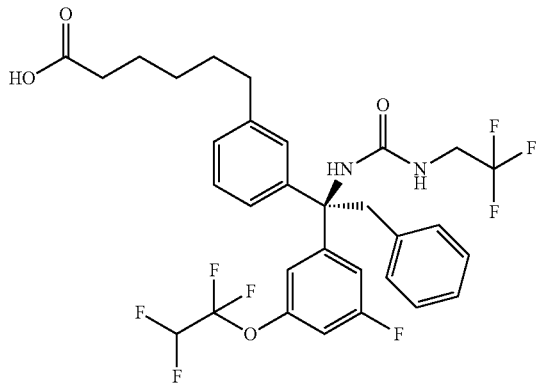

(R)-6-(3-(1-(3-fluoro-5-(1,1,2,2-tetrafluoroethoxy)phenyl)-2-phenyl-1-(3-(2,2,2-trifluoroethyl)ureido)ethyl)phenyl)hexanoic acid

Procedure 24

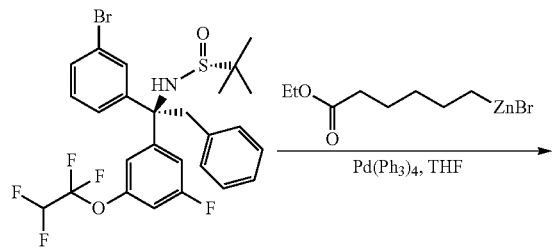

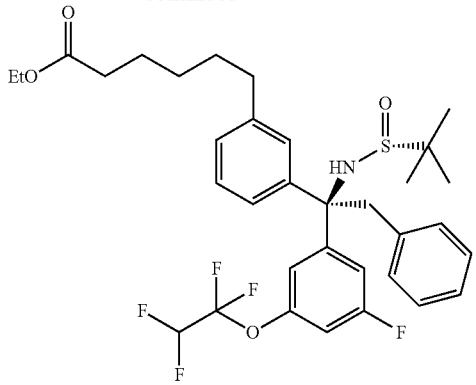

To a solution of (R)—N—((S)-1-(3-bromophenyl)-1-(3-fluoro-5-(1,1,2,2-tetrafluoroethoxy)phenyl)-2-phenylethyl)-2-methylpropane-2-sulfinamide (236 mg, 0.4 mmol), prepared as described in Procedure 3, 4, 5 and 6 (67% yield), in anhydrous THF (1 mL) was added (6-ethoxy-6-oxohexyl)zinc(II) bromide (2.4 ml, 1.2 mmol) followed by tetrakis(triphenylphosphine)palladium(0) (23 mg, 0.02 mmol). Under Ar atmosphere, the reaction mixture was heated to 130° C. under microwave irradiation for 15 min. The residue was diluted with EtOAc (10 mL) and washed with sat. NH$_4$Cl (2×5 mL). The organic layer was dried over Na$_2$SO$_4$, filtered and concentrated under reduced pressure. The resulting residue was dissolved in methanol and purified by preparative HPLC (Waters Sunfire C18 19×50 mm column eluting with 10-90% MeOH/H$_2$O over 7 min; 20 mL/min, monitoring at 220 nm) to give ethyl 6-(3-((R)-1-((R)-1,1-dimethylethylsulfinamido)-1-(3-fluoro-5-(1,1,2,2-tetrafluoroethoxy)phenyl)-2-phenylethyl)phenyl)hexanoate (60 mg, 23% yield). LCMS: RT=3.97 min [M+H] 654.52 (4 min YMC-ODS column, 4.6× 50 mm eluting with 10-90% MeOH/H$_2$O over 4 minutes containing 0.1% TFA; 4 mL/min, monitoring at 220 nm). $^1$H NMR (500 MHz, CDCl$_3$) δ ppm 7.24-7.33 (2H, m), 7.11-7.19 (5H, m), 6.89-6.94 (2H, m), 6.82 (1H, d, J=8.52 Hz), 6.67-6.73 (2H, m), 5.85 (1H, ttt, J=53.06, 2.61 Hz), 4.25 (1H, s), 4.11 (2H, q, J=7.15 Hz), 4.03 (1H, d, J=12.65 Hz), 3.60 (1H, d, J=12.65 Hz), 2.59 (2H, dd), 2.26 (2H, t, J=7.56 Hz), 1.61 (4H, tt, J=15.77, 7.87 Hz), 1.28-1.34 (2H, m) 1.22-1.27 (3H, m), 1.20 (9H, s).

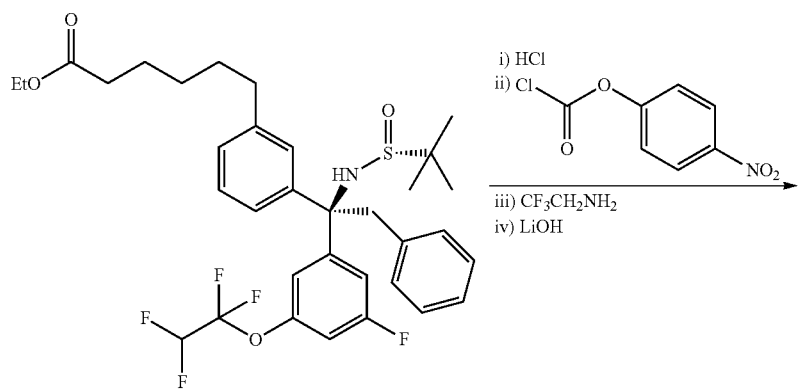

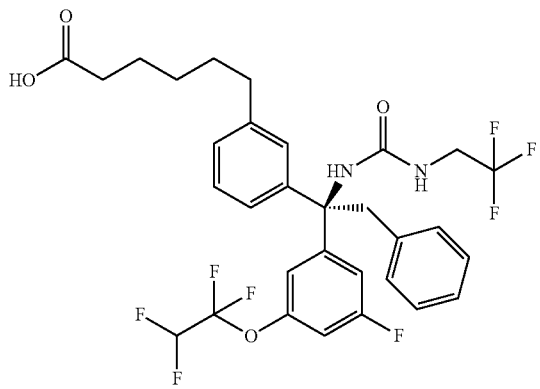 [SMILES: O=C(O)CCCCCc1cccc([C@@](Cc2ccccc2)(NC(=O)NCC(F)(F)F)c2cc(F)cc(OC(F)(F)C(F)F)c2)c1]

Example 236

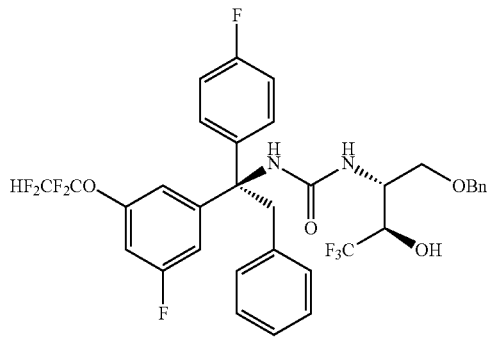

(R)-6-(3-(1-(3-fluoro-5-(1,1,2,2-tetrafluoroethoxy)phenyl)-2-phenyl-1-(3-(2,2,2-trifluoroethyl)ureido)ethyl)phenyl)hexanoic acid (Example 235, 13 mg, 50% yield) was prepared as described in Procedure 6, 12 and 23. LCMS: RT=4.10 min [M+H] 647.30 (Sunfire-S5-C18 column, 4.6× 50 mm eluting with 10-90% MeOH/H$_2$O over 4 minutes containing 0.1% TFA; 4 mL/min, monitoring at 220 nm). $^1$H NMR (500 MHz, CDCl$_3$) δ ppm 1.17-1.26 (m, 2H), 1.53-1.63 (m, 4H), 2.23-2.32 (m, 2H), 2.56 (t, J=7.15 Hz, 2H), 3.60 (ddd, J=15.05, 9.14, 5.77 Hz, 1H), 3.66 (d, J=12.92 Hz, 1H), 3.83 (ddd, J=15.67, 8.80, 7.15 Hz, 1H), 3.93 (d, J=12.92 Hz, 1H), 5.09 (t, J=5.91 Hz, 1H), 5.64 (s, 1H), 5.86 (ttt, J=53.06, 2.61 Hz, 1H), 6.69 (d, J=7.15 Hz, 2H), 6.87 (d, J=8.80 Hz, 1H), 6.90 (s, 1H), 6.96 (d, J=7.97 Hz, 1H), 6.99-7.02 (m, 2H), 7.06-7.12 (m, 3H), 7.16 (t, J=7.29 Hz, 1H), 7.22 (t, J=7.70 Hz, 1H), 7.26 (s, 1H).

1-((2R,3R)-1-(benzyloxy)-4,4,4-trifluoro-3-hydroxybutan-2-yl)-3-((R)-1-(3-fluoro-5-(1,1,2,2-tetrafluoroethoxy)phenyl)-1-(4-fluorophenyl)-2-phenylethyl)urea Procedure 25

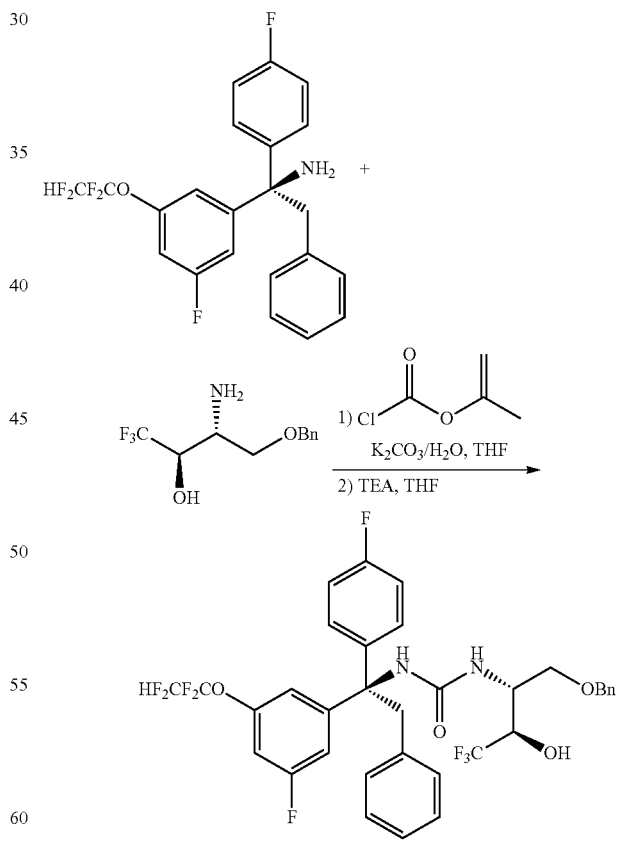

To a solution of (R)-1-(3-fluoro-5-(1,1,2,2-tetrafluoroethoxy)phenyl)-1-(4-fluorophenyl)-2-phenylethanamine (20 mg, 0.047 mmol), prepared as described in Procedure 3, 4, 5 and 6, in THF (0.5 mL) was added K$_2$CO$_3$ in H$_2$O (10 mg, 2 M in H$_2$O, 0.071 mmol), followed by the addition of prop-1- en-2-yl carbonochloridate (6 µL, 0.052 mmol). The reaction mixture was stirred at rt for 2 h, diluted with EtOAc (25 mL), washed with saturated NaCl (25 mL), dried over MgSO$_4$, filtered and concentrated under reduced pressure. To the residue was added (2R,3R)-3-amino-4-(benzyloxy)-1,1,1-trifluorobutan-2-ol (23 mg, 0.094 mmol), prepared according to the procedure described in J. Org. Chem., 68(19):7545 (2003), TEA (20 µL, 0.14 mmol) in THF (0.5 mL). The reaction mixture was heated at 70° C. for 18 h. The reaction solution was concentrated under reduced pressure and purified by ISCO chromatography (12 g column) using hexane/EtOAc (0-30% over 20 min) to give 1-((2R,3R)-1-(benzyloxy)-4,4,4-trifluoro-3-hydroxybutan-2-yl)-3-((R)-1-(3-fluoro-5-(1,1,2,2-tetrafluoroethoxy)phenyl)-1-(4-fluorophenyl)-2-phenylethyl)urea (Example 236) as a white solid at a retention time of 17 min (19 mg, 59% yield). LCMS: RT=2.138 min [M+H] 701.29 (Phenomenex Luna C18 column, 4.6×30 mm eluting with 10-90% MeOH/H$_2$O over 2 minutes containing 0.1% TFA, 5 mL/min, monitoring at 220 nm); HPLC: RT=4.335 min, Purity 94% (Phenomenex Luna C18 column, 4.6×50 mm eluting with 10-90% MeOH/H$_2$O over 4 minutes containing 0.2% PPA; 4 mL/min, monitoring at 220 nm); NMR: 400 MHz $^1$H (CDCl$_3$) 7.37 ppm, 3H, m; 7.25 ppm, 3H, m; 7.20 ppm, 1H, t, J=7.03 Hz; 7.13 ppm, 4H, m; 6.97 ppm, 2H, t, J=8.35 Hz; 6.89 ppm, 3H, m; 6.69 ppm, 2H, d, J=7.47 Hz; 5.86 ppm, 1H, m; 5.18 ppm, 1H, d, J=8.35 Hz; 5.13 ppm, 1H, s; 4.44 ppm, 2H, m; 4.26 ppm, 1H, d, J=9.67 Hz; 4.14 ppm, 1H, dd, J=8.13, 3.30 Hz; 3.99 ppm, 1H, m; 3.81 ppm, 2H, m; 3.71 ppm, 1H, m; 3.59 ppm, 1H, m.

Example 237

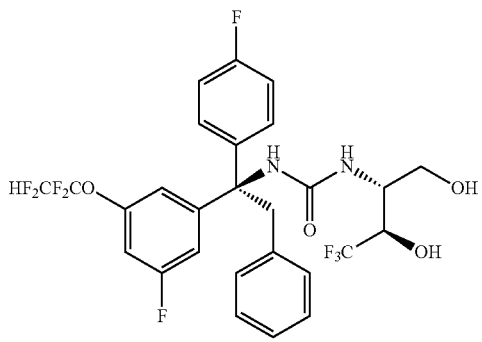

1-((R)-1-(3-fluoro-5-(1,1,2,2-tetrafluoroethoxy)phenyl)-1-(4-fluorophenyl)-2-phenylethyl)-3-((2R,3R)-4,4,4-trifluoro-1,3-dihydroxybutan-2-yl)urea Procedure 26

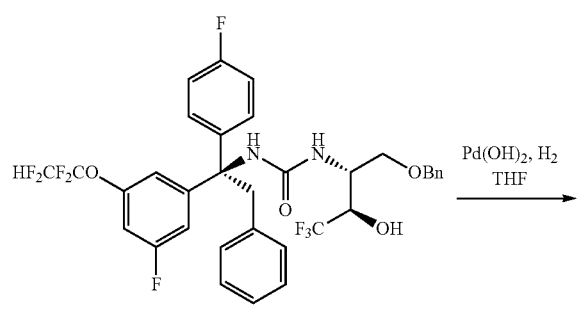

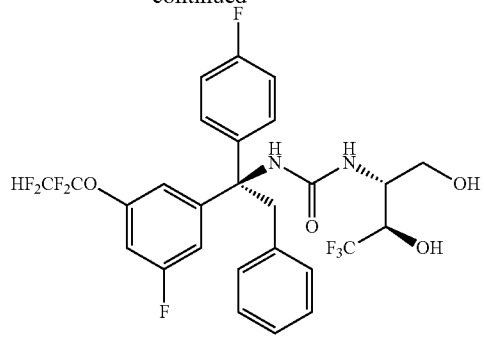

To a solution of 1-((2R,3R)-1-(benzyloxy)-4,4,4-trifluoro-3-hydroxybutan-2-yl)-3-((R)-1-(3-fluoro-5-(1,1,2,2-tetrafluoroethoxy)phenyl)-1-(4-fluorophenyl)-2-phenylethyl)urea (Example 236, 17 mg, 0.024 mmol) in THF (1 mL) was added 20% Pd(OH)$_2$/C (8 mg) and the slurry was subjected to balloon hydrogenation for 18 h. The reaction mixture was filtered and the filtrate was concentrated and purified by preparative HPLC (Shimadzu-YMC-ODS-A 5µ column, 30×100 mm eluting with 30-100% MeOH (90% in H$_2$O, 0.1% TFA) gradient over 12 min with flow rate 40 mL/min and UV detection at 220 nm) to yield 1-((R)-1-(3-fluoro-5-(1,1,2,2-tetrafluoroethoxy)phenyl)-1-(4-fluorophenyl)-2-phenylethyl)-3-((2R,3R)-4,4,4-trifluoro-1,3-dihydroxybutan-2-yl)urea (Example 237) eluting at a retention time of 11.54 min as a clear oil (11 mg, yield 78%). LCMS: RT=1.983 min [M+H] 611.26 (Phenomenex Luna C18 column, 4.6×30 mm eluting with 10-90% MeOH/H$_2$O over 2 minutes containing 0.1% TFA, 5 mL/min, monitoring at 220 nm); HPLC: RT=4.081 min, Purity 100% (Phenomenex Luna C18 column, 4.6×50 mm eluting with 10-90% MeOH/H$_2$O over 4 minutes containing 0.2% PPA; 4 mL/min, monitoring at 220 nm); NMR: 400 MHz $^1$H (CDCl$_3$) 7.20 ppm, 1H, s; 7.16 ppm, 5H, m; 6.99 ppm, 2H, m; 6.91 ppm, 3H, m; 6.70 ppm, 2H, d, J=7.47 Hz; 5.87 ppm, 1H, m; 5.38 ppm, 1H, d, J=7.47 Hz; 5.35 ppm, 1H, s; 4.28 ppm, 1H, d, J=5.71 Hz; 4.11 ppm, 2H, m; 3.94 ppm, 2H, d, J=7.91 Hz; 3.82 ppm, 1H, m; 3.73 ppm, 1H, m; 3.67 ppm, 1H, d, J=8.35 Hz.

Example 238

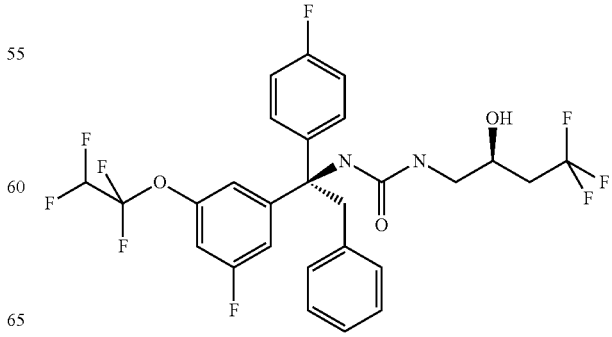

1-((R)-1-(3-fluoro-5-(1,1,2,2-tetrafluoroethoxy)phenyl)-1-(4-fluorophenyl)-2-phenylethyl)-3-((S)-4,4,4-trifluoro-2-hydroxybutyl)urea

Procedure 27

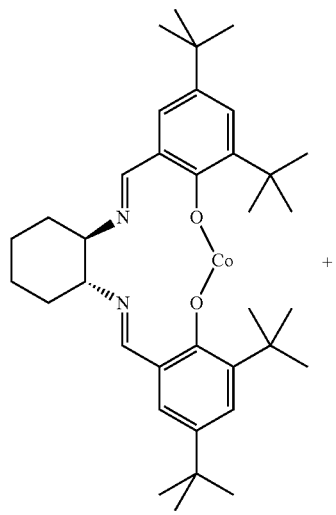

1) TsOH H₂O, DCM
2) pentane
3) H₂O

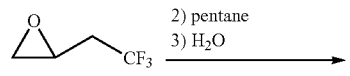

To a solution of (R,R)-(–)-N'N'-bis(3,5-di-tert-butylsalicylidene)-1,2-cyclo-hexanediamine (0.92 g, 1.53 mmol) in DCM (35 mL) was added TsOH H₂O (308 mg, 1.62 mmol) and the reaction mixture was stirred at room temperature while open to air for 1 h. The reaction mixture was concentrated under reduced pressure and pentane was added to the residue. The resulting solid was filtered, rinsed with pentane once, diluted with DCM and transferred to the reaction flask. DCM was then removed under reduced pressure and 2-(2,2,2-trifluoroethyl)oxirane (37 g, 294 mmol) was added to the resulting solid. The mixture was cooled to 0° C. and H₂O (3.7 mL, 206 mmol) was added dropwise. After addition was finished, the reaction mixture was stirred at room temperature for 72 h. (S)-2-(2,2,2-trifluoroethyl)oxirane was isolated as a clear oil (10 g, 28%) by vacuum distillation from the reaction mixture into a cooled (–78° C.) receiving flask. NMR: 400 MHz ¹H (CDCl₃) 3.16 ppm, 1H, m; 2.87 ppm, 1H, t, J=4.39 Hz; 2.59 ppm, 1H, dd, J=4.61, 2.42 Hz; 2.39 ppm, 1H, m; 2.29 ppm, 1H, m, J=10.44, 10.44, 5.05, 4.83 Hz.

The recovered epoxide was determined to be >99% ee according to the procedure used by Jacobsen (J. Am. Chem. Soc., 124(7):1307-1315 (2004)). (Chiral HPLC analysis of the 2-napthylsulfide derivative (obtained by ring opening with 2-napthalenethiol in MeOH using 1 equiv TEA and direct analysis of the product obtained, Chiralcel® AD, 95:5 hexanes:i-PrOH, 1 mL/min, 254 nm, RT (minor)=16.52 min, RT (major)=19.28 min).

Procedure 28

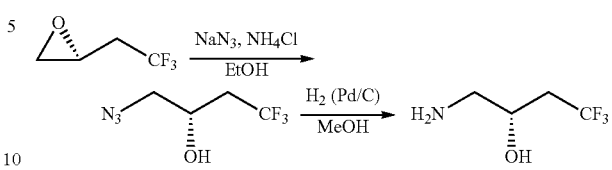

To a solution of (S)-2-(2,2,2-trifluoroethyl)oxirane (2.00 g, 16.0 mmol) in a mixture of EtOH (16 mL) and H₂O (4 mL) were added NaN₃ (2.06 g, 32.0 mmol) and NH₄Cl (1.70 g, 32.0 mmol). After stirring at room temperature for 18 h, the reaction mixture was diluted with H₂O (50 mL), extracted with Et₂O (2×75 mL). The combined organic layer was dried over MgSO₄, filtered and concentrated to give (S)-1-azido-4,4,4-trifluorobutan-2-ol as an oil (2.26 g, 83% yield). NMR: 400 MHz ¹H (CDCl₃) 4.17 ppm, 1H, ddd, J=6.81, 3.74, 3.52 Hz; 3.48 ppm, 1H, m; 3.37 ppm, 1H, m; 2.35 ppm, 2H, m.

The crude (S)-1-azido-4,4,4-trifluorobutan-2-ol (2.26 g, 13.0 mmol) was subjected to balloon hydrogenation for 18 h. After the filtration, the filtrate was concentrated to give (S)-1-amino-4,4,4-trifluorobutan-2-ol (1.02 g, 45% yield). NMR: 400 MHz ¹H (CDCl₃) 3.88 ppm, 1H, m, J=7.85, 7.85, 3.84, 3.74 Hz; 2.93 ppm, 1H, dd, J=12.74, 3.52 Hz; 2.61 ppm, 1H, dd, J=12.52, 8.13 Hz; 2.34 ppm, 1H, m; 2.21 ppm, 1H, m; 1.91 ppm, 3H, s.

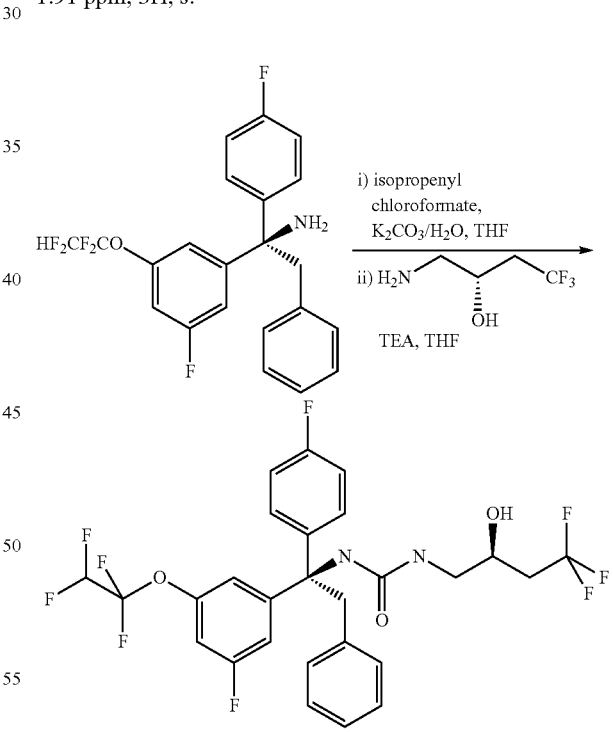

1-((R)-1-(3-fluoro-5-(1,1,2,2-tetrafluoroethoxy)phenyl)-1-(4-fluorophenyl)-2-phenylethyl)-3-((S)-4,4,4-trifluoro-2-hydroxybutyl)urea (Example 238) was prepared as described in Procedure 25 (27 mg, 65% yield). LCMS: RT=2.02 min [M+H] 595.28 (Phenomenex Luna C18 column, 4.6×30 mm eluting with 10-90% MeOH/H₂O over 2 minutes containing 0.1% TFA, 5 mL/min, monitoring at 220 nm); HPLC: RT=4.165 min, Purity 100% (Phenomenex Luna C18 column, 4.6×50 mm eluting with 10-90% MeOH/H₂O over 4 minutes containing 0.2% PPA; 4 mL/min, monitoring at 220 nm). $^1$H NMR (400 MHz, CDCl$_3$) δ ppm 7.16 ppm, 5H, m; 6.94 ppm, 5H, m; 6.69 ppm, 2H, d, J=7.03 Hz; 5.73 ppm, 1H, m; 4.10 ppm, 2H, m; 3.93 ppm, 1H, s; 3.84 ppm, 1H, m; 3.73 ppm, 1H, m; 3.52 ppm, 1H, s; 3.29 ppm, 1H, m; 3.04 ppm, 1H, m; 2.17 ppm, 2H, m.

Example 239

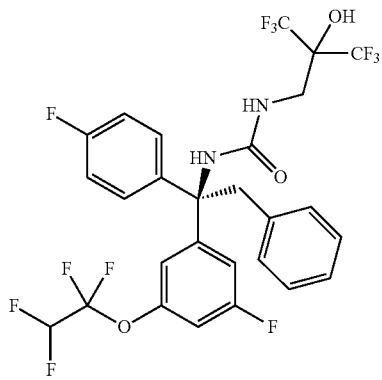 [SMILES: O=C(NCC(O)(C(F)(F)F)C(F)(F)F)N[C@](Cc1ccccc1)(c1ccc(F)cc1)c1cc(F)cc(OC(F)(F)C(F)F)c1]

(R)-1-(1-(3-fluoro-5-(1,1,2,2-tetrafluoroethoxy)phenyl)-1-(4-fluorophenyl)-2-phenylethyl)-3-(3,3,3-trifluoro-2-hydroxy-2-(trifluoromethyl)propyl)urea Procedure 29

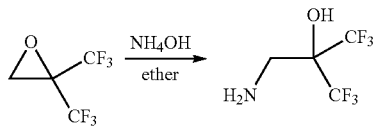

To a 1:1 mixture of ether (1.85 mL) and 30% ammonium hydroxide (1.85 mL) was added drop-wise 2,2-bis(trifluoromethyl)oxirane (1.00 g, 5.5 mmol). The reaction mixture was stirred for 2 h at rt, then diluted with ether and H$_2$O. The aqueous layer was extracted twice with ether and the combined ether layer was dried over MgSO$_4$, filtered and concentrated to give 2-(aminomethyl)-1,1,1,3,3,3-hexafluoropropan-2-ol as a semi solid (0.87 g, 81% yield). $^1$H NMR (400 MHz, CDCl$_3$) ppm 3.14 (s, 2H), 3.25 (s, 1H).

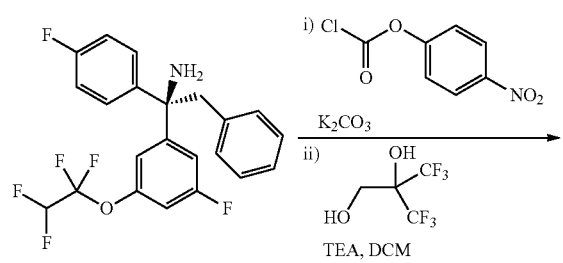

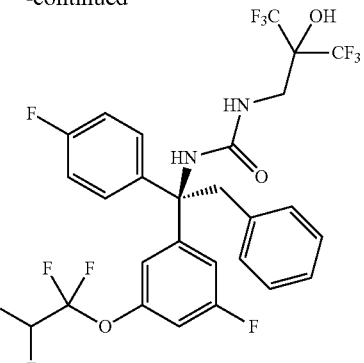

(R)-1-(1-(3-fluoro-5-(1,1,2,2-tetrafluoroethoxy)phenyl)-1-(4-fluorophenyl)-2-phenylethyl)-3-(3,3,3-trifluoro-2-hydroxy-2-(trifluoromethyl)propyl)urea was prepared as described in Procedure 12. The product was purified by ISCO chromatography (4 g column) using hexane/EtOAc (0-20% over 12 min) to give the (R)-1-(1-(3-fluoro-5-(1,1,2,2-tetrafluoroethoxy)phenyl)-1-(4-fluorophenyl)-2-phenylethyl)-3-(3,3,3-trifluoro-2-hydroxy-2-(trifluoromethyl)propyl)urea (Example 239) as a colorless oil (24 mg, 65% yield). LCMS: RT=4.11 min [M+H] 649.10 (Phenomenex Luna C18 column, 4.6×50 mm eluting with 10-90% MeOH/H$_2$O over 4 minutes containing 0.1% TFA; 4 mL/min, monitoring at 220 nm); $^1$H NMR (400 MHz, CDCl$_3$) ppm 3.60-3.90 (m, 4H), 5.13 (t, J=5.81 Hz, 1H), 5.50 (s, 1H), 5.69-6.05 (t, J=56 Hz, 1H), 6.68 (d, J=6.82 Hz, 2H), 6.81-6.95 (m, 3H), 6.96-7.05 (m, 3H), 7.06-7.24 (m, 5H).

Example 240

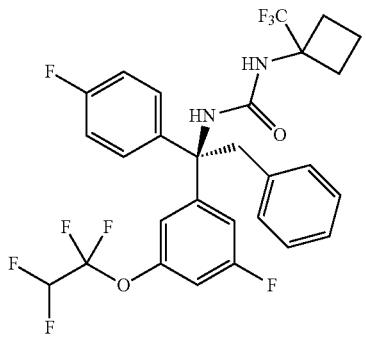 [SMILES: O=C(NC1(C(F)(F)F)CCC1)N[C@](Cc1ccccc1)(c1ccc(F)cc1)c1cc(F)cc(OC(F)(F)C(F)F)c1]

(R)-1-(1-(3-fluoro-5-(1,1,2,2-tetrafluoroethoxy)phenyl)-1-(4-fluorophenyl)-2-phenylethyl)-3-(1-(trifluoromethyl)cyclobutyl)urea Procedure 30

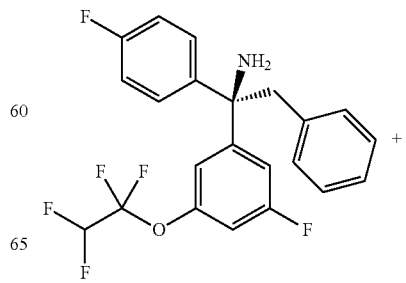

375

-continued

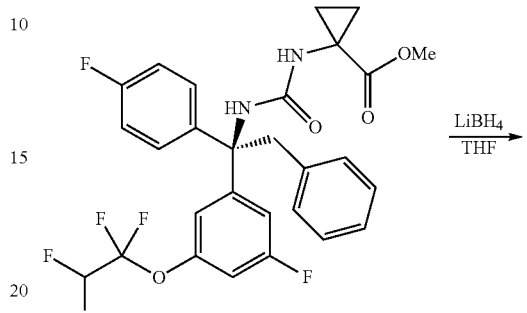

To a solution of 1-(trifluoromethyl)cyclobutanecarboxylic acid (54 mg, 0.354 mmol) in toluene (0.9 mL) was added TEA (36 mg, 0.354 mmol), followed by DPPA (76.4 uL, 0.354 mmol). The reaction mixture was heated at 90° C. for 2 h, then allowed to cool to rt. (R)-1-(3-fluoro-5-(1,1,2,2-tetrafluoroethoxy)phenyl)-1-(4-fluorophenyl)-2-phenylethanamine (50 mg, 0.117 mmol), prepared as described in Procedure 3, 4, 5 and 6, was added and the reaction mixture was stirred at rt for 4.5 h. The reaction mixture was concentrated under reduced pressure and purified by ISCO chromatography (12 g column, eluting with 0-30% hexane/EtOAc over 18 min). The product was further purified by preparative HPLC (Phenomenex AXIA Luna column, 30×100 mm, flow rate 40 mL/min, eluting with 40-100% ACN/H$_2$O/0.1% TFA over 10 min) to yield (R)-1-(1-(3-fluoro-5-(1,1,2,2-tetrafluoroethoxy)phenyl)-1-(4-fluorophenyl)-2-phenylethyl)-3-(1-(trifluoromethyl)cyclobutyl)urea (Example 240) as a white solid (45 mg, 65% yield). LCMS: RT=4.13 min [M+H] 519.18 (Phenomenex Luna C18 column, 4.6×50 mm eluting with 10-90% MeOH/H$_2$O over 4 minutes containing 0.1% TFA; 4 mL/min, monitoring at 220 nm); $^1$H NMR (400 MHz, CDCl$_3$) ppm 1.83-2.06 (m, 2H), 2.16-2.33 (m, 2H), 2.33-2.51 (m, 2H), 3.78 (qt, J=13 Hz, 2H), 4.71 (s, 1H), 5.02 (s, 1H), 5.85 (t, J=52 Hz, 1H), 6.65-6.75 (m, 2H), 6.83-7.06 (m, 5H), 7.05-7.23 (m, 5H).

Example 241

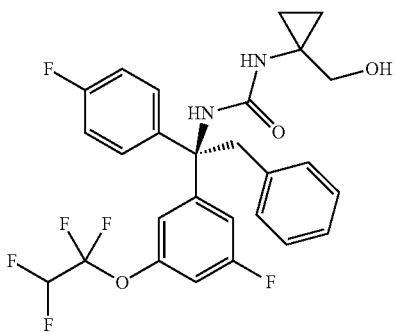 [SMILES: O=C(NC1(CO)CC1)N[C@](Cc1ccccc1)(c1ccc(F)cc1)c1cc(F)cc(OC(F)(F)C(F)F)c1]

376

(R)-1-(1-(3-fluoro-5-(1,1,2,2-tetrafluoroethoxy)phenyl)-1-(4-fluorophenyl)-2-phenylethyl)-3-(1-(hydroxymethyl)cyclopropyl)urea Procedure 31

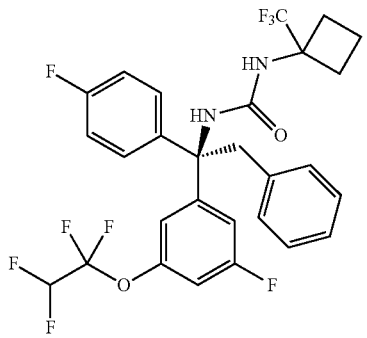

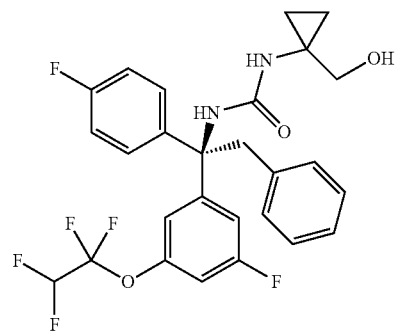

To a solution of (R)-methyl 1-(3-(1-(3-fluoro-5-(1,1,2,2-tetrafluoroethoxy)phenyl)-1-(4-fluorophenyl)-2-phenylethyl)ureido)-cyclopropanecarboxylate (112 mg, 0.2 mmol), prepared by the method described in Procedure 30, in THF (0.2 mL) was added LiBH$_4$ (0.2 mL, 2 M in THF, 0.4 mmol) at room temperature. The reaction mixture was stirred for 14 h, then cooled to 0° C. and 1 N HCl was added. The reaction mixture was diluted with ether. The organic layer was washed with H$_2$O and sat. NaCl, dried over MgSO$_4$, filtered and concentrated to give a colorless oil. The resulting oil was purified by ISCO chromatography (4 g column, eluting with 0-100% hexane/EtOAc over 16 min) to yield (R)-1-(1-(3-fluoro-5-(1,1,2,2-tetrafluoroethoxy)phenyl)-1-(4-fluorophenyl)-2-phenylethyl)-3-(1-(hydroxymethyl)cyclopropyl)urea (Example 241) as a white foam (91 mg, 84% yield). LCMS: RT=2.97 min [M+H] 539.2 (Phenomenex Luna C18 column, 4.6×50 mm eluting with 10-90% CH$_3$CN/H$_2$O over 4 minutes containing 0.1% NH$_4$OAc; 4 mL/min, monitoring at 220 nm); $^1$H NMR (400 MHz, CDCl$_3$) ppm 0.61-0.81 (m, 4H), 2.50 (brs, 1H), 3.31-3.50 (m, 2H), 3.84 (qt, J=12 Hz, 2H), 4.93 (s, 1H), 5.84 (t, J=53 Hz, 1H), 6.53-7.05 (m, 8H), 7.05-7.24 (m, 5H).

Example 242

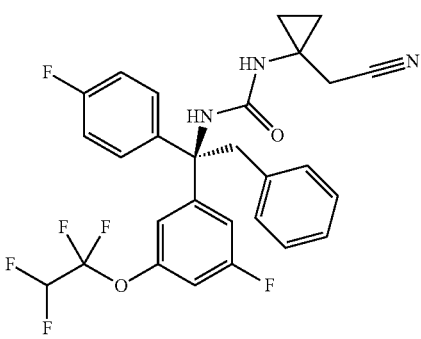 [SMILES: N#CCC1(NC(=O)N[C@](Cc2ccccc2)(c2ccc(F)cc2)c2cc(F)cc(OC(F)(F)C(F)F)c2)CC1]

(R)-1-(1-(cyanomethyl)cyclopropyl)-3-(1-(3-fluoro-5-(1,1,2,2-tetrafluoroethoxy)phenyl)-1-(4-fluorophenyl)-2-phenylethyl)urea Procedure 32

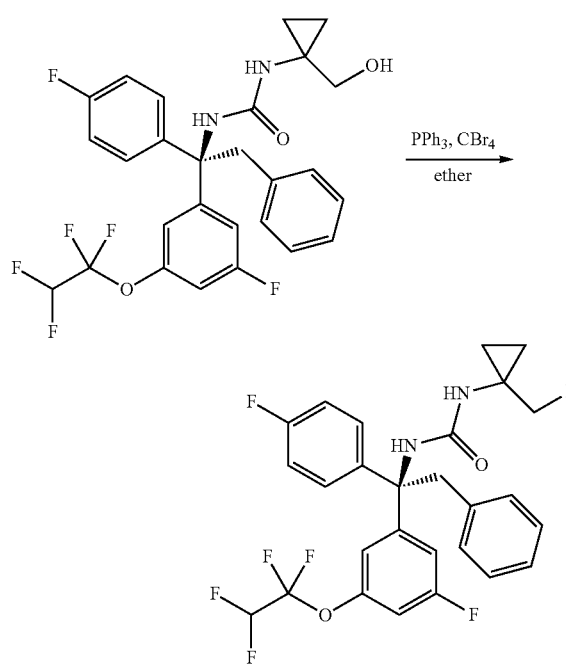

To a solution of (R)-1-(1-(3-fluoro-5-(1,1,2,2-tetrafluoroethoxy)phenyl)-1-(4-fluorophenyl)-2-phenylethyl)-3-(1-(hydroxymethyl)cyclopropyl)urea (Example 241, 43 mg, 0.08 mmol) in ether (0.4 mL) was added PPh$_3$ (48 mg, 0.18 mmol) and CBr$_4$ (58 mg, 0.18 mmol) at room temperature. The reaction mixture was stirred for 14 h and concentrated under reduced pressure and purified by ISCO chromatography (4 g column, eluting with 0-15% hexane/EtOAc over 14 min) to yield (R)-1-(1-(bromomethyl)cyclopropyl)-3-(1-(3-fluoro-5-(1,1,2,2-tetrafluoroethoxy)phenyl)-1-(4-fluorophenyl)-2-phenylethyl)urea as a white solid (8 mg, 17% yield). LCMS: RT=4.06 min [M+H] 601.2 (Phenomenex Luna C18 column, 4.6×50 mm eluting with 10-90% MeOH/H$_2$O over 4 minutes containing 0.1% TFA; 4 mL/min, monitoring at 220 nm); $^1$H NMR (400 MHz, CDCl$_3$) ppm 0.82-1.03 (m, 4H), 3.47 (qt, J=12 Hz, 2H), 3.81 (ABqt, J=12 Hz, 2H), 5.01 (s, 1H), 5.39 (s, 1H), 5.86 (t, J=53 Hz, 1H), 6.61-6.78 (m, 2H), 6.80-7.25 (m, 10H).

Procedure 33

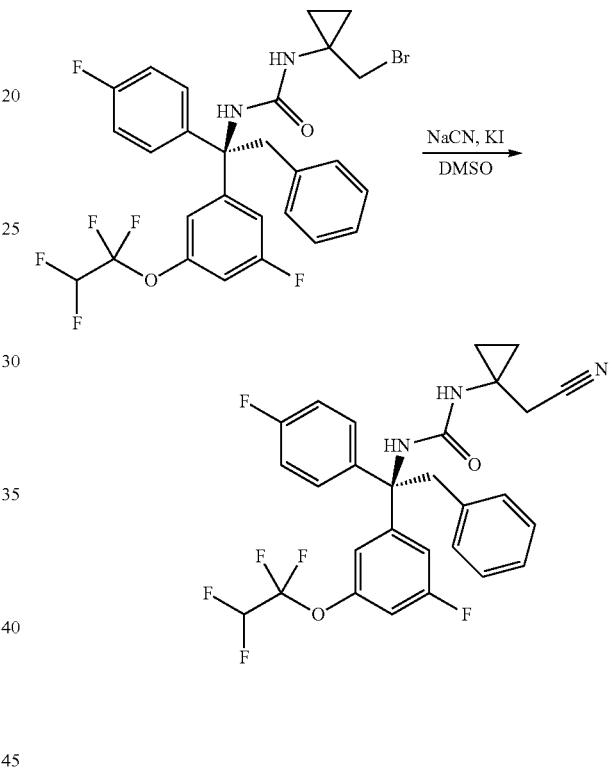

To a solution of (R)-1-(1-(bromomethyl)cyclopropyl)-3-(1-(3-fluoro-5-(1,1,2,2-tetrafluoroethoxy)phenyl)-1-(4-fluorophenyl)-2-phenylethyl)urea (8 mg, 0.013 mmol) in DMSO (0.3 mL) was added NaCN (18 mg, 0.37 mmol) and KI (20 mg, 0.12 mmol). The reaction mixture was stirred at rt for 3 days. The reaction mixture was concentrated under reduced pressure and purified by preparative HPLC (Phenomenex AXIA Luna column, 30×100 mm, flow rate 40 mL/min, 30-100% ACN/H$_2$O/0.1% TFA over 12 min) to yield (R)-1-(1-(cyanomethyl)cyclopropyl)-3-(1-(3-fluoro-5-(1,1,2,2-tetrafluoroethoxy)phenyl)-1-(4-fluorophenyl)-2-phenylethyl)urea (Example 242, 5 mg, 63% yield). LCMS: RT=3.88 min [M+H]548.3 (Phenomenex Luna C18 column, 4.6×50 mm eluting with 10-90% MeOH/H$_2$O over 4 minutes containing 0.1% TFA; 4 mL/min, monitoring at 220 nm); $^1$H NMR (400 MHz, CDCl$_3$) ppm 0.76-0.91 (m, 4H), 2.58 (qt, J=17 Hz, 2H), 3.78 (qt, J=12 Hz, 2H), 5.49 (s, 1H), 5.52 (s, 1H), 5.87 (t, J=53 Hz, 1H), 6.66 (d, J=6.6 Hz, 2H), 6.84-6.95 (m, 3H), 6.96-7.07 (m, 2H), 7.07-7.26 (m, 5H).

Example 243

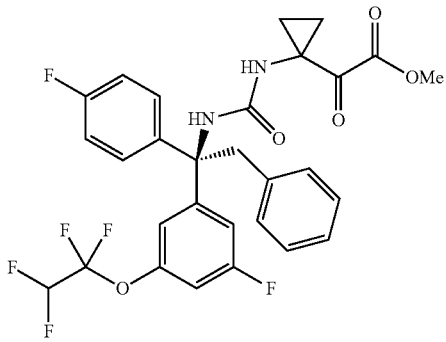 [SMILES: COC(=O)C(=O)C1(NC(=O)N[C@](Cc2ccccc2)(c2ccc(F)cc2)c2cc(F)cc(OC(F)(F)C(F)F)c2)CC1]

(R)-methyl 2-(1-(3-(1-(3-fluoro-5-(1,1,2,2-tetrafluoroethoxy)phenyl)-1-(4-fluorophenyl)-2-phenylethyl)ureido)cyclopropyl)-2-oxoacetate Procedure 34

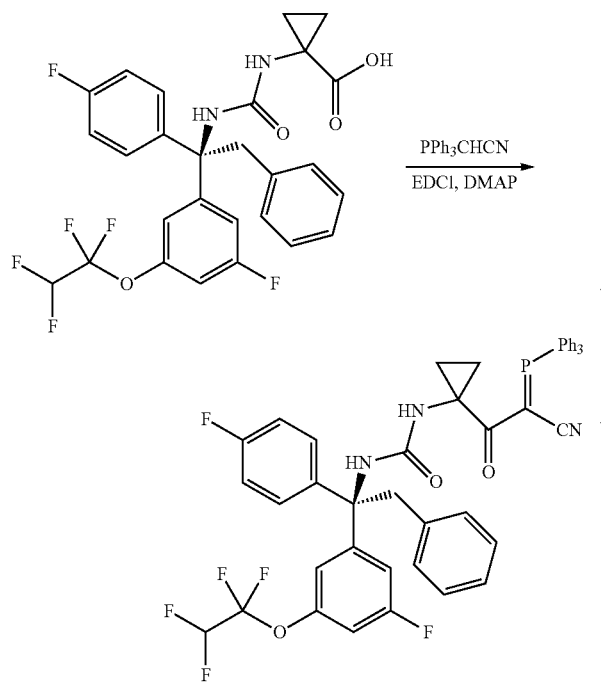

To a solution of (R)-1-(3-(1-(3-fluoro-5-(1,1,2,2-tetrafluoroethoxy)phenyl)-1-(4-fluorophenyl)-2-phenylethyl)ureido)-cyclopropanecarboxylic acid (84 mg, 0.153 mmol), prepared by the method described in Procedure 30, in DCM (0.5 mL) was added 2-(phenylphosphinylidene)acetonitrile compound with biphenyl (1:1) (51 mg, 0.168 mmol), EDCI (32 mg, 0.168 mmol) and DMAP (3 mg, 0.024 mmol). The reaction mixture was stirred at room temperature for 4.5 h, concentrated under reduced pressure and purified by ISCO chromatography (12 g column, eluting with 0-100% hexane/EtOAc) to yield (R)-1-(1-(2-cyano-2-(phenylphosphinylidene)acetyl)cyclopropyl)-3-(1-(3-fluoro-5-(1,1,2,2-tetrafluoroethoxy)phenyl)-1-(4-fluorophenyl)-2-phenylethyl)urea compound with biphenyl (1:1) as a white solid (53 mg, 42% yield). LCMS: RT=3.49 min [M+H] 836.4 (Phenomenex Luna C18 column, 4.6×50 mm eluting with 50-100% MeOH/H$_2$O over 4 minutes containing 0.1% TFA; 4 mL/min, monitoring at 220 nm); $^1$H NMR (400 MHz, CDCl$_3$) ppm 0.78-1.00 (m, 2H), 1.34-1.49 (m, 2H), 3.79-3.95 (m, 2H), 5.62-5.98 (m, 3H), 6.67-6.94 (m, 7H), 6.98-7.20 (m, 5H), 7.37-7.66 (m, 15H).

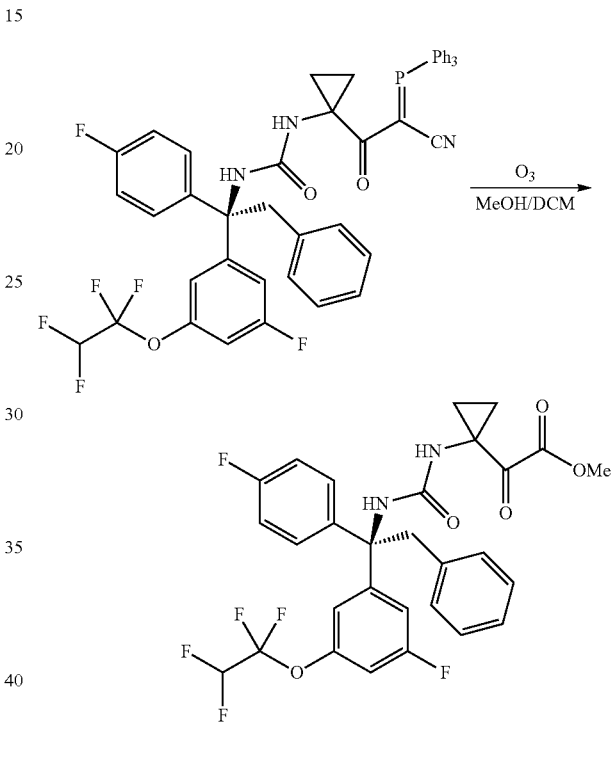

A solution of (R)-1-(1-(2-cyano-2-(phenylphosphinylidene)acetyl)cyclopropyl)-3-(1-(3-fluoro-5-(1,1,2,2-tetrafluoroethoxy)phenyl)-1-(4-fluorophenyl)-2-phenylethyl)urea with biphenyl (1:1) (53 mg, 0.063 mmol) in DCM/MeOH (0.7 mL/0.3 mL) was cooled to −78° C. O$_3$ was bubbled into the solution until the solution became light blue. The reaction mixture was warmed to room temperature and concentrated under reduced pressure. The resulting residue was purified by ISCO chromatography (4 g column) using hexane/EtOAc (0-100%) to give (R)-methyl 2-(1-(3-(1-(3-fluoro-5-(1,1,2,2-tetrafluoroethoxy)phenyl)-1-(4-fluorophenyl)-2-phenylethyl)ureido)cyclopropyl)-2-oxoacetate (Example 243) as a white solid (33 mg, 86% yield). LCMS: RT=2.99 min [M+H] 595.3 (Phenomenex Luna C18 column, 4.6×50 mm eluting with 50-100% MeOH/H$_2$O over 4 minutes containing 0.1% TFA; 4 mL/min, monitoring at 220 nm); $^1$H NMR (400 MHz, CDCl$_3$) ppm 0.81-0.95 (m, 2H), 1.04-1.18 (m, 2H), 3.63-3.88 (m, 5H), 5.48 (s, 2H), 5.86 (t, J=53 Hz, 1H), 6.60-6.69 (m, 2H), 6.80-7.02 (m, 5H), 7.05-7.24 (m, 5H).

Example 244

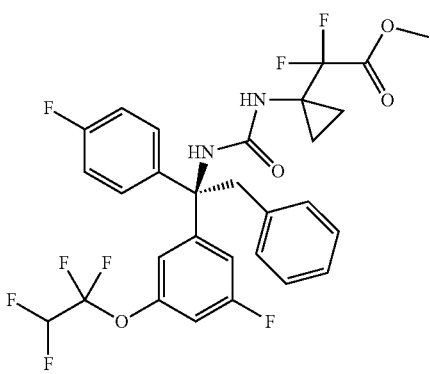 [SMILES: COC(=O)C(F)(F)C1(NC(=O)N[C@](Cc2ccccc2)(c2ccc(F)cc2)c2cc(F)cc(OC(F)(F)C(F)F)c2)CC1]

(R)-methyl 2,2-difluoro-2-(1-(3-(1-(3-fluoro-5-(1,1,2,2-tetrafluoroethoxy)phenyl)-1-(4-fluorophenyl)-2-phenylethyl)ureido)cyclopropyl)acetate

Procedure 35

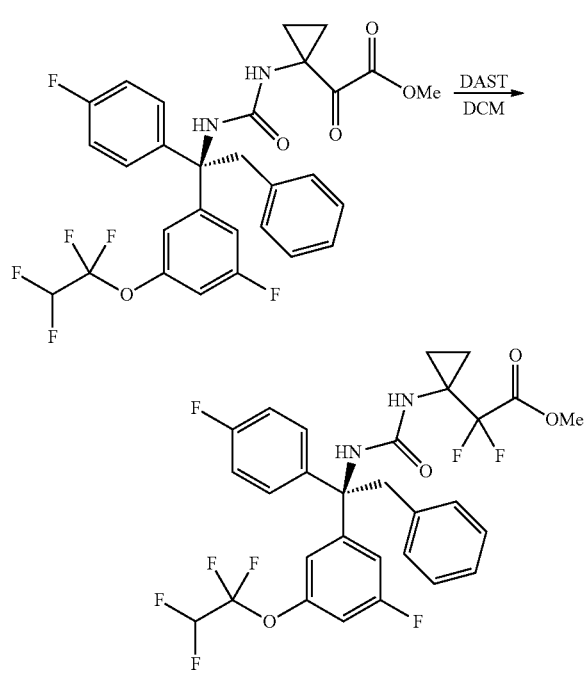

To a solution of (R)-methyl 2-(1-(3-(1-(3-fluoro-5-(1,1,2,2-tetrafluoroethoxy)phenyl)-1-(4-fluorophenyl)-2-phenylethyl)ureido)cyclopropyl)-2-oxoacetate (Example 243, 24 mg, 0.040 mmol) in DCM (0.5 mL) at 0° C. was added DAST (40 mg, 0.24 mmol). The reaction mixture was allowed to warm to room temperature and stirred for 1 h. The reaction mixture was quenched by addition of sat. NaHCO₃ (0.5 mL), concentrated under reduced pressure and purified by preparative HPLC (Phenomenex Axia column, 30×100 mm, flow rate 40 mL/min, 30-100% CH₃CN/H₂O/0.1% TFA over 13 min) to yield (R)-methyl 2,2-difluoro-2-(1-(3-(1-(3-fluoro-5-(1,1,2,2-tetrafluoroethoxy)phenyl)-1-(4-fluorophenyl)-2-phenylethyl)ureido)cyclopropyl)acetate (Example 244) as a white solid (3 mg, 12% yield). LCMS: RT=2.12 min [M+H] 617.5 (Phenomenex Luna C18 column, 4.6×30 mm eluting with 10-90% MeOH/H₂O over 2 minutes containing 0.1% TFA; 5 mL/min, monitoring at 220 nm); $^1$H NMR (400 MHz, CDCl₃) ppm 0.81-0.98 (m, 2H), 1.21-1.35 (m, 2H), 3.62-3.94 (m, 5H), 4.96 (s, 1H), 5.57-6.08 (m, 2H), 6.61-6.72 (m, 2H), 6.84-7.25 (m, 21H).

Example 245

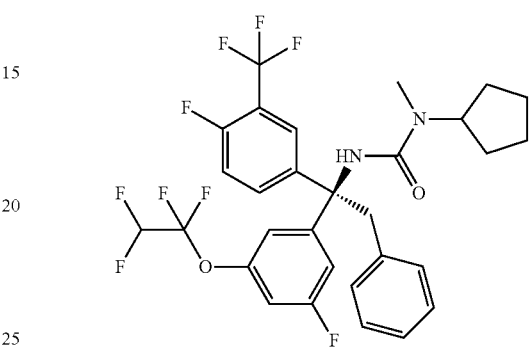

(R)-1-cyclopentyl-3-(1-(4-fluoro-3-(trifluoromethyl)phenyl)-1-(3-fluoro-5-(1,1,2,2-tetrafluoroethoxy)phenyl)-2-phenylethyl)-1-methylurea

Procedure 36

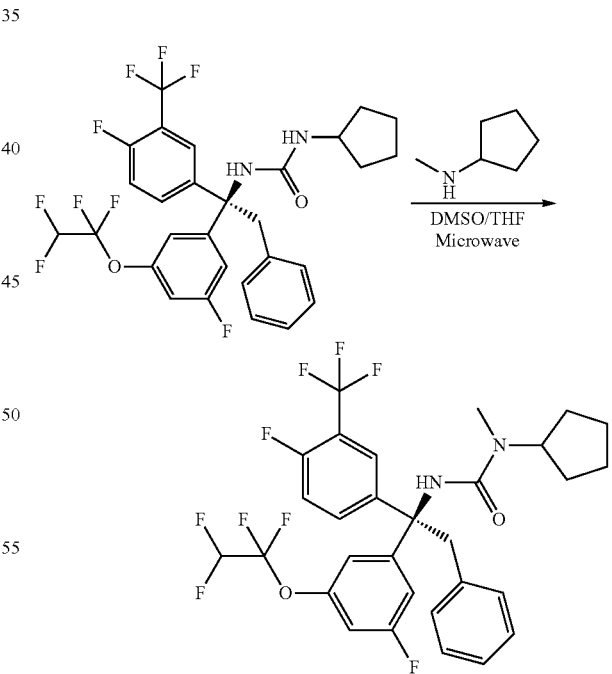

To a solution of (R)-1-cyclopentyl-3-(1-(4-fluoro-3-(trifluoromethyl)phenyl)-1-(3-fluoro-5-(1,1,2,2-tetrafluoroethoxy)phenyl)-2-phenylethyl)urea (20 mg, 0.033 mmol), prepared as described in Procedure 3, 4, 5, 6 and 2, in DMSO/THF (0.1 mL/0.1 mL) was added N-methylcyclopentanamine (32 mg, 0.33 mmol). The resulting solution was stirred at 120° C. under microwave irradiation for 1800 sec. The reaction mixture was filtered and the solid was washed with EtOAc. The filtrate was then washed with H₂O, sat. NaCl and dried over Na₂SO₄. The organic solvent was evaporated under reduced pressure and the resulting residue was purified by prep HPLC (Phenomenex AXIA Luna 75×30 mm, 5µ column eluting with 10-90% ACN/H₂O over 10 minutes containing 0.1% TFA; 40 mL/min, monitoring at 220 nm) to afford (R)-1-cyclopentyl-3-(1-(4-fluoro-3-(trifluoromethyl)phenyl)-1-(3-fluoro-5-(1,1,2,2-tetrafluoroethoxy)phenyl)-2-phenylethyl)-1-methylurea (Example 246) as white lyophillate (13 mg, 65% yield). LCMS: [M+H] 619.2 (Phenomenex Luna C18 column, 4.6×50 mm eluting with 10-90% MeOH/H₂O over 4 minutes containing 0.1% TFA; 4 mL/min, monitoring at 220 nm).

Example 246 rinsed with EtOH. The filtrate was concentrated to yield (1R, 2R)-2-aminocyclopentanol TFA salt (4.3 g, 100% yield) as a yellow oil. ¹H NMR (400 MHz, DMSO-D6) ppm 1.00-1.13 (m, 1H), 1.39-1.57 (m, 2H), 1.56-1.76 (m, 2H), 1.79-1.94 (m, 1H), 1.94-2.10 (m, 1H), 3.06-3.23 (m, 1H), 3.88-4.02 (m, 1H), 7.84-8.07 (m, 2H).

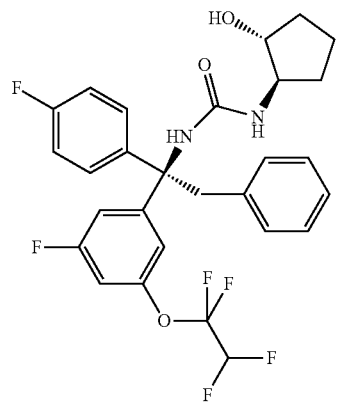 [SMILES: O=C(N[C@@H]1CCC[C@H]1O)N[C@](Cc1ccccc1)(c1ccc(F)cc1)c1cc(F)cc(OC(F)(F)C(F)F)c1]

1-((R)-1-(3-fluoro-5-(1,1,2,2-tetrafluoroethoxy)phenyl)-1-(4-fluorophenyl)-2-phenylethyl)-3-((1R,2R)-2-hydroxycyclopentyl)urea Procedure 37

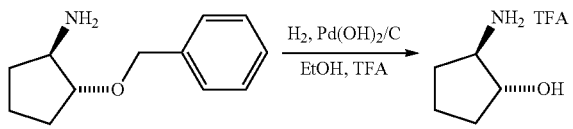 [SMILES: N[C@@H]1CCC[C@H]1OCc1ccccc1 ; N[C@@H]1CCC[C@H]1O]

To a solution of (1R,2R)-2-(benzyloxy)cyclopentanamine (3.5 g, 18.3 mmol) in EtOH (20 mL) was added TFA (1.6 mL, 21.5 mmol), followed by Pd(OH)₂/C (20% wt, 627 mg). The reaction mixture was degassed with Ar and stirred at rt under H₂ atmosphere for 3 days. The resulting solid was filtered and

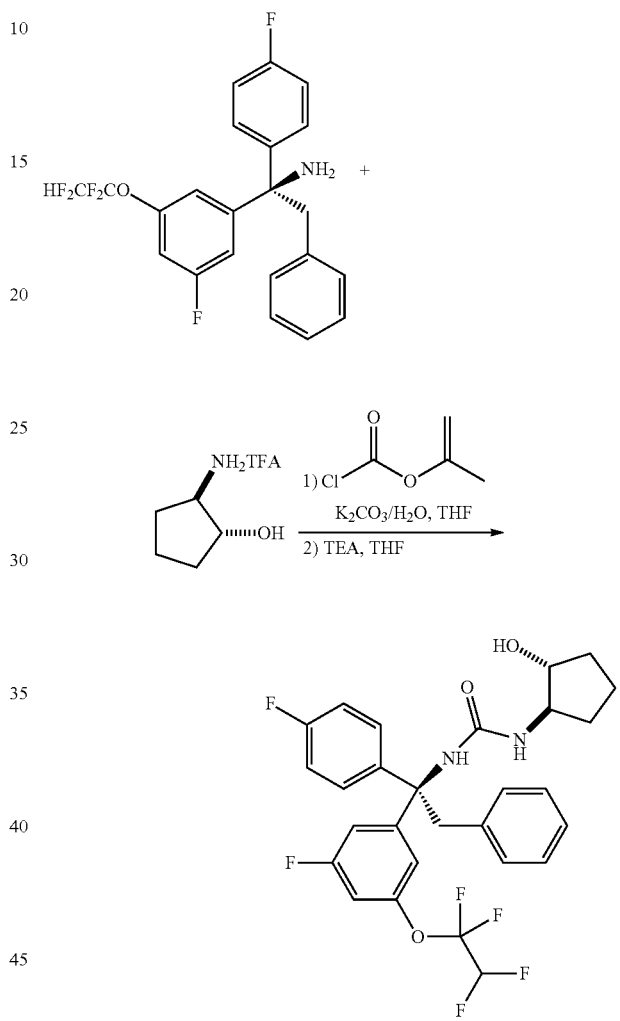

1-((R)-1-(3-fluoro-5-(1,1,2,2-tetrafluoroethoxy)phenyl)-1-(4-fluorophenyl)-2-phenylethyl)-3-((1R,2R)-2-hydroxycyclopentyl)urea (Example 246) was prepared as described in Procedure 25. HPLC: RT=3.94 min [M+H] 553.08 (Phenomenex Luna C18 column, 4.6×50 mm eluting with 10-90% MeOH/H₂O over 4 minutes containing 0.1% TFA; 4 mL/min, monitoring at 220 nm); ¹H NMR (400 MHz, CDCl₃) δ ppm 1.07-1.35 (m, 1H), 1.43-1.78 (m, 3H), 1.80-1.98 (m, 2H), 3.42-3.60 (m, 1H), 3.61-3.73 (m, 1H), 3.74-3.83 (m, 1H), 3.83-3.96 (m, 1H), 4.52-4.92 (m, 1H), 5.66-6.03 (m, 2H), 6.64-6.77 (m, 2H), 6.80-6.89 (m, 1H), 6.89-7.04 (m, 4H), 7.04-7.22 (m, 4H).

Example 247

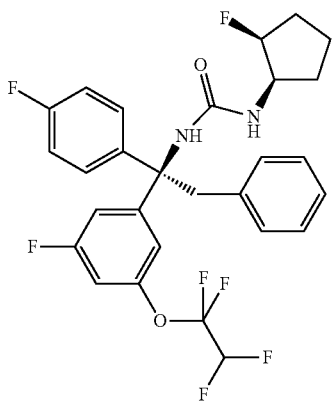 [SMILES: O=C(N[C@@H]1CCC[C@@H]1F)N[C@](Cc1ccccc1)(c1ccc(F)cc1)c1cc(F)cc(OC(F)(F)C(F)F)c1]

1-((R)-1-(3-fluoro-5-(1,1,2,2-tetrafluoroethoxy)phenyl)-1-(4-fluorophenyl)-2-phenylethyl)-3-((1R,2S)-2-fluorocyclopentyl)urea

Procedure 38

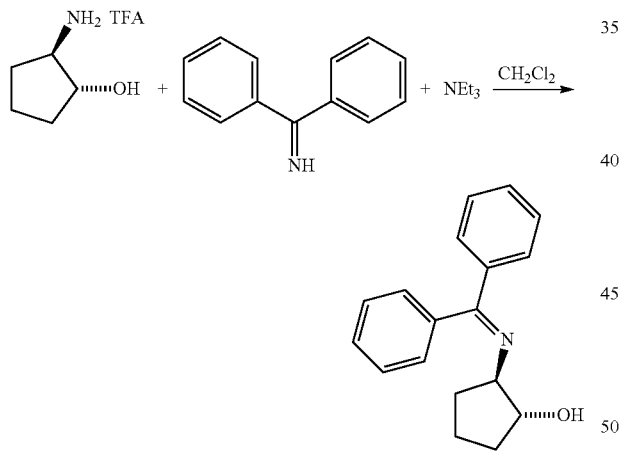

To a solution of (1R,2R)-2-aminocyclopentanol TFA salt (630 mg, 2.93 mmol) was added diphenylmethanimine (490 uL, 2.93 mmol) and TEA (0.5 mL, 3.58 mmol) in CH₂Cl₂ (3 mL). The reaction mixture was stirred at rt for 2 h and concentrated under reduced pressure and purified by ISCO flash chromatography using EtOAc and hexane as eluting solvent to yield (1R,2R)-2-(diphenylmethyleneamino)cyclopentanol (697 mg, 90% yield) as a colorless gum. HPLC: RT=1.96 min [M+H] 266.13 (Phenomenex Luna C18 column, 4.6×50 mm eluting with 10-90% MeOH/H₂O over 4 minutes containing 0.1% TFA; 4 mL/min, monitoring at 220 nm); ¹H NMR (400 MHz, CDCl₃) δ ppm 1.49-1.64 (m, 2H), 1.66-1.91 (m, 3H), 2.08-2.24 (m, 1H), 3.55-3.71 (m, 1H), 4.31-4.47 (m, 1H), 7.15-7.25 (m, 2H), 7.29-7.53 (m, 6H), 7.61-7.67 (m, 2H).

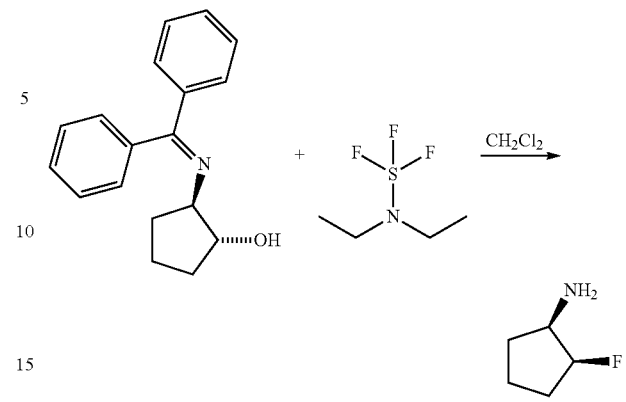

To a solution of (1R,2R)-2-(diphenylmethyleneamino)cyclopentanol (112 mg, 0.42 mmol) in CH₂Cl₂ (1 mL) at −20° C. was added dropwise DAST (67 uL, 0.5 mmol). The reaction mixture was allowed to warm up rt and stirred for 16 h. The solution was concentrated under reduced pressure to yield crude (1R,2R)-2-fluorocyclopentanamine (120 mg) which was used to next step without further purification.

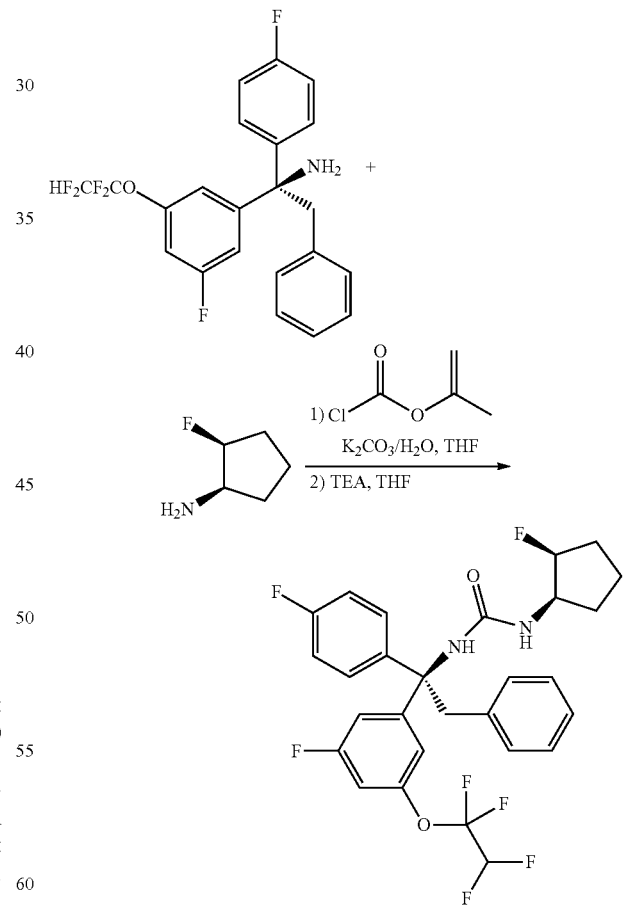

1-((R)-1-(3-fluoro-5-(1,1,2,2-tetrafluoroethoxy)phenyl)-1-(4-fluorophenyl)-2-phenylethyl)-3-((1R,2S)-2-fluorocyclopentyl)urea (Example 247) was prepared as described in Procedure 25. LCMS: RT=4.07 min [M+H] 555.20 (Phenomenex Luna C18 column, 4.6×50 mm eluting with 10-90%

MeOH/H$_2$O over 4 minutes containing 0.1% TFA; 4 mL/min, monitoring at 220 nm); $^1$H NMR (400 MHz, CD$_3$CN) δ ppm 1.02-1.12 (m, 6H), 3.15-3.33 (m, 2H), 3.89 (dd, 2H), 5.10-5.24 (m, 1H), 6.22 (t, 1H), 6.71-6.82 (m, 2H), 6.93-7.00 (m, 1H), 7.01-7.33 (m, 9H).

Example 248

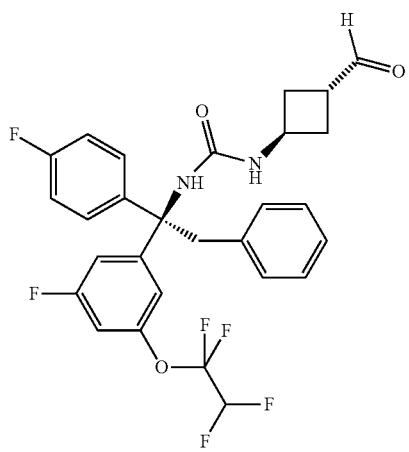

1-((R)-1-(3-fluoro-5-(1,1,2,2-tetrafluoroethoxy)phenyl)-1-(4-fluorophenyl)-2-phenylethyl)-3-((1r,3R)-3-formylcyclobutyl)urea Procedure 39

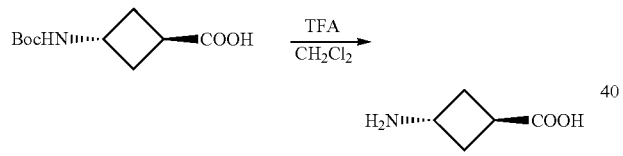

To a suspension of (1r,3r)-3-(tert-butoxycarbonylamino)cyclobutanecarboxylic acid (217 mg, 1 mmol) in CH$_2$Cl$_2$ (5 ml) at ambient temperature was added TFA (0.37 mL, 2.7 mmol) in one portion, and the reaction mixture was stirred at ambient temperature for 16 h, then concentrated to yield (1r,3r)-3-aminocyclobutanecarboxylic acid (227 mg, 100% yield) as a colorless oil. $^1$H NMR (500 MHz, DMSO-D6) δ ppm 2.21-2.34 (m, 2H), 2.35-2.46 (m, 2H), 3.01-3.17 (m, 1H), 3.65-3.85 (m, 1H), 7.90-8.13 (m, 3H).

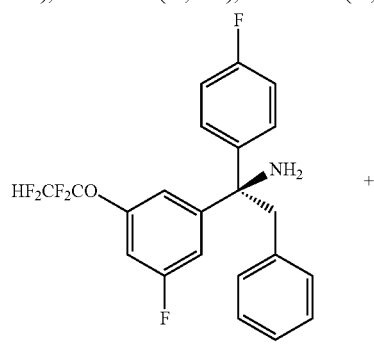

+

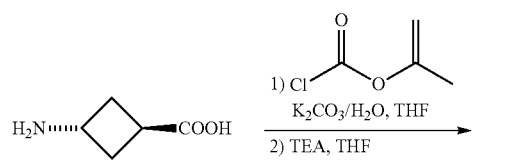

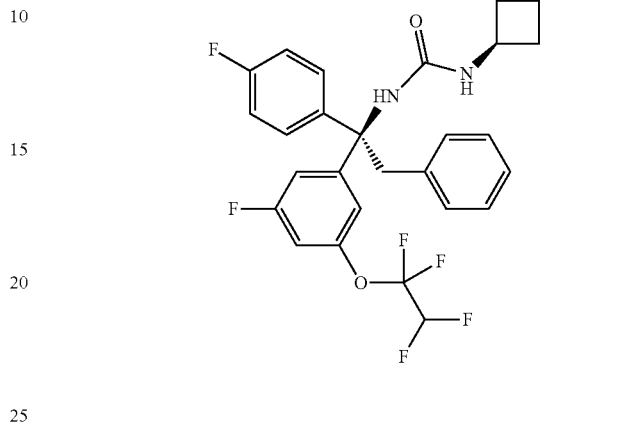

Using the method described in Procedure 25, (1R,3r)-3-(3-((R)-1-(3-fluoro-5-(1,1,2,2-tetrafluoroethoxy)phenyl)-1-(4-fluorophenyl)-2-phenylethyl)ureido)cyclobutanecarboxylic acid was prepared as a white solid (372 mg, 66% yield). HPLC: RT=3.90 min [M+H] 567.69 (Phenomenex Luna C18 column, 4.6×50 mm eluting with 10-90% MeOH/H$_2$O over 4 minutes containing 0.1% TFA; 4 mL/min, monitoring at 220 nm).

Procedure 40

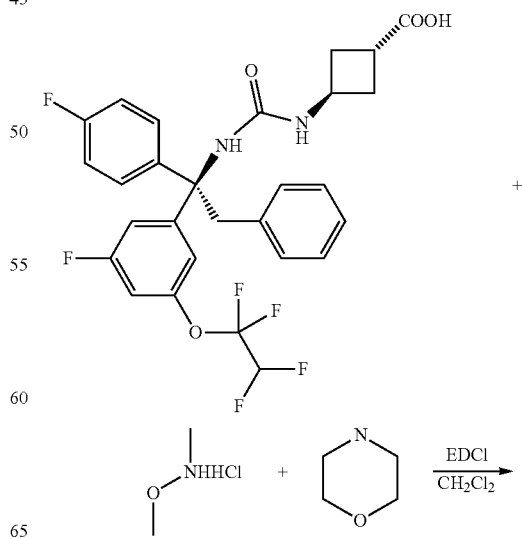

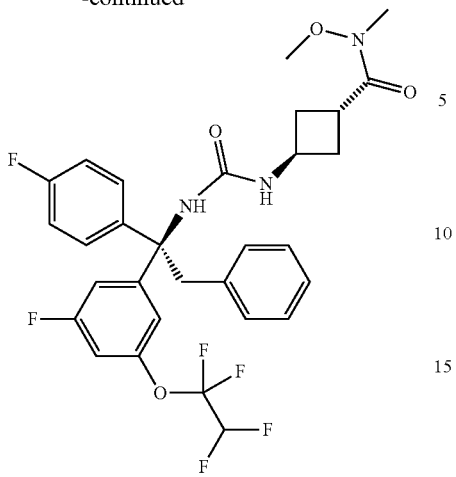

To a solution of (1R,3r)-3-(3-((R)-1-(3-fluoro-5-(1,1,2,2-tetrafluoroethoxy)phenyl)-1-(4-fluorophenyl)-2-phenyl-ethyl)ureido)cyclobutanecarboxylic acid (180 mg, 0.32 mmol) in CH$_2$Cl$_2$ (5 mL) was added N,O-dimethylhydroxyamine HCl (31 mg, 0.32 mmol) and N-methylmorpholine (32 mg, 0.37 mmol). The reaction mixture was cooled to −10° C. under Ar. After 5 min, EDCI (61 mg, 0.39 mmol) was added and the reaction mixture was allowed to reach rt and stirred for 15 min. The reaction mixture was concentrated and purified by ISCO flash chromatography to yield (1R,3r)-3-(3-((R)-1-(3-fluoro-5-(1,1,2,2-tetrafluoroethoxy)phenyl)-1-(4-fluorophenyl)-2-phenylethyl)ureido)-N-methoxy-N-methylcyclobutanecarboxamide as a white solid (194 mg, 100% yield). HPLC: RT=3.94 min [M+H] 610.72 (Phenomenex Luna C18 column, 4.6×50 mm eluting with 10-90% MeOH/H$_2$O over 4 minutes containing 0.1% TFA; 4 mL/min, monitoring at 220 nm); $^1$H NMR (400 MHz, DMSO) ppm 2.55-2.63 (m, 2H), 2.94-3.10 (m, 2H), 3.61-3.71 (m, 3H), 3.84-4.02 (m, 1H), 4.13-4.21 (m, 3H), 4.41 (dd, 2H), 4.58-4.75 (m, 1H), 5.92-6.05 (m, 2H), 6.75 (t, 1H), 7.24-7.33 (m, 2H), 7.43-7.52 (m, 2H), 7.54-7.64 (m, 3H), 7.64-7.83 (m, 5H).

Procedure 41

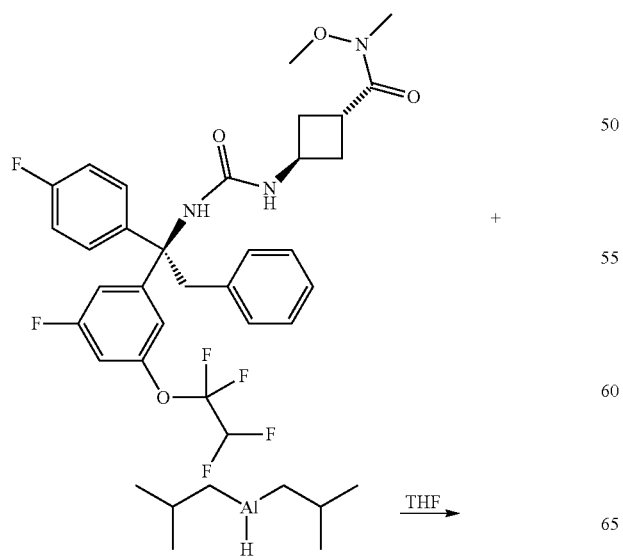

To a solution of (1R,3r)-3-(3-((R)-1-(3-fluoro-5-(1,1,2,2-tetrafluoroethoxy)phenyl)-1-(4-fluorophenyl)-2-phenyl-ethyl)ureido)-N-methoxy-N-methylcyclobutanecarboxamide (182 mg, 0.3 mmol) in THF (2 mL) at −78° C. under Ar was added dropwise DIBAL-H (1.0 M in hexane, 0.75 mL). The reaction mixture was stirred at −78° C. for 20 min. Acetone (1 mL) was added, followed by saturated aqueous potassium sodium tartrate (5 mL) and ether (2 mL). The resulting reaction mixture was stirred at rt for 16 h. The aqueous layer was extracted with ether (2×10 mL). The combined organic layers were dried over MgSO$_4$, filtered and concentrated under reduced pressure. The resulting residue was purified by ISCO flash chromatography using EtOAc and hexane as eluting solvent to yield 1-((R)-1-(3-fluoro-5-(1,1,2,2-tetrafluoroethoxy)phenyl)-1-(4-fluorophenyl)-2-phenyl-ethyl)-3-((1r,3R)-formylcyclobutyl)urea (Example 248) as a white solid (122 mg, 74% yield). HPLC: RT=3.89 min [M+H] 551.10 (Phenomenex Luna C18 column, 4.6×50 mm eluting with 10-90% MeOH/H$_2$O over 4 minutes containing 0.1% TFA; 4 mL/min, monitoring at 220 nm); $^1$H NMR (400 MHz, CDCl$_3$) δ ppm 1.73-1.88 (m, 2H), 2.35-2.49 (m, 2H), 2.80-2.94 (m, 1H), 3.64 (dd, 2H), 3.81-3.98 (m, 1H), 4.95 (d, 1H), 5.20-5.29 (m, 1H), 5.79 (t, 1H), 6.56 (d, 2H), 6.71-6.92 (m, 4H), 6.92-7.16 (m, 5H), 9.58-9.70 (m, 1H).

Example 249

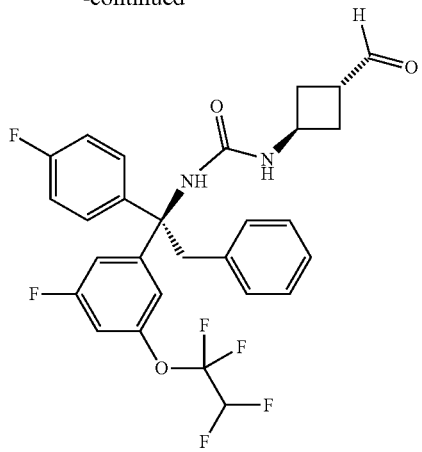

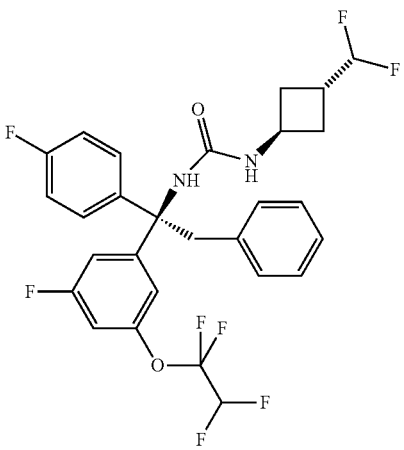 [SMILES: O=C[C@H]1C[C@H](NC(=O)N[C@](Cc2ccccc2)(c2ccc(F)cc2)c2cc(F)cc(OC(F)(F)C(F)F)c2)C1]

391

1-((1r,3R)-3-(difluoromethyl)cyclobutyl)-3-((R)-1-(3-fluoro-5-(1,1,2,2-tetrafluoroethoxy)phenyl)-1-(4-fluorophenyl)-2-phenylethyl)urea Procedure 42

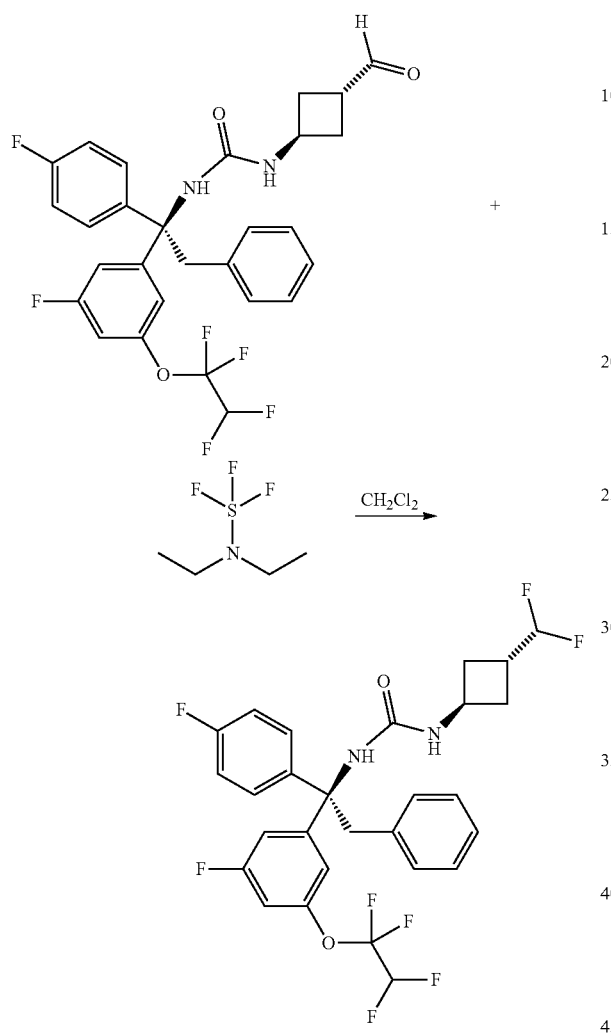

To a solution of 1-((R)-1-(3-fluoro-5-(1,1,2,2-tetrafluoroethoxy)phenyl)-1-(4-fluorophenyl)-2-phenylethyl)-3-((1r,3R)-formylcyclobutyl)urea (Example 248, 43 mg, 0.078 mmol) in CH$_2$Cl$_2$ (0.5 ml) at rt was added DAST (30 uL, 0.23 mmol) dropwise. The reaction mixture was stirred at rt for 16 h, concentrated under reduced pressure and purified by prep HPLC (phenomenex AXIA Luna 75×30 mm, 5µ column eluting with 10-90% ACN/H$_2$O over 10 minutes containing 0.1% TFA; 40 mL/min, monitoring at 220 nm). The product was further purified by ISCO flash chromatography to yield 1-((1r,3R)-3-(difluoromethyl)cyclobutyl)-3-((R)-1-(3-fluoro-5-(1,1,2,2-tetrafluoroethoxy)phenyl)-1-(4-fluorophenyl)-2-phenylethyl)urea (Example 249) as a white solid (18 mg, 40% yield). HPLC: RT=4.03 min [M+H] 573.69 (Phenomenex Luna C18 column, 4.6×50 mm eluting with 10-90% MeOH/H$_2$O over 4 minutes containing 0.1% TFA; 4 mL/min, monitoring at 220 nm); $^1$H NMR (500 MHz, CD$_3$CN) δ ppm 1.98-2.08 (m, 2H), 2.24-2.39 (m, 2H), 2.46-2.65 (m, 1H), 3.85 (dd, 2H), 4.08-4.22 (m, 1H), 5.45-5.56 (m, 1H), 5.96 (t, 1H), 6.19 (t, 1H), 6.65-6.78 (m, 2H), 6.88-6.97 (m, 2H).

392

Example 250

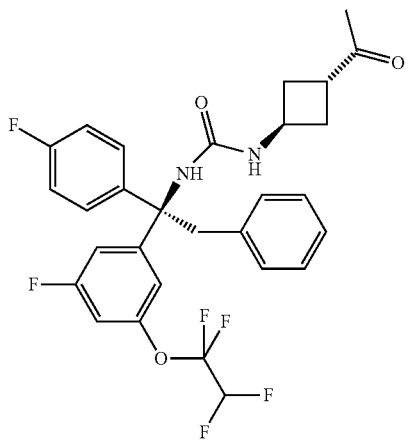 [SMILES: CC(=O)[C@H]1C[C@H](NC(=O)N[C@](Cc2ccccc2)(c2ccc(F)cc2)c2cc(F)cc(OC(F)(F)C(F)F)c2)C1]

1-((1r,3R)-3-acetylcyclobutyl)-3-((R)-1-(3-fluoro-5-(1,1,2,2-tetrafluoroethoxy)phenyl)-1-(4-fluorophenyl)-2-phenylethyl)urea Procedure 43

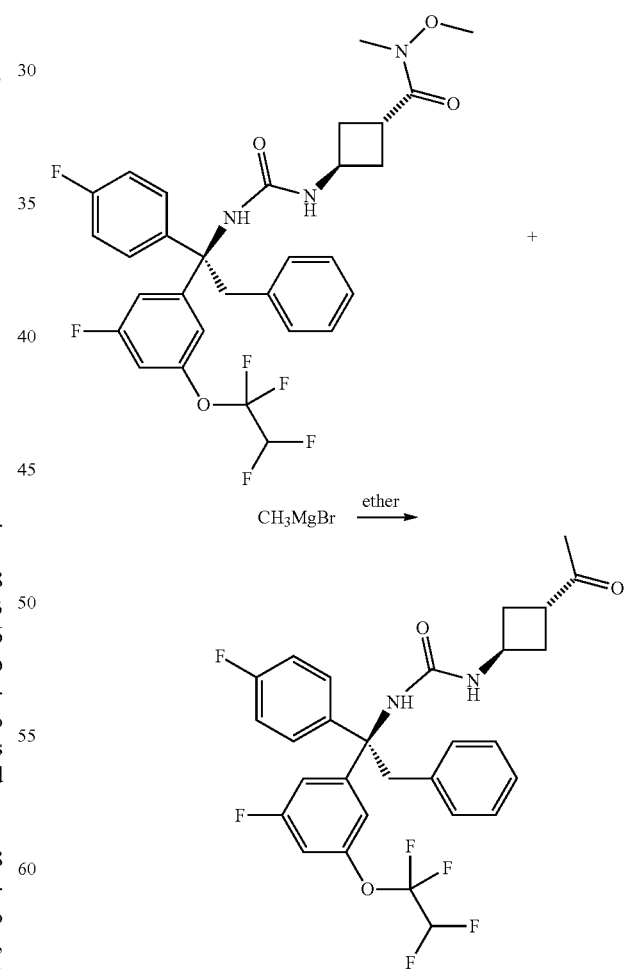

To a solution of (1R,3r)-3-(3-((R)-1-(3-fluoro-5-(1,1,2,2-tetrafluoroethoxy)phenyl)-1-(4-fluorophenyl)-2-phenylethyl)ureido)-N-methoxy-N-methylcyclobutanecarboxamide, prepared as described in Procedure 40, (160 mg, 0.26 mmol) in ether (5 mL) at −40° C., was added dropwise CH₃MgBr (3 M in ether, 0.2 mL). Then the reaction mixture was stirred at 0° C. for 4 h. The reaction was quenched with sat. NaCl and the aqueous layer was extracted with ether. The combined organic layers were dried over MgSO₄, filtered and concentrated under reduced pressure. The resulting oil was purified by ISCO flash chromatography using EtOAc and hexane as eluting solvent to yield 1-((1r,3R)-3-acetylcyclobutyl)-3-((R)-1-(3-fluoro-5-(1,1,2,2-tetrafluoroethoxy) phenyl)-1-(4-fluorophenyl)-2-phenylethyl)urea (Example 250) as a white solid (32 mg, 22% yield). HPLC: RT=3.90 min [M+H]565.3 (Phenomenex Luna C18 column, 4.6×50 mm eluting with 10-90% MeOH/H₂O over 4 minutes containing 0.1% TFA; 4 mL/min, monitoring at 220 nm); ¹H NMR (400 MHz, CD₃CN) δ ppm 2.03-2.09 (m, 2H), 2.08-2.12 (m, 3H), 2.41-2.54 (m, 2H), 3.10-3.23 (m, 1H), 3.88 (dd, 2H), 3.98-4.07 (m, 1H), 5.41-5.51 (m, 2H), 6.21 (t, 1H), 6.73-6.80 (m, 2H), 6.93-7.00 (m, 2H), 7.02-7.10 (m, 3H), 7.12-7.30 (m, 6H).

Example 251

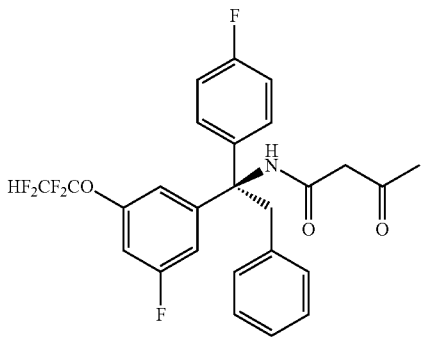

(R)—N-(1-(3-fluoro-5-(1,1,2,2-tetrafluoroethoxy) phenyl)-1-(4-fluorophenyl)-2-phenylethyl)-3-oxobutanamide Procedure 44

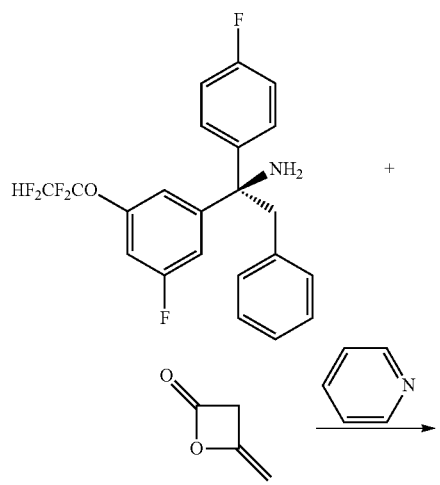

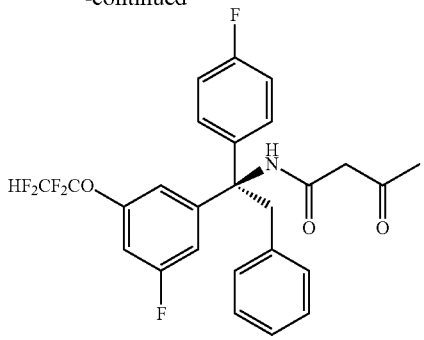

To a solution of (R)-1-(3-fluoro-5-(1,1,2,2-tetrafluoroethoxy)phenyl)-1-(4-fluorophenyl)-2-phenylethanamine (28 mg, 0.07 mmol), prepared as described in Procedure 3, 4, 5 and 6, in DCM (1 mL) was added pyridine (0.01 mL, 0.12 mmol). The reaction was cooled to 0° C., followed by the addition of 4-methyleneoxetan-2-one (0.01 mL, 0.13 mmol). The reaction mixture was stirred at rt for 2 h and concentrated. The residue was purified by preparative HPLC (Axia luna column, 30×75 mm, 40-100% ACN/H₂O with 0.1% TFA over 10 min, flow rate 40 mL/min, monitoring at 220 nm) to yield (R)—N-(1-(3-fluoro-5-(1,1,2,2-tetrafluoroethoxy)phenyl)-1-(4-fluorophenyl)-2-phenylethyl)-3-oxobutanamide (Example 251) as colorless oil (23 mg, 58% yield). LCMS: RT=3.71 min [M+H]510.2 (Phenomenex Luna C18 column, 4.6×50 mm eluting with 10-90% MeOH/H₂O over 4 minutes containing 0.1% TFA; 4 mL/min, monitoring at 220 nm). ¹H NMR (400 MHz, CDCl₃) δ ppm 8.23 (1H, s), 7.04-7.20 (5H, m), 6.96-7.02 (2H, m), 6.87-6.92 (3H, m), 6.61 (2H, d, J=7.07 Hz), 5.87 (1H, t, J=2.78 Hz), 3.94 (1H, d, J=12.88 Hz), 3.71 (1H, d, J=12.88 Hz), 3.43 (2H, s), 2.24 (3H, s).

Example 252

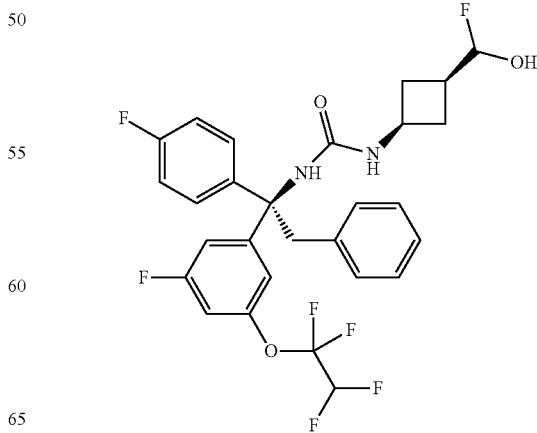

395

1-((1R,3S)-3-((S)-fluoro(hydroxy)methyl)cyclobutyl)-3-((R)-1-(3-fluoro-5-(1,1,2,2-tetrafluoroethoxy)phenyl)-1-(4-fluorophenyl)-2-phenylethyl)urea Procedure 45

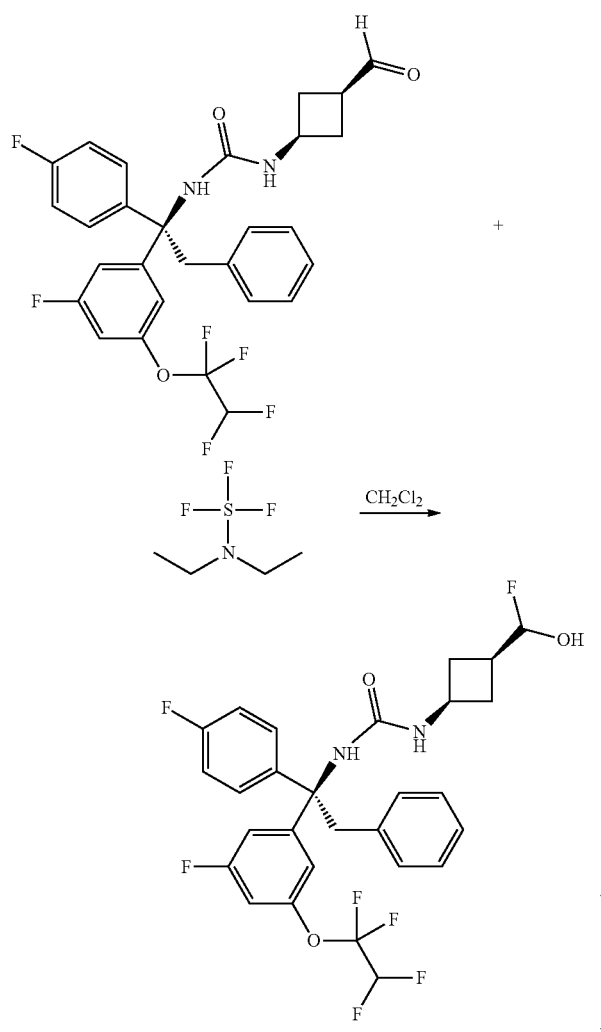

To a solution of 1-((R)-1-(3-fluoro-5-(1,1,2,2-tetrafluoroethoxy)phenyl)-1-(4-fluorophenyl)-2-phenylethyl)-3-((1s,3S)-3-formylcyclobutyl)urea (Example 248, 35 mg, 0.064 mmol) in CH$_2$Cl$_2$ (0.5 ml) was added DAST (50 uL, 0.37 mmol). The reaction mixture was stirred at rt for 3 days, then concentrated and purified by prep HPLC to yield 1-((1R,3S)-3-((S)-fluoro(hydroxy)methyl)cyclobutyl)-3-((R)-1-(3-fluoro-5-(1,1,2,2-tetrafluoroethoxy)phenyl)-1-(4-fluorophenyl)-2-phenylethyl)urea (Example 252) as a light yellow solid (20 mg, 56% yield). LCMS: RT=1.79 min [M+H] 553.2 (Phenomenex Luna C18 column, 4.6×30 mm eluting with 10-90% MeOH/H$_2$O over 2 minutes containing 0.1% TFA; 5 mL/min, monitoring at 220 nm); $^1$H NMR (400 MHz, CDCl$_3$) δ ppm 1.59-1.79 (m, 1H), 1.95-2.15 (m, 1H), 2.52-2.77 (m, 2H), 2.90-3.07 (m, 1H), 3.65-3.76 (m, 2H), 3.99-4.16 (m, 1H), 4.60-5.11 (m, 1H), 5.56-6.07 (m, 2H), 6.57-6.67 (m, 2H), 6.78-7.32 (m, 12H), 10.13-10.41 (m, 1H).

Example 253

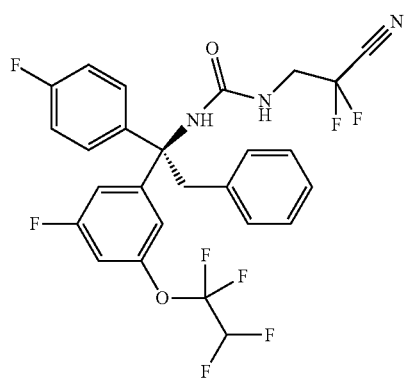 [SMILES: N#CC(F)(F)CNC(=O)N[C@](Cc1ccccc1)(c1ccc(F)cc1)c1cc(F)cc(OC(F)(F)C(F)F)c1]

(R)-1-(2-cyano-2,2-difluoroethyl)-3-(1-(3-fluoro-5-(1,1,2,2-tetrafluoroethoxy)phenyl)-1-(4-fluorophenyl)-2-phenylethyl)urea Procedure 46

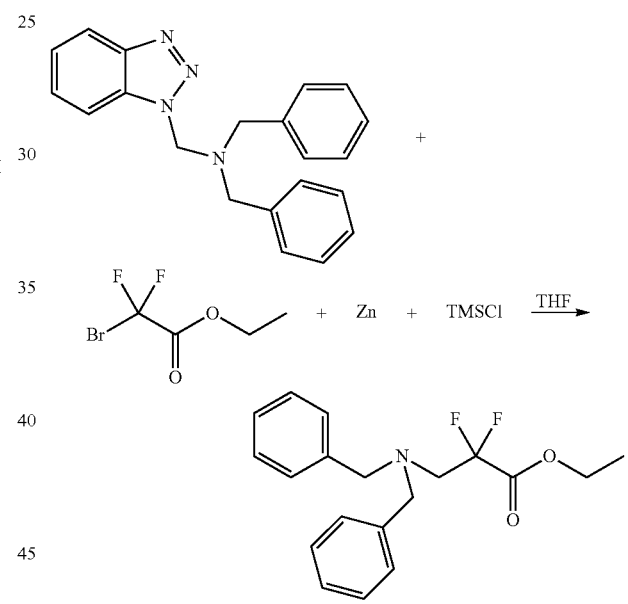

To a suspension of zinec dust (238 mg, 3.66 mmol) in THF (3 ml) under Ar was added TMSCl (234 uL, 1.83 mmol). The reaction mixture was stirred at rt for min followed by addition of ethyl bromodifluoroacetate (260 uL, 2.0 mmol) dropwise. After 10 min, N-((1H-benzo[d][1,2,3]triazol-1-yl)methyl)-N-benzyl-1-phenylmethanaime (600 mg, 1.83 mmol) in THF (3 ml) was added and the reaction mixture was stirred at room temperature for 1 h. The reaction mixture was quenched with 5% NaHCO$_3$ in H$_2$O (10 mL). The resulting solid was filtered and washed with EtOAc. The filtrate was extracted with EtOAc and the combined EtOAc layers were dried over MgSO$_4$, filtered and concentrated under reduced pressure. The resulting residue was purified by ISCO flash chromatography by using EtOAc and hexane as eluting solvent to yield ethyl 3-(dibenzylamino)-2,2-difluoropropanoate as a colorless oil (577 mg, 56% yield). LCMS: RT=4.09 min [M+H] 334.28 (Phenomenex Luna C18 column, 4.6×50 mm eluting with 10-90% MeOH/H$_2$O over 4 minutes containing 0.1% TFA; 4 mL/min, monitoring at 220 nm).

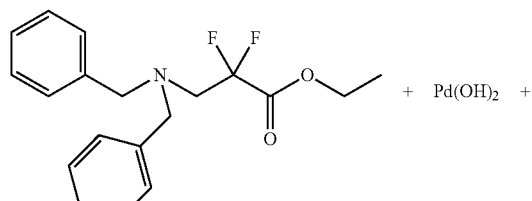

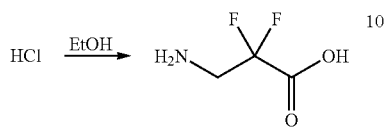

To a solution of ethyl 3-(dibenzylamino)-2,2-difluoropropanoate (517 mg, 1.55 mmol) in EtOH (1 mL) was added 0.5 N HCl (1 mL) and Pd(OH)$_2$/C (20%, 50 mg). The reaction mixture was stirred at room temperature under H$_2$ atmosphere for 3 days. The reaction mixture was filtered and the solid was rinsed with water and ether. The aqueous layer was separated from the ether layer and lyophilized to yield ethyl 3-amino-2,2-difluoropropanoic acid as a white solid (210 mg, 100% yield). $^1$H NMR (400 MHz, DMSO) ppm 3.27-3.46 (m, 2H), 8.06-8.64 (m, 3H).

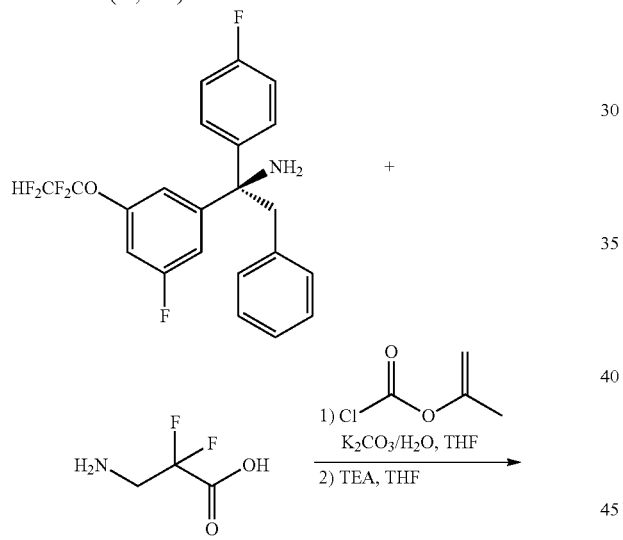

Using the method described in Procedure 25, (R)-2,2-difluoro-3-(3-(1-(3-fluoro-5-(1,1,2,2-tetrafluoroethoxy)phenyl)-1-(4-fluorophenyl)-2-phenylethyl)ureido)propanoic acid (60 mg, 0.1 mmol) was prepared as a white solid (62 mg, 54% yield). LCMS: RT=1.97 min [M+H] 577.2 (Phenomenex Luna C18 column, 4.6×30 mm eluting with 10-90% MeOH/H$_2$O over 2 minutes containing 0.1% TFA; 5 mL/min, monitoring at 220 nm).

Procedure 47

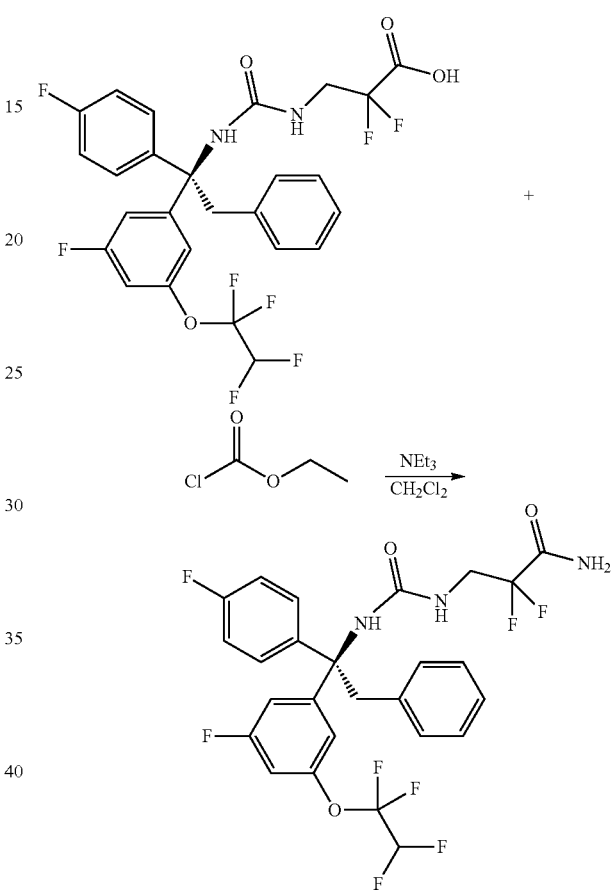

To a solution of (R)-2,2-difluoro-3-(3-(1-(3-fluoro-5-(1,1,2,2-tetrafluoroethoxy)phenyl)-1-(4-fluorophenyl)-2-phenylethyl)ureido)propanoic acid (60 mg, 0.1 mmol) in CH$_2$Cl$_2$ (1 mL) at 0° C. was added ethyl carbonochloridate (10 uL, 0.1 mmol), followed by NEt$_3$ (0.021 mL, 0.15 mmol) and NH$_3$*H$_2$O (0.1 mL, 2.6 mmol). The reaction mixture was stirred at rt for 30 min, then concentrated under reduced pressure and purified by prep HPLC (Phenomenex AXIA Luna 75×30 mm, 5µ column eluting with 10-90% ACN/H$_2$O over 10 minutes containing 0.1% TFA; 40 mL/min, monitoring at 220 nm) to yield (R)-2,2-difluoro-3-(3-(1-(3-fluoro-5-(1,1,2,2-tetrafluoroethoxy)phenyl)-1-(4-fluorophenyl)-2-phenylethyl)ureido)propanamide as a white solid (12 mg, 21% yield). LCMS: RT=3.85 min [M+H] 576.1 (Phenomenex Luna C18 column, 4.6×50 mm eluting with 10-90% MeOH/H$_2$O over 4 minutes containing 0.1% TFA; 4 mL/min, monitoring at 220 nm).

Procedure 48

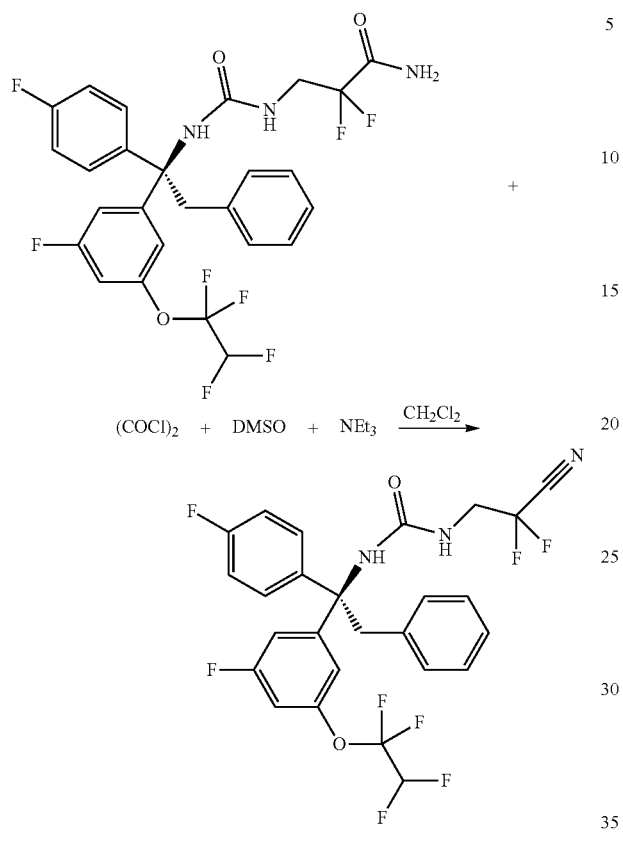

Example 254

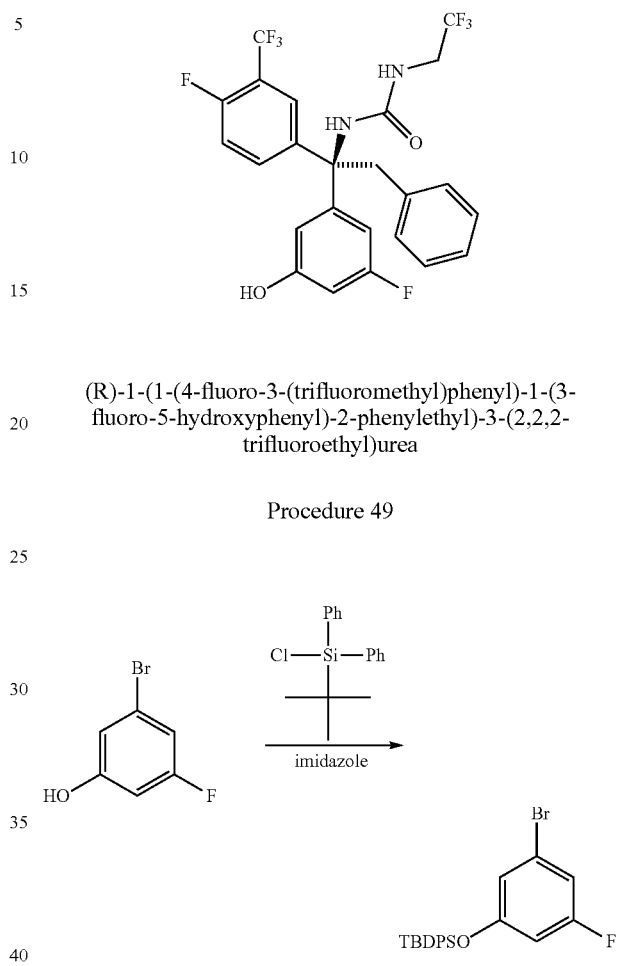

(R)-1-(1-(4-fluoro-3-(trifluoromethyl)phenyl)-1-(3-fluoro-5-hydroxyphenyl)-2-phenylethyl)-3-(2,2,2-trifluoroethyl)urea

Procedure 49

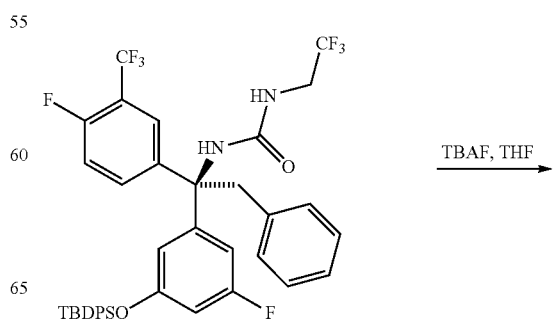

To a solution of (R)-2,2-difluoro-3-(3-(1-fluoro-5-(1,1,2,2-tetrafluoroethoxy)phenyl)-1-(4-fluorophenyl)-2-phenylethyl)ureido)propanamide (12 mg, 0.02 mmol) in CH$_2$Cl$_2$ (0.5 mL) at –78° C. was added DMSO (10 uL, 0.14 mmol), followed by addition of (COCl)$_2$ (2 M in CH$_2$Cl$_2$, 0.05 mmol). The reaction mixture was stirred at –78° C. for 15 min, then NEt$_3$ (0.03 mL, 0.2 mmol) was added dropwise. The reaction mixture was allowed to warm to rt and stirred for 16 h. The reaction mixture was concentrated under reduced pressure and the residue was purified by prep HPLC (Phenomenex AXIA Luna 75×30 mm, 5μ column eluting with 10-90% ACN/H$_2$O over 10 minutes containing 0.1% TFA; 40 mL/min, monitoring at 220 nm) to yield (R)-1-(2-cyano-2,2-difluoroethyl)-3-(1-(3-fluoro-5-(1,1,2,2-tetrafluoroethoxy)phenyl)-1-(4-fluorophenyl)-2-phenylethyl)urea (Example 253) as a white solid (7 mg, 62% yield). LCMS: RT=4.03 min [M+H] 558.2 (Phenomenex Luna C18 column, 4.6×50 mm eluting with 10-90% MeOH/H$_2$O over 4 minutes containing 0.1% TFA; 4 mL/min, monitoring at 220 nm). $^1$H NMR (500 MHz, CDCl$_3$) δ ppm 3.71 (d, 2H), 3.76-3.99 (m, 3H), 4.75-4.84 (m, 1H), 5.13-5.27 (m, 1H), 5.86 (t, 1H), 6.64-6.76 (m, 2H), 6.86-6.96 (m, 3H), 6.97-7.06 (m, 2H), 7.07-7.23 (m, 5H).

To a solution of 3-bromo-5-fluorophenol (5.7 g, 30 mmol), prepared as described in Procedure 3, and imidazole (4.0 g, 60 mmol, 2 eq) in anhydrous THF (100 mL) at 0° C. was added tert-butyldiphenyl-silyl chloride (9.6 mL, 1.3 eq). The resulting mixture was stirred at room temperature for 18 h. The reaction mixture was quenched with water and extracted with hexane/EtOAc (1:1). The combined organic layers were washed with H$_2$O (2×) and sat. NaCl (2×), dried over Na$_2$SO$_4$, filtered and concentrated under reduced pressure. The resulting residue was purified by silica gel chromatography (hexanes/EtOAc) to give (3-bromo-5-fluorophenoxy)(tert-butyl)diphenylsilane as colorless oil (7.5 g, yield 58%).

401

-continued

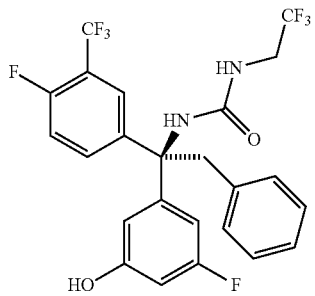

(R)-1-(1-(3-(tert-butyldiphenylsilyloxy)-5-fluorophenyl)-1-(4-fluoro-3-(trifluoromethyl)phenyl)-2-phenylethyl)-3-(2,2,2-trifluoroethyl)urea was prepared as described in Procedure 4, 5, 6 and 10 (85 mg, 37% overall yield). LCMS: RT=2.71 min [M+H] 757.3 (Phenomenex Luna C18 column, 4.6×30 mm eluting with 10-90% MeOH/H$_2$O over 2 minutes containing 0.1% TFA; 5 mL/min, monitoring at 220 nm).

To a solution of (R)-1-(1-(3-(tert-butyldiphenylsilyloxy)-5-fluorophenyl)-1-(4-fluoro-3-(trifluoromethyl)phenyl)-2-phenylethyl)-3-(2,2,2-trifluoroethyl)urea (85 mg, 0.11 mmol) in THF (1.5 mL) was added TBAF (1.0 M in THF, 0.12 mL, 0.12 mmol). The resulting mixture was stirred at room temperature for 45 min. The reaction was diluted with CH$_2$Cl$_2$ and washed with sat. NH$_4$Cl, H$_2$O and sat. NaCl, dried over Na$_2$SO$_4$, filtered and concentrated. The resulting residue was purified by flash chromatography (silica gel, hexanes/EtOAc) to give (R)-1-(1-(4-fluoro-3-(trifluoromethyl)phenyl)-1-(3-fluoro-5-hydroxyphenyl)-2-phenylethyl)-3-(2,2,2-trifluoroethyl)urea (Example 254, 45 mg, yield 77%). LCMS: RT=2.0 min [M+H] 519.1 (Phenomenex Luna C18 column, 4.6×30 mm eluting with 10-90% MeOH/H$_2$O over 2 minutes containing 0.1% TFA; 5 mL/min, monitoring at 220 nm). $^1$H NMR (400 MHz, CDCl$_3$) δ ppm 7.20-7.27 (3H, m), 7.09-7.18 (3H, m), 6.72 (1H, d, J=9.60 Hz), 6.66 (3H, d, J=7.07 Hz), 6.57 (1H, s), 3.73-3.78 (1H, m), 3.65-3.71 (1H, m), 3.63 (1H, d, J=8.59 Hz), 3.47-3.58 (1H, m).

Example 255

402

(R)-1-(1-(4-fluoro-3-(trifluoromethyl)phenyl)-1-(3-fluoro-5-(2,2,2-trifluoroethoxy)phenyl)-2-phenylethyl)-3-(2,2,2-trifluoroethyl)urea Procedure 50

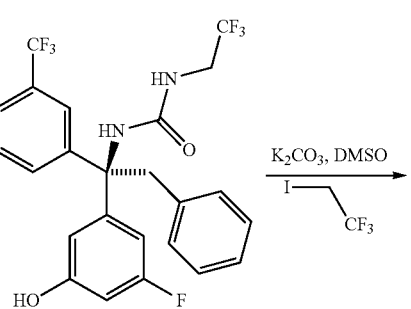

To a solution of (R)-1-(1-(4-fluoro-3-(trifluoromethyl)phenyl)-1-(3-fluoro-5-hydroxyphenyl)-2-phenylethyl)-3-(2,2,2-trifluoroethyl)urea (Example 254, 15 mg, 0.03 mmol) in DMSO (0.15 mL) was added ICH$_2$CF$_3$ (0.02 mL) and K$_2$CO$_3$ (20 mg, 0.2 mmol). The reaction mixture was heated at 70° C. overnight. The reaction was cooled to rt and diluted with CH$_3$CN, filtered and purified by prep HPLC (phenomenex AXIA Luna 75×30 mm, 5μ column eluting with 10-90% ACN/H$_2$O over 10 minutes containing 0.1% TFA; 40 mL/min, monitoring at 220 nm) to give (R)-1-(1-(4-fluoro-3-(trifluoromethyl)phenyl)-1-(3-fluoro-5-(2,2,2-trifluoroethoxy)phenyl)-2-phenylethyl)-3-(2,2,2-trifluoroethyl)urea (Example 255) as white solid (10 mg, yield 58%). LCMS: RT=2.18 min [M+H] 601.2 (Phenomenex Luna C18 column, 4.6×30 mm eluting with 10-90% MeOH/H$_2$O over 2 minutes containing 0.1% TFA; 5 mL/min, monitoring at 220 nm). $^1$H NMR (400 MHz, CDCl$_3$) δ ppm 7.33-7.43 (2H, m), 7.21 (1H, d, J=6.60 Hz), 7.12-7.19 (2H, m), 6.68 (2H, d, J=7.70 Hz), 6.54-6.63 (3H, m), 4.19-4.30 (2H, m), 3.73-3.84 (4H, m).

Example 256

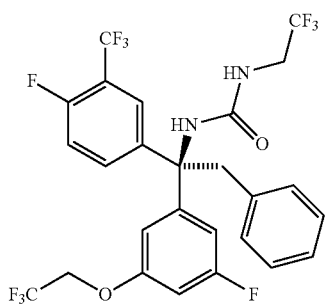 [SMILES: O=C(NCC(F)(F)F)N[C@@](Cc1ccccc1)(c1cc(F)cc(OCC(F)(F)F)c1)c1ccc(F)c(C(F)(F)F)c1]

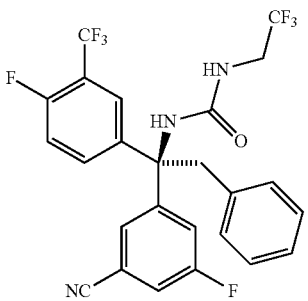 [SMILES: N#Cc1cc(F)cc([C@](Cc2ccccc2)(NC(=O)NCC(F)(F)F)c2ccc(F)c(C(F)(F)F)c2)c1]

403

(R)-1-(1-(3-cyano-5-fluorophenyl)-1-(4-fluoro-3-(trifluoromethyl)phenyl)-2-phenylethyl)-3-(2,2,2-trifluoroethyl)urea Procedure 51

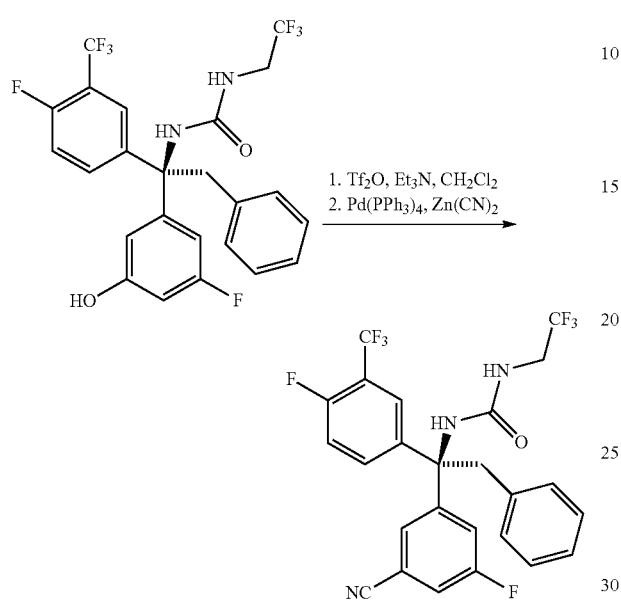

To a solution of (R)-1-(1-(4-fluoro-3-(trifluoromethyl)phenyl)-1-(3-fluoro-5-hydroxyphenyl)-2-phenylethyl)-3-(2,2,2-trifluoroethyl)urea (Example 254, 0.12 g, 0.23 mmol) in anhydrous CH$_2$Cl$_2$ (2 mL) at 0° C. under argon was added Et$_3$N (0.05 mL, 0.4 mmol) followed by dropwise addition of trifluoroacetic anhydride (0.05 mL). The reaction mixture was stirred at 0° C. for 30 min the diluted with CH$_2$Cl$_2$ (10 mL). The organic layer was washed with H$_2$O, sat. NaCl, dried over Na$_2$SO$_4$, filtered and concentrated under reduced pressure. The residue was purified by flash chromatography (silica gel, hexanes/EtOAc) to give (R)-3-(1-(4-fluoro-3-(trifluoromethyl)phenyl)-2-phenyl-1-(3-(2,2,2-trifluoroethyl)ureido)ethyl)phenyl trifluoromethanesulfonate (65 mg). LCMS: RT=2.34 min [M+H] 651.4 (Phenomenex Luna C18 column, 4.6×30 mm eluting with 10-90% MeOH/H$_2$O over 2 minutes containing 0.1% TFA; 5 mL/min, monitoring at 220 nm). To a solution of (R)-3-(1-(4-fluoro-3-(trifluoromethyl)phenyl)-2-phenyl-1-(3-(2,2,2-trifluoroethyl)ureido)ethyl)phenyl trifluoromethanesulfonate (65 mg, 0.1 mmol) in DMF (0.4 mL) was added Zn(CN)$_2$ (70 mg) and Pd(PPh$_3$)$_4$ (catalytic amount). The reaction mixture was heated to 105° C. in a sealed vial for 2 h. After cooling to rt, the reaction solution was filtered and the solid was rinsed with EtOAc. The filtrate was washed with sat. NaHCO$_3$, H$_2$O, and sat. NaCl, dried over Na$_2$SO$_4$, filtered and concentrated under reduced pressure. The resulting residue was purified by flash chromatography (silica gel, hexanes/EtOAc) to give (R)-1-(1-(3-cyano-5-fluorophenyl)-1-(4-fluoro-3-(trifluoromethyl)phenyl)-2-phenylethyl)-3-(2,2,2-trifluoroethyl)urea (Example 256, 37 mg, 30% yield for 2 steps). LCMS: RT=3.88 min [M+H] 528.2 (Phenomenex Luna C18 column, 4.6×30 mm eluting with 10-90% MeOH/H$_2$O over 2 minutes containing 0.1% TFA; 5 mL/min, monitoring at 220 nm). $^1$H NMR (400 MHz, CDCl$_3$) δ ppm 7.31 (m, 2H), 7.26-7.13 (m, 4H), 7.02-6.93 (m, 3H), 6.66 (d, J=7.7 Hz, 2H), 5.24 (s, br, 1H), 5.05 (t, J=6.0 Hz, 1H), 3.80 (AB, J=12.6 Hz, 2H), 3.74 (m, 2H).

Example 257

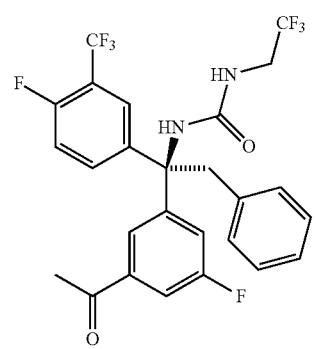 [SMILES: CC(=O)c1cc(F)cc([C@](Cc2ccccc2)(NC(=O)NCC(F)(F)F)c2ccc(F)c(C(F)(F)F)c2)c1]

(R)-1-(1-(3-acetyl-5-fluorophenyl)-1-(4-fluoro-3-(trifluoromethyl)phenyl)-2-phenylethyl)-3-(2,2,2-trifluoroethyl)urea Procedure 52

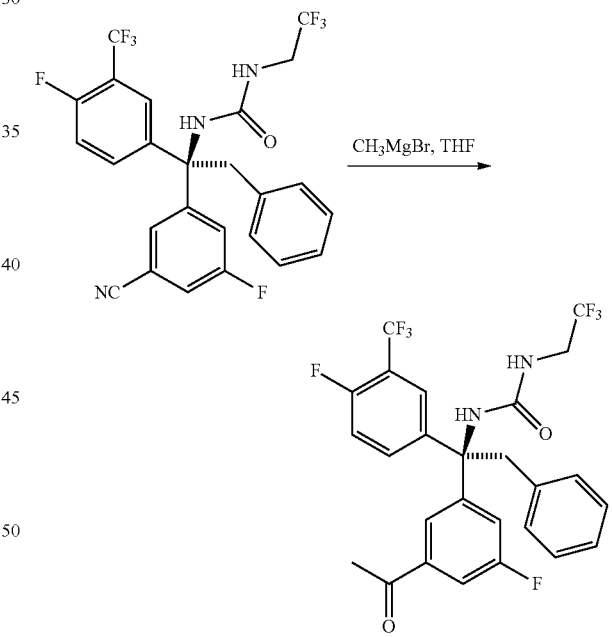

To a solution of (S)-1-(1-(3-cyanophenyl)-1-(4-fluoro-3-(trifluoromethyl)phenyl)-2-phenylethyl)-3-(2,2,2-trifluoroethyl)urea (Example 256, mg, 0.06 mmol) in THF (1 mL) at rt was added CH$_3$MgBr (3.0 M in Et$_2$O, 0.1 mL). The reaction mixture was heated at 48° C.-55° C. for 2.5 h. After cooling, 1N HCl was added and the reaction mixture was stirred for 10 min at rt. The reaction mixture was extracted with EtOAc, washed with H$_2$O, sat. NaCl, dried over Na$_2$SO$_4$, filtered and concentrated under reduced pressure. The resulting residue was purified by flash chromatography (silica gel, hexanes/EtOAc) to give pure (R)-1-(1-(3-acetyl-5-fluorophenyl)-1-(4-fluoro-3-(trifluoromethyl)phenyl)-2-phenylethyl)-3-(2,2, 2-trifluoroethyl)urea (Example 257, 26 mg, yield: 84%). LCMS: RT=3.90 min [M+H] 545.2 (Phenomenex Luna C18 column, 4.6×30 mm eluting with 10-90% MeOH/H₂O over 2 minutes containing 0.1% TFA; 5 mL/min, monitoring at 220 nm). ¹H NMR (400 MHz, CDCl₃) δ ppm 7.58 (m, 1H), 7.53 (m, 1H), 7.36 (m, 2H), 7.23 (m, 1H), 7.16 (m, 4H), 6.68 (d, J=6.8 Hz, 2H), 5.43 (s, br, 1H), 5.17 (m, 1H), 3.88 (dd, J=23.2, 12.9 Hz, 2H), 3.78 (m, 2H), 3.03 (s, 3H).

Example 258

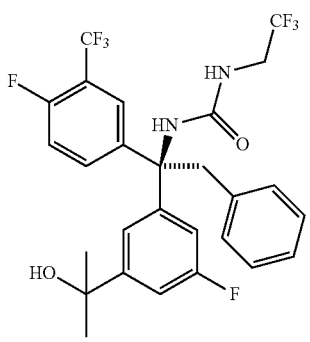 [SMILES: CC(C)(O)c1cc(F)cc([C@](Cc2ccccc2)(NC(=O)NCC(F)(F)F)c2ccc(F)c(C(F)(F)F)c2)c1]

(R)-1-(1-(4-fluoro-3-(trifluoromethyl)phenyl)-1-(3-fluoro-5-(2-hydroxypropan-2-yl)phenyl)-2-phenylethyl)-3-(2,2,2-trifluoroethyl)urea Procedure 53

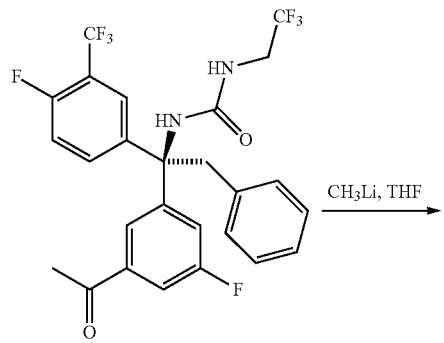

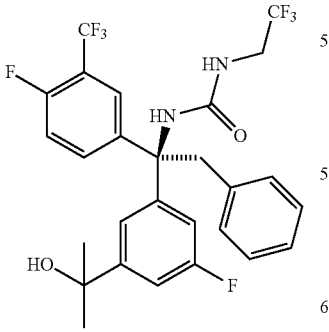

To a solution of (R)-1-(1-(3-acetyl-5-fluorophenyl)-1-(4-fluoro-3-(trifluoromethyl)phenyl)-2-phenylethyl)-3-(2,2,2-trifluoroethyl)urea (Example 257, mg, 0.037 mmol) in THF (1 mL) at 0° C. under argon was added dropwise CH₃Li (1.4 M in Et₂O, 0.04 mL, 0.056 mmol). The reaction mixture was stirred at room temperature for 2 h, then quenched with sat. NH₄Cl and 0.5 N HCl and the aqueous layer was extracted with EtOAc. The combined organic portions were washed with H₂O, sat. NaCl, dried over Na₂SO₄, filtered and concentrated under reduced pressure. The residue was purified by flash chromatography (silica gel, hexanes/EtOAc) to give (R)-1-(1-(4-fluoro-3-(trifluoromethyl)phenyl)-1-(3-fluoro-5-(2-hydroxypropan-2-yl)phenyl)-2-phenylethyl)-3-(2,2,2-trifluoroethyl)urea (Example 258, 8 mg, yield 39%). LCMS: RT=3.89 min [M+H] 559.4 (Phenomenex Luna C18 column, 4.6×50 mm eluting with 10-90% MeOH/H₂O over 4 minutes containing 0.1% NH₄Cl; 4 mL/min, monitoring at 220 nm). ¹H NMR (400 MHz, CDCl₃) ppm 7.51-7.45 (m, 2H), 7.21-6.96 (m, 6H), 6.68 (d, J=6.8 Hz, 2H), 6.61 (d, J=9.9 Hz, 1H), 5.43 (s, br, 1H), 5.17 (m, 1H), 4.01 (d, J=13.2 Hz, 1H), 3.85-3.62 (m, 3H), 1.46 (s, 3H), 1.44 (s, 3H).

Example 259

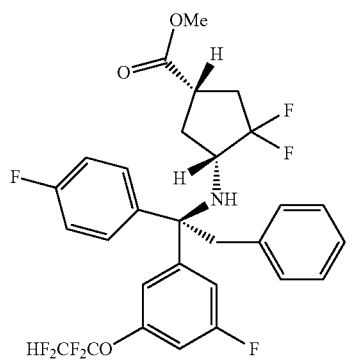

(1S,4R)-methyl 3,3-difluoro-4-(3-((R)-1-(3-fluoro-5-(1,1,2,2-tetra-fluoroethoxy)phenyl)-1-(4-fluorophenyl)-2-)ureido)cyclopentanecarboxylate Procedure 54

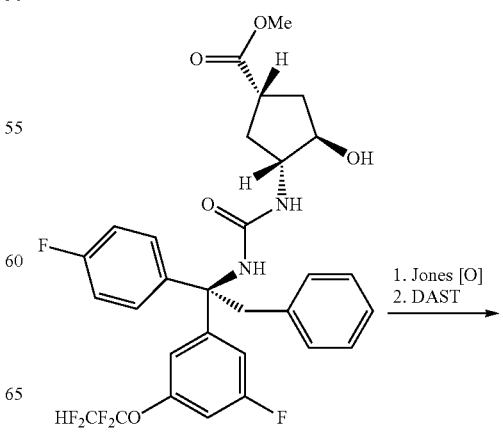

407
-continued

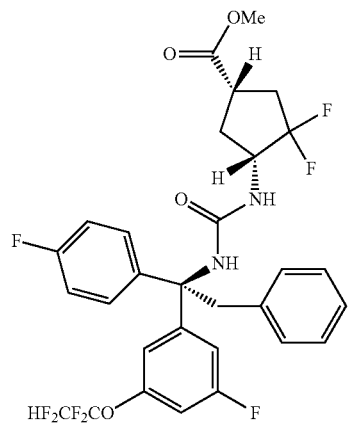

To a solution of (1S,3R,4R)-methyl 3-(3-((R)-1-(3-fluoro-5-(1,1,2,2-tetrafluoroethoxy)phenyl)-1-(4-fluorophenyl)-2-phenylethyl)ureido)-4-hydroxycyclopentanecarboxylate, prepared as described Procedure 12, (11 mg, 0.017 mmol) in acetone (430 µL) was added a solution of Jones reagent (17 µL, 1 M solution). The reaction mixture was stirred at rt for 1.5 h, then filtered through a celite pad. The pad was washed with acetone and the filtrate was concentrated under reduced pressure. The residue was dissolved in EtOAc and the solution was washed with $H_2O$. The organic layer was separated and the aqueous layer was further extracted with EtOAc (3×). The combined organics were dried over $Na_2SO_4$, filtered, and concentrated under reduced pressure. The residue was dissolved in $CH_2Cl_2$ (17 mL) and DAST (6.5 mL) was added at rt. The reaction mixture was stirred overnight, then quenched with sat. NaCl. The aqueous layer was extracted with $CH_2Cl_2$ (3×). The combined organic layers were dried over $Na_2SO_4$, filtered and concentrated under reduced pressure. The residue was purified by preparative HPLC (Phenoma Luna AXIA 10A, C18, eluting with $MeCN/H_2O$ containing 0.1% TFA, monitoring at 220 nm) to provide (1S,4R)-methyl 3,3-difluoro-4-(3-((R)-1-(3-fluoro-5-(1,1,2,2-tetra-fluoroethoxy)phenyl)-1-(4-fluorophenyl)-2-)ureido)cyclopentanecarboxylate (Example 259, 9 mg, 85% yield) as a film. $^1$H NMR (500 MHz, $CDC_3$) δ 7.16-7.07 (m, 6H), 7.00-6.83 (m, 6H), 6.62 (d, J=10 Hz, 2H), 5.93-5.68 (m, 1H), 5.37 (s, 1H), 3.77 (d, J=10 Hz, 1H), 3.64 (s, 3H), 3.68-5.58 (m, 2H), 2.90-2.84 (m, 1H), 2.47-2.26 (m, 3H), 1.60-1.53 (m, 1H); LC/MS: RT=3.97 min [M+H] 631.4 (Phenomenex Luna C18 column, 4.6×50 mm eluting with 10-90% $MeCN/H_2O$ over 4 minutes containing 0.1% $NH_4OAc$; 4 mL/min, monitoring at 220 nm).

408
Example 260

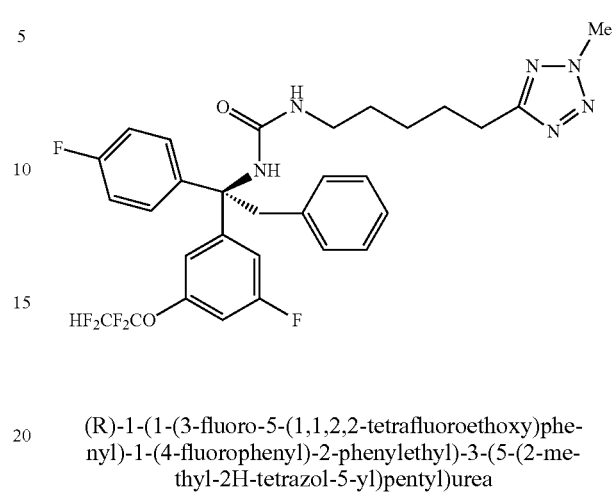

(R)-1-(1-(3-fluoro-5-(1,1,2,2-tetrafluoroethoxy)phenyl)-1-(4-fluorophenyl)-2-phenylethyl)-3-(5-(2-methyl-2H-tetrazol-5-yl)pentyl)urea Procedure 55

To a solution of (R)-1-(5-cyanopentyl)-3-(1-(3-fluoro-5-(1,1,2,2-tetrafluoroethoxy)phenyl)-1-(4-fluorophenyl)-2-phenylethyl)urea, prepared by the method described in Procedure 12 (45 mg, 0.080 mmol) in DME (161 µL) at rt was added $TMSN_3$ (0.013 mL, 0.16 mmol), followed by $n-Bu_2SnO_2$ (2 mg, 0.008 mmol). The reaction mixture was heated at 150° C. for 10 min under microwave irradiation. An additional amount of $TMSN_3$ (0.013 mL, 0.16 mmol) and $n-Bu_2SnO_2$ (2 mg, 0.008 mmol) was added, and the reaction mixture was heated at 150° C. for an additional 10 min under microwave irradiation. The reaction mixture was concentrated and the residue was dissolved in MeOH and purified by preparative HPLC (Phenoma Luna AXIA 10A, C18, eluting with $MeCN/H_2O$ containing 0.1% TFA, monitoring at 220 nm) to provide (R)-1-(5-(2H-tetrazol-5-yl)pentyl)-3-(1-(3-fluoro-5-(1,1,2,2-tetrafluoroethoxy)phenyl)-1-(4-fluorophenyl)-2-phenylethyl)urea (23 mg, 47% yield) as a white solid. $^1$H NMR (500 MHz, MeOH-$d_4$) δ 7.18-6.89 (m, 11H), 6.71 (d, J=5 Hz, 2H), 6.37-6.16 (m, 1H), 3.93 (d, J=15 Hz, 1H), 3.81 (d, J=15.0 Hz, 1H), 3.08 (t, J=5 Hz, 2H), 2.94 (t, J=5 Hz, 2H), 1.83-1.76 (m, 2H), 1.55-1.48 (m, 2H), 1.41-1.35 (m, 2H); LC/MS: RT=3.736 min [M+H] 607.3 (Phenomenex Luna C18 column, 4.6×50 mm eluting with 10-90% MeCN/H$_2$O over 4 minutes containing 0.1% NH$_4$OAc; 4 mL/min, monitoring at 220 nm).

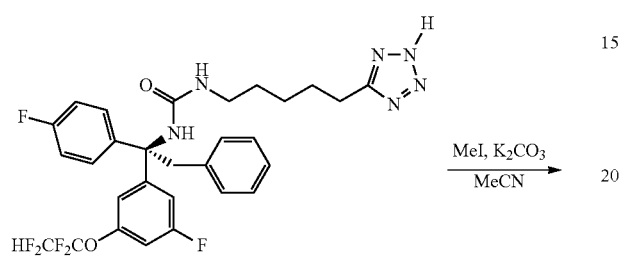

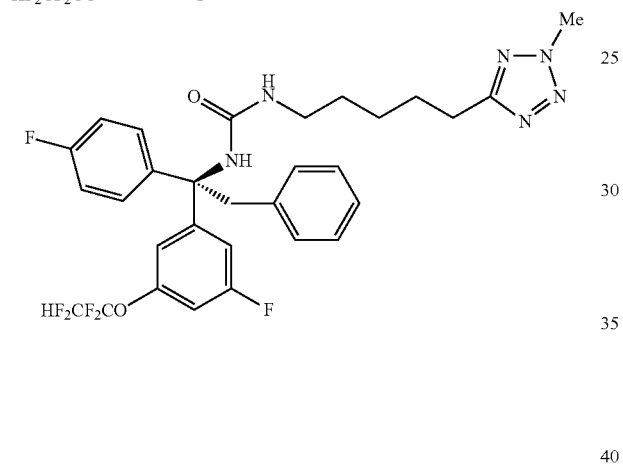

To a solution of (R)-1-(5-(2H-tetrazol-5-yl)pentyl)-3-(1-(3-fluoro-5-(1,1,2,2-tetrafluoroethoxy)phenyl)-1-(4-fluorophenyl)-2-phenylethyl)urea (12 mg, 0.019 mmol) in MeCN (115 µL) at rt was added K$_2$CO$_3$ (3.2 mg, 0.023 mmol) followed by MeI (1.5 µL, 0.023 mmol). The reaction mixture was heated to 80° C. overnight. The reaction mixture was quenched by addition of H$_2$O and the aqueous layer was extracted with EtOAc (3×). The combined organic layers were concentrated and the residue was dissolved in MeOH and purified by preparative HPLC (Phenoma Luna AXIA 10A, C18, eluting with MeCN/H$_2$O containing 0.1% TFA, monitoring at 220 nm) to provide (R)-1-(1-(3-fluoro-5-(1,1,2,2-tetrafluoroethoxy)phenyl)-1-(4-fluorophenyl)-2-phenylethyl)-3-(5-(2-methyl-2H-tetrazol-5-yl)pentyl)urea (Example 260, 2 mg, 18% yield) as white solid. $^1$H NMR (500 MHz, CDCl$_3$) ppm 7.17-7.08 (m, 5H), 6.99-6.85 (m, 5H), 6.67 (d, J=5 Hz, 2H), 5.98-5.75 (m, 1H), 4.23 (s, 3H), 3.82 (d, J=15 Hz, 1H), 3.68 (d, J=15 Hz, 1H), 3.10-3.07 (m, 2H), 2.85-2.82 (m, 2H), 1.77-1.71 (m, 2H), 1.46-1.40 (m, 2H), 1.32-1.26 (m, 2H); LC/MS: RT=3.218 min [M+H] 621.2 (Phenomenex Luna C18 column, 4.6×50 mm eluting with 10-90% MeCN/H$_2$O over 4 minutes containing 0.1% NH$_4$OAc; 4 mL/min, monitoring at 220 nm).

Example 261

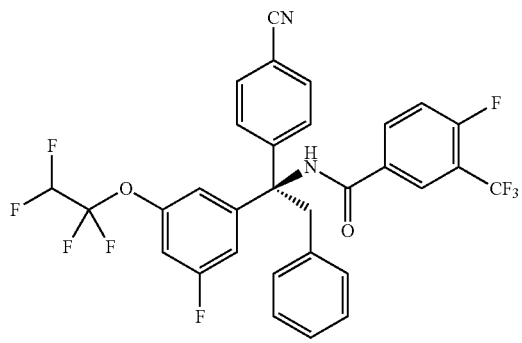 [SMILES: N#Cc1ccc([C@@](Cc2ccccc2)(NC(=O)c2ccc(F)c(C(F)(F)F)c2)c2cc(F)cc(OC(F)(F)C(F)F)c2)cc1]

(R)—N-(1-(4-cyanophenyl)-1-(3-fluoro-5-(1,1,2,2-tetrafluoroethoxy)phenyl)-2-phenylethyl)-4-fluoro-3-(trifluoromethyl)benzamide Procedure 56

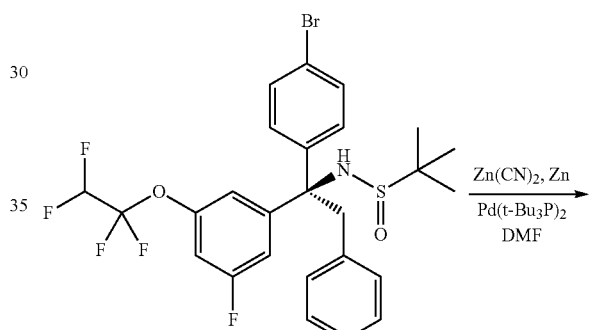

To a solution of (1,1,2,2-tetrafluoroethoxy)phenyl)-2-phenylethyl)-2-methylpropane-2-sulfinamide (2.44 g, 4.13 mmol), prepared as described in Procedure 3, 4, 5 and 6, in DMF (20 mL) were added zinc cyanide (970 mg, 8.27 mmol) and zinc dust (81 mg, 1.24 mmol). The reaction mixture was degassed with Ar and placed under nitrogen. Palladiumbis-tributylphosphine (41 mg, 0.20 mmol) was added and the reaction mixture was heated at 60° C. for 16 h. The reaction mixture was quenched with sat. sodium bicarbonate and extracted with ethyl acetate. The combined organic extracts were dried over Mg$_2$SO$_4$, filtered and concentrated to provide N—((R)-1-(4-cyanophenyl)-1-(3-fluoro-5-(1,1,2,2-tetrafluoroethoxy)phenyl)-2-phenylethyl)-2-methylpropane-2- sulfinamide as a white solid (2.08 g, 93% yield). LC/MS: RT=2.25 min [M+H] 537 (Chromolith Performance 18e 4.6×100 mm column, 10-90% CH₃OH/H₂O with 0.1% TFA gradient over 2 min, 5 mL/min, monitoring at 220 nm).

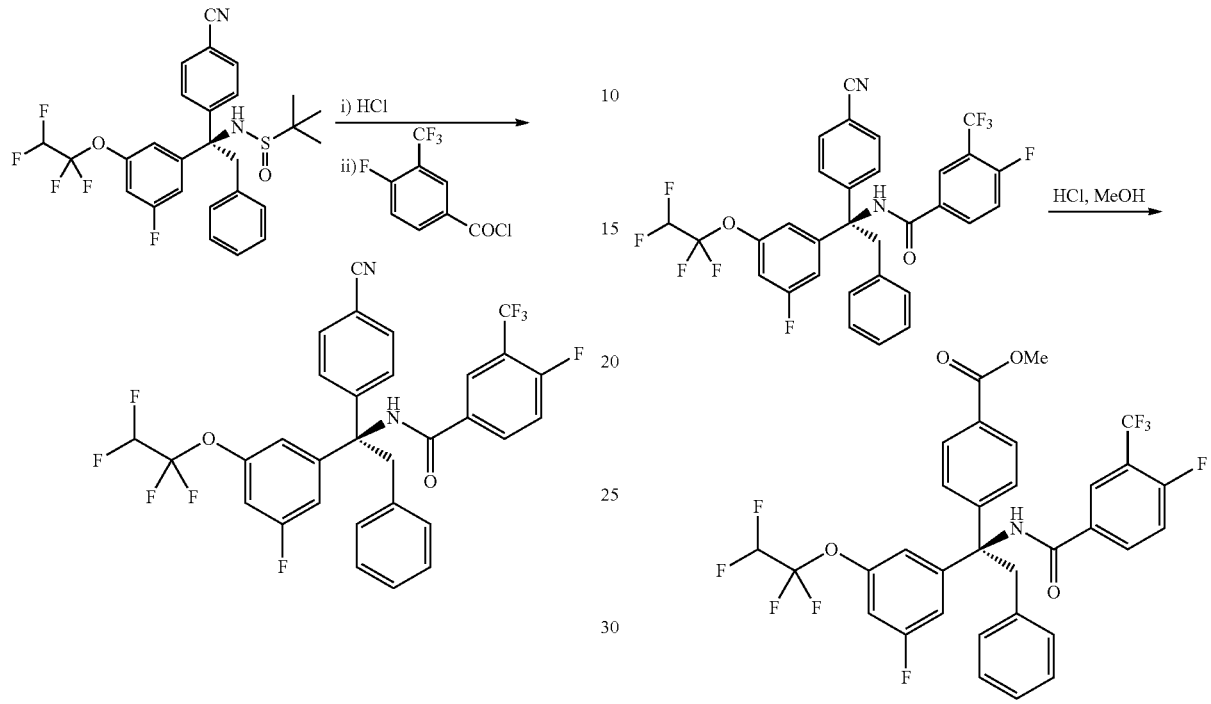

Following Procedure 6 and 7, (R)—N-(1-(4-cyanophenyl)-1-(3-fluoro-5-(1,1,2,2-tetrafluoroethoxy)phenyl)-2-phenylethyl)-4-fluoro-3-(trifluoromethyl)benzamide (Example 261) was prepared as a white powder (380 mg, 89% yield). LC/MS: RT=2.33 min [M+H] 623 (Chromolith Performance 18e 4.6×100 mm column, 10-90% CH₃OH/H₂O with 0.1% TFA gradient over 2 min, 5 mL/min, monitoring at 220 nm); ¹H NMR (400 MHz, CDCl₃) ppm 7.91 (1H, d, J=6.60 Hz), 7.81-7.86 (1H, m), 7.67 (2H, d, J=8.24 Hz), 7.38 (2H, d, J=8.25 Hz), 7.24 (CHCl₃) 7.24-7.31 (2H, m), 7.18 (2H, t, J=7.42 Hz), 7.05 (1H, m), 6.90 (2H, m), 6.64-6.75 (3H, m), 5.88 (1H, tt, J$_{HH}$=2.75 Hz, J$_{HF}$=53 Hz), 3.90 (2H, s).

Example 262

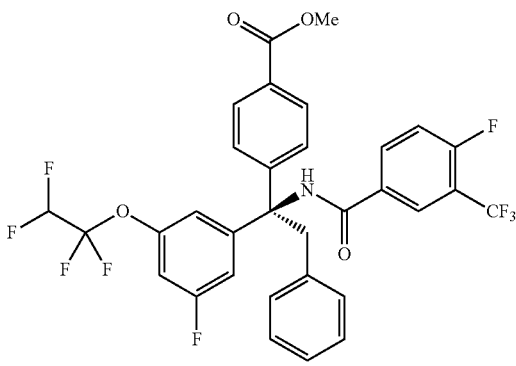 [SMILES: COC(=O)c1ccc([C@@](Cc2ccccc2)(NC(=O)c2ccc(F)c(C(F)(F)F)c2)c2cc(F)cc(OC(F)(F)C(F)F)c2)cc1]

(R)-methyl 4-(1-(4-fluoro-3-(trifluoromethyl)benzamido)-1-(3-fluoro-5-(1,1,2,2-tetrafluoroethoxy)phenyl)-2-phenylethyl)benzoate Procedure 57

(R)—N-(1-(4-Cyanophenyl)-1-(3-fluoro-5-(1,1,2,2-tetrafluoroethoxy)phenyl)-2-phenylethyl)-4-fluoro-3-(trifluoromethyl)benzamide (Example 261, 118 mg, 0.19 mmol) was dissolved in methanol (10 mL). Hydrogen chloride gas was bubbled into the solution for 5 min and the reaction mixture was stirred at 55° C. for 22 h. Then hydrogen chloride gas was bubbled to the mixture again for 4 min. After stirring for additional 22 h, the reaction was quenched with sat. NaHCO₃ and the mixture was extracted with ethyl acetate. The organic extracts were dried over MgSO₄, filtered and concentrated to yield a white solid. The resulting solid was purified by ISCO flash chromatography (12 g silica gel; 0-50% ethyl acetate/hexane gradient over 12 min., 30 mL/min) to provide (R)-methyl 4-(1-(4-fluoro-3-(trifluoromethyl)benzamido)-1-(3-fluoro-5-(1,1,2,2-tetrafluoroethoxy)phenyl)-2-phenylethyl)benzoate (Example 262) as a white solid (92 mg, 74% yield). LC/MS: RT=2.37 min [M+H] 656 (Chromolith Performance 18e 4.6×100 mm column, 10-90% CH₃OH/H₂O with 0.1% TFA gradient over 2 min, 5 mL/min, monitoring at 220 nm); ¹H NMR (400 MHz, CDCl₃) ppm 8.02 (2H, d, J=8.25 Hz), 7.92 (1H, d, J=6.60 Hz), 7.77-7.88 (2H, m), 7.21-7.30 (3H, m), 7.24 (s, CHCl₃), 7.15 (2H, t, J=7.42 Hz), 6.89-7.00 (3H, m), 6.64-6.72 (3H, m), 5.87 (1H, tt, J$_{HH}$=2.75 Hz, J$_{HF}$=53 Hz), 4.03 (1H, d, J=13.19 Hz), 3.93 (3H, s), 3.86 (1H, d, J=13.19 Hz).

Example 263

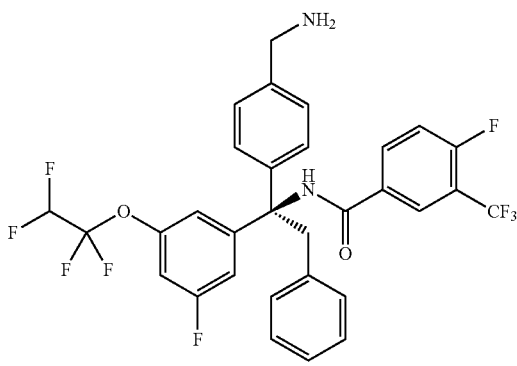 [SMILES: NCc1ccc([C@@](Cc2ccccc2)(NC(=O)c2ccc(F)c(C(F)(F)F)c2)c2cc(F)cc(OC(F)(F)C(F)F)c2)cc1]

(R)—N-(1-(4-(aminomethyl)phenyl)-1-(3-fluoro-5-(1,1,2,2-tetrafluoroethoxy)phenyl)-2-phenylethyl)-4-fluoro-3-(trifluoromethyl)benzamide Procedure 58

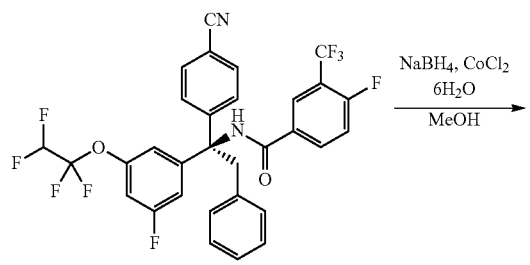

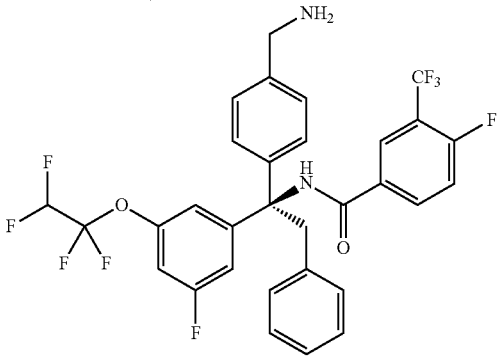

To a solution of (R)—N-(1-(4-Cyanophenyl)-1-(3-fluoro-5-(1,1,2,2-tetrafluoroethoxy)phenyl)-2-phenylethyl)-4-fluoro-3-(trifluoromethyl)benzamide (Example 261, 59 mg, 0.095 mmol) in methanol (2 mL) was added cobalt chloride hexahydrate (45 mg, 0.19 mmol), followed by sodium borohydride (36 mg, 0.95 mmol). The reaction mixture was stirred for 13 h, then quenched with HCl (1.0 M, 2 mL) and stirred for additional 1 h. The reaction mixture was diluted with sat. ammonium hydroxide then extracted with ethyl acetate. The organic extracts were dried over MgSO$_4$, filtered and concentrated to yield a white solid. The resulting solid was purified by preparative HPLC (YMC ODS-A s-5 20×100 mm column; 50-90% MeOH/H$_2$O with 0.1% TFA gradient over 10 min., 20 mL/min, monitoring at 220 nm) to provide (R)—N-(1-(4-(aminomethyl)phenyl)-1-(3-fluoro-5-(1,1,2,2-tetrafluoroethoxy)phenyl)-2-phenylethyl)-4-fluoro-(trifluoromethyl)benzamide (Example 263) as a white solid (39 mg, 56% yield). LC/MS: RT=1.65 min [M+H] 627 (Chromolith Performance 18e 4.6×100 mm column, 10-90% CH$_3$OH/H$_2$O with 0.1% TFA gradient over 2 min, 5 mL/min, monitoring at 220 nm); $^1$H NMR (400 MHz, CDCl$_3$) ppm 8.06 (2H, br s), 7.81 (1H, d, J=6.05 Hz), 7.67-7.77 (1H, m), 7.34 (2H, d, J=7.70 Hz), 7.18-7.27 (3H, m), 7.24 (CHCl$_3$, s), 7.13 (2H, t, J=7.42 Hz), 6.90 (1H, d, J=8.25 Hz), 6.72-6.81 (3H, m), 6.66 (2H, d, J=7.15 Hz), 5.88 (1H, tt, J$_{HH}$=2.75 Hz, J$_{HF}$=53 Hz), 4.01 (2H, br s), 3.77-(2H, dd, J=29.1 Hz, J=13.2 Hz).

Example 264

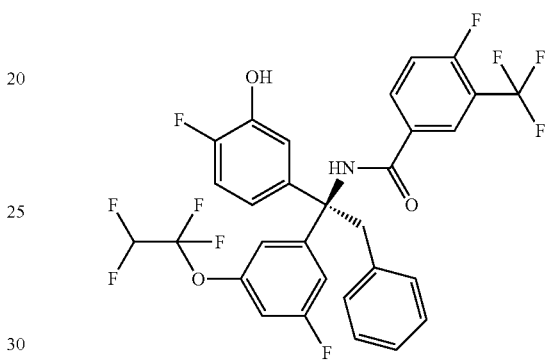

(R)-4-fluoro-N-(1-(4-fluoro-3-hydroxyphenyl)-1-(3-fluoro-5-(1,1,2,2)-tetrafluoro ethoxy)phenyl)-2-phenylethyl)-3-(trifluoromethyl)benzamide Procedure 59a

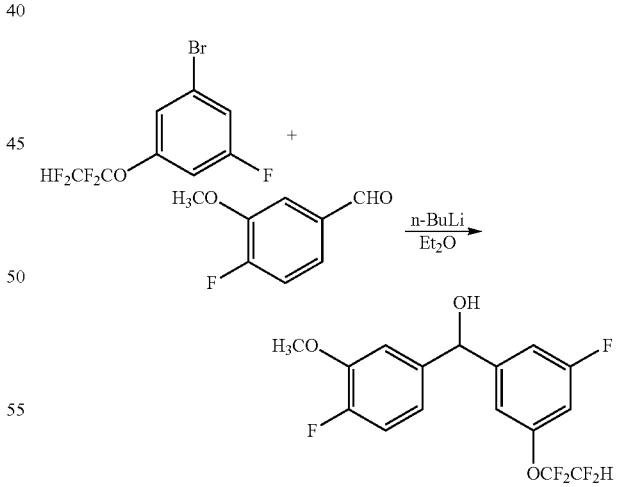

To a solution of 1-bromo-3-fluoro-5-(1,1,2,2-tetrafluoroethoxy)benzene, prepared as described in Procedure 3, (1.00 g, 3.44 mmol) in diethyl ether in (10 mL) at −72° C. was added 2.5 M n-BuLi (1.37 mL, 3.44 mmol) dropwise. Upon completion of addition, the reaction mixture was stirred for 15 minutes at −72° C., then 4-fluoro-3-methoxybenzaldehyde (0.53 g, 3.44 mmol) was added while the reaction mixture temperature was maintained below −52° C. The reaction mixture was stirred for 3 h at −72° C. The reaction mixture was quenched by the addition of 1N HCl and the aqueous portion was extracted with EtOAc (2×). The combined organic layers were washed with sat. NaCl, dried over MgSO₄ and concentrated under reduced pressure. The residue was purified by ISCO using a gradient of 0-50% EtOAc/hexane as eluent to yield (4-fluoro-3-methoxyphenyl)(3-fluoro-5-(1,1,2,2-tetrafluoroethoxy)phenyl)methanol (0.83 g, 66% yield). HPLC: RT=3.85 min (Phenomenex Luna C18 5μ column, eluting with 10-90% aqueous methanol containing 0.1% phosphoric acid over a 4 minute gradient, flow rate 4 mL/min, monitoring at 220 nm); ¹H NMR (CDCl₃): 7.05-6.8 (m, 6H), 5.87 (tt, J=2.8, 52.9 Hz), 5.75 (s, 1H), 3.85 (s, 3H).

Procedure 59b

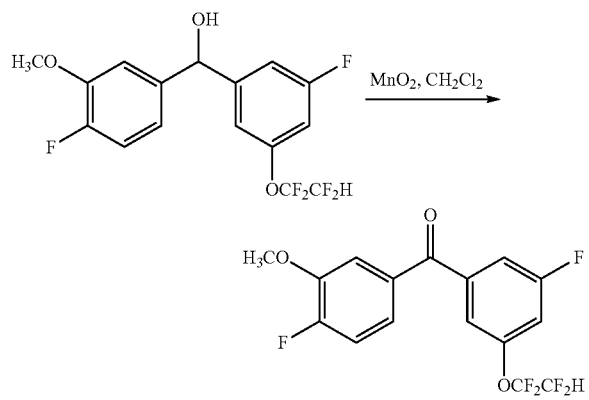

To a solution of (4-fluoro-3-methoxyphenyl)(3-fluoro-5-(1,1,2,2-tetrafluoroethoxy)phenyl)methanol (0.58 g, 1.57 mmol) in CH₂Cl₂ (5 mL) was added activated manganese dioxide (0.80 g, 7.86 mmol). The reaction mixture was stirred overnight at rt. Additional manganese dioxide (0.80 g, 7.86 mmol) was added and the reaction stirred at rt for another overnight. The reaction mixture was diluted with CH₂Cl₂ and filtered through celite and the solid was washed with CH₂Cl₂. The filtrate was concentrated under reduced pressure to yield (4-fluoro-3-methoxyphenyl)(3-fluoro-5-(1,1,2,2-tetrafluoroethoxy)phenyl)methanone (0.56 g, 98% yield). HPLC: RT=4.048 minutes (Phenomenex Luna C18 5μ column, eluting with 10-90% aqueous methanol containing 0.1% phosphoric acid over a 4 minute gradient, flow rate 4 mL/min, monitoring at 220 nm); LCMS: [M+H] 365.2 (Phenomenex Luna C18 5μ column, eluting with 10-90% aqueous methanol containing 0.1% TFA over a 2 minute gradient, flow rate 5 mL/min, monitoring at 220 nm); ¹H NMR (400 MHz, CDCl₃): 7.5-7.1 (m, 6H), 5.92 (tt, J=2.2, 53.6 Hz, 1H), 3.93 (s, 3H).

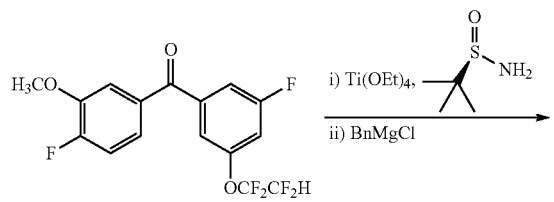

-continued

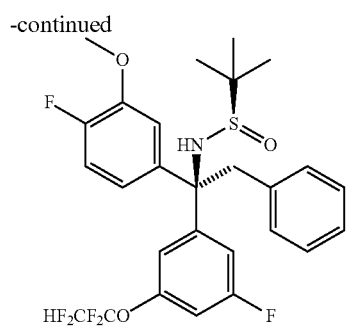

(R)—N—((R)-1-(3-fluoro-5-(1,1,2,2-tetrafluoroethoxy)phenyl)-1-(4-fluorophenyl)-2-phenylethyl)-2-methylpropane-2-sulfinamide may also be prepared by the methods described in Procedure 59c, 59d, 59e and 59f.

Procedure 59c

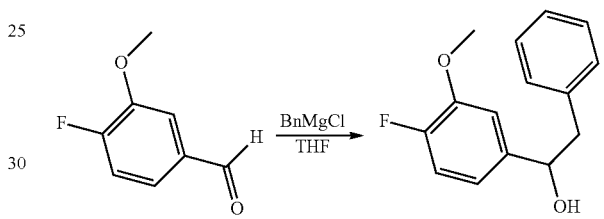

To a solution of 4-fluoro-3-methoxybenzaldehyde (25 g, 162 mmol) in THF (150 mL) was added a solution of benzyl magnesium chloride (2 M solution in THF, 122 mL, 243 mmol) in THF (50 mL). The reaction mixture was heated at 50° C. for 2 h. The reaction mixture was allowed to cool to rt and quenched by addition of sat. NH₄Cl. The reaction mixture was extracted with EtOAc (3×) and the combined organic layers were washed with sat. NaCl, dried over Na₂SO₄, filtered and concentrated under reduced pressure. The residue was purified by flash chromatography (SiO₂, eluting with 0-40% EtOAc/hexane) to yield 1-(4-fluoro-3-methoxyphenyl)-2-phenylethanol as a yellow oil (24 g, 60% yield). ¹H NMR (500 MHz, CDCl₃) δ ppm 7.27-7.32 (m, 2H), 7.21-7.27 (m, 1H), 7.16 (d, J=7 Hz, 2H), 7.01 (dd, J=11, 8 Hz, 1H), 6.92 (dd, J=8, 2 Hz, 1H), 6.82 (ddd, J=8, 4, 1 Hz, 1H), 4.80-4.88 (m, 1H), 4.66 (d, J=6 Hz, 1H), 3.84 (s, 3H), 2.91-3.04 (m, 2H).

Procedure 59d

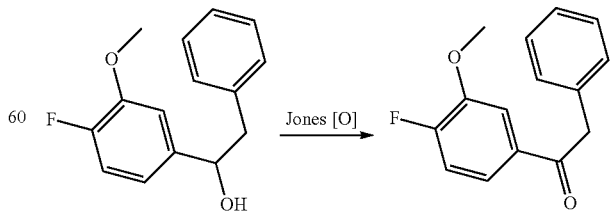

To a solution of 1-(4-fluoro-3-methoxyphenyl)-2-phenylethanol (23.7 g, 40.6 mmol) in acetone (240 mL) was added Jones reagent (64 mL) at rt. The reaction mixture was stirred overnight, quenched by the addition of isopropanol and diluted with EtOAc. The organic portion was washed with 1 N HCl (2×), dried over Na₂SO₄, filtered and concentrated under reduced pressure to yield the 1-(4-fluoro-3-methoxyphenyl)-2-phenylethanone (15 g, 66% yield). LCMS: RT=3.250 min [M+H] 245.1 (Phenomenex Luna C18 column, 4.6×50 mm eluting with 10-90% MeOH/H₂O over 4 minutes containing 0.1% NH₄OAc; 4 mL/min, monitoring at 220 nm); ¹H NMR (500 MHz, CDCl₃) δ ppm 7.62 (dd, J=8, 1 Hz, 1H), 7.60-7.55 (m, 1H), 7.35-7.29 (m, 2H), 7.26-7.23 (m, 3H), 7.10 (dd, J=10, 8 Hz, 1H), 4.24 (s, 2H), 3.89 (s, 3H).

Procedure 59e

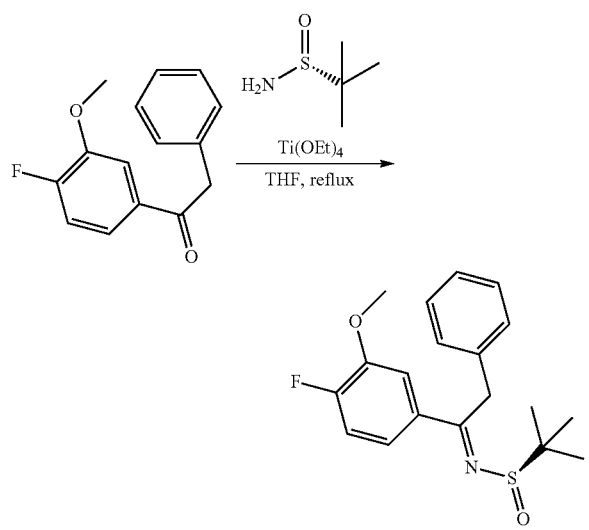

To a solution of 1-(4-fluoro-3-methoxyphenyl)-2-phenylethanone (13 g, 53 mmol) dissolved in THF (266 mL) was added (R)-2-methylpropane-2-sulfinamide (7.8 g, 64 mmol) at rt, followed by Ti(OEt)₄ (17 mL, 80 mmol). The reaction mixture was heated to reflux for 48 h, then allowed to cool to rt. The reaction mixture was concentrated under reduced pressure and the residue was diluted with Et₂O. H₂O was added and the solid was filtered and washed with Et₂O. The filtrate was washed with H₂O, dried over Na₂SO₄, filtered and concentrated under reduced pressure. The residue was purified by flash chromatography (SiO₂, eluting with 0-100% EtOAc/hexane) to yield (R,E)-N-(1-(4-fluoro-3-methoxyphenyl)-2-phenylethylidene)-2-methylpropane-2-sulfinamide (12 g, 67% yield). LCMS: RT=3.655 min [M+H] 348.2 (Phenomenex Luna C18 column, 4.6×50 mm eluting with 10-90% MeOH/H₂O over 4 minutes containing 0.1% NH₄OAc; 4 mL/min, monitoring at 220 nm); ¹H NMR (500 MHz, CDCl₃) δ ppm 7.60-7.53 (m, 1H), 7.43-7.36 (m, 1H), 7.29-7.15 (m, 5H), 7.03 (dd, J=11, 8 Hz, 1H), 4.75 (d, J=15 Hz, 1H), 4.54 (d, J=15 Hz, 1H), 3.84 (s, 3H), 1.34 (s, 9H).

Procedure 59f

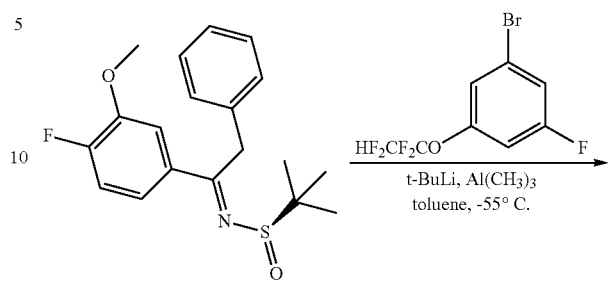

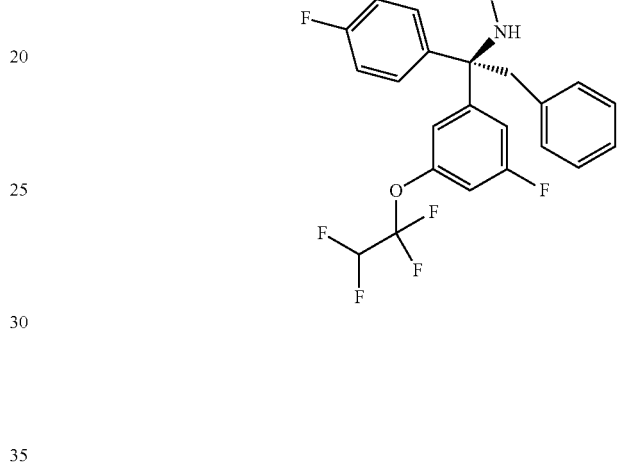

To a solution of 1-bromo-3-fluoro-5-(1,1,2,2-tetrafluoroethoxy)benzene (357 mg, 1.23 mmol) in toluene (1.5 mL) at −60° C. was added n-BuLi (2.5 M in hexane, 352 mL, 0.88 mmol). The reaction mixture was stirred for 1.5 h at −20° C. to −55° C. In a separate vial, to a −78° C. solution of (R,E)-N-(1-(4-fluoro-3-methoxyphenyl)-2-phenylethylidene)-2-methylpropane-2-sulfinamide (122 mg, 0.35 mmol) in toluene (1 mL) was added Al(CH₃)₃ (210 mL, 0.42 mmol). The resulting solution was stirred for 10-15 min, then added to the mixture of (3-fluoro-5-(1,1,2,2-tetrafluoroethoxy)phenyl) lithium. The combined reaction mixture was stirred at −55° C. overnight and then diluted with EtOAc. The organic portion was washed with H₂O and the aqueous portion was extracted with EtOAc (3×). The combined organic portions were concentrated under reduced pressure and the residue was purified by preparative HPLC (Phenomenex Luna AXIA 100A, C18, 5μ; 10%-90% ACN/H₂O containing 0.1% TFA, monitoring at 220 nm) to yield (R)—N—((R)-1-(4-fluoro-3-methoxyphenyl)-1-(3-fluoro-5-(1,1,2,2-tetrafluoroethoxy)phenyl)-2-phenylethyl)-2-methylpropane-2-sulfinamide (83 mg, 42% yield). LCMS: RT=3.49 min [M+H] 560.1 (Phenomenex Luna C18 column, 4.6×50 mm eluting with 10-90% MeOH/H₂O over 4 minutes containing 0.1% NH₄OAc; 4 mL/min, monitoring at 220 nm); ¹H NMR (500 MHz, CDCl₃) δ 7.21-7.12 (m, 3H), 7.08 (dd, J=11, 8 Hz, 1H), 7.00-6.94 (m, 1H), 6.91-6.81 (m, 4H), 6.72-6.62 (m, 2H), 5.99-5.70 (m, 1H), 4.36 (s, 1H), 3.96 (d, J=13 Hz, 1H), 3.77 (s, 3H), 3.55 (d, J=13 Hz, 1H), 1.21 (s, 9H).

419

Procedure 59 g

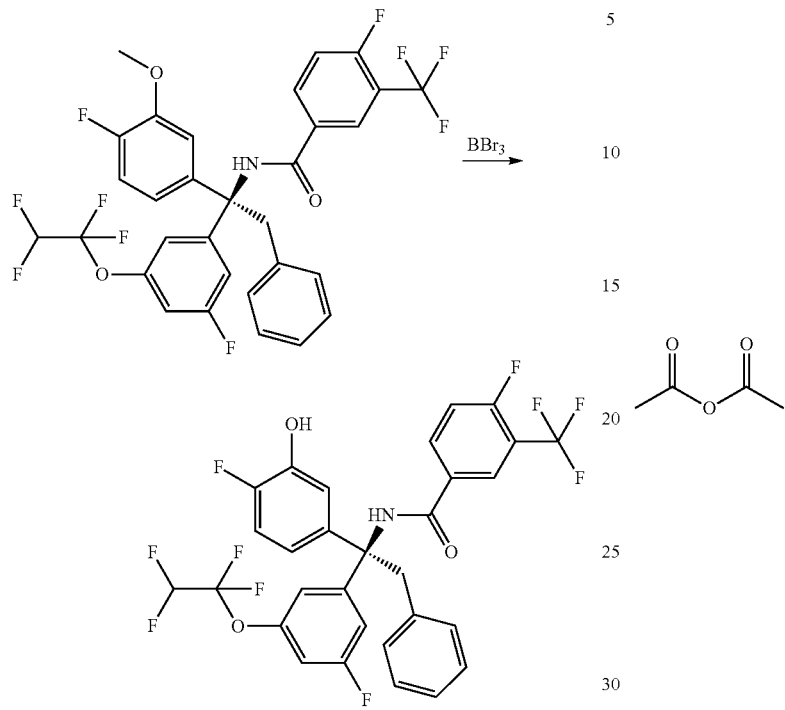

To a solution of (R)-4-fluoro-N-(1-(4-fluoro-3-methoxyphenyl)-1-(3-fluoro-5-(1,1,2,2-tetrafluoroethoxy)phenyl)-2-phenylethyl)-3-(trifluoromethyl)benzamide, prepared as described in Procedure 3, 59a-f, 6 and 7, (2.8 g, 4.43 mmol) in CH$_2$Cl$_2$ (15 mL) was added BBr$_3$ (12 mL, 12 mmol). The resulting mixture was stirred at room temperature for 2 h and quenched by addition of ice. The reaction mixture was diluted with EtOAc and washed with sat. NaHCO$_3$, sat. NaCl, dried over Na$_2$SO$_4$, filtered and concentrated to afford (R)-4-fluoro-N-(1-(4-fluoro-3-hydroxyphenyl)-1-(3-fluoro-5-(1,1,2,2)-tetrafluoro ethoxy)phenyl)-2-phenylethyl)-3-(trifluoromethyl)benzamide (Example 264) as clear oil (2.9 g, 100% yield). LCMS: RT=4.176 min [M+H] 632.2 (4 min Phenomenex Luna C18 column, 4.6×50 mm eluting with 10-90% MeOH/H$_2$O over 4 minutes containing 0.1% TFA; 4 mL/min, monitoring at 220 nm).

Example 265

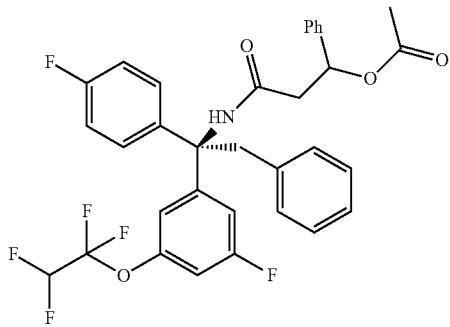 [SMILES: CC(=O)OC(CC(=O)N[C@](Cc1ccccc1)(c1ccc(F)cc1)c1cc(F)cc(OC(F)(F)C(F)F)c1)c1ccccc1]

420

3-((R)-1-(3-fluoro-5-(1,1,2,2-tetrafluoroethoxy)phenyl)-1-(4-fluorophenyl)-2-phenylethylamino)-3-oxo-1-phenylpropyl acetate Procedure 60

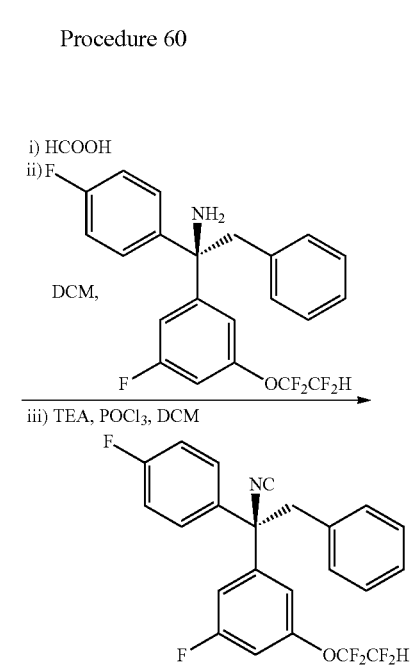

A solution of acetic anhydride (10 mL, 106 mmol) and formic acid (6 mL, 159 mmol) was heated at 60° C. for 3 h, then cooled to rt. An aliquot of the resulting solution (0.623 mL) was added to a solution of (R)-1-(3-fluoro-5-(1,1,2,2-tetrafluoroethoxy)phenyl)-1-(4-fluorophenyl)-2-phenylethanamine prepared as described in Procedure 3, 4, 5 and 6 (83 mg, 0.2 mmol) in DCE (1 mL). The reaction mixture was stirred at rt for 1.5 h, then concentrated under reduced pressure to yield a clear oil. The resulting oil was dissolved in DCM and purified by ISCO chromatography (12 g) with 0-30% EtOAc in hexane to yield (R)—N-(1-(3-fluoro-5-(1,1,2,2-tetrafluoroethoxy)phenyl)-1-(4-fluorophenyl)-2-phenylethyl)formamide as white solid (72 mg, 81% yield). LCMS: RT=2.02 min [M−NHCOH] 409.1 (2 min Phenomenex Luna C18 column, 4.6×30 mm eluting with 10-90% MeOH/H$_2$O over 2 minutes containing 0.1% TFA; 5 mL/min, monitoring at 220 nm). At 0° C. to a solution of (R)—N-(1-(3-fluoro-5-(1,1,2,2-tetrafluoroethoxy)phenyl)-1-(4-fluorophenyl)-2-phenylethyl)formamide (72 mg, 0.16 mmol) in DCM (2 mL) was added triethylamine (0.06 mL, 0.43 mmol) and POCl$_3$ (0.016 mL, 0.18 mmol). The reaction mixture was stirred at rt overnight, then diluted with EtOAc (15 mL). The organic layer was washed with sat. NaHCO$_3$ and sat. NaCl, dried over Na$_2$SO$_4$, filtered and concentrated under reduced pressure. The crude product was purified by ISCO chromatography (12 g) with 0-30% EtOAc in hexane to yield (R)-1-fluoro-3-(1-(4-fluorophenyl)-1-isocyano-2-phenylethyl)-5-(1,1,2,2-tetrafluoroethoxy)benzene as a white solid (60 mg, 87% yield). LCMS: RT=2.10 min [M−NC] 409.1 (2 min Phenomenex Luna C18 column, 4.6×30 mm eluting with 10-90% MeOH/H$_2$O over 2 minutes containing 0.1% TFA; 5 mL/min, monitoring at 220 nm). $^1$H NMR (400 MHz, CDCl$_3$) δ ppm 3.56-3.65 (m, 2H), 5.74-6.01 (m, 1H), 6.84 (d, J=7.03 Hz, 2H), 6.94 (d, J=7.03 Hz, 3H), 7.04-7.10 (m, 2H), 7.16-7.26 (m, 3H), 7.32 (dd, J=9.01, 5.05 Hz, 2H).

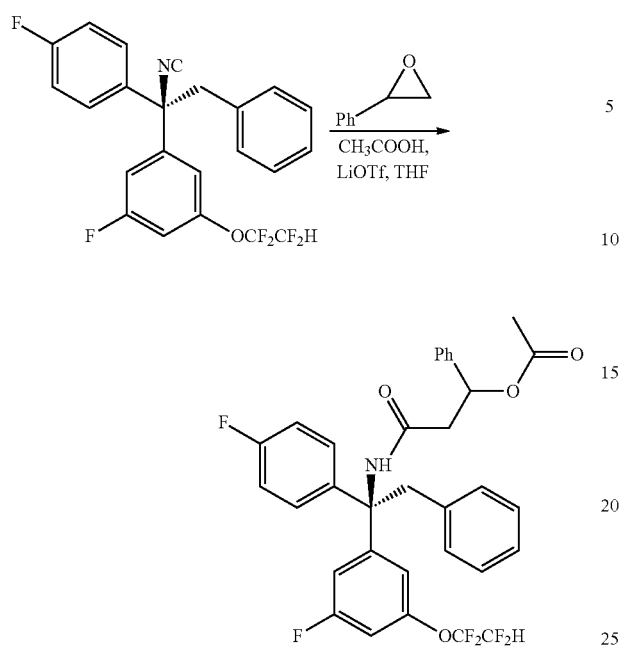

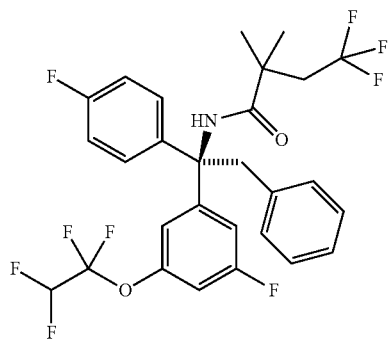 [SMILES: CC(C)(CC(F)(F)F)C(=O)N[C@](Cc1ccccc1)(c1ccc(F)cc1)c1cc(F)cc(OC(F)(F)C(F)F)c1]

Example 266

(R)-4,4,4-trifluoro-N-(1-(3-fluoro-5-(1,1,2,2-tetrafluoroethoxy)phenyl)-1-(4-fluorophenyl)-2-phenylethyl)-2,2-dimethylbutanamide Procedure 61

To a solution of 2-phenyloxirane (0.009 mL, 0.08 mmol) in THF (1.5 ml) was added LiOTf (12 mg, 0.08 mmol), (R)-1-fluoro-3-(1-(4-fluorophenyl)-1-isocyano-2-phenylethyl)-5-(1,1,2,2-tetrafluoroethoxy)benzene (30 mg, 0.07 mmol) and acetic acid (0.004 mL, 0.08 mmol) in succession. The reaction mixture was heated to reflux for 3 h. The reaction was allowed to cool to rt and diluted with EtOAc (15 mL). The organic layer was washed with sat. NaCl, dried over $Na_2SO_4$, filtered and concentrated under reduced pressure. The resulting crude mixture was purified by preparative HPLC YMC ODS S5 30×100 mm column 30-100% MeOH (90% in water, 0.1% TFA) gradient over 10 min with flow rate 40 mL/min and UV detection at 220 nm to yield 3-((R)-1-(3-fluoro-5-(1,1,2,2-tetrafluoroethoxy)phenyl)-1-(4-fluorophenyl)-2-phenylethylamino)-3-oxo-1-phenylpropyl acetate (Example 265) as a white solid (26 mg, yield 62%, 1:1 RR:RS diastereomer mixture). LCMS: RT=2.19 min [M+H] 616.3 (2 min Phenomenex Luna C18 column, 4.6×30 mm eluting with 10-90% MeOH/$H_2O$ over 2 minutes containing 0.1% TFA; 5 mL/min, monitoring at 220 nm); HPLC: RT=4.27 min, Purity 100% (Phenomenex Luna C18 column, 4.6×50 mm eluting with 10-90% MeOH/$H_2O$ over 4 minutes containing 0.2% PPA; 4 mL/min, monitoring at 220 nm); $^1$H NMR (400 MHz, $CDCl_3$) δ ppm 1.96 (d, J=4.95 Hz, 3H), 3.01 (ddd, J=14.30, 6.87, 3.02 Hz, 1H), 3.14 (td, J=8.94, 5.22 Hz, 1H), 3.523 (d, J=13.2 Hz, 0.5H), 3.62 (m, 0.5H), 3.72 (m, 0.5H), 3.82 (d, J=13.2 Hz, 0.5H), 5.30-5.34 (m, 1H), 5.74-5.97 (m, 1H), 6.46-6.53 (m, 2H), 6.60 (d, J=10.45 Hz, 1H), 6.67-6.72 (m, 1H), 6.80-7.31 (m, 13H).

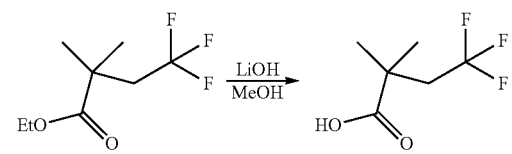

To a solution of ethyl 4,4,4-trifluoro-2,2-dimethylbutanoate (426 mg, 2.15 mmol) in MeOH (15 mL) was added a solution of LiOH in $H_2O$ (2 N, 5.35 mL, 10.75 mmol). The reaction mixture was stirred at room temperature overnight. The reaction was concentrated and the resulting mixture was diluted with DCM and washed with 3 N HCl. The aqueous layer was extracted twice with DCM. The combined organic layers were dried over $MgSO_4$, filtered and concentrated to yield 4,4,4-trifluoro-2,2-dimethylbutanoic acid as a colorless oil (370 mg, 100% yield). $^1$H NMR (400 MHz, $CDCl_3$) ppm 1.35 (s, 6H), 2.48 (ABqt, J=12 Hz, 2H).

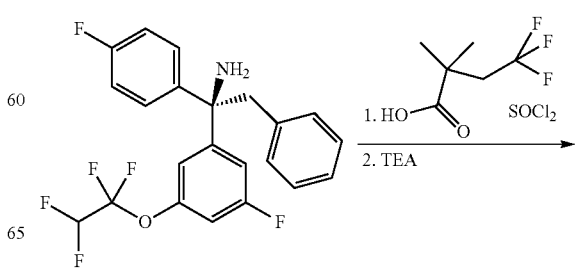

-continued

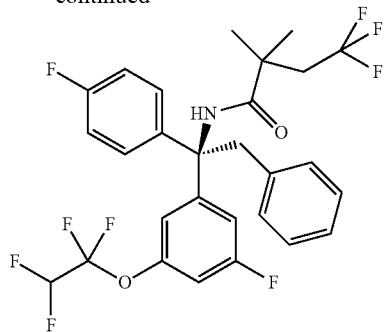

To a solution of 4,4,4-trifluoro-2,2-dimethylbutanoic acid (30 mg, 0.176 mmol) in DCE (1 mL) was added SOCl₂ (21 mg, 0.176 mmol) and the resulting mixture was refluxed for 2 h. After cooling to room temperature, TEA was added (82 uL, 0.59 mmol), followed by the addition of (R)-1-(3-fluoro-5-(1,1,2,2-tetrafluoroethoxy)phenyl)-1-(4-fluorophenyl)-2-phenylethanamine, prepared as described in Procedure 3, 4, 5 and 6, (25 mg, 0.059 mmol). The reaction mixture was heated to reflux overnight, concentrated and the residue was purified by preparative HPLC (Axia column, 30×100 mm, 40 mL/min, 40-100% ACN/H₂O/0.1% TFA over 12 min) to give (R)-4,4,4-trifluoro-N-(1-(3-fluoro-5-(1,1,2,2-tetrafluoroethoxy)phenyl)-1-(4-fluorophenyl)-2-phenylethyl)-2,2-dimethylbutanamide (Example 266) as a brownish oil (8 mg, 24% yield). LCMS: RT=2.13 min [M+H] 578.3 (Phenomenex Luna C18 column, 4.6×30 mm eluting with 10-90% MeOH/H₂O over 2 minutes containing 0.1% TFA; 5 mL/min, monitoring at 220 nm); ¹H NMR (400 MHz, CDCl₃) ppm 1.28 (s, 6H), 2.21-2.51 (m, 2H), 3.77 (ABqt, J=13 Hz, 2H), 5.83 (t, J=53 Hz, 1H), 6.37 (s, 1H), 6.65-6.74 (m, 2H), 6.75-6.95 (m, 3H), 6.94-7.09 (m, 4H), 7.09-7.31 (m, 3H).

Example 267

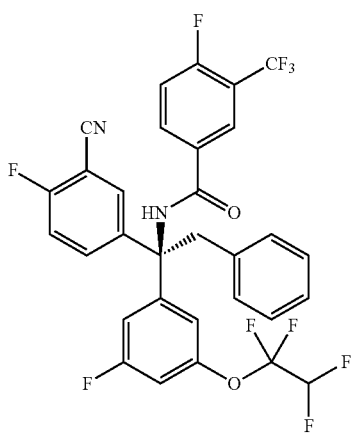 [SMILES: N#Cc1cc([C@@](Cc2ccccc2)(NC(=O)c2ccc(F)c(C(F)(F)F)c2)c2cc(F)cc(OC(F)(F)C(F)F)c2)ccc1F]

N-(1-(3-cyano-4-fluorophenyl)-1-(3-fluoro-5-(1,1,2,2-tetrafluoroethoxy)phenyl)-2-phenylethyl)-4-fluoro-3-(trifluoromethyl)benzamide Procedure 62

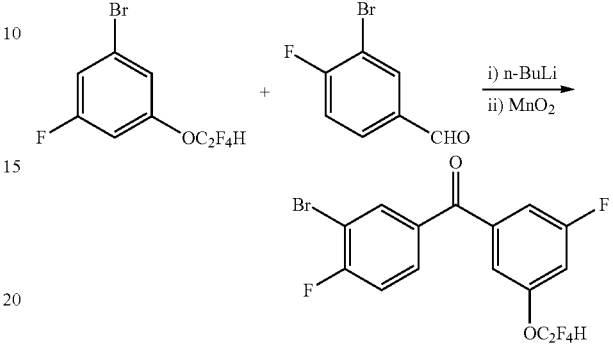

To a solution of 1-bromo-3-fluoro-5-(1,1,2,2-tetrafluoroethoxy)benzene (5.0 g, 17 mmol) in ether (40 mL) at −78° C. was added a solution of n-butyllithium (6.9 mL, 2.5 M, 17 mmol). The reaction mixture was stirred for 15 minutes and was added a solution of 3-bromo-4-fluorobenzaldehyde (3.5 g, 17 mmol) in ether (10 mL). The reaction was stirred at −78° C. for 2 h, then quenched with sat. NH₄Cl and warmed to room temperature. The ether layer was separated and dried over magnesium sulfate, filtered and concentrated to yield (3-bromo-4-fluorophenyl)(4-fluoro-2-(1,1,2,2-tetrafluoroethoxy)phenyl)methanol as an amber oil (6.5 g, 92% yield). The product was used in the next step without further purification. To a solution of (3-bromo-4-fluorophenyl)(4-fluoro-2-(1,1,2,2-tetrafluoroethoxy)phenyl)methanol (29.5 g, 71.3 mmol) in dichloromethane (600 mL) was added MnO₂ (30 g, 345 mmol). The reaction mixture was stirred for 6 h, then another 30 g of MnO₂ was added and the reaction continued to stir overnight. The MnO₂ addition was repeated twice and the reaction was stirred for a total of 48 h when the reaction was complete. The suspension was filtered through a pad of celite, the filtrate vas concentrated and the residue was purified by ISCO flash chromatography to yield (3-bromo-4-fluorophenyl)(4-fluoro-2-(1,1,2,2-tetrafluoroethoxy)phenyl)methanone as a yellow oil (60% yield). ¹H NMR (400 MHz, CDCl₃) δ ppm 8.06 (1H, d, J=6.59 Hz), 7.76 (1H, ddd, J=6.48, 4.50, 2.20 Hz), 7.38-7.44 (2H, m), 7.21-7.29 (2H, m), 6.09-5.83 (1H, t).

Alternatively, the following conditions may be used to oxidize 3-bromo-4-fluorophenyl)(4-fluoro-2-(1,1,2,2-tetrafluoroethoxy)phenyl)methanol to (3-bromo-4-fluorophenyl)(4-fluoro-2-(1,1,2,2-tetrafluoroethoxy)phenyl)methanone: To a solution of (3-bromo-4-fluorophenyl)(3-fluoro-5-(1,1,2,2-tetrafluoroethoxy)phenyl)methanol (3.6 g, 8.67 mmol) in CH₂Cl₂ (53.0 ml) was added pyridinium dichromate (4.89 g, 13.01 mmol), and activated molecular sieves (8.67 g, ~1 g/mmole). The resulting slurry was stirred at room temperature for 2 h. Celite (5 g) was added to the reaction mixture and the slurry stirred for 15 minutes then filtered. The filtrate was concentrated to in vacuo. The residue was dissolved in 20% EtOAc in Heptanes filtered through a 50 ml Isolute SPE filtration column (part #120-1028F) over Na₂SO₄ to give a clear pale yellow solution. The solvents were removed in vacuo to a give a yellow liquid which was purified by ISCO silica gel chromatography (80 g, 60 mL/min observation at 254 nm elution with heptane:EtOAc).

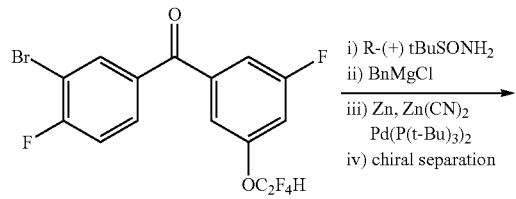

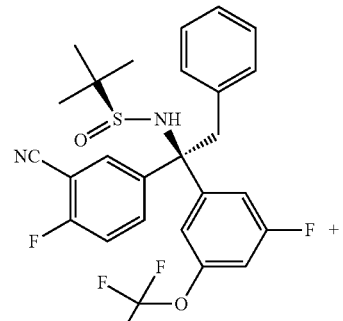

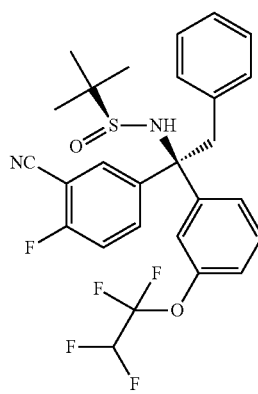

N-(1-(3-cyano-4-fluorophenyl)-1-(3-fluoro-5-(1,1,2,2-tetrafluoroethoxy)phenyl)-2-phenylethyl)-4-fluoro-3-(trifluoromethyl)benzamide was prepared as described in Procedure 5 and 6. The diastereomer mixture of N-(1-(3-cyano-4-fluorophenyl)-1-(3-fluoro-5-(1,1,2,2-tetrafluoroethoxy)phenyl)-2-phenylethyl)-4-fluoro-3-(trifluoromethyl)benzamide was separated by chiral preparative HPLC (chiralpak AD 20µ column, 5×50 cm, eluting with 60% IPA/Heptane with flow rate 50 mL/min). (R)—N—((S)-1-(3-cyano-4-fluorophenyl)-1-(3-fluoro-5-(1,1,2,2-tetrafluoroethoxy)phenyl)-2-phenylethyl)-2-methylpropane-2-sulfinamide (0.224 g, 18% yield) was eluted at a retention time of 19 min. LCMS: RT=2.23 min, Purity 71% [M+H] 555.3 (2 min Chromolith Performance RP 4.6×100 mm column, eluting with 10-90% MeOH/H$_2$O over 2 minutes containing 0.1% TFA with flow rate 5 mL/min, monitoring at 220 nm); Analytical Chiral HPLC: RT=4.01 min (Chiralpak AD 10 column 4.6×250 mm, isocratic elution with 50% IPA/Heptane with flow rate 1 mL/min, monitoring at 254 nm); $^1$H NMR (400 MHz, CDCl$_3$) ppm 1.23 (s, 9H), 3.55 (d, J=12.3 Hz, 1H), 3.97 (d, J=12.3 Hz, 1H), 5.89 (t, J=53.17 Hz, 1H) 6.85 (d, J=6.6 Hz, 2H), 6.94 (s, 1H), 7.00 (d, J=8.3 Hz, 1H), 7.12-7.22 (m, 4H), 7.24-7.29 (m, 2H), 7.37 (d, J=4.8 Hz, 1H). (R)—N—((R)-1-(3-cyano-4-fluorophenyl)-1-(3-fluoro-5-(1,1,2,2-tetrafluoroethoxy)phenyl)-2-phenylethyl)-2-methylpropane-2-sulfinamide (0.266 g, 22% yield) was eluted at a retention time of 41 min. LCMS: RT=2.23 min, purity 84% [M+H] 555.3 (2 min Chromolith Performance RP 4.6×100 mm column, eluting with 10-90% MeOH/H$_2$O over 2 minutes containing 0.1% TFA with flow rate 5 mL/min, monitoring at 220 nm); Analytical Chiral HPLC: RT=10.09 min (Chiralpak AD 10µ column 4.6×250 mm, isocratic elution with 50% IPA/Heptane with flow rate 1 mL/min, monitoring at 254 nm); $^1$H NMR (400 MHz, CDCl$_3$) ppm 1.18-1.25 (m, 9H), 3.59 (d, J=12.3 Hz, 1H), 3.99 (d, J=12.3 Hz, 1H), 4.30 (s, 1H), 5.87 (t, 1H) 6.64-6.71 (m, 2H), 6.90 (d, J=7.0 Hz, 3H), 7.15-7.22 (m, 3H), 7.23-7.29 (m, 2H), 7.64-7.71 (m, 2H).

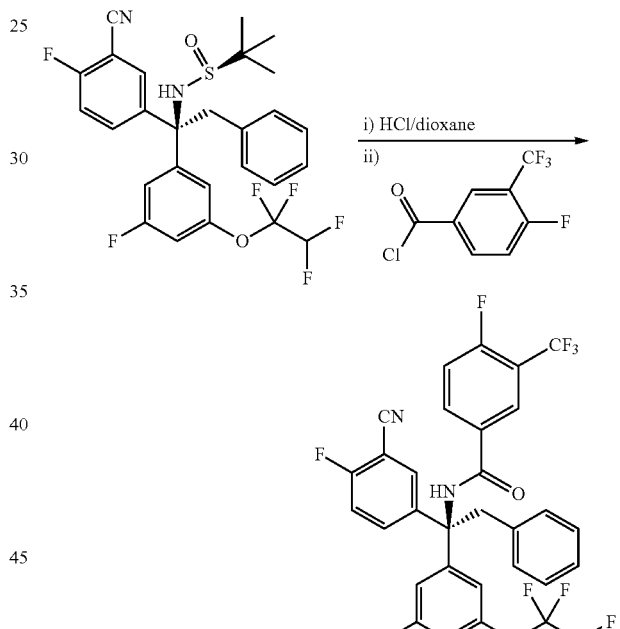

(R)—N-(1-(3-cyano-4-fluorophenyl)-1-(3-fluoro-5-(1,1,2,2-tetrafluoroethoxy)phenyl)-2-phenylethyl)-4-fluoro-3-(trifluoromethyl)benzamide (Example 267) was prepared as described in Procedure 6 and 7. LCMS: RT=2.342 min [M+H] 641.3 (2 min Chromolith Performance RP 4.6×100 mm column eluting with 10-90% MeOH/H$_2$O over 2 minutes containing 0.1% TFA with flow rate 5 mL/min. monitoring at 220 nm); HPLC: RT=4.358 min, Purity 95% (Phenomenex Luna C18 column, 4.6×50 mm eluting with 10-90% MeOH/H$_2$O over 4 minutes containing 0.2% PPA with flow rate 4 mL/min, monitoring at 220 nm); $^1$H NMR (400 MHz, CDCl$_3$) δ ppm 3.76-3.81 (m, 2H), 5.89 (t, J=53.1 Hz, 1H), 6.68-6.73 (m, 3H), 6.81-6.85 (m, 2H), 6.99 (d, J=8.3 Hz, 1H), 7.19-7.30 (m, 6H), 7.54-7.58 (m, 2H), 7.82-7.86 (m, 1H), 7.92 (d, J=6.6 Hz, 1H).

Example 268

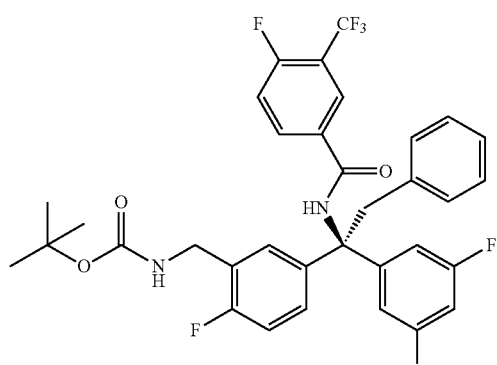

(R)-tert-butyl 2-fluoro-5-(1-(4-fluoro-3-(trifluoromethyl)benzamido)-1-(3-fluoro-5-(1,1,2,2-tetrafluoroethoxy)phenyl)-2-phenylethyl)benzylcarbamate Procedure 63

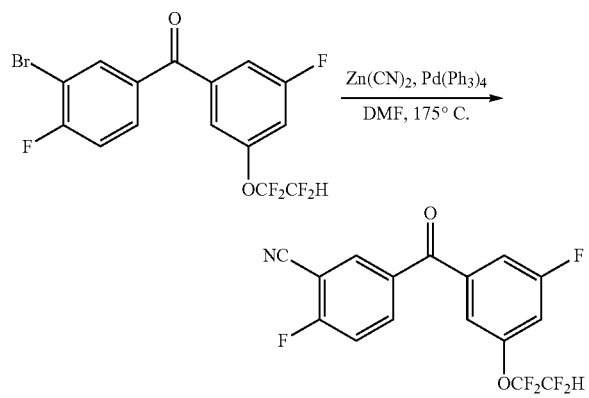

A mixture of (3-bromo-4-fluorophenyl)(3-fluoro-5-(1,1,2,2-tetrafluoroethoxy)phenyl)methanone, prepared as described in Procedure 3 and 62, (2.0 g, 4.84 mmol), zinc cyanide (568 mg, 4.84 mmol) and tetrakis(triphenyphoshine) palladium (559 mg, 0.48 mmol) in DMF was heated at 175° C. under microwave irradiation for 10 minutes. The reaction mixture was allowed to cool to room temperature, poured into H$_2$O and the aqueous layer was extracted with EtOAc. The organic layer was dried over Na$_2$SO$_4$, filtered and concentrated. The crude product was purified by ISCO chromatography (12 g column, 0-20% EtOAc/hexane) to yield 2-fluoro-5-(3-fluoro-5-(1,1,2,2-tetrafluoroethoxy)benzoyl)benzonitrile as a colorless oil (1.5 g, 86% yield). $^1$H NMR (400 MHz, CDC$_3$) δ ppm 8.11 (m, 2H), 7.41 (m, 3H), 7.27 (m, 1H), 5.97 (m, 1H).

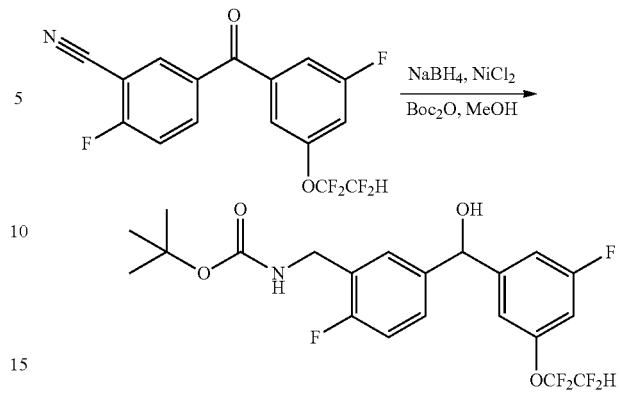

To a solution of 2-fluoro-5-(3-fluoro-5-(1,1,2,2-tetrafluoroethoxy)benzoyl)benzonitrile (1.30 g, 3.62 mmol), BOC$_2$O (1.68 mL, 7.24 mmol) and Nickel (II) chloride (0.47 g, 3.62 mmol) in MeOH at 0° C. was added sodium borohydride (0.96 g, 25.3 mmol). The reaction mixture was stirred at 0° C. for 30 minutes and then at room temperature for 6 h. The reaction mixture was filtered through celite and the filtrate was concentrated. The residue was diluted with EtOAc and the solution was washed with sat. NaHCO$_3$. The organic layer was dried over Na$_2$SO$_4$, filtered and concentrated to yield tert-butyl 2-fluoro-5-((3-fluoro-5-(1,1,2,2-tetrafluoroethoxy)phenyl)(hydroxy)methyl)benzylcarbamate as a clear, colorless oil (1.43 g, 85% yield). This product was used in the next step without further purification. $^1$H NMR (400 MHz, CDCl$_3$) δ ppm 7.32 (m, 1H), 7.22 (m, 1H), 7.03 (m, 3H),), 6.87 (d, J=8.84 Hz, 1H), 5.90 (m, 2H), 4.98 (br. s., 1H), 4.31 (d, J=5.05 Hz, 2H).

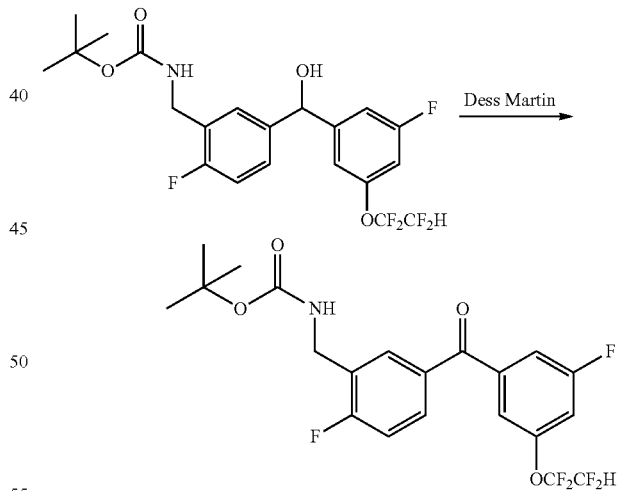

To a solution of tert-butyl 2-fluoro-5-(hydroxy(3-(1,1,2,2-tetrafluoroethoxy)-5-(trifluoromethyl)phenyl)methyl)benzylcarbamate (1.43 g, 2.77 mmol) in CH$_2$Cl$_2$ (25 mL) was added 1,1,1-tris(acetyloxy)-1,1-dihydro-1,2-benziodoxol-3-(1H)-one (1.77 g, 4.16 mmol) at rt. Water (0.2 mL) in CH$_2$Cl$_2$ (1 mL) was then added to the reaction mixture and the resulting solution was stirred at rt for 3 h, then the solid was filtered and the filtrate was concentrated. The residue was purified by ISCO chromatography (12 g column, 0-30% EtOAc/hexane) to yield tert-butyl 2-fluoro-5-(3-fluoro-5-(1,1,2,2-tetrafluoroethoxy)benzoyl) as a clear, colorless oil (915 mg, 64% yield). ¹H NMR (400 MHz, CDCl₃) δ ppm 7.85 (d, J=7.07 Hz, 1H), 7.73 (m, 1H), 7.40 (m, 2H), 7.18 (m, 2H), 7.00 (m, 1H), 5.96 (m, 1H), 1.41 (m, 9H).

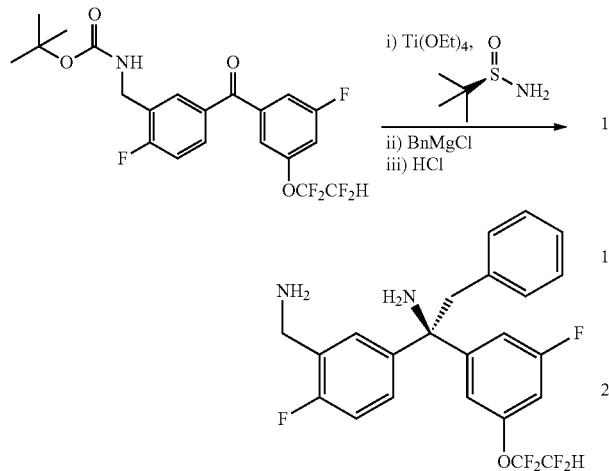

Following Procedure 5 and 6, tert-butyl 5-((1R)-1-(1,1-dimethylethylsulfinamido)-1-(3-fluoro-5-(1,1,2,2-tetrafluoroethoxy)phenyl)-2-phenylethyl)-2-fluorobenzylcarbamate was prepared and isolated by ISCO chromatography (40 g column, eluting with 0-40% EtOAc/hexane). Following Procedure 6, (R)-1-(3-(aminomethyl)-4-fluorophenyl)-1-(3-fluoro-5-(1,1,2,2-tetrafluoroethoxy)-phenyl)-2-phenylethanamine was prepared as a colorless oil (214 mg, 40% yield). ¹H NMR (500 MHz, CDCl₃) δ ppm 7.32 (d, J=5.50 Hz, 1H), 7.19 (m, 4H), 6.98 (br. s., 3H), 6.84 (d, J=7.70 Hz, 1H), 6.72 (d, J=6.60 Hz, 2H), 5.86 (t, J=53.06 Hz, 1H), 3.85 (br. s., 2H), 3.50 (m, 2H).

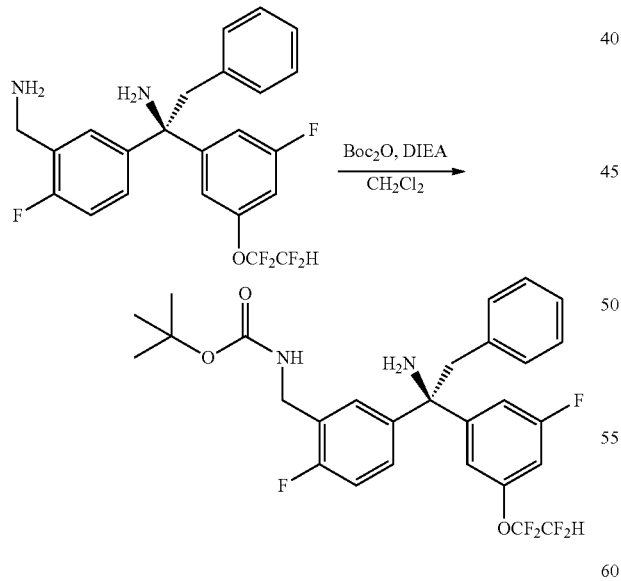

To a solution of (R)-1-(3-(aminomethyl)-4-fluorophenyl)-1-(3-fluoro-5-(1,1,2,2-tetrafluoroethoxy)phenyl)-2-phenylethanamine (229 mg, 0.50 mmol) at 0° C. in CH₂Cl₂ (5 mL) was added DIEA (0.11 mL, 0.61 mmol) and (Boc)₂O (0.12 mL, 0.50 mmol). The reaction mixture was stirred at 0° C. for 1.5 h and was then poured into sat. NH₄Cl and the aqueous layer was extracted with EtOAc. The organic phase was dried over Na₂SO₄, filtered and concentrated. The resulting residue was purified by ISCO column chromatography (12 g, 0-30% EtOAc/hexane) to yield (R)-tert-butyl 5-(1-amino-1-(3-fluoro-5-(1,1,2,2-tetrafluoroethoxy)phenyl)-2-phenylethyl)-2-fluorobenzylcarbamate as a white foam (202 mg, 72% yield). ¹H NMR (400 MHz, CDCl₃) δ ppm 3.49 (s, 2H), 7.34 (m, 1H), 7.17 (m, 4H), 6.97 (m, 3H), 6.83 (d, J=8.84 Hz, 1H), 6.73 (d, J=6.32 Hz, 2H), 5.86 (m, 1H), 4.86 (br. s., 1H), 4.31 (d, J=4.55 Hz, 2H), 3.49 (s, 2H), 1.42 (s, 9H).

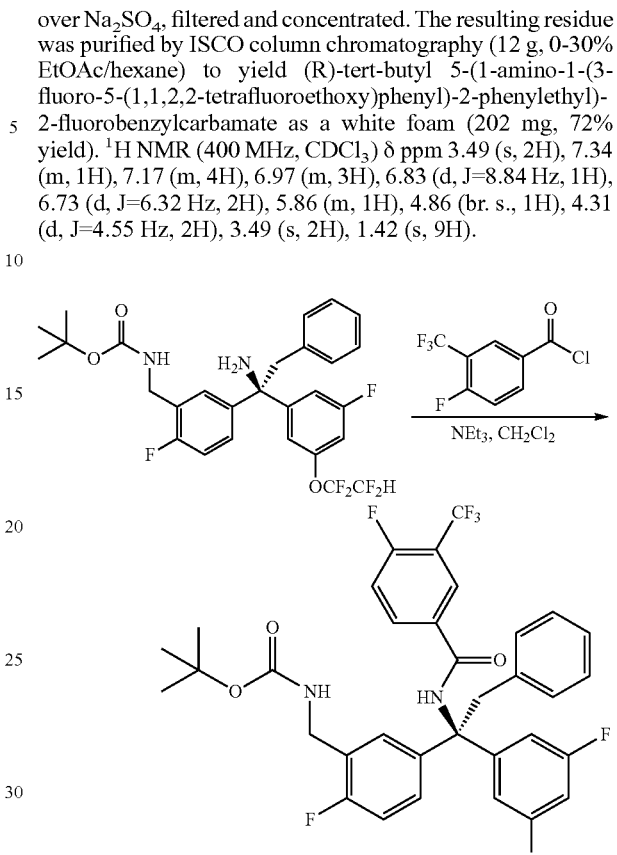

(R)-tert-Butyl 2-fluoro-5-(1-(4-fluoro-3-(trifluoromethyl)benzamido)-1-(3-fluoro-5-(1,1,2,2-tetrafluoroethoxy)phenyl)-2-phenylethyl)benzylcarbamate (Example 268) was prepared as a colorless oil (220 mg, 91% yield) using the method described in Procedure 7. LCMS: RT=3.47 min [M+H-17]538 (Phemonenex Luna C18, 50×4.6 mm, 4 min gradient, eluting with 105-90% MeOH/H₂O containing 0.1% TFA, monitoring at 220 nm); ¹H NMR (400 MHz, CDCl₃) δ ppm 7.97 (d, J=5.31 Hz, 1H), 7.84 (br. s., 1H), 7.24 (m, 2H), 7.15 (m, 3H), 6.96 (m, 5H), 6.71 (m, 3H), 5.86 (m, 1H), 4.84 (br. s., 1H), 4.27 (t, J=6.19 Hz, 2H), 4.02 (m, 1H), 3.79 (d, J=13.14 Hz, 1H), 1.37 (s, 9H).

Example 269

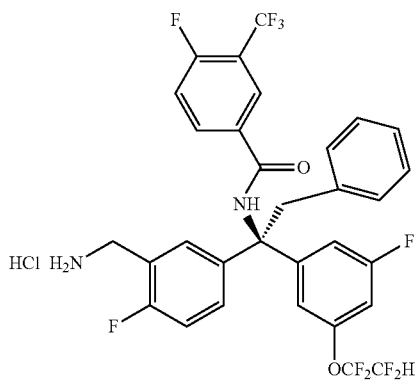

431

(R)—N-(1-(3-(aminomethyl)-4-fluorophenyl)-1-(3-fluoro-5-(1,1,2,2-tetrafluoroethoxy)phenyl)-2-phenylethyl)-4-fluoro-3-(trifluoromethyl)benzamide hydrochloride Procedure 64

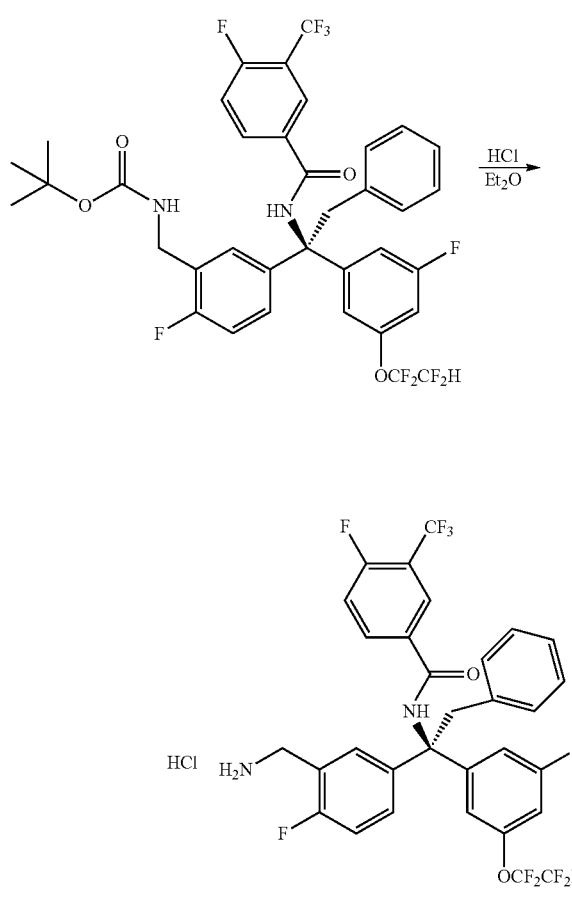

To a solution of (R)-tert-butyl 5-(1-amino-1-(3-fluoro-5-(1,1,2,2-tetrafluoroethoxy)phenyl)-2-phenylethyl)-2-fluorobenzylcarbamate (222 mg, 0.30 mmol) in DCM (5 ml) at rt was added 2 M HCl in diethyl ether (1.49 mL, 1.49 mmol). The reaction mixture was stirred for 2 h, then concentrated under reduced pressure to yield (R)—N-(1-(3-(aminomethyl)-4-fluorophenyl)-1-(3-fluoro-5-(1,1,2,2-tetrafluoroethoxy)phenyl)-2-phenylethyl)-4-fluoro-3-(trifluoromethyl)benzamide hydrochloride (Example 269) as a white foam (216 mg, 100%). $^1$H NMR (400 MHz, CDCl$_3$) δ ppm 7.95 (m, 1H), 7.84 (m, 1H), 7.19 (m, 4H), 6.91 (m, 3H), 6.70 (d, J=7.07 Hz, 2H), 5.88 (m, 1H), 4.24 (t, J=5.31 Hz, 1H), 4.06 (m, 1H), 3.79 (m, 2H).

432

Example 270

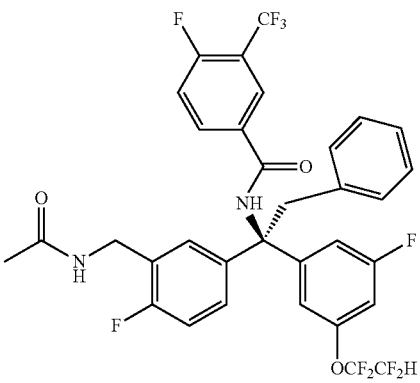

(R)—N-(1-(3-(acetamidomethyl)-4-fluorophenyl)-1-(3-fluoro-5-(1,1,2,2-tetrafluoroethoxy)phenyl)-2-phenylethyl)-4-fluoro-3-(trifluoromethyl)benzamide Procedure 65

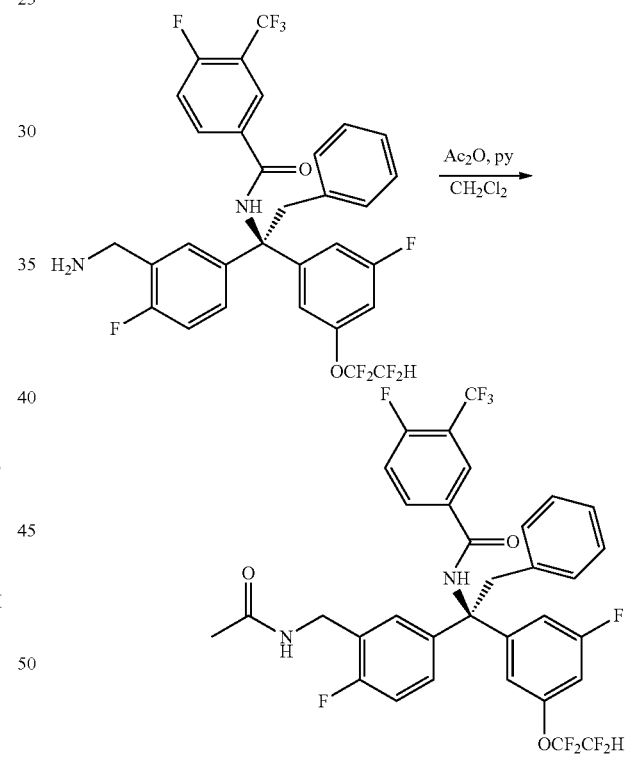

To a solution of (R)—N-(1-(3-(aminomethyl)-4-fluorophenyl)-1-(3-fluoro-5-(1,1,2,2-tetrafluoroethoxy)phenyl)-2-phenylethyl)-4-fluoro-3-(trifluoromethyl)benzamide hydrochloride (Example 269, 30 mg, 0.04 mmol) in DCM (2 mL) at rt was added pyridine (7.8 μL, 0.1 mmol) followed by acetic anhydride (4.6 μL, 0.05 mmol). The reaction mixture was stirred at rt for 1 h, then poured into 1N HCl and the aqueous layer was extracted with EtOAc. The organic layer was dried over Na$_2$SO$_4$, filtered and concentrated. The resulting residue was purified by ISCO column chromatography (4 g, 0-50% EtOAc/hexane) to yield (R)—N-(1-(3-(acetamidomethyl)-4-fluorophenyl)-1-(3-fluoro-5-(1,1,2,2-tetrafluoroethoxy)phenyl)-2-phenylethyl)-4-fluoro-3-(trifluoromethyl)benzamide (Example 270) as a white foam (21 mg, 100%). $^1$H NMR (400 MHz, CDCl$_3$) δ ppm 7.98 (dd, J=6.57, 2.02 Hz, 1H), 7.86 (dt, J=8.53, 2.18 Hz, 1H), 7.25 (m, 2H), 7.13 (m, 3H), 6.99 (m, 5H), 6.81 (s, 1H), 6.69 (m, 2H), 5.87 (m, 2H), 4.38 (m, 2H), 4.04 (d, J=13.14 Hz, 1H), 3.75 (d, J=13.14 Hz, 1H), 1.92 (s, 3H).

Example 271

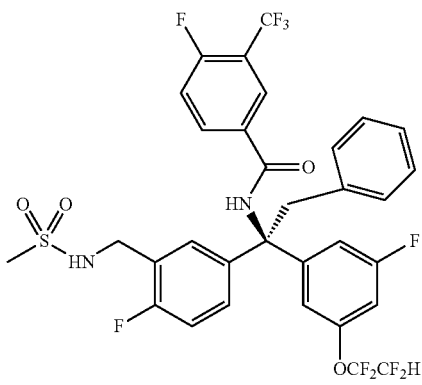

(R)-4-fluoro-N-(1-(4-fluoro-3-(methylsulfonamidoethyl)phenyl)-1-(3-fluoro-5-(1,1,2,2-tetrafluoroethoxy)phenyl)-2-phenylethyl)-3-(trifluoromethyl)benzamide Procedure 66

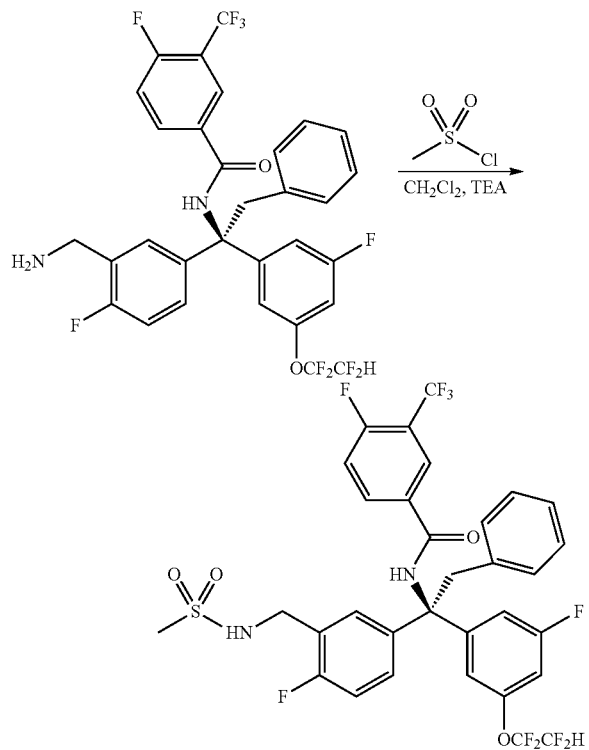

To a solution of (R)—N-(1-(3-(aminomethyl)-4-fluorophenyl)-1-(3-fluoro-5-(1,1,2,2-tetrafluoroethoxy)phenyl)-2-phenylethyl)-4-fluoro-3-(trifluoromethyl)benzamide hydrochloride (Example 269, 30 mg, 0.04 mmol) in DCM (2 mL) at rt was added TEA (6.8 µL, 0.05 mmol) followed by methanesulfonyl chloride (3.4 µL, 0.04 mmol). The reaction mixture was stirred at rt for 1 h and then poured into 1 N HCl. The aqueous layer was extracted with CH$_2$Cl$_2$ and the combined organic layers were dried over Na$_2$SO$_4$, filtered and concentrated. The residue was purified by ISCO column chromatography (4 g, 0-40% EtOAc/hexane) to yield (R)-4-fluoro-N-(1-(4-fluoro-3-(methylsulfonamidomethyl)phenyl)-1-(3-fluoro-5-(1,1,2,2-tetrafluoroethoxy)phenyl)-2-phenylethyl)-3-(trifluoromethyl)benzamide (Example 271) as a clear, colorless film (12 mg, 41%). $^1$H NMR (400 MHz, CDCl$_3$) 7.95 (dd, J=6.57, 2.02 Hz, 1H), 7.86 (m, 1H), 7.22 (m, 7H), 7.07 (t, J=8.97 Hz, 1H), 6.93 (m, 3H), 6.71 (m, 3H), 5.88 (m, 1H), 4.55 (t, J=6.32 Hz, 1H), 4.30 (t, J=5.81 Hz, 2H), 3.97 (m, 1H), 3.83 (m, 1H), 2.81 (s, 3H).

Example 272

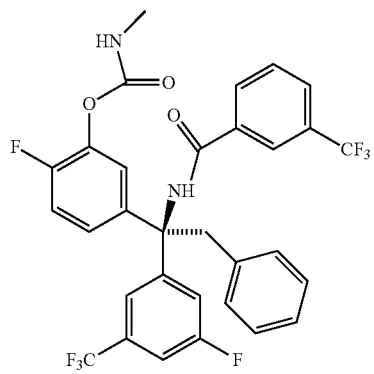 [SMILES: CNC(=O)Oc1cc([C@@](Cc2ccccc2)(NC(=O)c2cccc(C(F)(F)F)c2)c2cc(F)cc(C(F)(F)F)c2)ccc1F]

(R)-2-fluoro-5-(1-(3-fluoro-5-(trifluoromethyl)phenyl)-2-phenyl-1-(3-(trifluoromethyl)benzamido)ethyl)phenyl methylcarbamate Procedure 67

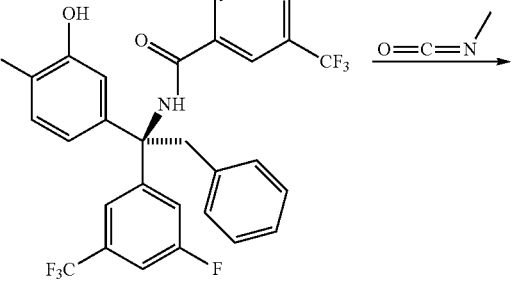

435

-continued

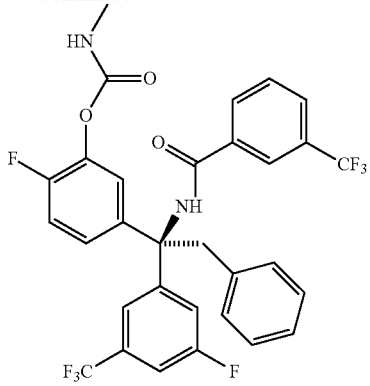

A solution of (R)—N-(1-(4-fluoro-3-hydroxyphenyl)-1-(3-fluoro-5-(trifluoromethyl)phenyl)-2-phenylethyl)-3-(trifluoromethyl)benzamide, prepared as described in Example 264, (15 mg, 0.027 mmol), methylisocyanate (0.01 mL), and Et$_3$N (0.02 mL) in CH$_2$Cl$_2$ (0.3 mL) was heated at 80° C. under microwave irradiation for 10 min. After cooling, the reaction mixture was diluted with EtOAc and the organic layer was washed with H$_2$O, sat. NaCl, dried over Na$_2$SO$_4$, filtered and concentrated. The residue was purified by ISCO flash chromatography (silica gel, hexanes/EtOAc) to yield (R)-2-fluoro-5-(1-(3-fluoro-5-(trifluoromethyl)phenyl)-2-phenyl-1-(3-(trifluoromethyl)-benzamido)-ethyl)phenyl methylcarbamate (Example 272, 11 mg, yield: 61%). LCMS: RT=2.13 min [M+H] 623.3 (Phenomenex Luna C18 column, 4.6×30 mm eluting with 10-90% MeOH/H$_2$O over 2 minutes containing 0.1% TFA; 5 mL/min, monitoring at 220 nm).

Example 273

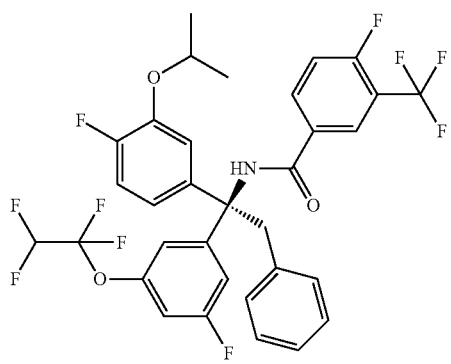 [SMILES: CC(C)Oc1cc([C@@](Cc2ccccc2)(NC(=O)c2ccc(F)c(C(F)(F)F)c2)c2cc(F)cc(OC(F)(F)C(F)F)c2)ccc1F]

436

(R)-4-fluoro-N-(1-(4-fluoro-3-isopropoxyphenyl)-1-(3-fluoro-5(1,1,2,2-tetrafluoro ethoxy)phenyl)-2-phenylethyl)-3-(trifluoromethyl)benzamide Procedure 68

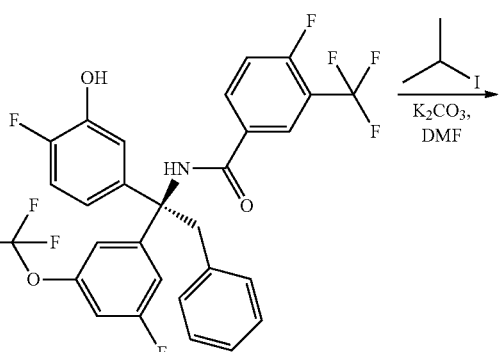

To a solution of (R)-4-fluoro-N-(1-(4-fluoro-3-hydroxyphenyl)-1-(3-fluoro-5-(1,1,2,2)-tetrafluoro ethoxy)phenyl)-2-phenylethyl)-3-(trifluoromethyl)benzamide (Example 264, 2.70 g, 4.27 mmol) in DMF (6 mL) was added K$_2$CO$_3$ (1.47 g, 10.69 mmol), followed by isopropyl iodide (0.64 mL, 6.40 mmol). The reaction mixture was stirred at 60° C. for 16 h. The reaction mixture was filtered and the solid was washed with EtOAc. The filtrate was washed with H$_2$O, sat. NaCl, dried over Na$_2$SO$_4$ and concentrated under reduced pressure. The residue was purified by ISCO silica gel column using 0 to 50% EtOAc in hexane as eluting solvents to yield (R)-4-fluoro-N-(1-(4-fluoro-3-isopropoxyphenyl)-1-(3-fluoro-5(1,1,2,2-tetrafluoro ethoxy)phenyl)-2-phenylethyl)-3-(trifluoromethyl)benzamide (Example 273) as white powder (2.4 g, 83% yield). LCMS: RT=4.05 min [M+H] 674.1 (Phenomenex Luna C18 column, 4.6×50 mm eluting with 10-90% MeOH/H$_2$O over 4 minutes containing 0.1% TFA; 5 mL/min, monitoring at 220 nm). $^1$H NMR (400 MHz, CD$_3$OD) δ ppm 7.95-8.00 (2H, m), 7.42-7.47 (1H, m), 7.19 (1H, t, J=7.47 Hz), 7.12 (3H, t, J=7.25 Hz), 6.99-7.07 (3H, m), 6.71-6.81 (4H, m), 6.14-6.41 (1H, m), 4.26-4.32 (1H, m, J=6.15, 6.15, 6.15, 6.15 Hz), 4.12 (1H, d, J=13.18 Hz), 3.85 (1H, d, J=12.74 Hz), 1.23 (3H, d, J=6.15 Hz), 1.17 (3H, d, J=6.15 Hz).

Example 274

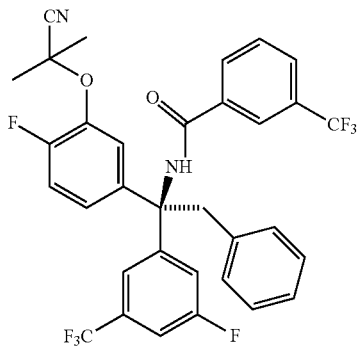 [SMILES: CC(C)(C#N)Oc1cc([C@@](Cc2ccccc2)(NC(=O)c2cccc(C(F)(F)F)c2)c2cc(F)cc(C(F)(F)F)c2)ccc1F]

(R)—N-(1-(3-(1-amino-2-methyl-1-oxopropan-2-yloxy)-4-fluorophenyl)-1-(3-fluoro-5-(trifluoromethyl)phenyl)-2-phenylethyl)-3-(trifluoromethyl)benzamide Procedure 69

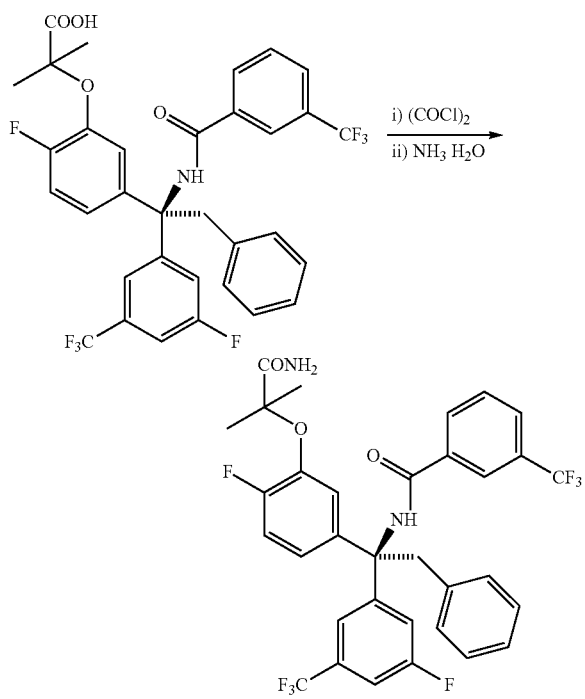

At 0° C. to a solution of (R)-2-(2-fluoro-5-(1-(3-fluoro-5-(trifluoromethyl)phenyl)-2-phenyl-1-(3-(trifluoromethyl)benzamido)ethyl)phenoxy)-2-methylpropanoic acid, prepared as described in Procedure 68 and 23, (60 mg, 0.092 mmol, yield 91%) in $CH_2Cl_2$ was added DMF (1 drop), followed by the addition of $(COCl)_2$ (0.02 mL). The reaction mixture was stirred at 0° C. for 30 min, then concentrated and dried in vacuo. The resulting residue was dissolved in THF (1 mL) and cooled to 0° C. followed by the addition of concentrated $NH_4OH$ (3 mL). The resulting mixture was stirred at rt for 1 h, then concentrated under reduced pressure. The residue was diluted with $CH_2Cl_2$ and the organic layer was washed with $H_2O$, saturated NaCl, dried over $Na_2SO_4$, filtered and concentrated. The residue was purified by flash chromatography (silica gel, hexanes/EtOAc) to give pure (R)—N-(1-(3-(1-amino-2-methyl-1-oxopropan-2-yloxy)-4-fluorophenyl)-1-(3-fluoro-5-(trifluoromethyl)phenyl)-2-phenylethyl)-3-(trifluoromethyl)benzamide (Example 274, 40 mg, yield: 67%). LCMS: RT=2.15 min [M+H] 651.2 (Phenomenex Luna C18 column, 4.6×30 mm eluting with 10-90% $MeOH/H_2O$ over 2 minutes containing 0.1% TFA; 5 mL/min, monitoring at 220 nm).

Example 275

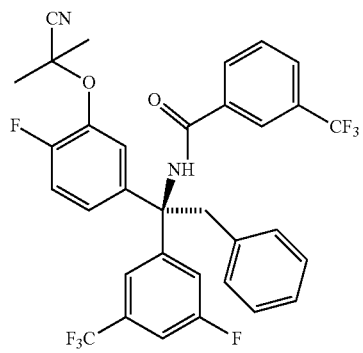 [SMILES: CC(C)(C#N)Oc1cc([C@@](Cc2ccccc2)(NC(=O)c2cccc(C(F)(F)F)c2)c2cc(F)cc(C(F)(F)F)c2)ccc1F]

(R)—N-(1-(3-(2-cyanopropane-2-yloxy)-4-fluorophenyl)-1-(3-fluoro-5-(trifluoromethyl)phenyl)-2-phenylethyl)-3-(trifluoromethyl)benzamide Procedure 70

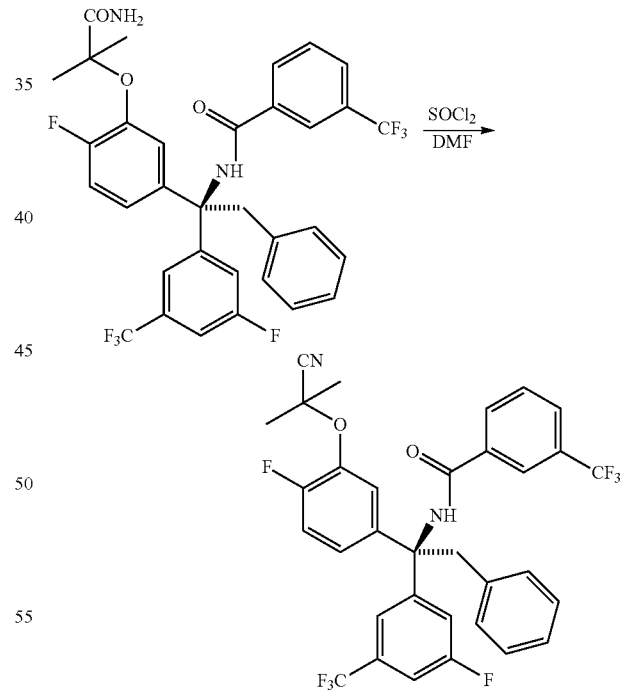

To a solution of (R)—N-(1-(3-(1-amino-2-methyl-1-oxopropan-2-yloxy)-4-fluorophenyl)-1-(3-fluoro-5-(trifluoromethyl)phenyl)-2-phenylethyl)-3-(trifluoromethyl)benzamide (Example 274, 30 mg, 0.046 mmol) in DMF (1 mL) at room temperature was added thionyl chloride (3 drops). The reaction mixture was stirred for 40 min and diluted with $H_2O$ and EtOAc. The organic layer was washed with $H_2O$, saturated $NaHCO_3$, $H_2O$ and saturated NaCl, dried over $Na_2SO_4$, filtered and concentrated under reduced pressure. The resulting residue was purified by flash chromatography (silica gel, hexanes/EtOAc) to give pure (R)—N-(1-(3-(2-cyanopropan-2-yloxy)-4-fluorophenyl)-1-(3-fluoro-5-(trifluoromethyl) phenyl)-2-phenylethyl)-3-(trifluoromethyl)benzamide (Example 275, 16 mg, yield: 55%). LCMS: RT=2.21 min [M+H] 633.3 (Phenomenex Luna C18 column, 4.6×30 mm eluting with 10-90% MeOH/H$_2$O over 2 minutes containing 0.1% TFA; 5 mL/min, monitoring at 220 nm).

Example 276

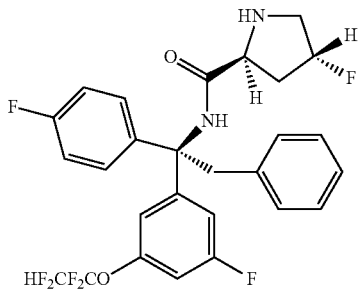

(2S,4R)-4-fluoro-N—((R)-1-(3-fluoro-5-(1,1,2,2-tetrafluoroethoxy)-phenyl)-1-(4-fluorophenyl)-2-phenylethyl)pyrrolidine-2-carboxamide Procedure 71

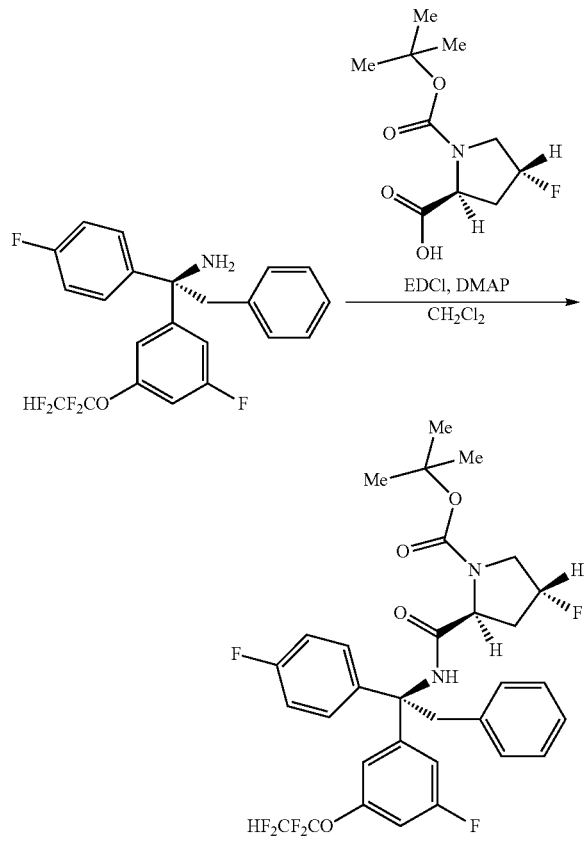

To a solution of (R)-1-(3-fluoro-5-(1,1,2,2-tetrafluoroethoxy)phenyl)-1-(4-fluorophenyl)-2-phenylethanamine (42 mg, 0.1 mmol), prepared as described in Procedure 3, 4, 5 and 6, and (2S,4R)-1-(tert-butoxycarbonyl)-4-fluoropyrrolidine-2-carboxylic acid (23 mg, 0.1 mmol) in CH$_2$Cl$_2$ (1 mL) was added EDCI (25 mg, 0.1 mmol) and DMAP (16 mg, 0.1 mmol). The reaction mixture was stirred overnight and concentrated to dryness under a stream of argon. The resulting residue was dissolved in MeOH and purified by preparative HPLC (Phenoma Luna AXIA 10A, C18, eluting with 10-90% MeCN/H$_2$O containing 0.1% TFA, monitoring at 220 nm) to provide (2S,4R)-tert-butyl 4-fluoro-2-((R)-1-(3-fluoro-5-(1,1,2,2-tetrafluoroethoxy)phenyl)-1-(4-fluorophenyl)-2-phenylethylcarbamoyl)pyrrolidine-1-carboxylate (40 mg, 64% yield) as a white solid. $^1$H NMR (500 MHz, CDCl$_3$) δ ppm 8.30 (s, 1H), 7.13-7.03 (m, 5H), 6.95-6.90 (m, 2H), 6.80-6.78 (m, 2H), 6.70 (bs, 1H), 6.51-6.47 (m, 2H), 5.88-5.67 (m, 1H, —CF$_2$H), 5.10 (app d, J=50 Hz, 1H, —CFH), 4.48-4.45 (m, 1H), 3.89-3.78 (m, 2H), 3.70 (d, J=10 Hz, 1H0, 3.29-3.18 (m, 1H), 2.79-2.55 (m, 2H), 2.25-2.11 (m, 1H), 1.32 (s, 9H); LC/MS: RT=3.746 min [M+H] 641.2 Phenomenex Luna C18 column, 4.6×50 mm eluting with 10-90% MeCN/H$_2$O over 4 minutes containing 0.1% NH$_4$OAc; 4 mL/min, monitoring at 220 nm.

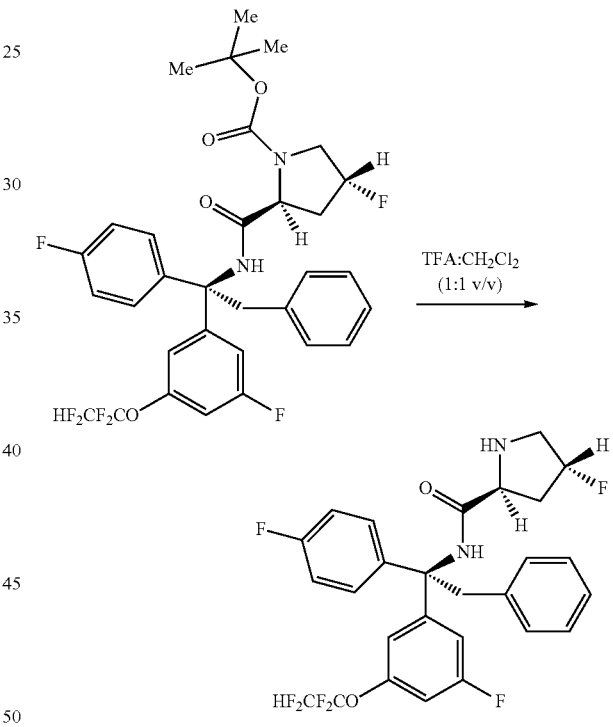

(2S,4R)-tert-butyl 4-fluoro-2-((R)-1-(3-fluoro-5-(1,1,2,2-tetrafluoroethoxy)phenyl)-1-(4-fluorophenyl)-2-phenylethylcarbamoyl)pyrrolidine-1-carboxylate (18 mg, 0.03 mmol) was dissolved in a solution of CH$_2$Cl$_2$ (1 mL)/TFA (1 mL) at rt. The reaction mixture was stirred overnight and concentrated to dryness under a stream of argon. The resulting residue was dissolved in MeOH and purified by preparative HPLC (Phenoma Luna AXIA 10A, C18, eluting with 10%-90% MeCN/H$_2$O containing 0.1% TFA, monitoring at 220 nm) to provide (2S,4R)-4-fluoro-N—((R)-1-(3-fluoro-5-(1,1,2,2-tetrafluoroethoxy)-phenyl)-1-(4-fluorophenyl)-2-phenylethyl)pyrrolidine-2-carboxamide (Example 276) as a white solid (13 mg, 83% yield). $^1$H NMR (500 MHz, MeOH-d$_4$) δ ppm 7.22-7.13 (m, 7H), 7.07-6.96 (m, 7H), 6.68 (d, J=5 Hz, 2H), 6.40-6.18 (m, 1H, —CF$_2$H), 5.43 (app d, J=50 Hz, 1H, —CFH), 4.55-4.51 (m, 1H), 4.01 (d, J=10 Hz, 1H), 3.92

(d, J=15 Hz, 1H), 3.65-3.49 (m, 2H), 2.72-2.64 (m, 1H), 2.10-1.96 (m, 1H); LC/MS: RT=3.310 min [M+H] 541.2 (Phenomenex Luna C18 column, 4.6×50 mm eluting with 10-90% MeCN/H₂O over 4 minutes containing 0.1% NH₄OAc; 4 mL/min, monitoring at 220 nm).

Example 277

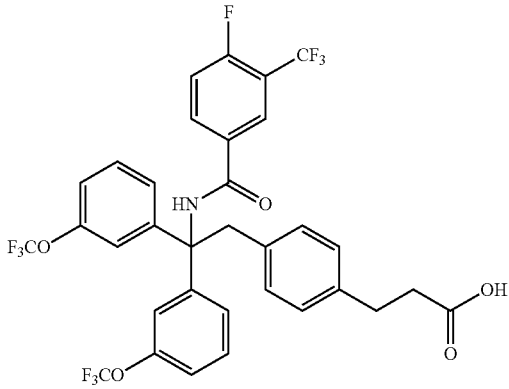 [SMILES: O=C(O)CCc1ccc(CC(NC(=O)c2ccc(F)c(C(F)(F)F)c2)(c2cccc(OC(F)(F)F)c2)c2cccc(OC(F)(F)F)c2)cc1]

3-(4-(2-(4-fluoro-3-(trifluoromethyl)benzamido)-2, 2-bis(3-(trifluoromethoxy)phenyl)ethyl)phenyl)propanoic acid Procedure 72

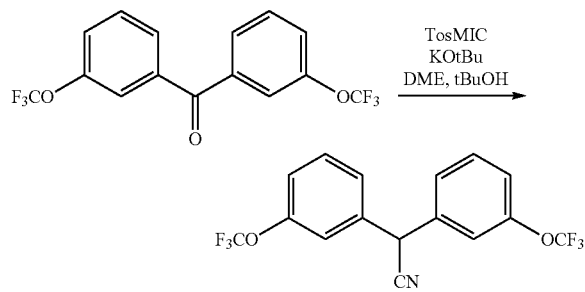

At 0° C. to a solution of bis(3-(trifluoromethoxy)phenyl)methanone (3 g, 8.6 mmol), prepared as described in Procedure 11, in DME (60 mL) was added 1-(isocyanomethylsulfonyl)-4-methylbenzene (3.3 g, 17.1 mmol) and tBuOK (25.7 mL, 1.0 M solution in tBuOH, 25.7 mmol). The reaction mixture was allowed to warm to rt and stirred for 18 h. H₂O (100 mL) was added to the reaction mixture and the aqueous layer was extracted with DCM (3×100 mL). The combined organic layers were washed with sat. NaCl (50 mL), dried over MgSO₄, filtered and concentrated under reduced pressure. The residue was purified by ISCO chromatography (150 g) using hexane/EtOAc (0-5% over 30 min, 5-20% over 20 min) to give 2,2-bis(3-(trifluoromethoxy)phenyl)acetonitrile as a yellow oil at a retention time of 46 min (1.4 g, 45% yield). HPLC: RT=4.13 min, Purity 100% (Phenomenex Luna C18 column, 4.6×50 mm eluting with 10-90% MeOH/H₂O over 4 minutes containing 0.2% PPA; 4 mL/min, monitoring at 220 nm). NMR: 400 MHz ¹H (CDCL₃) 7.45 ppm, 2H, t, J=8.13 Hz; 7.30 ppm, 2H, d, J=7.91 Hz; 7.23 ppm, 2H, d, J=9.23 Hz; 7.17 ppm, 2H, s; 5.17 ppm, 1H, s.

Procedure 73

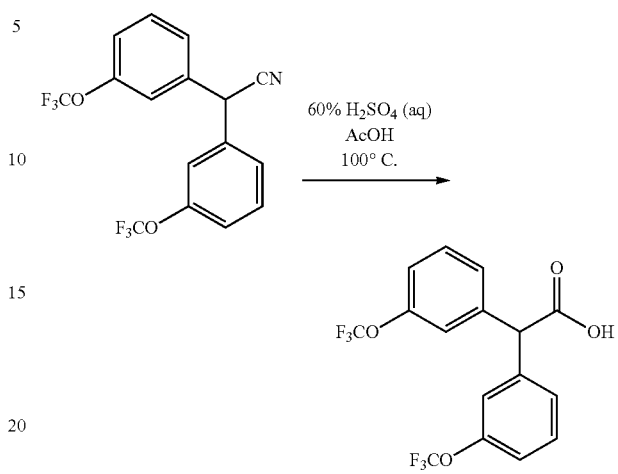

To a solution of 2,2-bis(3-(trifluoromethoxy)phenyl)acetonitrile (1.0 g, 2.8 mmol) in AcOH (15 mL) was added 60% H₂SO₄ (aq) (10 mL) and the reaction mixture was heated at 100° C. for 10 h. The reaction mixture was allowed to cool to rt and extracted with toluene (2×25 mL). The combined organic portions were washed with H₂O (25 mL) and sat. NaCl (25 mL), then extracted with 0.5 N NaOH (50 mL and 10 mL). The combined basic extracts were made acidic using concentrated HCl then extracted with toluene (2×25 mL). The combined organic extracts were dried over MgSO₄, filtered and concentrated under reduced pressure to give 2,2-bis(3-(trifluoromethoxy)phenyl)acetic acid (700 mg, 67% yield) as a pale tan oil. LCMS: RT=1.99 min [M+H] 381.1 (2 min Phenomenex Luna C18 column, 4.6×30 mm eluting with 10-90% MeOH/H₂O over 2 minutes containing 0.1% TFA; 5 mL/min, monitoring at 220 nm); NMR: 400 MHz ¹H (CDCL₃) δ ppm 5.05 (s, 1H), 7.14-7.19 (m, 4H), 7.25 (d, J=7.47 Hz, 2H), 7.37 (t, J=7.69 Hz, 2H).

Procedure 74

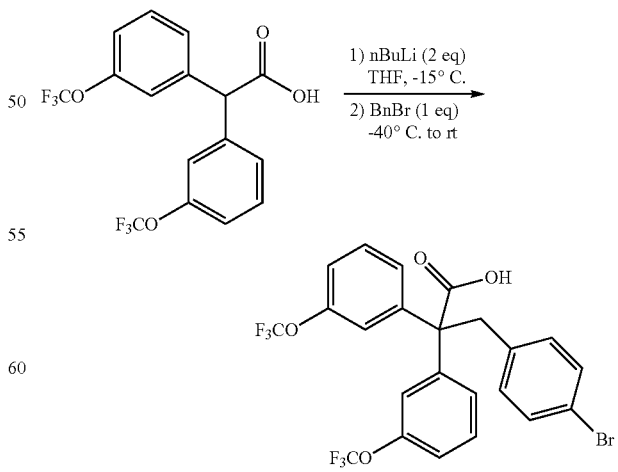

To a solution of 2,2-bis(3-(trifluoromethoxy)phenyl)acetic acid (198 mg, 0.52 mmol) in THF (3.5 mL) at −15° C. was added dropwise a 1.6 M solution of nBuLi in hexanes (0.65 mL, 1.04 mmol). The reaction mixture was stirred for 45 min. The solution was cooled to −40° C. and a solution of benzylbromide (130 mg, 0.52 mmol) in THF (0.6 mL) was added dropwise. The ice-bath was removed and the reaction mixture was allowed to warm up to rt. The reaction was quenched by addition of sat. NH$_4$Cl (5 mL) and extracted with Et$_2$O (3×5 mL). The combined organic portions were dried over Na$_2$SO$_4$, filtered and concentrated under reduced pressure. The residue was purified by silica chromatography, eluting with 30% EtOAc/hexane containing 1% AcOH to give 3-(4-bromophenyl)-2,2-bis(3-(trifluoromethoxy)phenyl)propanoic acid (232 mg, 81% yield) as a clear colorless oil. LCMS: RT=1.93 min [M+H] 549.0 (2 min Phenomenex Luna C18 column, 4.6×30 mm eluting with 10-90% MeOH/H$_2$O over 2 minutes containing 0.1% TFA; 5 mL/min, monitoring at 220 nm); NMR: 400 MHz $^1$H (CDCl$_3$) δ ppm 3.62 (s, 2H), 6.53 (d, J=8.35 Hz, 2H), 7.04 (s, 2H), 7.10 (d, J=7.91 Hz, 2H), 7.13-7.19 (m, 4H), 7.30 (t, J=8.13 Hz, 2H).

Procedure 75

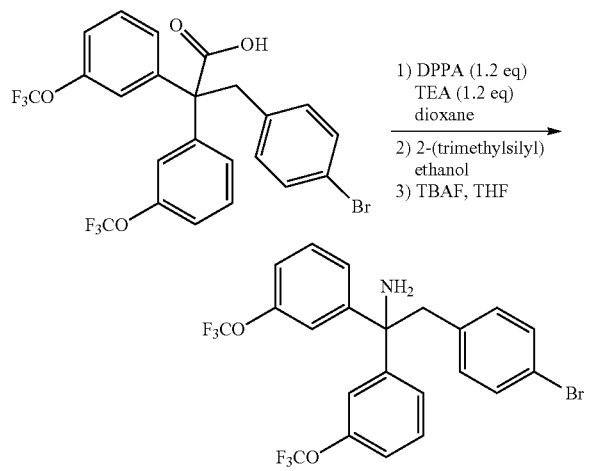

To a solution of 3-(4-bromophenyl)-2,2-bis(3-(trifluoromethoxy)phenyl)propanoic acid (224 mg, 0.41 mmol) in dioxane (5 mL) was added 4 Å molecular sieves (appx 100 mg), triethylamine (0.068 mL, 0.49 mmol) and diphenylphosphoryl azide (0.11 mL, 0.49 mmol) and the reaction mixture was stirred for 45 minutes. 2-(Trimethylsilyl)ethanol (0.176 mL, 1.23 mmol) was added and the reaction mixture was heated at reflux for 1 h. The reaction mixture was allowed to cool to rt and concentrated under reduced pressure. The residue was diluted with Et$_2$O (10 mL) and washed with sat. NH$_4$Cl (5 mL), sat. NaHCO$_3$ (5 mL) and sat. NaCl (5 mL). The organic layer was dried over Na$_2$SO$_4$, filtered and concentrated under reduced pressure. The residue was diluted with THF (5 mL) and cooled in an ice-bath, then a 1M solution of tetrabutylammonium fluoride in THF (0.80 mL, 0.80 mmol) was added dropwise. The reaction mixture was allowed to warm to rt and stirred for 3 h. The reaction mixture was diluted with CH$_2$Cl$_2$ (5 mL) and washed with H$_2$O (5 mL) and sat. NaCl (5 mL). The organic layer was dried over Na$_2$SO$_4$, filtered and concentrated under reduced pressure. The resulting residue was purified by ISCO silica chromatography with elution at 0 to 50% EtOAc/hexane to give 2-(4-bromophenyl)-1,1-bis(3-(trifluoromethoxy)phenyl)ethanamine (78 mg, 37% yield) as a clear colorless oil. LCMS: RT=1.87 min [M−NH$_2$] 505.0 (2 min Phenomenex Luna C18 column, 4.6×30 mm eluting with 10-90% MeOH/H$_2$O over 2 minutes containing 0.1% TFA; 5 mL/min, monitoring at 220 nm); NMR: 400 MHz $^1$H (CDCl$_3$) δ ppm 1.68 (bs, 2H), 3.46 (s, 2H), 6.57 (d, J=8.35 Hz, 2H), 7.10 (d, J=8.35 Hz, 2H), 7.18 (s, 2H), 7.21-7.26 (m, 4H), 7.32 (t, J=8.13 Hz, 2H).

Procedure 76

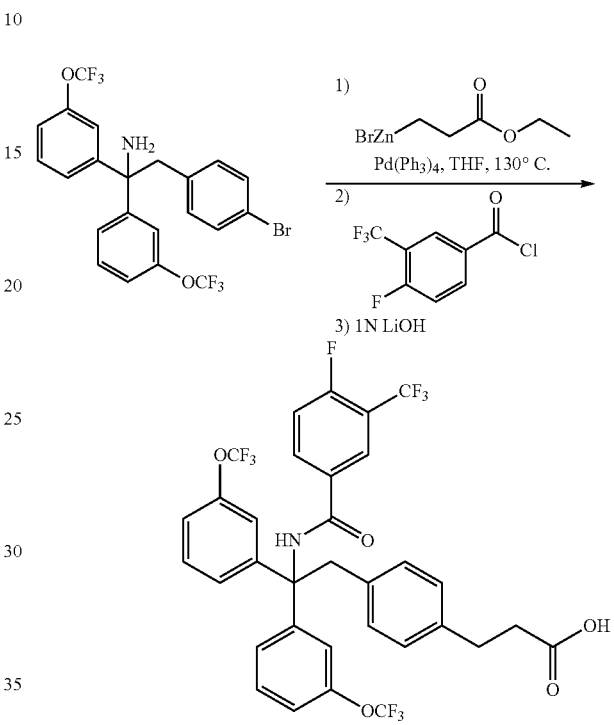

To a solution of 2-(4-bromophenyl)-1,1-bis(3-(trifluoromethoxy)phenyl)ethanamine (26 mg, 0.050 mmol) in THF (0.5 mL) was added a 0.5 M solution of 3-ethoxy-3-oxopropylzinc bromide in THF (0.18 mL, 0.090 mmol) followed by tetrakis(triphenylphosphine)palladium(0) (3 mg, 5 mol %). The reaction mixture was heated at 130° C. under microwave irradiation for 0.5 h. The reaction mixture was filtered through silica gel and eluted with THF. The solvents were removed under reduced pressure and the residue was dissolved into CH$_2$Cl$_2$ (0.5 mL) then triethylamine (0.020 mL, 0.15 mmol) was added followed by 4-fluoro-3-(trifluoromethyl)benzoylchloride (0.020 mL, 0.13 mmol). The reaction mixture was stirred at rt for 3 h then diluted with Et$_2$O (10 mL) and the organic layer was washed with sat. NH$_4$Cl (2 mL), sat. NaHCO$_3$ (2 mL) and sat. NaCl (2 mL). The organic layer was dried over Na$_2$SO$_4$, filtered and concentrated under reduced pressure. The residue was purified by prep TLC plate, eluting with 20% EtOAc/hexane to give ethyl 3-(4-(2-(4-fluoro-3-(trifluoromethyl)benzamido)-2,2-bis(3-(trifluoromethoxy)phenyl)ethyl)phenyl)propanoate (11 mg, 31% yield) as a clear, colorless oil. LCMS: RT=2.26 min [M+H] 731.93 (2 min Phenomenex Luna C18 column, 4.6×30 mm eluting with 10-90% MeOH/H$_2$O over 2 minutes containing 0.1% TFA; 5 mL/min, monitoring at 220 nm).

To a solution of ethyl 3-(4-(2-(4-fluoro-3-(trifluoromethyl)benzamido)-2,2-bis(3-(trifluoromethoxy)phenyl)ethyl)phenyl)propanoate (11 mg, 0.015 mmol) in THF (0.75 mL) was added 1 N LiOH (0.15 mL) and methanol (0.30 mL). The reaction mixture was heated at 50° C. for 0.5 h. The solvents were removed under a stream of nitrogen then 1 N HCl (2 mL) was added to the residue and the mixture was extracted with CH$_2$Cl$_2$ (2×5 mL). The combined organics were dried over Na$_2$SO$_4$, filtered and the volatiles removed. The resulting residue was purified on ISCO silica gel eluting with 0 to 10% MeOH/CH$_2$Cl$_2$ to give 3-(4-(2-(4-fluoro-3-(trifluoromethyl)benzamido)-2,2-bis(3-(trifluoromethoxy)phenyl)ethyl)phenyl)propanoic acid (Example 277) as a clear, colorless oil (9 mg, 85% yield). LCMS: RT=2.18 min [M+H] 704.1 (2 min Phenomenex Luna C18 column, 4.6×30 mm eluting with 10-90% MeOH/H$_2$O over 2 minutes containing 0.1% TFA; 5 mL/min, monitoring at 220 nm); NMR: 400 MHz $^1$H (CDCl$_3$) δ ppm 2.55 (t, J=7.69 Hz, 2H), 2.82 (t, J=7.69 Hz, 2H), 3.83 (s, 2H), 6.54 (d, J=8.35 Hz, 2H), 6.60 (s, 1H), 6.93 (d, J=7.91 Hz, 2H), 6.97 (s, 2H), 7.08-7.14 (m, 4H), 7.17-7.23 (m, 1H), 7.28-7.33 (m, 2H), 7.73-7.77 (m, 1H), 7.83-7.86 (m, 1H).

Example 278

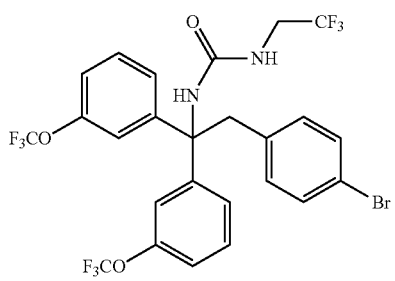 [SMILES: O=C(NCC(F)(F)F)NC(Cc1ccc(Br)cc1)(c1cccc(OC(F)(F)F)c1)c1cccc(OC(F)(F)F)c1]

1-(2-(4-bromophenyl)-1,1-bis(3-(trifluoromethoxy)phenyl)ethyl)-3-(2,2,2-trifluoroethyl)urea Procedure 77

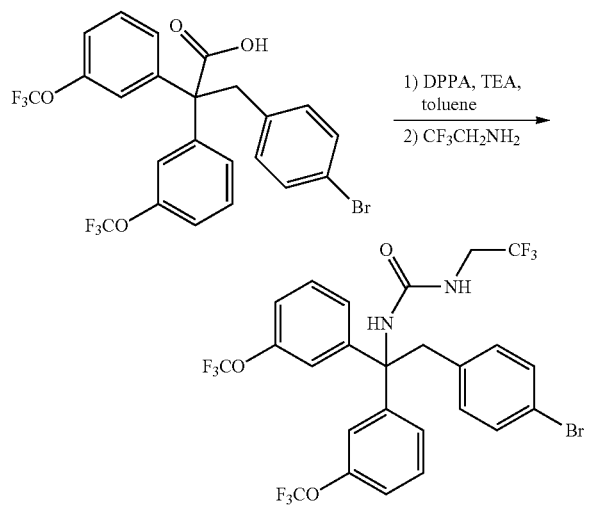

To a solution of 3-(4-bromophenyl)-2,2-bis(3-(trifluoromethoxy)phenyl)propanoic acid (260 mg, 0.47 mmol) in toluene (10 mL) was added diphenylphosphoryl azide (0.409 mL, 1.9 mmol) followed by triethylamine (0.264 mL, 1.9 mmol). The reaction mixture was heated at reflux for 1 h, then trifluoroethylamine was added and the reaction mixture was heated at reflux for another 1 h. The reaction mixture was allowed to cool to rt and diluted with EtOAc (30 mL) and washed successively with sat. NH$_4$Cl (10 mL), sat. NaHCO$_3$ (10 mL) and sat. NaCl (20 mL). The organic layer was dried over Na$_2$SO$_4$, filtered and concentrated under reduced pressure. The crude product was purified on a ISCO silica gel column (12 g) with elution at 0 to 20% EtOAc/hexane over 20 min, then further purified by preparative HPLC YMC ODS S5 30×100 mm column 40-100% MeOH/H$_2$O (90% in water, 0.1% TFA) gradient over 10 min with flow rate 40 mL/min and UV detection at 220 nm to yield 1-(2-(4-bromophenyl)-1,1-bis(3-(trifluoromethoxy)phenyl)ethyl)-3-(2,2,2-trifluoroethyl)urea (Example 278) as a white solid (200 mg, yield 65%). LCMS: RT=2.24 min [M+H] 645.0 (2 min Phenomenex Luna C18 column, 4.6×30 mm eluting with 10-90% MeOH/H$_2$O over 2 minutes containing 0.1% TFA; 5 mL/min, monitoring at 220 nm); HPLC: RT=4.476 min, Purity 100% (Phenomenex Luna C18 column, 4.6×50 mm eluting with 10-90% MeOH/H$_2$O over 4 minutes containing 0.2% PPA; 4 mL/min, monitoring at 220 nm); $^1$H NMR (400 MHz, CDCl$_3$) δ ppm 3.68-3.77 (m, 2H), 3.81 (s, 2H), 4.80 (t, J=6.15 Hz, 1H), 5.15 (s, 1H), 6.52 (d, J=7.91 Hz, 2H), 6.97 (s, 2H), 7.09-7.17 (m, 4H), 7.23-7.27 (m, 3H), 7.34 (t, J=7.91 Hz, 2H).

Example 279

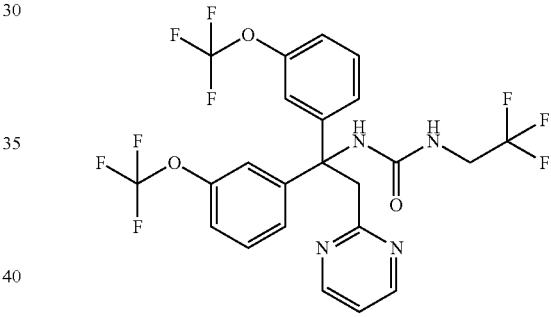

1-(2-(pyrimidin-2-yl)-1,1-bis(3-(trifluoromethoxy)phenyl)ethyl)-3-(2,2,2-trifluoroethyl)urea Procedure 78

To a solution of 2-methylpyrimidine (2.0 g, 21.3 mmol) in CCl$_4$ (80 mL) was added benzoyl peroxide (80 mg, 0.33 mmol). The reaction mixture was heated to reflux, then NBS (4.5 g, 25.56 mmol) was added in portions over 3.5 h. Reflux was maintained for 18 h and the reaction mixture was allowed to cool to rt, filtered through a celite pad and the celite was rinsed with ether (200 mL). The organic layer was concentrated and the residue was purified by ISCO chromatography (120 g column) using hexane/EtOAc (0-80% over 30 min) to give 2-(bromomethyl)pyrimidine as a yellow oil at a retention time of 18 min (412 mg, 11% yield). NMR: 400 MHz $^1$H (CDCl$_3$) 8.76 ppm, 2H, d, J=5.27 Hz; 7.23 ppm, 1H, m; 4.62 ppm, 2H, d, J=2.20 Hz.

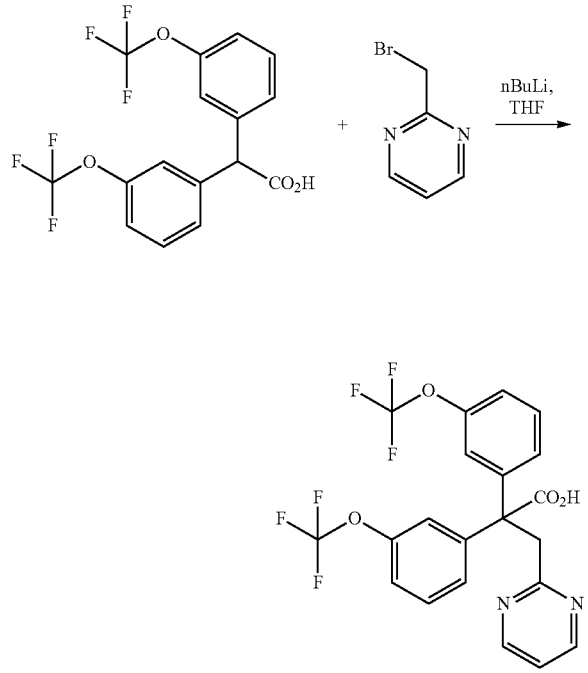 [SMILES: O=C(O)C(c1cccc(OC(F)(F)F)c1)c1cccc(OC(F)(F)F)c1 ; BrCc1ncccn1 ; O=C(O)C(Cc1ncccn1)(c1cccc(OC(F)(F)F)c1)c1cccc(OC(F)(F)F)c1]

At −15° C. to a solution of 2,2-bis(3-(trifluoromethoxy)phenyl)acetic acid prepared as described in Procedure 73 (607 mg, 1.6 mmol) in THF (6 mL) was added nBuLi (1.6 mL, 2M in hexane, 3.2 mmol). The mixture was stirred at −15° C. for 45 min. 2-(Bromomethyl)pyrimidine (412 mg, crude) in THF (1 mL) was added and the reaction mixture was allowed to warm to rt and stirred for 18 h, then quenched with saturated NH$_4$Cl. The aqueous layer was extracted with EtOAc (3×50 mL). The combined organic layer was dried over MgSO$_4$, filtered and concentrated to give 3-(pyrimidin-2-yl)-2,2-bis(3-(trifluoromethoxy)phenyl)propanoic acid as a yellow solid (437 mg, 58% crude). This crude solid was carried onto the next step without further purification.

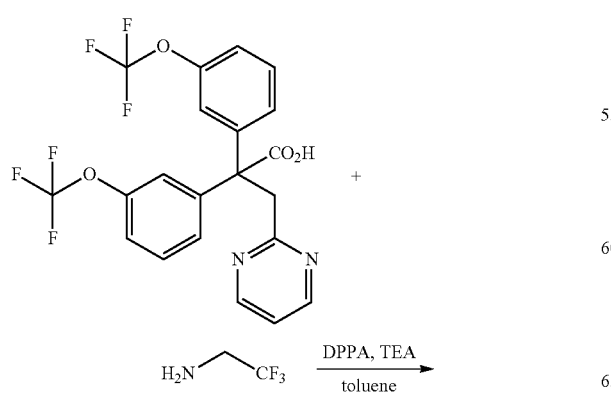

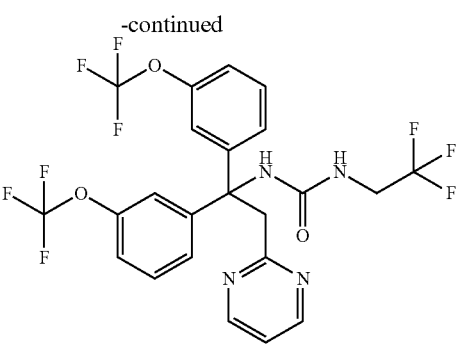

-continued

To a mixture of 3-(pyrimidin-2-yl)-2,2-bis(3-(trifluoromethoxy)phenyl)propanoic acid (20 mg, 0.042 mmol) and diphenyl phosphoryl azide (70 mg, 0.254 mmol) in toluene (1.5 mL) was added TEA (88 µL, 0.63 mmol) dropwise and the reaction mixture was heated at 110° C. for 20 min. 2,2,2-Trifluoroethanamine (7 µL, 0.084 mmol) was added and the reaction mixture was stirred at 110° C. for 1 h. The reaction mixture was allowed to cool to rt and diluted with EtOAc (25 mL). The organic layer was washed with H$_2$O (25 mL), 1 N HCl (25 mL) and saturated NaHCO$_3$ (25 mL), dried over MgSO$_4$, filtered and concentrated under reduced pressure. The residue was purified by preparative HPLC (Shimadzu-YMC-Sunfire 5µ column, 30×100 mm eluting with 40-100% MeOH (90% in H$_2$O, 0.1% TFA) gradient over 10 min with flow rate 40 mL/min and UV detection at 220 nm). The product that eluted at retention time of 9.42 min was isolated as a clear oil, and further purified by Prep TLC (Uniplate, Silica Gel GF, 20×20 cm, 1000 Microns) using Hexane/EtOAc (1/2) to yield 1-(2-(pyrimidin-2-yl)-1,1-bis(3-(trifluoromethoxy)phenyl)ethyl)-3-(2,2,2-trifluoroethyl)urea (Example 279) as a white solid (4 mg, 16% yield). LCMS: RT=1.867 min [M+H] 568.87 (Phenomenex Luna C18 column, 4.6×30 mm eluting with 10-90% MeOH/H$_2$O over 2 minutes containing 0.1% TFA, 5 mL/min, monitoring at 220 nm); HPLC: RT=3.973 min, Purity 100% (Phenomenex Luna C18 column, 4.6×50 mm eluting with 10-90% MeOH/H$_2$O over 4 minutes containing 0.2% PPA; 4 mL/min, monitoring at 220 nm); NMR: 400 MHz $^1$H (CDCl$_3$) 8.52 ppm, 2H, d, J=4.83 Hz; 7.98 ppm, 1H, s; 7.33 ppm, 5H, m; 7.23 ppm, 2H, s; 7.08 ppm, 3H, t, J=5.05 Hz; 4.61 ppm, 1H, t, J=6.37 Hz; 3.85 ppm, 2H, s; 3.77 ppm, 2H, ddd, J=15.71, 9.12, 9.01 Hz.

Example 280

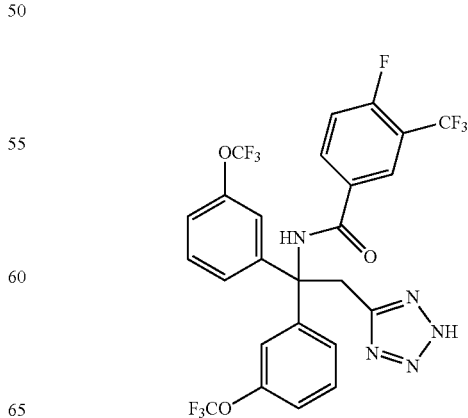

449

N-(2-(2H-tetrazol-5-yl)-1,1-bis(3-(trifluoromethoxy)phenyl)ethyl)-4-fluoro-3-(trifluoromethyl)benzamide Procedure 79

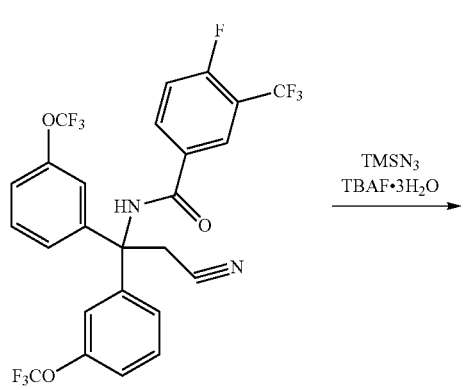

450

Example 281

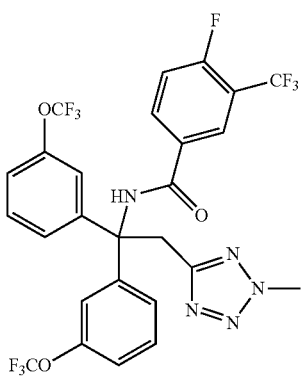 [SMILES: Cn1nnc(CC(NC(=O)c2ccc(F)c(C(F)(F)F)c2)(c2cccc(OC(F)(F)F)c2)c2cccc(OC(F)(F)F)c2)n1]

4-fluoro-N-(2-(2-methyl-2H-tetrazol-5-yl)-1,1-bis(3-(trifluoromethoxy)phenyl)ethyl)-3-(trifluoromethyl)benzamide Procedure 80

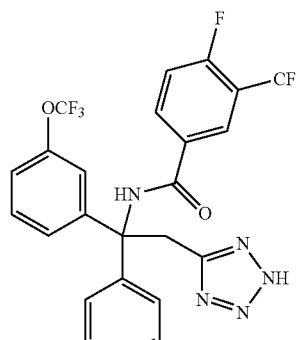

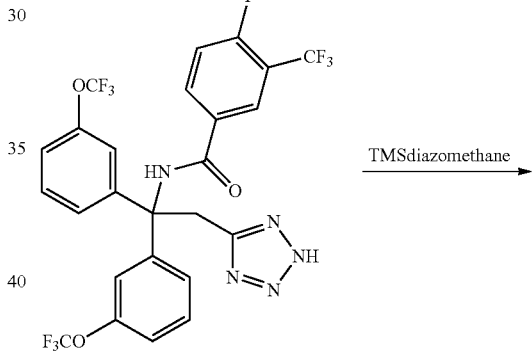

N-(2-cyano-1,1-bis(3-(trifluoromethoxy)phenyl)ethyl)-4-fluoro-3-(trifluoromethyl)benzamide was prepared as described in Procedure 11, 18, 6 and 7. LCMS: RT=4.04 min [M+H] 581.16 (Phenomenex Luna C18 column, 4.6×50 mm eluting with 10-90% MeOH/H$_2$O over 4 minutes containing 0.1% TFA; 4 mL/min, monitoring at 220 nm). A mixture of N-(2-cyano-1,1-bis(3-(trifluoromethoxy)phenyl)ethyl)-4-fluoro-3-(trifluoromethyl)benzamide (70 mg, 0.12 mmol), TMSN$_3$ (0.025 ml. 1.6 eq) and TBAF.3H$_2$O (19 mg, 0.5 eq) was heated in a sealed tube at 110° C. for 24 h. After allowing to cool to rt, the residue was dissolved in CH$_2$Cl$_2$, and purified by ISCO flash chromatography (silica gel, CH$_2$Cl$_2$/MeOH) to give N-(2-(2H-tetrazol-5-yl)-1,1-bis(3-(trifluoromethoxy)phenyl)ethyl)-4-fluoro-3-(trifluoromethyl)benzamide (Example 280, 54 mg, yield: 72%). LCMS: RT=3.91 min [M+H] 624.06, [M+Na] 647.06 (Phenomenex Luna C18 column, 4.6×50 mm eluting with 10-90% MeOH/H$_2$O over 4 minutes containing 0.1% TFA; 4 mL/min, monitoring at 220 nm).

To a solution of N-(2-(2H-tetrazol-5-yl)-1,1-bis(3-(trifluoromethoxy)phenyl)ethyl)-4-fluoro-3-(trifluoromethyl)benzamide (18 mg, 0.029 mmol) in THF (0.4 mL) and MeOH (0.1 mL) at rt was added (diazomethyl)trimethylsilane (0.02 mL, 2.0 M solution). The resulting solution was stirred at rt for 20 min. The solvents were evaporated and resulting residue was purified by ISCO flash chromatography (silica gel, hexane/EtOAc) to give 4-fluoro-N-(2-(2-methyl-2H-tetrazol-5-yl)-1,1-bis(3-(trifluoromethoxy)phenyl)ethyl)-3-(trifluoromethyl)benzamide (Example 281, 11 mg, yield: 60%). LCMS: RT=4.06 min [M+H] 638.23, [M+Na] 661.26 (Phenomenex Luna C18 column, 4.6×50 mm eluting with 10-90% MeOH/H$_2$O over 4 minutes containing 0.1% TFA; 4 mL/min, monitoring at 220 nm).

Example 282

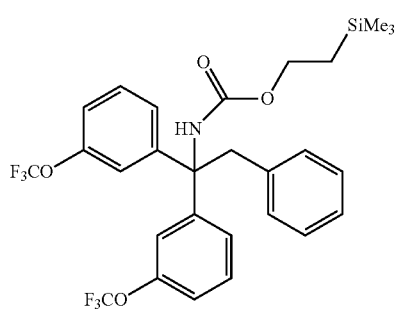 [SMILES: C[Si](C)(C)CCOC(=O)NC(Cc1ccccc1)(c1cccc(OC(F)(F)F)c1)c1cccc(OC(F)(F)F)c1]

2-(trimethylsilyl)ethyl 2-phenyl-1,1-bis(3-(trifluoromethoxy)phenyl)ethylcarbamate Procedure 81

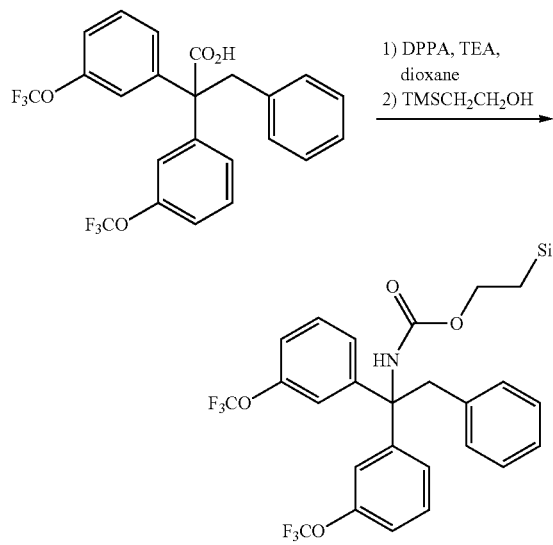

To a solution of 3-phenyl-2,2-bis(3-(trifluoromethoxy)phenyl)propanoic acid (0.055 g, 0.117 mmol) in 1,4-dioxane (2 mL) was added triethylamine (0.014 g, 20 µL, 0.14 mmol), 4 Å molecular sieves (0.05 g), diphenylphosphoryl azide (0.040 g, 31 µL, 0.14 mmol) and trimethylsilylethanol (0.042 g, 50 µL, 0.35 mmol). The reaction mixture was stirred for 1 h at rt, then heated at 75° C. for 1.5 h. The cooled reaction mixture was diluted with EtOAc and filtered through celite. The filtrate was concentrated under reduced pressure and purified by ISCO silica gel chromatography using a gradient of 0-20% EtOAc/hexane as eluent to yield 2-(trimethylsilyl)ethyl 2-phenyl-1,1-bis(3-(trifluoromethoxy)phenyl)ethylcarbamate (Example 282) as a colorless band (0.037 g, 54% yield). HPLC: RT=4.828 min (Phenomenex Luna C18 5µ column 4.6×50 mm, eluting with 10-90% MeOH/H$_2$O containing 0.1% PPA over a 4 minute gradient, monitoring at 220 nm). No molecular ion was obtained. $^1$H NMR (400 MHz, CDCl$_3$): 7.32 (t, J=8.1 Hz, 2H), 7.18-7.11 (m, 7H), 6.99 (s, 2H), 6.65 (d, J=7.1 Hz, 2H), 5.35 (s, 1H), 4.08 (t, J=8.8 Hz, 2H), 3.78 (s, 2H), 0.88 (br, 2H), 0.00 (s, 9H).

Example 283

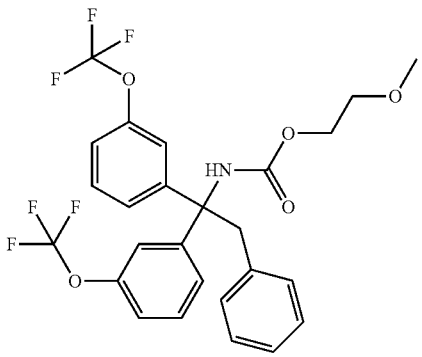 [SMILES: COCCOC(=O)NC(Cc1ccccc1)(c1cccc(OC(F)(F)F)c1)c1cccc(OC(F)(F)F)c1]

2-methoxyethyl 2-phenyl-1,1-bis(3-(trifluoromethoxy)phenyl)ethylcarbamate

Procedure 82

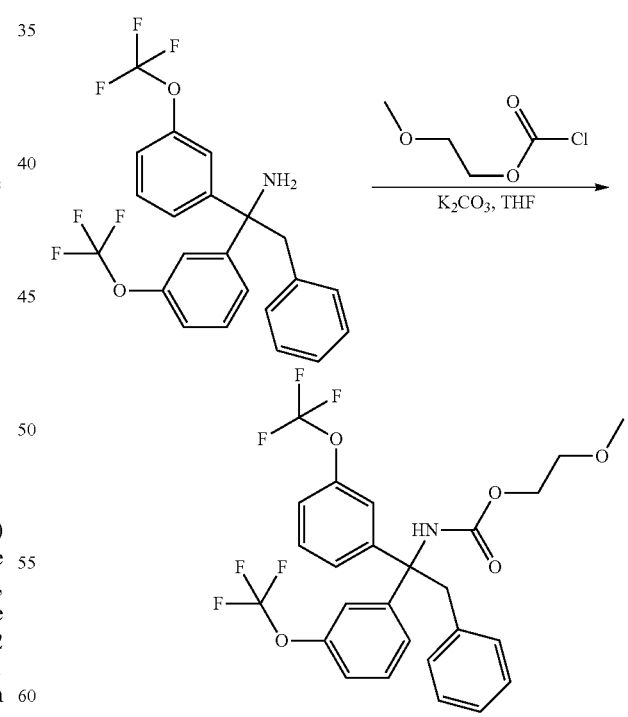

To a solution of 2-phenyl-1,1-bis(3-(trifluoromethoxy)phenyl)ethanamine (20 mg, 0.045 mmol) in THF (6 mL) was added 1M K$_2$CO$_3$ (20 mg in 0.1 mL), followed by 2-methoxyethyl carbonochloridate (0.106 mL, 0.91 mmol). The resulting mixture was stirred at rt for 16 h. The crude product was purified by prep HPLC (phenomenex AXIA Luna 75×30 mm, 5μ column eluting with 10-90% ACN/H₂O over 10 minutes containing 0.1% TFA; 40 mL/min, monitoring at 220 nm) to afford 2-methoxyethyl 2-phenyl-1,1-bis(3-(trifluoromethoxy)phenyl)ethylcarbamate (Example 283) as white lyophillate (12 mg, 51% yield). LCMS: RT=4.19 min [M+H] 544.2 (4 min Phenomenex Luna C18 column, 4.6×50 mm eluting with 10-90% MeOH/H₂O over 4 minutes containing 0.1% TFA; 4 mL/min, monitoring at 220 nm.

Example 284

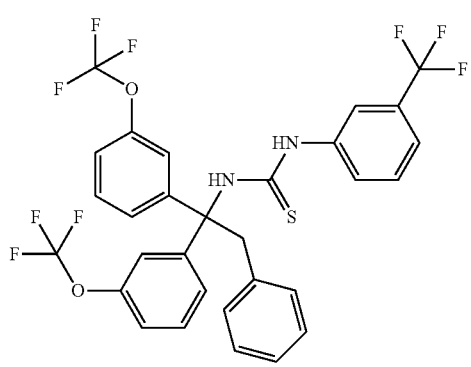 [SMILES: FC(F)(F)Oc1cccc(C(Cc2ccccc2)(NC(=S)Nc2cccc(C(F)(F)F)c2)c2cccc(OC(F)(F)F)c2)c1]

1-(2-phenyl-1,1-bis(3-(trifluoromethoxy)phenyl)ethyl)-3-(3-(trifluoromethyl)phenyl)thiourea Procedure 83

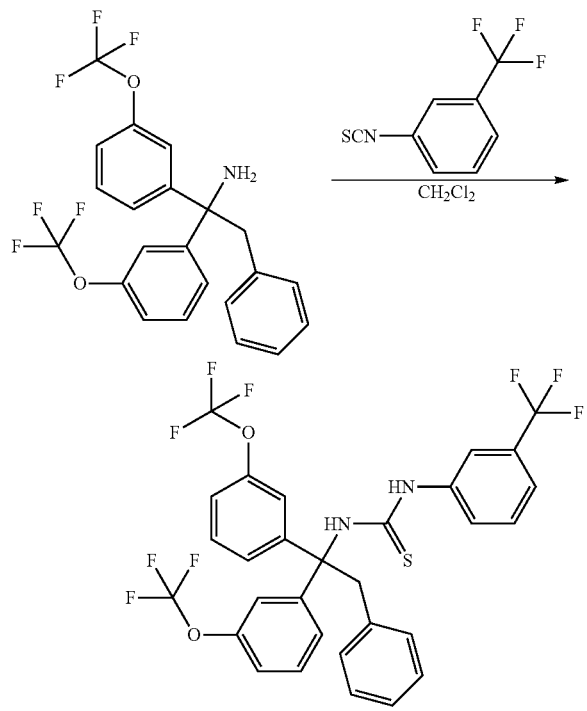

To a solution of bis(3-(trifluoromethoxy)phenyl)methanamine (20 mg, 0.057 mmol) in CH₂Cl₂ (0.1 mL) was added 1-isothiocyanato-3-(trifluoromethyl)benzene (35 mg, 0.17 mmol). The reaction mixture was stirred at rt for 16 h. The reaction mixture was concentrated and the residue was purified by prep HPLC (phenomenex AXIA Luna 75×30 mm, 5μ column eluting with 10-90% ACN/H₂O over 10 minutes containing 0.1% TFA; 40 mL/min, monitoring at 220 nm) to afford 1-(2-phenyl-1,1-bis(3-(trifluoromethoxy)phenyl)ethyl)-3-(3-(trifluoromethyl)phenyl)thiourea (Example 284) as white lyophillate (30 mg, 81%). LCMS: RT=4.51 min [M+H] 645.14 (Phenomenex Luna C18 column, 4.6×50 mm eluting with 10-90% MeOH/H₂O over 4 minutes containing 0.1% TFA; 4 mL/min, monitoring at 220 nm).

Example 285

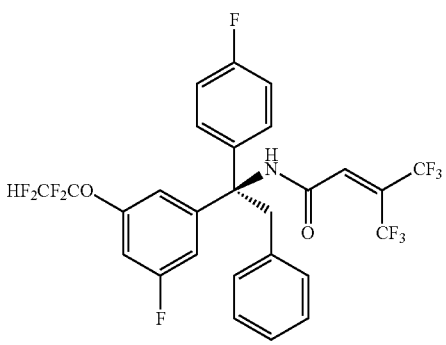

(R)-4,4,4-trifluoro-N-(1-(3-fluoro-5-(1,1,2,2-tetrafluoroethoxy)phenyl)-1-(4-fluorophenyl)-2-phenylethyl)-3-(trifluoromethyl)but-2-enamide Procedure 84

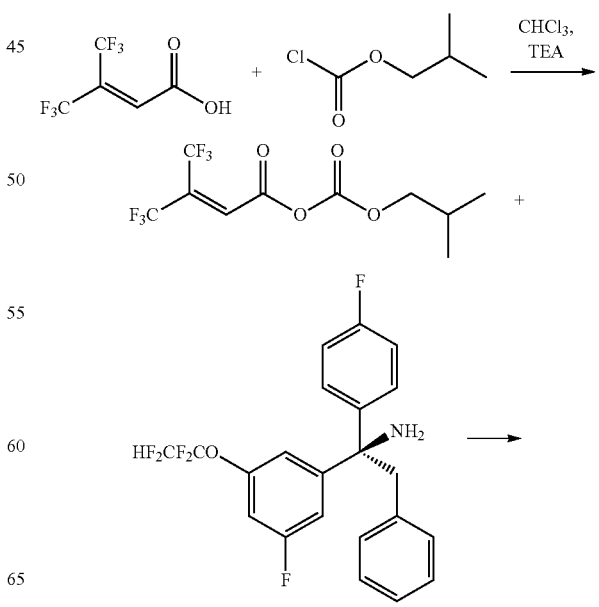

-continued

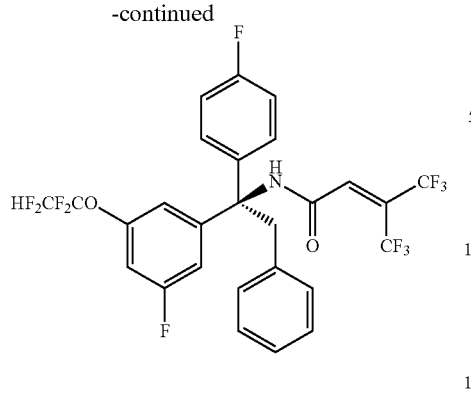

At 0° C. under argon to a solution of 4,4,4-trifluoro-3-(trifluoromethyl)crotonic acid (29 mg, 0.14 mmol) and TEA (25 μL, 0.18 mmol) in CHCl$_3$ (0.5 mL) was added isobutyl chloroformate (18 μL, 0.14 mmol). The reaction mixture was stirred at 0° C. for 10 min. A solution of (R)-1-(3-fluoro-5-(1,1,2,2-tetrafluoroethoxy)phenyl)-1-(4-fluorophenyl)-2-phenylethanamine, prepared as described in Procedure 3, 4, 5 and 6, (50 mg, 0.12 mmol) in CHCl$_3$ (0.5 mL) was added and the reaction was stirred at rt for 18 h. The reaction mixture was concentrated and purified by preparative HPLC Shimadzu-YMC Sunfire 5μ column, 30×100 mm eluting with 40-100% MeOH (90% in H$_2$O, 0.1% TFA) gradient over 10 min with flow rate 40 mL/min and UV detection at 220 nm. (R)-4,4,4-trifluoro-N-(1-(3-fluoro-5-(1,1,2,2-tetrafluoroethoxy)phenyl)-1-(4-fluorophenyl)-2-phenylethyl)-3-(trifluoromethyl)but-2-enamide (Example 285) was eluted at a retention time of 11.11 min and was isolated as a clear oil (63 mg, yield 73%). LCMS: RT=2.19 min [M+H] 616.1 (Phenomenex Luna C18 column, 4.6×30 mm eluting with 10-90% MeOH/H$_2$O over 2 minutes containing 0.1% TFA; 5 mL/min, monitoring at 220 nm); HPLC: RT=4.31 min, Purity 100% (Phenomenex Luna C18 column, 4.6×50 mm eluting with 10-90% MeOH/H$_2$O over 4 minutes containing 0.2% PPA; 4 mL/min, monitoring at 220 nm) NMR: 400 MHz $^1$H (CDCl$_3$) 7.36 ppm, 2H, s; 7.21 ppm, 3H, m; 7.09 ppm, 2H, m; 7.01 ppm, 2H, t, J=8.57 Hz; 6.91 ppm, 3H, m; 6.64 ppm, 2H, d, J=7.03 Hz; 6.43 ppm, 1H, s; 3.94 ppm, 1H, d, J=13.18 Hz; 3.78 ppm, 1H, d, J=13.18 Hz; 2.13 ppm, 2H, s.

Example 286

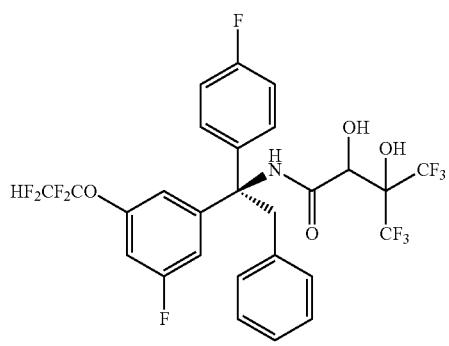

(4,4,4-trifluoro-N—((R)-1-(3-fluoro-5-(1,1,2,2-tetrafluoroethoxy)phenyl)-1-(4-fluorophenyl)-2-phenylethyl)-2,3-dihydroxy-3-(trifluoromethyl)butanamide Example 287A

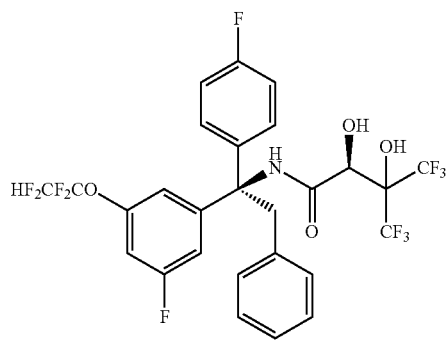

(S)-4,4,4-trifluoro-N—((R)-1-(3-fluoro-5-(1,1,2,2-tetrafluoroethoxy)phenyl)-1-(4-fluorophenyl)-2-phenylethyl)-2,3-dihydroxy-3-(trifluoromethyl)butanamide Example 287B

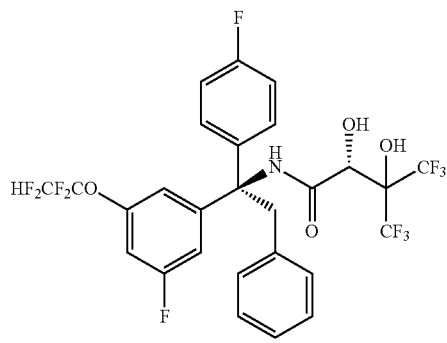

(R)-4,4,4-trifluoro-N—((R)-1-(3-fluoro-5-((1,1,2,2-tetrafluoroethoxy)phenyl)-1-(4-fluorophenyl)-2-phenylethyl)-2,3-dihydroxy-3-(trifluoromethyl)butanamide Procedure 85

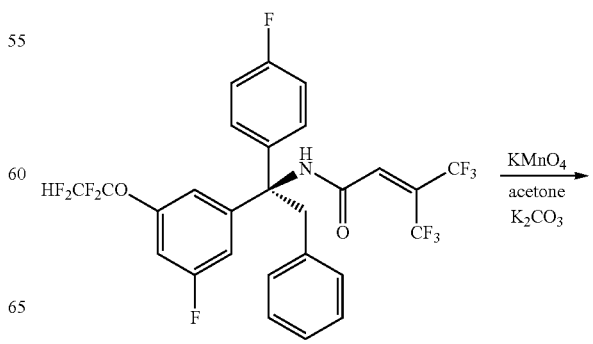

-continued

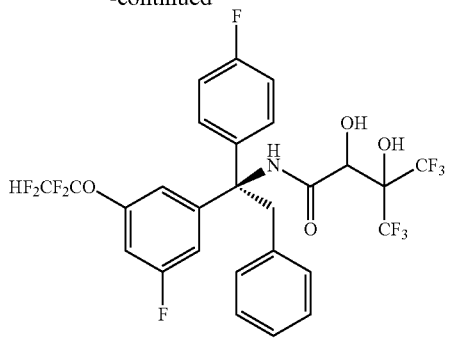

At −78° C. to a mixture of (R)-4,4,4-trifluoro-N-(1-(3-fluoro-5-(1,1,2,2-tetrafluoroethoxy)phenyl)-1-(4-fluorophenyl)-2-phenylethyl)-3-(trifluoromethyl)but-2-enamide (Example 285, 36 mg, 0.06 mmol) and $K_2CO_3$ (28 mg, 0.2 mmol) in acetone (0.5 mL) was added $KMnO_4$ (9 mg, 0.06 mmol). The resulted purple reaction mixture was stirred at −78° C. for 1 h, then at 0° C. for 30 min. The reaction mixture was diluted with EtOAc (25 mL) and the organic layer was washed by 1 N HCl (2×25 mL), dried over $MgSO_4$, filtered and concentrated. The resulting residue was purified by preparative HPLC Shimadzu-YMC Sunfire 5µ column, 30×100 mm eluting with 60-100% MeOH (90% in $H_2O$, 0.1% TFA) gradient over 14 min with flow rate 40 mL/min and UV detection at 220 nm. 4,4,4-Trifluoro-N—((R)-1-(3-fluoro-5-(1,1,2,2-tetrafluoroethoxy)phenyl)-1-(4-fluorophenyl)-2-phenylethyl)-2,3-dihydroxy-3-(trifluoromethyl)butanamide (Example 286) was eluted at a retention time of 12.86 min and was isolated as a clear oil (15 mg, yield 39%). LCMS: RT=2.12 min [M+H] 650.92 (Phenomenex Luna C18 column, 4.6×30 mm eluting with 10-90% MeOH/$H_2O$ over 2 minutes containing 0.1% TFA; 5 mL/min, monitoring at 220 nm); HPLC: RT=4.36 min, Purity 100% (Phenomenex Luna C18 column, 4.6×50 mm eluting with 10-90% MeOH/$H_2O$ over 4 minutes containing 0.2% PPA; 4 mL/min, monitoring at 220 nm) NMR: 400 MHz $^1$H (CDCl$_3$) 7.92 ppm, 1H, d, J=6.15 Hz; 7.19 ppm, 5H, m; 7.06 ppm, 1H, t, J=8.57 Hz; 6.97 ppm, 5H, m; 6.71 ppm, 1H, m; 6.62 ppm, 2H, t, J=6.37 Hz; 5.88 ppm, 1H, m; 4.51 ppm, 1H, s; 4.11 ppm, 1H, m; 3.56 ppm, 1H, m; 3.25 ppm, 1H, m.

The diastereomer mixture of 4,4,4-trifluoro-N—((R)-1-(3-fluoro-5-(1,1,2,2-tetrafluoroethoxy)phenyl)-1-(4-fluorophenyl)-2-phenylethyl)-2,3-dihydroxy-3-(trifluoromethyl)butanamide (Example 286, 189 mg, 0.3 mmol) was separated by chiral preparative HPLC chiralpak AD 20µ column, 5×50 cm, eluting with 5% IPA/Heptane with flow rate 50 mL/min. (S)-4,4,4-trifluoro-N—((R)-1-(3-fluoro-5-(1,1,2,2-tetrafluoroethoxy)phenyl)-1-(4-fluorophenyl)-2-phenylethyl)-2,3-dihydroxy-3-(trifluoromethyl)butanamide (Example 287A) was eluted at a retention time of 52 min and (R)-4,4,4-trifluoro-N—((R)-1-(3-fluoro-5-(1,1,2,2-tetrafluoroethoxy)phenyl)-1-(4-fluorophenyl)-2-phenylethyl)-2,3-dihydroxy-3-(trifluoromethyl)butanamide (Example 287B) was eluted at a retention time of 70 min. The stereochemistry of (S)-4,4,4-trifluoro-N—((R)-1-(3-fluoro-5-(1,1,2,2-tetrafluoroethoxy)phenyl)-1-(4-fluorophenyl)-2-phenylethyl)-2,3-dihydroxy-3-(trifluoromethyl)butanamide (Example 287A) and (R)-4,4,4-trifluoro-N—((R)-1-(3-fluoro-5-(1,1,2,2-tetrafluoroethoxy)phenyl)-1-(4-fluorophenyl)-2-phenylethyl)-2,3-dihydroxy-3-(trifluoromethyl)butanamide (Example 287B) was assigned arbitrarily.

(S)-4,4,4-trifluoro-N—((R)-1-(3-fluoro-5-(1,1,2,2-tetrafluoroethoxy)phenyl)-1-(4-fluorophenyl)-2-phenylethyl)-2,3-dihydroxy-3-(trifluoromethyl)butanamide (Example 287A) was further purified by ISCO chromatography (40 g column, flow rate 20 mL/min) using hexanes/EtOAc (0-30% over 30 min) to give (S)-4,4,4-trifluoro-N—((R)-1-(3-fluoro-5-(1,1,2,2-tetrafluoroethoxy)phenyl)-1-(4-fluorophenyl)-2-phenylethyl)-2,3-dihydroxy-3-(trifluoromethyl)butanamide (Example 287A) as a white solid at a retention time of 28 min (95 mg, 50% yield). LCMS: RT=2.12 min [M+H] 650.00 (Phenomenex Luna C18 column, 4.6×30 mm eluting with 10-90% MeOH/$H_2O$ over 2 minutes containing 0.1% TFA; 5 mL/min, monitoring at 220 nm); HPLC: RT=4.241 min, Purity 100% (Phenomenex Luna C18 column, 4.6×50 mm eluting with 10-90% MeOH/$H_2O$ over 4 minutes containing 0.2% PPA; 4 mL/min, monitoring at 220 nm) NMR: 400 MHz $^1$H (CDCl$_3$) 7.95 ppm, 1H, s; 7.22 ppm, 2H, m; 7.16 ppm, 2H, t, J=7.25 Hz; 6.99 ppm, 8H, m; 6.62 ppm, 2H, d, J=7.47 Hz; 5.89 ppm, 1H, t, J=52.95 Hz; 4.52 ppm, 1H, d, J=6.15 Hz; 4.08 ppm, 1H, d, J=3.95 Hz; 3.53 ppm, 2H, d, J=13.18 Hz.

(R)-4,4,4-trifluoro-N—((R)-1-(3-fluoro-5-(1,1,2,2-tetrafluoroethoxy)phenyl)-1-(4-fluorophenyl)-2-phenylethyl)-2,3-dihydroxy-3-(trifluoromethyl)butanamide (Example 287B) was further purified by ISCO chromatography (40 g column, flow rate 20 mL/min) using hexanes/EtOAc (0-30% over 30 min) to give (R)-4,4,4-trifluoro-N—((R)-1-(3-fluoro-5-(1,1,2,2-tetrafluoroethoxy)phenyl)-1-(4-fluorophenyl)-2-phenylethyl)-2,3-dihydroxy-3-(trifluoromethyl)butanamide (Example 287B) as a clear oil at a retention time of 28 min (57 mg, 30% yield). LCMS: RT=2.12 min [M+H] 650.00 (Phenomenex Luna C18 column, 4.6×30 mm eluting with 10-90% MeOH/$H_2O$ over 2 minutes containing 0.1% TFA; 5 mL/min, monitoring at 220 nm); HPLC: RT=4.285 min, Purity 100% (Phenomenex Luna C18 column, 4.6×50 mm eluting with 10-90% MeOH/$H_2O$ over 4 minutes containing 0.2% PPA; 4 mL/min, monitoring at 220 nm) NMR: 400 MHz $^1$H (CDCl$_3$) $^1$H NMR (400 MHz, Solvent) δ ppm 7.95 ppm, 1H, s; 7.20 ppm, 6H, m; 7.05 ppm, 2H, t, J=8.57 Hz; 6.93 ppm, 1H, d, J=8.79 Hz; 6.71 ppm, 2H, m; 6.63 ppm, 2H, d, J=7.03 Hz; 5.85 ppm, 1H, tt, J=52.95, 2.64 Hz; 4.49 ppm, 1H, d, J=6.15 Hz; 4.02 ppm, 1H, d, J=13.62 Hz; 3.79 ppm, 1H, d, J=6.15 Hz; 3.59 ppm, 1H, d, J=13.18 Hz.

Example 288

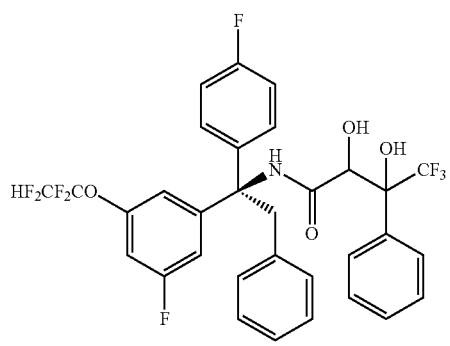

1,1,1-trifluoro-4-((R)-1-(3-fluoro-5-(1,1,2,2-tet-rafluoroethoxy)phenyl)-1-(4-fluorophenyl)-2-phenyl-ethylamino)-2-phenylbutane-2,3-diol Procedure 87

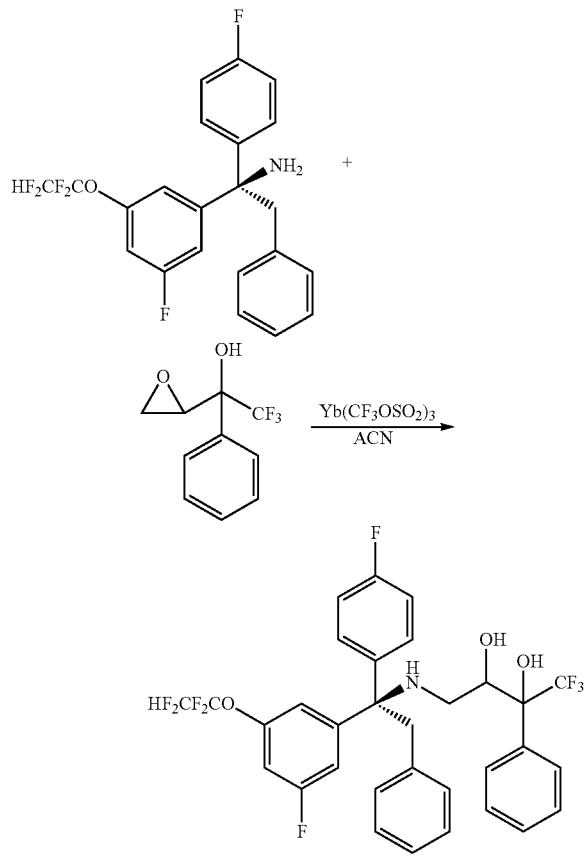

A mixture of (R)-1-(3-fluoro-5-(1,1,2,2-tetrafluoroethoxy)phenyl)-1-(4-fluorophenyl)-2-phenylethanamine, prepared as described in Procedure 3, 4, 5 and 6, (20 mg, 0.047 mmol), 2,2,2-trifluoro-1-(oxiran-2-yl)-1-phenylethanol (63 mg, 0.28 mmol), and Yb(CF$_3$OSO$_2$)$_3$ (10 mg) in dichloroethane (0.5 mL) were heated at 45° C. for 72 h. The reaction mixture was concentrated and the residue was purified by preparative HPLC Shimadzu-YMC Sunfire 5μ column, 30×100 mm eluting with 40-100% MeOH (90% in H$_2$O, 0.1% TFA) gradient over 10 min with flow rate 40 mL/min and UV detection at 220 nm. 1,1,1-Trifluoro-4-((R)-1-(3-fluoro-5-(1,1,2,2-tetrafluoroethoxy)phenyl)-1-(4-fluorophenyl)-2-phenylethylamino)-2-phenylbutane-2,3-diol (Example 288) was eluted at a retention time of 9.11 min and was isolated as a clear oil (11 mg, yield 37%). LCMS: RT=1.85 min [M+H] 643.95 (Phenomenex Luna C18 column, 4.6×30 mm eluting with 10-90% MeOH/H$_2$O over 2 minutes containing 0.1% TFA; 5 mL/min, monitoring at 220 nm); HPLC: RT=4.20 min, Purity 100% (Phenomenex Luna C18 column, 4.6×50 mm eluting with 10-90% MeOH/H$_2$O over 4 minutes containing 0.2% PPA; 4 mL/min, monitoring at 220 nm); NMR: 400 MHz $^1$H (CDCl$_3$) 7.34 ppm, 5H, m; 7.17 ppm, 1H, t, J=7.47 Hz; 7.07 ppm, 4H, m; 6.95 ppm, 2H, m; 6.84 ppm, 1H, m; 6.73 ppm, 2H, m; 6.44 ppm, 2H, d, J=7.47 Hz; 5.86 ppm, 1H, m; 4.02 ppm, 2H, dd, J=6.59, 3.95 Hz; 3.33 ppm, 2H, m; 2.32 ppm, 1H, dt, J=12.74, 4.61 Hz; 2.18 ppm, 1H, ddd, J=14.72, 12.52, 7.03 Hz.

Example 289

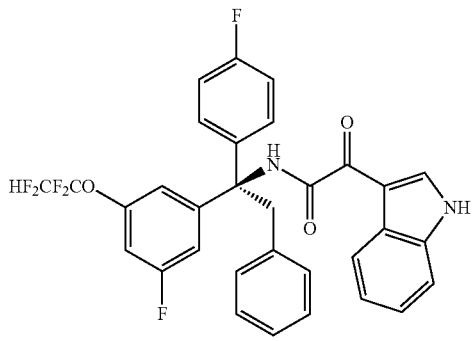

(R)—N-(1-(3-fluoro-5-(1,1,2,2-tetrafluoroethoxy)phenyl)-1-(4-fluorophenyl)-2-phenylethyl)-2-(1H-indol-3-yl)-2-oxoacetamide Procedure 88

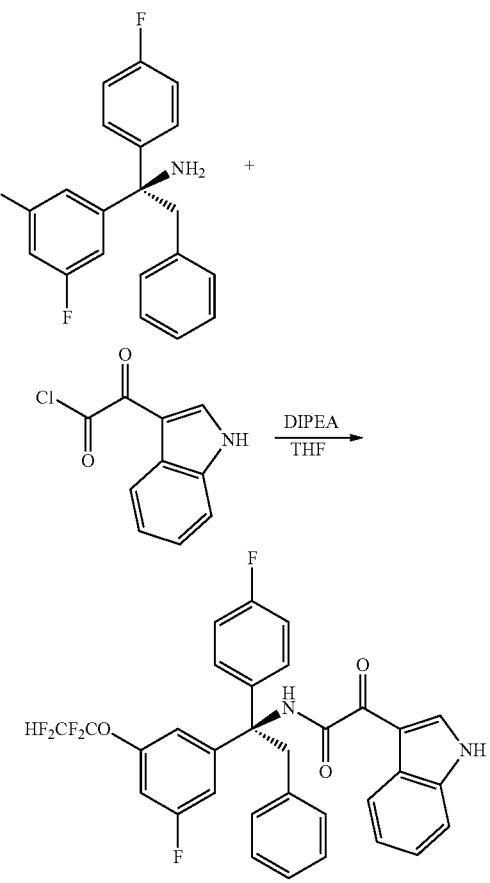

At 0° C., to a solution of (R)-1-(3-fluoro-5-(1,1,2,2-tetrafluoroethoxy)phenyl)-1-(4-fluorophenyl)-2-phenylethanamine, prepared as described in Procedure 3, 4, 5 and 6, (20 mg, 0.045 mmol) and 2-(1H-indol-3-yl)-2-oxoacetyl chloride (10 mg, 0.05 mmol) in THF (0.5 mL) was added dropwise diisopropylethylamine (10 μL, 0.06 mmol). The reaction mixture was stirred at 0° C. for 3 h. The reaction mixture was concentrated and the residue was purified by preparative HPLC Shimadzu-YMC Sunfire 5μ column, 30×100 mm eluting with 40-100% MeOH (90% in H₂O, 0.1% TFA) gradient over 10 min with flow rate 40 mL/min and UV detection at 220 nm. (R)—N-(1-(3-fluoro-5-(1,1,2,2-tetrafluoroethoxy) phenyl)-1-(4-fluorophenyl)-2-phenylethyl)-2-(1H-indol-3-yl)-2-oxoacetamide (Example 289) was eluted at a retention time of 11.65 min and was isolated as a clear oil (13 mg, yield 48%). LCMS: RT=2.20 min [M+H] 596.96 (Phenomenex Luna C18 column, 4.6×30 mm eluting with 10-90% MeOH/H₂O over 2 minutes containing 0.1% TFA; 5 mL/min, monitoring at 220 nm); HPLC: RT=4.45 min, Purity 100% (Phenomenex Luna C18 column, 4.6×50 mm eluting with 10-90% MeOH/H₂O over 4 minutes containing 0.2% PPA; 4 mL/min, monitoring at 220 nm). NMR: 400 MHz ¹H (CDCl₃) 8.98 ppm, 1H, d, J=3.52 Hz; 8.83 ppm, 1H, s; 8.43 ppm, 1H, s; 8.40 ppm, 1H, d, J=7.03 Hz; 7.42 ppm, 1H, m; 7.34 ppm, 2H, m; 7.14 ppm, 5H, m; 7.01 ppm, 2H, t, J=8.57 Hz; 6.93 ppm, 3H, m; 6.68 ppm, 2H, d, J=7.03 Hz; 5.86 ppm, 1H, tt, J=53.06, 2.86, 2.64 Hz; 3.96 ppm, 1H, d, J=12.74 Hz; 3.82 ppm, 1H, m.

Example 290

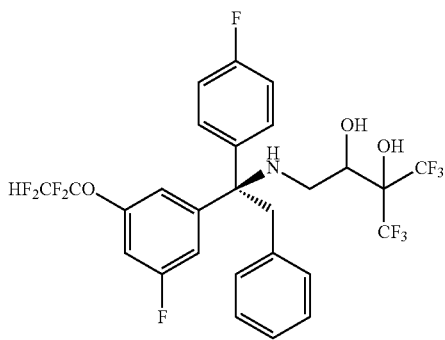

1,1,1-trifluoro-4-((R)-1-(3-fluoro-5-(1,1,2,2-tetrafluoroethoxy)phenyl)-1-(4-fluorophenyl)-2-phenylethylamino)-2-(trifluoromethyl)butane-2,3-diol Procedure 89

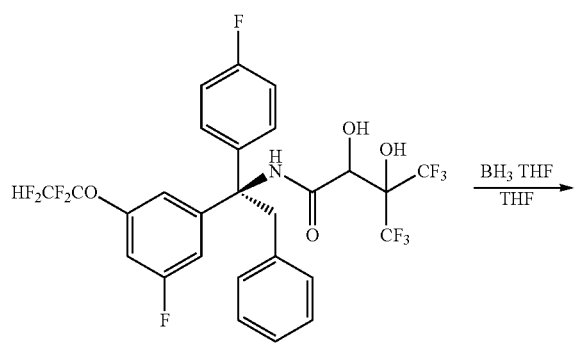

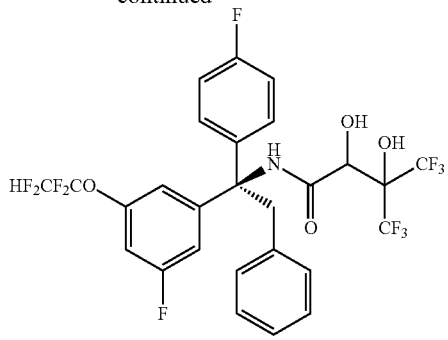

A mixture of 4,4,4-trifluoro-N—((R)-1-(3-fluoro-5-(1,1,2,2-tetrafluoroethoxy)phenyl)-1-(4-fluorophenyl)-2-phenylethyl)-2,3-dihydroxy-3-(trifluoromethyl)butanamide (Example 286, 20 mg, 0.031 mmol) and BH₃/THF (248 µL, 1.0 M solution in THF, 0.248 mmol) in THF (0.5 mL) was heated at 100° C. under microwave irradiation for 30 min. The reaction mixture was concentrated, diluted with EtOAc (25 mL) and the organic layer was washed with saturated Na₂CO₃ (25 mL), dried over MgSO₄, filtered and concentrated. The resulting residue was purified by preparative HPLC Shimadzu-YMC Sunfire 5µ column, 30×100 mm eluting with 40-100% MeOH (90% in H₂O, 0.1% TFA) gradient over 12 min with flow rate 40 mL/min and UV detection at 220 nm. 1,1,1-Trifluoro-4-((R)-1-(3-fluoro-5-(1,1,2,2-tetrafluoroethoxy)phenyl)-1-(4-fluorophenyl)-2-phenylethylamino)-2-(trifluoromethyl)butane-2,3-diol (Example 290) was eluted at a retention time of 11.09 min and isolated as a clear oil (12 mg, yield 62%). LCMS: RT=1.95 min [M+H] 636.38 (Phenomenex Luna C18 column, 4.6×30 mm eluting with 10-90% MeOH/H₂O over 2 minutes containing 0.1% TFA; 5 mL/min, monitoring at 220 nm); HPLC: RT=4.01 min, Purity 100% (Phenomenex Luna C18 column, 4.6×50 mm eluting with 10-90% MeOH/H₂O over 4 minutes containing 0.2% PPA; 4 mL/min, monitoring at 220 nm); NMR: 400 MHz ¹H (CDCl₃) 7.21 ppm, 4H, dd, J=8.57, 5.49 Hz; 7.15 ppm, 2H, t, J=7.25 Hz; 7.06 ppm, 2H, t, J=8.57 Hz; 6.90 ppm, 1H, d, J=8.35 Hz; 6.80 ppm, 1H, dd, J=9.67, 2.20 Hz; 6.77 ppm, 1H, s; 6.60 ppm, 2H, d, J=6.59 Hz; 5.87 ppm, 1H, tt, J=52.95, 2.86 Hz; 3.84 ppm, 1H, t, J=5.71 Hz; 3.59 ppm, 1H, m; 3.46 ppm, 1H, m; 3.07 ppm, 1H, dd, J=12.74, 6.15 Hz; 2.86 ppm, 1H, dd, J=12.96, 5.49 Hz.

Example 291

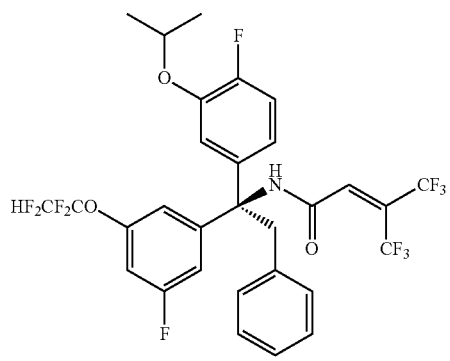

(R)-4,4,4-trifluoro-N-(1-(4-fluoro-3-isopropoxyphenyl)-1-(3-fluoro-5-(1,1,2,2-tetrafluoroethoxy)phenyl)-2-phenylethyl)-3-(trifluoromethyl)but-2-enamide Procedure 90

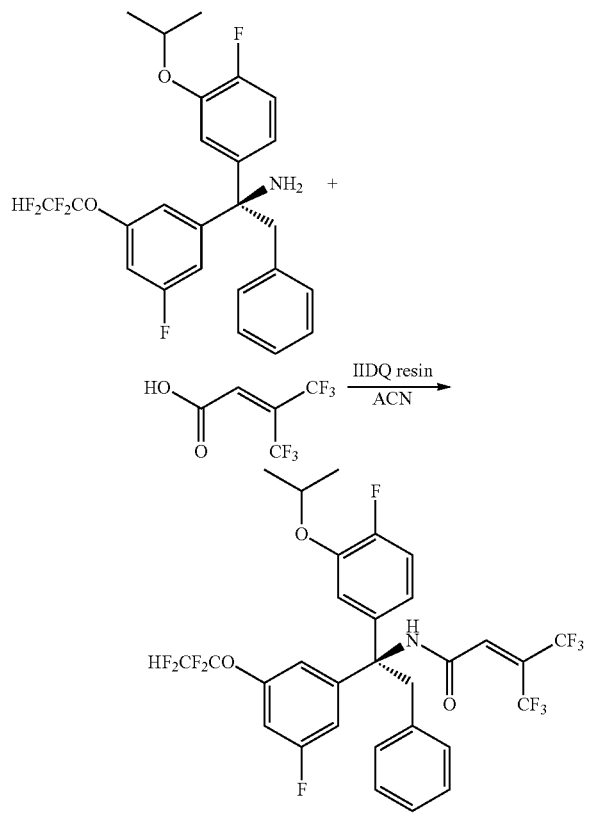

A round bottom flask was charged with IIDQ polystyrene resin (493 mg, 1.5 mmol/g, 0.74 mmol) and acetonitrile (5 mL) and sealed with a rubber septum. The suspension was vacuumed and reflushed with argon three times. To the resulting slurry was added a solution of (R)-1-(4-fluoro-3-isopropoxyphenyl)-1-(3-fluoro-5-(1,1,2,2-tetrafluoroethoxy)phenyl)-2-phenylethanamine, prepared as described in Procedures 109, 110, 111, 112, 113, 114, (180 mg, 0.37 mmol) and 4,4,4-trifluoro-3-(trifluoromethyl)crotonic acid (93 mg, 0.45 mmol) in acetonitrile (5 mL) and the reaction mixture was stirred at room temperature for 18 h. The reaction mixture was filtered and the filtrate was concentrated under reduced pressure and purified by ISCO chromatography (40 g column) using hexane/EtOAc (0-15% over 30 min) to give (R)-4,4,4-trifluoro-N-(1-(4-fluoro-3-isopropoxyphenyl)-1-(3-fluoro-5-(1,1,2,2-tetrafluoroethoxy)phenyl)-2-phenylethyl)-3-(trifluoromethyl)but-2-enamide (Example 291) as a white solid at a retention time of 20 min (199 mg, 74% yield). LCMS: RT=2.18 min [M+H] 674.33 (Phenomenex Luna C18 column, 4.6×30 mm eluting with 10-90% MeOH/H$_2$O over 2 minutes containing 0.1% TFA; 5 mL/min, monitoring at 220 nm); HPLC: RT=4.25 min, Purity 98% (Phenomenex Luna C18 column, 4.6×50 mm eluting with 10-90% MeOH/H$_2$O over 4 minutes containing 0.2% PPA; 4 mL/min, monitoring at 220 nm); NMR: 400 MHz $^1$H (CDCl$_3$) 7.19 ppm, 3H, m; 7.02 ppm, 1H, dd, J=10.55, 8.79 Hz; 6.95 ppm, 3H, m; 6.85 ppm, 1H, s; 6.67 ppm, 3H, d, J=7.03 Hz; 6.62 ppm, 1H, m; 6.13 ppm, 1H, s; 5.88 ppm, 1H, tt, J=53.00, 2.86, 2.75 Hz; 4.36 ppm, 1H, ddd, J=11.97, 6.15, 6.04 Hz; 3.99 ppm, 1H, d, J=13.18 Hz; 3.71 ppm, 1H, d, J=13.18 Hz; 1.26 ppm, 6H, m.

Example 292A

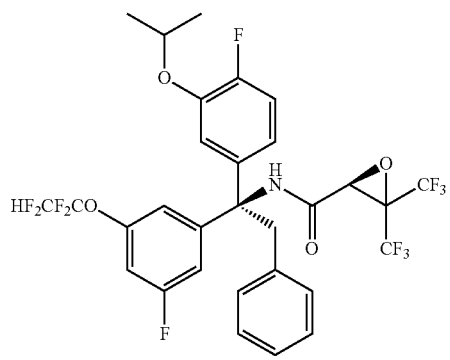

(S)—N—((R)-1-(4-fluoro-3-isopropoxyphenyl)-1-(3-fluoro-5-(1,1,2,2-tetrafluoroethoxy)phenyl)-2-phenylethyl)-3,3-bis(trifluoromethyl)oxirane-2-carboxamide Example 292B

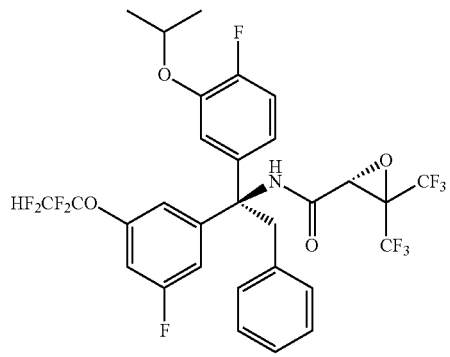

(R)—N—((R)-1-(4-fluoro-3-isopropoxyphenyl)-1-(3-fluoro-5-(1,1,2,2-tetrafluoroethoxy)phenyl)-2-phenylethyl)-3,3-bis(trifluoromethyl)oxirane-2-carboxamide Procedure 91

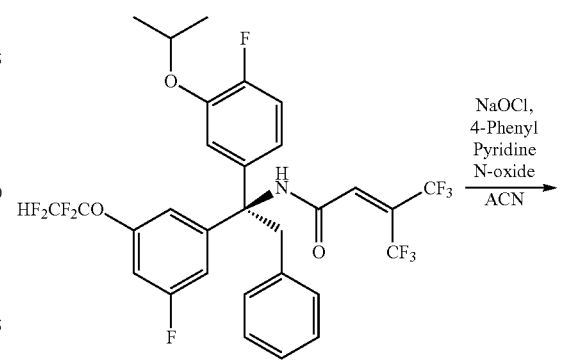

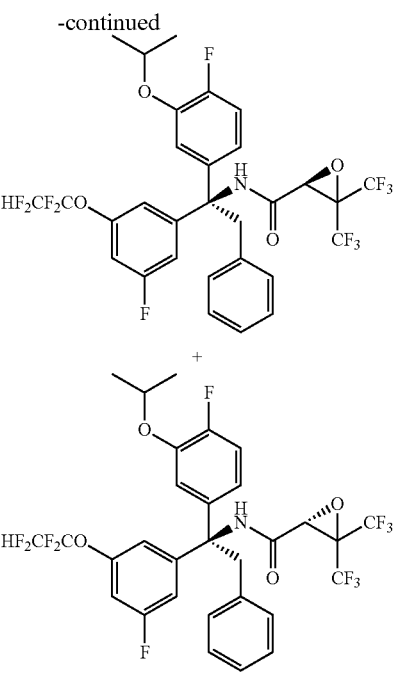

At 0° C. to a solution of (R)-4,4,4-trifluoro-N-(1-(4-fluoro-3-isopropoxyphenyl)-1-(3-fluoro-5-(1,1,2,2-tetrafluoroethoxy)phenyl)-2-phenylethyl)-3-(trifluoromethyl)but-2-enamide (Example 291, 130 mg, 0.19 mmol) and 4-phenyl pyridine N-oxide (26 mg, 0.15 mmol) in acetonitrile (5 mL) was added NaOCl solution (206 μL, chlorine wt % 10-3%, 0.58 mmol). The reaction mixture was stirred at 0° C. for 10 min, then at rt for 1 h. The solvents were removed under reduced pressure and the residue was diluted with EtOAc (30 mL), washed with saturated Na₂SO₃ (30 mL), dried over MgSO₄, filtered and concentrated. The resulting residue was right away purified by ISCO chromatography (40 g column, flow rate 25 mL/min) using hexanes/EtOAc (0-10% over 30 min) to give N—((R)-1-(4-fluoro-3-isopropoxyphenyl)-1-(3-fluoro-5-(1,1,2,2-tetrafluoroethoxy)phenyl)-2-phenylethyl)-3,3-bis(trifluoromethyl)oxirane-2-carboxamide as a diastereomer mixture at a retention time of 26 min (97 mg, 74% yield). The diastereomer mixture was separated by Chiral preparative HPLC chiralpak AD 20μ column, 5×50 cm, eluting with 5% IPA/Heptane with flow rate 50 mL/min.

(S)—N—((R)-1-(4-fluoro-3-isopropoxyphenyl)-1-(3-fluoro-5-(1,1,2,2-tetrafluoroethoxy)phenyl)-2-phenylethyl)-3,3-bis(trifluoromethyl)oxirane-2-carboxamide (Example 292A) was eluted at a retention time of 30 min and isolated as a clear oil (50 mg, yield 51%). LCMS: RT=2.25 min [M+H] 690.30 (Phenomenex Luna C18 column, 4.6×30 mm eluting with 10-90% MeOH/H₂O over 2 minutes containing 0.1% TFA; 5 mL/min, monitoring at 220 nm); HPLC: RT=4.225 min, Purity 100% (Phenomenex Luna C18 column, 4.6×50 mm eluting with 10-90% MeOH/H₂O over 4 minutes containing 0.2% PPA; 4 mL/min, monitoring at 220 nm); NMR: 400 MHz ¹H (CDCl₃) 7.20 ppm, 3H, ddd, J=14.72, 7.25, 7.03 Hz; 6.98 ppm, 3H, m; 6.90 ppm, 1H, s; 6.60 ppm, 5H, m; 5.87 ppm, 1H, t; 4.31 ppm, 1H, ddd, J=12.19, 6.04, 5.93 Hz; 4.10 ppm, 1H, d, J=13.18 Hz; 3.95 ppm, 1H, s; 3.51 ppm, 1H, d, J=13.18 Hz; 1.28 ppm, 3H, d, J=5.71 Hz; 1.21 ppm, 3H, d, J=5.71 Hz.

(R)—N—((R)-1-(4-fluoro-3-isopropoxyphenyl)-1-(3-fluoro-5-(1,1,2,2-tetrafluoroethoxy)phenyl)-2-phenylethyl)-3,3-bis(trifluoromethyl)oxirane-2-carboxamide (Example 292B) was eluted at a retention time of 40 min and isolated as a clear oil (38 mg, yield 39%). LCMS: RT=2.27 min [M+H] 690.30 (Phenomenex Luna C18 column, 4.6×30 mm eluting with 10-90% MeOH/H₂O over 2 minutes containing 0.1% TFA; 5 mL/min, monitoring at 220 nm); HPLC: RT=4.20 min, Purity 100% (Phenomenex Luna C18 column, 4.6×50 mm eluting with 10-90% MeOH/H₂O over 4 minutes containing 0.2% PPA; 4 mL/min, monitoring at 220 nm); NMR: 400 MHz ¹H (CDCl₃) 7.20 ppm, 3H, m; 7.05 ppm, 1H, m; 6.95 ppm, 1H, d, J=7.91 Hz; 6.85 ppm, 2H, m; 6.72 ppm, 2H, m; 6.64 ppm, 2H, d, J=7.47 Hz; 6.59 ppm, 1H, s; 5.87 ppm, 1H, m; 4.36 ppm, 1H, m; 3.92 ppm, 1H, m; 3.88 ppm, 1H, m; 3.70 ppm, 1H, m; 1.26 ppm, 6H, 9 m.

The relative stereochemistry of (S)—N—((R)-1-(4-fluoro-3-isopropoxyphenyl)-1-(3-fluoro-5-(1,1,2,2-tetrafluoroethoxy)phenyl)-2-phenylethyl)-3,3-bis(trifluoromethyl)oxirane-2-carboxamide (Example 292A) and (R)—N—((R)-1-(4-fluoro-3-isopropoxyphenyl)-1-(3-fluoro-5-(1,1,2,2-tetrafluoroethoxy)phenyl)-2-phenylethyl)-3,3-bis(trifluoromethyl)oxirane-2-carboxamide (Example 292B) was assigned arbitrarily.

Example 293

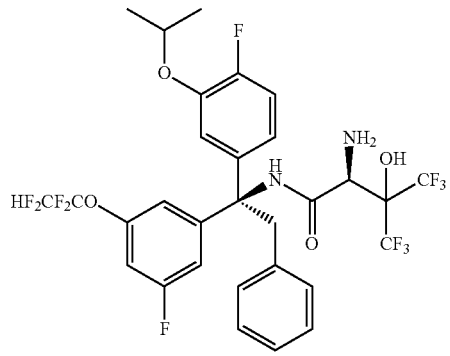

(S)-2-amino-4,4,4-trifluoro-N—((R)-1-(4-fluoro-3-isopropoxyphenyl)-1-(3-fluoro-5-(1,1,2,2-tetrafluoroethoxy)phenyl)-2-phenylethyl)-3-hydroxy-3-(trifluoromethyl)butanamide Procedure 92

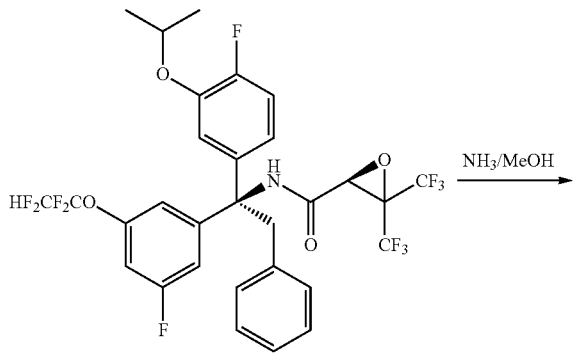

467

-continued

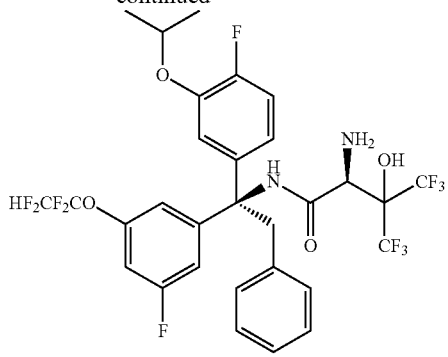

A solution of NH₃ in MeOH (7 M, 1.0 mL) was added to (S)—N—((R)-1-(4-fluoro-3-isopropoxyphenyl)-1-(3-fluoro-5-(1,1,2,2-tetrafluoroethoxy)phenyl)-2-phenylethyl)-3,3-bis(trifluoromethyl)oxirane-2-carboxamide (Example 292A, 28 mg, 0.04 mmol) and the reaction mixture was stirred at rt for 3 h. The reaction mixture was concentrated and purified by preparative HPLC (Shimadzu-Phenomenex Luna AXIA 5µ column, 21.2×100 mm eluting with 30-100% ACN (90% in H₂O, 0.1% TFA) gradient over 14 min with flow rate 20 mL/min and UV detection at 220 nm). (S)-2-amino-4,4,4-trifluoro-N—((R)-1-(4-fluoro-3-isopropoxyphenyl)-1-(3-fluoro-5-(1,1,2,2-tetrafluoroethoxy)phenyl)-2-phenylethyl)-3-hydroxy-3-(trifluoromethyl)butanamide (Example 293) was eluted at a retention time of 12.83 min and isolated as a clear oil (20 mg, yield 70%). LCMS: RT=2.11 min [M+H] 707.41 (Phenomenex Luna C18 column, 4.6×30 mm eluting with 10-90% MeOH/H₂O over 2 minutes containing 0.1% TFA; 5 mL/min, monitoring at 220 nm); HPLC: RT=3.99 min, Purity 100% (Phenomenex Luna C18 column, 4.6×50 mm eluting with 10-90% MeOH/H₂O over 4 minutes containing 0.2% PPA; 4 mL/min, monitoring at 220 nm) NMR: 400 MHz ¹H (CDCl₃) 9.00 ppm, 1H, s; 7.19 ppm, 3H, m; 7.04 ppm, 1H, m; 6.93 ppm, 1H, d, J=8.79 Hz; 6.76 ppm, 4H, m; 6.64 ppm, 2H, d, J=7.03 Hz; 5.8 ppm, 1H, m; 4.38 ppm, 1H, dq, J=6.15, 6.01 Hz; 3.87 ppm, 1H, m; 3.70 ppm, 2H, m; 1.89 ppm, 2H, s; 1.28 ppm, 6H, m.

Example 294

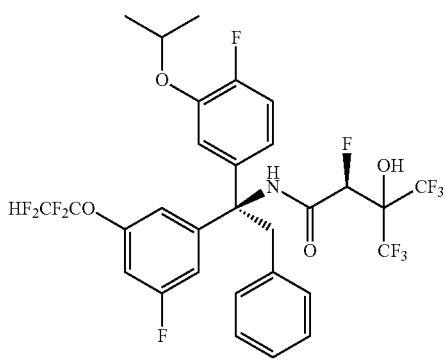

468

(S)-2,4,4,4-tetrafluoro-N—((R)-1-(4-fluoro-3-isopropoxyphenyl)-1-(3-fluoro-5-(1,1,2,2-tetrafluoroethoxy)phenyl)-2-phenylethyl)-3-hydroxy-3-(trifluoromethyl)butanamide Procedure 93

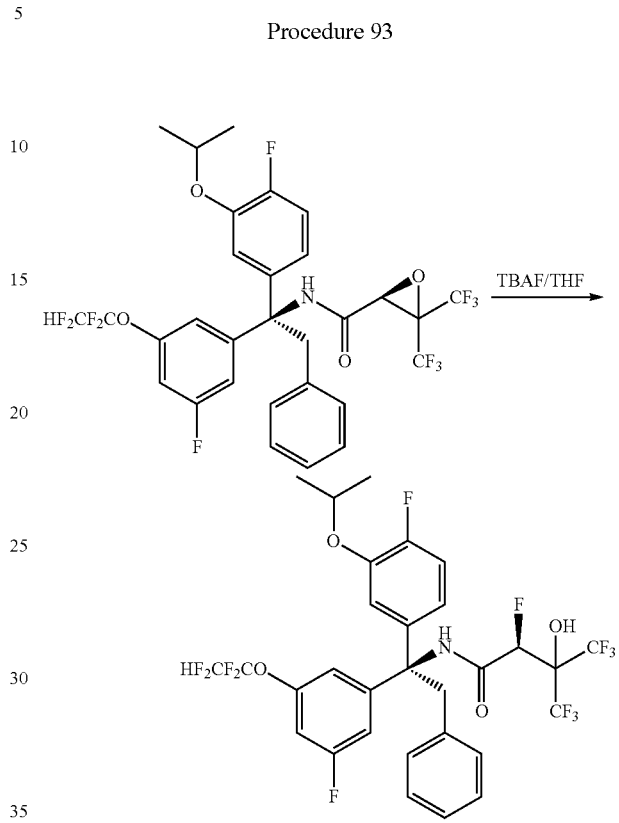

To a solution of (S)—N—((R)-1-(4-fluoro-3-isopropoxyphenyl)-1-(3-fluoro-5-(1,1,2,2-tetrafluoroethoxy)phenyl)-2-phenylethyl)-3,3-bis(trifluoromethyl)oxirane-2-carboxamide (Example 292A, 25 mg, 0.036 mmol) in THF (0.5 mL) was added TBAF (72 µL, 1.0 M solution in THF, 0.072 mmol). The reaction mixture was heated at 60° C. under microwave irradiation for 10 min. The solvent was removed under reduced pressure and the residue was purified by preparative HPLC (Shimadzu-YMC ODS 5µ column, 20×100 mm eluting with 30-100% ACN (90% in H₂O, 0.1% TFA) gradient over 18 min with flow rate 20 mL/min and UV detection at 220 nm). (S)-2,4,4,4-tetrafluoro-N—((R)-1-(4-fluoro-3-isopropoxyphenyl)-1-(3-fluoro-5-(1,1,2,2-tetrafluoroethoxy)phenyl)-2-phenylethyl)-3-hydroxy-3-(trifluoromethyl)butanamide (Example 294) was eluted at a retention time of 17.28 min and was isolated as a clear oil (14 mg, yield 55%). The stereochemistry of (S)-2,4,4,4-tetrafluoro-N—((R)-1-(4-fluoro-3-isopropoxyphenyl)-1-(3-fluoro-5-(1,1,2,2-tetrafluoroethoxy)phenyl)-2-phenylethyl)-3-hydroxy-3-(trifluoromethyl)butanamide (Example 294) was assigned arbitrarily. LCMS: RT=2.22 min [M+H] 710.39 (Phenomenex Luna C18 column, 4.6×30 mm eluting with 10-90% MeOH/H₂O over 2 minutes containing 0.1% TFA; 5 mL/min, monitoring at 220 nm); HPLC: RT=4.18 min, Purity 100% (Phenomenex Luna C18 column, 4.6×50 mm eluting with 10-90% MeOH/H₂O over 4 minutes containing 0.2% PPA; 4 mL/min, monitoring at 220 nm); NMR: 400 MHz ¹H (CDCl₃) 7.26 ppm, 1H, m; 7.21 ppm, 3H, m; 7.07 ppm, 1H, m; 6.96 ppm, 1H, d, J=8.79 Hz; 6.78 ppm, 4H, m; 6.64 ppm, 2H, d, J=7.15 Hz; 6.50 ppm, 1H, s; 5.87 ppm, 1H, tt, J=52.97, 2.61, 2.47 Hz; 5.10 ppm, 1H, d, J=46.17 Hz; 4.41 ppm, 1H, dt, J=12.09, 6.05 Hz; 3.97 ppm, 1H, d, J=13.19 Hz; 3.58 ppm, 1H, d, J=13.19 Hz; 1.30 ppm, 6H, t, J=6.32 Hz.

Example 295A

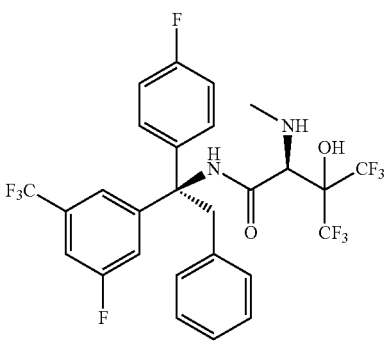 [SMILES: CN[C@H](C(=O)N[C@](Cc1ccccc1)(c1ccc(F)cc1)c1cc(F)cc(C(F)(F)F)c1)C(O)(C(F)(F)F)C(F)(F)F]

(S)-4,4,4-trifluoro-N—((R)-1-(3-fluoro-5-(trifluoromethyl)phenyl)-1-(4-fluorophenyl)-2-phenylethyl)-3-hydroxy-2-(methylamino)-3-(trifluoromethyl)butanamide

Example 295B

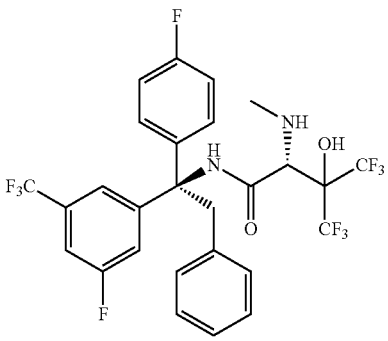 [SMILES: CN[C@@H](C(=O)N[C@](Cc1ccccc1)(c1ccc(F)cc1)c1cc(F)cc(C(F)(F)F)c1)C(O)(C(F)(F)F)C(F)(F)F]

(R)-4,4,4-trifluoro-N—((R)-1-(3-fluoro-5-(trifluoromethyl)phenyl)-1-(4-fluorophenyl)-2-phenylethyl)-3-hydroxy-2-(methylamino)-3-(trifluoromethyl)butanamide

Procedure 94

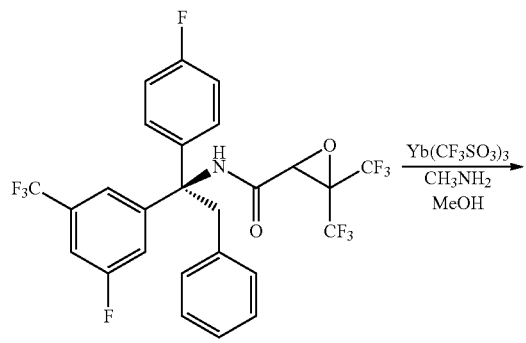

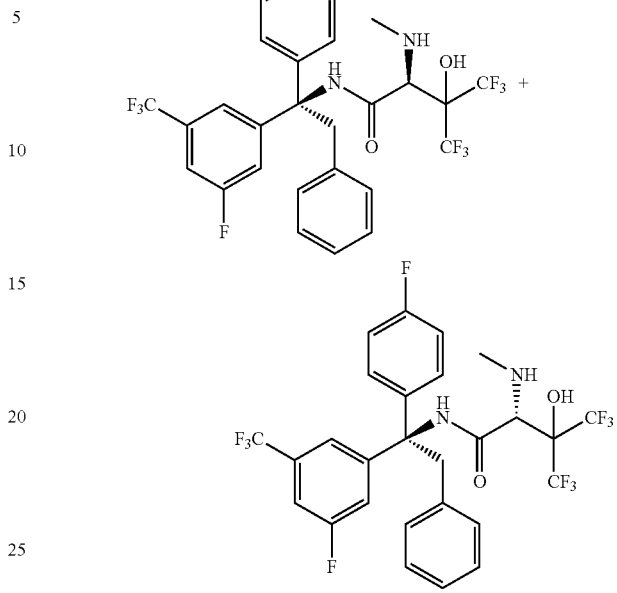

To a mixture of diastereomers of N—((R)-1-(3-fluoro-5-(trifluoromethyl)phenyl)-1-(4-fluorophenyl)-2-phenylethyl)-3,3-bis(trifluoromethyl)oxirane-2-carboxamide (40 mg, 0.069 mmol), prepared as described in Procedure 90 and 91, was added Yb(CF$_3$SO$_3$)$_3$ (10 mg) and methylamine in MeOH (0.2 mL, 2 M solution in MeOH). The reaction was heated at 60° C. under microwave irradiation for 10 min and then concentrated under reduced pressure. The residue was diluted with EtOAc (25 mL) and washed with saturated Na$_2$CO$_3$, dried over MgSO$_4$, filtered and concentrated under reduced pressure. The resulting residue was purified by preparative HPLC Shimadzu-YMC-ODS-A 5µ column, 20×100 mm eluting with 30-100% MeOH (90% in H$_2$O, 0.1% TFA) gradient over 30 min with flow rate 20 mL/min and UV detection at 220 nm.

(S)-4,4,4-trifluoro-N—((R)-1-(3-fluoro-5-(trifluoromethyl)phenyl)-1-(4-fluorophenyl)-2-phenylethyl)-3-hydroxy-2-(methylamino)-3-(trifluoromethyl)butanamide (Example 295A) was eluted at a retention time of 22.96 min and isolated as a clear oil (4 mg, yield 9%). LCMS: RT=4.17 min [M+H] 615.3 (Phenomenex Luna C18 column, 4.6×50 mm eluting with 10-90% MeOH/H$_2$O over 4 minutes containing 10 mM NH$_4$OAc; 4 mL/min, monitoring at 220 nm); HPLC: RT=3.87 min, Purity 100% (Phenomenex Luna C18 column, 4.6×50 mm eluting with 10-90% MeOH/H$_2$O over 4 minutes containing 0.2% PPA; 4 mL/min, monitoring at 220 nm); NMR: 400 MHz $^1$H (CDCl$_3$) 9.24 ppm, 1H, s; 7.54 ppm, 1H, s; 7.30 ppm, 3H, m; 7.20 ppm, 3H, m; 7.01 ppm, 2H, t, J=8.35 Hz; 6.85 ppm, 2H, m; 6.60 ppm, 2H, d, J=7.03 Hz; 4.29 ppm, 1H, d, J=12.74 Hz; 3.47 ppm, 1H, d, J=12.74 Hz; 3.32 ppm, 1H, s; 2.32 ppm, 3H, s.

(R)-4,4,4-trifluoro-N—((R)-1-(3-fluoro-5-(trifluoromethyl)phenyl)-1-(4-fluorophenyl)-2-phenylethyl)-3-hydroxy-2-(methylamino)-3-(trifluoromethyl)butanamide (Example 295B) was eluted at a retention time of 23.45 min and isolated as a clear oil (5 mg, yield 11%). LCMS: 4.16 min [M+H] 615.3 (Phenomenex Luna C18 column, 4.6×50 mm eluting with 10-90% MeOH/H$_2$O over 4 minutes containing 10 mM NH$_4$OAc; 4 mL/min, monitoring at 220 nm); HPLC:

RT=3.93 min, Purity 92% (Phenomenex Luna C18 column, 4.6×50 mm eluting with 10-90% MeOH/H₂O over 4 minutes containing 0.2% PPA; 4 mL/min, monitoring at 220 nm) NMR: 400 MHz ¹H (CDCl₃) 9.06 ppm, 1H, s; 7.30 ppm, 2H, m; 7.23 ppm, 3H, d, J=5.71 Hz; 7.17 ppm, 2H, t, J=7.25 Hz; 7.08 ppm, 2H, t, J=8.57 Hz; 7.00 ppm, 1H, m; 6.91 ppm, 1H, d, J=10.11 Hz; 6.60 ppm, 2H, d, J=7.03 Hz; 4.14 ppm, 1H, m; 3.98 ppm, 1H, s; 3.52 ppm, 2H, m; 3.39 ppm, 2H, m; 2.37 ppm, 3H, s.

The stereochemistry of (S)-4,4,4-Trifluoro-N—((R)-1-(3-fluoro-5-(trifluoromethyl)phenyl)-1-(4-fluorophenyl)-2-phenylethyl)-3-hydroxy-2-(methylamino)-3-(trifluoromethyl)butanamide (Example 295A) and (R)-4,4,4-trifluoro-N—((R)-1-(3-fluoro-5-(trifluoromethyl)phenyl)-1-(4-fluorophenyl)-2-phenylethyl)-3-hydroxy-2-(methylamino)-3-(trifluoromethyl)butanamide isomer B (Example 295B) was assigned arbitrarily.

Example 296

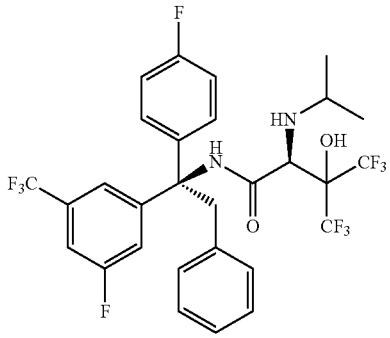 [SMILES: CC(C)N[C@H](C(=O)N[C@](Cc1ccccc1)(c1ccc(F)cc1)c1cc(F)cc(C(F)(F)F)c1)C(O)(C(F)(F)F)C(F)(F)F]

(S)-4,4,4-trifluoro-N—((R)-1-(3-fluoro-5-(trifluoromethyl)phenyl)-1-(4-fluorophenyl)-2-phenylethyl)-3-hydroxy-2-(isopropylamino)-3-(trifluoromethyl) butanamide

Procedure 95

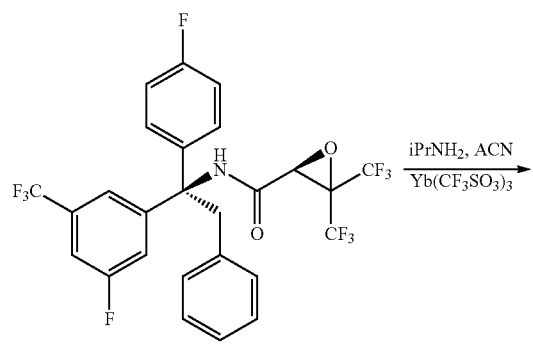

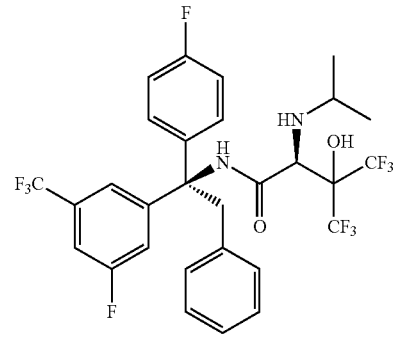

To a solution of (S)—N—((R)-1-(3-fluoro-5-(trifluoromethyl)phenyl)-1-(4-fluorophenyl)-2-phenylethyl)-3,3-bis(trifluoromethyl)oxirane-2-carboxamide (20 mg, 0.034 mmol), prepared as described in Procedure 90 and 91, in ACN (0.5 mL) was added Yb(CF₃SO₃)₃ (10 mg) and isopropylamine (10 µL, 0.1 mmol). The reaction mixture was heated at 60° C. under microwave irradiation for 10 min and then concentrated under reduced pressure. The residue was diluted with EtOAc (25 mL) and the organic layer was washed by saturated Na₂CO₃, dried over MgSO₄, filtered and concentrated under reduced pressure. The resulting residue was purified by preparative HPLC Shimadzu-YMC-ODS-A 5µ column, 20×100 mm eluting with 30-100% MeOH (90% in H₂O, 0.1% TFA) gradient over 30 min with flow rate 20 mL/min and UV detection at 220 nm. (S)-4,4,4-trifluoro-N—((R)-1-(3-fluoro-5-(trifluoromethyl)phenyl)-1-(4-fluorophenyl)-2-phenylethyl)-3-hydroxy-2-(isopropylamino)-3-(trifluoromethyl)butanamide (Example 296) was eluted at a retention time of 27.36 min and isolated as a clear oil (12 mg, yield 54%). LCMS: RT=2.15 min [M+H] 643.4 (Phenomenex Luna C18 column, 4.6×30 mm eluting with 10-90% MeOH/H₂O over 2 minutes containing 0.1% TFA, 5 mL/min, monitoring at 220 nm); HPLC: RT=4.293 min, Purity 100% (Phenomenex Luna C18 column, 4.6×50 mm eluting with 10-90% MeOH/H₂O over 4 minutes containing 0.2% PPA; 4 mL/min, monitoring at 220 nm). NMR: 400 MHz ¹H (CDCl₃) 9.23 ppm, 1H, s; 7.77 ppm, 1H, s; 7.30 ppm, 3H, m; 7.20 ppm, 1H, m; 7.14 ppm, 2H, t, J=7.25 Hz; 7.02 ppm, 2H, t, J=8.35 Hz; 6.93 ppm, 1H, d, J=4.83 Hz; 6.60 ppm, 2H, d, J=7.03 Hz; 4.29 ppm, 1H, d, J=13.18 Hz; 3.51 ppm, 1H, d, J=5.27 Hz; 3.47 ppm, 1H, d, J=12.74 Hz; 2.74 ppm, 1H, m; 1.87 ppm, 1H, s; 1.04 ppm, 3H, d, J=6.15 Hz; 0.71 ppm, 3H, d, J=6.15 Hz. The stereochemistry of (S)-4,4,4-trifluoro-N—((R)-1-(3-fluoro-5-(trifluoromethyl)phenyl)-2-phenylethyl)-3-hydroxy-2-(isopropylamino)-3-(trifluoromethyl)butanamide (Example 296) was assigned arbitrarily.

Example 297

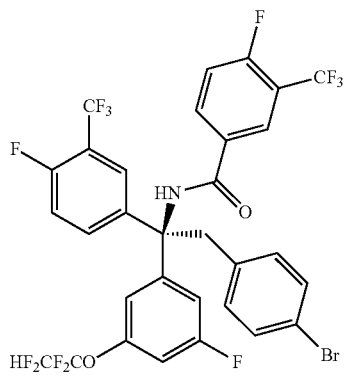

(R)—N-(2-(4-bromophenyl)-1-(4-fluoro-3-(trifluoromethyl)phenyl)-1-(3-fluoro-5-(1,1,2,2-tetrafluoroethoxy)phenyl)ethyl)-4-fluoro-3-(trifluoromethyl)benzamide

Procedure 96

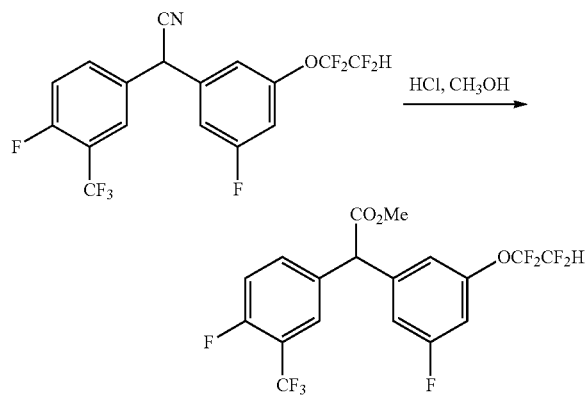

A solution of 2-(4-fluoro-3-(trifluoromethyl)phenyl)-2-(3-fluoro-5-(1,1,2,2-tetrafluoroethoxy)phenyl)acetonitrile prepared as described in Procedure 3, 4 and 73 (72% yield, 453 mg, 1.1 mmol) in MeOH (18 mL) was cooled to 0° C. and saturated with HCl gas. The resulting solution was heated at reflux overnight. The reaction mixture was concentrated under reduced pressure and the residue was partitioned between EtOAc and sat. NaCl. The organic layer was separated, dried over magnesium sulfate, filtered and concentrated under reduced pressure. The residue was purified by ISCO (40 g silica gel column, 0-40% EtOAc/hexane over 50 min) to yield methyl 2-(4-fluoro-3-(trifluoromethyl)phenyl)-2-(3-fluoro-5-(1,1,2,2-tetrafluoroethoxy)phenyl)acetate as a colorless oil (394 mg, 80% yield). LCMS: RT=2.05 min [M+H] 446.97 (Phenomenex Luna C18 4.6×30 mm column, eluting with 10-90% MeOH/H$_2$O containing 0.% TFA, 2 min gradient, flow rate 5 mL/min, wavelength 220 nm); HPLC: RT=4.22 min (Phenomenex Luna C18 4.6×50 mm column, eluting with 10-90% MeOH/H$_2$O containing 0.2% PPA, flow rate 4 mL/min, wavelength 220 nm); $^1$H NMR (400 MHz, CDCl$_3$) δ ppm 7.53 (1H, d, J=6.59 Hz), 7.47-7.51 (1H, m), 7.19 (1H, t, J=9.23 Hz), 6.9-6.97 (3H, m), 5.76-6.03 (1H, m), 3.78 (3H, s).

Procedure 97

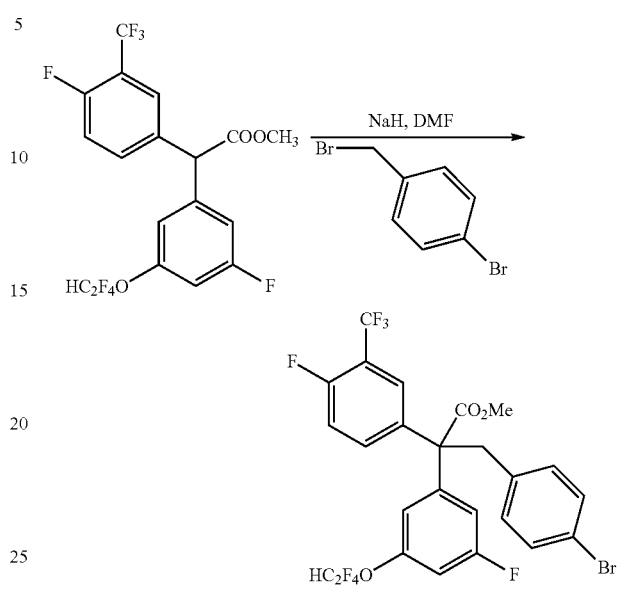

To a suspension of NaH (60% in oil, 66 mg, 1.65 mmol) in DMF (3 mL) at 0° C. was added a solution of methyl 2-(4-fluoro-3-(trifluoromethyl)phenyl)-2-(3-fluoro-5-(1,1,2,2-tetrafluoroethoxy)phenyl)acetate (600 mg, 1.34 mmol) in one portion. The reaction mixture was stirred at 0° C. for 10 min followed by addition of a solution of 4-bromobenzylbromide (343 mg, 1.37 mmol) in DMF (2 mL). The reaction was stirred at 0° C. for 5 min and quenched by the addition of saturated NH$_4$Cl. The mixture was extracted with EtOAc (2×30 mL). The combined organic layers were dried over magnesium sulfate, filtered and concentrated to give methyl 3-(4-bromophenyl)-2-(4-fluoro-3-(trifluoromethyl)phenyl)-2-(3-fluoro-5-(1,1,2,2-tetrafluoroethoxy)phenyl)propanoate as a colorless oil (865 mg, 100% yield). LCMS: RT=2.26 min, no ionization (Phenomenex Luna C18 4.6×30 mm column, eluting with 10-90% MeOH/H$_2$O containing 0.1% TFA, 2 min gradient, flow rate 5 mL/min, wavelength 220 nm); HPLC: RT=4.48 min (Phenomenex Luna C18 4.6×50 mm column, eluting with 10-90% MeOH/H$_2$O containing 0.2% PPA, flow rate 4 mL/min, wavelength 220 nm); $^1$H NMR (400 MHz, CDCl$_3$) δ ppm 7.29-7.33 (1H, m), 7.21-7.27 (4H, m), 7.11 (1H, t, J=9.23 Hz), 6.94 (1H, d, J=8.79 Hz), 6.82 (1H, d, J=9.67 Hz), 6.80 (1H, s), 6.52 (2H, d, J=8.35 Hz), 5.87 (1H, t, J=53.2 Hz), 3.75 (3H, s), 3.56-3.66 (2H, m).

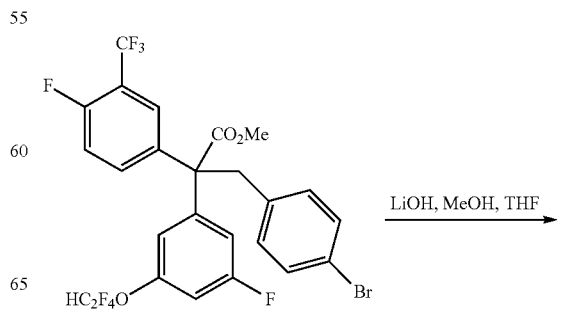

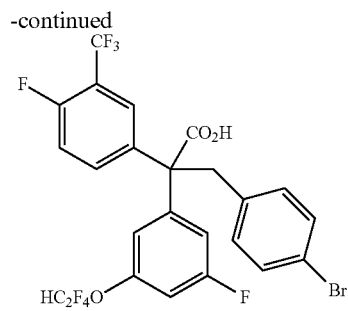

A mixture of methyl 3-(4-bromophenyl)-2-(4-fluoro-3-(trifluoromethyl)phenyl)-2-(3-fluoro-5-(1,1,2,2-tetrafluoroethoxy)phenyl)propanoate (865 mg, 1.34 mmol) in MeOH (10 mL)/THF (20 mL) and LiOH (2 N, 10 mL) was stirred at rt overnight. The reaction mixture was made acidic by addition of 1 N HCl to pH=1~2 and concentrated. The resulting residue was partitioned between EtOAc and sat. NaCl. The organic layer was separated, dried over magnesium sulfate, filtered and concentrated under reduced pressure. The residue was purified by ISCO (40 g siligel column, 0-10% MeOH/DCM over 30 min) to yield 3-(4-bromophenyl)-2-(4-fluoro-3-(trifluoromethyl)phenyl)-2-(3-fluoro-5-(1,1,2,2-tetrafluoroethoxy)phenyl)propanoic acid as a colorless oil (650 mg, 81% yield). LCMS: RT=2.17 min [M+H] 600.88 (Phenomenex Luna C18 4.6×30 mm column, eluting with 10-90% MeOH/H$_2$O containing 0.% TFA, 2 min gradient, flow rate 5 mL/min, wavelength 220 nm); HPLC: RT=4.45 min (Phenomenex Luna C18 4.6×50 mm column, eluting with 10-90% MeOH/H$_2$O containing 0.2% PPA, flow rate 4 mL/min, wavelength 220 nm).

Procedure 98

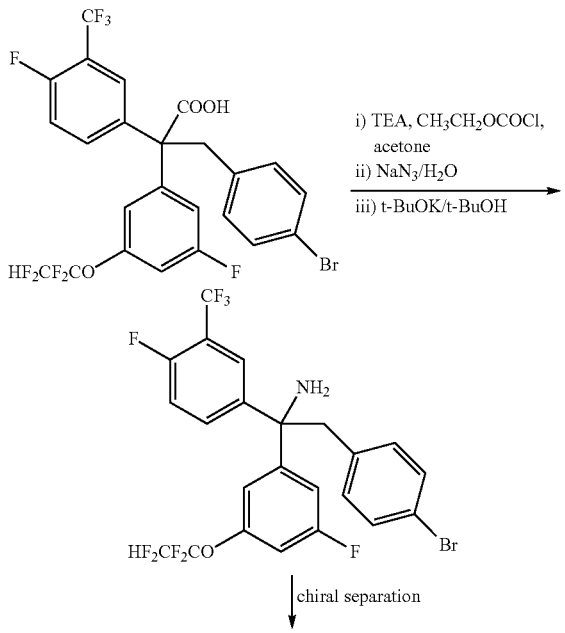

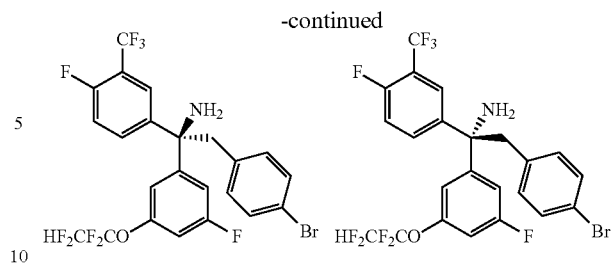

At 0° C. to a solution of 3-(4-bromophenyl)-2-(4-fluoro-3-(trifluoromethyl)phenyl)-2-(3-fluoro-5-(1,1,2,2-tetrafluoroethoxy)phenyl)propanoic acid (1.59 g, 2.64 mmol) in acetone (30 mL) was added TEA (442 µL, 3.17 mmol) followed by ethyl chloroformate (303 µL, 3.17 mmol). The reaction mixture was stirred at 0° C. for 45 min and NaN$_3$ (343 mg, 5.28 mmol) was added. The reaction was stirred at 0° C. for 1 h, quenched by the addition of water and the aqueous layer was extracted with toluene (3×30 mL). The combined organic layers were washed with sat. NaCl, dried over magnesium sulfate, filtered and concentrated under reduced pressure. The resulting residue was diluted with toluene (10 mL) and heated at 90° C. for 6 h. The reaction mixture was concentrated under reduced pressure and the residue was dissolved in t-BuOH/THF (1:1, 20 mL) and treated with t-BuOK/t-BuOH (1 N, 13.2 mL, 13.2 mmol). The reaction mixture was stirred at rt overnight, then heated at 85° C. for 3 h. The reaction mixture was quenched by the addition of water and the aqueous layer was extracted with EtOAc. The combined organic layers were washed with sat. NaCl, dried over magnesium sulfate, filtered and concentrated. The residue was purified by ISCO (40 g siligel column, 0-40% EtOAc/hexane over 40 min to yield 2-(4-bromophenyl)-1-(4-fluoro-3-(trifluoromethyl)phenyl)-1-(3-fluoro-5-(1,1,2,2-tetrafluoroethoxy)phenyl)ethanamine as a colorless oil (1.2 g, 82% yield). LCMS: RT=1.82 min [M+H] 556.8 (Phenomenex Luna C18 4.6×30 mm column, eluting with 10-90% MeOH/H$_2$O containing 0.1% TFA, 2 min gradient, flow rate 5 mL/min, wavelength 220 nm). $^1$H NMR (400 MHz, CDCl$_3$) δ ppm 7.61 (1H, d, J=6.15 Hz), 7.48-7.53 (1H, m), 7.30 (1H, d, J=7.91 Hz), 7.15 (1H, t, J=9.23 Hz), 6.96-7.00 (2H, m), 6.89 (1H, d, J=8.79 Hz), 6.61 (2H, d, J=7.91 Hz), 5.89 (1H, t, J=53 Hz), 3.49 (1H, d, J=13.6 Hz), 3.43 (1H, d, J=13.6 Hz), 1.50-1.65 (2H, m).

2-(4-Bromophenyl)-1-(4-fluoro-3-(trifluoromethyl)phenyl)-1-(3-fluoro-5-(1,1,2,2-tetrafluoroethoxy)phenyl)ethanamine (racemic, 510 mg) was subjected to chiral preparative HPLC separation (chiral OD 10 micron 4.6×250 mm column, eluting with 20% iPA/heptane/0.1% DEA) to give (R)-2-(4-bromophenyl)-1-(4-fluoro-3-(trifluoromethyl)phenyl)-1-(3-fluoro-5-(1,1,2,2-tetrafluoroethoxy)phenyl)ethanamine (211 mg) as a colorless oil and (S)-2-(4-bromophenyl)-1-(4-fluoro-3-(trifluoromethyl)phenyl)-1-(3-fluoro-5-(1,1,2,2-tetrafluoroethoxy)phenyl)ethanamine (195 mg) as colorless oil. For (R)-2-(4-bromophenyl)-1-(4-fluoro-3-(trifluoromethyl)phenyl)-1-(3-fluoro-5-(1,1,2,2-tetrafluoroethoxy)phenyl)ethanamine: chiral analytical HPLC: RT=6.0 min, 100% ee (chiral OD 10 micron 4.6×250 mm column, eluting with 20% IPA/heptane/0.1% DEA, flow rate 1 mL/min, wavelength 220 nm); LCMS: RT=1.82 min [M+H] 556.8 (Phenomenex Luna C18 4.6×30 mm column, eluting with 10-90% MeOH/H$_2$O containing 0.1% TFA, 2 min gradient, flow rate 5 mL/min, wavelength 220 nm). $^1$H NMR (400 MHz, CDCl$_3$) δ ppm 7.61 (1H, d, J=6.15 Hz), 7.48-7.53 (1H, m), 7.30 (1H, d, J=7.91 Hz), 7.15 (1H, t, J=9.23 Hz), 6.96-7.00 (2H, m), 6.89 (1H, d, J=8.79 Hz), 6.61 (2H, d, J=7.91 Hz), 5.89 (1H, t, J=53 Hz), 3.49 (1H, d, J=13.6 Hz), 3.43 (1H, d, J=13.6 Hz), 1.50-1.65 (2H, m). For (S)-2-(4-bromophenyl)-1-(4-fluoro-3-(trifluoromethyl)phenyl)-1-(3-fluoro-5-(1,1,2,2-tetrafluoroethoxy)phenyl)ethanamine isomer B: chiral analytical HPLC: RT=7.5 min, 100% ee (chiral OD 10 micron 4.6×250 mm column, eluting with 20% IPA/heptane/0.1% DEA, flow rate 1 mL/min, wavelength 220 nm); LCMS: RT=1.82 min [M+H] 556.8 (Phenomenex Luna C18 4.6×30 mm column, eluting with 10-90% MeOH/H₂O containing 0.1% TFA, 2 min gradient, flow rate 5 mL/min, wavelength 220 nm). ¹H NMR (400 MHz, CDCL₃) δ ppm 7.61 (1H, d, J=6.15 Hz), 7.48-7.53 (1H, m), 7.30 (1H, d, J=7.91 Hz), 7.15 (1H, t, J=9.23 Hz), 6.96-7.00 (2H, m), 6.89 (1H, d, J=8.79 Hz), 6.61 (2H, d, J=7.91 Hz), 5.89 (1H, t, J=53 Hz), 3.49 (1H, d, J=13.6 Hz), 3.43 (1H, d, J=13.6 Hz), 1.50-1.65 (2H, m).

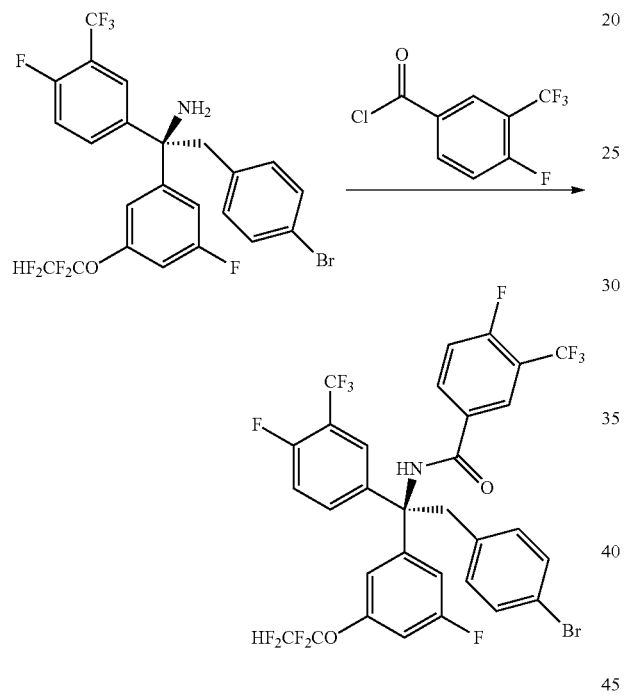

Following Procedure 7, (R)—N-(2-(4-bromophenyl)-1-(4-fluoro-3-(trifluoromethyl)phenyl)-1-(3-fluoro-5-(1,1,2,2-tetrafluoroethoxy)phenyl)ethyl)-4-fluoro-3-(trifluoromethyl)benzamide (Example 297) was prepared as a white foam (471 mg, 88% yield). LCMS: RT=2.25 min [M+H] 761.8 (Phenomenex Luna C18 4.6×30 mm column, eluting with 10-90% MeOH/H₂O containing 0.1% TFA, 2 min gradient, flow rate 5 mL/min, wavelength 220 nm); HPLC: RT=4.52 min (Phenomenex Luna C18 4.6×50 mm column, eluting with 10-90% MeOH/H₂O containing 0.2% PPA, flow rate 4 mL/min, wavelength 220 nm); ¹H NMR (400 MHz, CDCl₃) δ ppm 7.96 (1H, dd, J=6.59, 2.20 Hz), 7.81-7.85 (1H, m), 7.39-7.44 (2H, m), 7.30-7.34 (2H, m), 7.21 (1H, t, J=9.45 Hz), 6.99 (1H, d, J=8.79 Hz), 6.79-6.84 (2H, m), 6.57 (1H, s), 6.55 (2H, d, J=8.35 Hz), 5.89 (1H, t, J=54 Hz), 3.95 (1H, d, J=13.2 Hz), 3.86 (1H, d, J=13.2 Hz).

Example 298

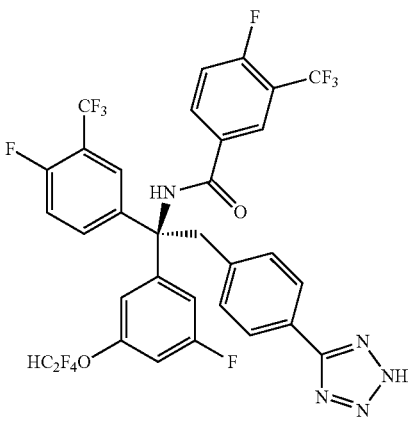

(R)—N-(2-(4-(2H-tetrazol-5-yl)phenyl)-1-(4-fluoro-3-(trifluoromethyl)phenyl)-1-(3-fluoro-5-(1,1,2,2-tetrafluoroethyl)phenyl)ethyl)-4-fluoro-3-(trifluoromethyl)benzamide Procedure 99

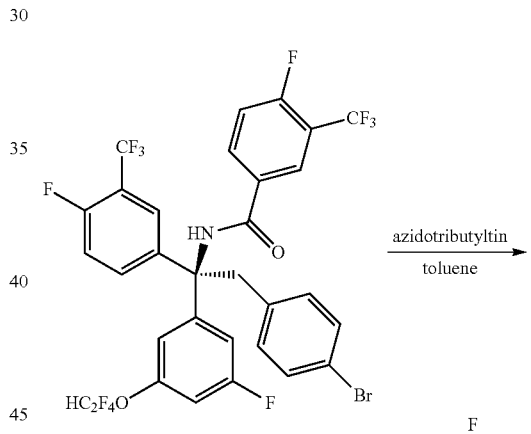

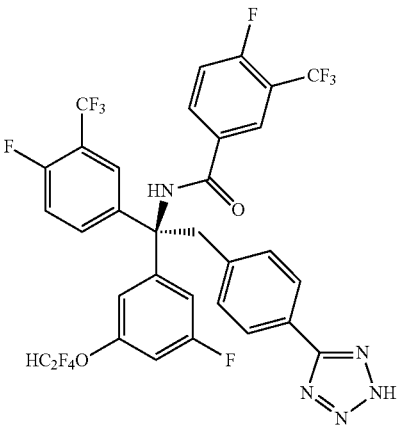

A mixture of (R)—N-(2-(4-bromophenyl)-1-(4-fluoro-3-(trifluoromethyl)phenyl)-1-(3-fluoro-5-(1,1,2,2-tetrafluoroethoxy)phenyl)ethyl)-4-fluoro-3-(trifluoromethyl)benzamide (Example 297, 20 mg, 0.028 mmol) and azidotributyltin (38 μL, 0.14 mmol) in toluene was heated at 100° C. overnight. The reaction mixture was concentrated under reduced pressure and the residue was purified by ISCO (4 g silica gel column, 0-10% MeOH/DCM) to give (R)—N-(2-(4-(2H-tetrazol-5-yl)phenyl)-1-(4-fluoro-3-(trifluoromethyl)phenyl)-1-(3-fluoro-5-(1,1,2,2-tetrafluoroethyl)phenyl)ethyl)-4-fluoro-3-(trifluoromethyl)benzamide (Example 298) as a white solid (11 mg, 52% yield). LCMS: RT=2.07 min [M+H] 752.3 (Phenomenex Luna C18 4.6×30 mm column, eluting with 10-90% MeOH/H$_2$O containing 0.1% TFA, 2 min gradient, flow rate 5 mL/min, wavelength 220 nm); HPLC: RT=4.26 min (Phenomenex Luna C18 4.6×50 mm column, eluting with 10-90% MeOH/H$_2$O containing 0.2% PPA, flow rate 4 mL/min, wavelength 220 nm). $^1$H NMR (400 MHz, CD$_3$OD) δ ppm 8.98 (1H, s), 7.95-7.98 (2H, m), 7.71 (2H, d, J=8.35 Hz), 7.49 (1H, dd, J=7.47, 3.95 Hz), 7.34-7.42 (2H, m), 7.22 (1H, t, J=9.45 Hz), 7.04 (1H, d, J=10.11 Hz), 6.94-6.98 (2H, m), 6.84 (2H, d, J=8.35 Hz), 6.18 (1H, t, J=52.3 Hz), 4.11 (1H, d, J=12.7), 4.11 (1H, d, J=12.7).

Example 299

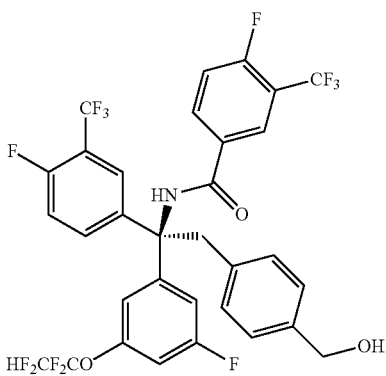

(R)-4-fluoro-N-(1-(4-fluoro-3-(trifluoromethyl)phenyl)-1-(3-fluoro-5-(1,1,2,2-tetrafluoroethoxy)phenyl)-2-(4-(hydroxymethyl)phenyl)ethyl)-3-(trifluoromethyl)benzamide Procedure 100

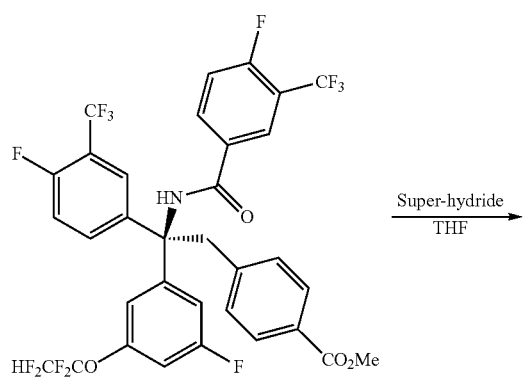

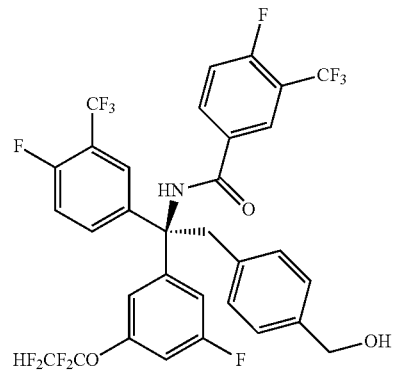

To a solution of (R)-methyl 4-(2-(4-fluoro-3-(trifluoromethyl)benzamido)-2-(4-fluoro-3-(trifluoromethyl)phenyl)-2-(3-fluoro-5-(1,1,2,2-tetrafluoroethoxy)phenyl)ethyl)benzoate prepared as described in Procedure 96, 97, 98, 56 and 57 (29 mg, 0.039 mmol) in THF at –78° C. was added a solution of lithium triethylborohydride (1.0 M in THF, 0.5 mL, 0.5 mmol). The resulting mixture was stirred at –78° C. for 1.5 h. The reaction was quenched by addition of 1 N NaOH (1 mL) and the aqueous layer was extracted with EtOAc (15 mL). The organic layer was dried over magnesium sulfate, filtered and concentrated under reduced pressure. The residue was purified by ISCO (12 g silica gel column, 0-50% EtOAc/hexane over min) to yield (R)-4-fluoro-N-(1-(4-fluoro-3-(trifluoromethyl)phenyl)-1-(3-fluoro-5-(1,1,2,2-tetrafluoroethoxy)phenyl)-2-(4-(hydroxymethyl)phenyl)ethyl)-3-(trifluoromethyl)benzamide (Example 299) as a colorless film (22 mg, 79% yield). LCMS: RT=2.10 min [M+H] 714.31 (Phenomenex Luna C18 4.6×30 mm column, eluting with 10-90% MeOH/H$_2$O containing 0.1% TFA, 2 min gradient, flow rate 5 mL/min, wavelength 220 nm); HPLC: RT=4.0 min (Phenomenex Luna C18 4.6×50 mm column, eluting with 10-90% MeOH/H$_2$O containing 0.2% PPA, flow rate 4 mL/min, wavelength 220 nm); $^1$H NMR (400 MHz, CDCl$_3$) δ ppm 7.98-7.80 (1H, m), 7.85-7.89 (1H, m), 7.39-7.43 (3H, m), 7.31 (1H, t, J=9.23 Hz), 7.19-7.27 (1H, m), 6.99 (1H, d, J=8.79 Hz), 6.76-6.83 (5H, m), 5.89 (1H, t, J=53.0 Hz), 4.16 (1H, d, J=13.18 Hz), 4.02 (1H, d, J=13.18 Hz).

Example 300

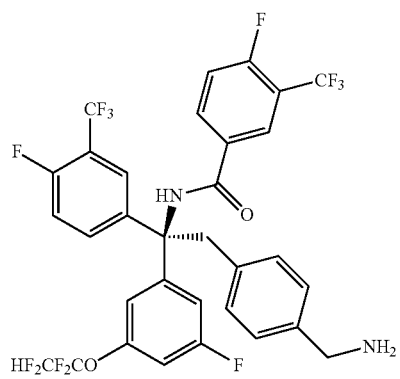

481

(R)—N-(2-(4-(aminomethyl)phenyl)-1-(4-fluoro-3-(trifluoromethyl)phenyl)-1-(3-fluoro-5-(1,1,2,2-tetrafluoroethoxy)phenyl)ethyl)-4-fluoro-3-(trifluoromethyl)benzamide Procedure 101

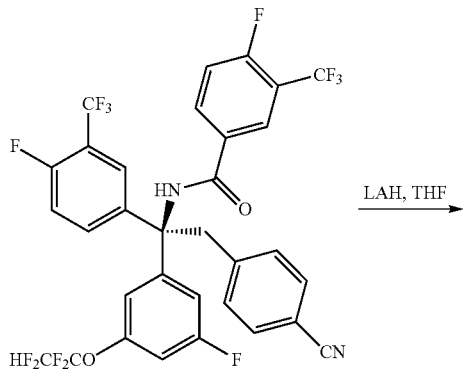

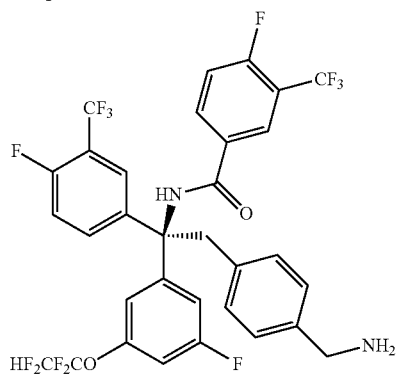

To a solution of (R)—N-(2-(4-cyanophenyl)-1-(4-fluoro-3-(trifluoromethyl)phenyl)-1-(3-fluoro-5-(1,1,2,2-tetrafluoroethoxy)phenyl)ethyl)-4-fluoro-3-(trifluoromethyl)benzamide, prepared as described in Procedure 56, (77% yield, 20 mg, 0.02 mmol) in THF (1.5 mL) at rt was added LAH (1.0 M in THF). The reaction mixture was stirred at rt for 5 h, then quenched by addition of 2 N LiOH. The solid was removed by filtration and the filtrate was concentrated. The resulting residue was purified by prep HPLC (YMC Sunfire 5μ C18 30×100 mm column, eluting with 20-90% MeOH/H$_2$O containing 0.1% TFA, 10 min gradient, flow rate 40 mL/min, wavelength 220 nm) to provide (R)—N-(2-(4-(aminomethyl)phenyl)-1-(4-fluoro-3-(trifluoromethyl)phenyl)-1-(3-fluoro-5-(1,1,2,2-tetrafluoroethoxy)phenyl)ethyl)-4-fluoro-3-(trifluoromethyl)benzamide (Example 300) as a colorless film (5 mg, 36% yield). LCMS: RT=1.8 min [M+H] 713.26 (Phenomenex Luna C18 4.6×30 mm column, eluting with 10-90% MeOH/H$_2$O containing 0.1% TFA, 2 min gradient, flow rate 5 mL/min, wavelength 220 nm); HPLC: RT=4.31 min (Phenomenex Luna C18 4.6×50 mm column, eluting with 10-90% MeOH/H$_2$O containing 0.2% PPA, flow rate 4 mL/min, wavelength 220 nm). $^1$H NMR (400 MHz, CD$_3$OD) δ ppm 7.95 (1H, d, J=6.59 Hz), 7.46-7.48 (1H, m), 7.36 7.41 (2H, m), 7.22 (1H, t, J=9.45 Hz), 7.16 (2H, d, J=7.91 Hz), 6.99 (2H, dd, J=16.48, 9.45 Hz), 6.93 (1H, s), 6.73 (2H, d, J=7.91 Hz), 6.21H, t, J=49.7 Hz), 4.01-4.06 (1H, m), 3.93-3.99 (3H, m).

482

Example 301

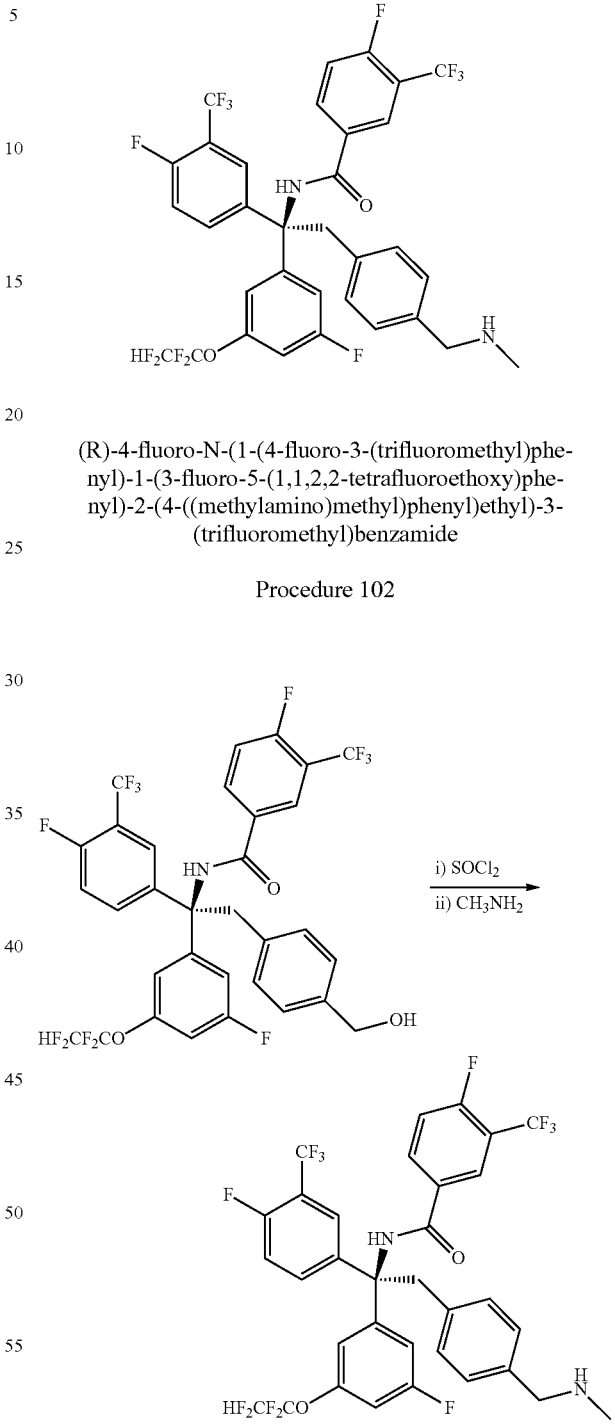

(R)-4-fluoro-N-(1-(4-fluoro-3-(trifluoromethyl)phenyl)-1-(3-fluoro-5-(1,1,2,2-tetrafluoroethoxy)phenyl)-2-(4-((methylamino)methyl)phenyl)ethyl)-3-(trifluoromethyl)benzamide Procedure 102

A solution of (R)-4-fluoro-N-(1-(4-fluoro-3-(trifluoromethyl)phenyl)-1-(3-fluoro-5-(1,1,2,2-tetrafluoroethoxy)phenyl)-2-(4-(hydroxymethyl)phenyl)ethyl)-3-(trifluoromethyl)benzamide (Example 299, 20 mg, 0.028 mmol) in SOCl$_2$ was stirred at rt overnight. The reaction mixture was concentrated and the residue was treated with a solution of methyl amine in methanol (1.0 M, 2.0 mL, 2.0 mmol) at rt overnight. The solvent was removed and the residue was purified by prep HPLC (YMC Sunfire 5μ C18 30×100 mm column, eluting with 20-90% MeOH/H$_2$O containing 0.1% TFA, 10 min gradient, flow rate 40 mL/min, wavelength 220 nm) to provide (R)-4-fluoro-N-(1-(4-fluoro-3-(trifluoromethyl)phenyl)-1-(3-fluoro-5-(1,1,2,2-tetrafluoroethoxy)phenyl)-2-(4-((methylamino)methyl)phenyl)ethyl)-3-(trifluoromethyl)benzamide (Example 301) as a white solid (13 mg, 65% yield). LCMS: RT=2.02 min [M+H]=727.48 (Phenomenex Luna C18 4.6×30 mm column, eluting with 10-90% MeOH/H$_2$O containing 0.1% TFA, 2 min gradient, flow rate 5 mL/min, wavelength 220 nm); HPLC: RT=3.11 min (Phenomenex Luna C18 4.6×50 mm column, eluting with 10-90% MeOH/H$_2$O containing 0.2% PPA, flow rate 4 mL/min, wavelength 220 nm). $^1$H NMR (400 MHz, CD$_3$OD) δ ppm 7.57-8.06 (2H, m), 7.48-7.57 (1H, m), 7.43-7.49 (2H, m), 7.30 (1H, t, J=9.45 Hz), 7.25 (2H, d, J=7.91 Hz), 7.00-7.10 (3H, m), 6.82 (2H, d, J=8.35 Hz), 6.29 (1H, t, J=46.6 Hz), 4.03-4.15 (4H, m), 2.65 (3H, s).

Example 302

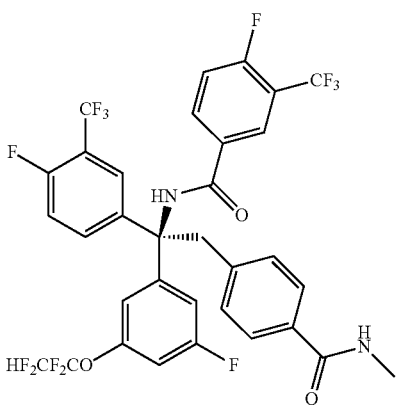

(R)-4-fluoro-N-(1-(4-fluoro-3-(trifluoromethyl)phenyl)-1-(3-fluoro-5-(1,1,2,2-tetrafluoroethoxy)phenyl)-2-(4-(methylcarbamoyl)phenyl)ethyl)-3-(trifluoromethyl)benzamide Procedure 103

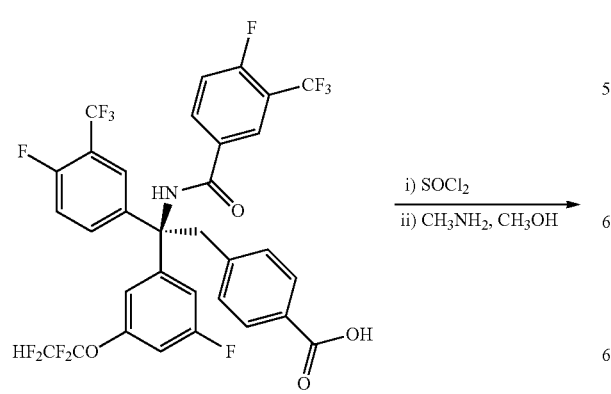

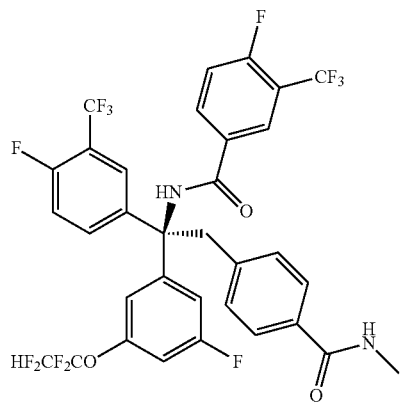

A solution of (R)-4-(2-(4-fluoro-3-(trifluoromethyl)benzamido)-2-(4-fluoro-3-(trifluoromethyl)phenyl)-2-(3-fluoro-5-(1,1,2,2-tetrafluoroethoxy)phenyl)ethyl)benzoic acid, prepared as described in Procedure 97, 98, 99 and 100, (65 mg, 0.09 mmol) in SOCl$_2$ was heated at 60° C. overnight. The reaction mixture was concentrated and 25 mg of the resulting residue was treated with a solution of methyl amine in methanol (1.0 M, 2.0 mL, 2.0 mmol) at rt overnight. The solvent was removed and the residue was purified by ISCO (12 g column, 0-20% EtOAc/hexane) to yield (R)-4-fluoro-N-(1-(4-fluoro-3-(trifluoromethyl)phenyl)-1-(3-fluoro-5-(1,1,2,2-tetrafluoroethoxy)phenyl)-2-(4-(methylcarbamoyl)phenyl)ethyl)-3-(trifluoromethyl)benzamide (Example 302) as a white solid (14 mg, 85% yield). LCMS: RT=2.16 min [M+H] 741.55 (Phenomenex Luna C18 4.6×30 mm column, eluting with 10-90% MeOH/H$_2$O containing 0.1% TFA, 2 min gradient, flow rate 5 mL/min, wavelength 220 nm); HPLC: RT=4.0 min (Phenomenex Luna C18 4.6×50 mm column, eluting with 10-90% MeOH/H$_2$O containing 0.2% PPA, flow rate 4 mL/min, wavelength 220 nm). $^1$H NMR (400 MHz, CDCl$_3$) δ ppm 7.97 (1H, d, J=5.71 Hz), 7.81-7.86 (1H, m), 7.50 (2H, d, J=7.91 Hz), 7.43 (2H, d, J=5.27 Hz), 7.25-7.31 (1H, m), 7.19 (1H, t, J=9.45 Hz), 6.97 (1H, d, J=8.35 Hz), 6.82 (2H, d, J=4.83 Hz), 6.74 (2H, d, J=7.91 Hz), 6.05 (1H, d, J=4.83 Hz), 5.88 (1H, t, J=52.1), 4.04 (1H, d, J=13.2), 3.95 (1H, d, J=13.2), 2.94 (3H, d, J=4.83 Hz).

Example 303

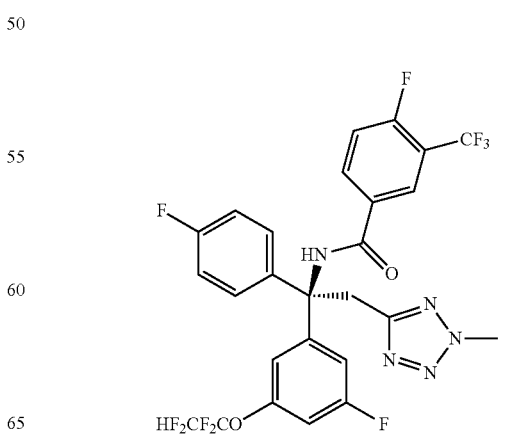

(R)-4-fluoro-N-(1-(3-fluoro-5-(1,1,2,2-tetrafluoroethoxy)phenyl)-1-(4-fluorophenyl)-2-(2-methyl-2H-tetrazol-5-yl)ethyl)-3-(trifluoromethyl)benzamide Procedure 104

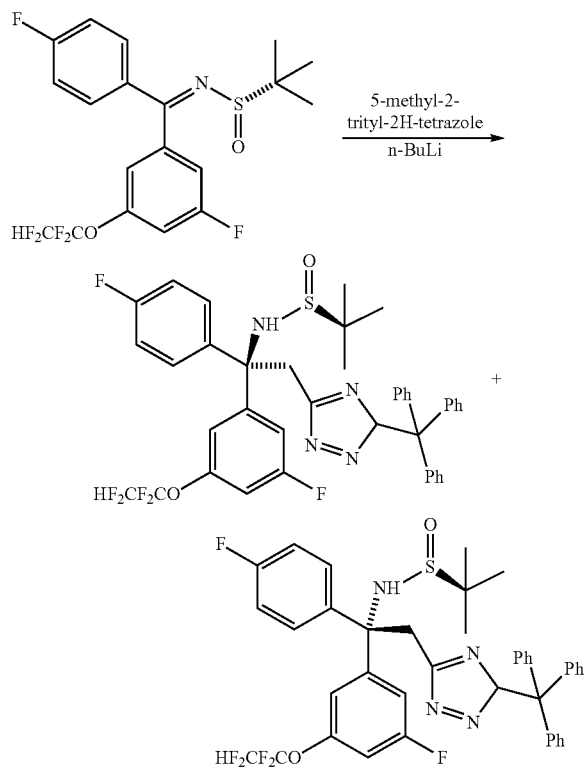

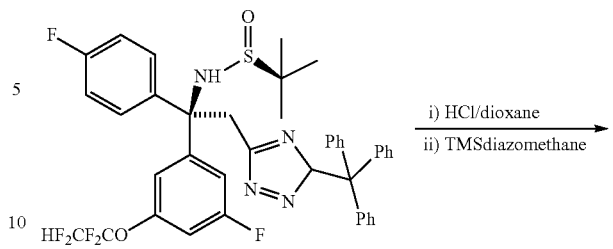

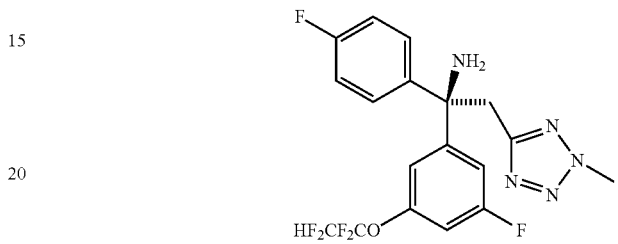

To a solution of 5-methyl-2-trityl-2H-tetrazole (0.90 g, 2.76 mmol) in dry THF (20 mL) at −78° C. under argon was added dropwise n-BuLi (2.5 M in hexane, 1.2 mL, 3 mmol). The resulting solution was stirred at −78° C. for 1 h, followed by the dropwise addition of a solution of (R)—N-((3-fluoro-5-(1,1,2,2-tetrafluoroethoxy)phenyl)(4-fluorophenyl)methylene)-2-methylpropane-2-sulfinamide, prepared as described in Procedure 3, 4 and 5, (0.40 g, 0.91 mmol) in THF (5 mL). The reaction mixture was stirred at −78° C. to −70° C. overnight. The reaction mixture was quenched by addition of sat. NH₄Cl and the aqueous layer was extracted with Et₂O (2×) and the combined organic layers were washed with H₂O, sat. NaCl, dried over Na₂SO₄, filtered and concentrated. The residue was purified by ISCO flash chromatography (silica gel, hexanes/EtOAc) to give (R)—N—(S)-1-(3-fluoro-5-(1,1,2,2-tetrafluoroethoxy)phenyl)-1-(4-fluorophenyl)-2-(2-trityl-2H-tetrazol-5-yl)ethyl)-2-methylpropane-2-sulfinamide as the fast eluting diastereomer (90 mg, 13% yield) and (R)—N—((R)-1-(3-fluoro-5-(1,1,2,2-tetrafluoroethoxy)phenyl)-1-(4-fluorophenyl)-2-(2-trityl-2H-tetrazol-5-yl)ethyl)-2-methylpropane-2-sulfinamide as the slow eluting diastereomer (85 mg, 12% yield).

To a solution of (R)—N—((R)-1-(3-fluoro-5-(1,1,2,2-tetrafluoroethoxy)phenyl)-1-(4-fluorophenyl)-2-(2-trityl-2H-tetrazol-5-yl)ethyl)-2-methylpropane-2-sulfinamide (60 mg, 0.079 mmol) in MeOH (3 mL) was added 4 N HCl in dioxane (1 mL). The reaction mixture was stirred at room temperature for 20 min, then concentrated to yield (R)-1-(3-fluoro-5-(1,1,2,2-tetrafluoroethoxy)phenyl)-1-(4-fluorophenyl)-2-(2H-tetrazol-5-yl)ethanamine. LCMS: RT=2.66 min [M+H] 418.55 (Phenomenex Luna C18 4.6×50 mm column, eluting with 10-90% MeOH/H₂O containing 0.1% TFA, 4 min gradient, flow rate 4 mL/min, wavelength 220 nm). To a solution of ((R)-1-(3-fluoro-5-(1,1,2,2-tetrafluoroethoxy)phenyl)-1-(4-fluorophenyl)-2-(2H-tetrazol-5-yl)ethanamine in THF (3 mL) and MeOH (0.5 mL) was added (diazomethyl)trimethylsilane (2.0 M in hexanes, 0.05 mL). After stirring at room temperate for 20 min, the reaction mixture was concentrated and purified by ISCO flash column chromatography (silica gel, EtOAc) to give ((R)-1-(3-fluoro-5-(1,1,2,2-tetrafluoroethoxy)phenyl)-1-(4-fluorophenyl)-2-(2-methyl-2H-tetrazol-5-yl)ethanamine (10 mg, yield: 30%). LCMS: RT=2.83 min [M+H] 432.57 (Phenomenex Luna C18 column, 4.6×50 mm eluting with 10-90% MeOH/H₂O over 4 minutes containing 0.1% TFA; 4 mL/min, monitoring at 220 nm).

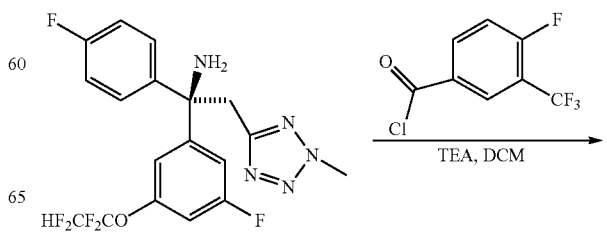

487

-continued

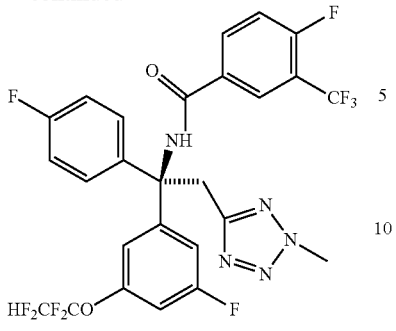

Following Procedure 7, ((R)-1-(3-fluoro-5-(1,1,2,2-tetrafluoroethoxy)phenyl)-1-(4-fluorophenyl)-2-(2-methyl-2H-tetrazol-5-yl)ethanamine (Example 303) was obtained (10 mg, yield 67%). LCMS: RT=3.86 min [M+H] 622.01 (Phenomenex Luna C18 column, 4.6×50 mm eluting with 10-90% MeOH/H$_2$O over 4 minutes containing 0.1% TFA; 4 mL/min, monitoring at 220 nm). $^1$H NMR (400 MHz, CDCL$_3$) ppm 8.30 (m, 2H), 8.19 (m, 1H), 7.37 (m, 3H), 7.05 (m, 4H), 6.92 (d, J=8.6 Hz, 1H), 5.89 (tt, J=53.05, 3.03 Hz, 1H), 4.26 (s, 3H), Example 304

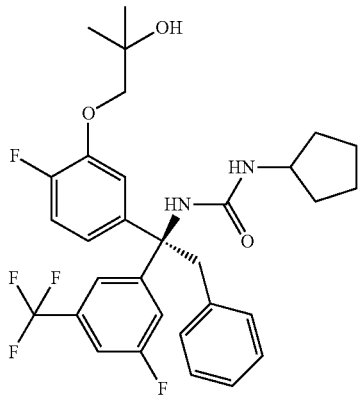 [SMILES: CC(C)(O)COc1cc([C@@](Cc2ccccc2)(NC(=O)NC2CCCC2)c2cc(F)cc(C(F)(F)F)c2)ccc1F]

(R)-1-cyclopentyl-3-(1-(4-fluoro-3-(2-hydroxy-2-methylpropoxy)phenyl)-1-(3-fluoro-5-(trifluoromethyl)phenyl)-2-phenylethyl)urea Procedure 105

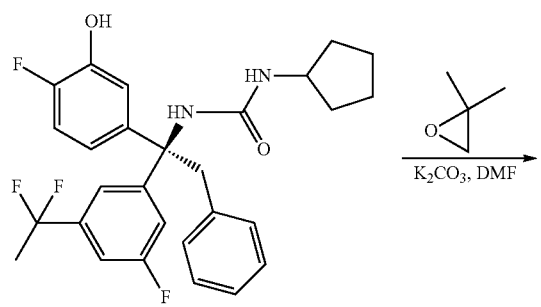

488

-continued

To a solution of (R)-1-cyclopentyl-3-(1-(4-fluoro-3-hydroxyphenyl)-1-(3-fluoro-5-(trifluoromethyl)phenyl)-2-phenylethyl)urea, prepared as described in Procedure 59, (20 mg, 0.039 mmol) in DMF (0.1 mL) was added K$_2$CO$_3$ (12 mg, 0.086 mmol), followed by 2,2-dimethyloxirane (28 mg, 0.39 mmol). The resulting mixture was stirred at 60° C. for 16 h. The reaction mixture was filtered and the solid was washed with EtOAc. The filtrate was washed with H$_2$O, sat. NaCl and dried over Na$_2$SO$_4$ and filtered. The organic solvent was evaporated under reduced pressure and the residue was purified by Prep HPLC (phenomenex AXIA Luna 75×30 mm, 5μ column eluting with 10-90% ACN/H$_2$O over 10 minutes containing 0.1% TFA; 40 mL/min, monitoring at 220 nm) to afford (R)-1-cyclopentyl-3-(1-(4-fluoro-3-(2-hydroxy-2-methylpropoxy)phenyl)-1-(3-fluoro-5-(trifluoromethyl)phenyl)-2-phenylethyl)urea (Example 304) as white lyophillate (11 mg, 56% yield). LCMS: RT=4.066 min [M+H] 577.3 (4 min Phenomenex Luna C18 column, 4.6×50 mm eluting with 10-90% MeOH/H$_2$O over 4 minutes containing 0.1% TFA; 4 mL/min, monitoring at 220 nm (retention time, column type, size, solvent, flow rate, gradient). NMR: 400 MHz $^1$H (CD$_3$OD) ppm 1.27 (d, J=2.20 Hz, 6H), 1.32-1.49 (m, 2H), 1.54-1.76 (m, 4H), 1.81-1.98 (m, 2H), 3.53 (d, J=9.23 Hz, 1H), 3.69 (d, J=9.23 Hz, 1H), 3.78 (d, J=12.74 Hz, 1H), 3.91 (t, J=6.15 Hz, 1H), 4.02 (d, J=12.74 Hz, 1H), 6.63-6.70 (m, 1H), 6.72-6.79 (m, 3H), 7.01 (dd, J=10.99, 8.79 Hz, 1H), 7.09-7.20 (m, 3H), 7.27-7.42 (m, 3H).

Example 305

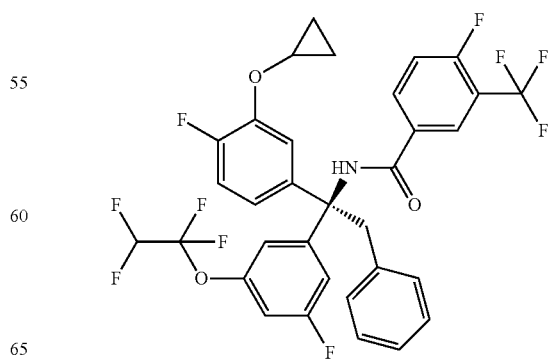

489

(R)—N-(1-(3-cyclopropoxy-4-fluorophenyl)-1-(3-fluoro-5-(1,1,2,2-tetrafluoroethoxy)phenyl)-2-phenylethyl)-4-fluoro-3-(trifluoromethyl)benzamide Procedure 106

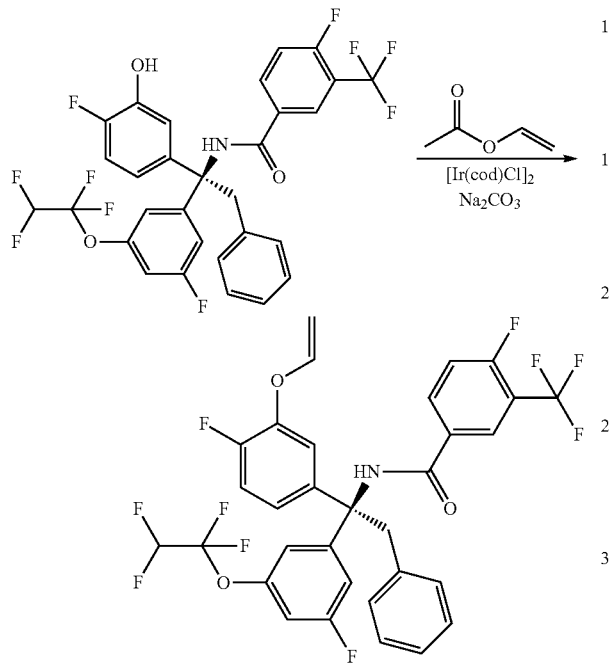

490

Procedure 107

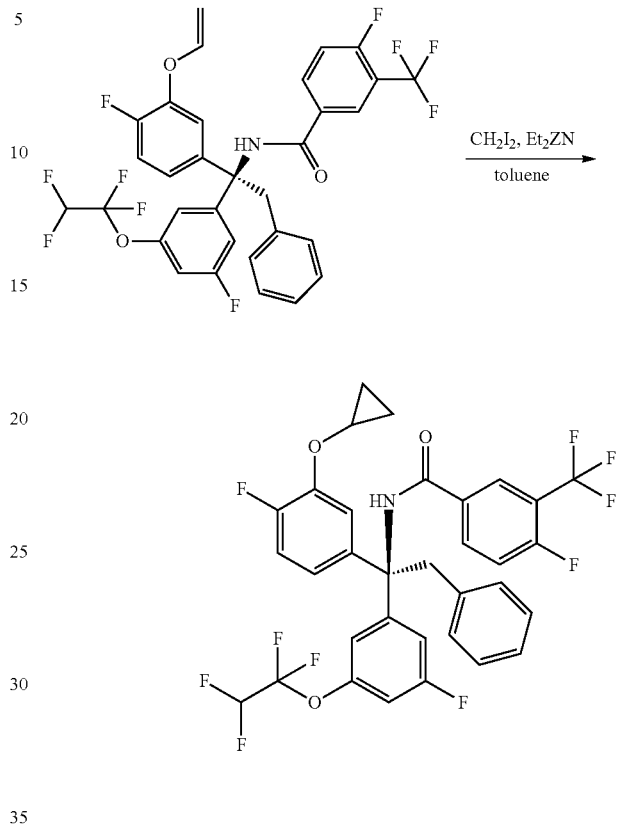

To a solution of (R)-4-fluoro-N-(1-(4-fluoro-3-hydroxyphenyl)-1-(3-fluoro-5-(1,1,2,2-tetrafluoroethoxy)phenyl)-2-phenyethyl)-3-(trifluoromethyl)benzamide (Example 264, 100 mg, 0.158 mmol) in toluene (0.2 ml) was added Na$_2$CO$_3$ (25 mg, 0.235 mmol) and catalystical amount of [Ir(cod)Cl]$_2$ (2 mg), followed by vinyl acetate (68 mg, 0.79 mmol). The reaction mixture was stirred at 100° C. for 16 h. The resulting mixture was filtered and the solid was washed with CH$_2$Cl$_2$. The CH$_2$Cl$_2$ layer was washed with 1 N NaOH, H$_2$O and dried over Na$_2$SO$_4$ and filtered. The solvent was evaporated under reduced pressure and the residue was purified by silica gel column using 0 to 60% EtOAc in hexane to afford (R)-4-fluoro-N-(1-(4-fluoro-3-(vinyloxy)phenyl)-1-(3-fluoro-5-(1,1,2,2-tetrafluoroethoxy)phenyl)-2-phenylethyl)-3-(trifluoromethyl)benzamide eluting out at 20% EtOAc in hexane as colorless oil (80 mg, 77%). LCMS: RT=2.237 min [M+H] 658.3 (2 min Phenomenex Luna C18 column, 4.6×30 mm eluting with 10-90% MeOH/H$_2$O over 2 minutes containing 0.1% TFA; 5 mL/min, monitoring at 220 nm. NMR: 400 MHz $^1$H (CD$_3$OD) ppm 3.87 (d, J=12.74 Hz, 1H), 4.05-4.15 (m, 1H), 4.35 (dd, J=5.93, 1.98 Hz, 1H), 4.55 (dd, J=13.84, 1.98 Hz, 1H), 6.12-6.41 (m, 1H), 6.48 (dd, J=13.62, 6.15 Hz, 1H), 6.72 (d, J=7.03 Hz, 2H), 6.87-7.24 (m, 9H), 7.37-7.51 (m, 1H), 7.88-8.04 (m, 2H).

To a solution of (R)-4-fluoro-N-(1-(4-fluoro-3-(vinyloxy)phenyl)-1-(3-fluoro-5-(1,1,2,2-tetrafluoroethoxy)phenyl)-2-phenylethyl)-3-(trifluoromethyl)benzamide (66 mg, 0.10 mmol) in 0.5 ml toluene was added Et$_2$Zn (1 N, 0.2 ml, 0.2 mmol), followed by CH$_2$I$_2$ (16 ml, 0.2 mmol). The reaction mixture was stirred at 120° C. for 3 h. The reaction mixture was quenched by addition of 1 N HCl and the aqueous layer was extracted with CH$_2$Cl$_2$. The organic layer was washed with sat. NaHCO$_3$ and concentrated under reduced pressure. The resulting residue was purified by ISCO silica gel column using 0 to 50% to EtOAc in hexane as eluting solvents and Prep HPLC (phenomenex AXIA Luna 75×30 mm, 5u column eluting with 10-90% ACN/H$_2$O over 10 minutes containing 0.1% TFA; 40 mL/min, monitoring at 220 nm) to afford (R)—N-(1-(3-cyclopropoxy-4-fluorophenyl)-1-(3-fluoro-5-(1,1,2,2-tetrafluoroethoxy)phenyl)-2-phenylethyl)-4-fluoro-3-(trifluoromethyl)benzamide (Example 305) as white lyophillate (36 mg, 52% yield). LCMS: RT=4.268 min [M+H] 672.3 (4 min Phenomenex Luna C18 column, 4.6×50 mm eluting with 10-90% MeOH/H$_2$O over 4 minutes containing 0.1% TFA; 4 mL/min, monitoring at 220 nm. NMR: 400 MHz $^1$H (CDCl$_3$) ppm 0.45-0.73 (m, 4H), 3.51-3.59 (m, 1H), 3.76 (d, J=13.18 Hz, 1H), 4.22 (d, J=12.74 Hz, 1H), 6.13-6.44 (m, 1H), 6.66-6.76 (m, 3H), 6.97-7.08 (m, 3H), 7.10-7.23 (m, 5H), 7.42-7.50 (m, 1H), 7.95-8.03 (m, 2H).

Example 306

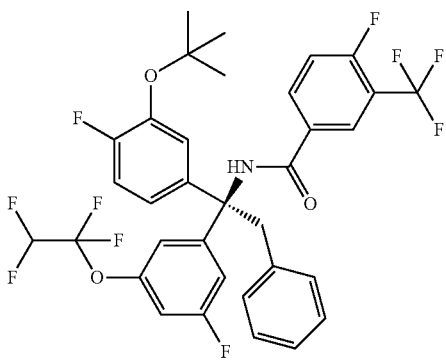 [SMILES: CC(C)(C)Oc1cc([C@@](Cc2ccccc2)(NC(=O)c2ccc(F)c(C(F)(F)F)c2)c2cc(F)cc(OC(F)(F)C(F)F)c2)ccc1F]

(R)—N-(1-(3-tert-butoxy-4-fluorophenyl)-1-(3-fluoro-5-(1,1,2,2-tetrafluoroethoxy)phenyl)-2-phenylethyl)-4-fluoro-3-(trifluoromethyl)benzamide Procedure 108

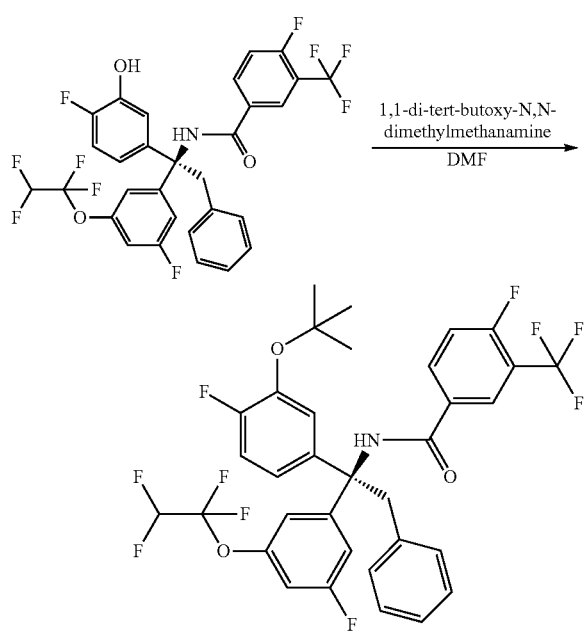

To a solution of (R)-4-fluoro-N-(1-(4-fluoro-3-hydroxyphenyl)-1-(3-fluoro-5-(1,1,2,2-tetrafluoroethoxy)phenyl)-2-phenylethyl)-3-(trifluoromethyl)benzamide (Example 264, 50 mg, 0.079 mmol) in DMF (0.2 mL) was added 1,1-di-tert-butoxy-N,N-dimethylmethanamine (100 µL, 0.49 mmol). The reaction mixture was stirred at 110° C. for 5 h. The reaction mixture was concentrated and purified by prep HPLC (phenomenex AXIA Luna 75×30 mm, 5µ column eluting with 10-90% ACN/H$_2$O over 10 minutes containing 0.1% TFA; 40 mL/min, monitoring at 220 nm) to afford (R)—N-(1-(3-tert-butoxy-4-fluorophenyl)-1-(3-fluoro-5-(1,1,2,2-tetrafluoroethoxy)phenyl)-2-phenylethyl)-4-fluoro-3-(trifluoromethyl)benzamide (Example 306) as white lyophillate (46 mg, 81% yield). LCMS: RT=4.341 min [M+H] 688.2 (4 min Phenomenex Luna C18 column, 4.6×50 mm eluting with 10-90% MeOH/H$_2$O over 4 minutes containing 0.1% TFA; 4 mL/min, monitoring at 220 nm. NMR: 400 MHz $^1$H (CDCl$_3$) ppm 1.22 (s, 9H), 3.89 (s, 1H), 4.06 (d, J=13.19 Hz, 1H), 6.08-6.42 (m, 1H), 6.73 (d, J=7.15 Hz, 2H), 6.91-7.21 (m, 9H), 7.39-7.44 (m, 1H), 7.94-8.00 (m, 2H).

Example 307

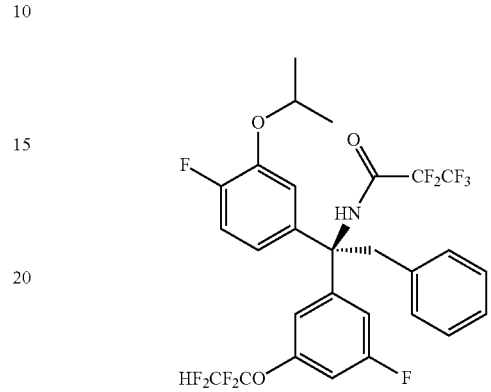

(R)-2,2,3,3,3-pentafluoro-N-(1-(4-fluoro-3-isopropoxyphenyl)-1-(3-fluoro-5-(1,1,2,2-tetrafluoroethoxy)phenyl)-2-phenylethyl)

Procedure 109

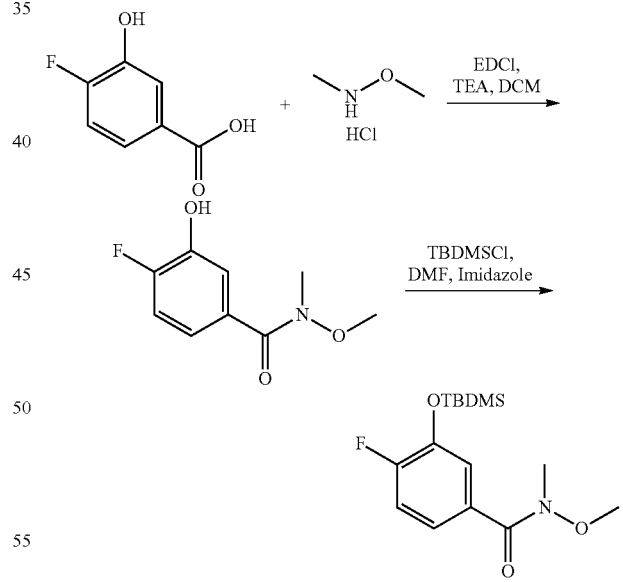

To a solution of 4-fluoro-3-hydroxybenzoic acid (1.49 g, 9.55 mmol) in DCM (40 mL) was added TEA (1.2 mL, 8.61 mmol) followed by N,O-dimethylhydroxylamine hydrochloride (1.12 g, 11.5 mmol). The reaction mixture was stirred at room temperature for 3 h, then diluted with DCM, washed with water twice, dried over Na$_2$SO$_4$, filtered and concentrated to yield 4-fluoro-3-hydroxy-N-methoxy-N-methylbenzamide as a colorless oil (1.90 g, 100% yield). LCMS: RT=0.89 min [M+H] 200.10 (Phenomenex Luna C18 column, 4.6×30 mm eluting with 10-90% MeOH/H₂O over 2 minutes containing 0.1% TFA; 5 mL/min, monitoring at 220 nm).

To a solution of 4-fluoro-3-hydroxy-N-methoxy-N-methylbenzamide (1.90 g, 9.55 mmol) in DMF (8 mL) was added imidazole (740 mg, 10.8 mmol) and TBDMSCl (1.62 g, 10.8 mmol) at room temperature. The reaction mixture was stirred for 48 h and quenched with saturated NaHCO₃. The solution was extracted with ether (3×) and the combined ether portions washed with LiCl (10%), dried over Na₂SO₄, filtered and concentrated. The resulted colorless oil was purified by ISCO chromatography (120 g column) using hexanes/EtOAc (0-100% over 30 min) to give 3-(tert-butyldimethylsilyloxy)-4-fluoro-N-methoxy-N-methylbenzamide (RT=10-12 minutes) as a colorless oil (2.00 g, 67% yield). LCMS: RT=2.06 min [M+H] 314.22 (Phenomenex Luna C18 column, 4.6×30 mm eluting with 10-90% MeOH/H₂O over 2 minutes containing 0.1% TFA; 5 mL/min, monitoring at 220 nm); NMR: 400 MHz $^1$H (CDCl₃) 7.26 ppm, 2H, m; 7.02 ppm, 1H, m; 3.50 ppm, 3H, s; 3.31 ppm, 3H, s; 0.97 ppm, 9H, s, 0.16 ppm, 6H, s.

Procedure 110

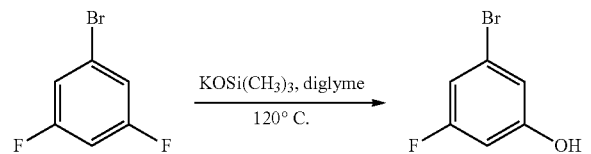 [SMILES: Fc1cc(F)cc(Br)c1 ; Oc1cc(F)cc(Br)c1]

To a N₂ flushed, 2 L four necked flask equipped with a mechanical stirrer, a condenser, temperature controller and a N₂ inlet, was added potassium trimethylsilanolate (225.0 g, 1.75 mol, tech. purify 90%), 1-bromo-3,5-difluorobenzene (96.5 g, 0.5 mol) and diglyme (300 mL). The reaction mixture was heated to 120° C. under N₂ for 5 h. After cooling to rt, the heating mantle was replaced with an ice bath. The reaction mixture was acidified with 3 N HCl solution (600 mL) below 30° C. TBME (1 L) was added and the resulting mixture was stirred below 20° C. for 30 min then transferred to a 5 L separatory funnel. The organic layer was separated and washed with water (3×500 mL), sat. NaCl (500 mL), dried over MgSO₄, filtered and concentrated in vacuo to give the crude reddish product (145.0 g). The crude material was then distillated at 52-55° C./0.1 mm Hg to yield 3-bromo-5-fluorophenol as a slightly yellow oil (88.0 g, 92% yield). $^1$H NMR (300 MHz, CDCl₃) δ 5.34 (s, H), 6.47-6.52 (m, 1H), 6.77-6.83 (m, 2H).

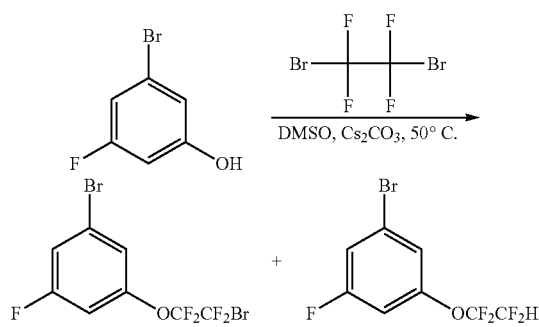

To a flame dried, 1 L, three necked round bottom flask (1 L) equipped with a temperature controller, a mechanical stirrer, a condenser and a N₂ inlet was charged 3-bromo-5-fluorophenol (57.3 g, 300 mmol), 1,2-dibromotetrafluoroethane (156.0 g, 600 mmol), dry DMSO (300 mL) and Cs₂CO₃ (146.6 g, 450 mmol) under N₂. The reaction mixture was heated to 50° C. for 5 h. After cooling to rt, water (300 mL) and hexane (300 mL) were added. The resulting mixture was stirred at rt for 30 min. The organic phase was separated and the aqueous layer was extracted with hexane (300 mL). The combined organic extracts were washed with water (500 mL), sat. NaCl (500 mL), dried over MgSO₄, filtered and concentrated in vacuo to give 1-bromo-3-(2-bromo-1,1,2,2-tetrafluoroethoxy)-5-fluorobenzene (104.2 g, 94% yield) containing 5% of 1-bromo-3-fluoro-5-(1,1,2,2-tetrafluoroethoxy)benzene (5.2 g). 1-Bromo-3-(2-bromo-1,1,2,2-tetrafluoroethoxy)-5-fluorobenzene: $^1$H NMR (300 MHz, CDCl₃) δ 6.91-6.94 (m, 1H), 7.18-7.23 (m, 2H).

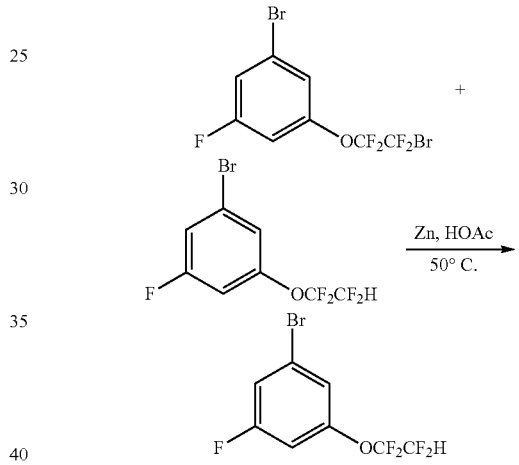

To a 1 L four necked round bottom flask equipped with a temperature controller, a mechanical stirrer, and a N₂ inlet, was added 1-bromo-3-(2-bromo-1,1,2,2,-tetrafluoroethoxy)-5-fluorobenzene (104.0 g, 281 mmol) and 1-bromo-3-fluoro-5-(1,1,2,2-tetrafluoroethoxy)benzene (5.2 g, 18 mmol), acetic acid (300 mL). The reaction mixture was then heated to 50° C. Zinc dust (91.9 g, 1.405 mol) was added portion wise. The reaction mixture was stirred at 50° C. for 1 h and allowed to cool to rt. Water (300 mL) and hexane (300 mL) were added. The resulting mixture was stirred at rt for 30 min. The organic phase was separated and the aqueous layer was extracted with hexane (2×300 mL). The combined organic extracts were washed with water (500 mL), sat. NaCl (500 mL), dried over MgSO4, filtered and concentrated in vacuo to yield 1-bromo-3-fluoro-5-(1,1,2,2-tetrafluoroethoxy)benzene as a slightly yellow liquid (71 g, 87% yield). $^1$H NMR (300 MHz, CDCl₃) δ ppm 5.87 (tt, J=52.7 and 2.9 Hz, 1H), 6.91 (d, J=8.7 Hz, 1H), 7.16-7.18 (m, 2H).

Procedure 111

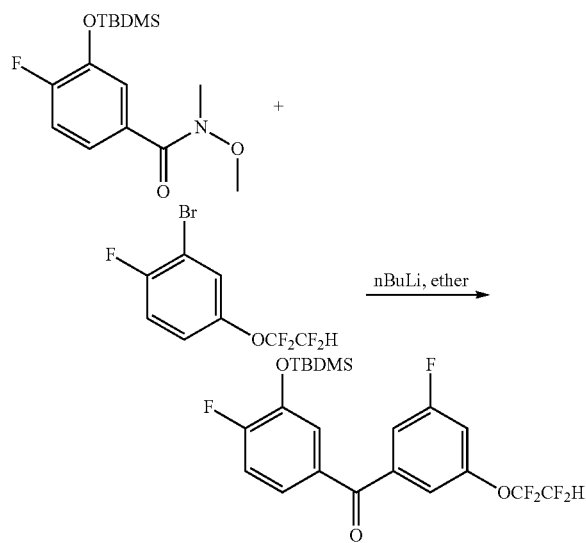

At −78° C. under argon, to a solution of 1-bromo-3-fluoro-5-(1,1,2,2-tetrafluoroethoxy)benzene (2.04 g, 7.01 mmol) in anhydrous ether (20 mL) was added nBuLi (3.5 mL, 2.0 M in cyclohexane, 7.0 mmol) dropwise and the reaction mixture was stirred for 1 h. 3-(Tert-butyldimethylsilyloxy)-4-fluoro-N-methoxy-N-methylbenzamide (2.00 g, 6.38 mmol) was added in one portion and the reaction mixture was stirred at −78° C. for 1.5 h. The pale yellow solution was poured into 1 N HCl aqueous solution (30 mL) and ether (30 mL) was used to rinse the reaction flask. The aqueous phase was separated and extracted with ether (20 mL). The combined ether portions were dried over $Na_2SO_4$, filtered and concentrated. The resulting oil was purified by ISCO chromatography (120 g column) using hexanes/EtOAc (0-100% over 30 min) to give (3-(tert-butyldimethylsilyloxy)-4-fluorophenyl)(3-fluoro-5-(1,1,2,2-tetrafluoroethoxy)phenyl)methanone at a retention time of 7 min (2.11 g, 71% yield). LCMS: RT=2.41 min [M+H] 465.19 (Phenomenex Luna C18 column, 4.6×30 mm eluting with 10-90% MeOH/$H_2O$ over 2 minutes containing 0.1% TFA; mL/min, monitoring at 220 nm); NMR: 400 MHz $^1$H (CDCl$_3$) 7.33 ppm, 3H, m; 7.28 ppm, 1H, m; 7.11 ppm, 2H, m; 5.86 ppm, 1H, t, J=53.39 Hz; 0.95 ppm, 9H, s; 0.15 ppm, 6H, s.

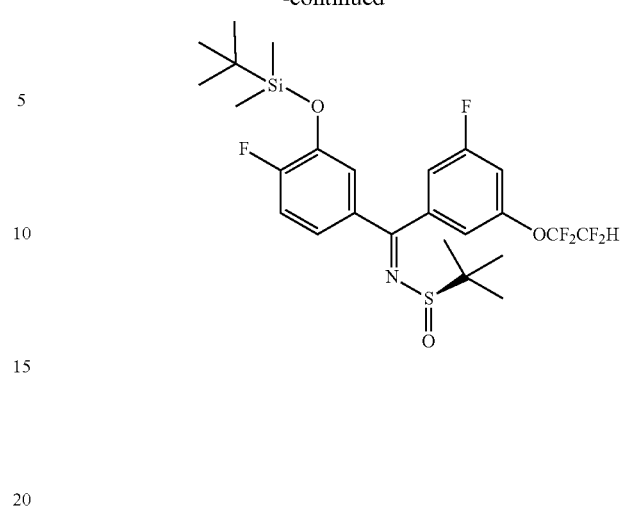

A round bottom flask was charged with (3-(tert-butyldimethylsilyloxy)-4-fluorophenyl)(3-fluoro-5-(1,1,2,2-tetrafluoroethoxy)phenyl)methanone (2.09 g, 4.50 mmol), (R)-2-methylpropane-2-sulfinamide (653 mg, 5.4 mmol), Ti(OEt)$_4$ (1.54 g, 6.76 mmol) and anhydrous THF (40 mL). The resulting solution was heated at 75° C. under argon for 14 h. The solvents were removed and the residue was diluted with ether (50 mL) and sat. NaCl (20 mL). The resulting mixture was filtered through a glass frit and the filtrate transferred to a separatory funnel. The organic portion was separated and the aqueous extracted with ether (2×20 mL). The combined organic portions were dried over $Na_2SO_4$, filtered and concentrated. The residue was dissolved in hexane:EtOAc and purified by ISCO chromatography (2×120 g column) using hexanes/EtOAc (0-100% over 30 min) to yield (R)—N-((3-(tert-butyldimethylsilyloxy)-4-fluorophenyl)(3-fluoro-5-(1,1,2,2-tetrafluoroethoxy)phenyl)methylene)-2-methylpropane-2-sulfinamide at a retention time of 14 min (2.05 g, 80% yield) LCMS: RT=2.37 min [M+H] 568.24 (Phenomenex Luna C18 column, 4.6×30 mm eluting with 10-90% MeOH/$H_2O$ over 2 minutes containing 0.1% TFA; 5 mL/min, monitoring at 220 nm). NMR: 400 MHz $^1$H (CDCl$_3$) 7.36 ppm, 1H, m; 7.11 ppm, 5H, m; 5.90 ppm, 1H, t, J=52.73 Hz; 0.97 ppm, 9H, s; 0.18 ppm, 6H, s.

Procedure 112

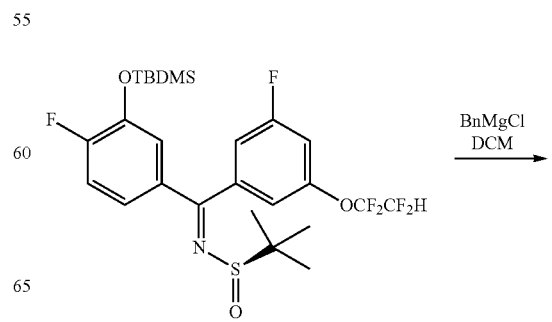

-continued

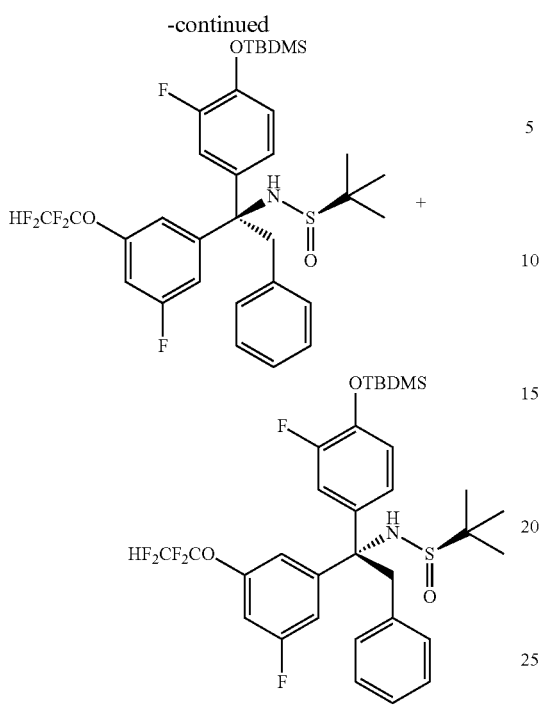

At −78° C. to a solution of (R)—N-((3-(tert-butyldimethylsilyloxy)-4-fluorophenyl)(3-fluoro-5-(1,1,2,2-tetrafluoroethoxy)phenyl)methylene)-2-methylpropane-2-sulfinamide (1.0 g, 1.76 mmol) in DCM (50 mL) was added BF$_3$.Et$_2$O (0.77 mL, 3.52 mmol) via syringe. After 5 min, BnMgCl solution (3.5 mL, 1.0 M solution in ether, 3.5 mmol) was added dropwise and the reaction mixture was stirred at −78° C. for 1 h. An additional portion of BnMgCl (3.5 mL, 1.0 M solution in ether, 3.5 mmol) was added dropwise and the reaction was stirred for an additional 1 h at −78° C. The reaction mixture was poured into saturated NaCl (50 mL) and the organic layer was separated. The aqueous layer was extracted with DCM (2×20 mL) and the combined organic layers were dried over Na$_2$SO$_4$, filtered and concentrated. The resulting oil was purified by ISCO chromatography (120 g column) using hexanes/EtOAc (0-100% over 30 min) to give an approximate 4:1 mixture of (R)—N-(1-(4-(tert-butyldimethylsilyloxy)-3-fluorophenyl)-1-(3-fluoro-5-(1,1,2,2-tetrafluoroethoxy)phenyl)-2-phenylethyl)-2-methylpropane-2-sulfinamide and (S)—N-(1-(4-(tert-butyldimethylsilyloxy)-3-fluorophenyl)-1-(3-fluoro-5-(1,1,2,2-tetrafluoroethoxy)phenyl)-2-phenylethyl)-2-methylpropane-2-sulfinamide at a retention time of 12 min (824 mg, 71% yield) LCMS: RT=2.43 min [M+H] 660.39 (Phenomenex Luna C18 column, 4.6×30 mm eluting with 10-90% MeOH/H$_2$O over 2 minutes containing 0.1% TFA; 5 mL/min, monitoring at 220 nm). The diastereomeric ratio of the product was determined to be 4:1 by Chiral HPLC analysis (Chiralcel® AD, 90:10 heptane:i-PrOH, 1 mL/min, 254 nm, RT (minor)=4.43 min, PA=17%; RT (major)=19.28 min, PA=71%) and the diastereomeric mixture was taken on directly to the next step, Procedure 112, or the diastereomers were separated as described in Procedure 114. NMR: 400 MHz $^1$H (CDCl$_3$) 7.30 ppm, 2H, m; 7.06 ppm, 5H, m; 6.85 ppm, 2H, m; 6.76 ppm, 1H, m; 6.62 ppm, 2H, m; 5.79 ppm, 1H, m; 4.13 ppm, 1H, s; 3.84 ppm, 1H, m; 3.47 ppm, 1H, m; 1.12 ppm, 9H, s; 0.84 ppm, 9H, s; 0.01 ppm, 6H, d, J=4.39 Hz.

Procedure 113

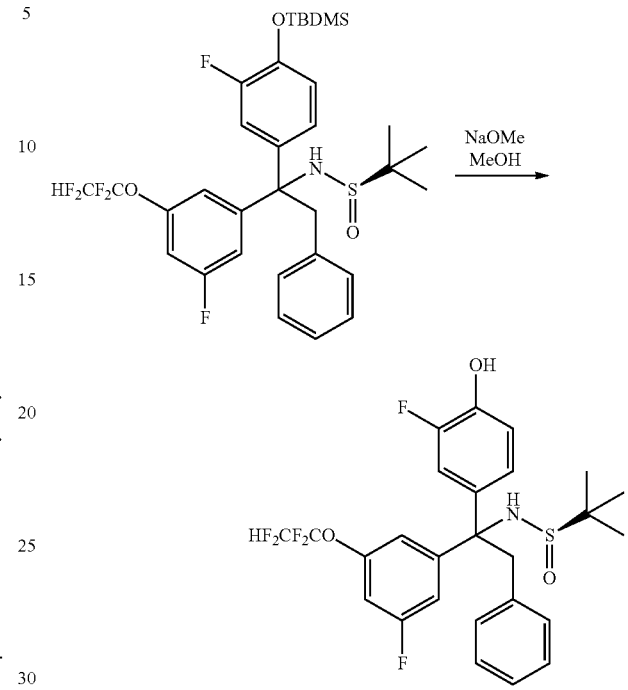

At room temperature a solution of NaOMe (5 mL, 0.5 M solution in MeOH) was added to the 4:1 diastereomeric mixture of (R)—N-(1-(4-(tert-butyldimethylsilyloxy)-3-fluorophenyl)-1-(3-fluoro-5-(1,1,2,2-tetrafluoroethoxy)phenyl)-2-phenylethyl)-2-methylpropane-2-sulfinamide (801 mg, 1.22 mmol). The reaction mixture was stirred for 15 minutes, MeOH was removed then the residue dissolved in EtOAc (50 mL) and transferred to a separation funnel. HCl (20 mL, 1.0 N solution) was added and the EtOAc layer was separated. The aqueous layer was extracted with EtOAc (2×10 mL) and the combined organic layers were dried over Na$_2$SO$_4$, filtered and concentrated to yield (R)—N-(1-(3-fluoro-4-hydroxyphenyl)-1-(3-fluoro-5-(1,1,2,2-tetrafluoroethoxy)phenyl)-2-phenylethyl)-2-methylpropane-2-sulfinamide as a white foam (578 mg, 87% yield). LCMS: RT=1.987 min [M+H] 546.35 (Phenomenex Luna C18 column, 4.6×30 mm eluting with 10-90% MeOH/H$_2$O over 2 minutes containing 0.1% TFA; 5 mL/min, monitoring at 220 nm).

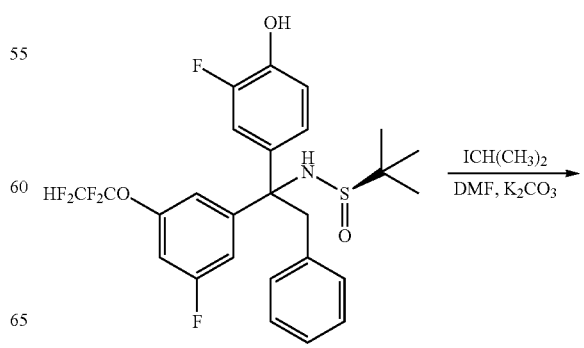

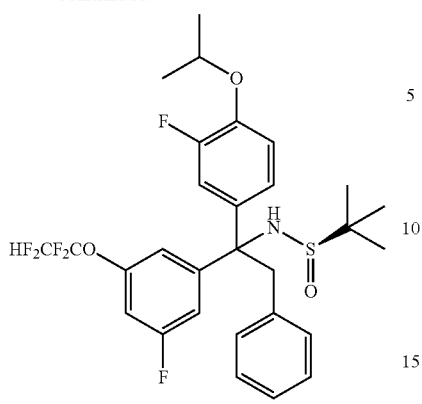

At rt to a solution of (R)—N-(1-(3-fluoro-4-hydroxyphenyl)-1-(3-fluoro-5-(1,1,2,2-tetrafluoroethoxy)phenyl)-2-phenylethyl)-2-methylpropane-2-sulfinamide (578 mg, 1.06 mmol) in DMF (10 mL) was added K$_2$CO$_3$ (800 mg, 5.80 mmol) and the slurry was stirred vigorously. 2-Iodopropane (220 mg, 1.27 mmol) was added and the reaction mixture was stirred at rt for 16 h. The reaction mixture was diluted with ether (50 mL), washed successively with 10% LiCl (2×20 mL) and water (20 mL). The organic portion was dried over Na$_2$SO$_4$, filtered and concentrated to yield (R)—N-(1-(3-fluoro-4-isopropoxyphenyl)-1-(3-fluoro-5-(1,1,2,2-tetrafluoroethoxy)phenyl)-2-phenylethyl)-2-methylpropane-2-sulfinamide as a pale orange foam (780 mg, 100% yield).

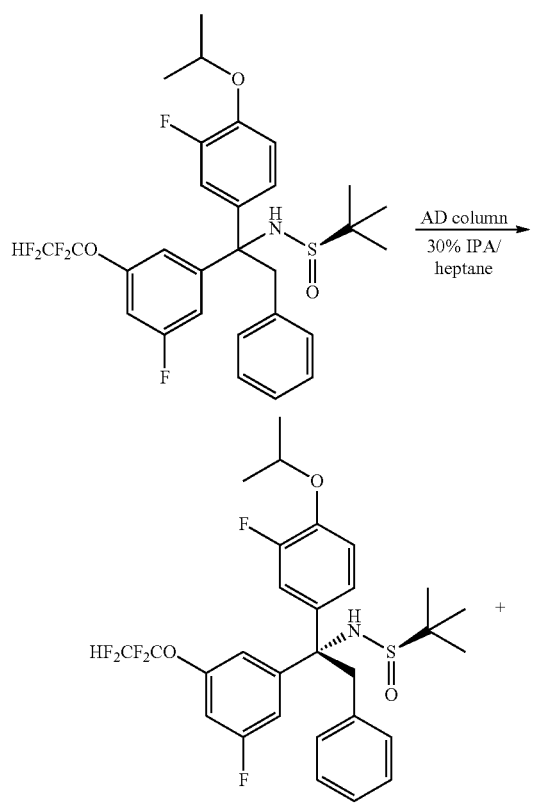

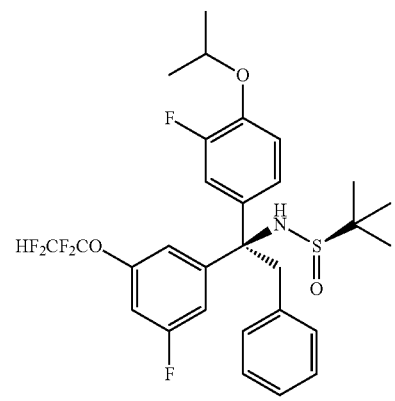

The diastereomeric mixture of (R)—N-(1-(3-fluoro-4-isopropoxyphenyl)-1-(3-fluoro-5-(1,1,2,2-tetrafluoroethoxy)phenyl)-2-phenylethyl)-2-methylpropane-2-sulfinamide (780 mg, 1.06 mmol crude) was separated by Chiral preparative HPLC chiralpak AD 20μ column, 5×50 cm, eluting with 30% IPA/Heptane with flow rate 50 mL/min.

(R)—N—((S)-1-(3-fluoro-4-isopropoxyphenyl)-1-(3-fluoro-5-(1,1,2,2-tetrafluoroethoxy)phenyl)-2-phenylethyl)-2-methylpropane-2-sulfinamide was eluted at a retention time of 17 min and isolated as a colorless oil (101 mg, yield 16%). LCMS: RT=2.128 min [M+H] 588.38 (Phenomenex Luna C18 column, 4.6×30 mm eluting with 10-90% MeOH/H$_2$O over 2 minutes containing 0.1% TFA; 5 mL/min, monitoring at 220 nm); Chiral HPLC: RT=4.35 min, ee 100% (Diacel Chiralpak AD 10μ column, 4.6×250 mm isocratic elution with IPA (20%) and heptane; 1 mL/min, monitoring at 254 nm).

(R)—N—((R)-1-(3-fluoro-4-isopropoxyphenyl)-1-(3-fluoro-5-(1,1,2,2-tetrafluoroethoxy)phenyl)-2-phenylethyl)-2-methylpropane-2-sulfinamide was eluted at a retention time of 39 min and isolated and was isolated as a colorless oil (398 mg, yield 64%). LCMS: RT=2.138 min [M+H] 588.38 (Phenomenex Luna C18 column, 4.6×30 mm eluting with 10-90% MeOH/H$_2$O over 2 minutes containing 0.1% TFA; mL/min, monitoring at 220 nm); Chiral HPLC: RT=9.98 min, ee 100% (Diacel Chiralpak AD 10μ column, 4.6×250 mm isocratic elution with IPA (20%) and heptane; 1 mL/min, monitoring at 254 nm) NMR: 400 MHz $^1$H (CDCl$_3$) 7.08 ppm, 5H, m; 6.84 ppm, 2H, d, J=7.47 Hz; 6.77 ppm, 2H, d, J=7.47 Hz; 6.63 ppm, 2H, m; 5.79 ppm, 1H, t, J=52.95 Hz; 4.33 ppm, 1H, m; 4.15 ppm, 1H, s; 3.92 ppm, 1H, d, J=12.30 Hz; 3.48 ppm, 1H, d, J=12.30 Hz; 1.22 ppm, 3H, d, J=6.15 Hz; 1.18 ppm, 3H, d, J=5.71 Hz; 1.14 ppm, 9H, s.

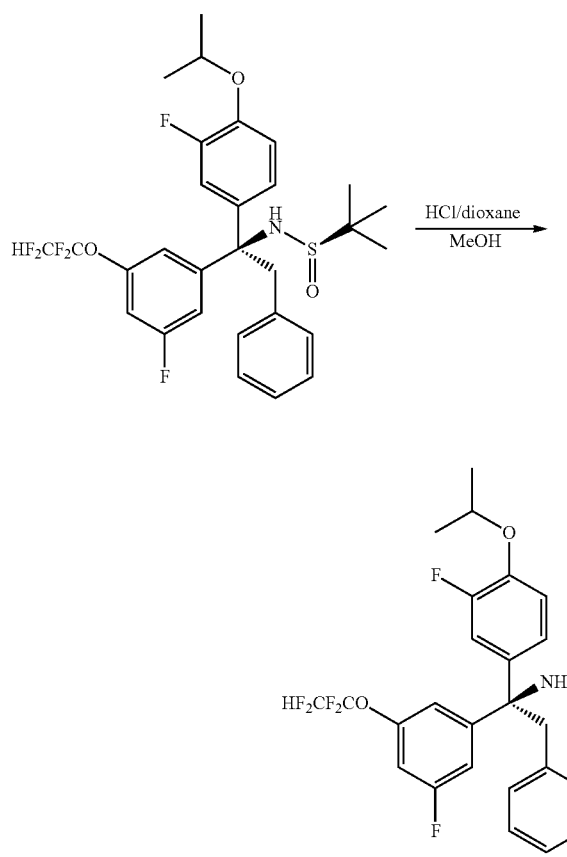

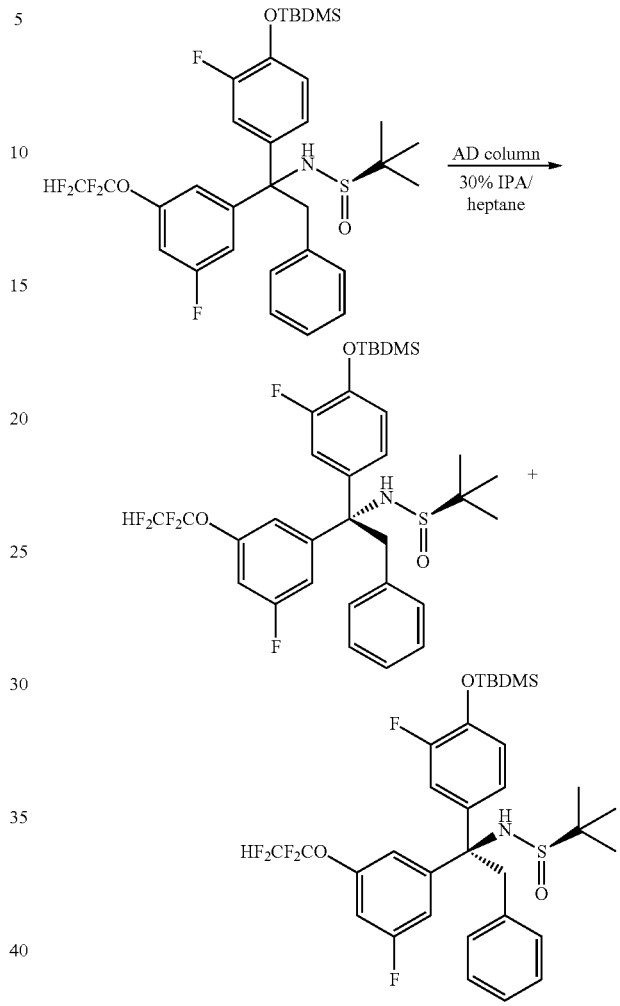

Procedure 114

To a solution of (R)—N—((R)-1-(3-fluoro-4-isopropoxyphenyl)-1-(3-fluoro-5-(1,1,2,2-tetrafluoroethoxy)phenyl)-2-phenylethyl)-2-methylpropane-2-sulfinamide (398 mg, 0.678 mmol) in MeOH (1.5 mL) was added HCl (1.5 mL, 4 M solution in dioxane) and the reaction mixture was stirred for 30 min. The reaction mixture was diluted with ether (50 mL) and the organic layer was washed with sat. $NaHCO_3$ (20 mL), dried over $Na_2SO_4$, filtered and concentrated to give (R)-1-(3-fluoro-4-isopropoxyphenyl)-1-(3-fluoro-5-(1,1,2,2-tetrafluoroethoxy)phenyl)-2-phenylethanamine as a colorless oil (334 mg, 100% yield). LCMS: RT=1.76 min [M–$NH_2$] 467.24 (Phenomenex Luna C18 column, 4.6×30 mm eluting with 10-90% MeOH/$H_2O$ over 2 minutes containing 0.1% TFA; 5 mL/min, monitoring at 220 nm); HPLC: RT=3.04 min, Purity 95% (Phenomenex Luna C18 column, 4.6×50 mm eluting with 10-90% MeOH/$H_2O$ over 4 minutes containing 0.2% PPA; 4 mL/min, monitoring at 220 nm) NMR: 400 MHz $^1H$ ($CDCl_3$) 7.15 ppm, 3H, m; 6.99 ppm, 4H, m; 6.89 ppm, 1H, m; 6.84 ppm, 1H, d, J=8.79 Hz; 6.74 ppm, 2H, d, J=6.15 Hz; 5.87 ppm, 1H, m; 4.42 ppm, 1H, m; 3.47 ppm, 2H, s; 1.27 ppm, 6H, dd, J=7.91, 6.15 Hz.

An alternative route used to prepare (R)-1-(3-fluoro-4-isopropoxyphenyl)-1-(3-fluoro-5-(1,1,2,2-tetrafluoroethoxy)phenyl)-2-phenylethanamine was as follows:

The diastereomer mixture of (R)—N-(1-(4-(tert-butyldimethylsilyloxy)-3-fluorophenyl)-1-(3-fluoro-5-(1,1,2,2-tetrafluoroethoxy)phenyl)-2-phenylethyl)-2-methylpropane-2-sulfinamide (1.14 g, 1.73 mmol) was separated by Chiral preparative HPLC chiralpak AD 20μ column, 5×50 cm, eluting with 30% IPA/Heptane with flow rate 50 mL/min.

(R)—N—((S)-1-(4-(tert-butyldimethylsilyloxy)-3-fluorophenyl)-1-(3-fluoro-5-(1,1,2,2-tetrafluoroethoxy)phenyl)-2-phenylethyl)-2-methylpropane-2-sulfinamide was eluted at a retention time of 19 min (114 mg, yield 10%). LCMS: RT=2.45 min [M+H] 660.41 (Phenomenex Luna C18 column, 4.6×30 mm eluting with 10-90% MeOH/$H_2O$ over 2 minutes containing 0.1% TFA; 5 mL/min, monitoring at 220 nm).

(R)—N—((R)-1-(4-(tert-butyldimethylsilyloxy)-3-fluorophenyl)-1-(3-fluoro-5-(1,1,2,2-tetrafluoroethoxy)phenyl)-2-phenylethyl)-2-methylpropane-2-sulfinamide was eluted at a retention time of 36 min (634 mg, yield 56%). LCMS: RT=2.41 min [M+H] 660.39 (Phenomenex Luna C18 column, 4.6×30 mm eluting with 10-90% MeOH/$H_2O$ over 2 minutes containing 0.1% TFA; 5 mL/min, monitoring at 220 nm); Chiral HPLC: RT=8.54 min, ee 100% (Diacel Chiralpak AD 10 column, 4.6×250 mm isocratic elution with IPA (20%)

and heptane; 1 mL/min, monitoring at 254 nm) NMR: 400 MHz ¹H (CDCl₃) 7.03 ppm, 5H, m; 6.84 ppm, 2H, m; 6.74 ppm, 1H, d, J=8.79 Hz; 6.66 ppm, 1H, dd, J=8.13, 1.98 Hz; 6.61 ppm, 2H, m; 5.76 ppm, 1H, m; 4.12 ppm, 1H, s; 3.90 ppm, 1H, d, J=12.74 Hz; 3.46 ppm, 1H, d, J=12.30 Hz; 1.11 ppm, 9H, s; 0.84 ppm, 9H, s; 0.01 ppm, 6H, d, J=4.83 Hz.

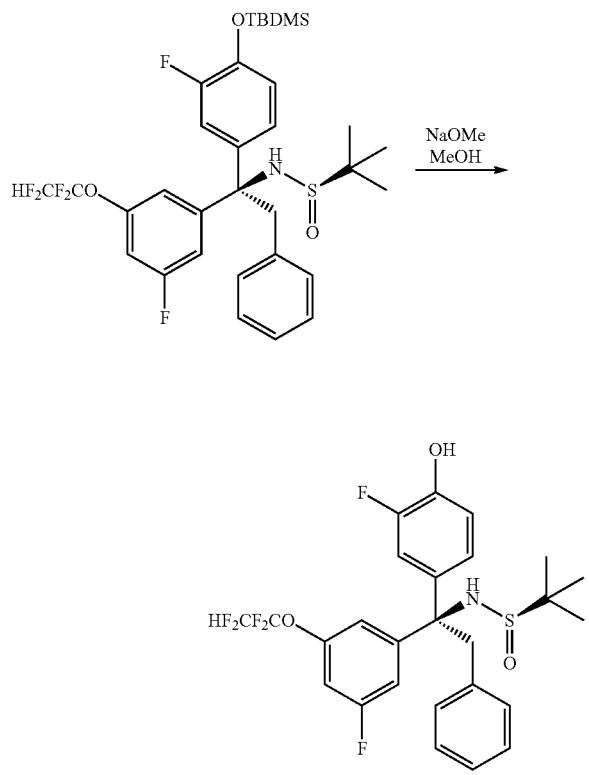

(R)—N—((R)-1-(3-fluoro-4-hydroxyphenyl)-1-(3-fluoro-5-(1,1,2,2-tetrafluoroethoxy)phenyl)-2-phenylethyl)-2-methylpropane-2-sulfinamide was prepared from (R)—N—((R)-1-(4-(tert-butyldimethylsilyloxy)-3-fluorophenyl)-1-(3-fluoro-5-(1,1,2,2-tetrafluoroethoxy)phenyl)-2-phenylethyl)-2-methylpropane-2-sulfinamide as described in Procedure 112 in quantitative yield. LCMS: RT=1.998 min [M+H] 546.28 (Phenomenex Luna C18 column, 4.6×30 mm eluting with 10-90% MeOH/H₂O over 2 minutes containing 0.1% TFA; 5 mL/min, monitoring at 220 nm). HPLC: RT=3.83 min, Purity 98% (Phenomenex Luna C18 column, 4.6×50 mm eluting with 10-90% MeOH/H₂O over 4 minutes containing 0.2% PPA; 4 mL/min, monitoring at 220 nm) NMR: 400 MHz ¹H (CDCl₃) 7.61 ppm, 1H, s; 7.40 ppm, 1H, dd, J=8.13, 1.98 Hz; 7.13 ppm, 3H, m; 6.99 ppm, 1H, dd, J=10.33, 8.57 Hz; 6.84 ppm, 3H, m; 6.68 ppm, 2H, m; 6.61 ppm, 1H, m; 5.85 ppm, 1H, tt, J=52.95, 2.64 Hz; 4.30 ppm, 1H, s; 4.02 ppm, 1H, d, J=12.30 Hz; 3.50 ppm, 1H, d, J=12.30 Hz; 1.24 ppm, 9H, s.

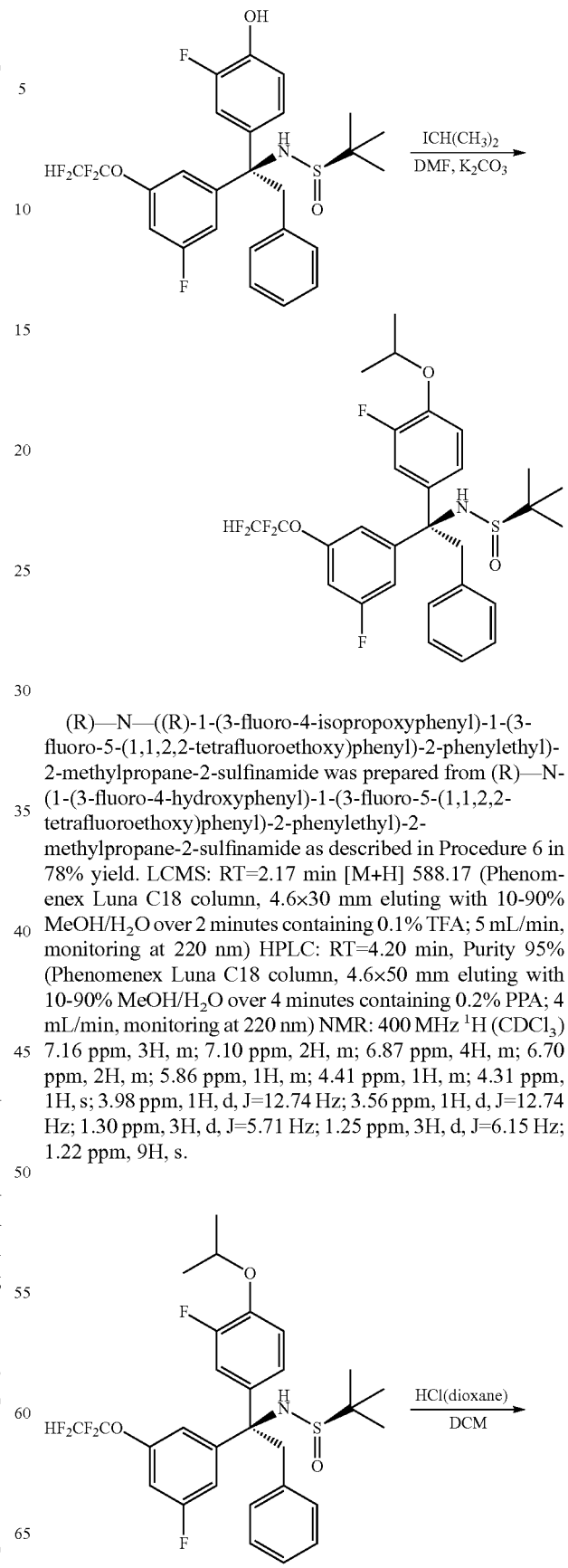

(R)—N—((R)-1-(3-fluoro-4-isopropoxyphenyl)-1-(3-fluoro-5-(1,1,2,2-tetrafluoroethoxy)phenyl)-2-phenylethyl)-2-methylpropane-2-sulfinamide was prepared from (R)—N—(1-(3-fluoro-4-hydroxyphenyl)-1-(3-fluoro-5-(1,1,2,2-tetrafluoroethoxy)phenyl)-2-phenylethyl)-2-methylpropane-2-sulfinamide as described in Procedure 6 in 78% yield. LCMS: RT=2.17 min [M+H] 588.17 (Phenomenex Luna C18 column, 4.6×30 mm eluting with 10-90% MeOH/H₂O over 2 minutes containing 0.1% TFA; 5 mL/min, monitoring at 220 nm) HPLC: RT=4.20 min, Purity 95% (Phenomenex Luna C18 column, 4.6×50 mm eluting with 10-90% MeOH/H₂O over 4 minutes containing 0.2% PPA; 4 mL/min, monitoring at 220 nm) NMR: 400 MHz ¹H (CDCl₃) 7.16 ppm, 3H, m; 7.10 ppm, 2H, m; 6.87 ppm, 4H, m; 6.70 ppm, 2H, m; 5.86 ppm, 1H, m; 4.41 ppm, 1H, m; 4.31 ppm, 1H, s; 3.98 ppm, 1H, d, J=12.74 Hz; 3.56 ppm, 1H, d, J=12.74 Hz; 1.30 ppm, 3H, d, J=5.71 Hz; 1.25 ppm, 3H, d, J=6.15 Hz; 1.22 ppm, 9H, s.

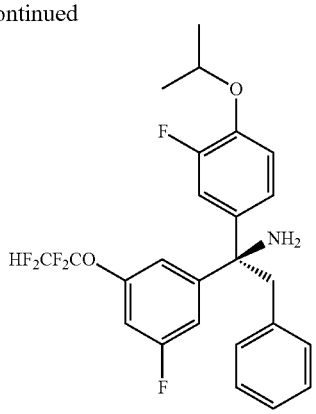

(R)-1-(3-fluoro-4-isopropoxyphenyl)-1-(3-fluoro-5-(1,1,2,2-tetrafluoroethoxy)phenyl)-2-phenylethanamine was prepared from (R)—N—((R)-1-(3-fluoro-4-isopropoxyphenyl)-1-(3-fluoro-5-(1,1,2,2-tetrafluoroethoxy)phenyl)-2-phenylethyl)-2-methylpropane-2-sulfinamide as described in Procedure 6 in 97% yield. LCMS: RT=1.83 min [M−NH$_2$] 467.24 (Phenomenex Luna C18 column, 4.6×30 mm eluting with 10-90% MeOH/H$_2$O over 2 minutes containing 0.1% TFA; 5 mL/min, monitoring at 220 nm); HPLC: RT=3.17 min, Purity 100% (Phenomenex Luna C18 column, 4.6×50 mm eluting with 10-90% MeOH/H$_2$O over 4 minutes containing 0.2% PPA; 4 mL/min, monitoring at 220 nm) NMR: 400 MHz $^1$H (CDCl$_3$) 7.16 ppm, 3H, m; 7.01 ppm, 3H, m; 6.92 ppm, 2H, m; 6.84 ppm, 1H, d, J=8.79 Hz; 6.74 ppm, 2H, d, J=7.03 Hz; 5.86 ppm, 1H, m; 4.41 ppm, 1H, m; 3.49 ppm, 2H, s; 1.25 ppm, 6H, m.

Procedure 115

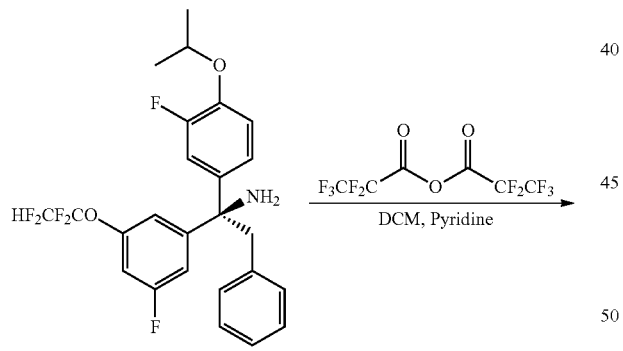

At rt, to a solution of (R)-1-(3-fluoro-4-isopropoxyphenyl)-1-(3-fluoro-5-(1,1,2,2-tetrafluoroethoxy)phenyl)-2-phenylethanamine (25 mg, 0.05 mmol) in anhydrous DCM (0.5 mL) was added pyridine (1 drop) and 2,2,3,3,3-pentafluoropropanoic anhydride (19 mg, 0.08 mmol). The resulting solution was stirred for 5 min, diluted with MeOH (0.5 mL) and purified by preparative HPLC (YMC Sunfire 30×100 mm column, eluting with 10-90% MeOH/H$_2$O over 10 minutes containing 0.1% TFA; 40 mL/min, monitoring at 220 nm). (R)-2,2,3,3,3-pentafluoro-N-(1-(4-fluoro-3-isopropoxyphenyl)-1-(3-fluoro-5-(1,1,2,2-tetrafluoroethoxy)phenyl)-2-phenylethyl)propanamide (Example 307) was isolated as a colorless oil (7 mg, 21% yield) at a retention time of 11.84 min. LCMS: RT=2.19 min [M+H] 630.32 (Phenomenex Luna C18 column, 4.6×30 mm eluting with 10-90% MeOH/H$_2$O over 2 minutes containing 0.1% TFA; 5 mL/min, monitoring at 220 nm); HPLC: RT=4.21 min, Purity 100% (Phenomenex Luna C18 column, 4.6×50 mm eluting with 10-90% MeOH/H$_2$O over 4 minutes containing 0.2% PPA; 4 mL/min, monitoring at 220 nm) NMR: 400 MHz $^1$H (CDCl$_3$) 7.25 ppm, 3H, m; 7.03 ppm, 1H, t, J=8.0 Hz; 6.86-6.97 ppm, 4H, m; 6.66 ppm, 2H, d, J=8.0 Hz; 6.58 ppm, 2H, d, J=8.0 Hz; 5.87 ppm, 1H, d, J=57.8 Hz; 4.32 ppm, 1H, sept, J=8.0 Hz; 3.93 ppm, 1H, d, J=12.0 Hz; 3.68 ppm, 1H, d, J=12.0 Hz; 1.28 ppm, 3H, d, J=8.0 Hz; 1.22 ppm, 3H, d, J=8.0 Hz.

Example 308

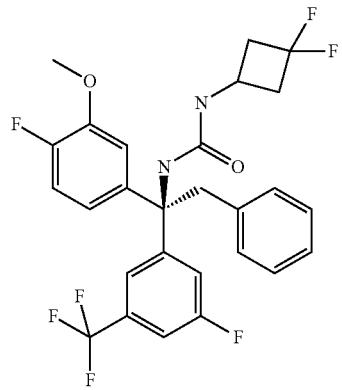 [SMILES: COc1cc([C@@](Cc2ccccc2)(NC(=O)NC2CC(F)(F)C2)c2cc(F)cc(C(F)(F)F)c2)ccc1F]

(R)-1-(3,3-difluorocyclobutyl)-3-(1-(4-fluoro-3-methoxyphenyl)-1-(3-fluoro-5-(trifluoromethyl)phenyl)-2-phenylethyl)urea Procedure 116

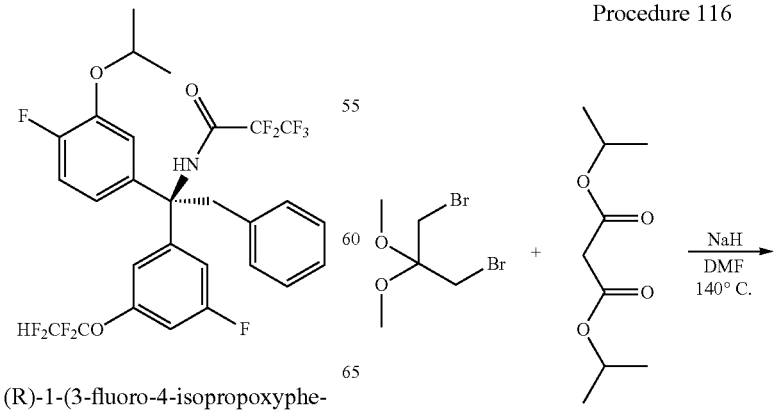

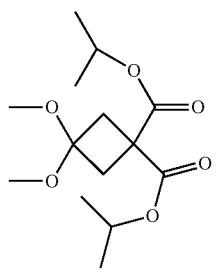

To a suspension of sodium hydride (60% in mineral oil, 3.7 g, 92 mmol) in dry DMF (32 mL) under nitrogen was added dropwise diisopropyl malonate (16 mL, 84 mmol) and the temperature was maintained below 0° C. On cessation of hydrogen evolution, 1,3-dibromo-2,2-dimethoxypropane (11.0 g, 42 mmol) was added at rt and the reaction mixture was heated at 140° C. for 24 h. The cooled mixture was poured into saturated ammonium chloride (100 mL) and extracted with hexane (3×75 mL). The combined organic extracts were washed with water (100 mL), sat. NaHCO$_3$ (50 mL), dried over magnesium sulfate and the solvent was evaporated to give 17.42 g of pale yellow oil. Distillation of the residue through Vigreux column with an air condenser and further purification by an Analogix silica column (12 g, 20% ethyl acetate in hexane) afforded diisopropyl 3,3-dimethoxycyclobutane-1,1-dicarboxylate (6.2 g, 51% yield). LCMS: RT=3.26 min, No parent ion (Phenominex, Luna C18, 4.6×50 mm, 4 min gradient from 10% methanol, 90% water, 0.1% TFA to 90% methanol, 10% water, 0.1% TFA); $^1$H NMR (500 MHz, CDCl$_3$) δ ppm 5.06 (2H, dq), 3.15 (6H, s), 2.69 (4H, s), 1.24 (12H, d, J=6.0 Hz); $^{13}$C NMR (126 MHz, CDCl$_3$) δ ppm 170.34 (2C, s), 98.50, 69.03 (2C, s), 48.59 (2C, s), 45.01, 39.63 (2C, s), 21.47 (4C, s).

Procedure 117

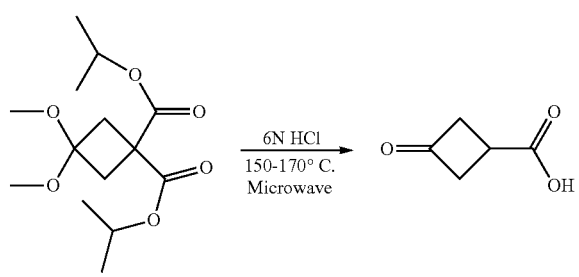

A solution of diisopropyl 3,3-dimethoxycyclobutane-1,1-dicarboxylate (2.2 g, 7.63 mmol) in HCl (6 N, 6 mL) was heated at 155-160° C. under microwave irradiation for 60 min. The reaction mixture was diluted with ether (150 mL) and vigorously stirred over the weekend. The ether layer was dried with MgSO$_4$, filtered and concentrated to give 3-oxo-cyclobutanecarboxylic acid (1.0 g, 118% yield) as a brown solid. $^1$H NMR (500 MHz, CDCl$_3$) δ ppm 10.80 (1H, br. s.), 3.43-3.51 (2H, m), 3.26-3.40 (3H, m); $^{13}$C NMR (126 MHz, CDCl3) δ ppm 203.14, 180.17, 51.64 (2C, s), 27.32 (1C, s).

Procedure 118

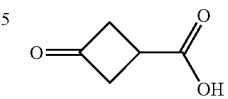

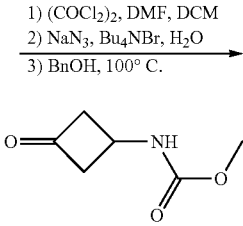

To a solution of 3-oxocyclobutanecarboxylic acid (3.34 g, 29.2 mmol) in dichloromethane (29 mL) at 0° C. was added oxalyl chloride (19.0 mL, 38.0 mmol) followed by DMF (0.057 mL, 0.731 mmol). The reaction mixture was stirred for 2 h at room temperature. The reaction mixture was concentrated under reduced pressure and the residue was dissolved in dichloromethane (15 mL). At 0° C., to the resulting solution was added sodium azide (3.23 g, 49.7 mmol) in water (7 mL) followed by tetrabutylammonium bromide. The reaction mixture was vigorously stirred for 2 h. The aqueous phase was separated and extracted with dichloromethane (2×40 mL). The combined organic portions were dried over MgSO$_4$, filtered rapidly and benzyl alcohol (30.4 ml, 292 mmol) was added and the solvent volume was reduced under reduced pressure. The reaction mixture was heated at 95° C. for 1 h. Benzyl alcohol was removed under reduced pressure and the residue oil was purified by ISCO flash chromatography (80 g column, hexane/ethyl acetate) to give benzyl 3-oxocyclobutylcarbamate as a pale yellow solid (693 mg, 11% yield). HPLC: RT=1.16 min, 90% pure (Phenomenex, Onyx C18, 4.6×100 mm, 2 min gradient from 10% MeCN, 90% water, 0.1% TFA to 90% MeCN, 10% water, 0.1% TFA); LCMS: RT=2.37 min, 75% purity, [M+H] 220.1 (Phenominex, Luna C18, 4.6×50 mm, 4 min gradient from 10% methanol, 90% water, 0.1% TFA to 90% methanol, 10% water, 0.1% TFA); $^1$H NMR (500 MHz, CDCl$_3$) δ ppm 7.32-7.38 (5H, m), 5.27 (1H, d, J=3.3 Hz), 5.12 (2H, s), 4.33 (1H, d, J=5.5 Hz), 3.40 (2H, dd, J=13.2, 6.6 Hz), 3.08 (2H, d, J=14.3 Hz). $^{13}$C NMR (101 MHz, CDCl$_3$) δ ppm 204.50, 155.87, 136.06, 128.56 (2C, s), 128.28, 128.13 (2C, s), 66.97, 54.59 (2C, s), 37.08.

Procedure 119

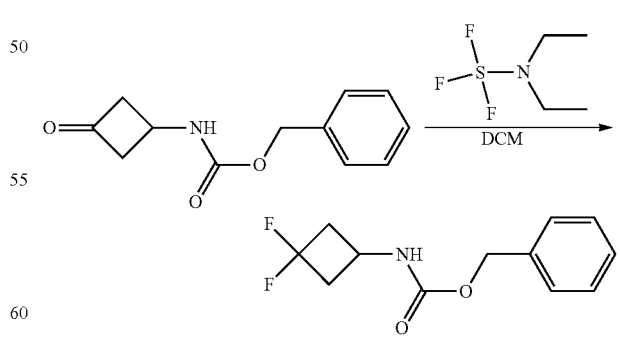

To a solution of benzyl 3-ocyclobutylcarbamate (2.58 g, 11.77 mmol) in dichloromethane (23.5 mL) at 0° C. to −5° C. was added dropwise DAST (4.66 mL, 35.3 mmol). The reaction mixture was stirred for 4.5 h at room temperature, then diluted with sat. NaCl at 0° C. and the aqueous layers were extracted with dichloromethane (3×50 mL). The combined organic layers were dried over MgSO4, filtered and concentrated. The resulting oil was purified by ISCO flash chromatography (120 g column, hexanes to ethyl acetate) to yield benzyl 3,3-difluorocyclobutylcarbamate (1.7 g, yield 60%). LCMS: RT=2.95 min [M+H] 242.1 (Phenomenex Luna C18 column, 4.6×50 mm eluting with 10-90% MeOH/H$_2$O over 4 minutes containing 0.1% TFA; 4 mL/min, monitoring at 220 nm); $^1$H NMR (500 MHz, CDCl$_3$) δ ppm 7.30-7.41 (5H, m), 5.10 (2H, br. s.), 4.99 (1H, br. s.), 4.04-4.16 (1H, m), 2.90-3.04 (2H, m), 2.42-2.56 (2H, m); $^{13}$C NMR (126 MHz, CDCl$_3$) δ ppm 155.52, 136.07, 128.58 (2C, s), 128.30, 128.18 (2C, s), 66.97, 42.72-43.57 (1C, m), 35.71-36.66 (2C, m), the triplet for the difluorocarbon signal did not rise above baseline; $^{19}$F NMR (471 MHz, CDCl$_3$) δ ppm −84.90 (1F, d, J=195.8 Hz), −97.62 (1F, d, J=201.5 Hz).

Procedure 120

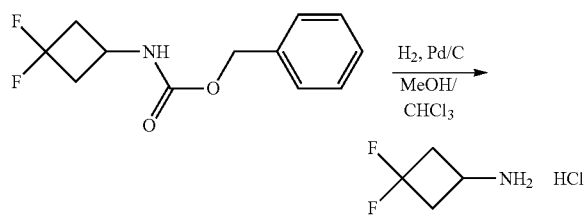

To a solution of benzyl 3,3-difluorocyclobutylcarbamate (1.86 g, 7.71 mmol) in methanol (49 mL) and chloroform (2 mL) was added 10% palladium on carbon (0.41 g, 0.39 mmol) and the slurry was subjected to balloon hydrogenation overnight. The reaction mixture was filtered, washed with methanol and HCl (1.0 M) in ether (1 mL) and the filtrate concentrated. The residue was triturated with ether, filtered, washed with ether and dried to give 3,3-difluorocyclobutanamine hydrochloride as a pale yellow solid (1.01 g, 92% yield). $^1$H NMR (400 MHz, DMSO-D6). δ ppm 8.48 (m, 3H), 3.60-3.69 (m, 1H), 2.72-3.02 (m, 4H); $^{19}$F NMR (376 MHz, DMSO-D6) δ ppm −81.57 (1F, d, J=189.6 Hz), −97.13 (1F, ddd, J=198.8 Hz, 18.5 Hz).

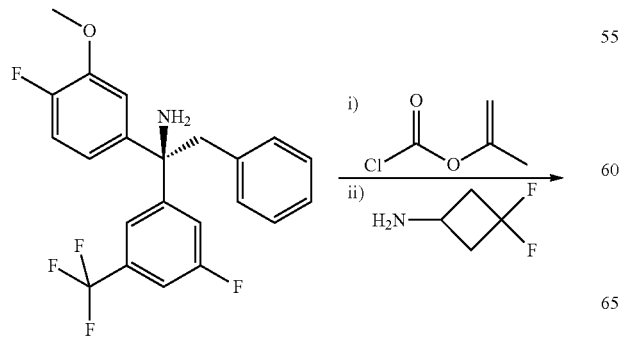

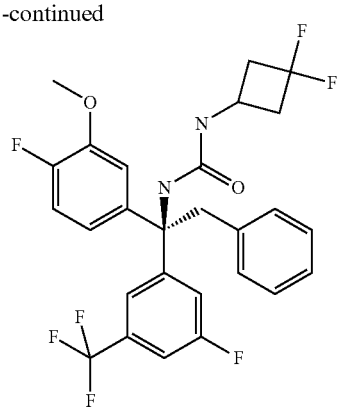

(R)-1-(3,3-difluorocyclobutyl)-3-(1-(4-fluoro-3-methoxyphenyl)-1-(3-fluoro-5-(trifluoromethyl)phenyl)-2-phenylethyl)urea (Example 308) was prepared as described in Procedure 10. LCMS: RT=2.003 min [M+H] 639 (2 min Phenomenex Luna C18 column, 4.6×30 mm eluting with 10-90% MeOH/H$_2$O over 2 minutes containing 0.1% TFA; 5 mL/min, monitoring at 220 nm). HPLC: RT=4.10 min, 100% purity (Phenomenex Luna C18 column, 4.6×50 mm eluting with 10-90% MeOH/H$_2$O over 4 minutes containing 0.2% PPA; 4 mL/min, monitoring at 220 nm). $^1$H NMR (400 MHz, Solvent) δ ppm 2.33-2.44 (m, 2H), 2.86-2.97 (m, J=15.25, 7.83, 7.70, 3.30 Hz, 2H), 3.63-3.72 (m, 3H), 3.74-3.85 (m, 1H), 3.93-4.03 (m, 1H), 4.09 (d, J=7.15 Hz, 1H), 6.62-6.69 (m, 1H), 6.70-6.78 (m, 3H), 7.00 (ddd, J=11.13, 8.11, 3.30 Hz, 1H), 7.10-7.21 (m, 3H), 7.29-7.40 (m, 3H).

Example 309

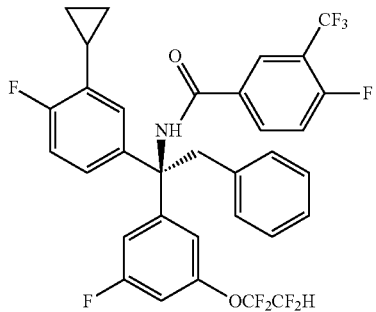

(R)—N-(1-(3-cyclopropyl-4-fluorophenyl)-1-(3-fluoro-5-(1,1,2,2-tetrafluoroethoxy)phenyl)-2-phenylethyl)-4-fluoro-3-(trifluoromethyl)benzamide

Procedure 121

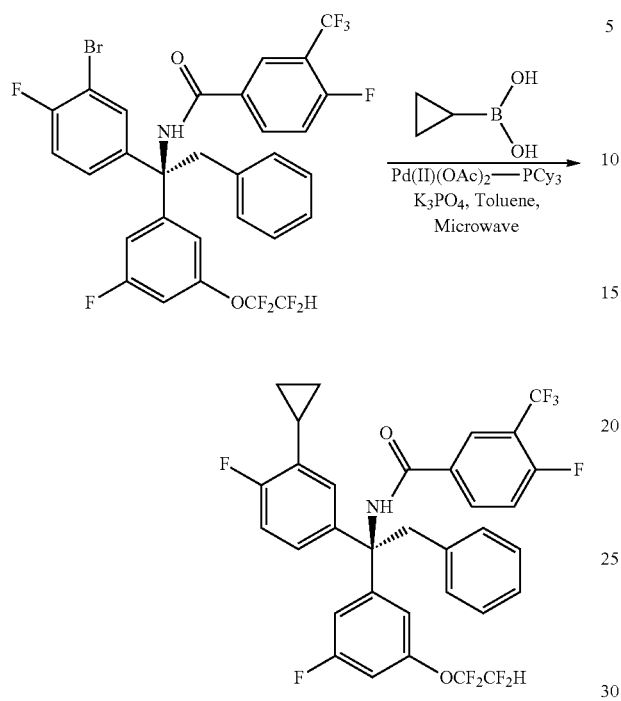

To a mixture of (S)—N-(1-(3-bromo-4-fluorophenyl)-1-(3-fluoro-5-(1,1,2,2-tetrafluoroethoxy)phenyl)-2-phenylethyl)-4-fluoro-3-(trifluoromethyl)benzamide, prepared as described in Procedures 3, 62, 5, 6 and 7, (50 mg, 0.07 mmol), (50 mg, 0.07 mmol), cyclopropylboronic acid (6 mg, 0.07 mmol), palladium (II) acetate (1 mg, 0.004 mmol) and tricyclohexylphosphine (2 mg, 0.007 mmol) in toluene (2 mL) was added $K_3PO_4$ (0.072 mL, 0.22 mmol). The reaction mixture was heated at 100° C. under microwave irradiation for 15 min. The reaction mixture was filtered, concentrated and the resulting residue was purified by preparative HPLC (Sunfire-S5-C18 18×50 mm column, eluting with 10-90% MeOH/$H_2O$ gradient over 8 min, with flow rate 20 mL/min and UV detection at 220 nm) to yield (R)—N-(1-(3-cyclopropyl-4-fluorophenyl)-1-(3-fluoro-5-(1,1,2,2-tetrafluoroethoxy)phenyl)-2-phenylethyl)-4-fluoro-3-(trifluoromethyl)benzamide (Example 309, 14 mg, 30% yield). LCMS: RT=4.37 min [M+H] 656.38 (Waters Sunfire-S5-C18 4.6×50 mm, eluting with 10-90% MeOH/$H_2O$ over 4 minutes containing 0.1% TFA; 4 mL/min, monitoring at 220 nm). $^1H$ NMR (500 MHz, $CDCl_3$) δ ppm 7.90 (1H, dd, J=6.60, 1.92 Hz), 7.81-7.84 (1H, m), 7.22-7.30 (5H, m), 7.16 (2H, t, J=7.56 Hz), 6.93-7.00 (4H, m), 6.77-6.81 (1H, m), 6.68 (2H, d, J=7.42 Hz), 6.62 (1H, s), 6.54 (1H, dd, J=6.87, 2.47 Hz), 5.88 (1H, t, J=52.73 Hz), 4.08 (1H, d, J=13.20 Hz), 3.66 (1H, d, J=13.20 Hz), 2.03 (1H, ddd, J=13.75, 8.52, 5.22 Hz), 0.92-0.96 (2H, m), 0.52-0.56 (1H, m), 0.43-0.47 (1H, m).

Example 310

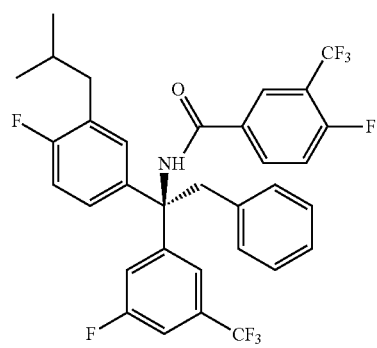 [SMILES: CC(C)Cc1cc([C@@](Cc2ccccc2)(NC(=O)c2ccc(F)c(C(F)(F)F)c2)c2cc(F)cc(C(F)(F)F)c2)ccc1F]

(R)-4-fluoro-N-(1-(4-fluoro-3-isobutylphenyl)-1-(3-fluoro-5-(trifluoromethyl)phenyl)-2-phenylethyl)-3-(trifluoromethyl)benzamide

Procedure 122

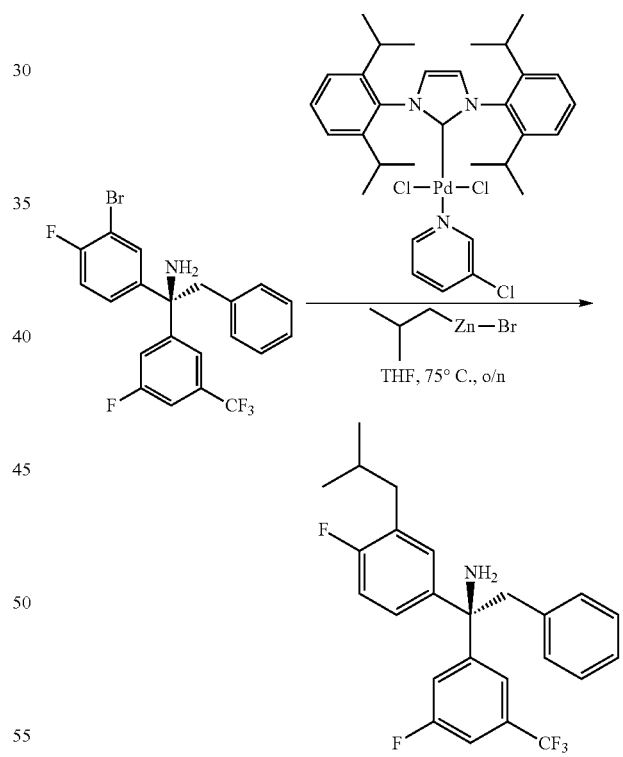

To a solution of [1,3-bis(2,6-diisopropylphenyl)imidazol-2-ylidene](3-chloropyridyl)palladium(II) dichloride (8 mg, 0.01 mmol) in NMP (0.5 mL) was added isobutylzinc(II) bromide in THF (0.5 M, 0.7 mL, 0.35 mmol) followed by (S)-1-(3-bromo-4-fluorophenyl)-1-(3-fluoro-5-(trifluoromethyl)phenyl)-2-phenylethanamine, prepared as described Procedure 62, 5 and 6, (50 mg, 0.11 mmol) in anhydrous THF. The reaction mixture was heated at 75° C. overnight. The reaction mixture was diluted with EtOAc and the organic layer was washed with sat. $NH_4Cl$, dried over $Na_2SO_4$ and concentrated to yield (R)-1-(4-fluoro-3-isobutylphenyl)-1-(3-fluoro-5-(trifluoromethyl)phenyl)-2-phenylethanamine. LCMS: RT=3.62 min [M−NH$_2$] 417 (Waters Sunfire-S5-C18 4.6×50 mm, eluting with 10-90% MeOH/H$_2$O over 4 minutes containing 0.1% TFA; 4 mL/min, monitoring at 220 nm).

(S)-4-fluoro-N-(2-hydroxy-2-phenyl-1,1-bis(3-(trifluoromethoxy)phenyl)ethyl)-3-(trifluoromethyl)benzamide Procedure 123

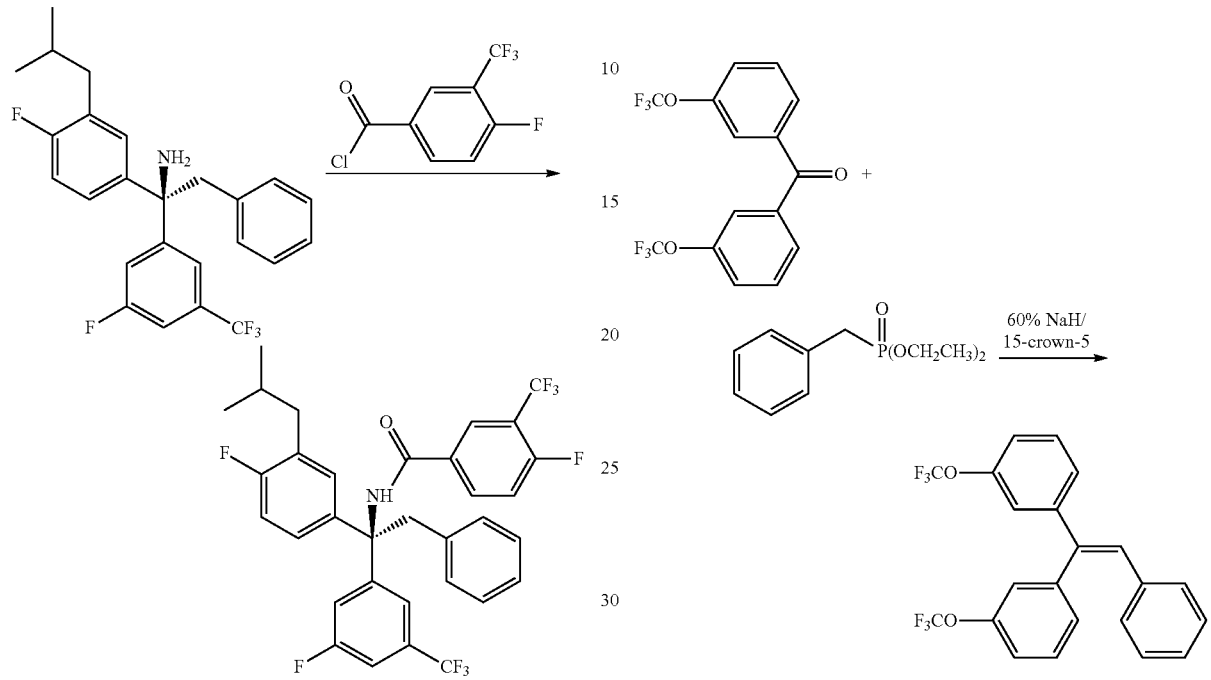

Following Procedure 7, (R)-4-fluoro-N-(1-(4-fluoro-3-isobutylphenyl)-1-(3-fluoro-5-(trifluoromethyl)phenyl)-2-phenylethyl)-3-(trifluoromethyl)benzamide (Example 310) was prepared (13 mg, 18% yield). LCMS: RT=4.68 min [M+H] 624.33 (Waters Sunfire-S5-C18 4.6×50 mm, eluting with 10-90% MeOH/H$_2$O over 4 minutes containing 0.1% TFA; 4 mL/min, monitoring at 220 nm). $^1$H NMR (500 MHz, CDCl$_3$) δ ppm 7.89 (1H, dd, J=6.46, 2.06 Hz), 7.82 (1H, ddd, J=8.45, 4.61, 2.34 Hz), 7.37 (1H, s), 7.22-7.30 (6H, m), 7.16 (2H, t, J=7.56 Hz), 6.98 (1H, t, J=8.80 Hz), 6.87-6.90 (1H, m), 6.83 (1H, dd, J=6.74, 2.61 Hz), 6.71 (1H, s), 6.69 (2H, d, J=7.15 Hz), 4.07 (1H, d, J=12.92 Hz), 3.78 (1H, d, J=13.20 Hz), 2.47-2.52 (1H, m), 2.40-2.45 (1H, m), 1.80 (1H, dt, J=13.54, 6.84 Hz), 0.85 (6H, dd, J=9.62, 6.60 Hz).

Example 311

To a suspension of NaH (60% in oil, 0.24 g, 6 mmol) in dry THF (25 mL) under nitrogen was added 15-crown-5 (0.06 g). The suspension was cooled in an ice bath. Bis(3-(trifluoromethoxy)phenyl)methanone (2.10 g, 6 mmol) and diethyl benzylphosphonate (1.37 g, 6 mmol) were dissolved in THF (12 mL) and added to the suspension. The reaction mixture was stirred at ice bath temperature for 15 min, allowed to warm to rt and stirred overnight. The reaction mixture was poured into water and extracted with ether (2×). The combined ether layers were washed with 10% NaHSO$_3$, sat. NaCl, dried over K$_2$CO$_3$, filtered and purified by ISCO using a gradient of 0-4% EtOAc/hexanes as eluent to give 3,3'-(2-phenylethene-1,1-diyl)bis((trifluoromethoxy)benzene) as a colorless oil (1.34 g, 53% yield). $^1$H NMR (400 MHz, CDC$_3$) δ ppm 7.33 (m, 2H), 7.2-7.1 (m, 8H), 7.04 (s, 1H), 7.0-6.97 (m, 3H).

Procedure 124

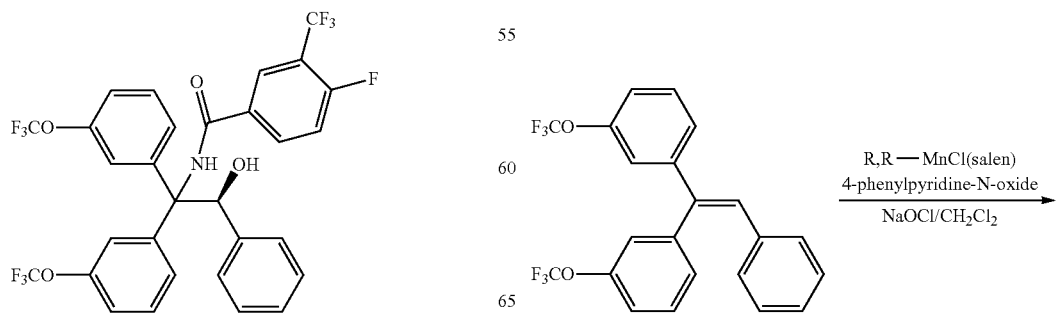

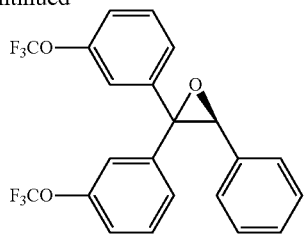

A mixture of 3,3'-(2-phenylethene-1,1-diyl)bis((trifluoromethoxy)benzene) (1.30 g, 3.06 mmol), R,R—MnCl (salen) (0.40 g, 0.64 mmol), 4-phenylpyridine-N-oxide (0.22 g, 1.27 mmol) in CH$_2$Cl$_2$ (30 mL) was cooled in an ice bath. A cold bleach (6.2% NaOCl in water, 11.54 g, 9.52 mmol) was added and the reaction mixture was allowed to warm to rt and stirred for 48 h. The dark brown reaction mixture was diluted with CH$_2$Cl$_2$ and filtered through celite. The organic layer was separated, washed with water, sat. NaCl, dried over MgSO$_4$, filtered and concentrated to yield a dark brown oil. The resulting oil was purified by ISCO using a gradient of 0-7% EtOAc/hexanes to give (S)-3-Phenyl-2,2-bis(trifluoromethoxy)phenyl)oxirane as a light yellow oil (0.96 g, 71% yield). HPLC: RT=4.68 min (Phenomenex Luna C18 5 u column, eluting with 10-90% MeOH/H$_2$O containing 0.1% phosphoric acid over a 4 minute gradient, monitoring at 220 nm). $^1$H NMR (400 MHz, CDCl$_3$) δ ppm 7.4-7.0 (m, 13H), 4.32 (s, 1H).

Procedure 125

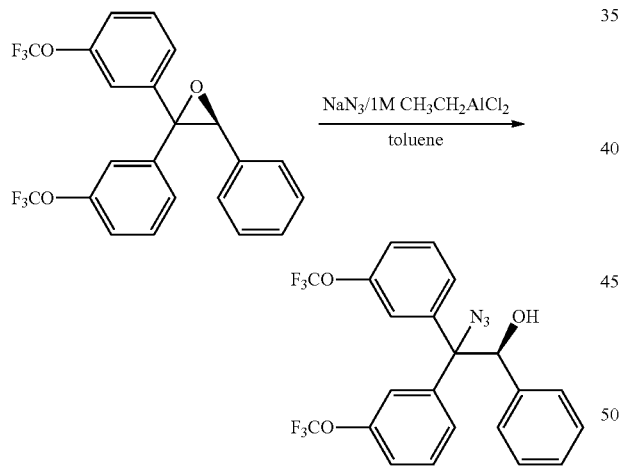

To a suspension of sodium azide (65 mg, 1 mmol) in toluene (9.1 mL) cooled at −78° C. was added 1 M ethylaluminum dichloride (0.91 mL, 0.91 mmol). The reaction mixture was stirred for 4 h at −78° C. (S)-3-Phenyl-2,2-bis(trifluoromethoxy)phenyl)oxirane (0.2 g, 0.45 mmol) was dissolved in toluene (0.5 mL) and added dropwise via syringe. The reaction mixture was stirred at −78° C. for min and then allowed to warm to rt and stirred overnight. The reaction mixture was diluted with EtOAc (5 mL) and NaN$_3$ (1 g) and water (1 mL) were added and stirred for 1 h. The resulting mixture was filtered through a pad of sodium sulfate and the filtrate was concentrated to a yellow oil. The residue was purified by ISCO using a gradient of 0-30% EtOAc/hexane as eluent to give (S)-2-azido-1-phenyl-2,2-bis(3-(trifluoromethoxy)phenyl)ethanol as a light yellow oil (69 mg, 31% yield). HPLC: RT=4.438 min (Phenomenex Luna C18 5 u column, eluting with 10-90% MeOH/H$_2$O containing 0.1% phosphoric acid over a 4 minute gradient, monitoring at 220 nm). $^1$H NMR (400 MHz, CDCl$_3$) δ ppm 7.5-7.0 (m, 13H), 5.63 (d, 1H), 2.35 (d, 1H).

Procedure 126

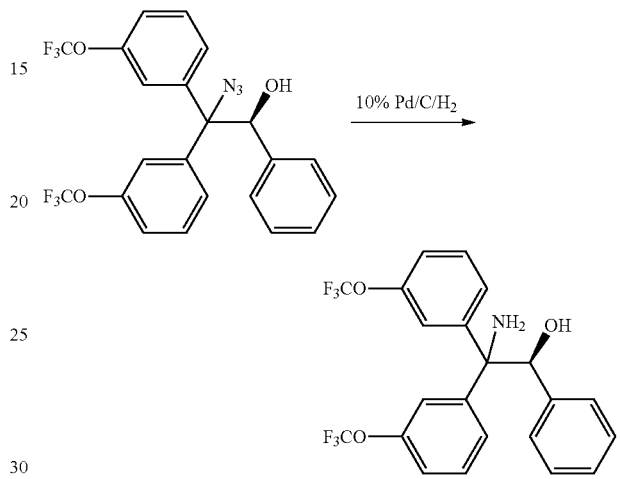

A slurry of (S)-2-azido-1-phenyl-2,2-bis(3-(trifluoromethoxy)phenyl)ethanol (64 mg, 0.132 mmol) and 10% Pd on C (40 mg) in methanol (2 mL) was subjected to balloon hydrogenation overnight at rt. The reaction mixture was filtered through celite and the filtrate was concentrated to give (S)-2-amino-1-phenyl-2,2-bis(3-(trifluoromethoxy)phenyl) ethanol as a light yellow oil (53 mg, 87% yield). HPLC: RT=3.40 min (Phenomenex Luna C18 5 u column, eluting with 10-90% MeOH/H$_2$O containing 0.1% phosphoric acid over a 4 minute gradient, monitoring at 220 nm). LCMS: [M+H] 458.1 (Phenomenex Luna C18 column, 4.6×30 mm eluting with 10-90% MeOH/H$_2$O over 2 minutes containing 0.1% TFA; 5 mL/min, monitoring at 220 nm).

Procedure 127

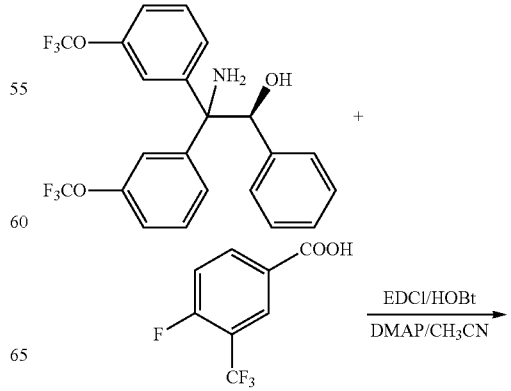

517
-continued

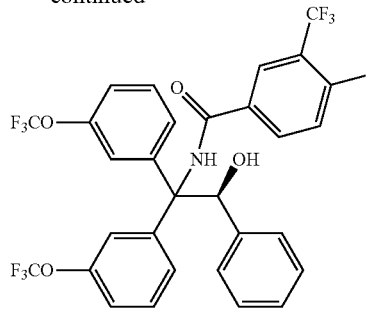

A solution of (S)-2-amino-1-phenyl-2,2-bis(3-(trifluoromethoxy)phenyl)ethanol (44 mg, 0.096 mmol), 4-fluoro-3-(trifluoromethyl)benzoic acid (20 mg, 0.096 mmol), EDCI (28 mg, 0.14 mmol), HOBT (14 mg, 0.096 mmol) and a catalytic amount of DMAP in acetonitrile (3 mL) was stirred for 24 h at rt. The reaction mixture was diluted with EtOAc and washed successively with 1 N HCl, 1 N NaOH, sat. NaCl, dried over MgSO$_4$, filtered and concentrated. The residue was purified by preparative HPLC Shimadzu-YMC Sunfire 5 µcolumn, 30×100 mm eluting with 50-100% MeOH (90% in H$_2$O, 0.1% TFA) gradient over 10 min with flow rate 40 mL/min and UV detection at 220 nm. (S)-4-Fluoro-N-(2-hydroxy-2-phenyl-1,1-bis(3-(trifluoromethoxy)phenyl)ethyl)-3-(trifluoromethyl)benzamide (Example 311) was isolated as a colorless film (10 mg, 15% yield). HPLC: RT=4.143 minutes (Phenomenex Luna C18 5 u column eluting with 10-90% aqueous methanol containing 0.1% phosphoric acid over a 4 minute gradient monitoring at 220 nm). LCMS: [M+H] 648.0 (Phenomenex Luna C18 column, 4.6×30 mm eluting with 10-90% MeOH/H$_2$O over 2 minutes containing 0.1% TFA; 5 mL/min, monitoring at 220 nm). $^1$H NMR (400 MHz, CDCl$_3$) δ ppm 8.23 (m, 1H), 7.37-6.9 (m, 15H), 5.41 (s, 1H).

Example 312

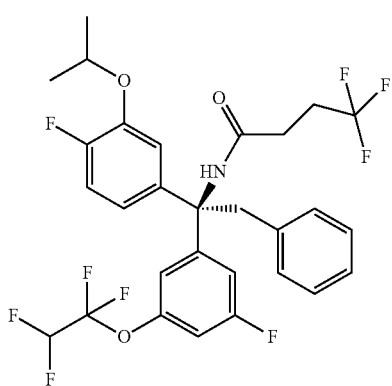 [SMILES: CC(C)Oc1cc([C@@](Cc2ccccc2)(NC(=O)CCC(F)(F)F)c2cc(F)cc(OC(F)(F)C(F)F)c2)ccc1F]

518
(R)-4,4,4-trifluoro-N-(1-(4-fluoro-3-isopropoxyphenyl)-1-(3-fluoro-5-(1,1,2,2-tetrafluoroethoxy)phenyl)-2-phenylethyl)butanamide Procedure 128

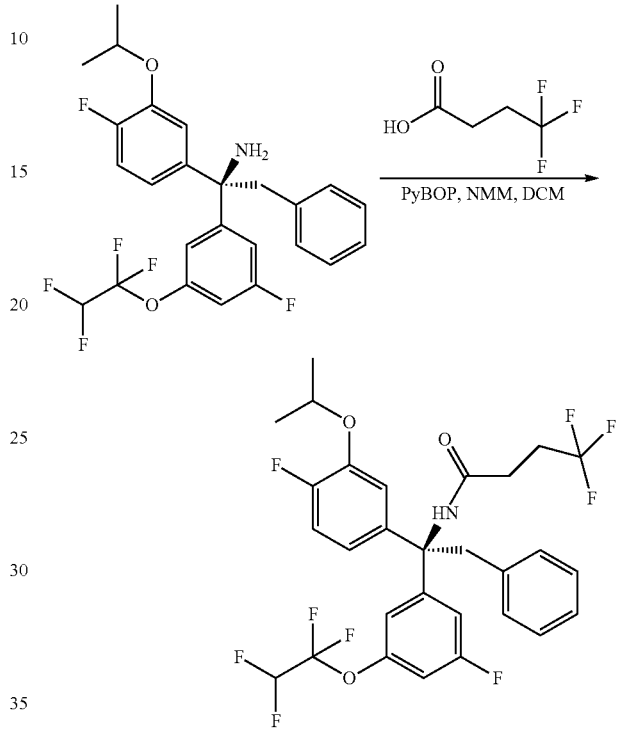

To a solution of 4,4,4-trifluorobutyric acid (13 mg, 0.09 mmol) in DCM (0.8 mL) was added (benzotriazol-1-yloxy)tripyrrolidinophosphonium hexafluorophosphate (52 mg, 0.1 mmol), (R)-1-(4-fluoro-3-isopropoxyphenyl)-1-(3-fluoro-5-(1,1,2,2-tetrafluoroethoxy)phenyl)-2-phenylethanamine (40 mg, 0.08 mmol), followed by NMM (28 µl, 0.25 mmol). The reaction mixture was stirred at room temperature for 16 h, then another 16 h at 60° C. The reaction mixture was diluted with EtOAc (10 mL) and the organic layer was washed with H$_2$O, dried over MgSO$_4$, filtered and concentrated. The residue was purified by preparative HPLC Phenomenex Luna C18 column, 30×50 mm eluting with 10-90% ACN/H$_2$O over 10 minutes containing 0.1% TFA; 40 mL/min, monitoring at 220 nm; 40-100% ACN (90% in water, 0.1% TFA) gradient over 10 min with flow rate 40 mL/min and UV detection at 220 nm. (R)-4,4,4-trifluoro-N-(1-(4-fluoro-3-isopropoxyphenyl)-1-(3-fluoro-5-(1,1,2,2,-tetrafluoroethoxy)phenyl)-2-phenylethyl)butanamide (Example 312) was isolated as a lyophillate (27 mg, 55% yield). LCMS: RT=2.15 min [M+H] 608.2 (2 min Phenomenex Luna C18 column, 4.6×30 mm eluting with 10-90% MeOH/H$_2$O over 2 minutes containing 0.1% TFA; 5 mL/min, monitoring at 220 nm); HPLC: RT=3.79 min, Purity 100% (Phenomenex Luna C18 column, 4.6×50 mm eluting with 10-90% ACN/H$_2$O over 4 minutes containing 0.1% TFA; 4 mL/min, monitoring at 220 nm); $^1$H NMR (400 MHz, CDCl$_3$) δ ppm 1.18 (d, J=6.05 Hz, 3H), 1.24 (d, J=6.05 Hz, 3H), 2.34-2.48 (m, 2H), 2.51-2.61 (m, 2H), 3.79 (d, J=13.19 Hz, 1H), 3.98 (d, J=13.19 Hz, 1H), 4.29-4.39 (m, 1H), 6.12-6.44 (m, 1H), 6.67-6.82 (m, 4H), 6.91-7.07 (m, 4H), 7.10-7.19 (m, 3H), 8.29 (s, 1H).

Example 313

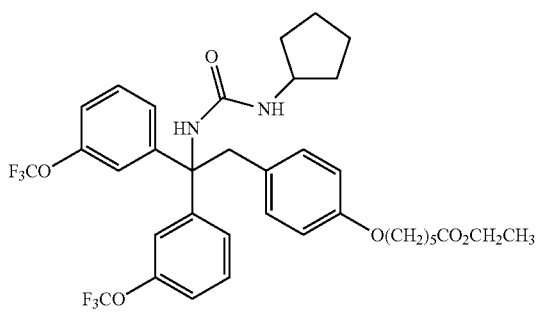

Ethyl 6-(4-(2-(3-cyclopentylureido)-2,2-bis(3-(trifluoromethoxy)phenyl)ethyl)phenoxy)hexanoate Procedure 129

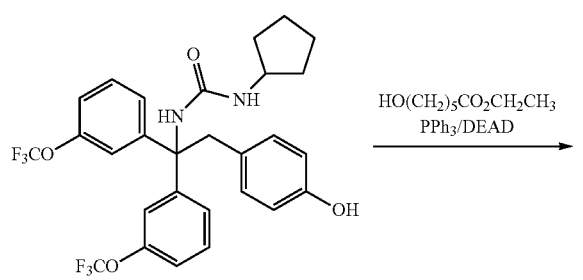

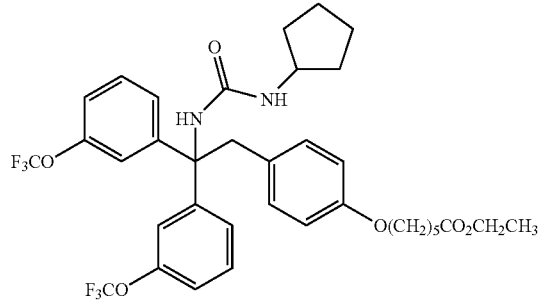

To an oven-dried 3-necked 10 mL round-bottom flask under nitrogen was added 1-cyclopentyl-3-(2-(4-hydroxyphenyl)-1,1-bis(3-(trifluoromethoxy)phenyl)ethyl)urea, prepared as described in Procedure 11, 6, 2 and 59, (50 mg, 0.1 mmol), triphenylphosphine (34 mg, 0.1 mmol), ethyl 6-hydroxyhexanoate (17 mg, 0.1 mmol) and dry THF (0.5 mL). The reaction mixture was cooled in an ice-methanol bath and diethylazodicarboxylate (23 mg, 0.13 mmol) was added via syringe. The reaction was allowed to warm to rt and stirred overnight. The reaction mixture was concentrated in vacuo and purified by ISCO silica gel chromatography using a gradient of 5-25% EtOAc/hexanes as eluent to yield ethyl 6-(4-(2-(3-cyclopentylureido)-2,2-bis(3-(trifluoromethoxy)phenyl)ethyl)phenoxy)hexanoate (Example 313) was isolated as a white solid (43 mg, 61% yield). HPLC: RT=4.69 minutes (Phenomenex Luna C18 5μ column 4.6×50 mm eluting with 10-90% aqueous methanol containing 0.1% phosphoric acid over a 4 minute gradient monitoring at 220 nm). LC/MS [M+H] 711.3 (Phenomenex Luna C18 5μ column 4.6×30 mm eluting with 10-90% aqueous methanol containing 0.1% TFA over a 4 minute gradient monitoring at 220 nm). $^1$H NMR (400 MHz, CDCl$_3$) δ ppm 7.33 (t, J=7.9 Hz, 2H), 7.20 (d, J=7.9 Hz, 2H), 7.12 (d, J=7.9 Hz, 2H), 7.07 (s, 2H), 6.62 (d, J=8.8 Hz, 2H), 6.56 (d, J=8.8 Hz, 2H), 4.10 (q, J=7.1 Hz, 2H), 3.86t, J=6.1 Hz, 2H), 3.68 (s, 1H), 3.62 (t, J=6.6 Hz, 1H), 2.30-2.27 (m, 2H), 1.82-1.14 (m, 17H), 1.23 (t, J=7.1 Hz, 3H).

Example 314

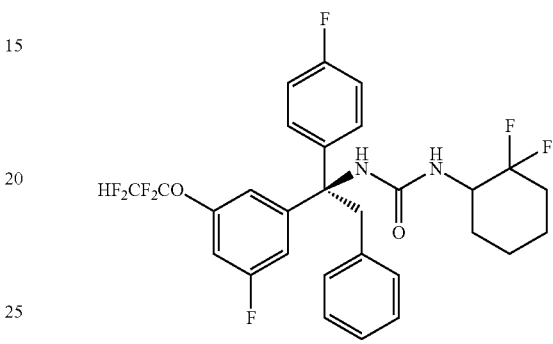

1-(2,2-difluorocyclohexyl)-3-((R)-1-(3-fluoro-5-(1,1,2,2-tetrafluoroethoxy)phenyl)-1-(4-fluorophenyl)-2-phenylethyl)urea Procedure 130

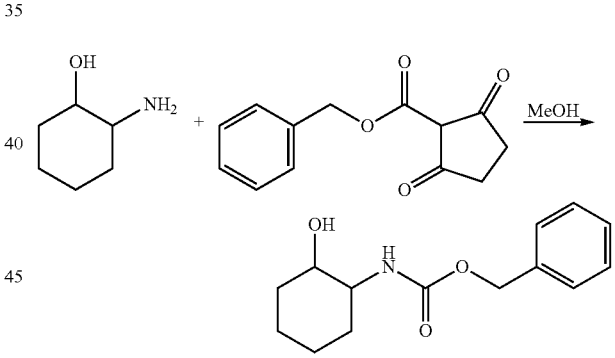

At 0° C. to a solution of benzyl 2,5-dioxocyclopentanecarboxylate (2.58 g, 10.35 mmol) in MeOH (20 mL) was added 2-aminocyclohexanol (1.25 g, 10.87 mmol). The reaction mixture was stirred at room temperature for 18 h and quenched with 0.25 N HCl (8 mL). MeOH was removed under vacuum and the aqueous layer was extracted with CH$_2$Cl$_2$ (4×10 mL). The combined organic layers were washed with sat. NaCl (20 mL), dried over Na$_2$SO$_4$, filtered and concentrated. The residue was purified by ISCO chromatography (40 g column) using hexanes/EtOAc (0-5% over 15 min, 5-10% over 7 min) to give benzyl 2-hydroxycyclohexylcarbamate as a light yellow solid at a retention time of 11-13 min (2.15 g, 83% yield). HPLC: RT=2.83 min, Purity 95% (Phenomenex Luna C18 column, 4.6×50 mm eluting with 10-90% MeOH/H$_2$O over 4 minutes containing 0.2% PPA; 4 mL/min, monitoring at 220 nm) NMR: 400 MHz $^1$H (CDCl$_3$) 7.33 ppm, 5H, m; 5.16 ppm, 1H, m; 5.09 ppm, 2H, s; 3.95 ppm, 1H, s; 3.68 ppm, 1H, m; 1.54 ppm, 8H, m.

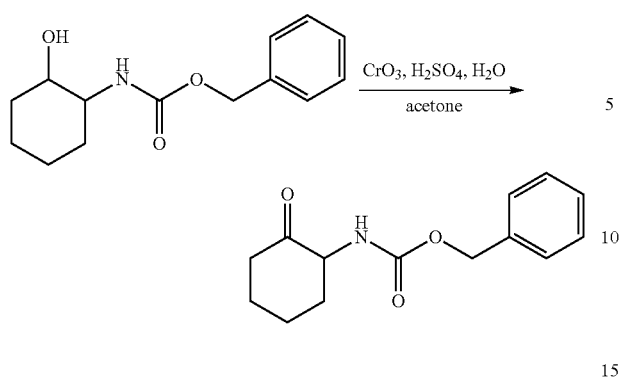

A mixture of CrO$_3$ (0.70 g) in concentrated H$_2$SO$_4$ (0.61 mL) was diluted with H$_2$O to the volume of 6 mL. To a solution of benzyl 2-hydroxycyclohexylcarbamate (1.60 g, 6.43 mmol) in acetone (5.4 mL) at 0° C. was added Jones Reagent (5.51 mL, 1.17 M, 6.43 mmol) dropwise over 5 min. The reaction mixture was stirred at room temperature for 1.5 h, quenched with 20% aq. K$_2$CO$_3$ to pH=8. The aqueous layer was extracted with EtOAc (3×15 mL). The combined organic layers were washed with sat. NaCl (20 mL), dried over Na$_2$SO$_4$, filtered and concentrated. The resulted crude yellow oil was purified by ISCO chromatography (40 g column) using hexanes/EtOAc (0-30% over 8 min, 30-45% over 10 min) to give benzyl 2-oxocyclohexylcarbamate as a colorless oil at a retention time of 8.5-11 min (1.26 g, 79% yield). HPLC: RT=2.69 min, Purity 99% (Phenomenex Luna C18 column, 4.6×50 mm eluting with 10-90% MeOH/H$_2$O over 4 minutes containing 0.2% PPA; 4 mL/min, monitoring at 220 nm). NMR: 400 MHz $^1$H (CDCl$_3$) 7.33 ppm, 5H, m; 5.76 ppm, 1H, s; 5.11 ppm, 2H, m; 4.27 ppm, 1H, m; 2.65 ppm, 1H, dd, J=6.60, 2.75 Hz; 2.52 ppm, 1H, m; 2.38 ppm, 1H, m; 2.13 ppm, 1H, m; 1.89 ppm, 1H, m; 1.77 ppm, 1H, m; 1.64 ppm, 1H, m; 1.42 ppm, 1H, m.

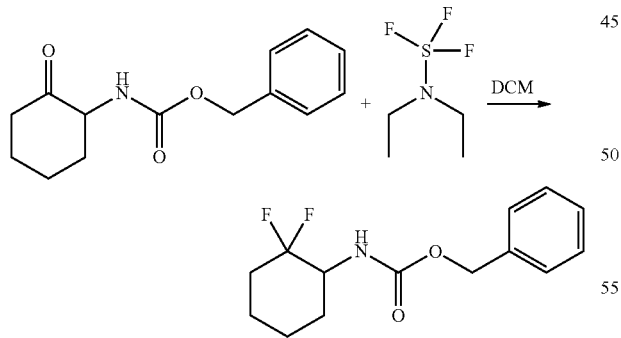

At room temperature to a solution of benzyl 2-oxocyclohexylcarbamate (294 mg, 1.19 mmol) in DCM (5 mL) was added DAST (0.5 mL, 3.92 mmol). The reaction mixture was stirred for 18 h, cooled to 0° C. and quenched by addition of sat. NaCl (1 mL). The aqueous phase was separated and extracted with DCM (3×8 mL). The combined organic layers were dried over Na$_2$SO$_4$, filtered and concentrated. The residue was purified by ISCO chromatography (12 g column) using hexanes/EtOAc (0-30% over 15 min, 30-45% over 10 min) to give benzyl 2,2-difluorocyclohexylcarbamate as a brown oil at a retention time of 7-10 min (272 mg, 85% yield). HPLC: RT=3.03 min, Purity 100% (Phenomenex Luna C18 column, 4.6×50 mm eluting with 10-90% MeOH/H$_2$O over 4 minutes containing 0.2% PPA; 4 mL/min, monitoring at 220 nm). NMR: 400 MHz $^1$H (CDCl$_3$) 7.34 ppm, 5H, m; 5.12 ppm, 2H, m; 4.99 ppm, 1H, d, J=8.35 Hz; 3.93 ppm, 1H, m; 2.18 ppm, 1H, m; 2.04 ppm, 1H, m; 1.77 ppm, 2H, m; 1.46 ppm, 4H, m.

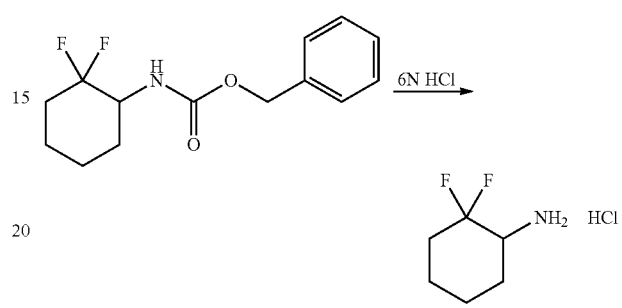

A solution of benzyl 2,2-difluorocyclohexylcarbamate (38 mg, 0.14 mmol) in 6 N HCl (2 mL) was heated at 100° C. for 2 h. The cooled reaction mixture was extracted with ether (3×1 mL) and the combined organic layers were concentrated to give 2,2-difluorocyclohexanamine hydrochloride as a light brown solid (23 mg, 96% crude).

1-(2,2-Difluorocyclohexyl)-3-((R)-1-(3-fluoro-5-(1,1,2, 2-tetrafluoroethoxy)phenyl)-1-(4-fluorophenyl)-2-phenylethyl)urea (Example 314) was prepared as described in Procedure 12 (43 mg, 60% yield). LC/MS: RT=4.07 min [M+H] 587.3 (Phenomenex Luna C18 column, 4.6×50 mm eluting with 10-90% MeCN/H$_2$O over 4 minutes containing 0.1% NH$_4$OAc; 4 mL/min, monitoring at 220 nm).

Example 315

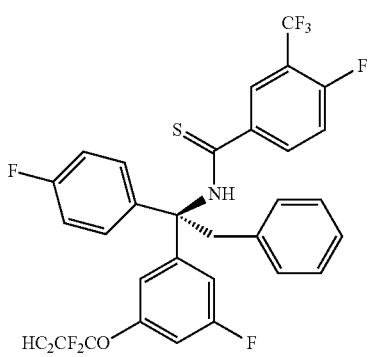

(R)-4-fluoro-N-(1-(3-fluoro-5-(1,1,2,2-tetrafluoroethoxy)phenyl)-1-(4-fluorophenyl)-2-phenylethyl)-3-(trifluoromethyl)benzothioamide

Procedure 131

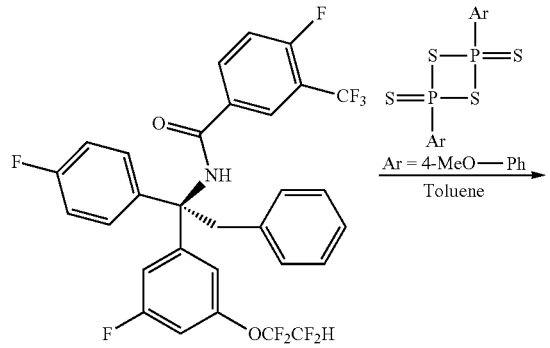

To a stirred solution of (R)-4-fluoro-N-(1-(3-fluoro-5-(1,1,2,2-tetrafluoroethoxy)phenyl)-1-(4-fluorophenyl)-2-phenylethyl)-3-(trifluoromethyl)benzamide (105 mg, 0.17 mmol), prepared as described in Procedure 3, 4, 5, 6 and 7, in toluene (5.2 mL) was added Lawesson's reagent (83 mg, 0.20 mmol). The reaction mixture was heated at 110° C. After 8 h, the reaction mixture was concentrated and the residue was purified by ISCO column chromatography (EtOAc/hexane 0-100%, SiO$_2$) to provide (R)-4-fluoro-N-(1-(3-fluoro-5-(1,1,2,2-tetrafluoroethoxy)phenyl)-1-(4-fluorophenyl)-2-phenylethyl)-3-(trifluoromethyl)benzothioamide (Example 315, 89 mg, 83% yield) as a yellow oil. $^1$H NMR (500 MHz, CDCl$_3$) δ ppm 7.92 (s, 1H), 7.74-7.72 (m, 1H), 7.68-7.66 (m, 1H), 7.22-6.86 (m, 11H), 6.72 (d, J=5 Hz, 2H), 5.92-5.70 (m, 1H), 4.36 (d, J=15 Hz, 1H), 3.82 (d, J=10 Hz, 1H); $^{13}$C NMR (125 MHz, CDCl$_3$) δ ppm 195 (C=S); LC/MS: RT=4.393 min [M+H] 632.4 (Phenomenex Luna C18 column, 4.6×50 mm eluting with 10-90% MeCN/H$_2$O over 4 minutes containing 0.1% NH$_4$OAc; 4 mL/min, monitoring at 220 nm).

Example 316

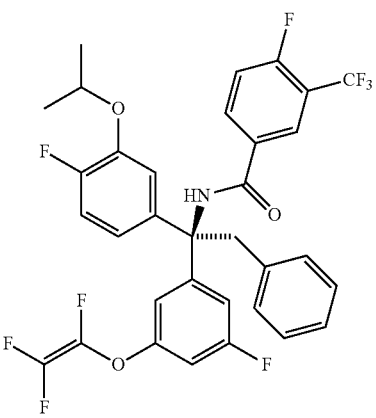 [SMILES: CC(C)Oc1cc([C@@](Cc2ccccc2)(NC(=O)c2ccc(F)c(C(F)(F)F)c2)c2cc(F)cc(OC(F)=C(F)F)c2)ccc1F]

(R)-4-fluoro-N-(1-(4-fluoro-3-isopropoxyphenyl)-1-(3-fluoro-5-(1,2,2-trifluorovinyloxy)phenyl)-2-phenylethyl)-3-(trifluoromethyl)benzamide

Procedure 132

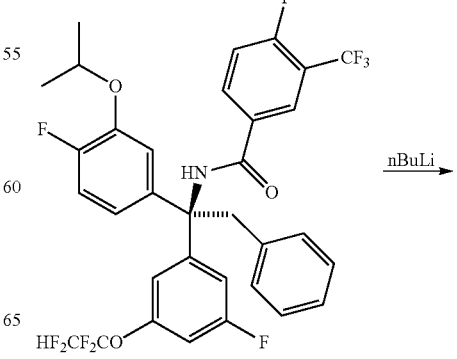

525
-continued

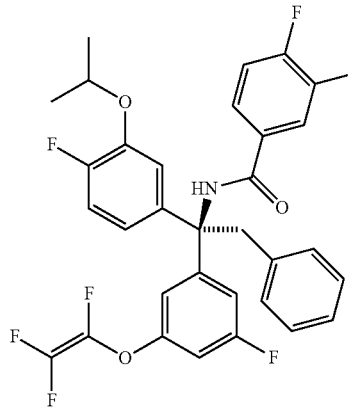

Example 317

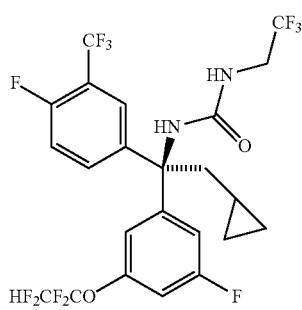

At −78° C. under argon, to a solution of (R)-4-fluoro-N-(1-(4-fluoro-3-isopropoxyphenyl)-1-(3-fluoro-5-(1,1,2,2-tetrafluoroethoxy)phenyl)-2-phenylethyl)-3-(trifluoromethyl)benzamide (31 mg, 0.046 mmol), prepared as described in Procedure 3, 4, 5, 6, 7, 59 and 68, in dry THF (0.7 mL) was added nBuLi (2.5 M in hexane, 0.25 mL, 0.625 mmol) dropwise. The reaction mixture was allowed to warm to −5° C. over 1.5 h period. After stirring for total 2 h, the reaction mixture was quenched by addition of sat. NH₄Cl and the aqueous phase was extracted with EtOAc and the organic layer was concentrated. The resulting residue was purified by reverse phase HPLC to give pure desired product (7 mg, 23% yield). LC-MS: RT=4.19 min [M+H] 654.3 (Phenomenex Luna C18 column, 4.6×30 mm eluting with 10-90% MeOH/H₂O over 2 minutes containing 0.1% TFA; 5 mL/min, monitoring at 220 nm). ¹H NMR (400 MHz, Methanol-d₄) δ ppm 8.85 (m, 1H), 8.00 (m, 2H), 7.47 (t, J=8.8 Hz, 1H), 7.22 (m, 1H), 7.15 (t, J=7.7 Hz, 2H), 7.07 (m, 1H), 7.01-6.94 (m, 2H), 6.90 (m, 1H), 6.88-6.83 (m, 2H), 6.75 (m, 1H), 4.01 (AB, J=12.9 Hz, 2H), 1.27, 1.21 (d, J=6.1 Hz, 6H).

526
(R)-1-(2-cyclopropyl-1-(4-fluoro-3-(trifluoromethyl)phenyl)-1-(3-fluoro-5-(1,1,2,2-tetrafluoroethoxy)phenyl)ethyl)-3-(2,2,2-trifluoroethyl)urea Procedure 133

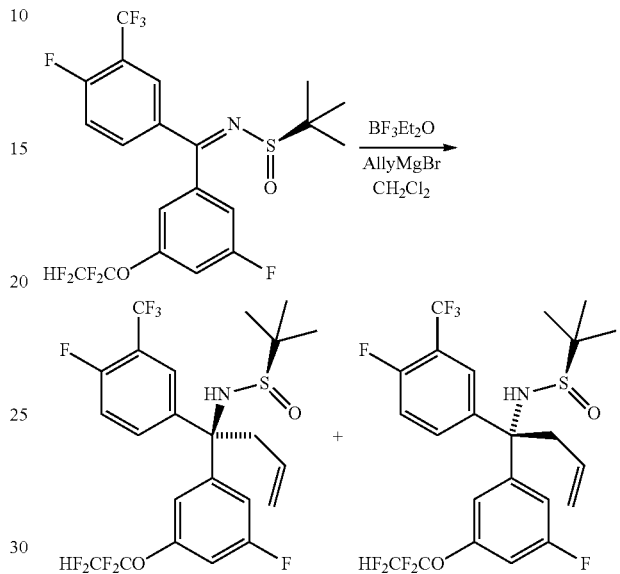

Following Procedure 14, (R)—N-(1-(4-fluoro-3-(trifluoromethyl)phenyl)-1-(3-fluoro-5-(1,1,2,2-tetrafluoroethoxy)phenyl)but-3-enyl)-2-methylpropane-2-sulfinamide was prepared (1.9 g, 92% yield). The two diastereomers were separated via chiral AD column (20% isopropanol/heptanes// 0.1% DEA) to give (R)—N—((S)-1-(4-fluoro-3-(trifluoromethyl)phenyl)-1-(3-fluoro-5-(1,1,2,2-tetrafluoroethoxy)phenyl)but-3-enyl)-2-methylpropane-2-sulfinamide (1.02 g) as the fast eluting isomer and (R)—N—((R)-1-(4-fluoro-3-(trifluoromethyl)phenyl)-1-(3-fluoro-5-(1,1,2,2-tetrafluoroethoxy)phenyl)but-3-enyl)-2-methylpropane-2-sulfinamide (0.88 g) as the slow eluting isomer. (R)—N—((R)-1-(4-fluoro-3-(trifluoromethyl)phenyl)-1-(3-fluoro-5-(1,1,2,2-tetrafluoroethoxy)phenyl)but-3-enyl)-2-methylpropane-2-sulfinamide: LCMS: RT=4.08 min [M+H] 548.2 (Phenomenex Luna C18 column, 4.6×30 mm eluting with 10-90% MeOH/H₂O over 2 minutes containing 0.1% TFA; 5 mL/min, monitoring at 220 nm).

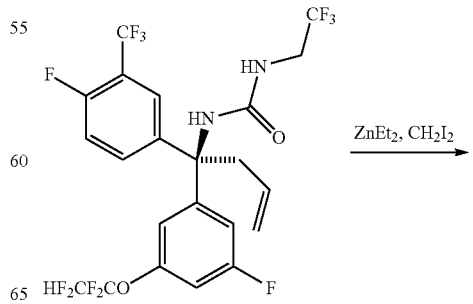

-continued

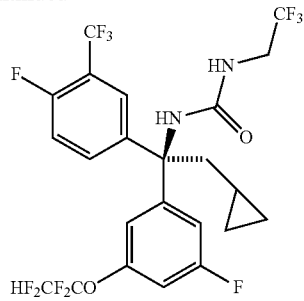

At 0° C. under argon, to a solution of (R)-1-(1-(4-fluoro-3-(trifluoromethyl)phenyl)-1-(3-fluoro-5-(1,1,2,2-tetrafluoroethoxy)phenyl)but-3-enyl)-3-(2,2,2-trifluoroethyl)urea (40 mg, 0.070 mmol), prepared as described in Procedure 6 and 10, in dry toluene (1 mL) was added diethyl Zinc (1.0 M in hexane, 1.2 mL, 1.2 mmol), followed by dropwise addition of diiodomethane (0.2 mL). The reaction mixture was gradually warmed to 110° C., and heated at 110° C. for 1 h. After cooling, 1 N HCl was added and the reaction mixture was stirred at room temperature for 5 min. The reaction mixture was extracted with EtOAc and the organic layer was washed with $H_2O$, sat. $NaHCO_3$, sat. NaCl, dried over $Na_2SO_4$, filtered and concentrated. The residue was purified by Prep HPLC (phenomenex AXIA Luna 75×30 mm, 5 u column eluting with 50-100% MeOH in $H_2O$ with 0.1% TFA, 40 mL/min, monitoring at 220 nm) to give (R)-1-(2-cyclopropyl-1-(4-fluoro-3-(trifluoromethyl)-phenyl)-1-(3-fluoro-5-(1,1,2,2-tetrafluoroethoxy)phenyl)ethyl)-3-(2,2,2-trifluoroethyl)urea (Example 317) as white solid (13 mg, yield 32%). LCMS: RT=3.26 min [M+H] 583.2 (Phenomenex Luna C18 column, 4.6×50 mm eluting with 50-90% MeOH/$H_2O$ over 4 minutes containing 0.1% TFA; 4 mL/min, monitoring at 220 nm). $^1$H NMR (400 MHz, $CDCl_3$) δ ppm 7.55 (d, J=6.6 Hz, 1H), 7.46 (m, 1H), 7.12 (t, J=9.3 Hz, 1H), 6.94-6.85 (m, 3H), 5.84 (tt, J=52.8, 2.8 Hz, 1H), 5.61 (br, s, 1H), 4.78 (br, t, J=6.1 Hz, 1H), 3.69 (m, 2H), 2.31 (m, 2H), 0.36 (m, 3H), 0.00 (m, 2H).

Example 318

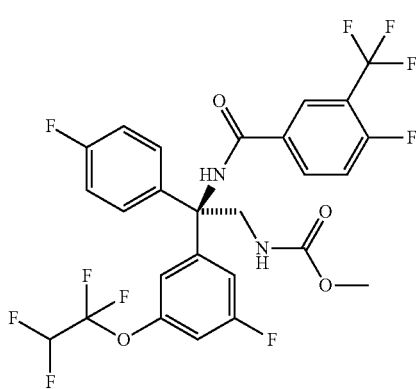 [SMILES: COC(=O)NC[C@@](NC(=O)c1ccc(F)c(C(F)(F)F)c1)(c1ccc(F)cc1)c1cc(F)cc(OC(F)(F)C(F)F)c1]

(R)-methyl 3-(4-fluoro-3-(trifluoromethyl)benzamido)-3-(3-fluoro-5-(1,1,2,2-tetrafluoroethoxy)phenyl)-3-(4-fluorophenyl)propanoate Procedure 134

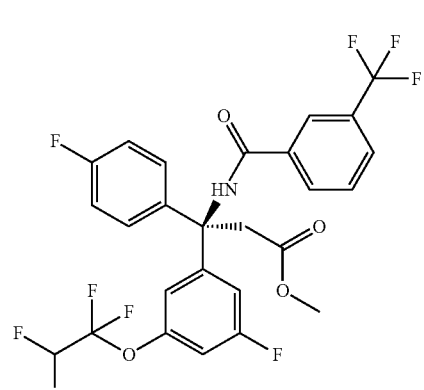

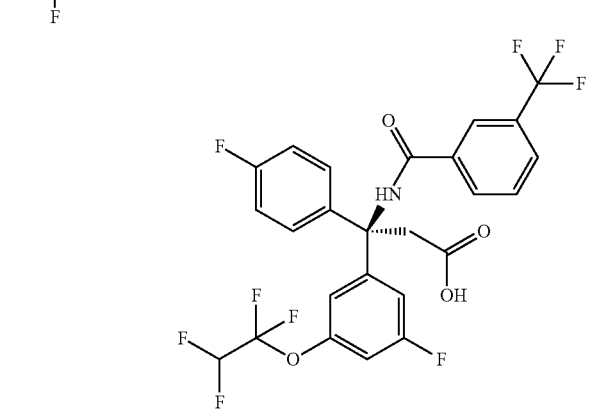

(R)-3-(4-fluoro-3-(trifluoromethyl)benzamido)-3-(3-fluoro-5-(1,1,2,2-tetrafluoroethoxy)phenyl)-3-(4-fluorophenyl)propanoic acid was prepared as described in Procedure 3, 4, 5, 14, 6, 7 and 23 (32 mg, 79% yield). LCMS: 2.03 min [M+H] 584.2 (2 min Phenomenex Luna C18 column, 4.6×30 mm eluting with 10-90% MeOH/$H_2O$ over 2 minutes containing 0.1% TFA; 5 mL/min, monitoring at 220 nm). $^1$H NMR (400 MHz, $CDCl_3$) δ ppm 3.70 (s, 2H), 6.18 (t, J=53 Hz, 1H), 6.97 (d, J=8.79 Hz, 1H), 7.08 (t, J=8.79 Hz, 2H), 7.14 (s, 1H), 7.19 (d, J=10.44 Hz, 1H), 7.34-7.50 (m, 3H), 8.05-8.18 (m, 3H).

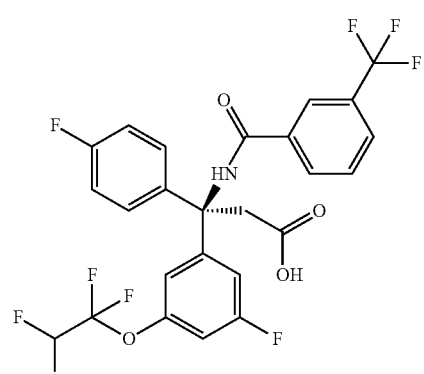

529
-continued

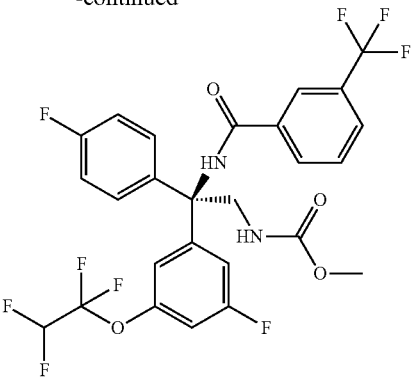

To a solution of (R)-3-(4-fluoro-3-(trifluoromethyl)benzamido)-3-(3-fluoro-5-(1,1,2,2-tetrafluoroethoxy)phenyl)-3-(4-fluorophenyl)propanoic acid (32 mg, 0.055 mmol) in toluene (0.5 mL) was added DPPA (18 mg, 0.066 mmol) and TEA (7 mg, 0.066 mmol). The reaction mixture was heated at 100° C. for 1 h followed by the addition of MeOH and TEA. The reaction was heated at 65° C. overnight. Excess K$_2$CO$_3$ was added and the reaction was heated to reflux for 3 h. The reaction mixture was concentrated and the resulting residue was purified by preparative HPLC (phenominex 30×100 mm column, 30-100% MeOH (90% in water, 0.1% TFA) gradient over 12 min with flow rate 40 mL/min and UV detection at 220 nm) to yield (R)-methyl 3-(4-fluoro-3-(trifluoromethyl)benzamido)-3-(3-fluoro-5-(1,1,2,2-tetrafluoroethoxy)phenyl)-3-(4-fluorophenyl)propanoate (Example 318) as a white solid (5 mg, 15% yield). LCMS: RT=3.92 min [M+H] 613.3 (4 min Phenomenex Luna C18 column, 4.6×30 mm eluting with 10-90% MeOH/H$_2$O over 4 minutes containing 0.1% TFA; 5 mL/min, monitoring at 220 nm). $^1$H NMR (400 MHz, CDCl$_3$) ppm 3.74 (s, 3H), 3.87-4.11 (m, 2H), 4.89 (m, 1H), 5.86 (t, 1H), 6.95 (d, 1H), 6.99-7.13 (m, 5H), 7.28-7.40 (m, 3H), 8.09-8.16 (m, 1H), 8.26 (d, 1H), 8.94 (s, 1H).

Example 319

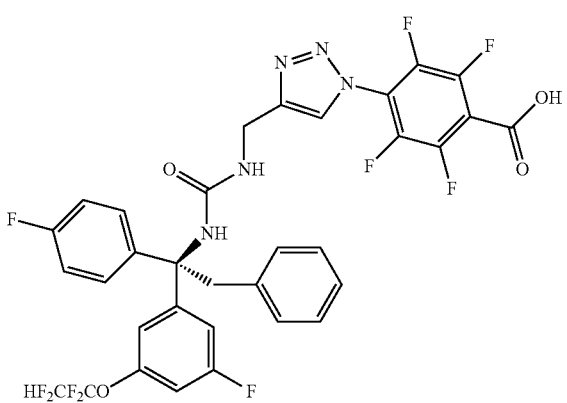

530

(R)-2,3,5,6-tetrafluoro-4-(4-((3-(1-(3-fluoro-5-(1,1,2,2-tetrafluoroethoxy)phenyl)-1-(4-fluorophenyl)-2-phenylethyl)ureido)methyl)-1H-1,2,3-triazol-1-yl)benzoic acid Procedure 135

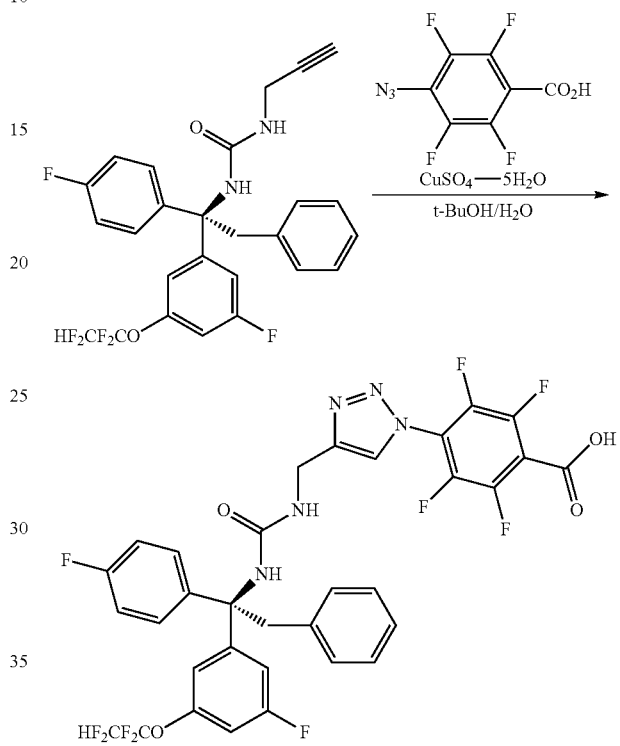

To a suspension of (R)-1-(1-(3-fluoro-5-(1,1,2,2-tetrafluoroethoxy)phenyl)-1-(4-fluorophenyl)-2-phenylethyl)-3-(prop-2-ynyl)urea (5.0 mg, 0.01 mmol), prepared as described in Procedure 3, 4, 5, 6 and 12, in a 1:1 mixture of water and tert-butyl alcohol (100 μL) was added 4-azido-2,3,5,6-tetrafluorobenzoic acid (2.3 mg, 0.01 mmol), followed by sodium ascorbate (1 M solution in H$_2$O, 100 μL) and CuSO$_4$.5H$_2$O (1 mg). The reaction mixture was stirred vigorously overnight in a sealed vial. The reaction mixture was diluted with H$_2$O and extracted with EtOAc (3×). The combined organic portions were concentrated and the residue was dissolved in MeOH and purified by preparative HPLC (Phenoma Onyx Monolithic 10×100 mm; eluting with 10%-90% MeCN/H$_2$O with 0.1% TFA, monitoring at 220 nm) to provide (R)-2,3,5,6-tetrafluoro-4-(4-((3-(1-(3-fluoro-5-(1,1,2,2-tetrafluoroethoxy)phenyl)-1-(4-fluorophenyl)-2-phenylethyl)ureido)methyl)-1H-1,2,3-triazol-1-yl)benzoic acid (Example 319, 5.7 mg, 78% yield). LC/MS: RT=3.610 min [M+H] 742.3 (Phenomenex Luna C18 column, 4.6×50 mm eluting with 10-90% MeOH/H$_2$O over 4 minutes containing 0.1% NH$_4$OAc; 4 mL/min, monitoring at 220 nm). $^1$H NMR (500 MHz, MeOH-d$_4$) δ 8.02 (s, 1H), 7.10-6.79 (m, 11H), 6.53 (d, J=5 Hz, 2H), 6.27-6.04 (m, 1H), 4.38-4.31 (m, 2H), 3.81 (d, J=15 Hz, 1H), 3.73 (d, J=10 Hz, 1H).

Example 320

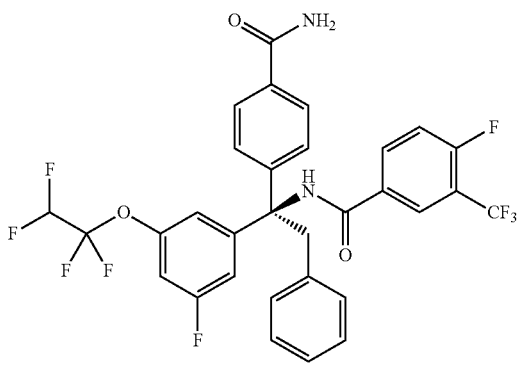

(R)—N-(1-(4-carbamoylphenyl)-1-(3-fluoro-5-(1,1,2,2-tetrafluoroethoxy)phenyl)-2-phenylethyl)-4-fluoro-3-(trifluoromethyl)benzamide Procedure 136

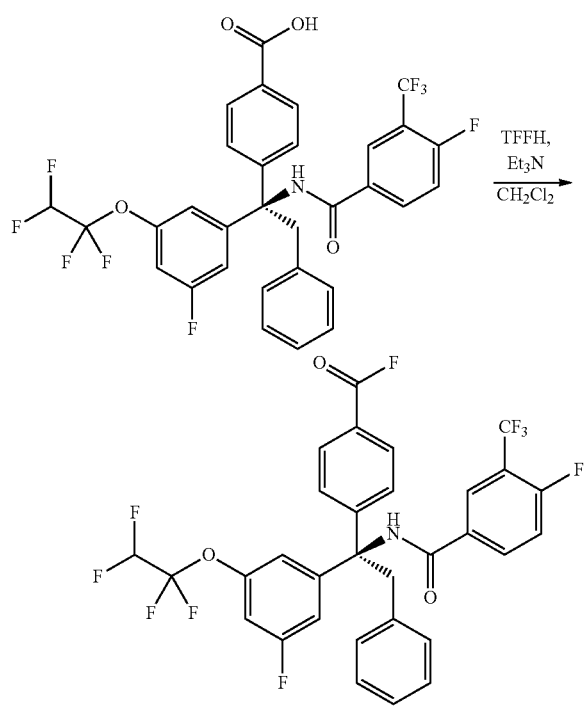

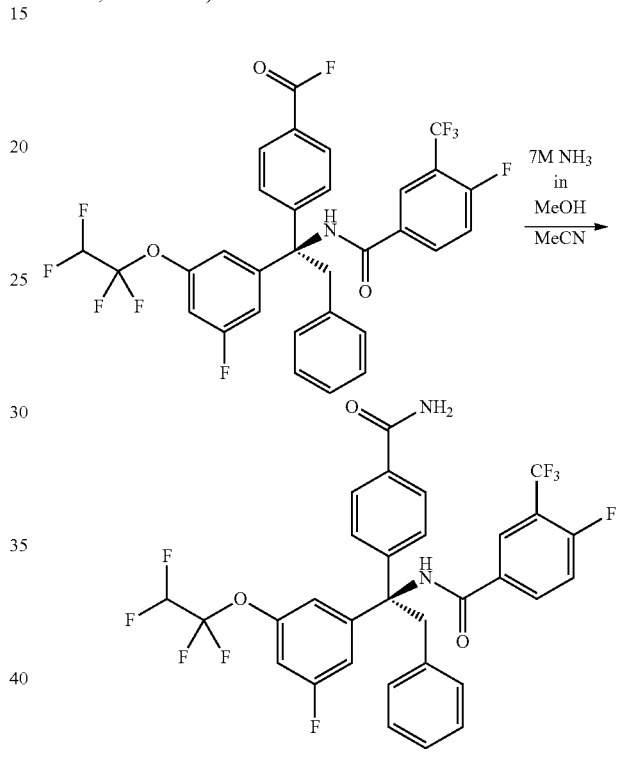

To a suspension of (R)-4-(1-(4-fluoro-3-(trifluoromethyl)benzamido)-1-(3-fluoro-5-(1,1,2,2-tetrafluoroethoxy)phenyl)-2-phenylethyl)benzoic acid (224 mg, 0.4 mmol), prepared as described in Procedure 3, 4, 5, 6, 7, 56, 57 and 23, in dichloromethane (3 mL) was added triethyl amine (97 µL, 0.70 mmol) followed by fluoro-N,N,N',N'-tetramethylformamidinium hexafluorophosphate (TFFH) (138 mg, 0.5 mmol). The reaction mixture was stirred for 18 h. The reaction mixture was concentrated and the residue was purified by flash chromatography (40 g silica gel; 0-40% ethyl acetate, hexane gradient over 14 min., 40 mL/min) to provide (R)-4-(1-(4-fluoro-3-(trifluoromethyl)benzamido)-1-(3-fluoro-5-(1,1,2,2-tetrafluoroethoxy)phenyl)-2-phenylethyl)benzoyl fluoride (127 mg, 56% yield). LCMS: RT=2.39 min [M+H] 644 (Chromolith Performance 18e 4.6×100 mm column, 10-90% methanol, water with 0.1% trifluoroacetic acid gradient over 2 min, 5 mL/min)

To a suspension of (R)-4-(1-(4-fluoro-3-(trifluoromethyl)benzamido)-1-(3-fluoro-5-(1,1,2,2-tetrafluoroethoxy)phenyl)-2-phenylethyl)benzoyl fluoride (20 mg, 0.03 mmol) in acetonitrile (1 mL) was added ammonia (7 M in methanol, 20 µL, 0.14 mmol). The reaction mixture was stirred for 24 h. The reaction mixture was concentrated and the residue was purified by flash chromatography (4 g silica gel; 0-100% ethyl acetate, hexane gradient over 14 min., 18 mL/min) to provide (R)—N-(1-(4-carbamoylphenyl)-1-(3-fluoro-5-(1,1,2,2-tetrafluoroethoxy)phenyl)-2-phenylethyl)-4-fluoro-3-(trifluoromethyl)benzamide (Example 320, 13 mg, 65% yield). LCMS: RT=1.81 min [M+H] 631 (Chromolith Performance 18e 4.6×100 mm column, 50-90% methanol, water with 0.1% trifluoroacetic acid gradient over 2 min, 5 mL/min). $^1$H NMR (400 MHz, CDCl$_3$) ppm 7.86 (1H, d, J=4.83 Hz), 7.77 (1H, dt, J=8.35, 2.20 Hz), 7.71 (2H, d, J=8.35 Hz), 7.14-7.25 (3H, m), 7.08 (3H, t, J=7.47 Hz), 6.85-6.90 (3H, m), 6.71 (1H, s), 6.63 (2H, d, J=7.03 Hz), 6.05 (1H, s), 5.88 (1H, tt, J$_{HH}$=2.75 Hz, J$_{HF}$=53 Hz), 5.70 (1H, s), 3.86 (2H, dd, J=37.4, 13.2 Hz).

Example 321

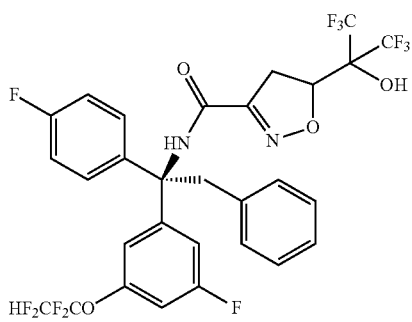

N—((R)-1-(3-fluoro-5-(1,1,2,2-tetrafluoroethoxy)
phenyl)-1-(4-fluorophenyl)-2-phenylethyl)-5-(1,1,1,
3,3,3-hexafluoro-2-hydroxypropan-2-yl)-4,5-dihy-
droisoxazole-3-carboxamide Procedure 137

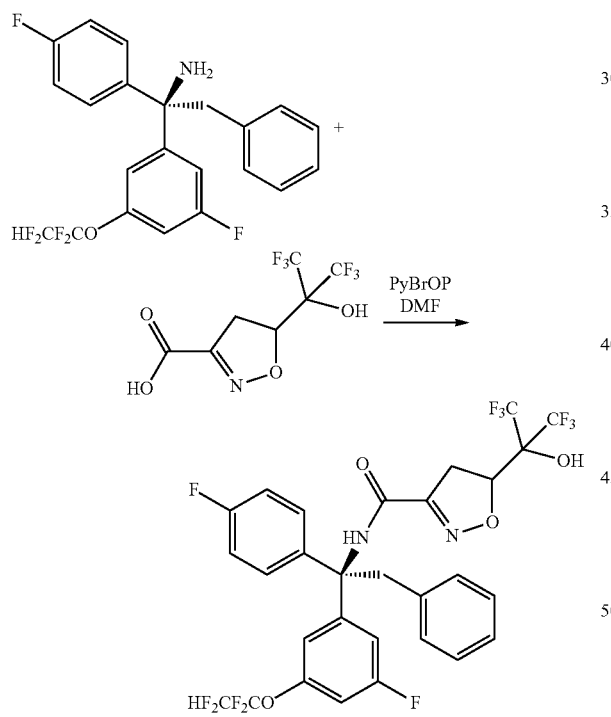

(R)-1-(3-fluoro-5-(1,1,2,2-tetrafluoroethoxy)phenyl)-1-(4-fluorophenyl)-2-phenylethanamine was prepared by the methods described in Procedure 3, 4, 5 and 6. 5-(1,1,1,3,3,3-Hexafluoro-2-hydroxypropan-2-yl)-4,5-dihydroisoxazole-3-carboxylic acid was prepared as described in Journal of Medicinal Chemistry, 2006, 49, 14, 4055. To a solution of (R)-1-(3-fluoro-5-(1,1,2,2-tetrafluoroethoxy)phenyl)-1-(4-fluorophenyl)-2-phenylethanamine (60 mg, 0.14 mmol), in anhydrous DMF (1 mL) was added N-methylmorpholine (26 mg, 0.28 mmol), PyBrOP (73 mg, 0.14 mmol) and 5-(1,1,1,3,3,3-hexafluoro-2-hydroxypropan-2-yl)-4,5-dihydroisoxazole-3-carboxylic acid (40 mg, 0.14 mmol). The resulting solution was stirred at rt for 16 h. The resulting solution was diluted with MeOH (0.5 mL) and purified by preparative HPLC (YMC Sunfire 30×100 mm column, eluting with 10-90% MeOH/H$_2$O over 10 minutes containing 0.1% TFA; 40 mL/min, monitoring at 220 nm). (N—((R)-1-(3-fluoro-5-(1,1,2,2-tetrafluoroethoxy)phenyl)-1-(4-fluorophenyl)-2-phenylethyl)-5-(1,1,1,3,3,3-hexafluoro-2-hydroxypropan-2-yl)-4,5-dihydroisoxazole-3-carboxamide (Example 321, 3 mg, 3% yield) was isolated as a colorless oil at a retention time of 11.29 min. LCMS: RT=2.18 min [M+H] 689.45 (Phenomenex Luna C18 column, 4.6×30 mm eluting with 10-90% MeOH/H$_2$O over 2 minutes containing 0.1% TFA; mL/min, monitoring at 220 nm); HPLC: RT=4.14 min, Purity 100% (Phenomenex Luna C18 column, 4.6×50 mm eluting with 10-90% MeOH/H$_2$O over 4 minutes containing 0.2% PPA; 4 mL/min, monitoring at 220 nm) NMR: 400 MHz $^1$H (CDCl$_3$) Diastereomeric ratio is 1:1; 7.28-6.86 ppm, 24H, m; 6.64 ppm, 1H, m; 6.61 ppm, 1H, m; 5.88 ppm, 2H, t, J=60.0 Hz; 5.16 ppm, 2H, t, J=16.0 Hz; 3.94 ppm, 1H, d, J=12.0 Hz; 3.88 ppm, 1H, d, J=12.0 Hz; 3.75 ppm, 1H, d, J=12.0 Hz; 3.68 ppm, 1H, d, J=12.0 Hz; 3.61 ppm, 2H, m; 3.40 ppm, 1H, dm, J=12.0 Hz; 3.33 ppm, 1H, dm, J=12.0 Hz.

Example 322

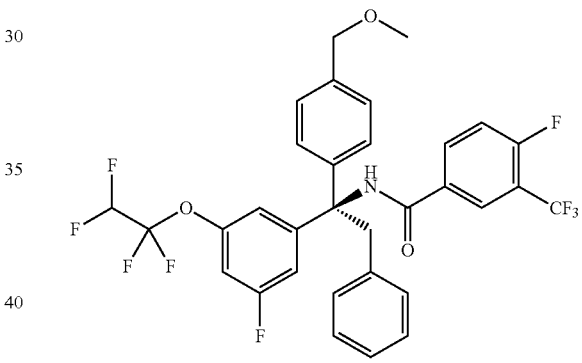

(R)-4-fluoro-N-(1-(3-fluoro-5-(1,1,2,2-tetrafluoroethoxy)phenyl)-1-(4-(methoxymethyl)phenyl)-2-phenylethyl)-3-(trifluoromethyl)benzamide Procedure 138

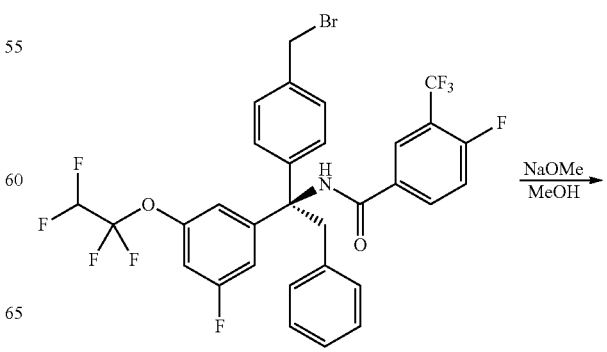

535
-continued

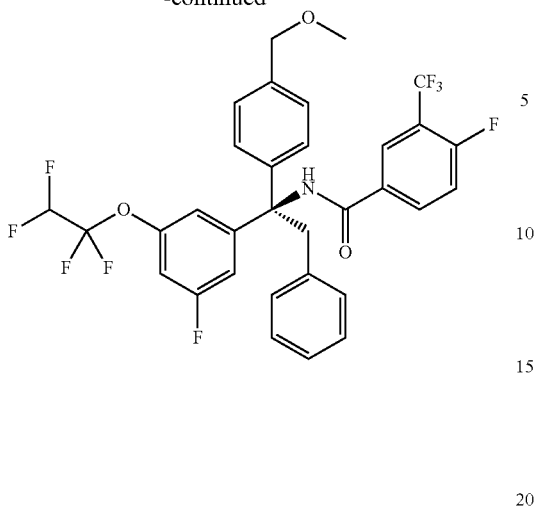

(R)—N-(1-(4-(bromomethyl)phenyl)-1-(3-fluoro-5-(1,1,2,2-tetrafluoroethoxy)phenyl)-2-phenylethyl)-4-fluoro-3-(trifluoromethyl)benzamide (prepared as described in Procedure 3, 4, 5, 6, 7, 56, 57, 100 and 32, 24 mg, 0.035 mmol) was dissolved in 0.5 mL of methanol. To this solution was added sodium methoxide (25% by wt, 0.5 mL) and the reaction mixture was stirred for 40 min. The reaction was quenched with 1.0 M HCl and extracted with ethyl acetate. The organic layer was dried over magnesium sulfate, filtered and concentrated. The resulting oil was purified by flash chromatography (4 g silica gel column, 0-100% EtOAc/hexane gradient over 11 min., flow rate 18 mL/min) to provide (R)-4-fluoro-N-(1-(3-fluoro-5-(1,1,2,2-tetrafluoroethoxy)phenyl)-1-(4-(methoxymethyl)phenyl)-2-phenylethyl)-3-(trifluoromethyl)benzamide (Example 321) as a white solid (15 mg, 67% yield). LC/MS: RT=1.62 min [M+H] 642 (Chromolith Performance 18e 4.6×100 mm column, 50-90% acetonitrile, water with 0.1% trifluoroacetic acid gradient over 2 min, 5 mL/min); $^1$H NMR (400 MHz, CDCl$_3$) ppm 7.91 (1H, d, J=7.15 Hz), 7.77-7.87 (1H, m), 7.08-7.44 (7H, m), 6.97-7.05 (2H, m), 6.92 (1H, d, J=8.79 Hz), 6.66-6.75 (3H, m), 5.87 (1H, tt, $J_{HH}$=2.75 Hz, $J_{HF}$=53 Hz), 4.47 (2H, s), 4.09 (1H, d, J=13.2 Hz), 3.81 (1H, d, J=13.2 Hz), 3.42 (3H, s).

Example 323A

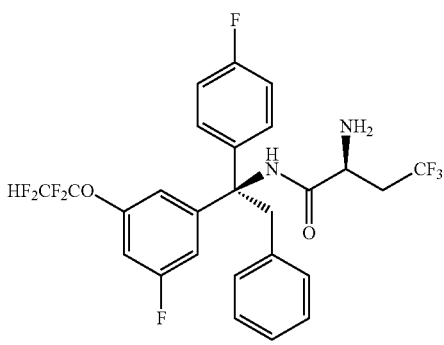

536

(S)-2-amino-4,4,4-trifluoro-N—((R)-1-(3-fluoro-5-(1,1,2,2-tetrafluoroethoxy)phenyl)-1-(4-fluorophenyl)-2-phenylethyl)butanamide Example 323B

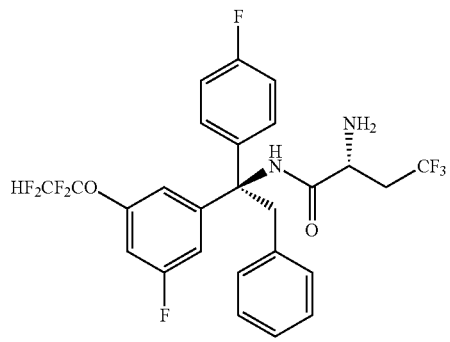

(R)-2-amino-4,4,4-trifluoro-N—((R)-1-(3-fluoro-5-(1,1,2,2-tetrafluoroethoxy)phenyl)-1-(4-fluorophenyl)-2-phenylethyl)butanamide Procedure 139

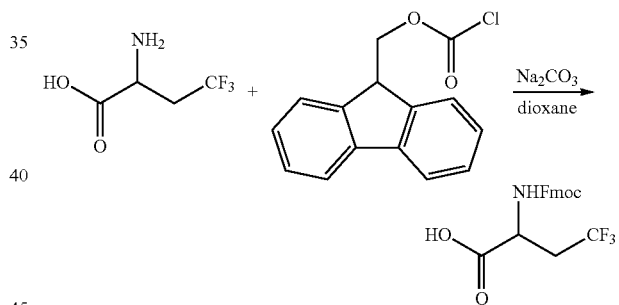

To a solution of 2-amino-4,4,4-trifluorobutanoic acid (239.0 mg, 1.52 mmol)) in dioxane (6 mL) was added 10% Na$_2$CO$_3$, followed by (9H-fluoren-9-yl)methyl carbonochloridate (394.0 mg, 1.52 mmol). The reaction mixture was stirred at 0° C. for 1 h, then at rt for 1 h. The reaction mixture was poured into a mixture of ether and water. The aqueous layer was treated with concentrated HCl, then extracted with 3×EtOAc. The organic layers were combined and dried over MgSO$_4$ and concentrated. The residue was purified by ISCO chromatography (10 g column, eluting with 0-30% EtOAc/hexane containing 0.1% AcOH) to yield (9H-fluoren-9-yl) methyl 1-amino-4,4,4-trifluoro-1-oxobutan-2-ylcarbamate as a white solid (260.0 mg, yield 45%). LCMS: RT=3.06 min [M+H] 380.2 (Phenomenex Luna C18 column, 4.6×50 mm eluting with 10-90% MeOH/H$_2$O over 4 minutes containing 0.1% TFA; 4 mL/min, monitoring at 220 nm).

Procedure 140

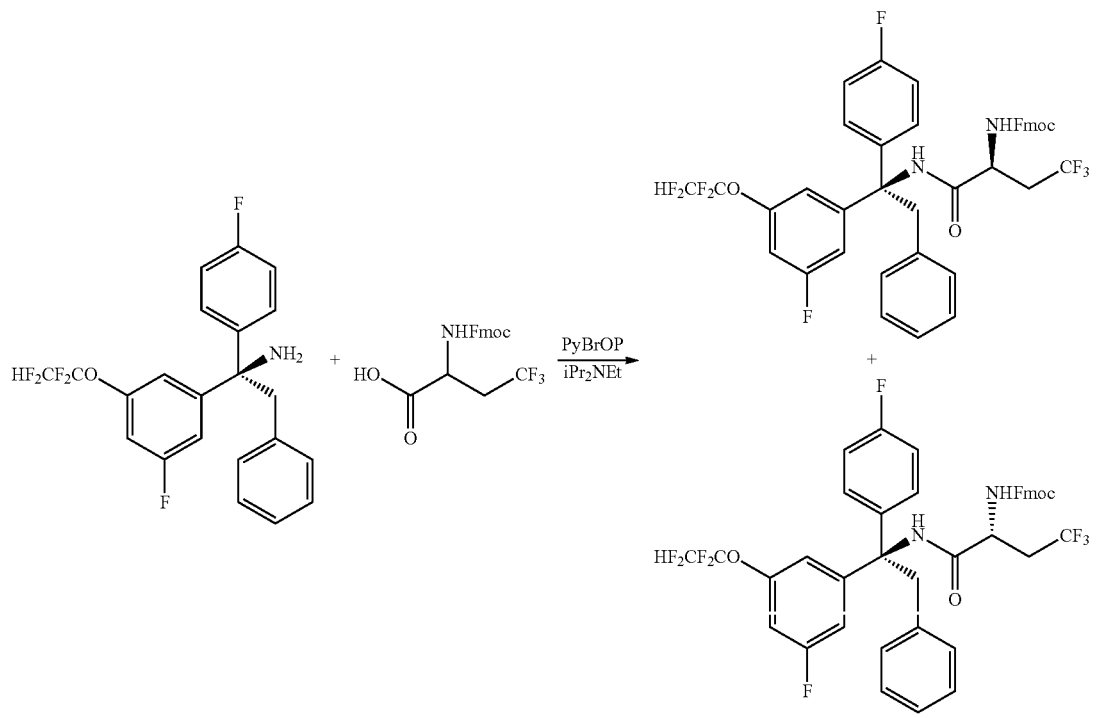

To a solution of (R)-1-(3-fluoro-5-(1,1,2,2-tetrafluoroethoxy)phenyl)-1-(4-fluorophenyl)-2-phenylethanamine (31 mg, 0.07 mmol), prepared as described in Procedure 3, 4, 5 and 6, in DCM (1 mL) was added (9H-fluoren-9-yl)methyl 1-amino-4,4,4-trifluoro-1-oxobutan-2-ylcarbamate (31 mg, 0.08 mmol), followed by PyBrOP and iPr$_2$NEt. The reaction mixture was stirred at rt for 72 h and concentrated. The residue was purified by preparative HPLC (Axia column, 30×100 mm, 60-100% MeOH/H$_2$O with 0.1% TFA over 12 min, flow rate 40 mL/min, monitoring at 220 nm) to yield (9H-fluoren-9-yl)methyl 4,4,4-trifluoro-1-((R)-1-(3-fluoro-5-(1,1,2,2-tetrafluoroethoxy)phenyl)-1-(4-fluorophenyl)-2-phenylethylamino)-1-oxobutan-2-ylcarbamate as white solid (20 mg, 38% yield). LCMS: RT=4.5 min [M+H] 787.3 (Phenomenex Luna C18 column, 4.6×50 mm eluting with 10-90% MeOH/H$_2$O over 4 minutes containing 0.1% TFA; 4 mL/min, monitoring at 220 nm). This diastereomer mixture was separated by Chiralpak AD column eluting with 10% MeOH/EtOH (1:1)/90% heptane with flow rate 20 mL/min. (9H-fluoren-9-yl)methyl (S)-4,4,4-trifluoro-1-((R)-1-(3-fluoro-5-(1,1,2,2-tetrafluoroethoxy)phenyl)-1-(4-fluorophenyl)-2-phenylethylamino)-1-oxobutan-2-ylcarbamate was eluted at a retention time of 8.26 min and isolated as a white solid (10 mg). (9H-fluoren-9-yl)methyl (R)-4,4,4-trifluoro-1-((R)-1-(3-fluoro-5-(1,1,2,2-tetrafluoroethoxy)phenyl)-1-(4-fluorophenyl)-2-phenylethylamino)-1-oxobutan-2-ylcarbamate was eluted at a retention time of 12.97 min and isolated as a white solid (10 mg). The stereochemistry of (9H-fluoren-9-yl)methyl (S)-4,4,4-trifluoro-1-((R)-1-(3-fluoro-5-(1,1,2,2-tetrafluoroethoxy)phenyl)-1-(4-fluorophenyl)-2-phenylethylamino)-1-oxobutan-2-ylcarbamate and (9H-fluoren-9-yl)methyl (R)-4,4,4-trifluoro-1-((R)-1-(3-fluoro-5-(1,1,2,2-tetrafluoroethoxy)phenyl)-1-(4-fluorophenyl)-2-phenylethylamino)-1-oxobutan-2-ylcarbamate was assigned arbitrarily.

Procedure 141

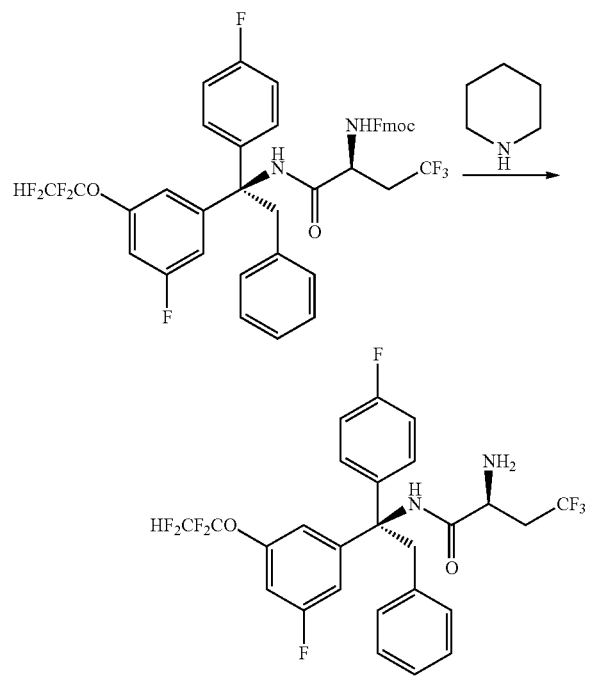

To a solution of (9H-fluoren-9-yl)methyl (S)-4,4,4-trifluoro-1-((R)-1-(3-fluoro-5-(1,1,2,2-tetrafluoroethoxy)phenyl)-1-(4-fluorophenyl)-2-phenylethylamino)-1-oxobutan-2-ylcarbamate (10 mg, 0.01 mmol) in DCM (0.5 mL) was added piperidine (20 mg, 0.1 mmol). The reaction mixture was stirred at rt for 1.5 h and concentrated. The residue was purified by preparative HPLC (Axia column, 30×100 mm, 30-100% MeOH/H$_2$O with 0.1% TFA over 12 min, flow rate 40 mL/min, monitoring at 220 nm) to yield (S)-2-amino-4,4,4-trifluoro-N—((R)-1-(3-fluoro-5-(1,1,2,2-tetrafluoroethoxy)phenyl)-1-(4-fluorophenyl)-2-phenylethyl)butanamide (Example 323A) as a white solid (6 mg, 82% yield). LCMS: RT=3.1 min [M+H] 565.22 (Phenomenex Luna C18 column, 4.6×50 mm eluting with 10-90% MeOH/H$_2$O over 4 minutes containing 0.1% TFA; 4 mL/min, monitoring at 220 nm). $^1$H NMR (400 MHz, CDCl$_3$) δ ppm 8.14 (1H, s), 7.17-7.22 (1H, m), 7.12 (2H, t, J=7.33 Hz), 7.03-7.08 (2H, m), 6.96-7.02 (2H, m), 6.88 (3H, s), 6.59 (2H, d, J=7.07 Hz), 5.85 (1H, t, J=2.53 Hz), 4.09 (1H, s), 3.91 (1H, d, J=13.14 Hz), 3.71 (1H, d, J=13.39 Hz), 2.66 (2H, m). (R)-2-amino-4,4,4-trifluoro-N—((R)-1-(3-fluoro-5-(1,1,2,2-tetrafluoroethoxy)phenyl)-1-(4-fluorophenyl)-2-phenylethyl)butanamide (Example 323B) was prepared in the same method here and isolated as a white solid (6 mg, 82% yield). LCMS: RT=3.1 min [M+H] 565.22 (Phenomenex Luna C18 column, 4.6×50 mm eluting with 10-90% MeOH/H$_2$O over 4 minutes containing 0.1% TFA; 4 mL/min, monitoring at 220 nm). $^1$H NMR (400 MHz, CDCl$_3$) δ ppm 7.80 (1H, s), 7.19 (1H, t, J=7.33 Hz), 7.08-7.15 (4H, m), 6.93-7.00 (2H, m), 6.84-6.92 (2H, m), 6.81 (1H, s), 6.58 (2H, d, J=7.07 Hz), 5.84 (1H, t, J=2.65 Hz), 4.26 (1H, d, J=5.56 Hz), 3.76-3.86 (2H, m), 2.53 (1H, d, J=10.61 Hz), 2.43-2.49 (1H, m). The stereochemistry of (S)-2-amino-4,4,4-trifluoro-N—((R)-1-(3-fluoro-5-(1,1,2,2-tetrafluoroethoxy)phenyl)-1-(4-fluorophenyl)-2-phenylethyl)butanamide (Example 323A) and (R)-2-amino-4,4,4-trifluoro-N—((R)-1-(3-fluoro-5-(1,1,2,2-tetrafluoroethoxy)phenyl)-1-(4-fluorophenyl)-2-phenylethyl)butanamide (Example 323B) was assigned arbitrarily.

Example 324

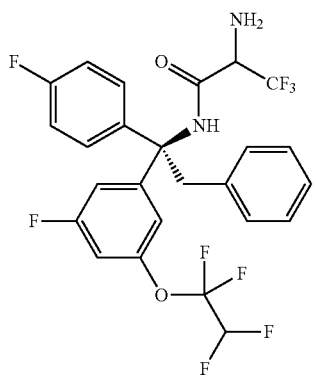 [SMILES: NC(C(=O)N[C@](Cc1ccccc1)(c1ccc(F)cc1)c1cc(F)cc(OC(F)(F)C(F)F)c1)C(F)(F)F]

2-amino-3,3,3-trifluoro-N—((R)-1-(3-fluoro-5-(1,1,2,2-tetrafluoroethoxy)phenyl)-1-(4-fluorophenyl)-2-phenylethyl)propanamide Procedure 142

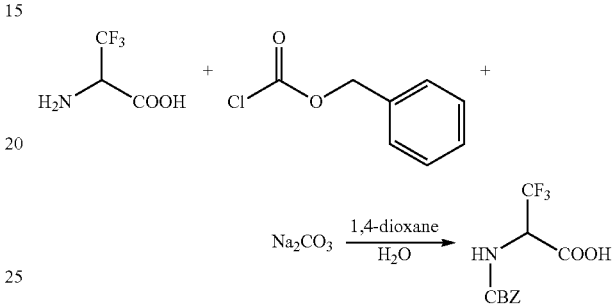

At 0° C. to a solution of 2-amino-3,3,3-difluoropropanoic acid (143 mg, 0.1 mmol) in 1,4-dioxane (1.3 mL) was added 10% aqueous Na$_2$CO$_3$ (2.6 mL), followed by dropwise addition of benzyl carbonochloridate (170 mg, 0.1 mmol) in 1,4-dioxane (2.6 mL). The reaction mixture was stirred at 0° C. for 1 h, then allowed to warm up rt and stirred at rt for 72 h. The reaction mixture was concentrated and the residue was purified by prep HPLC (Phenomenex Luna AXIA 5µ 21.2× 100 mm, 10%-90% ACN/H$_2$O containing 0.1% TFA, flow rate 20 mL/min, gradient time 10 min) to yield 2-(benzyloxycarbonylamino)-3,3,3-trifluoropropanoic acid as a white solid (108 mg, 76% yield). HPLC: RT=2.64 min [M+Na] 300.1 (Phenomenex Luna C18 column, 4.6×50 mm eluting with 10-90% MeOH/H$_2$O over 4 minutes containing 0.1% TFA; 4 mL/min, monitoring at 220 nm); $^1$H NMR (400 MHz, CDCl$_3$) δ ppm 7.12-7.22, m, H, 4.96, s, 2H, 4.92-4.99, m, 1H.

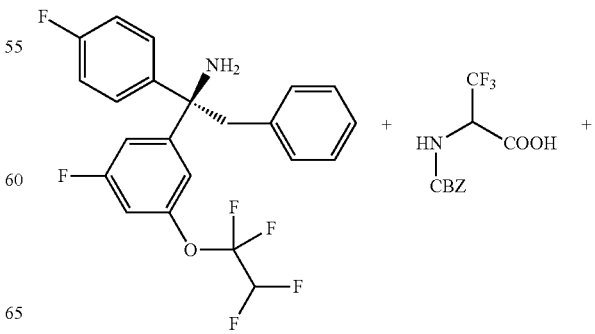

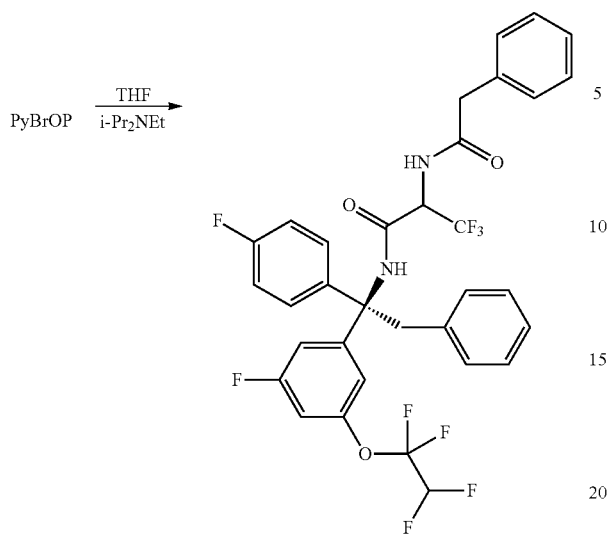
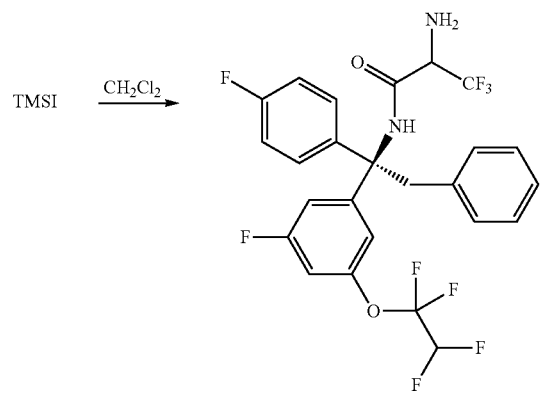

Following Procedure 140, benzyl 1,1,1-trifluoro-3-((R)-1-(3-fluoro-5-(1,1,2,2-tetrafluoroethoxy)phenyl)-1-(4-fluorophenyl)-2-phenylethylamino)-3-oxopropan-2-ylcarbamate was prepared as yellow solid (13 mg, 25% yield). HPLC: RT=4.15 min [M+H] 685.2 (Phenomenex Luna C18 column, 4.6×50 mm eluting with 10-90% MeOH/H$_2$O over 4 minutes containing 0.1% TFA; 4 mL/min, monitoring at 220 nm); $^1$H NMR (400 MHz, CDCl$_3$) δ ppm 7.26-7.51, m, 6H, 7.18-7.23, m, 1H, 6.97-7.15, m, 7H, 6.84-6.93, m, 3H, 6.58-6.61, m, 2H, 5.71-5.98, t, J=34, 1H, 5.73, m, 1H, 5.07-5.11, m, 2H, 4.87, m, 1H, 3.81-3.90, m, 1H, 3.69-3.73, m, 1H.

To a solution of benzyl 1,1,1-trifluoro-3-((R)-1-(3-fluoro-5-(1,1,2,2-tetrafluoroethoxy)phenyl)-1-(4-fluorophenyl)-2-phenylethylamino)-3-oxopropan-2-ylcarbamate (10 mg, 0.014 mmol) in CH$_2$Cl$_2$ (0.5 m) was added TMSI (18 mg, 0.094 mmol). The reaction mixture was sealed and stirred at rt for 20 h. The reaction mixture was concentrated under reduced pressure and the residue was purified by prep HPLC (Phenomenex Luna AXIA 5μ 21.2×100 mm, 10%-90% ACN/H$_2$O containing 0.1% TFA, flow rate 20 mL/min, gradient time 10 min) to yield 2-amino-3,3,3-trifluoro-N—((R)-1-(3-fluoro-5-(1,1,2,2-tetrafluoroethoxy)phenyl)-1-(4-fluorophenyl)-2-phenylethyl)propanamide (Example 324) as a white solid (5 mg, 65% yield). HPLC: RT=1.90 min [M+H] 551.5 (Phenomenex Luna C18 column, 4.6×50 mm eluting with 10-90% MeOH/H$_2$O over 2 minutes containing 0.1% TFA; 5 mL/min, monitoring at 220 nm); $^1$H NMR (400 MHz, CDCl$_3$) δ ppm 7.82-7.85, m, 1H, 7.19-7.23, m, 1H, 7.11-7.17, m, 2H, 7.07-7.11, m, 1H, 6.98-7.03, m, 3H, 6.89-6.93, m, 2H, 6.80-6.86, m, 1H, 6.61-6.64, m, 2H, 5.73-5.99, t, J=52, 1H, 4.00-4.03, J=12, d, 1H, 3.98, m, 1H, 3.63-3.67, d, J=12, 1H;

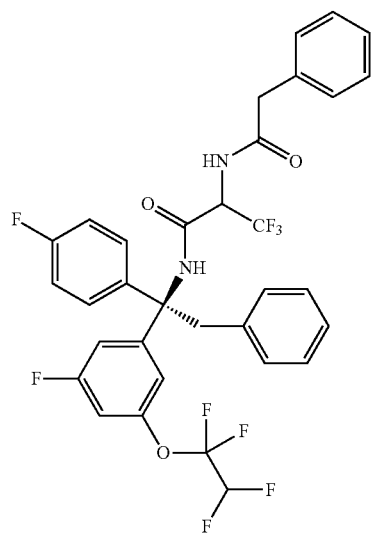

+

Example 325

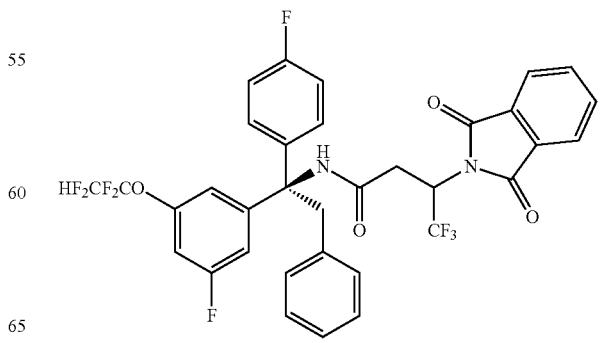

3-(1,3-dioxoisoindolin-2-yl)-4,4,4-trifluoro-N—((R)-1-(3-fluoro-5-(1,1,2,2-tetrafluoroethoxy)phenyl)-1-(4-fluorophenyl)-2-phenylethyl)butanamide Procedure 143

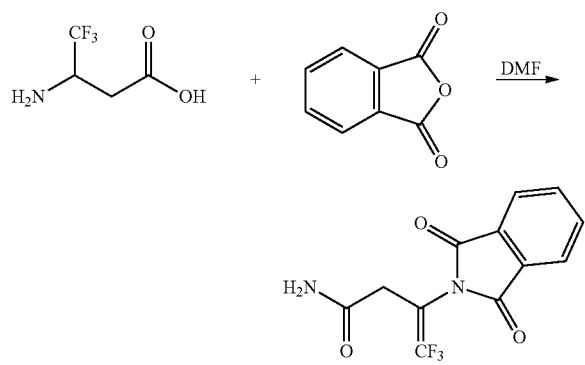

A solution of 3-amino-4,4,4-trifluorobutanoic acid (628 mg, 4 mmol) and isobenzofuran-1,3-dione (592 mg, 4 mmol) in DMF (5 mL) was heated to 140° C. under microwave irradiation for 15 min. The reaction mixture was purified by preparative HPLC (Axia luna column, 30×75 mm, 10-100% ACN/H₂O with 0.1% TFA over 10 min, flow rate 40 mL/min, monitoring at 220 nm) to yield 3-(1,3-dioxoisoindolin-2-yl)-4,4,4-trifluorobutanamide (620 mg, 54% yield). LCMS: RT=1.54 min [M+H] 288.2 (Phenomenex Luna C18 column, 4.6×30 mm eluting with 10-90% MeOH/H₂O over 2 minutes containing 0.1% TFA; 5 mL/min, monitoring at 220 nm).

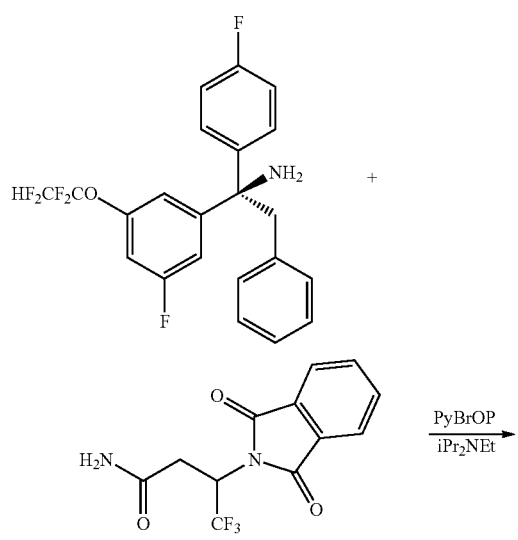

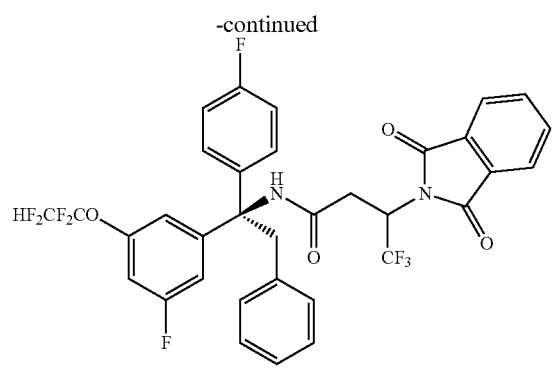

3-(1,3-Dioxoisoindolin-2-yl)-4,4,4-trifluoro-N—((R)-1-(3-fluoro-5-(1,1,2,2-tetrafluoroethoxy)phenyl)-1-(4-fluorophenyl)-2-phenylethyl)butanamide (Example 325) was prepared as white solid (12 mg, 27% yield) as described in Procedure 140. LCMS: RT=3.62 min [M+H] 695.3 (Phenomenex Luna C18 column, 4.6×50 mm eluting with 10-90% MeOH/H₂O over 4 minutes containing 0.1% TFA; 4 mL/min, monitoring at 220 nm). $^1$H NMR (400 MHz, CDCl₃) δ ppm 7.76-7.88 (4H, m), 7.15-7.01 (3H, m), 6.91-6.97 (2H, m), 6.80-6.86 (2H, m), 6.61-6.72 (3H, m), 6.54 (2H, dd, J=13.26, 7.71 Hz), 6.21 (1H, d, J=4.55 Hz), 5.84 (1H, t, J=2.78 Hz), 5.25 (1H, m), 3.87 (1H, d, J=13.14 Hz), 3.71 (1H, ddd, J=15.66, 11.49, 4.42 Hz), 3.62-3.55 (1H, m), 2.85-2.95 (1H, m).

Example 326

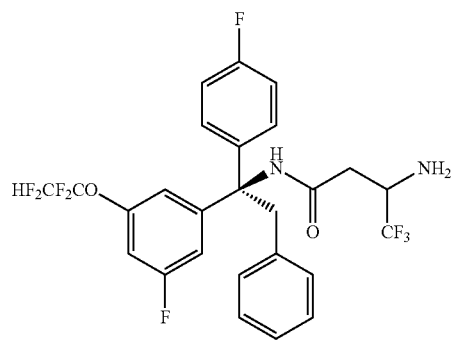

3-amino-4,4,4-trifluoro-N—((R)-1-(3-fluoro-5-(1,1,2,2-tetrafluoroethoxy)phenyl)-1-(4-fluorophenyl)-2-phenylethyl)butanamide Procedure 144

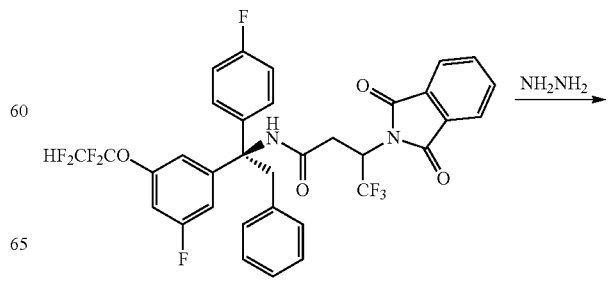

545
-continued

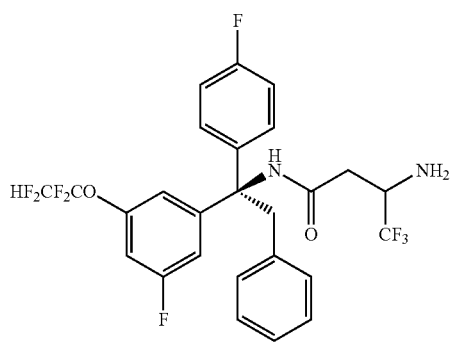

To a solution of 3-(1,3-dioxoisoindolin-2-yl)-4,4,4-trifluoro-N—((R)-1-(3-fluoro-5-(1,1,2,2-tetrafluoroethoxy)phenyl)-1-(4-fluorophenyl)-2-phenylethyl)butanamide (Example 325, 30 mg, 0.04 mmol) in MeOH (1 mL) was added hydrazine (0.03 mL, 1 mmol) and the reaction mixture was heated at 50° C. for 4 h. The reaction mixture was purified by preparative HPLC (Axia luna column, 30×75 mm, 10-100% ACN/$H_2O$ with 0.1% TFA over 10 min, flow rate 40 mL/min, monitoring at 220 nm) to yield 3-amino-4,4,4-trifluoro-N—((R)-1-(3-fluoro-5-(1,1,2,2-tetrafluoroethoxy)phenyl)-1-(4-fluorophenyl)-2-phenylethyl)butanamide (Example 326) as white solid (7 mg, 24% yield). LCMS: RT=3.62 min [M+H] 565.2 (Phenomenex Luna C18 column, 4.6×50 mm eluting with 10-90% MeOH/$H_2O$ over 4 minutes containing 0.1% TFA; 4 mL/min, monitoring at 220 nm). $^1H$ NMR (400 MHz, $CDCl_3$) δ ppm 7.34 (1H, d, J=17.94 Hz), 7.13-7.24 (3H, m), 6.96-7.11 (4H, m), 6.82-6.92 (3H, m), 6.62 (2H, d, J=7.83 Hz), 5.86 (1H, t, J=1.77 Hz), 3.88 (1H, t, J=12.63 Hz), 3.75-3.84 (1H, m), 3.70 (1H, d, J=13.14 Hz), 2.82-2.93 (1H, m), 2.77 (1H, m).

Example 327

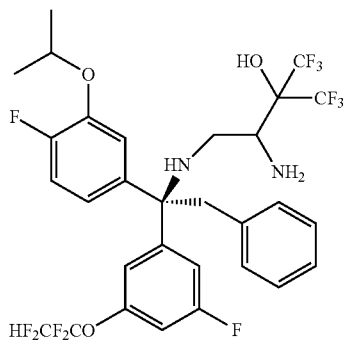

3-amino-1,1,1-trifluoro-4-((R)-1-(4-fluoro-3-isopropoxyphenyl)-1-(3-fluoro-5-(1,1,2,2-tetrafluoroethoxy)phenyl)-2-phenylethylamino)-2-(trifluoromethyl)butan-2-ol Procedure 145

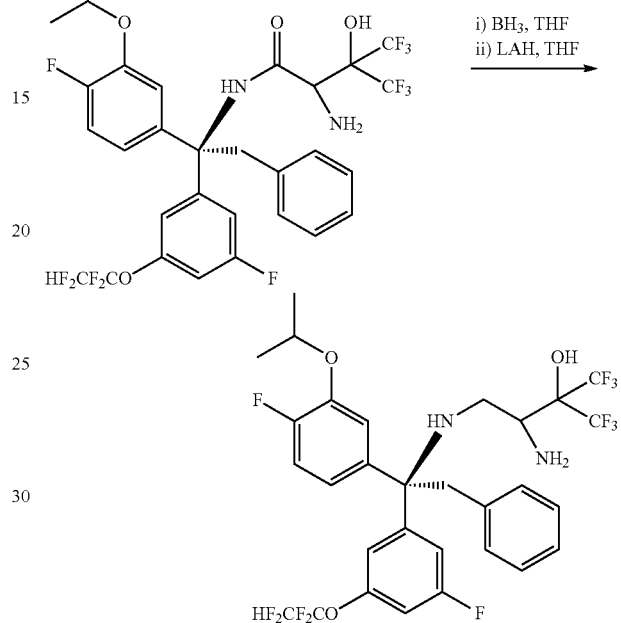

To a solution of 2-amino-4,4,4-trifluoro-N—((R)-1-(4-fluoro-3-isopropoxyphenyl)-1-(3-fluoro-5-(1,1,2,2-tetrafluoroethoxy)phenyl)-2-phenylethyl)-3-hydroxy-3-(trifluoromethyl)butanamide, prepared as described in Example 293, (20 mg, 0.028 mmol) in THF (0.5 mL) was added borane (0.2 mL, 1.0 M solution in THF). After hydrogen evolution ceased, the solution was heated in a sealed microwave vial under microwave irradiation at 100° C. for 5 min. The solvents were removed under a stream of nitrogen then THF (0.5 mL) was added to the residue followed by $BF_3 \cdot Et_2O$ (30 mg, 0.21 mmol) and LAH (0.2 mL, 1.0 M solution in THF). After evolution of hydrogen gas had ceased, the sealed microwave vial was heated at 100° C. for 10 min. The solvents were removed under a stream of nitrogen and the residue dissolved in $NH_4OH$ (ca. 10 mL). LiCl (10%, ca. 10 mL) was added and the aqueous extracted with DCM (3×10 mL). The combined organic portions were concentrated under reduced pressure and purified by preparative TLC (25×25 mm, silica gel 1 mm elution with hexane:EtOAc 4:1). 3-Amino-1,1,1-trifluoro-4-((R)-1-(4-fluoro-3-isopropoxyphenyl)-1-(3-fluoro-5-(1,1,2,2-tetrafluoroethoxy)phenyl)-2-phenylamino)-2-(trifluoromethyl)butan-2-ol (Example 327, 5 mg, 20% yield) was isolated as a colorless oil at $R_f$ of 0.5. LCMS: RT=3.88 min [M+H] 693.1 (Phenomenex Luna C18 column, 4.6×50 mm eluting with 10-90% MeOH/$H_2O$ over 4 minutes containing 0.1% TFA; 5 mL/min, monitoring at 220 nm); HPLC: RT=3.88 min, Purity 91% (Phenomenex Luna C18 column, 4.6×50 mm eluting with 10-90% MeOH/$H_2O$ over 4 minutes containing 0.2% PPA; 4 mL/min, monitoring at 220 nm) NMR: 400 MHz $^1H$ ($CDCl_3$) 7.15 ppm, 3H, m; 7.05 ppm, 1H, m; 6.86 ppm, 2H, d, J=8.0 Hz; 6.83 ppm, 3H, m; 6.61 ppm, 2H, d, J=8.0 Hz; 5.87 ppm, 1H, t, t, J=52.0 Hz and J=4.0 Hz; 4.41 ppm, 1H, sept, J=8.0 Hz; 3.57 ppm, 1H, d, J=12.0 Hz; 3.48 ppm, 1H, d, J=12.0 Hz; 2.99 ppm, 2H, m; 2.53 ppm, 1H, brt; 1.27 ppm, 3H, d, J=8.0 Hz; 1.25 ppm, 3H, d, J=8.0 Hz.

Example 328

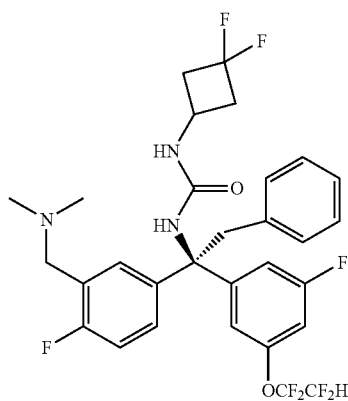

(R)-1-(3,3-difluorocyclobutyl)-3-(1-(3-((dimethylamino)methyl)-4-fluorophenyl)-1-(3-fluoro-5-(1,1,2,2-tetrafluoroethoxy)phenyl)-2-phenylethyl)urea Procedure 146

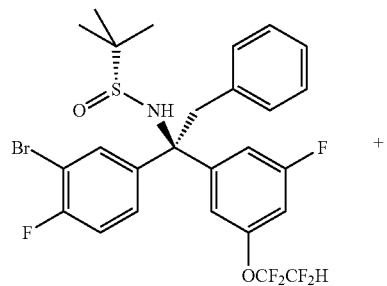

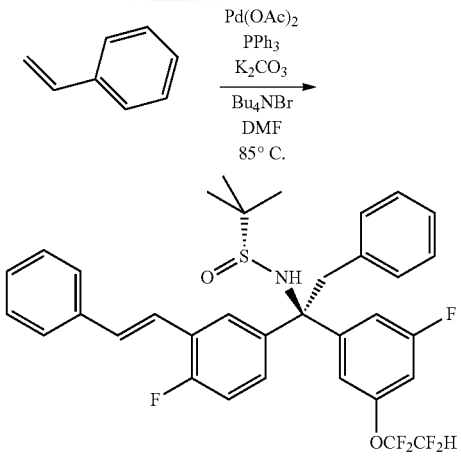

Following Procedure 3, 62, 5 and 6, N-(1-(3-bromo-4-fluorophenyl)-1-(3-fluoro-5-(1,1,2,2-tetrafluoroethoxy)phenyl)-2-phenylethyl)-2-methylpropane-2-sulfinamide was prepared and the diastereomer mixture was separated by chiral preparative HPLC (Chiralpak AD column, 5×50 cm isocratic elution with 60% IPA/heptane, 50 mL/min, monitoring at 254 nm) to yield (R)—N—((S)-1-(3-bromo-4-fluorophenyl)-1-(3-fluoro-5-(1,1,2,2-tetrafluoroethoxy)phenyl)-2-phenylethyl)-2-methylpropane-2-sulfinamide as a white foam (3.92 g, 33% yield) with a retention time of 40 min.

To a suspension of Pd(OAc)$_2$ (9 mg, 0.04 mmol) and PPh$_3$ (2 mg, 0.008 mmol) in DMF was added Bu$_4$NBr (265 mg, 0.8 mmol), (R)—N—((S)-1-(3-bromo-4-fluorophenyl)-1-(3-fluoro-5-(1,1,2,2-tetrafluoroethoxy)phenyl)-2-phenylethyl)-2-methylpropane-2-sulfinamide, prepared as described in Procedure 62, (500 mg, 0.8 mmol), styrene (137 mg, 1.3 mmol) and K$_2$CO$_3$ (136 mg, 1.0 mmol). The reaction mixture was degassed and backfilled with argon several times. The reaction mixture was heated at 85° C. for 16 h. The reaction mixture was then poured into sat. NH$_4$Cl and the aqueous phase was extracted with EtOAc. The combined organic portions were dried over Na$_2$SO$_4$, filtered and concentrated under reduced pressure. The residue was purified by ISCO chromatography (12 g column, 0-30% EtOAc/hexane) to yield (R)—N—((R)-1-(4-fluoro-3-styrylphenyl)-1-(3-fluoro-5-(1,1,2,2-tetrafluoroethoxy)phenyl)-2-phenylethyl)-2-methylpropane-2-sulfinamide (119 mg, 23% yield). LCMS: RT=4.62 min [M+H] 632 (Phenomenex Luna C18, 50×4.6 mm, 10%-90% H$_2$O/ACN with 0.1% TFA, 4 min gradient, flow rate 4 mL/min, monitoring at 220 nm).

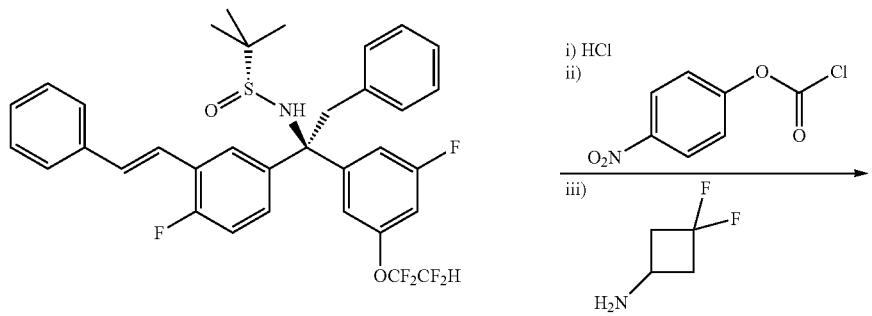

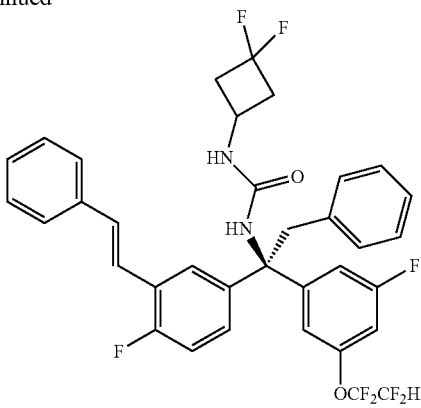

Using the methods described in Procedure 6 and 12, (R,E)-1-(3,3-difluorocyclobutyl)-3-(1-(4-fluoro-3-styrylphenyl)-1-(3-fluoro-5-(1,1,2,2-tetrafluoroethoxy)phenyl)-2-phenylethyl)urea was prepared as a clear oil (170 mg, 57% yield). LCMS: RT=4.19 min [M+H] 661 (Phenomenex Luna C18, 50×4.6 mm, 10%-90% H$_2$O/ACN with 0.1% TFA, 4 min gradient, flow rate 4 mL/min, monitoring at 220 nm).

Procedure 147 resulting yellow solution for 10 min. The reaction solvent was removed and the residue was purified by ISCO chromatography (12 g column, 0-30% EtOAc/hexane) to yield (R)-1-(3,3-difluorocyclobutyl)-3-(1-(4-fluoro-3-formylphenyl)-1-(3-fluoro-5-(1,1,2,2-tetrafluoroethoxy)phenyl)-2-phenylethyl)urea as a colorless oil (106 mg, 23% yield). $^1$H NMR (400 MHz, CDCl$_3$) δ ppm 10.22 (s, 1H), 8.06 (m, 1H), 7.67 (dd, J=6.19, 2.65 Hz, 1H), 7.16 (m, 4H), 6.85 (m, 3H), 6.69 (m, 3H), 5.85 (m, 1H), 5.40 (d, J=6.57 Hz, 1H), 4.00 (m, 1H), 2.90 (m, 2H).

Procedure 148

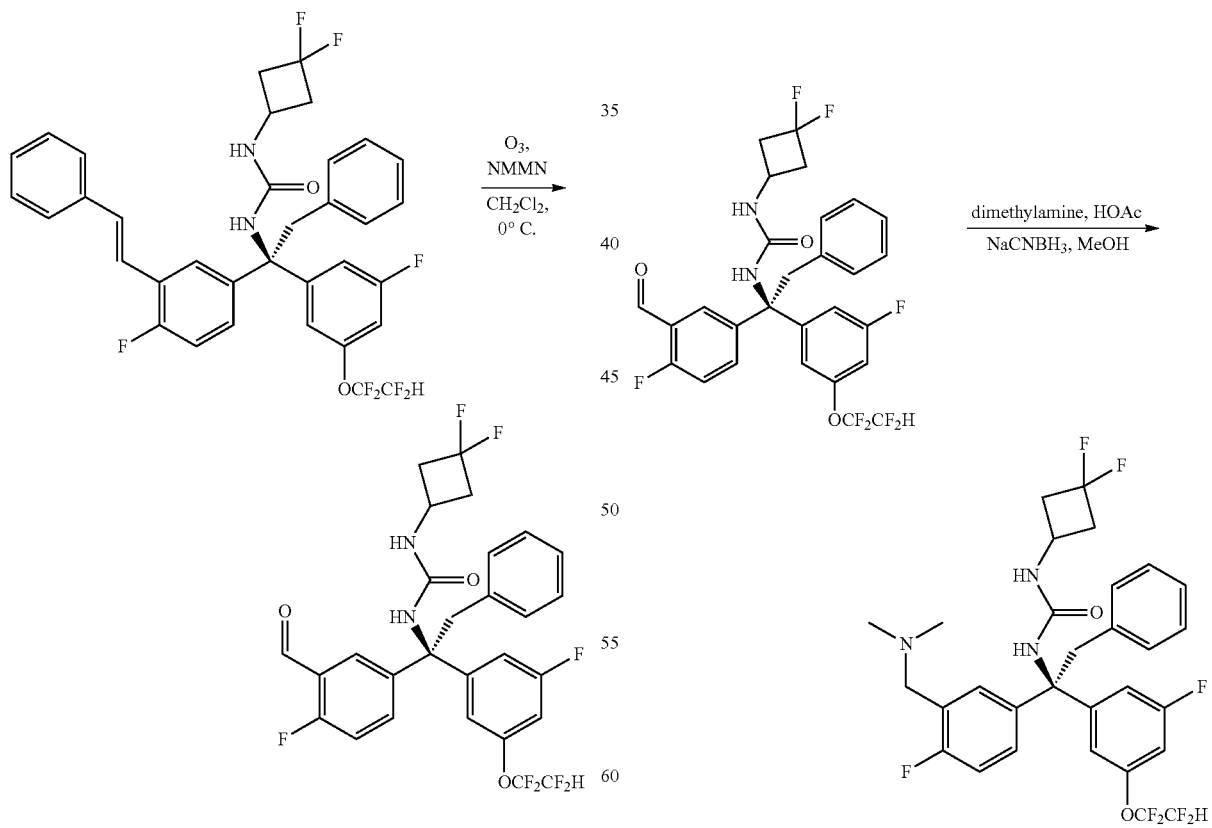

To a solution of (R,E)-1-(3,3-difluorocyclobutyl)-3-(1-(4-fluoro-3-styrylphenyl)-1-(3-fluoro-5-(1,1,2,2-tetrafluoroethoxy)phenyl)-2-phenylethyl)urea (509 mg, 0.8 mmol) in DCM (10 ml) at 0° C. was added 4-methylmorpholine N-oxide (104 mg, 0.8 mmol). Ozone was bubbled through the To a solution of (R)-1-(3,3-difluorocyclobutyl)-3-(1-(4-fluoro-3-formylphenyl)-1-(3-fluoro-5-(1,1,2,2-tetrafluoroethoxy)phenyl)-2-phenylethyl)urea (20 mg, 0.03 mmol) in MeOH (2 mL) was added NHMe$_2$ (0.009 mL) and a drop of acetic acid. The reaction mixture was stirred at rt for 30 min, followed by addition of NaCNBH$_3$ (2 mg, 0.03 mmol). The reaction mixture was stirred at rt for 1 h. The solvent was removed under reduced pressure and the residue was partitioned between sat. NaHCO$_3$ and EtOAc. The organic phase was concentrated and purified by prep HPLC (Phemomenex Luna 5u C18 Axia column, 21×100 mm, 10%-90% H$_2$O/ACN with 0.1% TFA/, monitoring at 220 nm) to yield (R)-1-(3,3-difluorocyclobutyl)-3-(1-(3-((dimethylamino)methyl)-4-fluorophenyl)-1-(3-fluoro-5-(1,1,2,2-tetrafluoroethoxy)phenyl)-2-phenylethyl)urea (Example 328, 8 mg, 44% yield). $^1$H NMR (400 MHz, CDCl$_3$) δ ppm 7.28 (d, J=2.27 Hz, 1H), 7.09 (m, 7H), 6.88 (d, J=8.84 Hz, 1H), 6.63 (d, J=7.07 Hz, 2H), 6.51 (br. s., 1H), 5.88 (m, 1H), 4.34 (d, J=12.63 Hz, 1H), 4.10 (m, 2H), 3.87 (m, 1H), 3.31 (d, J=12.63 Hz, 2H), 2.92 (m, 3H), 2.74 (d, J=2.78 Hz, 3H), 2.70 (d, J=3.28 Hz, 3H), 2.46 (m, 2H).

Example 329A

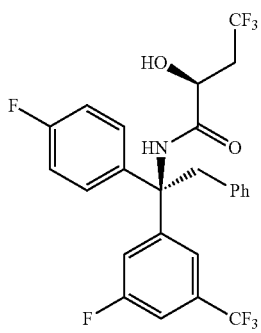 [SMILES: O=C(N[C@](Cc1ccccc1)(c1ccc(F)cc1)c1cc(F)cc(C(F)(F)F)c1)[C@@H](O)CC(F)(F)F]

(S)-4,4,4-trifluoro-N—((R)-1-(3-fluoro-5-(trifluoromethyl)phenyl)-1-(4-fluorophenyl)-2-phenylethyl)-2-hydroxybutanamide Example 329B

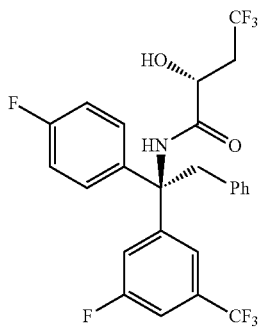 [SMILES: O=C(N[C@](Cc1ccccc1)(c1ccc(F)cc1)c1cc(F)cc(C(F)(F)F)c1)[C@H](O)CC(F)(F)F]

(R)-4,4,4-trifluoro-N—((R)-1-(3-fluoro-5-(trifluoromethyl)phenyl)-1-(4-fluorophenyl)-2-phenylethyl)-2-hydroxybutanamide Procedure 149

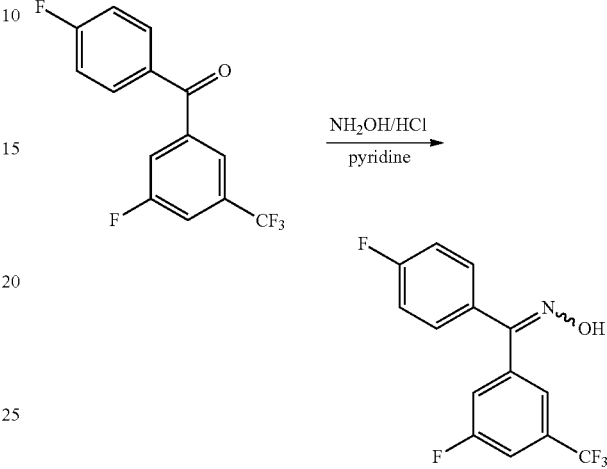

To a solution of (3-fluoro-5-(trifluoromethyl)phenyl)(4-fluorophenyl)methanone, prepared as described in Procedure 4, (860 mg, 3.0 mmol) in pyridine (6 mL) was added hydroxylamine hydrochloride (830 mg, 12.0 mmol) and the reaction mixture was heated at 100° C. for 2 h. The reaction mixture was concentrated under reduced pressure and the residue was dissolved in EtOAc (50 mL), washed with 1 N HCl (2×20 mL), water (20 mL) and sat. NaCl (20 mL), then dried over MgSO$_4$, filtered and concentrated under reduced pressure to yield (3-fluoro-5-(trifluoromethyl)phenyl)(4-fluorophenyl)methanone oxime (912 mg, 100% yield) as a white solid. TLC (30% EtOAc/hexane) shows two spots, the cis and trans isomers of (3-fluoro-5-(trifluoromethyl)phenyl)(4-fluorophenyl)methanone oxime, that were not separated. LCMS: RT=1.59 min [M+H] 302.1 (2 min Phenomenex Luna C18 column, 4.6×30 mm eluting with 10-90% acetonitrile/H$_2$O over 2 minutes containing 0.1% TFA; 5 mL/min, monitoring at 220 nm).

Procedure 150

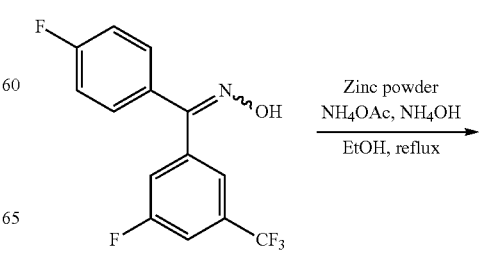

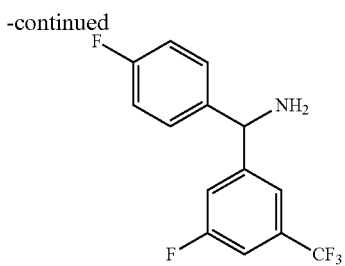

To a suspension of (3-fluoro-5-(trifluoromethyl)phenyl)(4-fluorophenyl)methanone oxime (904 mg, 3.0 mmol) in EtOH (3 mL) and conc. $NH_4OH$ (15 mL) was added ammonium acetate (120 mg, 1.6 mmol) followed by zinc powder (1.05 g, 16.2 mmol) and the reaction mixture was heated at reflux for 2 h. The reaction mixture was allowed to cool to rt then filtered. The filtered solid was washed with 10 N NaOH (15 mL) and EtOAc (15 mL). The combined filtrate was extracted with EtOAc (2×30 mL). The combined organic fractions were washed with sat. NaCl (2×10 mL) then dried over $MgSO_4$, filtered and concentrated under reduced pressure to yield (3-fluoro-5-(trifluoromethyl)phenyl)(4-fluorophenyl)methanamine (804 mg, 93% yield) as a clear, colorless oil. LCMS: RT=0.96 min [M−$NH_2$] 271.0 (2 min Phenomenex Luna C18 column, 4.6×30 mm eluting with 10-90% acetonitrile/$H_2O$ over 2 minutes containing 0.1% TFA; 5 mL/min, monitoring at 220 nm); NMR: 400 MHz $^1H$ ($CDCl_3$) δ ppm 1.68 (bs, 2H), 5.25 (s, 1H), 7.03 (t, J=8.57 Hz, 2H), 7.19 (d, J=7.91 Hz, 1H), 7.29-7.35 (m, 3H), 7.48 (s, 1H).

Procedure 151

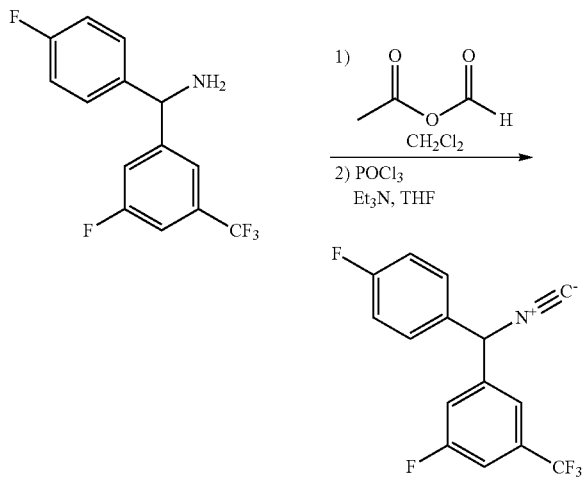

To a solution of (3-fluoro-5-(trifluoromethyl)phenyl)(4-fluorophenyl)methanamine (315 mg, 1.1 mmol) in $CH_2Cl_2$ (2 mL) at 0° C. was added acetic formic anhydride (314 uL, formed by heating a 2:1 v/v ratio of acetic anhydride and formic acid at 60° C. for 2 h). The reaction mixture was allowed to warm to room temperature and stirred for 0.5 h. The reaction mixture was concentrated under reduced pressure and the residue was purified on a 40 g column of silica gel, eluting with 0 to 100% EtOAc/hexane, to give N-((3-fluoro-5-(trifluoromethyl)phenyl)(4-fluorophenyl)methyl)formamide (327 mg, 94% yield) as a clear, viscous oil. LCMS: RT=1.37 min [M+H] 316.1 (2 min Phenomenex Luna C18 column, 4.6×30 mm eluting with 10-90% acetonitrile/$H_2O$ over 2 minutes containing 0.1% TFA; 5 mL/min, monitoring at 220 nm); NMR: 400 MHz $^1H$ ($CDCl_3$) δ ppm 6.13 (bs, 1H), 6.34 (d, J=7.47 Hz, 1H), 7.05-7.20 (m, 5H), 7.27-7.34 (m, 2H), 8.35 (s, 1H). To a solution of N-((3-fluoro-5-(trifluoromethyl)phenyl)(4-fluorophenyl)methyl)formamide (327 mg, 1.04 mmol) in THF (5 mL) at 0° C. was added $Et_3N$ (0.79 mL, 5.7 mmol) followed by phosphorous oxychloride (0.125, 1.35 mmol). The reaction mixture was allowed to warm to room temperature and stirred for 16 h. The reaction mixture was diluted with ice-water (25 mL) and extracted with $Et_2O$ (3×20 mL). The combined organic layers were washed with sat. NaCl (20 mL), dried over anhydrous $Na_2SO_4$, the filtered through basic alumina. The filtrate was concentrated to give 1-fluoro-3-((4-fluorophenyl)(isocyano)methyl)-5-(trifluoromethyl)benzene (268 mg, 93% yield) as a pale brown oil. LCMS: RT=1.71 min [M−NC] 271.0 (2 min Phenomenex Luna C18 column, 4.6×30 mm eluting with 10-90% acetonitrile/$H_2O$ over 2 minutes containing 0.1% TFA; 5 mL/min, monitoring at 220 nm); IR $v_{max}$ $cm^{-1}$ neat: 2139 (N≡C); NMR: 500 MHz $^1H$ ($CDCl_3$) δ ppm 5.94 (s, 1H), 7.12 (t, J=8.52 Hz, 2H), 7.25-7.29 (m, 1H), 7.30-7.35 (m, 3H), 7.41 (s, 1H).

Procedure 152

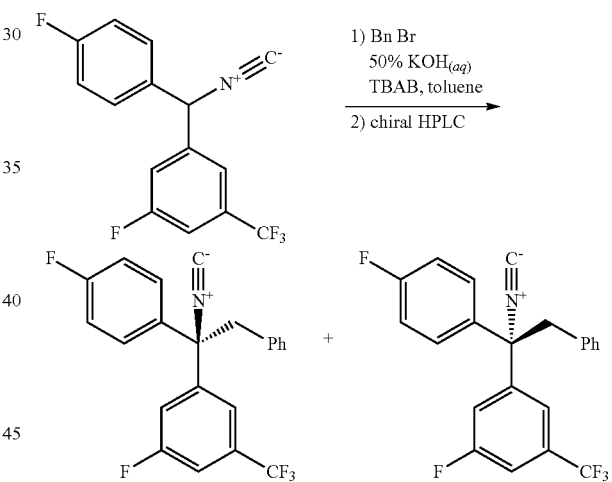

To a solution of 1-fluoro-3-((4-fluorophenyl)(isocyano)methyl)-5-(trifluoromethyl)benzene (234 mg, 0.79 mmol) in toluene (8 mL) was added tetrabutylammonium bromide (75 mg, 0.23 mmol) and benzyl bromide (0.185 mL, 1.56 mmol) followed by 50% KOH(aq) (2.5 mL). The reaction mixture was vigorously stirred for 3 minutes. The reaction mixture was transferred to a separatory funnel and washed with $H_2O$ (2.5 mL). The organic fraction was dried over $Na_2SO_4$, filtered through a pad of basic alumina and concentrated under reduced pressure. The residue was purified by chiral prep HPLC (Chiralcel OD-H column, 20×250 mm isocratic elution with isopropyl alcohol (10%) and heptane, 20 mL/min, monitoring at 254 nm) to give (R)-1-fluoro-3-(1-(4-fluorophenyl)-1-isocyano-2-phenylethyl)-5-(trifluoromethyl)benzene (RT=6.2 minutes, 128 mg, 42% yield) and (S)-1-fluoro-3-(1-(4-fluorophenyl)-1-isocyano-2-phenylethyl)-5-(trifluoromethyl)benzene (RT=7.8 minutes, 128 mg, 42% yield) as clear colorless oils. LCMS: RT=1.94 min [M−NC] 361.1 (2 min Phenomenex Luna C18 column, 4.6×30 mm eluting with 10-90% acetonitrile/H$_2$O over 2 minutes containing 0.1% TFA; 5 mL/min, monitoring at 220 nm); NMR: 400 MHz $^1$H (CDCl$_3$) δ ppm 3.61 (d, J=13.18 Hz, 1H), 3.67 (d, J=13.18 Hz, 1H), 6.83 (d, J=7.47 Hz, 2H), 7.08 (t, J=8.57 Hz, 2H), 7.17-7.34 (m, 8H).

The reaction could be run in 16% ee of the (R) isomer by substituting N-benzylcinchoninium chloride in place of tetrabutylammonium bromide and running the reaction at 0° C. for 1 h.

Procedure 153

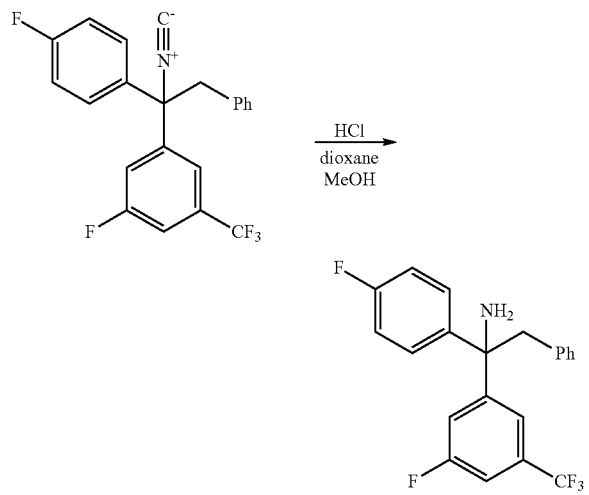

To a solution of 1-fluoro-3-(1-(4-fluorophenyl)-1-isocyano-2-phenylethyl)-5-(trifluoromethyl)benzene (20 mg, 0.052 mmol) in MeOH (0.4 mL) was added 4 N HCl in dioxane (0.3 mL) and the reaction mixture was stirred for 3 minutes. The reaction solvent was evaporated under a stream of nitrogen. The residue was diluted with 1 N NaOH (5 mL) and the aqueous portion was extracted with Et$_2$O (3×5 mL). The combined organic fractions were washed with sat. NaCl (5 mL), dried over Na$_2$SO$_4$, filtered and evaporated under vacuum to yield 1-(3-fluoro-5-(trifluoromethyl)phenyl)-1-(4-fluorophenyl)-2-phenylethanamine (19 mg, 97% yield) as a clear glass.

Procedure 154

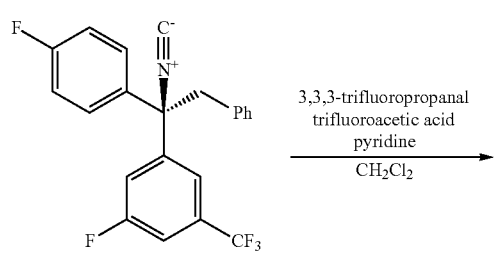

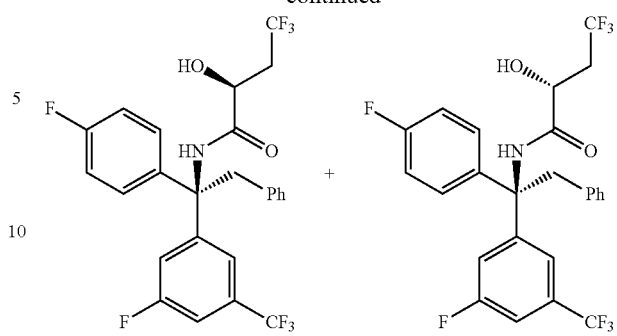

To a solution of (R)-1-fluoro-3-(1-(4-fluorophenyl)-1-isocyano-2-phenylethyl)-5-(trifluoromethyl)benzene (22 mg, 0.057 mmol) in CH$_2$Cl$_2$ (0.10 mL) was added 3,3,3-trifluoropropanal (0.010 mL, 0.11 mmol) and pyridine (0.018 mL, 0.23 mmol) followed by trifluoroacetic acid (0.009 mL, 0.11 mmol). The reaction mixture was heated at 40° C. for 4 h. Additional 3,3,3-trifluoropropanal (0.010 mL, 0.11 mmol) was added and heating at 40° C. for was continued for 2 h. The reaction mixture was allowed to cool to room temperature and the solvent was removed under a stream of nitrogen. The residue was purified by prep TLC plate, eluting with 40% Et$_2$O/hexane, to yield (S)-4,4,4-trifluoro-N—((R)-1-(3-fluoro-5-(trifluoromethyl)phenyl)-1-(4-fluorophenyl)-2-phenylethyl)-2-hydroxybutanamide (Example 329A, 11 mg, 36% yield) and (R)-4,4,4-trifluoro-N—((R)-1-(3-fluoro-5-(trifluoromethyl)phenyl)-1-(4-fluorophenyl)-2-phenylethyl)-2-hydroxybutanamide (Example 329B, 11 mg, 36% yield) as clear colorless oils. (S)-4,4,4-trifluoro-N—((R)-1-(3-fluoro-5-(trifluoromethyl)phenyl)-1-(4-fluorophenyl)-2-phenylethyl)-2-hydroxybutanamide (Example 329A): LCMS: RT=1.81 min [M+H] 518.2 (2 min Phenomenex Luna C18 column, 4.6×30 mm eluting with 10-90% acetonitrile/H$_2$O over 2 minutes containing 0.1% TFA; 5 mL/min, monitoring at 220 nm); NMR: 400 MHz $^1$H (CDCl$_3$) δ ppm 2.24-2.36 (m, 1H) 2.81-2.91 (m, 2H), 3.74 (d, J=13.18 Hz, 1H), 3.99 (d, J=13.18 Hz, 1H), 4.43 (dd, J=10.11, 3.52 Hz, 1H), 6.60 (d, J=7.47 Hz, 2H), 6.99-7.07 (m, 4H), 7.12-7.28 (m, 6H), 7.70 (s, 1H). (R)-4,4,4-trifluoro-N—((R)-1-(3-fluoro-5-(trifluoromethyl)phenyl)-1-(4-fluorophenyl)-2-phenylethyl)-2-hydroxybutanamide (Example 329B): LCMS: RT=1.82 min [M+H] 518.2 (2 min Phenomenex Luna C18 column, 4.6×30 mm eluting with 10-90% acetonitrile/H$_2$O over 2 minutes containing 0.1% TFA; 5 mL/min, monitoring at 220 nm); NMR: 400 MHz $^1$H (CDCl$_3$) δ ppm 2.23-2.35 (m, 1H), 2.77-2.88 (m, 2H), 3.73 (d, J=12.75 Hz, 1H), 3.99 (d, J=12.74 Hz, 1H), 4.45 (dd, J=8.35, 3.95 Hz, 1H), 6.61 (d, J=7.47 Hz, 2H), 6.98-7.04 (m, 4H), 7.16-7.28 (m, 6H), 7.69 (s, 1H). The stereochemistry of (S)-4,4,4-trifluoro-N—((R)-1-(3-fluoro-5-(trifluoromethyl)phenyl)-1-(4-fluorophenyl)-2-phenylethyl)-2-hydroxybutanamide (Example 329A) and (R)-4,4,4-trifluoro-N—((R)-1-(3-fluoro-5-(trifluoromethyl)phenyl)-1-(4-fluorophenyl)-2-phenylethyl)-2-hydroxybutanamide (Example 329B) was assigned arbitrarily.

Example 330

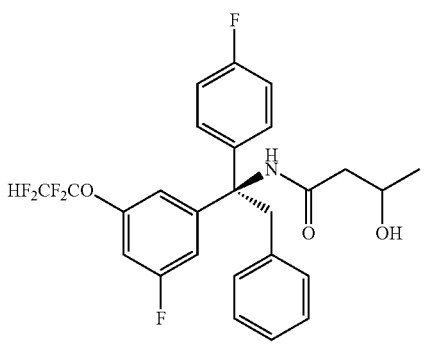

N—((R)-1-(3-fluoro-5-(1,1,2,2-tetrafluoroethoxy)phenyl)-1-(4-fluorophenyl)-2-phenylethyl)-3-hydroxybutanamide Procedure 155

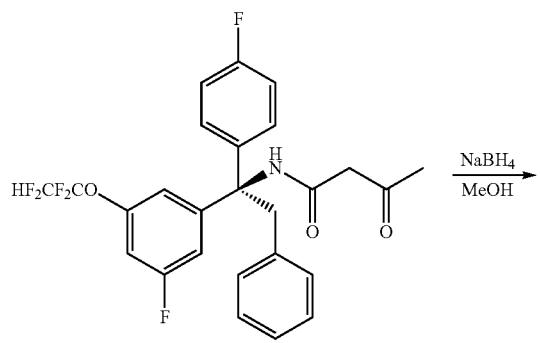

To a solution of (R)—N-(1-(3-fluoro-5-(1,1,2,2-tetrafluoroethoxy)phenyl)-1-(4-fluorophenyl)-2-phenylethyl)-3-oxobutanamide (Example 251, 51 mg, 0.1 mmol), in MeOH (1 mL) was added NaBH₄ (10 mL, 0.26 mmol). The reaction mixture was stirred at rt for 1 h and concentrated under reduced pressure. The residue was purified by preparative HPLC (Axia luna column, 30×100 mm, 40-100% MeOH/H₂O with 0.1% TFA over 10 min, flow rate 40 mL/min, monitoring at 220 nm) to yield N—((R)-1-(3-fluoro-5-(1,1,2,2-tetrafluoroethoxy)phenyl)-1-(4-fluorophenyl)-2-phenylethyl)-3-hydroxybutanamide (Example 330) as a pale yellow oil (28 mg, 55% yield). LCMS: RT=2.66 min [M+H] 512.2 (Phenomenex Luna C18 column, 4.6×50 mm eluting with 10-90% MeOH/H₂O over 4 minutes containing 0.1% TFA; 4 mL/min, monitoring at 220 nm). $^1$H NMR (400 MHz, CDCl₃) δ ppm 7.13-7.23 (3H, m), 7.02-7.08 (2H, m, J=4.96, 4.56, 4.56, 2.43, 2.43 Hz), 6.96-7.02 (2H, m), 6.85-6.93 (4H, m), 6.67 (2H, d, J=7.07 Hz), 5.87 (1H, t, J=2.78 Hz), 4.10-4.20 (1H, m), 3.95 (1H, dd, J=12.76, 10.74 Hz), 3.73 (1H, dd, J=12.76, 10.74 Hz), 2.32-2.38 (2H, m), 1.22 (3H, d, J=6.32 Hz).

Example 331

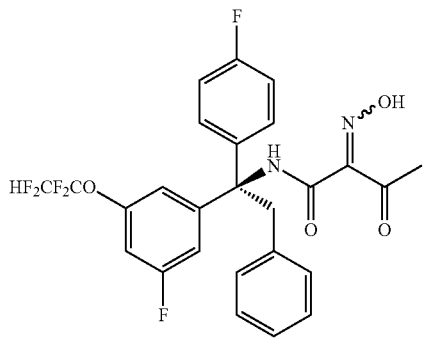

(R)—N-(1-(3-fluoro-5-(1,1,2,2-tetrafluoroethoxy)phenyl)-1-(4-fluorophenyl)-2-phenylethyl)-2-(hydroxyimino)-3-oxobutanamide Procedure 156

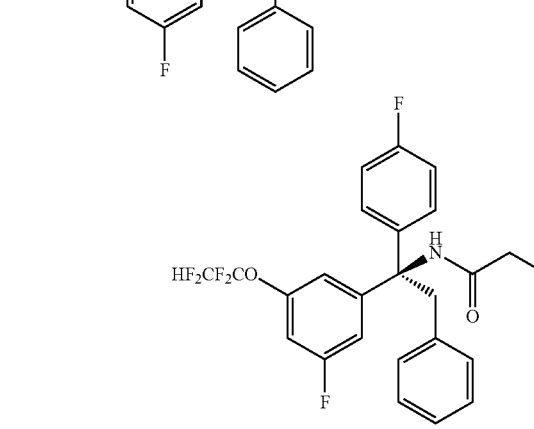

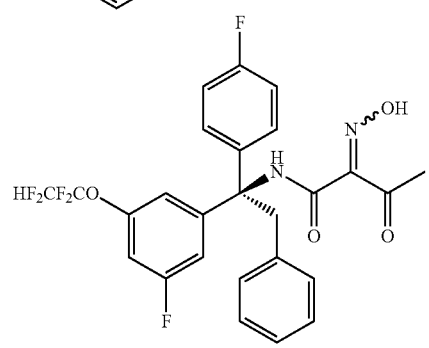

To a solution of (R)—N-(1-(3-fluoro-5-(1,1,2,2-tetrafluoroethoxy)phenyl)-1-(4-fluorophenyl)-2-phenylethyl)-3-oxobutanamide (Example 251, 62 mg, 0.12 mmol), in acetic acid (0.5 mL) was added dropwise a solution of NaNO$_2$ (25 mg, 0.36 mmol) in H$_2$O (0.5 mL). The reaction mixture was stirred at rt for 10 min and diluted with H$_2$O (10 mL). The aqueous portion was extracted with EtOAc (3×10 mL). The combined organic layers were dried over MgSO$_4$, filtered and concentrated under reduced pressure to yield (R)—N-(1-(3-fluoro-5-(1,1,2,2-tetrafluoroethoxy)phenyl)-1-(4-fluorophenyl)-2-phenylethyl)-2-(hydroxyimino)-3-oxobutanamide (Example 331) as a yellow solid (65 mg, 100% yield). LCMS: RT=1.99 min [M+H] 539.4 (Phenomenex Luna C18 column, 4.6×30 mm eluting with 10-90% MeOH/H$_2$O over 2 minutes containing 0.1% TFA; 5 mL/min, monitoring at 220 nm). $^1$H NMR (400 MHz, CDCl$_3$) δ ppm 10.07 (1H, s), 7.15-7.21 (2H, m), 7.07-7.14 (7H, m), 7.00-7.05 (4H, m), 6.84-6.96 (6H, m), 6.55-6.60 (2H, m), 5.88 (1H, t, J=2.78 Hz), 3.91 (1H, d, J=13.14 Hz), 3.72-3.80 (1H, m), 2.52 (3H, s).

Example 332A

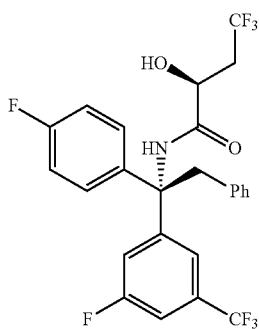 [SMILES: O=C(N[C@@](Cc1ccccc1)(c1ccc(F)cc1)c1cc(F)cc(C(F)(F)F)c1)[C@@H](O)CC(F)(F)F]

(S)-4,4,4-trifluoro-N-((S)-1-(3-fluoro-5-(trifluoromethyl)phenyl)-1-(4-fluorophenyl)-2-phenylethyl)-2-hydroxybutanamide Example 332B

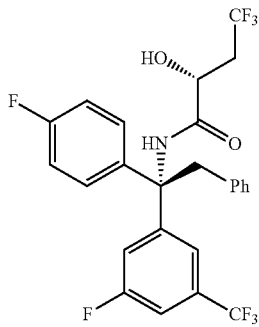 [SMILES: O=C(N[C@@](Cc1ccccc1)(c1ccc(F)cc1)c1cc(F)cc(C(F)(F)F)c1)[C@H](O)CC(F)(F)F]

(R)-4,4,4-trifluoro-N-((S)-1-(3-fluoro-5-(trifluoromethyl)phenyl)-1-(4-fluorophenyl)-2-phenylethyl)-2-hydroxybutanamide Procedure 157

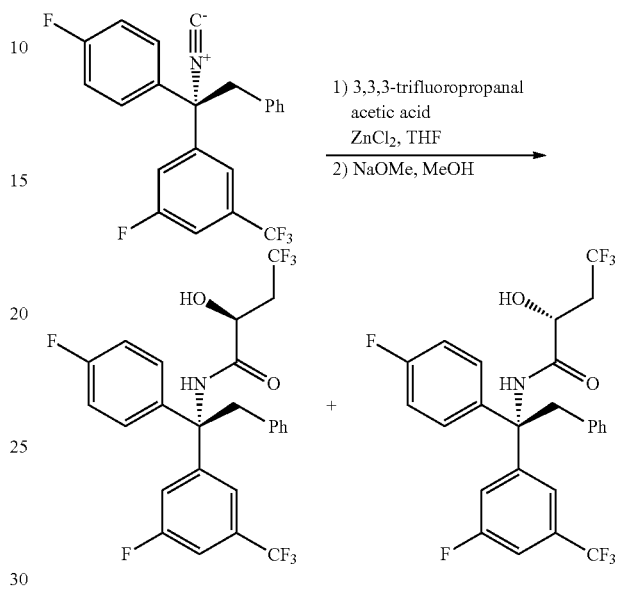

To a solution of (S)-1-fluoro-3-(1-(4-fluorophenyl)-1-isocyano-2-phenylethyl)-5-(trifluoromethyl)benzene prepared as described in Procedure 149, 150, 151 and 152 (23 mg, 0.060 mmol) in THF (0.25 mL) was added 3,3,3-trifluoropropanal (0.006 mL, 0.071 mmol) and acetic acid (0.004 mL, 0.071 mmol) followed by a 0.5M solution of zinc chloride in THF (0.142 mL, 0.071 mmol). The reaction mixture was heated at 55° C. for 16 h. The reaction mixture was allowed to cool to room temperature then a solution of 25% NaOMe in MeOH (25 uL) was added and the reaction mixture was heated at 40° C. for 18 h. The reaction mixture was allowed to cool to room temperature then a drop of acetic acid was added and the solvent was removed under a stream of nitrogen. The residue was purified by prep TLC plate, eluting with 25% EtOAc/hexanes, to yield (S)-4,4,4-trifluoro-N-((S)-1-(3-fluoro-5-(trifluoromethyl)phenyl)-1-(4-fluorophenyl)-2-phenylethyl)-2-hydroxybutanamide (Example 332A, 7 mg, 22% yield) and (R)-4,4,4-trifluoro-N-((S)-1-(3-fluoro-5-(trifluoromethyl)phenyl)-1-(4-fluorophenyl)-2-phenylethyl)-2-hydroxybutanamide (Example 332B, 6 mg, 18% yield) as clear colorless oils. (S)-4,4,4-trifluoro-N-((S)-1-(3-fluoro-5-(trifluoromethyl)phenyl)-1-(4-fluorophenyl)-2-phenylethyl)-2-hydroxybutanamide (Example 332A): LCMS: RT=1.82 min [M+H] 518.2 (2 min Phenomenex Luna C18 column, 4.6×30 mm eluting with 10-90% acetonitrile/H$_2$O over 2 minutes containing 0.1% TFA; 5 mL/min, monitoring at 220 nm); NMR: 400 MHz $^1$H (CDCl$_3$) δ ppm 2.23-2.35 (m, 1H) 2.77-2.88 (m, 2H) 3.73 (d, J=12.75 Hz, 1H) 3.99 (d, J=12.74 Hz, 1H) 4.45 (dd, J=8.57, 4.17 Hz, 1H) 6.61 (d, J=7.47 Hz, 2H) 6.98-7.04 (m, 4H) 7.16-7.28 (m, 6H) 7.69 (s, 1H). (R)-4,4,4-trifluoro-N-((S)-1-(3-fluoro-5-(trifluoromethyl)phenyl)-1-(4-fluorophenyl)-2-phenylethyl)-2-hydroxybutanamide (Example 332B): LCMS: RT=1.81 min [M+H] 518.2 (2 min Phenomenex Luna C18 column, 4.6×30 mm eluting with 10-90% acetonitrile/H$_2$O over 2 minutes containing 0.1% TFA; 5 mL/min, monitoring at 220 nm); NMR: 400 MHz $^1$H (CDCl$_3$) δ ppm 2.23-2.34 (m, 1H) 2.77-2.88 (m, 2H) 3.73 (d, J=12.75 Hz, 1H) 3.99 (d, J=12.74 Hz, 1H) 4.44-4.47 (m, 1H) 6.61 (d, J=7.47 Hz, 2H) 6.98-7.07 (m, 4H) 7.14-7.28 (m, 6H) 7.69 (s, 1H). The stereochemistry of (S)-4,4,4-trifluoro-N-((S)-1-(3-fluoro-5-(trifluoromethyl)phenyl)-1-(4-fluorophenyl)-2-phenylethyl)-2-hydroxybutanamide (Example 332A) and (R)-4,4,4-trifluoro-N-((S)-1-(3-fluoro-5-(trifluoromethyl)phenyl)-1-(4-fluorophenyl)-2-phenylethyl)-2-hydroxybutanamide (Example 332B) was assigned arbitrarily.

Example 333

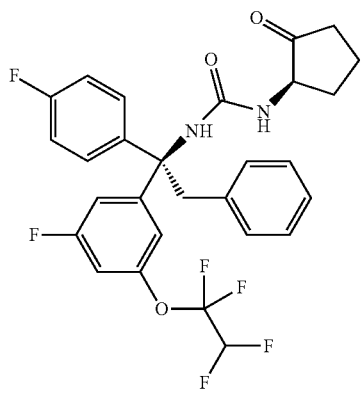 [SMILES: O=C(N[C@@H]1CCCC1=O)N[C@](Cc1ccccc1)(c1ccc(F)cc1)c1cc(F)cc(OC(F)(F)C(F)F)c1]

1-((R)-1-(3-fluoro-5-(1,1,2,2-tetrafluoroethoxy)phenyl)-1-(4-fluorophenyl)-2-phenylethyl)-3-((R)-2-oxocyclopentyl)urea Example 334

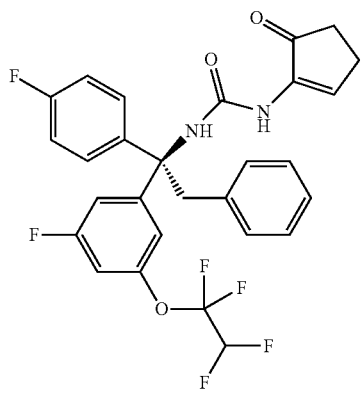 [SMILES: O=C(NC1=CCCC1=O)N[C@](Cc1ccccc1)(c1ccc(F)cc1)c1cc(F)cc(OC(F)(F)C(F)F)c1]

(R)-1-(1-(3-fluoro-5-(1,1,2,2-tetrafluoroethoxy)phenyl)-1-(4-fluorophenyl)-2-phenylethyl)-3-(5-oxocyclopent-1-enyl)urea Procedure 158

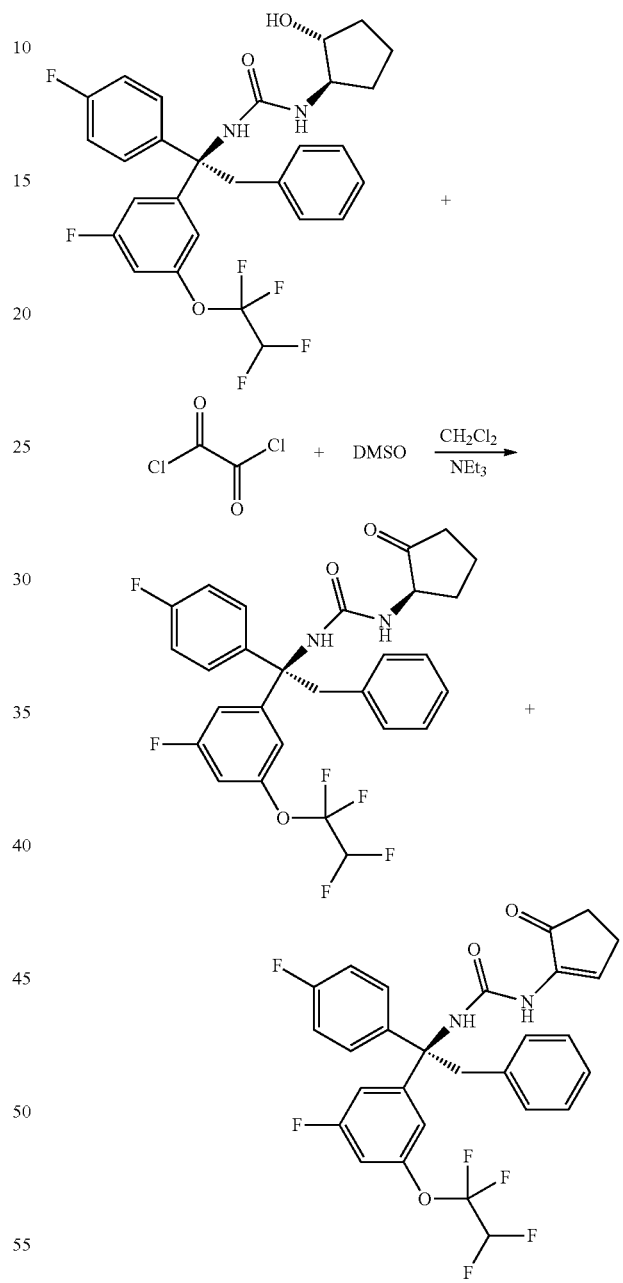

To a solution of oxalyl chloride (2 M in CH$_2$Cl$_2$, 150 uL) at −78° C. was added DMSO (47 mg, 0.60 mmol) dropwise. The reaction mixture was stirred at −78° C. for 15 min, then 1-((R)-1-(3-fluoro-5-(1,1,2,2-tetrafluoroethoxy)phenyl)-1-(4-fluorophenyl)-2-phenylethyl)-3-((1R,2R)-2-hydroxycyclopentyl)urea (Example 246, 113 mg, 0.20 mmol) in CH$_2$Cl$_2$ (1 mL) was added dropwise. The reaction mixture was allowed to warm to rt and stirred for 16 h. The reaction mixture was concentrated under reduced pressure and purified by ISCO flash chromatography with EtOAc and hexane as eluting solvent to yield (R)-1-(1-(3-fluoro-5-(1,1,2,2-tetrafluoroethoxy)phenyl)-1-(4-fluorophenyl)-2-phenylethyl)-3-(5-oxocyclopent-1-enyl)urea (Example 333) as a white solid (15 mg, 14% yield) and 1-((R)-1-(3-fluoro-5-(1,1,2,2-tetrafluoroethoxy)phenyl)-1-(4-fluorophenyl)-2-phenylethyl)-3-((R)-2-oxocyclopentyl)urea (Example 334) as a white solid (66 mg, 60% yield). (R)-1-(1-(3-fluoro-5-(1,1,2,2-tetrafluoroethoxy)phenyl)-1-(4-fluorophenyl)-2-phenylethyl)-3-(5-oxocyclopent-1-enyl)urea: HPLC: RT=3.99 min [M+H] 551.09 (Phenomenex Luna C18 column, 4.6×50 mm eluting with 10-90% MeOH/H$_2$O over 4 minutes containing 0.1% TFA; 4 mL/min, monitoring at 220 nm); $^1$H NMR (400 MHz, CDCl$_3$) δ ppm 1.24-1.37 (m, 1H), 1.36-1.58 (m, 1H), 1.68-1.84 (m, 1H), 1.84-2.00 (m, 2H), 2.12-2.30 (m, 3H), 2.48-2.73 (m, 1H), 3.58-4.05 (m, 3H), 5.35-5.52 (m, 1H), 5.64-6.03 (m, 2H), 6.62-6.78 (m, 2H), 6.78-7.02 (m, 5H), 7.04-7.23 (m, 5H). 1-((R)-1-(3-fluoro-5-(1,1,2,2-tetrafluoroethoxy)phenyl)-1-(4-fluorophenyl)-2-phenylethyl)-3-((R)-2-oxocyclopentyl)urea: HPLC: RT=4.09 min [M+H] 549.1 (Phenomenex Luna C18 column, 4.6×50 mm eluting with 10-90% MeOH/H$_2$O over 4 minutes containing 0.1% TFA; 4 mL/min, monitoring at 220 nm); $^1$H NMR (400 MHz, CDCl$_3$) δ ppm 1.84-1.94 (m, 2H), 2.43-2.62 (m, 2H) 3.92 (dd, 2H) 5.82 (t, 1H) 6.62-6.78 (m, 2H) 6.79-6.88 (m, 1H) 6.90-7.01 (m, 5H), 7.01-7.15 (m, 3H), 7.14-7.25 (m, 2H), 7.62-7.74 (m, 1H), 8.09-8.25 (m, 1H).

Example 335

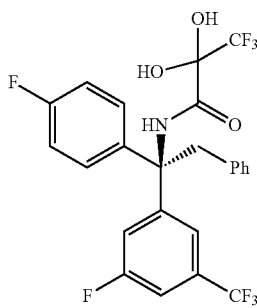 [SMILES: O=C(N[C@](Cc1ccccc1)(c1ccc(F)cc1)c1cc(F)cc(C(F)(F)F)c1)C(O)(O)C(F)(F)F]

(R)-3,3,3-trifluoro-N-(1-(3-fluoro-5-(trifluoromethyl)phenyl)-1-(4-fluorophenyl)-2-phenylethyl)-2,2-dihydroxypropanamide Procedure 159

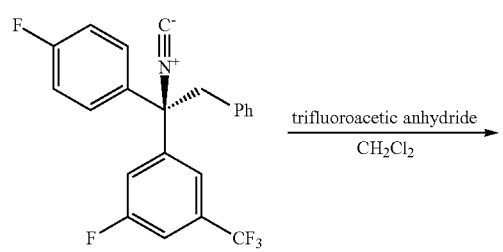

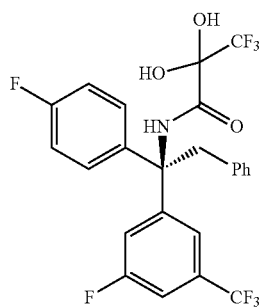

To a solution of (R)-1-fluoro-3-(1-(4-fluorophenyl)-1-isocyano-2-phenylethyl)-5-(trifluoromethyl)benzene (26 mg, 0.067 mmol) prepared as described in Procedure 4, 149, 150, 151 and 152, in CH$_2$Cl$_2$ (0.7 mL) at −78° C. was added trifluoroacetic anhydride (0.06 mL, 0.42 mmol) and the reaction mixture was allowed to warm to −40° C. over 6 h. The reaction mixture was quenched by the addition of H$_2$O (5 mL) then allowed to warm to room temperature. The mixture was extracted with CH$_2$Cl$_2$ (3×5 mL) then dried over Na$_2$SO$_4$, filtered and volatiles removed under vacuum. The residue was purified using silica gel (4 g), eluting with 0 to 100% Et$_2$O/hexane, to give (R)-3,3,3-trifluoro-N-(1-(3-fluoro-5-(trifluoromethyl)phenyl)-1-(4-fluorophenyl)-2-phenylethyl)-2,2-dihydroxypropanamide (Example 335, 11 mg, 32%) as a clear colorless glass. LCMS: RT=1.69 min [M−H] 518.0 (2 min Phenomenex Luna C18 column, 4.6×30 mm eluting with 10-90% acetonitrile/H$_2$O over 2 minutes containing 0.1% NH$_4$Ac; 5 mL/min, monitoring at 220 nm); NMR: 400 MHz $^1$H (CDCl$_3$) δ ppm 3.71 (d, J=13.18 Hz, 1H) 3.92 (d, J=13.18 Hz, 1H) 6.61 (d, J=7.47 Hz, 2H) 6.98-7.06 (m, 4H) 7.12-7.30 (m, 7H).

Example 336

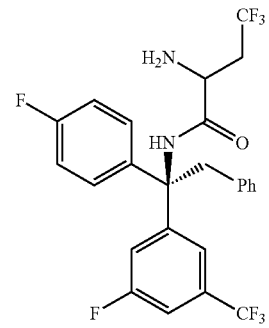

2-amino-4,4-trifluoro-N—((R)-1-(3-fluoro-5-(trifluoromethyl)phenyl)-1-(4-fluorophenyl)-2-phenylethyl)butanamide Procedure 160

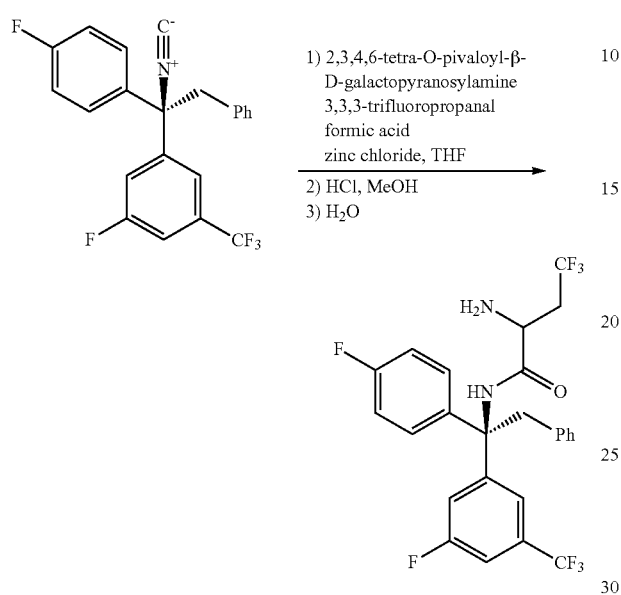

To a solution of (R)-1-fluoro-3-(1-(4-fluorophenyl)-1-isocyano-2-phenylethyl)-5-(trifluoromethyl)benzene (35 mg, 0.09 mmol) prepared as described in Procedure 4, 149, 150, 151 and 152, in THF (0.7 mL) was added 3,3,3-trifluoropropanal (0.008 mL, 0.095 mmol), 2, 3,4,6-O-pivaloyl-β-D-galactopyranosylamine (49 mg, 0.095 mmol) and formic acid (0.004 mL, 0.10 mmol). The reaction mixture was cooled to −20° C. then a 0.5 M solution of zinc chloride in THF (0.19 mL, 0.095 mmol) was added and the reaction mixture was stirred at 0° C. for 16 h. Additional 3,3,3-trifluoropropanal (0.016 mL, 0.19 mmol), 2, 3,4,6-O-pivaloyl-β-D-galactopyranosylamine (98 mg, 0.19 mmol), formic acid (0.008 mL, 0.20 mmol) and zinc chloride solution (0.38 mL, 0.19 mmol) were added and the reaction mixture was allowed to warm to room temperature and stirred for 3 h. The volatiles were removed under vacuum and the residue was dissolved in CH$_2$Cl$_2$ (5 mL) and washed with sat. NaHCO$_3$ (2×10 mL) and H$_2$O (10 mL) then dried over MgSO$_4$, filtered and volatiles removed under vacuum. The flask containing the residue was cooled in an ice bath then sat. HCl in methanol (2 mL) was added and the reaction mixture was stirred for 0.5 h at 0° C. then rt for 1.5 h. H$_2$O (0.5 mL) and MeOH (1.5 mL) were added and the reaction mixture was stirred for 24 h. Most of MeOH was removed under a stream of nitrogen then the reaction mixture was diluted with 1 N NaOH (5 mL) and extracted with CH$_2$Cl$_2$ (3×5 mL). The combined organic fractions were washed with H$_2$O (5 mL), dried over Na$_2$SO$_4$, filtered and volatiles removed under vacuum. The residue was purified by prep HPLC (RT=6.2 min using Axia Luna 5µ C18 30×100 mm column with flow rate of 40 mL/min over 10 min period. 20 to 100% solvent B. Solvent A=10/90/0.1% ACN/H$_2$O/TFA. Solvent B=90/10/0.1%) to give the trifluoroacetic acid salt of 2-amino-4,4-trifluoro-N—((R)-1-(3-fluoro-5-(trifluoromethyl)phenyl)-1-(4-fluorophenyl)-2-phenylethyl)butanamide (Example 336, 9 mg, 15% yield) as a clear colorless glass. LCMS: RT=1.34 min [M+H] 517.2 (2 min Phenomenex Luna C18 column, 4.6×30 mm eluting with 10-90% acetonitrile/H$_2$O over 2 minutes containing 0.1% TFA; 5 mL/min, monitoring at 220 nm); NMR: 400 MHz $^1$H (CD$_3$Cl) δ ppm 2.59-2.70 (m, 1H), 2.72-2.84 (m, 1H), 3.93-4.03 (m, 2H), 4.34 (dd, J=9.01, 3.73 Hz, 1H), 6.68-6.72 (m, 2H), 7.02-7.09 (m, 2H), 7.11-7.22 (m, 3H), 7.25-7.40 (m, 5H).

Example 337

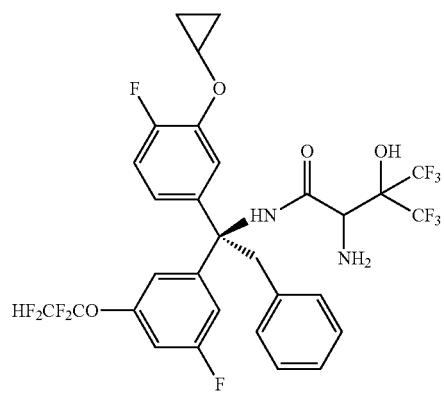

2-amino-N—((R)-1-(3-cyclopropoxy-4-fluorophenyl)-1-(3-fluoro-5-(1,1,2,2-tetrafluoroethoxy)phenyl)-2-phenylethyl)-4,4,4-trifluoro-3-hydroxy-3-(trifluoromethyl)butanamide Procedure 161

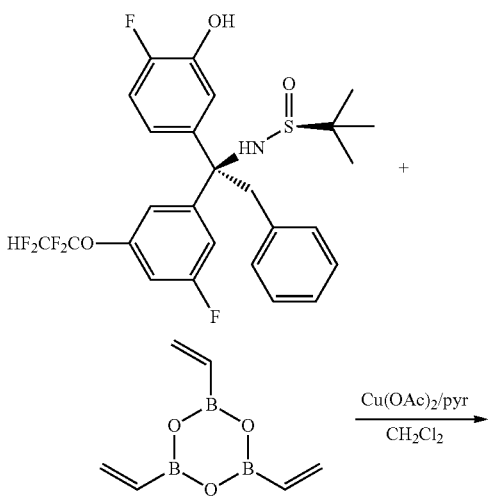

567
-continued

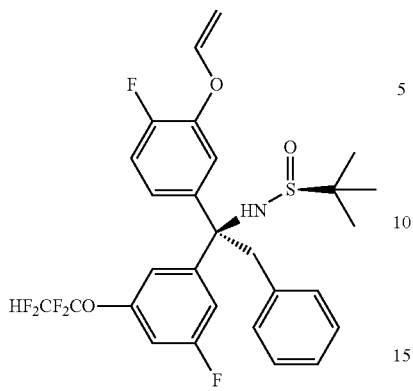

568
-continued

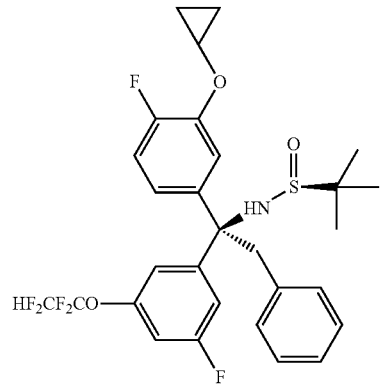

To a solution of (S)—N—((R)-1-(4-fluoro-3-hydroxyphenyl)-1-(3-fluoro-5-(1,1,2,2-tetrafluoroethoxy)phenyl)-2-phenylethyl)-2-methylpropane-2-sulfinamide, prepared as described in Procedure 109, 110, 111, 112, 113, 114, (0.545 g, 1 mmol) in CH$_2$Cl$_2$ (10 mL) was added Cu(OAc)$_2$ (0.182 g, 1 mmol), followed by pyridine (0.79 g, 10 mmol) and 2,4,6-trivinyl-1,3,5,2,4,6-trioxatriborinane (0.159 g, 0.66 mmol). The reaction mixture was stirred overnight under ambient air and filtered through a plug of celite and neutral alumina. The solid was washed with ethyl acetate and the filtrate was concentrated under reduced pressure to yield (S)—N—((R)-1-(4-fluoro-3-(vinyloxy)phenyl)-1-(3-fluoro-5-(1,1,2,2-tetrafluoroethoxy)phenyl)-2-phenylethyl)-2-methylpropane-2-sulfinamide as an off-white foam (0.495 g, 87% yield). LCMS: RT=3.653 min [M+H] 572.2 (Phenomenex Luna C18 5μ column, eluting with 10-90% aqueous acetonitrile containing 0.1% trifluoroacetic acid over a 4 minute gradient, monitoring at 220 nM). $^1$H NMR (CDCl$_3$) ppm 7.2-7.1 (m, 5H), 7.02 (d, J=6.2 Hz, 1H), 6.89 (d, J=6.2 Hz, 2H), 6.82 (d, J=8.8 Hz, 1H), 6.68 (br, 2H), 6.54 (dd, J=6.2 Hz, 13.6 Hz, 1H), 5.84 (t, J=52.7 Hz, 1H), 4.62 (dd, J=2.2 Hz, 13.6 Hz, 1H), 4.40 (dd, J=2.2 Hz, 5.7 Hz, 1H), 4.21 (s, 1H), 3.95 (d, J=12.8 Hz, 1H), 3.55 (d, J=12.7 Hz, 1H), 1.19 (s, 9H).

To an oven-dried 3-necked 25 mL RB flask under nitrogen was added CH$_2$Cl$_2$ (3.5 mL) and 1 M diethylzinc solution in hexane (3.43 mL, 3.43 mmol). The flask was cooled in an ice-bath and a solution of trifluoroacetic acid (0.391 g, 3.43 mmol) in CH$_2$Cl$_2$ (1 mL) was added dropwise via syringe. After stirring for 15 min, a solution of diiodomethane (0.918 g, 3.43 mmol) in CH$_2$Cl$_2$ (1 mL) was added. The reaction mixture was stirred at rt for 15 min, followed by addition of (S)—N—((R)-1-(4-fluoro-3-(vinyloxy)phenyl)-1-(3-fluoro-5-(1,1,2,2-tetrafluoroethoxy)phenyl)-2-phenylethyl)-2-methylpropane-2-sulfinamide (0.495 g, 0.87 mmol) in CH$_2$Cl$_2$ (1 mL). The reaction mixture was allowed to warm to rt and stirred for 4 h. The reaction mixture was diluted with CH$_2$Cl$_2$ and washed successively with sat. sodium bicarbonate, water, sat. NaCl, dried over MgSO$_4$, filtered and concentrated under reduced pressure. The residue was purified by ISCO using a gradient of 5-70% EtOAc/hexane as eluent to yield (S)—N—((R)-1-(3-cyclopropoxy-4-fluorophenyl)-1-(3-fluoro-5-(1,1,2,2-tetrafluoroethoxy)phenyl)-2-phenylethyl)-2-methylpropane-2-sulfinamide as a white foam (0.347 g, 71% yield). HPLC: RT=3.668 min [M+H] 586.3 (Phenomenex Luna C18 5μ column, eluting with 10-90% aqueous acetonitrile containing 0.1% trifluoroacetic acid over a 4 minute gradient, monitoring at 220 nm). $^1$H NMR (CDCL$_3$) ppm 7.2-7.05 (m, 6H), 6.91 (d, J=6.6 Hz, 2H), 6.83 (d, J=8.4 Hz, 1H), 6.71 (m, 2H), 5.84 (t, J=53.1 Hz, 1H), 4.21 (s, 1H), 3.99 (d, J=12.3 Hz, 1H), 3.62 (m, 1H), 3.56 (d, J=12.8 Hz, 1H), 1.22 (s, 9H), 0.72-0.65 (m, 4H).

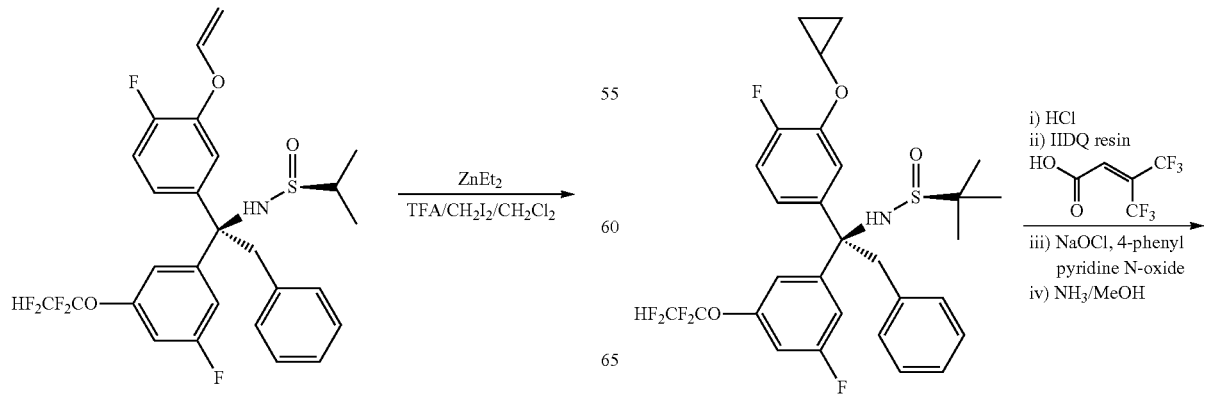

-continued

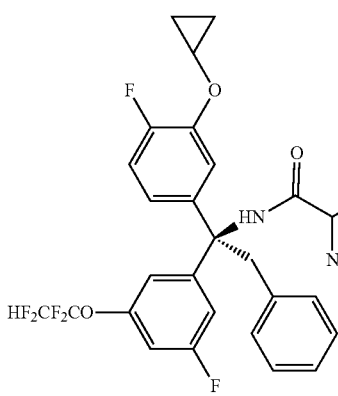

Following Procedure 6, 90, 91 and 92, 2-amino-N—((R)-1-(3-cyclopropoxy-4-fluorophenyl)-1-(3-fluoro-5-(1,1,2,2-tetrafluoroethoxy)phenyl)-2-phenylethyl)-4,4,4-trifluoro-3-hydroxy-3-(trifluoromethyl)butanamide (Example 337) was prepared. HPLC: RT=3.466 min [M+H] 705.3 (Phenomenex Luna C18 5μ column, eluting with 10-90% aqueous acetonitrile containing 0.1% trifluoroacetic acid over a 4 minute gradient, monitoring at 220 nM). $^1$H NMR (CD$_2$Cl$_2$) ppm 8.97 (s, 1H), 7.14-6.5 (m, 11H), 5.84 (t, J=53.1 Hz, 1H), 3.79 (d, J=12.3 Hz, 1H), 3.67 (s, 1H), 3.62 (d, J=13.1 Hz, 1H), 3.52 (m, 1H), 1.48 (br, 1H), 0.55 (m, 4H).

Example 338

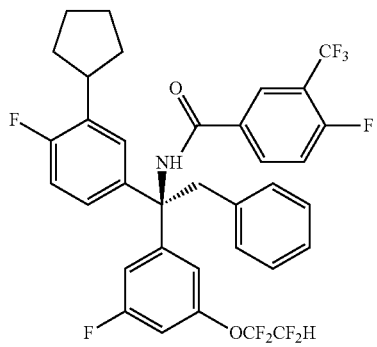

(R)—N-(1-(3-cyclopentyl-4-fluorophenyl)-1-(3-fluoro-5-(1,1,2,2-tetrafluoroethoxy)phenyl)-2-phenylethyl)-4-fluoro-3-(trifluoromethyl)benzamide Procedure 162

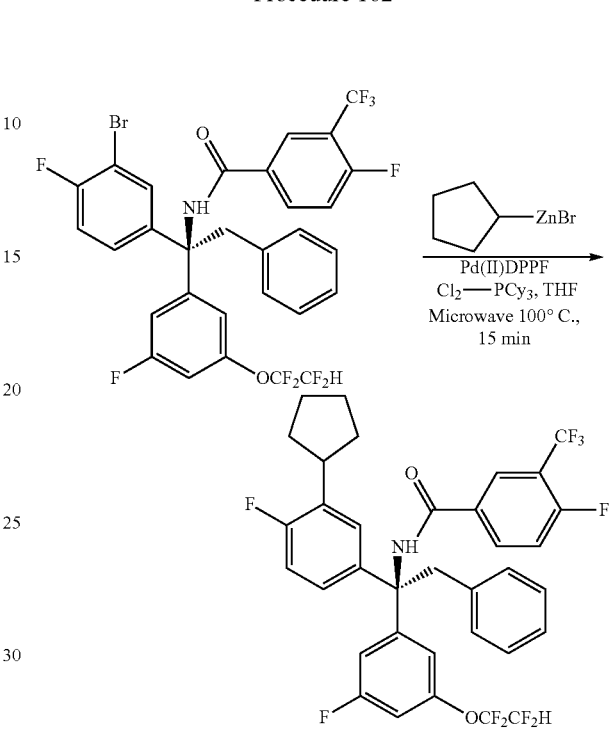

To a solution of (S)—N-(1-(3-bromo-4-fluorophenyl)-1-(3-fluoro-5-(1,1,2,2-tetrafluoroethoxy)phenyl)-2-phenylethyl)-4-fluoro-3-(trifluoromethyl)benzamide, prepared as described in Procedure 3, 62, 5, 6 and 7 in THF (0.1 M, 0.5 mL, 0.05 mmol) was added dichloro[1,1'-bis(diphenylphosphino)ferrocene]palladium(II) dichloromethane (4 mg, 0.0054 mmol) and tricyclohexylphosphine (1.0 M in toluene, 0.05 mL, 0.05 mmol), followed by cyclopentyl zinc bromide (0.5 M in THF, 0.04 mL, 0.2 mmol). The reaction mixture was heated at 100° C. under microwave irradiation for 15 min. The reaction mixture was cooled and filtered through a plug of silica. The solid was washed with THF (2 mL) and the filtrate was concentrated under reduced pressure. The residue was dissolved in methanol (1 mL) and purified by preparative HPLC (RT=14.89 min, Sunfire Prep C18 OBD 19×100 mm eluting with 18-90% MeCN/H$_2$O over 12 minutes and at 90% for 8 additional minutes containing 0.1% TFA; 20 mL/min, monitoring at 220 nm) to yield (R)—N-(1-(3-cyclopentyl-4-fluorophenyl)-1-(3-fluoro-5-(1,1,2,2-tetrafluoroethoxy)phenyl)-2-phenylethyl)-4-fluoro-3-(trifluoromethyl)benzamide (Example 338) as a colorless gum (13 mg, 19% yield). LCMS: RT=4.56 min [M+H] 684.3 (4 min Sunfire S5 C18 column, 4.6×50 mm eluting with 10-90% MeOH/H$_2$O over 4 minutes containing 0.1% TFA; 4 mL/min, monitoring at 220 nm). $^1$H NMR (500 MHz, CD$_3$Cl) δ ppm 7.90 (1H, d, J=6.60 Hz), 7.84 (1H, dd, J=8.25, 4.40 Hz), 7.28 (1H, t, J=9.07 Hz), 7.23 (1H, t, J=7.42 Hz), 7.16 (2H, t, J=7.42 Hz), 7.01-7.05 (2H, m), 6.92-6.96 (2H, m), 6.86 (1H, dd, J=6.60, 2.75 Hz), 6.79-6.82 (1H, m), 6.69 (2H, d, J=7.15 Hz), 6.65 (1H, s), 5.75-5.98 (1H, t), 4.12 (1H, d, J=13.20 Hz), 3.66 (1H, d, J=13.20 Hz), 3.14-3.21 (1H, min), 1.94-2.03 (2H, m), 1.62-1.72 (4H, m), 1.43-1.48 (1H, m), 1.36-1.42 (1H, m).

Example 339

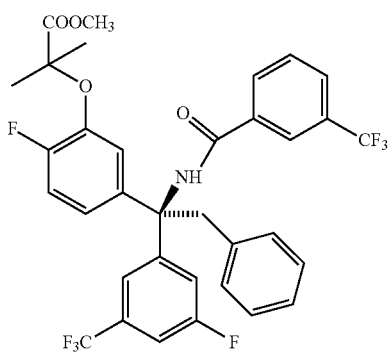 [SMILES: COC(=O)C(C)(C)Oc1cc([C@@](Cc2ccccc2)(NC(=O)c2cccc(C(F)(F)F)c2)c2cc(F)cc(C(F)(F)F)c2)ccc1F]

(R)-methyl 2-(2-fluoro-5-(1-(3-fluoro-5-(trifluoromethyl)phenyl)-2-phenyl-1-(3-(trifluoromethyl)benzamido)ethyl)phenoxy)-2-methylpropanoate Procedure 163

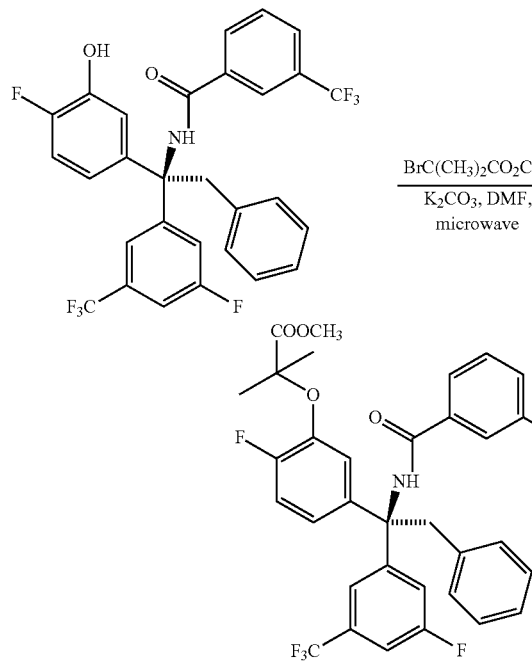

A solution of (R)—N-(1-(4-fluoro-3-hydroxyphenyl)-1-(3-fluoro-5-(trifluoromethyl)phenyl)-2-phenylethyl)-3-(trifluoromethyl)benzamide benzamide, prepared as described in Example 264, (226 mg, 0.4 mmol), methyl 2-bromo-2-methylpropanoate (0.10 mL) and $K_2CO_3$ (326 mg, 2.36 mmol) in DMF (1 mL) was heated at 180° C. under microwave condition for 1200 seconds. The reaction mixture was allowed to cool, diluted with EtOAc and the organic layer was washed with $H_2O$ (2×), saturated NaCl, dried over $Na_2SO_4$, filtered and concentrated. The residue was purified by ISCO flash chromatography (silica gel, hexanes/EtOAc) to give (R)-methyl 2-(2-fluoro-5-(1-(3-fluoro-5-(trifluoromethyl)phenyl)-2-phenyl-1-(3-(trifluoromethyl)benzamido)ethyl)phenoxy)-2-methylpropanoate (Example 273, 76 mg, yield: 29%). LCMS: RT=2.26 min [M+H] 666.4 (Phenomenex Luna C18 column, 4.6×30 mm eluting with 10-90% MeOH/$H_2O$ over 2 minutes containing 0.1% TFA; 5 mL/min, monitoring at 220 nm).

Example 340

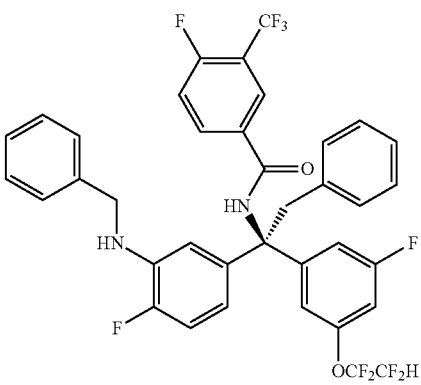

(R)—N-(1-(3-(benzylamino)-4-fluorophenyl)-1-(3-fluoro-5-(1,1,2,2-tetrafluoroethoxy)phenyl)-2-phenylethyl)-4-fluoro-3-(trifluoromethyl)benzamide Procedure 164

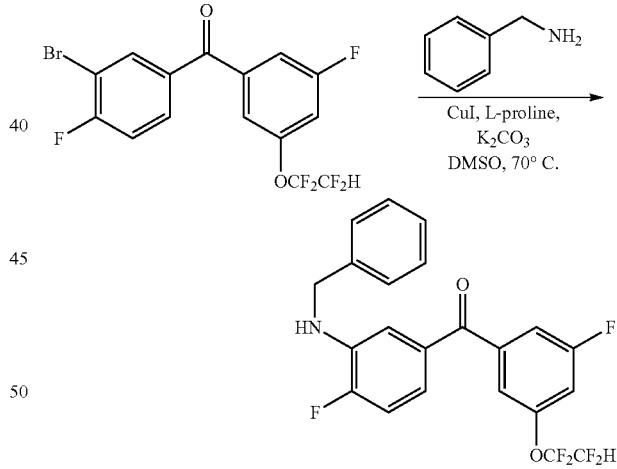

To a solution of (3-bromo-4-fluorophenyl)(3-fluoro-5-(1,1,2,2-tetrafluoroethoxy)-phenyl)methanone, prepared as described in Procedure 62, (110 mg, 0.27 mol) in DMSO (2 mL) at rt was added benzylamine (43 μL, 0.4 mol), copper (I) iodide (5 mg, 0.03 mol), L-proline (23 mg, 0.05 mol), and potassium carbonate (55 mg, 0.4 mol). The reaction mixture was degassed and heated for 4 h at 70° C. After cooling to rt, the reaction mixture was partitioned between water and EtOAc. The organic phase was dried over $MgSO_4$, filtered and concentrated under reduced pressure. The residue was purified via ISCO chromatography (4 g column, 0-30% EtOAc/hexane) to yield (3-(benzylamino)-4-fluorophenyl)(3-fluoro-5-(1,1,2,2-tetrafluoroethoxy)phenyl)methanonea as a clear, colorless oil (95 mg, 81% yield). ¹H NMR (400 MHz, CDCl₃) δ ppm 7.90 (dd, J=6.57, 2.02 Hz, 1H), 7.79 (m, 1H), 7.27 (m, 10H), 6.95 (m, 3H), 6.87 (dd, J=8.59, 2.53 Hz, 1H), 6.73 (d, J=7.07 Hz, 2H), 6.54 (m, 2H), 5.87 (m, 1H), 4.40 (s, 2H), 3.75 (d, J=13.14 Hz, 1H).

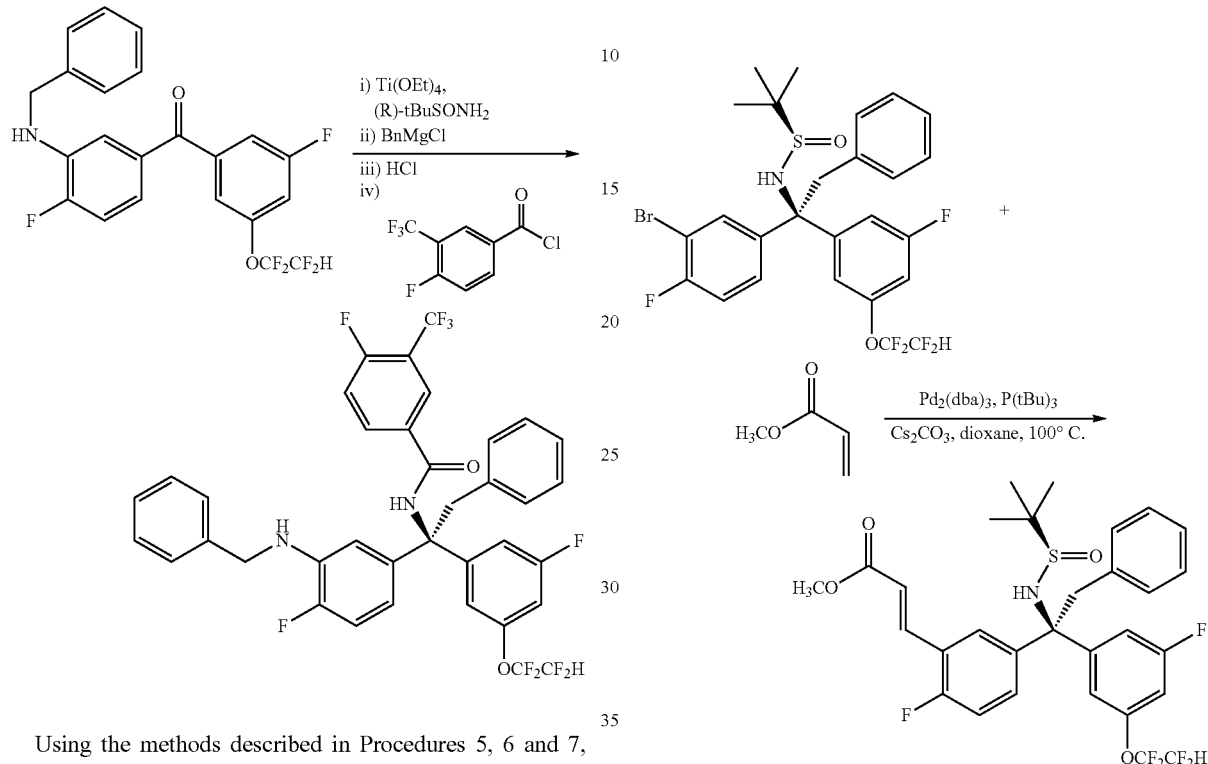

Using the methods described in Procedures 5, 6 and 7, (R)—N-(1-(3-(benzylamino)-4-fluorophenyl)-1-(3-fluoro-5-(1,1,2,2-tetrafluoroethoxy)phenyl)-2-phenylethyl)-4-fluoro-3-(trifluoromethyl)benzamide (Example 340) was prepared as a white solid (8 mg, 59% yield). ¹H NMR (400 MHz, CDCl₃) δ ppm 7.90 (dd, J=6.57, 2.02 Hz, 1H), 7.79 (m, 1H), 7.27 (m, 10H), 6.95 (m, 3H), 6.87 (dd, J=8.59, 2.53 Hz, 1H), 6.73 (d, J=7.07 Hz, 2H), 6.54 (m, 2H), 5.87 (m, 1H), 4.40 (s, 2H), 3.75 (d, J=13.14 Hz, 1H).

Example 341

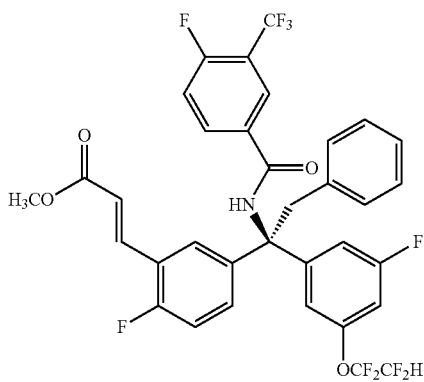

(R,E)-methyl 3-(2-fluoro-5-(1-(4-fluoro-3-(trifluoromethyl)benzamido)-1-(3-fluoro-5-(1,1,2,2-tetrafluoroethoxy)phenyl)-2-phenylethyl)phenyl)acrylate Procedure 165

To a solution of (R)—N—((S)-1-(3-bromo-4-fluorophenyl)-1-(3-fluoro-5-(1,1,2,2-tetrafluoroethoxy)-phenyl)-2-phenylethyl)-2-methylpropane-2-sulfinamide, prepared as described in Procedure 3, 62, 5 and 6, (500 mg, 0.82 mmol) in DMF (5 mL) at rt was added methyl acrylate (0.74 mL, 8.22 mmol), Pd₂(dba)₃ (75 mg, 0.082 mmol), tri-t-butyl phosphine (89 µL, 0.33 mmol), and cesium carbonate (536 mg, 1.64 mmol). The reaction mixture was degassed with argon and was heated at 100° C. for 4 h. The reaction mixture was poured into water and the aqueous phase extracted with ethyl acetate. The combined organic phase was dried over MgSO₄, filtered and concentrated under reduced pressure. The residue was purified by ISCO chromatography (4 g column, 0-40% EtOAc/hexane) to yield (E)-methyl 3-(5-((R)-1-((R)-1,1-dimethylethylsulfinamido)-1-(3-fluoro-5-(1,1,2,2-tetrafluoroethoxy)phenyl)-2-phenylethyl)-2-fluorophenyl)acrylate as a white foam (485 mg, 96% yield). ¹H NMR (400 MHz, CDCl₃) δ ppm 7.77 (d, J=16.42 Hz, 1H), 7.59 (dd, J=6.69, 2.15 Hz, 1H), 7.41 (m, 1H), 7.16 (m, 4H), 6.94 (dd, J=7.33, 1.77 Hz, 2H), 6.86 (d, J=8.84 Hz, 1H), 6.73 (t, J=4.93 Hz, 2H), 6.53 (d, J=16.17 Hz, 1H), 5.88 (m, 1H), 4.29 (s, 1H), 4.03 (d, J=12.38 Hz, 1H), 3.79 (s, 3H), 3.62 (d, J=12.38 Hz, 1H), 1.24 (m, 9H).

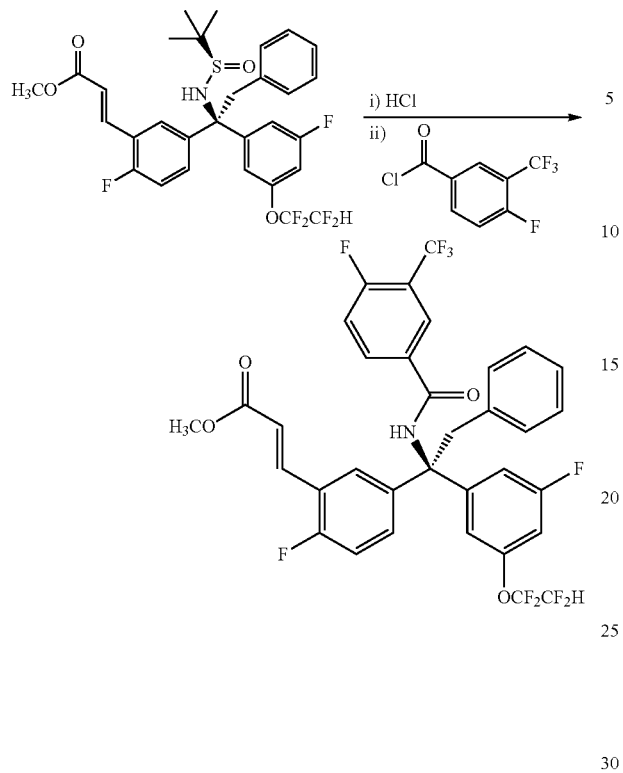

Using the methods described in Procedures 6 and 7, (R,E)-methyl 3-(2-fluoro-5-(1-(4-fluoro-3-(trifluoromethyl)benzamido)-1-(3-fluoro-5-(1,1,2,2-tetrafluoroethoxy)phenyl)-2-phenylethyl)phenyl)acrylate (Example 341) was prepared as a white solid. LCMS: RT=4.46 min [M+H+60] 781 (Phenomenex Luna C18, 50×4.6 mm, 4 min gradient, eluting with 105-90% MeOH/H$_2$O containing 0.1% TFA, monitoring at 220 nm). $^1$H NMR (400 MHz, CDCl$_3$) δ ppm 7.92 (m, 1H), 7.83 (m, 1H), 7.69 (d, J=16.42 Hz, 1H), 7.28 (m, 3H), 7.18 (m, 2H), 7.09 (t, J=9.35 Hz, 1H), 6.94 (m, 3H), 6.72 (m, 3H), 6.51 (m, 1H), 6.42 (d, J=16.42 Hz, 1H), 6.42 (d, J=16.42 Hz, 1H),), 5.88 (m, 1H), 3.95 (d, J=14.91 Hz, 1H), 3.82 (m, 4H).

Example 342

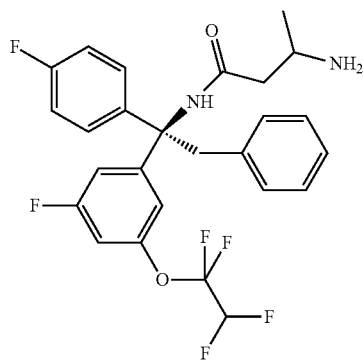 [SMILES: CC(N)CC(=O)N[C@](Cc1ccccc1)(c1ccc(F)cc1)c1cc(F)cc(OC(F)(F)C(F)F)c1]

3-amino-N—((R)-1-(3-fluoro-5-(1,1,2,2-tetrafluoroethoxy)phenyl)-1-(4-fluorophenyl)-2-phenylethyl) butanamide Procedure 166

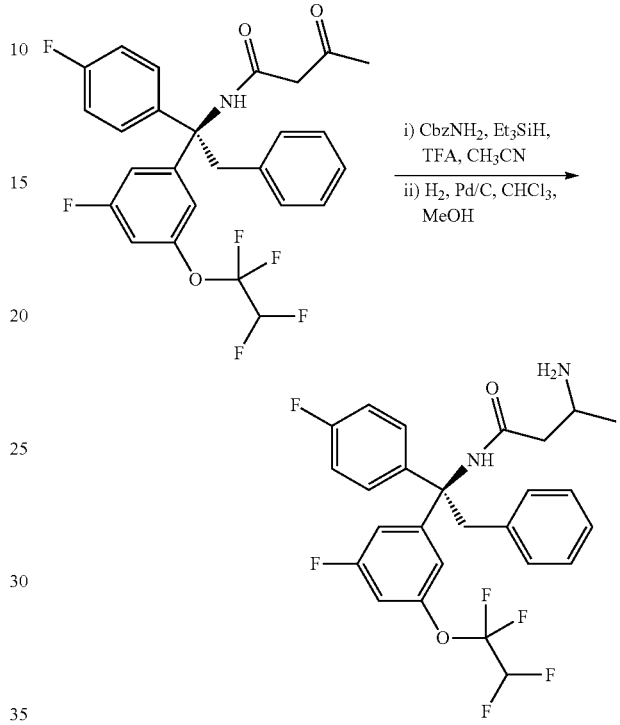

To a solution of (R)—N-(1-(3-fluoro-5-(1,1,2,2-tetrafluoroethoxy)phenyl)-1-(4-fluorophenyl)-2-phenylethyl)-3-oxobutamide (Example 251, 27 mg, 0.053 mmol) in CH$_3$CN (1 mL) was added Cbz-NH$_2$ (24 mg, 0.16 mmol), followed by triethylsilane (0.5 mL, 3 mmol), and TFA (0.4 mL, 5.3 mmol). The reaction mixture was stirred at rt for 3 days. The reaction mixture was concentrated and the residue was dissolved in a mixture of CH$_3$OH (1 mL) and CHCl$_3$ (1 mL) and 10 wt % Pd/C (20 mg) was added. The reaction mixture was stirred under H$_2$ for 16 h and the solid was filtered. The filtrate was concentrated under reduced pressure and the residue was purified by prep HPLC (Phenomenex Luna Axia, 5u 30×100, eluting with 10%-90% MeOH/H$_2$O containing 0.1% TFA, gradient time 10 min, flow rate 40 ml/min, monitoring at 220 nm) to yield 3-amino-N—((R)-1-(3-fluoro-5-(1,1,2,2-tetrafluoroethoxy)phenyl)-1-(4-fluorophenyl)-2-phenylethyl) butanamide (Example 342, 5 mg, 19% yield). HPLC: RT=3.28 min [M+H] 511.3 (Phenomenex Luna C18 column, 4.6×50 mm eluting with 10-90% MeOH/H$_2$O over 4 minutes containing 0.1% TFA; 4 mL/min, monitoring at 220 nm); $^1$H NMR (400 MHz, CDCl$_3$) δ ppm 7.15-7.24, m, 3H, 6.97-7.10, m, 4H, 6.83-6.92, m, 3H, 6.60-6.64, m, 3H, 5.73-6.60, t, J=54, 3.81-3.91, m, 1H, 3.67-3.76, m, 1H, 3.59, m, 1H, 2.70, m, 2H, 1.31, m, 3H.

Example 343

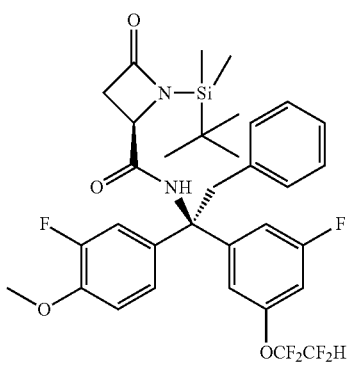

(R)-1-(tert-Butyldimethylsilyl)-N—((R)-1-(3-fluoro-4-methoxyphenyl)-1-(3-fluoro-5-(1,1,2,2-tetrafluoroethoxy)phenyl)-2-phenylethyl)-4-oxoazetidine-2-carboxamide

Procedure 167

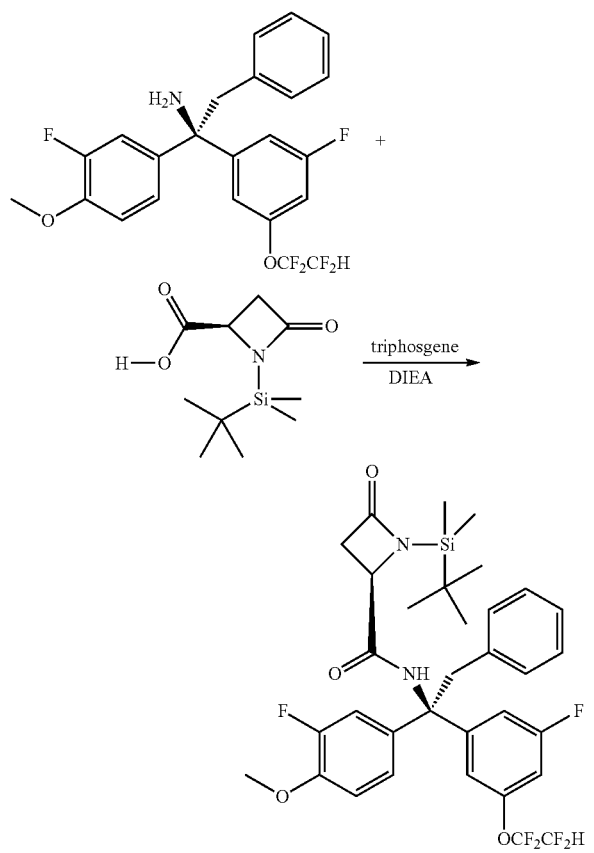

To a solution of (R)-1-(tert-butyldimethylsilyl)-4-oxoazetidine-2-carboxylic acid (126 mg, 0.55 mmol) in THF (1.5 mL) was added to a solution of triphosgene (54 mg, 0.18 mmol). The reaction mixture was stirred for 5 min at rt, followed by addition of 2,4,6-trimethylpyridine (203 μL, 1.54 mmol), a solution of (R)-1-(3-fluoro-4-methoxyphenyl)-1-(3-fluoro-5-(1,1,2,2-tetrafluoroethoxy)phenyl)-2-phenylethanamine, prepared as described in Procedure 3, 62, 5 and 6, (50 mg, 0.11 mmol) in THF (0.6 mL), and N,N-diisopropylethylamine (268 μL, 1.54 mmol). The reaction mixture was stirred at room temperature for 40 min. Water (10 mL) was added and the reaction mixture was extracted with dichloromethane (3×15 mL) and the combined organic layers were washed with 2 N potassium carbonate and then sat. NaCl. The organic layers were dried over magnesium sulfate, filtered and concentrated under reduced pressure. The residue was purified by ISCO Flash chromatography (Analogix column 4.2 g, eluting with hexane/EtOAc) to yield (R)-1-(tert-Butyldimethylsilyl)-N—((R)-1-(3-fluoro-4-methoxyphenyl)-1-(3-fluoro-5-(1,1,2,2-tetrafluoroethoxy)phenyl)-2-phenylethyl)-4-oxoazetidine-2-carboxamide (Example 343, 41 mg, 55% yield). LCMS: RT=4.18 min [M+H] 667.1 (Phenominex, Luna C18, 4.6×50 mm, 10%-90% MeOH/H$_2$O containing 0.1% TFA, flow rate 4 mL/min, 4 min gradient, monitoring at 220 nm); $^1$H NMR (500 MHz, CDCl$_3$) δ ppm −0.04 (s, 3H), 0.24 (s, 3H), 0.91 (s, 9H), 2.79 (dd, J=15.4, 2.7 Hz, 1H), 3.32 (dd, J=15.4, 6.6 Hz, 1H), 3.79-3.85 (m, 1H), 3.86-3.90 (m, 2H), 3.91 (s, 3H), 5.87 (none, 2H), 6.59 (s, 1H), 6.64 (d, J=7.1 Hz, 2H), 6.75 (s, 1H), 6.80 (d, J=9.3 Hz, 1H), 6.87-6.94 (m, 4H), 7.15 (t, J=7.4 Hz, 2H), 7.20 (d, J=7.1 Hz, 1H).

Example 344

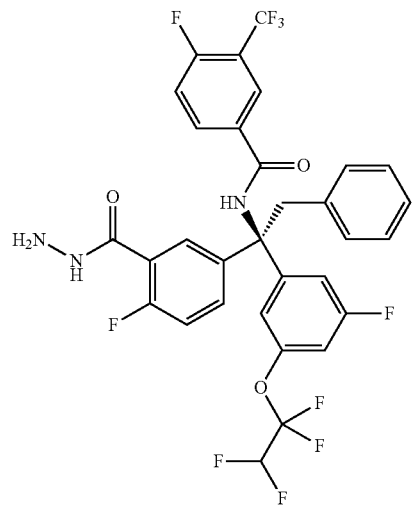 [SMILES: NNC(=O)c1cc([C@@](Cc2ccccc2)(NC(=O)c2ccc(F)c(C(F)(F)F)c2)c2cc(F)cc(OC(F)(F)C(F)F)c2)ccc1F]

579

((R)-4-fluoro-N-(1-(4-fluoro-3-(hydrazinecarbonyl)phenyl)-1-(3-fluoro-5-(1,1,2,2-tetrafluoroethoxy)phenyl)-2-phenylethyl)-3-(trifluoromethyl)benzamide Procedure 168

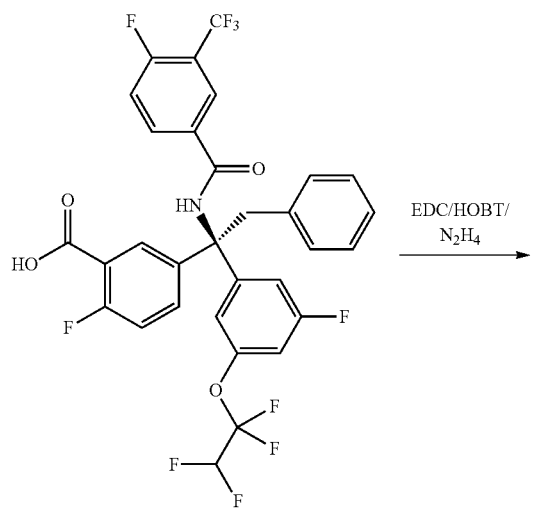

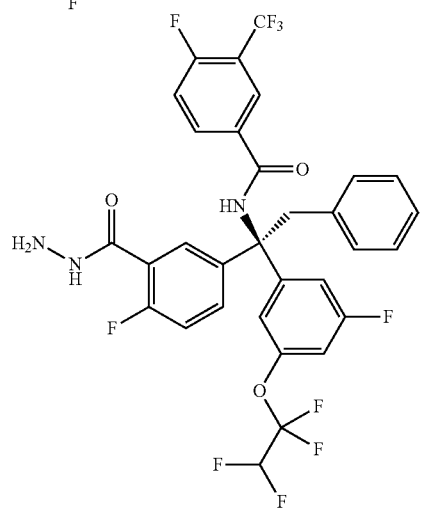

To a solution of (R)-2-fluoro-5-(1-(4-fluoro-3-(trifluoromethyl)benzamido)-1-(3-fluoro-5-(1,1,2,2-tetrafluoroethoxy)phenyl)-2-phenylethyl)benzoic acid, prepared as described in Procedures 3, 62, 5, 6, 7, 56, 57 and 23, (30 mg, 0.045 mmol) in dichloromethane (1 mL) was added hydroxybenzotriazole (8 mg, 0.058 mmol), followed by EDCI (11 mg, 0.058 mmol). The reaction mixture was stirred for 15 min at rt, then hydrazine hydrate was added (3 µL, 0.001 mmol) and the reaction mixture was stirred for an additional 15 min. The reaction mixture was loaded on an ISCO cartridge (4 g column) and eluted with 0 to 100% EtOAc in hexane to yield (R)-4-fluoro-N-(1-(4-fluoro-3-(hydrazinecarbonyl)phenyl)-1-(3-fluoro-5-(1,1,2,2-tetrafluoroethoxy)phenyl)-2-phenylethyl)-3-(trifluoromethyl)benzamide (Example 344, 25 mg, 81% yield) as a white solid. LCMS: RT=1.78 min [M+H] 674 (Chromolith Performance RP-18e column, 4.6×100 mm eluting with 10-90% ACN/H$_2$O over 2 minutes containing 0.1% TFA, 5 mL/min, monitoring at 220 nm).

580

Example 345

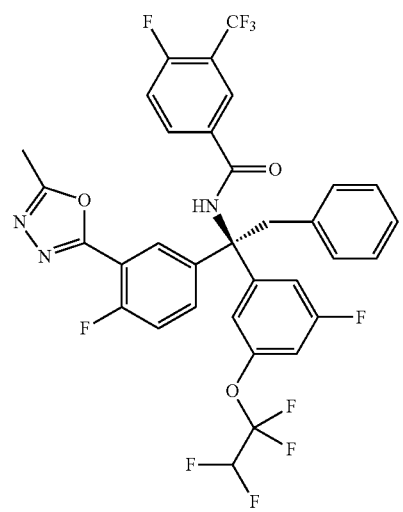 [SMILES: Cc1nnc(-c2cc([C@@](Cc3ccccc3)(NC(=O)c3ccc(F)c(C(F)(F)F)c3)c3cc(F)cc(OC(F)(F)C(F)F)c3)ccc2F)o1]

(R)-4-fluoro-N-(1-(4-fluoro-3-(5-methyl-1,3,4-oxadiazol-2-yl)phenyl)-1-(3-fluoro-5-(1,1,2,2-tetrafluoroethoxy)phenyl)-2-phenylethyl)-3-(trifluoromethyl)benzamide Procedure 169

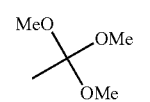

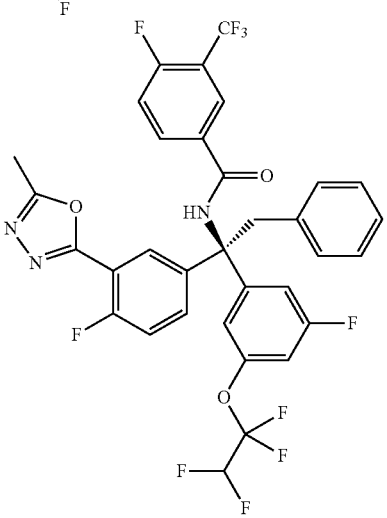

A solution of (R)-4-fluoro-N-(1-(4-fluoro-3-(hydrazinecarbonyl)phenyl)-1-(3-fluoro-5-(1,1,2,2-tetrafluoroethoxy)phenyl)-2-phenylethyl)-3-(trifluoromethyl)benzamide (Example 344, 35 mg, 0.052 mmol) in trimethyl orthoformate (1 mL) was heated at 100° C. for 16 h. The reaction mixture was concentrated under reduced pressure and the residue was purified by ISCO chromatography (4 g column, eluting with 0 to 100% EtOAc in hexane) to yield (R)-4-fluoro-N-(1-(4-fluoro-3-(5-methyl-1,3,4-oxadiazol-2-yl)phenyl)-1-(3-fluoro-5-(1,1,2,2-tetrafluoroethoxy)phenyl)-2-phenylethyl)-3-(trifluoromethyl)benzamide (Example 345, 16 mg, 45% yield) as a white solid. LCMS RT=2.06 min [M+H] 698 (Chromolith Performance RP-18e column, 4.6×100 mm eluting with 10-90% ACN/H$_2$O over 2 minutes containing 0.1% TFA; 5 mL/min, monitoring at 220 nm).

Example 346

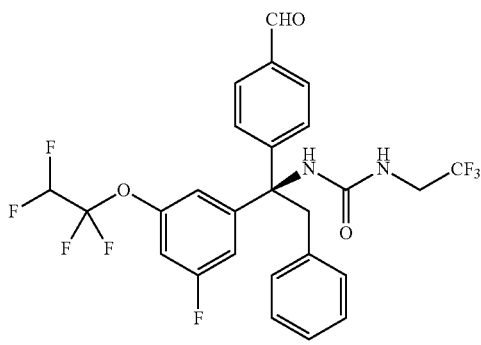

(R)-1-(1-(3-fluoro-5-(1,1,2,2-tetrafluoroethoxy)phenyl)-1-(4-formylphenyl)-2-phenylethyl)-3-(2,2,2-trifluoroethyl)urea Procedure 170

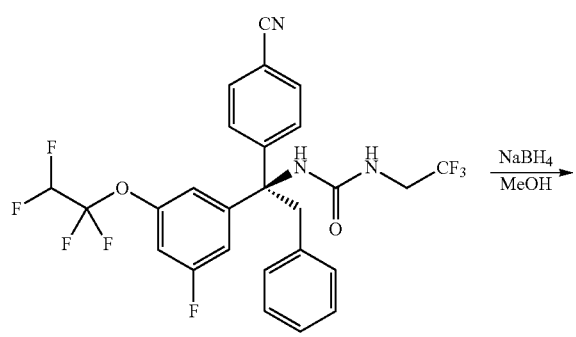

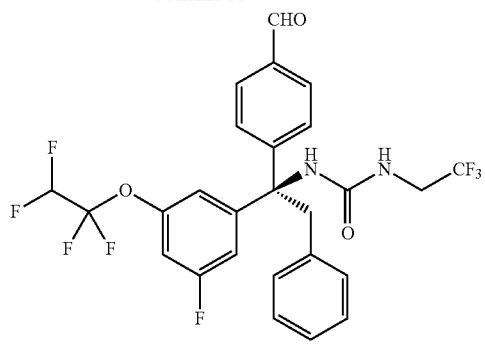 [SMILES: O=Cc1ccc([C@@](Cc2ccccc2)(NC(=O)NCC(F)(F)F)c2cc(F)cc(OC(F)(F)C(F)F)c2)cc1]

To a solution of (R)-1-(1-(4-cyanophenyl)-1-(3-fluoro-5-(1,1,2,2-tetrafluoroethoxy)phenyl)-2-phenylethyl)-3-(2,2,2-trifluoroethyl)urea, prepared as described in Procedure 3, 4, 5, 6, 25 and 56, (59 mg, 0.11 mmol) in methanol (2 mL) was added cobalt chloride hexahydrate (50 mg, 0.22 mmol), followed by sodium borohydride (40 mg, 1.1 mmol). The reaction mixture was stirred for 21 h at room temperature then quenched by addition of hydrochloric acid (1.0 M, 2 mL). The reaction mixture was extracted with ethyl acetate and the combined organic extracts were dried over magnesium sulfate, filtered and concentrated under reduced pressure. The residue was purified by ISCO flash chromatography (12 g silica gel, 0-100% ethyl acetate/hexane gradient over 11 min., flow rate 30 mL/min), then further purified by preparative HPLC (Phenomenex Onyx Monolithic 10×100 mm column; 10-90% acetonitrile/water with 0.1% trifluoroacetic acid gradient over 5 min., 25 mL/min) to yield (R)-1-(1-(3-fluoro-5-(1,1,2,2-tetrafluoroethoxy)phenyl)-1-(4-formylphenyl)-2-phenylethyl)-3-(2,2,2-trifluoroethyl)urea (Example 346) as a white solid (2 mg, 3% yield). LCMS: RT=1.07 min [M+H] 561 (Chromolith Performance 18e 4.6×100 mm column, 50-90% methanol/water with 0.1% trifluoroacetic acid gradient over 2 min, 5 mL/min); $^1$H NMR (400 MHz, CDCl$_3$) δ ppm 10.00 (1H, s), 7.84 (2H, d, J=8.24 Hz), 7.41 (2H, d, J=8.79 Hz), 7.1-7.20 (5H, m), 6.90 (3H, m), 6.70 (2H, d, J=7.15 Hz), 5.88 (1H, tt, J$_{HH}$=2.75 Hz, J$_{HF}$=53 Hz), 5.16 (1H, s), 4.88 (1H, t, J=6.32 Hz), 3.79 (2H, ddd, J=15.67, 9.07, 8.79 Hz).

Example 347

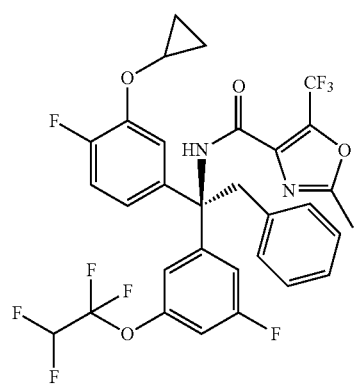 [SMILES: Cc1nc(C(=O)N[C@@](Cc2ccccc2)(c2cc(F)cc(OC(F)(F)C(F)F)c2)c2ccc(F)c(OC3CC3)c2)c(C(F)(F)F)o1]

583

(R)—N-(1-(3-cyclopropoxy-4-fluorophenyl)-1-(3-fluoro-5-(1,1,2,2-tetrafluoroethoxy)phenyl)-2-phenylethyl)-2-methyl-5-(trifluoromethyl)oxazole-4-carboxamide Procedure 171

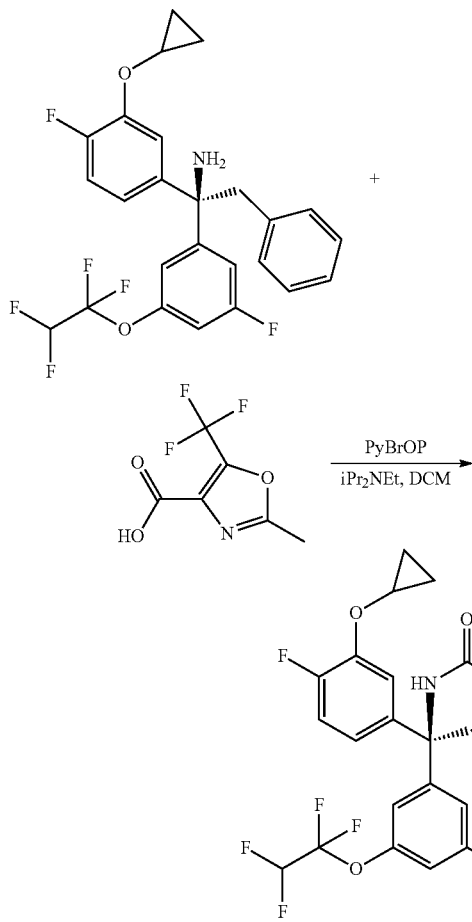

To a solution of (R)-1-(3-cyclopropoxy-4-fluorophenyl)-1-(3-fluoro-5-(1,1,2,2-tetrafluoroethoxy)phenyl)-2-phenylethanamine, prepared as described in Procedure 109, 110, 111, 112, 113, 114, 161, (24 mg, 0.05 mmol) in CH$_2$Cl$_2$ (0.5 mL) was added 2-methyl-5(trifluoromethyl)-oxazole-4-carboxylic acid (12 mg, 0.06 mmol), followed by PyBrOP (28 mg, 0.06 mmol) and iPr$_2$NEt (9 mg, 0.065 mmol). The reaction mixture was stirred at rt for 72 h. The reaction mixture was concentrated under reduced pressure and the residue was purified by prep HPLC (Phenomenex Luna 5μ, 30×100 mm, eluting with 10%-90% MeOH/H$_2$O containing 0.1% TFA, gradient time 10 min, flow rate 40 mL/min) to yield (R)—N-(1-(3-cyclopropoxy-4-fluorophenyl)-1-(3-fluoro-5-(1,1,2,2-tetrafluoroethoxy)phenyl)-2-phenylethyl)-2-methyl-5-(trifluoromethyl)oxazole-4-carboxamide (Example 347) as a white solid (23 mg, 70% yield). HPLC: RT=2.18 min [M+H] 659.5 (Phenomenex Luna C18 column, 4.6×50 mm eluting with 10-90% MeOH/H$_2$O over 2 minutes containing 0.1% TFA; 5 mL/min, monitoring at 220 nm); $^1$H NMR (400 MHz, CDCl$_3$) δ ppm 7.79, s, 1H, 7.10-7.20, m, 3H, 6.90-7.03, m, 5H, 6.70, s, 1H, 6.68, s, 1H, 6.55-6.58, m, 1H, 5.74-6.00, t, J=52; 4.15, 4.19, d, J=16, 1H, 3.66-3.69, d, J=12, 1H, 3.51-3.54, m, 1H, 0.73-0.80, m, 1H, 0.61-0.69, m, 2H, 0.55-0.60, m, 1H.

Example 348

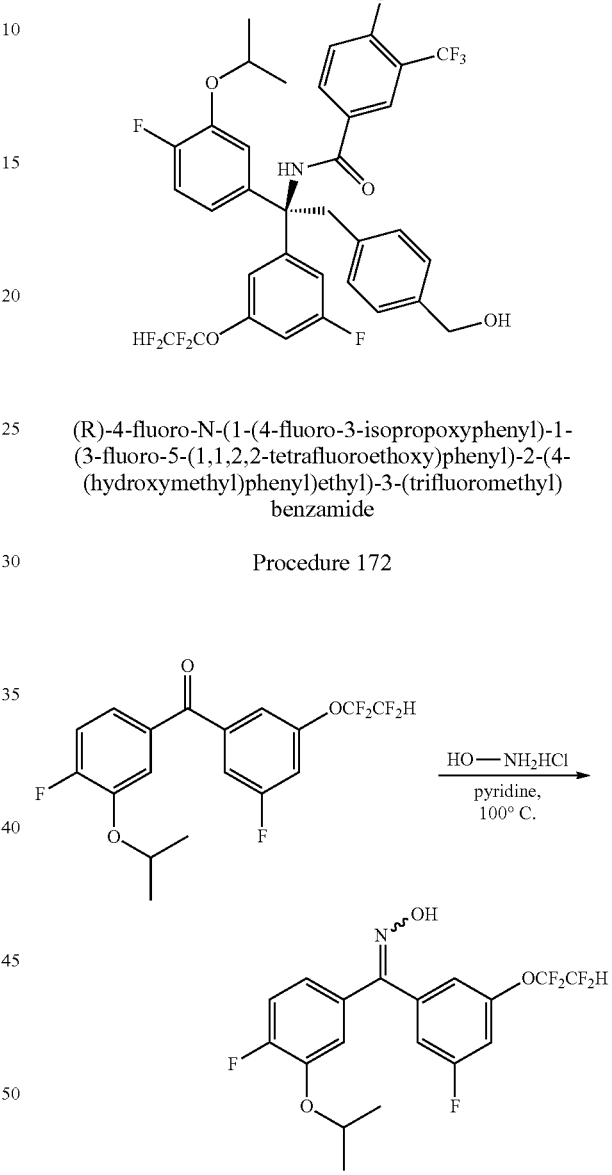

(R)-4-fluoro-N-(1-(4-fluoro-3-isopropoxyphenyl)-1-(3-fluoro-5-(1,1,2,2-tetrafluoroethoxy)phenyl)-2-(4-(hydroxymethyl)phenyl)ethyl)-3-(trifluoromethyl)benzamide Procedure 172

To a solution of (4-fluoro-3-isopropoxyphenyl)(3-fluoro-5-(1,1,2,2-tetrafluoroethoxy)phenyl)methanone, prepared as described in Procedure 3, 4, 59 and 68, (207 mg, 0.53 mmol) in pyridine (1.5 mL) was added hydroxylamine hydrochloride (192 mg, 2.8 mmol) and the reaction mixture was heated at 100° C. for 2 h. The reaction mixture was concentrated under reduced pressure and the residue was dissolved in EtOAc (50 mL). The organic portion was washed with 1 N HCl (2×20 mL), water (20 mL) and sat. NaCl (20 mL), then dried over MgSO$_4$, filtered and concentrated under reduced pressure. The residue was purified by ISCO (40 g silica gel column, 0-30% EtOAc/hexane over 30 min) to yield (4-fluoro-3-isopropoxyphenyl)(3-fluoro-5-(1,1,2,2-tetrafluoroethoxy)phenyl)methanone oxime (216 mg, 77% yield) as a colorless oil. LCMS: RT=2.13 min [M+H] 408.2 (2 min Phenomenex Luna C18 column, 4.6×30 mm eluting with 10-90% MeOH/H$_2$O over 2 minutes containing 0.1% TFA; 5 mL/min, monitoring at 220 nm).

Procedure 173

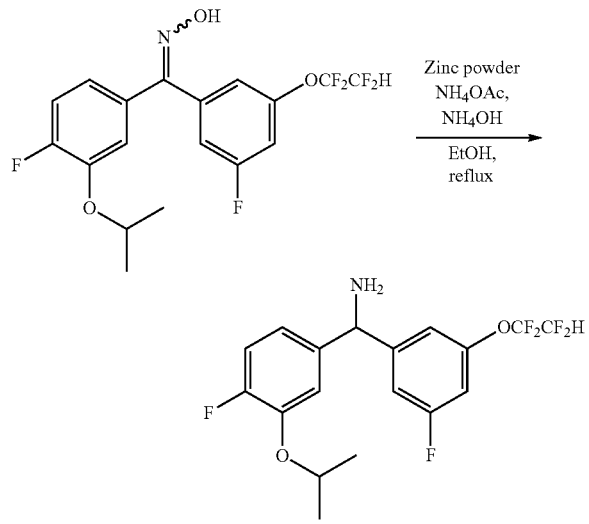

To a suspension of (4-fluoro-3-isopropoxyphenyl)(3-fluoro-5-(1,1,2,2-tetrafluoroethoxy)phenyl)methanone oxime (3.5 g, 8.6 mmol) in EtOH (30 mL) and conc. NH$_4$OH (50 mL) was added ammonium acetate (754 mg, 19.8 mmol), followed by zinc powder (3.2 g, 49.1 mmol) and the reaction mixture was heated at reflux for 3 h. The reaction mixture was allowed to cool to rt then filtered through celite. The solid was washed with 1 N NaOH (10 mL) and MeOH (10 mL). The combined filtrate was extracted concentrated and the residue was partitioned between EtOAc and water. The organic layer was separated and washed with 1 N NaOH (15 mL), sat. NaCl (2×10 mL), dried over MgSO$_4$, filtered and concentrated under reduced pressure to yield (4-fluoro-3-isopropoxyphenyl)(3-fluoro-5-(1,1,2,2-tetrafluoroethoxy)phenyl)methanamine (2.8 g, 83% yield) as a light yellow oil. LCMS: RT=1.76 min [M–NH$_2$] 377.1 (2 min Phenomenex Luna C18 column, 4.6×30 mm eluting with 10-90% MeOH/H$_2$O over 2 minutes containing 0.1% TFA; 5 mL/min, monitoring at 220 nm); $^1$H NMR (400 MHz, CDCl$_3$) δ ppm 6.97-7.09 (4H, m), 6.81-6.89 (2H, m), 5.76-6.03 (1H, m), 5.14 (1H, s), 4.52 (1H, ddd, J=11.97, 6.15, 6.04 Hz), 1.73 (2H, bs), 1.29-1.36 (6H, m).

Procedure 174

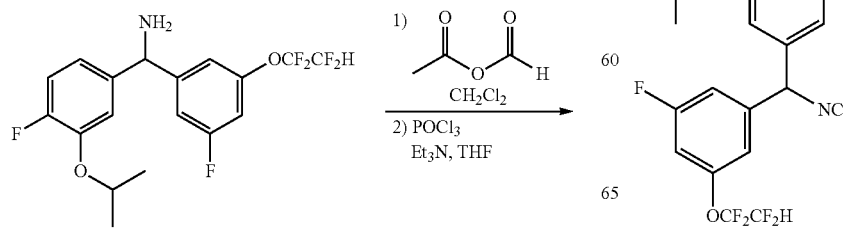

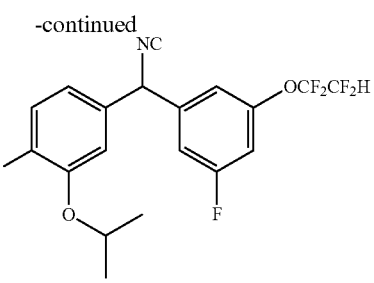

To a solution of (4-fluoro-3-isopropoxyphenyl)(3-fluoro-5-(1,1,2,2-tetrafluoroethoxy)phenyl)methanamine (2.8 g, 7.1 mmol) in CH$_2$Cl$_2$ (30 mL) at 0° C. was added acetic formic anhydride (2.8 mL, formed by heating a 2:1 v/v ratio of acetic anhydride and formic acid at 60° C. for 2 h). The reaction mixture was allowed to warm to room temperature and stirred for 0.5 h. The reaction mixture was concentrated under reduced pressure and the residue was purified by ISCO (120 g silica gel column, 0 to 60% EtOAc/hexane over 60 min gradient) to give N-((4-fluoro-3-isopropoxyphenyl)(3-fluoro-5-(1,1,2,2-tetrafluoroethoxy)phenyl)methyl)formamide (2.56 g, 85% yield) as a colorless oil. LCMS: RT=1.99 min [M+H] 422.0 (Phenomenex Luna C18 4.6×30 mm column, eluting with 10-90% MeOH/H$_2$O containing 0.1% TFA, 2 min gradient, flow rate 5 mL/min, wavelength 220 nm). To a solution of N-((4-fluoro-3-isopropoxyphenyl)(3-fluoro-5-(1,1,2,2-tetrafluoroethoxy)phenyl)methyl)formamide (225 mg, 0.53 mmol) in THF (2 mL) at 0° C. was added Et$_3$N (0.4 mL, 2.9 mmol) followed by phosphorous oxychloride (74 μL, 0.80 mmol). The reaction mixture was allowed to warm to room temperature and stirred for 4 h. The reaction mixture was diluted with ice water (15 mL) and extracted with Et$_2$O (3×15 mL). The combined organic layers were washed with sat. NaCl (20 mL), dried over anhydrous MgSO$_4$, filtered and concentrated. The residue was purified by ISCO (12 g silica gel column, 0-50% EtOAc/hexane over 30 min) to yield 1-fluoro-4-((3-fluoro-5-(1,1,2,2-tetrafluoroethoxy)phenyl)(isocyano)methyl)-2-isopropoxybenzene (143 mg, 67% yield) as a pale yellow oil. LCMS: RT=2.13 min [M–NC] 377 (Phenomenex Luna C18 4.6×30 mm column, eluting with 10-90% MeOH/H$_2$O containing 0.% TFA, 2 min gradient, flow rate 5 mL/min, wavelength 220 nm); $^1$H NMR (400 MHz, CDCl$_3$) δ ppm 7.07-7.13 (1H, m), 6.91-7.03 (4H, m), 6.84-6.86 (1H, m), 5.78-6.04 (1H, m), 5.82 (1H, s), 4.54 (1H, ddd, J=11.97, 6.15, 6.04 Hz), 1.35 (6H, t, J=5.05 Hz).

Procedure 175

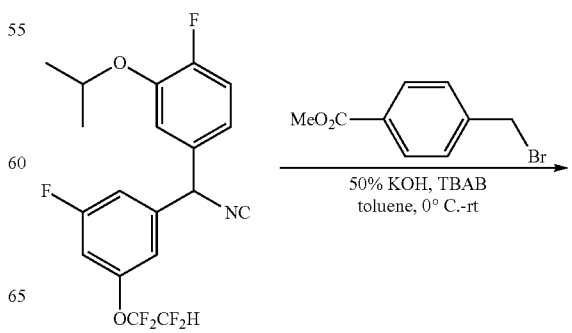

-continued

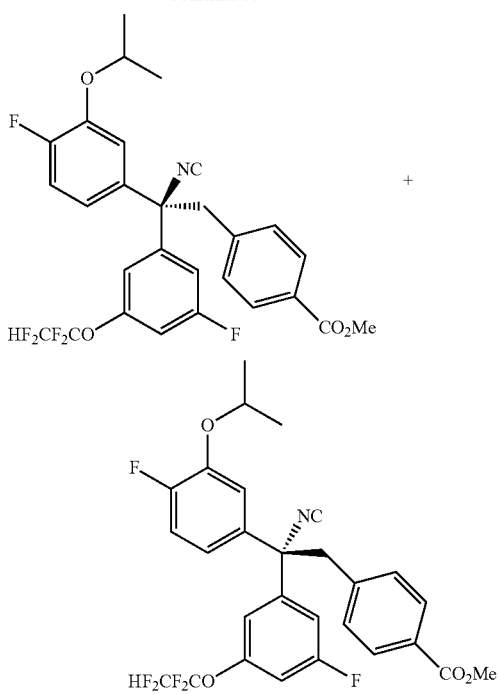

To a solution of 1-fluoro-4-((3-fluoro-5-(1,1,2,2-tetrafluoroethoxy)phenyl)(isocyano)methyl)-2-isopropoxybenzene (81 mg, 0.2 mmol) in toluene (2 mL) was added tetrabutylammonium bromide (19 mg, 0.06 mmol) and benzyl bromide (50 mg, 0.22 mmol), followed by 50% KOH(aq) (650 µL). The reaction mixture was vigorously stirred for 3 minutes. The reaction mixture was diluted with EtOAc (20 mL). The organic layer was separated, washed with sat. NaCl (2 mL), dried over MgSO$_4$, filtered and concentrated under reduced pressure. The residue was purified by ISCO (12 g silica gel column, 0-40% EtOAc/hexane over 35 min) to yield racemic (±)-methyl 4-(2-(4-fluoro-3-isopropoxyphenyl)-2-(3-fluoro-5-(1,1,2,2-tetrafluoroethoxy)phenyl)-2-isocyanoethyl)benzoate as a colorless film (87 mg, 79% yield). LCMS RT=2.24 min [M−NC] 525.1 (Phenomenex Luna C18 4.6×30 mm column, eluting with 10-90% MeOH/H$_2$O containing 0.% TFA, 2 min gradient, flow rate 5 mL/min, wavelength 220 nm); $^1$H NMR (400 MHz, CDCl$_3$) δ ppm 7.87 (2H, d, J=7.47 Hz), 7.08 (1H, t, J=9.67 Hz), 6.93-6.99 (5H, m), 6.87 (2H, d, J=6.59 Hz), 5.76-6.03 (1H, m), 4.40-4.46 (1H, m), 3.90 (3H, s), 3.65 (2H, s), 1.27 (6H, dd, J=17.58, 5.71 Hz).

A solution of (±)-methyl 4-(2-(4-fluoro-3-isopropoxyphenyl)-2-(3-fluoro-5-(1,1,2,2-tetrafluoroethoxy)phenyl)-2-isocyanoethyl)benzoate (87 mg) in isopropyl alcohol was subjected to chiral preparative HPLC (Chiralpak AD column, 5×50 cm isocratic elution with 10% IPA/heptane, 50 mL/min, monitoring at 254 nm) to yield (R)-methyl 4-(2-(4-fluoro-3-isopropoxyphenyl)-2-(3-fluoro-5-(1,1,2,2-tetrafluoroethoxy)phenyl)-2-isocyanoethyl)benzoate (35 mg) (chiral analytical HPLC: RT=8.9 min, chiralpak AD 4.6×250 mm column, isocratic elution with 10% IPA/heptane) and (S)-methyl 4-(2-(4-fluoro-3-isopropoxyphenyl)-2-(3-fluoro-5-(1,1,2,2-tetrafluoroethoxy)phenyl)-2-isocyanoethyl)benzoate (38 mg) (chiral analytical HPLC: RT=6.3 min, chiralpak AD 4.6×250 mm column, isocratic elution with 10% IPA/heptane) as clear colorless oils.

Procedure 176

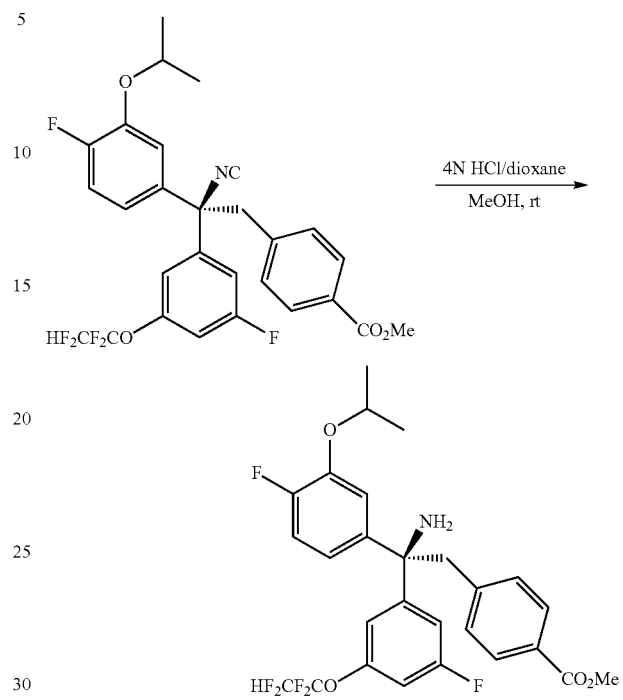

To a solution of (R)-methyl 4-(2-(4-fluoro-3-isopropoxyphenyl)-2-(3-fluoro-5-(1,1,2,2-tetrafluoroethoxy)phenyl)-2-isocyanoethyl)benzoate (120 mg, 0.22 mmol) in MeOH (2 mL) was added 4 N HCl in dioxane (0.5 mL) and the reaction mixture was stirred for 3 minutes. The reaction solvent was evaporated under a stream of nitrogen. The residue was diluted with EtOAc (15 mL), washed with saturated sodium bicarbonate solution (10 mL) and sat. NaCl, dried over MgSO$_4$, filtered and evaporated to yield (R)-methyl 4-(2-amino-2-(4-fluoro-3-isopropoxyphenyl)-2-(3-fluoro-5-(1,1,2,2-tetrafluoroethoxy)phenyl)ethyl)benzoate (103 mg, 86% yield) as a clear glass. LCMS: RT=1.87 min [M−NH$_2$] 525.1 (Phenomenex Luna C18 4.6×30 mm column, eluting with 10-90% MeOH/H$_2$O containing 0.% TFA, 2 min gradient, flow rate 5 mL/min, wavelength 220 nm).

Procedure 177

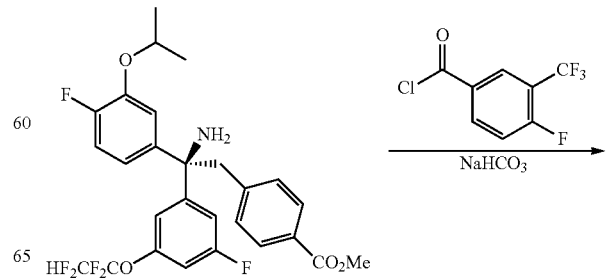

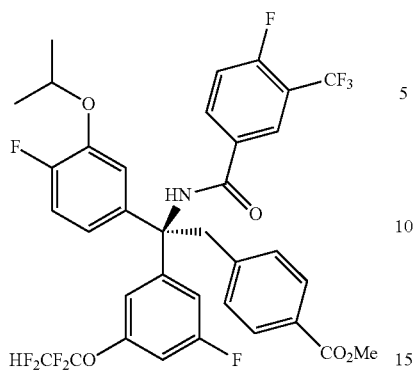

To a solution of (R)-methyl 4-(2-amino-2-(4-fluoro-3-isopropoxyphenyl)-2-(3-fluoro-5-(1,1,2,2-tetrafluoroethoxy) phenyl)ethyl)benzoate (50 mg, 0.09 mmol) in THF (2 mL) was added sodium bicarbonate (30 mg, 0.36 mmol). The reaction mixture was stirred at rt overnight. The reaction mixture was filtered and the filtrate was concentrated under reduced pressure. The residue was purified by ISCO (4 g silica gel column, 0-50% EtOAc/hexane over 30 min) to yield (R)-methyl 4-(2-(4-fluoro-3-(trifluoromethyl)benzamido)-2-(4-fluoro-3-isopropoxyphenyl)-2-(3-fluoro-5-(1,1,2,2-tetrafluoroethoxy)phenyl)ethyl)benzoate (53 mg, 79% yield) as a colorless film. LCMS: RT=2.28 min [M+H] 731.9 (Phenomenex Luna C18 4.6×30 mm column, eluting with 10-90% MeOH/H$_2$O containing 0.% TFA, 2 min gradient, flow rate 5 mL/min, wavelength 220 nm); HPLC: RT=4.28 min (Phenomenex Luna C18 4.6×50 mm column, eluting with 10-90% MeOH/H$_2$O containing 0.2% PPA, flow rate 4 mL/min, wavelength 220 nm); $^1$H NMR (400 MHz, CDCl$_3$) δ ppm 7.95 (1H, d, J=4.83 Hz), 7.81-7.84 (3H, m), 7.28-7.32 (1H, m), 6.94-7.04 (4H, m), 6.77-6.79 (2H, m), 6.53-6.63 (3H, m), 5.77-6.01 (1H, m), 4.30-4.35 (1H, m), 4.25 (1H, d, J=12.74 Hz), 3.89 (3H, s), 3.78 (1H, d, J=12.74 Hz), 1.28 (3H, d, J=6.15 Hz), 1.21 (3H, d, J=6.15 Hz).

To a solution of (R)-methyl 4-(2-(4-fluoro-3-(trifluoromethyl)benzamido)-2-(4-fluoro-3-isopropoxyphenyl)-2-(3-fluoro-5-(1,1,2,2-tetrafluoroethoxy)phenyl)ethyl)benzoate (20 mg, 0.027 mmol) in THF (2 mL) at −78° C. was added a solution of lithium triethylborohydride (1.0 M in THF, 0.5 mL, 0.5 mmol). The reaction mixture was stirred at −78° C. for 1.5 h. The reaction was quenched by the addition of 1 N NaOH (1 mL) and diluted with EtOAc (15 mL). The organic portion was washed with sat. NaCl (2×10 mL), dried over magnesium sulfate, filtered and concentrated under reduced pressure. The residue was purified by preparative HPLC (YMC Sunfire 5μ C18 30×100 mm column, eluting with 20-90% MeOH/H$_2$O containing 0.1% TFA, 10 min gradient, flow rate 40 mL/min, wavelength 220 nm) to yield (R)-4-fluoro-N-(1-(4-fluoro-3-isopropoxyphenyl)-1-(3-fluoro-5-(1,1,2,2-tetrafluoroethoxy)phenyl)-2-(4-(hydroxymethyl)phenyl)ethyl)-3-(trifluoromethyl)benzamide (Example 348, 13 mg, 78% yield) as a colorless film. LCMS: RT=2.17 min [M+H] 704.1 (Phenomenex Luna C18 4.6×30 mm column, eluting with 10-90% MeOH/H$_2$O containing 0.1% TFA, 2 min gradient, flow rate 5 mL/min, wavelength 220 nm); HPLC: RT=4.0 min (Phenomenex Luna C18 4.6×50 mm column, eluting with 10-90% MeOH/H$_2$O containing 0.2% PPA, flow rate 4 mL/min, wavelength 220 nm); $^1$H NMR (400 MHz, CDCl$_3$) δ ppm 7.91 (1H, d, J=6.59 Hz), 7.85-7.87 (1H, m) 7.26-7.31 (1H, m), 7.16 (2H, d, J=7.91 Hz), 6.93-7.05 (4H, m), 6.68-6.73 (3H, m), 6.60-6.66 (2H, m), 5.75-6.01 (1H, m), 4.64 (3H, s), 4.35 (1H, m), 4.06 (1H, d, J=13.2 Hz), 3.74 (1H, d, J=13.2 Hz), 1.29 (3H, d, J=6.15 Hz), 1.26 (1H, s), 1.23 (3H, d, J=6.15 Hz).

Example 273 can also be prepared by alternate procedures as set forth below.

Procedure 178

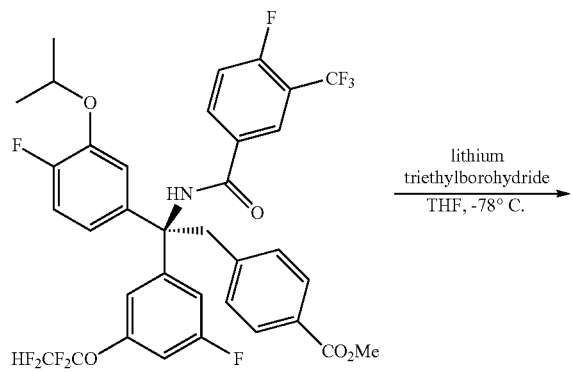

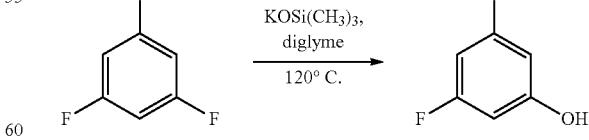

To a N$_2$ flushed, 2 L four necked flask equipped with a mechanical stirrer, a condenser, a temperature controller and a N$_2$ inlet, was added potassium trimethylsilanolate (225.0 g, 1.75 mol, tech. purify 90%), 1-bromo-3,5-difluorobenzene (96.5 g, 0.5 mol) and diglyme (300 mL). The reaction mixture was heated to 120° C. under N$_2$ for 5 h. After cooling to rt, the heating mantle was replaced with an ice bath. The reaction mixture was acidified with a 3 N HCl solution (600 mL) while keeping the reaction temperature below 30° C. Tertiary butyl methyl ether (1 L) was added and the resulting mixture was stirred below 20° C. for 30 min then transferred to a 5 L separatory funnel. The organic layer was separated and washed with water (3×500 mL), sat. NaCl (500 mL), dried over MgSO₄, filtered and concentrated in vacuo to give the crude red solid (145.0 g). The crude material was then distillated at 52-55° C./0.1 mm Hg to yield 3-bromo-5-fluorophenol as a slightly yellow oil (88.0 g, 92% yield). $^1$H NMR (300 MHz, CDCl₃) δ 5.34 (s, H), 6.47-6.52 (m, 1H), 6.77-6.83 (m, 2H).

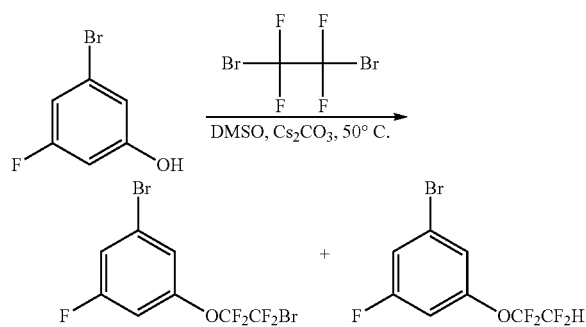

To a flame dried, 1 L, three necked round bottom flask equipped with a temperature controller, a mechanical stirrer, a condenser and a N₂ inlet was charged 3-bromo-5-fluorophenol (57.3 g, 300 mmol), 1,2-dibromo-1,1',2,2'-tetrafluoroethane (156.0 g, 600 mmol), dry DMSO (300 mL) and Cs₂CO₃ (146.6 g, 450 mmol) under N₂. The reaction mixture was heated to 50° C. for 5 h. After cooling to rt, water (300 mL) and hexane (300 mL) were added. The resulting mixture was stirred at rt for 30 min. The organic phase was separated and the aqueous layer was extracted with hexane (300 mL). The combined organic extracts were washed with water (500 mL), sat. NaCl (500 mL), dried over MgSO₄, filtered and concentrated in vacuo to give 1-bromo-3-(2-bromo-1,1,2,2-tetrafluoroethoxy)-5-fluorobenzene (104.2 g, 94% yield) containing 5% of 1-bromo-3-fluoro-5-(1,1,2,2-tetrafluoroethoxy)benzene (5.2 g). 1-Bromo-3-(2-bromo-1,1,2,2-tetrafluoroethoxy)-5-fluorobenzene: $^1$H NMR (300 MHz, CDCl₃) δ 6.91-6.94 (m, 1H), 7.18-7.23 (m, 2H).

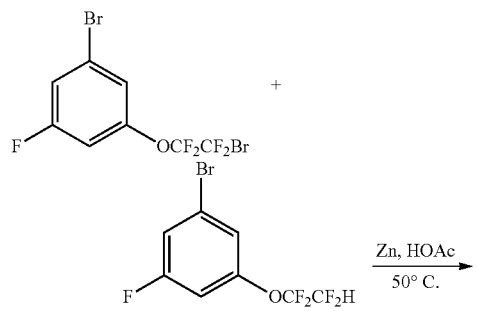

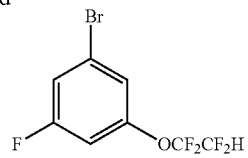

To a 1 L four necked round bottom flask equipped with a temperature controller, a mechanical stirrer, and a N₂ inlet, was added the crude mixture of 1-bromo-3-(2-bromo-1,1,2,2,-tetrafluoro-ethoxy)-5-fluorobenzene (104.0 g, 281 mmol) and 1-bromo-3-fluoro-5-(1,1,2,2-tetrafluoroethoxy)benzene (5.2 g, 18 mmol), acetic acid (300 mL). The reaction mixture was then heated to 50° C. Zinc dust (91.9 g, 1.405 mol) was added portion wise. The reaction mixture was stirred at 50° C. for 1 h and allowed to cool to rt. Water (300 mL) and hexane (300 mL) were added. The resulting mixture was stirred at rt for 30 min. The organic phase was separated and the aqueous layer was extracted with hexane (2×300 mL). The combined organic extracts were washed with water (500 mL), sat. NaCl (500 mL), dried over MgSO4, filtered and concentrated in vacuo to yield 1-bromo-3-fluoro-5-(1,1,2,2-tetrafluoroethoxy)benzene as a slightly yellow liquid (71 g, 87% yield). $^1$H NMR (300 MHz, CDCl₃) δ ppm 5.87 (tt, J=52.7 and 2.9 Hz, 1H), 6.91 (d, J=8.7 Hz, 1H), 7.16-7.18 (m, 2H). 1-bromo-3-fluoro-5-(1,1,2,2-tetrafluoroethoxy)benzene may be distilled at 0.6 mm Hg, 47-48° C. (bath 77-100° C.) to a colorless oil.

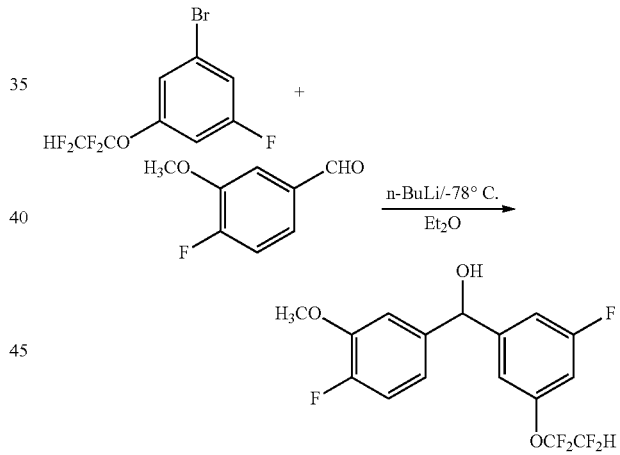

To a solution of 1-bromo-3-fluoro-5-(1,1,2,2-tetrafluoroethoxy)benzene, prepared as described in Procedure N, (1.00 g, 3.44 mmol) in diethyl ether in (10 mL) at −72° C. was added 2.5 M n-BuLi (1.37 mL, 3.44 mmol) dropwise. Upon completion of addition, the reaction mixture was stirred for 15 minutes at −72° C., then 4-fluoro-3-methoxybenzaldehyde (0.53 g, 3.44 mmol) was added while the reaction mixture temperature was maintained below −52° C. The reaction mixture was stirred for 3 h at −72° C. The reaction mixture was quenched by the addition of 1N HCl and the aqueous portion was extracted with EtOAc (2×). The combined organic layers were washed with sat. NaCl, dried over MgSO₄ and concentrated under reduced pressure. The residue was purified by ISCO using a gradient of 0-50% EtOAc/hexane as eluent to yield (4-fluoro-3-methoxyphenyl)(3-fluoro-5-(1,1,2,2-tetrafluoroethoxy)phenyl)methanol (0.83 g, 66% yield). HPLC: RT=3.85 min (Phenomenex Luna C18 5µ column, eluting with 10-90% aqueous methanol containing 0.1% phosphoric acid over a 4 minute gradient, flow rate 4 mL/min, monitoring at 220 nm); $^1$H NMR (CDCl$_3$): 7.05-6.8 (m, 6H), 5.87 (tt, J=2.8, 52.9 Hz), 5.75 (s, 1H), 3.85 (s, 3H).

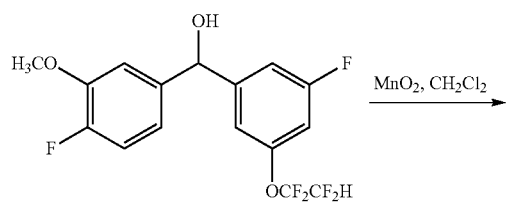

filtrate was concentrated under reduced pressure to yield (4-fluoro-3-methoxyphenyl)(3-fluoro-5-(1,1,2,2-tetrafluoroethoxy)phenyl)methanone (0.56 g, 98% yield). HPLC: RT=4.048 minutes (Phenomenex Luna C18 5µ column, eluting with 10-90% aqueous methanol containing 0.1% phosphoric acid over a 4 minute gradient, flow rate 4 mL/min, monitoring at 220 nm); LCMS: [M+H] 365.2 (Phenomenex Luna C18 5µ column, eluting with 10-90% aqueous methanol containing 0.1% TFA over a 2 minute gradient, flow rate 5 mL/min, monitoring at 220 nm); $^1$H NMR (400 MHz, CDCl$_3$): 7.5-7.1 (m, 6H), 5.92 (tt, J=2.2, 53.6 Hz, 1H), 3.93 (s, 3H).

Alternatively, (4-fluoro-3-methoxyphenyl)(3-fluoro-5-(1,1,2,2-tetrafluoroethoxy)phenyl)methanone may be prepared by the methods described in Procedure 4 from 4-fluoro-3-methoxybenzonitrile in 68% yield.

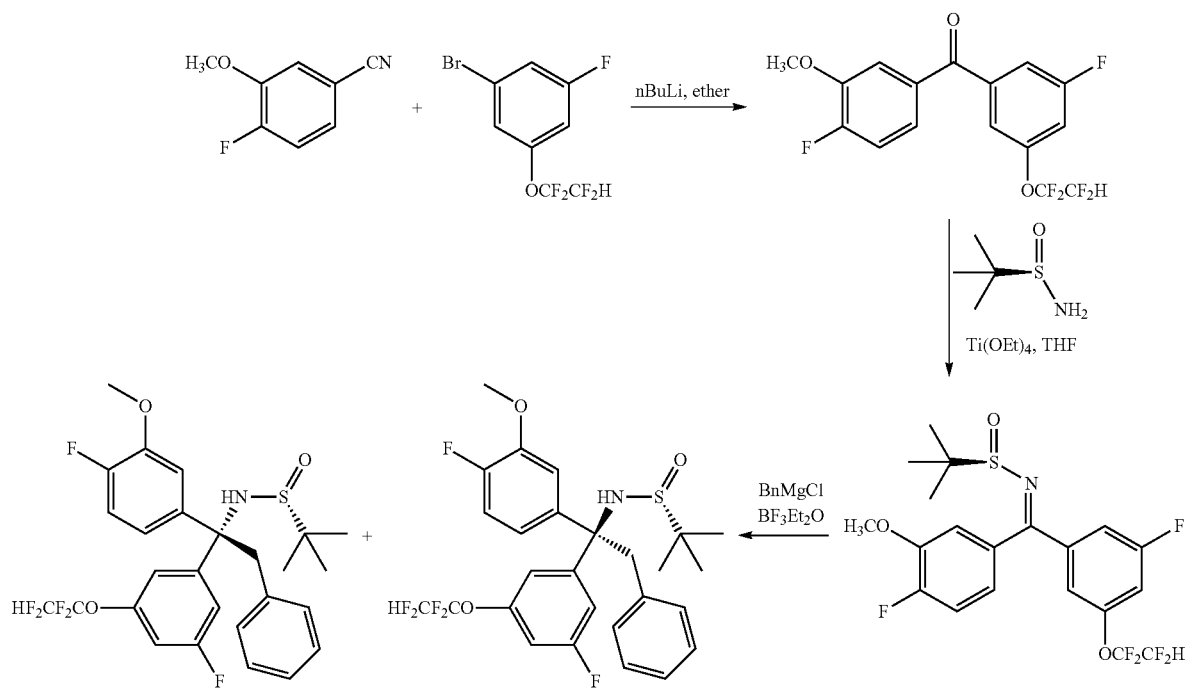

-continued

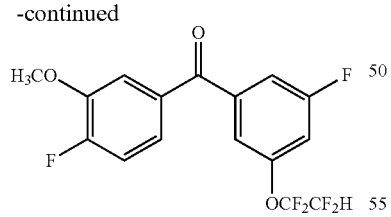

To a solution of (4-fluoro-3-methoxyphenyl)(3-fluoro-5-(1,1,2,2-tetrafluoroethoxy)phenyl)methanol (0.58 g, 1.57 mmol) in CH$_2$Cl$_2$ (5 mL) was added activated manganese dioxide (0.80 g, 7.86 mmol). The reaction mixture was stirred overnight at rt. Additional manganese dioxide (0.80 g, 7.86 mmol) was added and the reaction stirred at rt overnight. The reaction mixture was diluted with CH$_2$Cl$_2$ and filtered through celite and the solid was washed with CH$_2$Cl$_2$. The (R)—N-((4-fluoro-3-methoxyphenyl)(3-fluoro-5-(1,1,2,2-tetrafluoroethoxy)phenyl)methylene)-2-methylpropane-2-sulfinamide was prepared by the methods described in Procedures 5 yielding a 3:1 diastereomeric mixture of (R)—N—((R)-1-(4-fluoro-3-methoxyphenyl)-1-(3-fluoro-5-(1,1,2,2-tetrafluoroethoxy)phenyl)-2-methylpropane-2-sulfinamide and (S)—N—((R)-1-(4-fluoro-3-methoxyphenyl)-1-(3-fluoro-5-(1,1,2,2-tetrafluoroethoxy)phenyl)-2-phenylethyl)-2-methylpropane-2-sulfinamide in 90% yield. The diastereomers were separated by Chiralcel AD column chromatography elution with Heptane IPA (68% yield). Analytical data and yield for diastereomers in here. Isomer A: LCMS: [M+H] 560.2, retention time=4.08 min (Phenomenex Luna C18 5µ column, eluting with 10-90% aqueous methanol containing 0.1% TFA over a 4 minute gradient, flow rate 5 mL/min, monitoring at 220 nm); $^1$H NMR (400 MHz, CHLOROFORM-d) δ ppm 1.23 (s, 9H), 3.63 (d, J=12 Hz, 1H), 3.73 (s, 3H), 3.89 (d, J=12 Hz, 1H), 5.94 (tt, J=53, 2.4 Hz, 1H), 6.67-6.74 (m, 2H), 6.96-7.03 (m, 3H), 7.36-7.14 (m, 6H) ppm. Chiral HPLC: RT=8.21 min (Chiral AD column 4.6×

250 mm; 20% Isocratic; Solvent A=Heptane, Solvent B=0.1% DEA in IPA). Isomer B: LCMS: RT=4.022 min [M+H] 560.2 (4 min Phenomenex Luna C18 column, 4.6×50 mm eluting with 10-90% MeOH/H$_2$O over 4 minutes containing 0.1% TFA; 4 mL/min, monitoring at 220 nm). $^1$H NMR (400 MHz, CDCl$_3$) δ ppm 1.20 (s, 9H) 3.56 (d, J=12.09 Hz, 1H) 3.77 (s, 3H) 3.98 (d, J=12.64 Hz, 1H) 4.20 (s, 1H) 5.69-6.00 (m, 1H) 6.67-6.74 (m, 2H) 6.80-6.89 (m, 2H) 6.91 (d, J=7.70 Hz, 2H) 7.02-7.08 (m, 1H) 7.10 (s, 1H) 7.11-7.20 (m, 3H). Chiral HPLC: RT=10.34 min (Chiral AD column 4.6×250 mm; 20% Isocratic; Solvent A=Heptane, Solvent B=0.1% DEA in IPA).

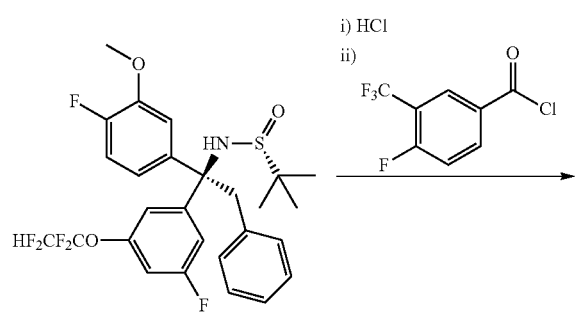

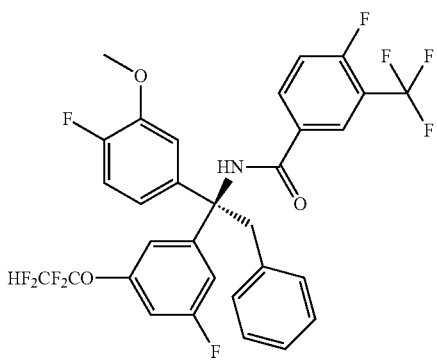

(R)—N—((R)-1-(4-fluoro-3-methoxyphenyl)-1-(3-fluoro-5-(1,1,2,2-tetrafluoroethoxy)phenyl)-2-phenylethyl)-2-methylpropane-2-sulfinamide was converted to (R)-4-fluoro-N-(1-(4-fluoro-3-methoxyphenyl)-1-(3-fluoro-5-(1,1,2,2-tetrafluoroethoxy)phenyl)-2-phenylethyl)-3-(trifluoromethyl)benzamide by the methods described in Procedure 6 and Procedure 7.

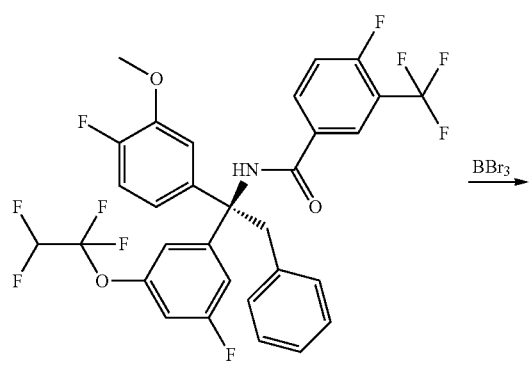

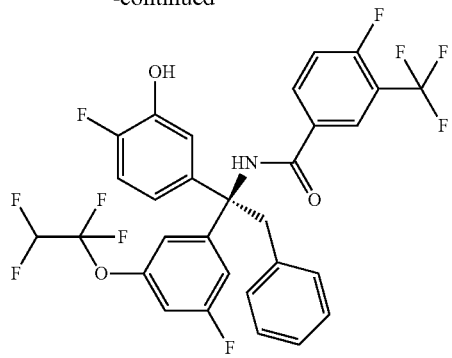

To a solution of (R)-4-fluoro-N-(1-(4-fluoro-3-methoxyphenyl)-1-(3-fluoro-5-(1,1,2,2-tetrafluoroethoxy)phenyl)-2-phenylethyl)-3-(trifluoromethyl)benzamide (2.8 g, 4.43 mmol), prepared as described in Procedure 5, 6 and 7 (44% yield), in CH$_2$Cl$_2$ (15 mL) was added BBr$_3$ (12 m, 12 mmol). The resulting mixture was stirred at room temperature for 2 h and quenched by addition of ice. The reaction mixture was diluted with EtOAc and washed with sat. NaHCO$_3$, sat. NaCl, dried over Na$_2$SO$_4$, filtered and concentrated to afford (R)-4-fluoro-N-(1-(4-fluoro-3-hydroxyphenyl)-1-(3-fluoro-5-(1,1,2,2)-tetrafluoro ethoxy)phenyl)-2-phenylethyl)-3-(trifluoromethyl)benzamide (Example 264) as clear oil (2.9 g, 100% yield). LCMS: RT=4.176 min [M+H] 632.2 (4 min Phenomenex Luna C18 column, 4.6×50 mm eluting with 10-90% MeOH/H$_2$O over 4 minutes containing 0.1% TFA;

To a solution of (R)-4-fluoro-N-(1-(4-fluoro-3-hydroxyphenyl)-1-(3-fluoro-5-(1,1,2,2)-tetrafluoro ethoxy)phenyl)-2-phenylethyl)-3-(trifluoromethyl)benzamide (Example 264, 2.70 g, 4.27 mmol) in DMF (6 mL) was added K$_2$CO$_3$ (1.47 g, 10.69 mmol), followed by isopropyl iodide (0.64 m, 6.40 mmol). The reaction mixture was stirred at 60° C. for 16 h. The reaction mixture was filtered and the solid was washed with EtOAc. The filtrate was washed with H₂O, sat. NaCl, dried over Na₂SO₄ and concentrated under reduced pressure. The residue was purified by ISCO silica gel column using 0 to 50% EtOAc in hexane as eluting solvents to yield (R)-4-fluoro-N-(1-(4-fluoro-3-isopropoxyphenyl)-1-(3-fluoro-5(1,1,2,2-tetrafluoro ethoxy)phenyl)-2-phenylethyl)-3-(trifluoromethyl)benzamide (Example 273) as white powder (2.4 g, 83% yield). LCMS: RT=4.05 min [M+H] 674.1 (Phenomenex Luna C18 column, 4.6×50 mm eluting with 10-90% MeOH/H₂O over 4 minutes containing 0.1% TFA; 5 mL/min, monitoring at 220 nm). ¹H NMR (400 MHz, CD₃OD) δ ppm 7.95-8.00 (2H, m), 7.42-7.47 (1H, m), 7.19 (1H, t, J=7.47 Hz), 7.12 (3H, t, J=7.25 Hz), 6.99-7.07 (3H, m), 6.71-6.81 (4H, m), 6.14-6.41 (1H, m), 4.26-4.32 (1H, m, J=6.15, 6.15, 6.15, 6.15 Hz), 4.12 (1H, d, J=13.18 Hz), 3.85 (1H, d, J=12.74 Hz), 1.23 (3H, d, J=6.15 Hz), 1.17 (3H, d, J=6.15 Hz).

Alternatively, (R)-4-fluoro-N-(1-(4-fluoro-3-isopropoxyphenyl)-1-(3-fluoro-5(1,1,2,2-tetrafluoro ethoxy)phenyl)-2-phenylethyl)-3-(trifluoromethyl)benzamide may be prepared by the following Procedures:

Procedure 179

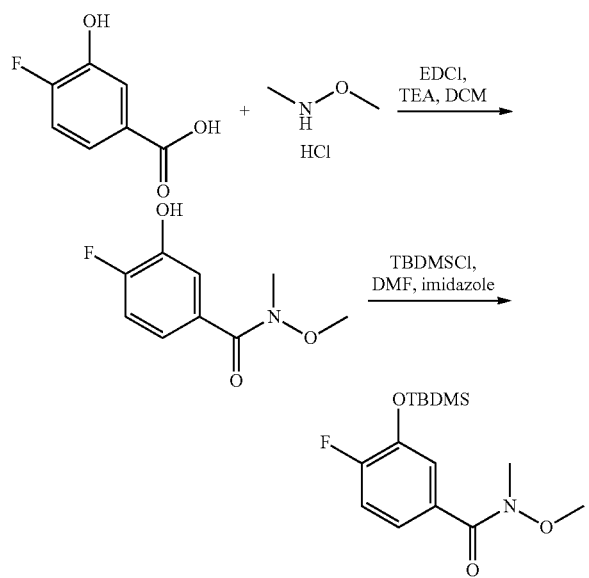

To a solution of 4-fluoro-3-hydroxybenzoic acid (1.49 g, 9.55 mmol) in DCM (40 mL) was added TEA (1.2 mL, 8.61 mmol) followed by N,O-dimethylhydroxylamine hydrochloride (1.12 g, 11.5 mmol). The reaction mixture was stirred at room temperature for 3 h, then diluted with DCM, washed with water twice, dried over Na₂SO₄, filtered and concentrated to yield 4-fluoro-3-hydroxy-N-methoxy-N-methylbenzamide as a colorless oil (1.90 g, 100% yield). LCMS: RT=0.89 min [M+H] 200.10 (Phenomenex Luna C18 column, 4.6×30 mm eluting with 10-90% MeOH/H₂O over 2 minutes containing 0.1% TFA; 5 mL/min, monitoring at 220 nm).

To a solution of 4-fluoro-3-hydroxy-N-methoxy-N-methylbenzamide (1.90 g, 9.55 mmol) in DMF (8 mL) was added imidazole (740 mg, 10.8 mmol) and TBDMSCl (1.62 g, 10.8 mmol) at room temperature. The reaction mixture was stirred for 48 h and quenched with saturated NaHCO₃. The solution was extracted with ether (3×) and the combined ether portions were washed with LiCl (10%), dried over Na₂SO₄, filtered and concentrated. The resulting colorless oil was purified by ISCO chromatography (120 g column) using hexanes/EtOAc (0-100% over 30 min) to give 3-(tert-butyldimethylsilyloxy)-4-fluoro-N-methoxy-N-methylbenzamide (RT=10-12 minutes) as a colorless oil (2.00 g, 67% yield). LCMS: RT=2.06 min [M+H] 314.22 (Phenomenex Luna C18 column, 4.6×30 mm eluting with 10-90% MeOH/H₂O over 2 minutes containing 0.1% TFA; 5 mL/min, monitoring at 220 nm); NMR: 400 MHz ¹H (CDCl₃) 7.26 ppm, 2H, m; 7.02 ppm, 1H, m; 3.50 ppm, 3H, s; 3.31 ppm, 3H, s; 0.97 ppm, 9H, s, 0.16 ppm, 6H, s.

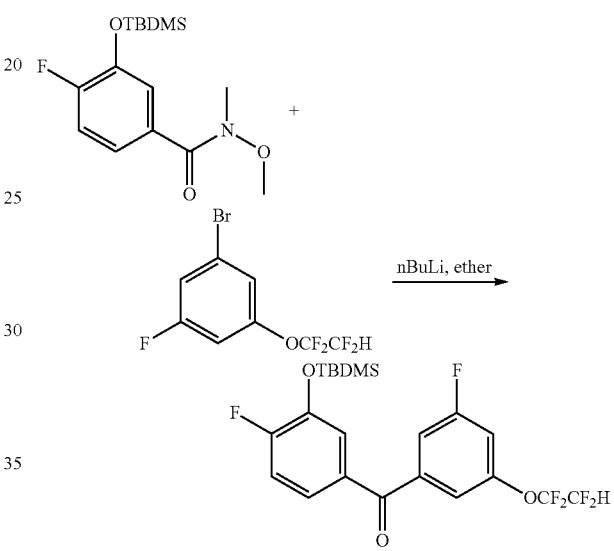

At −78° C. under argon, to a solution of 1-bromo-3-fluoro-5-(1,1,2,2-tetrafluoroethoxy)benzene (2.04 g, 7.01 mmol) in anhydrous ether (20 mL) was added nBuLi (3.5 mL, 2.0 M in cyclohexane, 7.0 mmol) dropwise and the reaction mixture was stirred for 1 h. 3-(Tert-butyldimethylsilyloxy)-4-fluoro-N-methoxy-N-methylbenzamide (2.00 g, 6.38 mmol) was added in one portion and the reaction mixture was stirred at −78° C. for 1.5 h. The pale yellow solution was poured into a 1 N HCl aqueous solution (30 mL) and ether (30 mL) was used to rinse the reaction flask. The aqueous phase was separated and extracted with diethyl ether (20 mL). The combined ether portions were dried over Na₂SO₄, filtered and concentrated. The resulting oil was purified by ISCO chromatography (120 g column) using hexanes/EtOAc (0-100% over 30 min) to give (3-(tert-butyldimethylsilyloxy)-4-fluorophenyl)(3-fluoro-5-(1,1,2,2-tetrafluoroethoxy)phenyl)methanone at a retention time of 7 min (2.11 g, 71% yield). LCMS: RT=2.41 min [M+H] 465.19 (Phenomenex Luna C18 column, 4.6×30 mm eluting with 10-90% MeOH/H₂O over 2 minutes containing 0.1% TFA; 5 mL/min, monitoring at 220 nm); NMR: 400 MHz ¹H (CDCl₃) 7.33 ppm, 3H, m; 7.28 ppm, 1H, m; 7.11 ppm, 2H, m; 5.86 ppm, 1H, t, J=53.39 Hz; 0.95 ppm, 9H, s; 0.15 ppm, 6H, s.

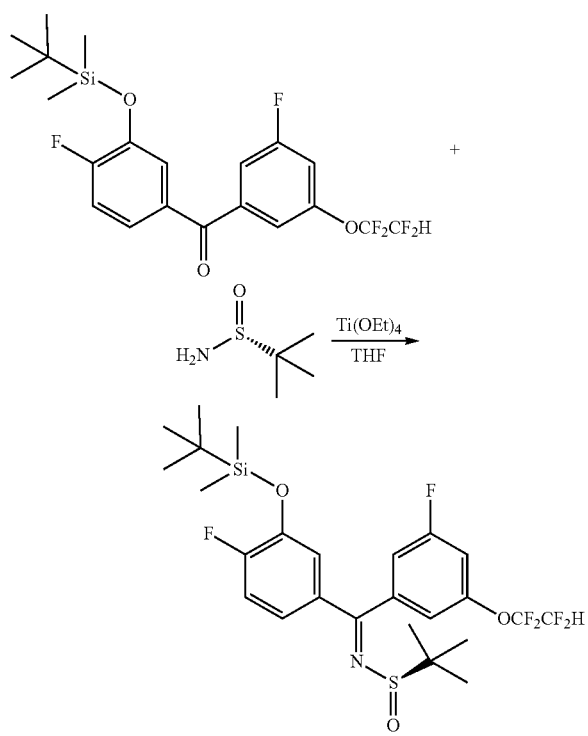

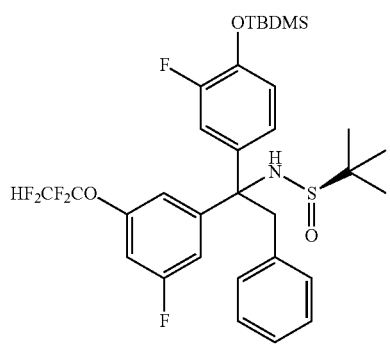

A round bottom flask was charged with (3-(tert-butyldimethylsilyloxy)-4-fluorophenyl)(3-fluoro-5-(1,1,2,2-tetrafluoroethoxy)phenyl)methanone (2.09 g, 4.50 mmol), (R)-2-methylpropane-2-sulfinamide (653 mg, 5.4 mmol), Ti(OEt)$_4$ (1.54 g, 6.76 mmol) and anhydrous THF (40 mL). The resulting solution was heated at 75° C. under argon for 14 h. The solvents were removed and the residue was diluted with ether (50 mL) and sat. NaCl (20 mL). The resulting mixture was filtered through a glass frit and the filtrate transferred to a separatory funnel. The organic portion was separated and the aqueous phase extracted with diethyl ether (2×20 mL). The combined organic portions were dried over Na$_2$SO$_4$, filtered and concentrated. The residue was dissolved in hexane:EtOAc and purified by ISCO chromatography (2×120 g column) using hexanes/EtOAc (0-100% over 30 min) to yield (R)—N-((3-(tert-butyldimethylsilyloxy)-4-fluorophenyl)(3-fluoro-5-(1,1,2,2-tetrafluoroethoxy)phenyl)methylene)-2-methylpropane-2-sulfinamide at a retention time of 14 min (2.05 g, 80% yield) LCMS: RT=2.37 min [M+H] 568.24 (Phenomenex Luna C18 column, 4.6×30 mm eluting with 10-90% MeOH/H$_2$O over 2 minutes containing 0.1% TFA; 5 mL/min, monitoring at 220 nm). NMR: 400 MHz $^1$H (CDCl$_3$) 7.36 ppm, 1H, m; 7.11 ppm, 5H, m; 5.90 ppm, 1H, t, J=52.73 Hz; 0.97 ppm, 9H, s; 0.18 ppm, 6H, s.

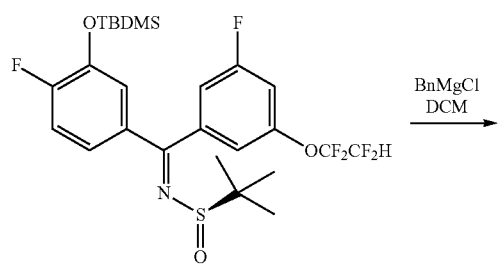

At −78° C. to a solution of (R)—N-((3-(tert-butyldimethylsilyloxy)-4-fluorophenyl)(3-fluoro-5-(1,1,2,2-tetrafluoroethoxy)phenyl)methylene)-2-methylpropane-2-sulfinamide (1.0 g, 1.76 mmol) in DCM (50 mL) was added BF$_3$.Et$_2$O (0.77 mL, 3.52 mmol) via syringe. After 5 min, BnMgCl solution (3.5 mL, 1.0 M solution in ether, 3.5 mmol) was added dropwise and the reaction mixture was stirred at −78° C. for 1 h. An additional portion of BnMgCl (3.5 mL, 1.0 M solution in ether, 3.5 mmol) was added dropwise and the reaction was stirred for an additional 1 h at −78° C. The reaction mixture was poured into saturated NaCl (50 mL) and the organic layer was separated. The aqueous layer was extracted with DCM (2×20 mL) and the combined organic layers were dried over Na$_2$SO$_4$, filtered and concentrated. The resulting oil was purified by ISCO chromatography (120 g column) using hexanes/EtOAc (0-100% over 30 min) to give an approximate 4:1 mixture of (R)—N-(1-(4-(tert-butyldimethylsilyloxy)-3-fluorophenyl)-1-(3-fluoro-5-(1,1,2,2-tetrafluoroethoxy)phenyl)-2-phenylethyl)-2-methylpropane-2-sulfinamide and (S)—N-(1-(4-(tert-butyldimethylsilyloxy)-3-fluorophenyl)-1-(3-fluoro-5-(1,1,2,2-tetrafluoroethoxy)phenyl)-2-phenylethyl)-2-methylpropane-2-sulfinamide at a retention time of 12 min (824 mg, 71% yield) LCMS: RT=2.43 min [M+H] 660.39 (Phenomenex Luna C18 column, 4.6×30 mm eluting with 10-90% MeOH/H$_2$O over 2 minutes containing 0.1% TFA; 5 mL/min, monitoring at 220 nm). The diastereomeric ratio of the product was determined to be 4:1 by Chiral HPLC analysis (Chiralcel® AD, 90:10 heptane:i-PrOH, 1 mL/min, 254 nm, RT (minor)=4.43 min, PA=17%; RT (major)=19.28 min, PA=71%) and the diastereomeric mixture was taken on directly to the next step, Procedure 112, or the diastereomers were separated as described in Procedure 114. NMR: 400 MHz $^1$H (CDCl$_3$) 7.30 ppm, 2H, m; 7.06 ppm, 5H, m; 6.85 ppm, 2H, m; 6.76 ppm, 1H, m; 6.62 ppm, 2H, m; 5.79 ppm, 1H, m; 4.13 ppm, 1H, s; 3.84 ppm, 1H, m; 3.47 ppm, 1H, m; 1.12 ppm, 9H, s; 0.84 ppm, 9H, s; 0.01 ppm, 6H, d, J=4.39 Hz.

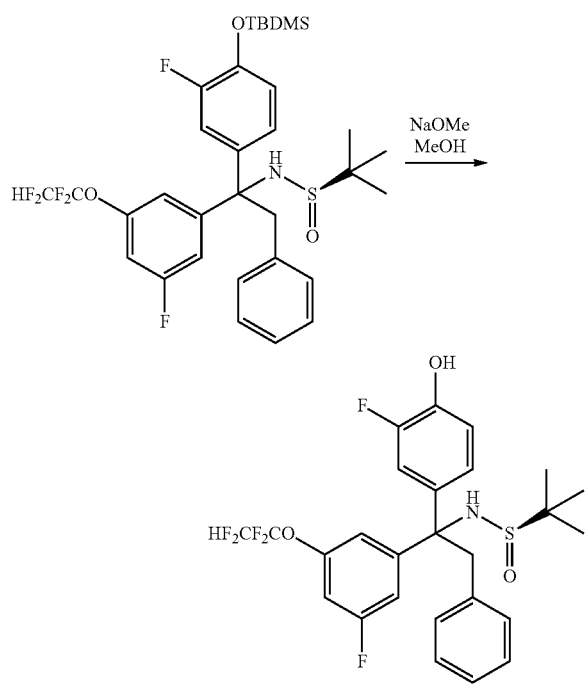

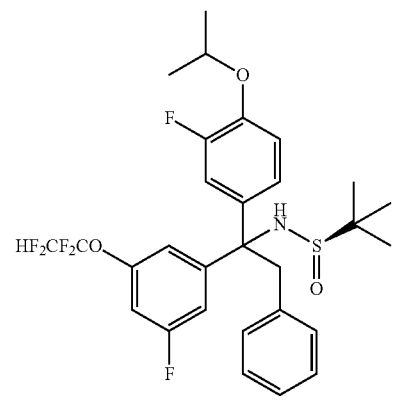

At rt to a solution of 4:1 diastereomeric mixture (R)—N-(1-(3-fluoro-4-hydroxyphenyl)-1-(3-fluoro-5-(1,1,2,2-tetrafluoroethoxy)phenyl)-2-phenylethyl)-2-methylpropane-2-sulfinamide (578 mg, 1.06 mmol) in DMF (10 mL) was added $K_2CO_3$ (800 mg, 5.80 mmol) and the slurry was stirred vigorously. 2-Iodopropane (220 mg, 1.27 mmol) was added and the reaction mixture was stirred at rt for 16 h. The reaction mixture was diluted with ether (50 mL), washed successively with 10% LiCl (2×20 mL) and water (20 mL). The organic portion was dried over $Na_2SO_4$, filtered and concentrated to yield (R)—N-(1-(3-fluoro-4-isopropoxyphenyl)-1-(3-fluoro-5-(1,1,2,2-tetrafluoroethoxy)phenyl)-2-phenylethyl)-2-methylpropane-2-sulfinamide as a pale orange foam (780 mg, 100% yield).

At room temperature a solution of NaOMe (5 mL, 0.5 M solution in MeOH) was added to the 4:1 diastereomeric mixture of (R)—N-(1-(4-(tert-butyldimethylsilyloxy)-3-fluorophenyl)-1-(3-fluoro-5-(1,1,2,2-tetrafluoroethoxy)phenyl)-2-phenylethyl)-2-methylpropane-2-sulfinamide (801 mg, 1.22 mmol). The reaction mixture was stirred for 15 minutes, MeOH was removed then the residue dissolved in EtOAc (50 mL) and transferred to a separation funnel. HCl (20 mL, 1.0 N solution) was added and the EtOAc layer was separated. The aqueous layer was extracted with EtOAc (2×10 mL) and the combined organic layers were dried over $Na_2SO_4$, filtered and concentrated to yield (R)—N-(1-(3-fluoro-4-hydroxyphenyl)-1-(3-fluoro-5-(1,1,2,2-tetrafluoroethoxy)phenyl)-2-phenylethyl)-2-methylpropane-2-sulfinamide as a white foam (578 mg, 87% yield). LCMS: RT=1.987 min [M+H] 546.35 (Phenomenex Luna C18 column, 4.6×30 mm eluting with 10-90% MeOH/$H_2O$ over 2 minutes containing 0.1% TFA; 5 mL/min, monitoring at 220 nm).

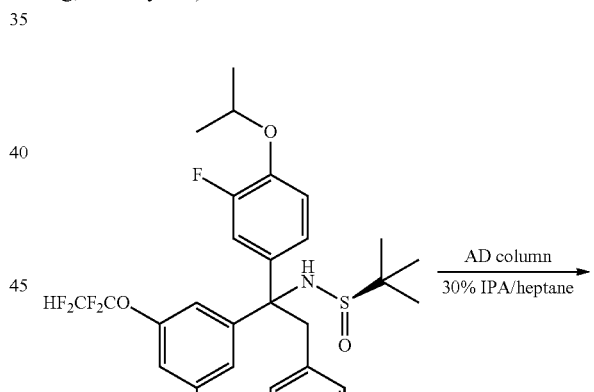

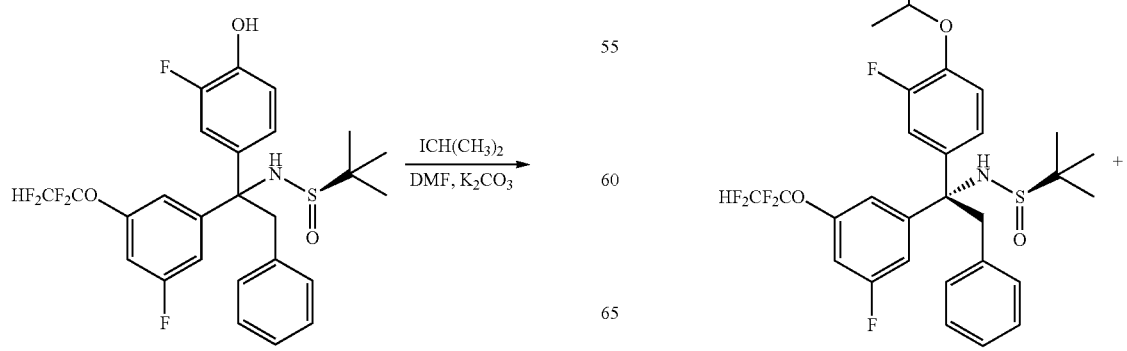

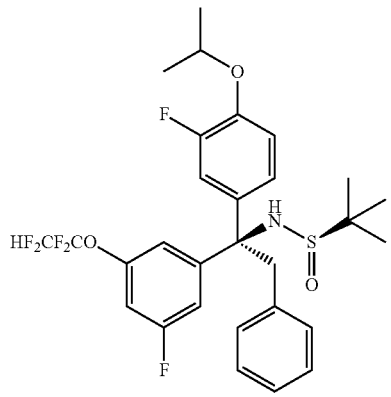

The 4:1 diastereomeric mixture of (R)—N-(1-(3-fluoro-4-isopropoxyphenyl)-1-(3-fluoro-5-(1,1,2,2-tetrafluoroethoxy)phenyl)-2-phenylethyl)-2-methylpropane-2-sulfinamide (780 mg, 1.06 mmol crude) was separated by Chiral preparative HPLC chiralpak AD 20μ column, 5×50 cm, eluting with 30% IPA/Heptane with flow rate 50 mL/min.

(R)—N—((S)-1-(3-fluoro-4-isopropoxyphenyl)-1-(3-fluoro-5-(1,1,2,2-tetrafluoroethoxy)phenyl)-2-phenylethyl)-2-methylpropane-2-sulfinamide was eluted at a retention time of 17 min and isolated as a colorless oil (101 mg, yield 16%). LCMS: RT=2.128 min [M+H] 588.38 (Phenomenex Luna C18 column, 4.6×30 mm eluting with 10-90% MeOH/$H_2O$ over 2 minutes containing 0.1% TFA; 5 mL/min, monitoring at 220 nm); Chiral HPLC: RT=4.35 min, ee 100% (Diacel Chiralpak AD 10μ column, 4.6×250 mm isocratic elution with IPA (20%) and heptane; 1 mL/min, monitoring at 254 nm).

(R)—N—((R)-1-(3-fluoro-4-isopropoxyphenyl)-1-(3-fluoro-5-(1,1,2,2-tetrafluoroethoxy)phenyl)-2-phenylethyl)-2-methylpropane-2-sulfinamide was eluted at a retention time of 39 min and isolated and was isolated as a colorless oil (398 mg, yield 64%). LCMS: RT=2.138 min [M+H] 588.38 (Phenomenex Luna C18 column, 4.6×30 mm eluting with 10-90% MeOH/$H_2O$ over 2 minutes containing 0.1% TFA; 5 mL/min, monitoring at 220 nm); Chiral HPLC: RT=9.98 min, ee 100% (Diacel Chiralpak AD 10μ column, 4.6×250 mm isocratic elution with IPA (20%) and heptane; 1 mL/min, monitoring at 254 nm) NMR: 400 MHz $^1H$ ($CDCl_3$) 7.08 ppm, 5H, m; 6.84 ppm, 2H, d, J=7.47 Hz; 6.77 ppm, 2H, d, J=7.47 Hz; 6.63 ppm, 2H, m; 5.79 ppm, 1H, t, J=52.95 Hz; 4.33 ppm, 1H, m; 4.15 ppm, 1H, s; 3.92 ppm, 1H, d, J=12.30 Hz; 3.48 ppm, 1H, d, J=12.30 Hz; 1.22 ppm, 3H, d, J=6.15 Hz; 1.18 ppm, 3H, d, J=5.71 Hz; 1.14 ppm, 9H, s.

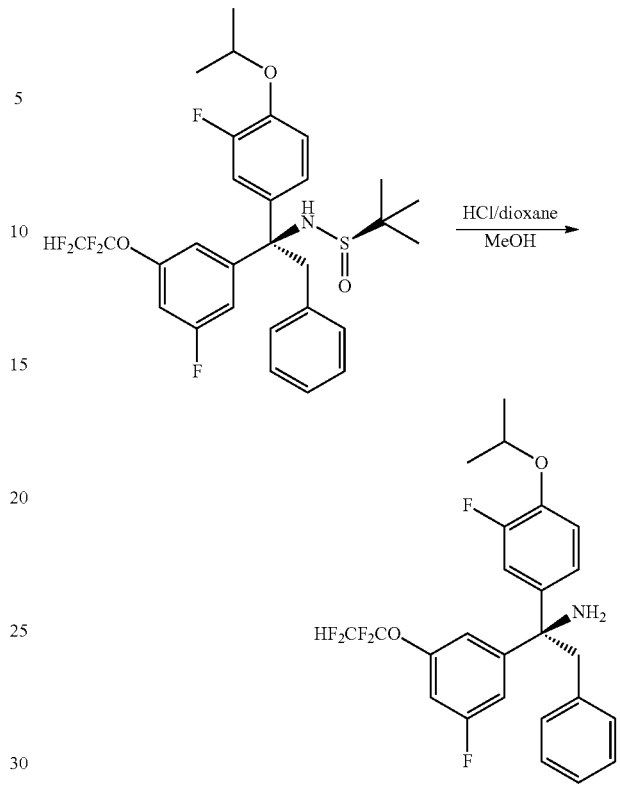

To a solution of (R)—N—((R)-1-(3-fluoro-4-isopropoxyphenyl)-1-(3-fluoro-5-(1,1,2,2-tetrafluoroethoxy)phenyl)-2-phenylethyl)-2-methylpropane-2-sulfinamide (398 mg, 0.678 mmol) in MeOH (1.5 mL) was added HCl (1.5 mL, 4 M solution in dioxane) and the reaction mixture was stirred for 30 min. The reaction mixture was diluted with ether (50 mL) and the organic layer was washed with sat. $NaHCO_3$ (20 mL), dried over $Na_2SO_4$, filtered and concentrated to give (R)-1-(3-fluoro-4-isopropoxyphenyl)-1-(3-fluoro-5-(1,1,2,2-tetrafluoroethoxy)phenyl)-2-phenylethanamine as a colorless oil (334 mg, 100% yield). LCMS: RT=1.76 min [M−$NH_2$] 467.24 (Phenomenex Luna C18 column, 4.6×30 mm eluting with 10-90% MeOH/$H_2O$ over 2 minutes containing 0.1% TFA; 5 mL/min, monitoring at 220 nm); HPLC: RT=3.04 min, Purity 95% (Phenomenex Luna C18 column, 4.6×50 mm eluting with 10-90% MeOH/$H_2O$ over 4 minutes containing 0.2% PPA; 4 mL/min, monitoring at 220 nm) NMR: 400 MHz $^1H$ ($CDCl_3$) 7.15 ppm, 3H, m; 6.99 ppm, 4H, m; 6.89 ppm, 1H, m; 6.84 ppm, 1H, d, J=8.79 Hz; 6.74 ppm, 2H, d, J=6.15 Hz; 5.87 ppm, 1H, m; 4.42 ppm, 1H, m; 3.47 ppm, 2H, s; 1.27 ppm, 6H, dd, J=7.91, 6.15 Hz.

Alternatively, the diastereomeric mixture of (R)—N-(1-(4-(tert-butyldimethylsilyloxy)-3-fluorophenyl)-1-(3-fluoro-5-(1,1,2,2-tetrafluoroethoxy)phenyl)-2-phenylethyl)-2-methylpropane-2-sulfinamide can be separated as described in Procedure 114 and the individual diastereomers converted to (R) and (S)-1-(3-fluoro-4-isopropoxyphenyl)-1-(3-fluoro-5-(1,1,2,2-tetrafluoroethoxy)phenyl)-2-phenylethanamine by the methods described in Procedure 113.

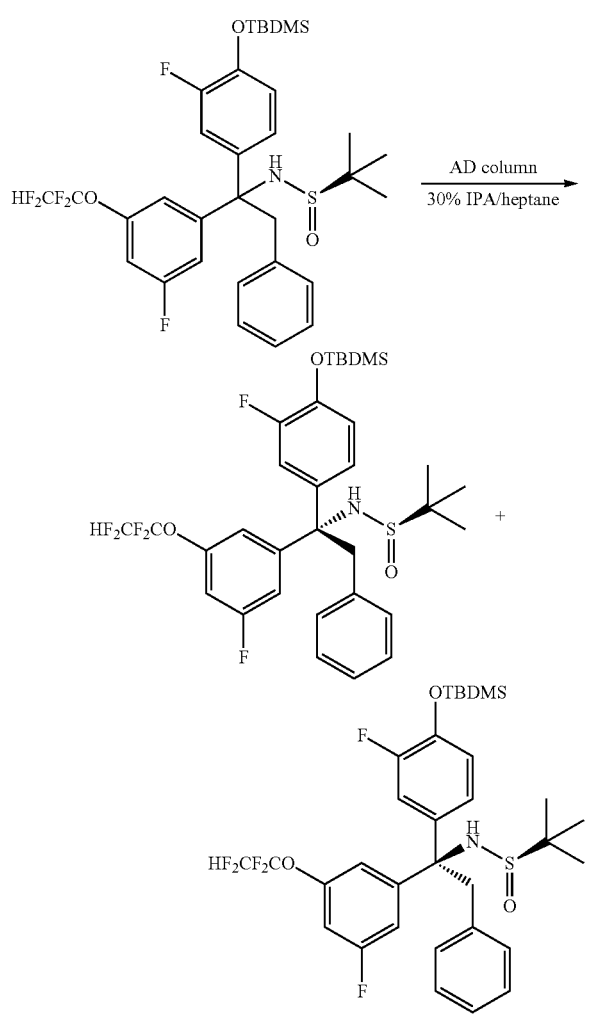

The diastereomer mixture of (R)—N-(1-(4-(tert-butyldimethylsilyloxy)-3-fluorophenyl)-1-(3-fluoro-5-(1,1,2,2-tetrafluoroethoxy)phenyl)-2-phenylethyl)-2-methylpropane-2-sulfinamide (1.14 g, 1.73 mmol) was separated by Chiral preparative HPLC chiralpak AD 20μ column, 5×50 cm, eluting with 30% IPA/Heptane with flow rate 50 mL/min.

(R)—N—((S)-1-(4-(tert-butyldimethylsilyloxy)-3-fluorophenyl)-1-(3-fluoro-5-(1,1,2,2-tetrafluoroethoxy)phenyl)-2-phenylethyl)-2-methylpropane-2-sulfinamide was eluted at a retention time of 19 min (114 mg, yield 10%). LCMS: RT=2.45 min [M+H] 660.41 (Phenomenex Luna C18 column, 4.6×30 mm eluting with 10-90% MeOH/H₂O over 2 minutes containing 0.1% TFA; 5 mL/min, monitoring at 220 nm).

(R)—N—((R)-1-(4-(tert-butyldimethylsilyloxy)-3-fluorophenyl)-1-(3-fluoro-5-(1,1,2,2-tetrafluoroethoxy)phenyl)-2-phenylethyl)-2-methylpropane-2-sulfinamide was eluted at a retention time of 36 min (634 mg, yield 56%). LCMS: RT=2.41 min [M+H] 660.39 (Phenomenex Luna C18 column, 4.6×30 mm eluting with 10-90% MeOH/H₂O over 2 minutes containing 0.1% TFA; 5 mL/min, monitoring at 220 nm); Chiral HPLC: RT=8.54 min, ee 100% (Diacel Chiralpak AD 10 column, 4.6×250 mm isocratic elution with IPA (20%) and heptane; 1 mL/min, monitoring at 254 nm) NMR: 400 MHz ¹H (CDCl₃) 7.03 ppm, 5H, m; 6.84 ppm, 2H, m; 6.74 ppm, 1H, d, J=8.79 Hz; 6.66 ppm, 1H, dd, J=8.13, 1.98 Hz; 6.61 ppm, 2H, m; 5.76 ppm, 1H, m; 4.12 ppm, 1H, s; 3.90 ppm, 1H, d, J=12.74 Hz; 3.46 ppm, 1H, d, J=12.30 Hz; 1.11 ppm, 9H, s; 0.84 ppm, 9H, s; 0.01 ppm, 6H, d, J=4.83 Hz.

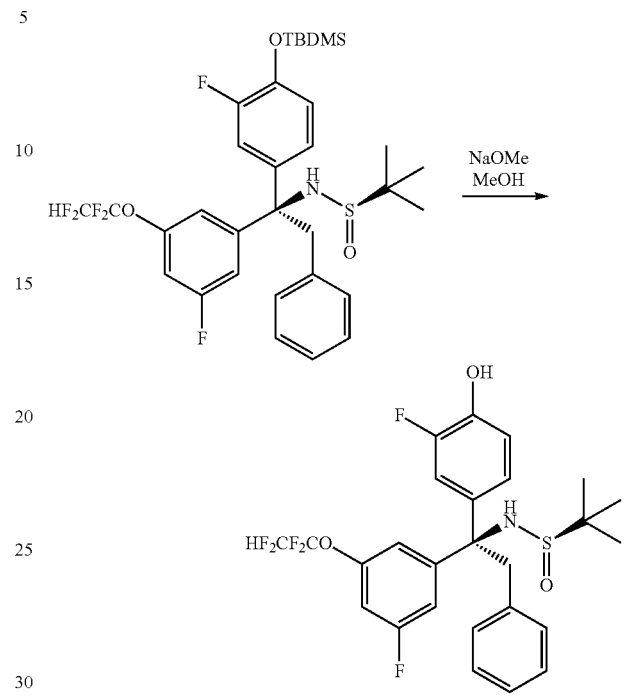

(R)—N—((R)-1-(3-fluoro-4-hydroxyphenyl)-1-(3-fluoro-5-(1,1,2,2-tetrafluoroethoxy)phenyl)-2-phenylethyl)-2-methylpropane-2-sulfinamide was prepared from (R)—N—((R)-1-(4-(tert-butyldimethylsilyloxy)-3-fluorophenyl)-1-(3-fluoro-5-(1,1,2,2-tetrafluoroethoxy)phenyl)-2-phenylethyl)-2-methylpropane-2-sulfinamide as described in Procedure 112 in quantitative yield. LCMS: RT=1.998 min [M+H] 546.28 (Phenomenex Luna C18 column, 4.6×30 mm eluting with 10-90% MeOH/H₂O over 2 minutes containing 0.1% TFA; 5 mL/min, monitoring at 220 nm). HPLC: RT=3.83 min, Purity 98% (Phenomenex Luna C18 column, 4.6×50 mm eluting with 10-90% MeOH/H₂O over 4 minutes containing 0.2% PPA; 4 mL/min, monitoring at 220 nm) NMR: 400 MHz ¹H (CDCl₃) 7.61 ppm, 1H, s; 7.40 ppm, 1H, dd, J=8.13, 1.98 Hz; 7.13 ppm, 3H, m; 6.99 ppm, 1H, dd, J=10.33, 8.57 Hz; 6.84 ppm, 3H, m; 6.68 ppm, 2H, m; 6.61 ppm, 1H, m; 5.85 ppm, 1H, tt, J=52.95, 2.64 Hz; 4.30 ppm, 1H, s; 4.02 ppm, 1H, d, J=12.30 Hz; 3.50 ppm, 1H, d, J=12.30 Hz; 1.24 ppm, 9H, s.

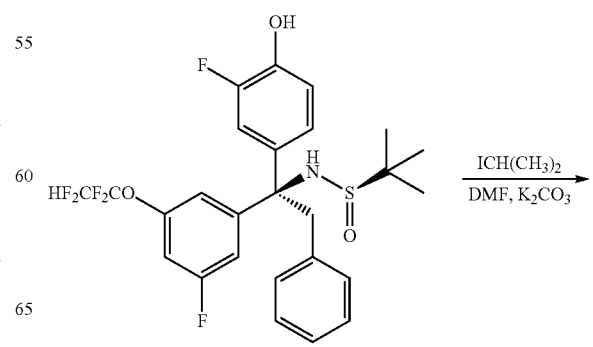

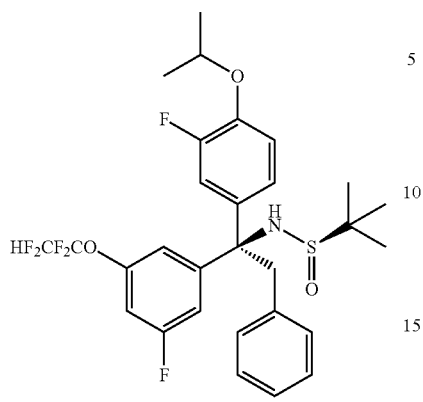

(R)—N—((R)-1-(3-fluoro-4-isopropoxyphenyl)-1-(3-fluoro-5-(1,1,2,2-tetrafluoroethoxy)phenyl)-2-phenylethyl)-2-methylpropane-2-sulfinamide was prepared from (R)—N-(1-(3-fluoro-4-hydroxyphenyl)-1-(3-fluoro-5-(1,1,2,2-tetrafluoroethoxy)phenyl)-2-phenylethyl)-2-methylpropane-2-sulfinamide as described in Procedure 6 in 78% yield. LCMS: RT=2.17 min [M+H] 588.17 (Phenomenex Luna C18 column, 4.6×30 mm eluting with 10-90% MeOH/H₂O over 2 minutes containing 0.1% TFA; 5 mL/min, monitoring at 220 nm) HPLC: RT=4.20 min, Purity 95% (Phenomenex Luna C18 column, 4.6×50 mm eluting with 10-90% MeOH/H₂O over 4 minutes containing 0.2% PPA; 4 mL/min, monitoring at 220 nm) NMR: 400 MHz ¹H (CDCl₃) 7.16 ppm, 3H, m; 7.10 ppm, 2H, m; 6.87 ppm, 4H, m; 6.70 ppm, 2H, m; 5.86 ppm, 1H, m; 4.41 ppm, 1H, m; 4.31 ppm, 1H, s; 3.98 ppm, 1H, d, J=12.74 Hz; 3.56 ppm, 1H, d, J=12.74 Hz; 1.30 ppm, 3H, d, J=5.71 Hz; 1.25 ppm, 3H, d, J=6.15 Hz; 1.22 ppm, 9H, s.

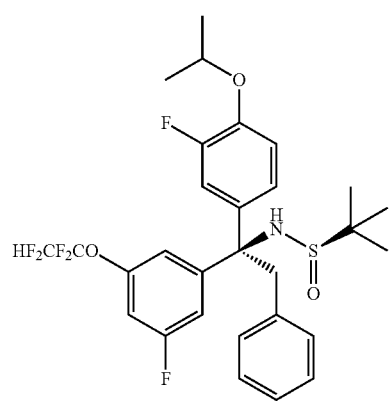

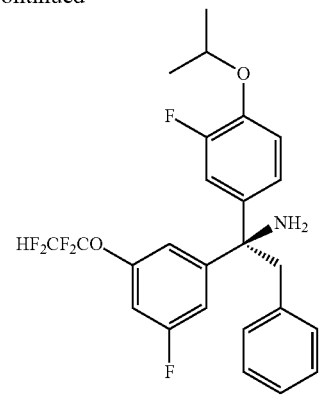

(R)-1-(3-fluoro-4-isopropoxyphenyl)-1-(3-fluoro-5-(1,1,2,2-tetrafluoroethoxy)phenyl)-2-phenylethanamine was prepared from (R)—N—((R)-1-(3-fluoro-4-isopropoxyphenyl)-1-(3-fluoro-5-(1,1,2,2-tetrafluoroethoxy)phenyl)-2-phenylethyl)-2-methylpropane-2-sulfinamide as described in Procedure 6 in 97% yield. LCMS: RT=1.83 min [M−NH₂] 467.24 (Phenomenex Luna C18 column, 4.6×30 mm eluting with 10-90% MeOH/H₂O over 2 minutes containing 0.1% TFA; 5 mL/min, monitoring at 220 nm); HPLC: RT=3.17 min, Purity 100% (Phenomenex Luna C18 column, 4.6×50 mm eluting with 10-90% MeOH/H₂O over 4 minutes containing 0.2% PPA; 4 mL/min, monitoring at 220 nm) NMR: 400 MHz ¹H (CDCl₃) 7.16 ppm, 3H, m; 7.01 ppm, 3H, m; 6.92 ppm, 2H, m; 6.84 ppm, 1H, d, J=8.79 Hz; 6.74 ppm, 2H, d, J=7.03 Hz; 5.86 ppm, 1H, m; 4.41 ppm, 1H, m; 3.49 ppm, 2H, s; 1.25 ppm, 6H, m.

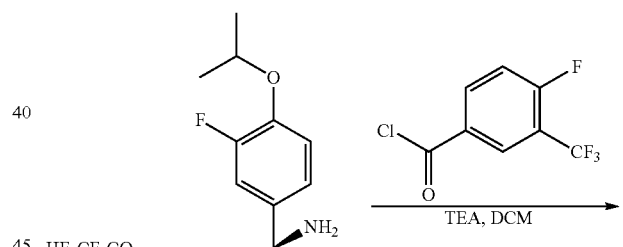

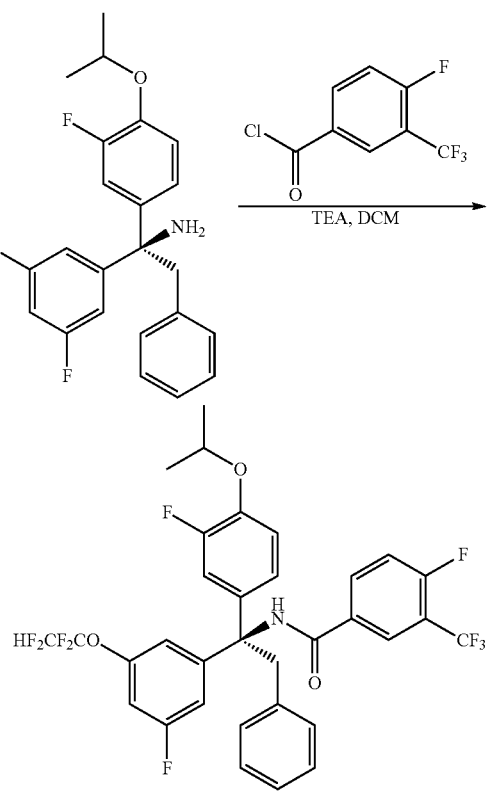

(R)-4-fluoro-N-(1-(4-fluoro-3-isopropoxyphenyl)-1-(3-fluoro-5(1,1,2,2-tetrafluoro ethoxy)phenyl)-2-phenylethyl)-3-(trifluoromethyl)benzamide may be prepared from (R)-1-(3-fluoro-4-isopropoxyphenyl)-1-(3-fluoro-5-(1,1,2,2-tetrafluoroethoxy)phenyl)-2-phenylethanamine by the methods described in Procedure 7.

Alternatively, (R)-4-fluoro-N-(1-(4-fluoro-3-isopropoxyphenyl)-1-(3-fluoro-5(1,1,2,2-tetrafluoro ethoxy)phenyl)-2-phenylethyl)-3-(trifluoromethyl)benzamide may be prepared by the following procedures:

Procedure 180

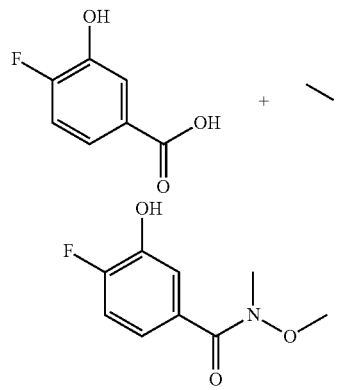

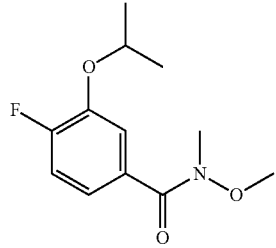

To a 5 L four necked round bottom flask was added 3-hydroxy-4-fluorobenzoic acid (100 g, 0.64 mol) and $CH_2Cl_2$ (2.3 L). Triethylamine (107 mL, 0.768 mol) was then added to the suspension. The solution was cooled to 78° C., and EDCI (184.2 g, 0.961 mol) was added portion wise followed by the addition of N,O-dimethylhydroxyamine hydrochloride (93.6 g, 0.96 mol). The reaction mixture was stirred at −78° C. for 1 h and then allowed to warm to 0° C. over a period of 2 h. The reaction mixture was transferred to a separatory funnel and washed water (2×1.2 L). The organic portion was dried over $Na_2SO_4$, filtered and concentrated in vacuo to give 4-fluoro-3-hydroxy-N-methoxy-N-methylbenzamide as a white solid (94.4 g, 74%).

A 2 L round bottom flask equipped with a mechanical stirrer, a $N_2$ inlet, a condenser and a temperature controller, was charged 4-fluoro-3-hydroxy-N-methoxy-N-methylbenzamide (99.6 g, 0.5 mol), isopropyl iodide (110.5 g, 0.65 mol) and $Cs_2CO_3$ (195.5 g) and DMF (300 mL). The reaction mixture was heated at 50° C. for 3 h. Isopropyl iodide (17.0 g, 0.1 mol) was added and the reaction was heated at 50° C. for 12 h. The reaction mixture was allowed to cool to rt and water (1 L) and $CH_2Cl_2$ (500 mL) were added. The reaction mixture was stirred at rt for 0.5 h, and the organic phase was separated. The aqueous layer was extracted with CH2Cl2 (3×500 mL). The combined organic extracts were washed with water (2×1 L), brine (1 L), dried over MgSO4, filtered and concentrated in vacuo at 40° C. for 18 h to give 4-fluoro-3-isopropoxy-N-methoxy-N-methlbenzamide as an off-white solid (120.0 g, 100%).

Procedure 181

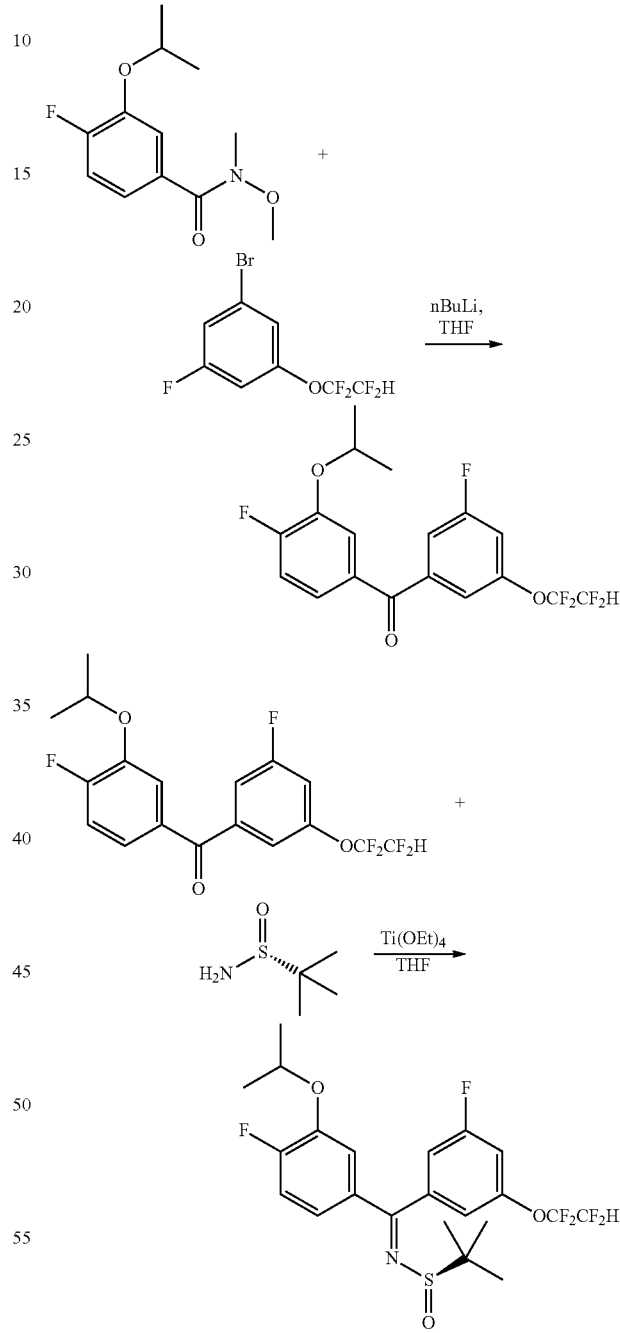

A 3-liter four neck round-bottomed flask (flame dried) was charged 1-bromo-3-fluoro-5-(1,1,2,2-tetrafluoroethoxy)benzene (72.88 g, 0.25 mol), 4-fluoro-3-isopropoxy-N-methoxy-N-methylbenzamide (60.39 g, 0.25 mol) and dry THF (700 mL) under $N_2$. The solution was cooled to −76° C., and a solution of n-BuLi in hexane (2.5M, 100 mL, 0.25 mol) was drop-wise maintaining the reaction mixture temperature below −70° C. over a period of 40 min. The reaction mixture was stirred at −76° C. for 1.5 h then quenched with 1N HCl (500 mL). The mixture was concentrated in vacuo to half the volume and was partitioned between EtOAc and H₂O (v/v 1:0.3, 1 L). The organic phase was separated and the aqueous layer was extracted with EtOAc (500 mL). The combined organic extracts were washed with brine and then concentrated in vacuo to give a yellow oil which was purified by column chromatography using CH₂Cl₂ in hexanes (0% to 20%) to give (4-fluoro-3-isopropoxyphenyl)(3-fluoro-5-(1,1,2,2-tetrafluoroethoxy)phenyl)methanone as a colorless oil contaminated with a by-product (49.0 g, 50%). LC-MS (10-90% MeOH in H₂O with 0.1% TFA in a 2-min gradient) 393.2 (M+H), retention time=2.15 min.

A solution of (4-fluoro-3-isopropoxyphenyl)(3-fluoro-5-(1,1,2,2-tetrafluoroethoxy)phenyl)methanone (49.0 g, 0.125 mol), (R)-(+)-2-methylpropane-2-sulfinamide (30.2 g, 0.25 mol), and Ti(Oet)₄ (51.9 mL, 0.25 mol) in dry THF was heated to reflux under N₂ for 20 h. After allowing to cool to rt, the reaction mixture was poured into ice water (800 mL) with stirring. The reaction flask was washed with small amount of EtOAc. The yellow suspension was then filtered through a Celite pad and the pad rinsed with EtOAc (ca. 500 mL). The filtrate was concentrated in vacuo to remove most of THF (<30° C.). The remaining filtrate was partitioned between EtOAc and H₂O (1:1, 1 L). The organic phase was separated and washed with brine (1 L). After concentration in vacuo, the orange oily residue was dissolved in CH₂Cl₂ (ca. 100 mL). The solution was purified by silica gel flash column using EtOAc in Hexane (0-20%) to give (R,Z/E)-N-((4-fluoro-3-isopropoxyphenyl)(3-fluoro-5-(1,1,2,2-tetrafluoroethoxy)phenyl)methylene)-2-methylpropane-2-sulfinamide (24.4 g). The mixed fractions were subjected to an additional silica gel flash column to give an additional 9.9 g of (R,Z/E)-N-((4-fluoro-3-isopropoxyphenyl)(3-fluoro-5-(1,1,2,2-tetrafluoroethoxy)phenyl)methylene)-2-methylpropane-2-sulfinamide. The residual mixed fraction (ca. 9.7 g) was dissolved in EtOAc in hexane (25%, 80 mL) and subjected to an additional silica gel flash chromatography column to give (R,Z/E)-N-((4-fluoro-3-isopropoxyphenyl)(3-fluoro-5-(1,1,2,2-tetrafluoroethoxy)phenyl)methylene)-2-methylpropane-2-sulfinamide (6.90 g). Total yield: 41.2 g (67%). LC-MS (10-90% MeOH in H₂O with 0.1% TFA in a 4-min gradient) 496.1 (M+H), retention time=4.23 min.

Procedure 182

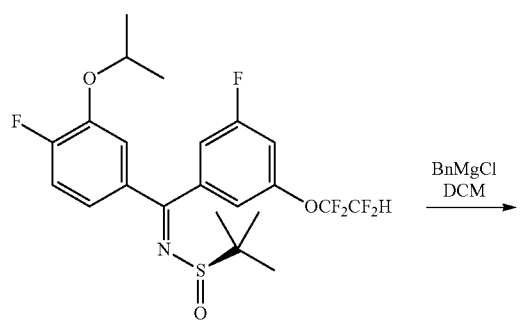

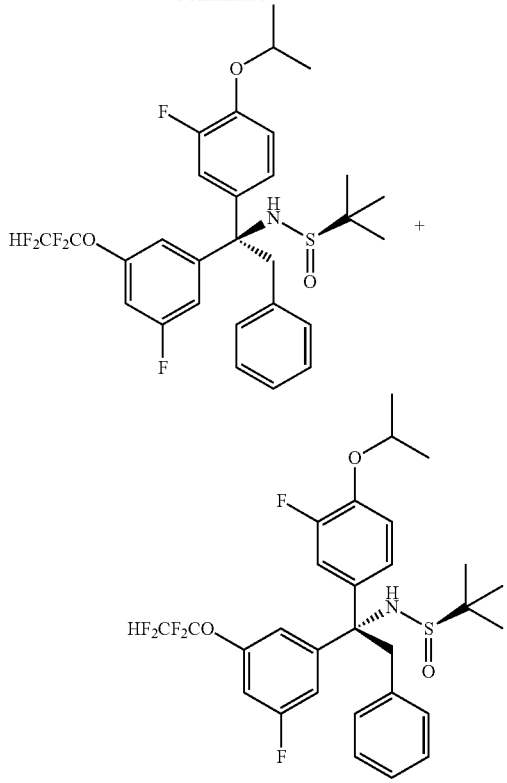

A flame dried 3 L round bottom flask equipped with a mechanical stirrer, a thermometer, a N₂ inlet and a dropping funnel, was charged a solution of (R,Z/E)-N-((4-fluoro-3-isopropoxyphenyl)(3-fluoro-5-(1,1,2,2-tetrafluoroethoxy)phenyl)methyne)methylene)-2-methylpropane-2-ethylpropane-2-sulfinamide (40.5 g, 81.7 mol) in dry CH₂Cl₂ (1 L). The solution was cooled to −76° C. and BF₃·Et₂O (12.3 mL, 90.0 mol, 1.2 eq) was added in one portion. The reaction mixture was stirred at −76° C. for 15 min, and a solution of phenyl magnesium chloride (1.0 M in ether, 105.7 mL, 105.7 mol) was added dropwise below −70° C. over a period of 1 h before the reaction mixture was quenched with brine (800 mL). The resulting solution was stirred for 10 min, then transferred a 2 L separatory funnel. The organic phase was separated and the aqueous layer was extracted with CH₂Cl₂ (500 mL). The combined organic phases were dried over MgSO₄. The solution was filtered and concentrated to ca. 100 mL. The residue was then purified by silica gel column chromatography using 0-20% of EtOAc in hexanes to give a yellow oil (48.5 g, 100%). LC-MS (10-90% MeOH in H₂O with 0.1% TFA in a 4-min gradient) 588.3 (M+H), retention time=4.36 min. Analytical chiral HPLC (AD column, 25% IPA in heptane with 0.01% DEA, isocratic), $t_{R1}$=4.16 min for (R)—N—((S)-1-(3-fluoro-4-isopropoxyphenyl)-1-(3-fluoro-5-(1,1,2,2-tetrafluoroethoxy)phenyl)-2-phenylethyl)-2-methylpropane-2-sulfinamide, $t_{R2}$=8.60 min for (R)—N—((R)-1-(3-fluoro-4-isopropoxyphenyl)-1-(3-fluoro-5-(1,1,2,2-tetrafluoroethoxy)phenyl)-2-phenylethyl)-2-methylpropane-2-sulfinamide. 48.5 g of the diastereomeric mixture compound (4/1 ratio) was separated by SFC on the Thar 350 system. A total of 33.5 g of (R)—N—((R)-1-(3-fluoro-4-isopropoxyphenyl)-1-(3-fluoro-5-(1,1,2,2-tetrafluoroethoxy)phenyl)-2-phenylethyl)-2-methylpropane-2-sulfinamide (yield: 69.3%) was obtained. Chiral preparative conditions are listed here.

613

Sample Preparation:

The sample is dissolved in IPA to a concentration of 110 mg/ml. at a concentration of 50 mg/ml. Sample readily dissolves.

| Preparative conditions on Thar SFC-350 | |
|---|---|
| column | Chiralcel AD-H  5 × 25 cm |
| mobile phase | 20% IPA in $CO_2$ |
| pressure (bar) | 100 |
| flow rate (ml/min) | 240 |
| solution concentration (mg/ml) | 110 |
| injection amount (ml) | 10 |
| Cycle time (min/inj) | 6.5 |
| Temperature (° C.) | 35 |
| throughput (g/hr) | 10 |
| Detector wavelength (nm) | 254 |

(R)—N—((R)-1-(3-fluoro-4-isopropoxyphenyl)-1-(3-fluoro-5-(1,1,2,2-tetrafluoroethoxy)phenyl)-2-phenylethyl)-2-methylpropane-2-sulfinamide was converted to (R)-4-fluoro-N-(1-(4-fluoro-3-isopropoxyphenyl)-1-(3-fluoro-5(1,1,2,2-tetrafluoro ethoxy)phenyl)-2-phenylethyl)-3-(trifluoromethyl)benzamide as described in 114.

Example 349A

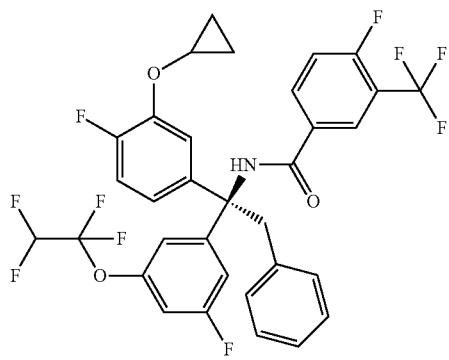 [SMILES: O=C(N[C@@](Cc1ccccc1)(c1cc(F)cc(OC(F)(F)C(F)F)c1)c1ccc(F)c(OC2CC2)c1)c1ccc(F)c(C(F)(F)F)c1]

(R)—N-(1-(3-cyclopropoxy-4-fluorophenyl)-1-(3-fluoro-5-(1,1,2,2-tetrafluoroethoxy)phenyl)-2-phenylethyl)-4-fluoro-3-(trifluoromethyl)benzamide Procedure 183

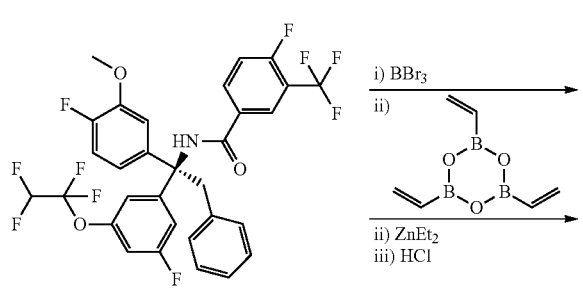

614

-continued

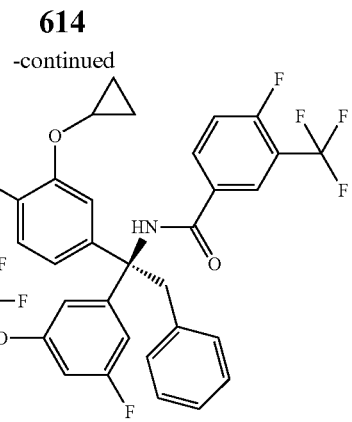

(R)-4-fluoro-N-(1-(4-fluoro-3-methoxyphenyl)-1-(3-fluoro-5-(1,1,2,2-tetrafluoroethoxy)phenyl)-2-phenylethyl)-3-(trifluoromethyl)benzamide (Example 273) was converted to (R)-4-fluoro-N-(1-(4-fluoro-3-hydroxyphenyl)-1-(3-fluoro-5-(1,1,2,2-tetrafluoroethoxy)phenyl)-2-phenylethyl)-3-(trifluoromethyl)benzamide as described in Procedure 59. (R)-4-fluoro-N-(1-(4-fluoro-3-hydroxyphenyl)-1-(3-fluoro-5-(1,1,2,2-tetrafluoroethoxy)phenyl)-2-phenylethyl)-3-(trifluoromethyl)benzamide was subsequently converted to (R)—N-(1-(3-cyclopropoxy-4-fluorophenyl)-1-(3-fluoro-5-(1,1,2,2-tetrafluoroethoxy)phenyl)-2-phenylethyl)-4-fluoro-3-(trifluoromethyl)benzamide by the methods described in Procedure 161.

Alternatively, (R)—N-(1-(3-cyclopropoxy-4-fluorophenyl)-1-(3-fluoro-5-(1,1,2,2-tetrafluoroethoxy)phenyl)-2-phenylethyl)-4-fluoro-3-(trifluoromethyl)benzamide may be prepared by the following Procedures:

Procedure 184

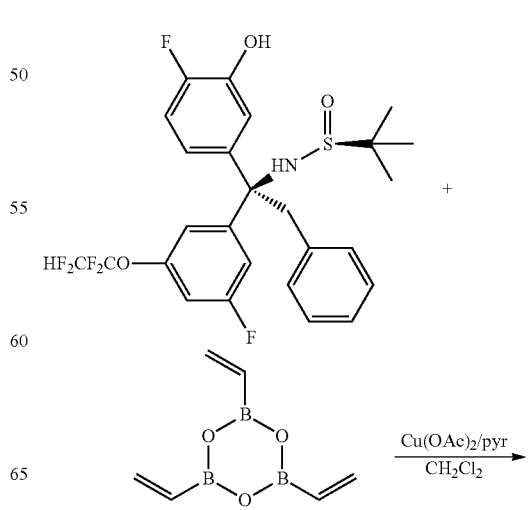

615
-continued

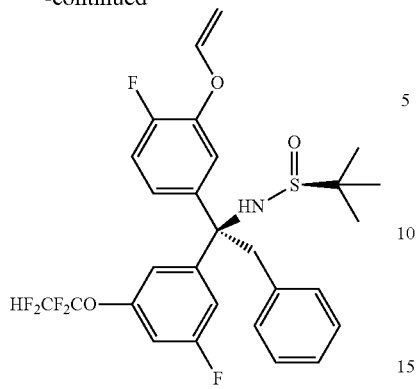

616
-continued

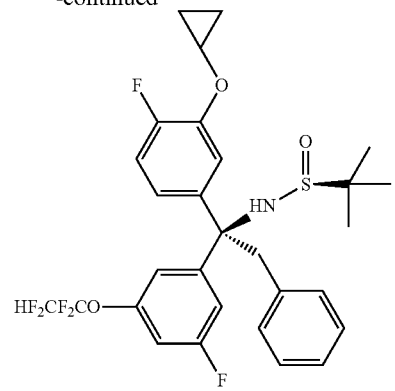

To a solution of (S)—N—((R)-1-(4-fluoro-3-hydroxyphenyl)-1-(3-fluoro-5-(1,1,2,2-tetrafluoroethoxy)phenyl)-2-phenylethyl)-2-methylpropane-2-sulfinamide prepared as described in Procedure 3, 4, 5, 6 and 59 (0.545 g, 1 mmol) in CH$_2$Cl$_2$ (10 mL) was added Cu(OAc)$_2$ (0.182 g, 1 mmol), followed by pyridine (0.79 g, 10 mmol) and 2,4,6-trivinyl-1,3,5,2,4,6-trioxatriborinane (0.159 g, 0.66 mmol). The reaction mixture was stirred overnight under ambient air and filtered through a plug of celite and neutral alumina. The solid was washed with ethyl acetate and the filtrate was concentrated under reduced pressure to yield (S)—N—((R)-1-(4-fluoro-3-(vinyloxy)phenyl)-1-(3-fluoro-5-(1,1,2,2-tetrafluoroethoxy)phenyl)-2-phenyl)-2-methylpropane-2-sulfinamide as an off-white foam (0.495 g, 87% yield). LCMS: RT=3.653 min [M+H] 572.2 (Phenomenex Luna C18 5μ column, eluting with 10-90% aqueous acetonitrile containing 0.1% trifluoroacetic acid over a 4 minute gradient, monitoring at 220 nM). $^1$H NMR (CDCl$_3$) ppm 7.2-7.1 (m, 5H), 7.02 (d, J=6.2 Hz, 1H), 6.89 (d, J=6.2 Hz, 2H), 6.82 (d, J=8.8 Hz, 1H), 6.68 (br, 2H), 6.54 (dd, J=6.2 Hz, 13.6 Hz, 1H), 5.84 (t, J=52.7 Hz, 1H), 4.62 (dd, J=2.2 Hz, 13.6 Hz, 1H), 4.40 (dd, J=2.2 Hz, 5.7 Hz, 1H), 4.21 (s, 1H), 3.95 (d, J=12.8 Hz, 1H), 3.55 (d, J=12.7 Hz, 1H), 1.19 (s, 9H).

To an oven-dried 3-necked 25 mL RB flask under nitrogen was added CH$_2$Cl$_2$ (3.5 mL) and 1 M diethylzinc solution in hexane (3.43 mL, 3.43 mmol). The flask was cooled in an ice-bath and a solution of trifluoroacetic acid (0.391 g, 3.43 mmol) in CH$_2$Cl$_2$ (1 mL) was added dropwise via syringe. After stirring for 15 min, a solution of diiodomethane (0.918 g, 3.43 mmol) in CH$_2$Cl$_2$ (1 mL) was added. The reaction mixture was stirred at rt for 15 min, followed by addition of (S)—N—((R)-1-(4-fluoro-3-(vinyloxy)phenyl)-1-(3-fluoro-5-(1,1,2,2-tetrafluoroethoxy)phenyl)-2-phenylethyl)-2-methylpropane-2-sulfinamide (0.495 g, 0.87 mmol) in CH$_2$Cl$_2$ (1 mL). The reaction mixture was allowed to warm to rt and stirred for 4 h. The reaction mixture was diluted with CH$_2$Cl$_2$ and washed successively with sat. sodium bicarbonate, water, sat. NaCl, dried over MgSO$_4$, filtered and concentrated under reduced pressure. The residue was purified by ISCO using a gradient of 5-70% EtOAc/hexane as eluent to yield (S)—N—((R)-1-(3-cyclopropoxy-4-fluorophenyl)-1-(3-fluoro-5-(1,1,2,2-tetrafluoroethoxy)phenyl)-2-phenylethyl)-2-methylpropane-2-sulfinamide as a white foam (0.347 g, 71% yield). HPLC: RT=3.668 min [M+H] 586.3 (Phenomenex Luna C18 5μ column, eluting with 10-90% aqueous acetonitrile containing 0.1% trifluoroacetic acid over a 4 minute gradient, monitoring at 220 nm). $^1$H NMR (CDCL$_3$) ppm 7.2-7.05 (m, 6H), 6.91 (d, J=6.6 Hz, 2H), 6.83 (d, J=8.4 Hz, 1H), 6.71 (m, 2H), 5.84 (t, J=53.1 Hz, 1H), 4.21 (s, 1H), 3.99 (d, J=12.3 Hz, 1H), 3.62 (m, 1H), 3.56 (d, J=12.8 Hz, 1H), 1.22 (s, 9H), 0.72-0.65 (m, 4H).

Procedure 185

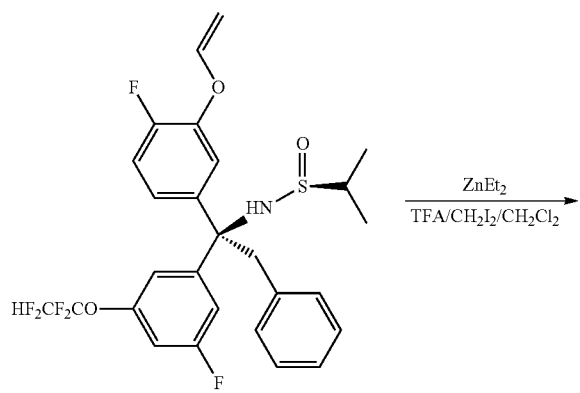

Procedure 186

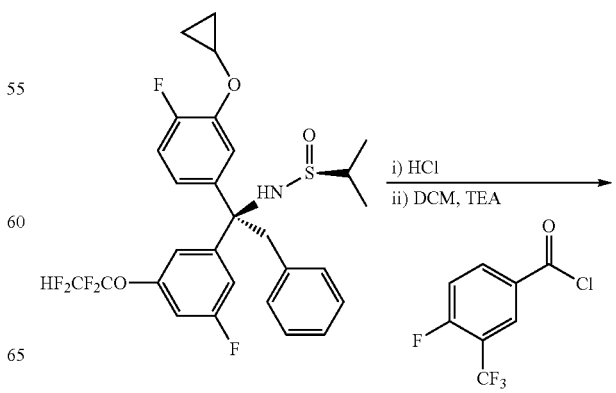

-continued

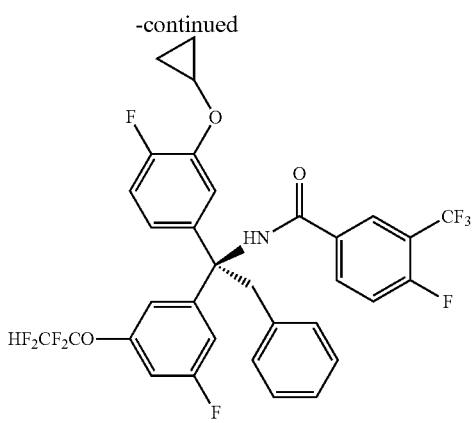

(S)—N—((R)-1-(3-cyclopropoxy-4-fluorophenyl)-1-(3-fluoro-5-(1,1,2,2-tetrafluoroethoxy)phenyl)-2-phenylethyl)-2-methylpropane-2-sulfinamide was converted to (R)—N-(1-(3-cyclopropoxy-4-fluorophenyl)-1-(3-fluoro-5-(1,1,2,2-tetrafluoroethoxy)phenyl)-2-phenylethyl)-4-fluoro-3-(trifluoromethyl)benzamide by the methods described in Procedures 6 and 7.

Alternatively, R)—N-(1-(3-cyclopropoxy-4-fluorophenyl)-1-(3-fluoro-5-(1,1,2,2-tetrafluoroethoxy)phenyl)-2-phenylethyl)-4-fluoro-3-(trifluoromethyl)benzamide may be prepared from (R)-4-fluoro-N-(1-(4-fluoro-3-hydroxyphenyl)-1-(3-fluoro-5-(1,1,2,2-tetrafluoroethoxy)phenyl)-2-phenylethyl)-3-(trifluoromethyl)benzamide by the following methods:

Procedure 187

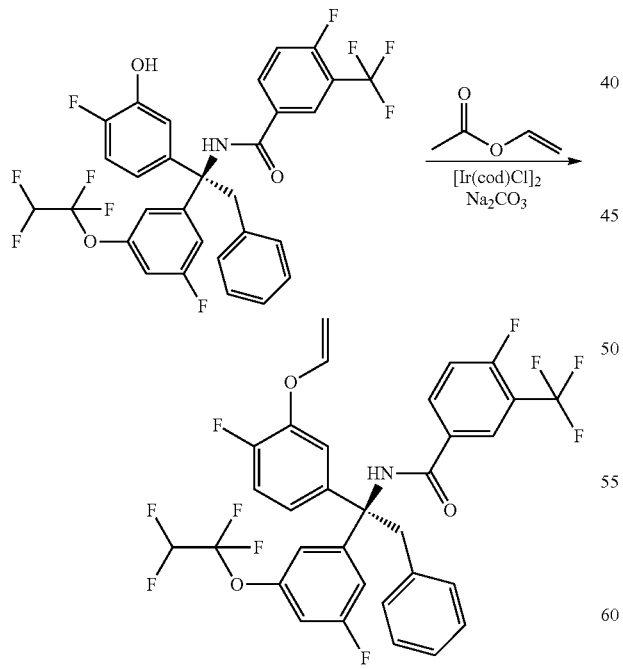

To a solution of (R)-4-fluoro-N-(1-(4-fluoro-3-hydroxyphenyl)-1-(3-fluoro-5-(1,1,2,2-tetrafluoroethoxy)phenyl)-2-phenylethyl)-3-(trifluoromethyl)benzamide (Example 264, 100 mg, 0.158 mmol) in toluene (0.2 ml) was added Na$_2$CO$_3$ (25 mg, 0.235 mmol) and catalytic amount of [Ir(cod)Cl]$_2$ (2 mg), followed by vinyl acetate (68 mg, 0.79 mmol). The reaction mixture was stirred at 100° C. for 16 h. The resulting mixture was filtered and the solid was washed with CH$_2$Cl$_2$. The CH$_2$Cl$_2$ layer was washed with 1 N NaOH, H$_2$O and the organic portion dried over Na$_2$SO$_4$ and filtered. The solvent was evaporated under reduced pressure and the residue was purified by silica gel column using 0 to 60% EtOAc in hexane to afford (R)-4-fluoro-N-(1-(4-fluoro-3-(vinyloxy)phenyl)-1-(3-fluoro-5-(1,1,2,2-tetrafluoroethoxy)phenyl)-2-phenylethyl)-3-(trifluoromethyl)benzamide eluting out at 20% EtOAc in hexane as colorless oil (80 mg, 77%). LCMS: RT=2.237 min [M+H] 658.3 (2 min Phenomenex Luna C18 column, 4.6×30 mm eluting with 10-90% MeOH/H$_2$O over 2 minutes containing 0.1% TFA; 5 mL/min, monitoring at 220 nm. NMR: 400 MHz $^1$H (CD$_3$OD) ppm 3.87 (d, J=12.74 Hz, 1H), 4.05-4.15 (m, 1H), 4.35 (dd, J=5.93, 1.98 Hz, 1H), 4.55 (dd, J=13.84, 1.98 Hz, 1H), 6.12-6.41 (m, 1H), 6.48 (dd, J=13.62, 6.15 Hz, 1H), 6.72 (d, J=7.03 Hz, 2H), 6.87-7.24 (m, 9H), 7.37-7.51 (m, 1H), 7.88-8.04 (m, 2H).

Procedure 188

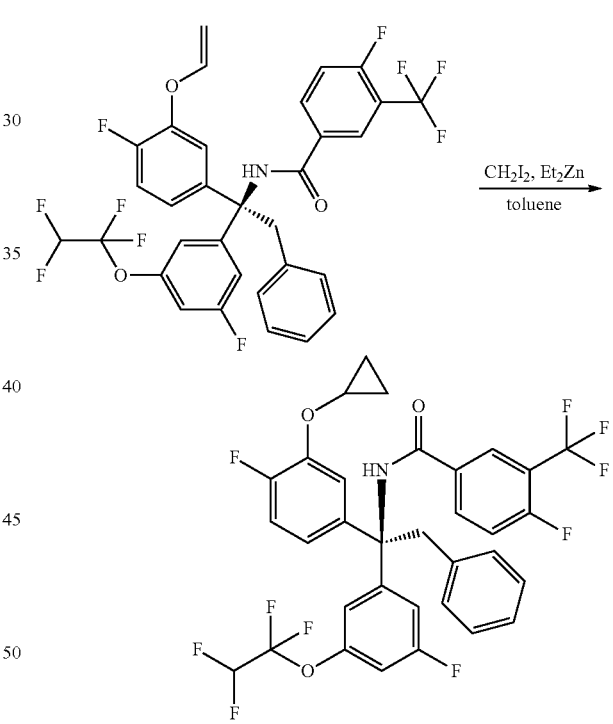

To a solution of (R)-4-fluoro-N-(1-(4-fluoro-3-(vinyloxy)phenyl)-1-(3-fluoro-5-(1,1,2,2-tetrafluoroethoxy)phenyl)-2-phenylethyl)-3-(trifluoromethyl)benzamide (66 mg, 0.10 mmol) in 0.5 ml toluene was added Et$_2$Zn (1 N, 0.2 ml, 0.2 mmol), followed by CH$_2$I$_2$ (16 ml, 0.2 mmol). The reaction mixture was stirred at 120° C. for 3 h. The reaction mixture was quenched by addition of 1 N HCl and the aqueous layer was extracted with CH$_2$Cl$_2$. The organic layer was washed with sat. NaHCO$_3$ and concentrated under reduced pressure. The resulting residue was purified by ISCO silica gel column using 0 to 50% to EtOAc in hexane as eluting solvents and Prep HPLC (phenomenex AXIA Luna 75×30 mm, 5u column eluting with 10-90% ACN/H$_2$O over 10 minutes containing 0.1% TFA; 40 mL/min, monitoring at 220 nm) to afford (R)—N-(1-(3-cyclopropoxy-4-fluorophenyl)-1-(3-fluoro-5-(1,1,2,2-tetrafluoroethoxy)phenyl)-2-phenylethyl)-4-fluoro-3-(trifluoromethyl)benzamide (Example 305) as white lyophillate (36 mg, 52% yield). LCMS: RT=4.268 min [M+H] 672.3 (4 min Phenomenex Luna C18 column, 4.6×50 mm eluting with 10-90% MeOH/H$_2$O over 4 minutes containing 0.1% TFA; 4 mL/min, monitoring at 220 nm. NMR: 400 MHz $^1$H (CDCl$_3$) ppm 0.45-0.73 (m, 4H), 3.51-3.59 (m, 1H), 3.76 (d, J=13.18 Hz, 1H), 4.22 (d, J=12.74 Hz, 1H), 6.13-6.44 (m, 1H), 6.66-6.76 (m, 3H), 6.97-7.08 (m, 3H), 7.10-7.23 (m, 5H), 7.42-7.50 (m, 1H), 7.95-8.03 (m, 2H).

TABLE 9

| Ex. No. | Structure | Name | Retention Time Min./ Molecular Mass | Prepared in the manner described in: |
|---|---|---|---|---|
| 349B | 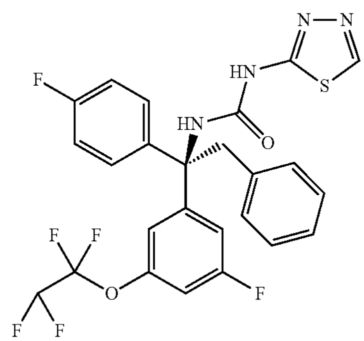 [SMILES: O=C(Nc1nncs1)N[C@](Cc1ccccc1)(c1ccc(F)cc1)c1cc(F)cc(OC(F)(F)C(F)F)c1] | (R)-1-(1-(3-fluoro-5-(1,1,2,2-tetrafluoroethoxy)phenyl)-1-(4-fluorophenyl)-2-phenylethyl)-3-(1,3,4-thiadiazol-2-yl)urea | 4.02 LC (1) 553.27 [M + H]$^+$ | Procedures 3, 4, 5, 6 and 10 |
| 350 | 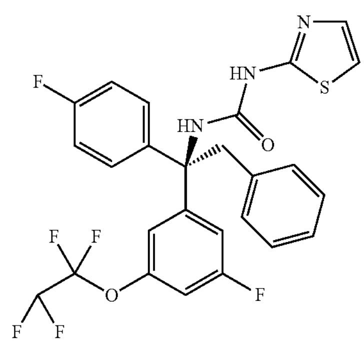 [SMILES: O=C(Nc1nccs1)N[C@](Cc1ccccc1)(c1ccc(F)cc1)c1cc(F)cc(OC(F)(F)C(F)F)c1] | (R)-1-(1-(3-fluoro-5-(1,1,2,2-tetrafluoroethoxy)phenyl)-1-(4-fluorophenyl)-2-phenylethyl)-3-(thiazol-2-yl)urea | 4.12 LC (1) 552.28 [M + H]$^+$ | Procedures 3, 4, 5, 6 and 10 |
| 351 | 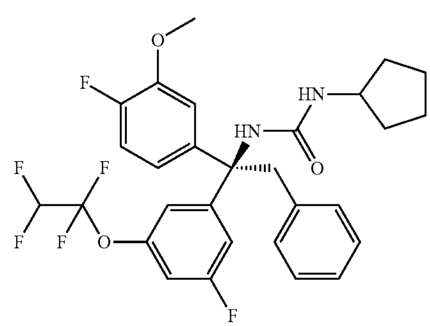 [SMILES: COc1cc([C@@](Cc2ccccc2)(NC(=O)NC2CCCC2)c2cc(F)cc(OC(F)(F)C(F)F)c2)ccc1F] | (R)-1-cyclopentyl-3-(1-(4-fluoro-3-methoxyphenyl)-1-(3-fluoro-5-(1,1,2,2-tetrafluoroethoxy)phenyl)-2-phenylethyl)urea | 3.524 LC (1) 567.01 [M + H]$^+$ | Procedures 3, 4, 5, 6 and 2 |
| 352 | 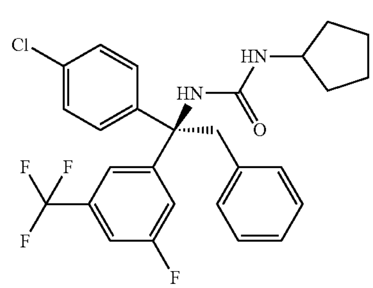 [SMILES: O=C(NC1CCCC1)N[C@](Cc1ccccc1)(c1ccc(Cl)cc1)c1cc(F)cc(C(F)(F)F)c1] | (R)-1-(1-(4-chlorophenyl)-1-(3-fluoro-5-(trifluoromethyl)phenyl)-2-phenylethyl)-3-cyclopentylurea | 3.803 LC (1) 505.37 [M + H]$^+$ | Procedures 4, 5, 6 and 2 |

TABLE 9-continued

| Ex. No. | Structure | Name | Retention Time Min./ Molecular Mass | Prepared in the manner described in: |
|---|---|---|---|---|
| 353 | 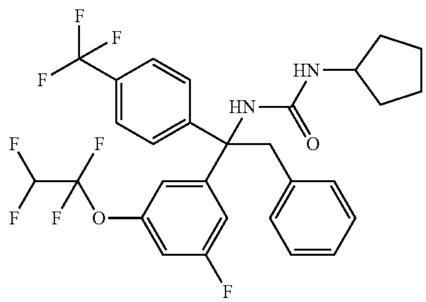 [SMILES: O=C(NC1CCCC1)NC(Cc1ccccc1)(c1ccc(C(F)(F)F)cc1)c1cc(F)cc(OC(F)(F)C(F)F)c1] | 1-cyclopentyl-3-(1-(3-fluoro-5-(1,1,2,2-tetrafluoroethoxy)phenyl)-2-phenyl-1-(4-(trifluoromethyl)phenyl)ethyl)urea | 3.845 LC (1) 587.11 [M + H]+ | Procedures 3, 1, 2 and 23 |
| 354 | 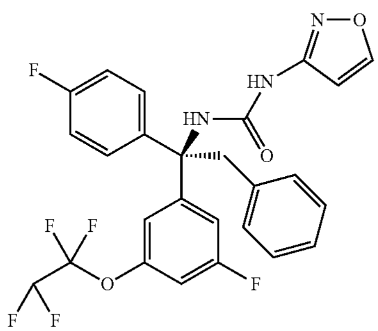 [SMILES: O=C(Nc1ccon1)N[C@](Cc1ccccc1)(c1ccc(F)cc1)c1cc(F)cc(OC(F)(F)C(F)F)c1] | (R)-1-(1-(3-fluoro-5-(1,1,2,2-tetrafluoroethoxy)phenyl)-1-(4-fluorophenyl)-2-phenylethyl)-3-(isoxazol-3-yl)urea | 4.11 LC (1) 536.2 [M + H]+ | Procedures 3, 4, 5, 6 and 10 |
| 355 | 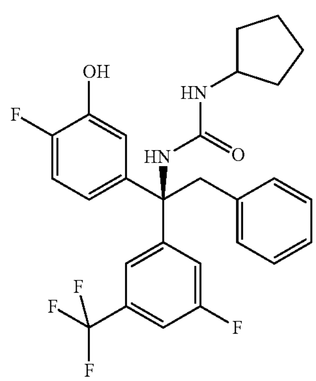 [SMILES: O=C(NC1CCCC1)N[C@@](Cc1ccccc1)(c1cc(F)cc(C(F)(F)F)c1)c1ccc(F)c(O)c1] | (R)-1-cyclopentyl-3-(1-(4-fluoro-3-hydroxyphenyl)-1-(3-fluoro-5-(trifluoromethyl)phenyl)-2-phenylethyl)urea | 3.176 LC (1) 505.22 [M + H]+ | Procedures 4, 5, 6, 2 and 59 |
| 356 | 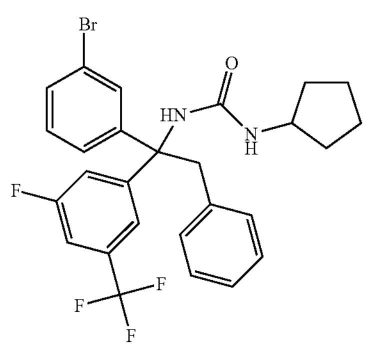 [SMILES: O=C(NC1CCCC1)NC(Cc1ccccc1)(c1cccc(Br)c1)c1cc(F)cc(C(F)(F)F)c1] | 1-(1-(3-bromophenyl)-1-(3-fluoro-5-(trifluoromethyl)phenyl)-2-phenylethyl)-3-cyclopentylurea | 4.25 LC (4) 549.21 [M + H]+ | Procedures 1 and 2 |

TABLE 9-continued

| Ex. No. | Structure | Name | Retention Time Min./ Molecular Mass | Prepared in the manner described in: |
|---|---|---|---|---|
| 357 | 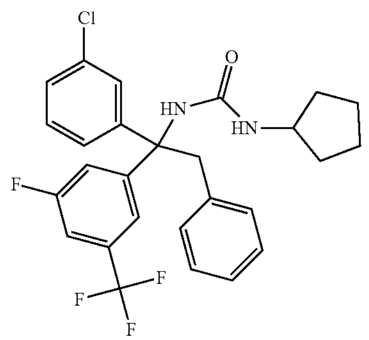 [SMILES: O=C(NC1CCCC1)NC(Cc1ccccc1)(c1cccc(Cl)c1)c1cc(F)cc(C(F)(F)F)c1] | 1-(1-(3-chlorophenyl)-1-(3-fluoro-5-(trifluoromethyl)phenyl)-2-phenylethyl)-3-cyclopentylurea | 4.23 LC (4) 505.26 [M + H]$^+$ | Procedures 1 and 2 |
| 358 | 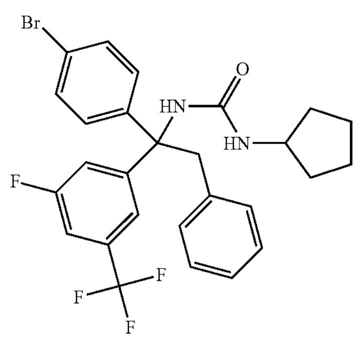 [SMILES: O=C(NC1CCCC1)NC(Cc1ccccc1)(c1ccc(Br)cc1)c1cc(F)cc(C(F)(F)F)c1] | 1-(1-(4-bromophenyl)-1-(3-fluoro-5-(trifluoromethyl)phenyl)-2-phenylethyl)-3-cyclopentylurea | 4.29 LC (4) 549.16 [M + H]$^+$ | Procedures 1 and 2 |
| 359 | 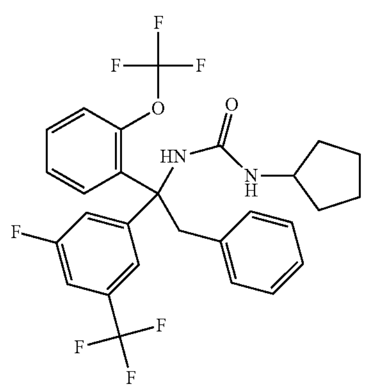 [SMILES: O=C(NC1CCCC1)NC(Cc1ccccc1)(c1cc(F)cc(C(F)(F)F)c1)c1ccccc1OC(F)(F)F] | 1-cyclopentyl-3-(1-(3-fluoro-5-(trifluoromethyl)phenyl)-2-phenyl-1-(2-(trifluoromethoxy)phenyl)ethyl)urea | 4.21 LC (4) 555.21 [M + H]$^+$ | Procedures 1 and 2 |
| 360 | 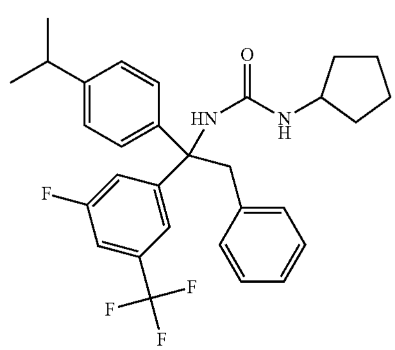 [SMILES: CC(C)c1ccc(C(Cc2ccccc2)(NC(=O)NC2CCCC2)c2cc(F)cc(C(F)(F)F)c2)cc1] | 1-cyclopentyl-3-(1-(3-fluoro-5-(trifluoromethyl)phenyl)-1-(4-isopropylphenyl)-2-phenylethyl)urea | 4.40 LC (4) 513.32 [M + H]$^+$ | Procedures 1 and 2 |

TABLE 9-continued

| Ex. No. | Structure | Name | Retention Time Min./ Molecular Mass | Prepared in the manner described in: |
|---|---|---|---|---|
| 361 | 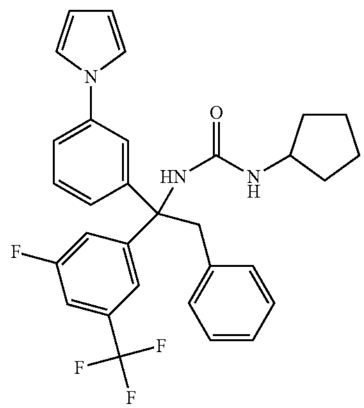 [SMILES: O=C(NC1CCCC1)NC(Cc1ccccc1)(c1cccc(-n2cccc2)c1)c1cc(F)cc(C(F)(F)F)c1] | 1-(1-(3-(1H-pyrrol-1-yl)phenyl)-1-(3-fluoro-5-(trifluoro-methyl)phenyl)-2-phenylethyl)-3-cyclopentylurea | 4.26 LC (4) 536.28 [M + H]⁺ | Procedures 1 and 2 |
| 362 | 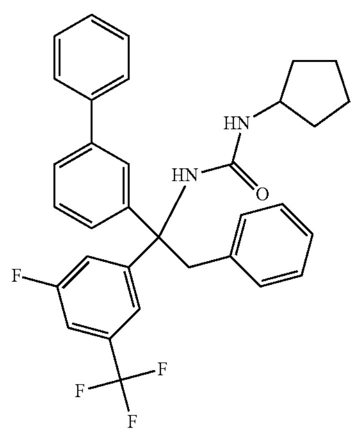 [SMILES: O=C(NC1CCCC1)NC(Cc1ccccc1)(c1cccc(-c2ccccc2)c1)c1cc(F)cc(C(F)(F)F)c1] | 1-cyclopentyl-3-(1-(biphenyl-3-yl)-1-(3-fluoro-5-(trifluoro-methyl)phenyl)-2-phenylethyl)urea | 4.40 LC (4) 547.28 [M + H]⁺ | Procedures 1 and 2 |
| 363 | 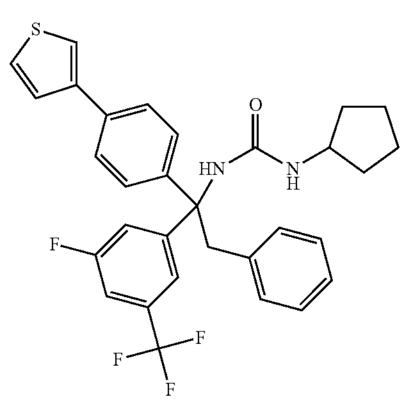 [SMILES: O=C(NC1CCCC1)NC(Cc1ccccc1)(c1ccc(-c2ccsc2)cc1)c1cc(F)cc(C(F)(F)F)c1] | 1-cyclopentyl-3-(1-(3-fluoro-5-(trifluoromethyl)phenyl)-2-phenyl-1-(4-(thiophen-3-yl)phenyl)ethyl)urea | 4.33 LC (4) 553.23 [M + H]⁺ | Procedures 1 and 2 |

TABLE 9-continued

| Ex. No. | Structure | Name | Retention Time Min./ Molecular Mass | Prepared in the manner described in: |
|---|---|---|---|---|
| 364 | 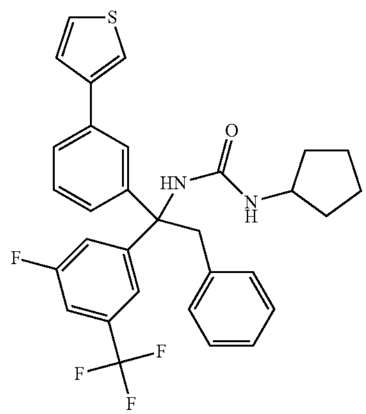 [SMILES: O=C(NC1CCCC1)NC(Cc1ccccc1)(c1cccc(-c2ccsc2)c1)c1cc(F)cc(C(F)(F)F)c1] | 1-cyclopentyl-3-(1-(3-fluoro-5-(trifluoromethyl)phenyl)-2-phenyl-1-(3-(thiophen-3-yl)phenyl)ethyl)urea | 4.33 LC (4) 553.26 [M + H]$^+$ | Procedures 1 and 2 |
| 365 | 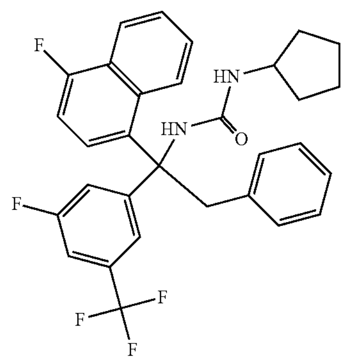 [SMILES: O=C(NC1CCCC1)NC(Cc1ccccc1)(c1cc(F)cc(C(F)(F)F)c1)c1ccc(F)c2ccccc12] | 1-cyclopentyl-3-(1-(3-fluoro-5-(trifluoromethyl)phenyl)-1-(4-fluoronaphthalen-1-yl)-2-phenylethyl)urea | 4.29 LC (4) 539.27 [M + H]$^+$ | Procedures 1 and 2 |
| 366 | 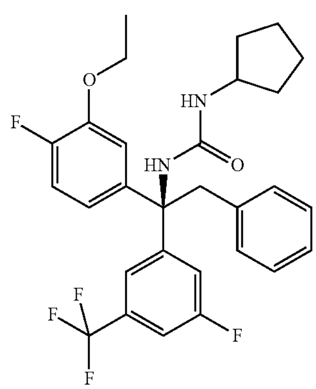 [SMILES: CCOc1cc([C@@](Cc2ccccc2)(NC(=O)NC2CCCC2)c2cc(F)cc(C(F)(F)F)c2)ccc1F] | (R)-1-cyclopentyl-3-(1-(3-ethoxy-4-fluorophenyl)-1-(3-fluoro-5-(trifluoromethyl)phenyl)-2-phenylethyl)urea | 3.683 LC (1) 533.36 [M + H]$^+$ | Procedures 4, 5, 6, 2, 59 and 68 |
| 367 | 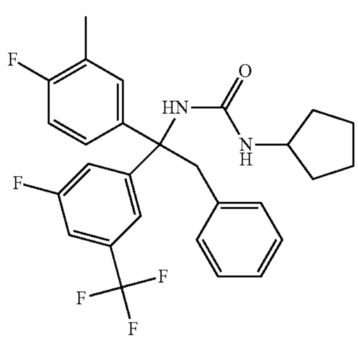 [SMILES: Cc1cc(C(Cc2ccccc2)(NC(=O)NC2CCCC2)c2cc(F)cc(C(F)(F)F)c2)ccc1F] | 1-cyclopentyl-3-(1-(4-fluoro-3-methylphenyl)-1-(3-fluoro-5-(trifluoromethyl)phenyl)-2-phenylethyl)urea | 4.23 LC (4) 503.31 [M + H]$^+$ | Procedures 1 and 2 |

TABLE 9-continued

| Ex. No. | Structure | Name | Retention Time Min./ Molecular Mass | Prepared in the manner described in: |
|---|---|---|---|---|
| 368 | 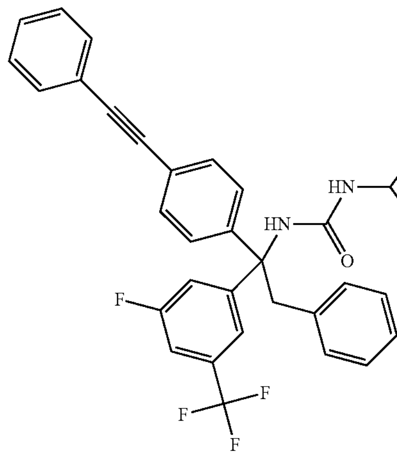 | 1-cyclopentyl-3-(1-(3-fluoro-5-(trifluoromethyl)phenyl)-2-phenyl-1-(4-(2-phenyl-ethynyl)phenyl)ethyl)urea | 4.49 LC (4) 571.28 [M + H]+ | Procedures 1 and 2 |
| 369 | 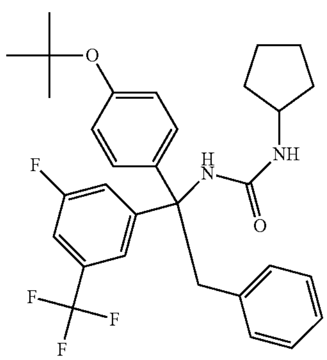 [SMILES: CC(C)(C)Oc1ccc(C(Cc2ccccc2)(NC(=O)NC2CCCC2)c2cc(F)cc(C(F)(F)F)c2)cc1] | 1-(1-(4-tert-butoxyphenyl)-1-(3-fluoro-5-(trifluoromethyl)phenyl)-2-phenylethyl)-3-cyclopentylurea | 4.29 LC (4) 543.34 [M + H]+ | Procedures 1 and 2 |
| 370 | 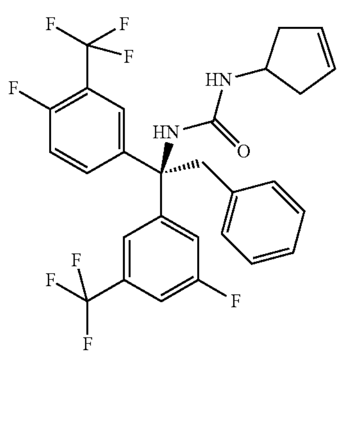 [SMILES: O=C(NC1CC=CC1)N[C@@](Cc1ccccc1)(c1cc(F)cc(C(F)(F)F)c1)c1ccc(F)c(C(F)(F)F)c1] | (R)-1-(cyclopent-3-enyl)-3-(1-(4-fluoro-3-(trifluoromethyl)phenyl)-1-(3-fluoro-5-(trifluoro-methyl)phenyl)-2-phenylethyl)urea | 4.24 LC (1) 555.23 [M + H]+ | Procedures 4, 5, 6 and 10 |

TABLE 9-continued

| Ex. No. | Structure | Name | Retention Time Min./ Molecular Mass | Prepared in the manner described in: |
|---|---|---|---|---|
| 371 | 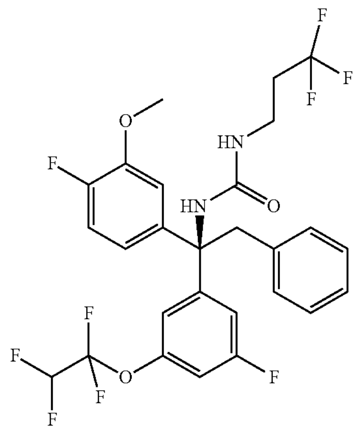 [SMILES: COc1cc([C@@](Cc2ccccc2)(NC(=O)NCCC(F)(F)F)c2cc(F)cc(OC(F)(F)C(F)F)c2)ccc1F] | (R)-1-(1-(4-fluoro-3-methoxyphenyl)-1-(3-fluoro-5-(1,1,2,2-tetrafluoroethoxy)phenyl)-2-phenylethyl)-3-(3,3,3-trifluoropropyl)urea | 3.39 LC (1) 595.63 [M + H]+ | Procedures 3, 4, 5, 6 and 10 |
| 372 | 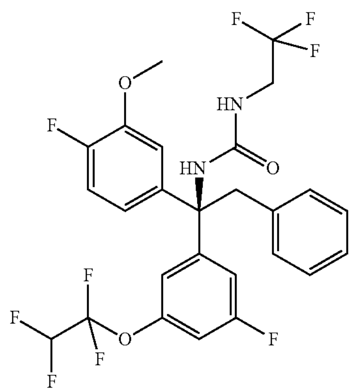 [SMILES: COc1cc([C@@](Cc2ccccc2)(NC(=O)NCC(F)(F)F)c2cc(F)cc(OC(F)(F)C(F)F)c2)ccc1F] | (R)-1-(1-(4-fluoro-3-methoxyphenyl)-1-(3-fluoro-5-(1,1,2,2-tetrafluoroethoxy)phenyl)-2-phenylethyl)-3-(2,2,2-trifluoroethyl)urea | 3.391 LC (1) 581.15 [M + H]+ | Procedures 3, 4, 5, 6 and 10 |
| 373 | 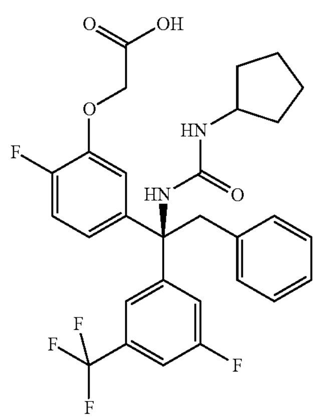 [SMILES: O=C(O)COc1cc([C@@](Cc2ccccc2)(NC(=O)NC2CCCC2)c2cc(F)cc(C(F)(F)F)c2)ccc1F] | (R)-2-(5-(1-(3-cyclopentylureido)-1-(3-fluoro-5-(trifluoromethyl)phenyl)-2-phenylethyl)-2-fluorophenoxy)acetic acid | 3.210 LC (1) 563.29 [M + H]+ | Procedures 4, 5, 6, 2, 59, 68 and 23 |

TABLE 9-continued

| Ex. No. | Structure | Name | Retention Time Min./ Molecular Mass | Prepared in the manner described in: |
|---|---|---|---|---|
| 374 | 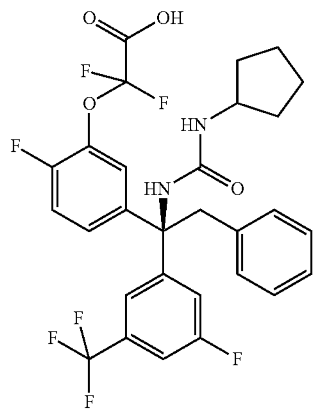 [SMILES: O=C(NC1CCCC1)N[C@@](Cc1ccccc1)(c1cc(F)cc(C(F)(F)F)c1)c1ccc(F)c(OC(F)(F)C(=O)O)c1] | (R)-2-(5-(1-(3-cyclopentylureido)-1-(3-fluoro-5-(trifluoro-methyl)phenyl)-2-phenylethyl)-2-fluorophenoxy)-2,2-difluoroacetic acid | 3.131 LC (1) 599.27 [M + H]⁺ | Procedures 4, 5, 6, 2, 59, 68 and 23 |
| 375 | 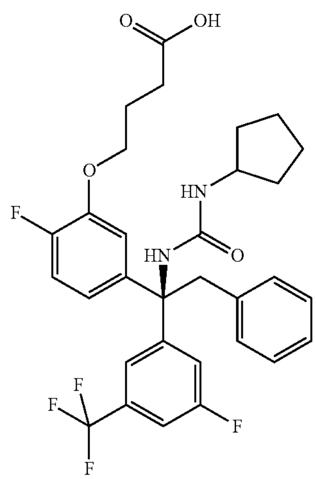 [SMILES: O=C(O)CCCOc1cc([C@@](Cc2ccccc2)(NC(=O)NC2CCCC2)c2cc(F)cc(C(F)(F)F)c2)ccc1F] | (R)-4-(5-(1-(3-cyclopentylureido)-1-(3-fluoro-5-(trifluoro-methyl)phenyl)-2-phenylethyl)-2-fluorophenoxy)butanoic acid | 3.068 LC (1) 591.31 [M + H]⁺ | Procedures 4, 5, 6, 2, 59, 68 and 23 |
| 376 | 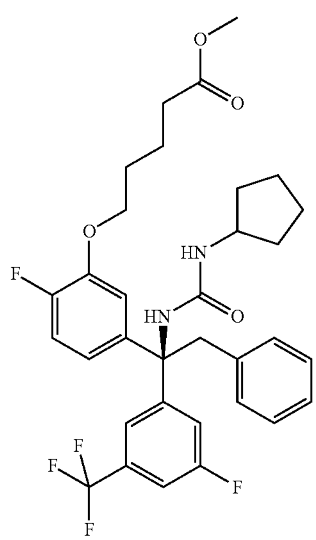 [SMILES: COC(=O)CCCCOc1cc([C@@](Cc2ccccc2)(NC(=O)NC2CCCC2)c2cc(F)cc(C(F)(F)F)c2)ccc1F] | (R)-methyl 5-(5-(1-(3-cyclopentylureido)-1-(3-fluoro-5-(trifluoromethyl)phenyl)-2-phenylethyl)-2-fluoro-phenoxy)pentanoate | 3.715 LC (1) 619.33 [M + H]⁺ | Procedures 4, 5, 6, 2, 59 and 68 |

TABLE 9-continued

| Ex. No. | Structure | Name | Retention Time Min./ Molecular Mass | Prepared in the manner described in: |
|---|---|---|---|---|
| 377 | 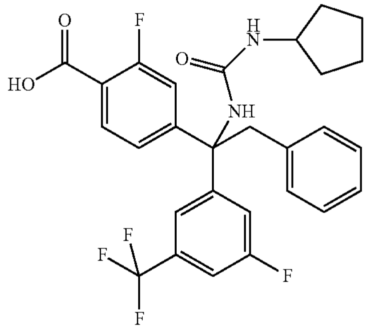 [SMILES: O=C(NC1CCCC1)NC(Cc1ccccc1)(c1cc(F)cc(C(F)(F)F)c1)c1ccc(C(=O)O)c(F)c1] | 4-(1-(3-cyclopentylureido)-1-(3-fluoro-5-(trifluoromethyl)phenyl)-2-phenylethyl)-2-fluorobenzoic acid | 3.46 LC (5) 533.24 [M + H]$^+$ | Procedures 1 and 2 |
| 378 | 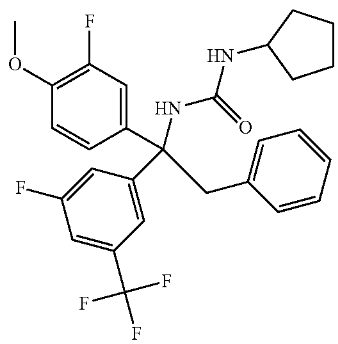 [SMILES: COc1ccc(C(Cc2ccccc2)(NC(=O)NC2CCCC2)c2cc(F)cc(C(F)(F)F)c2)cc1F] | 1-cyclopentyl-3-(1-(3-fluoro-4-methoxyphenyl)-1-(3-fluoro-5-(trifluoromethyl)phenyl)-2-phenylethyl)urea | 4.08 LC (4) 519.22 [M + H]$^+$ | Procedures 1 and 2 |
| 379 | 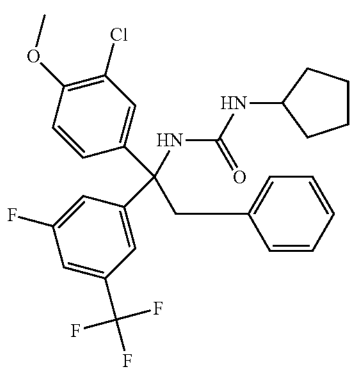 | 1-(1-(3-chloro-4-methoxyphenyl)-1-(3-fluoro-5-(trifluoromethyl)phenyl)-2-phenylethyl)-3-cyclopentylurea | 4.15 LC (4) 535.20 [M + H]$^+$ | Procedures 1 and 2 |
| 380 | 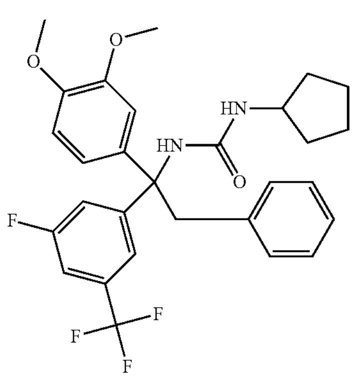 [SMILES: COc1ccc(C(Cc2ccccc2)(NC(=O)NC2CCCC2)c2cc(F)cc(C(F)(F)F)c2)cc1OC] | 1-cyclopentyl-3-(1-(3,4-dimethoxyphenyl)-1-(3-fluoro-5-(trifluoromethyl)phenyl)-2-phenylethyl)urea | 3.99 LC (4) 531.27 [M + H]$^+$ | Procedures 1 and 2 |

TABLE 9-continued

| Ex. No. | Structure | Name | Retention Time Min./ Molecular Mass | Prepared in the manner described in: |
|---|---|---|---|---|
| 381 | 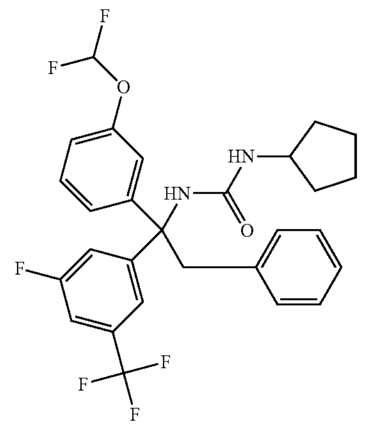 [SMILES: O=C(NC1CCCC1)NC(Cc1ccccc1)(c1cccc(OC(F)F)c1)c1cc(F)cc(C(F)(F)F)c1] | 1-cyclopentyl-3-(1-(3-(difluoromethoxy)phenyl)-1-(3-fluoro-5-(trifluoromethyl)phenyl)-2-phenylethyl)urea | 4.10 LC (4) 537.20 [M + H]$^+$ | Procedures 1 and 2 |
| 382 | 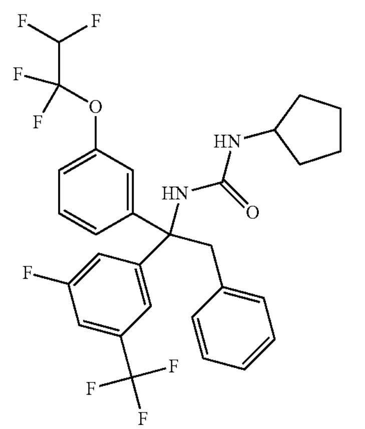 [SMILES: O=C(NC1CCCC1)NC(Cc1ccccc1)(c1cccc(OC(F)(F)C(F)F)c1)c1cc(F)cc(C(F)(F)F)c1] | 1-cyclopentyl-3-(1-(3-fluoro-5-(trifluoromethyl)phenyl)-2-phenyl-1-(3-(1,1,2,2-tetrafluoro-ethoxy)phenyl)ethyl)urea | 4.15 LC (4) 587.17 [M + H]$^+$ | Procedures 1 and 2 |
| 383 | 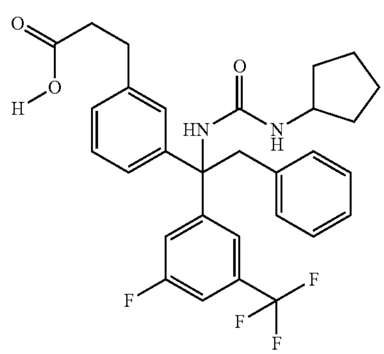 [SMILES: O=C(O)CCc1cccc(C(Cc2ccccc2)(NC(=O)NC2CCCC2)c2cc(F)cc(C(F)(F)F)c2)c1] | 3-(3-(1-(3-cyclopentylureido)-1-(3-fluoro-5-(trifluoromethyl)phenyl)-2-phenylethyl)phenyl)propanoic acid | 4.251 LC (4) 554.2 [M + H]$^+$ | Procedures 1, 2, 24 and 23 |
| 384 | 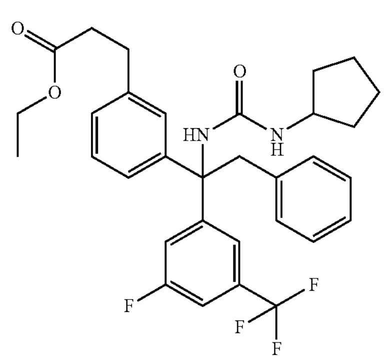 [SMILES: CCOC(=O)CCc1cccc(C(Cc2ccccc2)(NC(=O)NC2CCCC2)c2cc(F)cc(C(F)(F)F)c2)c1] | ethyl 3-(3-(1-(3-cyclopentylureido)-1-(3-fluoro-5-(trifluoromethyl)phenyl)-2-phenylethyl)phenyl)propanoate | 4.285 LC (4) 571.3 [M + H]$^+$ | Procedures 1, 2 and 24 |

TABLE 9-continued

| Ex. No. | Structure | Name | Retention Time Min./ Molecular Mass | Prepared in the manner described in: |
|---|---|---|---|---|
| 385 | 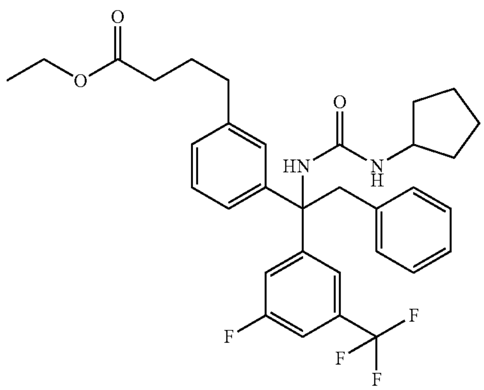 [SMILES: CCOC(=O)CCCc1cccc(C(Cc2ccccc2)(NC(=O)NC2CCCC2)c2cc(F)cc(C(F)(F)F)c2)c1] | ethyl 4-(3-(1-(3-cyclopentylureido)-1-(3-fluoro-5-(trifluoromethyl)phenyl)-2-phenylethyl)phenyl)butanoate | 4.376 LC (4) 585.3 [M + H]⁺ | Procedures 1, 2 and 24 |
| 386 | 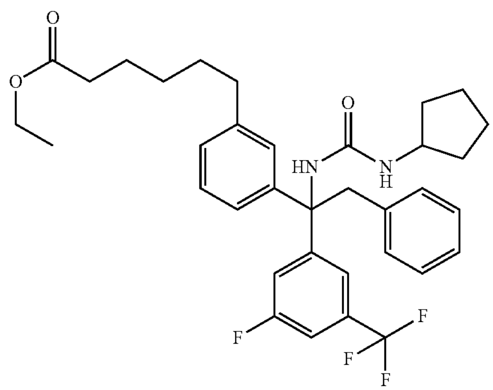 [SMILES: CCOC(=O)CCCCCc1cccc(C(Cc2ccccc2)(NC(=O)NC2CCCC2)c2cc(F)cc(C(F)(F)F)c2)c1] | ethyl 6-(3-(1-(3-cyclopentylureido)-1-(3-fluoro-5-(trifluoromethyl)phenyl)-2-phenylethyl)phenyl)hexanoate | 4.536 LC (4) 613.4 [M + H]⁺ | Procedures 1, 2 and 24 |
| 387 | 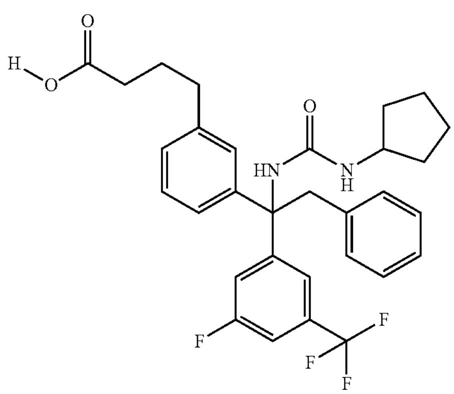 [SMILES: O=C(O)CCCc1cccc(C(Cc2ccccc2)(NC(=O)NC2CCCC2)c2cc(F)cc(C(F)(F)F)c2)c1] | 4-(3-(1-(3-cyclopentylureido)-1-(3-fluoro-5-(trifluoromethyl)phenyl)-2-phenylethyl)phenyl)butanoic acid | 4.135 LC (4) 557.3 [M + H]⁺ | Procedures 1, 2, 24 and 23 |
| 388 | 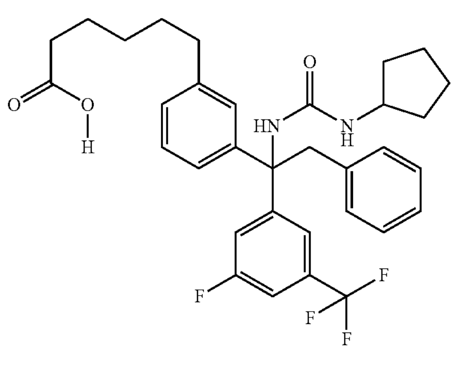 [SMILES: O=C(O)CCCCCc1cccc(C(Cc2ccccc2)(NC(=O)NC2CCCC2)c2cc(F)cc(C(F)(F)F)c2)c1] | 6-(3-(1-(3-cyclopentylureido)-1-(3-fluoro-5-(trifluoromethyl)phenyl)-2-phenylethyl)phenyl)hexanoic acid | 4.288 LC (4) 585.3 [M + H]⁺ | Procedures 1, 2, 24 and 23 |

TABLE 9-continued

| Ex. No. | Structure | Name | Retention Time Min./ Molecular Mass | Prepared in the manner described in: |
|---|---|---|---|---|
| 389 | 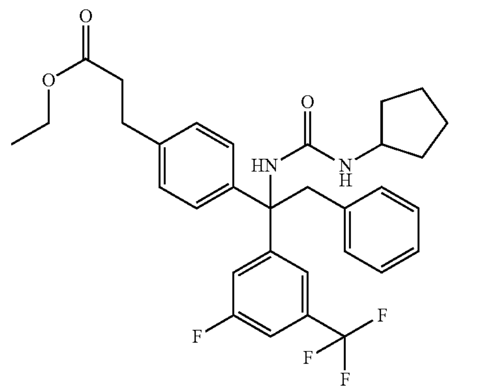 [SMILES: CCOC(=O)CCc1ccc(C(Cc2ccccc2)(NC(=O)NC2CCCC2)c2cc(F)cc(C(F)(F)F)c2)cc1] | ethyl 3-(4-(1-(3-cyclopentylureido)-1-(3-fluoro-5-(trifluoromethyl)phenyl)-2-phenylethyl)phenyl)propanoate | 4.286 LC (4) 571.3 [M + H]$^+$ | Procedures 1, 2 and 24 |
| 390 | 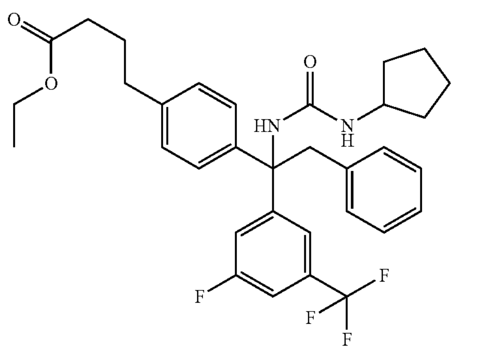 [SMILES: CCOC(=O)CCCc1ccc(C(Cc2ccccc2)(NC(=O)NC2CCCC2)c2cc(F)cc(C(F)(F)F)c2)cc1] | ethyl 4-(4-(1-(3-cyclopentylureido)-1-(3-fluoro-5-(trifluoromethyl)phenyl)-2-phenylethyl)phenyl)butanoate | 4.391 LC (4) 585.3 [M + H]$^+$ | Procedures 1, 2 and 24 |
| 391 | 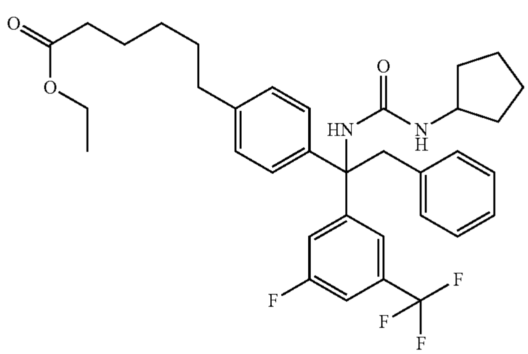 [SMILES: CCOC(=O)CCCCCc1ccc(C(Cc2ccccc2)(NC(=O)NC2CCCC2)c2cc(F)cc(C(F)(F)F)c2)cc1] | ethyl 6-(4-(1-(3-cyclopentylureido)-1-(3-fluoro-5-(trifluoromethyl)phenyl)-2-phenylethyl)phenyl)hexanoate | 4.54 LC (4) 613.3 [M + H]$^+$ | Procedures 1, 2 and 24 |
| 392 | 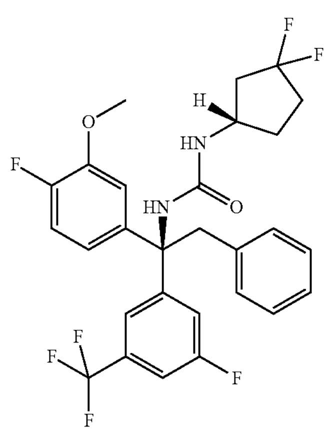 [SMILES: COc1cc([C@@](Cc2ccccc2)(NC(=O)N[C@H]2CCC(F)(F)C2)c2cc(F)cc(C(F)(F)F)c2)ccc1F] | 1-((S)-3,3-difluorocyclopentyl)-3-((R)-1-(4-fluoro-3-methoxyphenyl)-1-(3-fluoro-5-(trifluoromethyl)phenyl)-2-phenylethyl)urea | 3.456 LC (1) 555.27 [M + H]$^+$ | Procedures 4, 5, 6 and 12 |

TABLE 9-continued

| Ex. No. | Structure | Name | Retention Time Min./ Molecular Mass | Prepared in the manner described in: |
|---|---|---|---|---|
| 393 | 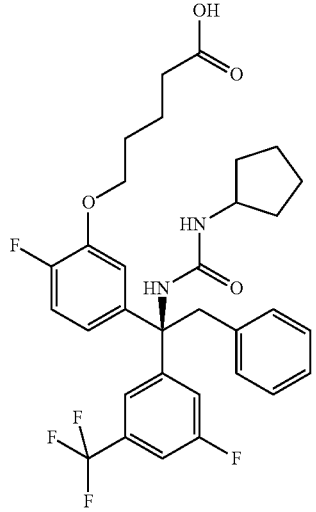 [SMILES: O=C(O)CCCCOc1cc([C@@](Cc2ccccc2)(NC(=O)NC2CCCC2)c2cc(F)cc(C(F)(F)F)c2)ccc1F] | (R)-5-(5-(1-(3-cyclopentylureido)-1-(3-fluoro-5-(trifluoromethyl)phenyl)-2-phenylethyl)-2-fluorophenoxy)pentanoic acid | 3.265 LC (1) 605.15 [M + H]+ | Procedures 4, 5, 6, 2, 59, 68 and 23 |
| 394 | 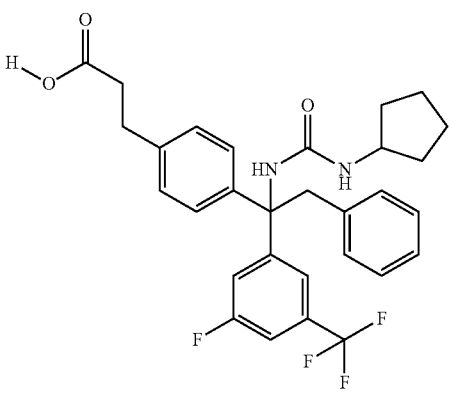 [SMILES: O=C(O)CCc1ccc(C(Cc2ccccc2)(NC(=O)NC2CCCC2)c2cc(F)cc(C(F)(F)F)c2)cc1] | 3-(4-(1-(3-cyclopentylureido)-1-(3-fluoro-5-(trifluoromethyl)phenyl)-2-phenylethyl)phenyl)propanoic acid | 4.045 LC (4) 543.3 [M + H]+ | Procedures 1, 2, 24 and 23 |
| 395 | 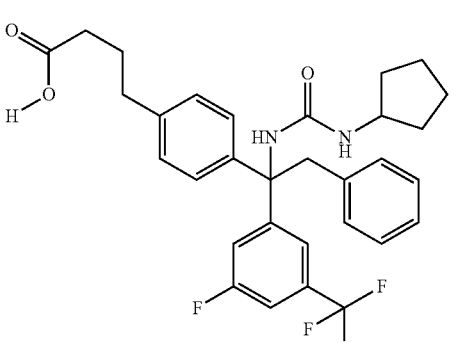 | 4-(4-(1-(3-cyclopentylureido)-1-(3-fluoro-5-(trifluoromethyl)phenyl)-2-phenylethyl)phenyl)butanoic acid | 4.098 LC (4) 557.2 [M + H]+ | Procedures 1, 2, 24 and 23 |

TABLE 9-continued

| Ex. No. | Structure | Name | Retention Time Min./ Molecular Mass | Prepared in the manner described in: |
|---|---|---|---|---|
| 396 | 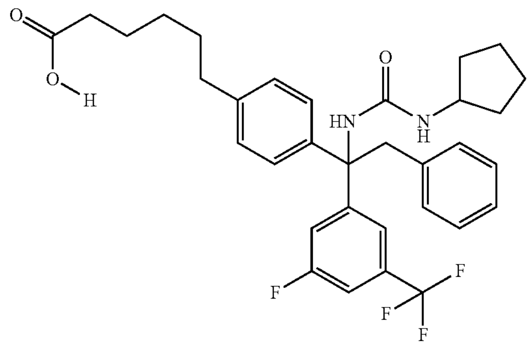 [SMILES: O=C(O)CCCCCc1ccc(C(Cc2ccccc2)(NC(=O)NC2CCCC2)c2cc(F)cc(C(F)(F)F)c2)cc1] | 6-(4-(1-(3-cyclopentylureido)-1-(3-fluoro-5-(trifluoromethyl)phenyl)-2-phenylethyl)phenyl)hexanoic acid | 4.275 LC (4) 585.2 [M + H]$^+$ | Procedures 1, 24 and 23 |
| 397 | 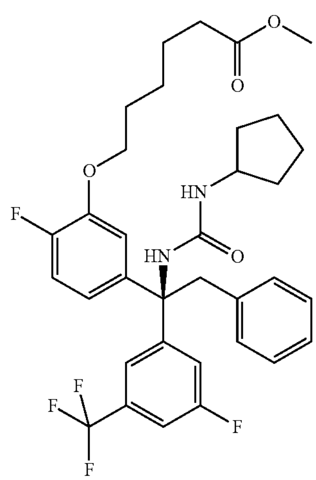 [SMILES: COC(=O)CCCCCOc1cc([C@@](Cc2ccccc2)(NC(=O)NC2CCCC2)c2cc(F)cc(C(F)(F)F)c2)ccc1F] | (R)-methyl 6-(5-(1-(3-cyclopentylureido)-1-(3-fluoro-5-(trifluoromethyl)phenyl)-2-phenylethyl)-2-fluoro-phenoxy)hexanoate | 3.818 LC (1) 633.45 [M + H]$^+$ | Procedures 4, 5, 6, 2, 59, 68 and 23 |
| 398 | 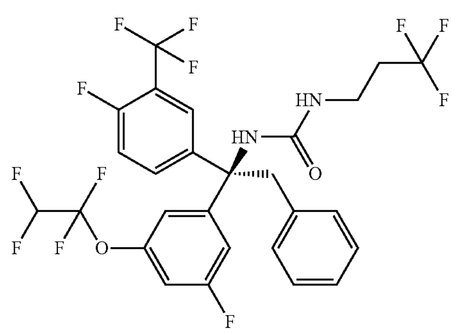 [SMILES: O=C(NCCC(F)(F)F)N[C@@](Cc1ccccc1)(c1cc(F)cc(OC(F)(F)C(F)F)c1)c1ccc(F)c(C(F)(F)F)c1] | (R)-1-(1-(4-fluoro-3-(trifluoromethyl)phenyl)-1-(3-fluoro-5-(1,1,2,2-tetrafluoro-ethoxy)phenyl)-2-phenylethyl)-3-(3,3,3-trifluoropropyl)urea | 3.653 LC (1) 633.14 [M + H]$^+$ | Procedures 3, 4, 5, 6 and 10 |
| 399 | 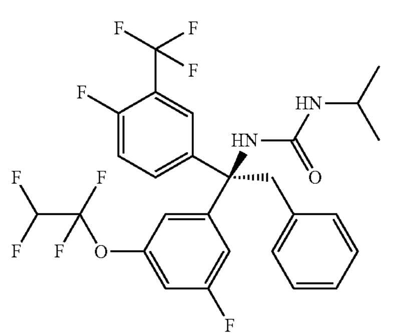 [SMILES: CC(C)NC(=O)N[C@@](Cc1ccccc1)(c1cc(F)cc(OC(F)(F)C(F)F)c1)c1ccc(F)c(C(F)(F)F)c1] | (R)-1-(1-(4-fluoro-3-(trifluoromethyl)phenyl)-1-(3-fluoro-5-(1,1,2,2-tetrafluoro-ethoxy)phenyl)-2-phenylethyl)-3-isopropylurea | 3.59 LC (1) 579.03 [M + H]$^+$ | Procedures 3, 4, 5, 6 and 10 |

TABLE 9-continued

| Ex. No. | Structure | Name | Retention Time Min./ Molecular Mass | Prepared in the manner described in: |
|---|---|---|---|---|
| 400 | 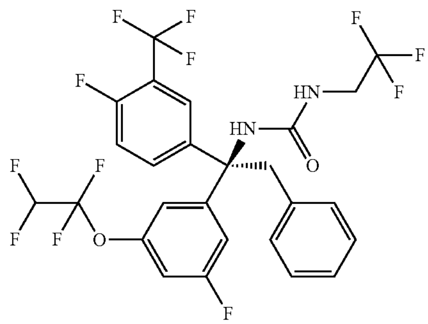 [SMILES: O=C(NCC(F)(F)F)N[C@@](Cc1ccccc1)(c1cc(F)cc(OC(F)(F)C(F)F)c1)c1ccc(F)c(C(F)(F)F)c1] | (R)-1-(1-(4-fluoro-3-(trifluoromethyl)phenyl)-1-(3-fluoro-5-(1,1,2,2-tetrafluoro-ethoxy)phenyl)-2-phenylethyl)-3-(2,2,2-trifluoroethyl)urea | 4.06 LC (1) 619.64 [M + H]$^+$ | Procedures 3, 4, 5, 6 and 10 |
| 401 | 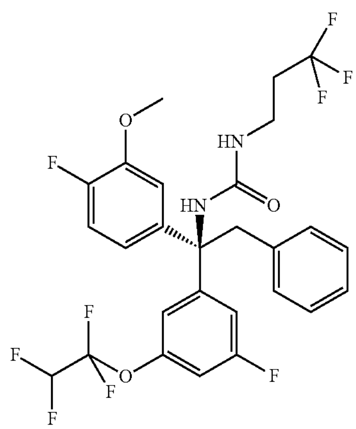 [SMILES: COc1cc([C@@](Cc2ccccc2)(NC(=O)NCCC(F)(F)F)c2cc(F)cc(OC(F)(F)C(F)F)c2)ccc1F] | (R)-1-(1-(4-fluoro-3-methoxyphenyl)-1-(3-fluoro-5-(1,1,2,2-tetrafluoroethoxy)phenyl)-2-phenylethyl)-3-(3,3,3-trifluoropropyl)urea | 3.39 LC (1) 595.63 [M + H]$^+$ | Procedures 3, 4, 5, 6 and 10 |
| 402 | 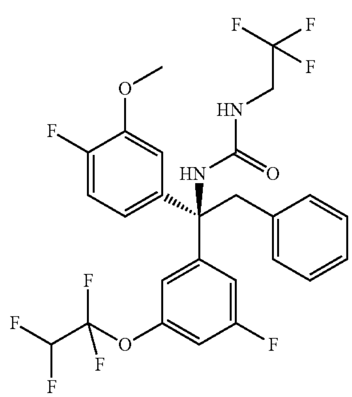 [SMILES: COc1cc([C@@](Cc2ccccc2)(NC(=O)NCC(F)(F)F)c2cc(F)cc(OC(F)(F)C(F)F)c2)ccc1F] | (R)-1-(1-(4-fluoro-3-methoxyphenyl)-1-(3-fluoro-5-(1,1,2,2-tetrafluoroethoxy)phenyl)-2-phenylethyl)-3-(2,2,2-trifluoroethyl)urea | 3.4 LC (1) 581.1 [M + H]$^+$ | Procedures 3, 4, 5, 6 and 10 |

TABLE 9-continued

| Ex. No. | Structure | Name | Retention Time Min./ Molecular Mass | Prepared in the manner described in: |
|---|---|---|---|---|
| 403 | 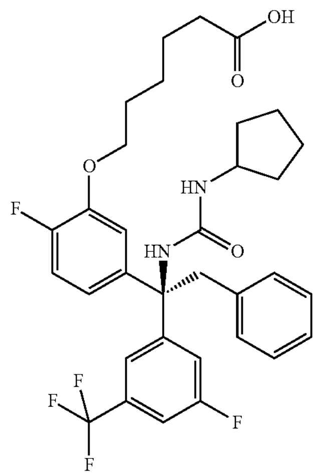 [SMILES: O=C(O)CCCCCOc1cc([C@@](Cc2ccccc2)(NC(=O)NC2CCCC2)c2cc(F)cc(C(F)(F)F)c2)ccc1F] | (R)-6-(5-(1-(3-cyclopentylureido)-1-(3-fluoro-5-(trifluoromethyl)phenyl)-2-phenylethyl)-2-fluorophenoxy)hexanoic acid | 3.37 LC (1) 619.39 $[M + H]^+$ | Procedures 4, 5, 6, 2, 59, 68 and 23 |
| 404 | 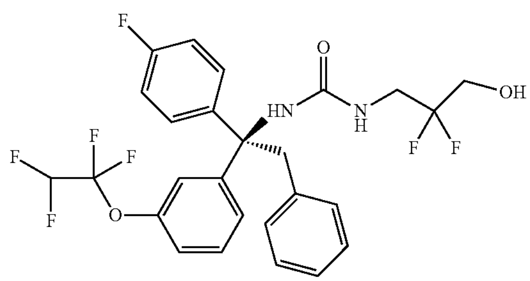 [SMILES: O=C(NCC(F)(F)CO)N[C@](Cc1ccccc1)(c1ccc(F)cc1)c1cccc(OC(F)(F)C(F)F)c1] | (R)-1-(2,2-difluoro-3-hydroxypropyl)-3-(1-(3-fluoro-5-(1,1,2,2-tetrafluoroethoxy)phenyl)-1-(4-fluorophenyl)-2-phenylethyl)urea | 3.82 LC (1) 563.16 $[M + H]^+$ | Procedures 3, 4, 5, 6 and 25 |
| 405 | 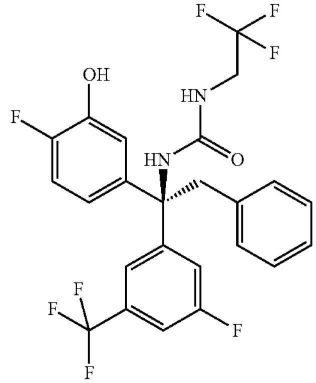 | (R)-1-(1-(4-fluoro-3-hydroxyphenyl)-1-(3-fluoro-5-(trifluoromethyl)phenyl)-2-phenylethyl)-3-(2,2,2-trifluoroethyl)urea | 3.07 LC (1) 519.14 $[M + H]^+$ | Procedures 4, 5, 6, 10 and 59 |

TABLE 9-continued

| Ex. No. | Structure | Name | Retention Time Min./ Molecular Mass | Prepared in the manner described in: |
|---|---|---|---|---|
| 406 | 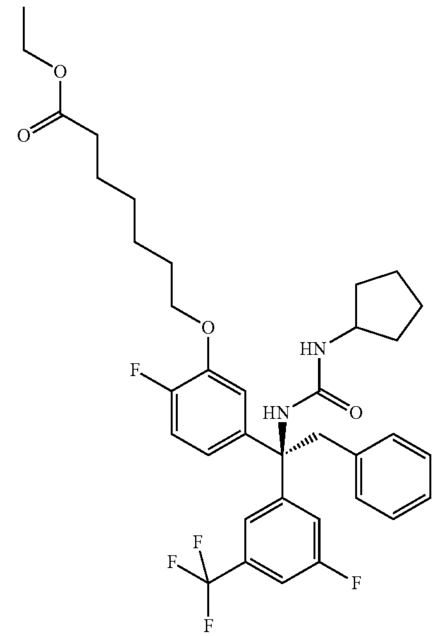 [SMILES: CCOC(=O)CCCCCCOc1cc([C@@](Cc2ccccc2)(NC(=O)NC2CCCC2)c2cc(F)cc(C(F)(F)F)c2)ccc1F] | (R)-ethyl 7-(5-(1-(3-cyclopentylureido)-1-(3-fluoro-5-(trifluoromethyl)phenyl)-2-phenylethyl)-2-fluorophenoxy)heptanoate | 4.09 LC (1) 661.37 [M + H]$^+$ | Procedures 4, 5, 6, 2, 59 and 68 |
| 407 | 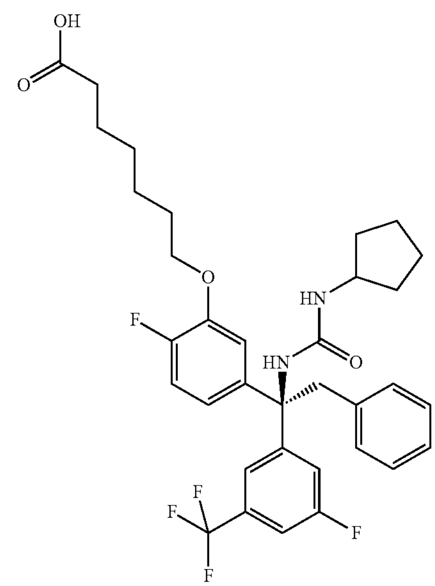 [SMILES: O=C(O)CCCCCCOc1cc([C@@](Cc2ccccc2)(NC(=O)NC2CCCC2)c2cc(F)cc(C(F)(F)F)c2)ccc1F] | (R)-7-(5-(1-(3-cyclopentylureido)-1-(3-fluoro-5-(trifluoromethyl)phenyl)-2-phenylethyl)-2-fluorophenoxy)heptanoic acid | 3.48 LC (1) 633.21 [M + H]$^+$ | Procedures 4, 5, 6, 2, 59 68 and 23 |
| 408 | 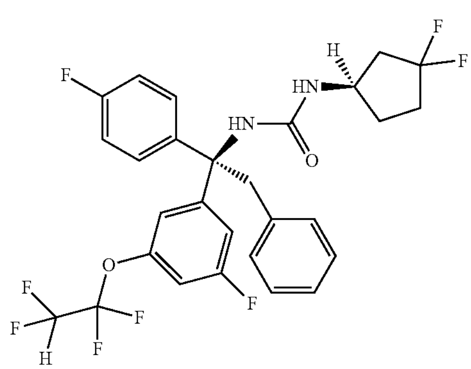 [SMILES: O=C(N[C@@H]1CCC(F)(F)C1)N[C@](Cc1ccccc1)(c1ccc(F)cc1)c1cc(F)cc(OC(F)(F)C(F)F)c1] | 1-((R)-3,3-difluorocyclopentyl)-3-((R)-1-(3-fluoro-5-(1,1,2,2-tetrafluoroethoxy)phenyl)-1-(4-fluorophenyl)-2-phenylethyl)urea | 4.011 LC (3) 573.4 [M + H]$^+$ | Procedures 3, 4, 5, 6 and 12 |

TABLE 9-continued

| Ex. No. | Structure | Name | Retention Time Min./ Molecular Mass | Prepared in the manner described in: |
|---|---|---|---|---|
| 409 | 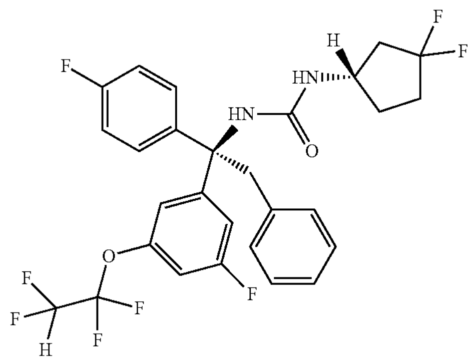 [SMILES: O=C(N[C@H]1CCC(F)(F)C1)N[C@](Cc1ccccc1)(c1ccc(F)cc1)c1cc(F)cc(OC(F)(F)C(F)F)c1] | 1-((S)-3,3-difluorocyclopentyl)-3-((R)-1-(3-fluoro-5-(1,1,2,2-tetrafluoroethoxy)phenyl)-1-(4-fluorophenyl)-2-phenylethyl)urea | 3.455 LC (3) 573.4 [M + H]⁺ | Procedures 3, 4, 5, 6 and 12 |
| 410 | 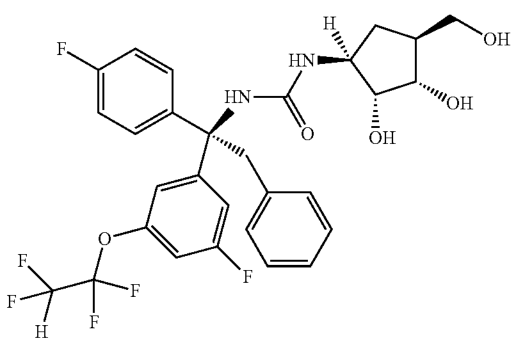 [SMILES: O=C(N[C@H]1C[C@@H](CO)[C@H](O)[C@@H]1O)N[C@](Cc1ccccc1)(c1ccc(F)cc1)c1cc(F)cc(OC(F)(F)C(F)F)c1] | 1-((1S,2R,3S,4S)-2,3-dihydroxy-4-(hydroxymethyl)cyclopentyl)-3-((R)-1-(3-fluoro-5-(1,1,2,2-tetrafluoroethoxy)phenyl)-1-(4-fluorophenyl)-2-phenylethyl)urea | 3.736 LC (3) 599.4 [M + H]⁺ | Procedures 3, 4, 5, 6 and 12 |
| 411 | 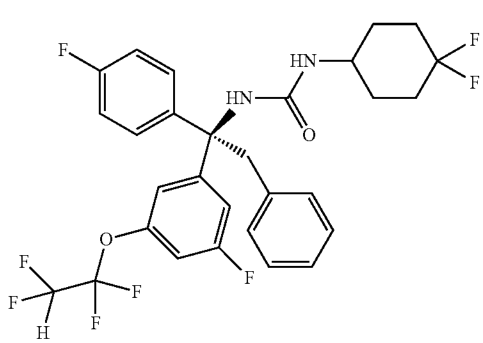 [SMILES: O=C(NC1CCC(F)(F)CC1)N[C@](Cc1ccccc1)(c1ccc(F)cc1)c1cc(F)cc(OC(F)(F)C(F)F)c1] | (R)-1-(4,4-difluorocyclohexyl)-3-(1-(3-fluoro-5-(1,1,2,2-tetrafluoroethoxy)phenyl)-1-(4-fluorophenyl)-2-phenylethyl)urea | 4.046 LC (3) 585.3 [M − H]⁻ | Procedures 3, 4, 5, 6, 130 and 12 |

| Ex. No. | Structure | Name | Retention Time Min./ Molecular Mass | Prepared in the manner described in: |
|---|---|---|---|---|
| 412 | 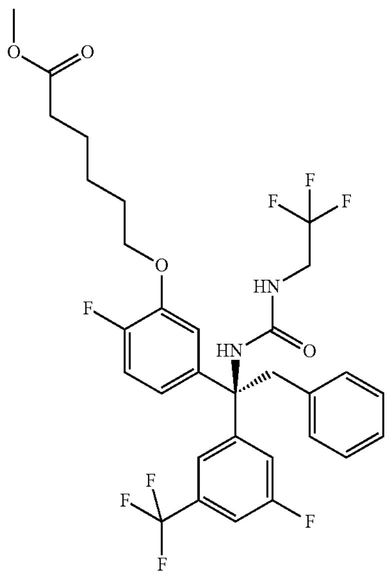 [SMILES: COC(=O)CCCCCOc1cc([C@@](Cc2ccccc2)(NC(=O)NCC(F)(F)F)c2cc(F)cc(C(F)(F)F)c2)ccc1F] | (R)-methyl 6-(2-fluoro-5-(1-(3-fluoro-5-(trifluoromethyl)phenyl)-2-phenyl-1-(3-(2,2,2-trifluoroethyl)ureido)ethyl)phenoxy)hexanoate | 3.69 LC (1) 647.11 [M + H]⁺ | Procedures 4, 5, 6, 10, 59 and 68 |
| 413 | 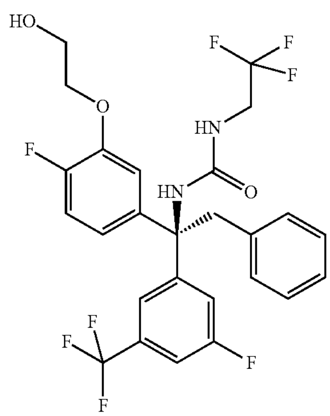 [SMILES: O=C(NCC(F)(F)F)N[C@@](Cc1ccccc1)(c1cc(F)cc(C(F)(F)F)c1)c1ccc(F)c(OCCO)c1] | (R)-1-(1-(4-fluoro-3-(2-hydroxyethoxy)phenyl)-1-(3-fluoro-5-(trifluoromethyl)phenyl)-2-phenylethyl)-3-(2,2,2-trifluoroethyl)urea | 3.03 LC (1) 563.17 [M + H]⁺ | Procedures 4, 5, 6, 10, 59 and 68 |
| 414 | 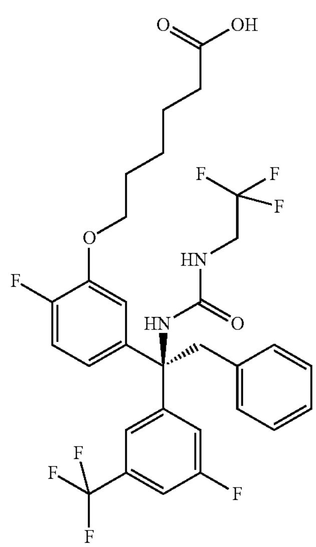 [SMILES: O=C(O)CCCCCOc1cc([C@@](Cc2ccccc2)(NC(=O)NCC(F)(F)F)c2cc(F)cc(C(F)(F)F)c2)ccc1F] | (R)-6-(2-fluoro-5-(1-(3-fluoro-5-(trifluoromethyl)phenyl)-2-phenyl-1-(3-(2,2,2-trifluoroethyl)ureido)ethyl)phenoxy)hexanoic acid | 3.28 LC (1) 633.17 [M + H]⁺ | Procedures 4, 5, 6, 10, 59, 68 and 23 |

TABLE 9-continued

| Ex. No. | Structure | Name | Retention Time Min./ Molecular Mass | Prepared in the manner described in: |
|---|---|---|---|---|
| 415 | 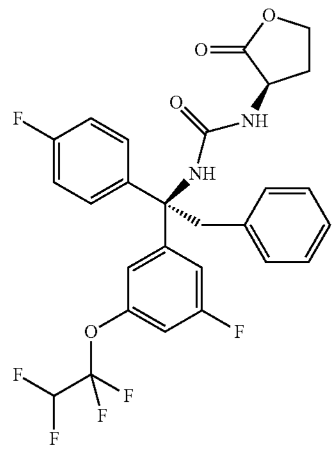 [SMILES: O=C(N[C@@H]1CCOC1=O)N[C@](Cc1ccccc1)(c1ccc(F)cc1)c1cc(F)cc(OC(F)(F)C(F)F)c1] | 1-((R)-1-(3-fluoro-5-(1,1,2,2-tetrafluoroethoxy)phenyl)-1-(4-fluorophenyl)-2-phenylethyl)-3-((R)-2-oxotetrahydrofuran-3-yl)urea | 3.85 LC (1) 553.1 [M + H]+ | Procedures 3, 4, 5, 6 and 25 |
| 416 | 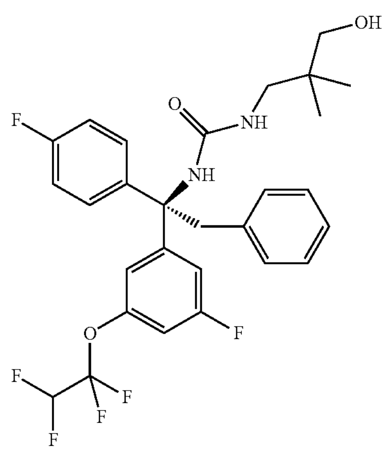 [SMILES: CC(C)(CO)CNC(=O)N[C@](Cc1ccccc1)(c1ccc(F)cc1)c1cc(F)cc(OC(F)(F)C(F)F)c1] | (R)-1-(1-(3-fluoro-5-(1,1,2,2-tetrafluoroethoxy)phenyl)-1-(4-fluorophenyl)-2-phenylethyl)-3-(3-hydroxy-2,2-dimethylpropyl)urea | 3.97 LC (1) 555.14 [M + H]+ | Procedures 3, 4, 5, 6 and 12 |
| 417 | 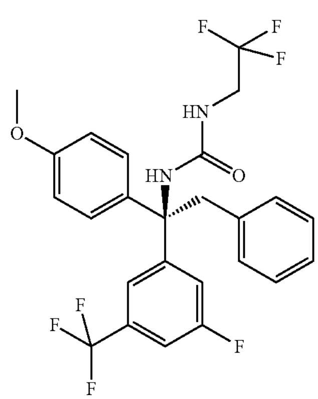 [SMILES: COc1ccc([C@@](Cc2ccccc2)(NC(=O)NCC(F)(F)F)c2cc(F)cc(C(F)(F)F)c2)cc1] | (R)-1-(1-(3-fluoro-5-(trifluoromethyl)phenyl)-1-(4-methoxyphenyl)-2-phenylethyl)-3-(2,2,2-trifluoroethyl)urea | 3.438 LC (1) 515.10 [M + H]+ | Procedures 4, 5, 6 and 10 |

TABLE 9-continued

| Ex. No. | Structure | Name | Retention Time Min./ Molecular Mass | Prepared in the manner described in: |
|---|---|---|---|---|
| 418 | 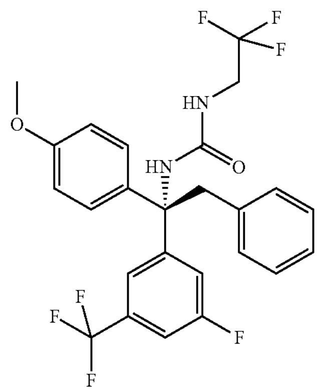 [SMILES: COc1ccc([C@](Cc2ccccc2)(NC(=O)NCC(F)(F)F)c2cc(F)cc(C(F)(F)F)c2)cc1] | (S)-1-(1-(3-fluoro-5-(trifluoromethyl)phenyl)-1-(4-methoxyphenyl)-2-phenylethyl)-3-(2,2,2-trifluoroethyl)urea | 3.436 LC (1) 515.11 [M + H]+ | Procedures 4, 5, 6 and 10 |
| 419 | 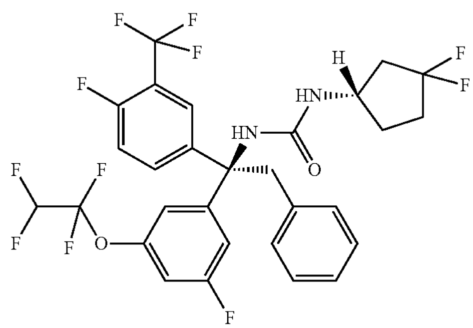 [SMILES: O=C(N[C@H]1CCC(F)(F)C1)N[C@@](Cc1ccccc1)(c1cc(F)cc(OC(F)(F)C(F)F)c1)c1ccc(F)c(C(F)(F)F)c1] | 1-((S)-3,3-difluorocyclopentyl)-3-((R)-1-(4-fluoro-3-(trifluoromethyl)phenyl)-1-(3-fluoro-5-(1,1,2,2-tetrafluoroethoxy)phenyl)-2-phenylethyl)urea | 3.66 LC (1) 641.68 [M + H]+ | Procedures 3, 4, 5, 6 and 12 |
| 420 | 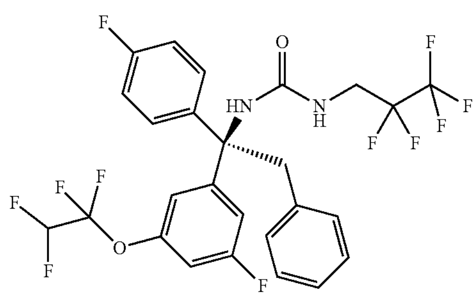 [SMILES: O=C(NCC(F)(F)C(F)(F)F)N[C@](Cc1ccccc1)(c1ccc(F)cc1)c1cc(F)cc(OC(F)(F)C(F)F)c1] | (R)-1-(1-(3-fluoro-5-(1,1,2,2-tetrafluoroethoxy)phenyl)-1-(4-fluorophenyl)-2-phenylethyl)-3-(2,2,3,3,3-pentafluoropropyl)urea | 4.06 LC (1) 601.4 [M + H]+ | Procedures 3, 4, 5, 6 and 25 |
| 421 | 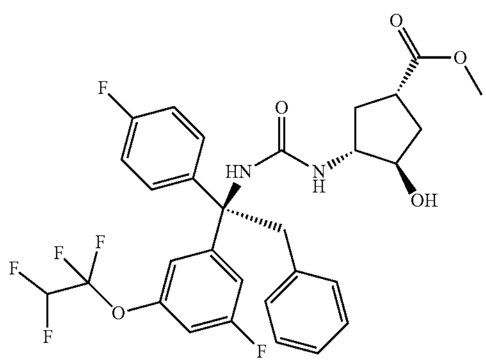 [SMILES: COC(=O)[C@@H]1C[C@@H](O)[C@H](NC(=O)N[C@](Cc2ccccc2)(c2ccc(F)cc2)c2cc(F)cc(OC(F)(F)C(F)F)c2)C1] | (1S,3R,4R)-methyl 3-(3-((R)-1-(3-fluoro-5-(1,1,2,2-tetrafluoro-ethoxy)phenyl)-1-(4-fluorophenyl)-2-phenylethyl)ureido)-4-hydroxycyclopentanecarboxylate | 3.87 LC (3) 611.5 [M + H]+ | Procedures 3, 4, 5, 6 and 25 |

TABLE 9-continued

| Ex. No. | Structure | Name | Retention Time Min./ Molecular Mass | Prepared in the manner described in: |
|---|---|---|---|---|
| 422 | 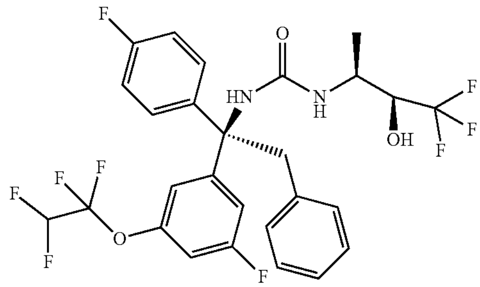 [SMILES: C[C@H](NC(=O)N[C@](Cc1ccccc1)(c1ccc(F)cc1)c1cc(F)cc(OC(F)(F)C(F)F)c1)[C@H](O)C(F)(F)F] | 1-((R)-1-(3-fluoro-5-(1,1,2,2-tetrafluoroethoxy)phenyl)-1-(4-fluorophenyl)-2-phenylethyl)-3-((2S,3S)-4,4,4-trifluoro-3-hydroxybutan-2-yl)urea | 3.99 LC (1) 595.12 [M + H]$^+$ | Procedures 3, 4, 5, 6 and 25 |
| 423 | 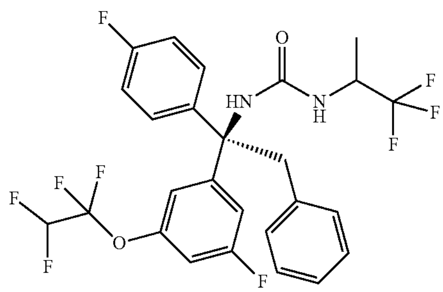 [SMILES: CC(NC(=O)N[C@](Cc1ccccc1)(c1ccc(F)cc1)c1cc(F)cc(OC(F)(F)C(F)F)c1)C(F)(F)F] | 1-((R)-1-(3-fluoro-5-(1,1,2,2-tetrafluoroethoxy)phenyl)-1-(4-fluorophenyl)-2-phenylethyl)-3-(1,1,1-trifluoropropan-2-yl)urea | 4.05 LC (1) 565.65 [M + H]$^+$ | Procedures 3, 4, 5, 6 and 25 |
| 424 | 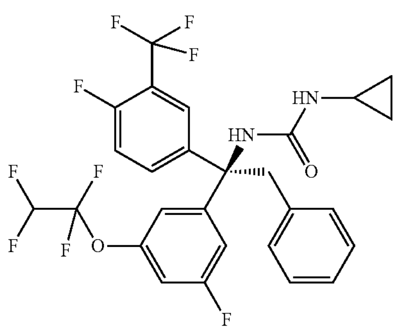 [SMILES: O=C(NC1CC1)N[C@@](Cc1ccccc1)(c1cc(F)cc(OC(F)(F)C(F)F)c1)c1ccc(F)c(C(F)(F)F)c1] | (R)-1-cyclopropyl-3-(1-(4-fluoro-3-(trifluoromethyl)phenyl)-1-(3-fluoro-5-(1,1,2,2-tetrafluoroethoxy)phenyl)-2-phenylethyl)urea | 3.46 LC (1) 577.03 [M + H]$^+$ | Procedures 3, 4, 5, 6 and 10 |
| 425 | 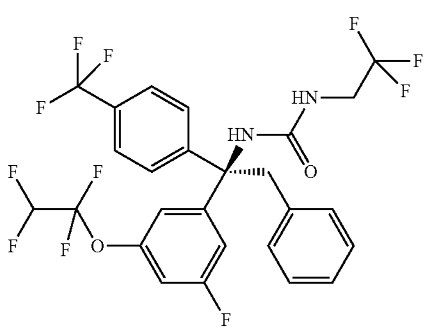 [SMILES: O=C(NCC(F)(F)F)N[C@](Cc1ccccc1)(c1ccc(C(F)(F)F)cc1)c1cc(F)cc(OC(F)(F)C(F)F)c1] | (R)-1-(1-(3-fluoro-5-(1,1,2,2-tetrafluoroethoxy)phenyl)-2-phenyl-1-(4-(trifluoromethyl)phenyl)ethyl)-3-(2,2,2-trifluoroethyl)urea | 3.62 LC (1) 600.98 [M + H]$^+$ | Procedures 3, 4, 5, 6, 2 and 9 |

TABLE 9-continued

| Ex. No. | Structure | Name | Retention Time Min./ Molecular Mass | Prepared in the manner described in: |
|---|---|---|---|---|
| 426 | 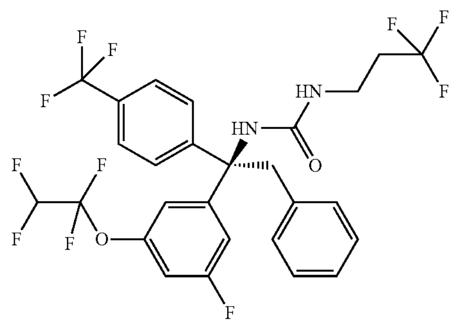 [SMILES: O=C(NCCC(F)(F)F)N[C@](Cc1ccccc1)(c1ccc(C(F)(F)F)cc1)c1cc(F)cc(OC(F)(F)C(F)F)c1] | (R)-1-(1-(3-fluoro-5-(1,1,2,2-tetrafluoroethoxy)phenyl)-2-phenyl-1-(4-(trifluoromethyl)phenyl)ethyl)-3-(3,3,3-trifluoropropyl)urea | 3.64 LC (1) 615.65 [M + H]$^+$ | Procedures 3, 4, 5, 6, 2 and 9 |
| 427 | 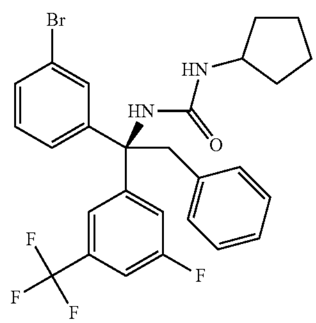 [SMILES: O=C(NC1CCCC1)N[C@](Cc1ccccc1)(c1cccc(Br)c1)c1cc(F)cc(C(F)(F)F)c1] | (S)-1-(1-(3-bromophenyl)-1-(3-fluoro-5-(trifluoromethyl)phenyl)-2-phenylethyl)-3-cyclopentylurea | 4.30 LC (4) 549.13 [M + H]$^+$ | Procedures 4, 5, 6 and 2 |
| 428 | 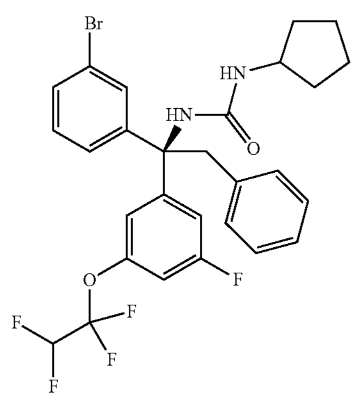 [SMILES: O=C(NC1CCCC1)N[C@](Cc1ccccc1)(c1cccc(Br)c1)c1cc(F)cc(OC(F)(F)C(F)F)c1] | (S)-1-(1-(3-bromophenyl)-1-(3-fluoro-5-(1,1,2,2-tetrafluoroethoxy)phenyl)-2-phenylethyl)-3-cyclopentylurea | 4.23 LC (4) 597.15 [M + H]$^+$ | Procedures 3, 4, 5, 6 and 2 |
| 429 | 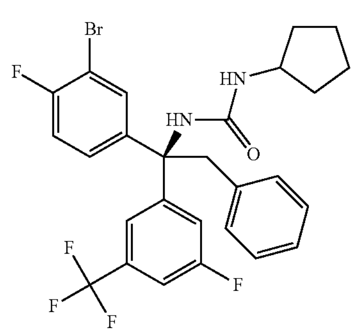 [SMILES: O=C(NC1CCCC1)N[C@@](Cc1ccccc1)(c1cc(F)cc(C(F)(F)F)c1)c1ccc(F)c(Br)c1] | (S)-1-(1-(3-bromo-4-fluorophenyl)-1-(3-fluoro-5-(trifluoromethyl)phenyl)-2-phenylethyl)-3-cyclopentylurea | 4.30 LC (4) 567.14 [M + H]$^+$ | Procedures 62, 5, 6 and 2 |

TABLE 9-continued

| Ex. No. | Structure | Name | Retention Time Min./ Molecular Mass | Prepared in the manner described in: |
|---|---|---|---|---|
| 430 | 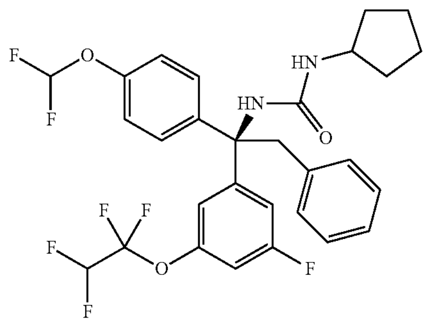 [SMILES: O=C(NC1CCCC1)N[C@](Cc1ccccc1)(c1ccc(OC(F)F)cc1)c1cc(F)cc(OC(F)(F)C(F)F)c1] | (R)-1-cyclopentyl-3-(1-(4-(difluoromethoxy)phenyl)-1-(3-fluoro-5-(1,1,2,2-tetrafluoro-ethoxy)phenyl)-2-phenylethyl)urea | 4.10 LC (4) 585.20 [M + H]+ | Procedures 3, 4, 5, 6 and 2 |
| 431 | 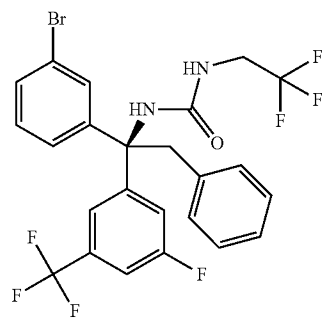 [SMILES: O=C(NCC(F)(F)F)N[C@](Cc1ccccc1)(c1cccc(Br)c1)c1cc(F)cc(C(F)(F)F)c1] | (S)-1-(1-(3-bromophenyl)-1-(3-fluoro-5-(trifluoromethyl)phenyl)-2-phenylethyl)-3-(2,2,2-trifluoroethyl)urea | 4.21 LC (4) 563.07 [M + H]+ | Procedures 4, 5, 6 and 12 |
| 432 | 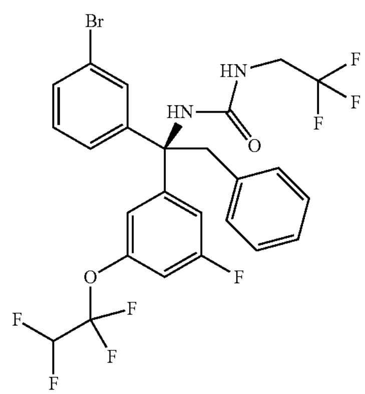 [SMILES: O=C(NCC(F)(F)F)N[C@](Cc1ccccc1)(c1cccc(Br)c1)c1cc(F)cc(OC(F)(F)C(F)F)c1] | (S)-1-(1-(3-bromophenyl)-1-(3-fluoro-5-(1,1,2,2-tetrafluoro-ethoxy)phenyl)-2-phenylethyl)-3-(2,2,2-trifluoroethyl)urea | 4.13 LC (4) 611.06 [M + H]+ | Procedures 4, 5, 6 and 12 |
| 433 | 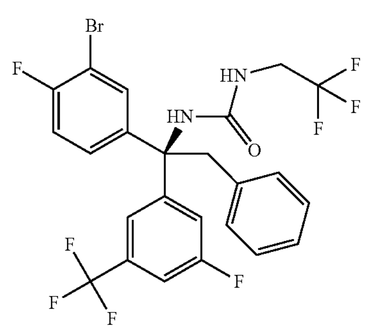 [SMILES: O=C(NCC(F)(F)F)N[C@@](Cc1ccccc1)(c1cc(F)cc(C(F)(F)F)c1)c1ccc(F)c(Br)c1] | (S)-1-(1-(3-bromo-4-fluorophenyl)-1-(3-fluoro-5-(trifluoromethyl)phenyl)-2-phenylethyl)-3-(2,2,2-trifluoroethyl)urea | 4.19 LC (4) 581.04 [M + H]+ | Procedures 62, 5, 6 and 12 |

TABLE 9-continued

| Ex. No. | Structure | Name | Retention Time Min./ Molecular Mass | Prepared in the manner described in: |
|---|---|---|---|---|
| 434 | 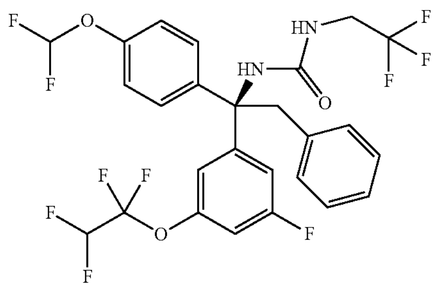 [SMILES: O=C(NCC(F)(F)F)N[C@](Cc1ccccc1)(c1ccc(OC(F)F)cc1)c1cc(F)cc(OC(F)(F)C(F)F)c1] | (R)-1-(1-(4-(difluoro-methoxy)phenyl)-1-(3-fluoro-5-(1,1,2,2-tetrafluoroethoxy)phenyl)-2-phenylethyl)-3-(2,2,2-trifluoroethyl)urea | 4.01 LC (4) 599.15 [M + H]$^+$ | Procedures 3, 4, 5, 6 and 12 |
| 435 | 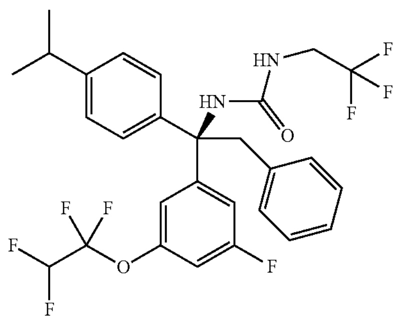 [SMILES: CC(C)c1ccc([C@@](Cc2ccccc2)(NC(=O)NCC(F)(F)F)c2cc(F)cc(OC(F)(F)C(F)F)c2)cc1] | (R)-1-(1-(3-fluoro-5-(1,1,2,2-tetrafluoroethoxy)phenyl)-1-(4-isopropylphenyl)-2-phenylethyl)-3-(2,2,2-trifluoroethyl)urea | 4.27 LC (4) 575.23 [M + H]$^+$ | Procedures 3, 4, 5, 6 and 12 |
| 436 | 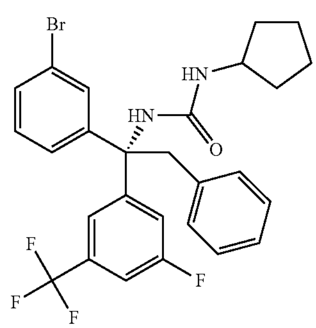 [SMILES: O=C(NC1CCCC1)N[C@@](Cc1ccccc1)(c1cccc(Br)c1)c1cc(F)cc(C(F)(F)F)c1] | (R)-1-(1-(3-bromophenyl)-1-(3-fluoro-5-(trifluoromethyl)phenyl)-2-phenylethyl)-3-cyclopentylurea | 4.30 LC (4) 549.13 [M + H]$^+$ | Procedures 4, 5, 6 and 2 |
| 437 | 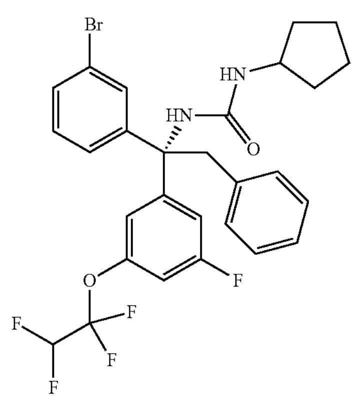 [SMILES: O=C(NC1CCCC1)N[C@@](Cc1ccccc1)(c1cccc(Br)c1)c1cc(F)cc(OC(F)(F)C(F)F)c1] | (R)-1-(1-(3-bromophenyl)-1-(3-fluoro-5-(1,1,2,2-tetrafluoro-ethoxy)phenyl)-2-phenylethyl)-3-cyclopentylurea | 4.22 LC (4) 597.12 [M + H]$^+$ | Procedures 3, 4, 5, 6 and 2 |

TABLE 9-continued

| Ex. No. | Structure | Name | Retention Time Min./ Molecular Mass | Prepared in the manner described in: |
|---|---|---|---|---|
| 438 | 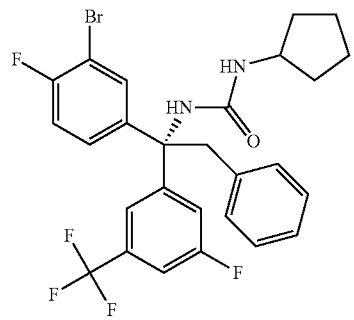 [SMILES: O=C(NC1CCCC1)N[C@](Cc1ccccc1)(c1cc(F)cc(C(F)(F)F)c1)c1ccc(F)c(Br)c1] | (R)-1-(1-(3-bromo-4-fluorophenyl)-1-(3-fluoro-5-(trifluoromethyl)phenyl)-2-phenylethyl)-3-cyclopentylurea | 4.30 LC (4) 567.11 [M + H]+ | Procedures 62, 5, 6 and 2 |
| 439 | 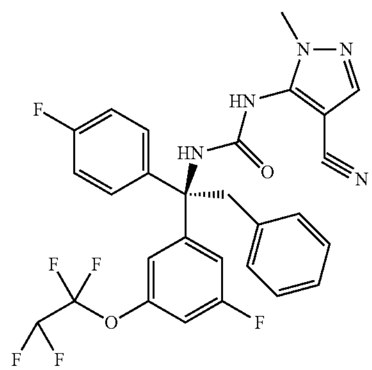 [SMILES: Cn1ncc(C#N)c1NC(=O)N[C@](Cc1ccccc1)(c1ccc(F)cc1)c1cc(F)cc(OC(F)(F)C(F)F)c1] | (R)-1-(4-cyano-1-methyl-1H-pyrazol-5-yl)-3-(1-(3-fluoro-5-(1,1,2,2-tetrafluoroethoxy)phenyl)-1-(4-fluorophenyl)-2-phenyl-ethyl)urea | 3.91 LC (3) 574.67 [M + H]+ | Procedures 3, 4, 5, 6 and 12 |
| 440 | 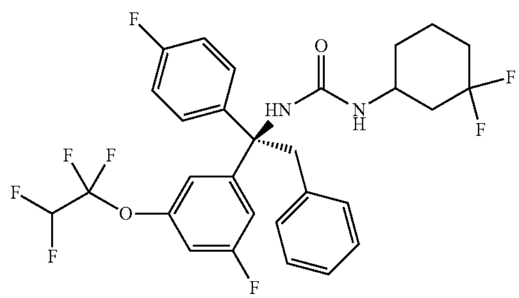 [SMILES: O=C(NC1CCCC(F)(F)C1)N[C@](Cc1ccccc1)(c1ccc(F)cc1)c1cc(F)cc(OC(F)(F)C(F)F)c1] | 1-(3,3-difluorocyclohexyl)-3-((R)-1-(3-fluoro-5-(1,1,2,2-tetrafluoroethoxy)phenyl)-1-(4-fluorophenyl)-2-phenylethyl)urea | 4.048 LC (3) 587.4 [M + H]+ | Procedures 3, 4, 5, 6, 130 and 12 |
| 441 | 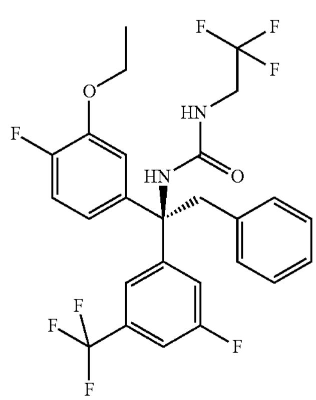 [SMILES: CCOc1cc([C@@](Cc2ccccc2)(NC(=O)NCC(F)(F)F)c2cc(F)cc(C(F)(F)F)c2)ccc1F] | (R)-1-(1-(3-ethoxy-4-fluorophenyl)-1-(3-fluoro-5-(trifluoromethyl)phenyl)-2-phenylethyl)-3-(2,2,2-trifluoroethyl)urea | 3.57 LC (1) 547.3 [M + H]+ | Procedures 4, 5, 6, 2, 9, 59 and 68 |

TABLE 9-continued

| Ex. No. | Structure | Name | Retention Time Min./ Molecular Mass | Prepared in the manner described in: |
|---|---|---|---|---|
| 442 | 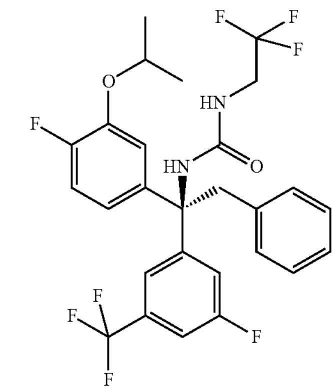 [SMILES: CC(C)Oc1cc([C@@](Cc2ccccc2)(NC(=O)NCC(F)(F)F)c2cc(F)cc(C(F)(F)F)c2)ccc1F] | (R)-1-(1-(4-fluoro-3-isopropoxyphenyl)-1-(3-fluoro-5-(trifluoromethyl)phenyl)-2-phenylethyl)-3-(2,2,2-trifluoroethyl)urea | 3.68 LC (1) 561.1 [M + H]$^+$ | Procedures 4, 5, 6, 2, 9, 59 and 68 |
| 443 | 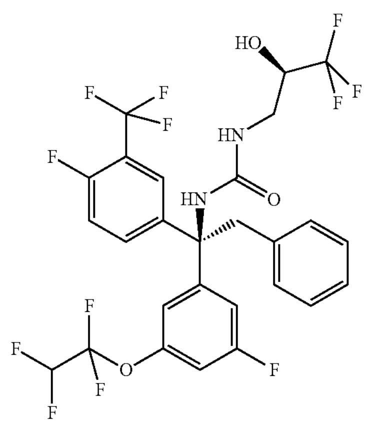 [SMILES: O=C(NC[C@@H](O)C(F)(F)F)N[C@@](Cc1ccccc1)(c1cc(F)cc(OC(F)(F)C(F)F)c1)c1ccc(F)c(C(F)(F)F)c1] | 1-((R)-1-(4-fluoro-3-(trifluoromethyl)phenyl)-1-(3-fluoro-5-(1,1,2,2-tetrafluoro-ethoxy)phenyl)-2-phenylethyl)-3-((R)-3,3,3-trifluoro-2-hydroxypropyl)urea | 3.81 LC (1) 649.66 [M + H]$^+$ | Procedures 3, 4, 5, 6, 27, 28 and 10 |
| 444 | 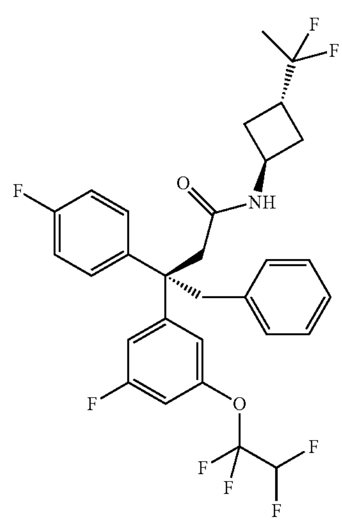 [SMILES: CC(F)(F)[C@H]1C[C@H](NC(=O)C[C@](Cc2ccccc2)(c2ccc(F)cc2)c2cc(F)cc(OC(F)(F)C(F)F)c2)C1] | 1-((1r,3R)-3-(1,1-difluoro-ethyl)cyclobutyl)-3-((R)-1-(3-fluoro-5-(1,1,2,2-tetrafluoroethoxy)phenyl)-1-(4-fluorophenyl)-2-phenylethyl)urea | 4.10 LC (3) 587.13 [M + H]$^+$ | Procedures 3, 4, 5, 6 and 12 |

TABLE 9-continued

| Ex. No. | Structure | Name | Retention Time Min./ Molecular Mass | Prepared in the manner described in: |
|---|---|---|---|---|
| 445 | 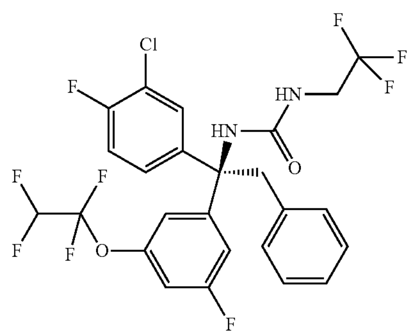 [SMILES: O=C(NCC(F)(F)F)N[C@@](Cc1ccccc1)(c1cc(F)cc(OC(F)(F)C(F)F)c1)c1ccc(F)c(Cl)c1] | (S)-1-(1-(3-chloro-4-fluorophenyl)-1-(3-fluoro-5-(1,1,2,2-tetrafluoroethoxy)phenyl)-2-phenylethyl)-3-(2,2,2-trifluoroethyl)urea | 3.558 LC (1) 585.01 [M + H]$^+$ | Procedures 3, 4, 5, 6, 2 and 9 |
| 446 | 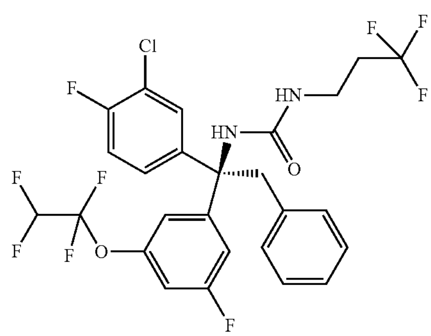 [SMILES: O=C(NCCC(F)(F)F)N[C@@](Cc1ccccc1)(c1cc(F)cc(OC(F)(F)C(F)F)c1)c1ccc(F)c(Cl)c1] | (S)-1-(1-(3-chloro-4-fluorophenyl)-1-(3-fluoro-5-(1,1,2,2-tetrafluoroethoxy)phenyl)-2-phenylethyl)-3-(3,3,3-trifluoropropyl)urea | 3.593 LC (1) 599.04 [M + H]$^+$ | Procedures 3, 4, 5, 6, 2 and 9 |
| 447 | 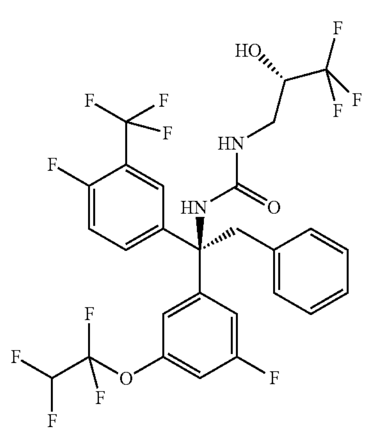 [SMILES: O=C(NC[C@H](O)C(F)(F)F)N[C@@](Cc1ccccc1)(c1cc(F)cc(OC(F)(F)C(F)F)c1)c1ccc(F)c(C(F)(F)F)c1] | 1-((R)-1-(4-fluoro-3-(trifluoromethyl)phenyl)-1-(3-fluoro-5-(1,1,2,2-tetrafluoro-ethoxy)phenyl)-2-phenylethyl)-3-((S)-3,3,3-trifluoro-2-hydroxypropyl)urea | 3.445 LC (1) 649.1 [M + H]$^+$ | Procedures 3, 4, 5, 6, 27, 28 and 10 |
| 448 | 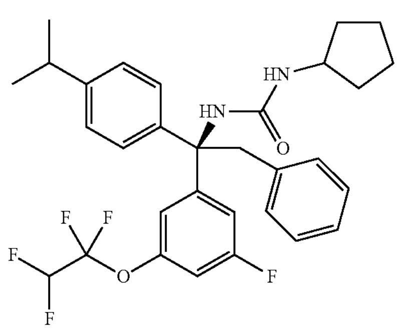 [SMILES: CC(C)c1ccc([C@@](Cc2ccccc2)(NC(=O)NC2CCCC2)c2cc(F)cc(OC(F)(F)C(F)F)c2)cc1] | (R)-1-cyclopentyl-3-(1-(3-fluoro-5-(1,1,2,2-tetrafluoroethoxy)phenyl)-1-(4-isopropylphenyl)-2-phenylethyl)urea | 4.35 LC (4) 561.36 [M + H]$^+$ | Procedures 3, 4, 5, 6 and 2 |

TABLE 9-continued

| Ex. No. | Structure | Name | Retention Time Min./ Molecular Mass | Prepared in the manner described in: |
|---|---|---|---|---|
| 449 | 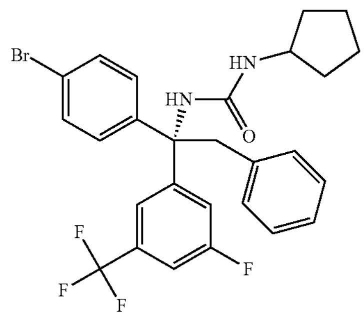 [SMILES: O=C(NC1CCCC1)N[C@@](Cc1ccccc1)(c1ccc(Br)cc1)c1cc(F)cc(C(F)(F)F)c1] | (S)-1-(1-(4-bromophenyl)-1-(3-fluoro-5-(trifluoromethyl)phenyl)-2-phenylethyl)-3-cyclopentylurea | 4.32 LC (4) 549.25 [M + H]$^+$ | Procedures 4, 5, 6 and 2 |
| 450 | 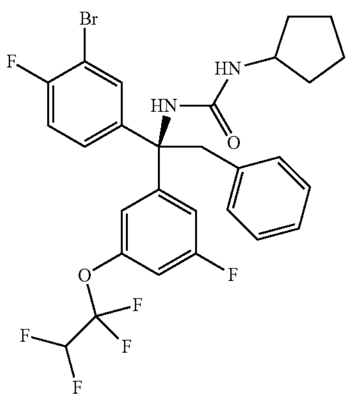 [SMILES: O=C(NC1CCCC1)N[C@@](Cc1ccccc1)(c1cc(F)cc(OC(F)(F)C(F)F)c1)c1ccc(F)c(Br)c1] | (S)-1-(1-(3-bromo-4-fluorophenyl)-1-(3-fluoro-5-(1,1,2,2-tetrafluoroethoxy)phenyl)-2-phenylethyl)-3-cyclopentylurea | 4.23 LC (4) 615.24 [M + H]$^+$ | Procedures 62, 3, 5, 6 and 2 |
| 451 | 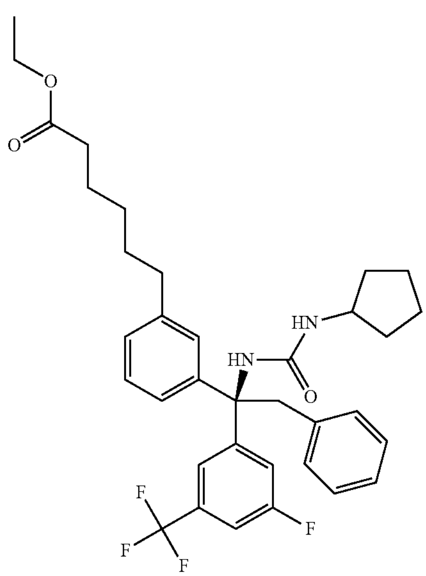 [SMILES: CCOC(=O)CCCCCc1cccc([C@@](Cc2ccccc2)(NC(=O)NC2CCCC2)c2cc(F)cc(C(F)(F)F)c2)c1] | (R)-ethyl 6-(3-(1-(3-cyclopentylureido)-1-(3-fluoro-5-(trifluoromethyl)phenyl)-2-phenylethyl)phenyl)hexanoate | 4.48 LC (4) 613.43 [M + H]$^+$ | Procedures 4, 5, 6, 24 and 2 |

TABLE 9-continued

| Ex. No. | Structure | Name | Retention Time Min./ Molecular Mass | Prepared in the manner described in: |
|---|---|---|---|---|
| 452 | 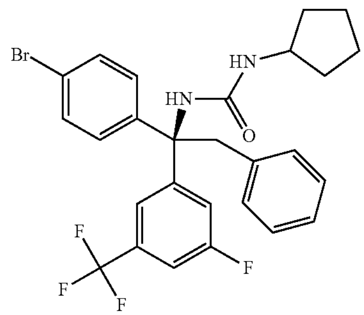 [SMILES: O=C(NC1CCCC1)N[C@](Cc1ccccc1)(c1ccc(Br)cc1)c1cc(F)cc(C(F)(F)F)c1] | (R)-1-(1-(4-bromophenyl)-1-(3-fluoro-5-(trifluoromethyl)phenyl)-2-phenylethyl)-3-cyclopentylurea | 4.33 LC (4) 549.21 [M + H]$^+$ | Procedures 4, 5, 6 and 2 |
| 453 | 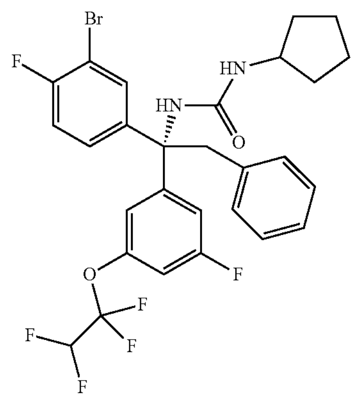 [SMILES: O=C(NC1CCCC1)N[C@](Cc1ccccc1)(c1cc(F)cc(OC(F)(F)C(F)F)c1)c1ccc(F)c(Br)c1] | (R)-1-(1-(3-bromo-4-fluorophenyl)-1-(3-fluoro-5-(1,1,2,2-tetrafluoroethoxy)phenyl)-2-phenylethyl)-3-cyclopentylurea | 4.23 LC (4) 615.26 [M + H]$^+$ | Procedures 62, 3, 5, 6 and 2 |
| 454 | 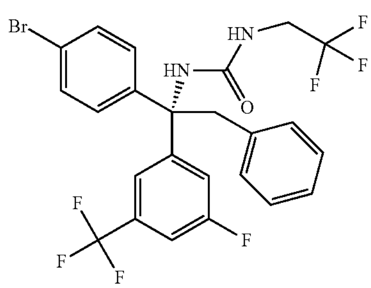 [SMILES: O=C(NCC(F)(F)F)N[C@@](Cc1ccccc1)(c1ccc(Br)cc1)c1cc(F)cc(C(F)(F)F)c1] | (S)-1-(1-(4-bromophenyl)-1-(3-fluoro-5-(trifluoromethyl)phenyl)-2-phenylethyl)-3-(2,2,2-trifluoroethyl)urea | 4.22 LC (4) 563.16 [M + H]$^+$ | Procedures 4, 5, 6 and 12 |
| 455 | 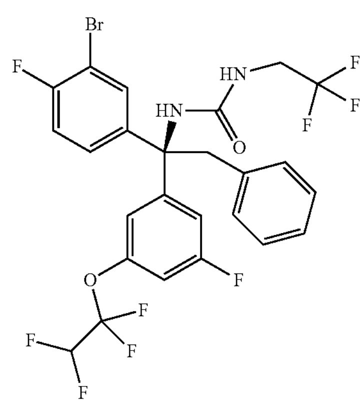 [SMILES: O=C(NCC(F)(F)F)N[C@@](Cc1ccccc1)(c1cc(F)cc(OC(F)(F)C(F)F)c1)c1ccc(F)c(Br)c1] | (S)-1-(1-(3-bromo-4-fluorophenyl)-1-(3-fluoro-5-(1,1,2,2-tetrafluoroethoxy)phenyl)-2-phenylethyl)-3-(2,2,2-trifluoroethyl)urea | 4.14 LC (4) 629.11 [M + H]$^+$ | Procedures 62, 3, 5, 6 and 12 |

TABLE 9-continued
| Ex. No. | Structure | Name | Retention Time Min./ Molecular Mass | Prepared in the manner described in: |
|---|---|---|---|---|
| 456 | 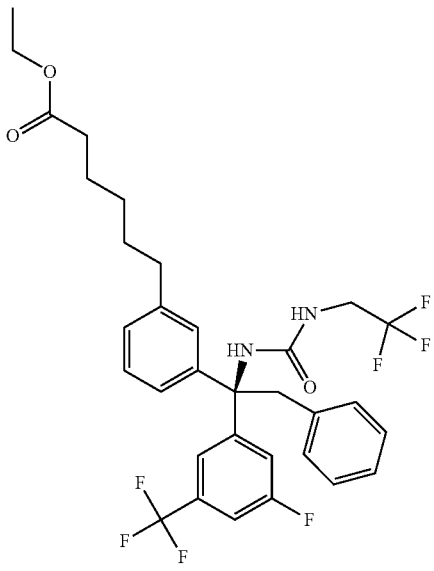 [SMILES: CCOC(=O)CCCCCc1cccc([C@@](Cc2ccccc2)(NC(=O)NCC(F)(F)F)c2cc(F)cc(C(F)(F)F)c2)c1] | (R)-ethyl 6-(3-(1-(3-fluoro-5-(trifluoromethyl)phenyl)-2-phenyl-1-(3-(2,2,2-trifluoroethyl)ureido)ethyl)phenyl)hexanoate | 4.36 LC (4) 627.31 [M + H]$^+$ | Procedures 4, 5, 6, 12 and 22 |
| 457 | 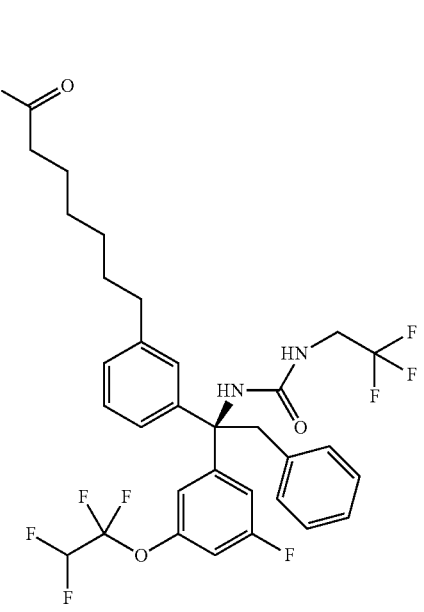 | (R)-ethyl 7-(3-(1-(3-fluoro-5-(1,1,2,2-tetrafluoroethoxy)phenyl)-2-phenyl-1-(3-(2,2,2-trifluoroethyl)ureido)ethyl)phenyl)heptanoate | 4.36 LC (4) 689.31 [M + H]$^+$ | Procedures 3, 4, 5, 6, 12 and 22 |

TABLE 9-continued

| Ex. No. | Structure | Name | Retention Time Min./ Molecular Mass | Prepared in the manner described in: |
|---|---|---|---|---|
| 458 | 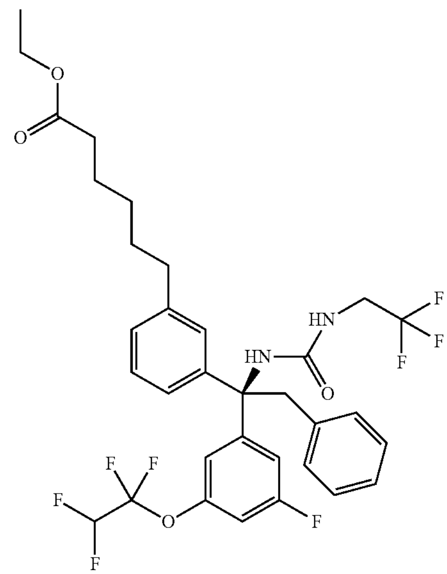 [SMILES: CCOC(=O)CCCCCc1cccc([C@@](Cc2ccccc2)(NC(=O)NCC(F)(F)F)c2cc(F)cc(OC(F)(F)C(F)F)c2)c1] | (R)-ethyl 6-(3-(1-(3-fluoro-5-(1,1,2,2-tetrafluoroethoxy)phenyl)-2-phenyl-1-(3-(2,2,2-trifluoro-ethyl)ureido)ethyl)phenyl)hex-anoate | 4.29 LC (4) 675.31 [M + H]⁺ | Procedures 3, 4, 5, 6, 12 and 22 |
| 459 | 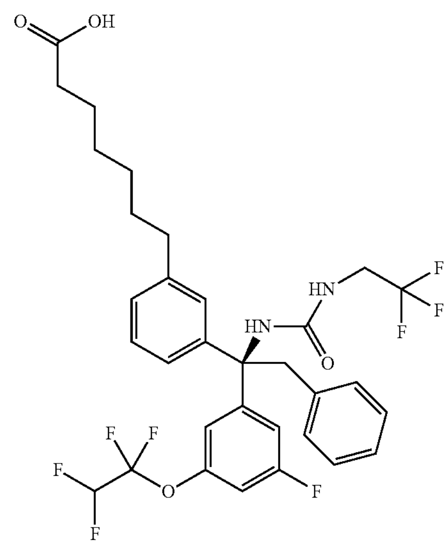 [SMILES: O=C(O)CCCCCCc1cccc([C@@](Cc2ccccc2)(NC(=O)NCC(F)(F)F)c2cc(F)cc(OC(F)(F)C(F)F)c2)c1] | (R)-7-(3-(1-(3-fluoro-5-(1,1,2,2-tetrafluoroethoxy)phenyl)-2-phenyl-1-(3-(2,2,2-trifluoro-ethyl)ureido)ethyl)phenyl)hep-tanoic acid | 4.17 LC (4) 661.31 [M + H]⁺ | Procedures 3, 4, 5, 6, 12, 22 and 23 |
| 460 | 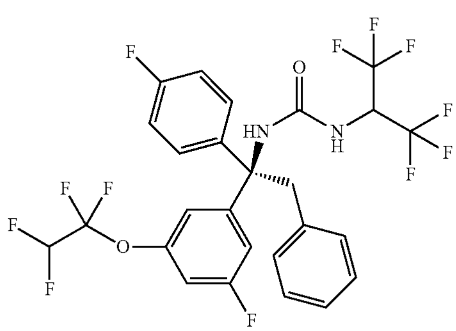 [SMILES: O=C(NC(C(F)(F)F)C(F)(F)F)N[C@](Cc1ccccc1)(c1ccc(F)cc1)c1cc(F)cc(OC(F)(F)C(F)F)c1] | (R)-1-(1-(3-fluoro-5-(1,1,2,2-tetrafluoroethoxy)phenyl)-1-(4-fluorophenyl)-2-phenylethyl)-3-(1,1,1,3,3,3-hexafluoropropan-2-yl)urea | 4.23 LC (1) 619.04 [M + H]⁺ | Procedures 3, 4, 5, 6 and 25 |

TABLE 9-continued

| Ex. No. | Structure | Name | Retention Time Min./ Molecular Mass | Prepared in the manner described in: |
|---|---|---|---|---|
| 461 | 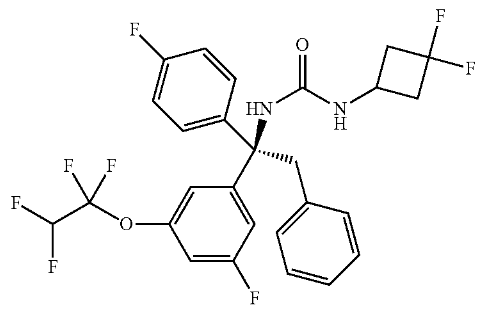 [SMILES: O=C(NC1CC(F)(F)C1)N[C@](Cc1ccccc1)(c1ccc(F)cc1)c1cc(F)cc(OC(F)(F)C(F)F)c1] | (R)-1-(3,3-difluorocyclobutyl)-3-(1-(3-fluoro-5-(1,1,2,2-tetrafluoroethoxy)phenyl)-1-(4-fluorophenyl)-2-phenylethyl)urea | 3.383 LC (3) 559.4 [M + H]$^+$ | Procedures 3, 4, 5, 6, 116, 117, 118, 119, 120 and 25 |
| 462 | 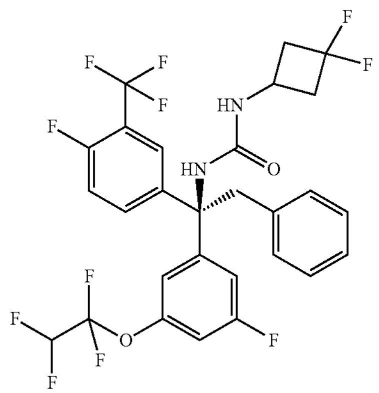 [SMILES: O=C(NC1CC(F)(F)C1)N[C@@](Cc1ccccc1)(c1cc(F)cc(OC(F)(F)C(F)F)c1)c1ccc(F)c(C(F)(F)F)c1] | (R)-1-(3,3-difluorocyclobutyl)-3-(1-(4-fluoro-3-(trifluoromethyl)phenyl)-1-(3-fluoro-5-(1,1,2,2-tetrafluoroethoxy)phenyl)-2-phenylethyl)urea | 3.611 LC (3) 627.15 [M + H]$^+$ | Procedures 3, 4, 5, 6, 116, 117, 118, 119, 120 and 10 |
| 463 | 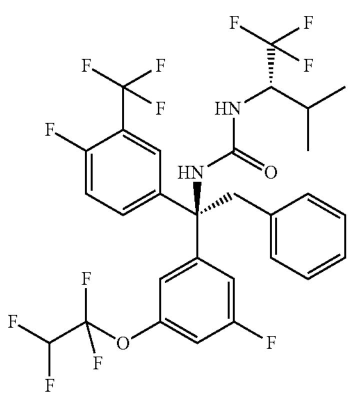 [SMILES: CC(C)[C@H](NC(=O)N[C@@](Cc1ccccc1)(c1cc(F)cc(OC(F)(F)C(F)F)c1)c1ccc(F)c(C(F)(F)F)c1)C(F)(F)F] | 1-((R)-1-(4-fluoro-3-(trifluoromethyl)phenyl)-1-(3-fluoro-5-(1,1,2,2-tetrafluoroethoxy)phenyl)-2-phenylethyl)-3-((S)-1,1,1-trifluoro-3-methylbutan-2-yl)urea | 3.891 LC (1) 661.11 [M + H]$^+$ | Procedures 3, 4, 5, 6 and 10 |
| 464 | 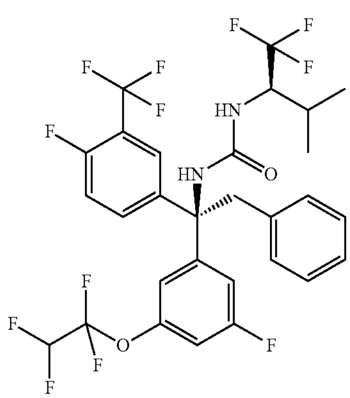 [SMILES: CC(C)[C@@H](NC(=O)N[C@@](Cc1ccccc1)(c1cc(F)cc(OC(F)(F)C(F)F)c1)c1ccc(F)c(C(F)(F)F)c1)C(F)(F)F] | 1-((R)-1-(4-fluoro-3-(trifluoromethyl)phenyl)-1-(3-fluoro-5-(1,1,2,2-tetrafluoroethoxy)phenyl)-2-phenylethyl)-3-((R)-1,1,1-trifluoro-3-methylbutan-2-yl)urea | 3.885 LC (1) 661.12 [M + H]$^+$ | Procedures 3, 4, 5, 6 and 10 |

TABLE 9-continued

| Ex. No. | Structure | Name | Retention Time Min./ Molecular Mass | Prepared in the manner described in: |
|---|---|---|---|---|
| 465 | 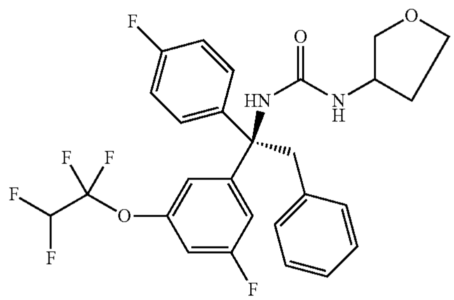 [SMILES: O=C(NC1CCOC1)N[C@](Cc1ccccc1)(c1ccc(F)cc1)c1cc(F)cc(OC(F)(F)C(F)F)c1] | 1-((R)-1-(3-fluoro-5-(1,1,2,2-tetrafluoroethoxy)phenyl)-1-(4-fluorophenyl)-2-phenylethyl)-3-(tetrahydrofuran-3-yl)urea | 3.97 LC (1) 539.09 [M + H]+ | Procedures 3, 4, 5, 6 and 25 |
| 466 | 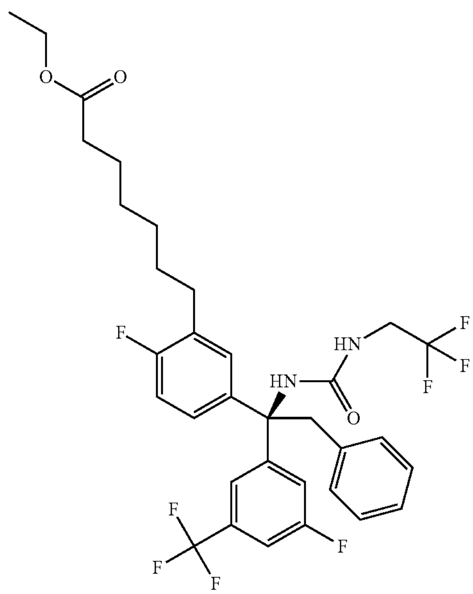 [SMILES: CCOC(=O)CCCCCCc1cc([C@@](Cc2ccccc2)(NC(=O)NCC(F)(F)F)c2cc(F)cc(C(F)(F)F)c2)ccc1F] | (R)-ethyl 7-(2-fluoro-5-(1-(3-fluoro-5-(trifluoromethyl)phenyl)-2-phenyl-1-(3-(2,2,2-trifluoro-ethyl)ureido)ethyl)phenyl)heptanoate | 4.45 LC (4) 659.46 [M + H]+ | Procedures 62, 3, 5, 6, 12 and 22 |
| 467 | 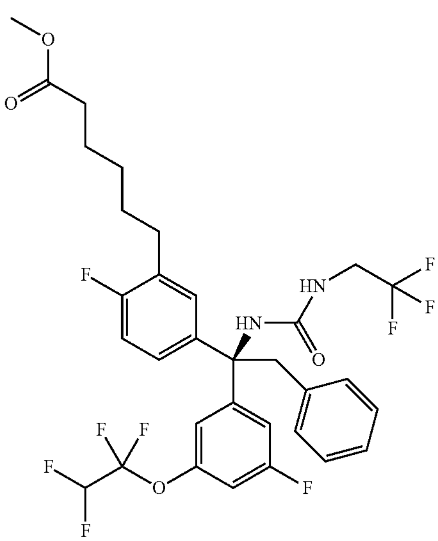 [SMILES: COC(=O)CCCCCc1cc([C@@](Cc2ccccc2)(NC(=O)NCC(F)(F)F)c2cc(F)cc(OC(F)(F)C(F)F)c2)ccc1F] | (R)-methyl 6-(2-fluoro-5-(1-(3-fluoro-5-(1,1,2,2-tetrafluoro-ethoxy)phenyl)-2-phenyl-1-(3-(2,2,2-trifluoro-ethyl)ureido)ethyl)phenyl)hexanoate | 4.24 LC (4) 679.45 [M + H]+ | Procedures 62, 3, 5, 6, 12 and 22 |

TABLE 9-continued

| Ex. No. | Structure | Name | Retention Time Min./ Molecular Mass | Prepared in the manner described in: |
|---|---|---|---|---|
| 468 | 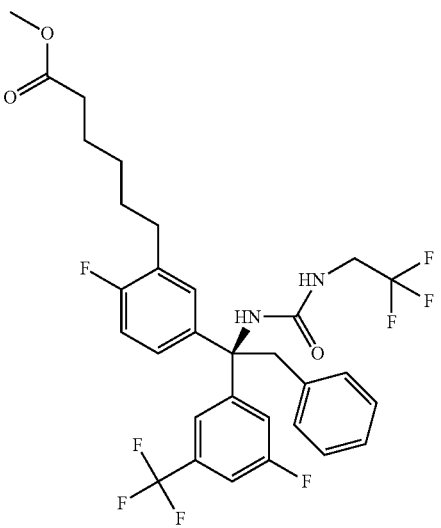 [SMILES: COC(=O)CCCCCc1cc([C@@](Cc2ccccc2)(NC(=O)NCC(F)(F)F)c2cc(F)cc(C(F)(F)F)c2)ccc1F] | (R)-methyl 6-(2-fluoro-5-(1-(3-fluoro-5-(trifluoromethyl)phenyl)-2-phenyl-1-(3-(2,2,2-trifluoroethyl)ureido)ethyl)phenyl)hexanoate | 4.30 LC (4) 631.41 [M + H]$^+$ | Procedures 62, 5, 6, 12 and 22 |
| 469 | 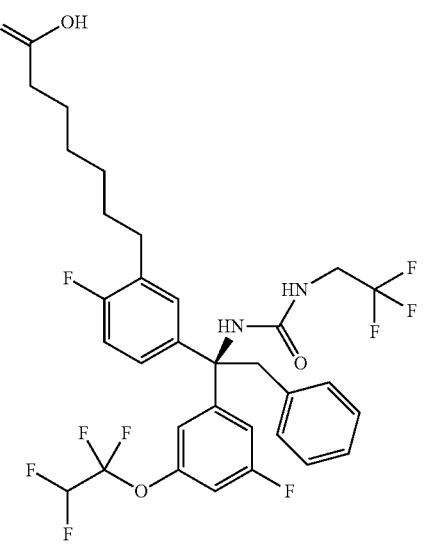 | (R)-7-(2-fluoro-5-(1-(3-fluoro-5-(1,1,2,2-tetrafluoroethoxy)phenyl)-2-phenyl-1-(3-(2,2,2-trifluoroethyl)ureido)ethyl)phenyl)heptanoic acid | 4.18 LC (4) 679.43 [M + H]$^+$ | Procedures 62, 3, 5, 6, 12, 22 and 23 |

TABLE 9-continued

| Ex. No. | Structure | Name | Retention Time Min./ Molecular Mass | Prepared in the manner described in: |
|---|---|---|---|---|
| 470 | 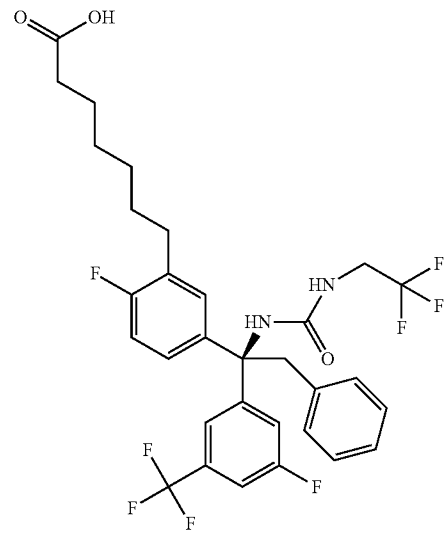 [SMILES: O=C(O)CCCCCCc1cc([C@@](Cc2ccccc2)(NC(=O)NCC(F)(F)F)c2cc(F)cc(C(F)(F)F)c2)ccc1F] | (R)-7-(2-fluoro-5-(1-(3-fluoro-5-(trifluoromethyl)phenyl)-2-phenyl-1-(3-(2,2,2-trifluoro-ethyl)ureido)ethyl)phenyl)hep-tanoic acid | 4.23 LC (4) 631.42 [M + H]$^+$ | Procedures 62, 3, 5, 6, 12, 22 and 23 |
| 471 | 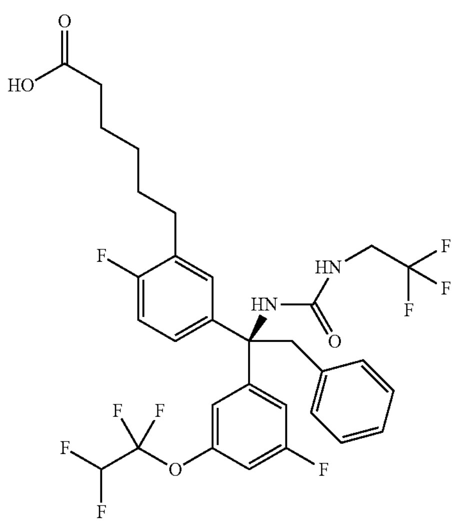 [SMILES: O=C(O)CCCCCc1cc([C@@](Cc2ccccc2)(NC(=O)NCC(F)(F)F)c2cc(F)cc(OC(F)(F)C(F)F)c2)ccc1F] | (R)-6-(2-fluoro-5-(1-(3-fluoro-5-(1,1,2,2-tetrafluoroethoxy)phenyl)-2-phenyl-1-(3-(2,2,2-trifluoro-ethyl)ureido)ethyl)phenyl)hex-anoic acid | 4.11 LC (4) 665.40 [M + H]$^+$ | Procedures 62, 3, 5, 6, 12, 22 and 23 |
| 472 | 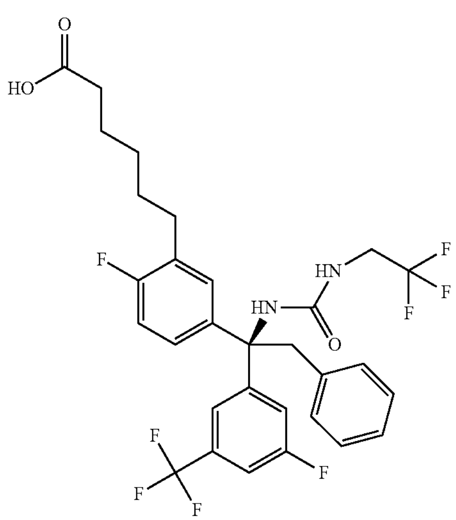 [SMILES: O=C(O)CCCCCc1cc([C@@](Cc2ccccc2)(NC(=O)NCC(F)(F)F)c2cc(F)cc(C(F)(F)F)c2)ccc1F] | (R)-6-(2-fluoro-5-(1-(3-fluoro-5-(trifluoromethyl)phenyl)-2-phenyl-1-(3-(2,2,2-trifluoro-ethyl)ureido)ethyl)phenyl)hex-anoic acid | 4.17 LC (4) 617.37 [M + H]$^+$ | Procedures 62, 3, 5, 6, 12, 22 and 23 |

TABLE 9-continued

| Ex. No. | Structure | Name | Retention Time Min./ Molecular Mass | Prepared in the manner described in: |
|---|---|---|---|---|
| 473 | 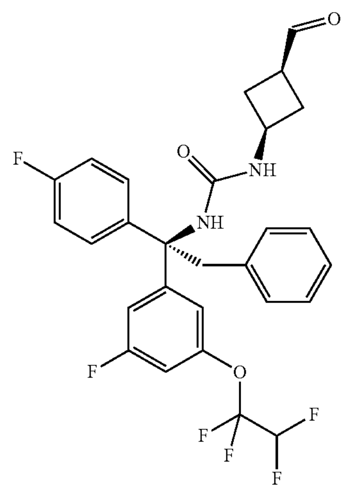 [SMILES: O=C[C@H]1C[C@@H](NC(=O)N[C@](Cc2ccccc2)(c2ccc(F)cc2)c2cc(F)cc(OC(F)(F)C(F)F)c2)C1] | 1-((R)-1-(3-fluoro-5-(1,1,2,2-tetrafluoroethoxy)phenyl)-1-(4-fluorophenyl)-2-phenylethyl)-3-((1s,3S)-3-formylcyclobutyl)urea | 2.01 LC (3) 550.2 [M + H]+ | Procedures 3, 4, 5, 6, 25, 39, 40 and 41 |
| 474 | 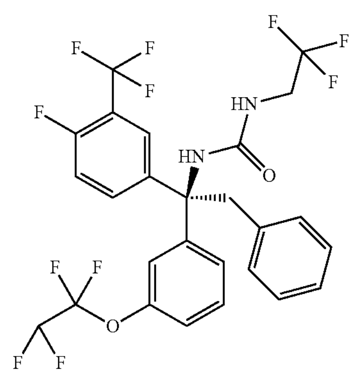 [SMILES: O=C(NCC(F)(F)F)N[C@@](Cc1ccccc1)(c1cccc(OC(F)(F)C(F)F)c1)c1ccc(F)c(C(F)(F)F)c1] | (R)-1-(1-(4-fluoro-3-(trifluoromethyl)phenyl)-2-phenyl-1-(3-(1,1,2,2-tetrafluoro-ethoxy)phenyl)ethyl)-3-(2,2,2-trifluoroethyl)urea | 4.13 LC (1) 601.9 [M + H]+ | Procedures 3, 4, 5, 6, 2 and 9 |
| 475 | 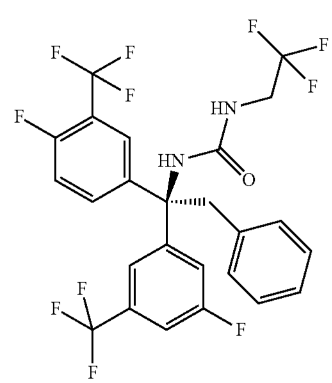 [SMILES: O=C(NCC(F)(F)F)N[C@@](Cc1ccccc1)(c1cc(F)cc(C(F)(F)F)c1)c1ccc(F)c(C(F)(F)F)c1] | (R)-1-(1-(4-fluoro-3-(trifluoromethyl)phenyl)-1-(3-fluoro-5-(trifluoromethyl)phenyl)-2-phenylethyl)-3-(2,2,2-trifluoroethyl)urea | 4.21 LC (1) 571.08 [M + H]+ | Procedures 4, 5, 6, 2 and 9 |

TABLE 9-continued

| Ex. No. | Structure | Name | Retention Time Min./ Molecular Mass | Prepared in the manner described in: |
|---|---|---|---|---|
| 476 | 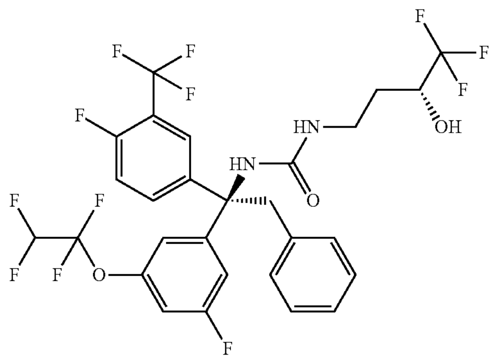 [SMILES: O=C(NCC[C@@H](O)C(F)(F)F)N[C@@](Cc1ccccc1)(c1cc(F)cc(OC(F)(F)C(F)F)c1)c1ccc(F)c(C(F)(F)F)c1] | 1-((R)-1-(4-fluoro-3-(trifluoromethyl)phenyl)-1-(3-fluoro-5-(1,1,2,2-tetrafluoro-ethoxy)phenyl)-2-phenyl-ethyl)-3-((R)-4,4,4-trifluoro-3-hydroxybutyl)urea | 3.486 LC (1) 663.15 [M + H]$^+$ | Procedures 3, 4, 5, 6, 27, 28 and 10 |
| 477 | 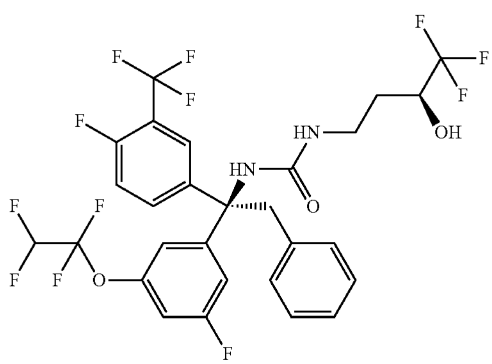 [SMILES: O=C(NCC[C@H](O)C(F)(F)F)N[C@@](Cc1ccccc1)(c1cc(F)cc(OC(F)(F)C(F)F)c1)c1ccc(F)c(C(F)(F)F)c1] | 1-((R)-1-(4-fluoro-3-(trifluoromethyl)phenyl)-1-(3-fluoro-5-(1,1,2,2-tetrafluoro-ethoxy)phenyl)-2-phenylethyl)-3-((S)-4,4,4-trifluoro-3-hydroxybutyl)urea | 3.486 LC (1) 663.16 [M + H]$^+$ | Procedures 3, 4, 5, 6, 27, 28 and 25 |
| 478 | 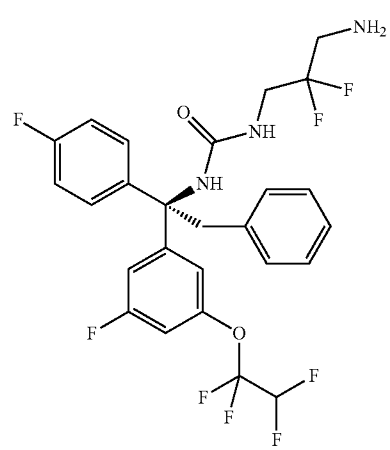 [SMILES: NCC(F)(F)CNC(=O)N[C@](Cc1ccccc1)(c1ccc(F)cc1)c1cc(F)cc(OC(F)(F)C(F)F)c1] | (R)-1-(3-amino-2,2-difluoropropyl)-3-(1-(3-fluoro-5-(1,1,2,2-tetrafluoroethoxy)phenyl)-1-(4-fluorophenyl)-2-phenylethyl)urea | 1.86 LC (2) 562.2 [M + H]$^+$ | Procedures 3, 4, 5, 6, 25 and 39 |

TABLE 9-continued

| Ex. No. | Structure | Name | Retention Time Min./ Molecular Mass | Prepared in the manner described in: |
|---|---|---|---|---|
| 479 | 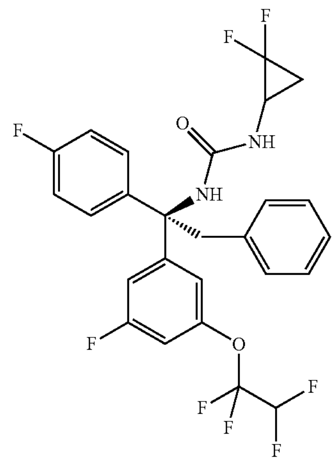 [SMILES: O=C(NC1CC1(F)F)N[C@](Cc1ccccc1)(c1ccc(F)cc1)c1cc(F)cc(OC(F)(F)C(F)F)c1] | 1-(2,2-difluorocyclopropyl)-3-((R)-1-(3-fluoro-5-(1,1,2,2-tetrafluoroethoxy)phenyl)-1-(4-fluorophenyl)-2-phenylethyl)urea | 2.05 LC (2) 545.2 [M + H]+ | Procedures 3, 4, 5, 6 and 25 |
| 480 | 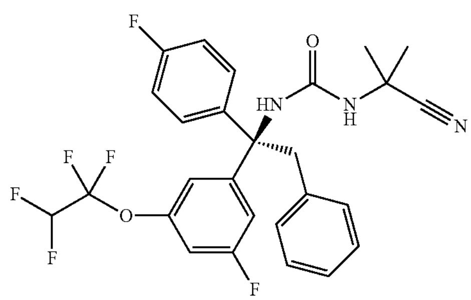 [SMILES: CC(C)(C#N)NC(=O)N[C@](Cc1ccccc1)(c1ccc(F)cc1)c1cc(F)cc(OC(F)(F)C(F)F)c1] | (R)-1-(2-cyanopropan-2-yl)-3-(1-(3-fluoro-5-(1,1,2,2-tetrafluoroethoxy)phenyl)-1-(4-fluorophenyl)-2-phenylethyl)urea | 3.93 LC (1) 536.1 [M + H]+ | Procedures 3, 4, 5, 6 and 25 |
| 481 | 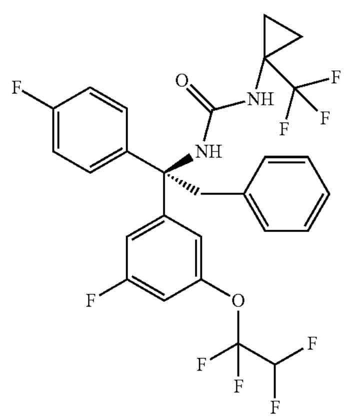 [SMILES: O=C(NC1(C(F)(F)F)CC1)N[C@](Cc1ccccc1)(c1ccc(F)cc1)c1cc(F)cc(OC(F)(F)C(F)F)c1] | (R)-1-(1-(3-fluoro-5-(1,1,2,2-tetrafluoroethoxy)phenyl)-1-(4-fluorophenyl)-2-phenylethyl)-3-(1-(trifluoromethyl)cyclopropyl)urea | 2.08 LC (2) 577.2 [M + H]+ | Procedures 3, 4, 5, 6 and 30 |
| 482 | 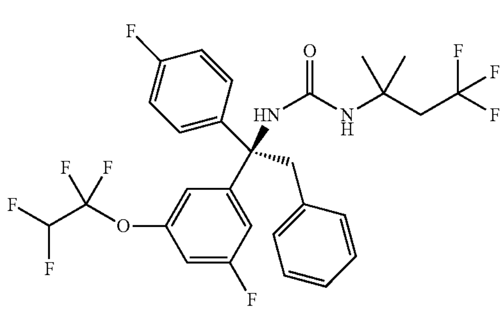 [SMILES: CC(C)(CC(F)(F)F)NC(=O)N[C@](Cc1ccccc1)(c1ccc(F)cc1)c1cc(F)cc(OC(F)(F)C(F)F)c1] | (R)-1-(1-(3-fluoro-5-(1,1,2,2-tetrafluoroethoxy)phenyl)-1-(4-fluorophenyl)-2-phenylethyl)-3-(4,4,4-trifluoro-2-methylbutan-2-yl)urea | 2.16 LC (2) 593.3 [M + H]+ | Procedures 3, 4, 5, 6 and 30 |

TABLE 9-continued

| Ex. No. | Structure | Name | Retention Time Min./ Molecular Mass | Prepared in the manner described in: |
|---|---|---|---|---|
| 483 | 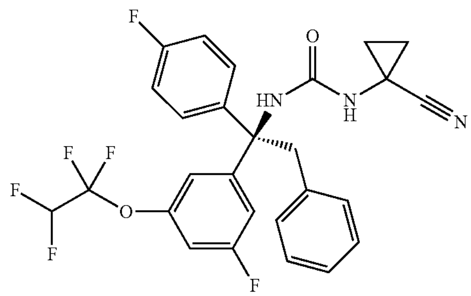 [SMILES: N#CC1(NC(=O)N[C@](Cc2ccccc2)(c2ccc(F)cc2)c2cc(F)cc(OC(F)(F)C(F)F)c2)CC1] | (R)-1-(1-cyanocyclopropyl)-3-(1-(3-fluoro-5-(1,1,2,2-tetrafluoroethoxy)phenyl)-1-(4-fluorophenyl)-2-phenylethyl)urea | 1.97 LC (2) 534.2 [M + H]$^+$ | Procedures 3, 4, 5, 6 and 30 |
| 484 | 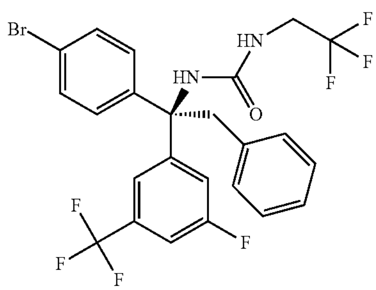 [SMILES: O=C(NCC(F)(F)F)N[C@](Cc1ccccc1)(c1ccc(Br)cc1)c1cc(F)cc(C(F)(F)F)c1] | (R)-1-(1-(4-bromophenyl)-1-(3-fluoro-5-(trifluoromethyl)phenyl)-2-phenylethyl)-3-(2,2,2-trifluoroethyl)urea | 3.68 LC (4) 561.1 [M + H]$^+$ | Procedures 4, 5, 6 and 12 |
| 485 | 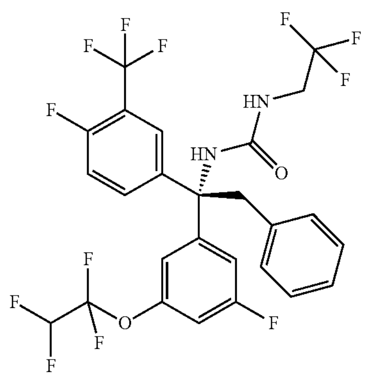 [SMILES: O=C(NCC(F)(F)F)N[C@](Cc1ccccc1)(c1cc(F)cc(OC(F)(F)C(F)F)c1)c1ccc(F)c(C(F)(F)F)c1] | (S)-1-(1-(4-fluoro-3-(trifluoromethyl)phenyl)-1-(3-fluoro-5-(1,1,2,2-tetrafluoroethoxy)phenyl)-2-phenylethyl)-3-(2,2,2-trifluoroethyl)urea | 2.16 LC (2) 619.2 [M + H]$^+$ | Procedures 3, 4, 5, 6, 2 and 9 |
| 486 | 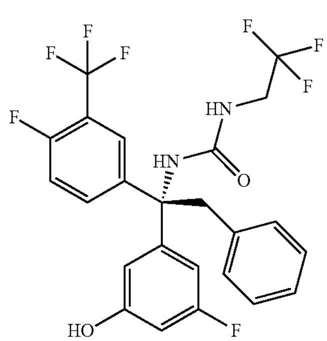 [SMILES: O=C(NCC(F)(F)F)N[C@](Cc1ccccc1)(c1cc(O)cc(F)c1)c1ccc(F)c(C(F)(F)F)c1] | (S)-1-(1-(4-fluoro-3-(trifluoromethyl)phenyl)-1-(3-fluoro-5-hydroxyphenyl)-2-phenylethyl)-3-(2,2,2-trifluoroethyl)urea | 2.0 LC (2) 519.1 [M + H]$^+$ | Procedures 49 and 10 |

TABLE 9-continued

| Ex. No. | Structure | Name | Retention Time Min./ Molecular Mass | Prepared in the manner described in: |
|---|---|---|---|---|
| 487 | 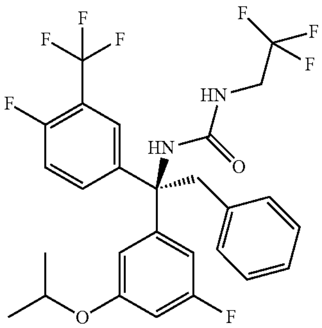 [SMILES: CC(C)Oc1cc(F)cc([C@](Cc2ccccc2)(NC(=O)NCC(F)(F)F)c2ccc(F)c(C(F)(F)F)c2)c1] | (R)-1-(1-(4-fluoro-3-(trifluoromethyl)phenyl)-1-(3-fluoro-5-isopropoxyphenyl)-2-phenylethyl)-3-(2,2,2-trifluoroethyl)urea | 2.20 LC (2) 561.2 [M + H]$^+$ | Procedures 49, 10 and 68 |
| 488 | 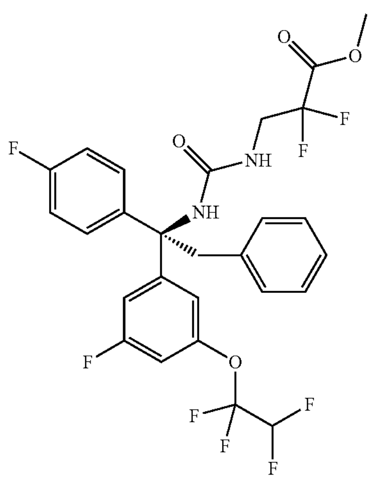 [SMILES: COC(=O)C(F)(F)CNC(=O)N[C@](Cc1ccccc1)(c1ccc(F)cc1)c1cc(F)cc(OC(F)(F)C(F)F)c1] | (R)-methyl 2,2-difluoro-3-(3-(1-(3-fluoro-5-(1,1,2,2-tetrafluoro-ethoxy)phenyl)-1-(4-fluorophenyl)-2-phenylethyl)ureido)propanoate | 4.01 LC (1) 591.1 [M + H]$^+$ | Procedures 3, 4, 5, 6, 46, 25 and 127 |
| 489 | 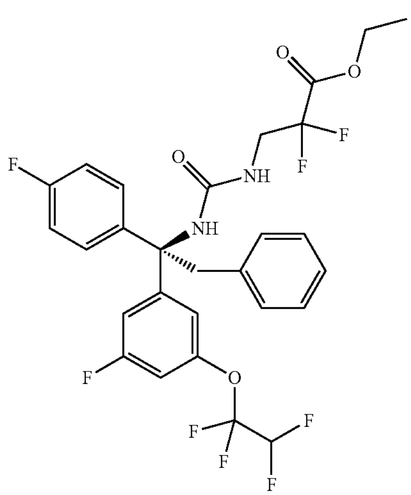 [SMILES: CCOC(=O)C(F)(F)CNC(=O)N[C@](Cc1ccccc1)(c1ccc(F)cc1)c1cc(F)cc(OC(F)(F)C(F)F)c1] | (R)-ethyl 2,2-difluoro-3-(3-(1-(3-fluoro-5-(1,1,2,2-tetrafluoro-ethoxy)phenyl)-1-(4-fluorophenyl)-2-phenylethyl)ureido)propanoate | 4.06 LC (1) 605.2 [M + H]$^+$ | Procedures 3, 4, 5, 6, 46, 25 and 127 |

TABLE 9-continued

| Ex. No. | Structure | Name | Retention Time Min./ Molecular Mass | Prepared in the manner described in: |
|---|---|---|---|---|
| 490 | 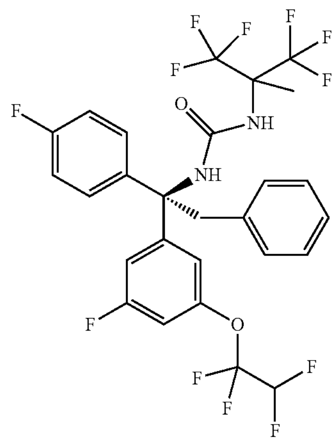 [SMILES: CC(NC(=O)N[C@](Cc1ccccc1)(c1ccc(F)cc1)c1cc(F)cc(OC(F)(F)C(F)F)c1)(C(F)(F)F)C(F)(F)F] | (R)-1-(1-(3-fluoro-5-(1,1,2,2-tetrafluoroethoxy)phenyl)-1-(4-fluorophenyl)-2-phenylethyl)-3-(1,1,1,3,3,3-hexafluoro-2-methylpropan-2-yl)urea | 2.19 LC (2) 633.3 [M + H]$^+$ | Procedures 3, 4, 5, 6 and 30 |
| 491 | 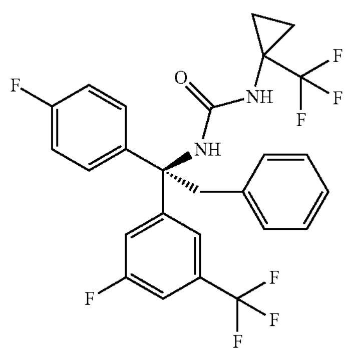 [SMILES: O=C(NC1(C(F)(F)F)CC1)N[C@](Cc1ccccc1)(c1ccc(F)cc1)c1cc(F)cc(C(F)(F)F)c1] | (R)-1-(1-(3-fluoro-5-(trifluoromethyl)phenyl)-1-(4-fluorophenyl)-2-phenylethyl)-3-(1-(trifluoromethyl)cyclopropyl)urea | 2.12 LC (2) 529.31 [M + H]$^+$ | Procedures 4, 5, 6 and 30 |
| 492 | 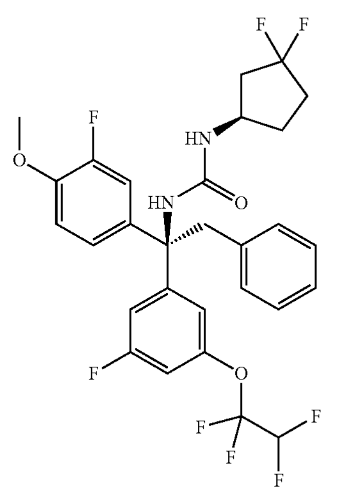 [SMILES: COc1ccc([C@@](Cc2ccccc2)(NC(=O)N[C@@H]2CCC(F)(F)C2)c2cc(F)cc(OC(F)(F)C(F)F)c2)cc1F] | 1-((R)-3,3-difluorocyclopentyl)-3-((R)-1-(3-fluoro-4-methoxyphenyl)-1-(3-fluoro-5-(1,1,2,2-tetrafluoroethoxy)phenyl)-2-phenylethyl)urea | 10.11 LC (7) 603 [M + H]$^+$ | Procedures 3, 4, 5, 6 and 12 |

TABLE 9-continued

| Ex. No. | Structure | Name | Retention Time Min./ Molecular Mass | Prepared in the manner described in: |
|---|---|---|---|---|
| 493 | 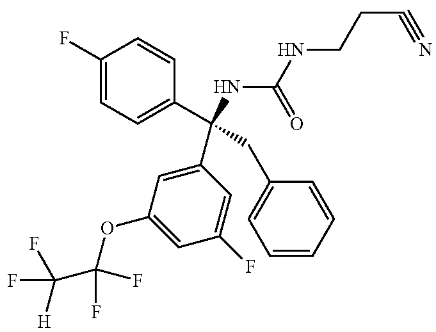 [SMILES: N#CCCNC(=O)N[C@](Cc1ccccc1)(c1ccc(F)cc1)c1cc(F)cc(OC(F)(F)C(F)F)c1] | (R)-1-(2-cyanoethyl)-3-(1-(3-fluoro-5-(1,1,2,2-tetrafluoro-ethoxy)phenyl)-1-(4-fluorophenyl)-2-phenylethyl)urea | 3.075 LC (3) 522.1 [M + H]$^+$ | Procedures 3, 4, 5, 6 and 25 |
| 494 | 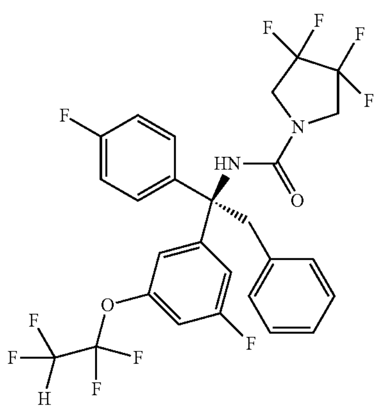 [SMILES: O=C(N[C@](Cc1ccccc1)(c1ccc(F)cc1)c1cc(F)cc(OC(F)(F)C(F)F)c1)N1CC(F)(F)C(F)(F)C1] | (R)-3,3,4,4-tetrafluoro-N-(1-(3-fluoro-5-(1,1,2,2-tetrafluoro-ethoxy)phenyl)-1-(4-fluorophenyl)-2-phenylethyl)pyrrolidine-1-carboxamide | 3.603 LC (3) 595.1 [M + H]$^+$ | Procedures 3, 4, 5, 6 and 12 |
| 495 | 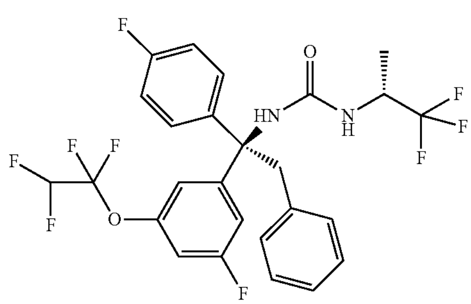 [SMILES: C[C@@H](NC(=O)N[C@](Cc1ccccc1)(c1ccc(F)cc1)c1cc(F)cc(OC(F)(F)C(F)F)c1)C(F)(F)F] | 1-((R)-1-(3-fluoro-5-(1,1,2,2-tetrafluoroethoxy)phenyl)-1-(4-fluorophenyl)-2-phenylethyl)-3-((R)-1,1,1-trifluoropropan-2-yl)urea | 2.12 LC (2) 565.3 [M + H]$^+$ | Procedures 3, 4, 5, 6 and 25 |
| 496 | 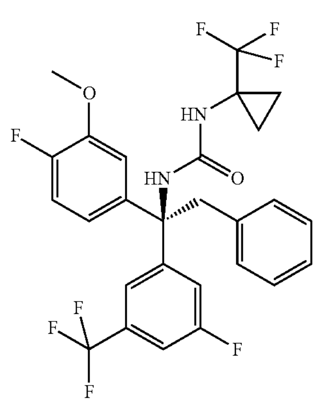 [SMILES: COc1cc([C@@](Cc2ccccc2)(NC(=O)NC2(C(F)(F)F)CC2)c2cc(F)cc(C(F)(F)F)c2)ccc1F] | (R)-1-(1-(4-fluoro-3-methoxyphenyl)-1-(3-fluoro-5-(trifluoromethyl)phenyl)-2-phenylethyl)-3-(1-(trifluoro-methyl)cyclopropyl)urea | 3.50 LC (1) 559.3 [M + H]$^+$ | Procedures 4, 5, 6 and 30 |

TABLE 9-continued

| Ex. No. | Structure | Name | Retention Time Min./ Molecular Mass | Prepared in the manner described in: |
|---|---|---|---|---|
| 497 | 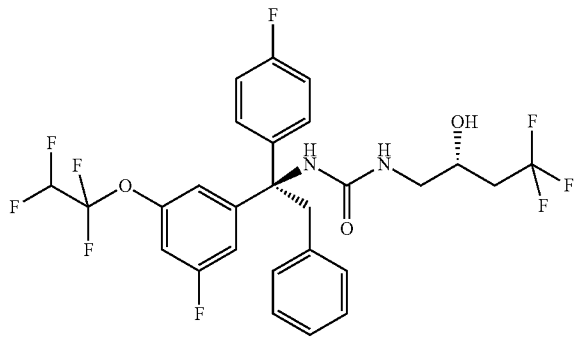 [SMILES: O=C(NC[C@H](O)CC(F)(F)F)N[C@](Cc1ccccc1)(c1ccc(F)cc1)c1cc(F)cc(OC(F)(F)C(F)F)c1] | 1-((R)-1-(3-fluoro-5-(1,1,2,2-tetrafluoroethoxy)phenyl)-1-(4-fluorophenyl)-2-phenylethyl)-3-((R)-4,4,4-trifluoro-2-hydroxybutyl)urea | 4.271 LC (1) 595.27 [M + H]$^+$ | Procedures 3, 4, 5, 6, 27, 28 and 25 |
| 498 | 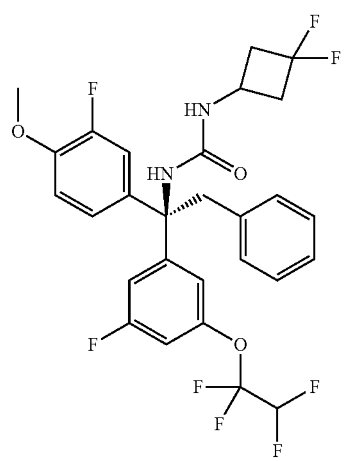 [SMILES: COc1ccc([C@@](Cc2ccccc2)(NC(=O)NC2CC(F)(F)C2)c2cc(F)cc(OC(F)(F)C(F)F)c2)cc1F] | (R)-1-(3,3-difluorocyclobutyl)-3-(1-(3-fluoro-4-methoxyphenyl)-1-(3-fluoro-5-(1,1,2,2-tetrafluoroethoxy)phenyl)-2-phenylethyl)urea | 9.97 LC (7) 589 [M + H]$^+$ | Procedures 3, 4, 5, 6, 116, 117, 118, 119, 120 and 10 |
| 499 | 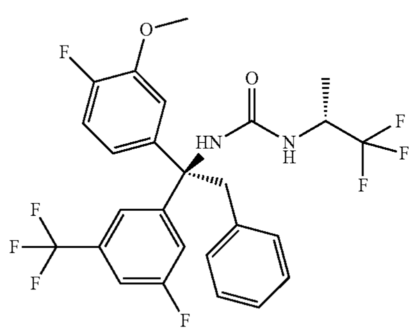 [SMILES: COc1cc([C@@](Cc2ccccc2)(NC(=O)N[C@H](C)C(F)(F)F)c2cc(F)cc(C(F)(F)F)c2)ccc1F] | 1-((R)-1-(4-fluoro-3-methoxyphenyl)-1-(3-fluoro-5-(trifluoromethyl)phenyl)-2-phenylethyl)-3-((R)-1,1,1-trifluoropropan-2-yl)urea | 2.10 LC (2) 547.3 [M + H]$^+$ | Procedures 4, 5, 6 and 25 |

TABLE 9-continued

| Ex. No. | Structure | Name | Retention Time Min./ Molecular Mass | Prepared in the manner described in: |
|---|---|---|---|---|
| 500 | 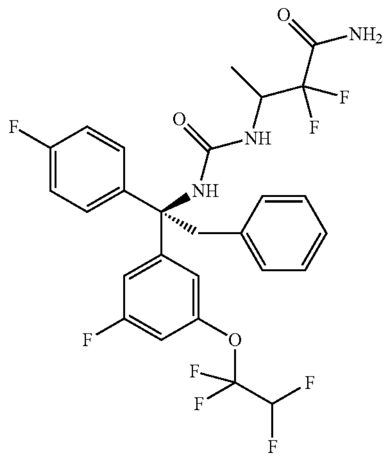 [SMILES: CC(NC(=O)N[C@](Cc1ccccc1)(c1ccc(F)cc1)c1cc(F)cc(OC(F)(F)C(F)F)c1)C(F)(F)C(N)=O] | 2,2-difluoro-3-(3-((R)-1-(3-fluoro-5-(1,1,2,2-tetrafluoro-ethoxy)phenyl)-1-(4-fluorophenyl)-2-phenylethyl)ureido)butanamide | 2.00 LC (2) 590.3 [M + H]$^+$ | Procedures 3, 4, 5, 6, 25, 46 and 47 |
| 501 | 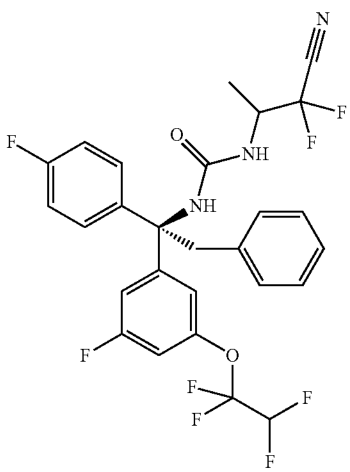 [SMILES: CC(NC(=O)N[C@](Cc1ccccc1)(c1ccc(F)cc1)c1cc(F)cc(OC(F)(F)C(F)F)c1)C(F)(F)C#N] | 1-(1-cyano-1,1-difluoropropan-2-yl)-3-((R)-1-(3-fluoro-5-(1,1,2,2-tetrafluoroethoxy)phenyl)-1-(4-fluorophenyl)-2-phenylethyl)urea | 2.10 LC (2) 572.3 [M + H]$^+$ | Procedures 3, 4, 5, 6, 25, 46, 47 and 48 |
| 502 | 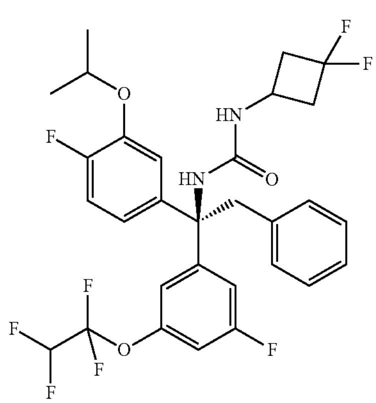 [SMILES: CC(C)Oc1cc([C@@](Cc2ccccc2)(NC(=O)NC2CC(F)(F)C2)c2cc(F)cc(OC(F)(F)C(F)F)c2)ccc1F] | (R)-1-(3,3-difluorocyclobutyl)-3-(1-(4-fluoro-3-isopropoxyphenyl)-1-(3-fluoro-5-(1,1,2,2-tetrafluoroethoxy)phenyl)-2-phenylethyl)urea | 3.72 LC (1) 617.4 [M + H]$^+$ | Procedures 3, 4, 5, 6, 116, 117, 118, 119, 120, 59, 68 and 10 |

TABLE 9-continued

| Ex. No. | Structure | Name | Retention Time Min./ Molecular Mass | Prepared in the manner described in: |
|---|---|---|---|---|
| 503 | 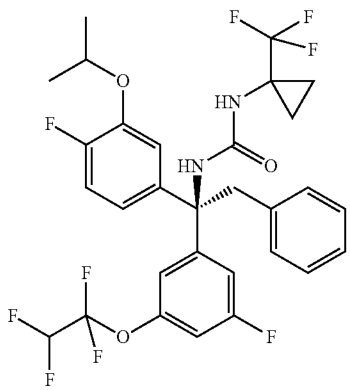 [SMILES: CC(C)Oc1cc([C@@](Cc2ccccc2)(NC(=O)NC2(C(F)(F)F)CC2)c2cc(F)cc(OC(F)(F)C(F)F)c2)ccc1F] | (R)-1-(1-(4-fluoro-3-isopropoxyphenyl)-1-(3-fluoro-5-(1,1,2,2-tetrafluoroethoxy)phenyl)-2-phenylethyl)-3-(1-(trifluoromethyl)cyclopropyl)urea | 3.60 LC (1) 635.4 [M + H]$^+$ | Procedures 3, 4, 5, 6, 59, 68 and 30 |
| 504 | 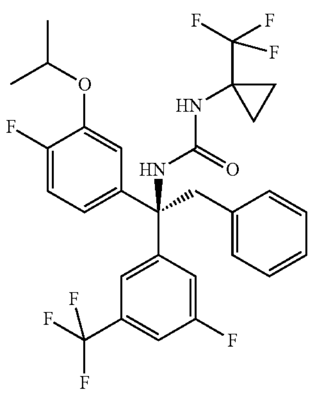 [SMILES: CC(C)Oc1cc([C@@](Cc2ccccc2)(NC(=O)NC2(C(F)(F)F)CC2)c2cc(F)cc(C(F)(F)F)c2)ccc1F] | (R)-1-(1-(4-fluoro-3-isopropoxyphenyl)-1-(3-fluoro-5-(trifluoromethyl)phenyl)-2-phenylethyl)-3-(1-(trifluoromethyl)cyclopropyl)urea | 3.745 LC (1) 587.4 [M + H]$^+$ | Procedures 4, 5, 6, 59, 68 and 30 |
| 505 | 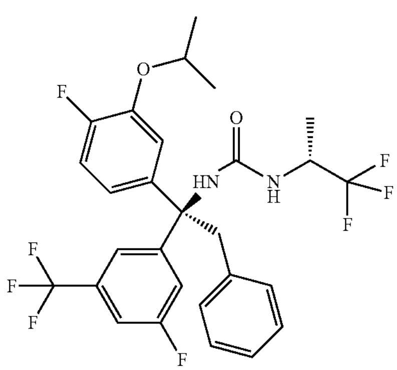 [SMILES: CC(C)Oc1cc([C@@](Cc2ccccc2)(NC(=O)N[C@H](C)C(F)(F)F)c2cc(F)cc(C(F)(F)F)c2)ccc1F] | 1-((R)-1-(4-fluoro-3-isopropoxyphenyl)-1-(3-fluoro-5-(trifluoromethyl)phenyl)-2-phenylethyl)-3-((R)-1,1,1-trifluoropropan-2-yl)urea | 2.20 LC (2) 575.4 [M + H]$^+$ | Procedures 3, 4, 5, 6, 59, 68 and 25 |
| 506 | 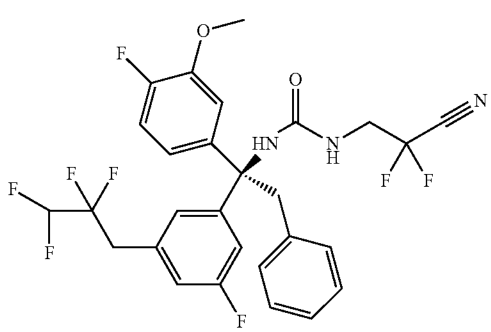 [SMILES: COc1cc([C@@](Cc2ccccc2)(NC(=O)NCC(F)(F)C#N)c2cc(F)cc(CC(F)(F)C(F)F)c2)ccc1F] | (R)-1-(2-cyano-2,2-difluoroethyl)-3-(1-(4-fluoro-3-methoxyphenyl)-1-(3-fluoro-5-(1,1,2,2-tetrafluoroethoxy)phenyl)-2-phenylethyl)urea | 3.96 LC (1) 588.2 [M + H]$^+$ | Procedures 3, 4, 5, 6, 25, 46, 47 and 48 |

TABLE 9-continued

| Ex. No. | Structure | Name | Retention Time Min./ Molecular Mass | Prepared in the manner described in: |
|---|---|---|---|---|
| 507 | 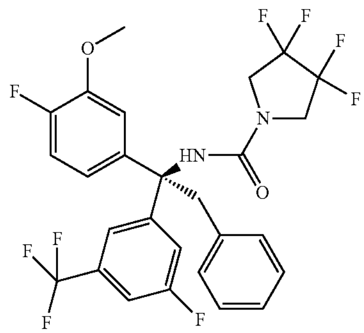 [SMILES: COc1cc([C@@](Cc2ccccc2)(NC(=O)N2CC(F)(F)C(F)(F)C2)c2cc(F)cc(C(F)(F)F)c2)ccc1F] | (R)-3,3,4,4-tetrafluoro-N-(1-(4-fluoro-3-methoxyphenyl)-1-(3-fluoro-5-(trifluoromethyl)phenyl)-2-phenylethyl)pyrrolidine-1-carboxamide | 3.596 LC (3) 577.2 [M + H]$^+$ | Procedures 4, 5, 6 and 12 |
| 508 | 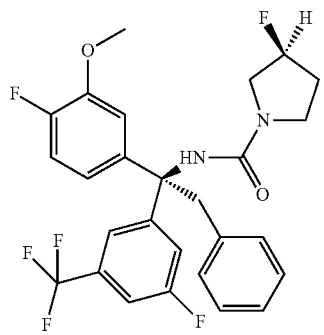 [SMILES: COc1cc([C@@](Cc2ccccc2)(NC(=O)N2CC[C@H](F)C2)c2cc(F)cc(C(F)(F)F)c2)ccc1F] | (S)-3-fluoro-N-((R)-1-(4-fluoro-3-methoxyphenyl)-1-(3-fluoro-5-(trifluoromethyl)phenyl)-2-phenylethyl)pyrrolidine-1-carboxamide | 3.233 LC (3) 523.2 [M + H]$^+$ | Procedures 4, 5, 6 and 12 |
| 509 | 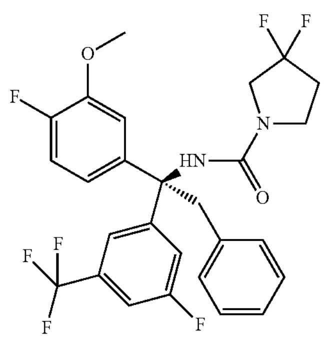 [SMILES: COc1cc([C@@](Cc2ccccc2)(NC(=O)N2CCC(F)(F)C2)c2cc(F)cc(C(F)(F)F)c2)ccc1F] | (R)-3,3-difluoro-N-(1-(4-fluoro-3-methoxyphenyl)-1-(3-fluoro-5-(trifluoromethyl)phenyl)-2-phenylethyl)pyrrolidine-1-carboxamide | 3.403 LC (3) 541.2 [M + H]$^+$ | Procedures 4, 5, 6 and 12 |
| 510 | 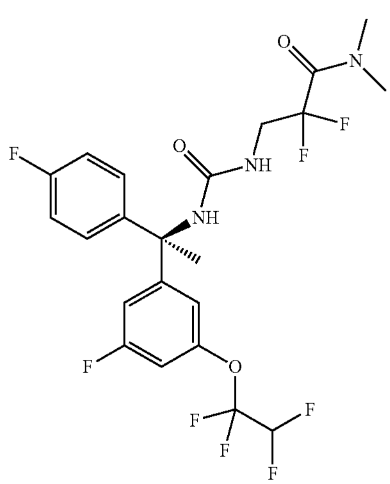 | (R)-2,2-difluoro-3-(3-(1-(3-fluoro-5-(1,1,2,2-tetrafluoroethoxy)phenyl)-1-(4-fluorophenyl)-2-phenylethyl)ureido)-N,N-dimethylpropanamide | 3.21 LC (1) 604.2 [M + H]$^+$ | Procedures 3, 4, 5, 6, 25 and 127 |

TABLE 9-continued

| Ex. No. | Structure | Name | Retention Time Min./ Molecular Mass | Prepared in the manner described in: |
|---|---|---|---|---|
| 511 | 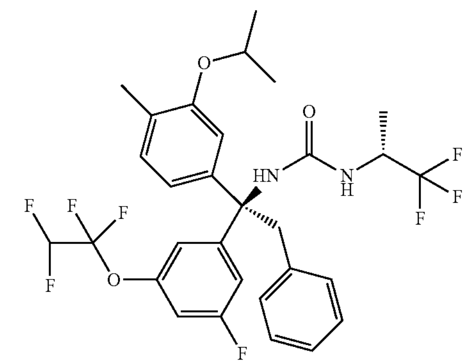 | 1-((R)-1-(4-fluoro-3-isopropoxyphenyl)-1-(3-fluoro-5-(1,1,2,2-tetrafluoroethoxy)phenyl)-2-phenylethyl)-3-((R)-1,1,1-trifluoropropan-2-yl)urea | 3.66 LC (1) 623.2 [M + H]$^+$ | Procedures 3, 4, 5, 6, 59, 68 and 25 |
| 512 | 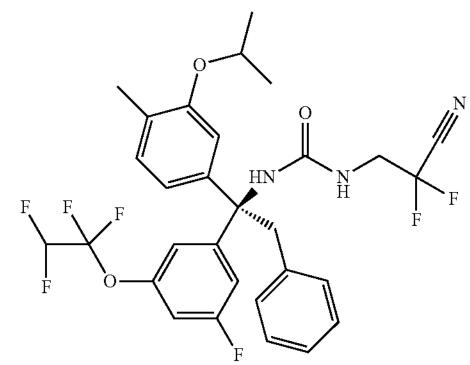 | (R)-1-(2-cyano-2,2-difluoroethyl)-3-(1-(4-fluoro-3-isopropoxyphenyl)-1-(3-fluoro-5-(1,1,2,2-tetrafluoroethoxy)phenyl)-2-phenylethyl)urea | 2.26 LC (2) 616.5 [M + H]$^+$ | Procedures 3, 4, 5, 6, 59, 68, 46, 25, 47 and 48 |
| 513 | 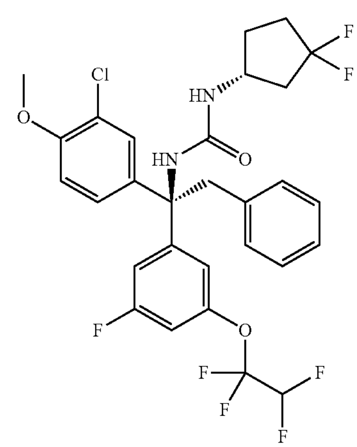 [SMILES: COc1ccc([C@@](Cc2ccccc2)(NC(=O)N[C@@H]2CCC(F)(F)C2)c2cc(F)cc(OC(F)(F)C(F)F)c2)cc1Cl] | 1-((S)-1-(3-chloro-4-methoxyphenyl)-1-(3-fluoro-5-(1,1,2,2-tetrafluoroethoxy)phenyl)-2-phenylethyl)-3-((R)-3,3-difluorocyclopentyl)urea | 10.28 LC (7) 619 [M + H]$^+$ | Procedures 3, 4, 5, 6 and 12 |
| 514 | 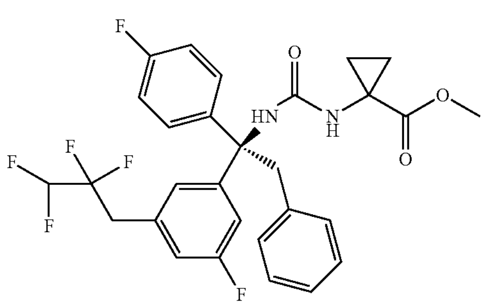 [SMILES: COC(=O)C1(NC(=O)N[C@](Cc2ccccc2)(c2ccc(F)cc2)c2cc(F)cc(CC(F)(F)C(F)F)c2)CC1] | (R)-methyl 1-(3-(1-(3-fluoro-5-(1,1,2,2-tetrafluoroethoxy)phenyl)-1-(4-fluorophenyl)-2-phenylethyl)ureido)cyclopropanecarboxylate | 3.89 LC (1) 567.2 [M + H]$^+$ | Procedures 3, 4, 5, 6 and 12 |

TABLE 9-continued

| Ex. No. | Structure | Name | Retention Time Min./ Molecular Mass | Prepared in the manner described in: |
|---|---|---|---|---|
| 515 | 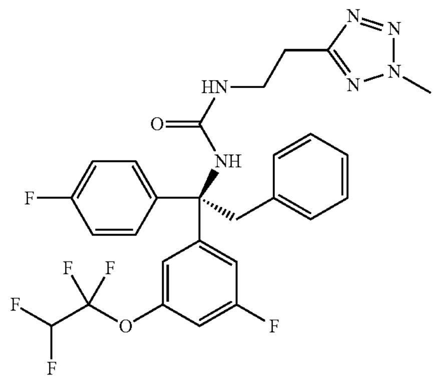 [SMILES: Cn1nnc(CCNC(=O)N[C@](Cc2ccccc2)(c2ccc(F)cc2)c2cc(F)cc(OC(F)(F)C(F)F)c2)n1] | (R)-1-(1-(3-fluoro-5-(1,1,2,2-tetrafluoroethoxy)phenyl)-1-(4-fluorophenyl)-2-phenylethyl)-3-(2-(2-methyl-2H-tetrazol-5-yl)ethyl)urea | 3.005 LC (3) 579.2 [M + H]$^+$ | Procedures 3, 4, 5, 6, 12 and 55 |
| 516 | 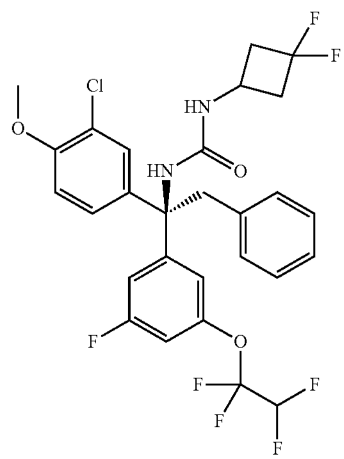 | (S)-1-(1-(3-chloro-4-methoxyphenyl)-1-(3-fluoro-5-(1,1,2,2-tetrafluoroethoxy)phenyl)-2-phenylethyl)-3-(3,3-difluorocyclobutyl)urea | 10.16 LC (7) 606 [M + H]$^+$ | Procedures 3, 4, 5, 6, 116, 117, 118, 119, 120 and 25 |
| 517 | 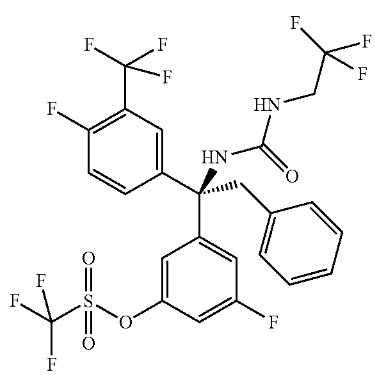 [SMILES: O=C(NCC(F)(F)F)N[C@@](Cc1ccccc1)(c1cc(F)cc(OS(=O)(=O)C(F)(F)F)c1)c1ccc(F)c(C(F)(F)F)c1] | (R)-3-fluoro-5-(1-(4-fluoro-3-(trifluoromethyl)phenyl)-2-phenyl-1-(3-(2,2,2-trifluoro-ethyl)ureido)ethyl)phenyltri-fluoromethanesulfonate | 2.34 LC (2) 651.4 [M + H]$^+$ | Procedures 49 and 66 |
| 518 | 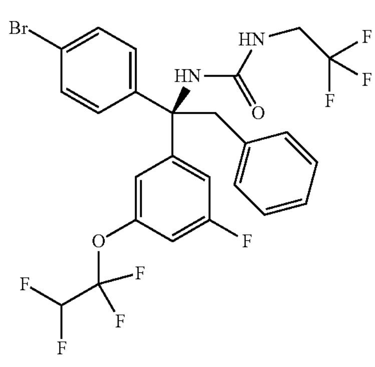 [SMILES: O=C(NCC(F)(F)F)N[C@](Cc1ccccc1)(c1ccc(Br)cc1)c1cc(F)cc(OC(F)(F)C(F)F)c1] | (R)-1-(1-(4-bromophenyl)-1-(3-fluoro-5-(1,1,2,2-tetrafluoro-ethoxy)phenyl)-2-phenylethyl)-3-(2,2,2-trifluoroethyl)urea | 3.76 LC (4) 611.3 [M + H]$^+$ | Procedures 3, 4, 5, 6 and 12 |

TABLE 9-continued

| Ex. No. | Structure | Name | Retention Time Min./ Molecular Mass | Prepared in the manner described in: |
|---|---|---|---|---|
| 519 | 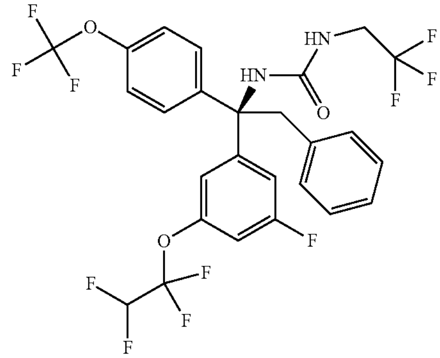 [SMILES: O=C(NCC(F)(F)F)N[C@](Cc1ccccc1)(c1ccc(OC(F)(F)F)cc1)c1cc(F)cc(OC(F)(F)C(F)F)c1] | (R)-1-(1-(3-fluoro-5-(1,1,2,2-tetrafluoroethoxy)phenyl)-2-phenyl-1-(4-(trifluoromethoxy)phenyl)ethyl)-3-(2,2,2-trifluoroethyl)urea | 3.79 LC (4) 617.4 [M + H]+ | Procedures 3, 4, 5, 6 and 12 |
| 520 | 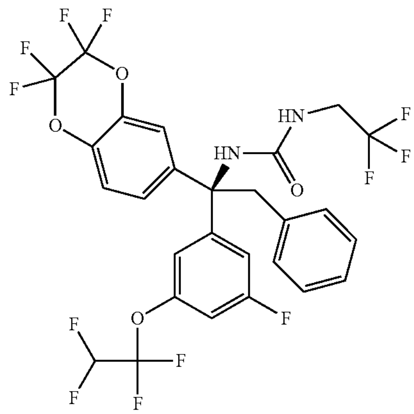 [SMILES: O=C(NCC(F)(F)F)N[C@@](Cc1ccccc1)(c1cc(F)cc(OC(F)(F)C(F)F)c1)c1ccc2c(c1)OC(F)(F)C(F)(F)O2] | (R)-1-(1-(3-fluoro-5-(1,1,2,2-tetrafluoroethoxy)phenyl)-2-phenyl-1-(2,2,3,3-tetrafluoro-2,3-dihydrobenzo[b][1,4]dioxin-6-yl)ethyl)-3-(2,2,2-trifluoroethyl)urea | 3.88 LC (4) 663.5 [M + H]+ | Procedures 3, 4, 5, 6 and 12 |
| 521 | 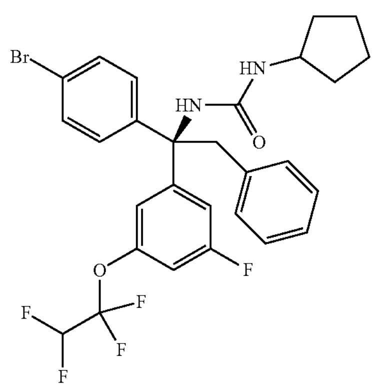 [SMILES: O=C(NC1CCCC1)N[C@](Cc1ccccc1)(c1ccc(Br)cc1)c1cc(F)cc(OC(F)(F)C(F)F)c1] | (R)-1-(1-(4-bromophenyl)-1-(3-fluoro-5-(1,1,2,2-tetrafluoroethoxy)phenyl)-2-phenylethyl)-3-cyclopentylurea | 3.87 LC (4) 597.4 [M + H]+ | Procedures 3, 4, 5, 6 and 2 |
| 522 | 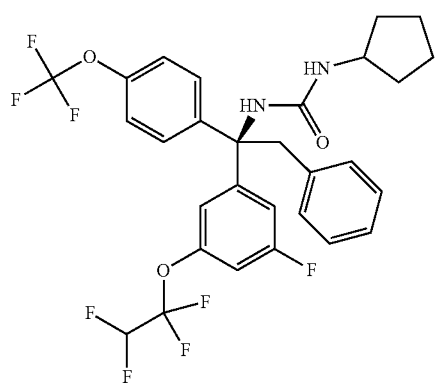 [SMILES: O=C(NC1CCCC1)N[C@](Cc1ccccc1)(c1ccc(OC(F)(F)F)cc1)c1cc(F)cc(OC(F)(F)C(F)F)c1] | (R)-1-cyclopentyl-3-(1-(3-fluoro-5-(1,1,2,2-tetrafluoroethoxy)phenyl)-2-phenyl-1-(4-(trifluoromethoxy)phenyl)ethyl)urea | 3.90 LC (4) 603.5 [M + H]+ | Procedures 3, 4, 5, 6 and 2 |

TABLE 9-continued

| Ex. No. | Structure | Name | Retention Time Min./ Molecular Mass | Prepared in the manner described in: |
|---|---|---|---|---|
| 523 | 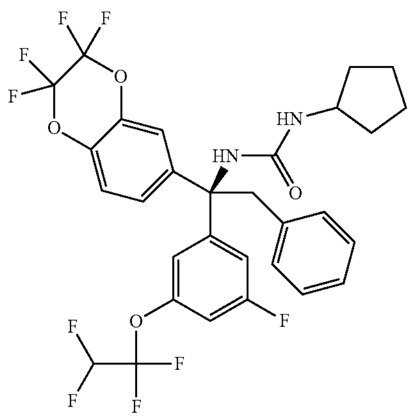 [SMILES: O=C(NC1CCCC1)N[C@@](Cc1ccccc1)(c1cc(F)cc(OC(F)(F)C(F)F)c1)c1ccc2c(c1)OC(F)(F)C(F)(F)O2] | (R)-1-cyclopentyl-3-(1-(3-fluoro-5-(1,1,2,2-tetrafluoroethoxy)phenyl)-2-phenyl-1-(2,2,3,3-tetrafluoro-2,3-dihydrobenzo[b][1,4]dioxin-6-yl)ethyl)urea | 4.02 LC (4) 649.4 $[M + H]^+$ | Procedures 3, 4, 5, 6 and 2 |
| 524 | 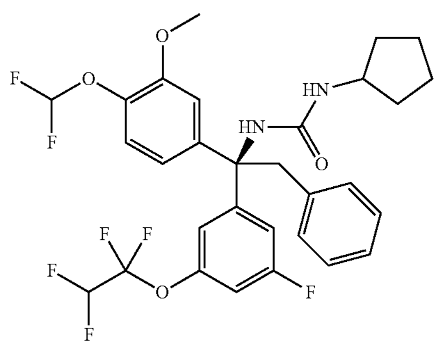 [SMILES: COc1cc([C@@](Cc2ccccc2)(NC(=O)NC2CCCC2)c2cc(F)cc(OC(F)(F)C(F)F)c2)ccc1OC(F)F] | (R)-1-cyclopentyl-3-(1-(4-(difluoromethoxy)-3-methoxyphenyl)-1-(3-fluoro-5-(1,1,2,2-tetrafluoroethoxy)phenyl)-2-phenylethyl)urea | 3.68 LC (4) 615.5 $[M + H]^+$ | Procedures 3, 4, 5, 6 and 2 |
| 525 | 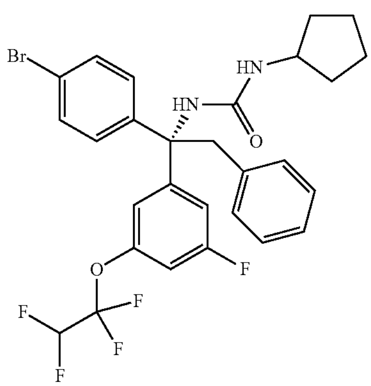 [SMILES: O=C(NC1CCCC1)N[C@@](Cc1ccccc1)(c1ccc(Br)cc1)c1cc(F)cc(OC(F)(F)C(F)F)c1] | (S)-1-(1-(4-bromophenyl)-1-(3-fluoro-5-(1,1,2,2-tetrafluoro-ethoxy)phenyl)-2-phenylethyl)-3-cyclopentylurea | 3.87 LC (4) 597.4 $[M + H]^+$ | Procedures 3, 4, 5, 6 and 2 |
| 526 | 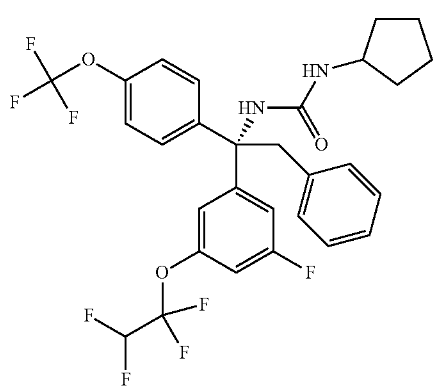 [SMILES: O=C(NC1CCCC1)N[C@@](Cc1ccccc1)(c1ccc(OC(F)(F)F)cc1)c1cc(F)cc(OC(F)(F)C(F)F)c1] | (S)-1-cyclopentyl-3-(1-(3-fluoro-5-(1,1,2,2-tetrafluoroethoxy)phenyl)-2-phenyl-1-(4-(trifluoro-methoxy)phenyl)ethyl)urea | 3.90 LC (4) 603.5 $[M + H]^+$ | Procedures 3, 4, 5, 6 and 2 |

TABLE 9-continued

| Ex. No. | Structure | Name | Retention Time Min./ Molecular Mass | Prepared in the manner described in: |
|---|---|---|---|---|
| 527 | 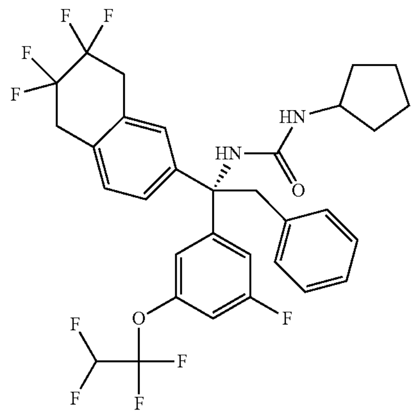 [SMILES: O=C(NC1CCCC1)N[C@](Cc1ccccc1)(c1cc(F)cc(OC(F)(F)C(F)F)c1)c1ccc2c(c1)CC(F)(F)C(F)(F)C2] | (S)-1-cyclopentyl-3-(1-(3-fluoro-5-(1,1,2,2-tetrafluoroethoxy)phenyl)-2-phenyl-1-(2,2,3,3-tetrafluoro-2,3-dihydrobenzo[b][1,4]dioxin-6-yl)ethyl)urea | 4.02 LC (4) 649.4 [M + H]$^+$ | Procedures 3, 4, 5, 6 and 2 |
| 528 | 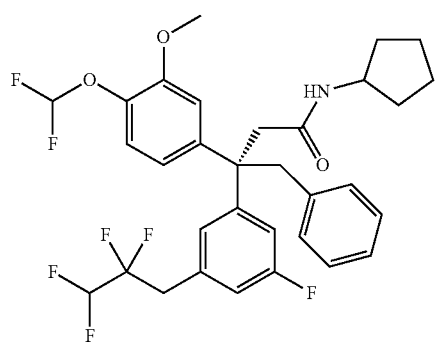 | (S)-1-cyclopentyl-3-(1-(4-(difluoromethoxy)-3-methoxyphenyl)-1-(3-fluoro-5-(1,1,2,2-tetrafluoroethoxy)phenyl)-2-phenylethyl)urea | 3.68 LC (4) 615.5 [M + H]$^+$ | Procedures 3, 4, 5, 6 and 2 |
| 529 | 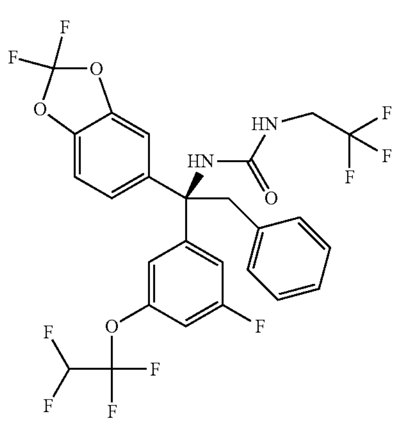 [SMILES: O=C(NCC(F)(F)F)N[C@@](Cc1ccccc1)(c1cc(F)cc(OC(F)(F)C(F)F)c1)c1ccc2c(c1)OC(F)(F)O2] | (R)-1-(1-(2,2-difluoro-benzo[d][1,3]dioxol-5-yl)-1-(3-fluoro-5-(1,1,2,2-tetrafluoroethoxy)phenyl)-2-phenylethyl)-3-(2,2,2-trifluoroethyl)urea | 3.74 LC (4) 613.4 [M + H]$^+$ | Procedures 3, 4, 5, 6 and 2 |

TABLE 9-continued

| Ex. No. | Structure | Name | Retention Time Min./ Molecular Mass | Prepared in the manner described in: |
|---|---|---|---|---|
| 530 | 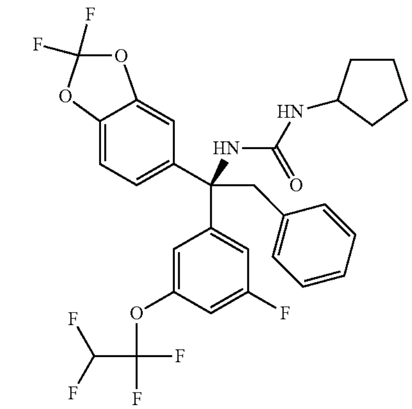 [SMILES: O=C(NC1CCCC1)N[C@@](Cc1ccccc1)(c1cc(F)cc(OC(F)(F)C(F)F)c1)c1ccc2c(c1)OC(F)(F)O2] | (R)-1-cyclopentyl-3-(1-(2,2-difluorobenzo[d][1,3]dioxol-5-yl)-1-(3-fluoro-5-(1,1,2,2-tetrafluoroethoxy)phenyl)-2-phenylethyl)urea | 3.85 LC (4) 599.5 [M + H]$^+$ | Procedures 3, 4, 5, 6 and 2 |
| 531 | 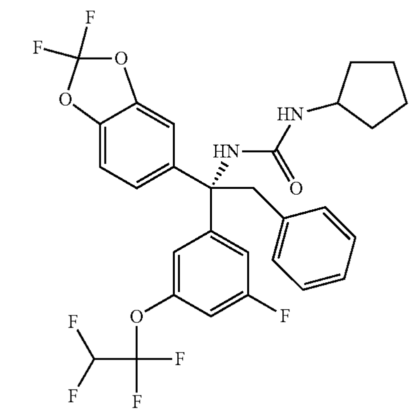 [SMILES: O=C(NC1CCCC1)N[C@](Cc1ccccc1)(c1cc(F)cc(OC(F)(F)C(F)F)c1)c1ccc2c(c1)OC(F)(F)O2] | (S)-1-cyclopentyl-3-(1-(2,2-difluorobenzo[d][1,3]dioxol-5-yl)-1-(3-fluoro-5-(1,1,2,2-tetrafluoroethoxy)phenyl)-2-phenylethyl)urea | 3.85 LC (4) 599.5 [M + H]$^+$ | Procedures 3, 4, 5, 6 and 2 |
| 532 | 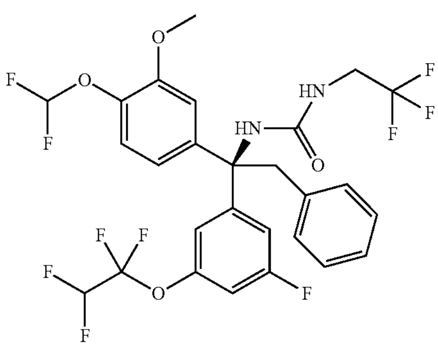 [SMILES: COc1cc([C@@](Cc2ccccc2)(NC(=O)NCC(F)(F)F)c2cc(F)cc(OC(F)(F)C(F)F)c2)ccc1OC(F)F] | (R)-1-(1-(4-(difluoromethoxy)-3-methoxyphenyl)-1-(3-fluoro-5-(1,1,2,2-tetrafluoroethoxy)phenyl)-2-phenylethyl)-3-(2,2,2-trifluoroethyl)urea | 3.59 LC (4) 629.09 [M + H]$^+$ | Procedures 3, 4, 5, 6 and 2 |
| 533 | 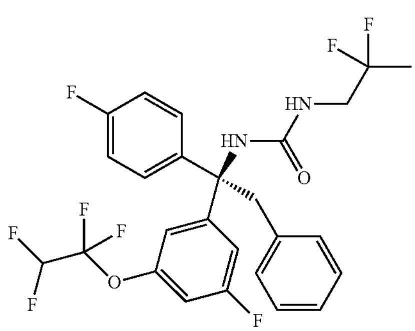 [SMILES: CC(F)(F)CNC(=O)N[C@](Cc1ccccc1)(c1ccc(F)cc1)c1cc(F)cc(OC(F)(F)C(F)F)c1] | (R)-1-(2,2-difluoropropyl)-3-(1-(3-fluoro-5-(1,1,2,2-tetrafluoroethoxy)phenyl)-1-(4-fluorophenyl)-2-phenylethyl)urea | 3.955 LC (3) 547.3 [M + H]$^+$ | Procedures 3, 4, 5, 6 and 12 |

TABLE 9-continued

| Ex. No. | Structure | Name | Retention Time Min./ Molecular Mass | Prepared in the manner described in: |
|---|---|---|---|---|
| 534 | 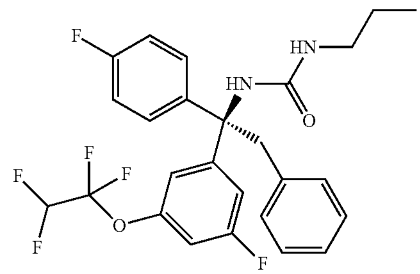 [SMILES: CCCNC(=O)N[C@](Cc1ccccc1)(c1ccc(F)cc1)c1cc(F)cc(OC(F)(F)C(F)F)c1] | (R)-1-(1-(3-fluoro-5-(1,1,2,2-tetrafluoroethoxy)phenyl)-1-(4-fluorophenyl)-2-phenylethyl)-3-propylurea | 3.985 LC (3) 511.3 [M + H]+ | Procedures 3, 4, 5, 6 and 12 |
| 535 | 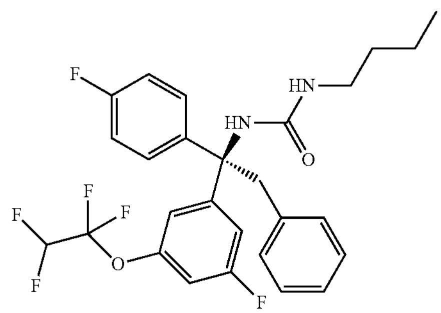 [SMILES: CCCCNC(=O)N[C@](Cc1ccccc1)(c1ccc(F)cc1)c1cc(F)cc(OC(F)(F)C(F)F)c1] | (R)-1-butyl-3-(1-(3-fluoro-5-(1,1,2,2-tetrafluoroethoxy)phenyl)-1-(4-fluorophenyl)-2-phenyl-ethyl)urea | 4.063 LC (3) 525.3 [M + H]+ | Procedures 3, 4, 5, 6 and 12 |
| 536 | 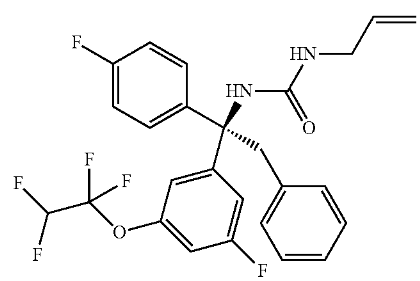 [SMILES: C=CCNC(=O)N[C@](Cc1ccccc1)(c1ccc(F)cc1)c1cc(F)cc(OC(F)(F)C(F)F)c1] | (R)-1-allyl-3-(1-(3-fluoro-5-(1,1,2,2-tetrafluoroethoxy)phenyl)-1-(4-fluorophenyl)-2-phenyl-ethyl)urea | 3.948 LC (3) 509.2 [M + H]+ | Procedures 3, 4, 5, 6 and 12 |
| 537 | 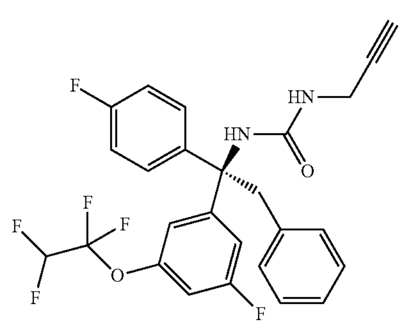 [SMILES: C#CCNC(=O)N[C@](Cc1ccccc1)(c1ccc(F)cc1)c1cc(F)cc(OC(F)(F)C(F)F)c1] | (R)-1-(1-(3-fluoro-5-(1,1,2,2-tetrafluoroethoxy)phenyl)-1-(4-fluorophenyl)-2-phenylethyl)-3-(prop-2-ynyl)urea | 3.866 LC (3) [M + H]+ | Procedures 3, 4, 5, 6 and 12 |

TABLE 9-continued

| Ex. No. | Structure | Name | Retention Time Min./ Molecular Mass | Prepared in the manner described in: |
|---|---|---|---|---|
| 538 | 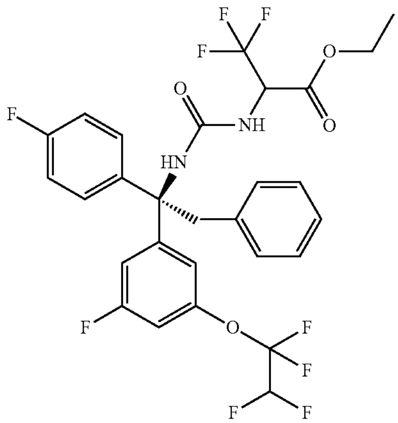 | ethyl 3,3,3-trifluoro-2-(3-((R)-1-(3-fluoro-5-(1,1,2,2-tetrafluoro-ethoxy)phenyl)-1-(4-fluorophenyl)-2-phenylethyl)ureido)propanoate | 2.15 LC (2) 623.5 [M + H]$^+$ | Procedures 3, 4, 5, 6 and 25 |
| 539 | 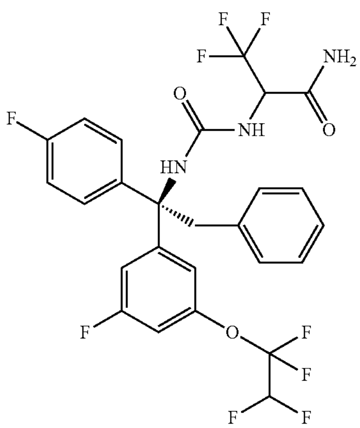 [SMILES: NC(=O)C(NC(=O)N[C@](Cc1ccccc1)(c1ccc(F)cc1)c1cc(F)cc(OC(F)(F)C(F)F)c1)C(F)(F)F] | 3,3,3-trifluoro-2-(3-((R)-1-(3-fluoro-5-(1,1,2,2-tetrafluoro-ethoxy)phenyl)-1-(4-fluorophenyl)-2-phenylethyl)ureido)propanamide | 3.04 LC (8) 594.1 [M + H]$^+$ | Procedures 3, 4, 5, 6, 25, 23 and 47 |
| 540 | 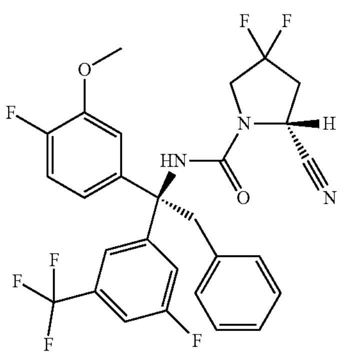 [SMILES: COc1cc([C@@](Cc2ccccc2)(NC(=O)N2CC(F)(F)C[C@@H]2C#N)c2cc(F)cc(C(F)(F)F)c2)ccc1F] | (R)-2-cyano-4,4-difluoro-N-((R)-1-(4-fluoro-3-methoxyphenyl)-1-(3-fluoro-5-(trifluoromethyl)phenyl)-2-phenylethyl)pyrrolidine-1-carboxamide | 3.895 LC (3) 566.3 [M + H]$^+$ | Procedures 4, 5, 6, 12 and 48 |
| 541 | 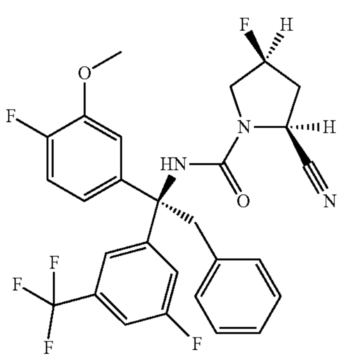 [SMILES: COc1cc([C@@](Cc2ccccc2)(NC(=O)N2C[C@@H](F)C[C@H]2C#N)c2cc(F)cc(C(F)(F)F)c2)ccc1F] | (2S,4S)-2-cyano-4-fluoro-((R)-1-(4-fluoro-3-methoxyphenyl)-1-(3-fluoro-5-(trifluoromethyl)phenyl)-2-phenylethyl)pyrrolidine-1-carboxamide | 3.82 LC (3) 548.3 [M + H]$^+$ | Procedures 4, 5, 6, 12 and 48 |

TABLE 9-continued

| Ex. No. | Structure | Name | Retention Time Min./ Molecular Mass | Prepared in the manner described in: |
|---|---|---|---|---|
| 542 | 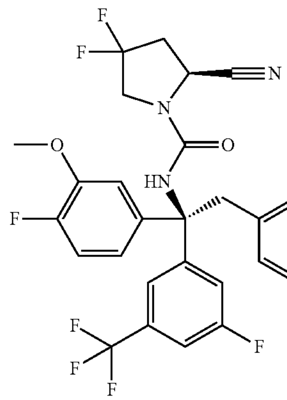 | (S)-2-cyano-4,4-difluoro-N-((R)-1-(4-fluoro-3-methoxyphenyl)-1-(3-fluoro-5-(trifluoromethyl)phenyl)-2-phenylethyl)pyrrolidine-1-carboxamide | 3.925 LC (3) 566.3 [M + H]⁺ | Procedures 4, 5, 6, 12 and 48 |
| 543 | 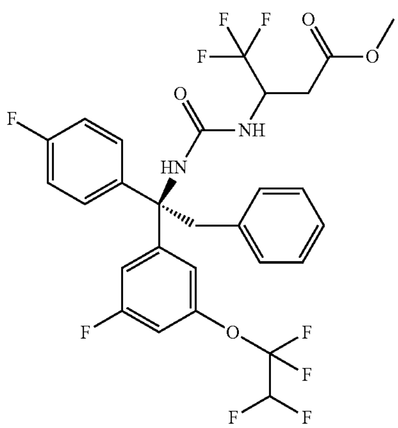 [SMILES: COC(=O)CC(NC(=O)N[C@](Cc1ccccc1)(c1ccc(F)cc1)c1cc(F)cc(OC(F)(F)C(F)F)c1)C(F)(F)F] | methyl 4,4,4-trifluoro-3-(3-((R)-1-(3-fluoro-5-(1,1,2,2-tetrafluoroethoxy)phenyl)-1-(4-fluorophenyl)-2-phenyl-ethyl)ureido)butanoate | 4.0 LC (1) 623.3 [M + H]⁺ | Procedures 3, 4, 5, 6 and 25 |
| 544 | 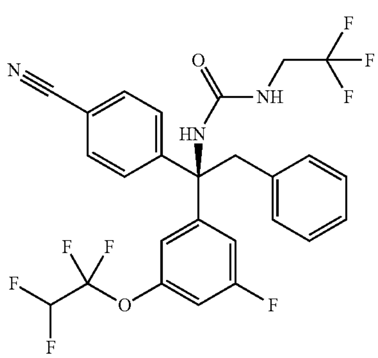 [SMILES: N#Cc1ccc([C@@](Cc2ccccc2)(NC(=O)NCC(F)(F)F)c2cc(F)cc(OC(F)(F)C(F)F)c2)cc1] | (R)-1-(1-(4-cyanophenyl)-1-(3-fluoro-5-(1,1,2,2-tetrafluoro-ethoxy)phenyl)-2-phenylethyl)-3-(2,2,2-trifluoroethyl)urea | 1.12 LC (9) 558 [M + H]⁺ | Procedures 3, 4, 5, 6, 56 and 25 |
| 545 | 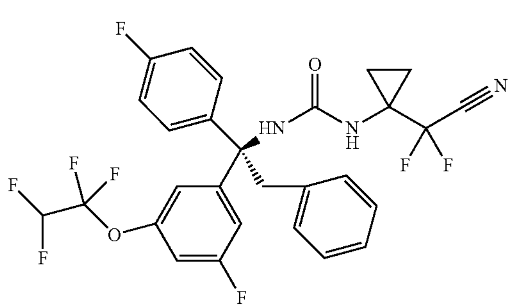 [SMILES: N#CC(F)(F)C1(NC(=O)N[C@](Cc2ccccc2)(c2ccc(F)cc2)c2cc(F)cc(OC(F)(F)C(F)F)c2)CC1] | (R)-1-(1-(cyanodifluoro-methyl)cyclopropyl)-3-(1-(3-fluoro-5-(1,1,2,2-tetrafluoroethoxy)phenyl)-1-(4-fluorophenyl)-2-phenyl-ethyl)urea | 3.44 LC (8) 584.1 [M + H]⁺ | Procedures 3, 4, 5, 6, 25, 34, 35, 47 and 48 |

TABLE 9-continued

| Ex. No. | Structure | Name | Retention Time Min./ Molecular Mass | Prepared in the manner described in: |
| --- | --- | --- | --- | --- |
| 546 | 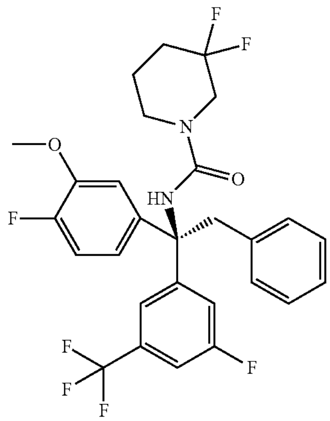 [SMILES: COc1cc([C@@](Cc2ccccc2)(NC(=O)N2CCCC(F)(F)C2)c2cc(F)cc(C(F)(F)F)c2)ccc1F] | (R)-3,3-difluoro-N-(1-(4-fluoro-3-methoxyphenyl)-1-(3-fluoro-5-(trifluoromethyl)phenyl)-2-phenylethyl)piperidine-1-carboxamide | 4.023 LC (3) 555.3 [M + H]+ | Procedures 4, 5, 6 and 12 |
| 547 | 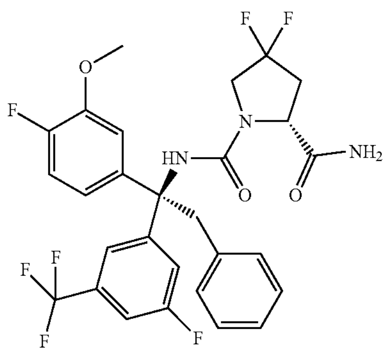 [SMILES: COc1cc([C@@](Cc2ccccc2)(NC(=O)N2CC(F)(F)C[C@@H]2C(N)=O)c2cc(F)cc(C(F)(F)F)c2)ccc1F] | (R)-4,4-difluoro-N1-((R)-1-(4-fluoro-3-methoxyphenyl)-1-(3-fluoro-5-(trifluoromethyl)phenyl)-2-phenylethyl)pyrrolidine-1,2-dicarboxamide | 3.901 LC (3) 584.3 [M + H]+ | Procedures 4, 5, 6 and 12 |
| 548 | 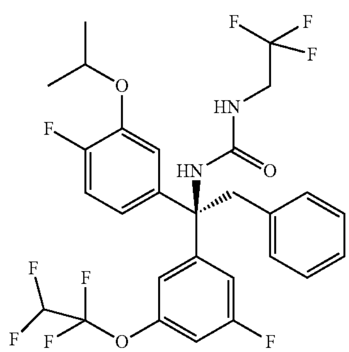 [SMILES: CC(C)Oc1cc([C@@](Cc2ccccc2)(NC(=O)NCC(F)(F)F)c2cc(F)cc(OC(F)(F)C(F)F)c2)ccc1F] | (R)-1-(1-(4-fluoro-3-isopropoxyphenyl)-1-(3-fluoro-5-(1,1,2,2-tetrafluoroethoxy)phenyl)-2-phenylethyl)-3-(2,2,2-trifluoroethyl)urea | 3.633 LC (1) 609.4 [M + H]+ | Procedures 3, 4, 5, 6, 10, 59 and 68 |
| 549 | 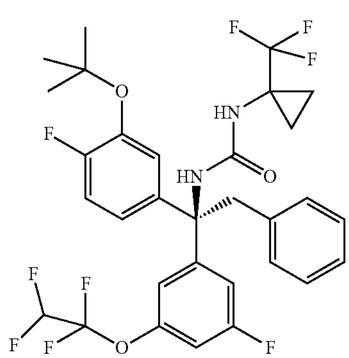 [SMILES: CC(C)(C)Oc1cc([C@@](Cc2ccccc2)(NC(=O)NC2(C(F)(F)F)CC2)c2cc(F)cc(OC(F)(F)C(F)F)c2)ccc1F] | (R)-1-(1-(3-tert-butoxy-4-fluorophenyl)-1-(3-fluoro-5-(1,1,2,2-tetrafluoroethoxy)phenyl)-2-phenylethyl)-3-(1-(trifluoromethyl)cyclopropyl)urea | 3.798 LC (1) 649.6 [M + H]+ | Procedures 3, 4, 5, 6, 30, 59 and 108 |

TABLE 9-continued

| Ex. No. | Structure | Name | Retention Time Min./ Molecular Mass | Prepared in the manner described in: |
|---|---|---|---|---|
| 550 | 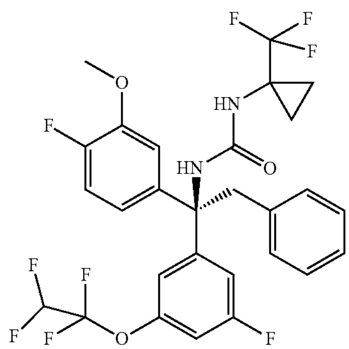 [SMILES: COc1cc([C@@](Cc2ccccc2)(NC(=O)NC2(C(F)(F)F)CC2)c2cc(F)cc(OC(F)(F)C(F)F)c2)ccc1F] | (R)-1-(1-(4-fluoro-3-methoxyphenyl)-1-(3-fluoro-5-(1,1,2,2-tetrafluoroethoxy)phenyl)-2-phenylethyl)-3-(1-(trifluoromethyl)cyclopropyl)urea | 3.46 LC (1) 607.5 [M + H]$^+$ | Procedures 3, 4, 5, 6 and 30 |
| 551 | 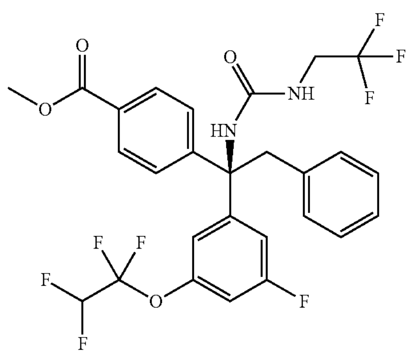 [SMILES: COC(=O)c1ccc([C@@](Cc2ccccc2)(NC(=O)NCC(F)(F)F)c2cc(F)cc(OC(F)(F)C(F)F)c2)cc1] | (R)-methyl 4-(1-(3-fluoro-5-(1,1,2,2-tetrafluoroethoxy)phenyl)-2-phenyl-1-(3-(2,2,2-trifluoroethyl)ureido)ethyl)benzoate | 1.19 LC (12) 591 [M + H]$^+$ | Procedures 3, 4, 5, 6, 25, 56 and 57 |
| 552 | 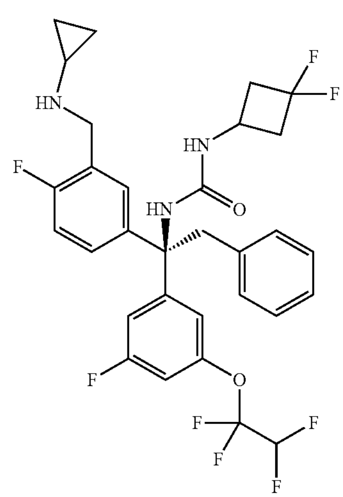 [SMILES: O=C(NC1CC(F)(F)C1)N[C@@](Cc1ccccc1)(c1cc(F)cc(OC(F)(F)C(F)F)c1)c1ccc(F)c(CNC2CC2)c1] | (R)-1-(1-(3-((cyclopropylamino)methyl)-4-fluorophenyl)-1-(3-fluoro-5-(1,1,2,2-tetrafluoroethoxy)phenyl)-2-phenylethyl)-3-(3,3-difluorocyclobutyl)urea | 3.331 LC (15) 628 [M + H]$^+$ | Procedures 3, 62, 5, 6, 146, 116-120, 12, 147 and 148 |

TABLE 9-continued

| Ex. No. | Structure | Name | Retention Time Min./ Molecular Mass | Prepared in the manner described in: |
|---|---|---|---|---|
| 553 | 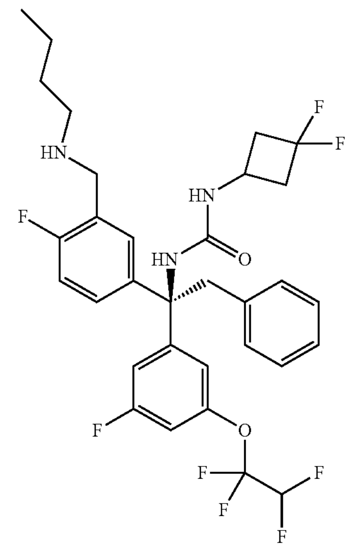 [SMILES: CCCCNCc1cc([C@@](Cc2ccccc2)(NC(=O)NC2CC(F)(F)C2)c2cc(F)cc(OC(F)(F)C(F)F)c2)ccc1F] | (R)-1-(1-(3-((butylamino)methyl)-4-fluorophenyl)-1-(3-fluoro-5-(1,1,2,2-tetrafluoroethoxy)phenyl)-2-phenylethyl)-3-(3,3-difluorocyclobutyl)urea | 3.488 LC (15) 644 [M + H]+ | Procedures 3, 62, 5, 6, 146, 116-120, 12, 147 and 148 |
| 554 | 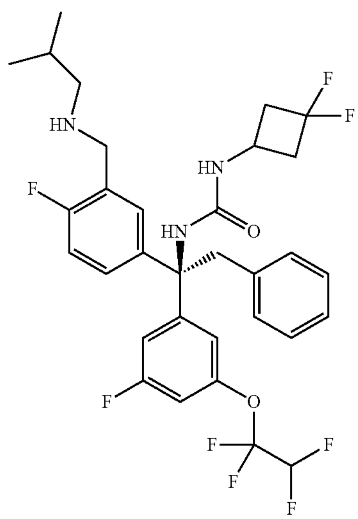 [SMILES: CC(C)CNCc1cc([C@@](Cc2ccccc2)(NC(=O)NC2CC(F)(F)C2)c2cc(F)cc(OC(F)(F)C(F)F)c2)ccc1F] | (R)-1-(3,3-difluorocyclobutyl)-3-(1-(4-fluoro-3-((isobutyl-amino)methyl)phenyl)-1-(3-fluoro-5-(1,1,2,2-tetrafluoroethoxy)phenyl)-2-phenylethyl)urea | 3.458 LC (15) 644 [M + H]+ | Procedures 3, 62, 5, 6, 146, 116-120, 12, 147 and 148 |
| 555 | 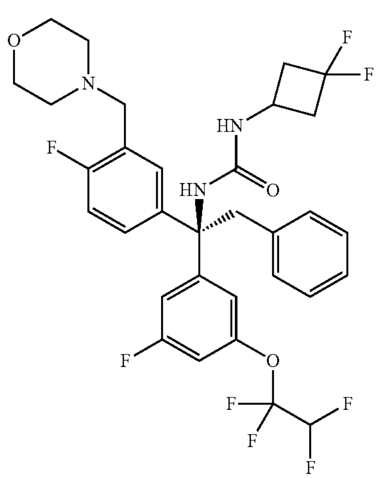 [SMILES: O=C(NC1CC(F)(F)C1)N[C@@](Cc1ccccc1)(c1cc(F)cc(OC(F)(F)C(F)F)c1)c1ccc(F)c(CN2CCOCC2)c1] | (R)-1-(3,3-difluorocyclobutyl)-3-(1-(4-fluoro-3-(morpholino-methyl)phenyl)-1-(3-fluoro-5-(1,1,2,2-tetrafluoroethoxy)phenyl)-2-phenylethyl)urea | 3.636 LC (15) 658 [M + H]+ | Procedures 3, 62, 5, 6, 146, 116-120, 12, 147 and 148 |

TABLE 9-continued

| Ex. No. | Structure | Name | Retention Time Min./ Molecular Mass | Prepared in the manner described in: |
|---|---|---|---|---|
| 556 | 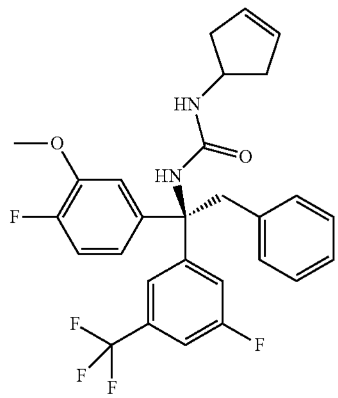 [SMILES: COc1cc([C@@](Cc2ccccc2)(NC(=O)NC2CC=CC2)c2cc(F)cc(C(F)(F)F)c2)ccc1F] | (R)-1-(cyclopent-3-enyl)-3-(1-(4-fluoro-3-methoxyphenyl)-1-(3-fluoro-5-(trifluoromethyl)phenyl)-2-phenylethyl)urea | 4.068 LC (3) 517.3 [M + H]$^+$ | Procedures 4, 5, 6 and 12 |
| 557 | 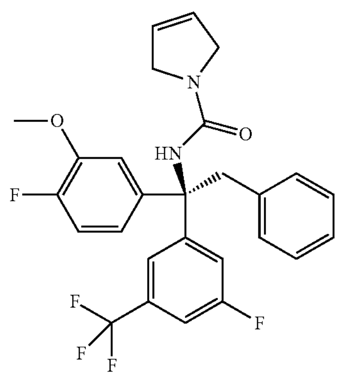 [SMILES: COc1cc([C@@](Cc2ccccc2)(NC(=O)N2CC=CC2)c2cc(F)cc(C(F)(F)F)c2)ccc1F] | (R)-N-(1-(4-fluoro-3-methoxyphenyl)-1-(3-fluoro-5-(trifluoromethyl)phenyl)-2-phenylethyl)-2,5-dihydro-1H-pyrrole-1-carboxamide | 3.986 LC (3) 503.3 [M + H]$^+$ | Procedures 4, 5, 6 and 12 |
| 558 | 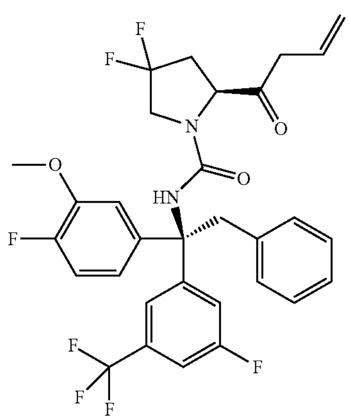 [SMILES: C=CCC(=O)[C@@H]1CC(F)(F)CN1C(=O)N[C@@](Cc1ccccc1)(c1cc(F)cc(C(F)(F)F)c1)c1ccc(F)c(OC)c1] | (S)-2-but-3-enoyl-4,4-difluoro-N-((R)-1-(4-fluoro-3-methoxyphenyl)-1-(3-fluoro-5-(trifluoromethyl)phenyl)-2-phenylethyl)pyrrolidine-1-carboxamide | 4.09 LC (3) 609.3 [M + H]$^+$ | Procedure 4, 5, 6 and 12 |
| 559 | 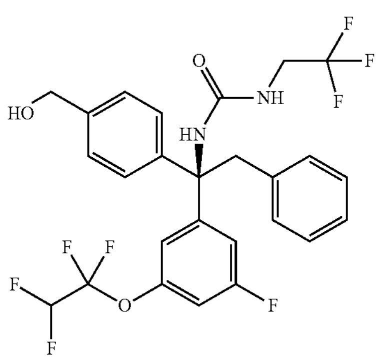 [SMILES: O=C(NCC(F)(F)F)N[C@](Cc1ccccc1)(c1ccc(CO)cc1)c1cc(F)cc(OC(F)(F)C(F)F)c1] | (R)-1-(1-(3-fluoro-5-(1,1,2,2-tetrafluoroethoxy)phenyl)-1-(4-(hydroxymethyl)phenyl)-2-phenylethyl)-3-(2,2,2-trifluoroethyl)urea | 1.78 LC (9) 563 [M + H]$^+$ | Procedures 3, 4, 5, 6, 25, 56, 57 and 100 |

TABLE 9-continued

| Ex. No. | Structure | Name | Retention Time Min./ Molecular Mass | Prepared in the manner described in: |
|---|---|---|---|---|
| 560 | 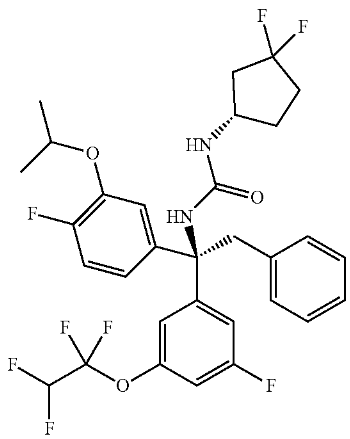 | 1-((S)-3,3-difluorocyclopentyl)-3-((R)-1-(4-fluoro-3-isopropoxyphenyl)-1-(3-fluoro-5-(1,1,2,2-tetrafluoroethoxy)phenyl)-2-phenylethyl)urea | 3.633 LC (3) 661.2 [M + H]$^+$ | Procedures 638, 4, 5, 6, 12, 59 and 68 |
| 561 | 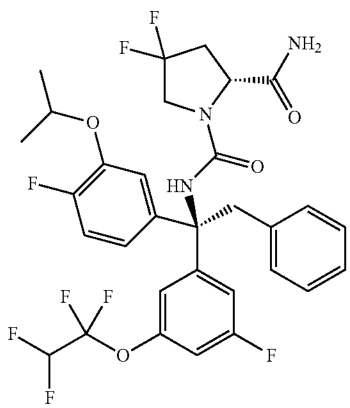 [SMILES: CC(C)Oc1cc([C@@](Cc2ccccc2)(NC(=O)N2CC(F)(F)C[C@@H]2C(N)=O)c2cc(F)cc(OC(F)(F)C(F)F)c2)ccc1F] | (R)-4,4-difluoro-N1-((R)-1-(4-fluoro-3-isopropoxyphenyl)-1-(3-fluoro-5-(1,1,2,2-tetrafluoroethoxy)phenyl)-2-phenylethyl)pyrrolidine-1,2-dicarboxamide | 3.221 LC (3) 660.2 [M + H]$^+$ | Procedures 3, 4, 5, 6, 12, 59 and 68 |

TABLE 10

| Ex. No. | Structure | Name | Retention Time Min./ Molecular Mass | Prepared in the manner described in: |
|---|---|---|---|---|
| 562 | 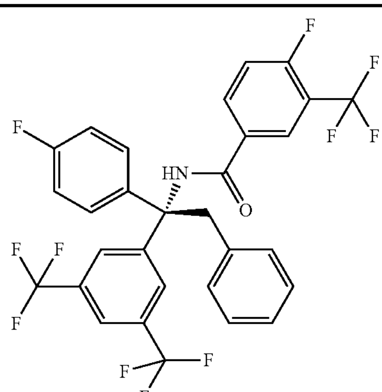 | (S)-N-(1-(3,5-bis(trifluoromethyl)phenyl)-1-(4-fluorophenyl)-2-phenylethyl)-4-fluoro-3-(trifluoromethyl)benzamide | 4.120 LC (1) 617.97 [M + H]$^+$ | Procedures 4, 5, 6 and 7 |

TABLE 10-continued

| Ex. No. | Structure | Name | Retention Time Min./ Molecular Mass | Prepared in the manner described in: |
|---|---|---|---|---|
| 563 | 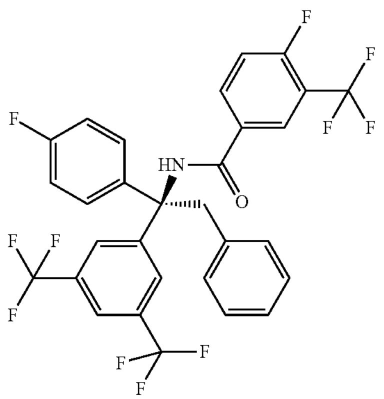 [SMILES: O=C(N[C@](Cc1ccccc1)(c1ccc(F)cc1)c1cc(C(F)(F)F)cc(C(F)(F)F)c1)c1ccc(F)c(C(F)(F)F)c1] | (R)-N-(1-(3,5-bis(trifluoromethyl)phenyl)-1-(4-fluorophenyl)-2-phenylethyl)-4-fluoro-3-(trifluoromethyl)benzamide | 4.528 LC (1) 617.97 [M + H]$^+$ | Procedures 4, 5, 6 and 7 |
| 564 | 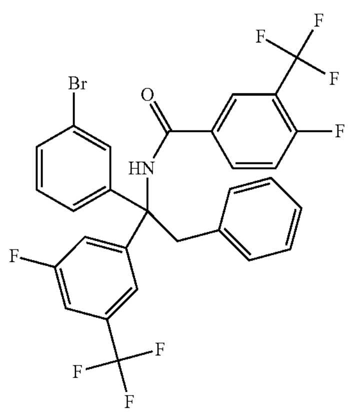 [SMILES: O=C(NC(Cc1ccccc1)(c1cccc(Br)c1)c1cc(F)cc(C(F)(F)F)c1)c1ccc(F)c(C(F)(F)F)c1] | N-(1-(3-bromophenyl)-1-(3-fluoro-5-(trifluoromethyl)phenyl)-2-phenylethyl)-4-fluoro-3-(trifluoromethyl)benzamide | 4.33 LC (4) 628.12 [M + H]$^+$ | Procedures 1 and 7 |
| 565 | 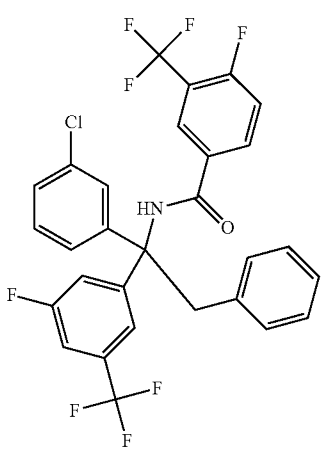 [SMILES: O=C(NC(Cc1ccccc1)(c1cccc(Cl)c1)c1cc(F)cc(C(F)(F)F)c1)c1ccc(F)c(C(F)(F)F)c1] | N-(1-(3-chlorophenyl)-1-(3-fluoro-5-(trifluoromethyl)phenyl)-2-phenylethyl)-4-fluoro-3-(trifluoromethyl)benzamide | 4.31 LC (4) 584.15 [M + H]$^+$ | Procedures 1 and 7 |

TABLE 10-continued

| Ex. No. | Structure | Name | Retention Time Min./ Molecular Mass | Prepared in the manner described in: |
|---|---|---|---|---|
| 566 | 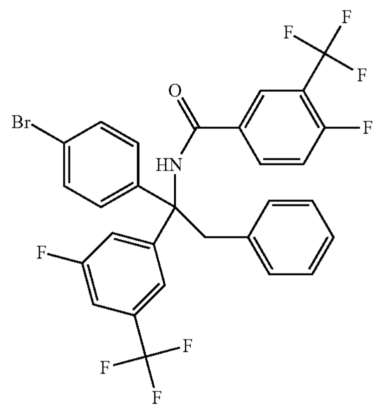 [SMILES: O=C(NC(Cc1ccccc1)(c1ccc(Br)cc1)c1cc(F)cc(C(F)(F)F)c1)c1ccc(F)c(C(F)(F)F)c1] | N-(1-(4-bromophenyl)-1-(3-fluoro-5-(trifluoromethyl)phenyl)-2-phenylethyl)-4-fluoro-3-(trifluoromethyl)benzamide | 4.37 LC (4) 628.10 [M + H]+ | Procedures 1 and 7 |
| 567 | 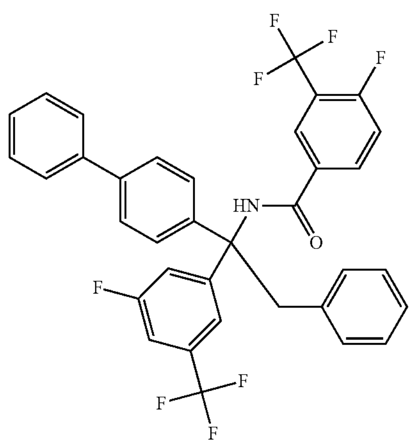 [SMILES: O=C(NC(Cc1ccccc1)(c1ccc(-c2ccccc2)cc1)c1cc(F)cc(C(F)(F)F)c1)c1ccc(F)c(C(F)(F)F)c1] | N-(1-(biphenyl-4-yl)-1-(3-fluoro-5-(trifluoromethyl)phenyl)-2-phenylethyl)-4-fluoro-3-(trifluoromethyl)benzamide | 4.50 LC (4) 626.26 [M + H]+ | Procedures 1 and 7 |
| 568 | 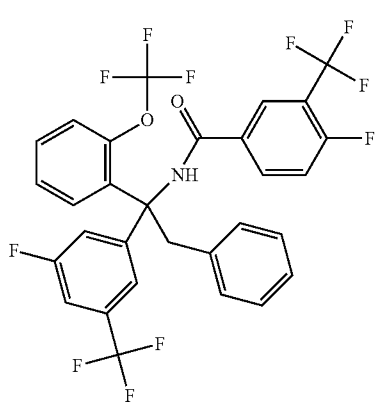 [SMILES: O=C(NC(Cc1ccccc1)(c1cc(F)cc(C(F)(F)F)c1)c1ccccc1OC(F)(F)F)c1ccc(F)c(C(F)(F)F)c1] | 4-fluoro-N-(1-(3-fluoro-5-(trifluoromethyl)phenyl)-2-phenyl-1-(2-(trifluoromethoxy)phenyl)ethyl)-3-(trifluoromethyl)benzamide | 4.32 LC (4) 634.18 [M + H]+ | Procedures 1 and 7 |

TABLE 10-continued

| Ex. No. | Structure | Name | Retention Time Min./ Molecular Mass | Prepared in the manner described in: |
|---|---|---|---|---|
| 569 | 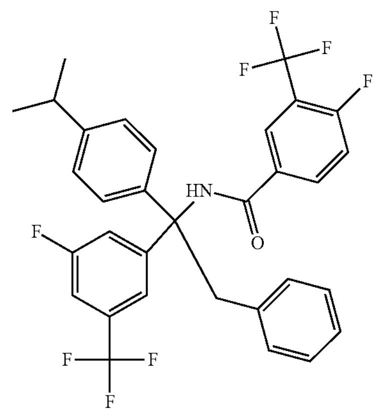 [SMILES: CC(C)c1ccc(C(Cc2ccccc2)(NC(=O)c2ccc(F)c(C(F)(F)F)c2)c2cc(F)cc(C(F)(F)F)c2)cc1] | 4-fluoro-N-(1-(3-fluoro-5-(trifluoromethyl) phenyl)-1-(4-isopropylphenyl)-2-phenylethyl)-3-(trifluoromethyl)benzamide | 4.50 LC (4) 592.23 [M + H]$^+$ | Procedures 1 and 7 |
| 570 | 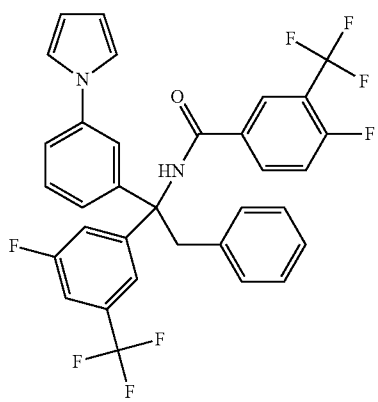 [SMILES: O=C(NC(Cc1ccccc1)(c1cccc(-n2cccc2)c1)c1cc(F)cc(C(F)(F)F)c1)c1ccc(F)c(C(F)(F)F)c1] | N-(1-(3-(1H-pyrrol-1-yl)phenyl)-1-(3-fluoro-5-(trifluoromethyl)phenyl)-2-phenylethyl)-4-fluoro-3-(trifluoromethyl)benzamide | 4.34 LC (4) 615.24 [M + H]$^+$ | Procedures 1 and 7 |
| 571 | 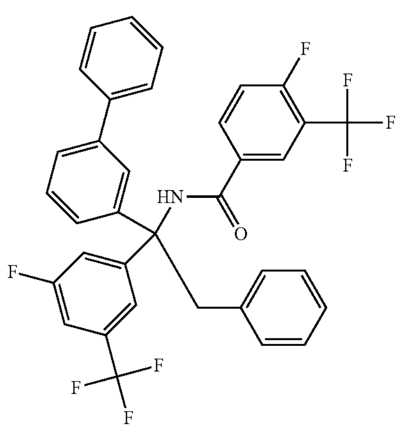 [SMILES: O=C(NC(CCc1ccccc1)(c1cccc(-c2ccccc2)c1)c1cc(F)cc(C(F)(F)F)c1)c1ccc(F)c(C(F)(F)F)c1] | N-(1-(biphenyl-3-yl)-1-(3-fluoro-5-(trifluoromethyl)phenyl)-2-phenylethyl)-4-fluoro-3-(trifluoromethyl)benzamide | 4.48 LC (4) 626.25 [M + H]$^+$ | Procedures 1 and 7 |

TABLE 10-continued

| Ex. No. | Structure | Name | Retention Time Min./ Molecular Mass | Prepared in the manner described in: |
|---|---|---|---|---|
| 572 | 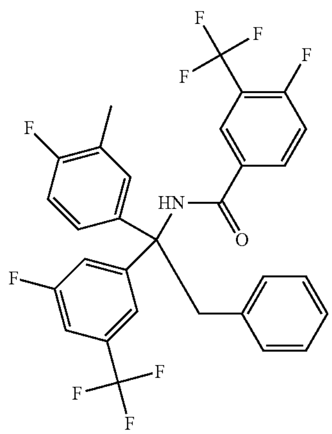 | 4-fluoro-N-(1-(4-fluoro-3-methylphenyl)-1-(3-fluoro-5-(trifluoromethyl)phenyl)-2-phenylethyl)-3-(trifluoromethyl)benzamide | 4.33 LC (4) 582.22 [M + H]$^+$ | Procedures 1 and 7 |
| 573 | 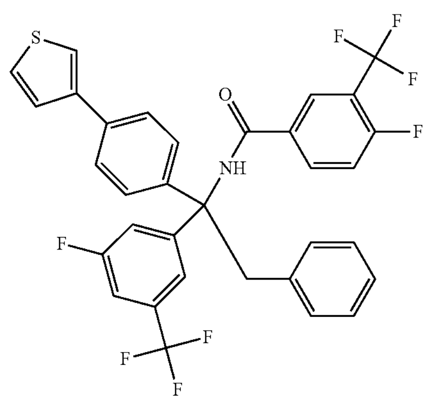 [SMILES: O=C(NC(CCc1ccccc1)(c1ccc(-c2ccsc2)cc1)c1cc(F)cc(C(F)(F)F)c1)c1ccc(F)c(C(F)(F)F)c1] | 4-fluoro-N-(1-(3-fluoro-5-(trifluoromethyl)phenyl)-2-phenyl-1-(4-(thiophen-3-yl)phenyl)ethyl)-3-(trifluoromethyl)benzamide | 4.41 LC (4) 632.16 [M + H]$^+$ | Procedures 1 and 7 |
| 574 | 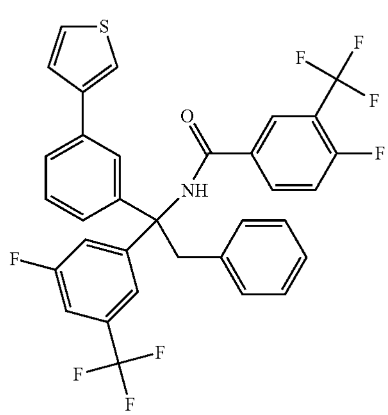 [SMILES: O=C(NC(Cc1ccccc1)(c1cccc(-c2ccsc2)c1)c1cc(F)cc(C(F)(F)F)c1)c1ccc(F)c(C(F)(F)F)c1] | 4-fluoro-N-(1-(3-fluoro-5-(trifluoromethyl)phenyl)-2-phenyl-1-(3-(thiophen-3-yl)phenyl)ethyl)-3-(trifluoromethyl)benzamide | 4.43 LC (4) 632.18 [M + H]$^+$ | Procedures 1 and 7 |

TABLE 10-continued

| Ex. No. | Structure | Name | Retention Time Min./ Molecular Mass | Prepared in the manner described in: |
|---|---|---|---|---|
| 575 | 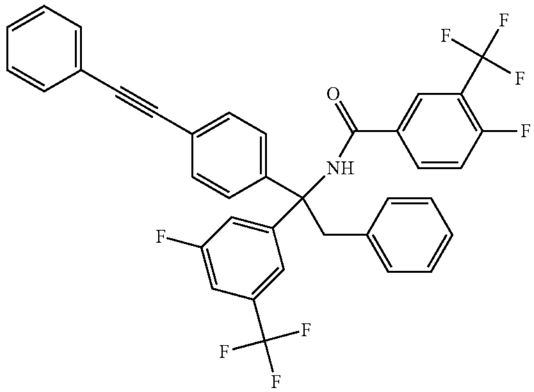 [SMILES: O=C(NC(Cc1ccccc1)(c1ccc(C#Cc2ccccc2)cc1)c1cc(F)cc(C(F)(F)F)c1)c1ccc(F)c(C(F)(F)F)c1] | 4-fluoro-N-(1-(3-fluoro-5-(trifluoromethyl)phenyl)-2-phenyl-1-(4-(2-phenylethynyl)phenyl)ethyl)-3-(trifluoromethyl)benzamide | 4.59 LC (4) 650.20 [M + H]+ | Procedures 1 and 7 |
| 576 | 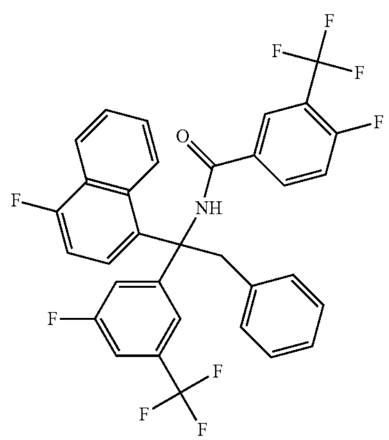 [SMILES: O=C(NC(Cc1ccccc1)(c1cc(F)cc(C(F)(F)F)c1)c1ccc(F)c2ccccc12)c1ccc(F)c(C(F)(F)F)c1] | 4-fluoro-N-(1-(3-fluoro-5-(trifluoromethyl)phenyl)-1-(4-fluoronaphthalen-1-yl)-2-phenylethyl)-3-(trifluoromethyl)benzamide | 4.40 LC (4) 618.20 [M + H]+ | Procedures 1 and 7 |
| 577 | 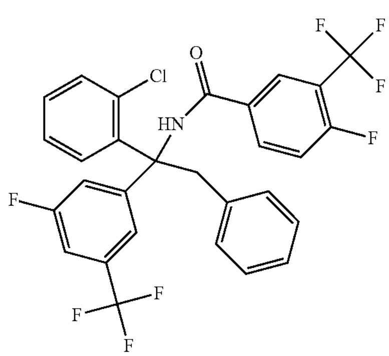 [SMILES: O=C(NC(Cc1ccccc1)(c1cc(F)cc(C(F)(F)F)c1)c1ccccc1Cl)c1ccc(F)c(C(F)(F)F)c1] | N-(1-(2-chlorophenyl)-1-(3-fluoro-5-(trifluoromethyl)phenyl)-2-phenylethyl)-4-fluoro-3-(trifluoromethyl)benzamide | 4.33 LC (4) 584.19 [M + H]+ | Procedures 1 and 7 |

TABLE 10-continued

| Ex. No. | Structure | Name | Retention Time Min./ Molecular Mass | Prepared in the manner described in: |
|---|---|---|---|---|
| 578 | 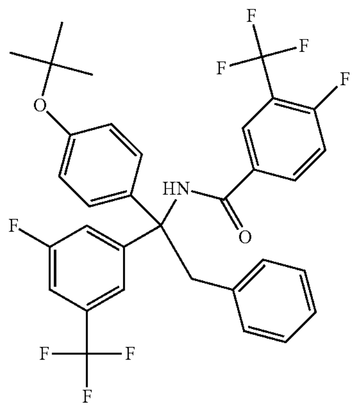 [SMILES: CC(C)(C)Oc1ccc(C(Cc2ccccc2)(NC(=O)c2ccc(F)c(C(F)(F)F)c2)c2cc(F)cc(C(F)(F)F)c2)cc1] | N-(1-(4-tert-butoxyphenyl)-1-(3-fluoro-5-(trifluoromethyl)phenyl)-2-phenylethyl)-4-fluoro-3-(trifluoromethyl)benzamide | 4.40 LC (4) 622.28 [M + H]$^+$ | Procedures 1 and 7 |
| 579 | 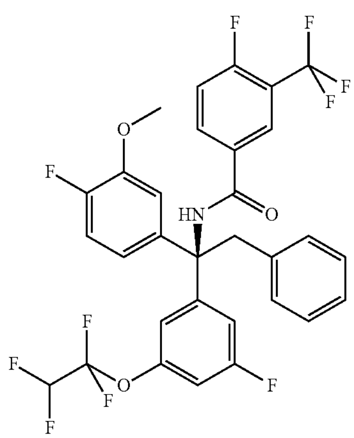 [SMILES: COc1cc([C@@](Cc2ccccc2)(NC(=O)c2ccc(F)c(C(F)(F)F)c2)c2cc(F)cc(OC(F)(F)C(F)F)c2)ccc1F] | (R)-4-fluoro-N-(1-(4-fluoro-3-methoxyphenyl)-1-(3-fluoro-5-(1,1,2,2-tetrafluoroethoxy)phenyl)-2-phenylethyl)-3-(trifluoromethyl)benzamide | 3.833 LC (1) 646.14 [M + H]$^+$ | Procedures 3, 4, 5, 6 and 7 |
| 580 | 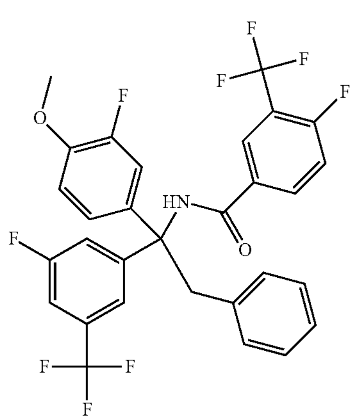 [SMILES: COc1ccc(C(Cc2ccccc2)(NC(=O)c2ccc(F)c(C(F)(F)F)c2)c2cc(F)cc(C(F)(F)F)c2)cc1F] | 4-fluoro-N-(1-(3-fluoro-4-methoxyphenyl)-1-(3-fluoro-5-(trifluoromethyl)phenyl)-2-phenylethyl)-3-(trifluoromethyl)benzamide | 4.20 LC (4) 598.10 [M + H]$^+$ | Procedures 1 and 7 |

TABLE 10-continued

| Ex. No. | Structure | Name | Retention Time Min./ Molecular Mass | Prepared in the manner described in: |
|---|---|---|---|---|
| 581 | 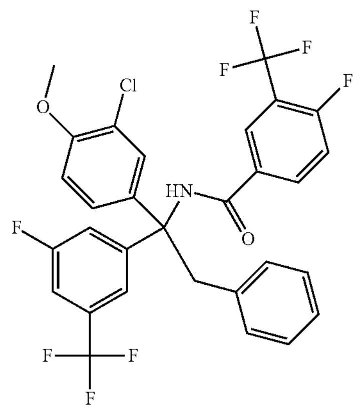 [SMILES: COc1ccc(C(Cc2ccccc2)(NC(=O)c2ccc(F)c(C(F)(F)F)c2)c2cc(F)cc(C(F)(F)F)c2)cc1Cl] | N-(1-(3-chloro-4-methoxyphenyl)-1-(3-fluoro-5-(trifluoromethyl)phenyl)-2-phenylethyl)-4-fluoro-3-(trifluoromethyl)benzamide | 4.26 LC (4) 614.07 [M + H]$^+$ | Procedures 1 and 7 |
| 582 | 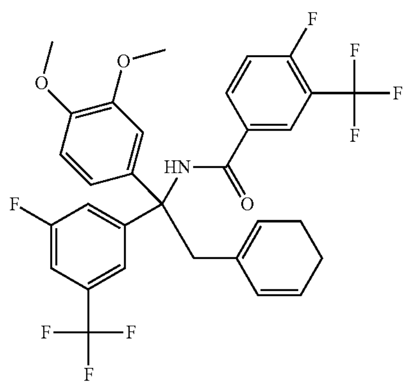 [SMILES: COc1ccc(C(CC2=CCCC=C2)(NC(=O)c2ccc(F)c(C(F)(F)F)c2)c2cc(F)cc(C(F)(F)F)c2)cc1OC] | N-(1-(3,4-dimethoxyphenyl)-1-(3-fluoro-5-(trifluoromethyl)phenyl)-2-phenylethyl)-4-fluoro-3-(trifluoromethyl)benzamide | 4.15 LC (4) 610.13 [M + H]$^+$ | Procedures 1 and 7 |
| 583 | 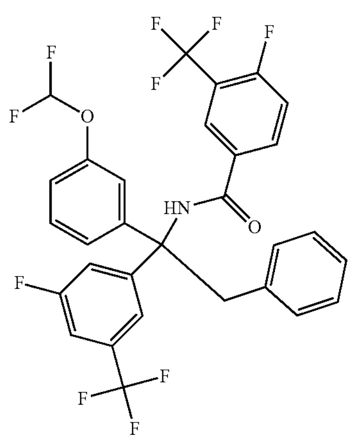 [SMILES: O=C(NC(Cc1ccccc1)(c1cccc(OC(F)F)c1)c1cc(F)cc(C(F)(F)F)c1)c1ccc(F)c(C(F)(F)F)c1] | N-(1-(3-(difluoromethoxy)phenyl)-1-(3-fluoro-5-(trifluoromethyl)phenyl)-2-phenylethyl)-4-fluoro-3-(trifluoromethyl)benzamide | 4.21 LC (4) 616.10 [M + H]$^+$ | Procedures 1 and 7 |

TABLE 10-continued

| Ex. No. | Structure | Name | Retention Time Min./ Molecular Mass | Prepared in the manner described in: |
|---|---|---|---|---|
| 584 | 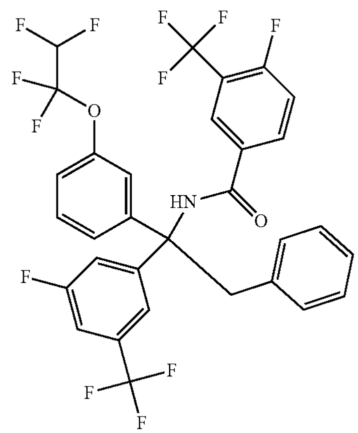 [SMILES: O=C(NC(Cc1ccccc1)(c1cccc(OC(F)(F)C(F)F)c1)c1cc(F)cc(C(F)(F)F)c1)c1ccc(F)c(C(F)(F)F)c1] | 4-fluoro-N-(1-(3-fluoro-5-(trifluoromethyl)phenyl)-2-phenyl-1-(3-(1,1,2,2-tetrafluoroethoxy)phenyl)ethyl)-3-(trifluoromethyl)benzamide | 4.24 LC (4) 666.13 [M + H]$^+$ | Procedures 1 and 7 |
| 585 | 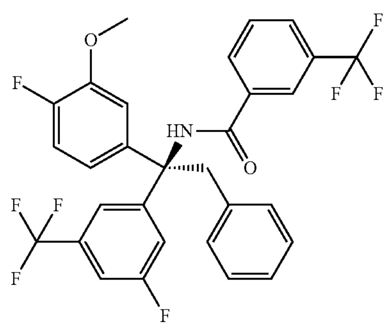 [SMILES: COc1cc([C@@](Cc2ccccc2)(NC(=O)c2cccc(C(F)(F)F)c2)c2cc(F)cc(C(F)(F)F)c2)ccc1F] | (R)-N-(1-(4-fluoro-3-methoxyphenyl)-1-(3-fluoro-5-(trifluoromethyl)phenyl)-2-phenylethyl)-3-(trifluoromethyl)benzamide | 3.92 LC (1) 580.1 [M + H]$^+$ | Procedures 4, 5, 6 and 7 |
| 586 | 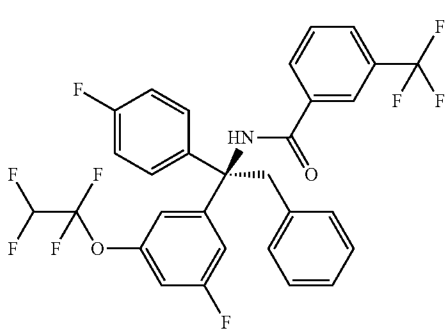 [SMILES: O=C(N[C@](Cc1ccccc1)(c1ccc(F)cc1)c1cc(F)cc(OC(F)(F)C(F)F)c1)c1cccc(C(F)(F)F)c1] | (R)-N-(1-(3-fluoro-5-(1,1,2,2-tetrafluoroethoxy)phenyl)-1-(4-fluorophenyl)-2-phenylethyl)-3-(trifluoromethyl)benzamide | 3.84 LC (1) 598.15 [M + H]$^+$ | Procedures 3, 4, 5, 6 and 7 |

TABLE 10-continued

| Ex. No. | Structure | Name | Retention Time Min./ Molecular Mass | Prepared in the manner described in: |
| --- | --- | --- | --- | --- |
| 587 | 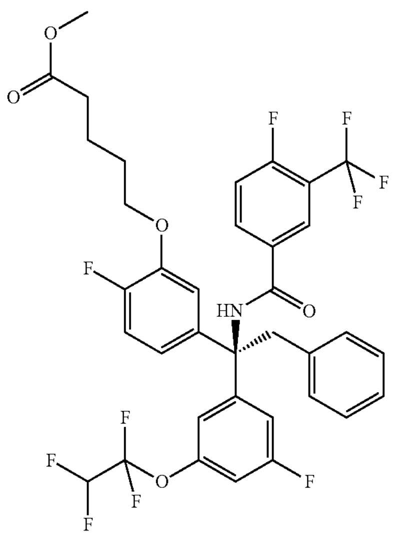 [SMILES: COC(=O)CCCCOc1cc([C@@](Cc2ccccc2)(NC(=O)c2ccc(F)c(C(F)(F)F)c2)c2cc(F)cc(OC(F)(F)C(F)F)c2)ccc1F] | (R)-methyl 5-(2-fluoro-5-(1-(4-fluoro-3-(trifluoromethyl)benzamido)-1-(3-fluoro-5-(1,1,2,2-tetrafluoroethoxy)phenyl)-2-phenylethyl)phenoxy)pentanoate | 3.95 LC (1) 746.12 [M + H]+ | Procedures 3, 4, 5, 6, 7, 59 and 68 |
| 588 | 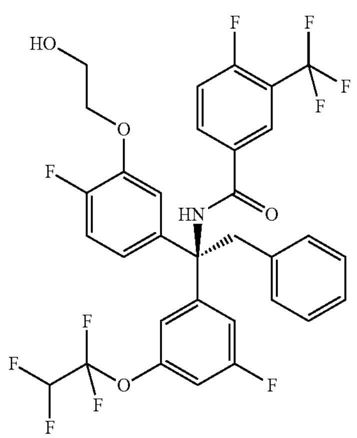 [SMILES: O=C(N[C@@](Cc1ccccc1)(c1cc(F)cc(OC(F)(F)C(F)F)c1)c1ccc(F)c(OCCO)c1)c1ccc(F)c(C(F)(F)F)c1] | (R)-4-fluoro-N-(1-(4-fluoro-3-(2-hydroxyethoxy)phenyl)-1-(3-fluoro-5-(1,1,2,2-tetrafluoroethoxy)phenyl)-2-phenylethyl)-3-(trifluoromethyl)benzamide | 3.48 LC (1) 676.10 [M + H]+ | Procedures 3, 4, 5, 6, 7, 59 and 68 |
| 589 | 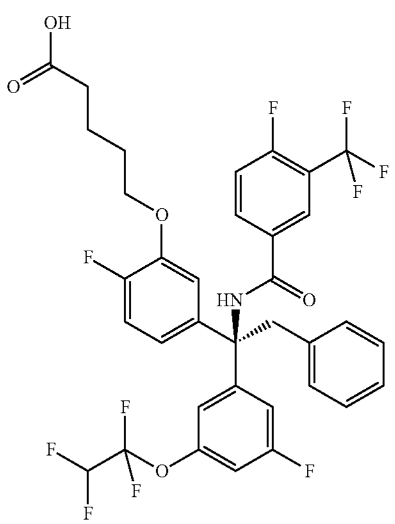 [SMILES: O=C(O)CCCCOc1cc([C@@](Cc2ccccc2)(NC(=O)c2ccc(F)c(C(F)(F)F)c2)c2cc(F)cc(OC(F)(F)C(F)F)c2)ccc1F] | (R)-5-(2-fluoro-5-(1-(4-fluoro-3-(trifluoromethyl)benzamido)-1-(3-fluoro-5-(1,1,2,2-tetrafluoroethoxy)phenyl)-2-phenylethyl)phenoxy)pentanoic acid | 3.59 LC (1) 732.08 [M + H]+ | Procedures 3, 4, 5, 6, 7, 59, 68 and 23 |

TABLE 10-continued

| Ex. No. | Structure | Name | Retention Time Min./ Molecular Mass | Prepared in the manner described in: |
|---|---|---|---|---|
| 590 | 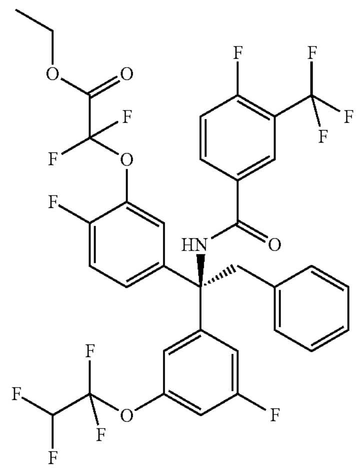 [SMILES: CCOC(=O)C(F)(F)Oc1cc([C@@](Cc2ccccc2)(NC(=O)c2ccc(F)c(C(F)(F)F)c2)c2cc(F)cc(OC(F)(F)C(F)F)c2)ccc1F] | (R)-ethyl 2,2-difluoro-2-(2-fluoro-5-(1-(4-fluoro-3-(trifluoromethyl)benzamido)-1-(3-fluoro-5-(1,1,2,2-tetrafluoroethoxy)phenyl)-2-phenylethyl)phenoxy)acetate | 3.92 LC (1) 754.30 $[M + H]^+$ | Procedures 3, 4, 5, 6, 7, 59 and 68 |
| 591 | 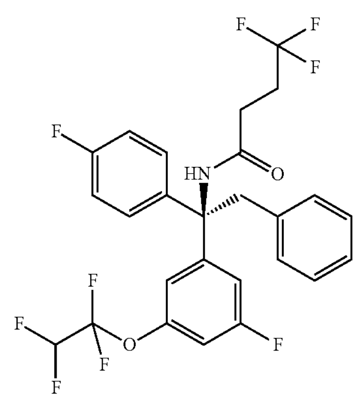 [SMILES: O=C(CCC(F)(F)F)N[C@](Cc1ccccc1)(c1ccc(F)cc1)c1cc(F)cc(OC(F)(F)C(F)F)c1] | (R)-4,4,4-trifluoro-N-(1-(3-fluoro-5-(1,1,2,2-tetrafluoroethoxy)phenyl)-1-(4-fluorophenyl)-2-phenylethyl)butanamide | 3.60 LC (1) 550.2 $[M + H]^+$ | Procedures 3, 4, 5, 6 and 128 |
| 592 | 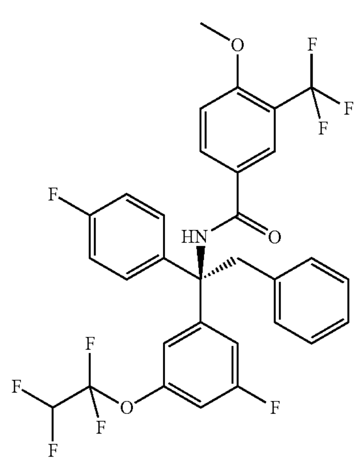 [SMILES: COc1ccc(C(=O)N[C@](Cc2ccccc2)(c2ccc(F)cc2)c2cc(F)cc(OC(F)(F)C(F)F)c2)cc1C(F)(F)F] | (R)-N-(1-(3-fluoro-5-(1,1,2,2-tetrafluoroethoxy)phenyl)-1-(4-fluorophenyl)-2-phenylethyl)-4-methoxy-3-(trifluoromethyl)benzamide | 3.81 LC (1) 628.21 $[M + H]^+$ | Procedures 3, 4, 5, 6 and 7 |

TABLE 10-continued

| Ex. No. | Structure | Name | Retention Time Min./ Molecular Mass | Prepared in the manner described in: |
|---|---|---|---|---|
| 593 | 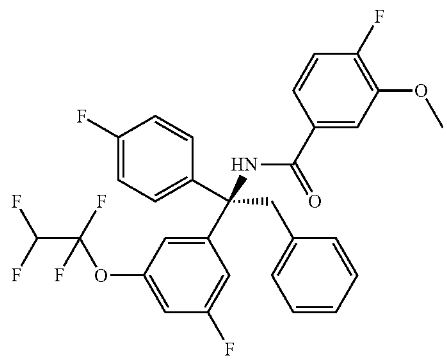 [SMILES: COc1cc(C(=O)N[C@](Cc2ccccc2)(c2ccc(F)cc2)c2cc(F)cc(OC(F)(F)C(F)F)c2)ccc1F] | (R)-4-fluoro-N-(1-(3-fluoro-5-(1,1,2,2-tetrafluoroethoxy)phenyl)-1-(4-fluorophenyl)-2-phenylethyl)-3-methoxybenzamide | 3.68 LC (1) 578.12 [M + H]+ | Procedures 3, 4, 5, 6 and 7 |
| 594 | 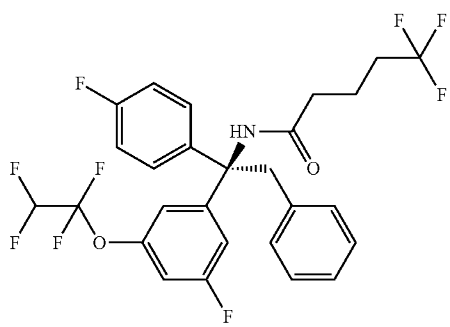 [SMILES: O=C(CCCC(F)(F)F)N[C@](Cc1ccccc1)(c1ccc(F)cc1)c1cc(F)cc(OC(F)(F)C(F)F)c1] | (R)-5,5,5-trifluoro-N-(1-(3-fluoro-5-(1,1,2,2-tetrafluoroethoxy)phenyl)-1-(4-fluorophenyl)-2-phenylethyl)pentanamide | 3.65 LC (1) 564.09 [M + H]+ | Procedures 3, 4, 5, 6 and 128 |
| 595 | 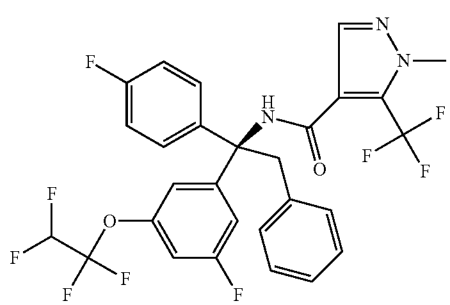 [SMILES: Cn1ncc(C(=O)N[C@](Cc2ccccc2)(c2ccc(F)cc2)c2cc(F)cc(OC(F)(F)C(F)F)c2)c1C(F)(F)F] | (R)-N-(1-(3-fluoro-5-(1,1,2,2-tetrafluoroethoxy)phenyl)-1-(4-fluorophenyl)-2-phenylethyl)-1-methyl-5-(trifluoromethyl)-1H-pyrazole-4-carboxamide | 4.01 LC (4) 602.17 [M + H]+ | Procedures 3, 4, 5, 6 and 127 |
| 596 | 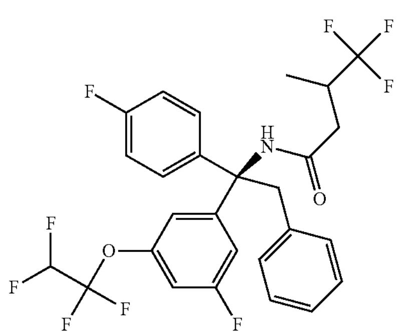 [SMILES: CC(CC(=O)N[C@](Cc1ccccc1)(c1ccc(F)cc1)c1cc(F)cc(OC(F)(F)C(F)F)c1)C(F)(F)F] | 4,4,4-trifluoro-N-((R)-1-(3-fluoro-5-(1,1,2,2-tetrafluoroethoxy)phenyl)-1-(4-fluorophenyl)-2-phenylethyl)-3-methylbutanamide | 4.14 LC (4) 564.21 [M + H]+ | Procedures 3, 4, 5, 6 and 127 |

TABLE 10-continued

| Ex. No. | Structure | Name | Retention Time Min./ Molecular Mass | Prepared in the manner described in: |
|---|---|---|---|---|
| 597 | 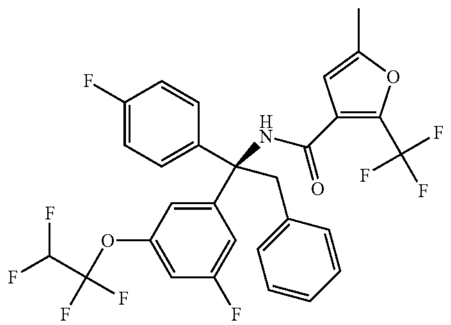 [SMILES: Cc1cc(C(=O)N[C@](Cc2ccccc2)(c2ccc(F)cc2)c2cc(F)cc(OC(F)(F)C(F)F)c2)c(C(F)(F)F)o1] | (R)-N-(1-(3-fluoro-5-(1,1,2,2-tetrafluoroethoxy)phenyl)-1-(4-fluorophenyl)-2-phenylethyl)-5-methyl-2-(trifluoromethyl)furan-3-carboxamide | 4.12 LC (4) 602.17 [M + H]$^+$ | Procedures 3, 4, 5, 6 and 127 |
| 598 | 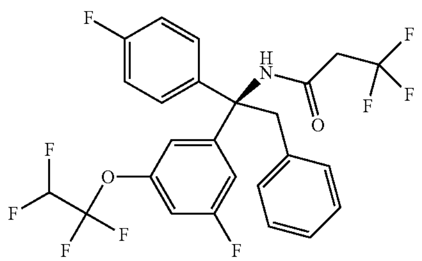 [SMILES: O=C(CC(F)(F)F)N[C@](Cc1ccccc1)(c1ccc(F)cc1)c1cc(F)cc(OC(F)(F)C(F)F)c1] | (R)-3,3,3-trifluoro-N-(1-(3-fluoro-5-(1,1,2,2-tetrafluoroethoxy)phenyl)-1-(4-fluorophenyl)-2-phenylethyl)propanamide | 3.99 LC (4) 535.21 [M + H]$^+$ | Procedures 3, 4, 5, 6 and 127 |
| 599 | 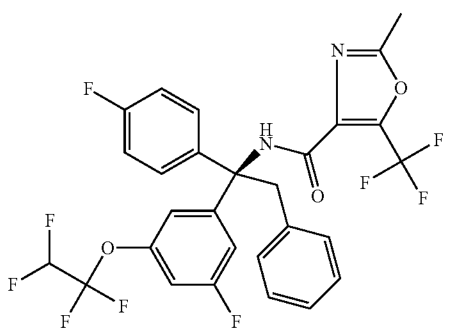 [SMILES: Cc1nc(C(=O)N[C@](Cc2ccccc2)(c2ccc(F)cc2)c2cc(F)cc(OC(F)(F)C(F)F)c2)c(C(F)(F)F)o1] | (R)-N-(1-(3-fluoro-5-(1,1,2,2-tetrafluoroethoxy)phenyl)-1-(4-fluorophenyl)-2-phenylethyl)-2-methyl-5-(trifluoromethyl)oxazole-4-carboxamide | 4.15 LC (4) 603.14 [M + H]$^+$ | Procedures 3, 4, 5, 6 and 127 |
| 600 | 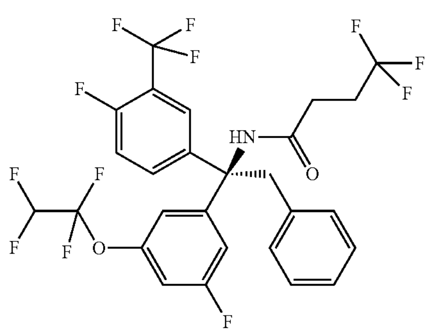 [SMILES: O=C(CCC(F)(F)F)N[C@@](Cc1ccccc1)(c1cc(F)cc(OC(F)(F)C(F)F)c1)c1ccc(F)c(C(F)(F)F)c1] | (R)-4,4,4-trifluoro-N-(1-(4-fluoro-3-(trifluoromethyl)phenyl)-1-(3-fluoro-5-(1,1,2,2-tetrafluoroethoxy)phenyl)-2-phenylethyl)butanamide | 3.751 LC (1) 617.96 [M + H]$^+$ | Procedures 3, 4, 5, 6 and 128 |

TABLE 10-continued

| Ex. No. | Structure | Name | Retention Time Min./ Molecular Mass | Prepared in the manner described in: |
|---|---|---|---|---|
| 601 | 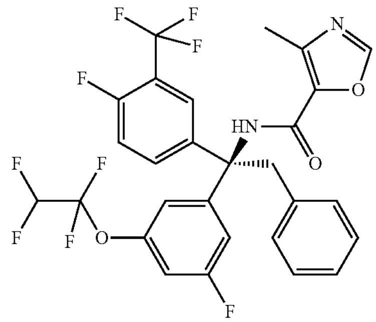 [SMILES: Cc1ncoc1C(=O)N[C@@](Cc1ccccc1)(c1cc(F)cc(OC(F)(F)C(F)F)c1)c1ccc(F)c(C(F)(F)F)c1] | (R)-N-(1-(4-fluoro-3-(trifluoromethyl)phenyl)-1-(3-fluoro-5-(1,1,2,2-tetrafluoroethoxy)phenyl)-2-phenylethyl)-4-methyloxazole-5-carboxamide | 3.513 LC (1) 603.69 [M + H]$^+$ | Procedures 3, 4, 5, 6 and 128 |
| 602 | 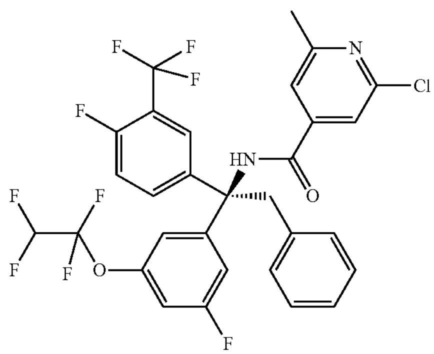 [SMILES: Cc1cc(C(=O)N[C@@](Cc2ccccc2)(c2cc(F)cc(OC(F)(F)C(F)F)c2)c2ccc(F)c(C(F)(F)F)c2)cc(Cl)n1] | (R)-2-chloro-N-(1-(4-fluoro-3-(trifluoromethyl)phenyl)-1-(3-fluoro-5-(1,1,2,2-tetrafluoroethoxy)phenyl)-2-phenylethyl)-6-methylisonicotinamide | 3.836 LC (1) 647.69 [M + H]$^+$ | Procedures 3, 4, 5, 6 and 128 |
| 603 | 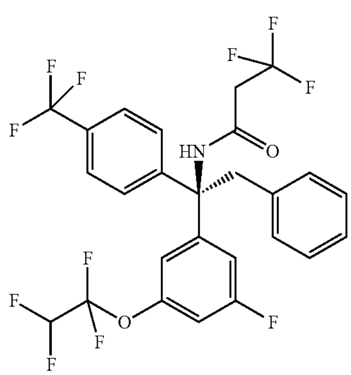 [SMILES: O=C(CC(F)(F)F)N[C@](Cc1ccccc1)(c1ccc(C(F)(F)F)cc1)c1cc(F)cc(OC(F)(F)C(F)F)c1] | (R)-3,3,3-trifluoro-N-(1-(3-fluoro-5-(1,1,2,2-tetrafluoroethoxy)phenyl)-2-phenyl-1-(4-(trifluoromethyl)phenyl)ethyl)propanamide | 3.61 LC (1) 586.67 [M + H]$^+$ | Procedures 3, 4, 5, 6 and 128 |
| 604 | 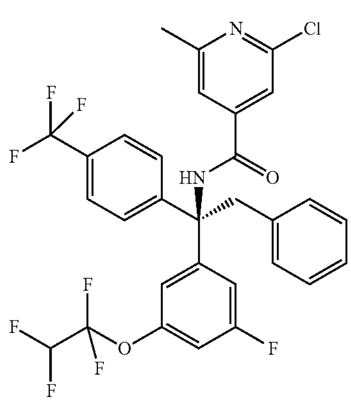 [SMILES: Cc1cc(C(=O)N[C@](Cc2ccccc2)(c2ccc(C(F)(F)F)cc2)c2cc(F)cc(OC(F)(F)C(F)F)c2)cc(Cl)n1] | (R)-2-chloro-N-(1-(3-fluoro-5-(1,1,2,2-tetrafluoroethoxy)phenyl)-2-phenyl-1-(4-(trifluoromethyl)phenyl)ethyl)-6-methylisonicotinamide | 3.72 LC (1) 629.70 [M + H]$^+$ | Procedures 3, 4, 5, 6 and 128 |

TABLE 10-continued

| Ex. No. | Structure | Name | Retention Time Min./ Molecular Mass | Prepared in the manner described in: |
|---|---|---|---|---|
| 605 | 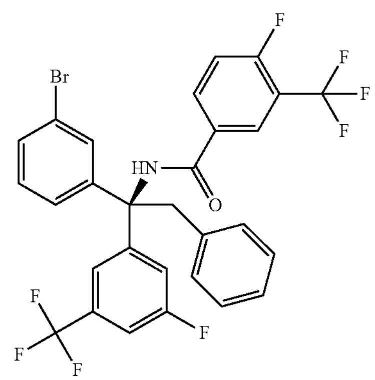 [SMILES: O=C(N[C@](Cc1ccccc1)(c1cccc(Br)c1)c1cc(F)cc(C(F)(F)F)c1)c1ccc(F)c(C(F)(F)F)c1] | (S)-N-(1-(3-bromophenyl)-1-(3-fluoro-5-(trifluoromethyl)phenyl)-2-phenylethyl)-4-fluoro-3-(trifluoromethyl)benzamide | 4.41 LC (4) 628.08 [M + H]+ | Procedures 4, 5, 6 and 7 |
| 606 | 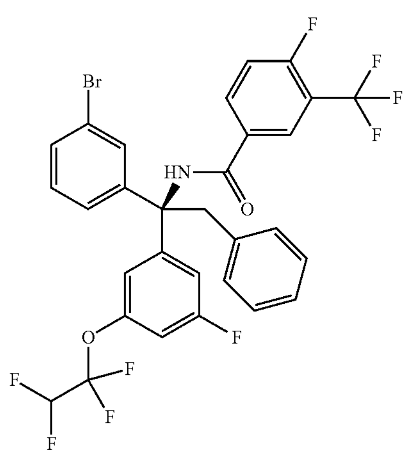 [SMILES: O=C(N[C@](Cc1ccccc1)(c1cccc(Br)c1)c1cc(F)cc(OC(F)(F)C(F)F)c1)c1ccc(F)c(C(F)(F)F)c1] | (S)-N-(1-(3-bromophenyl)-1-(3-fluoro-5-(1,1,2,2-tetrafluoroethoxy)phenyl)-2-phenylethyl)-4-fluoro-3-(trifluoromethyl)benzamide | 4.32 LC (4) 676.06 [M + H]+ | Procedures 3, 4, 5, 6 and 7 |
| 607 | 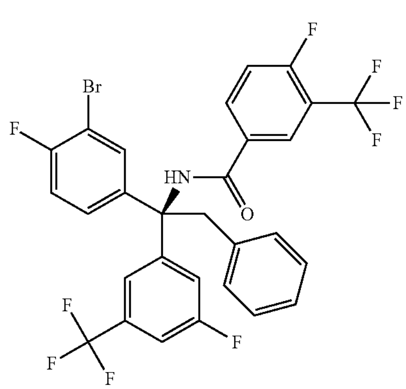 [SMILES: O=C(N[C@@](Cc1ccccc1)(c1cc(F)cc(C(F)(F)F)c1)c1ccc(F)c(Br)c1)c1ccc(F)c(C(F)(F)F)c1] | (S)-N-(1-(3-bromo-4-fluorophenyl)-1-(3-fluoro-5-(trifluoromethyl)phenyl)-2-phenylethyl)-4-fluoro-3-(trifluoromethyl)benzamide | 4.43 LC (4) 646.05 [M + H]+ | Procedures 62, 5, 6 and 7 |

TABLE 10-continued

| Ex. No. | Structure | Name | Retention Time Min./ Molecular Mass | Prepared in the manner described in: |
|---|---|---|---|---|
| 608 | 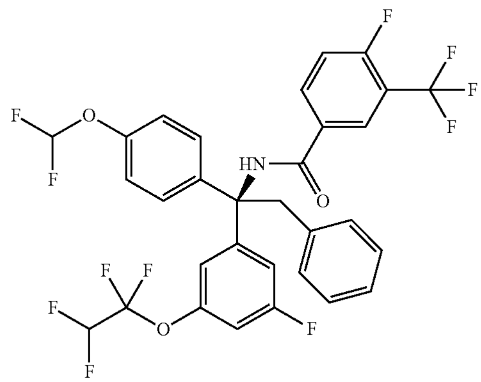 [SMILES: O=C(N[C@](Cc1ccccc1)(c1ccc(OC(F)F)cc1)c1cc(F)cc(OC(F)(F)C(F)F)c1)c1ccc(F)c(C(F)(F)F)c1] | (R)-N-(1-(4-(difluoromethoxy)phenyl)-1-(3-fluoro-5-(1,1,2,2-tetrafluoroethoxy)phenyl)-2-phenylethyl)-4-fluoro-3-(trifluoromethyl)benzamide | 4.22 LC (4) 664.14 [M + H]$^+$ | Procedures 3, 4, 5, 6 and 7 |
| 609 | 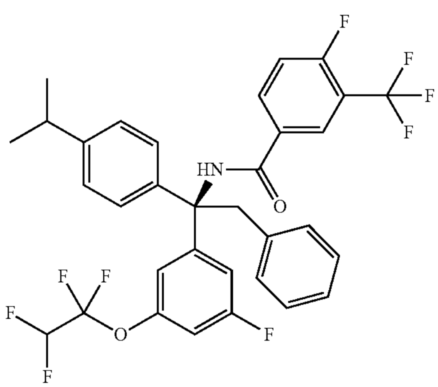 [SMILES: CC(C)c1ccc([C@@](Cc2ccccc2)(NC(=O)c2ccc(F)c(C(F)(F)F)c2)c2cc(F)cc(OC(F)(F)C(F)F)c2)cc1] | (R)-4-fluoro-N-(1-(3-fluoro-5-(1,1,2,2-tetrafluoroethoxy)phenyl)-1-(4-isopropylphenyl)-2-phenylethyl)-3-(trifluoromethyl)benzamide | 4.47 LC (4) 640.20 [M + H]$^+$ | Procedures 3, 4, 5, 6 and 7 |
| 610 | 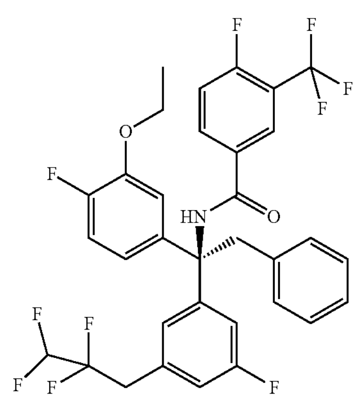 [SMILES: CCOc1cc([C@@](Cc2ccccc2)(NC(=O)c2ccc(F)c(C(F)(F)F)c2)c2cc(F)cc(CC(F)(F)C(F)F)c2)ccc1F] | (R)-N-(1-(3-ethoxy-4-fluorophenyl)-1-(3-fluoro-5-(1,1,2,2-tetrafluoroethoxy)phenyl)-2-phenylethyl)-4-fluoro-3-(trifluoromethyl)benzamide | 3.606 LC (1) 660.3 [M + H]$^+$ | Procedures 3, 4, 5, 6, 7, 59 and 68 |

TABLE 10-continued

| Ex. No. | Structure | Name | Retention Time Min./ Molecular Mass | Prepared in the manner described in: |
|---|---|---|---|---|
| 611 | 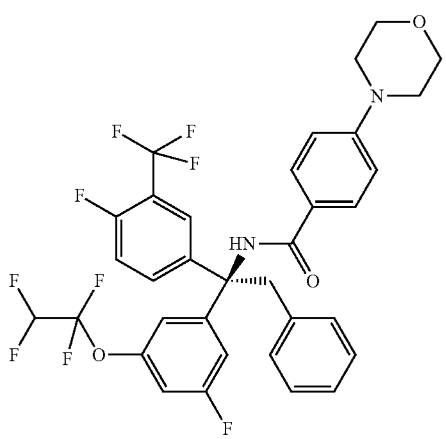 [SMILES: O=C(N[C@@](Cc1ccccc1)(c1cc(F)cc(OC(F)(F)C(F)F)c1)c1ccc(F)c(C(F)(F)F)c1)c1ccc(N2CCOCC2)cc1] | (R)-N-(1-(4-fluoro-3-(trifluoromethyl)phenyl)-1-(3-fluoro-5-(1,1,2,2-tetrafluoroethoxy)phenyl)-2-phenylethyl)-4-morpholinobenzamide | 3.66 LC (1) 683.3 [M + H]+ | Procedures 3, 4, 5, 6 and 128 |
| 612 | 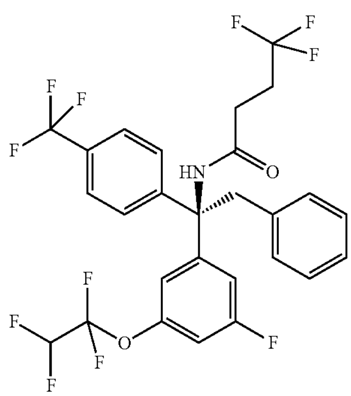 [SMILES: O=C(CCC(F)(F)F)N[C@](Cc1ccccc1)(c1ccc(C(F)(F)F)cc1)c1cc(F)cc(OC(F)(F)C(F)F)c1] | (R)-4,4,4-trifluoro-N-(1-(3-fluoro-5-(1,1,2,2-tetrafluoroethoxy)phenyl)-2-phenyl-1-(4-(trifluoromethyl)phenyl)ethyl)butanamide | 3.455 LC (1) 600.2 [M + H]+ | Procedures 3, 4, 5, 6 and 128 |
| 613 | 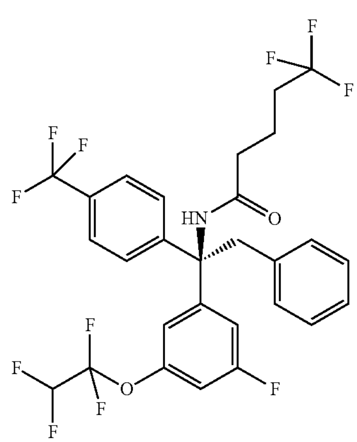 [SMILES: O=C(CCCC(F)(F)F)N[C@](Cc1ccccc1)(c1ccc(C(F)(F)F)cc1)c1cc(F)cc(OC(F)(F)C(F)F)c1] | (R)-5,5,5-trifluoro-N-(1-(3-fluoro-5-(1,1,2,2-tetrafluoroethoxy)phenyl)-2-phenyl-1-(4-(trifluoromethyl)phenyl)ethyl)pentanamide | 3.773 LC (1) 614.66 [M + H]+ | Procedures 3, 4, 5, 6 and 128 |

TABLE 10-continued

| Ex. No. | Structure | Name | Retention Time Min./ Molecular Mass | Prepared in the manner described in: |
|---|---|---|---|---|
| 614 | 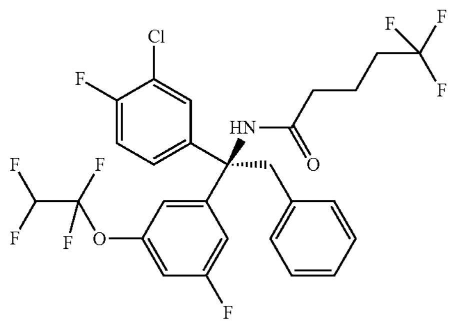 [SMILES: O=C(CCCC(F)(F)F)N[C@@](Cc1ccccc1)(c1cc(F)cc(OC(F)(F)C(F)F)c1)c1ccc(F)c(Cl)c1] | (S)-N-(1-(3-chloro-4-fluorophenyl)-1-(3-fluoro-5-(1,1,2,2-tetrafluoroethoxy)phenyl)-2-phenylethyl)-5,5,5-trifluoropentanamide | 3.76 LC (1) 598.05 [M + H]+ | Procedures 3, 4, 5, 6 and 128 |
| 615 | 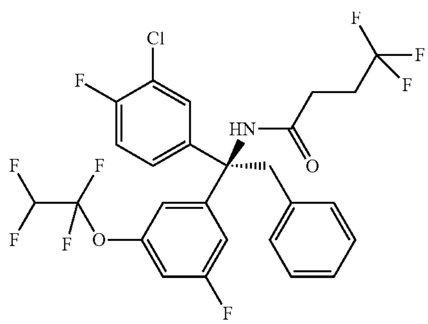 [SMILES: O=C(CCC(F)(F)F)N[C@@](Cc1ccccc1)(c1cc(F)cc(OC(F)(F)C(F)F)c1)c1ccc(F)c(Cl)c1] | (S)-N-(1-(3-chloro-4-fluorophenyl)-1-(3-fluoro-5-(1,1,2,2-tetrafluoroethoxy)phenyl)-2-phenylethyl)-4,4,4-trifluorobutanamide | 3.73 LC (1) 587.04 [M + H]+ | Procedures 3, 4, 5, 6 and 128 |
| 616 | 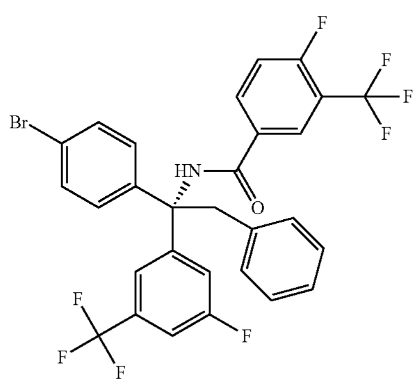 [SMILES: O=C(N[C@@](Cc1ccccc1)(c1ccc(Br)cc1)c1cc(F)cc(C(F)(F)F)c1)c1ccc(F)c(C(F)(F)F)c1] | (S)-N-(1-(4-bromophenyl)-1-(3-fluoro-5-(trifluoromethyl)phenyl)-2-phenylethyl)-4-fluoro-3-(trifluoromethyl)benzamide | 4.44 LC (4) 628.19 [M + H]+ | Procedures 4, 5, 6 and 7 |
| 617 | 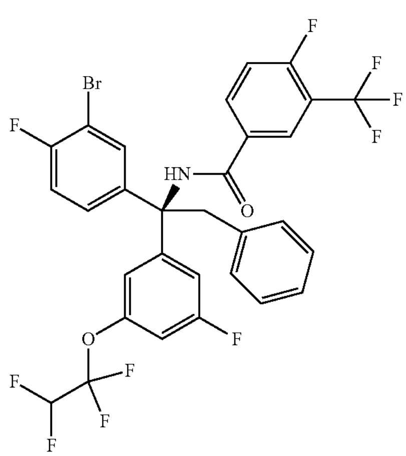 [SMILES: O=C(N[C@@](Cc1ccccc1)(c1cc(F)cc(OC(F)(F)C(F)F)c1)c1ccc(F)c(Br)c1)c1ccc(F)c(C(F)(F)F)c1] | (S)-N-(1-(3-bromo-4-fluorophenyl)-1-(3-fluoro-5-(1,1,2,2-tetrafluoroethoxy)phenyl)-2-phenylethyl)-4-fluoro-3-(trifluoromethyl)benzamide | 4.33 LC (4) 694.21 [M + H]+ | Procedures 62, 3, 5, 6 and 7 |

TABLE 10-continued

| Ex. No. | Structure | Name | Retention Time Min./ Molecular Mass | Prepared in the manner described in: |
|---|---|---|---|---|
| 618 | 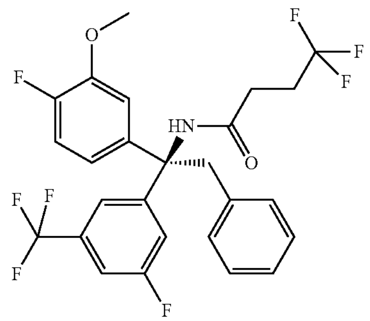 [SMILES: COc1cc([C@@](Cc2ccccc2)(NC(=O)CCC(F)(F)F)c2cc(F)cc(C(F)(F)F)c2)ccc1F] | (R)-4,4,4-trifluoro-N-(1-(4-fluoro-3-methoxyphenyl)-1-(3-fluoro-5-(trifluoromethyl)phenyl)-2-phenylethyl)butanamide | 3.628 LC (1) 532.15 [M + H]$^+$ | Procedures 4, 5, 6 and 128 |
| 619 | 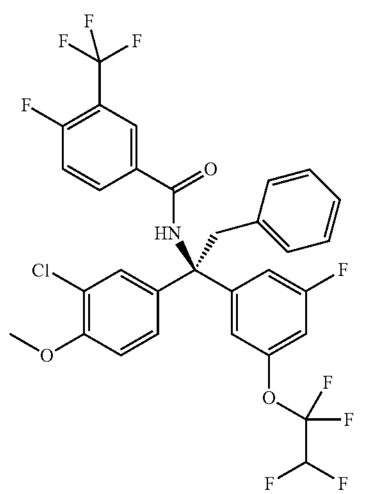 [SMILES: COc1ccc([C@@](Cc2ccccc2)(NC(=O)c2ccc(F)c(C(F)(F)F)c2)c2cc(F)cc(OC(F)(F)C(F)F)c2)cc1Cl] | (S)-N-(1-(3-chloro-4-methoxyphenyl)-1-(3-fluoro-5-(1,1,2,2-tetrafluoroethoxy)phenyl)-2-phenylethyl)-4-fluoro-3-(trifluoromethyl)benzamide | 10.93 LC (7) 662.0 [M + H]$^+$ | Procedures 3, 4, 5, 6 and 7 |
| 620 | 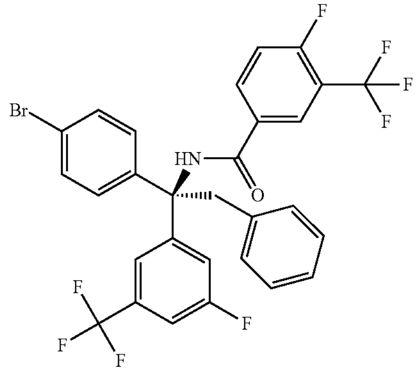 [SMILES: O=C(N[C@](Cc1ccccc1)(c1ccc(Br)cc1)c1cc(F)cc(C(F)(F)F)c1)c1ccc(F)c(C(F)(F)F)c1] | (R)-N-(1-(4-bromophenyl)-1-(3-fluoro-5-(trifluoromethyl)phenyl)-2-phenylethyl)-4-fluoro-3-(trifluoromethyl)benzamide | 4.43 LC (4) 628.30 [M + H]$^+$ | Procedures 4, 5, 6 and 7 |

TABLE 10-continued

| Ex. No. | Structure | Name | Retention Time Min./ Molecular Mass | Prepared in the manner described in: |
|---|---|---|---|---|
| 621 | 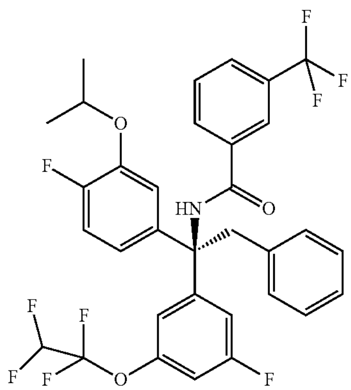 [SMILES: CC(C)Oc1cc([C@@](Cc2ccccc2)(NC(=O)c2cccc(C(F)(F)F)c2)c2cc(F)cc(OC(F)(F)C(F)F)c2)ccc1F] | (R)-N-(1-(4-fluoro-3-isopropoxyphenyl)-1-(3-fluoro-5-(1,1,2,2-tetrafluoroethoxy)phenyl)-2-phenylethyl)-3-(trifluoromethyl)benzamide | 4.00 LC (1) 656.2 [M + H]+ | Procedures 3, 4, 5, 6, 7, 59 and 68 |
| 622 | 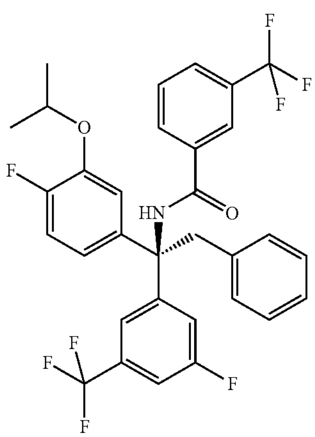 [SMILES: CC(C)Oc1cc([C@@](Cc2ccccc2)(NC(=O)c2cccc(C(F)(F)F)c2)c2cc(F)cc(C(F)(F)F)c2)ccc1F] | (R)-N-(1-(4-fluoro-3-isopropoxyphenyl)-1-(3-fluoro-5-(trifluoromethyl)phenyl)-2-phenylethyl)-3-(trifluoromethyl)benzamide | 4.10 LC (1) 608.4 [M + H]+ | Procedures 4, 5, 6, 7, 59 and 68 |
| 623 | 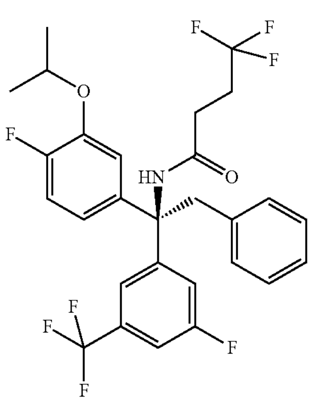 [SMILES: CC(C)Oc1cc([C@@](Cc2ccccc2)(NC(=O)CCC(F)(F)F)c2cc(F)cc(C(F)(F)F)c2)ccc1F] | (R)-4,4,4-trifluoro-N-(1-(4-fluoro-3-isopropoxyphenyl)-1-(3-fluoro-5-(trifluoromethyl)phenyl)-2-phenylethyl)butanamide | 3.85 LC (1) 560.2 [M + H]+ | Procedures 4, 5, 6, 128, 59 and 68 |

TABLE 10-continued

| Ex. No. | Structure | Name | Retention Time Min./ Molecular Mass | Prepared in the manner described in: |
|---|---|---|---|---|
| 624 | 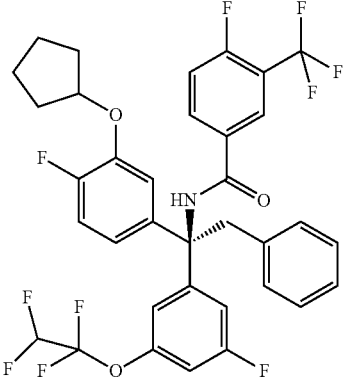 [SMILES: O=C(N[C@@](Cc1ccccc1)(c1cc(F)cc(OC(F)(F)C(F)F)c1)c1ccc(F)c(OC2CCCC2)c1)c1ccc(F)c(C(F)(F)F)c1] | (R)-N-(1-(3-(cyclopentyloxy)-4-fluorophenyl)-1-(3-fluoro-5-(1,1,2,2-tetrafluoroethoxy)phenyl)-2-phenylethyl)-4-fluoro-3-(trifluoromethyl)benzamide | 4.24 LC (1) 700.1 [M + H]+ | Procedures 3, 4, 5, 6, 7, 59 and 68 |
| 625 | 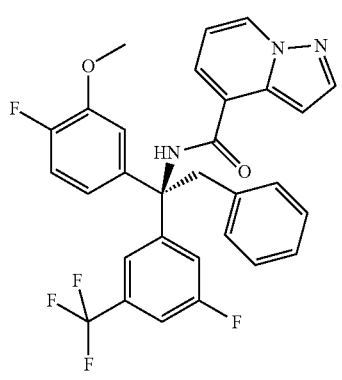 [SMILES: COc1cc([C@@](Cc2ccccc2)(NC(=O)c2cccn3nccc23)c2cc(F)cc(C(F)(F)F)c2)ccc1F] | (R)-N-(1-(4-fluoro-3-methoxyphenyl)-1-(3-fluoro-5-(trifluoromethyl)phenyl)-2-phenylethyl)pyrazolo[1,5-a]pyridine-4-carboxamide | 2.12 LC (1) 552.3 [M + H]+ | Procedures 4, 5, 6 and 127 |
| 626 | 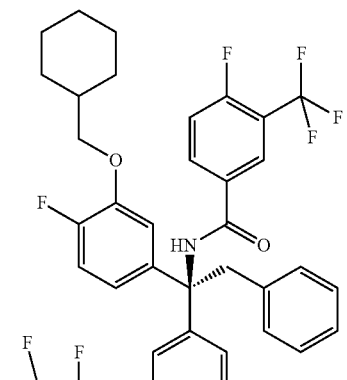 | (R)-N-(1-(3-(cyclohexylmethoxy)-4-fluorophenyl)-1-(3-fluoro-5-(1,1,2,2-tetrafluoroethoxy)phenyl)-2-phenylethyl)-4-fluoro-3-(trifluoromethyl)benzamide | 4.51 LC (1) 729.3 [M + H]+ | Procedures 3, 4, 5, 6, 7, 59 and 68 |

TABLE 10-continued

| Ex. No. | Structure | Name | Retention Time Min./ Molecular Mass | Prepared in the manner described in: |
|---|---|---|---|---|
| 627 | 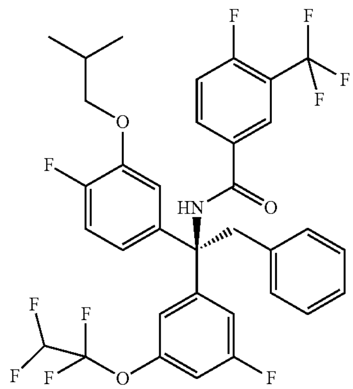 [SMILES: CC(C)COc1cc([C@@](Cc2ccccc2)(NC(=O)c2ccc(F)c(C(F)(F)F)c2)c2cc(F)cc(OC(F)(F)C(F)F)c2)ccc1F] | (R)-4-fluoro-N-(1-(4-fluoro-3-isobutoxyphenyl)-1-(3-fluoro-5-(1,1,2,2-tetrafluoroethoxy)phenyl)-2-phenylethyl)-3-(trifluoromethyl)benzamide | 4.23 LC (1) 688.4 [M + H]$^+$ | Procedures 3, 4, 5, 6, 7, 59 and 68 |
| 628 | 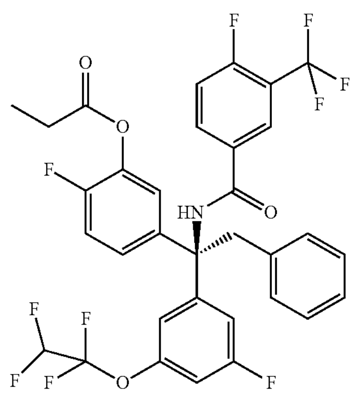 [SMILES: CCC(=O)Oc1cc([C@@](Cc2ccccc2)(NC(=O)c2ccc(F)c(C(F)(F)F)c2)c2cc(F)cc(OC(F)(F)C(F)F)c2)ccc1F] | (R)-2-fluoro-5-(1-(4-fluoro-3-(trifluoromethyl)benzamido)-1-(3-fluoro-5-(1,1,2,2-tetrafluoroethoxy)phenyl)-2-phenylethyl)phenylpropionate | 3.905 LC (1) 688.4 [M + H]$^+$ | Procedures 3, 4, 5, 6, 7, 59 and 68 |
| 629 | 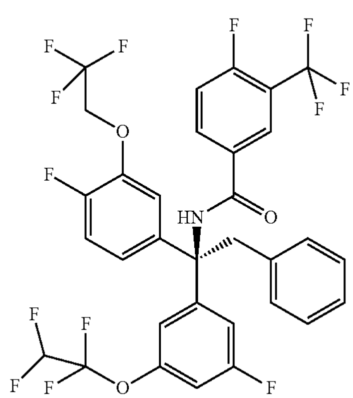 [SMILES: O=C(N[C@@](Cc1ccccc1)(c1cc(F)cc(OC(F)(F)C(F)F)c1)c1ccc(F)c(OCC(F)(F)F)c1)c1ccc(F)c(C(F)(F)F)c1] | (R)-4-fluoro-N-(1-(4-fluoro-3-(2,2,2-trifluoroethoxy)phenyl)-1-(3-fluoro-5-(1,1,2,2-tetrafluoroethoxy)phenyl)-2-phenylethyl)-3-(trifluoromethyl)benzamide | 3.95 LC (1) 714.1 [M + H]$^+$ | Procedures 3, 4, 5, 6, 7, 59 and 68 |

TABLE 10-continued

| Ex. No. | Structure | Name | Retention Time Min./ Molecular Mass | Prepared in the manner described in: |
|---|---|---|---|---|
| 630 | 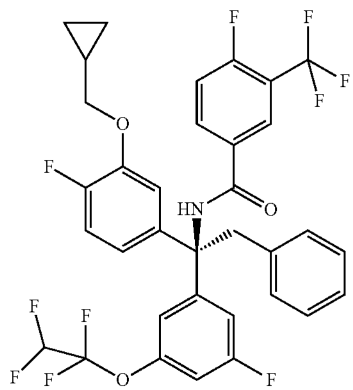 [SMILES: O=C(N[C@@](Cc1ccccc1)(c1cc(F)cc(OC(F)(F)C(F)F)c1)c1ccc(F)c(OCC2CC2)c1)c1ccc(F)c(C(F)(F)F)c1] | (R)-N-(1-(3-(cyclopropylmethoxy)-4-fluorophenyl)-1-(3-fluoro-5-(1,1,2,2-tetrafluoroethoxy)phenyl)-2-phenylethyl)-4-fluoro-3-(trifluoromethyl)benzamide | 4.04 LC (1) 686.2 [M + H]+ | Procedures 3, 4, 5, 6, 7, 59 and 68 |
| 631 | 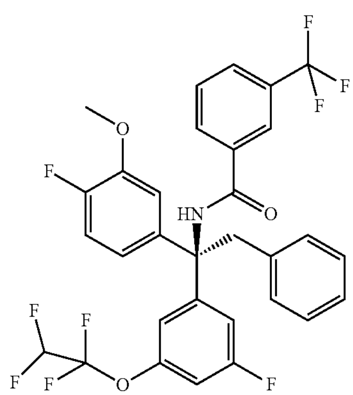 [SMILES: COc1cc([C@@](Cc2ccccc2)(NC(=O)c2cccc(C(F)(F)F)c2)c2cc(F)cc(OC(F)(F)C(F)F)c2)ccc1F] | (R)-N-(1-(4-fluoro-3-methoxyphenyl)-1-(3-fluoro-5-(1,1,2,2-tetrafluoroethoxy)phenyl)-2-phenylethyl)-3-(trifluoromethyl)benzamide | 3.88 LC (1) 628.2 [M + H]+ | Procedures 3, 4, 5, 6 and 7 |
| 632 | 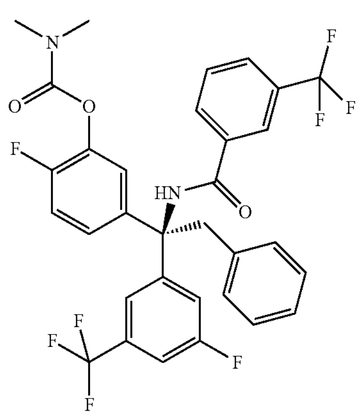 [SMILES: CN(C)C(=O)Oc1cc([C@@](Cc2ccccc2)(NC(=O)c2cccc(C(F)(F)F)c2)c2cc(F)cc(C(F)(F)F)c2)ccc1F] | (R)-2-fluoro-5-(1-(3-fluoro-5-(trifluoromethyl)phenyl)-2-phenyl-1-(3-(trifluoromethyl)benzamido)ethyl)phenyldimethylcarbamate | 2.21 LC (2) 637.3 [M + H]+ | Procedures 3, 4, 5, 6, 7, 59 and 68 |

TABLE 10-continued

| Ex. No. | Structure | Name | Retention Time Min./ Molecular Mass | Prepared in the manner described in: |
|---|---|---|---|---|
| 633 | 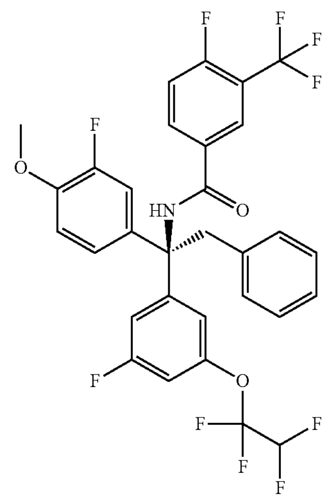 [SMILES: COc1ccc([C@@](Cc2ccccc2)(NC(=O)c2ccc(F)c(C(F)(F)F)c2)c2cc(F)cc(OC(F)(F)C(F)F)c2)cc1F] | (R)-4-fluoro-N-(1-(3-fluoro-4-methoxyphenyl)-1-(3-fluoro-5-(1,1,2,2-tetrafluoroethoxy)phenyl)-2-phenylethyl)-3-(trifluoromethyl)benzamide | 645.487 | Procedures 3, 4, 5, 6 and 7 |
| 634 | 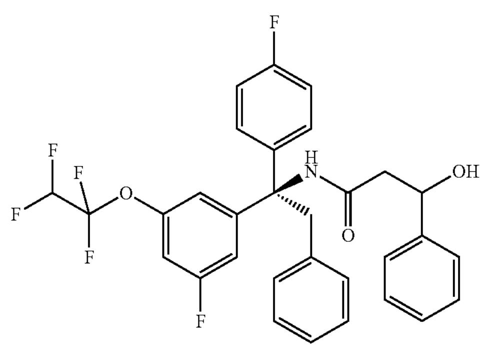 [SMILES: O=C(CC(O)c1ccccc1)N[C@](Cc1ccccc1)(c1ccc(F)cc1)c1cc(F)cc(OC(F)(F)C(F)F)c1] | N-((R)-1-(3-fluoro-5-(1,1,2,2-tetrafluoroethoxy)phenyl)-1-(4-fluorophenyl)-2-phenylethyl)-3-hydroxy-3-phenylpropanamide | 4.28 LC (11) 574.3 [M + H]$^+$ | Procedures 3, 4, 5, 6, 60 and 23 |
| 635 | 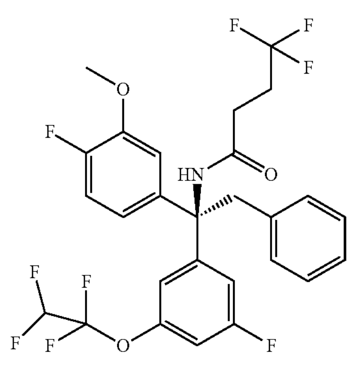 [SMILES: COc1cc([C@@](Cc2ccccc2)(NC(=O)CCC(F)(F)F)c2cc(F)cc(OC(F)(F)C(F)F)c2)ccc1F] | (R)-4,4,4-trifluoro-N-(1-(4-fluoro-3-methoxyphenyl)-1-(3-fluoro-5-(1,1,2,2-tetrafluoroethoxy)phenyl)-2-phenylethyl)butanamide | 3.56 LC (1) 580.3 [M + H]$^+$ | Procedures 3, 4, 5, 6 and 128 |

TABLE 10-continued

| Ex. No. | Structure | Name | Retention Time Min./ Molecular Mass | Prepared in the manner described in: |
|---|---|---|---|---|
| 636 | 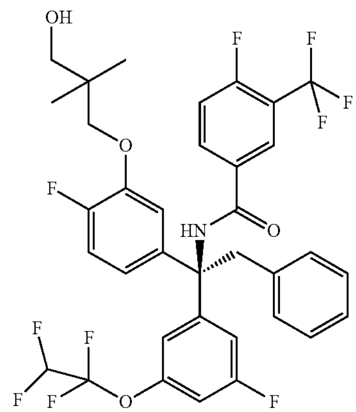 [SMILES: CC(C)(CO)COc1cc([C@@](Cc2ccccc2)(NC(=O)c2ccc(F)c(C(F)(F)F)c2)c2cc(F)cc(OC(F)(F)C(F)F)c2)ccc1F] | (R)-4-fluoro-N-(1-(4-fluoro-3-(3-hydroxy-2,2-dimethylpropoxy)phenyl)-1-(3-fluoro-5-(1,1,2,2-tetrafluoroethoxy)phenyl)-2-phenylethyl)-3-(trifluoromethyl)benzamide | 3.833 LC (1) 718.4 [M + H]$^+$ | Procedures 3, 4, 5, 6, 7, 59 and 68 |
| 637 | 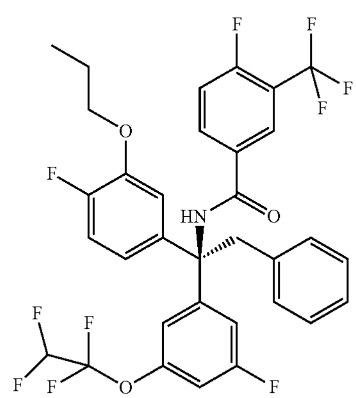 [SMILES: CCCOc1cc([C@@](Cc2ccccc2)(NC(=O)c2ccc(F)c(C(F)(F)F)c2)c2cc(F)cc(OC(F)(F)C(F)F)c2)ccc1F] | (R)-4-fluoro-N-(1-(4-fluoro-3-propoxyphenyl)-1-(3-fluoro-5-(1,1,2,2-tetrafluoroethoxy)phenyl)-2-phenylethyl)-3-(trifluoromethyl)benzamide | 4.08 LC (1) 674.3 [M + H]$^+$ | Procedures 3, 4, 5, 6, 7, 59 and 68 |
| 638 | 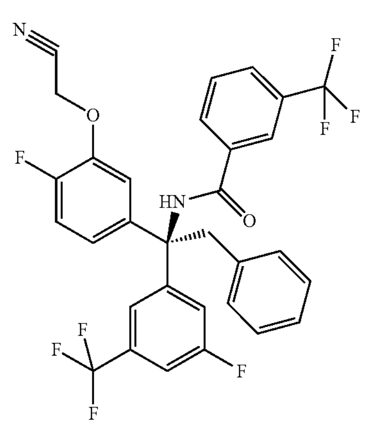 [SMILES: N#CCOc1cc([C@@](Cc2ccccc2)(NC(=O)c2cccc(C(F)(F)F)c2)c2cc(F)cc(C(F)(F)F)c2)ccc1F] | (R)-N-(1-(3-(cyanomethoxy)-4-fluorophenyl)-1-(3-fluoro-5-(trifluoromethyl)phenyl)-2-phenylethyl)-3-(trifluoromethyl)benzamide | 4.24 LC (1) 605.2 [M + H]$^+$ | Procedures 4, 5, 6, 7, 59 and 68 |

TABLE 10-continued

| Ex. No. | Structure | Name | Retention Time Min./ Molecular Mass | Prepared in the manner described in: |
|---|---|---|---|---|
| 639 | 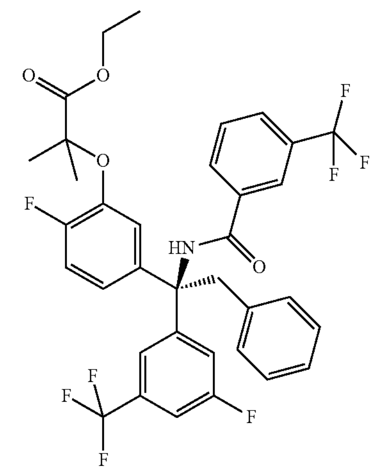 [SMILES: CCOC(=O)C(C)(C)Oc1cc([C@@](Cc2ccccc2)(NC(=O)c2cccc(C(F)(F)F)c2)c2cc(F)cc(C(F)(F)F)c2)ccc1F] | (R)-ethyl 2-(2-fluoro-5-(1-(3-fluoro-5-(trifluoromethyl)phenyl)-2-phenyl-1-(3-(trifluoromethyl)benzamido)ethyl)phenoxy)-2-methylpropanoate | 4.44 LC (1) 680.2 [M + H]$^+$ | Procedures 4, 5, 6, 7, 59 and 68 |
| 640 | 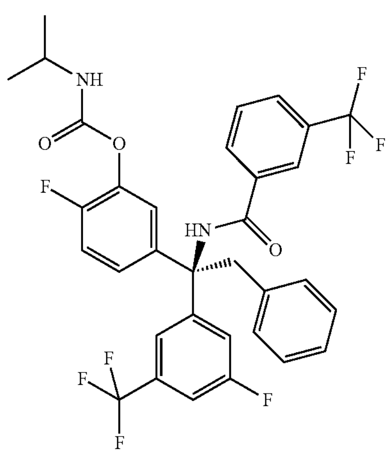 [SMILES: CC(C)NC(=O)Oc1cc([C@@](Cc2ccccc2)(NC(=O)c2cccc(C(F)(F)F)c2)c2cc(F)cc(C(F)(F)F)c2)ccc1F] | (R)-2-fluoro-5-(1-(3-fluoro-5-(trifluoromethyl)phenyl)-2-phenyl-1-(3-(trifluoromethyl)benzamide)ethyl)phenylisopropylcarbamate | 2.20 LC (2) 651.3 [M + H]$^+$ | Procedures 4, 5, 6, 7, 59 and 68 |
| 641 | 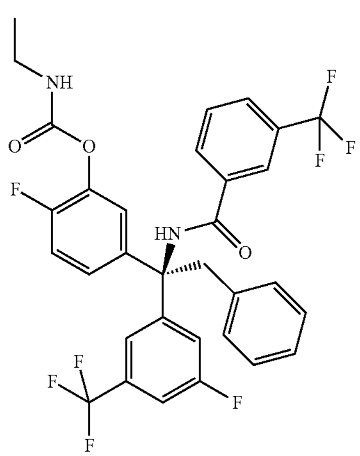 [SMILES: CCNC(=O)Oc1cc([C@@](Cc2ccccc2)(NC(=O)c2cccc(C(F)(F)F)c2)c2cc(F)cc(C(F)(F)F)c2)ccc1F] | (R)-2-fluoro-5-(1-(3-fluoro-5-(trifluoromethyl)phenyl)-2-phenyl-1-(3-(trifluoromethyl)benzamido)ethyl)phenylethylcarbamate | 2.15 LC (2) 637.2 [M + H]$^+$ | Procedures 4, 5, 6, 7, 59 and 68 |

TABLE 10-continued

| Ex. No. | Structure | Name | Retention Time Min./ Molecular Mass | Prepared in the manner described in: |
|---|---|---|---|---|
| 642 | 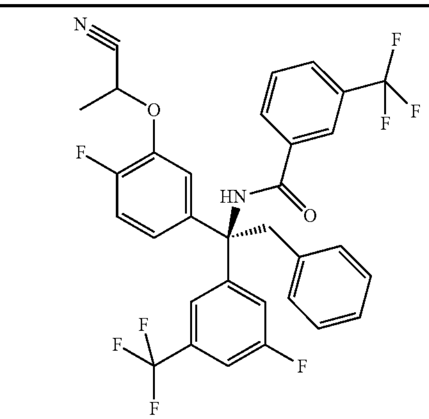 | N-((1R)-1-(3-(1-cyanoethoxy)-4-fluorophenyl)-1-(3-fluoro-5-(trifluoromethyl) phenyl)-2-phenylethyl)-3-(trifluoromethyl) benzamide | 2.18 LC (2) 619.3 [M + H]+ | Procedures 4, 5, 6, 7, 59 and 68 |
| 643 | 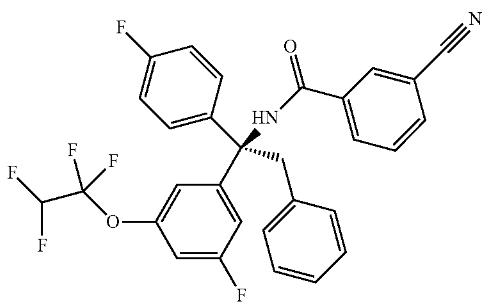 [SMILES: N#Cc1cccc(C(=O)N[C@](Cc2ccccc2)(c2ccc(F)cc2)c2cc(F)cc(OC(F)(F)C(F)F)c2)c1] | (R)-3-cyano-N-(1-(3-fluoro-5-(1,1,2,2-tetrafluoroethoxy)phenyl)-1-(4-fluorophenyl)-2-phenylethyl)benzamide | 2.07 LC (2) 555.3 [M + H]+ | Procedures 3, 4, 5, 6 and 7 |
| 644 | 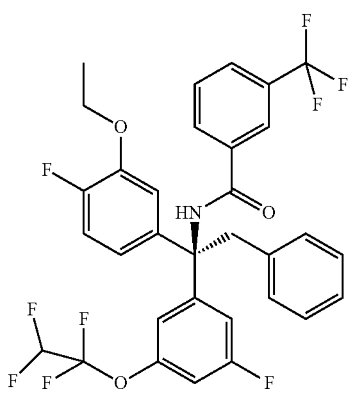 [SMILES: CCOc1cc([C@@](Cc2ccccc2)(NC(=O)c2cccc(C(F)(F)F)c2)c2cc(F)cc(OC(F)(F)C(F)F)c2)ccc1F] | (R)-N-(1-(3-ethoxy-4-fluorophenyl)-1-(3-fluoro-5-(1,1,2,2-tetrafluoroethoxy)phenyl)-2-phenylethyl)-3-(trifluoromethyl)benzamide | 3.91 LC (1) 642.2 [M + H]+ | Procedures 3, 4, 5, 6, 7, 59 and 68 |
| 645 | 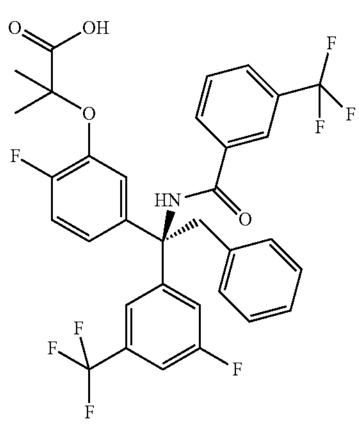 [SMILES: CC(C)(Oc1cc([C@@](Cc2ccccc2)(NC(=O)c2cccc(C(F)(F)F)c2)c2cc(F)cc(C(F)(F)F)c2)ccc1F)C(=O)O] | (R)-2-(2-fluoro-5-(1-(3-fluoro-5-(trifluoromethyl)phenyl)-2-phenyl-1-(3-(trifluoromethyl)benzamido)ethyl)phenoxy)-2-methylpropanoic acid | 2.23 LC (2) 652.3 [M + H]+ | Procedures 4, 5, 6, 7 59, 68 and 23 |

TABLE 10-continued

| Ex. No. | Structure | Name | Retention Time Min./ Molecular Mass | Prepared in the manner described in: |
|---|---|---|---|---|
| 646 | 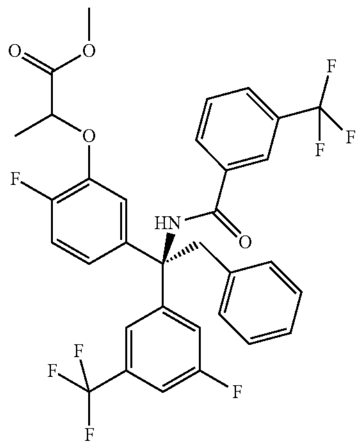 [SMILES: COC(=O)C(C)Oc1cc([C@@](Cc2ccccc2)(NC(=O)c2cccc(C(F)(F)F)c2)c2cc(F)cc(C(F)(F)F)c2)ccc1F] | methyl 2-(2-fluoro-5-((R)-1-(3-fluoro-5-(trifluoromethyl)phenyl)-2-phenyl-1-(3-(trifluoromethyl)benzamido)ethyl)phenoxy) propanoate | 2.24 LC (2) 652.4 [M + H]$^+$ | Procedures 4, 5, 6, 7, 59 and 68 |
| 647 | 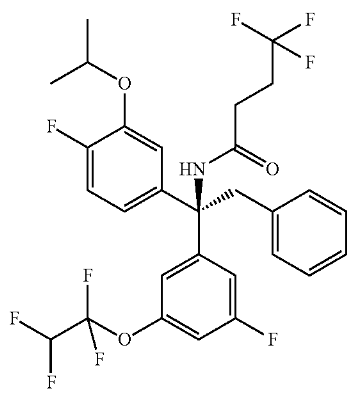 [SMILES: CC(C)Oc1cc([C@@](Cc2ccccc2)(NC(=O)CCC(F)(F)F)c2cc(F)cc(OC(F)(F)C(F)F)c2)ccc1F] | (R)-4,4,4-trifluoro-N-(1-(4-fluoro-3-isopropoxyphenyl)-1-(3-fluoro-5-(1,1,2,2-tetrafluoroethoxy)phenyl)-2-phenylethyl) butanamide | 3.79 LC (1) 608.4 [M + H]$^+$ | Procedures 3, 4, 5, 6, 59, 68 and 128 |
| 648 | 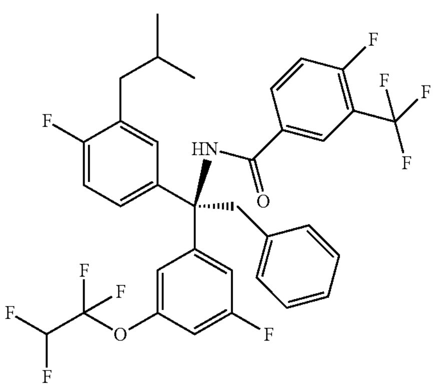 [SMILES: CC(C)Cc1cc([C@@](Cc2ccccc2)(NC(=O)c2ccc(F)c(C(F)(F)F)c2)c2cc(F)cc(OC(F)(F)C(F)F)c2)ccc1F] | (R)-4-fluoro-N-(1-(4-fluoro-3-isobutylphenyl)-1-(3-fluoro-5-(1,1,2,2-tetrafluoroethoxy)phenyl)-2-phenylethyl)-3-(trifluoromethyl)benzamide | 4.54 LC (4) 672.40 [M + H]$^+$ | Procedures 3, 62, 5, 6, 122 and 7 |
| 649 | 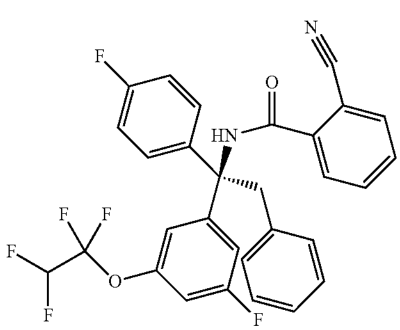 [SMILES: N#Cc1ccccc1C(=O)N[C@](Cc1ccccc1)(c1ccc(F)cc1)c1cc(F)cc(OC(F)(F)C(F)F)c1] | (R)-2-cyano-N-(1-(3-fluoro-5-(1,1,2,2-tetrafluoroethoxy)phenyl)-1-(4-fluorophenyl)-2-phenylethyl)benzamide | 2.14 LC (2) 577.4 [M + Na]$^+$ | Procedures 3, 4, 5, 6 and 7 |

TABLE 10-continued

| Ex. No. | Structure | Name | Retention Time Min./ Molecular Mass | Prepared in the manner described in: |
|---|---|---|---|---|
| 650 | 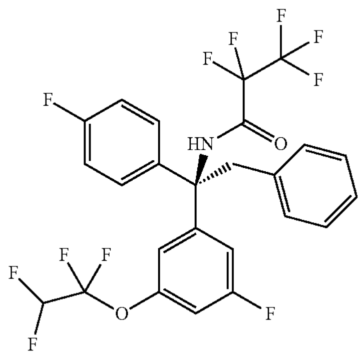 [SMILES: O=C(N[C@](Cc1ccccc1)(c1ccc(F)cc1)c1cc(F)cc(OC(F)(F)C(F)F)c1)C(F)(F)C(F)(F)F] | (R)-2,2,3,3,3-pentafluoro-N-(1-(3-fluoro-5-(1,1,2,2-tetrafluoroethoxy)phenyl)-1-(4-fluorophenyl)-2-phenylethyl)propanamide | 2.11 LC (2) 409.2 [M-amide] | Procedures 3, 109, 110, 111, 112, 113, 114 and 115 |
| 651 | 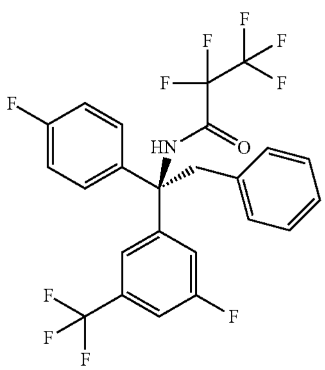 [SMILES: O=C(N[C@](Cc1ccccc1)(c1ccc(F)cc1)c1cc(F)cc(C(F)(F)F)c1)C(F)(F)C(F)(F)F] | (R)-2,2,3,3,3-pentafluoro-N-(1-(3-fluoro-5-(trifluoromethyl)phenyl)-1-(4-fluorophenyl)-2-phenylethyl)propanamide | 2.15 LC (2) no ionizable peak | Procedures 4, 5, 6 and 115 |
| 652 | 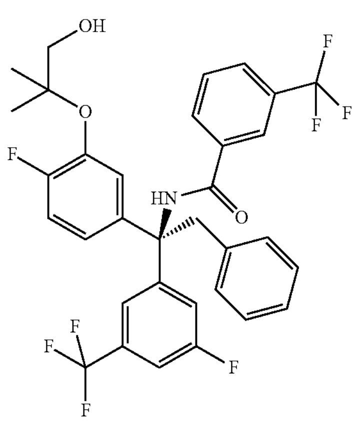 [SMILES: CC(C)(CO)Oc1cc([C@@](Cc2ccccc2)(NC(=O)c2cccc(C(F)(F)F)c2)c2cc(F)cc(C(F)(F)F)c2)ccc1F] | (R)-N-(1-(4-fluoro-3-(1-hydroxy-2-methylpropan-2-yloxy)phenyl)-1-(3-fluoro-5-(trifluoromethyl)phenyl)-2-phenylethyl)-3-(trifluoromethyl)benzamide | 2.33 LC (2) 660.5 [M + Na]$^+$ | Procedures 4, 5, 6, 7, 59 and 68 |

TABLE 10-continued

| Ex. No. | Structure | Name | Retention Time Min./ Molecular Mass | Prepared in the manner described in: |
|---|---|---|---|---|
| 653 | 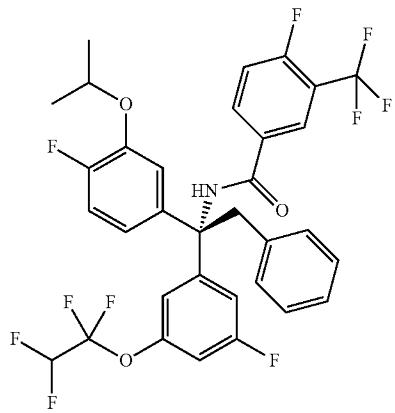 [SMILES: CC(C)Oc1cc([C@](Cc2ccccc2)(NC(=O)c2ccc(F)c(C(F)(F)F)c2)c2cc(F)cc(OC(F)(F)C(F)F)c2)ccc1F] | (S)-4-fluoro-N-(1-(4-fluoro-3-isopropoxyphenyl)-1-(3-fluoro-5-(1,1,2,2-tetrafluoroethoxy)phenyl)-2-phenylethyl)-3-(trifluoromethyl)benzamide | 4.35 LC (4) 674.3 [M + H]$^+$ | Procedures 3, 4, 5, 6, 7, 59 and 68 |
| 654 | 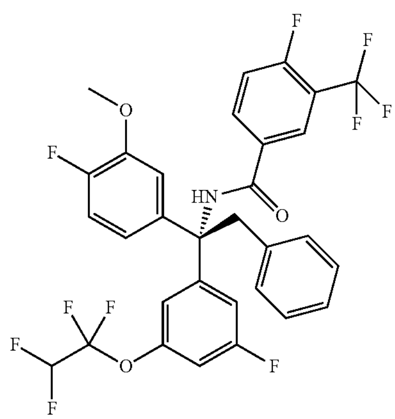 [SMILES: COc1cc([C@](Cc2ccccc2)(NC(=O)c2ccc(F)c(C(F)(F)F)c2)c2cc(F)cc(OC(F)(F)C(F)F)c2)ccc1F] | (S)-4-fluoro-N-(1-(4-fluoro-3-methoxyphenyl)-1-(3-fluoro-5-(1,1,2,2-tetrafluoroethoxy)phenyl)-2-phenylethyl)-3-(trifluoromethyl)benzamide | 4.21 LC (1) 645.14 [M + H]$^+$ | Procedures 3, 4, 5, 6 and 7 |
| 655 | 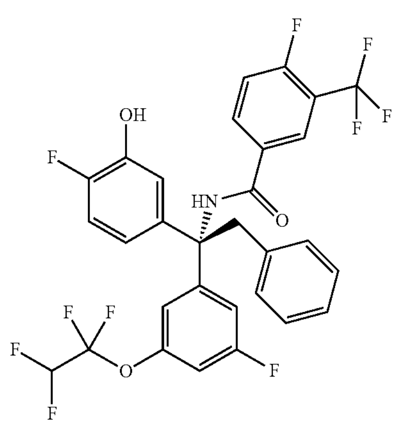 [SMILES: O=C(N[C@](Cc1ccccc1)(c1cc(F)cc(OC(F)(F)C(F)F)c1)c1ccc(F)c(O)c1)c1ccc(F)c(C(F)(F)F)c1] | (S)-4-fluoro-N-(1-(4-fluoro-3-hydroxyphenyl)-1-(3-fluoro-5-(1,1,2,2-tetrafluoroethoxy)phenyl)-2-phenylethyl)-3-(trifluoromethyl)benzamide | 4.06 LC (1) 632.2 [M + H]$^+$ | Procedures 3, 4, 5, 6, 7 and 59 |

TABLE 10-continued

| Ex. No. | Structure | Name | Retention Time Min./ Molecular Mass | Prepared in the manner described in: |
|---|---|---|---|---|
| 656 | 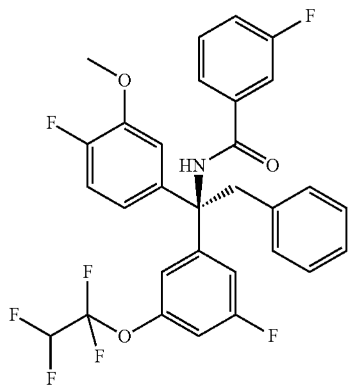 [SMILES: COc1cc([C@@](Cc2ccccc2)(NC(=O)c2cccc(F)c2)c2cc(F)cc(OC(F)(F)C(F)F)c2)ccc1F] | (R)-3-fluoro-N-(1-(4-fluoro-3-methoxyphenyl)-1-(3-fluoro-5-(1,1,2,2-tetrafluoroethoxy)phenyl)-2-phenylethyl) benzamide | 3.63 LC (1) 578.2 [M + H]$^+$ | Procedures 3, 4, 5, 6 and 7 |
| 657 | 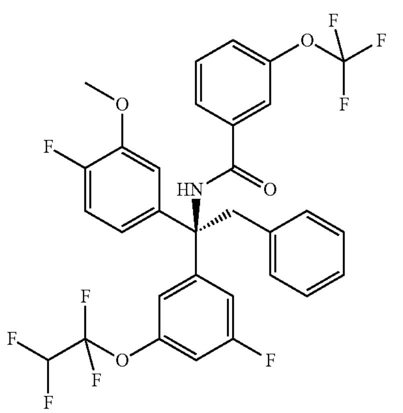 [SMILES: COc1cc([C@@](Cc2ccccc2)(NC(=O)c2cccc(OC(F)(F)F)c2)c2cc(F)cc(OC(F)(F)C(F)F)c2)ccc1F] | (R)-N-(1-(4-fluoro-3-methoxyphenyl)-1-(3-fluoro-5-(1,1,2,2-tetrafluoroethoxy)phenyl)-2-phenylethyl)-3-(trifluoromethoxy) benzamide | 3.87 LC (1) 644.5 [M + H]$^+$ | Procedures 3, 4, 5, 6 and 7 |
| 658 | 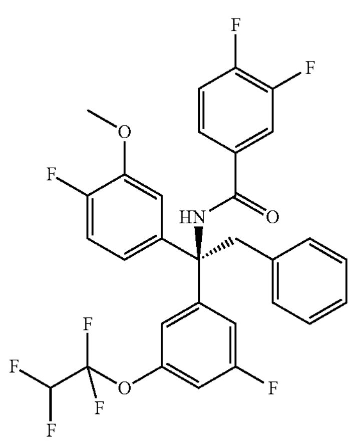 [SMILES: COc1cc([C@@](Cc2ccccc2)(NC(=O)c2ccc(F)c(F)c2)c2cc(F)cc(OC(F)(F)C(F)F)c2)ccc1F] | (R)-3,4-difluoro-N-(1-(4-fluoro-3-methoxyphenyl)-1-(3-fluoro-5-(1,1,2,2-tetrafluoroethoxy)phenyl)-2-phenylethyl) benzamide | 3.701 LC (1) 596.5 [M + H]$^+$ | Procedures 3, 4, 5, 6 and 7 |

TABLE 10-continued

| Ex. No. | Structure | Name | Retention Time Min./ Molecular Mass | Prepared in the manner described in: |
|---|---|---|---|---|
| 659 | 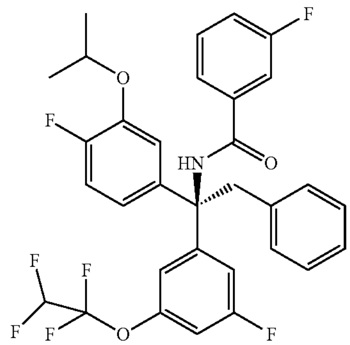 [SMILES: CC(C)Oc1cc([C@@](Cc2ccccc2)(NC(=O)c2cccc(F)c2)c2cc(F)cc(OC(F)(F)C(F)F)c2)ccc1F] | (R)-3-fluoro-N-(1-(4-fluoro-3-isopropoxyphenyl)-1-(3-fluoro-5-(1,1,2,2-tetrafluoroethoxy)phenyl)-2-phenylethyl)benzamide | 3.85 LC (1) 606.5 [M + H]+ | Procedures 3, 4, 5, 6, 7, 59 and 68 |
| 660 | 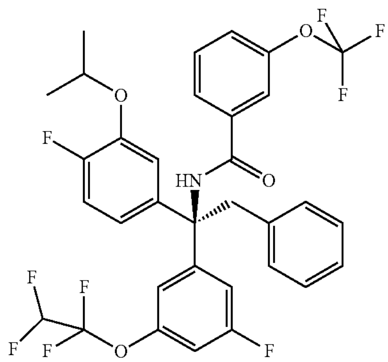 [SMILES: CC(C)Oc1cc([C@@](Cc2ccccc2)(NC(=O)c2cccc(OC(F)(F)F)c2)c2cc(F)cc(OC(F)(F)C(F)F)c2)ccc1F] | (R)-N-(1-(4-fluoro-3-isopropoxyphenyl)-1-(3-fluoro-5-(1,1,2,2-tetrafluoroethoxy)phenyl)-2-phenylethyl)-3-(trifluoromethoxy)benzamide | 4.06 LC (1) 672.6 [M + H]+ | Procedures 3, 4, 5, 6, 7, 59 and 68 |
| 661 | 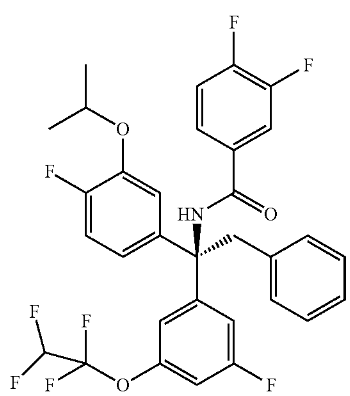 [SMILES: CC(C)Oc1cc([C@@](Cc2ccccc2)(NC(=O)c2ccc(F)c(F)c2)c2cc(F)cc(OC(F)(F)C(F)F)c2)ccc1F] | (R)-3,4-difluoro-N-(1-(4-fluoro-3-isopropoxyphenyl)-1-(3-fluoro-5-(1,1,2,2-tetrafluoroethoxy)phenyl)-2-phenylethyl)benzamide | 3.91 LC (1) 624.5 [M + H]+ | Procedures 3, 4, 5, 6, 7, 59 and 68 |
| 662 | 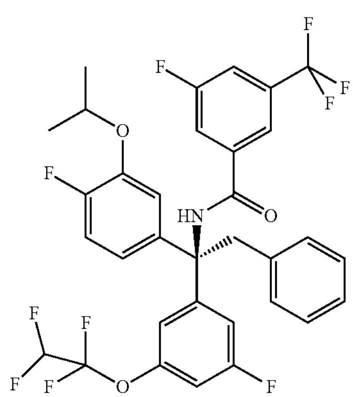 [SMILES: CC(C)Oc1cc([C@@](Cc2ccccc2)(NC(=O)c2cc(F)cc(C(F)(F)F)c2)c2cc(F)cc(OC(F)(F)C(F)F)c2)ccc1F] | (R)-3-fluoro-N-(1-(4-fluoro-3-isopropoxyphenyl)-1-(3-fluoro-5-(1,1,2,2-tetrafluoroethoxy)phenyl)-2-phenylethyl)-5-(trifluoromethyl)benzamide | 4.08 LC (1) 674.3 [M + H]+ | Procedures 3, 4, 5, 6, 7, 59 and 68 |

TABLE 10-continued

| Ex. No. | Structure | Name | Retention Time Min./ Molecular Mass | Prepared in the manner described in: |
|---|---|---|---|---|
| 663 | 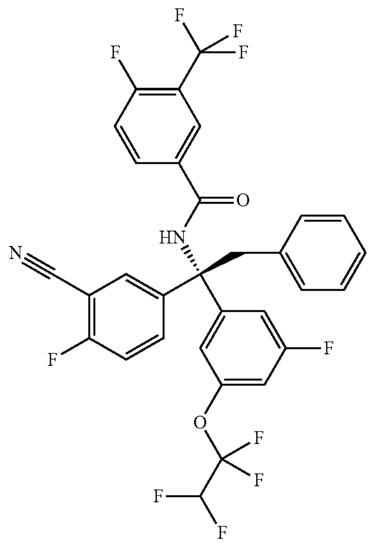 [SMILES: N#Cc1cc([C@](Cc2ccccc2)(NC(=O)c2ccc(F)c(C(F)(F)F)c2)c2cc(F)cc(OC(F)(F)C(F)F)c2)ccc1F] | N-(1-(3-cyano-4-fluorophenyl)-1-(3-fluoro-5-(1,1,2,2-tetrafluoroethoxy)phenyl)-2-phenylethyl)-4-fluoro-3-(trifluoromethyl)benzamide | 2.335 LC (2) 641.3 [M + H]+ | Procedures 3, 62, 5, 6, 7 and 56 |
| 664 | 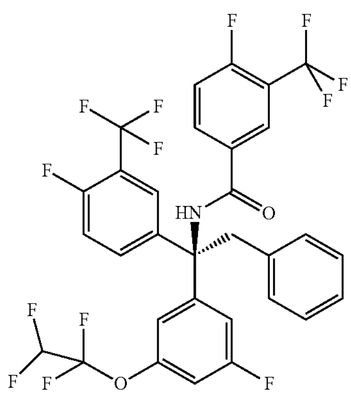 [SMILES: O=C(N[C@@](Cc1ccccc1)(c1cc(F)cc(OC(F)(F)C(F)F)c1)c1ccc(F)c(C(F)(F)F)c1)c1ccc(F)c(C(F)(F)F)c1] | (R)-4-fluoro-N-(1-(4-fluoro-3-(trifluoromethyl)phenyl)-1-(3-fluoro-5-(1,1,2,2-tetrafluoroethoxy)phenyl)-2-phenylethyl)-3-(trifluoromethyl)benzamide | 4.30 LC (1) 684.46 [M + H]+ | Procedures 3, 4, 5, 6 and 7 |
| 665 | 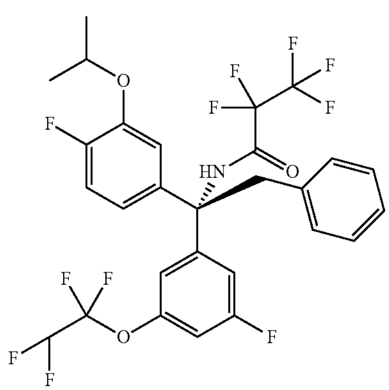 [SMILES: CC(C)Oc1cc([C@](Cc2ccccc2)(NC(=O)C(F)(F)C(F)(F)F)c2cc(F)cc(OC(F)(F)C(F)F)c2)ccc1F] | (S)-2,2,3,3,3-pentafluoro-N-(1-(4-fluoro-3-isopropoxyphenyl)-1-(3-fluoro-5-(1,1,2,2-tetrafluoroethoxy)phenyl)-2-phenylethyl)propanamide | 2.22 LC (2) no ionizable peak | Procedures 3, 109, 110, 111, 112, 113, 114 and 115 |

TABLE 10-continued

| Ex. No. | Structure | Name | Retention Time Min./ Molecular Mass | Prepared in the manner described in: |
|---|---|---|---|---|
| 666 | 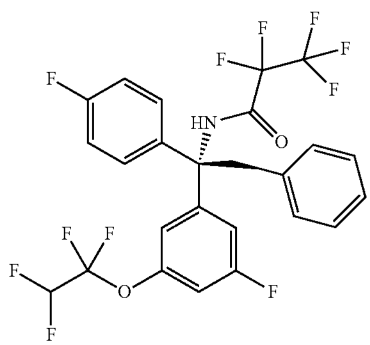 [SMILES: O=C(N[C@@](Cc1ccccc1)(c1ccc(F)cc1)c1cc(F)cc(OC(F)(F)C(F)F)c1)C(F)(F)C(F)(F)F] | (S)-2,2,3,3,3-pentafluoro-N-(1-(3-fluoro-5-(1,1,2,2-tetrafluoroethoxy)phenyl)-1-(4-fluorophenyl)-2-phenylethyl)propanamide | 2.14 LC (2) no ionizable peak | Procedures 3, 4, 5, 6 and 115 |
| 667 | 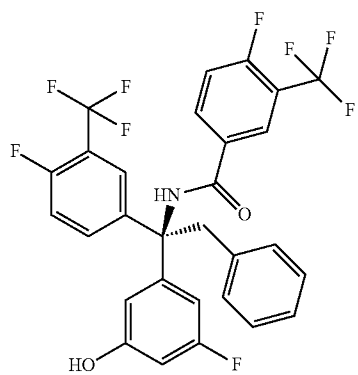 [SMILES: O=C(N[C@@](Cc1ccccc1)(c1cc(O)cc(F)c1)c1ccc(F)c(C(F)(F)F)c1)c1ccc(F)c(C(F)(F)F)c1] | (R)-4-fluoro-N-(1-(4-fluoro-3-(trifluoromethyl)phenyl)-1-(3-fluoro-5-hydroxyphenyl)-2-phenylethyl)-3-(trifluoromethyl)benzamide | 2.19 LC (2) 584.4 [M + H]$^+$ | Procedures 49 and 7 |
| 668 | 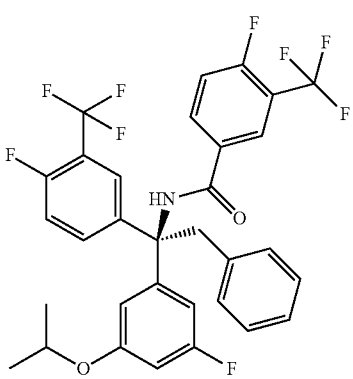 [SMILES: CC(C)Oc1cc(F)cc([C@](Cc2ccccc2)(NC(=O)c2ccc(F)c(C(F)(F)F)c2)c2ccc(F)c(C(F)(F)F)c2)c1] | (R)-4-fluoro-N-(1-(4-fluoro-3-(trifluoromethyl)phenyl)-1-(3-fluoro-5-isopropoxyphenyl)-2-phenylethyl)-3-(trifluoromethyl)benzamide | 2.34 LC (2) 626.5 [M + H]$^+$ | Procedures 49, 7 and 68 |
| 669 | 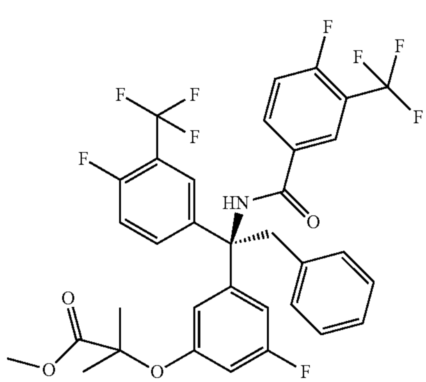 [SMILES: COC(=O)C(C)(C)Oc1cc(F)cc([C@](Cc2ccccc2)(NC(=O)c2ccc(F)c(C(F)(F)F)c2)c2ccc(F)c(C(F)(F)F)c2)c1] | (R)-methyl 2-(3-fluoro-5-(1-(4-fluoro-3-(trifluoromethyl)benzamido)-1-(4-fluoro-3-(trifluoromethyl)phenyl)-2-phenylethyl)phenoxy)-2-methylpropanoate | 2.26 LC (2) 684.6 [M + H]$^+$ | Procedures 49, 7 and 68 |

TABLE 10-continued

| Ex. No. | Structure | Name | Retention Time Min./ Molecular Mass | Prepared in the manner described in: |
|---|---|---|---|---|
| 670 | 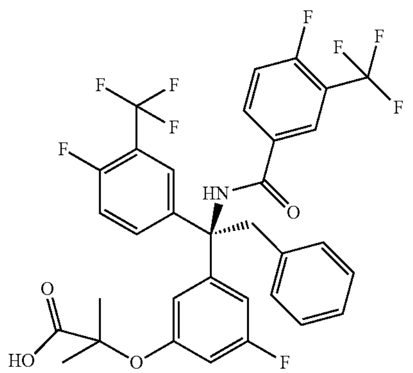 [SMILES: CC(C)(Oc1cc(F)cc([C@](Cc2ccccc2)(NC(=O)c2ccc(F)c(C(F)(F)F)c2)c2ccc(F)c(C(F)(F)F)c2)c1)C(=O)O] | (R)-2-(3-fluoro-5-(1-(4-fluoro-3-(trifluoromethyl)benzamido)-1-(4-fluoro-3-(trifluoromethyl)phenyl)-2-phenylethyl)phenoxy)-2-methylpropanoic acid | 2.25 LC (2) 670.6 [M + H]$^+$ | Procedures 49, 7, 68 and 23 |
| 671 | 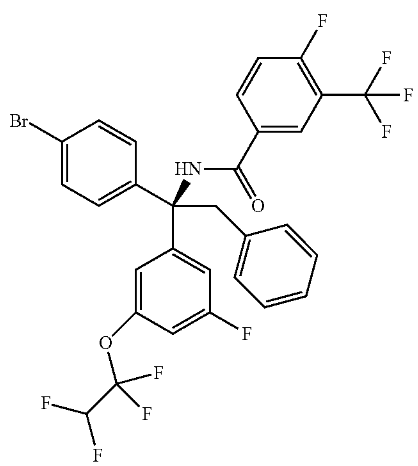 [SMILES: O=C(N[C@](Cc1ccccc1)(c1ccc(Br)cc1)c1cc(F)cc(OC(F)(F)C(F)F)c1)c1ccc(F)c(C(F)(F)F)c1] | (R)-N-(1-(4-bromophenyl)-1-(3-fluoro-5-(1,1,2,2-tetrafluoroethoxy)phenyl)-2-phenylethyl)-4-fluoro-3-(trifluoromethyl)benzamide | 4.13 LC (4) 676.4 [M + H]$^+$ | Procedures 3, 4, 5, 6 and 7 |
| 672 | 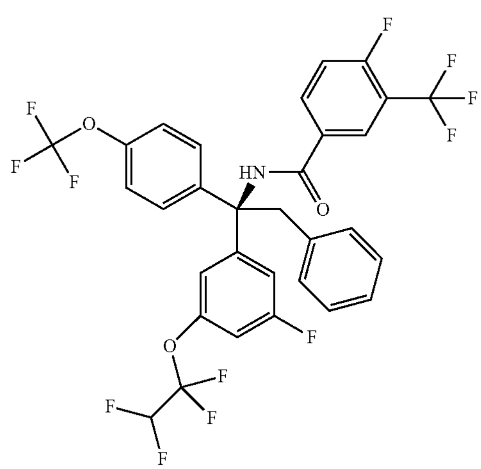 [SMILES: O=C(N[C@](Cc1ccccc1)(c1ccc(OC(F)(F)F)cc1)c1cc(F)cc(OC(F)(F)C(F)F)c1)c1ccc(F)c(C(F)(F)F)c1] | (R)-4-fluoro-N-(1-(3-fluoro-5-(1,1,2,2-tetrafluoroethoxy)phenyl)-2-phenyl-1-(4-(trifluoromethoxy)phenyl)ethyl)-3-(trifluoromethyl)benzamide | 4.13 LC (4) 682.4 [M + H]$^+$ | Procedures 3, 4, 5, 6 and 7 |

TABLE 10-continued

| Ex. No. | Structure | Name | Retention Time Min./ Molecular Mass | Prepared in the manner described in: |
|---|---|---|---|---|
| 673 | 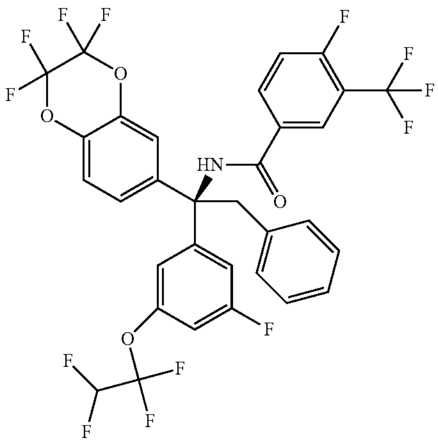 [SMILES: O=C(N[C@@](Cc1ccccc1)(c1cc(F)cc(OC(F)(F)C(F)F)c1)c1ccc2c(c1)OC(F)(F)C(F)(F)O2)c1ccc(F)c(C(F)(F)F)c1] | (R)-4-fluoro-N-(1-(3-fluoro-5-(1,1,2,2-tetrafluoroethoxy)phenyl)-2-phenyl-1-(2,2,3,3-tetrafluoro-2,3-dihydrobenzo[b][1,4]dioxin-6-yl)ethyl)-3-(trifluoromethyl)benzamide | 4.21 LC (4) 728.4 [M + H]$^+$ | Procedures 3, 4, 5, 6 and 7 |
| 674 | 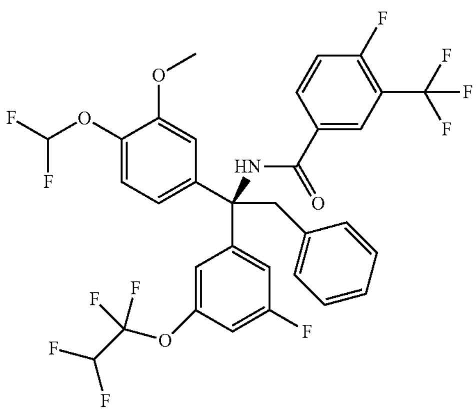 [SMILES: COc1cc([C@@](Cc2ccccc2)(NC(=O)c2ccc(F)c(C(F)(F)F)c2)c2cc(F)cc(OC(F)(F)C(F)F)c2)ccc1OC(F)F] | (R)-N-(1-(4-(difluoromethoxy)-3-methoxyphenyl)-1-(3-fluoro-5-(1,1,2,2-tetrafluoroethoxy)phenyl)-2-phenylethyl)-4-fluoro-3-(trifluoromethyl)benzamide | 3.95 LC (4) 694.4 [M + H]$^+$ | Procedures 3, 4, 5, 6 and 7 |
| 675 | 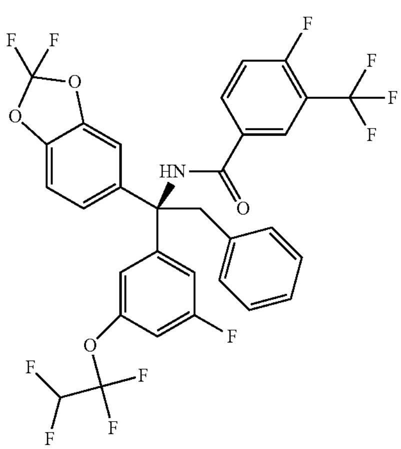 [SMILES: O=C(N[C@@](Cc1ccccc1)(c1cc(F)cc(OC(F)(F)C(F)F)c1)c1ccc2c(c1)OC(F)(F)O2)c1ccc(F)c(C(F)(F)F)c1] | (R)-N-(1-(2,2-difluorobenzo[d][1,3]dioxol-5-yl)-1-(3-fluoro-5-(1,1,2,2-tetrafluoroethoxy) phenyl)-2-phenylethyl)-4-fluoro-3-(trifluoromethyl)benzamide | 4.10 LC (4) 678.5 [M + H]$^+$ | Procedures 3, 4, 5, 6 and 7 |

TABLE 10-continued

| Ex. No. | Structure | Name | Retention Time Min./ Molecular Mass | Prepared in the manner described in: |
|---|---|---|---|---|
| 676 | 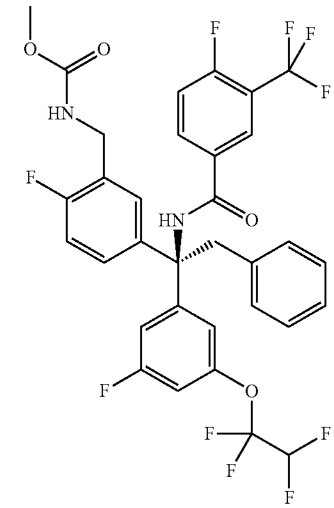 [SMILES: COC(=O)NCc1cc([C@@](Cc2ccccc2)(NC(=O)c2ccc(F)c(C(F)(F)F)c2)c2cc(F)cc(OC(F)(F)C(F)F)c2)ccc1F] | (R)-methyl 2-fluoro-5-(1-(4-fluoro-3-(trifluoromethyl)benzamido)-1-(3-fluoro-5-(1,1,2,2-tetrafluoroethoxy)phenyl)-2-phenylethyl)benzylcarbamate | 10.26 LC (7) 703.1 [M + H]$^+$ | Procedures 3, 62, 63, 7, 64 and 82 |
| 677 | 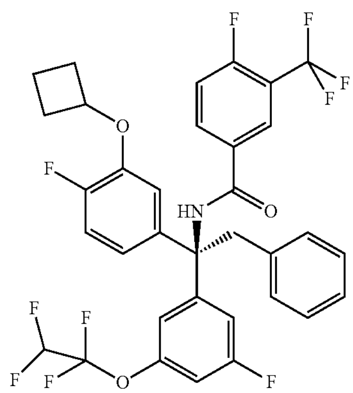 [SMILES: O=C(N[C@@](Cc1ccccc1)(c1cc(F)cc(OC(F)(F)C(F)F)c1)c1ccc(F)c(OC2CCC2)c1)c1ccc(F)c(C(F)(F)F)c1] | (R)-N-(1-(3-cyclobutoxy-4-fluorophenyl)-1-(3-fluoro-5-(1,1,2,2-tetrafluoroethoxy)phenyl)-2-phenylethyl)-4-fluoro-3-(trifluoromethyl)benzamide | 4.12 LC (1) 686.3 [M + H]$^+$ | Procedures 3, 4, 5, 6, 7, 59 and 68 |
| 678 | 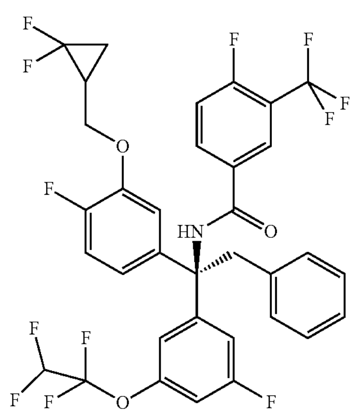 [SMILES: O=C(N[C@@](Cc1ccccc1)(c1cc(F)cc(OC(F)(F)C(F)F)c1)c1ccc(F)c(OCC2CC2(F)F)c1)c1ccc(F)c(C(F)(F)F)c1] | N-((1R)-1-(3-((2,2-difluorocyclopropyl)methoxy)-4-fluorophenyl)-1-(3-fluoro-5-(1,1,2,2-tetrafluoroethoxy)phenyl)-2-phenylethyl)-4-fluoro-3-(trifluoromethyl)benzamide | 3.94 LC (1) 722.3 [M + H]$^+$ | Procedures 3, 4, 5, 6, 7, 59 and 68 |

TABLE 10-continued

| Ex. No. | Structure | Name | Retention Time Min./ Molecular Mass | Prepared in the manner described in: |
|---|---|---|---|---|
| 679 | 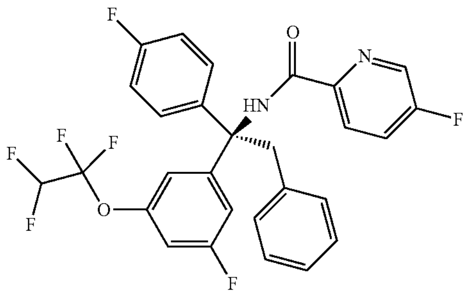 [SMILES: O=C(N[C@](Cc1ccccc1)(c1ccc(F)cc1)c1cc(F)cc(OC(F)(F)C(F)F)c1)c1ccc(F)cn1] | (R)-5-fluoro-N-(1-(3-fluoro-5-(1,1,2,2-tetrafluoroethoxy)phenyl)-1-(4-fluorophenyl)-2-phenylethyl)picolinamide | 4.13 LC (1) 549 [M + H]$^+$ | Procedures 3, 4, 5, 6 and 71 |
| 680 | 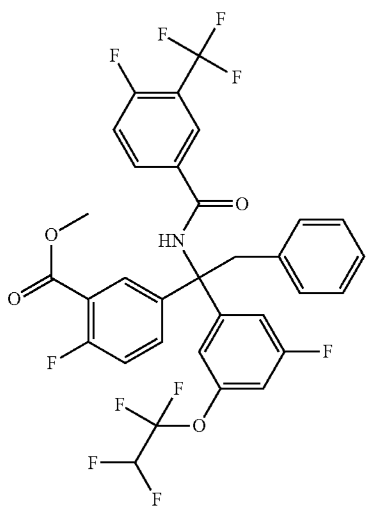 [SMILES: COC(=O)c1cc(C(Cc2ccccc2)(NC(=O)c2ccc(F)c(C(F)(F)F)c2)c2cc(F)cc(OC(F)(F)C(F)F)c2)ccc1F] | methyl 2-fluoro-5-(1-(4-fluoro-3-(trifluoromethyl)benzamido)-1-(3-fluoro-5-(1,1,2,2-tetrafluoroethoxy)phenyl)-2-phenylethyl)benzoate | 2.38 LC (9) 674 [M + H]$^+$ | Procedures 3, 62, 5, 6, 7, 56 and 57 |
| 681 | 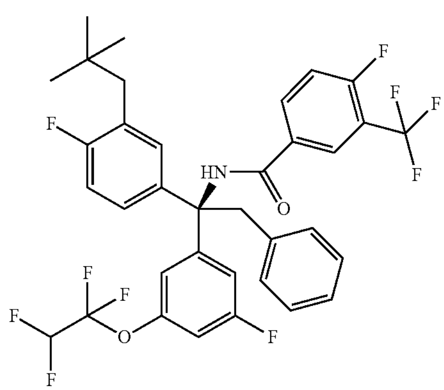 [SMILES: CC(C)(C)Cc1cc([C@@](Cc2ccccc2)(NC(=O)c2ccc(F)c(C(F)(F)F)c2)c2cc(F)cc(OC(F)(F)C(F)F)c2)ccc1F] | (R)-4-fluoro-N-(1-(4-fluoro-3-neopentylphenyl)-1-(3-fluoro-5-(1,1,2,2-tetrafluoroethoxy)phenyl)-2-phenylethyl)-3-(trifluoromethyl)benzamide | 4.60 LC (4) 686.43 [M + H]$^+$ | Procedures 3, 62, 5, 6, 122 and 7 |

TABLE 10-continued

| Ex. No. | Structure | Name | Retention Time Min./ Molecular Mass | Prepared in the manner described in: |
|---|---|---|---|---|
| 682 | 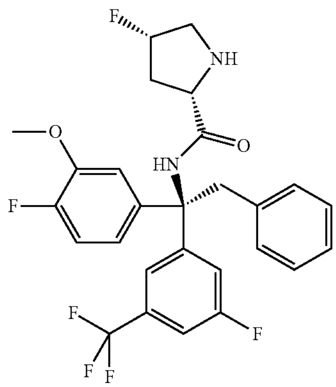 [SMILES: COc1cc([C@@](Cc2ccccc2)(NC(=O)[C@@H]2C[C@H](F)CN2)c2cc(F)cc(C(F)(F)F)c2)ccc1F] | (2S,4S)-4-fluoro-N-((R)-1-(4-fluoro-3-methoxyphenyl)-1-(3-fluoro-5-(trifluoromethyl)phenyl)-2-phenylethyl)pyrrolidine-2-carboxamide | 3.94 LC (3) 523.3 [M + H]$^+$ | Procedures 4, 5, 6, 71 and 39 |
| 683 | 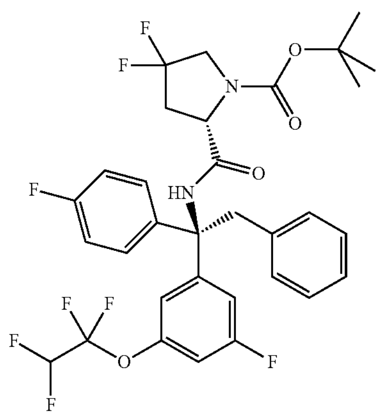 [SMILES: CC(C)(C)OC(=O)N1CC(F)(F)C[C@H]1C(=O)N[C@](Cc1ccccc1)(c1ccc(F)cc1)c1cc(F)cc(OC(F)(F)C(F)F)c1] | (S)-tert-butyl 4,4-difluoro-2-((R)-1-(3-fluoro-5-(1,1,2,2-tetrafluoroethoxy)phenyl)-1-(4-fluorophenyl)-2-phenylethylcarbamoyl)pyrrolidine-1-carboxylate | 4.218 LC (3) 659.4 [M + H]$^+$ | Procedures 3, 4, 5, 6 and 71 |
| 684 | 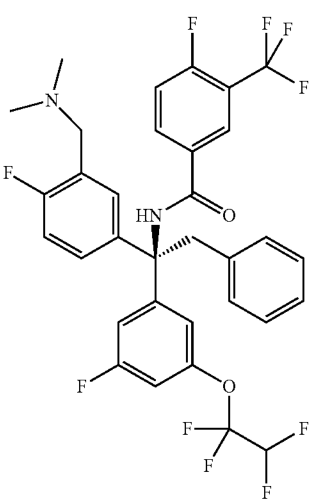 | (R)-N-(1-(3-((dimethylamino)methyl)-4-fluorophenyl)-1-(3-fluoro-5-(1,1,2,2-tetrafluoroethoxy)phenyl)-2-phenylethyl)-4-fluoro-3-(trifluoromethyl)benzamide | 4.48 LC (1) 632.4 [M + H]$^+$ | Procedures 3, 62, 5, 6, 7, 56, 57, 100 and 102 |

TABLE 10-continued

| Ex. No. | Structure | Name | Retention Time Min./ Molecular Mass | Prepared in the manner described in: |
|---|---|---|---|---|
| 685 | 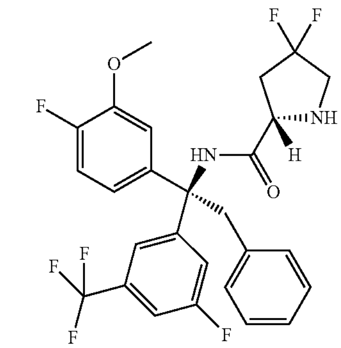 [SMILES: COc1cc([C@@](Cc2ccccc2)(NC(=O)[C@@H]2CC(F)(F)CN2)c2cc(F)cc(C(F)(F)F)c2)ccc1F] | (S)-4,4-difluoro-N-((R)-1-(4-fluoro-3-methoxyphenyl)-1-(3-fluoro-5-(trifluoromethyl)phenyl)-2-phenylethyl)pyrrolidine-2-carboxamide | 4.008 LC (3) 541.2 [M + H]$^+$ | Procedures 4, 5, 6, 71 and 39 |
| 686 | 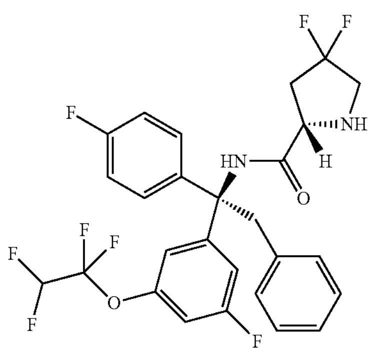 [SMILES: O=C(N[C@](Cc1ccccc1)(c1ccc(F)cc1)c1cc(F)cc(OC(F)(F)C(F)F)c1)[C@@H]1CC(F)(F)CN1] | (S)-4,4-difluoro-N-((R)-1-(3-fluoro-5-(1,1,2,2-tetrafluoroethoxy)phenyl)-1-(4-fluorophenyl)-2-phenylethyl)pyrrolidine-2-carboxamide | 3.963 LC (3) 559.3 [M + H]$^+$ | Procedures 4, 5, 6, 71 and 39 |
| 687 | 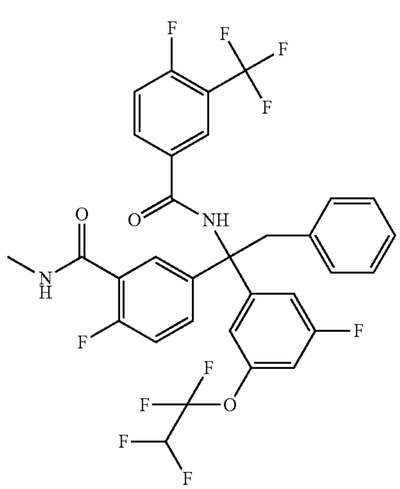 [SMILES: CNC(=O)c1cc(C(Cc2ccccc2)(NC(=O)c2ccc(F)c(C(F)(F)F)c2)c2cc(F)cc(OC(F)(F)C(F)F)c2)ccc1F] | 2-fluoro-5-(1-(4-fluoro-3-(trifluoromethyl)benzamido)-1-(3-fluoro-5-(1,1,2,2-tetrafluoroethoxy)phenyl)-2-phenylethyl)-N-methylbenzamide | 2.28 LC (9) 673 [M + H]$^+$ | Procedures 3, 4, 5, 6, 56, 57, 23 and 103 |

TABLE 10-continued

| Ex. No. | Structure | Name | Retention Time Min./ Molecular Mass | Prepared in the manner described in: |
|---|---|---|---|---|
| 688 | 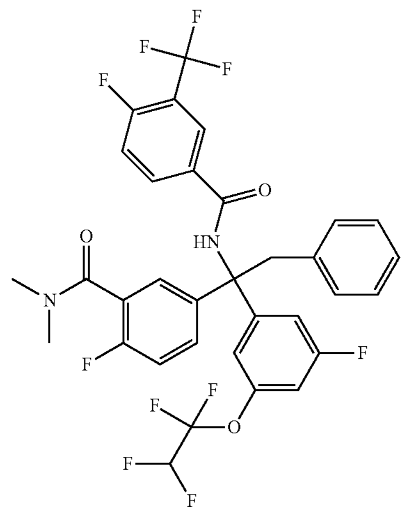 [SMILES: CN(C)C(=O)c1cc(C(Cc2ccccc2)(NC(=O)c2ccc(F)c(C(F)(F)F)c2)c2cc(F)cc(OC(F)(F)C(F)F)c2)ccc1F] | 2-fluoro-5-(1-(4-fluoro-3-(trifluoromethyl) benzamido)-1-(3-fluoro-5-(1,1,2,2-tetrafluoroethoxy)phenyl)-2-phenylethyl)-N,N-dimethylbenzamide | 4.213 LC (11) 687 [M + H]+ | Procedures 3, 4, 5, 6, 56, 57, 23 and 103 |
| 689 | 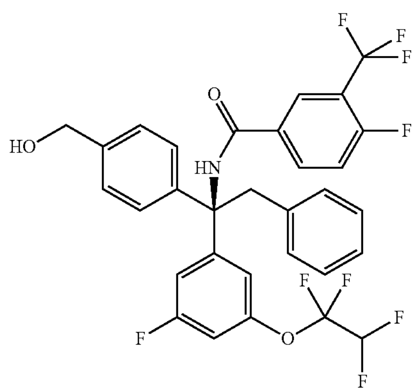 [SMILES: O=C(N[C@](Cc1ccccc1)(c1ccc(CO)cc1)c1cc(F)cc(OC(F)(F)C(F)F)c1)c1ccc(F)c(C(F)(F)F)c1] | (R)-4-fluoro-N-(1-(3-fluoro-5-(1,1,2,2-tetrafluoroethoxy)phenyl)-1-(4-(hydroxymethyl)phenyl)-2-phenylethyl)-3-(trifluoromethyl)benzamide | 1.90 LC (12) 628 [M + H]+ | Procedures 3, 4, 5, 6, 56, 57, and 100 |
| 690 | 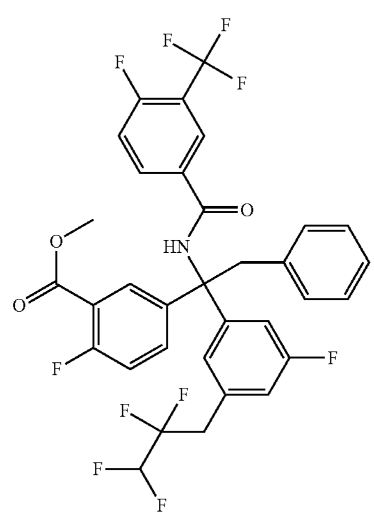 | methyl 2-fluoro-5-(1-(4-fluoro-3-(trifluoromethyl)benzamido)-1-(3-fluoro-5-(1,1,2,2-tetrafluoroethoxy)phenyl)-2-phenylethyl)benzoate | 2.353 LC (2) 674.0 [M + H]+ | Procedures 3, 62, 5, 6, 56 and 57 |

TABLE 10-continued

| Ex. No. | Structure | Name | Retention Time Min./ Molecular Mass | Prepared in the manner described in: |
|---|---|---|---|---|
| 691 | 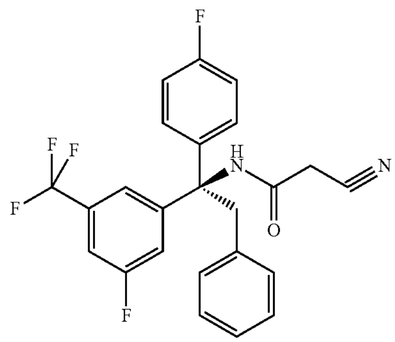 [SMILES: N#CCC(=O)N[C@](Cc1ccccc1)(c1ccc(F)cc1)c1cc(F)cc(C(F)(F)F)c1] | (R)-2-cyano-N-(1-(3-fluoro-5-(trifluoromethyl)phenyl)-1-(4-fluorophenyl)-2-phenylethyl)acetamide | 2.163 LC (1) 654.3 [M + H]$^+$ | Procedures 4, 5, 6 and 127 |
| 692 | 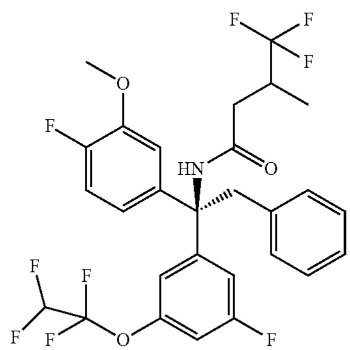 [SMILES: COc1cc([C@@](Cc2ccccc2)(NC(=O)CC(C)C(F)(F)F)c2cc(F)cc(OC(F)(F)C(F)F)c2)ccc1F] | 4,4,4-trifluoro-N-((R)-1-(4-fluoro-3-methoxyphenyl)-1-(3-fluoro-5-(1,1,2,2-tetrafluoroethoxy)phenyl)-2-phenylethyl)-3-methylbutanamide | 3.67 LC (1) 594.3 [M + H]$^+$ | Procedures 3, 4, 5, 6 and 128 |
| 693 | 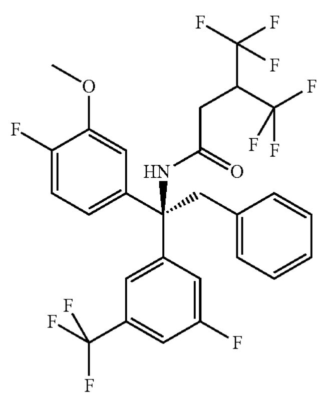 [SMILES: COc1cc([C@@](Cc2ccccc2)(NC(=O)CC(C(F)(F)F)C(F)(F)F)c2cc(F)cc(C(F)(F)F)c2)ccc1F] | (R)-4,4,4-trifluoro-N-(1-(4-fluoro-3-methoxyphenyl)-1-(3-fluoro-5-(trifluoromethyl)phenyl)-2-phenylethyl)-3-(trifluoromethyl)butanamide | 4.09 LC (1) 600.0 [M + H]$^+$ | Procedures 4, 5, 6 and 128 |
| 694 | 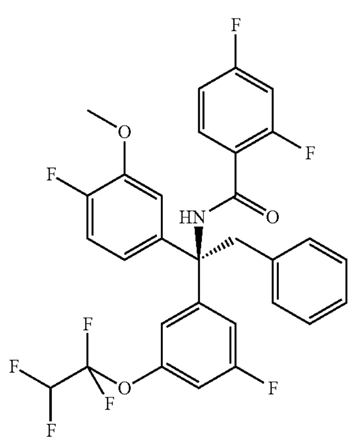 [SMILES: COc1cc([C@@](Cc2ccccc2)(NC(=O)c2ccc(F)cc2F)c2cc(F)cc(OC(F)(F)C(F)F)c2)ccc1F] | (R)-2,4-difluoro-N-(1-(4-fluoro-3-methoxyphenyl)-1-(3-fluoro-5-(1,1,2,2-tetrafluoroethoxy)phenyl)-2-phenylethyl)benzamide | 3.67 LC (1) 596.3 [M + H]$^+$ | Procedures 3, 4, 5, 6 and 7 |

TABLE 10-continued

| Ex. No. | Structure | Name | Retention Time Min./ Molecular Mass | Prepared in the manner described in: |
|---|---|---|---|---|
| 695 | 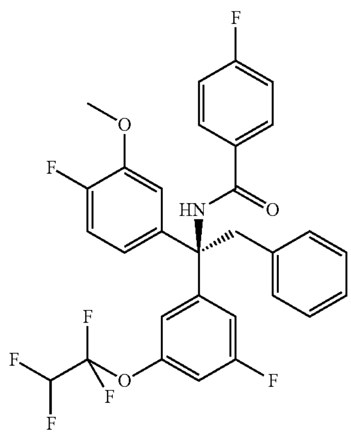 [SMILES: COc1cc([C@@](Cc2ccccc2)(NC(=O)c2ccc(F)cc2)c2cc(F)cc(OC(F)(F)C(F)F)c2)ccc1F] | (R)-4-fluoro-N-(1-(4-fluoro-3-methoxyphenyl)-1-(3-fluoro-5-(1,1,2,2-tetrafluoroethoxy)phenyl)-2-phenylethyl)benzamide | 3.61 LC (1) 578.1 [M + H]+ | Procedures 3, 4, 5, 6 and 7 |
| 696 | 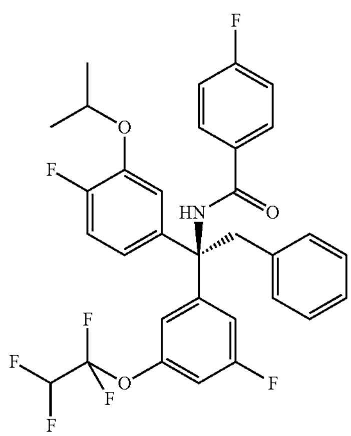 [SMILES: CC(C)Oc1cc([C@@](Cc2ccccc2)(NC(=O)c2ccc(F)cc2)c2cc(F)cc(OC(F)(F)C(F)F)c2)ccc1F] | (R)-4-fluoro-N-(1-(4-fluoro-3-isopropoxyphenyl)-1-(3-fluoro-5-(1,1,2,2-tetrafluoroethoxy)phenyl)-2-phenylethyl)benzamide | 3.836 LC (1) 606.5 [M + H]+ | Procedures 3, 4, 5, 6, 7, 59 and 68 |
| 697 | 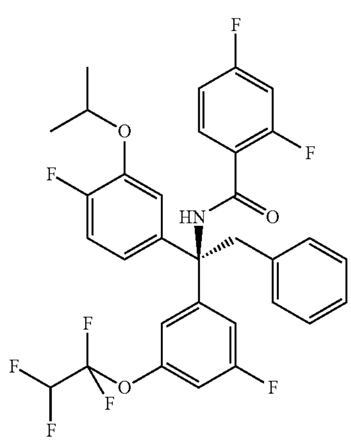 [SMILES: CC(C)Oc1cc([C@@](Cc2ccccc2)(NC(=O)c2ccc(F)cc2F)c2cc(F)cc(OC(F)(F)C(F)F)c2)ccc1F] | (R)-2,4-difluoro-N-(1-(4-fluoro-3-isopropoxyphenyl)-1-(3-fluoro-5-(1,1,2,2-tetrafluoroethoxy)phenyl)-2-phenylethyl)benzamide | 3.91 LC (1) 624.5 [M + H]+ | Procedures 4, 5, 6, 128, 59 and 68 |

TABLE 10-continued

| Ex. No. | Structure | Name | Retention Time Min./ Molecular Mass | Prepared in the manner described in: |
|---|---|---|---|---|
| 698 | 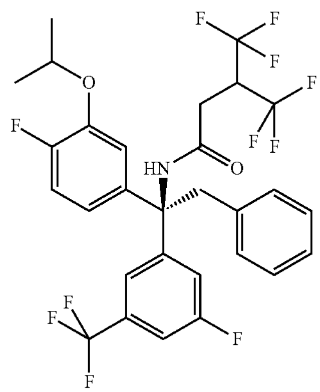 [SMILES: CC(C)Oc1cc([C@@](Cc2ccccc2)(NC(=O)CC(C(F)(F)F)C(F)(F)F)c2cc(F)cc(C(F)(F)F)c2)ccc1F] | (R)-4,4,4-trifluoro-N-(1-(4-fluoro-3-isopropoxyphenyl)-1-(3-fluoro-5-(trifluoromethyl)phenyl)-2-phenylethyl)-3-(trifluoromethyl)butanamide | 4.05 LC (1) 628.5 [M + H]$^+$ | Procedures 4, 5, 6, 128, 59 and 68 |
| 699 | 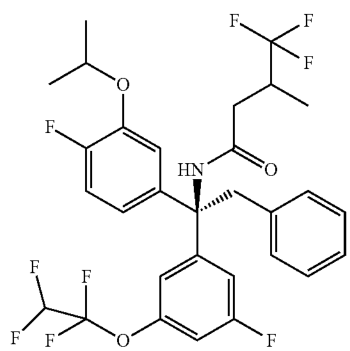 [SMILES: CC(C)Oc1cc([C@@](Cc2ccccc2)(NC(=O)CC(C)C(F)(F)F)c2cc(F)cc(OC(F)(F)C(F)F)c2)ccc1F] | 4,4,4-trifluoro-N-((R)-1-(4-fluoro-3-isopropoxyphenyl)-1-(3-fluoro-5-(1,1,2,2-tetrafluoroethoxy)phenyl)-2-phenylethyl)-3-methylbutanamide | 3.911 LC (1) 622.5 [M + H]$^+$ | Procedures 3, 4, 5, 6, 128, 59 and 68 |
| 700 | 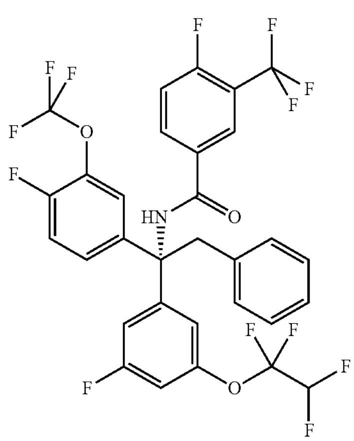 [SMILES: O=C(N[C@](Cc1ccccc1)(c1cc(F)cc(OC(F)(F)C(F)F)c1)c1ccc(F)c(OC(F)(F)F)c1)c1ccc(F)c(C(F)(F)F)c1] | (S)-4-fluoro-N-(1-(4-fluoro-3-(trifluoromethoxy)phenyl)-1-(3-fluoro-5-(1,1,2,2-tetrafluoroethoxy)phenyl)-2-phenylethyl)-3-(trifluoromethyl)benzamide | 4.36 LC (4) 700.32 [M + H]$^+$ | Procedures 3, 62, 5, 6 and 7 |

TABLE 10-continued

| Ex. No. | Structure | Name | Retention Time Min./ Molecular Mass | Prepared in the manner described in: |
|---|---|---|---|---|
| 701 | 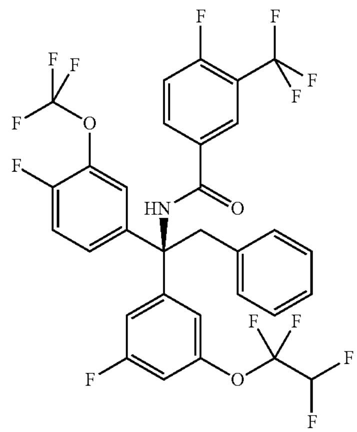 [SMILES: O=C(N[C@@](Cc1ccccc1)(c1cc(F)cc(OC(F)(F)C(F)F)c1)c1ccc(F)c(OC(F)(F)F)c1)c1ccc(F)c(C(F)(F)F)c1] | (R)-4-fluoro-N-(1-(4-fluoro-3-(trifluoromethoxy)phenyl)-1-(3-fluoro-5-(1,1,2,2-tetrafluoroethoxy)phenyl)-2-phenylethyl)-3-(trifluoromethyl)benzamide | 4.36 LC (4) 700.26 [M + H]$^+$ | Procedures 3, 62, 5, 6 and 7 |
| 702 | 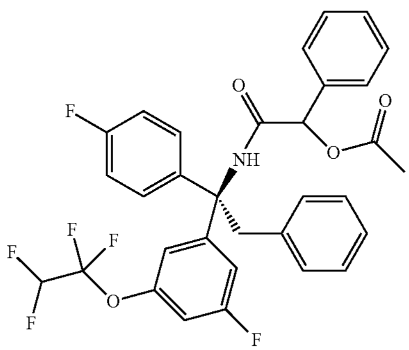 [SMILES: CC(=O)OC(C(=O)N[C@](Cc1ccccc1)(c1ccc(F)cc1)c1cc(F)cc(OC(F)(F)C(F)F)c1)c1ccccc1] | 2-((R)-1-(3-fluoro-5-(1,1,2,2-tetrafluoroethoxy)phenyl)-1-(4-fluorophenyl)-2-phenylethylamino)phenylethylacetate | 4.05 LC (1) 602.3 [M + H]$^+$ | Procedures 3, 4, 5, 6 and 7 |
| 703 | 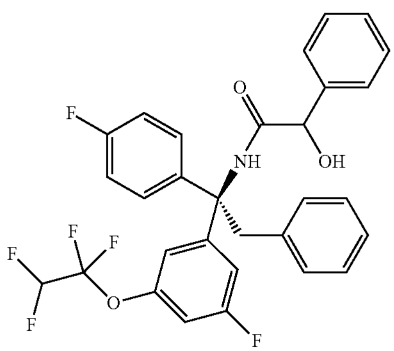 [SMILES: O=C(N[C@](Cc1ccccc1)(c1ccc(F)cc1)c1cc(F)cc(OC(F)(F)C(F)F)c1)C(O)c1ccccc1] | N-((R)-1-(3-fluoro-5-(1,1,2,2-tetrafluoroethoxy)phenyl)-1-(4-fluorophenyl)-2-phenylethyl)-2-hydroxy-2-phenylacetamide | 3.82 LC (1) 560.2 [M + H]$^+$ | Procedures 3, 4, 5, 6, 7 and 23 |
| 704 | 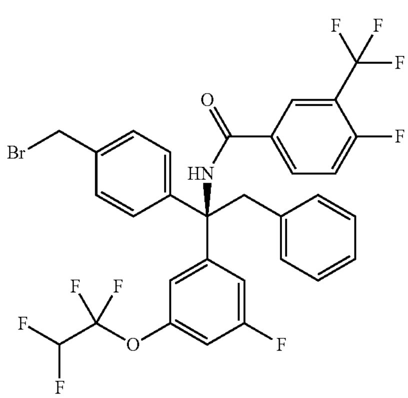 [SMILES: O=C(N[C@](Cc1ccccc1)(c1ccc(CBr)cc1)c1cc(F)cc(OC(F)(F)C(F)F)c1)c1ccc(F)c(C(F)(F)F)c1] | (R)-N-(1-(4-(bromomethyl)phenyl)-1-(3-fluoro-5-(1,1,2,2-tetrafluoroethoxy)phenyl)-2-phenylethyl)-4-fluoro-3-(trifluoromethyl)benzamide | 1.77 LC (9) 602.3 [M + H]$^+$ | Procedures 3, 4, 5, 6, 56, 57, 100 and 32 |

TABLE 10-continued

| Ex. No. | Structure | Name | Retention Time Min./ Molecular Mass | Prepared in the manner described in: |
|---|---|---|---|---|
| 705 | 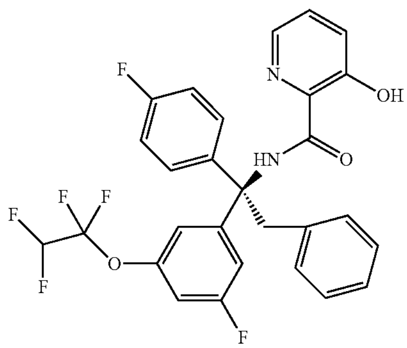 [SMILES: O=C(N[C@](Cc1ccccc1)(c1ccc(F)cc1)c1cc(F)cc(OC(F)(F)C(F)F)c1)c1ncccc1O] | (R)-N-(1-(3-fluoro-5-(1,1,2,2-tetrafluoroethoxy)phenyl)-1-(4-fluorophenyl)-2-phenylethyl)-3-hydroxypicolinamide | 2.22 LC (2) 547.4 $[M + H]^+$ | Procedures 3, 4, 5, 6 and 71 |
| 706 | 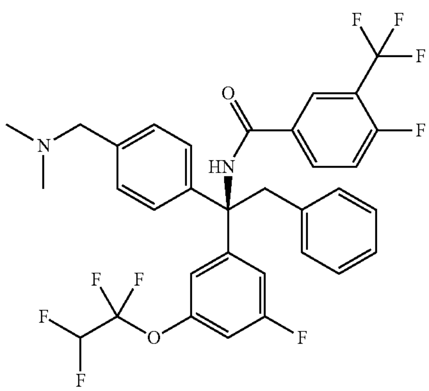 [SMILES: CN(C)Cc1ccc([C@@](Cc2ccccc2)(NC(=O)c2ccc(F)c(C(F)(F)F)c2)c2cc(F)cc(OC(F)(F)C(F)F)c2)cc1] | (R)-N-(1-(4-((dimethylamino)methyl)phenyl)-1-(3-fluoro-5-(1,1,2,2-tetrafluoroethoxy)phenyl)-2-phenylethyl)-4-fluoro-3-(trifluoromethyl)benzamide | 0.89 LC (12) 655 $[M + H]^+$ | Procedures 3, 4, 5, 6, 7, 56, 57, 100 and 102 |
| 707 | 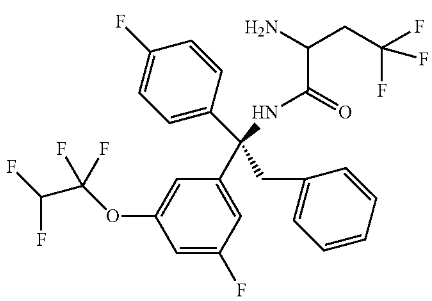 [SMILES: NC(CC(F)(F)F)C(=O)N[C@](Cc1ccccc1)(c1ccc(F)cc1)c1cc(F)cc(OC(F)(F)C(F)F)c1] | 2-amino-4,4,4-trifluoro-N-((R)-1-(3-fluoro-5-(1,1,2,2-tetrafluoroethoxy)phenyl)-1-(4-fluorophenyl)-2-phenylethyl)butanamide | 3.1 LC (1) 565.2 $[M + H]^+$ | Procedures 3, 4, 5, 6, 139, 140 and 141 |
| 708 | 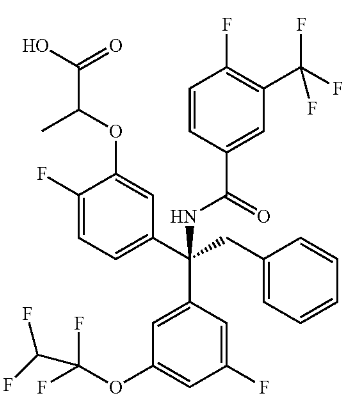 [SMILES: CC(Oc1cc([C@@](Cc2ccccc2)(NC(=O)c2ccc(F)c(C(F)(F)F)c2)c2cc(F)cc(OC(F)(F)C(F)F)c2)ccc1F)C(=O)O] | 2-(2-fluoro-5-((R)-1-(4-fluoro-3-(trifluoromethyl)benzamido)-1-(3-fluoro-5-(1,1,2,2-tetrafluoroethoxy)phenyl)-2-phenylethyl)phenoxy)propanoic acid | 3.51 LC (1) 704.5 $[M + H]^+$ | Procedures 3, 4, 5, 6, 7, 59, 68 and 23 |

TABLE 10-continued

| Ex. No. | Structure | Name | Retention Time Min./ Molecular Mass | Prepared in the manner described in: |
|---|---|---|---|---|
| 709 | 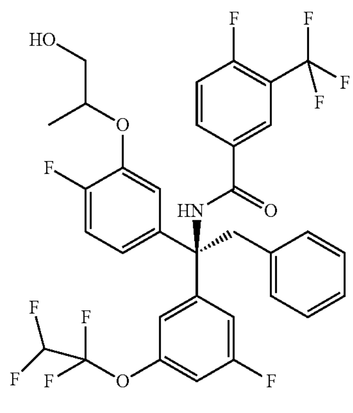 | 4-fluoro-N-((1R)-1-(4-fluoro-3-(1-hydroxypropan-2-yloxy)phenyl)-1-(3-fluoro-5-(1,1,2,2-tetrafluoroethoxy)phenyl)-2-phenylethyl)-3-(trifluoromethyl)benzamide | 3.588 LC (1) 690.6 [M + H]$^+$ | Procedures 3, 4, 5, 6, 7, 59, 68, 23 and 100 |
| 710 | 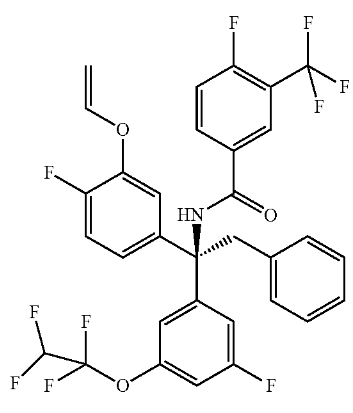 | (R)-4-fluoro-N-(1-(4-fluoro-3-(vinyloxy)phenyl)-1-(3-fluoro-5-(1,1,2,2-tetrafluoroethoxy)phenyl)-2-phenylethyl)-3-(trifluoromethyl)benzamide | 3.948 LC (1) 658.2 [M + H]$^+$ | Procedures 3, 4, 5, 6, 7, 59 and 106 |
| 711 | 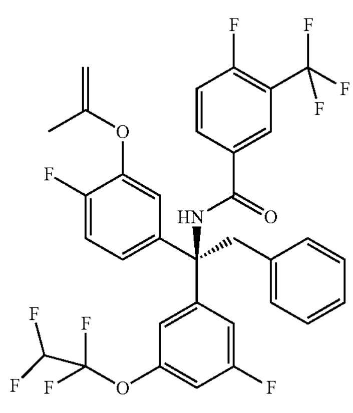 | (R)-4-fluoro-N-(1-(4-fluoro-3-(prop-1-en-2-yloxy)phenyl)-1-(3-fluoro-5-(1,1,2,2-tetrafluoroethoxy)phenyl)-2-phenylethyl)-3-(trifluoromethyl)benzamide | 4.053 LC (1) 672.3 [M + H]$^+$ | Procedures 3, 4, 5, 6, 7, 59 and 68 |

TABLE 10-continued

| Ex. No. | Structure | Name | Retention Time Min./ Molecular Mass | Prepared in the manner described in: |
|---|---|---|---|---|
| 712 | 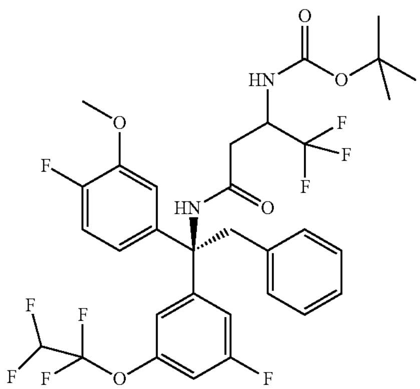 [SMILES: COc1cc([C@@](Cc2ccccc2)(NC(=O)CC(NC(=O)OC(C)(C)C)C(F)(F)F)c2cc(F)cc(OC(F)(F)C(F)F)c2)ccc1F] | tert-butyl 1,1,1-trifluoro-4-((R)-1-(4-fluoro-3-methoxyphenyl)-1-(3-fluoro-5-(1,1,2,2-tetrafluoroethoxy)phenyl)-2-phenylethylamino)-4-oxobutan-2-ylcarbamate | 3.7 LC (1) 695.3 [M + H]$^+$ | Procedures 3, 4, 5, 6 and 128 |
| 713 | 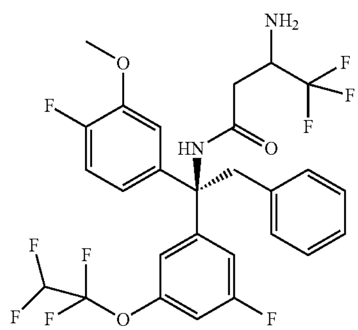 [SMILES: COc1cc([C@@](Cc2ccccc2)(NC(=O)CC(N)C(F)(F)F)c2cc(F)cc(OC(F)(F)C(F)F)c2)ccc1F] | 3-amino-4,4,4-trifluoro-N-((R)-1-(4-fluoro-3-methoxyphenyl)-1-(3-fluoro-5-(1,1,2,2-tetrafluoroethoxy)phenyl)-2-phenylethyl)butanamide | 2.518 LC (1) 595.5 [M + H]$^+$ | Procedures 3, 4, 5, 6, 128 and 39 |
| 714 | 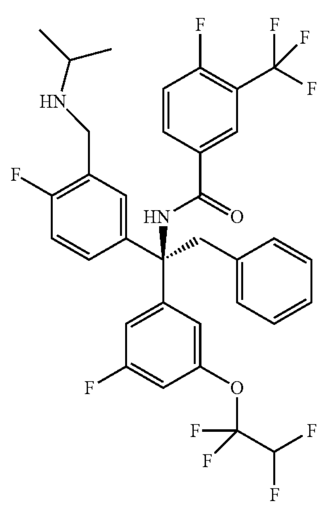 [SMILES: CC(C)NCc1cc([C@@](Cc2ccccc2)(NC(=O)c2ccc(F)c(C(F)(F)F)c2)c2cc(F)cc(OC(F)(F)C(F)F)c2)ccc1F] | (R)-4-fluoro-N-(1-(4-fluoro-3-((isopropylamino)methyl)phenyl)-1-(3-fluoro-5-(1,1,2,2-tetrafluoroethoxy)phenyl)-2-phenylethyl)-3-(trifluoromethyl)benzamide | 8.099 LC (7) 687 [M + H]$^+$ | Procedures 3, 62, 5, 6, 146, 7, 147 and 148 |

TABLE 10-continued

| Ex. No. | Structure | Name | Retention Time Min./ Molecular Mass | Prepared in the manner described in: |
|---|---|---|---|---|
| 715 | 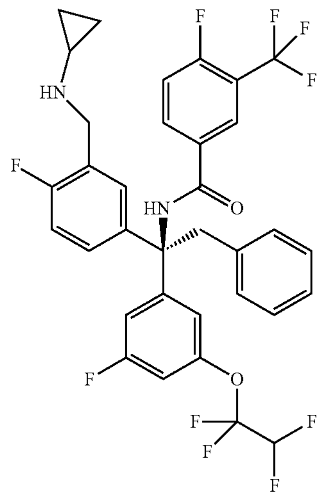 [SMILES: O=C(N[C@@](Cc1ccccc1)(c1cc(F)cc(OC(F)(F)C(F)F)c1)c1ccc(F)c(CNC2CC2)c1)c1ccc(F)c(C(F)(F)F)c1] | (R)-N-(1-(3-((cyclopropylamino)methyl)-4-fluorophenyl)-1-(3-fluoro-5-(1,1,2,2-tetrafluoroethoxy)phenyl)-2-phenylethyl)-4-fluoro-3-(trifluoromethyl)benzamide | 3.656 LC (15) 685 [M + H]+ | Procedures 3, 62, 5, 6, 146, 7, 147 and 148 |
| 716 | 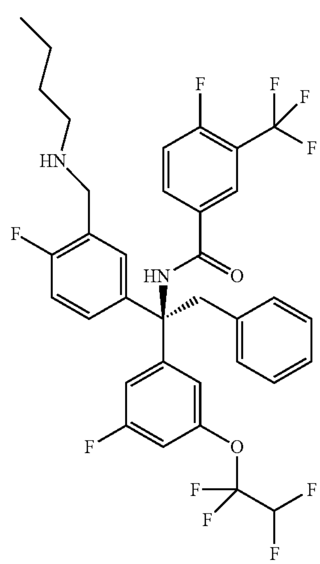 [SMILES: CCCCNCc1cc([C@@](Cc2ccccc2)(NC(=O)c2ccc(F)c(C(F)(F)F)c2)c2cc(F)cc(OC(F)(F)C(F)F)c2)ccc1F] | (R)-N-(1-(3-((butylamino)methyl)-4-fluorophenyl)-1-(3-fluoro-5-(1,1,2,2-tetrafluoroethoxy)phenyl)-2-phenylethyl)-4-fluoro-3-(trifluoromethyl)benzamide | 3.723 LC (15) 701 [M + H]+ | Procedures 3, 62, 5, 6, 146, 7, 147 and 148 |

TABLE 10-continued

| Ex. No. | Structure | Name | Retention Time Min./ Molecular Mass | Prepared in the manner described in: |
|---|---|---|---|---|
| 717 | 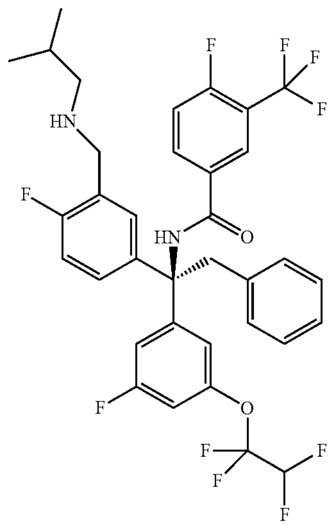 [SMILES: CC(C)CNCc1cc([C@@](Cc2ccccc2)(NC(=O)c2ccc(F)c(C(F)(F)F)c2)c2cc(F)cc(OC(F)(F)C(F)F)c2)ccc1F] | (R)-4-fluoro-N-(1-(4-fluoro-3-((isobutylamino)methyl)phenyl)-1-(3-fluoro-5-(1,1,2,2-tetrafluoroethoxy)phenyl)-2-phenylethyl)-3-(trifluoromethyl)benzamide | 3.725 LC (15) 701 [M + H]+ | Procedures 3, 62, 5, 6, 146, 7, 147 and 148 |
| 718 | 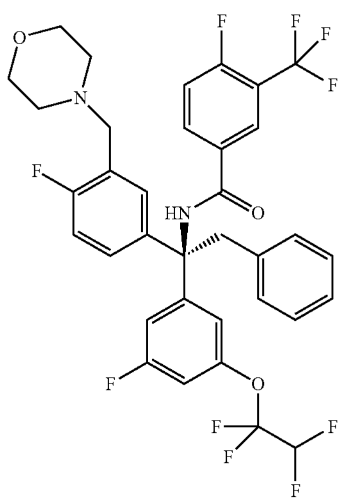 [SMILES: O=C(N[C@@](Cc1ccccc1)(c1cc(F)cc(OC(F)(F)C(F)F)c1)c1ccc(F)c(CN2CCOCC2)c1)c1ccc(F)c(C(F)(F)F)c1] | (R)-4-fluoro-N-(1-(4-fluoro-3-(morpholinomethyl)phenyl)-1-(3-fluoro-5-(1,1,2,2-tetrafluoroethoxy)phenyl)-2-phenylethyl)-3-(trifluoromethyl)benzamide | 3.650 LC (15) 715 [M + H]+ | Procedures 3, 62, 5, 6, 146, 7, 147 and 148 |
| 719 | 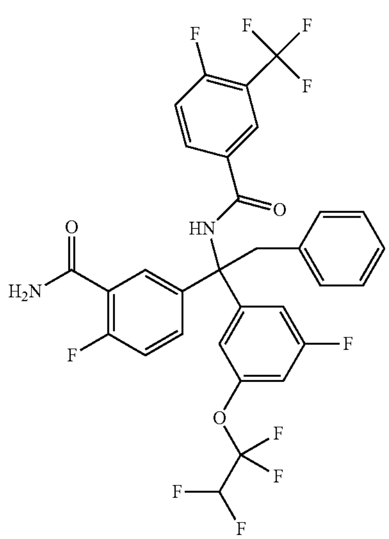 [SMILES: NC(=O)c1cc(C(Cc2ccccc2)(NC(=O)c2ccc(F)c(C(F)(F)F)c2)c2cc(F)cc(OC(F)(F)C(F)F)c2)ccc1F] | N-(1-(3-carbamoyl-4-fluorophenyl)-1-(3-fluoro-5-(1,1,2,2-tetrafluoroethoxy)phenyl)-2-phenylethyl)-4-fluoro-3-(trifluoromethyl)benzamide | 4.243 LC (13) 659 [M + H]+ | Procedures 3, 62, 5, 6, 7, 56, 57, 23 and 136 |

TABLE 10-continued

| Ex. No. | Structure | Name | Retention Time Min./ Molecular Mass | Prepared in the manner described in: |
|---|---|---|---|---|
| 720 | 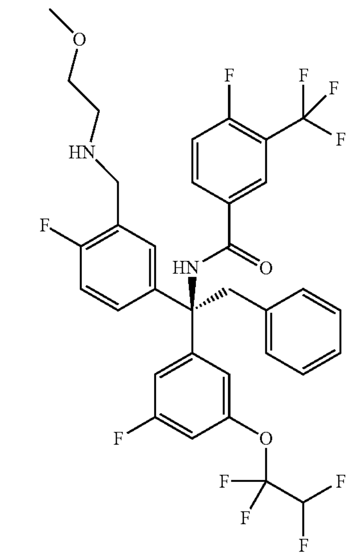 [SMILES: COCCNCc1cc([C@@](Cc2ccccc2)(NC(=O)c2ccc(F)c(C(F)(F)F)c2)c2cc(F)cc(OC(F)(F)C(F)F)c2)ccc1F] | (R)-4-fluoro-N-(1-(4-fluoro-3-((2-methoxyethylamino)methyl)phenyl)-1-(3-fluoro-5-(1,1,2,2-tetrafluoroethoxy)phenyl)-2-phenylethyl)-3-(trifluoromethyl)benzamide | 3.636 LC (15) 703 [M + H]+ | Procedures 3, 62, 5, 6, 146, 7, 147 and 148 |
| 721 | 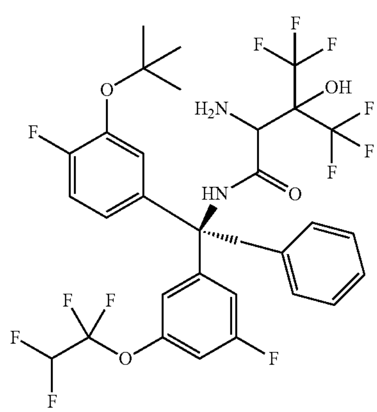 [SMILES: CC(C)(C)Oc1cc([C@@](Cc2ccccc2)(NC(=O)C(N)C(O)(C(F)(F)F)C(F)(F)F)c2cc(F)cc(OC(F)(F)C(F)F)c2)ccc1F] | 2-amino-N-((R)-1-(3-tert-butoxy-4-fluorophenyl)-1-(3-fluoro-5-(1,1,2,2-tetrafluoroethoxy)phenyl)-2-phenylethyl)-4,4,4-trifluoro-3-hydroxy-3-(trifluoromethyl)butanamide | 2.09 LC (1) 721.0 [M + H]+ | Procedures 3, 109, 110, 111, 112, 108, 90, 91 and 92 |
| 722 | 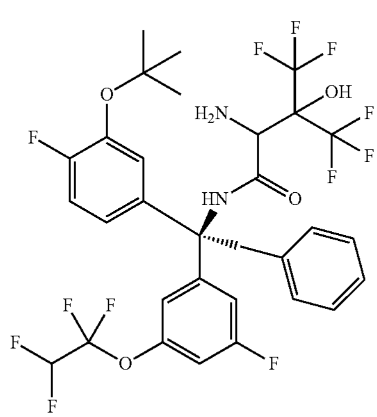 [SMILES: CC(C)(C)Oc1cc([C@@](Cc2ccccc2)(NC(=O)C(N)C(O)(C(F)(F)F)C(F)(F)F)c2cc(F)cc(OC(F)(F)C(F)F)c2)ccc1F] | 2-amino-N-((R)-1-(3-tert-butoxy-4-fluorophenyl)-1-(3-fluoro-5-(1,1,2,2-tetrafluoroethoxy)phenyl)-2-phenylethyl)-4,4,4-trifluoro-3-hydroxy-3-(trifluoromethyl)butanamide | 2.11 LC (1) 721.0 [M + H]+ | Procedures 3, 109, 110, 111, 112, 108, 90, 91 and 92 |

TABLE 10-continued

| Ex. No. | Structure | Name | Retention Time Min./ Molecular Mass | Prepared in the manner described in: |
|---|---|---|---|---|
| 723 | 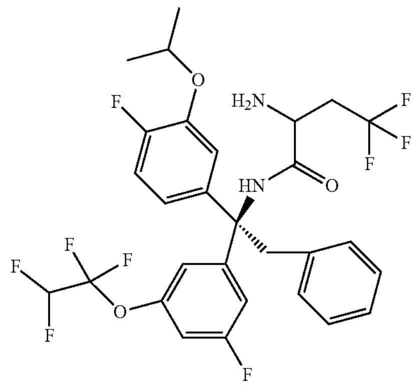 [SMILES: CC(C)Oc1cc([C@@](Cc2ccccc2)(NC(=O)C(N)CC(F)(F)F)c2cc(F)cc(OC(F)(F)C(F)F)c2)ccc1F] | 2-amino-4,4,4-trifluoro-N-((R)-1-(4-fluoro-3-isopropoxyphenyl)-1-(3-fluoro-5-(1,1,2,2-tetrafluoroethoxy)phenyl)-2-phenylethyl)butanamide | 2.01 LC (2) 623.4 [M + H]⁺ | Procedures 3, 4, 5, 6, 59, 68, 139, 140 and 141 |
| 724 | 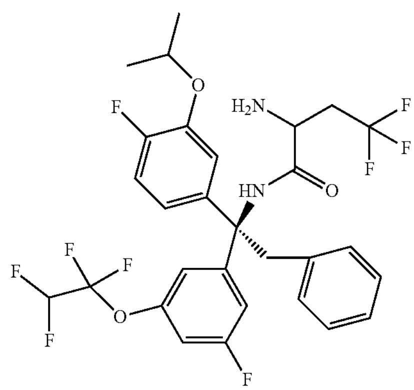 [SMILES: CC(C)Oc1cc([C@@](Cc2ccccc2)(NC(=O)C(N)CC(F)(F)F)c2cc(F)cc(OC(F)(F)C(F)F)c2)ccc1F] | 2-amino-4,4,4-trifluoro-N-((R)-1-(4-fluoro-3-isopropoxyphenyl)-1-(3-fluoro-5-(1,1,2,2-tetrafluoroethoxy)phenyl)-2-phenylethyl)butanamide | 2.04 LC (2) 623.4 [M + H]⁺ | Procedures 3, 4, 5, 6, 59, 68, 139, 140 and 141 |
| 725 | 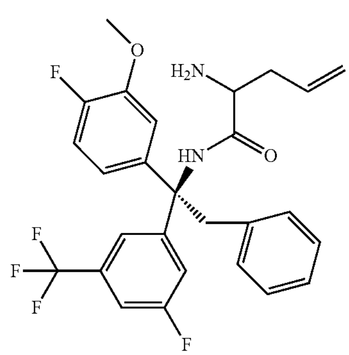 [SMILES: C=CCC(N)C(=O)N[C@@](Cc1ccccc1)(c1cc(F)cc(C(F)(F)F)c1)c1ccc(F)c(OC)c1] | 2-amino-N-((R)-1-(4-fluoro-3-methoxyphenyl)-1-(3-fluoro-5-(trifluoromethyl)phenyl)-2-phenylethyl)pent-4-enamide | 2.2 LC (2) 505.2 [M + H]⁺ | Procedures 4, 5, 6, 140 and 39 |

TABLE 10-continued

| Ex. No. | Structure | Name | Retention Time Min./ Molecular Mass | Prepared in the manner described in: |
|---|---|---|---|---|
| 726 | 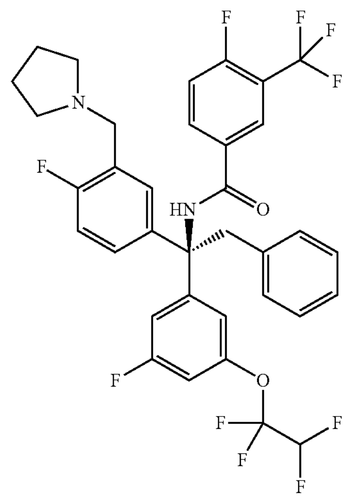 [SMILES: O=C(N[C@@](Cc1ccccc1)(c1cc(F)cc(OC(F)(F)C(F)F)c1)c1ccc(F)c(CN2CCCC2)c1)c1ccc(F)c(C(F)(F)F)c1] | (R)-4-fluoro-N-(1-(4-fluoro-3-(pyrrolidin-1-ylmethyl)phenyl)-1-(3-fluoro-5-(1,1,2,2-tetrafluoroethoxy)phenyl)-2-phenylethyl)-3-(trifluoromethyl)benzamide | 3.606 LC (15) 699 [M + H]+ | Procedures 3, 62, 5, 6, 146, 7, 147 and 148 |
| 727 | 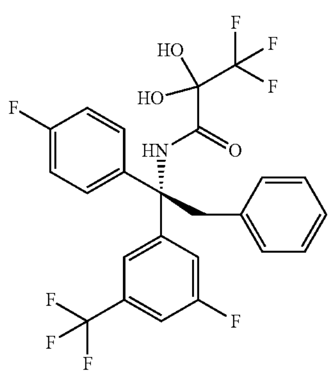 [SMILES: O=C(N[C@@](Cc1ccccc1)(c1ccc(F)cc1)c1cc(F)cc(C(F)(F)F)c1)C(O)(O)C(F)(F)F] | (S)-3,3,3-trifluoro-N-(1-(3-fluoro-5-(trifluoromethyl)phenyl)-1-(4-fluorophenyl)-2-phenylethyl)-2,2-dihydroxypropanamide | 1.70 LC (14) 518.1 [M − H]− | Procedures 3, 62, 5, 6, 146, 7, 147 and 148 |
| 728 | 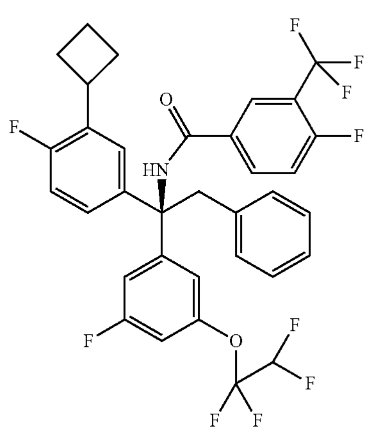 [SMILES: O=C(N[C@@](Cc1ccccc1)(c1cc(F)cc(OC(F)(F)C(F)F)c1)c1ccc(F)c(C2CCC2)c1)c1ccc(F)c(C(F)(F)F)c1] | (R)-N-(1-(3-cyclobutyl-4-fluorophenyl)-1-(3-fluoro-5-(1,1,2,2-tetrafluoroethoxy)phenyl)-2-phenylethyl)-4-fluoro-3-(trifluoromethyl) benzamide | 8.654 LC (16) 670.29 [M + H]+ | Procedures 3, 62, 5, 6, 7 and 121 |

TABLE 10-continued

| Ex. No. | Structure | Name | Retention Time Min./ Molecular Mass | Prepared in the manner described in: |
|---|---|---|---|---|
| 729 | 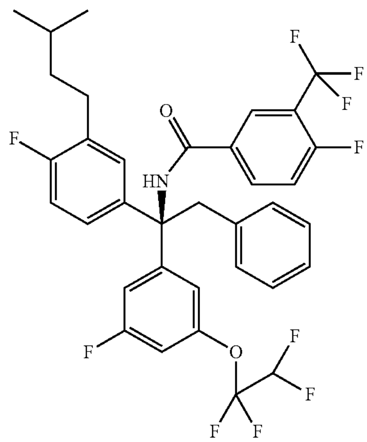 [SMILES: CC(C)CCc1cc([C@@](Cc2ccccc2)(NC(=O)c2ccc(F)c(C(F)(F)F)c2)c2cc(F)cc(OC(F)(F)C(F)F)c2)ccc1F] | (R)-4-fluoro-N-(1-(4-fluoro-3-isopentylphenyl)-1-(3-fluoro-5-(1,1,2,2-tetrafluoroethoxy)phenyl)-2-phenylethyl)-3-(trifluoromethyl)benzamide | 4.62 LC (4) 686.33 [M + H]$^+$ | Procedures 3, 62, 5, 6, 7 and 162 |
| 730 | 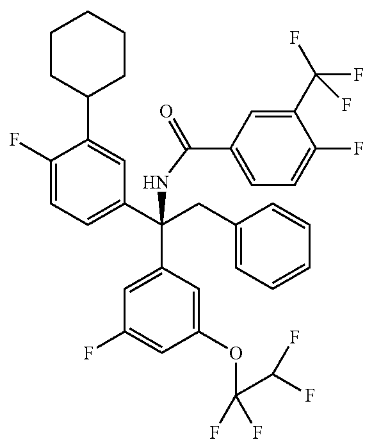 [SMILES: O=C(N[C@@](Cc1ccccc1)(c1cc(F)cc(OC(F)(F)C(F)F)c1)c1ccc(F)c(C2CCCCC2)c1)c1ccc(F)c(C(F)(F)F)c1] | (R)-N-(1-(3-cyclohexyl-4-fluorophenyl)-1-(3-fluoro-5-(1,1,2,2-tetrafluoroethoxy)phenyl)-2-phenylethyl)-4-fluoro-3-(trifluoromethyl)benzamide | 4.67 LC (4) 698.37 [M + H]$^+$ | Procedures 3, 62, 5, 6, 7 and 162 |
| 731 | 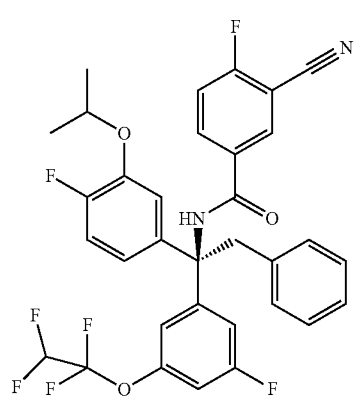 [SMILES: CC(C)Oc1cc([C@@](Cc2ccccc2)(NC(=O)c2ccc(F)c(C#N)c2)c2cc(F)cc(OC(F)(F)C(F)F)c2)ccc1F] | (R)-3-cyano-4-fluoro-N-(1-(4-fluoro-3-isopropoxyphenyl)-1-(3-fluoro-5-(1,1,2,2-tetrafluoroethoxy)phenyl)-2-phenylethyl)benzamide | 3.785 LC (1) 631.6 [M + H]$^+$ | Procedures 3, 4, 5, 6, 59, 68 and 7 |

TABLE 10-continued

| Ex. No. | Structure | Name | Retention Time Min./ Molecular Mass | Prepared in the manner described in: |
|---|---|---|---|---|
| 732 | 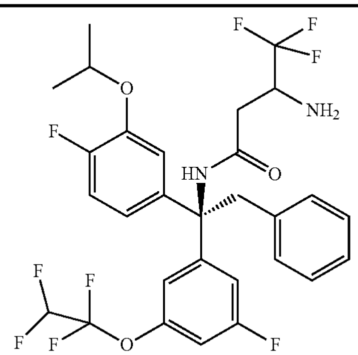 | 3-amino-4,4,4-trifluoro-N-((R)-1-(4-fluoro-3-isopropoxyphenyl)-1-(3-fluoro-5-(1,1,2,2-tetrafluoroethoxy)phenyl)-2-phenylethyl) butanamide | 2.69 LC (1) 623.5 [M + H]+ | Procedures 3, 4, 5, 6, 59, 68, 143 and 144 |
| 733 | 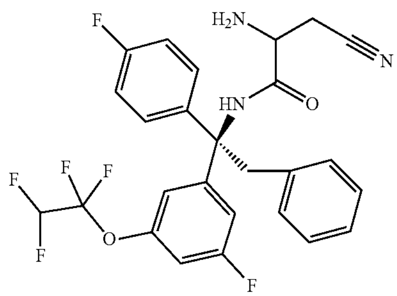 [SMILES: N#CCC(N)C(=O)N[C@](Cc1ccccc1)(c1ccc(F)cc1)c1cc(F)cc(OC(F)(F)C(F)F)c1] | 2-amino-3-cyano-N-((R)-1-(3-fluoro-5-(1,1,2,2-tetrafluoroethoxy)phenyl)-1-(4-fluorophenyl)-2-phenylethyl)propanamide | 1.83 LC (2) 522.3 [M + H]+ | Procedures 3, 4, 5, 6, 140 and 39 |
| 734 | 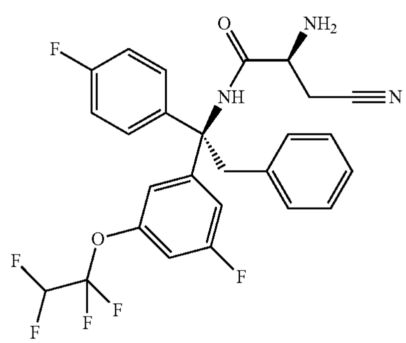 [SMILES: N#CC[C@H](N)C(=O)N[C@](Cc1ccccc1)(c1ccc(F)cc1)c1cc(F)cc(OC(F)(F)C(F)F)c1] | (S)-2-amino-3-cyano-N-((R)-1-(3-fluoro-5-(1,1,2,2-tetrafluoroethoxy)phenyl)-1-(4-fluorophenyl)-2-phenylethyl)propanamide | 3.12 LC (8) 522.0 [M + H]+ | Procedures 3, 4, 5, 6, 140 and 39 |

TABLE 11

| Ex. No. | Structure | Name | Retention Time Min./ Molecular Mass | Prepared in the manner described in: |
|---|---|---|---|---|
| 735 | 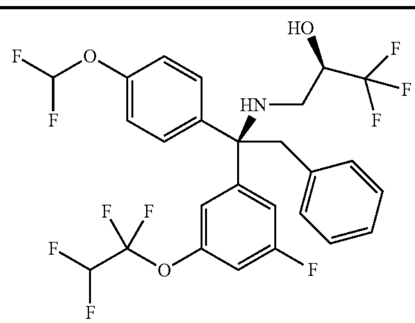 | (R)-3-((R)-1-(4-(difluoromethoxy)phenyl)-1-(3-fluoro-5-(1,1,2,2-tetrafluoroethoxy) phenyl)-2-phenylethylamino)-1,1,1-trifluoropropan-2-ol | 3.97 LC (4) 586.39 [M + H]+ | Procedures 3, 4, 5, 6, 27, and 8 |

TABLE 11-continued

| Ex. No. | Structure | Name | Retention Time Min./ Molecular Mass | Prepared in the manner described in: |
|---|---|---|---|---|
| 736 | 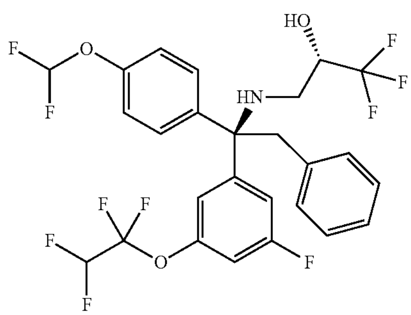 [SMILES: O[C@@H](CN[C@](Cc1ccccc1)(c1ccc(OC(F)F)cc1)c1cc(F)cc(OC(F)(F)C(F)F)c1)C(F)(F)F] | (S)-3-((R)-1-(4-(difluoromethoxy)phenyl)-1-(3-fluoro-5-(1,1,2,2-tetrafluoroethoxy)phenyl)-2-phenylethylamino)-1,1,1-trifluoropropan-2-ol | 3.98 LC (4) 586.41 [M + H]$^+$ | Procedures 3, 4, 5, 6, 27, and 8 |
| 737 | 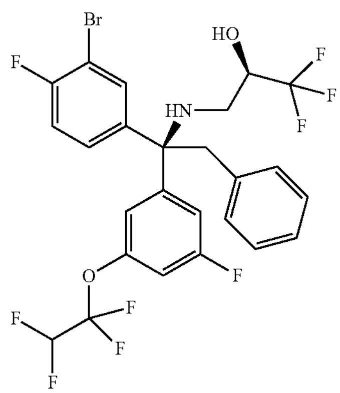 [SMILES: O[C@H](CN[C@@](Cc1ccccc1)(c1cc(F)cc(OC(F)(F)C(F)F)c1)c1ccc(F)c(Br)c1)C(F)(F)F] | (R)-3-((S)-1-(3-bromo-4-fluorophenyl)-1-(3-fluoro-5-(1,1,2,2-tetrafluoroethoxy(phenyl)-2-phenylethylamino)-1,1,1-trifluoropropan-2-ol | 4.23 LC (4) 616.31 [M + H]$^+$ | Procedures 3, 62, 5, 6, 27 and 8 |
| 738 | 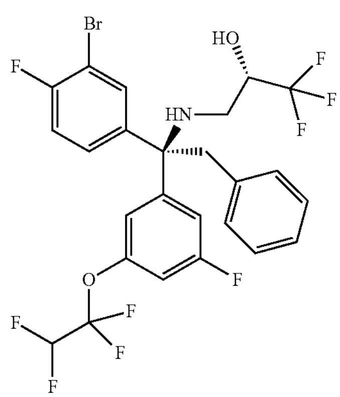 [SMILES: O[C@@H](CN[C@@](Cc1ccccc1)(c1cc(F)cc(OC(F)(F)C(F)F)c1)c1ccc(F)c(Br)c1)C(F)(F)F] | (S)-3-((S)-1-(3-bromo-4-fluorophenyl)-1-(3-fluoro-5-(1,1,2,2-tetrafluoroethoxy)phenyl)-2-phenylethylamino)-1,1,1-trifluoropropan-2-ol | 4.21 LC (4) 616.32 [M + H]$^+$ | Procedures 3, 62, 5, 6, 27 and 8 |
| 739 | 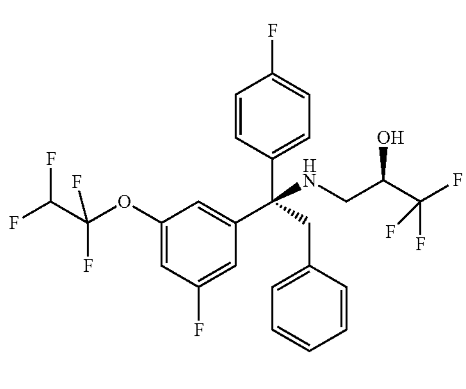 [SMILES: O[C@H](CN[C@](Cc1ccccc1)(c1ccc(F)cc1)c1cc(F)cc(OC(F)(F)C(F)F)c1)C(F)(F)F] | (R)-1,1,1-trifluoro-3-((R)-1-(3-fluoro-5-(1,1,2,2-tetrafluoroethoxy)pheny)-1-(4-fluorophenyl)-2-phenylethylamino)propan-2-ol | 2.098 LC (2) 538.2 [M + H]$^+$ | Procedures 3, 4, 5, 6, 27 and 8 |

TABLE 11-continued

| Ex. No. | Structure | Name | Retention Time Min./ Molecular Mass | Prepared in the manner described in: |
|---|---|---|---|---|
| 740 | 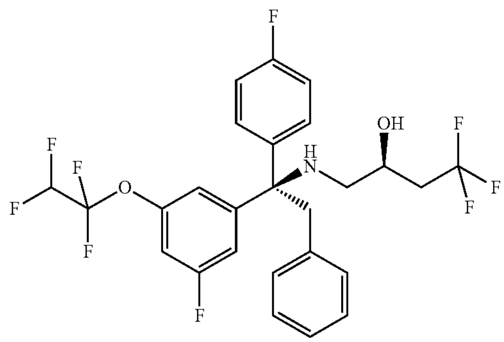 [SMILES: O[C@H](CN[C@](Cc1ccccc1)(c1ccc(F)cc1)c1cc(F)cc(OC(F)(F)C(F)F)c1)CC(F)(F)F] | (S)-4,4,4-trifluoro-1-(R)-1-(3-fluoro-5-(1,1,2,2-tetrafluoroethoxy)phenyl)-1-(4-fluorophenyl)-2-phenylethylamino)butan-2-ol | 3.805 LC (1) 552.33 [M + H]$^+$ | Procedures 3, 4, 5, 6, 27 and 8 |
| 741 | 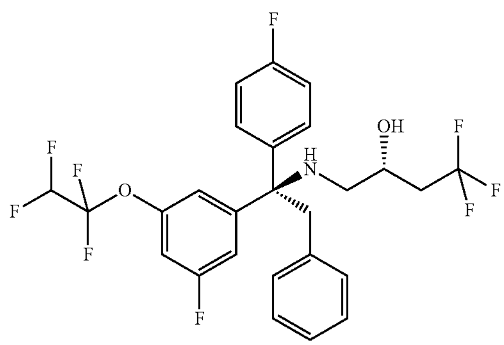 [SMILES: O[C@@H](CN[C@](Cc1ccccc1)(c1ccc(F)cc1)c1cc(F)cc(OC(F)(F)C(F)F)c1)CC(F)(F)F] | (R)-4,4,4-trifluoro-1-((R)-1-(3-fluoro-5-(1,1,2,2-tetrafluoroethoxy)phenyl)-1-(4-fluorophenyl)-2-phenylethylamino)butan-2-ol | 1.835 LC (2) 552.33 [M + H]$^+$ | Procedures 3, 4, 5, 6, 27 and 8 |
| 742 | 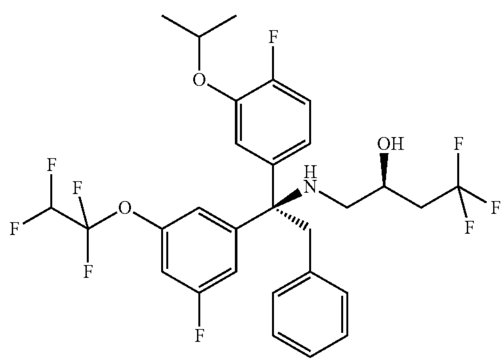 [SMILES: CC(C)Oc1cc([C@@](Cc2ccccc2)(NC[C@@H](O)CC(F)(F)F)c2cc(F)cc(OC(F)(F)C(F)F)c2)ccc1F] | (S)-4,4,4-trifluoro-1-((R)-1-(4-fluoro-3-isopropoxyphenyl)-1-(3-fluoro-5-(1,1,2,2-tetrafluoroethoxy)phenyl)-2-phenylethylamino)butan-2-ol | 2.00 LC (2) 610.4 [M + H]$^+$ | Procedures 3, 109, 110, 111, 112, 113, 114, 27 and 8 |
| 743 | 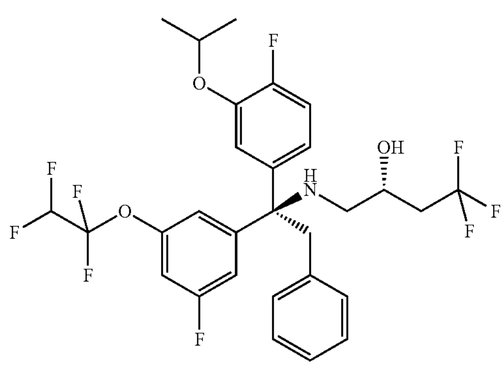 [SMILES: CC(C)Oc1cc([C@@](Cc2ccccc2)(NC[C@H](O)CC(F)(F)F)c2cc(F)cc(OC(F)(F)C(F)F)c2)ccc1F] | (R)-4,4,4-trifluoro-1-((R)-1-(4-fluoro-3-isopropoxyphenyl)-1-(3-fluoro-5-(1,1,2,2-tetrafluoroethoxy)phenyl)-2-phenylethylamino)butan-2-ol | 2.002 LC (2) 610.4 [M + H]$^+$ | Procedures 3, 109, 110, 111, 112, 113, 114, 27 and 8 |

TABLE 11-continued

| Ex. No. | Structure | Name | Retention Time Min./ Molecular Mass | Prepared in the manner described in: |
|---|---|---|---|---|
| 744 | 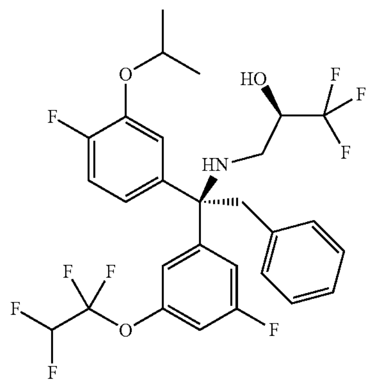 [SMILES: CC(C)Oc1cc([C@@](Cc2ccccc2)(NC[C@@H](O)C(F)(F)F)c2cc(F)cc(OC(F)(F)C(F)F)c2)ccc1F] | (R)-1,1,1-trifluoro-3-((R)-1-(4-fluoro-3-isopropoxyphenyl)-1-(3-fluoro-5-(1,1,2,2-tetrafluoroethoxy)phenyl)-2-phenylethylamino)propan-2-ol | 2.25 LC (2) 596.2 [M + H]$^+$ | Procedures 3, 109, 110, 111, 112, 113, 114, 27 and 8 |
| 745 | 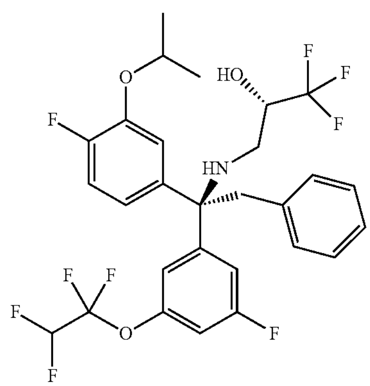 [SMILES: CC(C)Oc1cc([C@@](Cc2ccccc2)(NC[C@H](O)C(F)(F)F)c2cc(F)cc(OC(F)(F)C(F)F)c2)ccc1F] | (S)-1,1,1-trifluoro-3-((R)-1-(4-fluoro-3-isopropoxyphenyl)-1-(3-fluoro-5-(1,1,2,2-tetrafluoroethoxy)phenyl)-2-phenylethylamino)propan-2-ol | 2.21 LC (2) 596.1 [M + H]$^+$ | Procedures 3, 109, 110, 111, 112, 113, 114, 27 and 8 |
| 746 | 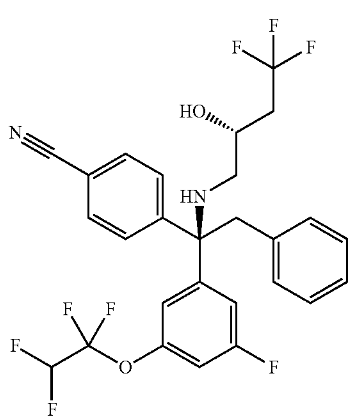 [SMILES: N#Cc1ccc([C@@](Cc2ccccc2)(NC[C@H](O)CC(F)(F)F)c2cc(F)cc(OC(F)(F)C(F)F)c2)cc1] | 4-((R)-1-(3-fluoro-5-(1,1,2,2-tetrafluoroethoxy)phenyl)-2-phenyl-1-((R)-4,4,4-trifluoro-2-hydroxybutylamino)ethyl)benzonitrile | 0.92 LC (12) 592 [M + H]$^+$ | Procedures 3, 4, 5, 6, 27, 8 and 56 |
| 747 | 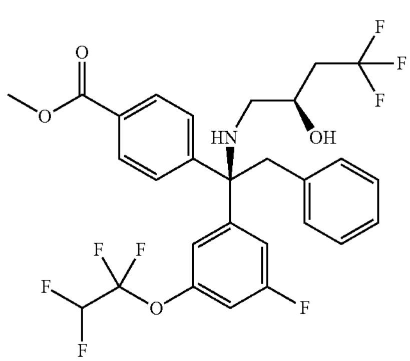 [SMILES: COC(=O)c1ccc([C@@](Cc2ccccc2)(NC[C@H](O)CC(F)(F)F)c2cc(F)cc(OC(F)(F)C(F)F)c2)cc1] | methyl 4-((R)-1-(3-fluoro-5-(1,1,2,2-tetrafluroethoxy)phenyl)-2-phenyl-1-((R)-4,4,4-trifluoro-2-hydroxybutylamino)ethyl)benzoate | 0.91 LC (12) 592 [M + H]$^+$ | Procedures 3, 4, 5, 6, 27, 8, 56 and 57 |

TABLE 11-continued

| Ex. No. | Structure | Name | Retention Time Min./ Molecular Mass | Prepared in the manner described in: |
|---|---|---|---|---|
| 748 | 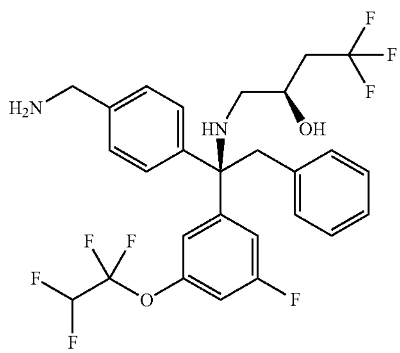 [SMILES: NCc1ccc([C@@](Cc2ccccc2)(NC[C@H](O)CC(F)(F)F)c2cc(F)cc(OC(F)(F)C(F)F)c2)cc1] | (R)-1-((R)-1-(4-(aminomethyl)phenyl)-1-(3-fluoro-5-(1,1,2,2-tetrafluoroethoxy)phenyl)-2-phenylethylamino)-4,4,4-trifluorobutan-2-ol | 1.33 LC (2) | Procedures 3, 4, 5, 6, 27, 8, 56 and 101 |
| 749 | 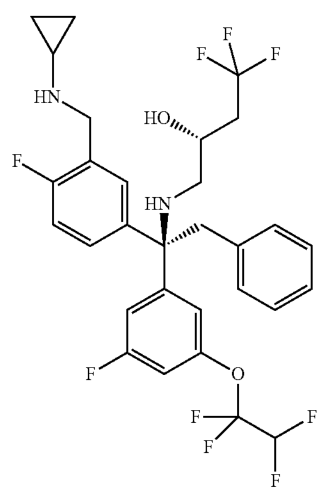 [SMILES: O[C@@H](CN[C@@](Cc1ccccc1)(c1cc(F)cc(OC(F)(F)C(F)F)c1)c1ccc(F)c(CNC2CC2)c1)CC(F)(F)F] | (R)-1-((R)-1-(3-((cyclopropylamino)methyl)-4-fluorophenyl)-1-(3-fluoro-5-(1,1,2,2-tetrafluoroethoxy)phenyl)-2-phenylethylamino)-4,4,4-trifluorobutan-2-ol | 7.418 LC (7) 621 $[M + H]^+$ | Procedures 3, 4, 5, 6, 27, 8, 146, 147 and 148 |
| 750 | 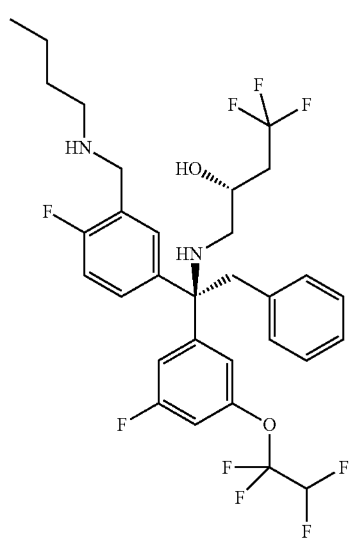 [SMILES: CCCCNCc1cc([C@@](Cc2ccccc2)(NC[C@H](O)CC(F)(F)F)c2cc(F)cc(OC(F)(F)C(F)F)c2)ccc1F] | (R)-1-((R)-1-(3-((butylamino)methyl)-4-fluorophenyl)-1-(3-fluoro-5-(1,1,2,2-tetrafluoroethoxy)phenyl)-2-phenylethylamino)-4,4,4-trifluorobutan-2-ol | 7.418 LC (7) 637 $[M + H]^+$ | Procedures 3, 4, 5, 6, 27, 8, 146, 147 and 148 |

TABLE 11-continued

| Ex. No. | Structure | Name | Retention Time Min./ Molecular Mass | Prepared in the manner described in: |
|---|---|---|---|---|
| 751 | 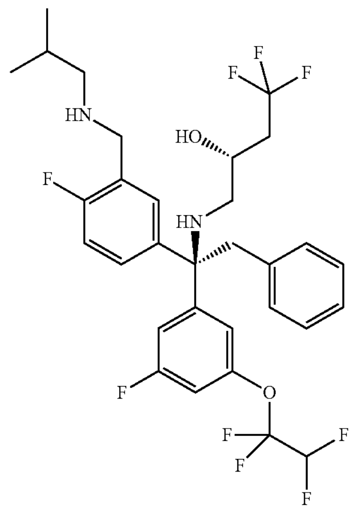 [SMILES: CC(C)CNCc1cc([C@@](Cc2ccccc2)(NC[C@H](O)CC(F)(F)F)c2cc(F)cc(OC(F)(F)C(F)F)c2)ccc1F] | (R)-4,4,4-trifluoro-1-((R)-1-(4-fluoro-3-((isobutylamino)methyl)phenyl)-1-(3-fluoro-5-(1,1,2,2-tetrafluoroethoxy)phenyl)-2-phenylethylamino)butan-2-ol | 4.46 LC (15) 637 [M + H]⁺ | Procedures 3, 4, 5, 6, 27, 8, 146 147 and 148 |
| 752 | 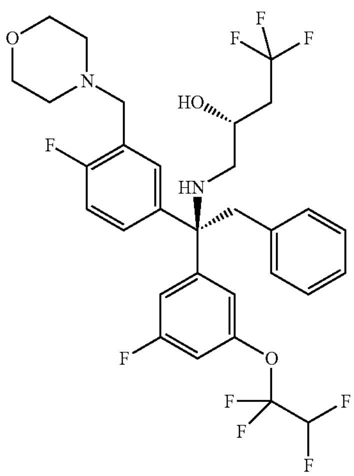 [SMILES: O[C@@H](CN[C@@](Cc1ccccc1)(c1cc(F)cc(OC(F)(F)C(F)F)c1)c1ccc(F)c(CN2CCOCC2)c1)CC(F)(F)F] | (R)-4,4,4-trifluoro-1-((R)-1-(4-fluoro-3-(morpholinomethyl)phenyl)-1-(3-fluoro-5-(1,1,2,2-tetrafluoroethoxy)phenyl)-2-phenylelhylamino)butan-2-ol | 7.033 LC (7) 651 [M + H]⁺ | Procedures 3, 62, 5, 6, 27, 8, 146 147 and 148 |
| 743 | 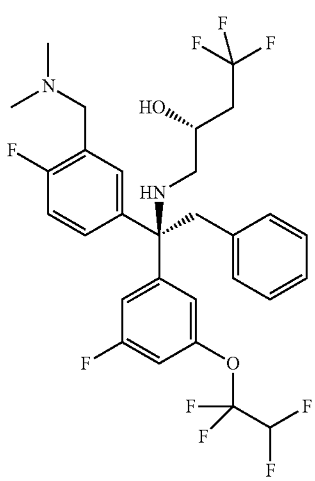 [SMILES: CN(C)Cc1cc([C@@](Cc2ccccc2)(NC[C@H](O)CC(F)(F)F)c2cc(F)cc(OC(F)(F)C(F)F)c2)ccc1F] | (R)-1-((R)-1-(3-((dimethylamino)methyl)-4-fluorophenyl)-1-fluoro-5-(1,1,2,2-tetrafluoroethoxy)phenyl)-2-phenylethylamino)-4,4,4-trifluorobutan-2-ol | 7.133 LC (7) 609 [M + H]⁺ | Procedures 3, 62, 5, 6, 27, 8, 146 147 and 148 |

TABLE 11-continued

| Ex. No. | Structure | Name | Retention Time Min./ Molecular Mass | Prepared in the manner described in: |
|---|---|---|---|---|
| 754 | 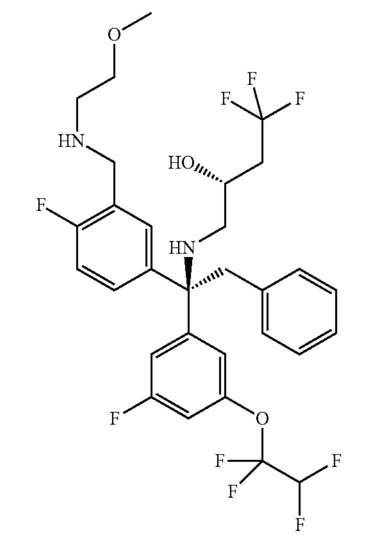 [SMILES: COCCNCc1cc([C@@](Cc2ccccc2)(NC[C@H](O)CC(F)(F)F)c2cc(F)cc(OC(F)(F)C(F)F)c2)ccc1F] | (R)-4,4,4-trifluoro-1-((R)-1-(4-fluoro-3-((2-methoxyelhylamino)methyl)phenyl)-1-(3-fluoro-5-(1,1,2,2-tetrafluoroethoxy)phenyl)-2-phenylethylamino)butan-2-ol | 6.90 LC (7) 639 [M + H]⁺ | Procedures 3, 62, 5, 6, 27, 8, 146 147 and 148 |
| 755 | 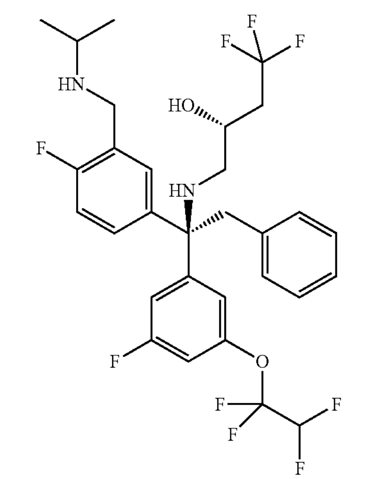 [SMILES: CC(C)NCc1cc([C@@](Cc2ccccc2)(NC[C@H](O)CC(F)(F)F)c2cc(F)cc(OC(F)(F)C(F)F)c2)ccc1F] | (R)-4,4,4-trifluoro-1-((R)-1-(4-fluoro-3-((isopropylamino)methyl)phenyl)-1-(3-fluoro-5-(1,1,2,2-tetrafluoroethoxy)phenyl)-2-phenylethylamino)butan-2-ol | 7.241 LC (7) 623 [M + H]⁺ | Procedures 3, 62, 5, 6, 27, 8, 146 147 and 148 |
| 756 | 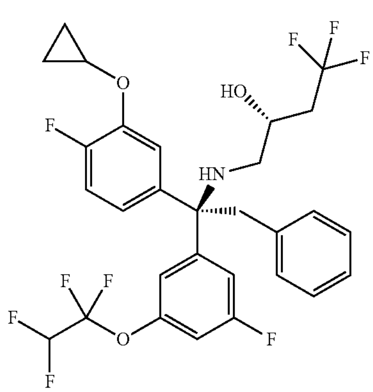 [SMILES: O[C@@H](CN[C@@](Cc1ccccc1)(c1cc(F)cc(OC(F)(F)C(F)F)c1)c1ccc(F)c(OC2CC2)c1)CC(F)(F)F] | (R)-1-((R)-1-(3-cyclopropoxy-4-fluorophenyl)-1-(3-fluoro-5-(1,1,2,2-tetrafluoroethoxy)phenyl)-2-phenylethylamino)-4,4,4-trifluorobutan-2-ol | 3.99 LC (1) 608.0 [M + H]⁺ | Procedures 3, 4, 5, 6, 27, 8, 59 106 and 107 |

TABLE 11-continued

| Ex. No. | Structure | Name | Retention Time Min./ Molecular Mass | Prepared in the manner described in: |
|---|---|---|---|---|
| 757 | 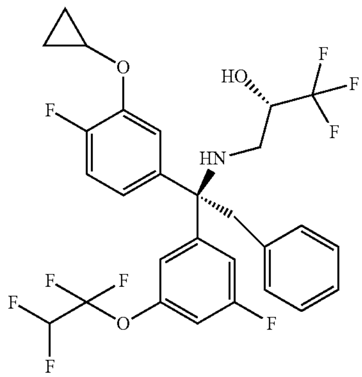 [SMILES: O[C@@H](CN[C@@](Cc1ccccc1)(c1cc(F)cc(OC(F)(F)C(F)F)c1)c1ccc(F)c(OC2CC2)c1)C(F)(F)F] | (S)-3-((R)-1-(3-cyclopropoxy-4-fluorophenyl)-1-(3-fluoro-5-(1,1,2,2-tetrafluoroethoxy)phenyl)-2-phenylethylamino)-1,1,1-trifluoropropan-2-ol | 4.19 LC (1) 594.0 [M + H]⁺ | Procedures 3, 4, 5, 6, 27, 8, 59 106 and 107 |

TABLE 12

| Ex. No. | Structure | Name | Retention Time Min./ Molecular Mass | Prepared in the manner described in: |
|---|---|---|---|---|
| 758 | 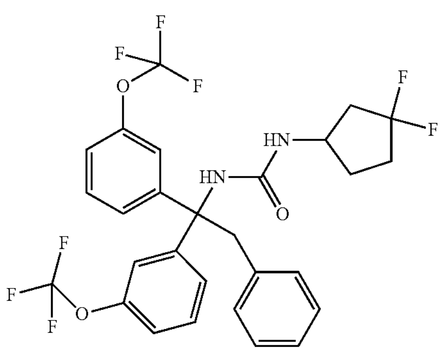 [SMILES: O=C(NC1CCC(F)(F)C1)NC(Cc1ccccc1)(c1cccc(OC(F)(F)F)c1)c1cccc(OC(F)(F)F)c1] | 1-(3,3-difluorocyclopentyl)-3-(2-phenyl-1,1-bis(3-(trifluoromethoxy)phenyl)ethyl)urea | 4.25 LC (3) 589.3 [M + H]⁺ | Procedures 11, 6 and 12 |
| 759 | 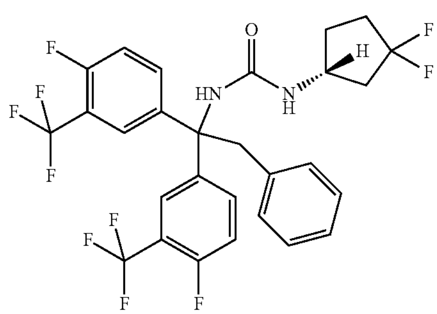 | (R)-1-(1,1-bis(4-fluoro-3-(trifluoromethyl)phenyl)-2-phenylethyl)-3-(3,3-difluorocyclopentyl)urea | 4.13 LC (3) 593.3 [M + H]⁺ | Procedures 11, 6 and 12 |

TABLE 12-continued

| Ex. No. | Structure | Name | Retention Time Min./ Molecular Mass | Prepared in the manner described in: |
|---|---|---|---|---|
| 760 | 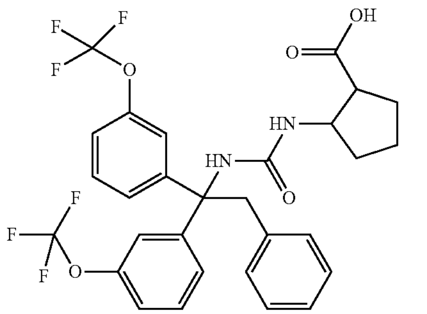 [SMILES: O=C(NC1CCCC1C(=O)O)NC(Cc1ccccc1)(c1cccc(OC(F)(F)F)c1)c1cccc(OC(F)(F)F)c1] | 2-(3-(2-phenyl-1,1-bis(3-(trifluoromethoxy) phenyl)ethyl)ureido)cyclopentanecarboxylic acid | 3.408 LC (1) 597.03 [M + H]+ | Procedures 11, 6 and 10 |
| 761 | 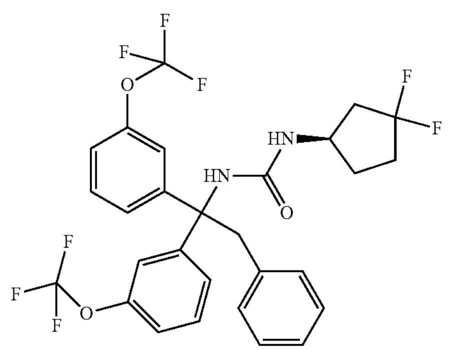 [SMILES: O=C(N[C@@H]1CCC(F)(F)C1)NC(Cc1ccccc1)(c1cccc(OC(F)(F)F)c1)c1cccc(OC(F)(F)F)c1] | (R)-1-(3,3-difluorocyclopentyl)-3-(2-phenyl-1,1-bis(3-(trifluoromethoxy)phenyl)ethyl) urea | 4.21 LC (3) 589.2 [M + H]+ | Procedures 11, 6 and 12 |
| 762 | 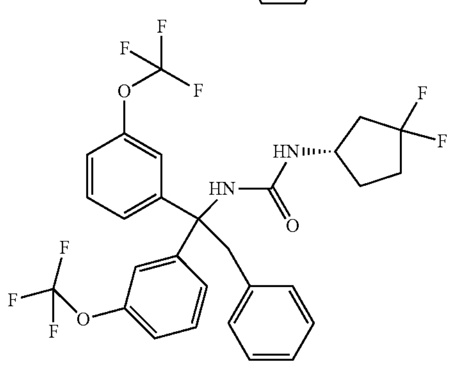 | (S)-1-(3,3-difluorocyclopentyl)-3-(2-phenyl-1,1-bis(3-(trifluoromethoxy)phenyl)ethyl) urea | 4.206 LC (3) 589.2 [M + H]+ | Procedures 11, 6 and 12 |
| 763 | 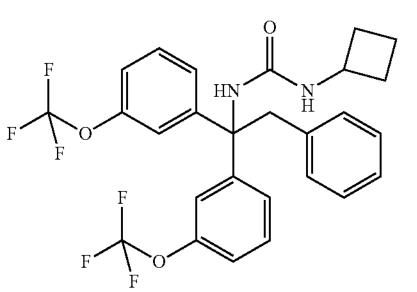 [SMILES: O=C(NC1CCC1)NC(Cc1ccccc1)(c1cccc(OC(F)(F)F)c1)c1cccc(OC(F)(F)F)c1] | 1-cyclobutyl-3-(2-phenyl-1,1-bis(3-(trifluoromethoxy)phenyl)ethyl)urea | 4.25 LC (4) 539.11 [M + H]+ | Procedures 11, 6 and 12 |

TABLE 12-continued

| Ex. No. | Structure | Name | Retention Time Min./ Molecular Mass | Prepared in the manner described in: |
|---|---|---|---|---|
| 764 | 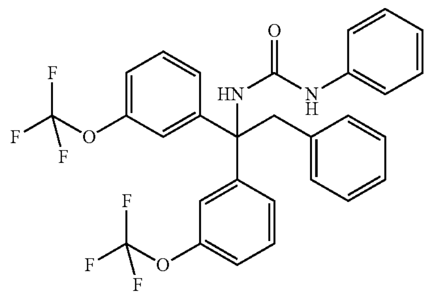 [SMILES: O=C(Nc1ccccc1)NC(Cc1ccccc1)(c1cccc(OC(F)(F)F)c1)c1cccc(OC(F)(F)F)c1] | 1-phenyl-3-(2-phenyl-1,1-bis(3-(trifluoromethoxy)phenyl)ethyl)urea | 4.281 LC (4) 561.06 [M + H]+ | Procedures 11, 6 and 12 |
| 765 | 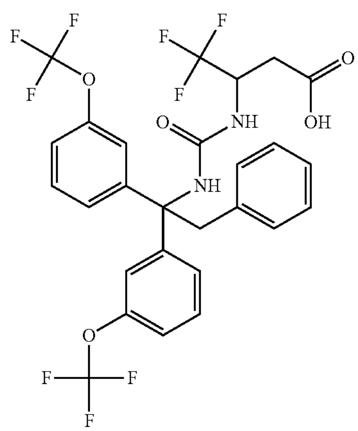 [SMILES: O=C(O)CC(NC(=O)NC(Cc1ccccc1)(c1cccc(OC(F)(F)F)c1)c1cccc(OC(F)(F)F)c1)C(F)(F)F] | 4,4,4-trifluoro-3-(3-(2-phenyl-1,1-bis(3-(trifluoromethoxy)phenyl)ethyl)ureido) butanoic acid | 624.452 LC (4) LC 625.10 [M + H]+ | Procedures 11, 6 and 12 |
| 766 | 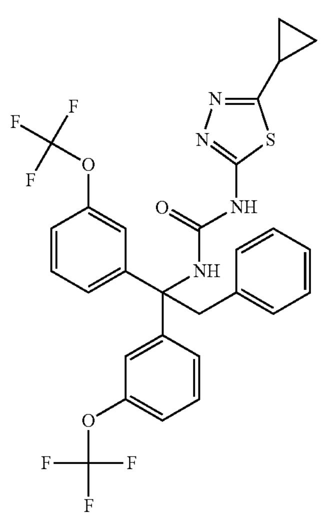 [SMILES: O=C(Nc1nnc(C2CC2)s1)NC(Cc1ccccc1)(c1cccc(OC(F)(F)F)c1)c1cccc(OC(F)(F)F)c1] | 1-(5-cyclopropyl-1,3,4-thiadiazol-2-yl)-3-(2-phenyl-1,1-bis(3-(trifluoromethoxy)phenyl) ethyl)urea | 4.39 LC (4) 609.11 [M + H]+ | Procedures 11, 6 and 12 |

TABLE 12-continued

| Ex. No. | Structure | Name | Retention Time Min./ Molecular Mass | Prepared in the manner described in: |
|---|---|---|---|---|
| 767 | 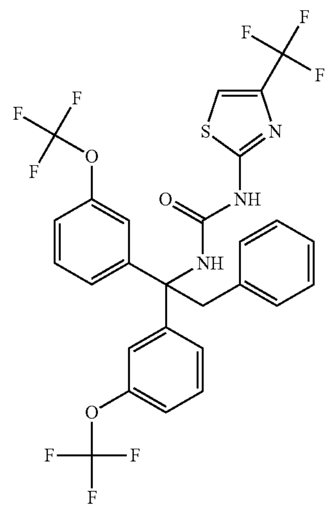 [SMILES: O=C(Nc1nc(C(F)(F)F)cs1)NC(Cc1ccccc1)(c1cccc(OC(F)(F)F)c1)c1cccc(OC(F)(F)F)c1] | 1-(2-phenyl-1,1-bis(3-(trifluoromethoxy)phenyl)ethyl)-3-(4-(trifluoromethyl)thiazol-2-yl)urea | 4.44 LC (4) 636.06 [M + H]$^+$ | Procedures 11, 6 and 12 |
| 768 | 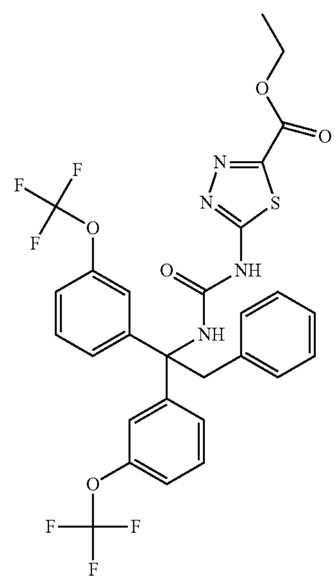 [SMILES: CCOC(=O)c1nnc(NC(=O)NC(Cc2ccccc2)(c2cccc(OC(F)(F)F)c2)c2cccc(OC(F)(F)F)c2)s1] | ethyl 5-(3-(2-phenyl-1,1-bis(3-(trifluoromethoxy)phenyl)ethyl)ureido)-1,3,4-thiadiazole-2-carboxylate | 4.42 LC (4) 641.09 [M + H]$^+$ | Procedures 11, 6 and 12 |
| 769 | 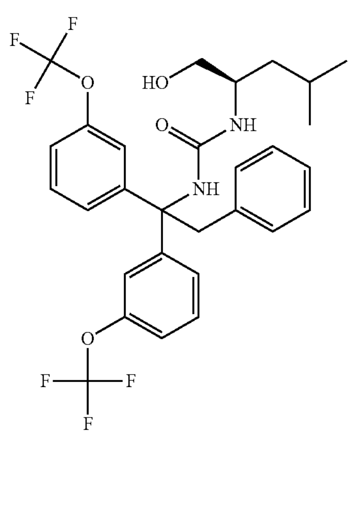 [SMILES: CC(C)C[C@H](CO)NC(=O)NC(Cc1ccccc1)(c1cccc(OC(F)(F)F)c1)c1cccc(OC(F)(F)F)c1] | (R)-1-(1-hydroxy-4-methylpentan-2-yl)-3-(2-phenyl-1,1-bis(3-(trifluoromethoxy)phenyl)ethyl)urea | 4.27 LC (4) 585.23 [M + H]$^+$ | Procedures 11, 6 and 12 |

TABLE 12-continued

| Ex. No. | Structure | Name | Retention Time Min./ Molecular Mass | Prepared in the manner described in: |
|---|---|---|---|---|
| 770 | 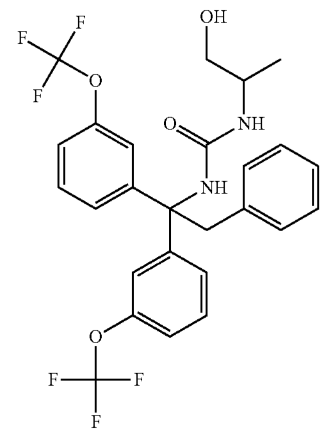 [SMILES: CC(CO)NC(=O)NC(Cc1ccccc1)(c1cccc(OC(F)(F)F)c1)c1cccc(OC(F)(F)F)c1] | 1-(1-hydroxypropan-2-yl)-3-(2-phenyl-1,1-bis(3-(trifluoromethoxy)phenyl)ethyl)urea | 4.18 LC (4) 543.21 [M + H]$^+$ | Procedures 11, 6 and 12 |
| 771 | 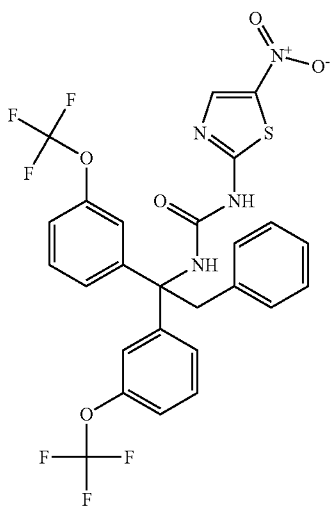 [SMILES: O=C(Nc1ncc([N+](=O)[O-])s1)NC(Cc1ccccc1)(c1cccc(OC(F)(F)F)c1)c1cccc(OC(F)(F)F)c1] | 1-(5-nitrothiazol-2-yl)-3-(2-phenyl-1,1-bis(3-(trifluoromethoxy)phenyl)ethyl)urea | 4.40 LC (4) 612.50 [M + H]$^+$ | Procedures 11, 6 and 12 |
| 772 | 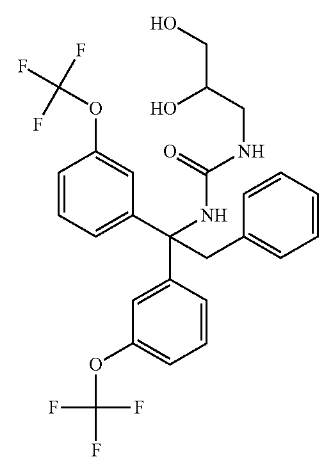 [SMILES: O=C(NCC(O)CO)NC(Cc1ccccc1)(c1cccc(OC(F)(F)F)c1)c1cccc(OC(F)(F)F)c1] | 1-(2,3-dihydroxypropyl)-3-(2-phenyl-1,1-bis(3-(trifluoromethoxy)phenyl)ethyl)urea | 4.11 LC (4) 559.19 [M + H]$^+$ | Procedures 11, 6 and 12 |

TABLE 12-continued

| Ex. No. | Structure | Name | Retention Time Min./ Molecular Mass | Prepared in the manner described in: |
|---|---|---|---|---|
| 773 | 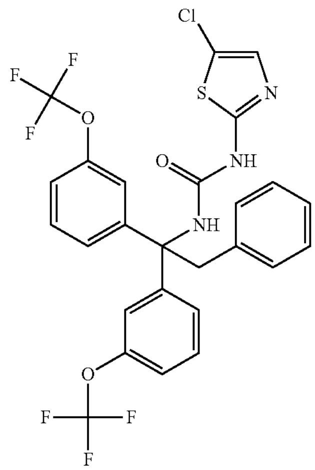 [SMILES: O=C(Nc1ncc(Cl)s1)NC(Cc1ccccc1)(c1cccc(OC(F)(F)F)c1)c1cccc(OC(F)(F)F)c1] | 1-(5-chlorothiazol-2-yl)-3-(2-phenyl-1,1-bis(3-(trifluoromethoxy)phenyl)ethyl)urea | 4.56 LC (4) 602.05 [M + H]$^+$ | Procedures 11, 6 and 12 |
| 774 | 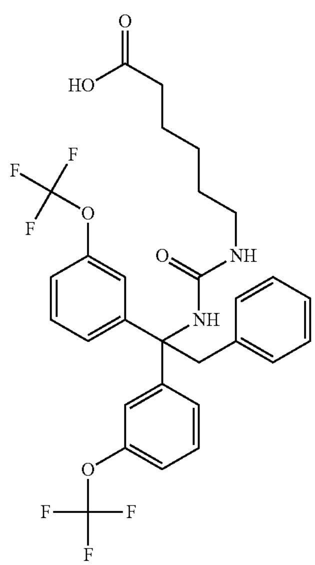 [SMILES: O=C(O)CCCCCNC(=O)NC(Cc1ccccc1)(c1cccc(OC(F)(F)F)c1)c1cccc(OC(F)(F)F)c1] | 6-(3-(2-phenyl-1,1-bis(3-(trifluoromethoxy)phenyl)ethyl)ureido)hexanoic acid | 4.20 LC (4) 599.18 [M + H]$^+$ | Procedures 11, 6 and 12 |
| 775 | 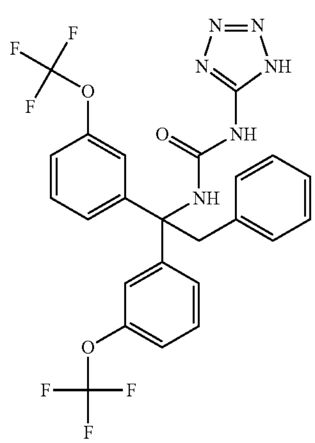 [SMILES: O=C(Nc1nnn[nH]1)NC(Cc1ccccc1)(c1cccc(OC(F)(F)F)c1)c1cccc(OC(F)(F)F)c1] | 1-(2-phenyl-1,1-bis(3-(trifluoromethoxy)phenyl)ethyl)-3-(1H-tetrazol-5-yl)urea | 4.06 LC (4) 553.16 [M + H]$^+$ | Procedures 11, 6 and 12 |

TABLE 12-continued

| Ex. No. | Structure | Name | Retention Time Min./ Molecular Mass | Prepared in the manner described in: |
|---|---|---|---|---|
| 776 | 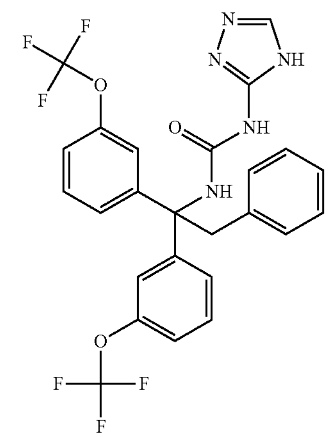 [SMILES: O=C(Nc1nnc[nH]1)NC(Cc1ccccc1)(c1cccc(OC(F)(F)F)c1)c1cccc(OC(F)(F)F)c1] | 1-(2-phenyl-1,1-bis(3-(trifluoromethoxy) phenyl)ethyl)-3-(4H-1,2,4-triazol-3-yl)urea | 4.05 LC (4) 552.17 [M + H]$^+$ | Procedures 11, 6 and 12 |
| 777 | 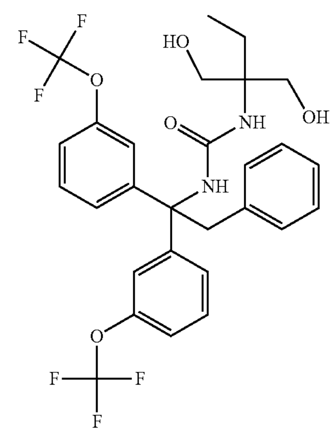 [SMILES: CCC(CO)(CO)NC(=O)NC(Cc1ccccc1)(c1cccc(OC(F)(F)F)c1)c1cccc(OC(F)(F)F)c1] | 1-(1-hydroxy-2-(hydroxymethyl)butan-2-yl)-3-(2-phenyl-1,1-bis(3-(trifluoromethoxy) phenyl)ethyl)urea | 4.20 LC (4) 587.19 [M + H]$^+$ | Procedures 11, 6 and 12 |
| 778 | 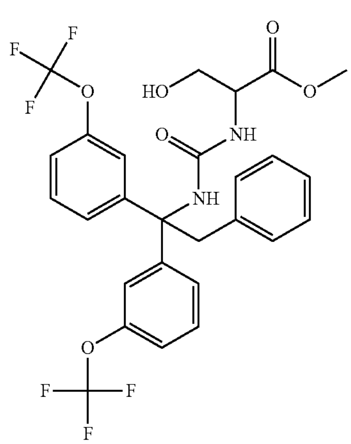 [SMILES: COC(=O)C(CO)NC(=O)NC(Cc1ccccc1)(c1cccc(OC(F)(F)F)c1)c1cccc(OC(F)(F)F)c1] | methyl 3-hydroxy-2-(3-(2-phenyl-1,1-bis(3-(trifluoromethoxy)phenyl)ethyl)ureido) propanoate | 4.07 LC (4) 587.16 [M + H]$^+$ | Procedures 11, 6 and 12 |

TABLE 12-continued

| Ex. No. | Structure | Name | Retention Time Min./ Molecular Mass | Prepared in the manner described in: |
|---|---|---|---|---|
| 779 | 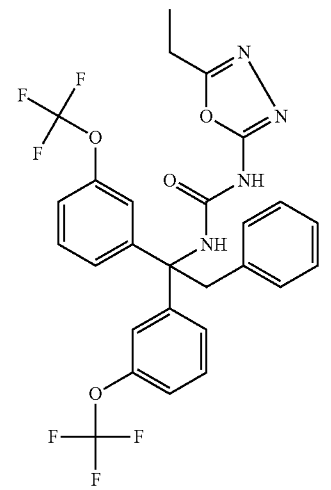 [SMILES: CCc1nnc(NC(=O)NC(Cc2ccccc2)(c2cccc(OC(F)(F)F)c2)c2cccc(OC(F)(F)F)c2)o1] | 1-(5-ethyl-1,3,4-oxadiazol-2-yl)-3-(2-phenyl-1,1-bis(3-(trifluoromethoxy)phenyl)ethyl)urea | 4.25 LC (4) 581.16 [M + H]$^+$ | Procedures 11, 6 and 12 |
| 780 | 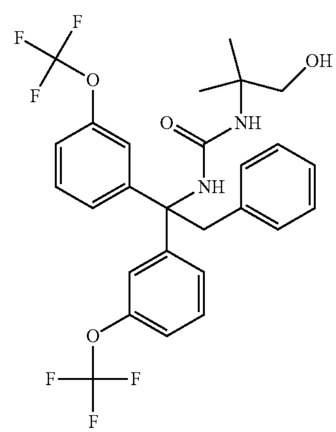 [SMILES: CC(C)(CO)NC(=O)NC(Cc1ccccc1)(c1cccc(OC(F)(F)F)c1)c1cccc(OC(F)(F)F)c1] | 1-(1-hydroxy-2-methylpropan-2-yl)-3-(2-phenyl-1,1-bis(3-(trifluoromethoxy)phenyl)ethyl)urea | 4.14 LC (4) 557.25 [M + H]$^+$ | Procedures 11, 6 and 12 |
| 781 | 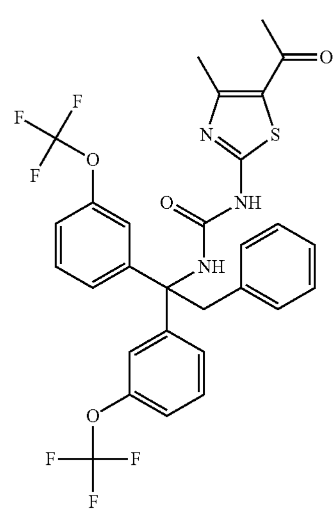 [SMILES: CC(=O)c1sc(NC(=O)NC(Cc2ccccc2)(c2cccc(OC(F)(F)F)c2)c2cccc(OC(F)(F)F)c2)nc1C] | 1-(5-acetyl-4-methylthiazole-2-yl)-3-(2-phenyl-1-bis(3-(trifluoromethoxy)phenyl)ethyl)urea | 4.28 LC (4) 624.11 [M + H]$^+$ | Procedures 11, 6 and 12 |

TABLE 12-continued

| Ex. No. | Structure | Name | Retention Time Min./ Molecular Mass | Prepared in the manner described in: |
|---|---|---|---|---|
| 782 | 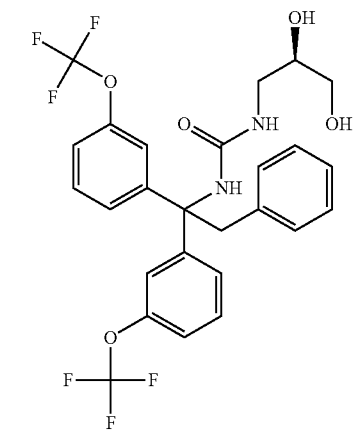 [SMILES: O=C(NC[C@@H](O)CO)NC(Cc1ccccc1)(c1cccc(OC(F)(F)F)c1)c1cccc(OC(F)(F)F)c1] | (R)-1-(2,3-dihydroxypropyl)-3-(2-phenyl-1,1-bis(3-(trifluromethoxy)phenyl)ethyl) urea | 4.04 LC (4) 559.19 [M + H]$^+$ | Procedures 11, 6 and 12 |
| 783 | 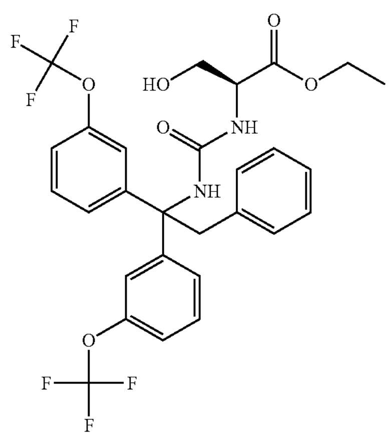 [SMILES: CCOC(=O)[C@H](CO)NC(=O)NC(Cc1ccccc1)(c1cccc(OC(F)(F)F)c1)c1cccc(OC(F)(F)F)c1] | (S)-ethyl 3-hydroxy-2-(3-(2-phenyl-1,1-bis(3-(trifluoromethoxy)phenyl)ethyl)ureido) propanoate | 4.13 LC (4) 601.17 [M + H]$^+$ | Procedures 11, 6 and 12 |
| 784 | 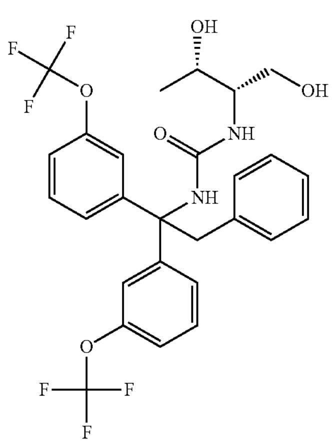 [SMILES: C[C@H](O)[C@H](CO)NC(=O)NC(Cc1ccccc1)(c1cccc(OC(F)(F)F)c1)c1cccc(OC(F)(F)F)c1] | 1-((2S,3S)-1,3-dihydroxybutan-2-yl)-3-(2-phenyl-1,1-bis(3-(trifluoromethoxy)phenyl) ethyl)urea | 4.07 LC (4) 573.19 [M + H]$^+$ | Procedures 11, 6 and 12 |

TABLE 12-continued

| Ex. No. | Structure | Name | Retention Time Min./ Molecular Mass | Prepared in the manner described in: |
|---|---|---|---|---|
| 785 | 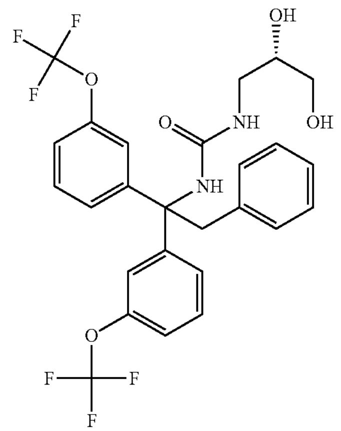 [SMILES: O=C(NC[C@H](O)CO)NC(Cc1ccccc1)(c1cccc(OC(F)(F)F)c1)c1cccc(OC(F)(F)F)c1] | (S)-1-(2,3-dihydroxypropyl)-3-(2-phenyl-1,1-bis(3-(trifluoromethoxy)phenyl)ethyl)urea | 4.03 LC (4) 559.19 [M + H]$^+$ | Procedures 11, 6 and 12 |
| 786 | 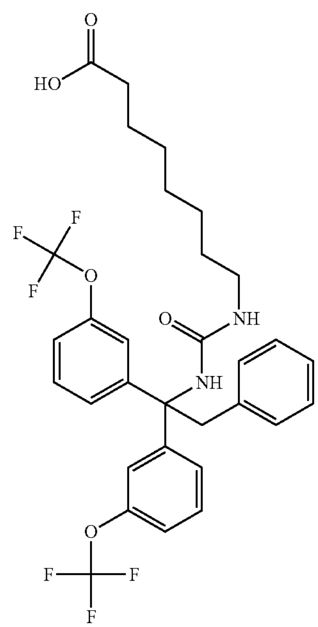 [SMILES: O=C(O)CCCCCCCNC(=O)NC(Cc1ccccc1)(c1cccc(OC(F)(F)F)c1)c1cccc(OC(F)(F)F)c1] | 8-(3-(2-phenyl-1,1-bis(3-(trifluoromethoxy)phenyl)ethyl) ureido)octanoic acid | 4.22 LC (4) 627.26 [M + H]$^+$ | Procedures 11, 6 and 12 |
| 787 | 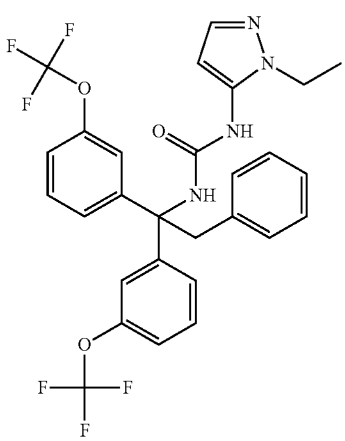 [SMILES: CCn1nccc1NC(=O)NC(Cc1ccccc1)(c1cccc(OC(F)(F)F)c1)c1cccc(OC(F)(F)F)c1] | 1-(1-ethyl-1H-pyrazol-5-yl)-3-(2-phenyl-1,1-bis(3-(trifluoromethoxy)phenyl)ethyl)urea | 4.09 LC (4) 579.21 [M + H]$^+$ | Procedures 11, 6 and 12 |

TABLE 12-continued

| Ex. No. | Structure | Name | Retention Time Min./ Molecular Mass | Prepared in the manner described in: |
|---|---|---|---|---|
| 788 | 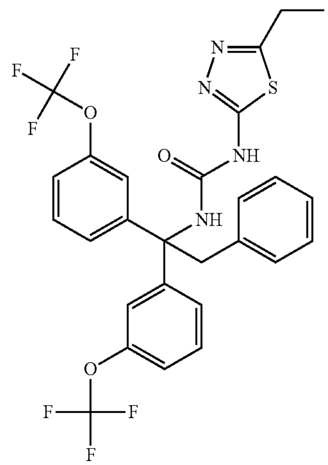 [SMILES: CCc1nnc(NC(=O)NC(Cc2ccccc2)(c2cccc(OC(F)(F)F)c2)c2cccc(OC(F)(F)F)c2)s1] | 1-(5-ethyl-1,3,4-thiadiazol-2-yl)-3-(2-phenyl-1,1-bis(3-(trifluoromethoxy)phenyl)ethyl)urea | 4.27 LC (4) 597.11 [M + H]$^+$ | Procedures 11, 6 and 12 |
| 789 | 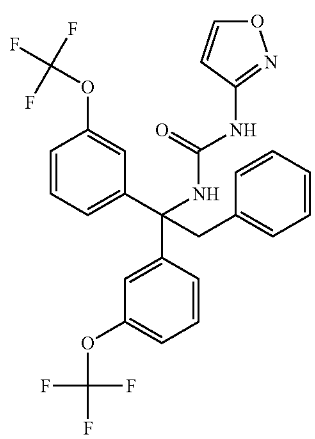 [SMILES: O=C(Nc1ccon1)NC(Cc1ccccc1)(c1cccc(OC(F)(F)F)c1)c1cccc(OC(F)(F)F)c1] | 1-(isoxazol-3-yl)-3-(2-phenyl-1,1-bis(3-(trifluoromethoxy)phenyl)ethyl)urea | 4.16 LC (4) 552.19 [M + H]$^+$ | Procedures 11, 6 and 12 |
| 791 | 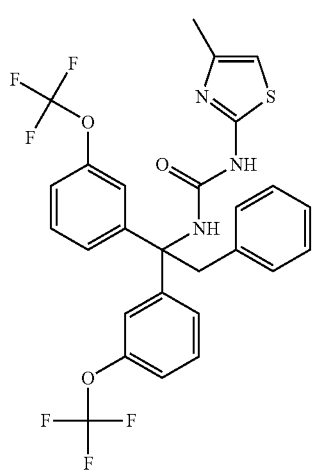 [SMILES: Cc1csc(NC(=O)NC(Cc2ccccc2)(c2cccc(OC(F)(F)F)c2)c2cccc(OC(F)(F)F)c2)n1] | 1-(4-methylthiazol-2-yl)-3-(2-phenyl-1,1-bis(3-(trifluoromethoxy)phenyl)ethyl)urea | 4.21 LC (4) 582.12 [M + H]$^+$ | Procedures 11, 6 and 12 |

TABLE 12-continued

| Ex. No. | Structure | Name | Retention Time Min./ Molecular Mass | Prepared in the manner described in: |
|---|---|---|---|---|
| 792 | 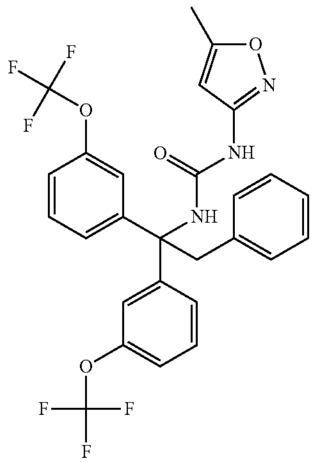 [SMILES: Cc1cc(NC(=O)NC(Cc2ccccc2)(c2cccc(OC(F)(F)F)c2)c2cccc(OC(F)(F)F)c2)no1] | 1-(5-methylisoxazol-3-yl)-3-(2-phenyl-1,1-bis(3-(trifluoromethoxy)phenyl)ethyl)urea | 4.23 LC (4) 566.18 [M + H]$^+$ | Procedures 11, 6 and 12 |
| 793 | 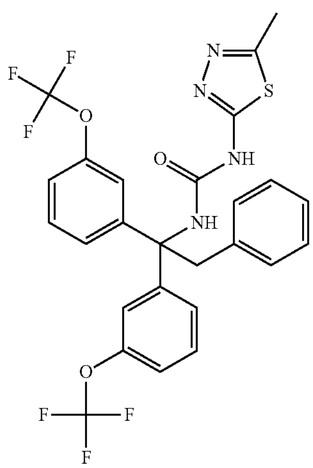 [SMILES: Cc1nnc(NC(=O)NC(Cc2ccccc2)(c2cccc(OC(F)(F)F)c2)c2cccc(OC(F)(F)F)c2)s1] | 1-(5-methyl-1,3,4-thiadiazol-2-yl)-3-(2-phenyl-1,1-bis(3-(trifluoromethoxy)phenyl)ethyl)urea | 4.18 LC (4) 583.12 [M + H]$^+$ | Procedures 11, 6 and 12 |
| 794 | 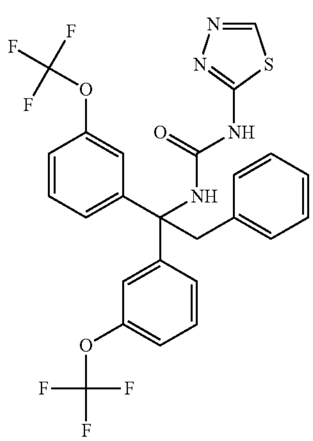 [SMILES: O=C(Nc1nncs1)NC(Cc1ccccc1)(c1cccc(OC(F)(F)F)c1)c1cccc(OC(F)(F)F)c1] | 1-(2-phenyl-1,1-bis(3-(trifluoromethoxy)phenyl)ethyl)-3-(1,3,4-thiadiazol-2-yl)urea | 4.13 LC (4) 569.13 [M + H]$^+$ | Procedures 11, 6 and 12 |

TABLE 12-continued

| Ex. No. | Structure | Name | Retention Time Min./ Molecular Mass | Prepared in the manner described in: |
|---|---|---|---|---|
| 795 | 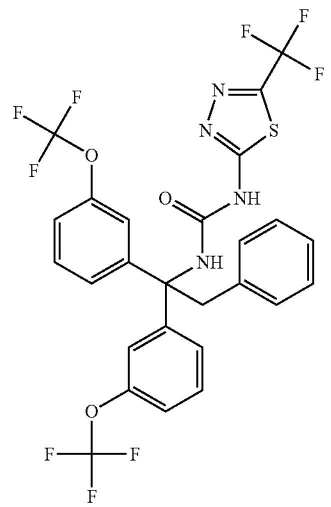 [SMILES: O=C(Nc1nnc(C(F)(F)F)s1)NC(Cc1ccccc1)(c1cccc(OC(F)(F)F)c1)c1cccc(OC(F)(F)F)c1] | 1-(2-phenyl-1,1-bis(3-(trifluoromethoxy) phenyl)ethyl)-3-(5-(trifluoromethyl)-1,3,4-thiadiazol-2-yl)urea | 4.49 LC (4) 637.07 [M + H]$^+$ | Procedures 11, 6 and 12 |
| 796 | 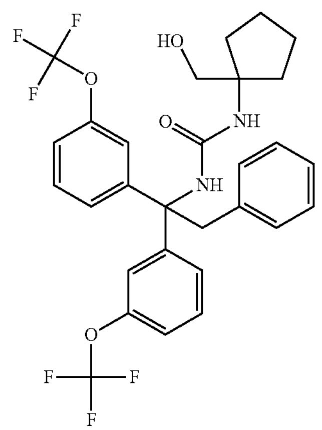 [SMILES: O=C(NC1(CO)CCCC1)NC(Cc1ccccc1)(c1cccc(OC(F)(F)F)c1)c1cccc(OC(F)(F)F)c1] | 1-(1-(hydroxymethyl)cyclopentyl)-3-(2-phenyl-1,1-bis(3-(trifluoromethoxy)phenyl) ethyl)urea | 4.22 LC (4) 583.23 [M + H]$^+$ | Procedures 11, 6 and 12 |
| 797 | 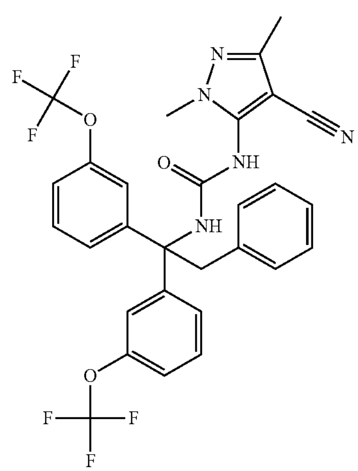 [SMILES: Cc1nn(C)c(NC(=O)NC(Cc2ccccc2)(c2cccc(OC(F)(F)F)c2)c2cccc(OC(F)(F)F)c2)c1C#N] | 1-(4-cyano-1,3-dimethyl-1H-pyrazol-5-yl)-3-(2-phenyl-1,1-bis(3-( trifluoromethoxy) phenyl)ethyl)urea | 4.04 LC (4) 603.98 [M + H]$^+$ | Procedures 11, 6 and 12 |

TABLE 12-continued

| Ex. No. | Structure | Name | Retention Time Min./ Molecular Mass | Prepared in the manner described in: |
|---|---|---|---|---|
| 798 | 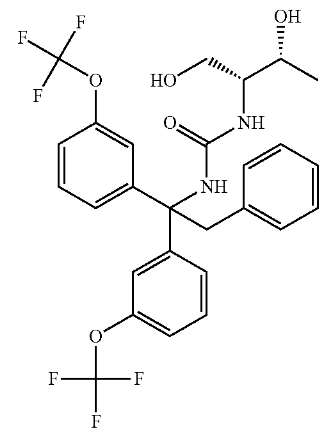 [SMILES: C[C@@H](O)[C@@H](CO)NC(=O)NC(Cc1ccccc1)(c1cccc(OC(F)(F)F)c1)c1cccc(OC(F)(F)F)c1] | 1-((2R,3R)-1,3-dihydroxybutan-2-yl)-3-(2-phenyl-1,1-bis(3-(trifluoromethoxy)phenyl)ethyl)urea | 4.07 LC (4) 573.19 [M + H]⁺ | Procedures 11, 6 and 12 |
| 799 | 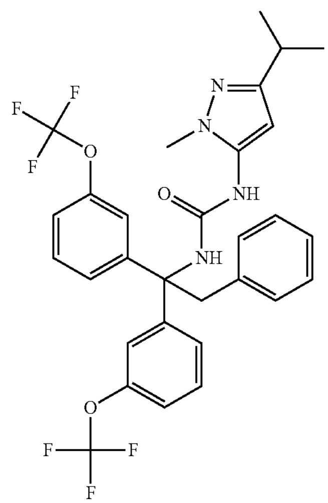 [SMILES: CC(C)c1cc(NC(=O)NC(Cc2ccccc2)(c2cccc(OC(F)(F)F)c2)c2cccc(OC(F)(F)F)c2)n(C)n1] | 1-(3-isopropyl-1-methyl-1H-pyrazol-5-yl)-3-(2-phenyl-1,1-bis(3-(trifluoromethoxy)phenyl)ethyl)urea | 4.12 LC (4) 607.23 [M + H]⁺ | Procedures 11, 6 and 12 |
| 800 | 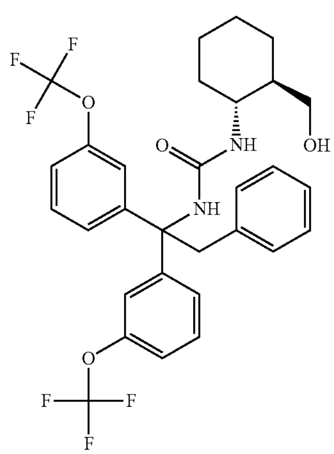 [SMILES: O=C(N[C@@H]1CCCC[C@H]1CO)NC(Cc1ccccc1)(c1cccc(OC(F)(F)F)c1)c1cccc(OC(F)(F)F)c1] | 1-((1R,2R)-2-(hydroxymethyl)cyclohexyl)-3-(2-phenyl-1,1-bis(3-(trifluoromethoxy)phenyl)tthyl)urea | 4.24 LC (4) 597.21 [M + H]⁺ | Procedures 11, 6 and 12 |

TABLE 12-continued

| Ex. No. | Structure | Name | Retention Time Min./ Molecular Mass | Prepared in the manner described in: |
|---|---|---|---|---|
| 801 | 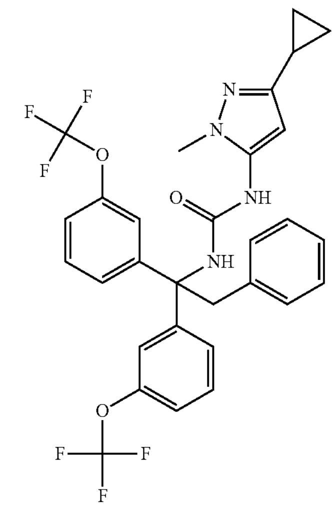 [SMILES: Cn1nc(C2CC2)cc1NC(=O)NC(Cc1ccccc1)(c1cccc(OC(F)(F)F)c1)c1cccc(OC(F)(F)F)c1] | 1-(3-cyclopropyl-1-methyl-1H-pyrazol-5-yl)-3-(2-phenyl-1,1-bis(3-(trifluoromethoxy)phenyl)ethyl)urea | 4.09 LC (4) 605.21 $[M + H]^+$ | Procedures 11, 6 and 12 |
| 802 | 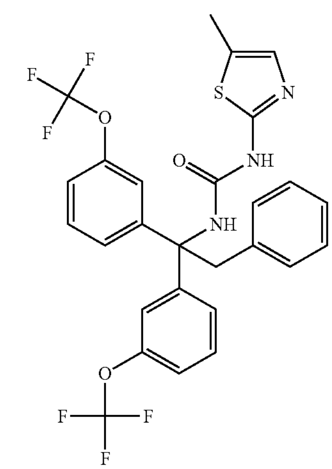 [SMILES: Cc1cnc(NC(=O)NC(Cc2ccccc2)(c2cccc(OC(F)(F)F)c2)c2cccc(OC(F)(F)F)c2)s1] | 1-(5-methylthiazol-2-yl)-3-(2-phenyl-1,1-bis(3-(trifluoromethoxy)phenyl)ethyl)urea | 4.21 LC (4) 582.12 $[M + H]^+$ | Procedures 11, 6 and 12 |
| 803 | 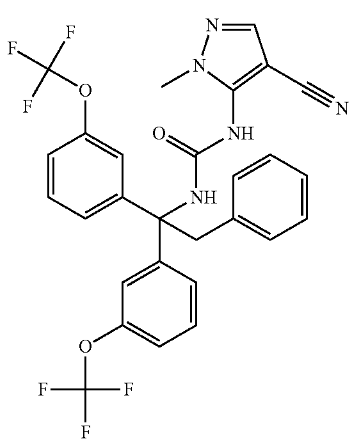 [SMILES: Cn1ncc(C#N)c1NC(=O)NC(Cc1ccccc1)(c1cccc(OC(F)(F)F)c1)c1cccc(OC(F)(F)F)c1] | 1-(4-cyano-1-methyl-1H-pyrazol-5-yl)-3-(2-phenyl-1,1-bis(3-(trifluoromethoxy)phenyl)ethyl)urea | 4.05 LC (4) 590.18 $[M + H]^+$ | Procedures 11, 6 and 12 |

TABLE 12-continued

| Ex. No. | Structure | Name | Retention Time Min./ Molecular Mass | Prepared in the manner described in: |
| --- | --- | --- | --- | --- |
| 804 | 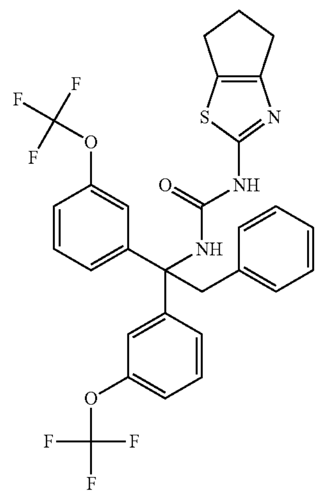 [SMILES: O=C(Nc1nc2c(s1)CCC2)NC(Cc1ccccc1)(c1cccc(OC(F)(F)F)c1)c1cccc(OC(F)(F)F)c1] | 1-(5,6-dihydro-4H-cyclopenta[d]thiazol-2-yl)-3-(2-phenyl-1,1-bis(3-(trifluoromethoxy)phenyl)ethyl)urea | 4.40 LC (4) 608.12 [M + H]+ | Procedures 11, 6 and 12 |
| 805 | 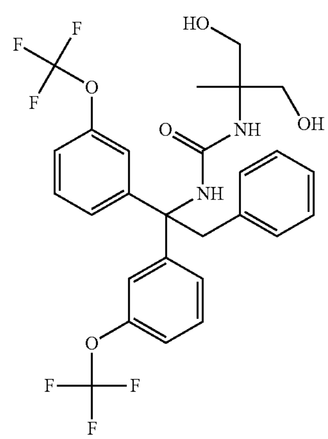 [SMILES: CC(CO)(CO)NC(=O)NC(Cc1ccccc1)(c1cccc(OC(F)(F)F)c1)c1cccc(OC(F)(F)F)c1] | 1-(1,3-dihydroxy-2-methylpropan-2-yl)-3-(2-phenyl-1,1-bis(3-(trifluoromethoxy)phenyl)ethyl)urea | 4.08 LC (4) 573.22 [M + H]+ | Procedures 11, 6 and 12 |
| 806 | 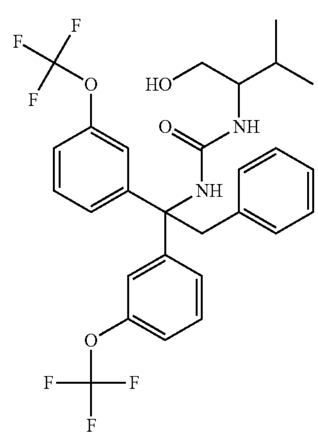 [SMILES: CC(C)C(CO)NC(=O)NC(Cc1ccccc1)(c1cccc(OC(F)(F)F)c1)c1cccc(OC(F)(F)F)c1] | 1-(1-hydroxy-3-methylbutan-2-yl)-3-(2-phenyl-1,1-bis(3-(trifluoromethoxy)phenyl)ethyl)urea | 4.20 LC (4) 571.24 [M + H]+ | Procedures 11, 6 and 12 |

TABLE 12-continued

| Ex. No. | Structure | Name | Retention Time Min./ Molecular Mass | Prepared in the manner described in: |
|---|---|---|---|---|
| 807 | 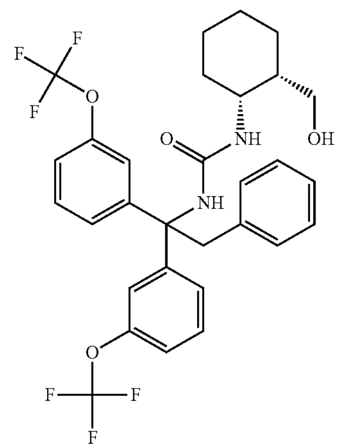 [SMILES: O=C(N[C@@H]1CCCC[C@@H]1CO)NC(Cc1ccccc1)(c1cccc(OC(F)(F)F)c1)c1cccc(OC(F)(F)F)c1] | 1-((1R,2S)-2-(hydroxymethyl)cyclohexyl)-3-(2-phenyl-1,1-bis(3-(trifluoromethoxy)phenyl)ethyl)urea | 4.23 LC (4) 597.23 [M + H]$^+$ | Procedures 11, 6 and 12 |
| 808 | 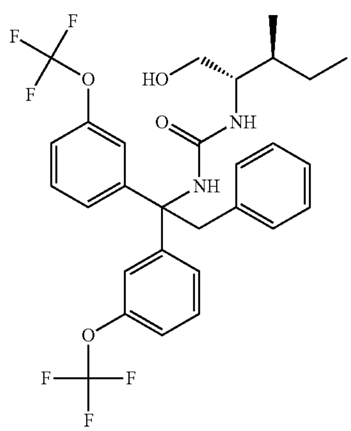 [SMILES: CC[C@H](C)[C@@H](CO)NC(=O)NC(Cc1ccccc1)(c1cccc(OC(F)(F)F)c1)c1cccc(OC(F)(F)F)c1] | 1-((2S,3S)-1-hydroxy-3-methylpentan-2-yl)-3-(2-phtnyl-1,1-bis(3-(trifluoromethoxy)phenyl)tthyl)urea | 4.26 LC (4) 585.24 [M + H]$^+$ | Procedures 11, 6 and 12 |
| 809 | 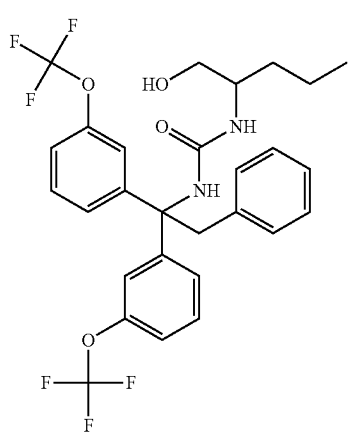 [SMILES: CCCC(CO)NC(=O)NC(Cc1ccccc1)(c1cccc(OC(F)(F)F)c1)c1cccc(OC(F)(F)F)c1] | 1-(1-hydroxypentan-2-yl)-3-(2-phenyl-1,1-bis(3-(trifluoromethoxy)phenyl)ethyl)urea | 4.21 LC (4) 571.23 [M + H]$^+$ | Procedures 11, 6 and 12 |

TABLE 12-continued

| Ex. No. | Structure | Name | Retention Time Min./ Molecular Mass | Prepared in the manner described in: |
|---|---|---|---|---|
| 810 | 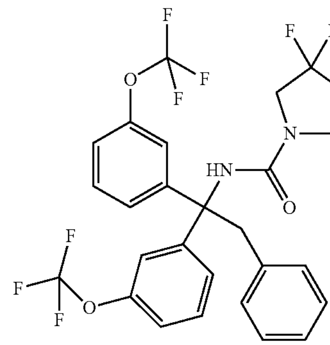 | 3,3,4,4-tetrafluoro-N-(2-phenyl-1,1-bis(3-(trifluoromethoxy)phenyl)ethyl)pyrrolidine-1-carboxamide | 3.868 LC (3) 611.1 [M + H]$^+$ | Procedures 11, 6 and 12 |
| 811 | 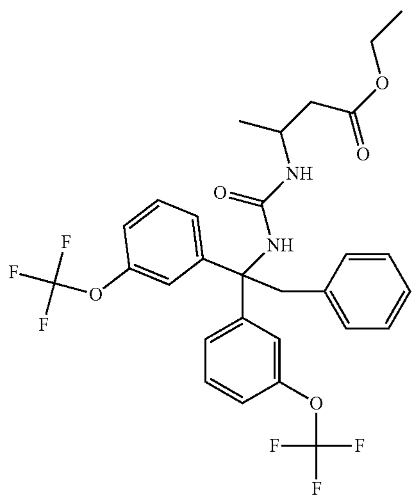 [SMILES: CCOC(=O)CC(C)NC(=O)NC(Cc1ccccc1)(c1cccc(OC(F)(F)F)c1)c1cccc(OC(F)(F)F)c1] | ethyl 3-(3-(2-phenyl-1,1-bis(3-(trifluoromethoxy)phenyl)ethyl)ureido)butanoate | 3.81 LC (10) 599.5 [M + H]$^+$ | Procedures 11, 6 and 12 |
| 812 | 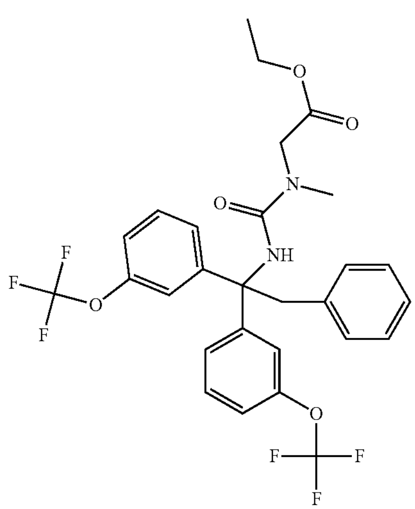 [SMILES: CCOC(=O)CN(C)C(=O)NC(Cc1ccccc1)(c1cccc(OC(F)(F)F)c1)c1cccc(OC(F)(F)F)c1] | ethyl 2-(1-methyl-3-(2-phenyl-1,1-bis(3-(trifluoromethoxy)phenyl)ethyl)ureido)acetate | 3.85 LC (10) 585.4 [M + H]$^+$ | Procedures 11, 6 and 12 |

TABLE 12-continued

| Ex. No. | Structure | Name | Retention Time Min./ Molecular Mass | Prepared in the manner described in: |
|---|---|---|---|---|
| 813 | 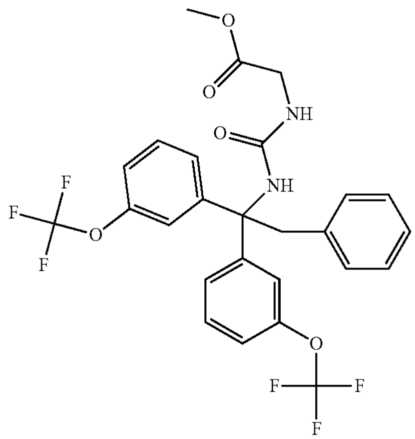 [SMILES: COC(=O)CNC(=O)NC(Cc1ccccc1)(c1cccc(OC(F)(F)F)c1)c1cccc(OC(F)(F)F)c1] | methyl 2-(3-(2-phenyl-1,1-bis(3-(trifluoromethoxy)phenyl)ethyl)ureido)acetate | 3.57 LC (10) 557.4 [M + H]$^+$ | Procedures 11, 6 and 12 |
| 814 | 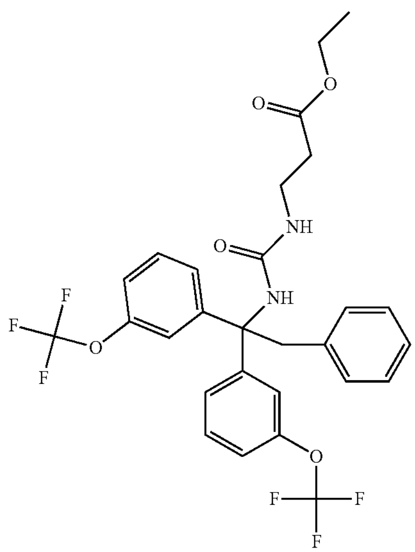 [SMILES: CCOC(=O)CCNC(=O)NC(Cc1ccccc1)(c1cccc(OC(F)(F)F)c1)c1cccc(OC(F)(F)F)c1] | ethyl 3-(3-(2-phenyl-1,1-bis(3-(trifluoromethoxy)phenyl)ethyl)ureido)propanoate | 3.71 LC (10) 585.5 [M + H]$^+$ | Procedures 11, 6 and 12 |
| 815 | 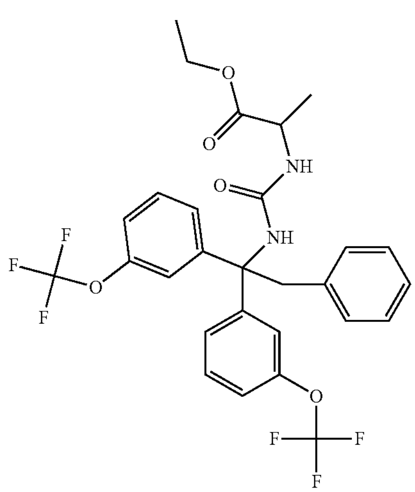 [SMILES: CCOC(=O)C(C)NC(=O)NC(Cc1ccccc1)(c1cccc(OC(F)(F)F)c1)c1cccc(OC(F)(F)F)c1] | ethyl 2-(3-(2-phenyl-1,1-bis(3-(trifluoromethoxy)phenyl)ethyl)ureido)propanoate | 3.78 LC (10) 585.5 [M + H]$^+$ | Procedures 11, 6 and 12 |

TABLE 12-continued

| Ex. No. | Structure | Name | Retention Time Min./ Molecular Mass | Prepared in the manner described in: |
|---|---|---|---|---|
| 816 | 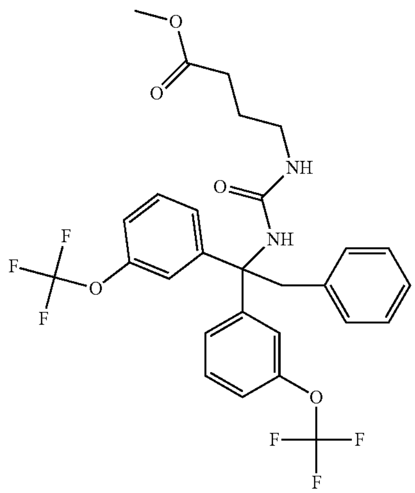 [SMILES: COC(=O)CCCNC(=O)NC(Cc1ccccc1)(c1cccc(OC(F)(F)F)c1)c1cccc(OC(F)(F)F)c1] | methyl 4-(3-(2-phenyl-1,1-bis(3-(trifluoromethoxy)phenyl)ethyl)ureido)butanoate | 3.62 LC (10) 585.5 [M + H]$^+$ | Procedures 11, 6 and 12 |
| 817 | 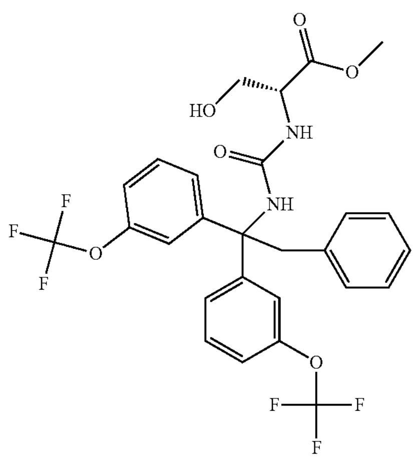 [SMILES: COC(=O)[C@@H](CO)NC(=O)NC(Cc1ccccc1)(c1cccc(OC(F)(F)F)c1)c1cccc(OC(F)(F)F)c1] | (R)-methyl 3-hydroxy-2-(3-(2-phenyl-1,1-bis(3-(trifluoromethoxy)phenyl)ethyl)ureido)propanoate | 3.39 LC (10) 587.4 [M + H]$^+$ | Procedures 11, 6 and 12 |
| 818 | 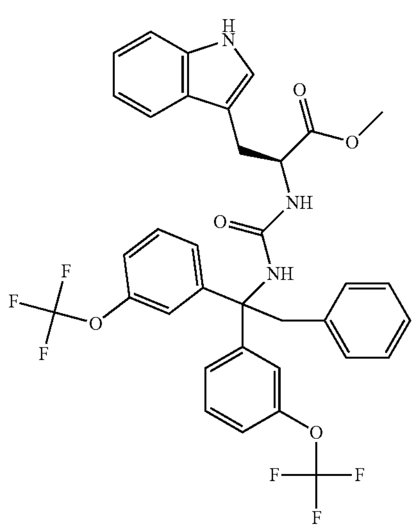 [SMILES: COC(=O)[C@H](Cc1c[nH]c2ccccc12)NC(=O)NC(Cc1ccccc1)(c1cccc(OC(F)(F)F)c1)c1cccc(OC(F)(F)F)c1] | (S)-methyl 3-(1H-indol-3-yl)-2-(3-(2-phenyl-1,1-bis(3-(trifluoromethoxy)phenyl)ethyl)ureido)propanoate | 3.85 LC (10) 685.5 [M + H]$^+$ | Procedures 11, 6 and 12 |

TABLE 12-continued

| Ex. No. | Structure | Name | Retention Time Min./ Molecular Mass | Prepared in the manner described in: |
|---|---|---|---|---|
| 819 | 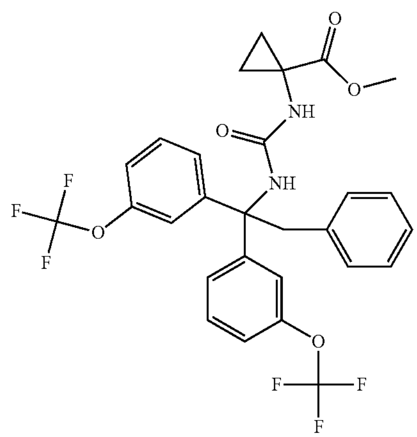 [SMILES: COC(=O)C1(NC(=O)NC(Cc2ccccc2)(c2cccc(OC(F)(F)F)c2)c2cccc(OC(F)(F)F)c2)CC1] | methyl 1-(3-(2-phenyl-1,1-bis(3-(trifluoromethoxy)phenyl)ethyl)ureido)cyclopropanecarboxylate | 3.63 LC (10) 583.4 [M + H]+ | Procedures 11, 6 and 12 |
| 820 | 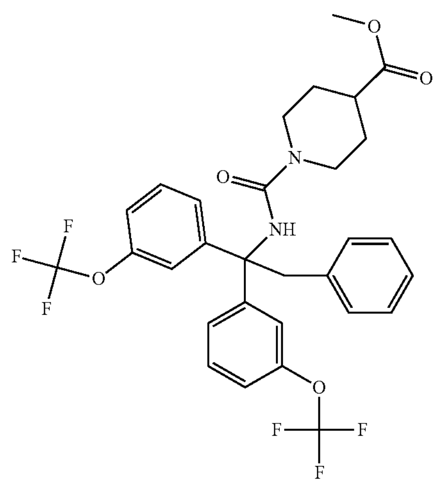 [SMILES: COC(=O)C1CCN(C(=O)NC(Cc2ccccc2)(c2cccc(OC(F)(F)F)c2)c2cccc(OC(F)(F)F)c2)CC1] | methyl 1-(2-phenyl-1,1-bis(3-(trifluoromethoxy)phenyl)ethylcarbamoyl)piperidine-4-carboxylate | 3.81 LC (10) 611.5 [M + H]+ | Procedures 11, 6 and 12 |
| 821 | 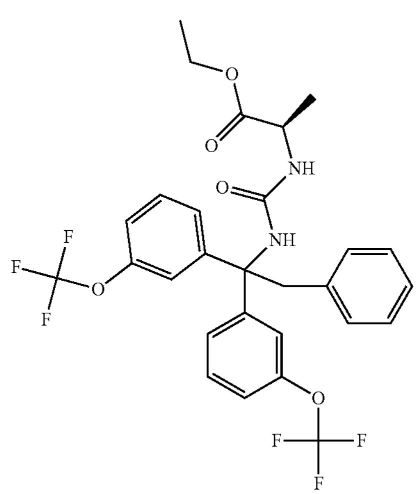 [SMILES: CCOC(=O)[C@@H](C)NC(=O)NC(Cc1ccccc1)(c1cccc(OC(F)(F)F)c1)c1cccc(OC(F)(F)F)c1] | (R)-ethyl 2-(3-(2-phenyl-1,1-bis(3-(trifluoromethoxy)phrnyl)rthyl)ureido)propanoate | 3.79 LC (10) 585.5 [M + H]+ | Procedures 11, 6 and 12 |

TABLE 12-continued

| Ex. No. | Structure | Name | Retention Time Min./ Molecular Mass | Prepared in the manner described in: |
|---|---|---|---|---|
| 822 | 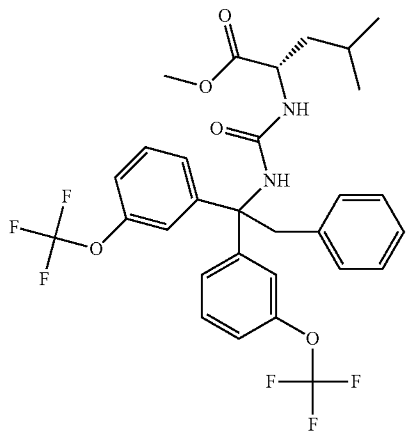 [SMILES: COC(=O)[C@H](CC(C)C)NC(=O)NC(Cc1ccccc1)(c1cccc(OC(F)(F)F)c1)c1cccc(OC(F)(F)F)c1] | (S)-methyl 4-methyl-2-(3-(2-phenyl-1,1-bis(3-(trifluoromethoxy)phenyl)ethyl)ureido)pentanoate | 4.04 LC (10) 613.2 [M + H]$^+$ | Procedures 11, 6 and 12 |
| 823 | 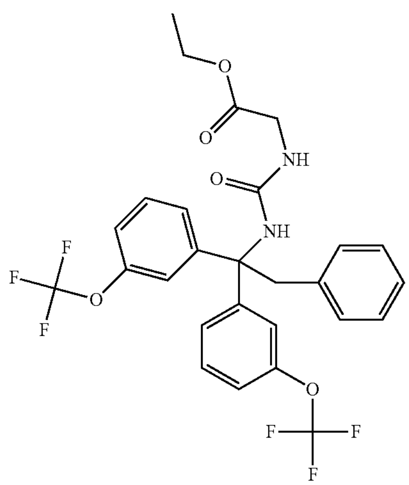 [SMILES: CCOC(=O)CNC(=O)NC(Cc1ccccc1)(c1cccc(OC(F)(F)F)c1)c1cccc(OC(F)(F)F)c1] | ethyl 2-(3-(2-phenyl-1,1-bis(3-(trifluoromethoxy)phenyl)ethyl)ureido)acetate | 3.74 LC (10) 571.1 [M + H]$^+$ | Procedures 11, 6 and 12 |
| 824 | 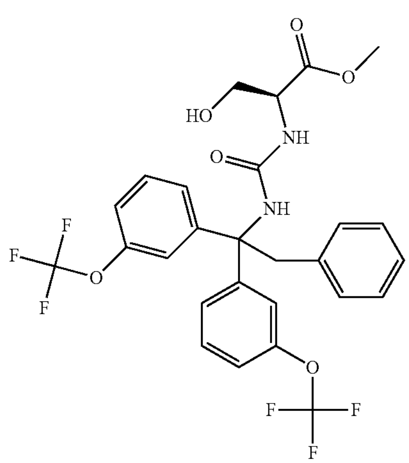 [SMILES: COC(=O)[C@H](CO)NC(=O)NC(Cc1ccccc1)(c1cccc(OC(F)(F)F)c1)c1cccc(OC(F)(F)F)c1] | (S)-methyl 3-hydroxy-2-(3-(2-phenyl-1,1-bis(3-(trifluoromethoxy)phenyl)ethyl)ureido)propanoate | 3.44 LC (10) 587.1 [M + H]$^+$ | Procedures 11, 6 and 12 |

TABLE 12-continued

| Ex. No. | Structure | Name | Retention Time Min./ Molecular Mass | Prepared in the manner described in: |
|---|---|---|---|---|
| 825 | 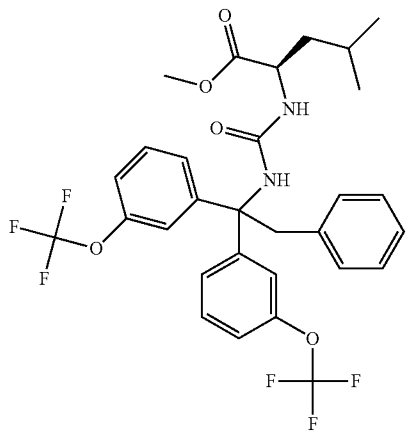 [SMILES: COC(=O)[C@@H](CC(C)C)NC(=O)NC(Cc1ccccc1)(c1cccc(OC(F)(F)F)c1)c1cccc(OC(F)(F)F)c1] | (R)-methyl 4-methyl-2-(3-(2-phenyl-1,1-bis(3-(trifluoromethoxy)phenyl)ethyl)ureido)pentanoate | 4.04 LC (10) 613.2 [M + H]$^+$ | Procedures 11, 6 and 12 |
| 826 | 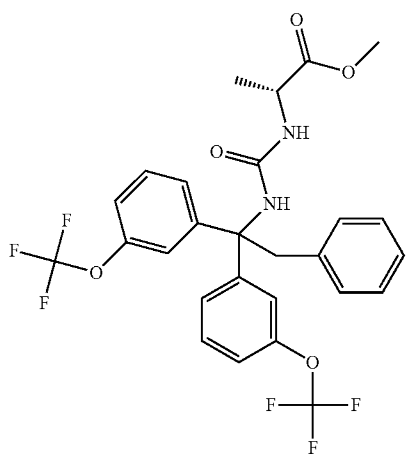 [SMILES: COC(=O)[C@@H](C)NC(=O)NC(Cc1ccccc1)(c1cccc(OC(F)(F)F)c1)c1cccc(OC(F)(F)F)c1] | (R)-methyl 2-(3-(2-phenyl-1,1-bis(3-(trifluoromethoxy)phenyl)ethyl)ureido)propanoate | 3.73 LC (10) 571.1 [M + H]$^+$ | Procedures 11, 6 and 12 |
| 827 | 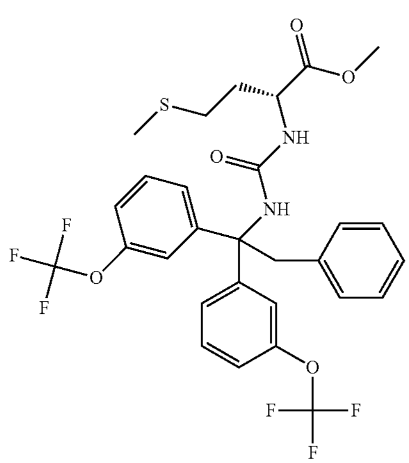 [SMILES: COC(=O)[C@@H](CCSC)NC(=O)NC(Cc1ccccc1)(c1cccc(OC(F)(F)F)c1)c1cccc(OC(F)(F)F)c1] | (R)-methyl 4-(methylthio)-2-(3-(2-phenyl-1,1-bis(3-(trifluoromethoxy)phenyl)ethyl)ureido)butanoate | 3.88 LC (10) 631.1 [M + H]$^+$ | Procedures 11, 6 and 12 |

TABLE 12-continued

| Ex. No. | Structure | Name | Retention Time Min./ Molecular Mass | Prepared in the manner described in: |
|---|---|---|---|---|
| 828 | 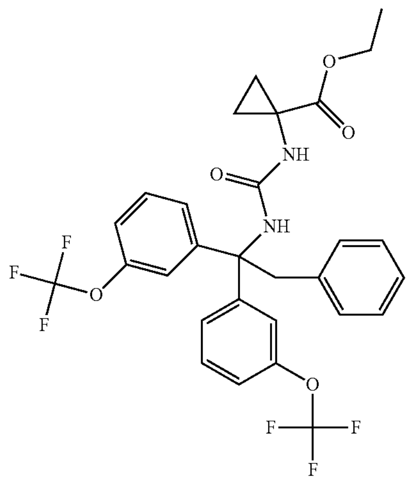 [SMILES: CCOC(=O)C1(NC(=O)NC(Cc2ccccc2)(c2cccc(OC(F)(F)F)c2)c2cccc(OC(F)(F)F)c2)CC1] | ethyl 1-(3-(2-phenyl-1,1-bis(3-(trifluoromcthoxy)phenyl)ethyl)ureido) cyclopropanecarboxylate | 3.80 LC (10) 597.1 [M + H]$^+$ | Procedures 11, 6 and 12 |
| 829 | 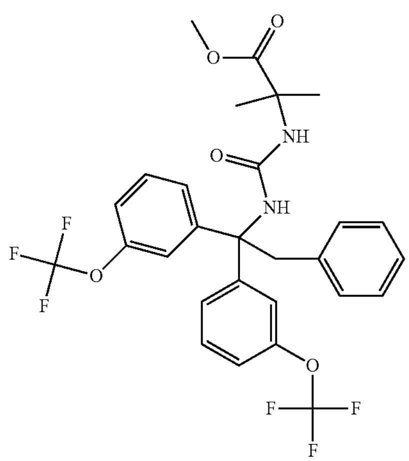 [SMILES: COC(=O)C(C)(C)NC(=O)NC(Cc1ccccc1)(c1cccc(OC(F)(F)F)c1)c1cccc(OC(F)(F)F)c1] | methyl 2-methyl-2-(3-(2-phenyl-1,1-bis(3-(trifluoromethoxy)phenyl)ethyl)ureido) propanoate | 3.80 LC (10) 585.0 [M + H]$^+$ | Procedures 11, 6 and 12 |
| 830 | 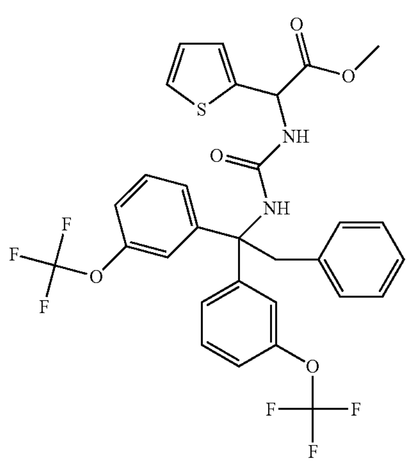 [SMILES: COC(=O)C(NC(=O)NC(Cc1ccccc1)(c1cccc(OC(F)(F)F)c1)c1cccc(OC(F)(F)F)c1)c1cccs1] | methyl 2-(3-(2-phenyl-1,1-bis(3-(trifluoromethoxy)phenyl)ethyl)ureido)-2-(thiophen-2-yl)acetate | 3.92 LC (10) 639.1 [M + H]$^+$ | Procedures 11, 6 and 12 |

TABLE 12-continued

| Ex. No. | Structure | Name | Retention Time Min./ Molecular Mass | Prepared in the manner described in: |
|---|---|---|---|---|
| 831 | 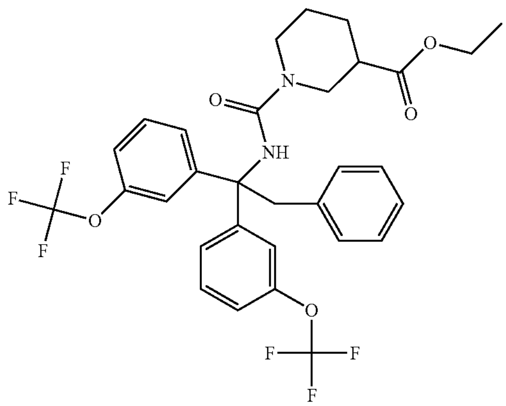 [SMILES: CCOC(=O)C1CCCN(C(=O)NC(Cc2ccccc2)(c2cccc(OC(F)(F)F)c2)c2cccc(OC(F)(F)F)c2)C1] | ethyl 1-(2-phenyl-1,1-bis(3-(trifluoromethoxy)phenyl)ethylcarbamoyl)piperidine-3-carboxylate | 3.99 LC (10) 625.2 [M + H]$^+$ | Procedures 11, 6 and 12 |
| 832 | 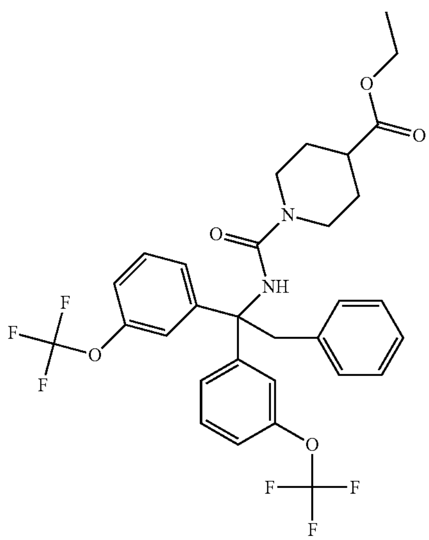 [SMILES: CCOC(=O)C1CCN(C(=O)NC(Cc2ccccc2)(c2cccc(OC(F)(F)F)c2)c2cccc(OC(F)(F)F)c2)CC1] | ethyl 1-(2-phenyl-1,1-bis(3-(trifluoromethoxy)phenyl)ethylcarbamoyl)piperidine-4-carboxylate | 3.90 LC (10) 625.2 [M + H]$^+$ | Procedures 11, 6 and 12 |
| 833 | 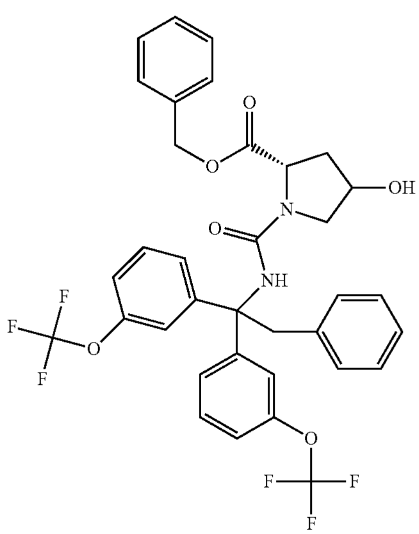 [SMILES: O=C(OCc1ccccc1)[C@@H]1CC(O)CN1C(=O)NC(Cc1ccccc1)(c1cccc(OC(F)(F)F)c1)c1cccc(OC(F)(F)F)c1] | (2S)-benzyl 4-hydroxy-1-(2-phenyl-1,1-bis(3-(trifluoromethoxy)phenyl)ethylcarbamoyl)pyrrolidine-2-carboxylate | 3.76 LC (10) 689.2 [M + H]$^+$ | Procedures 11, 6 and 12 |

TABLE 12-continued

| Ex. No. | Structure | Name | Retention Time Min./ Molecular Mass | Prepared in the manner described in: |
|---|---|---|---|---|
| 834 | 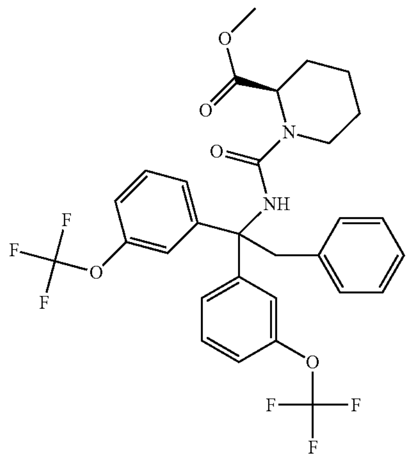 [SMILES: COC(=O)[C@H]1CCCCN1C(=O)NC(Cc1ccccc1)(c1cccc(OC(F)(F)F)c1)c1cccc(OC(F)(F)F)c1] | (R)-methyl 1-(2-phenyl-1,1-bis(3-(trifluoromethoxy)phenyl)ethylcarbamoyl)piperidine-2-carboxylate | 3.95 LC (10) 611.1 [M + H]$^+$ | Procedures 11, 6 and 12 |
| 835 | 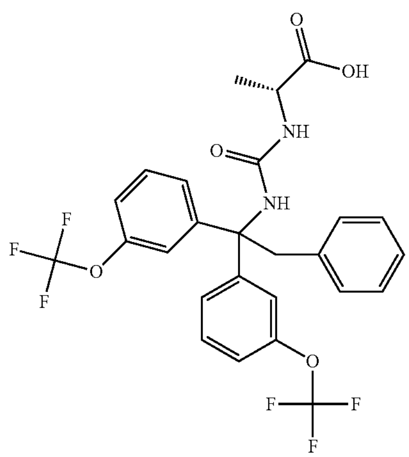 [SMILES: C[C@@H](NC(=O)NC(Cc1ccccc1)(c1cccc(OC(F)(F)F)c1)c1cccc(OC(F)(F)F)c1)C(=O)O] | (R)-2-(3-(2-phenyl-1,1-bis(3-(trifluoromethoxy)phenyl)ethyl)ureido)propanoic acid | 2.62 LC (10) 557.1 [M + H]$^+$ | Procedures 11, 6, 12 and 23 |
| 836 | 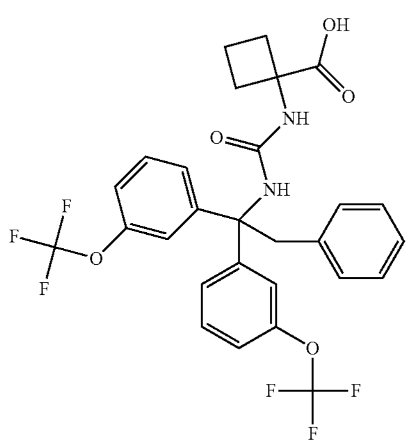 [SMILES: O=C(NC1(C(=O)O)CCC1)NC(Cc1ccccc1)(c1cccc(OC(F)(F)F)c1)c1cccc(OC(F)(F)F)c1] | 1-(3-(2-phenyl-1,1-bis(3-(trifluoromethoxy)phenyl)ethyl)ureido)cyclobutanecarboxylic acid | 2.94 LC (10) 583.1 [M + H]$^+$ | Procedures 11, 6, 12 and 23 |

TABLE 13

| Ex. No. | Structure | Name | Retention Time Min./ Molecular Mass | Prepared in the manner described in: |
|---|---|---|---|---|
| 837 | 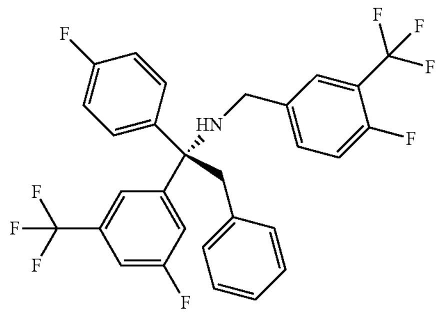 [SMILES: Fc1ccc([C@](Cc2ccccc2)(NCc2ccc(F)c(C(F)(F)F)c2)c2cc(F)cc(C(F)(F)F)c2)cc1] | (S)-N-(4-fluoro-3-(trifluoromethyl)benzyl)-1-(3-fluoro-5-(trifluoromethyl)phenyl)-1-(4-fluorophenyl)-2-phenylethanamine | 4.32 LC (1) 553.90 [M + H]⁺ | Procedures 4, 5, 6 and 13 |
| 838 | 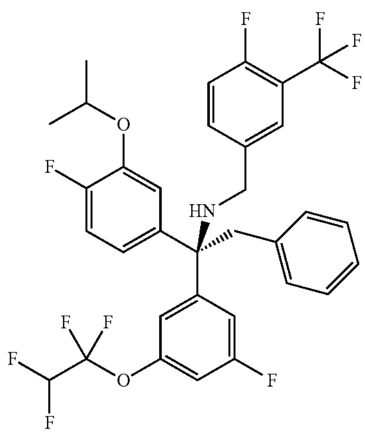 [SMILES: CC(C)Oc1cc([C@@](Cc2ccccc2)(NCc2ccc(F)c(C(F)(F)F)c2)c2cc(F)cc(OC(F)(F)C(F)F)c2)ccc1F] | (R)-N-(4-fluoro-3-(trifluoromethyl)benzyl)-1-(4-fluoro-3-isopropoxyphenyl)-1-(3-fluoro-5-(1,1,2,2-tetrafluoroethoxy)phenyl)-2-phenylethanamine | 2.23 LC (2) 660.39 [M + H]⁺ | Procedures 109, 110, 111, 112, 113, 114 and 13 |
| 839 | 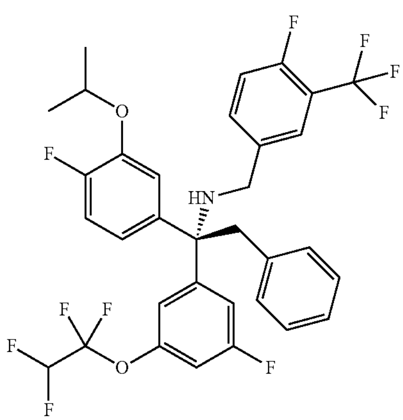 [SMILES: CC(C)Oc1cc([C@](Cc2ccccc2)(NCc2ccc(F)c(C(F)(F)F)c2)c2cc(F)cc(OC(F)(F)C(F)F)c2)ccc1F] | (S)-N-(4-fluoro-3-(trifluoromethyl)benzyl)-1-(4-fluoro-3-isopropoxyphenyl)-1-(3-fluoro-5-(1,1,2,2-tetrafluoroethoxy)phenyl)-2-phenylethanamine | 2.23 LC (2) 660.38 [M + H]⁺ | Procedures 109, 110, 111, 112, 113, 114 and 13 |
| 840 | 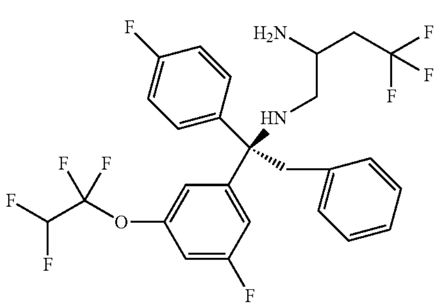 [SMILES: NC(CN[C@](Cc1ccccc1)(c1ccc(F)cc1)c1cc(F)cc(OC(F)(F)C(F)F)c1)CC(F)(F)F] | 4,4,4-trifluoro-N1-((R)-1-(3-fluoro-5-(1,1,2,2-tetrafluoroethoxy)phenyl)-1-(4-fluorophenyl)-2-phenylethyl)butane-1,2-diamine | 3.55 LC (1) 551.2 [M + H]⁺ | Procedures 3, 4, 5, 6, 13 and 141 |

TABLE 14

| Ex. No. | Structure | Name | Retention Time Min./ Molecular Mass | Prepared in the manner described in: |
|---|---|---|---|---|
| 841 | 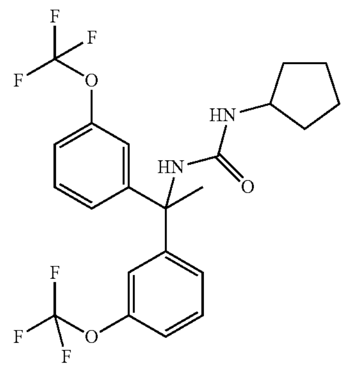 [SMILES: CC(NC(=O)NC1CCCC1)(c1cccc(OC(F)(F)F)c1)c1cccc(OC(F)(F)F)c1] | 1-(1,1-bis(3-(trifluoromethoxy) phenyl)ethyl)-3-cyclopentylurea | 4.26 LC (1) 477.34 [M + H]+ | Procedures 11, 6 and 2 |
| 842 | 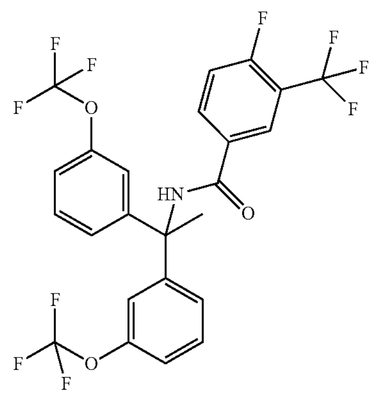 [SMILES: CC(NC(=O)c1ccc(F)c(C(F)(F)F)c1)(c1cccc(OC(F)(F)F)c1)c1cccc(OC(F)(F)F)c1] | N-(1,1-bis(3-(trifluoromethoxy) phenyl)ethyl)-4-fluoro-3-(trifluoromethyl)benzamide | 4.38 LC (1) 556.24 [M + H]+ | Procedures 11, 6 and 7 |
| 843 | 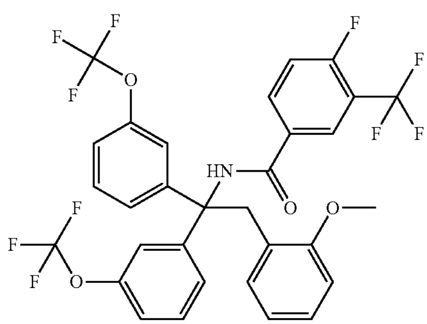 [SMILES: COc1ccccc1CC(NC(=O)c1ccc(F)c(C(F)(F)F)c1)(c1cccc(OC(F)(F)F)c1)c1cccc(OC(F)(F)F)c1] | 4-fluoro-N-(2-(2-methoxyphenyl)-1,1-bis(3-(trifluoromethoxy)phenyl) ethyl)-3-(trifluoromethyl) benzamide | 4.116 LC (1) 661.98 [M + H]+ | Procedures 11, 6 and 7 |
| 844 | 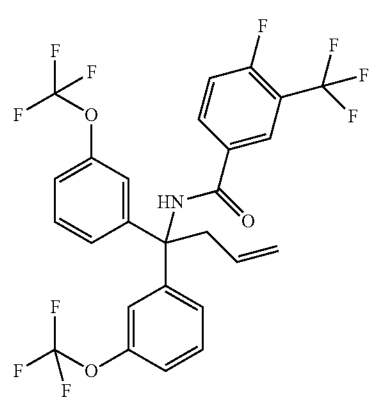 [SMILES: C=CCC(NC(=O)c1ccc(F)c(C(F)(F)F)c1)(c1cccc(OC(F)(F)F)c1)c1cccc(OC(F)(F)F)c1] | N-(1,1-bis(3-(trifluoromethoxy) phenyl)but-3-enyl)-4-fluoro-3-(trifluoromethyl)benzamide | 4.37 LC (1) 582.25 [M + H]+ | Procedures 11, 6 and 7 |

TABLE 14-continued

| Ex. No. | Structure | Name | Retention Time Min./ Molecular Mass | Prepared in the manner described in: |
|---|---|---|---|---|
| 845 | 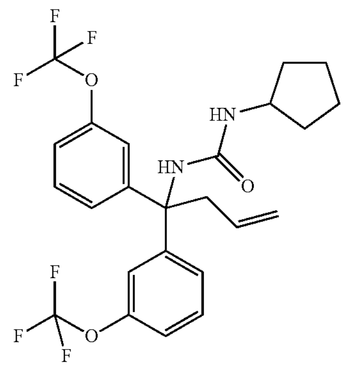 [SMILES: C=CCC(NC(=O)NC1CCCC1)(c1cccc(OC(F)(F)F)c1)c1cccc(OC(F)(F)F)c1] | 1-(1,1-bis(3-(trifluoromethoxy)phenyl)but-3-enyl)-3-cyclopentylurea | 4.26 LC (1) 503.33 [M + H]⁺ | Procedures 11, 6 and 2 |
| 846 | 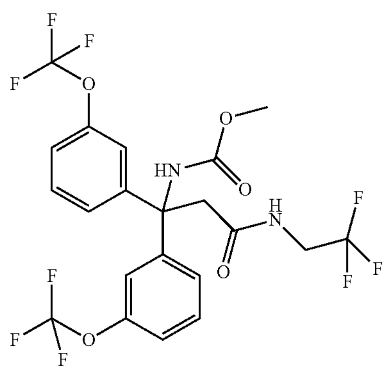 [SMILES: COC(=O)NC(CC(=O)NCC(F)(F)F)(c1cccc(OC(F)(F)F)c1)c1cccc(OC(F)(F)F)c1] | methyl 3-oxo-3-(2,2,2-trifluoroethylamino)-1,1-bis(3-(trifluoromethoxy)phenyl)propylcarbamate | 3.81 LC (1) 548.90 [M + H]⁺ | Procedures 11, 6, 14, 23, 128 and 82 |
| 847 | 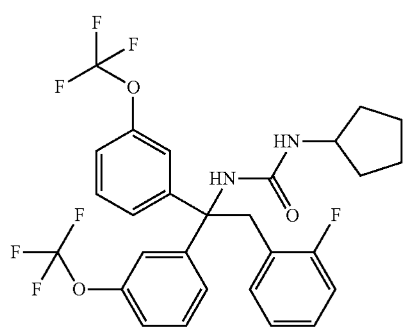 [SMILES: O=C(NC1CCCC1)NC(Cc1ccccc1F)(c1cccc(OC(F)(F)F)c1)c1cccc(OC(F)(F)F)c1] | 1-cyclopentyl-3-(2-(2-fluorophenyl)-1,1-bis(3-(trifluoromethoxy)phenyl)ethyl)urea | 3.766 LC (1) 571.06 [M + H]⁺ | Procedures 11, 6 and 2 |
| 848 | 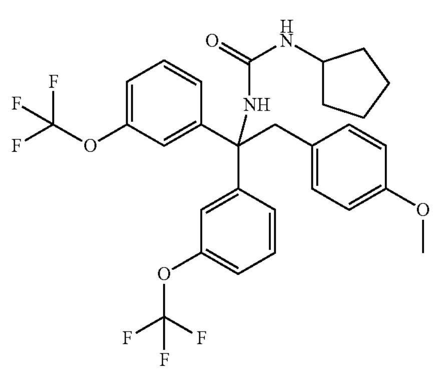 [SMILES: COc1ccc(CC(NC(=O)NC2CCCC2)(c2cccc(OC(F)(F)F)c2)c2cccc(OC(F)(F)F)c2)cc1] | 1-cyclopentyl-3-(2-(4-methoxyphenyl)-1,1-bis(3-(trifluoromethoxy)phenyl)ethyl)urea | 4.37 LC (11) 583.03 [M + H]⁺ | Procedures 11, 6 and 2 |

TABLE 14-continued

| Ex. No. | Structure | Name | Retention Time Min./ Molecular Mass | Prepared in the manner described in: |
|---|---|---|---|---|
| 849 | 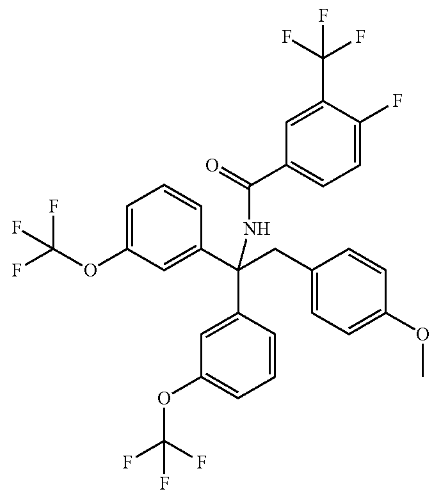 [SMILES: COc1ccc(CC(NC(=O)c2ccc(F)c(C(F)(F)F)c2)(c2cccc(OC(F)(F)F)c2)c2cccc(OC(F)(F)F)c2)cc1] | 4-fluoro-N-(2-(4-methoxyphenyl)-1,1-bis(3-(trifluoromethoxy)phenyl)ethyl)-3-(trifluoromethyl)benzamide | 4.52 LC (11) 661.96 [M + H]$^+$ | Procedures 11, 6 and 7 |
| 850 | 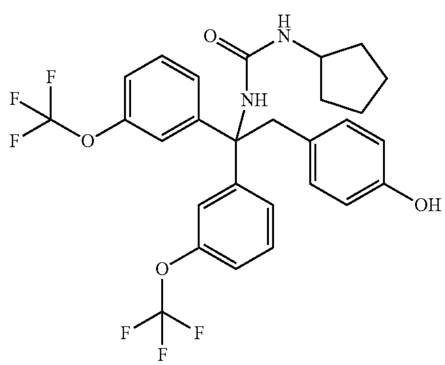 [SMILES: O=C(NC1CCCC1)NC(Cc1ccc(O)cc1)(c1cccc(OC(F)(F)F)c1)c1cccc(OC(F)(F)F)c1] | 1-cyclopentyl-3-(2-(4-hydroxyphenyl)-1,1-bis(3-(trifluoromethoxy)phenyl)ethyl)urea | 4.21 LC (11) 569.17 [M + H]$^+$ | Procedures 11, 6, 2 and 59 |
| 851 | 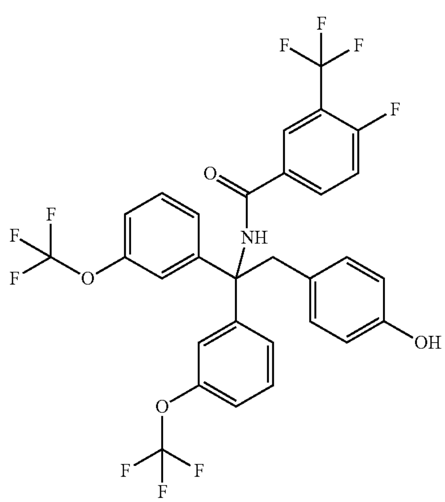 [SMILES: O=C(NC(Cc1ccc(O)cc1)(c1cccc(OC(F)(F)F)c1)c1cccc(OC(F)(F)F)c1)c1ccc(F)c(C(F)(F)F)c1] | 4-fluoro-N-(2-(4-hydroxyphenyl)-1,1-bis(3-(trifluoromethoxy)phenyl)ethyl)-3-(trifluoromethyl)benzamide | 4.28 LC (11) 648.12 [M + H]$^+$ | Procedures 11, 6, 7 and 59 |

TABLE 14-continued

| Ex. No. | Structure | Name | Retention Time Min./ Molecular Mass | Prepared in the manner described in: |
|---|---|---|---|---|
| 852 | 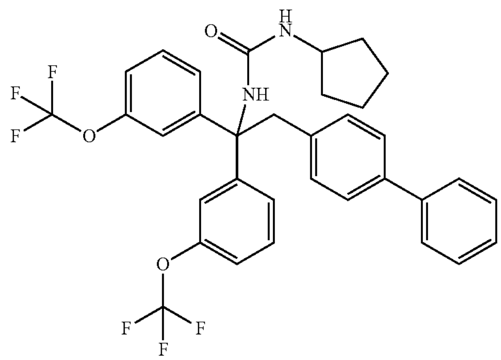 [SMILES: O=C(NC1CCCC1)NC(Cc1ccc(-c2ccccc2)cc1)(c1cccc(OC(F)(F)F)c1)c1cccc(OC(F)(F)F)c1] | 1-(2-(biphenyl-4-yl)-1,1-bis(3-(trifluoromethoxy)phenyl)ethyl)-3-cyclopentylurea | 4.74 LC (11) 629.20 $[M + H]^+$ | Procedures 11, 6 and 2 |
| 853 | 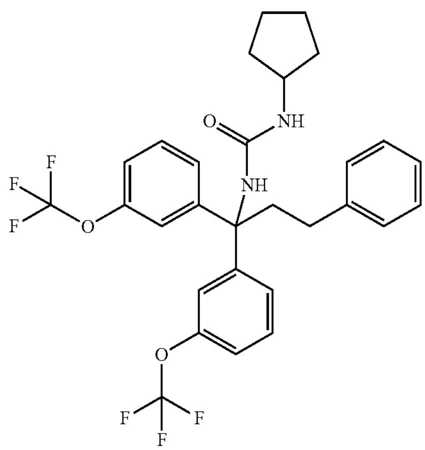 [SMILES: O=C(NC1CCCC1)NC(CCc1ccccc1)(c1cccc(OC(F)(F)F)c1)c1cccc(OC(F)(F)F)c1] | 1-cyclopentyl-3-(3-phenyl-1,1-bis(3-(trifluoromethoxy)phenyl)propyl)urea | 4.54 LC (11) 567.2 $[M + H]^+$ | Procedures 11, 6 and 2 |
| 854 | 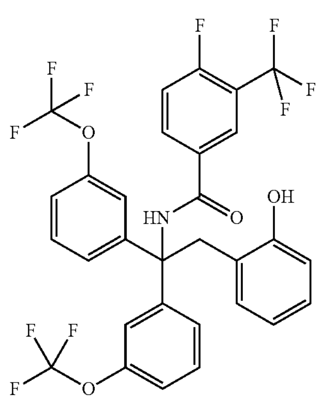 [SMILES: O=C(NC(Cc1ccccc1O)(c1cccc(OC(F)(F)F)c1)c1cccc(OC(F)(F)F)c1)c1ccc(F)c(C(F)(F)F)c1] | 4-fluoro-N-(2-(2-hydroxyphenyl)-1,1-bis(3-(trifluoromethoxy)phenyl)ethyl)-3-(trifluoromethyl)benzamide | 3.953 LC (1) 648.2 $[M + H]^+$ | Procedures 11, 6, 7 and 59 |

TABLE 14-continued

| Ex. No. | Structure | Name | Retention Time Min./ Molecular Mass | Prepared in the manner described in: |
|---|---|---|---|---|
| 855 | 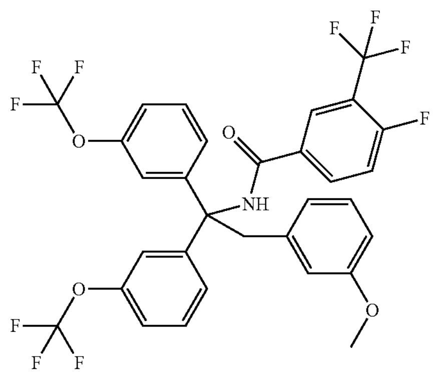 [SMILES: COc1cccc(CC(NC(=O)c2ccc(F)c(C(F)(F)F)c2)(c2cccc(OC(F)(F)F)c2)c2cccc(OC(F)(F)F)c2)c1] | 4-fluoro-N-(2-(3-methoxyphenyl)-1,1-bis(3-(trifluoromethoxy)phenyl)ethyl)-3-(trifluoromethyl)benzamide | 4.50 LC (11) 662.1 [M + H]$^+$ | Procedures 11, 6 and 7 |
| 856 | 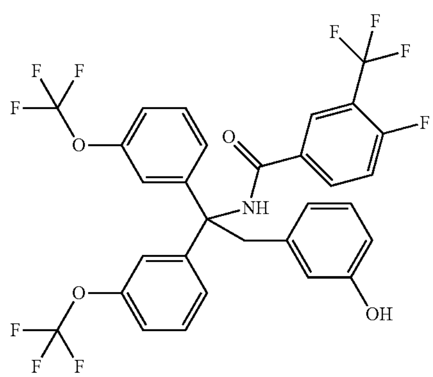 [SMILES: O=C(NC(Cc1cccc(O)c1)(c1cccc(OC(F)(F)F)c1)c1cccc(OC(F)(F)F)c1)c1ccc(F)c(C(F)(F)F)c1] | 4-fluoro-N-(2-(3-hydroxyphenyl)-1,1-bis(3-(trifluoromethoxy)phenyl)ethyl)-3-(trifluoromethyl)benzamide | 4.30 LC (11) 648.1 [M + H]$^+$ | Procedures 11, 6, 7 and 59 |
| 857 | 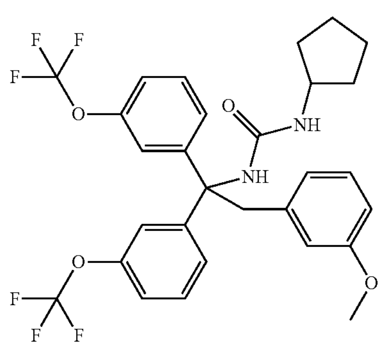 [SMILES: COc1cccc(CC(NC(=O)NC2CCCC2)(c2cccc(OC(F)(F)F)c2)c2cccc(OC(F)(F)F)c2)c1] | 1-cyclopentyl-3-(2-(3-methoxyphenyl)-1,1-bis(3-(trifluoromethoxy)phenyl)ethyl)urea | 4.44 LC (11) 583.2 [M + H]$^+$ | Procedures 11, 6 and 2 |
| 858 | 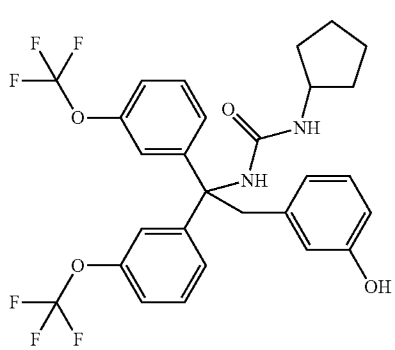 [SMILES: O=C(NC1CCCC1)NC(Cc1cccc(O)c1)(c1cccc(OC(F)(F)F)c1)c1cccc(OC(F)(F)F)c1] | 1-cyclopentyl-3-(2-(3-hydroxyphenyl)-1,1-bis(3-(trifluoromethoxy)phenyl)ethyl)urea | 4.19 LC (11) 569.2 [M + H]$^+$ | Procedures 11, 6, 2 and 59 |

TABLE 14-continued

| Ex. No. | Structure | Name | Retention Time Min./ Molecular Mass | Prepared in the manner described in: |
|---|---|---|---|---|
| 859 | 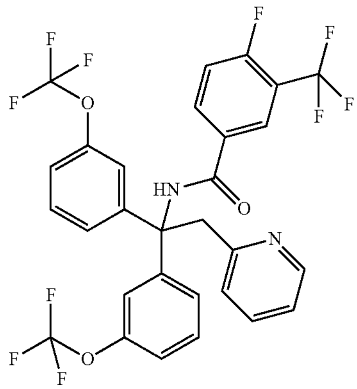 [SMILES: O=C(NC(Cc1ccccn1)(c1cccc(OC(F)(F)F)c1)c1cccc(OC(F)(F)F)c1)c1ccc(F)c(C(F)(F)F)c1] | 4-fluoro-N-(2-(pyridin-2-yl)-1,1-bis(3-(trifluoromethoxy)phenyl)ethyl)-3-(trifluoromethyl)benzamide | 4.03 LC (1) 633.13 [M + H]+ | Procedures 11, 20, 6 and 7 |
| 860 | 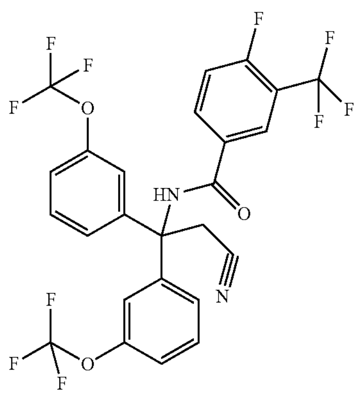 [SMILES: N#CCC(NC(=O)c1ccc(F)c(C(F)(F)F)c1)(c1cccc(OC(F)(F)F)c1)c1cccc(OC(F)(F)F)c1] | N-(2-cyano-1,1-bis(3-(trifluoromethoxy)phenyl)ethyl)-4-fluoro-3-(trifluoromethyl)benzamide | 4.04 LC (1) 581.16 [M + H]+ | Procedures 11, 18, 6 and 7 |
| 861 | 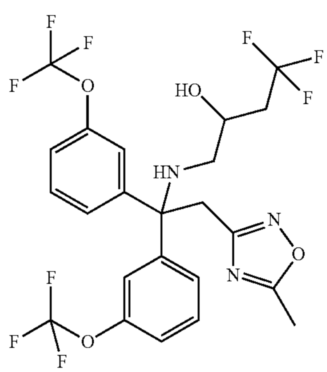 [SMILES: Cc1nc(CC(NCC(O)CC(F)(F)F)(c2cccc(OC(F)(F)F)c2)c2cccc(OC(F)(F)F)c2)no1] | 4,4,4-trifluoro-1-(2-(5-methyl-1,2,4-oxadiazol-3-yl)-1,1-bis(3-(trifluoromethoxy)phenyl)ethylamino)butan-2-ol | 3.78 LC (1) 574.22 [M + H]+ | Procedures 11, 17 and 8 |
| 862 | 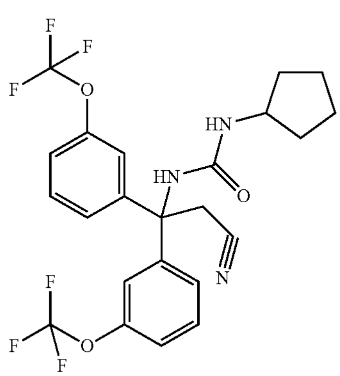 [SMILES: N#CCC(NC(=O)NC1CCCC1)(c1cccc(OC(F)(F)F)c1)c1cccc(OC(F)(F)F)c1] | 1-(2-cyano-1,1-bis(3-(trifluoromethoxy)phenyl)ethyl)-3-cyclopentylurea | 3.83 LC (1) 502.3 [M + H]+ | Procedures 11, 18, 6 and 2 |

TABLE 14-continued

| Ex. No. | Structure | Name | Retention Time Min./ Molecular Mass | Prepared in the manner described in: |
|---|---|---|---|---|
| 863 | 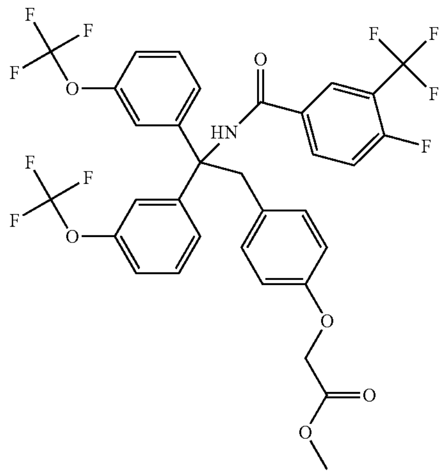 [SMILES: COC(=O)COc1ccc(CC(NC(=O)c2ccc(F)c(C(F)(F)F)c2)(c2cccc(OC(F)(F)F)c2)c2cccc(OC(F)(F)F)c2)cc1] | methyl 2-(4-(2-(4-fluoro-3-(trifluoromethyl)benzamido)-2,2-bis(3-(trifluoromethoxy)phenyl)ethyl)phenoxy)acetate | 4.37 LC (11) 720.2 [M + H]$^+$ | Procedures 11, 6, 7, 59 and 68 |
| 864 | 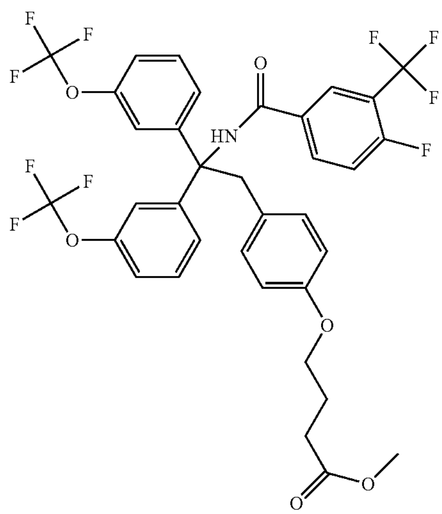 [SMILES: COC(=O)CCCOc1ccc(CC(NC(=O)c2ccc(F)c(C(F)(F)F)c2)(c2cccc(OC(F)(F)F)c2)c2cccc(OC(F)(F)F)c2)cc1] | methyl 4-(4-(2-(4-fluoro-3-(trifluoromethyl)benzamido)-2,2-bis(3-(trifluoromethoxy)phenyl)ethyl)phenoxy)butanoate | 4.50 LC (11) 748.2 [M + H]$^+$ | Procedures 11, 6, 7, 59 and 68 |
| 865 | 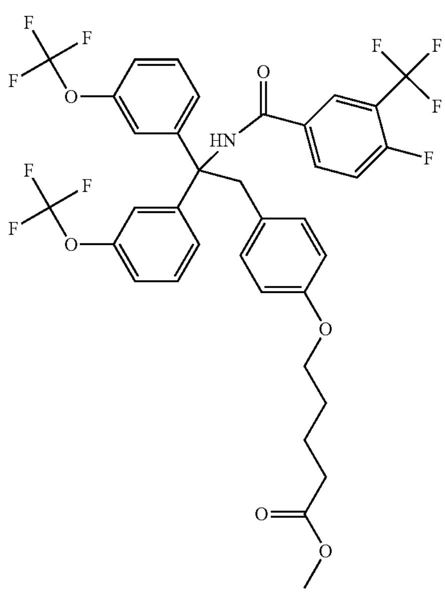 [SMILES: COC(=O)CCCCOc1ccc(CC(NC(=O)c2ccc(F)c(C(F)(F)F)c2)(c2cccc(OC(F)(F)F)c2)c2cccc(OC(F)(F)F)c2)cc1] | methyl 5-(4-(2-(4-fluoro-3-(trifluoromethyl)benzamido)-2,2-bis(3-(trifluoromethoxy)phenyl)ethyl)phenoxy)pentanoate | 4.59 LC (11) 762.2 [M + H]$^+$ | Procedures 11, 6, 7, 59 and 68 |

TABLE 14-continued

| Ex. No. | Structure | Name | Retention Time Min./ Molecular Mass | Prepared in the manner described in: |
|---|---|---|---|---|
| 866 | 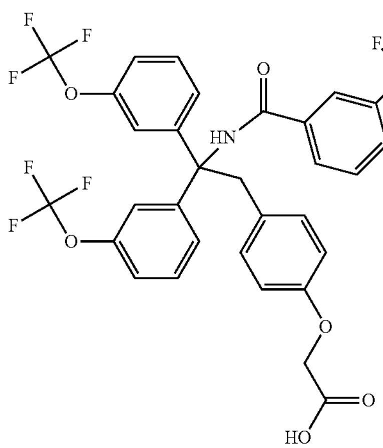 | 2-(4-(2-(4-fluoro-3-(trifluoromethyl)benzamido)-2,2-bis(3-(trifluoromethoxy)phenyl)ethyl)phenoxy)acetic acid | 4.28 LC (11) 706.1 $[M + H]^+$ | Procedures 11, 6, 7, 59, 68 and 23 |
| 867 | 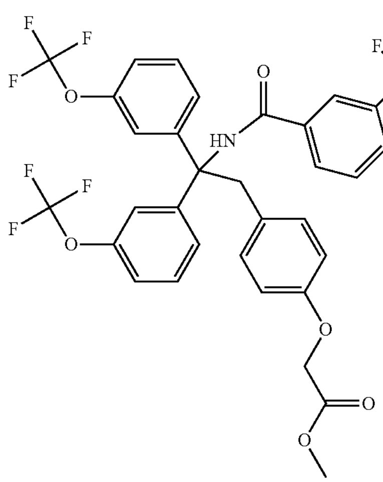 | methyl 2-(4-(2-(4-fluoro-3-(trifluoromethyl)benzamido)-2,2-bis(3-(trifluoromethoxy)phenyl)ethyl)phenoxy)acetate | 4.365 LC (11) 720.2 $[M + H]^+$ | Procedures 11, 6, 7, 59 and 68 |
| 868 | 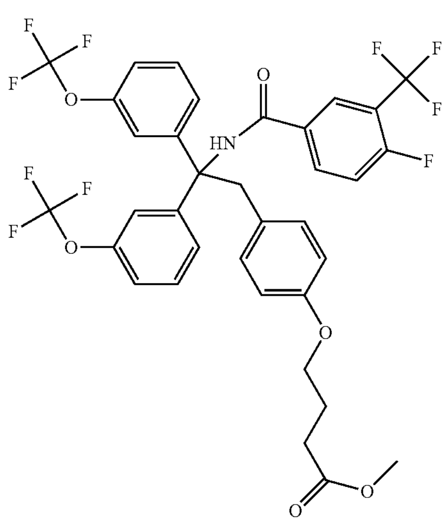 [SMILES: COC(=O)CCCOc1ccc(CC(NC(=O)c2ccc(F)c(C(F)(F)F)c2)(c2cccc(OC(F)(F)F)c2)c2cccc(OC(F)(F)F)c2)cc1] | methyl 4-(4-(2-(4-fluoro-3-(trifluoromethyl)benzamido)-2,2-bis(3-(trifluoromethoxy)phenyl)ethyl)phenoxy)butanoate | 4.503 LC (11) 748.2 $[M + H]^+$ | Procedures 11, 6, 7, 59 and 68 |

TABLE 14-continued

| Ex. No. | Structure | Name | Retention Time Min./ Molecular Mass | Prepared in the manner described in: |
|---|---|---|---|---|
| 869 | 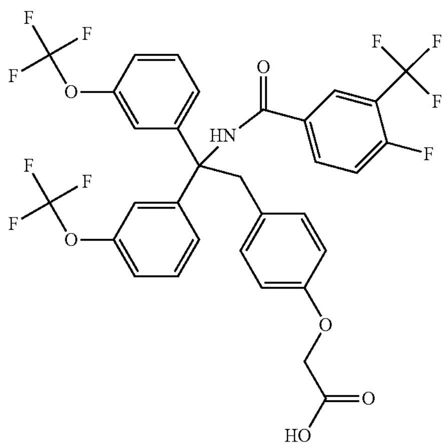 [SMILES: O=C(O)COc1ccc(CC(NC(=O)c2ccc(F)c(C(F)(F)F)c2)(c2cccc(OC(F)(F)F)c2)c2cccc(OC(F)(F)F)c2)cc1] | 2-(4-(2-(4-fluoro-3-(trifluoromethyl)benzamido)-2,2-bis(3-(trifluoromethoxy)phenyl)ethyl)phenoxy)acetic acid | 4.281 LC (11) 706.1 [M + H]$^+$ | Procedures 11, 6, 7, 59, 68 and 23 |
| 870 | 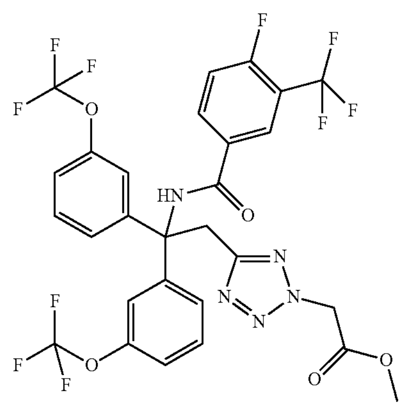 [SMILES: COC(=O)Cn1nnc(CC(NC(=O)c2ccc(F)c(C(F)(F)F)c2)(c2cccc(OC(F)(F)F)c2)c2cccc(OC(F)(F)F)c2)n1] | methyl 2-(5-(2-(4-fluoro-3-(trifluoromethyl)benzamido)-2,2-bis(3-(trifluoromethoxy)phenyl)ethyl)-2H-tetrazol-2-yl)acetate | 4.04 LC (1) 696.1 [M + H]$^+$ | Procedures 11, 18, 6, 7, 79 and 163 |
| 871 | 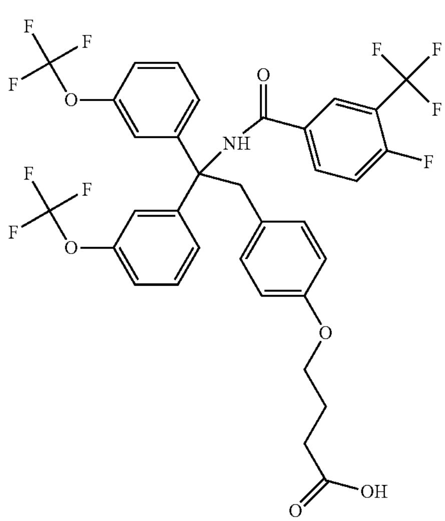 [SMILES: O=C(O)CCCOc1ccc(CC(NC(=O)c2ccc(F)c(C(F)(F)F)c2)(c2cccc(OC(F)(F)F)c2)c2cccc(OC(F)(F)F)c2)cc1] | 4-(4-(2-(4-fluoro-3-(trifluoromethyl)benzamido)-2,2-bis(3-(trifluoromethoxy)phenyl)ethyl)phenoxy)butanoic acid | 4.336 LC (11) 734.1 [M + H]$^+$ | Procedures 11, 6, 7, 59, 68 and 23 |

TABLE 14-continued

| Ex. No. | Structure | Name | Retention Time Min./ Molecular Mass | Prepared in the manner described in: |
|---|---|---|---|---|
| 872 | 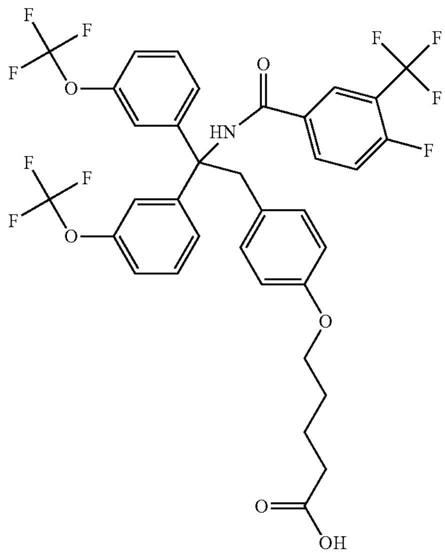 [SMILES: O=C(O)CCCCOc1ccc(CC(NC(=O)c2ccc(F)c(C(F)(F)F)c2)(c2cccc(OC(F)(F)F)c2)c2cccc(OC(F)(F)F)c2)cc1] | 5-(4-(2-(4-fluoro-3-(trifluoromethyl)benzamido)-2,2-bis(3-(trifluoromethoxy)phenyl)ethyl)phenoxy)pentanoic acid | 4.376 LC (11) 748.2 [M + H]$^+$ | Procedures 11, 6, 7, 59, 68 and 23 |
| 873 | 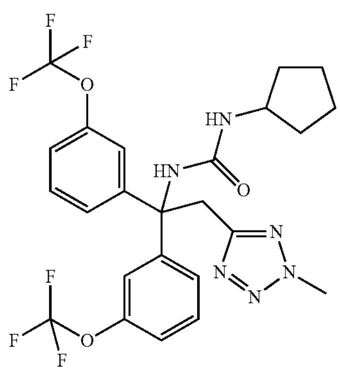 [SMILES: Cn1nnc(CC(NC(=O)NC2CCCC2)(c2cccc(OC(F)(F)F)c2)c2cccc(OC(F)(F)F)c2)n1] | 1-cyclopentyl-3-(2-(2-methyl-2H-tetrazol-5-yl)-1,1-bis(3-(trifluoromethoxy)phenyl)ethyl)urea | 3.89 LC (1) 559.26 [M + H]$^+$ | Procedures 11, 18, 6, 2, 79 and 80 |
| 874 | 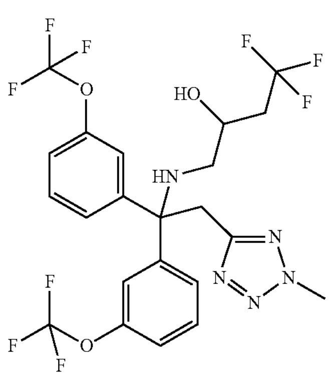 [SMILES: Cn1nnc(CC(NCC(O)CC(F)(F)F)(c2cccc(OC(F)(F)F)c2)c2cccc(OC(F)(F)F)c2)n1] | 4,4,4-trifluoro-1-(2-(2-methyl-2H-tetrazol-5-yl)-1,1-bis(3-(trifluoromethoxy)phenyl)ethylamino)butan-2-ol | 3.72 LC (1) 574.23 [M + H]$^+$ | Procedures 11, 18, 6, 8, 79 and 80 |

TABLE 14-continued

| Ex. No. | Structure | Name | Retention Time Min./ Molecular Mass | Prepared in the manner described in: |
|---|---|---|---|---|
| 875 | 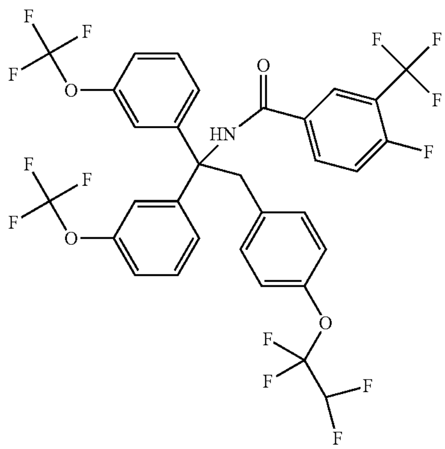 [SMILES: O=C(NC(Cc1ccc(OC(F)(F)C(F)F)cc1)(c1cccc(OC(F)(F)F)c1)c1cccc(OC(F)(F)F)c1)c1ccc(F)c(C(F)(F)F)c1] | 4-fluoro-N-(2-(4-(1,1,2,2-tetrafluoroethoxy)phenyl)-1,1-bis(3-(trifluoromethoxy)phenyl)ethyl)-3-(trifluoromethyl)benzamide | 4.305 LC (11) 748.1 [M + H]+ | Procedures 11, 6, 7, 59 and 3 |
| 876 | 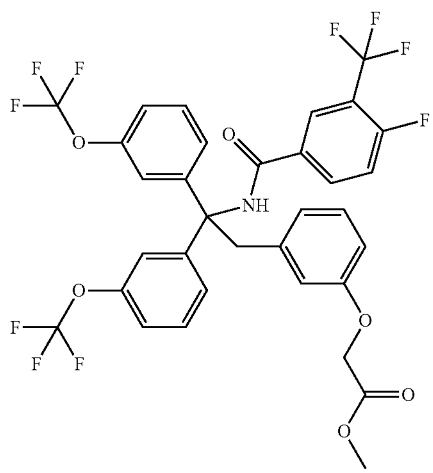 [SMILES: COC(=O)COc1cccc(CC(NC(=O)c2ccc(F)c(C(F)(F)F)c2)(c2cccc(OC(F)(F)F)c2)c2cccc(OC(F)(F)F)c2)c1] | methyl 2-(3-(2-(4-fluoro-3-(trifluoromethyl)benzamido)-2,2-bis(3-(trifluoromethoxy)phenyl)ethyl)phenoxy)acetate | 4.363 LC (11) 720.2 [M + H]+ | Procedures 11, 6, 7, 59 and 68 |
| 877 | 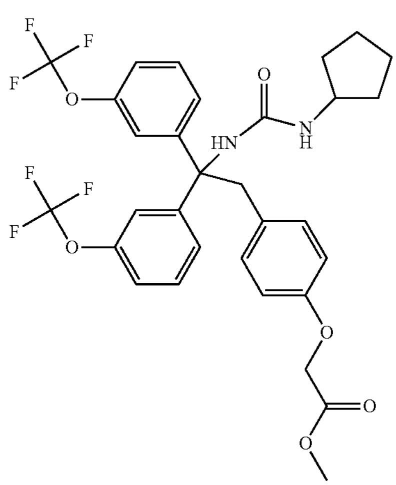 [SMILES: COC(=O)COc1ccc(CC(NC(=O)NC2CCCC2)(c2cccc(OC(F)(F)F)c2)c2cccc(OC(F)(F)F)c2)cc1] | methyl 2-(4-(2-(3-cyclopentylureido)-2,2-bis(3-(trifluoromethoxy)phenyl)ethyl)phenoxy)acetate | 4.293 LC (11) 641.2 [M + H]+ | Procedures 11, 6, 2, 59 and 68 |

TABLE 14-continued

| Ex. No. | Structure | Name | Retention Time Min./ Molecular Mass | Prepared in the manner described in: |
|---|---|---|---|---|
| 878 | 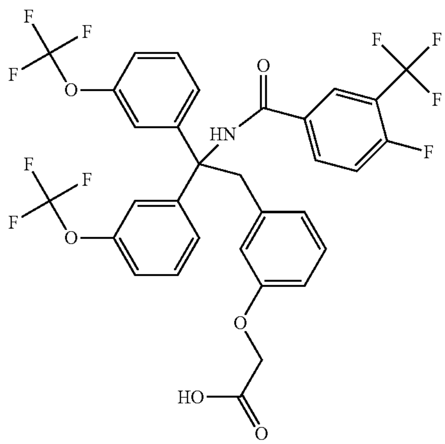 [SMILES: O=C(O)COc1cccc(CC(NC(=O)c2ccc(F)c(C(F)(F)F)c2)(c2cccc(OC(F)(F)F)c2)c2cccc(OC(F)(F)F)c2)c1] | 2-(3-(2-(4-fluoro-3-(trifluoromethyl)benzamido)-2,2-bis(3-(trifluoromethoxy)phenyl)ethyl)phenoxy)acetic acid | 4.286 LC (11) 706.1 [M + H]$^+$ | Procedures 11, 6, 7, 59, 68 and 23 |
| 879 | 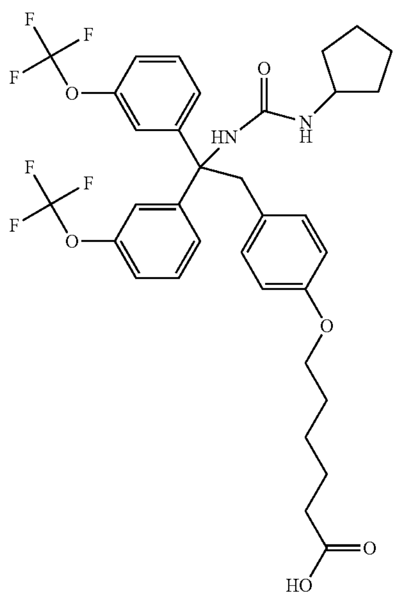 [SMILES: O=C(O)CCCCCOc1ccc(CC(NC(=O)NC2CCCC2)(c2cccc(OC(F)(F)F)c2)c2cccc(OC(F)(F)F)c2)cc1] | 6-(4-(2-(3-cyclopentylureido)-2,2-bis(3-(trifluoromethoxy)phenyl)ethyl)phenoxy)hexanoic acid | 4.39 LC (11) 683.2 [M + H]$^+$ | Procedures 11, 6, 2, 59, 129 and 23 |
| 880 | 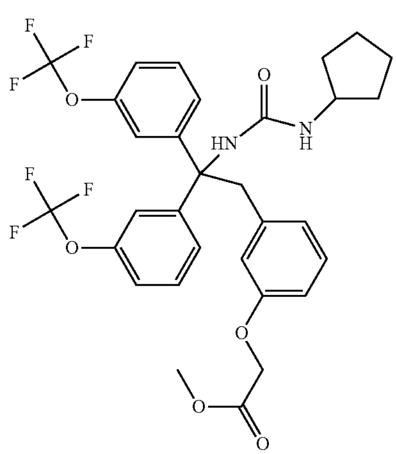 [SMILES: COC(=O)COc1cccc(CC(NC(=O)NC2CCCC2)(c2cccc(OC(F)(F)F)c2)c2cccc(OC(F)(F)F)c2)c1] | methyl 2-(3-(2-(3-cyclopentylureido)-2,2-bis(3-(trifluoromethoxy)phenyl)ethyl)phenoxy)acetate | 4.278 LC (11) 641.2 [M + H]$^+$ | Procedures 11, 6, 2, 59, and 68 |

TABLE 14-continued

| Ex. No. | Structure | Name | Retention Time Min./ Molecular Mass | Prepared in the manner described in: |
|---|---|---|---|---|
| 881 | 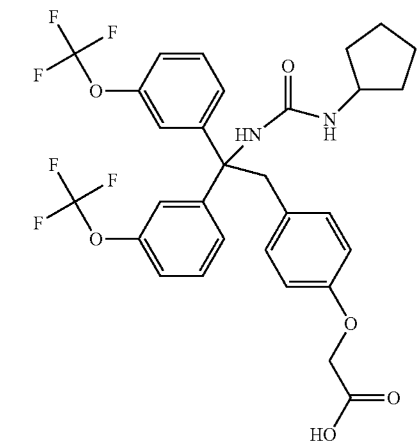 [SMILES: O=C(O)COc1ccc(CC(NC(=O)NC2CCCC2)(c2cccc(OC(F)(F)F)c2)c2cccc(OC(F)(F)F)c2)cc1] | 2-(4-(2-(3-cyclopentylureido)-2,2-bis(3-(trifluoromethoxy)phenyl)ethyl)phenoxy)acetic acid | 4.223 LC (11) 627.2 [M + H]⁺ | Procedures 11, 6, 2, 59, 68 and 23 |
| 882 | 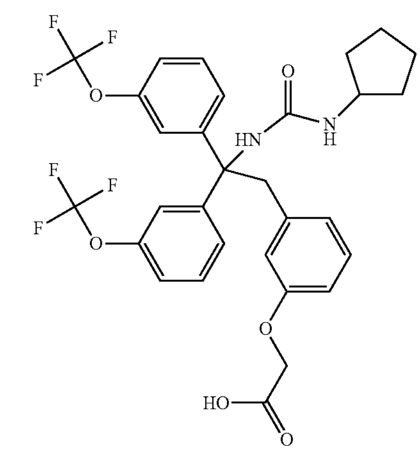 [SMILES: O=C(O)COc1cccc(CC(NC(=O)NC2CCCC2)(c2cccc(OC(F)(F)F)c2)c2cccc(OC(F)(F)F)c2)c1] | 2-(3-(2-(3-cyclopentylureido)-2,2-bis(3-(trifluoromethoxy)phenyl)ethyl)phenoxy)acetic acid | 4.198 LC (11) 627.2 [M + H]⁺ | Procedures 11, 6, 2, 59, 68 and 23 |
| 883 | 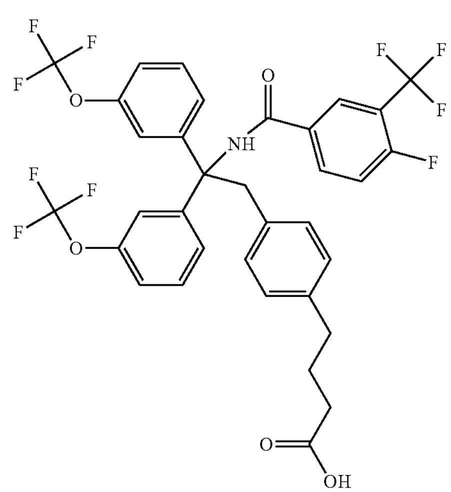 [SMILES: O=C(O)CCCc1ccc(CC(NC(=O)c2ccc(F)c(C(F)(F)F)c2)(c2cccc(OC(F)(F)F)c2)c2cccc(OC(F)(F)F)c2)cc1] | 4-(4-(2-(4-fluoro-3-(trifluoromethyl)benzamido)-2,2-bis(3-(trifluoromethoxy)phenyl)ethyl)phenyl)butanoic acid | 2.21 LC (2) 718.1 [M + H]⁺ | Procedures 11, 72, 73, 74, 75 and 76 |

TABLE 14-continued

| Ex. No. | Structure | Name | Retention Time Min./ Molecular Mass | Prepared in the manner described in: |
|---|---|---|---|---|
| 884 | 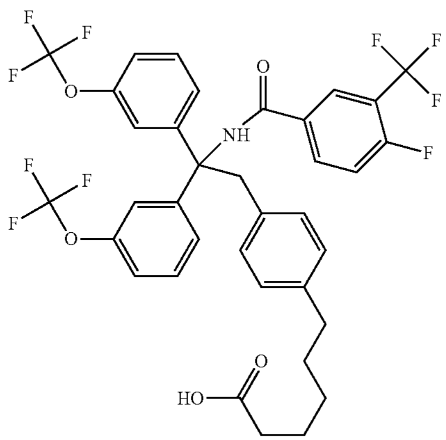 [SMILES: O=C(O)CCCCCc1ccc(CC(NC(=O)c2ccc(F)c(C(F)(F)F)c2)(c2cccc(OC(F)(F)F)c2)c2cccc(OC(F)(F)F)c2)cc1] | 6-(4-(2-(4-fluoro-3-(trifluoromethyl)benzamido)-2,2-bis(3-(trifluoromethoxy)phenyl)ethyl)phenyl)hexanoic acid | 2.28 LC (2) 746.2 [M + H]⁺ | Procedures 11, 72, 73, 74, 75 and 76 |
| 885 | 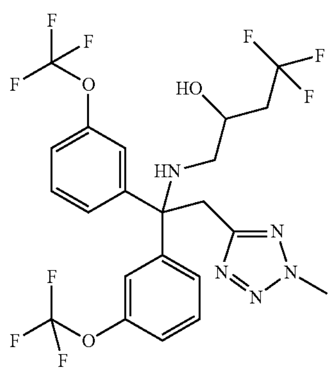 [SMILES: Cn1nnc(CC(NCC(O)CC(F)(F)F)(c2cccc(OC(F)(F)F)c2)c2cccc(OC(F)(F)F)c2)n1] | 4,4,4-trifluoro-1-(2-(2-methyl-2H-tetrazol-5-yl)-1,1-bis(3-(trifluoromethoxy)phenyl)ethylamino)butan-2-ol | 3.62 LC (1) 574.04 [M + H]⁺ | Procedures 11, 18, 6, 8, 79 and 80 |
| 886 | 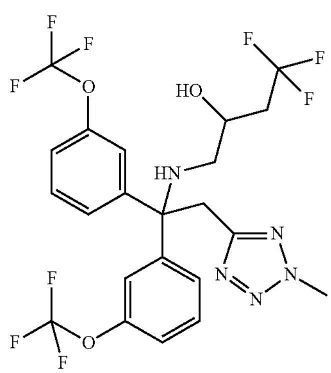 [SMILES: Cn1nnc(CC(NCC(O)CC(F)(F)F)(c2cccc(OC(F)(F)F)c2)c2cccc(OC(F)(F)F)c2)n1] | 4,4,4-trifluoro-1-(2-(2-methyl-2H-tetrazol-5-yl)-1,1-bis(3-(trifluoromethoxy)phenyl)ethylamino)butan-2-ol | 3.69 LC (1) 574.13 [M + H]⁺ | Procedures 11, 18, 6, 8, 79 and 80 |
| 887 | 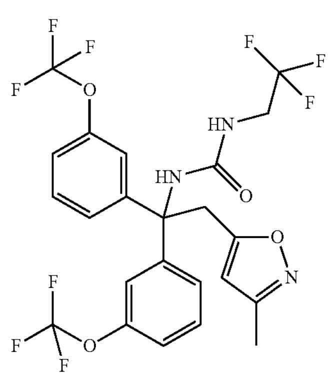 [SMILES: Cc1cc(CC(NC(=O)NCC(F)(F)F)(c2cccc(OC(F)(F)F)c2)c2cccc(OC(F)(F)F)c2)on1] | 1-(2-(3-methylisoxazol-5-yl)-1,1-bis(3-(trifluoromethoxy)phenyl)ethyl)-3-(2,2,2-trifluoroethyl)urea | 3.81 LC (1) 572.11 [M + H]⁺ | Procedures 11, 17, 2 and 9 |

TABLE 14-continued

| Ex. No. | Structure | Name | Retention Time Min./ Molecular Mass | Prepared in the manner described in: |
|---|---|---|---|---|
| 888 | 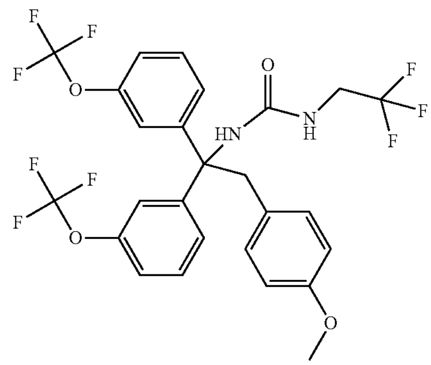 [SMILES: COc1ccc(CC(NC(=O)NCC(F)(F)F)(c2cccc(OC(F)(F)F)c2)c2cccc(OC(F)(F)F)c2)cc1] | 1-(2-(4-methoxyphenyl)-1,1-bis(3-(trifluoromethoxy)phenyl)ethyl)-3-(2,2,2-trifluoroethyl)urea | 4.291 LC (11) 597.2 [M + H]$^+$ | Procedures 11, 6 and 25 |
| 889 | 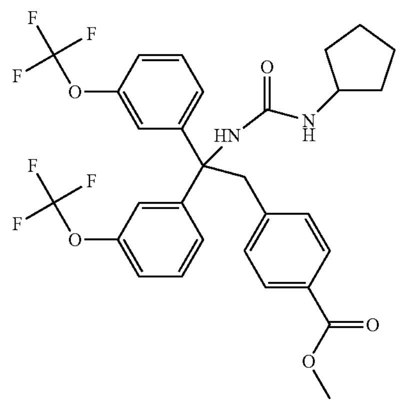 [SMILES: COC(=O)c1ccc(CC(NC(=O)NC2CCCC2)(c2cccc(OC(F)(F)F)c2)c2cccc(OC(F)(F)F)c2)cc1] | methyl 4-(2-(3-cyclopentylureido)-2,2-bis(3-(trifluoromethoxy)phenyl)ethyl)benzoate | 4.345 LC (11) 611.2 [M + H]$^+$ | Procedures 11, 72, 73, 74, 75 and 2 |
| 890 | 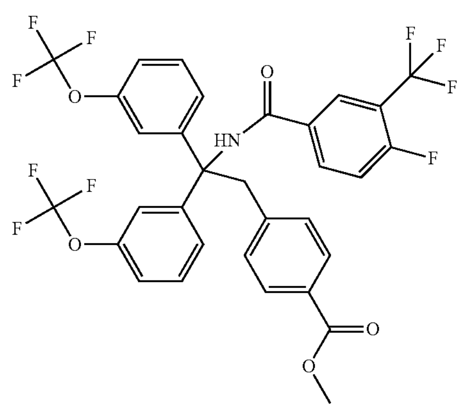 [SMILES: COC(=O)c1ccc(CC(NC(=O)c2ccc(F)c(C(F)(F)F)c2)(c2cccc(OC(F)(F)F)c2)c2cccc(OC(F)(F)F)c2)cc1] | methyl 4-(2-(4-fluoro-3-(trifluoromethyl)benzamido)-2,2-bis(3-(trifluoromethoxy)phenyl)ethyl)benzoate | 4.448 LC (11) 690.1 [M + H]$^+$ | Procedures 11, 72, 73, 74, 75 and 7 |
| 891 | 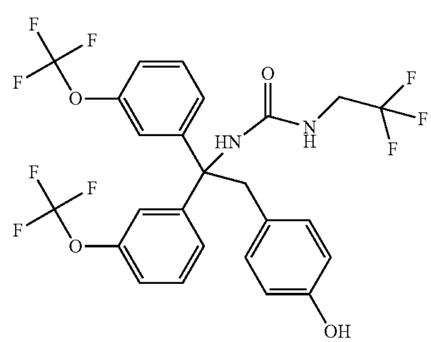 [SMILES: O=C(NCC(F)(F)F)NC(Cc1ccc(O)cc1)(c1cccc(OC(F)(F)F)c1)c1cccc(OC(F)(F)F)c1] | 1-(2-(4-hydroxyphenyl)-1,1-bis(3-(trifluoromethoxy)phenyl)ethyl)-3-(2,2,2-trifluoroethyl)urea | 4.101 LC (11) 583.2 [M + H]$^+$ | Procedures 11, 6, 25 and 59 |

TABLE 14-continued

| Ex. No. | Structure | Name | Retention Time Min./ Molecular Mass | Prepared in the manner described in: |
|---|---|---|---|---|
| 892 | 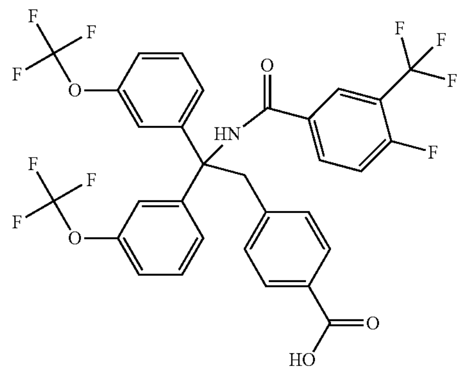 [SMILES: O=C(O)c1ccc(CC(NC(=O)c2ccc(F)c(C(F)(F)F)c2)(c2cccc(OC(F)(F)F)c2)c2cccc(OC(F)(F)F)c2)cc1] | 4-(2-(4-fluoro-3-(trifluoromethyl)benzamido)-2,2-bis(3-(trifluoromethoxy)phenyl)ethyl)benzoic acid | 4.286 LC (11) 676.1 [M + H]⁺ | Procedures 11, 72, 73, 74, 75, 7 and 23 |
| 893 | 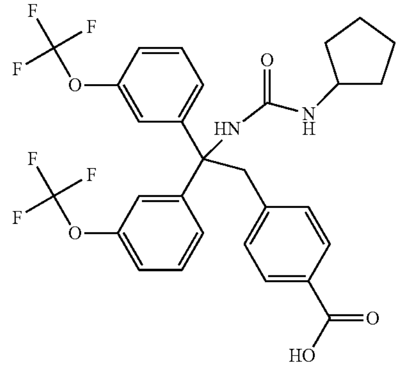 [SMILES: O=C(NC1CCCC1)NC(Cc1ccc(C(=O)O)cc1)(c1cccc(OC(F)(F)F)c1)c1cccc(OC(F)(F)F)c1] | 4-(2-(3-cyclopentylureido)-2,2-bis(3-(trifluoromethoxy)phenyl)ethyl)benzoic acid | 4.208 LC (11) 597.2 [M + H]⁺ | Procedures 11, 72, 73, 74, 75, 2 and 23 |
| 894 | 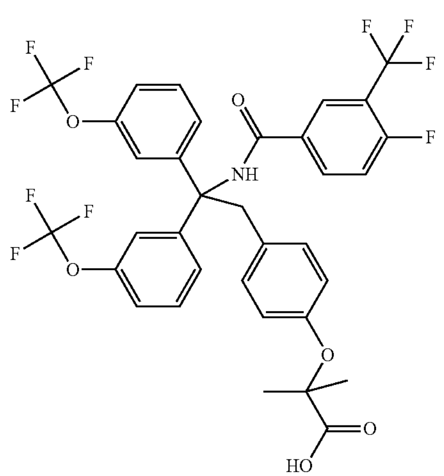 [SMILES: CC(C)(Oc1ccc(CC(NC(=O)c2ccc(F)c(C(F)(F)F)c2)(c2cccc(OC(F)(F)F)c2)c2cccc(OC(F)(F)F)c2)cc1)C(=O)O] | 2-(4-(2-(4-fluoro-3-(trifluoromethyl)benzamido)-2,2-bis(3-(trifluoromethoxy)phenyl)ethyl)phenoxy)-2-methylpropanoic acid | 4.366 LC (11) 734.1 [M + H]⁺ | Procedures 11, 6, 7, 59, 68 and 23 |

TABLE 14-continued

| Ex. No. | Structure | Name | Retention Time Min./ Molecular Mass | Prepared in the manner described in: |
|---|---|---|---|---|
| 895 | 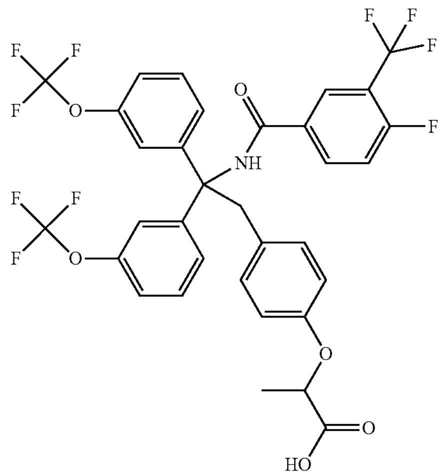 [SMILES: CC(Oc1ccc(CC(NC(=O)c2ccc(F)c(C(F)(F)F)c2)(c2cccc(OC(F)(F)F)c2)c2cccc(OC(F)(F)F)c2)cc1)C(=O)O] | 2-(4-(2-(4-fluoro-3-(trifluoromethyl)benzamido)-2,2-bis(3-(trifluoromethoxy)phenyl)ethyl)phenoxy)propanoic acid | 4.388 LC (11) 719.87 [M + H]$^+$ | Procedures 11, 6, 7, 59, 68 and 23 |
| 896 | 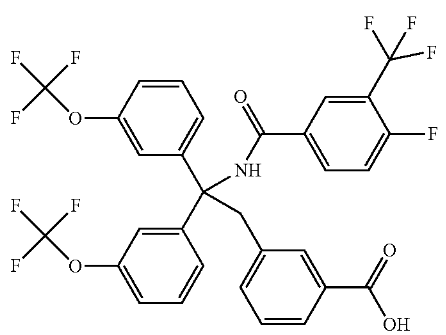 [SMILES: O=C(O)c1cccc(CC(NC(=O)c2ccc(F)c(C(F)(F)F)c2)(c2cccc(OC(F)(F)F)c2)c2cccc(OC(F)(F)F)c2)c1] | 3-(2-(4-fluoro-3-(trifluoromethyl)benzamido)-2,2-bis(3-(trifluoromethoxy)phenyl)ethyl)benzoic acid | 4.266 LC (11) 675.84 [M + H]$^+$ | Procedures 11, 72, 73, 74, 75, 7 and 23 |
| 897 | 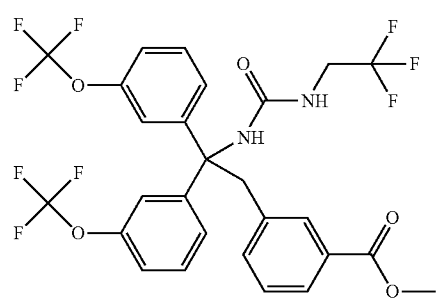 [SMILES: COC(=O)c1cccc(CC(NC(=O)NCC(F)(F)F)(c2cccc(OC(F)(F)F)c2)c2cccc(OC(F)(F)F)c2)c1] | methyl 3-(2-(3-(2,2,2-trifluoroethyl)ureido)-2,2-bis(3-(trifluoromethoxy)phenyl)ethyl)benzoate | 4.246 LC (11) 625.2 [M + H]$^+$ | Procedures 11, 72, 73, 74, 75 and 25 |

TABLE 14-continued

| Ex. No. | Structure | Name | Retention Time Min./ Molecular Mass | Prepared in the manner described in: |
|---|---|---|---|---|
| 898 | 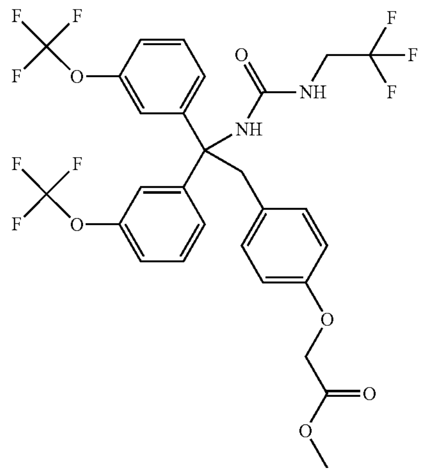 [SMILES: COC(=O)COc1ccc(CC(NC(=O)NCC(F)(F)F)(c2cccc(OC(F)(F)F)c2)c2cccc(OC(F)(F)F)c2)cc1] | methyl 2-(4-(2-(3-(2,2,2-trifluoroethyl)ureido)-2,2-bis(3-(tri-fluoromethoxy)phenyl)ethyl)phenoxy)acetate | 4.196 LC (11) 655.1 [M + H]⁺ | Procedures 11, 6, 25, 59 and 68 |
| 899 | 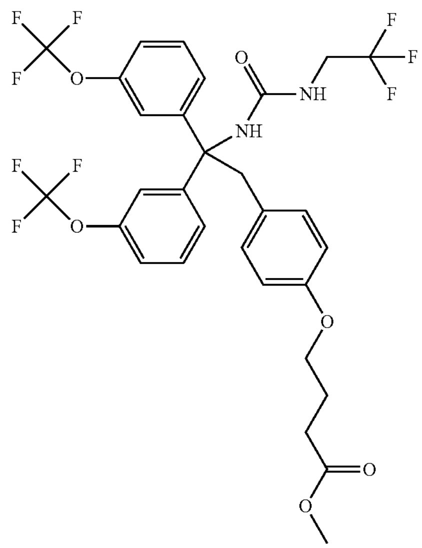 [SMILES: COC(=O)CCCOc1ccc(CC(NC(=O)NCC(F)(F)F)(c2cccc(OC(F)(F)F)c2)c2cccc(OC(F)(F)F)c2)cc1] | methyl 4-(4-(2-(3-(2,2,2-trifluoroethyl)ureido)-2,2-bis(3-(tri-fluoromethoxy)phenyl)ethyl)phenoxy)butanoate | 4.31 LC (11) 683.1 [M + H]⁺ | Procedures 11, 6, 25, 59 and 68 |
| 900 | 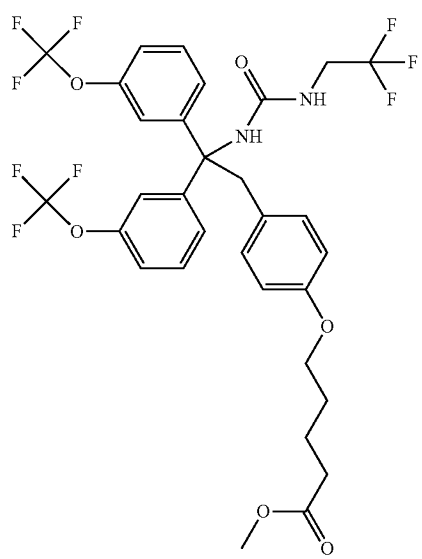 [SMILES: COC(=O)CCCCOc1ccc(CC(NC(=O)NCC(F)(F)F)(c2cccc(OC(F)(F)F)c2)c2cccc(OC(F)(F)F)c2)cc1] | methyl 5-(4-(2-(3-(2,2,2-trifluoroethyl)ureido)-2,2-bis(3-(tri-fluoromethoxy)phenyl)ethyl)phenoxy)pentanoate | 4.371 LC (11) 697.2 [M + H]⁺ | Procedures 11, 6, 25, 59 and 68 |

TABLE 14-continued

| Ex. No. | Structure | Name | Retention Time Min./ Molecular Mass | Prepared in the manner described in: |
|---|---|---|---|---|
| 901 | 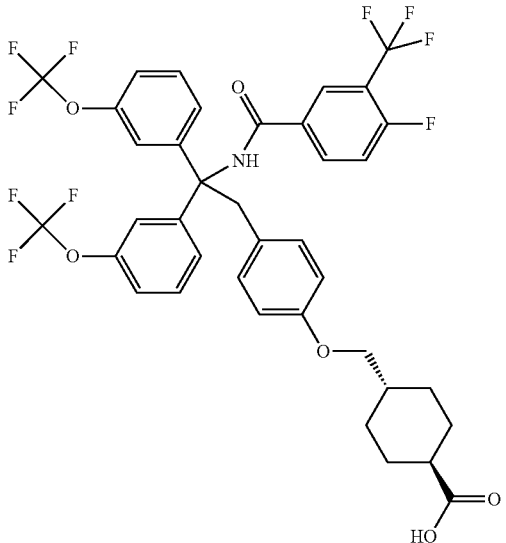 [SMILES: O=C(NC(Cc1ccc(OC[C@H]2CC[C@H](C(=O)O)CC2)cc1)(c1cccc(OC(F)(F)F)c1)c1cccc(OC(F)(F)F)c1)c1ccc(F)c(C(F)(F)F)c1] | (1r,4r)-4-((4-(2-(4-fluoro-3-(trifluoromethyl)benzamido)-2,2-bis(3-(trifluoromethoxy)phenyl)ethyl)phenoxy)methyl)cyclohexanecarboxylic acid | 4.546 LC (11) 788.3 [M + H]⁺ | Procedures 11, 6, 7, 59 and 129 |
| 902 | 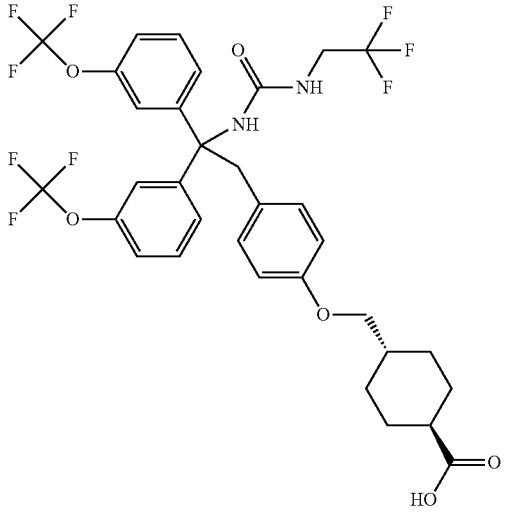 [SMILES: O=C(NCC(F)(F)F)NC(Cc1ccc(OC[C@H]2CC[C@H](C(=O)O)CC2)cc1)(c1cccc(OC(F)(F)F)c1)c1cccc(OC(F)(F)F)c1] | (1r,4r)-4-((4-(2-(3-(2,2,2-trifluoroethyl)ureido)-2,2-bis(3-(tri-fluoromethoxy)phenyl)ethyl)phenoxy)methyl)cyclohexanecarboxylic acid | 4.35 LC (11) 723.2 [M + H]⁺ | Procedures 11, 6, 25, 59 and 129 |
| 903 | 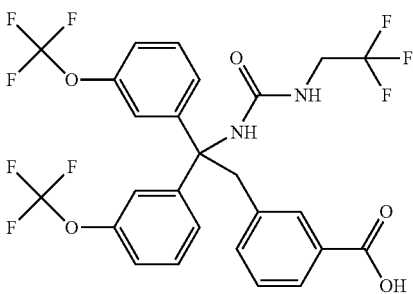 [SMILES: O=C(NCC(F)(F)F)NC(Cc1cccc(C(=O)O)c1)(c1cccc(OC(F)(F)F)c1)c1cccc(OC(F)(F)F)c1] | 3-(2-(3-(2,2,2-trifluoroethyl)ureido)-2,2-bis(3-(trifluoromethoxy)phenyl)ethyl)benzoic acid | 4.07 LC (11) 611.1 [M + H]⁺ | Procedures 11, 72, 73, 74, 75, 25 and 23 |

TABLE 14-continued

| Ex. No. | Structure | Name | Retention Time Min./ Molecular Mass | Prepared in the manner described in: |
|---|---|---|---|---|
| 904 | 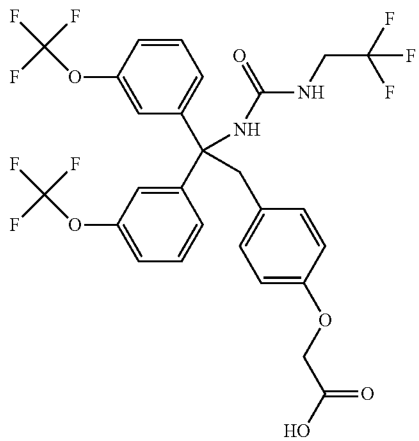 [SMILES: O=C(O)COc1ccc(CC(NC(=O)NCC(F)(F)F)(c2cccc(OC(F)(F)F)c2)c2cccc(OC(F)(F)F)c2)cc1] | 2-(4-(2-(3-(2,2,2-trifluoroethyl) ureido)-2,2-bis(3-(trifluoromethoxy)phenyl)ethyl) phenoxy)acetic acid | 4.13 LC (11) 641.1 [M + H]+ | Procedures 11, 6, 25, 59, 68 and 23 |
| 905 | 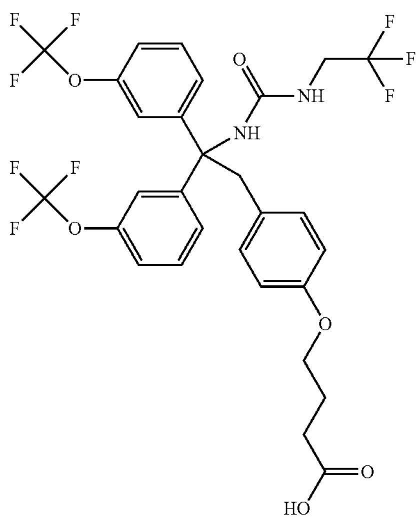 [SMILES: O=C(O)CCCOc1ccc(CC(NC(=O)NCC(F)(F)F)(c2cccc(OC(F)(F)F)c2)c2cccc(OC(F)(F)F)c2)cc1] | 4-(4-(2-(3-(2,2,2-trifluoroethyl) ureido)-2,2-bis(3-(trifluoromethoxy)phenyl)ethyl) phenoxy)butanoic acid | 4.188 LC (11) 669.2 [M + H]+ | Procedures 11, 6, 25, 59, 68 and 23 |
| 906 | 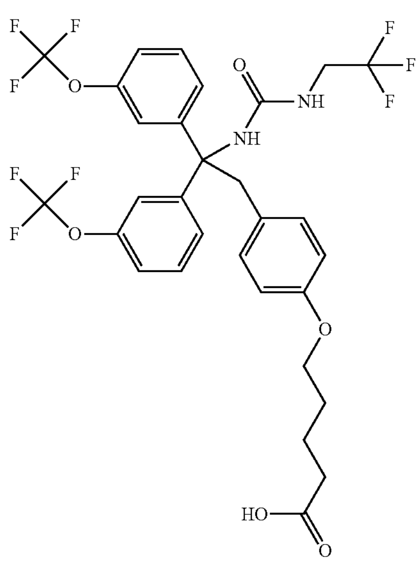 [SMILES: O=C(O)CCCCOc1ccc(CC(NC(=O)NCC(F)(F)F)(c2cccc(OC(F)(F)F)c2)c2cccc(OC(F)(F)F)c2)cc1] | 5-(4-(2-(3-(2,2,2-trifluoroethyl) ureido)-2,2-bis(3-(trifluoromethoxy)phenyl)ethyl) phenoxy)pentanoic acid | 4.243 LC (11) 683.2 [M + H]+ | Procedures 11, 6, 25, 59, 68 and 23 |

TABLE 14-continued

| Ex. No. | Structure | Name | Retention Time Min./ Molecular Mass | Prepared in the manner described in: |
|---|---|---|---|---|
| 907 | 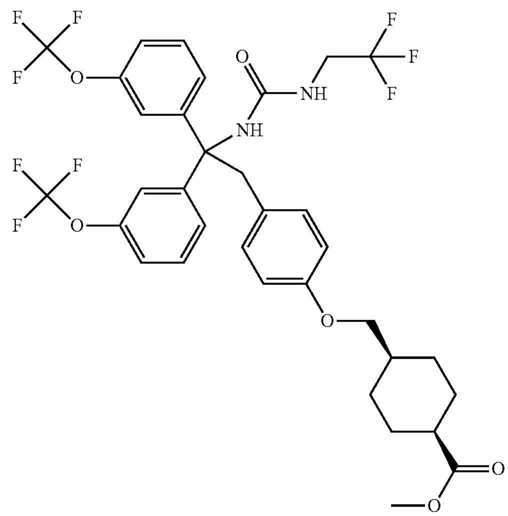 [SMILES: COC(=O)[C@H]1CC[C@@H](COc2ccc(CC(NC(=O)NCC(F)(F)F)(c3cccc(OC(F)(F)F)c3)c3cccc(OC(F)(F)F)c3)cc2)CC1] | (1s,4s)-methyl 4-((4-(2-(3-(2,2,2-trifluoroethyl)ureido)-2,2-bis(3-(trifluoromethoxy)phenyl)ethyl)phenoxy)methyl)cyclohexanecarboxylate | 4.611 LC (11) 737.2 [M + H]+ | Procedures 11, 6, 25, 59 and 129 |
| 908 | 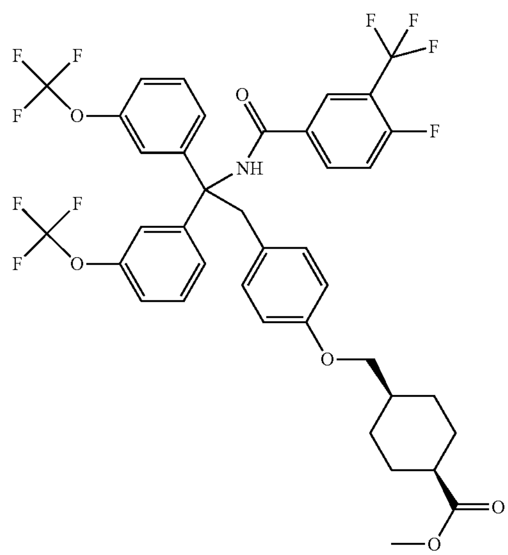 [SMILES: COC(=O)[C@H]1CC[C@@H](COc2ccc(CC(NC(=O)c3ccc(F)c(C(F)(F)F)c3)(c3cccc(OC(F)(F)F)c3)c3cccc(OC(F)(F)F)c3)cc2)CC1] | (1s,4s)-methyl 4-((4-(2-(4-fluoro-3-(trifluoromethyl)benzamido)-2,2-bis(3-(trifluoromethoxy)phenyl)ethyl)phenoxy)methyl)cyclohexanecarboxylate | 4.943 LC (11) 802.3 [M + H]+ | Procedures 11, 6, 7, 59 and 129 |
| 909 | 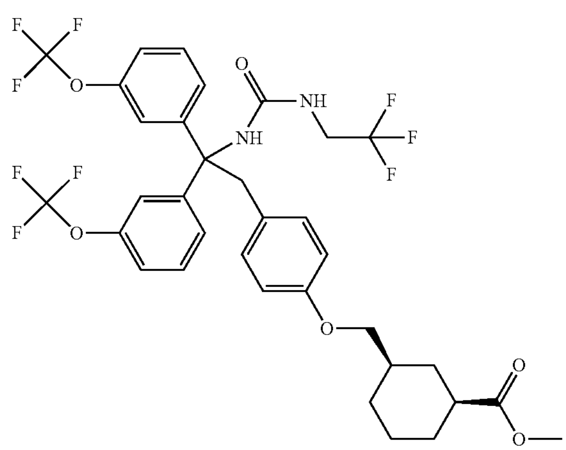 [SMILES: COC(=O)[C@H]1CCC[C@@H](COc2ccc(CC(NC(=O)NCC(F)(F)F)(c3cccc(OC(F)(F)F)c3)c3cccc(OC(F)(F)F)c3)cc2)C1] | (1S,3R)-methyl 3-((4-(2-(3-(2,2,2-trifluoroethyl)ureido)-2,2-bis(3-(trifluoromethoxy)phenyl)ethyl)phenoxy)methyl)cyclohexanecarboxylate | 4.61 LC (11) 737.3 [M + H]+ | Procedures 11, 6, 25, 59 and 129 |

TABLE 14-continued
| Ex. No. | Structure | Name | Retention Time Min./ Molecular Mass | Prepared in the manner described in: |
|---|---|---|---|---|
| 910 | 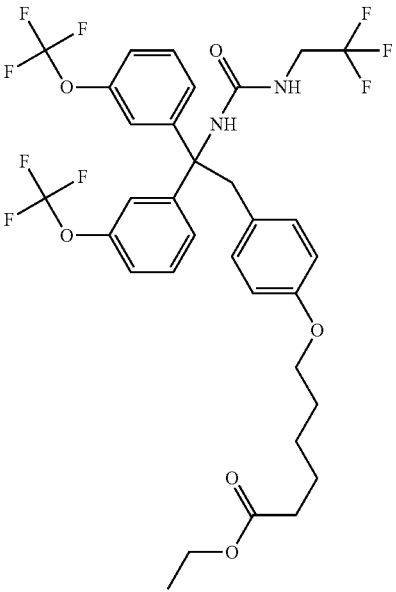 [SMILES: CCOC(=O)CCCCCOc1ccc(CC(NC(=O)NCC(F)(F)F)(c2cccc(OC(F)(F)F)c2)c2cccc(OC(F)(F)F)c2)cc1] | ethyl 6-(4-(2-(3-(2,2,2-trifluoroethyl)ureido)-2,2-bis(3-(trifluoromethoxy)phenyl)ethyl)phenoxy)hexanoate | 4.535 LC (11) 725.3 [M + H]$^+$ | Procedures 11, 6, 25, 59 and 129 |
| 911 | 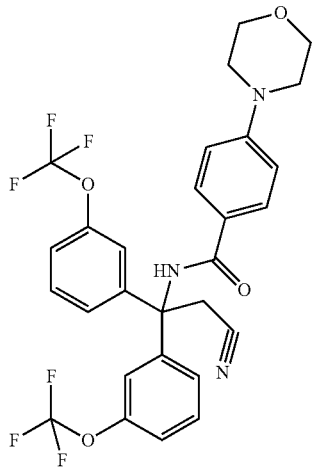 [SMILES: N#CCC(NC(=O)c1ccc(N2CCOCC2)cc1)(c1cccc(OC(F)(F)F)c1)c1cccc(OC(F)(F)F)c1] | N-(2-cyano-1,1-bis(3-(trifluoromethoxy)phenyl)ethyl)-4-morpholinobenzamide | 3.83 LC (1) 580.15 [M + H]$^+$ | Procedures 11, 18, 6, and 7 |

TABLE 14-continued

| Ex. No. | Structure | Name | Retention Time Min./ Molecular Mass | Prepared in the manner described in: |
|---|---|---|---|---|
| 912 | 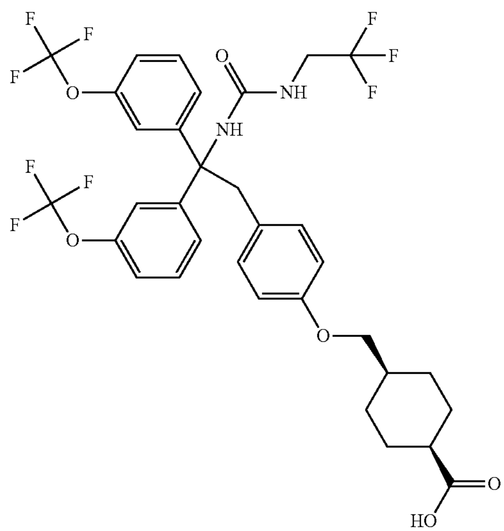 [SMILES: O=C(NCC(F)(F)F)NC(Cc1ccc(OC[C@H]2CC[C@@H](C(=O)O)CC2)cc1)(c1cccc(OC(F)(F)F)c1)c1cccc(OC(F)(F)F)c1] | (1s,4s)-4-((4-(2-(3-(2,2,2-trifluoroethyl)ureido)-2,2-bis(3-(trifluoromethoxy)phenyl)ethyl)phenoxy)methyl)cyclohexanecarboxylic acid | 4.413 LC (11) 723.2 [M + H]+ | Procedures 11, 6, 25, 59, 129 and 23 |
| 913 | 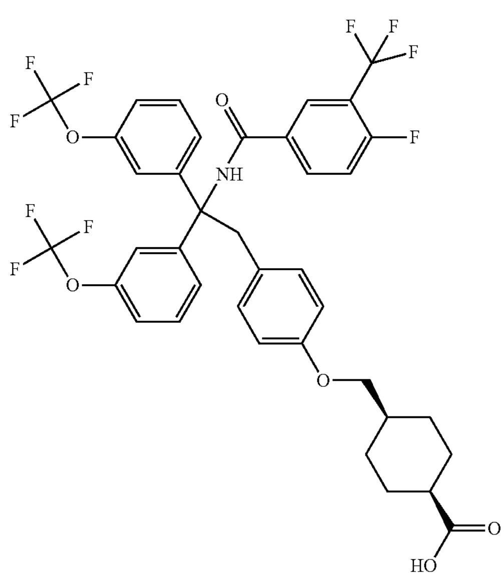 [SMILES: O=C(NC(Cc1ccc(OC[C@H]2CC[C@@H](C(=O)O)CC2)cc1)(c1cccc(OC(F)(F)F)c1)c1cccc(OC(F)(F)F)c1)c1ccc(F)c(C(F)(F)F)c1] | (1s,4s)-4-((4-(2-(4-fluoro-3-(trifluoromethyl)benzamido)-2,2-bis(3-(trifluoromethoxy)phenyl)ethyl)phenoxy)methyl)cyclohexanecarboxylic acid | 4.633 LC (11) 788.2 [M + H]+ | Procedures 11, 6, 7, 59, 129 and 23 |

TABLE 14-continued

| Ex. No. | Structure | Name | Retention Time Min./ Molecular Mass | Prepared in the manner described in: |
|---|---|---|---|---|
| 914 | 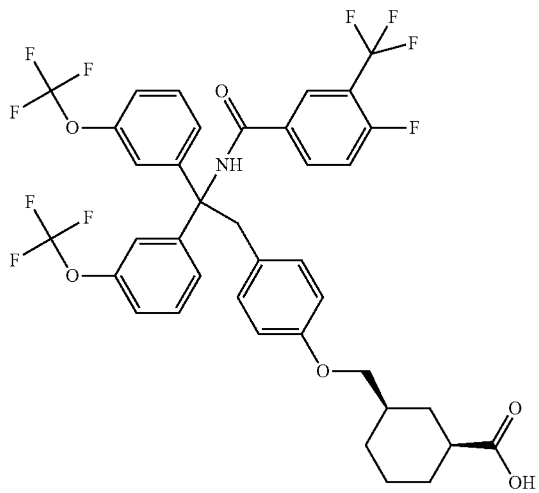 [SMILES: O=C(NC(Cc1ccc(OC[C@@H]2CCC[C@H](C(=O)O)C2)cc1)(c1cccc(OC(F)(F)F)c1)c1cccc(OC(F)(F)F)c1)c1ccc(F)c(C(F)(F)F)c1] | (1S,3R)-3-((4-(2-(4-fluoro-3-(trifluoromethyl)benzamido)-2,2-bis(3-(trifluoromethoxy)phenyl)ethyl)phenoxy)methyl)cyclohexanecarboxylic acid | 4.625 LC (11) 788.2 [M + H]$^+$ | Procedures 11, 6, 7, 59, 129 and 23 |
| 915 | 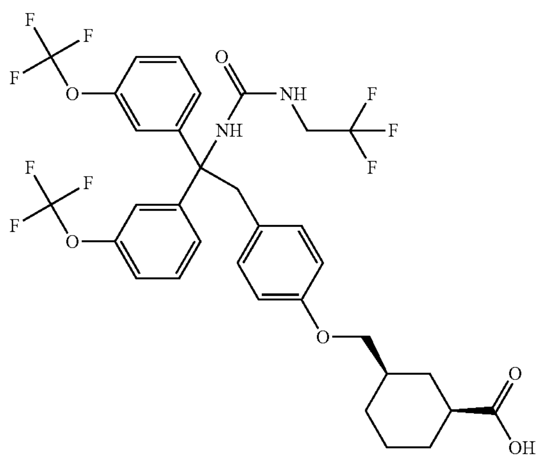 [SMILES: O=C(NCC(F)(F)F)NC(Cc1ccc(OC[C@@H]2CCC[C@H](C(=O)O)C2)cc1)(c1cccc(OC(F)(F)F)c1)c1cccc(OC(F)(F)F)c1] | (1S,3R)-3-((4-(2-(3-(2,2,2-trifluoroethyl)ureido)-2,2-bis(3-(trifluoromethoxy)phenyl)ethyl)phenoxy)methyl)cyclohexanecarboxylic acid | 4.431 LC (11) 723.2 [M + H]$^+$ | Procedures 11, 6, 25, 59, 129 and 23 |
| 916 | 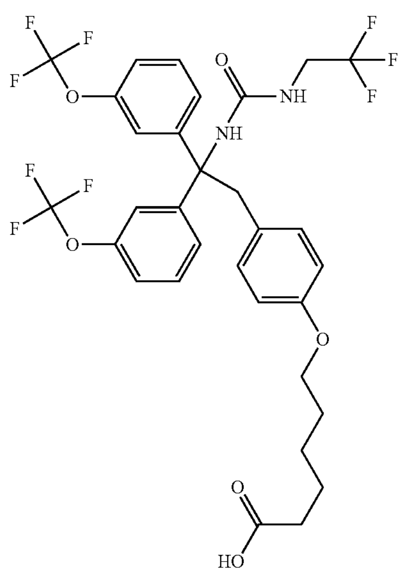 [SMILES: O=C(O)CCCCCOc1ccc(CC(NC(=O)NCC(F)(F)F)(c2cccc(OC(F)(F)F)c2)c2cccc(OC(F)(F)F)c2)cc1] | 6-(4-(2-(3-(2,2,2-trifluoroethyl)ureido)-2,2-bis(3-(trifluoromethoxy)phenyl)ethyl)phenoxy)hexanoic acid | 4.315 LC (11) 697.2 [M + H]$^+$ | Procedures 11, 6, 25, 59, 129 and 23 |

TABLE 14-continued

| Ex. No. | Structure | Name | Retention Time Min./ Molecular Mass | Prepared in the manner described in: |
|---|---|---|---|---|
| 917 | 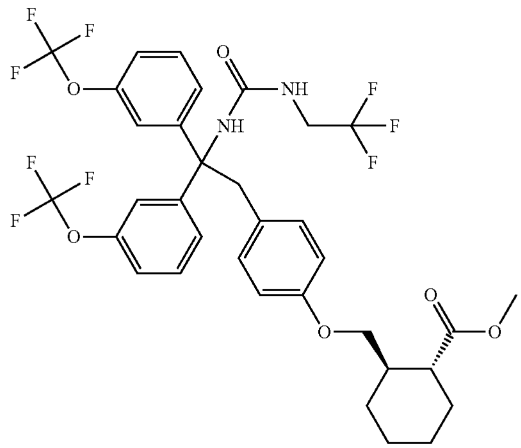 [SMILES: COC(=O)[C@@H]1CCCC[C@H]1COc1ccc(CC(NC(=O)NCC(F)(F)F)(c2cccc(OC(F)(F)F)c2)c2cccc(OC(F)(F)F)c2)cc1] | (1R,2R)-methyl 2-((4-(2-(3-(2,2,2-trifluoroethyl)ureido)-2,2-bis(3-(trifluoromethoxy)phenyl)ethyl)phenoxy)methyl)cyclohexanecarboxylate | 4.583 LC (11) 737.3 [M + H]+ | Procedures 11, 6, 25, 59 and 129 |
| 918 | 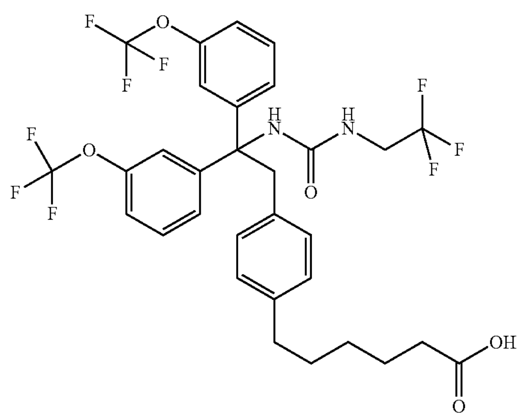 [SMILES: O=C(O)CCCCCc1ccc(CC(NC(=O)NCC(F)(F)F)(c2cccc(OC(F)(F)F)c2)c2cccc(OC(F)(F)F)c2)cc1] | 6-(4-(2-(3-(2,2,2-trifluoroethyl)ureido)-2,2-bis(3-(trifluoromethoxy)phenyl)ethyl)phenyl)hexanoic acid | 2.205 LC (2) 681.2 [M + H]+ | Procedures 11, 72, 73, 74, 77, 24 and 23 |
| 919 | 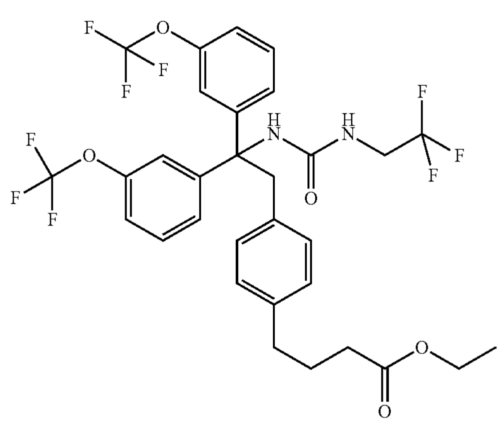 [SMILES: CCOC(=O)CCCc1ccc(CC(NC(=O)NCC(F)(F)F)(c2cccc(OC(F)(F)F)c2)c2cccc(OC(F)(F)F)c2)cc1] | ethyl 4-(4-(2-(3-(2,2,2-trifluoroethyl)ureido)-2,2-bis(3-(trifluoromethoxy)phenyl)ethyl)phenyl)butanoate | 2.233 LC (2) 681.2 [M + H]+ | Procedures 11, 72, 73, 74, 77 and 24 |

TABLE 14-continued

| Ex. No. | Structure | Name | Retention Time Min./ Molecular Mass | Prepared in the manner described in: |
|---|---|---|---|---|
| 920 | 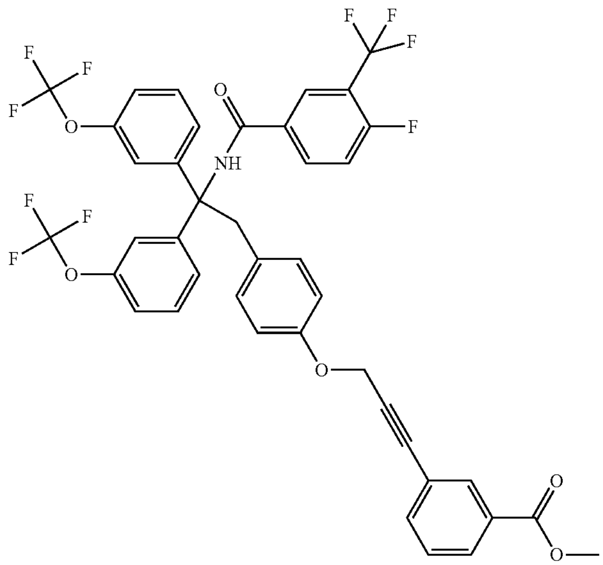 [SMILES: COC(=O)c1cccc(C#CCOc2ccc(CC(NC(=O)c3ccc(F)c(C(F)(F)F)c3)(c3cccc(OC(F)(F)F)c3)c3cccc(OC(F)(F)F)c3)cc2)c1] | methyl 3-(3-(4-(2-(4-fluoro-3-(trifluoromethyl)benzamido)-2,2-bis(3-(trifluoromethoxy)phenyl)ethyl)phenoxy)prop-1-ynyl)benzoate | 4.90 LC (11) 820.2 [M + H]+ | Procedures 11, 6, 7, 59 and 129 |
| 921 | 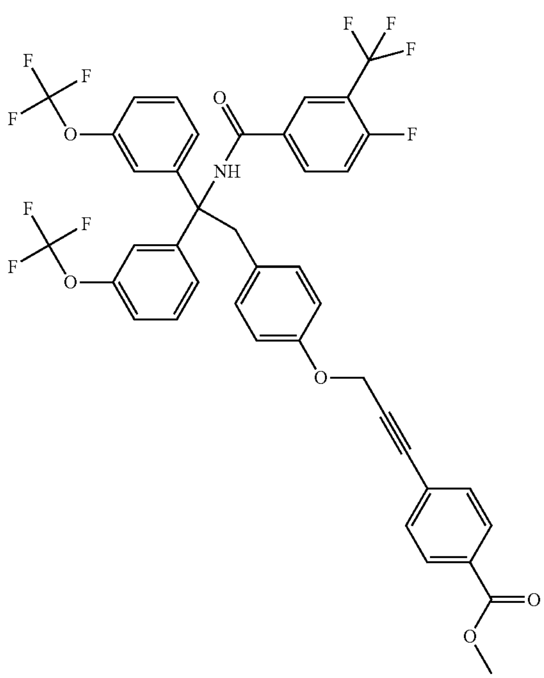 [SMILES: COC(=O)c1ccc(C#CCOc2ccc(CC(NC(=O)c3ccc(F)c(C(F)(F)F)c3)(c3cccc(OC(F)(F)F)c3)c3cccc(OC(F)(F)F)c3)cc2)cc1] | methyl 4-(3-(4-(2-(4-fluoro-3-(trifluoromethyl)benzamido)-2,2-bis(3-(trifluoromethoxy)phenyl)ethyl)phenoxy)prop-1-ynyl)benzoate | 4.856 LC (11) 820.2 [M + H]+ | Procedures 11, 6, 7, 59 and 129 |

TABLE 14-continued

| Ex. No. | Structure | Name | Retention Time Min./ Molecular Mass | Prepared in the manner described in: |
|---|---|---|---|---|
| 922 | 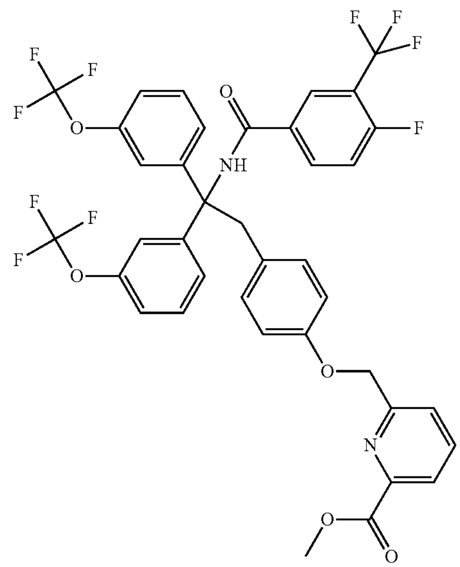 [SMILES: COC(=O)c1cccc(COc2ccc(CC(NC(=O)c3ccc(F)c(C(F)(F)F)c3)(c3cccc(OC(F)(F)F)c3)c3cccc(OC(F)(F)F)c3)cc2)n1] | methyl 6-((4-(2-(4-fluoro-3-(trifluoromethyl)benzamido)-2,2-bis(3-(trifluoromethoxy)phenyl)ethyl)phenoxy)methyl)picolinate | 4.506 LC (11) 797.2 [M + H]+ | Procedures 11, 6, 7, 59 and 129 |
| 923 | 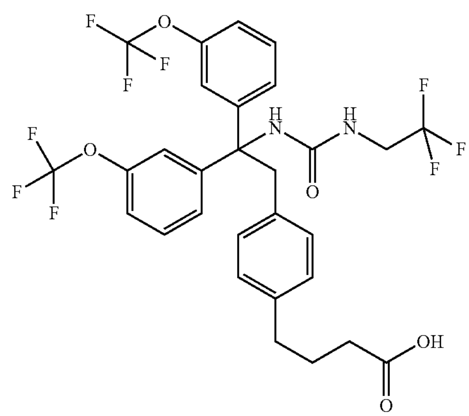 [SMILES: O=C(O)CCCc1ccc(CC(NC(=O)NCC(F)(F)F)(c2cccc(OC(F)(F)F)c2)c2cccc(OC(F)(F)F)c2)cc1] | 4-(4-(2-(3-(2,2,2-trifluoroethyl)ureido)-2,2-bis(3-(trifluoromethoxy)phenyl)ethyl)phenyl)butanoic acid | 2.128 LC (2) 653.2 [M + H]+ | Procedures 11, 72, 73, 74, 77, 24 and 23 |
| 924 | 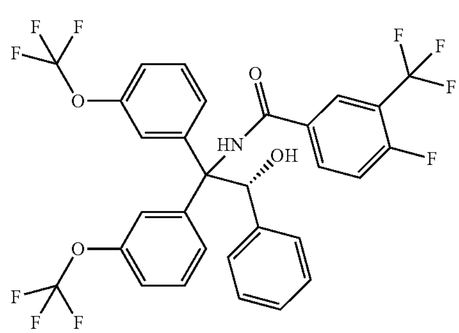 [SMILES: O=C(NC(c1cccc(OC(F)(F)F)c1)(c1cccc(OC(F)(F)F)c1)[C@H](O)c1ccccc1)c1ccc(F)c(C(F)(F)F)c1] | (R)-4-fluoro-N-(2-hydroxy-2-phenyl-1,1-bis(3-(trifluoromethoxy)phenyl)ethyl)-3-(trifluoromethyl)benzamide | 4.128 LC (11) 648.0 [M + H]+ | Procedures 11, 123, 124, 125, 126 and 127 |

TABLE 15

| Ex. No. | Structure | Name | Retention Time Min./ Molecular Mass | Prepared in the manner described in: |
|---|---|---|---|---|
| 925 | 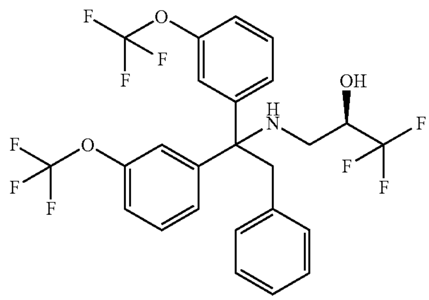 [SMILES: O[C@H](CNC(Cc1ccccc1)(c1cccc(OC(F)(F)F)c1)c1cccc(OC(F)(F)F)c1)C(F)(F)F] | (R)-1,1,1-trifluoro-3-(2-phenyl-1,1-bis(3-(trifluoromethoxy)phenyl)ethylamino)propan-2-ol | 2.188 LC (2) 554.2 [M + H]$^+$ | Procedures 11, 6, 27 and 8 |
| 926 | 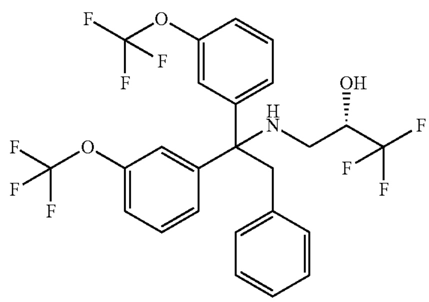 [SMILES: O[C@@H](CNC(Cc1ccccc1)(c1cccc(OC(F)(F)F)c1)c1cccc(OC(F)(F)F)c1)C(F)(F)F] | (S)-1,1,1-trifluoro-3-(2-phenyl-1,1-bis(3-(trifluoromethoxy)phenyl)ethylamino)propan-2-ol | 2.193 LC (2) 554.2 [M + H]$^+$ | Procedures 11, 6, 27 and 8 |

TABLE 16

| Ex. No. | Structure | Name | Retention Time Min./ Molecular Mass | Prepared in the manner described in: |
|---|---|---|---|---|
| 927 | 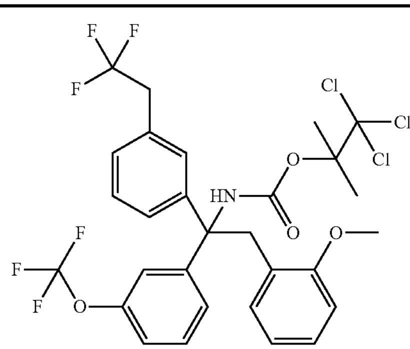 | 1,1,1-trichloro-2-methylpropan-2-yl 2-(2-methoxyphenyl)-1,1-bis(3-(trifluoromethoxy)phenyl)ethylcarbamate | 4.266 LC (1) 675.33 [M + H]$^+$ | Procedures 11, 6 and 82 |
| 928 | 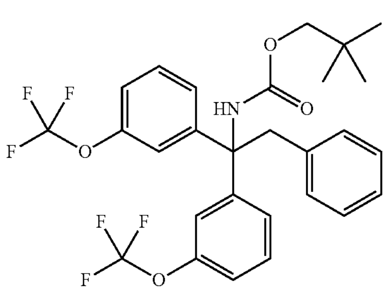 [SMILES: CC(C)(C)COC(=O)NC(Cc1ccccc1)(c1cccc(OC(F)(F)F)c1)c1cccc(OC(F)(F)F)c1] | neopentyl 2-phenyl-1,1-bis(3-(trifluoromethoxy)phenyl) ethylcarbamate | 4.45 LC (1) 556.25 [M + H]$^+$ | Procedures 11, 6 and 82 |

TABLE 16-continued

| Ex. No. | Structure | Name | Retention Time Min./ Molecular Mass | Prepared in the manner described in: |
|---|---|---|---|---|
| 929 | 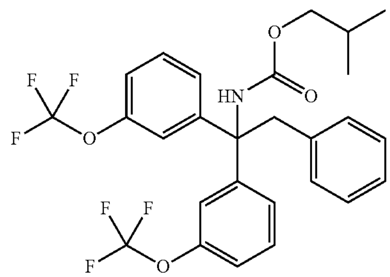 [SMILES: CC(C)COC(=O)NC(Cc1ccccc1)(c1cccc(OC(F)(F)F)c1)c1cccc(OC(F)(F)F)c1] | isobutyl 2-phenyl-1,1-bis(3-(trifluoromethoxy)phenyl)ethylcarbamate | 4.38 LC (1) 542.20 [M + H]$^+$ | Procedures 11, 6 and 82 |
| 930 | 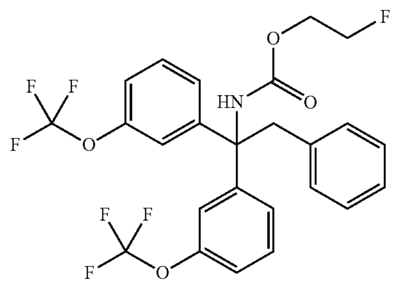 [SMILES: O=C(NC(Cc1ccccc1)(c1cccc(OC(F)(F)F)c1)c1cccc(OC(F)(F)F)c1)OCCF] | 2-fluoroethyl 2-phenyl-1,1-bis(3-(trifluoromethoxy)phenyl)ethylcarbamate | 4.17 LC (1) 532.17 [M + H]$^+$ | Procedures 11, 6 and 82 |
| 931 | 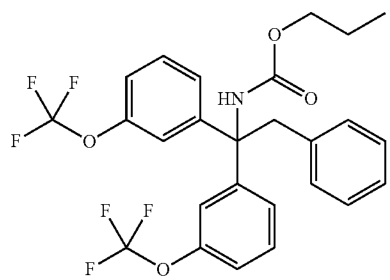 [SMILES: CCCOC(=O)NC(Cc1ccccc1)(c1cccc(OC(F)(F)F)c1)c1cccc(OC(F)(F)F)c1] | propyl 2-phenyl-1,1-bis(3-(trifluoromethoxy)phenyl)ethylcarbamate | 4.30 LC (1) 528.20 [M + H]$^+$ | Procedures 11, 6 and 82 |
| 932 | 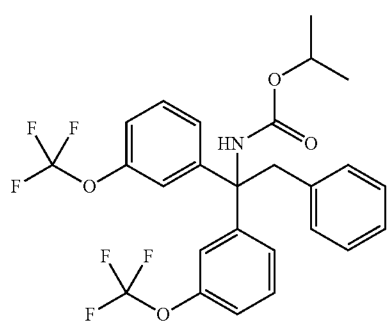 [SMILES: CC(C)OC(=O)NC(Cc1ccccc1)(c1cccc(OC(F)(F)F)c1)c1cccc(OC(F)(F)F)c1] | isopropyl 2-phenyl-1,1-bis(3-(trifluoromethoxy)phenyl)ethylcarbamate | 4.30 LC (1) 528.20 [M + H]$^+$ | Procedures 11, 6 and 82 |
| 933 | 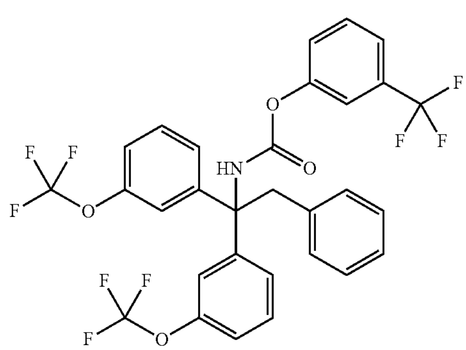 [SMILES: O=C(NC(Cc1ccccc1)(c1cccc(OC(F)(F)F)c1)c1cccc(OC(F)(F)F)c1)Oc1cccc(C(F)(F)F)c1] | 3-(trifluoromethyl)phenyl 2-phenyl-1,1-bis(3-(trifluoromethoxy)phenyl)ethylcarbamate | 4.42 LC (1) 630.26 [M + H]$^+$ | Procedures 11, 6 and 82 |

TABLE 16-continued

| Ex. No. | Structure | Name | Retention Time Min./ Molecular Mass | Prepared in the manner described in: |
|---|---|---|---|---|
| 934 | 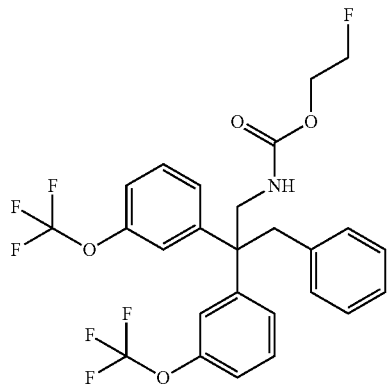 [SMILES: O=C(NCC(Cc1ccccc1)(c1cccc(OC(F)(F)F)c1)c1cccc(OC(F)(F)F)c1)OCCF] | 2-fluoroethyl 3-phenyl-2,2-bis(3-(trifluoromethoxy)phenyl) propylcarbamate | 4.20 LC (4) 546.14 [M + H]$^+$ | Procedures 11, 6 and 82 |
| 935 | 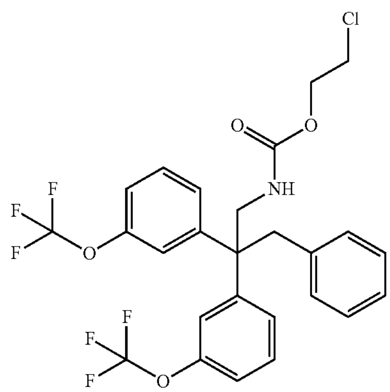 | 2-chloroethyl 3-phenyl-2,2-bis(3-(trifluoromethoxy)phenyl) propylcarbamate | 4.28 LC (4) 562.08 [M + H]$^+$ | Procedures 11, 6 and 82 |

TABLE 17

| Ex. No. | Structure | Name | Retention Time Min./ Molecular Mass | Prepared in the manner described in: |
|---|---|---|---|---|
| 936 | 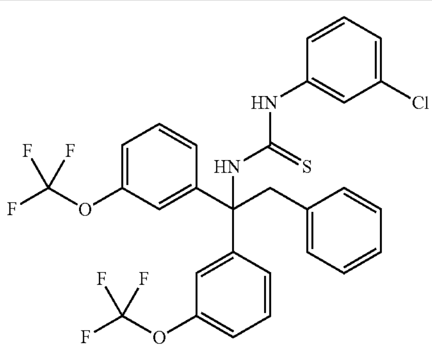 [SMILES: FC(F)(F)Oc1cccc(C(Cc2ccccc2)(NC(=S)Nc2cccc(Cl)c2)c2cccc(OC(F)(F)F)c2)c1] | 1-(3-chlorophenyl)-3-(2-phenyl-1,1-bis(3-(trifluoromethoxy)phenyl)ethyl)thiourea | 4.51 LC (1) 612.5 [M + H]$^+$ | Procedures 11, 6 and 83 |

TABLE 18

| Ex. No. | Structure | Name | Retention Time Min./Molecular Mass | Prepared in the manner described in: |
|---|---|---|---|---|
| 937 | 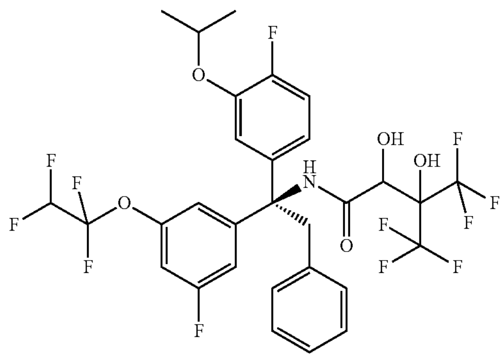 [SMILES: CC(C)Oc1cc([C@@](Cc2ccccc2)(NC(=O)C(O)C(O)(C(F)(F)F)C(F)(F)F)c2cc(F)cc(OC(F)(F)C(F)F)c2)ccc1F] | 4,4,4-trifluoro-N-((R)-1-(4-fluoro-3-isopropoxyphenyl)-1-(3-fluoro-5-(1,1,2,2-tetrafluoroethoxy)phenyl)-2-phenylethyl)-2,3-dihydroxy-3-(trifluoromethyl)butanamide | 4.181 LC (11) 708.38 [M + H]$^+$ RT = 40 min (AD, EtOH/MeOH/heptane, 4% isocratic, 40 mL/min) | Procedures 3, 109, 110, 111, 112, 113, 114, 84, 85 and 86 |
| 938 | 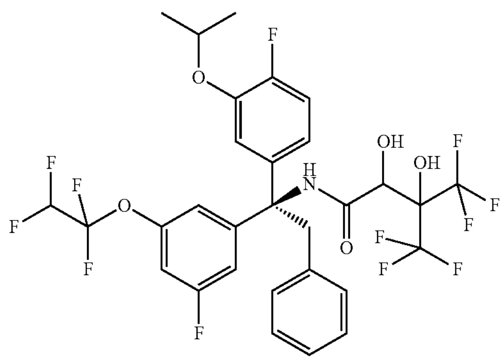 [SMILES: CC(C)Oc1cc([C@@](Cc2ccccc2)(NC(=O)C(O)C(O)(C(F)(F)F)C(F)(F)F)c2cc(F)cc(OC(F)(F)C(F)F)c2)ccc1F] | 4,4,4-trifluoro-N-((R)-1-(4-fluoro-3-isopropoxyphenyl)-1-(3-fluoro-5-(1,1,2,2-tetrafluoroethoxy)phenyl)-2-phenylethyl)-2,3-dihydroxy-3-(trifluoromethyl)butanamide | 4.178 LC (11) 708.39 [M + H]$^+$ RT = 50 min (AD, EtOH/MeOH/heptane, 4% isocratic, 40 mL/min) | Procedures 3, 109, 110, 111, 112, 113, 114, 84, 85 and 86 |
| 939 | 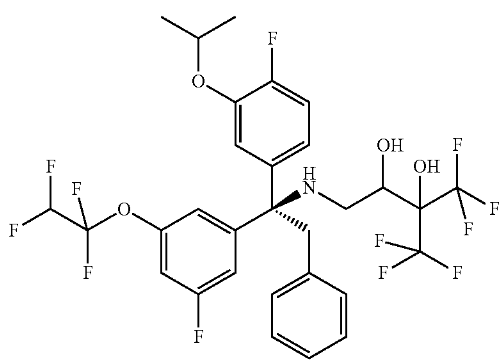 [SMILES: CC(C)Oc1cc([C@@](Cc2ccccc2)(NCC(O)C(O)(C(F)(F)F)C(F)(F)F)c2cc(F)cc(OC(F)(F)C(F)F)c2)ccc1F] | 1,1,1-trifluoro-4-((R)-1-(4-fluoro-3-isopropoxyphenyl)-1-(3-fluoro-5-(1,1,2,2-tetrafluoroethoxy)phenyl)-2-phenylethylamino)-2-(trifluoromethyl)butane-2,3-diol | 4.12 LC (11) 694.39 [M + H]$^+$ (prepared from precursor Example 937) | Procedures 3, 109, 110, 111, 112, 113, 114, 84, 85, 86 and 89 |
| 940 | 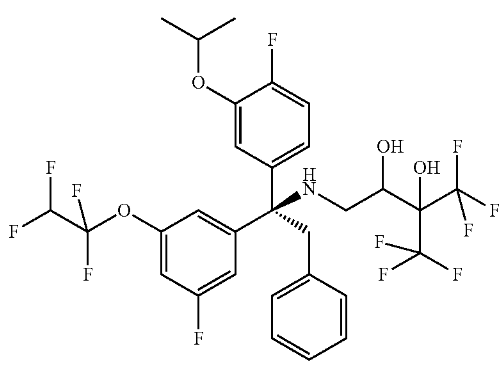 [SMILES: CC(C)Oc1cc([C@@](Cc2ccccc2)(NCC(O)C(O)(C(F)(F)F)C(F)(F)F)c2cc(F)cc(OC(F)(F)C(F)F)c2)ccc1F] | 1,1,1-trifluoro-4-((R)-1-(4-fluoro-3-isopropoxyphenyl)-1-(3-fluoro-5-(1,1,2,2-tetrafluoroethoxy)phenyl)-2-phenylethylamino)-2-(trifluoromethyl)butane-2,3-diol | 4.108 LC (11) 694.39 [M + H]$^+$ (prepared from precursor Example 938) | Procedures 3, 109, 110, 111, 112, 113, 114, 84, 85, 86 and 89 |

TABLE 18-continued

| Ex. No. | Structure | Name | Retention Time Min./Molecular Mass | Prepared in the manner described in: |
|---|---|---|---|---|
| 941 | 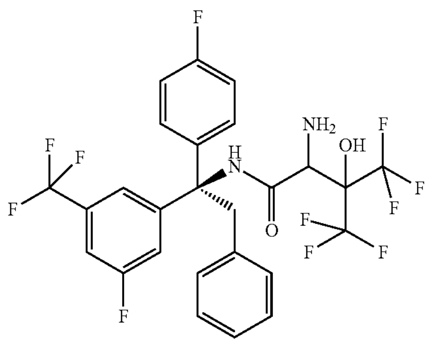 [SMILES: NC(C(=O)N[C@](Cc1ccccc1)(c1ccc(F)cc1)c1cc(F)cc(C(F)(F)F)c1)C(O)(C(F)(F)F)C(F)(F)F] | 2-amino-4,4,4-trifluoro-N-((R)-1-(3-fluoro-5-(trifluoromethyl)phenyl)-1-(4-fluorophenyl)-2-phenylethyl)-3-hydroxy-3-(trifluoromethyl)butanamide | 2.065 LC (2) 601.2 [M + H]⁺ RT = 11.458 min (PrepHPLC, YMC Sunfire 5μ, C18, 30 X 100 mm, MeOH/H₂O/TFA, 30-100% over 12 min) | Procedures 4, 5, 6, 90, 91 and 92 |
| 942 | 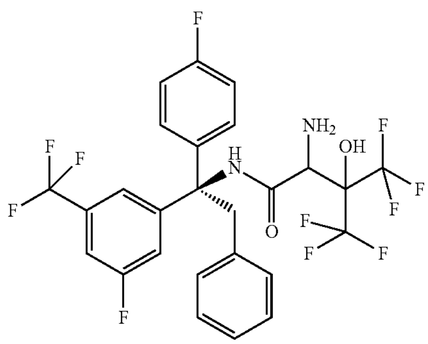 [SMILES: NC(C(=O)N[C@](Cc1ccccc1)(c1ccc(F)cc1)c1cc(F)cc(C(F)(F)F)c1)C(O)(C(F)(F)F)C(F)(F)F] | 2-amino-4,4,4-trifluoro-N-((R)-1-(3-fluoro-5-(trifluoromethyl)phenyl)-1-(4-fluorophenyl)-2-phenylethyl)-3-hydroxy-3-(trifluoromethyl)butanamide | 2.085 LC (2) 601.3 [M + H]⁺ RT = 11.619 min (PrepHPLC, YMC Sunfire 5μ, C18, 30 X 100 mm, MeOH/H₂O/TFA, 30-100% over 12 min) | Procedures 4, 5, 6, 90, 91 and 92 |
| 943 | 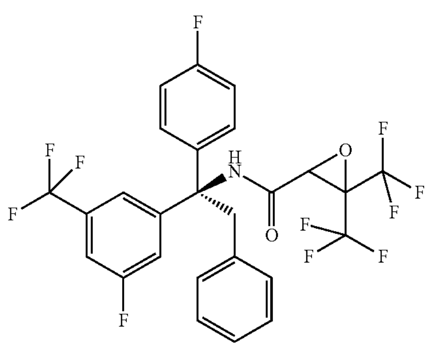 [SMILES: O=C(N[C@](Cc1ccccc1)(c1ccc(F)cc1)c1cc(F)cc(C(F)(F)F)c1)C1OC1(C(F)(F)F)C(F)(F)F] | N-((R)-1-(3-fluoro-5-(trifluoromethyl)phenyl)-1-(4-fluorophenyl)-2-phenylethyl)-3,3-bis(trifluoromethyl)oxirane-2-carboxamide | 4.186 LC 582.3 [M − H]⁻ RT = 28-30 min (AD, IPA/heptane, 5% isocratic, 50 mL/min) | Procedures 4, 5, 6, 90 and 91 |
| 944 | 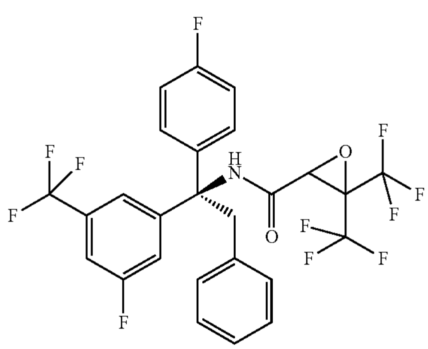 [SMILES: O=C(N[C@](Cc1ccccc1)(c1ccc(F)cc1)c1cc(F)cc(C(F)(F)F)c1)C1OC1(C(F)(F)F)C(F)(F)F] | N-((R)-1-(3-fluoro-5-(trifluoromethyl)phenyl)-1-(4-fluorophenyl)-2-phenylethyl)-3,3-bis(trifluoromethyl)oxirane-2-carboxamide | 4.161 LC 582.3 [M − H]⁻ RT = 40-45 min (AD, IPA/heptane, 5% isocratic, 50 mL/min) | Procedures 4, 5, 6, 90 and 91 |

TABLE 18-continued

| Ex. No. | Structure | Name | Retention Time Min./Molecular Mass | Prepared in the manner described in: |
|---|---|---|---|---|
| 945 | 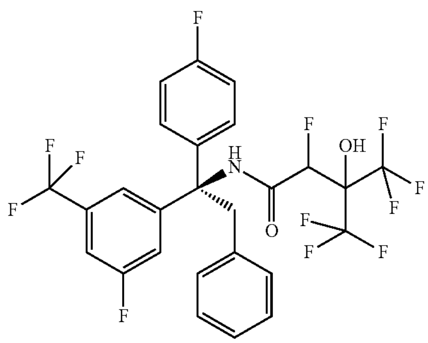 [SMILES: O=C(N[C@](Cc1ccccc1)(c1ccc(F)cc1)c1cc(F)cc(C(F)(F)F)c1)C(F)C(O)(C(F)(F)F)C(F)(F)F] | 2,4,4,4-tetrafluoro-N-((R)-1-(3-fluoro-5-(trifluoromethyl)phenyl)-1-(4-fluorophenyl)-2-phenylethyl)-3-hydroxy-3-(trifluoromethyl)butanamide | 3.98 LC (3) 602.3 [M − H]⁻ RT = 26.94 min (PrepHPLC, YMC Sunfire 5μ, C18, 30 X 100 mm, MeOH/H₂O/TFA, 40-100% over 30 min) | Procedures 4, 5, 6, 90, 91 and 93 |
| 946 | 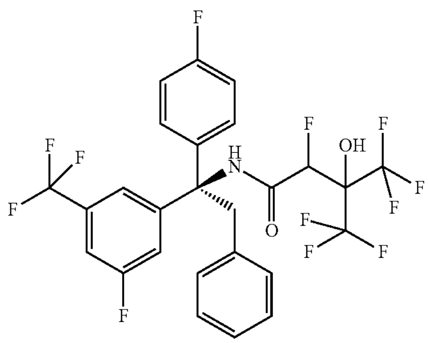 [SMILES: O=C(N[C@](Cc1ccccc1)(c1ccc(F)cc1)c1cc(F)cc(C(F)(F)F)c1)C(F)C(O)(C(F)(F)F)C(F)(F)F] | 2,4,4,4-tetrafluoro-N-((R)-1-(3-fluoro-5-(trifluoromethyl)phenyl)-1-(4-fluorophenyl)-2-phenylethyl)-3-hydroxy-3-(trifluoromethyl)butanamide | 4.043 LC (3) 602.3 [M − H]⁻ RT = 27.40 min (PrepHPLC, YMC Sunfire 5μ, C18, 30 X 100 mm, MeOH/H₂O/TFA, 40-100% over 30 min) | Procedures 4, 5, 6, 90, 91 and 93 |
| 947 | 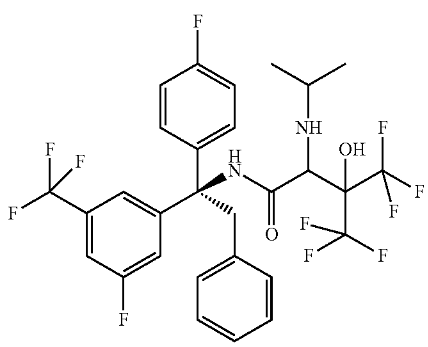 [SMILES: CC(C)NC(C(=O)N[C@](Cc1ccccc1)(c1ccc(F)cc1)c1cc(F)cc(C(F)(F)F)c1)C(O)(C(F)(F)F)C(F)(F)F] | 4,4,4-trifluoro-N-((R)-1-(3-fluoro-5-(trifluoromethyl)phenyl)-1-(4-fluorophenyl)-2-phenylethyl)-3-hydroxy-2-(isopropylamino)-3-(trifluoromethyl)butanamide | 4.258 LC 643.4 [M + H]⁺ (prepared from precursor Example 944) | Procedures 4, 5, 6, 90, 91 and 95 |
| 948 | 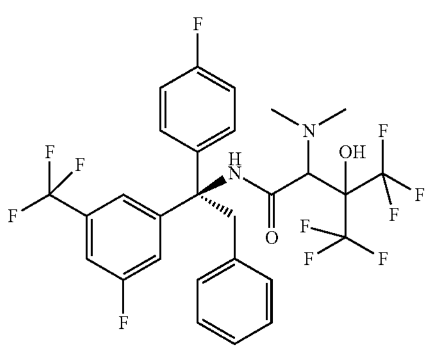 [SMILES: CN(C)C(C(=O)N[C@](Cc1ccccc1)(c1ccc(F)cc1)c1cc(F)cc(C(F)(F)F)c1)C(O)(C(F)(F)F)C(F)(F)F] | 2-(dimethylamino)-4,4,4-trifluoro-N-((R)-1-(3-fluoro-5-(trifluoromethyl)phenyl)-1-(4-fluorophenyl)-2-phenylethyl)-3-hydroxy-3-(trifluoromethyl) butanamide | 4.013 LC 629.2 [M + H]⁺ (prepared from precursor Example 944) | Procedures 4, 5, 6, 90, 91 and 95 |

TABLE 18-continued

| Ex. No. | Structure | Name | Retention Time Min./Molecular Mass | Prepared in the manner described in: |
|---|---|---|---|---|
| 949 | 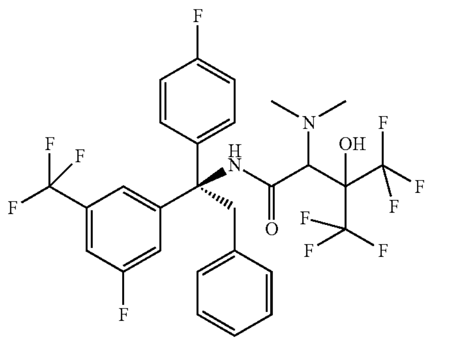 [SMILES: CN(C)C(C(=O)N[C@](Cc1ccccc1)(c1ccc(F)cc1)c1cc(F)cc(C(F)(F)F)c1)C(O)(C(F)(F)F)C(F)(F)F] | 2-(dimethylamino)-4,4,4-trifluoro-N-((R)-1-(3-fluoro-5-(trifluoromethyl)phenyl)-1-(4-fluorophenyl)-2-phenylethyl)-3-hydroxy-3-(trifluoromethyl) butanamide | 4.348 LC 629.3 [M + H]$^+$ (prepared from precursor Example 943) | Procedures 4, 5, 6, 90, 91 and 95 |
| 950 | 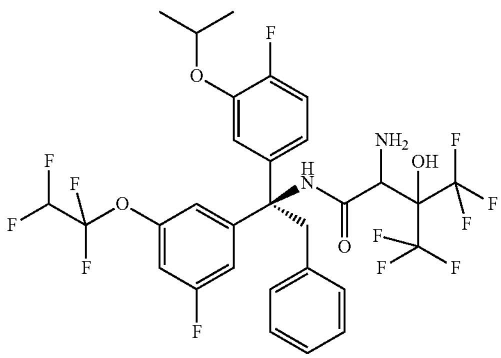 [SMILES: CC(C)Oc1cc([C@@](Cc2ccccc2)(NC(=O)C(N)C(O)(C(F)(F)F)C(F)(F)F)c2cc(F)cc(OC(F)(F)C(F)F)c2)ccc1F] | 2-amino-4,4,4-trifluoro-N-((R)-1-(4-fluoro-3-isopropoxyphenyl)-1-(3-fluoro-5-(1,1,2,2-tetrafluoroethoxy)phenyl)-2-phenylethyl)-3-hydroxy-3-(trifluoromethyl)butanamide | 2.118 LC (2) 707.4 [M + H]$^+$ (prepared from precursor Example 292B) | Procedures 3, 109, 110, 111, 112, 113, 114, 90, 91 and 92 |
| 951 | 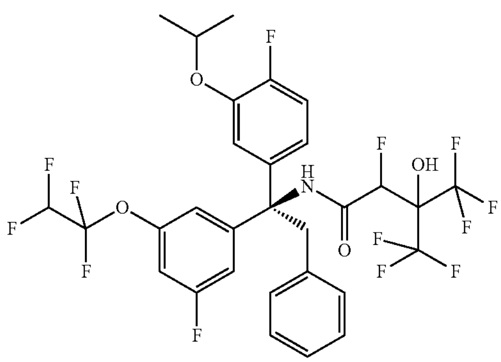 [SMILES: CC(C)Oc1cc([C@@](Cc2ccccc2)(NC(=O)C(F)C(O)(C(F)(F)F)C(F)(F)F)c2cc(F)cc(OC(F)(F)C(F)F)c2)ccc1F] | 2,4,4,4-tetrafluoro-N-((R)-1-(4-fluoro-3-isopropoxyphenyl)-1-(3-fluoro-5-(1,1,2,2-tetrafluoroethoxy)phenyl)-2-phenylethyl)-3-hydroxy-3-(trifluoromethyl)butanamide | 2.27 LC (2) 710.8 [M + H]$^+$ (prepared from precursor Example 292B) | Procedures 3, 109, 110, 111, 112, 113, 114, 90, 91 and 92 |
| 952 | 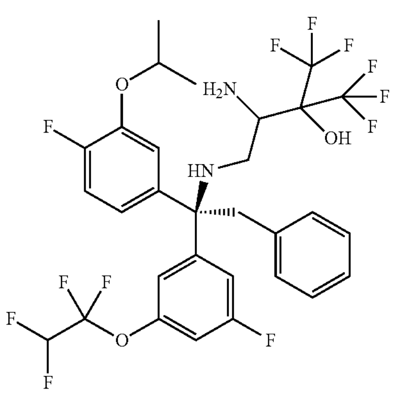 [SMILES: CC(C)Oc1cc([C@@](Cc2ccccc2)(NCC(N)C(O)(C(F)(F)F)C(F)(F)F)c2cc(F)cc(OC(F)(F)C(F)F)c2)ccc1F] | 3-amino-1,1,1-trifluoro-4-((R)-1-(4-fluoro-3-isopropoxyphenyl)-1-(3-fluoro-5-(1,1,2,2-tetrafluoroethoxy)phenyl)-2-phenylethylamino)-2-(trifluoromethyl)butan-2-ol | 2.06 LC (1) 693.1 [M + H]$^+$ (prepared from precursor Example 950) | Procedures 109, 110, 111, 112, 113, 114, 90, 91, 92 and 145 |

TABLE 18-continued

| Ex. No. | Structure | Name | Retention Time Min./Molecular Mass | Prepared in the manner described in: |
|---|---|---|---|---|
| 953 | 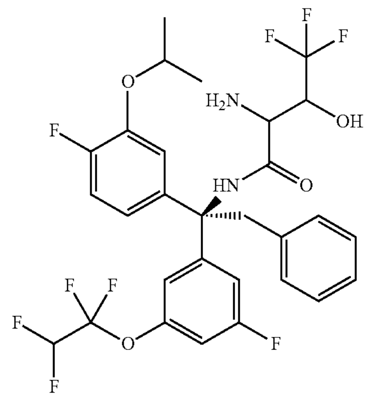 [SMILES: CC(C)Oc1cc([C@@](Cc2ccccc2)(NC(=O)C(N)C(O)C(F)(F)F)c2cc(F)cc(OC(F)(F)C(F)F)c2)ccc1F] | 2-amino-4,4,4-trifluoro-N-((R)-1-(4-fluoro-3-isopropoxyphenyl)-1-(3-fluoro-5-(1,1,2,2-tetrafluoroethoxy)phenyl)-2-phenylethyl)-3-hydroxybutanamide | 3.69 LC (1) 639.1 $[M + H]^+$ Precursor epoxide chiral retention time 12.52 min: Chiralpak AD 4.6 x 250 mm 10% heptane/IPA | Procedures 3, 109, 110, 111, 112, 113, 114, 90, 91 and 92 |
| 954 | 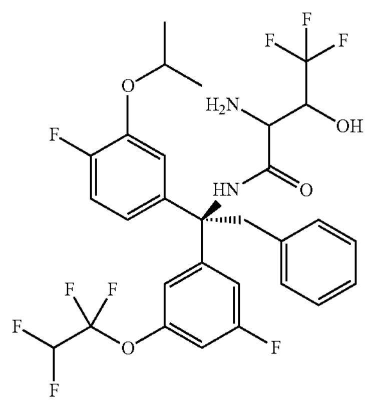 [SMILES: CC(C)Oc1cc([C@@](Cc2ccccc2)(NC(=O)C(N)C(O)C(F)(F)F)c2cc(F)cc(OC(F)(F)C(F)F)c2)ccc1F] | 2-amino-4,4,4-trifluoro-N-((R)-1-(4-fluoro-3-isopropoxyphenyl)-1-(3-fluoro-5-(1,1,2,2-tetrafluoroethoxy)phenyl)-2-phenylethyl)-3-hydroxybutanamide | 3.67 LC (1) 639.1 $[M + H]^+$ Precursor epoxide chiral retention time 7.77 min: Chiralpak AD 4.6 x 250 mm 10% heptane/IPA | Procedures 3, 109, 110, 111, 112, 113, 114, 90, 91 and 92 |

TABLE 19

| Ex. No. | Structure | Name | Retention Time Min./Molecular Mass | Prepared in the manner described in: |
|---|---|---|---|---|
| 955 | 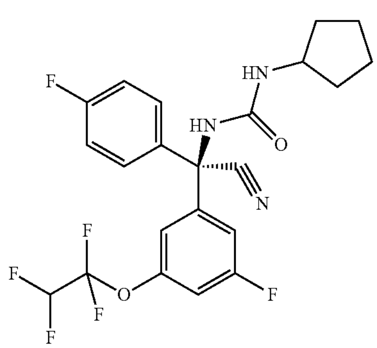 [SMILES: N#C[C@@](NC(=O)NC1CCCC1)(c1ccc(F)cc1)c1cc(F)cc(OC(F)(F)C(F)F)c1] | (R)-1-(cyano(3-fluoro-5-(1,1,2,2-tetrafluoroethoxy)phenyl)(4-fluorophenyl)methyl)-3-cyclopentylurea | 3.71 LC (1) 472.20 $[M + H]^+$ | Procedures 3, 4, 18, 6 and 2 |

TABLE 19-continued

| Ex. No. | Structure | Name | Retention Time Min./ Molecular Mass | Prepared in the manner described in: |
|---|---|---|---|---|
| 956 | 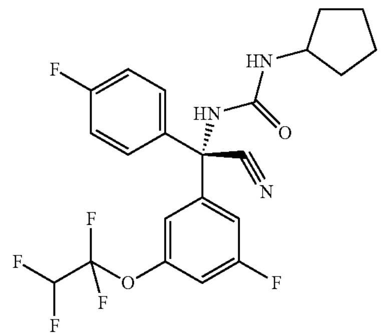 [SMILES: N#C[C@](NC(=O)NC1CCCC1)(c1ccc(F)cc1)c1cc(F)cc(OC(F)(F)C(F)F)c1] | (S)-1-(cyano(3-fluoro-5-(1,1,2,2-tetrafluoroethoxy)phenyl)(4-fluorophenyl)methyl)-3-cyclopentylurea | 3.71 LC (1) 472.20 [M + H]+ | Procedures 3, 4, 18, 6 and 2 |
| 957 | 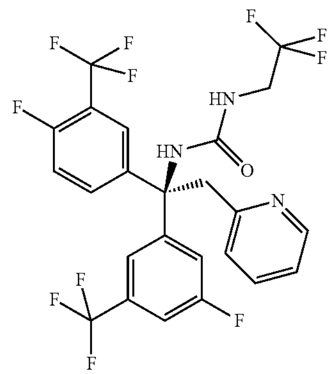 [SMILES: O=C(NCC(F)(F)F)N[C@@](Cc1ccccn1)(c1cc(F)cc(C(F)(F)F)c1)c1ccc(F)c(C(F)(F)F)c1] | (R)-1-(1-(4-fluoro-3-(trifluoromethyl)phenyl)-1-(3-fluoro-5-(trifluoromethyl)phenyl)-2-(pyridin-2-yl)ethyl)-3-(2,2,2-trifluoroethyl)urea | 3.25 LC (1) 572.04 [M + H]+ | Procedures 4, 5, 6, 2 and 9 |
| 958 | 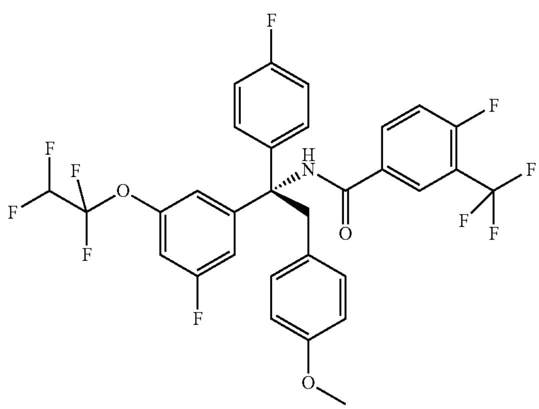 [SMILES: COc1ccc(C[C@](NC(=O)c2ccc(F)c(C(F)(F)F)c2)(c2ccc(F)cc2)c2cc(F)cc(OC(F)(F)C(F)F)c2)cc1] | (S)-4-fluoro-N-(1-(3-fluoro-5-(1,1,2,2-tetrafluoroethoxy)phenyl)-1-(4-fluorophenyl)-2-(4-methoxyphenyl)ethyl)-3-(trifluoromethyl)benzamide | 4.326 LC (11) 646.1 [M + H]+ | Procedures 3, 4, 5, 6 and 7 |
| 959 | 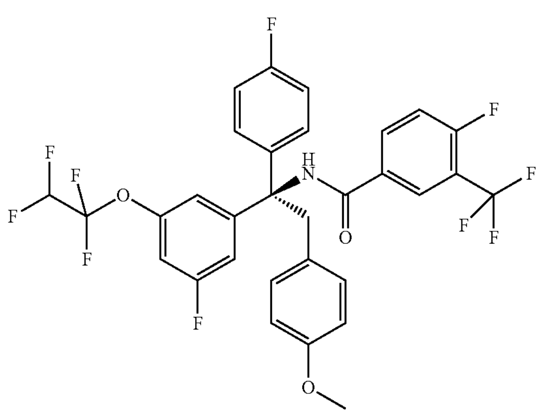 [SMILES: COc1ccc(C[C@@](NC(=O)c2ccc(F)c(C(F)(F)F)c2)(c2ccc(F)cc2)c2cc(F)cc(OC(F)(F)C(F)F)c2)cc1] | (R)-4-fluoro-N-(1-(3-fluoro-5-(1,1,2,2-tetrafluoroethoxy)phenyl)-1-(4-fluorophenyl)-2-(4-methoxyphenyl)ethyl)-3-(trifluoromethyl)benzamide | 4.326 LC (11) 646.1 [M + H]+ | Procedures 3, 4, 5, 6 and 7 |

TABLE 19-continued

| Ex. No. | Structure | Name | Retention Time Min./ Molecular Mass | Prepared in the manner described in: |
|---|---|---|---|---|
| 960 | 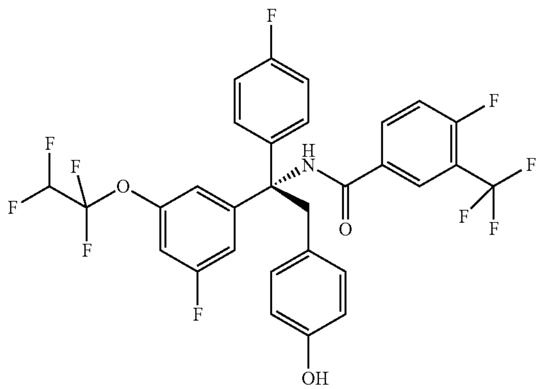 [SMILES: O=C(N[C@@](Cc1ccc(O)cc1)(c1ccc(F)cc1)c1cc(F)cc(OC(F)(F)C(F)F)c1)c1ccc(F)c(C(F)(F)F)c1] | (S)-4-fluoro-N-(1-(3-fluoro-5-(1,1,2,2-tetrafluoroethoxy)phenyl)-1-(4-fluorophenyl)-2-(4-hydroxyphenyl)ethyl)-3-(trifluoromethyl)benzamide | 4.146 LC (11) 632.1 [M + H]+ | Procedures 3, 4, 5, 6, 7 and 59 |
| 961 | 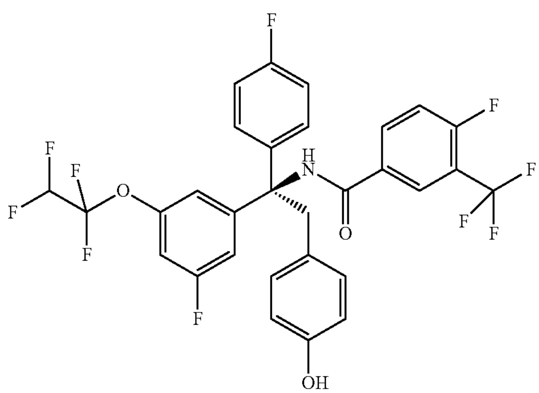 [SMILES: O=C(N[C@](Cc1ccc(O)cc1)(c1ccc(F)cc1)c1cc(F)cc(OC(F)(F)C(F)F)c1)c1ccc(F)c(C(F)(F)F)c1] | (R)-4-fluoro-N-(1-(3-fluoro-5-(1,1,2,2-tetrafluoroethoxy)phenyl)-1-(4-fluorophenyl)-2-(4-hydroxyphenyl)ethyl)-3-(trifluoromethyl)benzamide | 4.146 LC (11) 632.1 [M + H]+ | Procedures 3, 4, 5, 6, 7 and 59 |
| 962 | 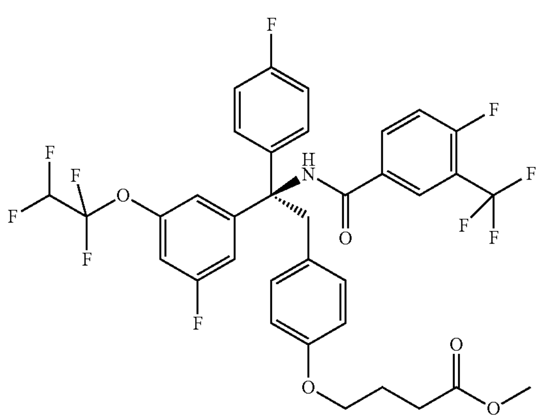 [SMILES: COC(=O)CCCOc1ccc(C[C@@](NC(=O)c2ccc(F)c(C(F)(F)F)c2)(c2ccc(F)cc2)c2cc(F)cc(OC(F)(F)C(F)F)c2)cc1] | (R)-methyl 4-(4-(2-(4-fluoro-3-(trifluoromethyl)benzamido)-2-(3-fluoro-5-(1,1,2,2-tetrafluoroethoxy)phenyl)-2-(4-fluorophenyl)ethyl)phenoxy)butanoate | 4.326 LC (11) 732.1 [M + H]+ | Procedures 3, 4, 5, 6, 7, 59 and 68 |

TABLE 19-continued

| Ex. No. | Structure | Name | Retention Time Min./ Molecular Mass | Prepared in the manner described in: |
|---|---|---|---|---|
| 963 | 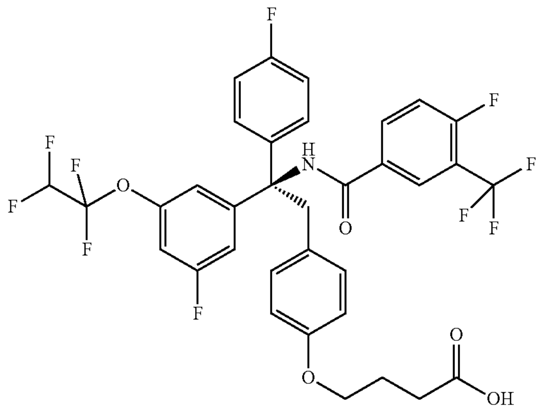 [SMILES: O=C(O)CCCOc1ccc(C[C@@](NC(=O)c2ccc(F)c(C(F)(F)F)c2)(c2ccc(F)cc2)c2cc(F)cc(OC(F)(F)C(F)F)c2)cc1] | (R)-4-(4-(2-(4-fluoro-3-(trifluoromethyl)benzamido)-2-(3-fluoro-5-(1,1,2,2-tetrafluoroethoxy)phenyl)-2-(4-fluorophenyl)ethyl)phenoxy)butanoic acid | 4.215 LC (11) 718.1 [M + H]$^+$ | Procedures 3, 4, 5, 6, 7, 59, 68 and 23 |
| 964 | 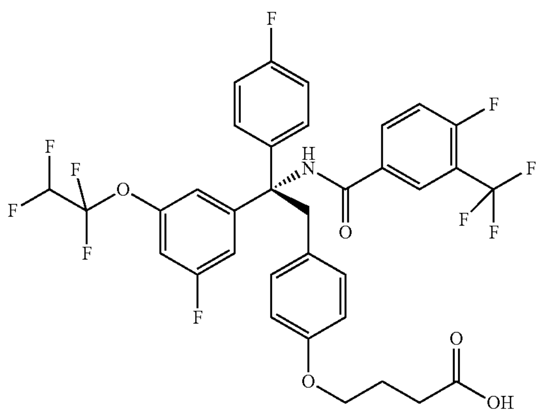 [SMILES: O=C(O)CCCOc1ccc(C[C@](NC(=O)c2ccc(F)c(C(F)(F)F)c2)(c2ccc(F)cc2)c2cc(F)cc(OC(F)(F)C(F)F)c2)cc1] | (S)-4-(4-(2-(4-fluoro-3-(trifluoromethyl)benzamido)-2-(3-fluoro-5-(1,1,2,2-tetrafluoroethoxy)phenyl)-2-(4-fluorophenyl)ethyl)phenoxy)butanoic acid | 4.193 LC (11) 718.1 [M + H]$^+$ | Procedures 3, 4, 5, 6, 7, 59, 68, and 23 |
| 965 | 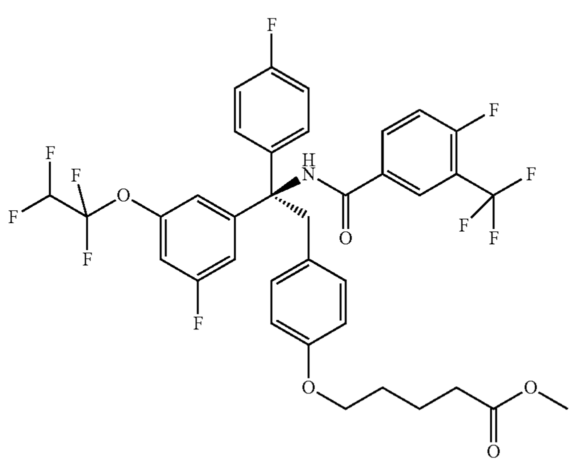 [SMILES: COC(=O)CCCCOc1ccc(C[C@@](NC(=O)c2ccc(F)c(C(F)(F)F)c2)(c2ccc(F)cc2)c2cc(F)cc(OC(F)(F)C(F)F)c2)cc1] | (R)-methyl 5-(4-(2-(4-fluoro-3-(trifluoromethyl)benzamido)-2-(3-fluoro-5-(1,1,2,2-tetrafluoroethoxy)phenyl)-2-(4-fluorophenyl)ethyl)phenoxy)pentanoate | 2.217 LC (2) 746.1 [M + H]$^+$ | Procedures 3, 4, 5, 6, 7, 59 and 68 |

TABLE 19-continued

| Ex. No. | Structure | Name | Retention Time Min./ Molecular Mass | Prepared in the manner described in: |
|---|---|---|---|---|
| 966 | 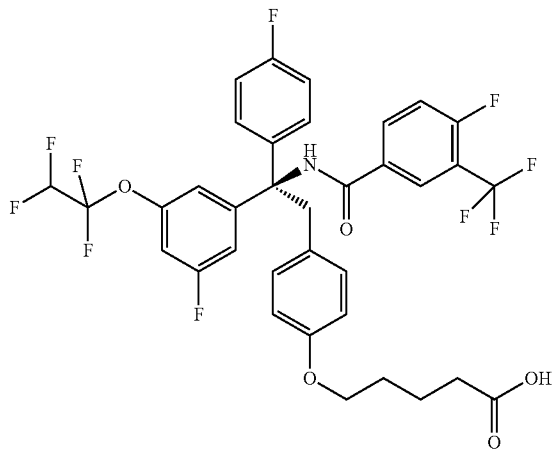 [SMILES: O=C(O)CCCCOc1ccc(C[C@@](NC(=O)c2ccc(F)c(C(F)(F)F)c2)(c2ccc(F)cc2)c2cc(F)cc(OC(F)(F)C(F)F)c2)cc1] | (R)-5-(4-(2-(4-fluoro-3-(trifluoromethyl)benzamide)-2-(3-fluoro-5-(1,1,2,2-tetrafluoroethoxy)phenyl)-2-(4-fluorophenyl)ethyl)phenoxy)pentanoic acid | 4.230 LC (11) 732.1 [M + H]+ | Procedures 3, 4, 5, 6, 7, 59, 68 and 23 |
| 967 | 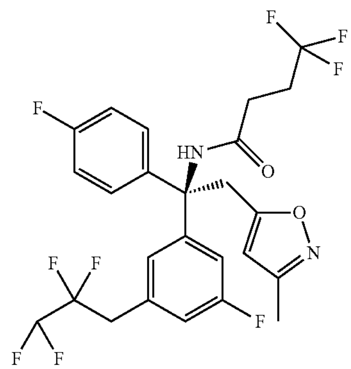 [SMILES: Cc1cc(C[C@@](NC(=O)CCC(F)(F)F)(c2ccc(F)cc2)c2cc(F)cc(CC(F)(F)C(F)F)c2)on1] | (R)-4,4,4-trifluoro-N-(1-(3-fluoro-5-(1,1,2,2-tetrafluoroethoxy)phenyl)-1-(4-fluorophenyl)-2-(3-methylisoxazol-5-yl)ethyl)butanamide | 3.73 LC (1) 555.65 [M + H]+ | Procedures 3, 4, 5, 6, 17 and 128 |
| 968 | 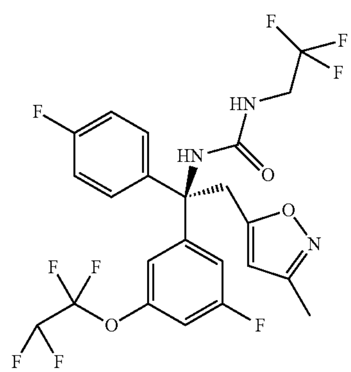 [SMILES: Cc1cc(C[C@@](NC(=O)NCC(F)(F)F)(c2ccc(F)cc2)c2cc(F)cc(OC(F)(F)C(F)F)c2)on1] | (R)-1-(1-(3-fluoro-5-(1,1,2,2-tetrafluoroethoxy)phenyl)-1-(4-fluorophenyl)-2-(3-methylisoxazol-5-yl)ethyl)-3-(2,2,2-trifluoroethyl)urea | 3.70 LC (1) 556.68 [M + H]+ | Procedures 3, 4, 5, 6, 17, 2 and 9 |
| 969 | 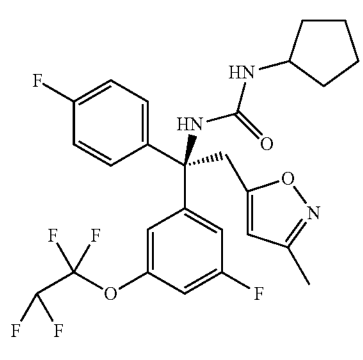 [SMILES: Cc1cc(C[C@@](NC(=O)NC2CCCC2)(c2ccc(F)cc2)c2cc(F)cc(OC(F)(F)C(F)F)c2)on1] | (R)-1-cyclopentyl-3-(1-(3-fluoro-5-(1,1,2,2-tetrafluoroethoxy)phenyl)-1-(4-fluorophenyl)-2-(3-methylisoxazol-5-yl)ethyl)urea | 3.80 LC (1) 542.74 [M + H]+ | Procedures 3, 4, 5, 6, 17 and 2 |

TABLE 19-continued

| Ex. No. | Structure | Name | Retention Time Min./ Molecular Mass | Prepared in the manner described in: |
|---|---|---|---|---|
| 970 | 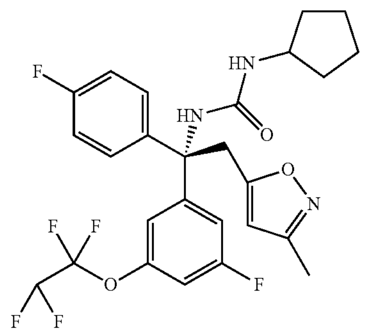 [SMILES: Cc1cc(C[C@](NC(=O)NC2CCCC2)(c2ccc(F)cc2)c2cc(F)cc(OC(F)(F)C(F)F)c2)on1] | (S)-1-cyclopentyl-3-(1-(3-fluoro-5-(1,1,2,2-tetrafluoroethoxy)phenyl)-1-(4-fluorophenyl)-2-(3-methylisoxazol-5-yl)ethyl)urea | 3.84 LC (1) 542.79 [M + H]+ | Procedures 3, 4, 5, 6, 17 and 2 |
| 971 | 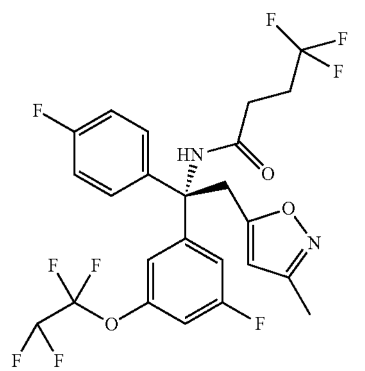 [SMILES: Cc1cc(C[C@](NC(=O)CCC(F)(F)F)(c2ccc(F)cc2)c2cc(F)cc(OC(F)(F)C(F)F)c2)on1] | (S)-4,4,4-trifluoro-N-(1-(3-fluoro-5-(1,1,2,2-tetrafluoroethoxy)phenyl)-1-(4-fluorophenyl)-2-(3-methylisoxazol-5-yl)ethyl)butanamide | 3.77 LC (1) 555.73 [M + H]+ | Procedures 3, 4, 5, 6, 17 and 128 |
| 972 | 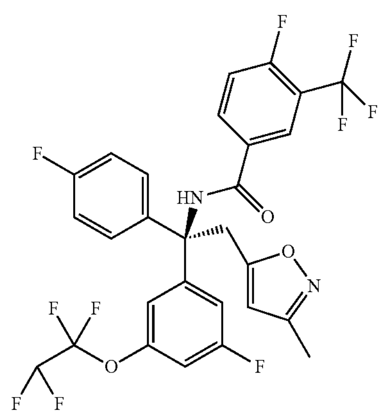 [SMILES: Cc1cc(C[C@@](NC(=O)c2ccc(F)c(C(F)(F)F)c2)(c2ccc(F)cc2)c2cc(F)cc(OC(F)(F)C(F)F)c2)on1] | (R)-4-fluoro-N-(1-(3-fluoro-5-(1,1,2,2-tetrafluoroethoxy)phenyl)-1-(4-fluorophenyl)-2-(3-methylisoxazol-5-yl)ethyl)-3-(trifluoromethyl)benzamide | 4.00 LC (1) 621.71 [M + H]+ | Procedures 3, 4, 5, 6, 17 and 7 |
| 973 | 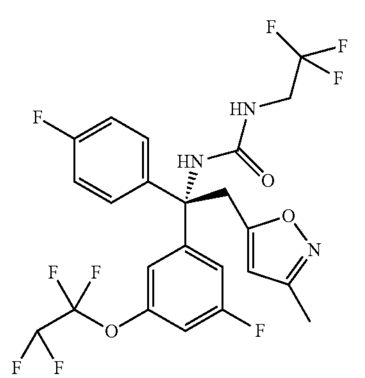 [SMILES: Cc1cc(C[C@](NC(=O)NCC(F)(F)F)(c2ccc(F)cc2)c2cc(F)cc(OC(F)(F)C(F)F)c2)on1] | (S)-1-(1-(3-fluoro-5-(1,1,2,2-tetrafluoroethoxy)phenyl)-1-(4-fluorophenyl)-2-(3-methylisoxazol-5-yl)ethyl)-3-(2,2,2-trifluoroethyl)urea | 3.71 LC (1) 556.68 [M + H]+ | Procedures 3, 4, 5, 6, 17, 2 and 9 |

TABLE 19-continued

| Ex. No. | Structure | Name | Retention Time Min./ Molecular Mass | Prepared in the manner described in: |
|---|---|---|---|---|
| 974 | 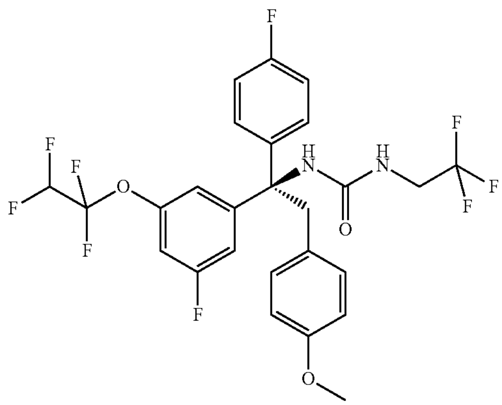 [SMILES: COc1ccc(C[C@@](NC(=O)NCC(F)(F)F)(c2ccc(F)cc2)c2cc(F)cc(OC(F)(F)C(F)F)c2)cc1] | (R)-1-(1-(3-fluoro-5-(1,1,2,2-tetrafluoroethoxy)phenyl)-1-(4-fluorophenyl)-2-(4-methoxyphenyl)ethyl)-3-(2,2,2-trifluoroethyl)urea | 4.118 LC 581.1 [M + H]$^+$ | Procedures 3, 4, 5, 6 and 25 |
| 975 | 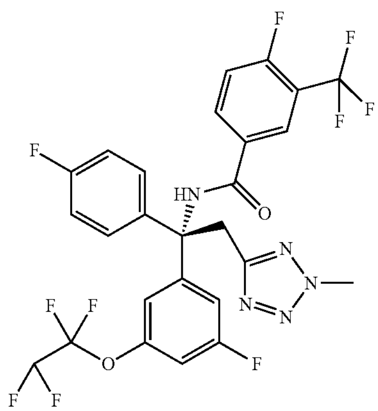 [SMILES: Cn1nnc(C[C@](NC(=O)c2ccc(F)c(C(F)(F)F)c2)(c2ccc(F)cc2)c2cc(F)cc(OC(F)(F)C(F)F)c2)n1] | (S)-4-fluoro-N-(1-(3-fluoro-5-(1,1,2,2-tetrafluoroethoxy)phenyl)-1-(4-fluorophenyl)-2-(2-methyl-2H-tetrazol-5-yl)ethyl)-3-(trifluoromethyl)benzamide | 3.97 LC 622.67 [M + H]$^+$ | Procedures 3, 4, 5, 18, 6, 7, 79 and 80 |
| 976 | 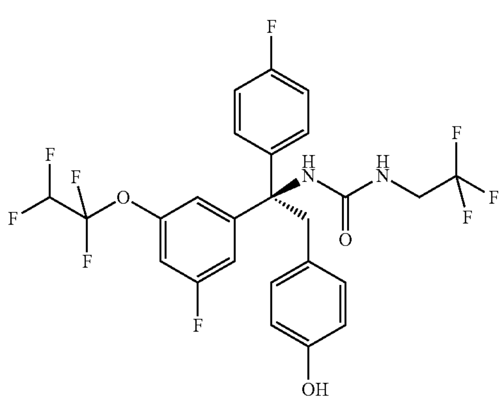 [SMILES: O=C(NCC(F)(F)F)N[C@](Cc1ccc(O)cc1)(c1ccc(F)cc1)c1cc(F)cc(OC(F)(F)C(F)F)c1] | (R)-1-(1-(3-fluoro-5-(1,1,2,2-tetrafluoroethoxy)phenyl)-1-(4-fluorophenyl)-2-(4-hydroxyphenyl)ethyl)-3-(2,2,2-trifluoroethyl)urea | 1.945 LC (2) 567.1 [M + H]$^+$ | Procedures 3, 4, 5, 6, 25 and 59 |

TABLE 19-continued

| Ex. No. | Structure | Name | Retention Time Min./ Molecular Mass | Prepared in the manner described in: |
|---|---|---|---|---|
| 977 | 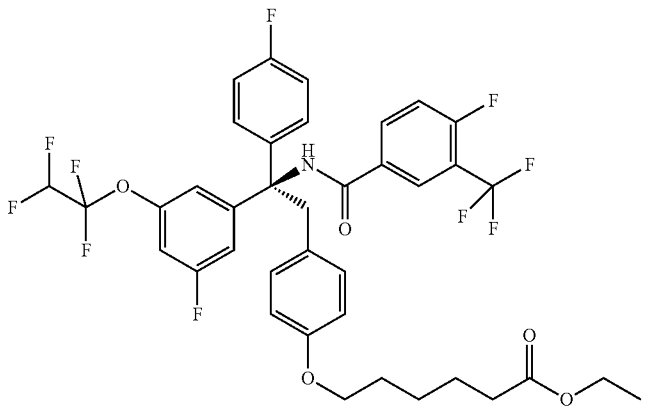 [SMILES: CCOC(=O)CCCCCOc1ccc(C[C@@](NC(=O)c2ccc(F)c(C(F)(F)F)c2)(c2ccc(F)cc2)c2cc(F)cc(OC(F)(F)C(F)F)c2)cc1] | (R)-ethyl 6-(4-(2-(4-fluoro-3-(trifluoromethyl)benzamide)-2-(3-fluoro-5-(1,1,2,2-tetrafluoroethoxy)phenyl)-2-(4-fluorophenyl)ethyl)phenoxy)hexanoate | 2.277 LC (2) 774.2 [M + H]$^+$ | Procedures 3, 4, 5, 6, 7, 59 and 129 |
| 978 | 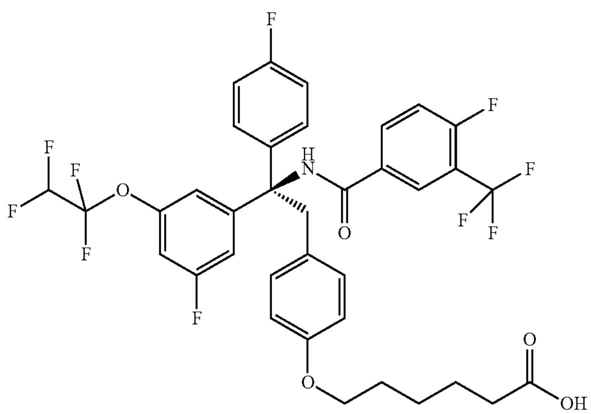 [SMILES: O=C(O)CCCCCOc1ccc(C[C@@](NC(=O)c2ccc(F)c(C(F)(F)F)c2)(c2ccc(F)cc2)c2cc(F)cc(OC(F)(F)C(F)F)c2)cc1] | (R)-6-(4-(2-(4-fluoro-3-(trifluoromethyl)benzamide)-2-(3-fluoro-5-(1,1,2,2-tetrafluoroethoxy)phenyl)-2-(4-fluorophenypethyl)phenoxy)hexanoic acid | 2.172 LC (2) 746.2 [M + H]$^+$ | Procedures 3, 4, 5, 6, 7, 59, 129 and 23 |
| 979 | 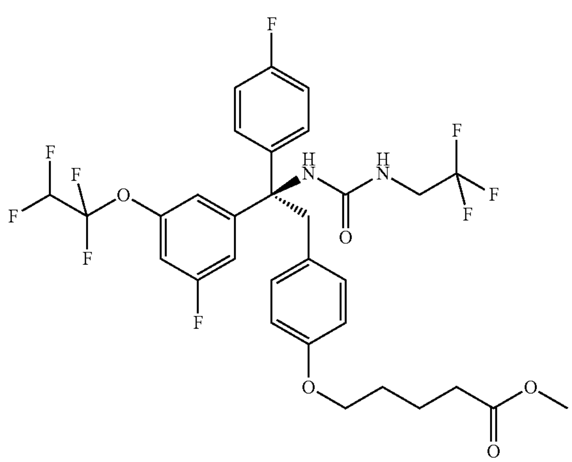 [SMILES: COC(=O)CCCCOc1ccc(C[C@@](NC(=O)NCC(F)(F)F)(c2ccc(F)cc2)c2cc(F)cc(OC(F)(F)C(F)F)c2)cc1] | (R)-methyl 5-(4-(2-(3-fluoro-5-(1,1,2,2-tetrafluoroethoxy)phenyl)-2-(4-fluorophenyl)-2-(3-(2,2,2-trifluoroethyl)ureido)ethyl)phenoxy)pentanoate | 2.092 LC (2) 681.1 [M + H]$^+$ | Procedures 3, 4, 5, 6, 25, 59 and 68 |

TABLE 19-continued

| Ex. No. | Structure | Name | Retention Time Min./ Molecular Mass | Prepared in the manner described in: |
|---|---|---|---|---|
| 980 | 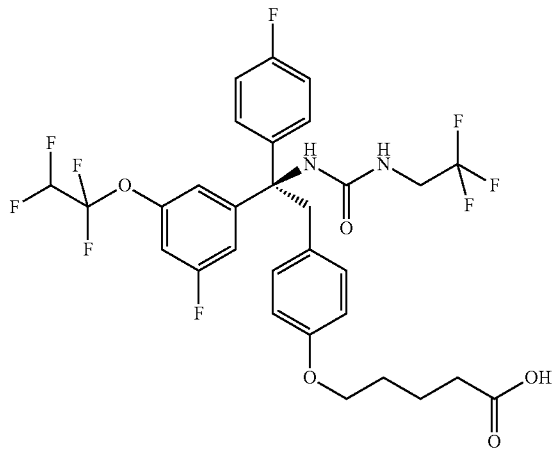 [SMILES: O=C(O)CCCCOc1ccc(C[C@@](NC(=O)NCC(F)(F)F)(c2ccc(F)cc2)c2cc(F)cc(OC(F)(F)C(F)F)c2)cc1] | (R)-5-(4-(2-(3-fluoro-5-(1,1,2,2-tetrafluoroethoxy)phenyl)-2-(4-fluorophenyl)-2-(3-(2,2,2-trifluoroethyl)ureido)ethyl)phenoxy)pentanoic acid | 2.058 LC (2) 667.1 [M + H]+ | Procedures 3, 4, 5, 6, 25, 59, 68 and 23 |
| 981 | 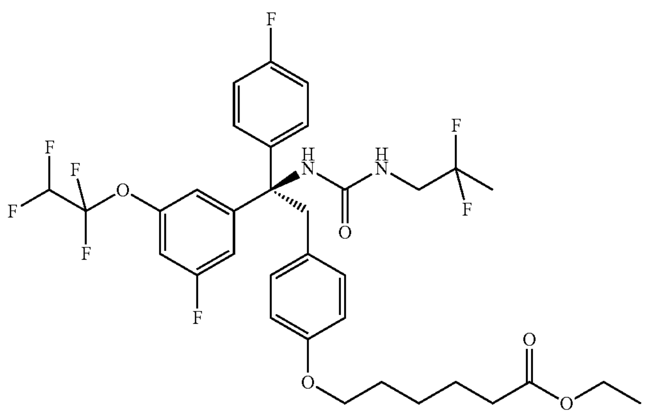 | (R)-ethyl 6-(4-(2-(3-fluoro-5-(1,1,2,2-tetrafluoroethoxy)phenyl)-2-(4-fluorophenyl-2-(3-(2,2,2-trifluoroethyl)ureido)ethyl)phenoxy)hexanoate | 2.188 LC (2) 709.2 [M + H]+ | Procedures 3, 4, 5, 6, 25, 59 and 129 |
| 982 | 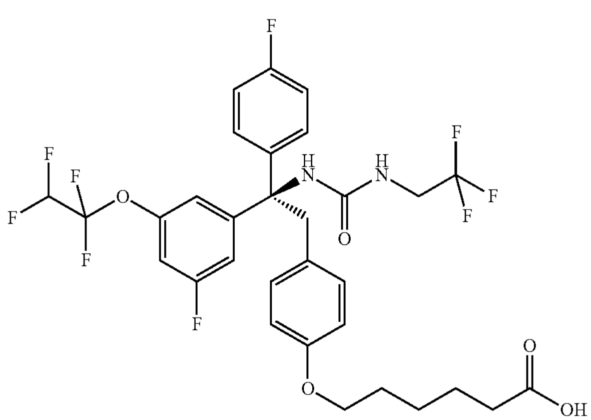 [SMILES: O=C(O)CCCCCOc1ccc(C[C@@](NC(=O)NCC(F)(F)F)(c2ccc(F)cc2)c2cc(F)cc(OC(F)(F)C(F)F)c2)cc1] | (R)-6-(4-(2-(3-fluoro-5-(1,1,2,2-tetrafluoroethoxy)phenyl)-2-(4-trifluoroethyl)ureido)ethyl)phenoxy)hexanoic acid | 2.097 LC (2) 681.1 [M + H]+ | Procedures 3, 4, 5, 6, 25, 59, 129 and 23 |

TABLE 19-continued

| Ex. No. | Structure | Name | Retention Time Min./ Molecular Mass | Prepared in the manner described in: |
|---|---|---|---|---|
| 983 | 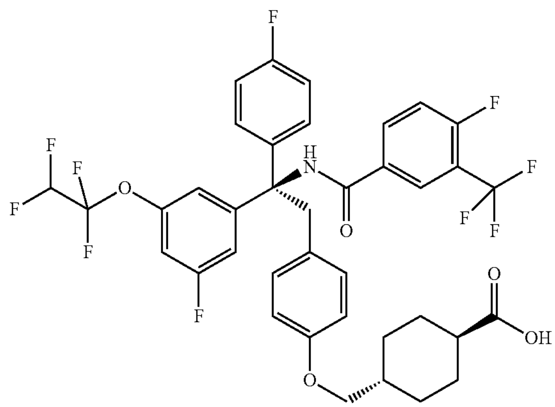 [SMILES: O=C(N[C@](Cc1ccc(OC[C@H]2CC[C@H](C(=O)O)CC2)cc1)(c1ccc(F)cc1)c1cc(F)cc(OC(F)(F)C(F)F)c1)c1ccc(F)c(C(F)(F)F)c1] | (1r,4r)-4-((4-((R)-2-(4-fluoro-3-(trifluoromethyl)benzamide)-2-(3-fluoro-5-(1,1,2,2-tetrafluoroethoxy)phenyl)-2-(4-fluorophenyl)ethyl)phenoxy)methyl)cyclohexanecarboxylic acid | 2.207 LC (2) 772.1 [M + H]$^+$ | Procedures 3, 4, 5, 6, 7, 59, 129 and 23 |
| 984 | 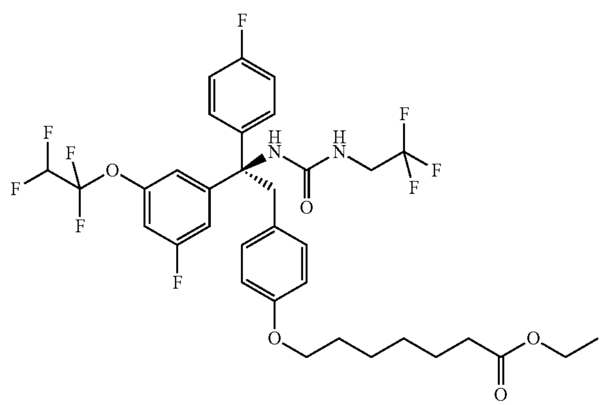 [SMILES: CCOC(=O)CCCCCCOc1ccc(C[C@@](NC(=O)NCC(F)(F)F)(c2ccc(F)cc2)c2cc(F)cc(OC(F)(F)C(F)F)c2)cc1] | (R)-ethyl 7-(4-(2-(3-fluoro-5-(1,1,2,2-tetrafluoroethoxy)phenyl)-2-(4-trifluoroethyl)ureido ethyl)phenoxy)heptanoate | 2.232 LC (2) 723.3 [M + H]$^+$ | Procedures 3, 4, 5, 6, 25, 59 and 129 |
| 985 | 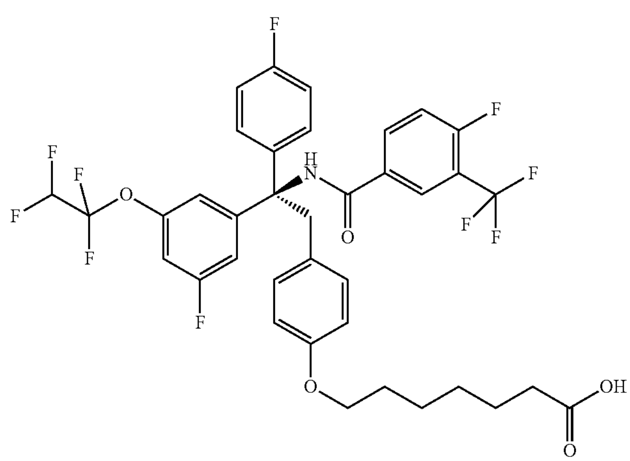 [SMILES: O=C(O)CCCCCCOc1ccc(C[C@@](NC(=O)c2ccc(F)c(C(F)(F)F)c2)(c2ccc(F)cc2)c2cc(F)cc(OC(F)(F)C(F)F)c2)cc1] | (R)-7-(4-(2-(4-fluoro-3-(trifluoromethyl)benzamido)-2-(3-fluoro-5-(1,1,2,2-tetrafluoroethoxy)phenyl)-2-(4-fluorophenyl)ethyl)phenoxy)heptanoic acid | 2.202 LC (2) 760.2 [M + H]$^+$ | Procedures 3, 4, 5, 6, 7, 59, 129 and 23 |

TABLE 19-continued

| Ex. No. | Structure | Name | Retention Time Min./ Molecular Mass | Prepared in the manner described in: |
|---|---|---|---|---|
| 986 | 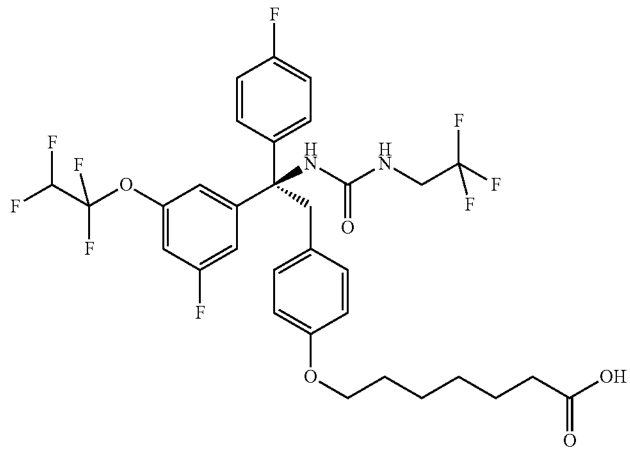 [SMILES: O=C(O)CCCCCCOc1ccc(C[C@@](NC(=O)NCC(F)(F)F)(c2ccc(F)cc2)c2cc(F)cc(OC(F)(F)C(F)F)c2)cc1] | (R)-7-(4-(2-(3-fluoro-5-(1,1,2,2-tetrafluoroethoxy) phenyl)-2-(4-fluorophenyl)-2-(3-(2,2,2-trifluoroethyl)ureido) ethyl)phenoxy)heptanoic acid | 2.130 LC (2) 695.2 [M + H]+ | Procedures 3, 4, 5, 6, 25, 59, 129 and 23 |
| 987 | 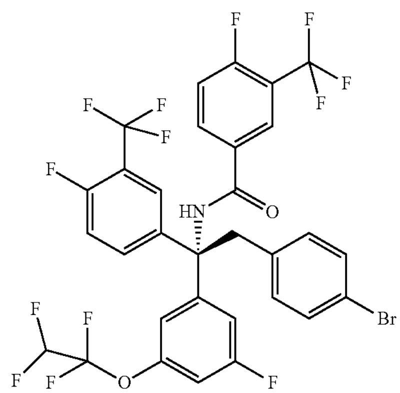 [SMILES: O=C(N[C@](Cc1ccc(Br)cc1)(c1cc(F)cc(OC(F)(F)C(F)F)c1)c1ccc(F)c(C(F)(F)F)c1)c1ccc(F)c(C(F)(F)F)c1] | (S)-N-(2-(4-bromophenyl)-1-(4-fluoro-3-(trifluoromethyl) phenyl)-1-(3-fluoro-5-(1,1,2,2-tetrafluoroethoxy)phenyl) ethyl)-4-fluoro-3-(trifluoromethyl) benzamide | 2.30 LC (2) 763.8 [M + H]+ | Procedures 3, 4, 72, 96, 97, 98 and 7 |
| 988 | 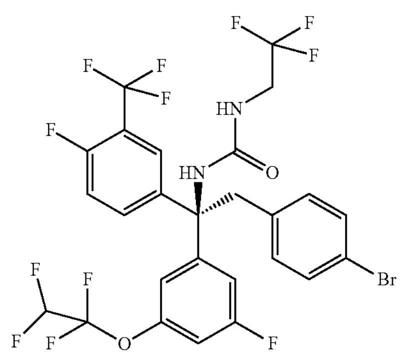 [SMILES: O=C(NCC(F)(F)F)N[C@@](Cc1ccc(Br)cc1)(c1cc(F)cc(OC(F)(F)C(F)F)c1)c1ccc(F)c(C(F)(F)F)c1] | (R)-1-(2-(4-bromophenyl)-1-(4-fluoro-3-(trifluoromethyl) phenyl)-1-(3-fluoro-5-(1,1,2,2-tetrafluoroethoxy)phenyl) ethyl)-3-(2,2,2-trifluoroethyl)urea | 4.04 LC (6) 698.0 [M + H]+ | Procedures 3, 4, 72, 96, 97, 98 and 25 |
| 989 | 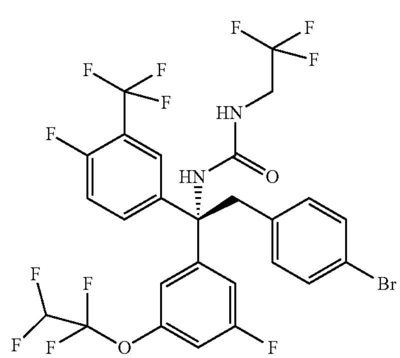 [SMILES: O=C(NCC(F)(F)F)N[C@](Cc1ccc(Br)cc1)(c1cc(F)cc(OC(F)(F)C(F)F)c1)c1ccc(F)c(C(F)(F)F)c1] | (S)-1-(2-(4-bromophenyl)-1-(4-fluoro-3-(trifluoromethyl) phenyl)-1-(3-fluoro-5-(1,1,2,2-tetrafluoroethoxy)phenyl) ethyl)-3-(2,2,2-trifluoroethyl)urea | 4.05 LC (6) 699.0 [M + H]+ | Procedures 3, 4, 72, 96, 97, 98 and 25 |

TABLE 19-continued

| Ex. No. | Structure | Name | Retention Time Min./ Molecular Mass | Prepared in the manner described in: |
|---|---|---|---|---|
| 990 | 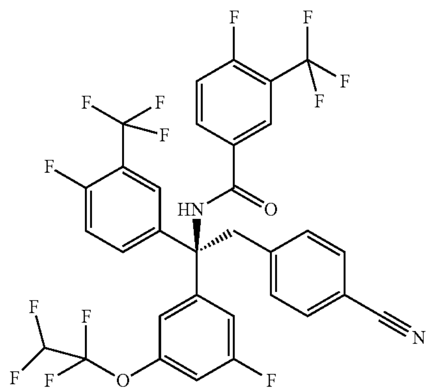 [SMILES: N#Cc1ccc(C[C@](NC(=O)c2ccc(F)c(C(F)(F)F)c2)(c2cc(F)cc(OC(F)(F)C(F)F)c2)c2ccc(F)c(C(F)(F)F)c2)cc1] | (R)-N-(2-(4-cyanophenyl)-1-(4-fluoro-3-(trifluoromethyl)phenyl)-1-(3-fluoro-5-(1,1,2,2-tetrafluoroethoxy)phenyl)ethyl)-4-fluoro-3-(trifluoromethyl)benzamide | 2.130 LC (2) 709.0 [M + H]$^+$ | Procedures 3, 4, 72, 96, 97, 98, 7 and 56 |
| 991 | 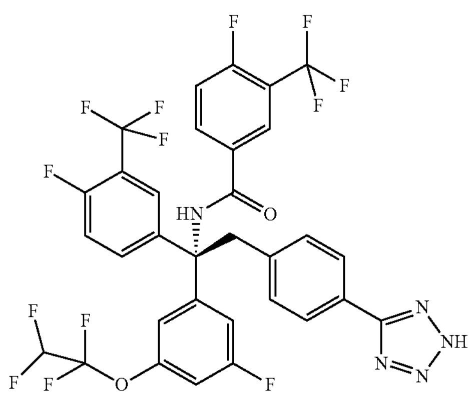 [SMILES: O=C(N[C@](Cc1ccc(-c2nn[nH]n2)cc1)(c1cc(F)cc(OC(F)(F)C(F)F)c1)c1ccc(F)c(C(F)(F)F)c1)c1ccc(F)c(C(F)(F)F)c1] | (S)-N-(2-(4-(2H-tetrazol-5-yl)phenyl)-1-(4-fluoro-3-(trifluoromethyl)phenyl)-1-(3-fluoro-5-(1,1,2,2-tetrafluoroethoxy)phenyl)ethyl)-4-fluoro-3-(trifluoromethyl)benzamide | 4.26 LC (6) 752.3 [M + H]$^+$ | Procedures 3, 4, 72, 96, 97, 98, 7 and 99 |
| 992 | 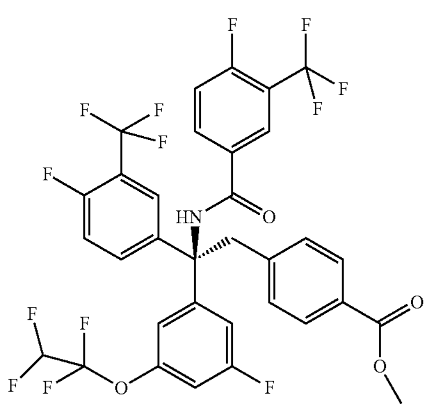 [SMILES: COC(=O)c1ccc(C[C@](NC(=O)c2ccc(F)c(C(F)(F)F)c2)(c2cc(F)cc(OC(F)(F)C(F)F)c2)c2ccc(F)c(C(F)(F)F)c2)cc1] | (R)-methyl 4-(2-(4-fluoro-3-(trifluoromethyl)benzamido)-2-(4-fluoro-3-(trifluoromethyl)phenyl)-2-(3-fluoro-5-(1,1,2,2-tetrafluoroethoxy)phenyl)ethyl)benzoate | 2.17 LC (2) 742.19 [M + H]$^+$ | Procedures 3, 4, 72, 96, 97, 98, 7, 56 and 57 |

TABLE 19-continued

| Ex. No. | Structure | Name | Retention Time Min./ Molecular Mass | Prepared in the manner described in: |
|---|---|---|---|---|
| 993 | 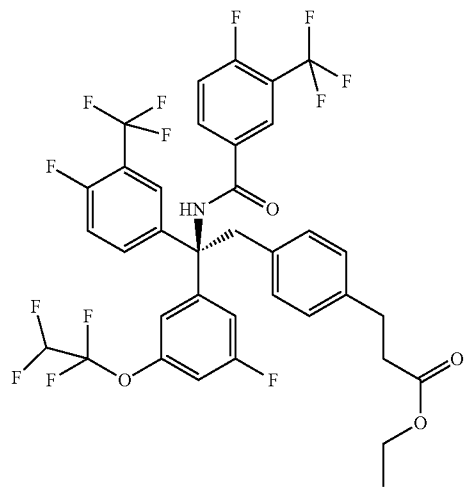 [SMILES: CCOC(=O)CCc1ccc(C[C@](NC(=O)c2ccc(F)c(C(F)(F)F)c2)(c2cc(F)cc(OC(F)(F)C(F)F)c2)c2ccc(F)c(C(F)(F)F)c2)cc1] | (R)-ethyl 3-(4-(2-(4-fluoro-3-(trifluoromethyl)benzamido)-2-(4-fluoro-3-(trifluoromethyl)phenyl)-2-(3-fluoro-5-(1,1,2,2-tetrafluoroethoxy)phenyl)ethyl)phenyl)propanoate | 4.49 LC (6) 784.34 [M + H]⁺ | Procedures 3, 4, 72, 96, 97, 98 and 24 |
| 994 | 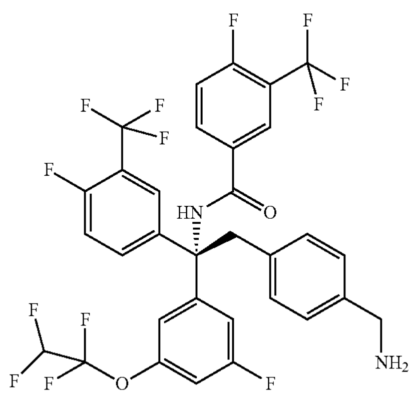 [SMILES: NCc1ccc(C[C@@](NC(=O)c2ccc(F)c(C(F)(F)F)c2)(c2cc(F)cc(OC(F)(F)C(F)F)c2)c2ccc(F)c(C(F)(F)F)c2)cc1] | (S)-N-(2-(4-(aminomethyl)phenyl)-1-(4-fluoro-3-(trifluoromethyl)phenyl)-1-(3-fluoro-5-(1,1,2,2-tetrafluoroethoxy)phenyl)ethyl)-4-fluoro-3-(trifluoromethyl)benzamide | 4.3 LC (6) 713.31 [M + H]⁺ | Procedures 3, 4, 72, 96, 97, 98, 7, 56 and 101 |
| 995 | 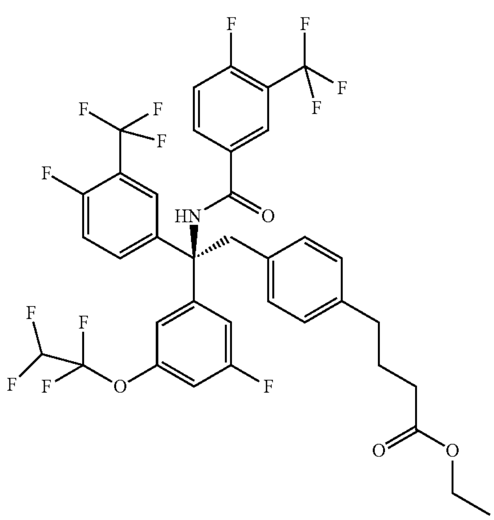 [SMILES: CCOC(=O)CCCc1ccc(C[C@](NC(=O)c2ccc(F)c(C(F)(F)F)c2)(c2cc(F)cc(OC(F)(F)C(F)F)c2)c2ccc(F)c(C(F)(F)F)c2)cc1] | (R)-ethyl 4-(4-(2-(4-fluoro-3-(trifluoromethyl)benzamido)-2-(4-fluoro-3-(trifluoromethyl)phenyl)-2-(3-fluoro-5-(1,1,2,2-tetrafluoroethoxy)phenyl)ethyl)phenyl)butanoate | 4.39 LC (6) 798.36 [M + H]⁺ | Procedures 3, 4, 72, 96, 97, 98, 7 and 25 |

TABLE 19-continued

| Ex. No. | Structure | Name | Retention Time Min./ Molecular Mass | Prepared in the manner described in: |
|---|---|---|---|---|
| 996 | 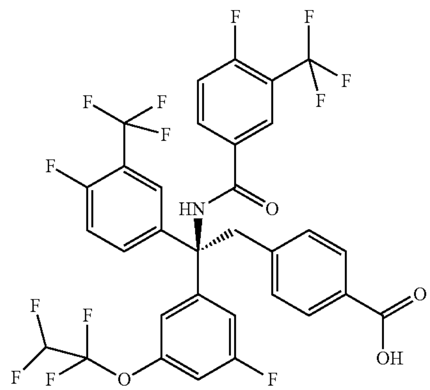 [SMILES: O=C(O)c1ccc(C[C@](NC(=O)c2ccc(F)c(C(F)(F)F)c2)(c2cc(F)cc(OC(F)(F)C(F)F)c2)c2ccc(F)c(C(F)(F)F)c2)cc1] | (R)-4-(2-(4-fluoro-3-(trifluoromethyl)benzamido)-2-(4-fluoro-3-(trifluoromethyl)phenyl)-2-(3-fluoro-5-(1,1,2,2-tetrafluoroethoxy)phenyl)ethyl)benzoic acid | 2.11 LC (2) 728.32 $[M + H]^+$ | Procedures 3, 4, 72, 96, 97, 98, 7, 56, 57 and 23 |
| 997 | 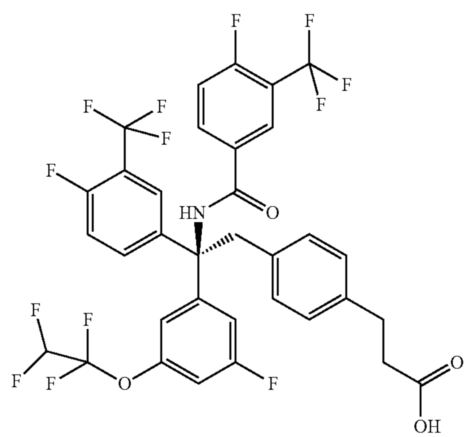 [SMILES: O=C(O)CCc1ccc(C[C@](NC(=O)c2ccc(F)c(C(F)(F)F)c2)(c2cc(F)cc(OC(F)(F)C(F)F)c2)c2ccc(F)c(C(F)(F)F)c2)cc1] | (R)-3-(4-(2-(4-fluoro-3-(trifluoromethyl)benzamido)-2-(4-fluoro-3-(trifluoromethyl)phenyl)-2-(3-fluoro-5-(1,1,2,2-tetrafluoroethoxy)phenyl)ethyl)phenyl)propanoic acid | 4.12 LC (6) 756.3 $[M + H]^+$ | Procedures 3, 4, 72, 96, 97, 98, 7, 24 and 23 |
| 998 | 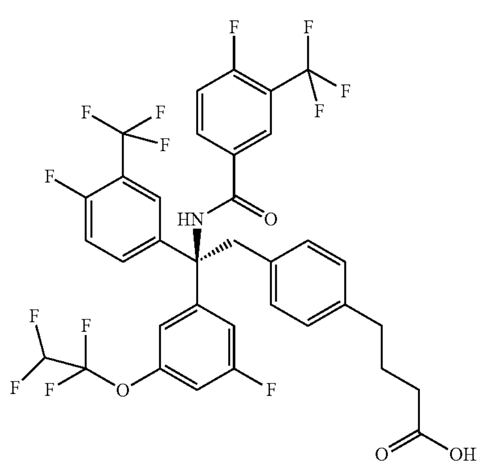 [SMILES: O=C(O)CCCc1ccc(C[C@](NC(=O)c2ccc(F)c(C(F)(F)F)c2)(c2cc(F)cc(OC(F)(F)C(F)F)c2)c2ccc(F)c(C(F)(F)F)c2)cc1] | (R)-4-(4-(2-(4-fluoro-3-(trifluoromethyl)benzamido)-2-(4-fluoro-3-(trifluoromethyl)phenyl)-2-(3-fluoro-5-(1,1,2,2-tetrafluoroethoxy)phenyl)ethyl)phenyl)butanoic acid | 4.18 LC (6) 770.0 $[M + H]^+$ | Procedures 3, 4, 72, 96, 97, 98, 7, 24 and 23 |

TABLE 19-continued

| Ex. No. | Structure | Name | Retention Time Min./ Molecular Mass | Prepared in the manner described in: |
|---|---|---|---|---|
| 999 | 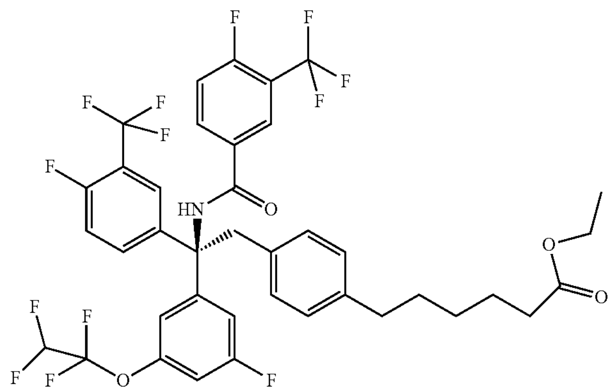 [SMILES: CCOC(=O)CCCCCc1ccc(C[C@](NC(=O)c2ccc(F)c(C(F)(F)F)c2)(c2cc(F)cc(OC(F)(F)C(F)F)c2)c2ccc(F)c(C(F)(F)F)c2)cc1] | (R)-ethyl 6-(4-(2-(4-fluoro-3-(trifluoromethyl)benzamido)-2-(4-fluoro-3-(trifluoromethyl)phenyl)-2-(3-fluoro-5-(1,1,2,2-tetrafluoroethoxy)phenyl)ethyl)phenyl)hexanoate | 4.54 LC (6) 826.52 [M + H]$^+$ | Procedures 3, 4, 72, 96, 97, 98, 7 and 24 |
| 1000 | 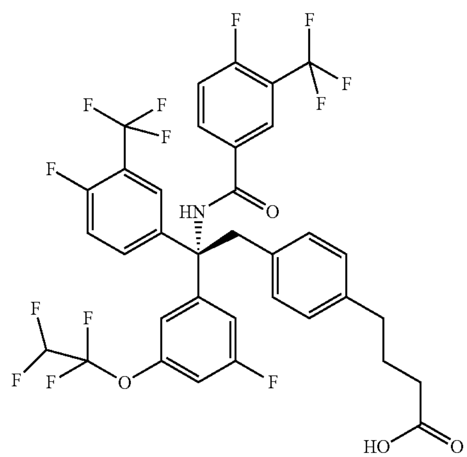 [SMILES: O=C(O)CCCc1ccc(C[C@@](NC(=O)c2ccc(F)c(C(F)(F)F)c2)(c2cc(F)cc(OC(F)(F)C(F)F)c2)c2ccc(F)c(C(F)(F)F)c2)cc1] | (S)-4-(4-(2-(4-fluoro-3-(trifluoromethyl)benzamido)-2-(4-fluoro-3-(trifluoromethyl)phenyl)-2-(3-fluoro-5-(1,1,2,2-tetrafluoroethoxy)phenyl)ethyl)phenyl)butanoic acid | 4.16 LC (6) 770.3 [M + H]$^+$ | Procedures 3, 4, 72, 96, 97, 98, 7, 24 and 23 |
| 1001 | 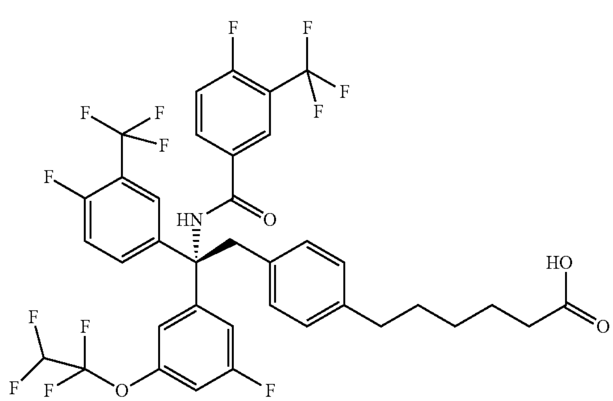 [SMILES: O=C(O)CCCCCc1ccc(C[C@@](NC(=O)c2ccc(F)c(C(F)(F)F)c2)(c2cc(F)cc(OC(F)(F)C(F)F)c2)c2ccc(F)c(C(F)(F)F)c2)cc1] | (S)-6-(4-(2-(4-fluoro-3-(trifluoromethyl)benzamido)-2-(4-fluoro-3-(trifluoromethyl)phenyl)-2-(3-fluoro-5-(1,1,2,2-tetrafluoroethoxy)phenyl)ethyl)phenyl)hexanoic acid | 4.20 LC (6) 798.47 [M + H]$^+$ | Procedures 3, 4, 72, 96, 97, 98, 7, 24 and 23 |

TABLE 19-continued

| Ex. No. | Structure | Name | Retention Time Min./ Molecular Mass | Prepared in the manner described in: |
|---|---|---|---|---|
| 1002 | 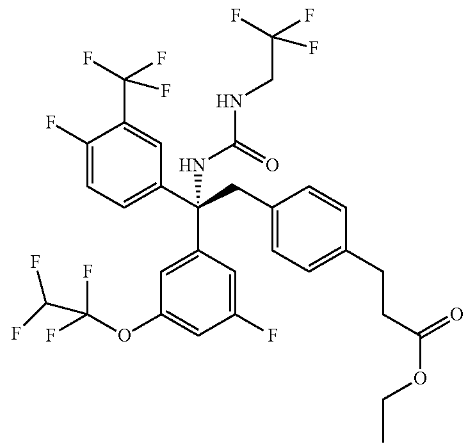 [SMILES: CCOC(=O)CCc1ccc(C[C@@](NC(=O)NCC(F)(F)F)(c2cc(F)cc(OC(F)(F)C(F)F)c2)c2ccc(F)c(C(F)(F)F)c2)cc1] | (S)-ethyl 3-(4-(2-(4-fluoro-3-(trifluoromethyl)phenyl)-2-(3-fluoro-5-(1,1,2,2-tetrafluoroethoxy)phenyl)-2-(3-(2,2,2-trifluoroethyl)ureido)ethyl)phenyl)propanoate | 4.15 LC (6) 719.37 [M + H]+ | Procedures 3, 4, 72, 96, 97, 98, 25 and 24 |
| 1003 | 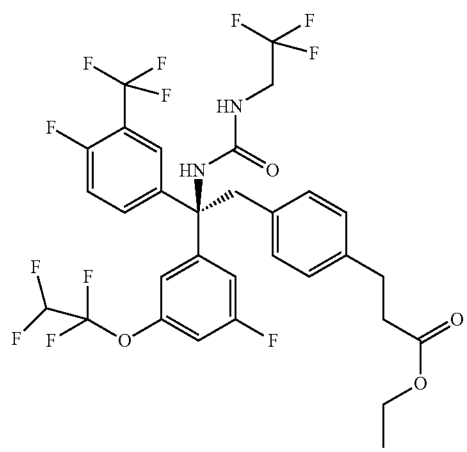 [SMILES: CCOC(=O)CCc1ccc(C[C@](NC(=O)NCC(F)(F)F)(c2cc(F)cc(OC(F)(F)C(F)F)c2)c2ccc(F)c(C(F)(F)F)c2)cc1] | (R)-ethyl 3-(4-(2-(4-fluoro-3-(trifluoromethyl)phenyl)-2-(3-fluoro-5-(1,1,2,2-tetrafluoroethoxy)phenyl)-2-(3-(2,2,2-trifluoroethyl)ureido)ethyl)phenyl)propanoate | 2.20 LC (2) 719.4 [M + H]+ | Procedures 3, 4, 72, 96, 97, 98, 25 and 24 |
| 1004 | 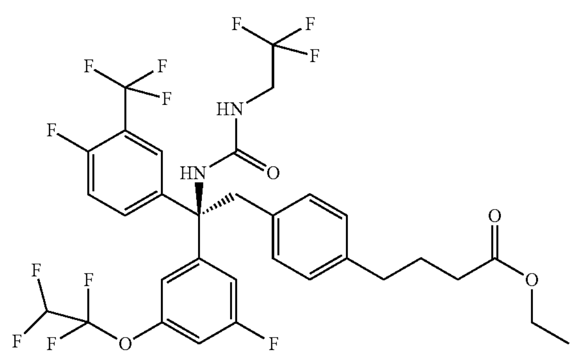 [SMILES: CCOC(=O)CCCc1ccc(C[C@](NC(=O)NCC(F)(F)F)(c2cc(F)cc(OC(F)(F)C(F)F)c2)c2ccc(F)c(C(F)(F)F)c2)cc1] | (R)-ethyl 4-(4-(2-(4-fluoro-3-(trifluoromethyl)phenyl)-2-(3-fluoro-5-(1,1,2,2-tetrafluoroethoxy)phenyl)-2-(3-(2,2,2-trifluoroethyl)ureido)ethyl)phenyl)butanoate | 4.22 LC (6) 733.39 [M + H]+ | Procedures 3, 4, 72, 96, 97, 98, 25 and 24 |

TABLE 19-continued

| Ex. No. | Structure | Name | Retention Time Min./ Molecular Mass | Prepared in the manner described in: |
|---|---|---|---|---|
| 1005 | 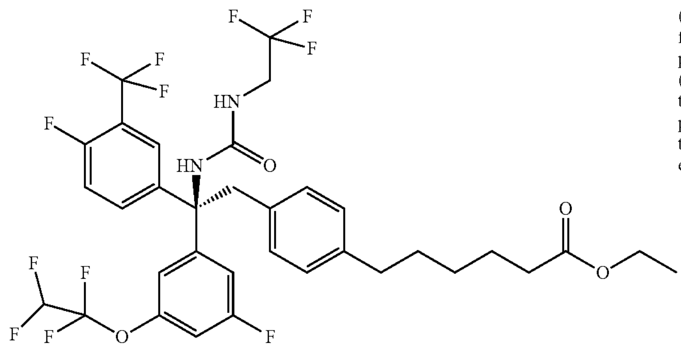 [SMILES: CCOC(=O)CCCCCc1ccc(C[C@](NC(=O)NCC(F)(F)F)(c2cc(F)cc(OC(F)(F)C(F)F)c2)c2ccc(F)c(C(F)(F)F)c2)cc1] | (R)-ethyl 6-(4-(2-(4-fluoro-3-(trifluoromethyl)phenyl)-2-(3-fluoro-5-(1,1,2,2-tetrafluoroethoxy)phenyl)-2-(3-(2,2,2-trifluoroethyl)ureido)ethyl)phenyl)hexanoate | 4.34 LC (6) 761.47 [M + H]+ | Procedures 3, 4, 72, 96, 97, 98, 25 and 24 |
| 1006 | 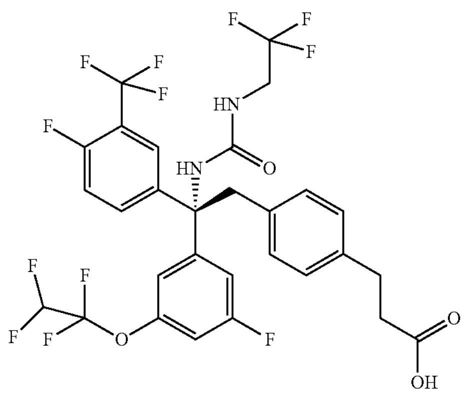 [SMILES: O=C(O)CCc1ccc(C[C@@](NC(=O)NCC(F)(F)F)(c2cc(F)cc(OC(F)(F)C(F)F)c2)c2ccc(F)c(C(F)(F)F)c2)cc1] | (S)-3-(4-(2-(4-fluoro-3-(trifluoromethyl)phenyl)-2-(3-fluoro-5-(1,1,2,2-tetrafluoroethoxy)phenyl)-2-(3-(2,2,2-trifluoroethyl)ureido)ethyl)phenyl)propanoic acid | 3.97 LC (6) 691.36 [M + H]+ | Procedures 3, 4, 72, 96, 97, 98, 25, 24 and 23 |
| 1007 | 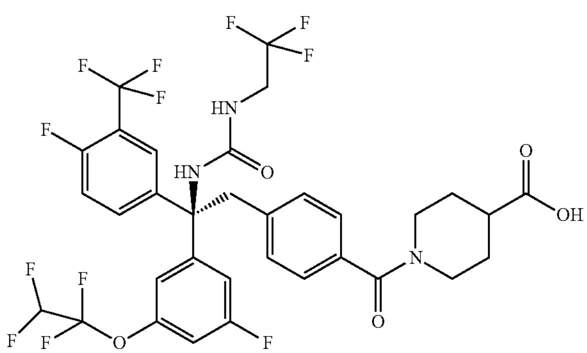 [SMILES: O=C(NCC(F)(F)F)N[C@@](Cc1ccc(C(=O)N2CCC(C(=O)O)CC2)cc1)(c1cc(F)cc(OC(F)(F)C(F)F)c1)c1ccc(F)c(C(F)(F)F)c1] | (R)-1-(4-(2-(4-fluoro-3-(trifluoromethyl)benzamido)-2-(4-fluoro-3-(trifluoromethyl)phenyl)-2-(3-fluoro-5-(1,1,2,2-tetrafluoroethoxy)phenyl)ethyl)benzoyl)piperidine-4-carboxylic acid | 4.0 LC (6) 839.5 [M + H]+ | Procedures 3, 4, 72, 96, 97, 98, 7, 56, 57, 23 and 103 |
| 1008 | 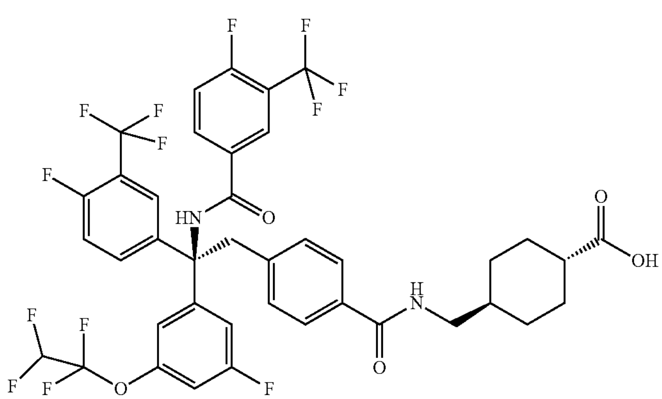 [SMILES: O=C(NC[C@H]1CC[C@H](C(=O)O)CC1)c1ccc(C[C@](NC(=O)c2ccc(F)c(C(F)(F)F)c2)(c2cc(F)cc(OC(F)(F)C(F)F)c2)c2ccc(F)c(C(F)(F)F)c2)cc1] | (1r,4r)-4-((4-((R)-2-(4-fluoro-3-(trifluoromethyl)benzamido)-2-(4-fluoro-phenyl)-2-(3-fluoro-5-3-(trifluoromethyl)(1,1,2,2-tetrafluoroethoxy)phenyl)ethyl)benzamido)methyl)cyclohexanecarboxylic acid | 4.0 LC (6) 867.5 [M + H]+ | Procedures 3, 4, 72, 96, 97, 98, 7, 56, 57, 23 and 103 |

TABLE 19-continued

| Ex. No. | Structure | Name | Retention Time Min./ Molecular Mass | Prepared in the manner described in: |
|---|---|---|---|---|
| 1009 | 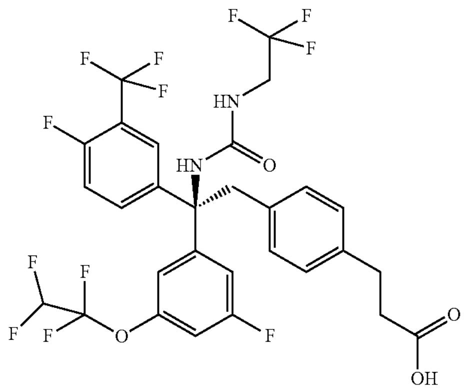 [SMILES: O=C(O)CCc1ccc(C[C@](NC(=O)NCC(F)(F)F)(c2cc(F)cc(OC(F)(F)C(F)F)c2)c2ccc(F)c(C(F)(F)F)c2)cc1] | (R)-3-(4-(2-(4-fluoro-3-(trifluoromethyl)phenyl)-2-(3-fluoro-5-(1,1,2,2-tetrafluoroethoxy)phenyl)-2-(3-(2,2,2-trifluoroethyl)ureido)ethyl)phenyl)propanoic acid | 4.0 LC (6) 691.37 [M + H]$^+$ | Procedures 3, 4, 72, 96, 97, 98, 25, 24 and 23 |
| 1010 | 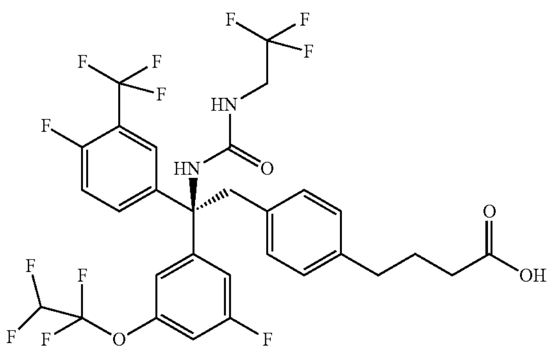 [SMILES: O=C(O)CCCc1ccc(C[C@](NC(=O)NCC(F)(F)F)(c2cc(F)cc(OC(F)(F)C(F)F)c2)c2ccc(F)c(C(F)(F)F)c2)cc1] | (R)-4-(4-(2-(4-fluoro-3-(trifluoromethyl)phenyl)-2-(3-fluoro-5-(1,1,2,2-tetrafluoroethoxy)phenyl)-2-(3-(2,2,2-trifluoroethyl)ureido)ethyl)phenyl)butanoic acid | 4.02 LC (6) 705.4 [M + H]+ | Procedures 3, 4, 72, 96, 97, 98, 25, 24 and 23 |
| 1011 | 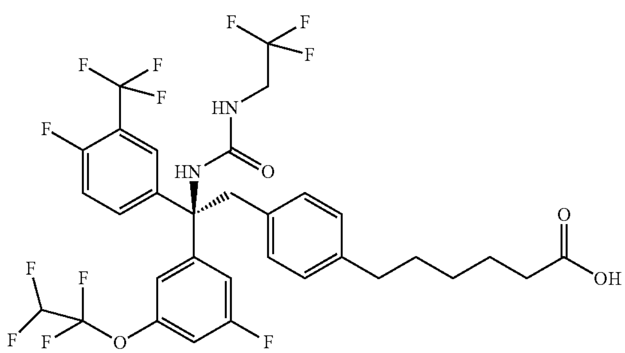 [SMILES: O=C(O)CCCCCc1ccc(C[C@](NC(=O)NCC(F)(F)F)(c2cc(F)cc(OC(F)(F)C(F)F)c2)c2ccc(F)c(C(F)(F)F)c2)cc1] | (R)-6-(4-(2-(4-fluoro-3-(trifluoromethyl)phenyl)-2-(3-fluoro-5-(1,1,2,2-tetrafluoroethoxy)phenyl)-2-(3-(2,2,2-trifluoroethyl)ureido)ethyl)phenyl)hexanoic acid | 4.2 LC (6) 733.5 [M + H]+ | Procedures 3, 4, 72, 96, 97, 98, 25, 24 and 23 |
| 1012 | 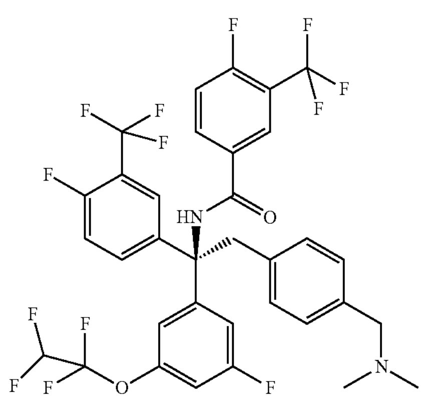 [SMILES: CN(C)Cc1ccc(C[C@](NC(=O)c2ccc(F)c(C(F)(F)F)c2)(c2cc(F)cc(OC(F)(F)C(F)F)c2)c2ccc(F)c(C(F)(F)F)c2)cc1] | (R)-N-(2-(4-((dimethylamino)methyl)phenyl)-1-(4-fluoro-3-(trifluoromethyl)phenyl)-1-(3-fluoro-5-(1,1,2,2-tetrafluoroethoxy)phenyl)ethyl)-4-fluoro-3-(trifluoromethyl)benzamide | 3.45 LC (6) 741.5 [M + H]$^+$ | Procedures 3, 4, 72, 96, 97, 98, 7, 56, 57, 100 and 102 |

TABLE 19-continued

| Ex. No. | Structure | Name | Retention Time Min./ Molecular Mass | Prepared in the manner described in: |
|---|---|---|---|---|
| 1013 | 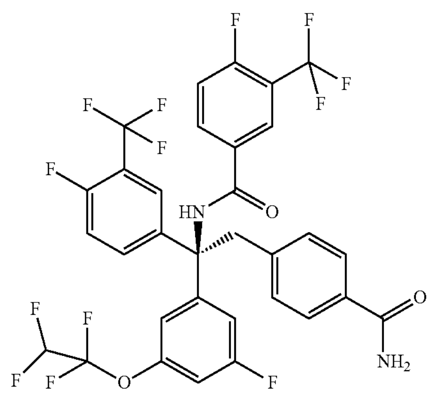 [SMILES: NC(=O)c1ccc(C[C@](NC(=O)c2ccc(F)c(C(F)(F)F)c2)(c2cc(F)cc(OC(F)(F)C(F)F)c2)c2ccc(F)c(C(F)(F)F)c2)cc1] | (R)-N-(2-(4-carbamoylphenyl)-1-(4-fluoro-3-(trifluoromethyl)phenyl)-1-(3-fluoro-5-(1,1,2,2-tetrafluoroethoxy)phenyl)ethyl)-4-fluoro-3-(trifluoromethyl)benzamide | 3.97 LC (6) 727.41 [M + H]$^+$ | Procedures 3, 4, 72, 96, 97, 98, 7, 56, 57, 23 and 103 |
| 1014 | 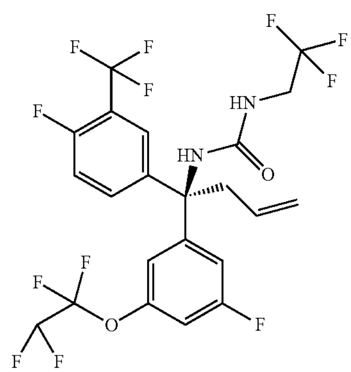 [SMILES: C=CC[C@](NC(=O)NCC(F)(F)F)(c1cc(F)cc(OC(F)(F)C(F)F)c1)c1ccc(F)c(C(F)(F)F)c1] | (R)-1-(1-(4-fluoro-3-(trifluoromethyl)phenyl)-1-(3-fluoro-5-(1,1,2,2-tetrafluoroethoxy)phenyl)but-3-enyl)-3-(2,2,2-trifluoroethyl)urea | 568.355 | Procedures 3, 4, 5, 6 and 10 |
| 1015 | 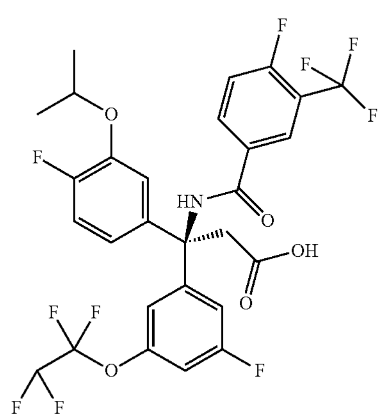 [SMILES: CC(C)Oc1cc([C@@](CC(=O)O)(NC(=O)c2ccc(F)c(C(F)(F)F)c2)c2cc(F)cc(OC(F)(F)C(F)F)c2)ccc1F] | (R)-3-(4-fluoro-3-(trifluoromethyl)benzamido)-3-(4-fluoro-3-isopropoxyphenyl)-3-(3-fluoro-5-(1,1,2,2-tetrafluoroethoxy)phenyl)propanoic acid | 641.454 | Procedures 3, 4, 5, 14, 6, 7, 59, 68 and 23 |

TABLE 19-continued

| Ex. No. | Structure | Name | Retention Time Min./ Molecular Mass | Prepared in the manner described in: |
|---|---|---|---|---|
| 1016 | 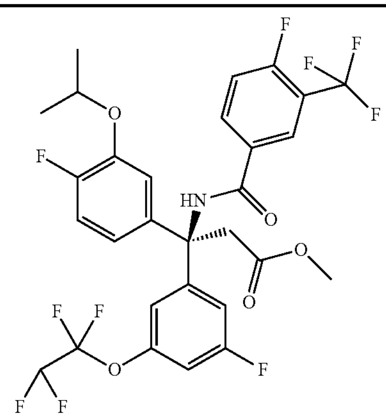 | (R)-methyl 3-(4-fluoro-3-(trifluoromethyl)benzamido)-3-(4-fluoro-3-isopropoxyphenyl)-3-(3-fluoro-5-(1,1,2,2-tetrafluoroethoxy)phenyl)propanoate | 655.481 | Procedures 3, 4, 5, 14, 6, 7, 59 and 68 |
| 1017 | 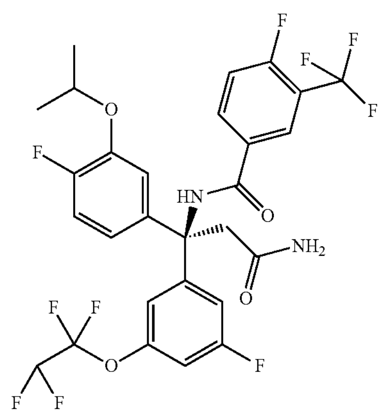 [SMILES: CC(C)Oc1cc([C@@](CC(N)=O)(NC(=O)c2ccc(F)c(C(F)(F)F)c2)c2cc(F)cc(OC(F)(F)C(F)F)c2)ccc1F] | (R)-N-(3-amino-1-(4-fluoro-3-isopropoxyphenyl)-1-(3-fluoro-5-(1,1,2,2-tetrafluoroethoxy)phenyl)-3-oxopropyl)-4-fluoro-3-(trifluoromethyl)benzamide | 2.0 LC (2) 641.2 $[M + H]^+$ | Procedures 3, 4, 5, 14, 6, 7, 59, 68, 23 and 103 |
| 1018 | 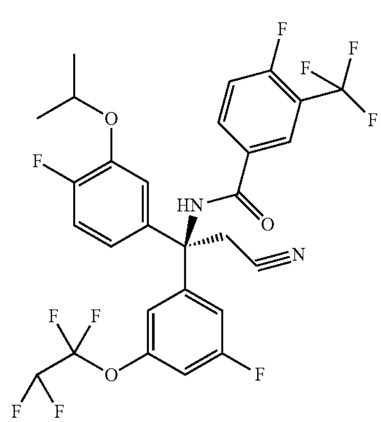 [SMILES: CC(C)Oc1cc([C@@](CC#N)(NC(=O)c2ccc(F)c(C(F)(F)F)c2)c2cc(F)cc(OC(F)(F)C(F)F)c2)ccc1F] | (R)-N-(2-cyano-1-(4-fluoro-3-isopropoxyphenyl)-1-(3-fluoro-5-(1,1,2,2-tetrafluoroethoxy)phenyl)ethyl)-4-fluoro-3-(trifluoromethyl)benzamide | 2.0 LC (2) 623.5 $[M + H]^+$ | Procedures 3, 4, 5, 18, 6, 7, 59 and 68 |

TABLE 19-continued

| Ex. No. | Structure | Name | Retention Time Min./ Molecular Mass | Prepared in the manner described in: |
|---|---|---|---|---|
| 1019 | 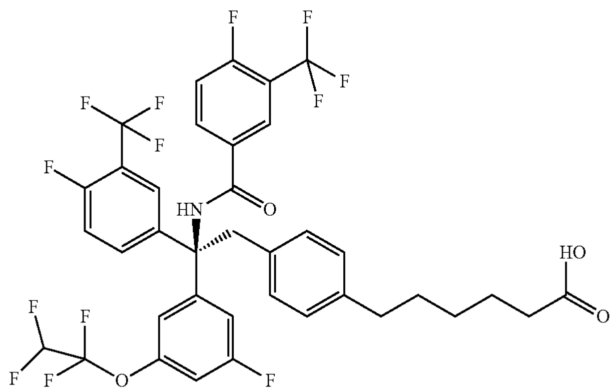 [SMILES: O=C(O)CCCCCc1ccc(C[C@](NC(=O)c2ccc(F)c(C(F)(F)F)c2)(c2cc(F)cc(OC(F)(F)C(F)F)c2)c2ccc(F)c(C(F)(F)F)c2)cc1] | (R)-6-(4-(2-(4-fluoro-3-(trifluoromethyl)benzamido)-2-(4-fluoro-3-(trifluoromethyl)phenyl)-2-(3-fluoro-5-(1,1,2,2-tetrafluoroethoxy)phenyl)ethyl)phenyl)hexanoic acid | 4.3 LC (6) 798.4 [M + H]+ | Procedures 3, 4, 96, 97, 98, 24 and 23 |
| 1020 | 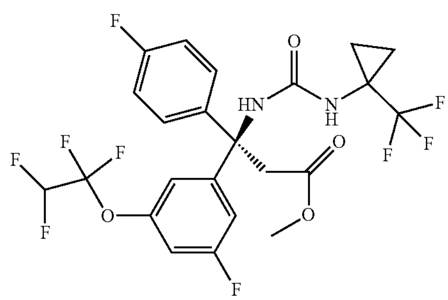 [SMILES: COC(=O)C[C@@](NC(=O)NC1(C(F)(F)F)CC1)(c1ccc(F)cc1)c1cc(F)cc(OC(F)(F)C(F)F)c1] | (R)-methyl 3-(3-fluoro-5-(1,1,2,2-tetrafluoroethoxy)phenyl)-3-(4-fluorophenyl)-3-(3-(1-(trifluoromethyl)cyclopropyl)ureido)propanoate | 1.94 LC (2) 559.4 [M + H]+ | Procedures 3, 4, 5, 14, 6 and 30 |
| 1021 | 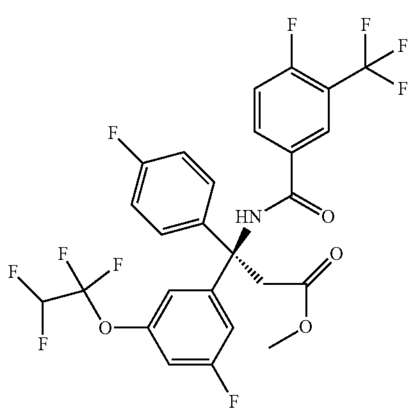 [SMILES: COC(=O)C[C@@](NC(=O)c1ccc(F)c(C(F)(F)F)c1)(c1ccc(F)cc1)c1cc(F)cc(OC(F)(F)C(F)F)c1] | (R)-methyl 3-(4-fluoro-3-(trifluoromethyl)benzamido)-3-(3-fluoro-5-(1,1,2,2-tetrafluoroethoxy)phenyl)-3-(4-fluorophenyl)propanoate | 3.95 LC (1) 598.2 [M + H]+ | Procedures 3, 4, 5, 14, 6 and 7 |
| 1022 | 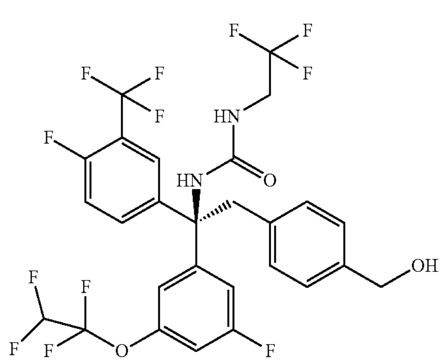 [SMILES: O=C(NCC(F)(F)F)N[C@@](Cc1ccc(CO)cc1)(c1cc(F)cc(OC(F)(F)C(F)F)c1)c1ccc(F)c(C(F)(F)F)c1] | (R)-1-(1-(4-fluoro-3-(trifluoromethyl)phenyl)-1-(3-fluoro-5-(1,1,2,2-tetrafluoroethoxy)phenyl)-2-(4-(hydroxymethyl)phenyl)ethyl)-3-(2,2,2-trifluoroethyl)urea | 3.8 LC (6) 649.3 [M + H]+ | Procedures 3, 4, 96, 97, 98, 56, and 100 |

TABLE 19-continued

| Ex. No. | Structure | Name | Retention Time Min./ Molecular Mass | Prepared in the manner described in: |
|---|---|---|---|---|
| 1023 | 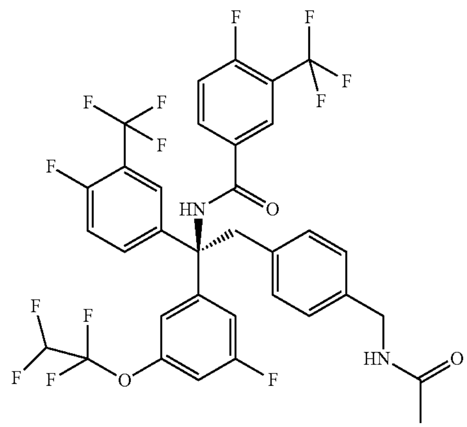 [SMILES: CC(=O)NCc1ccc(C[C@](NC(=O)c2ccc(F)c(C(F)(F)F)c2)(c2cc(F)cc(OC(F)(F)C(F)F)c2)c2ccc(F)c(C(F)(F)F)c2)cc1] | (R)-N-(2-(4-(acetamidomethyl)phenyl)-1-(4-fluoro-3-(trifluoromethyl)phenyl)-1-(3-fluoro-5-(1,1,2,2-tetrafluoroethoxy)phenyl)ethyl)-4-fluoro-3-(trifluoromethyl)benzamide | 4.0 LC (6) 755.38 [M + H]$^+$ | Procedures 3, 4, 96, 97, 98, 56, 101 and 65 |
| 1024 | 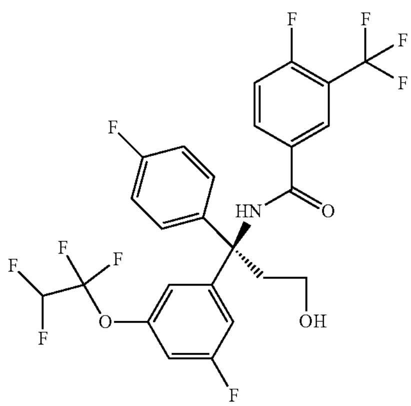 [SMILES: O=C(N[C@](CCO)(c1ccc(F)cc1)c1cc(F)cc(OC(F)(F)C(F)F)c1)c1ccc(F)c(C(F)(F)F)c1] | (R)-4-fluoro-N-(1-(3-fluoro-5-(1,1,2,2-tetrafluoroethoxy)phenyl)-1-(4-fluorophenyl)-3-hydroxypropyl)-3-(trifluoromethyl)benzamide | 2.05 LC (2) 570.5 [M + H]$^+$ | Procedures 3, 4, 5, 14, 6, 7 and 100 |
| 1025 | 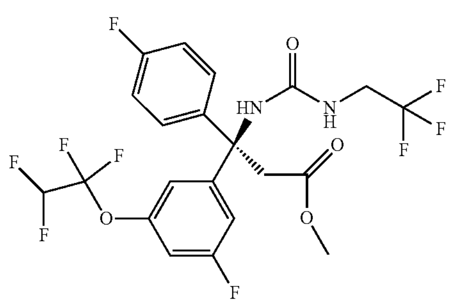 [SMILES: COC(=O)C[C@@](NC(=O)NCC(F)(F)F)(c1ccc(F)cc1)c1cc(F)cc(OC(F)(F)C(F)F)c1] | (R)-methyl 3-(3-fluoro-5-(1,1,2,2-tetrafluoroethoxy)phenyl)-3-(4-fluorophenyl)-3-(3-(2,2,2-trifluoroethyl)ureido)propanoate | 3.39 LC (1) 533.2 [M + H]$^+$ | Procedures 3, 4, 5, 14, 6 and 25 |
| 1026 | 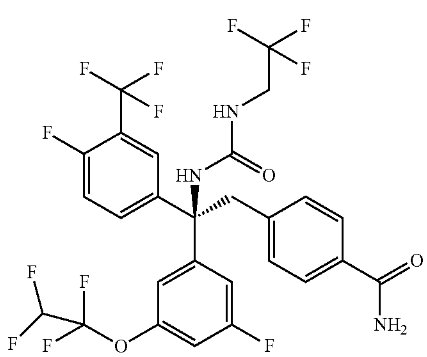 [SMILES: NC(=O)c1ccc(C[C@](NC(=O)NCC(F)(F)F)(c2cc(F)cc(OC(F)(F)C(F)F)c2)c2ccc(F)c(C(F)(F)F)c2)cc1] | (R)-4-(2-(4-fluoro-3-(trifluoromethyl)phenyl)-2-(3-fluoro-5-(1,1,2,2-tetrafluoroethoxy)phenyl)-2-(3-(2,2,2-trifluoroethyl)ureido)ethyl)benzamide | 3.74 LC (6) 662.3 [M + H]$^+$ | Procedures 3, 4, 96, 97, 98, 56, 57, 23 and 103 |

TABLE 19-continued

| Ex. No. | Structure | Name | Retention Time Min./ Molecular Mass | Prepared in the manner described in: |
|---|---|---|---|---|
| 1027 | 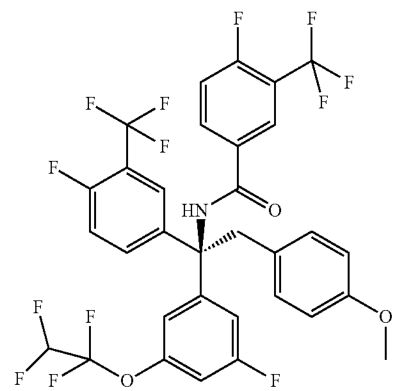 [SMILES: COc1ccc(C[C@](NC(=O)c2ccc(F)c(C(F)(F)F)c2)(c2cc(F)cc(OC(F)(F)C(F)F)c2)c2ccc(F)c(C(F)(F)F)c2)cc1] | (R)-4-fluoro-N-(1-(4-fluoro-3-(trifluoromethyl)phenyl)-1-(3-fluoro-5-(1,1,2,2-tetrafluoroethoxy)phenyl)-2-(4-methoxyphenyl)ethyl)-3-(trifluoromethyl)benzamide | 4.3 LC (6) 714.0 [M + H]⁺ | Procedures 3, 4, 5, 6 and 7 |
| 1028 | 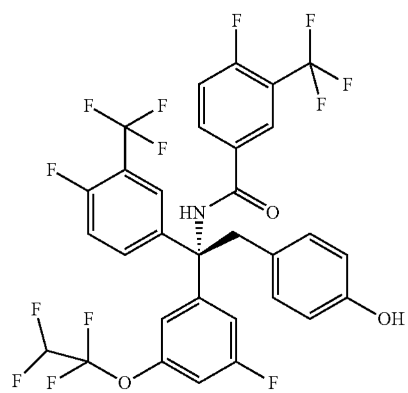 [SMILES: O=C(N[C@](Cc1ccc(O)cc1)(c1cc(F)cc(OC(F)(F)C(F)F)c1)c1ccc(F)c(C(F)(F)F)c1)c1ccc(F)c(C(F)(F)F)c1] | (S)-4-fluoro-N-(1-(4-fluoro-3-(trifluoromethyl)phenyl)-1-(3-fluoro-5-(1,1,2,2-tetrafluoroethoxy)phenyl)-2-(4-hydroxyphenypethyl)-3-(trifluoromethyl)benzamide | 2.2 LC (2) 700.0 [M + H]⁺ | Procedures 3, 4, 59, 68, 172, 173, 174, 175, 176, 7 and 59 |
| 1029 | 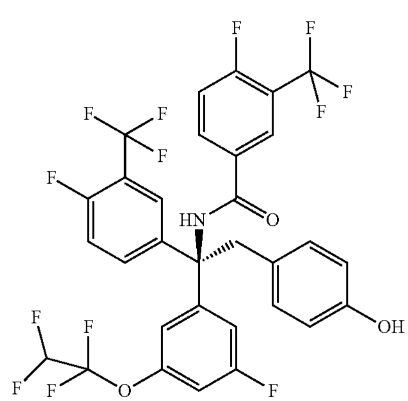 [SMILES: O=C(N[C@@](Cc1ccc(O)cc1)(c1cc(F)cc(OC(F)(F)C(F)F)c1)c1ccc(F)c(C(F)(F)F)c1)c1ccc(F)c(C(F)(F)F)c1] | (R)-4-fluoro-N-(1-(4-fluoro-3-(trifluoromethyl)phenyl)-1-(3-fluoro-5-(1,1,2,2-tetrafluoroethoxy)phenyl)-2-(4-hydroxyphenyl)ethyl)-3-(trifluoromethyl)benzamide | 2.2 LC (2) 700.0 [M + H]⁺ | Procedures 3, 4, 59, 68, 172, 173, 174, 175, 176, 7 and 59 |

TABLE 19-continued

| Ex. No. | Structure | Name | Retention Time Min./ Molecular Mass | Prepared in the manner described in: |
|---|---|---|---|---|
| 1030 | 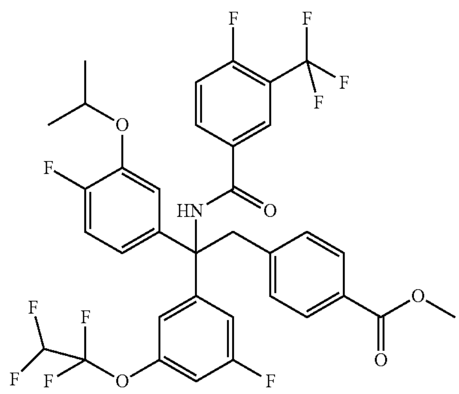 [SMILES: COC(=O)c1ccc(CC(NC(=O)c2ccc(F)c(C(F)(F)F)c2)(c2cc(F)cc(OC(F)(F)C(F)F)c2)c2ccc(F)c(OC(C)C)c2)cc1] | methyl 4-(2-(4-fluoro-3-(trifluoromethyl)benzamido)-2-(4-fluoro-3-isopropoxyphenyl)-2-(3-fluoro-5-(1,1,2,2-tetrafluoroethoxy)phenyl)ethyl)benzoate | 2.3 LC (2) 731.9 $[M + H]^+$ | Procedures 3, 4, 59, 68, 172, 173, 174, 175, 176, 7, 56 and 57 |
| 1031 | 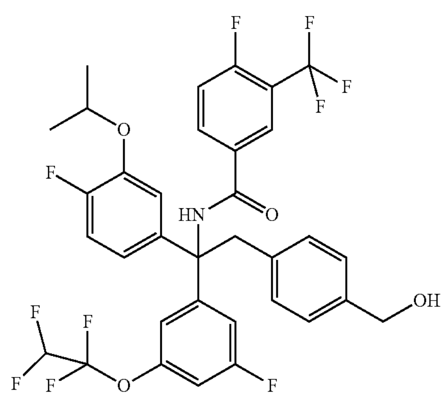 [SMILES: CC(C)Oc1cc(C(Cc2ccc(CO)cc2)(NC(=O)c2ccc(F)c(C(F)(F)F)c2)c2cc(F)cc(OC(F)(F)C(F)F)c2)ccc1F] | 4-fluoro-N-(1-(4-fluoro-3-isopropoxyphenyl)-1-(3-fluoro-5-(1,1,2,2-tetrafluoroethoxy)phenyl)-2-(4-(hydroxymethyl)phenyl)ethyl)-3-(trifluoromethyl)benzamide | 2.17 LC (2) 704.0 $[M + H]^+$ | Procedures 3, 4, 59, 68, 172, 173, 174, 175, 176, 7, 56, 57 and 100 |
| 1032 | 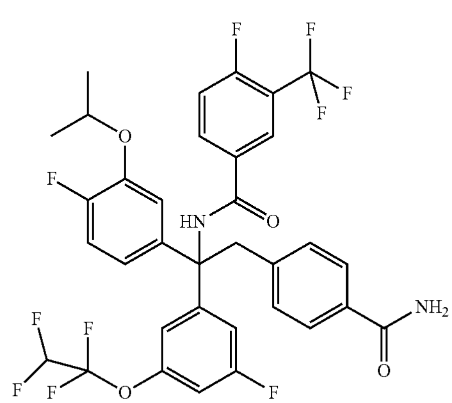 [SMILES: CC(C)Oc1cc(C(Cc2ccc(C(N)=O)cc2)(NC(=O)c2ccc(F)c(C(F)(F)F)c2)c2cc(F)cc(OC(F)(F)C(F)F)c2)ccc1F] | N-(2-(4-carbamoylphenyl)-1-(4-fluoro-3-isopropoxyphenyl)-1-(3-fluoro-5-(1,1,2,2-tetrafluoroethoxy)phenyl)ethyl)-4-fluoro-3-(trifluoromethyl)benzamide | 2.13 LC (2) 716.9 $[M + H]^+$ | Procedures 3, 4, 59, 68, 172, 173, 174, 175, 176, 7, 56, 57, 23 and 103 |

TABLE 19-continued

| Ex. No. | Structure | Name | Retention Time Min./ Molecular Mass | Prepared in the manner described in: |
|---|---|---|---|---|
| 1033 | 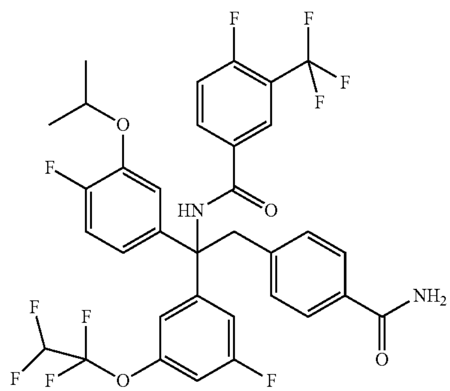 [SMILES: CC(C)Oc1cc(C(Cc2ccc(C(N)=O)cc2)(NC(=O)c2ccc(F)c(C(F)(F)F)c2)c2cc(F)cc(OC(F)(F)C(F)F)c2)ccc1F] | N-(2-(4-carbamoylphenyl)-1-(4-fluoro-3-isopropoxyphenyl)-1-(3-fluoro-5-(1,1,2,2-tetrafluoroethoxy)phenyl)ethyl)-4-fluoro-3-(trifluoromethyl)benzamide | 2.13 LC (2) 716.9 [M + H]$^+$ | Procedures 3, 4, 59, 68, 172, 173, 174, 175, 176, 7, 56, 57, 23 and 103 |
| 1034 | 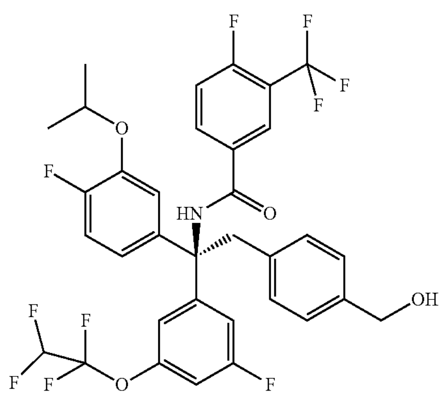 [SMILES: CC(C)Oc1cc([C@@](Cc2ccc(CO)cc2)(NC(=O)c2ccc(F)c(C(F)(F)F)c2)c2cc(F)cc(OC(F)(F)C(F)F)c2)ccc1F] | (R)-4-fluoro-N-(1-(4-fluoro-3-isopropoxyphenyl)-1-(3-fluoro-5-(1,1,2,2-tetrafluoroethoxy)phenyl)-2-(4-(hydroxymethyl)phenyl)ethyl)-3-(trifluoromethyl)benzamide | 2.17 LC (2) 704.1 [M + H]$^+$ | Procedures 3, 4, 59, 68, 172, 173, 174, 175, 176, 7, 56, 57 and 100 |
| 1035 | 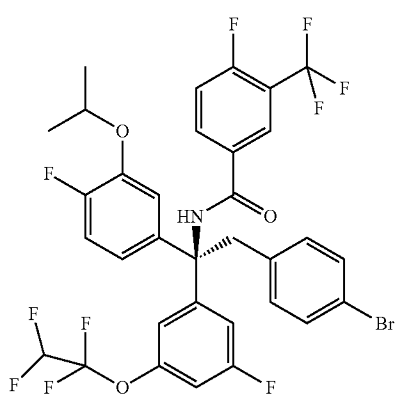 [SMILES: CC(C)Oc1cc([C@@](Cc2ccc(Br)cc2)(NC(=O)c2ccc(F)c(C(F)(F)F)c2)c2cc(F)cc(OC(F)(F)C(F)F)c2)ccc1F] | (R)-N-(2-(4-bromophenyl)-1-(4-fluoro-3-isopropoxyphenyl)-1-(3-fluoro-5-(1,1,2,2-tetrafluoroethoxy)phenyl)ethyl)-4-fluoro-3-(trifluoromethyl)benzamide | 2.17 LC (2) 753.8 [M + H]$^+$ | Procedures 3, 4, 59, 68, 172, 173, 174, 175, 176 and 7 |

TABLE 19-continued

| Ex. No. | Structure | Name | Retention Time Min./ Molecular Mass | Prepared in the manner described in: |
|---|---|---|---|---|
| 1036 | 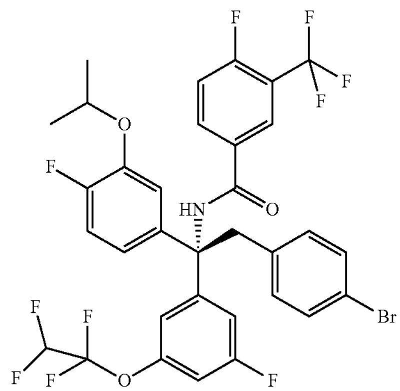 [SMILES: CC(C)Oc1cc([C@](Cc2ccc(Br)cc2)(NC(=O)c2ccc(F)c(C(F)(F)F)c2)c2cc(F)cc(OC(F)(F)C(F)F)c2)ccc1F] | (S)-N-(2-(4-bromophenyl)-1-(4-fluoro-3-isopropoxyphenyl)-1-(3-fluoro-5-(1,1,2,2-tetrafluoroethoxy)phenyl)ethyl)-4-fluoro-3-(trifluoromethyl)benzamide | 2.17 LC (2) 753.8 [M + H]⁺ | Procedures 3, 4, 59, 68, 172, 173, 174, 175, 176 and 7 |
| 1037 | 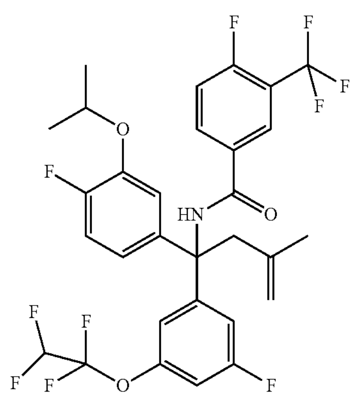 [SMILES: C=C(C)CC(NC(=O)c1ccc(F)c(C(F)(F)F)c1)(c1cc(F)cc(OC(F)(F)C(F)F)c1)c1ccc(F)c(OC(C)C)c1] | 4-fluoro-N-(1-(4-fluoro-3-isopropoxyphenyl)-1-(3-fluoro-5-(1,1,2,2-tetrafluoroethoxy)phenyl)-3-methylbut-3-enyl)-3-(trifluoromethyl)benzamide | 2.19 LC (2) 638.9 [M + H]⁺ | Procedures 3, 4, 59, 68, 172, 173, 174, 175, 176 and 7 |
| 1038 | 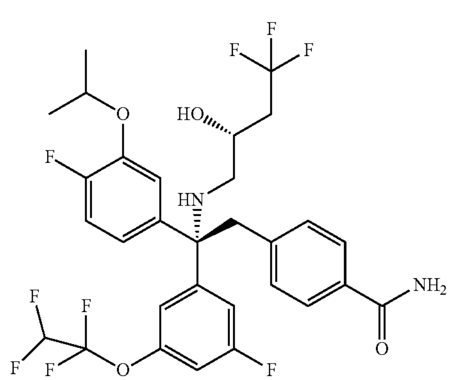 [SMILES: CC(C)Oc1cc([C@](Cc2ccc(C(N)=O)cc2)(NC[C@H](O)CC(F)(F)F)c2cc(F)cc(OC(F)(F)C(F)F)c2)ccc1F] | 4-((S)-2-(4-fluoro-3-isopropoxyphenyl)-2-(3-fluoro-5-(1,1,2,2-tetrafluoroethoxy)phenyl)-2-((R)-4,4,4-trifluoro-2-hydroxybutylamino)ethyl)benzamide | 1.93 LC (2) 653.0 [M + H]⁺ | Procedures 3, 4, 59, 68, 172, 173, 174, 175, 176, 56, 57, 23, 136, 27 and 8 |

TABLE 19-continued

| Ex. No. | Structure | Name | Retention Time Min./ Molecular Mass | Prepared in the manner described in: |
|---|---|---|---|---|
| 1039 | 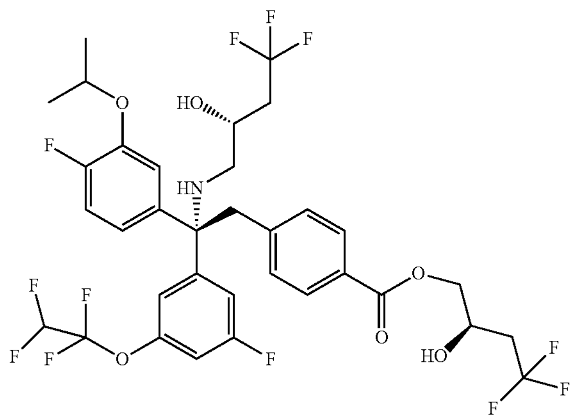 [SMILES: CC(C)Oc1cc([C@](Cc2ccc(C(=O)OC[C@H](O)CC(F)(F)F)cc2)(NC[C@H](O)CC(F)(F)F)c2cc(F)cc(OC(F)(F)C(F)F)c2)ccc1F] | (R)-4,4,4-trifluoro-2-hydroxybutyl 4-((S)-2-(4-fluoro-3-isopropoxyphenyl)-2-(3-fluoro-5-(1,1,2,2-tetrafluoroethoxy)phenyl)-2-((R)-4,4,4-trifluoro-2-hydroxybutylamino)ethyl)benzoate | 2.08 LC (2) 780.0 [M + H]$^+$ | Procedures 3, 4, 59, 68, 172, 173, 174, 175, 176, 56, 57, 23, 136, 27 and 8 |
| 1040 | 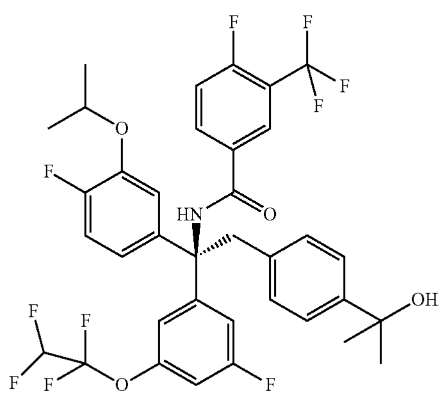 [SMILES: CC(C)Oc1cc([C@@](Cc2ccc(C(C)(C)O)cc2)(NC(=O)c2ccc(F)c(C(F)(F)F)c2)c2cc(F)cc(OC(F)(F)C(F)F)c2)ccc1F] | (R)-4-fluoro-N-(1-(4-fluoro-3-isopropoxyphenyl)-1-(3-fluoro-5-(1,1,2,2-tetrafluoroethoxy)phenyl)-2-(4-(2-hydroxypropan-2-yl)phenyl)ethyl)-3-(trifluoromethyl)benzamide | 2.2 LC (2) 714.0 [M + H]$^+$ | Procedures 3, 4, 59, 68, 172, 173, 174, 175, 176, 7, 56, 52 and 53 |
| 1041 | 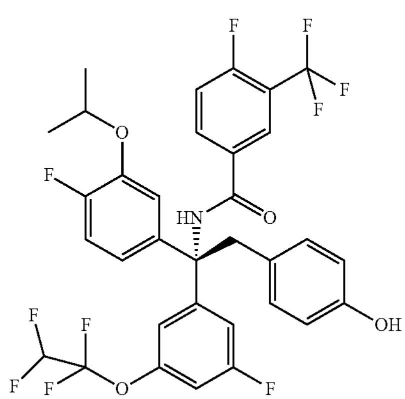 [SMILES: CC(C)Oc1cc([C@](Cc2ccc(O)cc2)(NC(=O)c2ccc(F)c(C(F)(F)F)c2)c2cc(F)cc(OC(F)(F)C(F)F)c2)ccc1F] | (S)-4-fluoro-N-(1-(4-fluoro-3-isopropoxyphenyl)-1-(3-fluoro-5-(1,1,2,2-tetrafluoroethoxy)phenyl)-2-(4-hydroxyphenyethyl)-3-(trifluoromethyl)benzamide | 2.15 LC (2) 689.9 [M + H]$^+$ | Procedures 3, 4, 59, 68, 172, 173, 174, 175, 176, 7 and 59 |

TABLE 19-continued

| Ex. No. | Structure | Name | Retention Time Min./ Molecular Mass | Prepared in the manner described in: |
|---|---|---|---|---|
| 1042 | 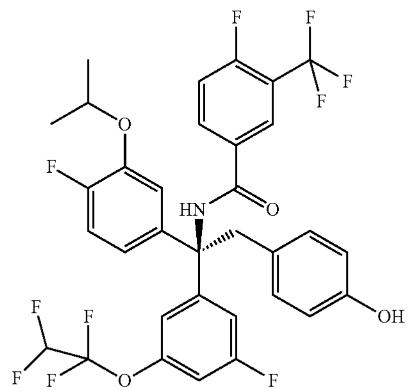 [SMILES: CC(C)Oc1cc([C@@](Cc2ccc(O)cc2)(NC(=O)c2ccc(F)c(C(F)(F)F)c2)c2cc(F)cc(OC(F)(F)C(F)F)c2)ccc1F] | (R)-4-fluoro-N-(1-(4-fluoro-3-isopropoxyphenyl)-1-(3-fluoro-5-(1,1,2,2-tetrafluoroethoxy)phenyl)-2-(4-hydroxyphenyl)ethyl)-3-(trifluoromethyl)benzamide | 2.15 LC (2) 689.9 $[M + H]^+$ | Procedures 3, 4, 59, 68, 172, 173, 174, 175, 176, 7 and 59 |

TABLE 20

| Ex. No. | Structure | Name | Retention Time Min./ Molecular Mass | Prepared in the manner described in: |
|---|---|---|---|---|
| 1043 | 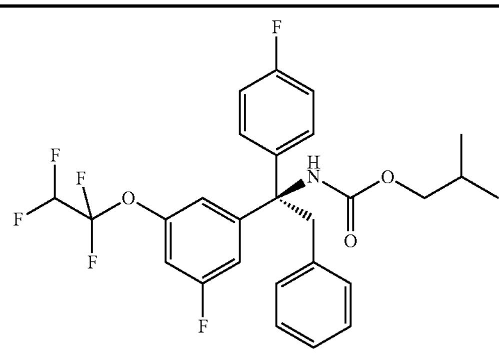 | (R)-isobutyl 1-(3-fluoro-5-(1,1,2,2-tetrafluoroethoxy)phenyl)-1-(4-fluorophenyl)-2-phenylethylcarbamate | 2.165 LC (2) 526.02 $[M + H]^+$ | Procedures 3, 4, 5, 6 and 82 |

TABLE 21

| Ex. No. | Structure | Name | Retention Time Min./ Molecular Mass | Prepared in the manner described in: |
|---|---|---|---|---|
| 1044 | 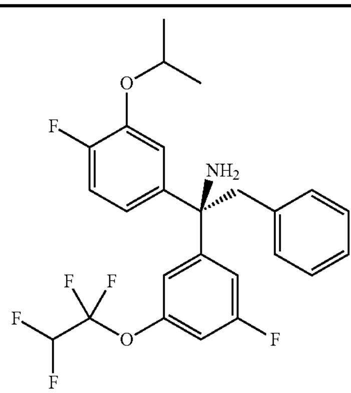 | (R)-1-(4-fluoro-3-isopropoxyphenyl)-1-(3-fluoro-5-(1,1,2,2-tetrafluoroethoxy)phenyl)-2-phenylethanamine | 1.89 LC (2) 467.46 $[M - NH_2]$ | Procedure 109, 110, 111, 112, 113 and 114 |

TABLE 21-continued

| Ex. No. | Structure | Name | Retention Time Min./ Molecular Mass | Prepared in the manner described in: |
|---|---|---|---|---|
| 1045 | 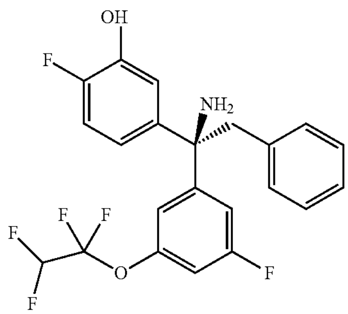 [SMILES: N[C@@](Cc1ccccc1)(c1cc(F)cc(OC(F)(F)C(F)F)c1)c1ccc(F)c(O)c1] | (R)-5-(1-amino-1-(3-fluoro-5-(1,1,2,2-tetrafluoroethoxy) phenyl)-2-phenylethyl)-2-fluorophenol | 1.70 LC (2) 425.1 [M − $NH_2$] | Procedure 109, 110, 111, 112, 113 and 114 |
| 1046 | 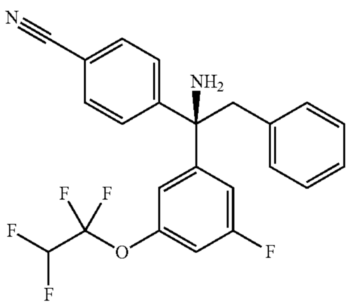 [SMILES: N#Cc1ccc([C@](N)(Cc2ccccc2)c2cc(F)cc(OC(F)(F)C(F)F)c2)cc1] | (R)-4-(1-amino-1-(3-fluoro-5-(1,1,2,2-tetrafluoroethoxy) phenyl)-2-phenylethyl)benzonitrile | 1.02 LC (12) 433 [M + H]$^+$ | Procedures 3, 4, 5, 6, and 56 |
| 1047 | 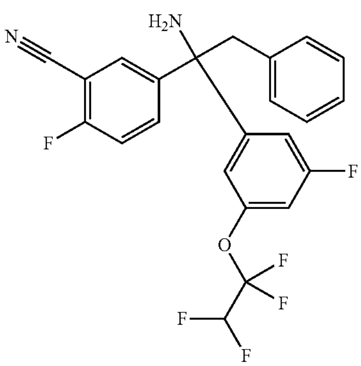 [SMILES: N#Cc1cc(C(N)(Cc2ccccc2)c2cc(F)cc(OC(F)(F)C(F)F)c2)ccc1F] | 5-(1-amino-1-(3-fluoro-5-(1,1,2,2-tetrafluoroethoxy) phenyl)-2-phenylethyl)-2-fluorobenzonitrile | 3.281 LC (11) 451 [M + H]$^+$ | Procedures 3, 62, 5, 6 and 56 |

It is noted that the proceeding examples, while illustrative of the present invention, are not in sequential order and some example numbers may be missing.

What is claimed is:

1. A compound of formula Ia or Ib

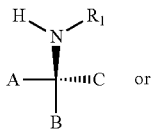

Ia

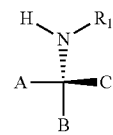

Ib or stereoisomers or pharmaceutically acceptable salt forms thereof, wherein:

A is phenyl, which is substituted with one or more substituents selected from the group consisting of: 1) halo, and 2) —$OR_6$;

B is
phenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) —$S(O)_pR_6$, 17) —$SO_2NHR_6$, 18) —$COOR_6$, 19) —$NHC(CN)NHR_6$, 20) —$CONR_6R_6$; and 21) cycloalkyl, which may be optionally substituted with one or more $R_{20}$'s;

C is:
- (a) alkyl, which may be optionally substituted with one or more substituents selected from aryl, which may be optionally substituted with one or more $R_{20}$'s; or
- (b) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl; and 15) cycloalkyl, which may be optionally substituted with one or more $R_{20}$'s;

$R_1$ is —$C(O)NR_2R_3$;

$R_2$ is:
- (a) H;
- (b) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) ($C_2$-$C_6$)-alkenyl, 15) ($C_2$-$C_6$)-alkynyl, 16) —$S(O)_pR_6$, 17) —$SO_2NHR_6$, 18) —$COOR_6$, 19) —$NHC(CN)NHR_6$; and 20) cycloalkyl, which may be optionally substituted with one or more $R_{20}$'s;
- (c) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ($C_2$-$C_6$)-alkynyl, 18) —$COR_6$, 19) —$S(O)_pR_6$, 20) —$SO_2NHR_6$, 21) —$COOR_6$, 22) —$NHC(CN)NHR_6$; and 23) cycloalkyl, which may be optionally substituted with one or more $R_{20}$'s; or
- (d) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CO(C_1$-$C_6$)-alkyl, 16) —COOH, 17) —$CO_2(C_1$-$C_6$)-alkyl, 18) —$CONR_6R_6$, 19) ($C_2$-$C_6$)-alkenyl, 20) ($C_2$-$C_6$)-alkynyl; and 21) cycloalkyl, which may be optionally substituted with one or more $R_{20}$'s;

$R_3$ is:
- (a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$CONR_6R_6$, 13) ($C_2$-$C_6$)-alkenyl, 14) ($C_2$-$C_6$)-alkynyl, 15) —$COR_6$, 16) —$S(O)_pR_6$, 17) —$SO_2NHR_6$, 18) —$COOR_6$, 19) —$NHC(CN)NHR_6$; and 20) cycloalkyl, which may be optionally substituted with one or more $R_{20}$'s;
- (b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, 23) —$NHC(CN)NHR_6$; and 24) cycloalkyl, which may be optionally substituted with one or more $R_{20}$'s;
- (c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12)

heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CONR$_6$R$_6$, 16) ($C_2$-$C_6$)-alkenyl, 17) =O, 18) ($C_2$-$C_6$)-alkynyl, 19) —COR$_6$, 20) —S(O)$_p$R$_6$, 21) —SO$_2$NHR$_6$, 22) —COOR$_6$, 23) —NHC(CN)NHR$_6$; and 24) cycloalkyl, which may be optionally substituted with one or more $R_{20}$'s;

(d) heteroaryl, which may be optionally substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CONR$_6$R$_6$, 16) ($C_2$-$C_6$)-alkenyl, 17) =O, 18) ($C_2$-$C_6$)-alkynyl, 19) —COR$_6$, 20) —S(O)$_p$R$_6$, 21) —SO$_2$NHR$_6$, 22) —COOR$_6$, 23) —NHC(CN)NHR$_6$; and 24) cycloalkyl, which may be optionally substituted with one or more $R_{20}$'s;

(e) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CONR$_6$R$_6$, 16) ($C_2$-$C_6$)-alkenyl, 17) =O, 18) ($C_2$-$C_6$)-alkynyl, 19) —COR$_6$, 20) —S(O)$_p$R$_6$, 21) —SO$_2$NHR$_6$, 22) —COOR$_6$, 23) —NHC(CN)NHR$_6$; and 24) cycloalkyl, which may be optionally substituted with one or more $R_{20}$'s; or (f) alkenyl, which may be optionally substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CONR$_6$R$_6$, 16) ($C_2$-$C_6$)-alkenyl, 17) (C2-C6)-alkynyl, 18) —COR$_6$, 19) —S(O)$_p$R$_6$, 20) —SO$_2$NHR$_6$, 21) —COOR$_6$, 22) —NHC(CN)NHR$_6$; and 23) cycloalkyl, which may be optionally substituted with one or more $R_{20}$'s;

$R_6$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —CONR$_{36}$R$_{36}$, 16) =O, 17) ($C_2$-$C_6$)-alkynyl, 18) —COR$_{36}$, 19) —S(O)$_p$R$_{36}$, 20) —SO$_2$NHR$_{36}$, 21) —COOR$_{36}$, 22) —NHC(CN)NHR$_{36}$, or 23) cycloalkyl, which may be optionally substituted with one or more $R_{20}$'s;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —CONR$_{36}$R$_{36}$, 18) =O, 19) ($C_2$-$C_6$)-alkynyl, 20) —COR$_{36}$, 21) —S(O)$_p$R$_{36}$, 22) —SO$_2$NHR$_{36}$, 23) —COOR$_{36}$, 24) —NHC(CN)NHR$_{36}$; and 25) cycloalkyl, which may be optionally substituted with one or more $R_{20}$'s;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, 25) —NHC(CN)NHR$_{36}$; and 26) cycloalkyl, which may be optionally substituted with one or more $R_{20}$'s;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, 25) —NHC(CN)NHR$_{36}$; and 26) cycloalkyl, which may be optionally substituted with one or more $R_{20}$'s;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —CONR$_{36}$R$_{36}$, 19) =O, 20) (C2-C6)-alkynyl, 21) —COR$_{36}$, 22) —S(O)$_p$R$_{36}$, 23) —SO$_2$NHR$_{36}$, 24) —COOR$_{36}$, 25) —NHC(CN)NHR$_{36}$; and 26) cycloalkyl, which may be optionally substituted with one or more $R_{20}$'s;

(f) hydrogen; or (g) alkynyl, which may be optionally substituted with one or more substituents selected from the group consisting of: 1) halo, 2) —OH, or 3) ($C_1$-$C_6$)-alkyl, which may be optionally substituted with one or more $R_{20}$'s;

$R_9$ and $R_{10}$ are independently: (a) hydrogen; (b) —[(C=O)O$_r$]$_s$aryl, wherein the aryl may be optionally substituted with one or more $R_{20}$'s; (c) —[(C=O)O$_r$]$_s$($C_2$-$C_8$)-alkenyl, wherein the alkenyl may be optionally substituted with one or more $R_{20}$'s; (d) —[(C=O)O$_r$]$_s$($C_1$-$C_8$) alkyl, wherein the alkyl may be optionally substituted with one or more $R_{20}$'s; (e) heterocyclyl optionally substituted with one or more $R_{20}$'s; (f) —CONR$_{26}$R$_{26}$; (g) —($C_2$-$C_6$)-alkynyl; (h) —COR$_{26}$; (i) —S(O)$_p$R$_{26}$; (j) —SO$_2$NHR$_{26}$; (k) —COOR$_{26}$; (l) —NHC(CN)NHR$_{26}$; or m) —[(C=O)O$_r$]$_s$cycloalkyl, which may be optionally substituted with one or more $R_{20}$'s;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is: (a) halo; (b) ($C_1$-$C_6$)-alkyl, which may be optionally substituted with one or more $R_{21}$'s; (c) —OR$_{26}$; (d) ($C_1$-$C_6$)-alkylthio; (e) cyano; (f) nitro; (g) —NR$_{29}$R$_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) =O; (q) —($C_2$-$C_6$)-alkynyl; (r) —COR$_{26}$; (s) —S(O)$_p$R$_{26}$; (t) —SO$_2$NHR$_{26}$; (u) —COOR$_{26}$; (v) —NHC(CN)NHR$_{26}$; (w) cycloalkyl, which may be optionally substituted with one or more $R_{21}$'s; (x) cycloalkylalkyl, which may be optionally substituted with one or more $R_{21}$'s; or (y) —CONR$_{26}$R$_{26}$;

$R_{21}$ is: (a) halo; (b) ($C_1$-$C_6$)-alkyl; (c) —OR$_{26}$; (d) ($C_1$-$C_6$)-alkylthio; (e) cyano; (f) nitro; (g) —NR$_{29}$R$_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —CONR$_{26}$R$_{26}$; (p) ($C_2$-$C_6$)-alkenyl; (q) =O; (r) ($C_2$-$C_6$)-alkynyl; (s) cycloalkyl; (t) cycloalkylalkyl; (u) —COR$_{26}$; (v) —S(O)$_p$R$_{26}$; (w) —SO$_2$NHR$_{26}$; (x) —COOR$_{26}$; or (y) —NHC(CN)NHR$_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{10}$'s, 12) halo($C_1$-$C_6$)alkyl, 13) ($C_2$-$C_6$)-alkenyl, 14) —COOH, 15) —CONR$_{36}$R$_{36}$, 16) =O, 17) ($C_2$-$C_6$)-alkynyl, 18) —COR$_{36}$, 19) —S(O)$_p$R$_{36}$, 20) —SO$_2$NHR$_{36}$, 21) —COOR$_{36}$, 22) —NHC(CN)NHR$_{36}$; and 23) cycloalkyl, which may be optionally substituted with one or more $R_{40}$'s;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —CONR$_{36}$R$_{36}$, 18) =O, 19) ($C_2$-$C_6$)-alkynyl, 20) —COR$_{36}$, 21) —S(O)$_p$R$_{36}$, 22) —SO$_2$NHR$_{36}$, 23) —COOR$_{36}$, 24) —NHC(CN)NHR$_{36}$; and 25) cycloalkyl, which may be optionally substituted with one or more $R_{40}$'s;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, 25) —NHC(CN)NHR$_{36}$; and 26) cycloalkyl, which may be optionally substituted with one or more $R_{40}$'s;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —S(O)$_p$$R_{36}$, 23) —$SO_2NHR_{36}$, 24) —$COOR_{36}$, 25) —NHC(CN)$NHR_{36}$; and 26) cycloalkyl, which may be optionally substituted with one or more $R_{40}$'s;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —S(O)$_p$$R_{36}$, 23) —$SO_2NHR_{36}$, 24) —$COOR_{36}$, 25) —NHC(CN)$NHR_{36}$; and 26) cycloalkyl, which may be optionally substituted with one or more $R_{40}$'s;

(f) hydrogen;

(g) alkynyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —S(O)$_p$$R_{36}$, 20) —$SO_2NHR_{36}$, 21) —$COOR_{36}$, 22) —NHC(CN)$NHR_{36}$, or 23) cycloalkyl, which may be optionally substituted with one or more $R_{20}$'s; or (h) alkenyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —S(O)$_p$$R_{36}$, 20) —$SO_2NHR_{36}$, 21) —$COOR_{36}$, 22) —NHC(CN)$NHR_{36}$, or 23) cycloalkyl, which may be optionally substituted with one or more $R_{40}$'s;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —[(C=O)O$_r$]$_s$aryl, —[(C=O)O$_r$]$_s$alkenyl, —[(C=O)O$_r$]$_s$alkyl, heterocyclyl, alkynyl, —$COR_{36}$, —S(O)$_p$$R_{36}$, —$SO_2NHR_{36}$, —$COOR_{36}$, —C(CN)$NHR_{36}$, or cycloalkyl, wherein the aryl, alkyl, alkenyl, cycloalkyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, =O, alkynyl, cycloalkyl, cycloalkylalkyl, —$COR_{49}$, —S(O)$_p$$R_{49}$, —$SO_2NHR_{49}$, —$COOR_{49}$, or —NHC(CN)$NHR_{49}$;

$R_{49}$ and $R_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2;

excluding compounds having the following formula:

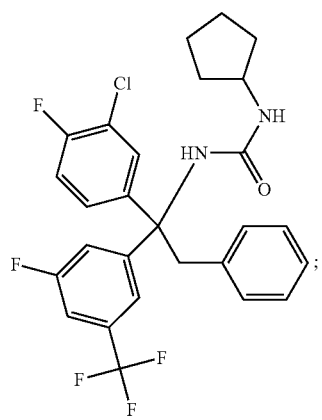

1049
-continued
1050
-continued
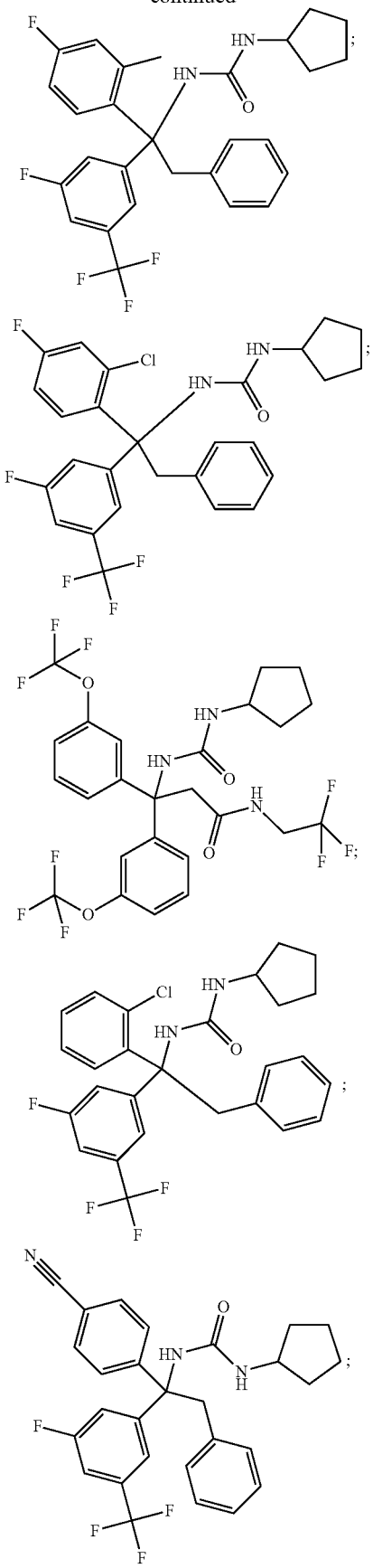
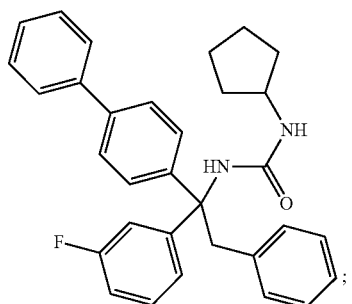

1051
-continued
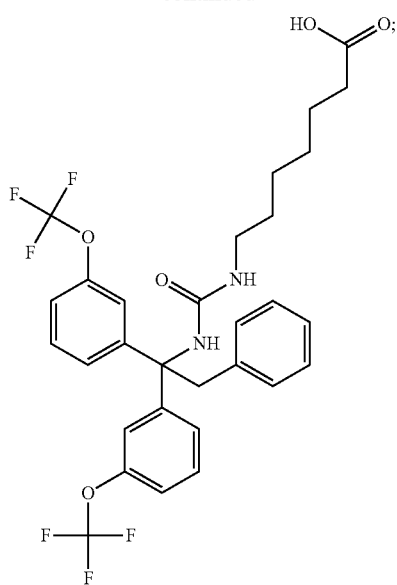
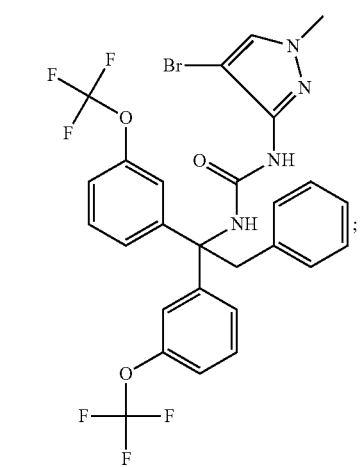
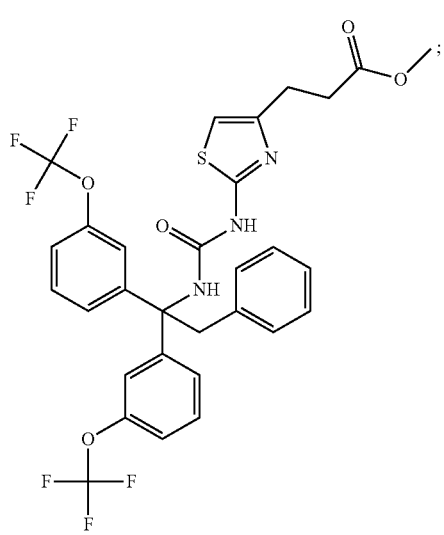
1052
-continued
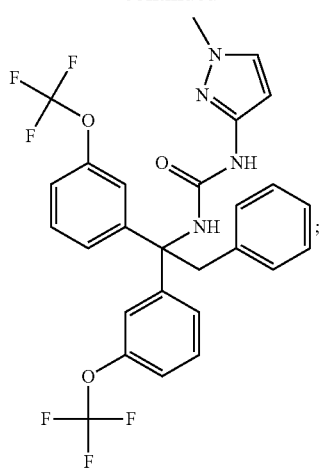
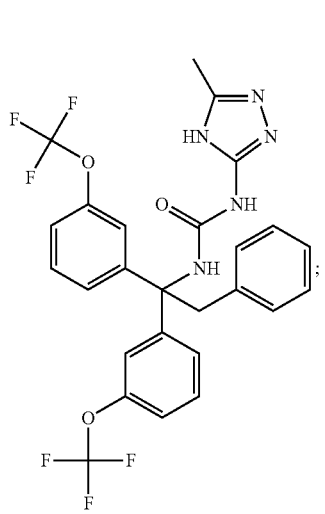
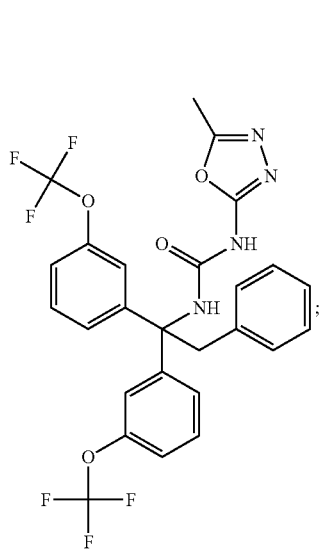

1053
-continued
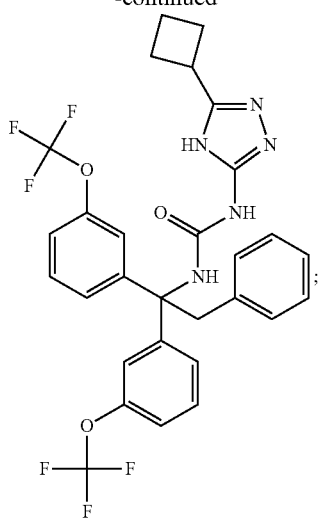
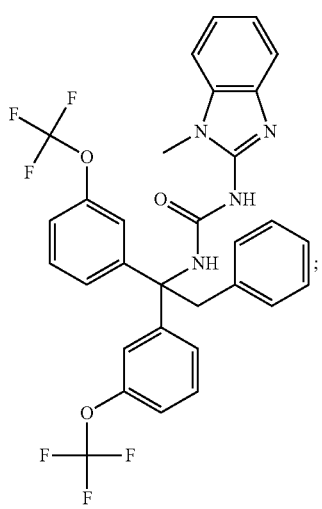
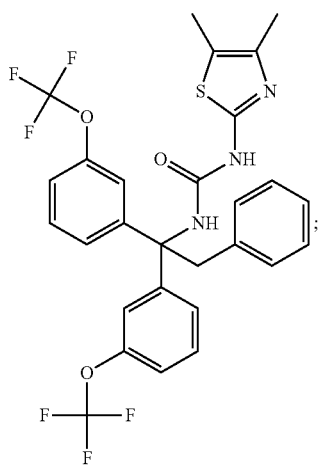
1054
-continued
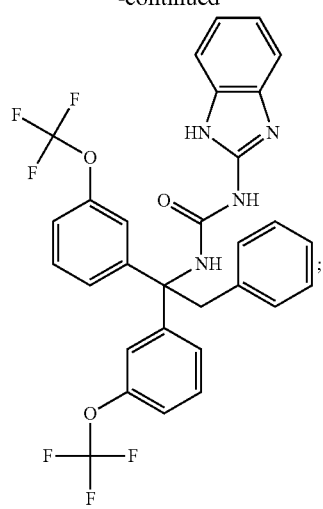
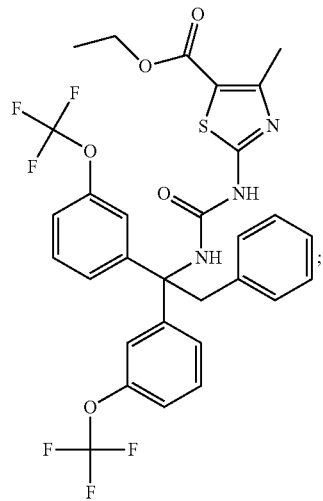
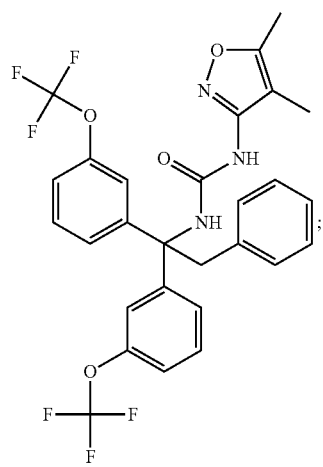

1055
-continued
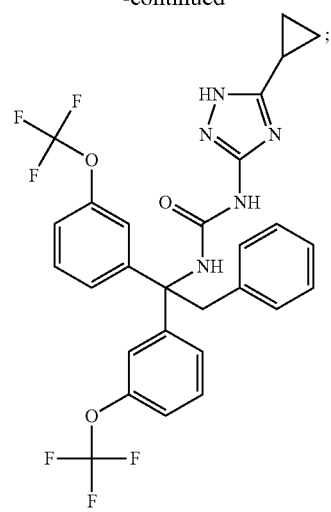
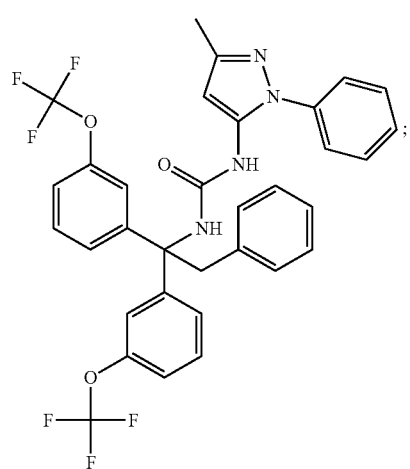
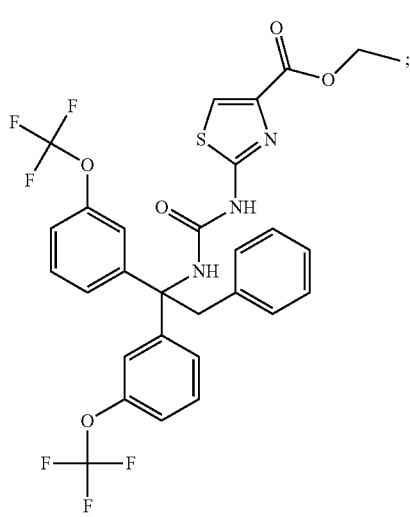
1056
-continued
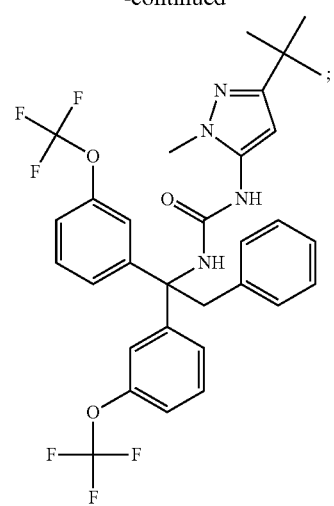
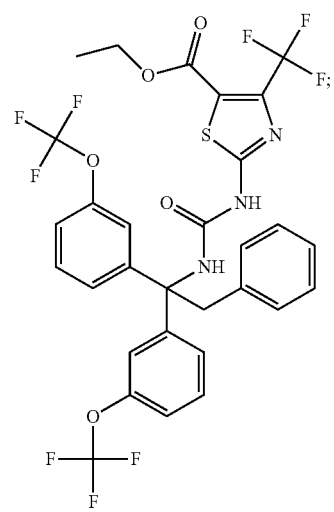
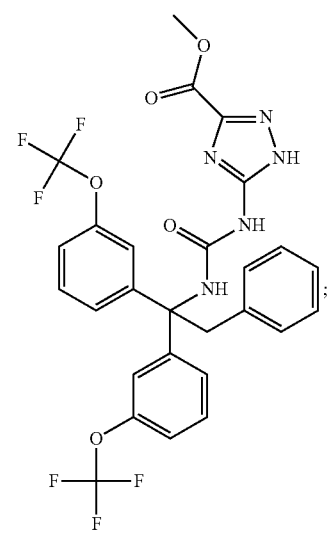

1057
-continued
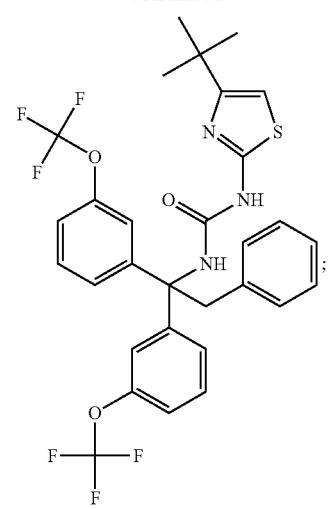
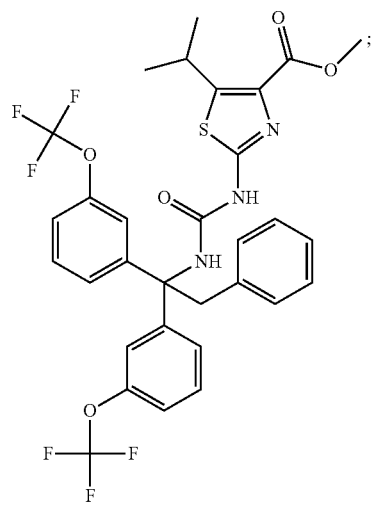
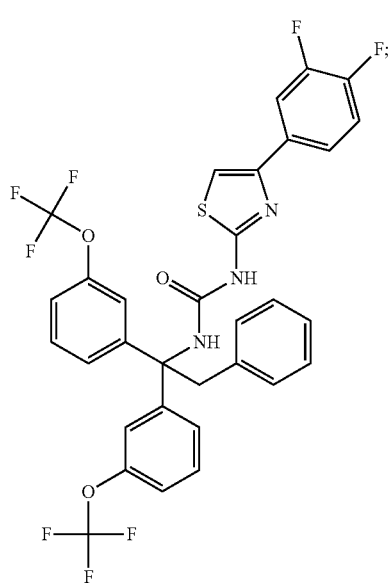
1058
-continued
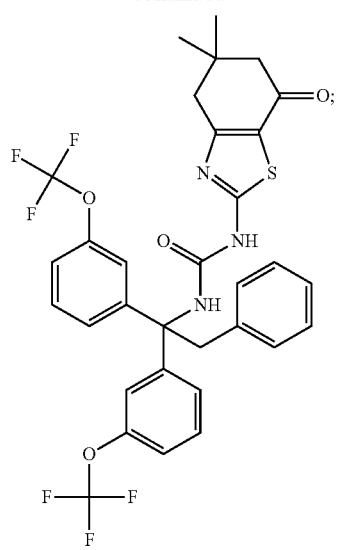
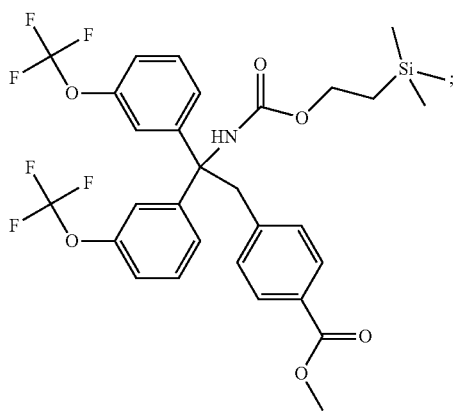
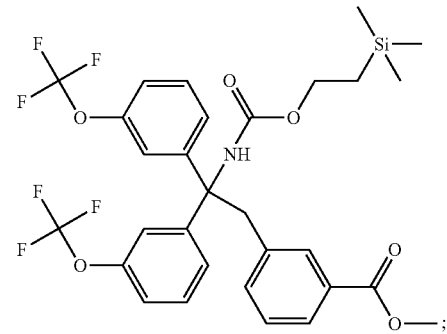

1059
-continued
1060
-continued
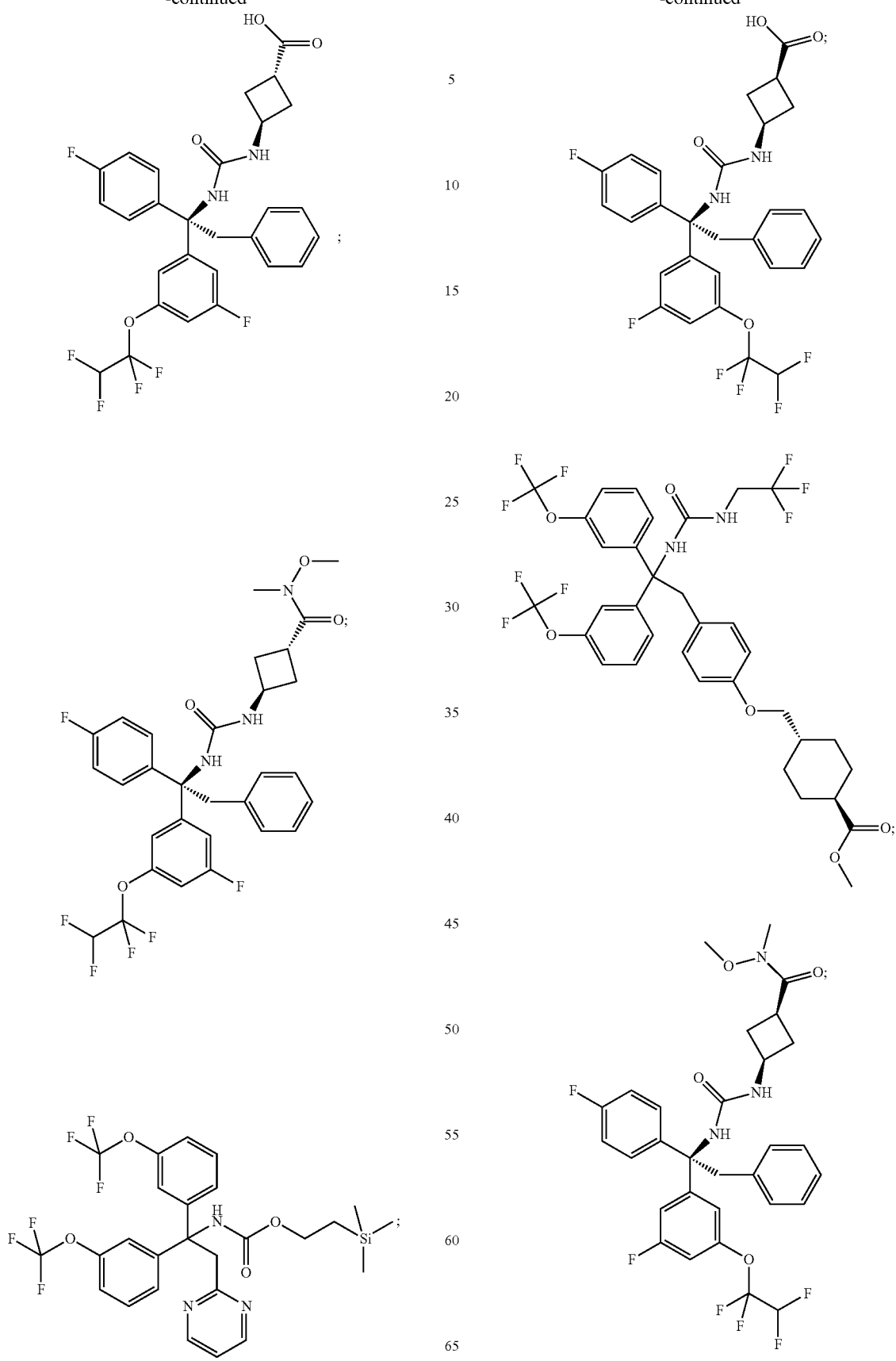

1061
-continued
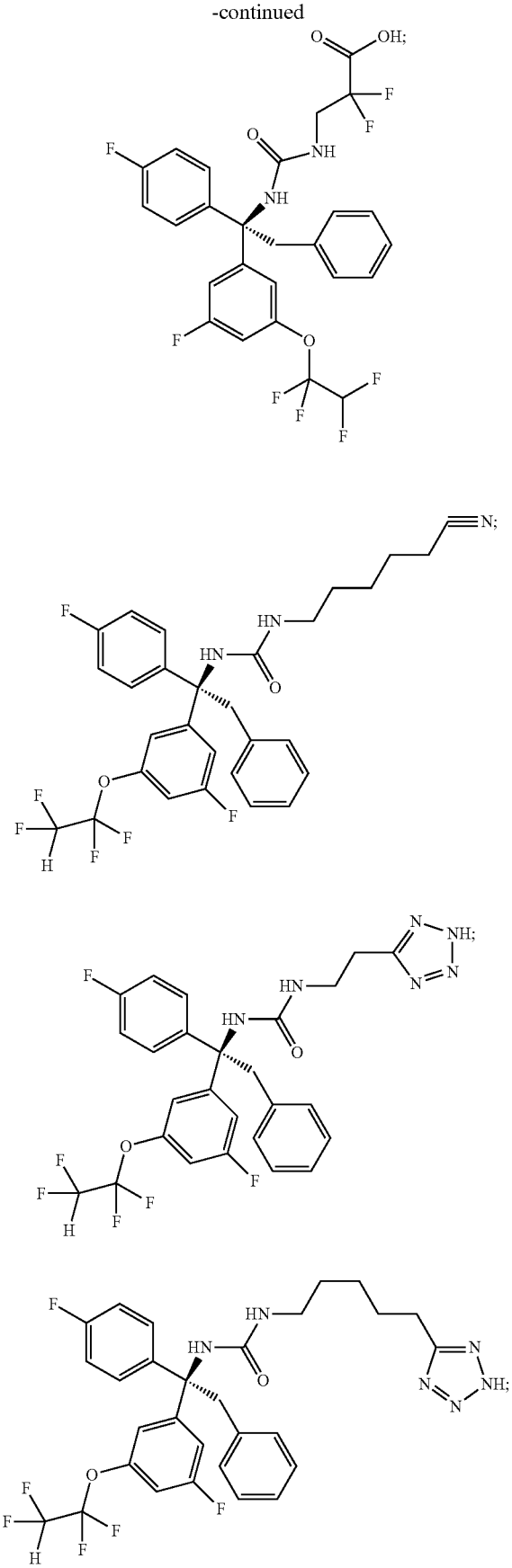
1062
-continued
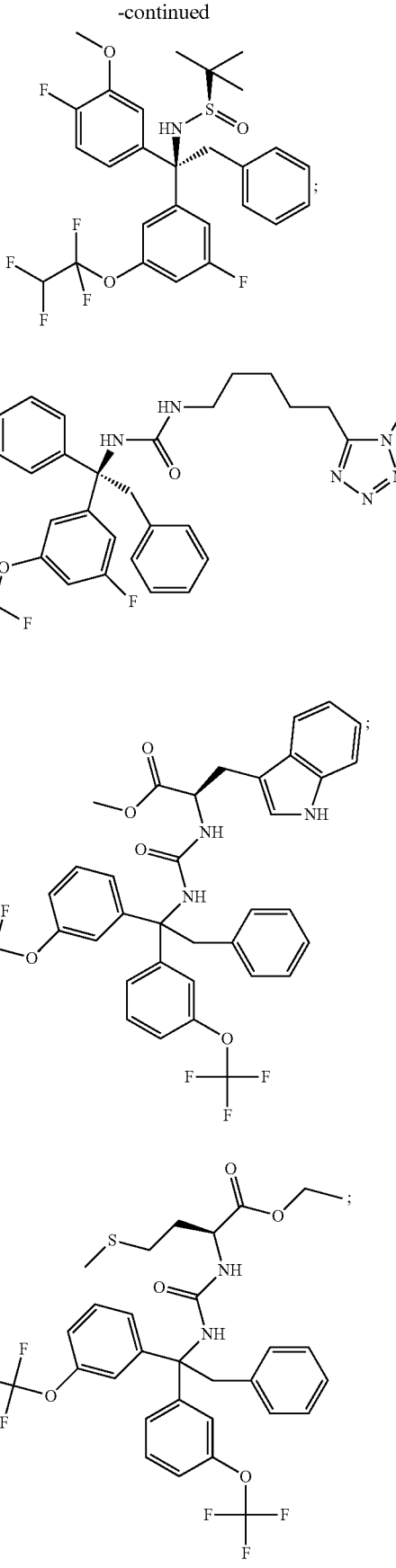

1063
-continued
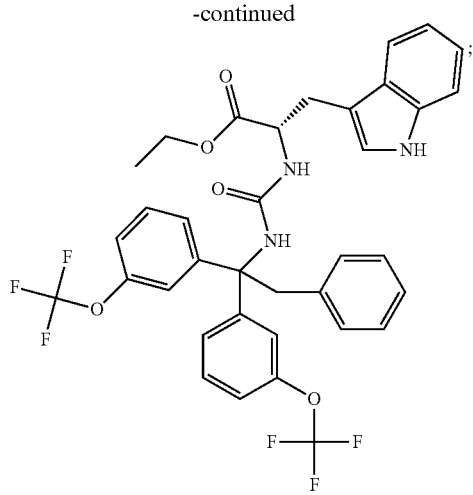
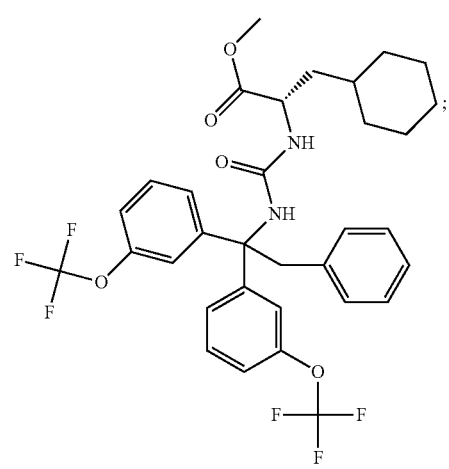
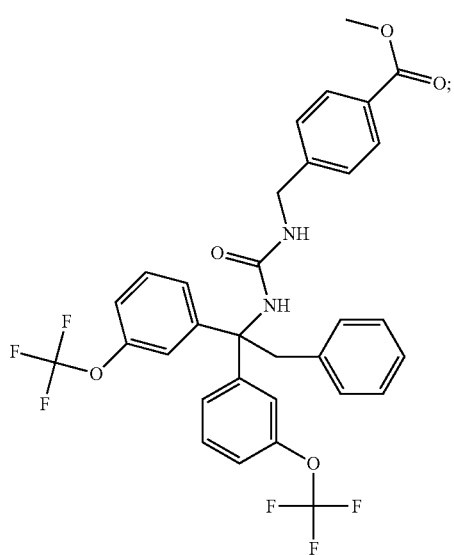
1064
-continued
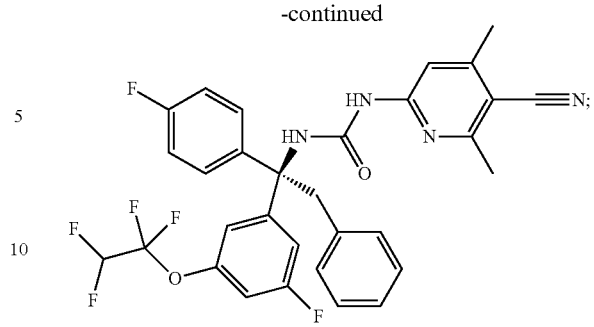
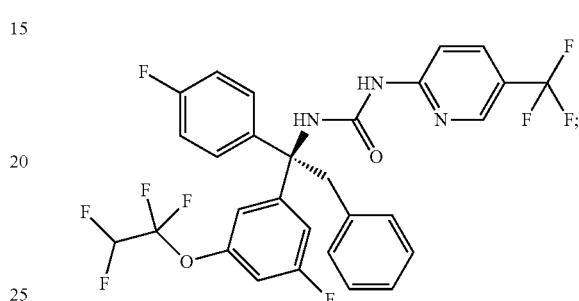
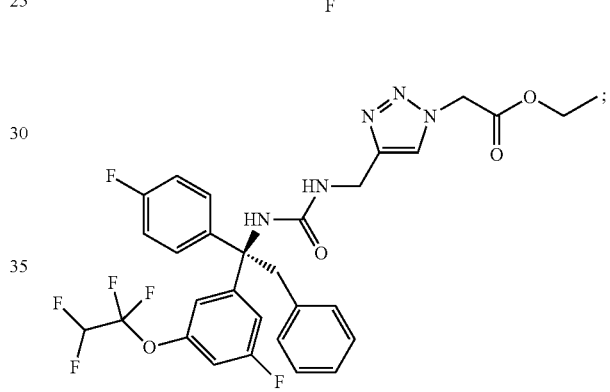
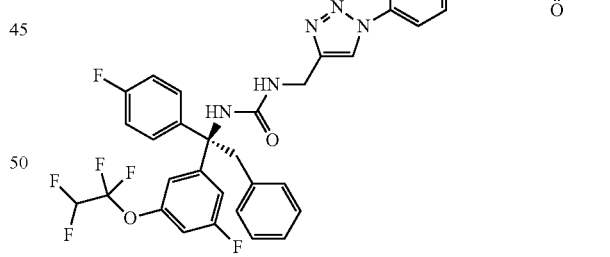
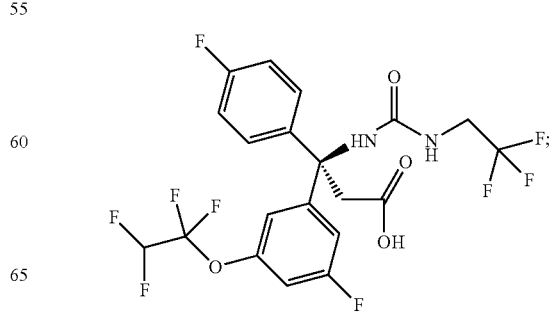

1065
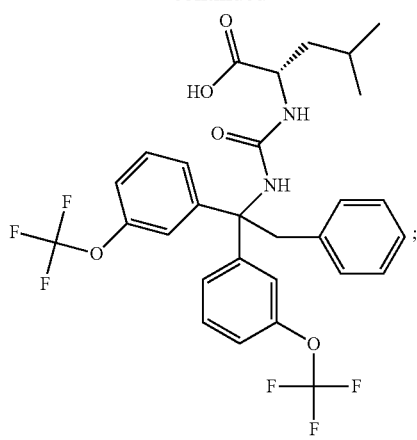
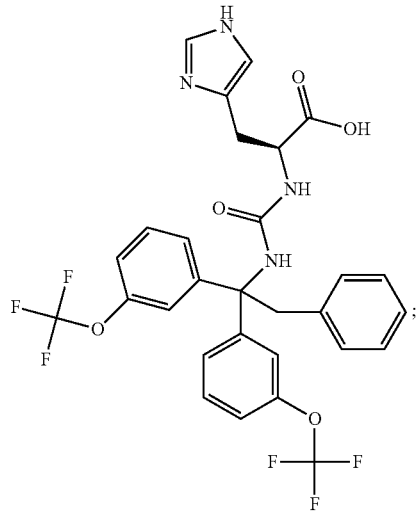
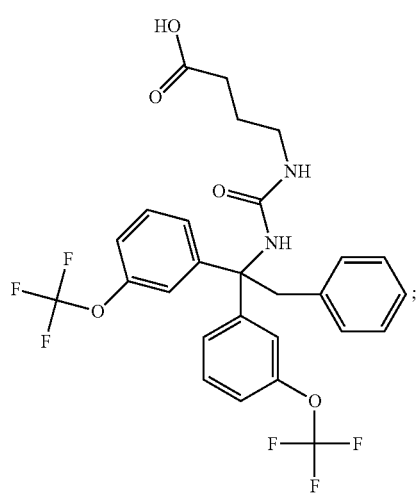
1066
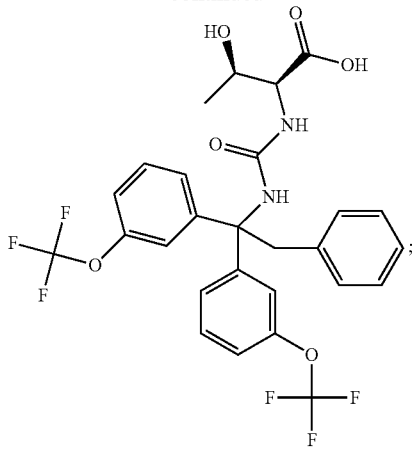
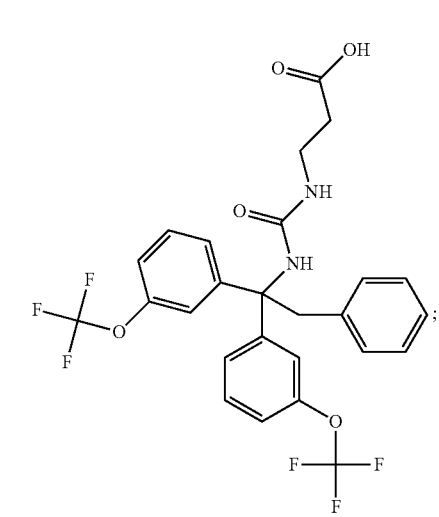

-continued

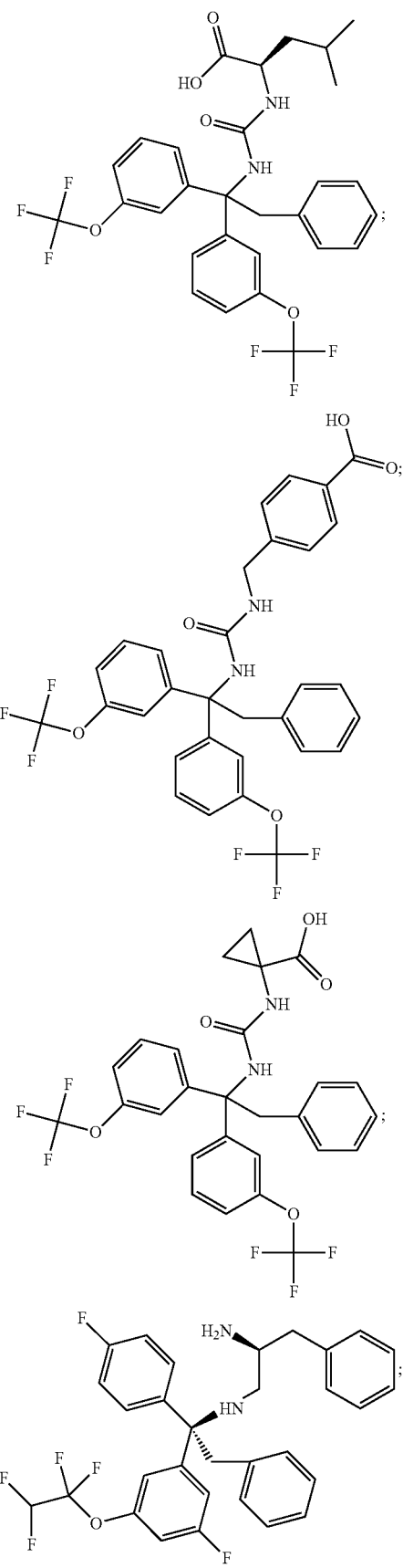

-continued

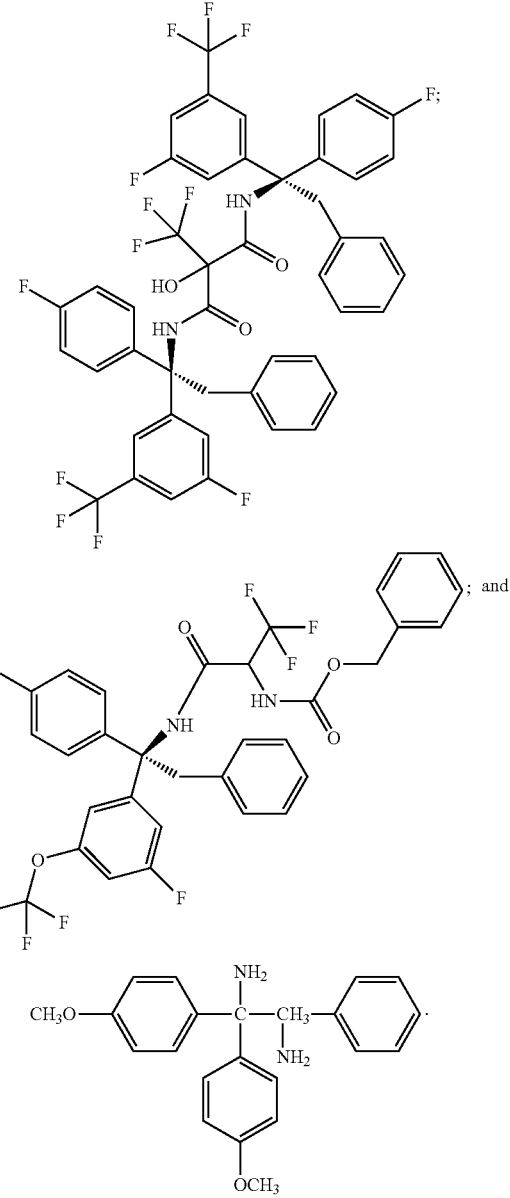

2. A compound of claim 1, wherein the compound is a compound of formula Ia

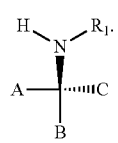

Ia

3. A compound of claim 1, wherein:
A is phenyl, which is substituted with one or more substituents selected from the group consisting of: 1) halo, and 2) —OR$_6$;
B is
phenyl, which is substituted with one or more substituents selected from the group consisting of: 1) halo, 2) (C$_1$-C$_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_E$, 16) —$S(O)_pR_6$, 17) —$SO_2NHR_6$, 18) —$COOR_6$, 19) —$NHC(CN)NHR_6$, and 20) —$CONR_6R_6$;

C is:
- (a) alkyl, which may be optionally substituted with one or more substituents selected from aryl, which may be optionally substituted with one or more $R_{20}$'s; or
- (b) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl;

$R_1$ is —$C(O)NR_2R_3$;

$R_2$ is:
- (a) H;
- (b) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) ($C_2$-$C_6$)-alkenyl, 15) ($C_2$-$C_6$)-alkynyl, 16) —$S(O)_pR_6$, 17) —$SO_2NHR_6$, 18) —$COOR_6$, and 19) —$NHC(CN)NHR_6$;
- (c) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ($C_2$-$C_6$)-alkynyl, 18) —$COR_6$, 19) —$S(O)_pR_6$, 20) —$SO_2NHR_6$, 21) —$COOR_6$, and 22) —$NHC(CN)NHR_6$; or
- (d) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CO(C_1$-$C_6)$-alkyl, 16) —COOH, 17) —$CO_2(C_1$-$C_6)$-alkyl, 18) —$CONR_6R_6$, 19) ($C_2$-$C_6$)-alkenyl, and 20) ($C_2$-$C_6$)-alkynyl;

$R_3$ is:
- (a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$CONR_6R_6$, 13) ($C_2$-$C_6$)-alkenyl, 14) ($C_2$-$C_6$)-alkynyl, 15) —$COR_6$, 16) —$S(O)_pR_6$, 17) —$SO_2NHR_6$, 18) —$COOR_6$, and 19) —$NHC(CN)NHR_6$;
- (b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, and 23) —$NHC(CN)NHR_6$;
- (c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)- alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, and 23) —$NHC(CN)NHR_6$;

(d) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, and 23) —$NHC(CN)NHR_6$;

(e) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, and 23) —$NHC(CN)NHR_6$; or (f) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ($C_2$-$C_6$)-alkynyl, 18) —$COR_6$, 19) —$S(O)_pR_6$, 20) —$SO_2NHR_6$, 21) —$COOR_6$, and 22) —$NHC(CN)NHR_6$;

or $R_2$ and $R_3$ are taken together to form a 3- to 9-membered ring, which optionally may contain 1-4 heteroatoms selected from N, O, and S and be optionally substituted with one or more $R_{20}$'s;

$R_6$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, 22) —$NHC(CN)NHR_{36}$, or 23) cycloalkyl, which may be optionally substituted with one or more $R_{20}$'s;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —$NHC(CN)NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$) alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(f) hydrogen;

(g) alkynyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) (C2-C6)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, 22) —$NHC(CN)NHR_{36}$, or 23) cycloalkyl, which may be optionally substituted with one or more $R_{20}$'s; or (h) alkenyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) (C2-C6)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, 22) —$NHC(CN)NHR_{36}$, or 23) cycloalkyl, which may be optionally substituted with one or more $R_{20}$'s;

or two $R_6$'s are taken together to form a 3- to 9-membered ring, which optionally may contain 1-4 heteroatoms selected from N, O, and S and be optionally substituted with one or more $R_{20}$'s;

$R_9$ and $R_{10}$ are independently: (a) hydrogen; (b) —[(C=O)$O_r]_s$aryl, wherein the aryl may be optionally substituted with one or more $R_{20}$'s; (c) —[(C=O)$O_r]_s$($C_2$-$C_8$)-alkenyl, wherein the alkenyl may be optionally substituted with one or more $R_{20}$'s; (d) —[(C=O)$O_r]_s$($C_1$-$C_8$) alkyl, wherein the alkyl may be optionally substituted with one or more $R_{20}$'s; (e) heterocyclyl optionally substituted with one or more $R_{20}$'s; (f) —$CONR_{26}R_{26}$; (g) —($C_2$-$C_6$)-alkynyl; (h) —$COR_{26}$; (i) —$S(O)_pR_{26}$; (j) —$SO_2NHR_{26}$; (k) —$COOR_{26}$; or (l) —$NHC(CN)NHR_{26}$;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) =O; (q) —($C_2$-$C_6$)-alkynyl; (r) —$COR_{26}$; (s) —$S(O)_pR_{26}$; (t) —$SO_2NHR_{26}$; (u) —$COOR_{26}$; (v) —$NHC(CN)NHR_{26}$; (w) cycloalkyl, which may be optionally substituted with one or more $R_{21}$'s; (x) cycloalkylalkyl, which may be optionally substituted with one or more $R_{21}$'s; or (y) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o)—$CONR_{26}R_{26}$; (p) ($C_2$-$C_6$)-alkenyl; (q) =O; (r) ($C_2$-$C_6$)-alkynyl; (s) cycloalkyl; (t) cycloalkylalkyl; (u) —$COR_{26}$; (v) —$S(O)_pR_{26}$; (w) —$SO_2NHR_{26}$; (x) —$COOR_{26}$; or (y) —$NHC(CN)NHR_{26}$;

$R_{26}$, at each occurrence, is independently:
(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —$NHC(CN)NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —$NHC(CN)NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8)

—NR$_{29}$R$_{30}$, 9) aryl, which may be optionally substituted with one or more R$_{40}$'s, 10) arylalkyl, which may be optionally substituted with one or more R$_{40}$'s, 11) heteroaryl, which may be optionally substituted with one or more R$_{40}$'s, 12) heteroarylalkyl, which may be optionally substituted with one or more R$_{40}$'s, 13) heterocyclyl, which may be optionally substituted with one or more R$_{40}$'s, 14) heterocyclylalkyl, which may be optionally substituted with one or more R$_{10}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(d) heteroaryl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) arylalkyl, which may be optionally substituted with one or more R$_{40}$'s, 11) heteroaryl, which may be optionally substituted with one or more R$_{40}$'s, 12) heteroarylalkyl, which may be optionally substituted with one or more R$_{40}$'s, 13) heterocyclyl, which may be optionally substituted with one or more R$_{40}$'s, 14) heterocyclylalkyl, which may be optionally substituted with one or more R$_{40}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(e) heterocyclyl, other than heteroaryl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) arylalkyl, which may be optionally substituted with one or more R$_{40}$'s, 11) heteroaryl, which may be optionally substituted with one or more R$_{40}$'s, 12) heteroarylalkyl, which may be optionally substituted with one or more R$_{40}$'s, 13) heterocyclyl, which may be optionally substituted with one or more R$_{40}$'s, 14) heterocyclylalkyl, which may be optionally substituted with one or more R$_{40}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(f) hydrogen;

(g) alkynyl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) heteroaryl, which may be optionally substituted with one or more R$_{40}$'s, 11) heterocyclyl, which may be optionally substituted with one or more R$_{40}$'s, 12) halo(C$_1$-C$_6$)alkyl, 13) (C$_2$-C$_6$)-alkenyl, 14) —COOH, 15) —CONR$_{36}$R$_{36}$, 16) =O, 17) (C$_2$-C$_6$)-alkynyl, 18) —COR$_{36}$, 19) —S(O)$_p$R$_{36}$, 20) —SO$_2$NHR$_{36}$, 21) —COOR$_{36}$, 22) —NHC(CN)NHR$_{36}$, or 23) cycloalkyl, which may be optionally substituted with one or more R$_{20}$'s; or (h) alkenyl, which may be optionally substituted with one or more substituents selected from the group consisting of: 1) halo, 2) —OH, 3) (C$_1$-C$_6$)-alkyl, which may be optionally substituted with one or more R$_{40}$'s, 4) —OR$_{36}$, 5) (C$_1$-C$_6$)-alkylthio, 6) cyano, 7) nitro, 8) —NR$_{29}$R$_{30}$, 9) aryl, which may be optionally substituted with one or more R$_{40}$'s, 10) heteroaryl, which may be optionally substituted with one or more R$_{40}$'s, 11) heterocyclyl, which may be optionally substituted with one or more R$_{40}$'s, 12) halo(C$_1$-C$_6$)alkyl, 13) (C$_2$-C$_6$)-alkenyl, 14) —COOH, 15) —CONR$_{36}$R$_{36}$, 16) =O, 17) (C$_2$-C$_6$)-alkynyl, 18) —COR$_{36}$, 19) —S(O)$_p$R$_{36}$, 20) —SO$_2$NHR$_{36}$, 21) —COOR$_{36}$, 22) —NHC(CN)NHR$_{36}$, or 23) cycloalkyl, which may be optionally substituted with one or more R$_{40}$'s;

or two R$_{26}$'s are taken together to form a 3- to 9-membered ring, which optionally may contain 1-4 heteroatoms selected from N, O, and S and be optionally substituted with one or more R$_{40}$'s;

R$_{29}$ and R$_{30}$ are independently hydrogen, —[(C=O)O$_r$]$_s$aryl, —[(C=O)O$_r$]$_s$alkenyl, —[(C=O)O$_r$]$_s$alkyl, heterocyclyl, alkynyl, —COR$_{36}$, —S(O)$_p$R$_{36}$, —SO$_2$NHR$_{36}$, —COOR$_{36}$, or —C(CN)NHR$_{36}$, wherein the aryl, alkyl, alkenyl or heterocyclyl may be optionally substituted with one or more R$_{40}$'s;

or R$_{29}$ and R$_{30}$ are taken together with the nitrogen to which both are attached to form a 3- to 8-membered ring, which may optionally contain 1-4 heteroatoms selected from N, O, and S and be optionally substituted with one or more R$_{40}$'s;

R$_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more R$_{40}$'s;

R$_{40}$ is halo, —OH, alkyl, alkyloxy, alkylthio, cyano, nitro, —NR$_{49}$R$_{50}$, aryl, arylalkyl, heteroaryl, heteroarylalkyl, heterocyclyl, heterocyclylalkyl, haloalkyl, haloalkyloxy, —CONR$_{49}$R$_{50}$, alkenyl, arylalkyloxy, =O, alkynyl, cycloalkyl, cycloalkylalkyl, —COR$_{49}$, —S(O)$_p$R$_{49}$, —SO$_2$NHR$_{49}$, —COOR$_{49}$, or —NHC(CN)NHR$_{49}$;

R$_{49}$ and R$_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2.

4. A compound of claim 1, wherein:

A is phenyl, which is substituted with one or more substituents selected from the group consisting of: 1) halo, and 2) —OR$_6$;

B is phenyl, which is substituted with one or more substituents selected from the group consisting of: 1) halo, 2) (C$_1$-C$_6$)-alkyl, which may be optionally substituted with one or more R$_{20}$'s, 3) —OR$_6$, 4) (C$_1$-C$_6$)-alkylthio, 5) cyano, 6) nitro, 7) —NR$_9$R$_{10}$, 8) aryl, which may be optionally substituted with one or more R$_{20}$'s, 9) arylalkyl, which may be optionally substituted with one or more R$_{20}$'s, 10) heteroaryl, which may be optionally substituted with one or more R$_{20}$'s, 11) heteroarylalkyl, which may be optionally substituted with one or more R$_{20}$'s, 12) heterocyclyl, which may be optionally substituted with one or more R$_{20}$'s, 13) heterocyclylalkyl, which may be optionally substituted with one or more $R_{20}$'s, 14) halo($C_1$-$C_6$)alkyl, 15) —$COR_6$, 16) —$COOR_6$, and 17) —$CONR_6R_6$;

C is alkyl, which is substituted with one or more substituents selected from aryl, which may be optionally substituted with one or more $R_{20}$'s;

$R_1$ is —C(O)$NR_2R_3$;

$R_2$ is:
 (a) H;
 (b) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) ($C_2$-$C_6$)-alkenyl, 15) ($C_2$-$C_6$)-alkynyl, and 16) —$COOR_6$;
 (c) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ($C_2$-$C_6$)-alkynyl, 18) —$COR_6$, and 19) —$COOR_6$; or
 (d) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CO($C_1$-$C_6$)-alkyl, 16) —COOH, 17) —$CO_2$($C_1$-$C_6$)-alkyl, 18) —$CONR_6R_6$, 19) ($C_2$-$C_6$)-alkenyl, and 20) ($C_2$-$C_6$)-alkynyl;

$R_3$ is:
 (a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$CONR_6R_6$, 13) ($C_2$-$C_6$)-alkenyl, 14) ($C_2$-$C_6$)-alkynyl, 15) —$COR_6$, and 16) —$COOR_6$;
 (b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;
 (c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;
 (d) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;
 (e) heterocyclyl, other than heteroaryl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CONR$_6$R$_6$, 16) (C$_2$-C$_6$)-alkenyl, 17) =O, 18) (C$_2$-C$_6$)-alkynyl, 19) —COR$_6$, and 20) —COOR$_6$; or
(f) alkenyl, which may be optionally substituted with one or more substituents selected from the group consisting of: 1) halo, 2) (C$_1$-C$_6$)-alkyl, which may be optionally substituted with one or more R$_{20}$'s, 3) —OR$_6$, 4) (C$_1$-C$_6$)-alkylthio, 5) cyano, 6) nitro, 7) —NR$_9$R$_{10}$, 8) aryl, which may be optionally substituted with one or more R$_{20}$'s, 9) arylalkyl, which may be optionally substituted with one or more R$_{20}$'s, 10) heteroaryl, which may be optionally substituted with one or more R$_{20}$'s, 11) heteroarylalkyl, which may be optionally substituted with one or more R$_{20}$'s, 12) heterocyclyl, which may be optionally substituted with one or more R$_{20}$'s, 13) heterocyclylalkyl, which may be optionally substituted with one or more R$_{20}$'s, 14) halo(C$_1$-C$_6$)alkyl, 15) —CONR$_6$R$_6$, 16) (C$_2$-C$_6$)-alkenyl, 17) (C$_2$-C$_6$)-alkynyl, 18) —COR$_6$, and 19) —COOR$_6$;

R$_6$, at each occurrence, is independently:
(a) alkyl, which may be optionally substituted with one or more substituents selected from the group consisting of: 1) halo, 2) —OH, 3) (C$_1$-C$_6$)-alkyl, which may be optionally substituted with one or more R$_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more R$_{20}$'s, 10) heteroaryl, which may be optionally substituted with one or more R$_{20}$'s, 11) heterocyclyl, which may be optionally substituted with one or more R$_{20}$'s, 12) halo(C$_1$-C$_6$)alkyl, 13) (C$_2$-C$_6$)-alkenyl, 14) —COOH, 15) —CONR$_{36}$R$_{36}$, 16) =O, 17) (C$_2$-C$_6$)-alkynyl, 18) —COR$_{36}$, 19) —S(O)$_p$R$_{36}$, 20) —SO$_2$NHR$_{36}$, 21) —COOR$_{36}$, and 22) —NHC(CN)NHR$_{36}$;
(b) aryl, which may be optionally substituted with one or more substituents selected from the group consisting of: 1) halo, 2) —OH, 3) (C$_1$-C$_6$)-alkyl, which may be optionally substituted with one or more R$_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more R$_{20}$'s, 10) arylalkyl, which may be optionally substituted with one or more R$_{20}$'s, 11) heteroaryl, which may be optionally substituted with one or more R$_{20}$'s, 12) heteroarylalkyl, which may be optionally substituted with one or more R$_{20}$'s, 13) heterocyclyl, which may be optionally substituted with one or more R$_{20}$'s, 14) heterocyclylalkyl, which may be optionally substituted with one or more R$_{20}$'s, 15) halo(C$_1$-C$_6$)alkyl, 16) —COOH, 17) —CONR$_{36}$R$_{36}$, 18) =O, 19) (C$_2$-C$_6$)-alkynyl, 20) —COR$_{36}$, 21) —S(O)$_p$R$_{36}$, 22) —SO$_2$NHR$_{36}$, 23) —COOR$_{36}$, and 24) —NHC(CN)NHR$_{36}$;
(c) cycloalkyl, which may be optionally substituted with one or more substituents selected from the group consisting of: 1) halo, 2) —OH, 3) (C$_1$-C$_6$)-alkyl, which may be optionally substituted with one or more R$_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more R$_{20}$'s, 10) arylalkyl, which may be optionally substituted with one or more R$_{20}$'s, 11) heteroaryl, which may be optionally substituted with one or more R$_{20}$'s, 12) heteroarylalkyl, which may be optionally substituted with one or more R$_{20}$'s, 13) heterocyclyl, which may be optionally substituted with one or more R$_{20}$'s, 14) heterocyclylalkyl, which may be optionally substituted with one or more R$_{20}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;
(d) heteroaryl, which may be optionally substituted with one or more substituents selected from the group consisting of: 1) halo, 2) —OH, 3) (C$_1$-C$_6$)-alkyl, which may be optionally substituted with one or more R$_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more R$_{20}$'s, 10) arylalkyl, which may be optionally substituted with one or more R$_{20}$'s, 11) heteroaryl, which may be optionally substituted with one or more R$_{20}$'s, 12) heteroarylalkyl, which may be optionally substituted with one or more R$_{20}$'s, 13) heterocyclyl, which may be optionally substituted with one or more R$_{20}$'s, 14) heterocyclylalkyl, which may be optionally substituted with one or more R$_{20}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;
(e) heterocyclyl, other than heteroaryl, which may be optionally substituted with one or more substituents selected from the group consisting of: 1) halo, 2) —OH, 3) (C$_1$-C$_6$)-alkyl, which may be optionally substituted with one or more R$_{20}$'s, 4) —OR$_{36}$, 5) (C$_1$-C$_6$)-alkylthio, 6) cyano, 7) nitro, 8) —NR$_9$R$_{10}$, 9) aryl, which may be optionally substituted with one or more R$_{20}$'s, 10) arylalkyl, which may be optionally substituted with one or more R$_{20}$'s, 11) heteroaryl, which may be optionally substituted with one or more R$_{20}$'s, 12) heteroarylalkyl, which may be optionally substituted with one or more R$_{20}$'s, 13) heterocyclyl, which may be optionally substituted with one or more R$_{20}$'s, 14) heterocyclylalkyl, which may be optionally substituted with one or more R$_{20}$'s, 15) halo(C$_1$-C$_6$)alkyl, 16) (C$_2$-C$_6$)-alkenyl, 17) —COOH, 18) —CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$; or
(f) hydrogen;

or two R$_6$'s are taken together to form a 3- to 9-membered ring, which optionally may contain 1-4 heteroatoms selected from N, O, and S and may be optionally substituted with one or more R$_{20}$'s;

R$_9$ and R$_{10}$ are independently: (a) hydrogen; (b) —[(C=O)O$_r$]$_s$aryl, wherein the aryl may be optionally substituted with one or more R$_{20}$'s; (c) —[(C=O)O$_r$]$_s$(C$_1$-C$_8$)alkyl, wherein the alkyl may be optionally substituted with one or more R$_{20}$'s; or (d) heterocyclyl optionally substituted with one or more R$_{20}$'s;

or R$_9$ and R$_{10}$ are taken together with the nitrogen to which both are attached to form a 3- to 8-membered ring, which may optionally contain 1-4 heteroatoms selected from N, O, and S and be optionally substituted with one or more R$_{20}$'s;

R$_{20}$ is: (a) halo; (b) (C$_1$-C$_6$)-alkyl, which may be optionally substituted with one or more R$_{21}$'s; (c) —OR$_{26}$; (d) (C$_1$-C$_6$)-alkylthio; (e) cyano; (f) nitro; (g) —NR$_{29}$R$_{30}$; (h) aryl, which may be optionally substituted with one or more R$_{21}$'s; (i) arylalkyl, which may be optionally substituted with one or more R$_{21}$'s; (j) heteroaryl, which may be optionally substituted with one or more R$_{21}$'s; (k) heteroarylalkyl, which may be optionally substituted with one or more R$_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) —($C_2$-$C_6$)-alkynyl; (q) —$COR_{26}$; (r) —$COOR_{26}$; (s) cycloalkyl, which may be optionally substituted with one or more $R_{21}$'s; (t) cycloalkylalkyl, which may be optionally substituted with one or more $R_{21}$'s; or (u) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) ($C_2$-$C_6$)-alkynyl; (r) cycloalkyl; (s) cycloalkylalkyl; (t) —$COR_{26}$; or (u) —$COOR_{26}$;

$R_{26}$, at each occurrence, is independently:
 (a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —$NHC(CN)NHR_{36}$;
 (b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —$NHC(CN)NHR_{36}$;
 (c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;
 (d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;
 (e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$; or
 (f) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —[(C=O)O$_r$]$_s$aryl, —[(C=O)O$_r$]$_s$alkyl, or heterocyclyl, wherein the aryl, alkyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, =O, alkynyl, cycloalkyl, cycloalkylalkyl, —$COR_{49}$ or —$COOR_{49}$;

$R_{49}$ and $R_{50}$, at each occurrence, are independently hydrogen, alkyl, aryl, heteroaryl or heterocyclyl, other than heteroaryl;

r is 0 to 3;
s is 0 to 2; and
p is 1 or 2.

5. A compound of claim 1, wherein:

A is phenyl, which is substituted with one or more substituents selected from the group consisting of: 1) halo, and 2) —$OR_6$;

B is:
  phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COOR_6$, and 16) —$CONR_6R_6$;

C is alkyl, which is substituted with one or more substituents selected from aryl, which may be optionally substituted with one or more $R_{20}$'s;

$R_1$ is —C(O)$NR_2R_3$;

$R_2$ is:
  (a) H;
  (b) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) ($C_2$-$C_6$)-alkenyl, 15) ($C_2$-$C_6$)-alkynyl, and 16) —$COOR_6$; or
  (c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CO($C_1$-$C_6$)-alkyl, 16) —COOH, 17) —$CO_2$($C_1$-$C_6$)-alkyl, 18) —$CONR_6R_6$, 19) ($C_2$-$C_6$)-alkenyl, and 20) ($C_2$-$C_6$)-alkynyl;

$R_3$ is:
  (a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$CONR_6R_6$, 13) ($C_2$-$C_6$)-alkenyl, 14) ($C_2$-$C_6$)-alkynyl, 15) —$COR_6$, and 16) —$COOR_6$;
  (b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;
  (c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;
  (d) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;
  (e) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CONR$_6$R$_6$, 16) ($C_2$-$C_6$)-alkenyl, 17) =O, 18) ($C_2$-$C_6$)-alkynyl, 19) —COR$_6$, and 20) —COOR$_6$; or (f) alkenyl, which may be optionally substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CONR$_6$R$_6$, 16) ($C_2$-$C_6$)-alkenyl, 17) ($C_2$-$C_6$)-alkynyl, 18) —COR$_6$, and 19) —COOR$_6$;

$R_6$, at each occurrence, is independently:
- (a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —CONR$_{36}$R$_{36}$, 16) =O, 17) ($C_2$-$C_6$)-alkynyl, 18) —COR$_{36}$, 19) —S(O)$_p$R$_{36}$, 20) —SO$_2$NHR$_{36}$, 21) —COOR$_{36}$, and 22) —NHC(CN)NHR$_{36}$;
- (b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —CONR$_{36}$R$_{36}$, 18) =O, 19) ($C_2$-$C_6$)-alkynyl, 20) —COR$_{36}$, 21) —S(O)$_p$R$_{36}$, 22) —SO$_2$NHR$_{36}$, 23) —COOR$_{36}$, and 24) —NHC(CN)NHR$_{36}$;
- (c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;
- (d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;
- (e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$; or
- (f) hydrogen;

or two $R_6$'s are taken together to form a 3- to 9-membered ring, which optionally may contain 1-4 heteroatoms selected from N, O, and S and may be optionally substituted with one or more $R_{20}$'s;

$R_9$ and $R_{10}$ are independently: (a) hydrogen, (b) —[(C=O)O$_r$]$_s$aryl, wherein the aryl may be optionally substituted with one or more $R_{20}$'s, or (c) —[(C=O)O$_r$]$_s$($C_1$-$C_8$) alkyl, wherein the alkyl may be optionally substituted with one or more $R_{20}$'s;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is: (a) halo; (b) ($C_1$-$C_6$)-alkyl, which may be optionally substituted with one or more $R_{21}$'s; (c) —OR$_{26}$; (d) ($C_1$-$C_6$)-alkylthio; (e) cyano; (f) nitro; (g) —NR$_{29}$R$_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s;

(k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) —($C_2$-$C_6$)-alkynyl; (q) —$COR_{26}$; (r) —$COOR_{26}$; (s) cycloalkyl, which may be optionally substituted with one or more $R_{21}$'s; (t) cycloalkylalkyl, which may be optionally substituted with one or more $R_{21}$'s; or (u) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) ($C_2$-$C_6$)-alkynyl; (r) cycloalkyl; (s) cycloalkylalkyl; (t) —$COR_{26}$; or (u) —$COOR_{26}$;

$R_{26}$, at each occurrence, is independently:
(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —$NHC(CN)NHR_{36}$;
(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —$NHC(CN)NHR_{36}$;
(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;
(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;
(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$; or
(f) hydrogen;
or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —[(C=O)$O_r$]$_s$aryl, or —[(C=O)$O_r$]$_s$alkyl, wherein the aryl or alkyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, =O, alkynyl, cycloalkyl, cycloalkylalkyl, —$COR_{49}$ or —$COOR_{49}$;

$R_{49}$ and $R_{50}$, at each occurrence, are independently hydrogen, alkyl, aryl or heteroaryl;

r is 0 to 2;
s is 0 to 1; and
p is 1 or 2.

6. A compound of claim 1, wherein:
A is phenyl, which is substituted with one or more substituents selected from the group consisting of: 1) halo, and 2) —$OR_6$;
B is
  phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, and 15) —$COOR_6$;
C is alkyl, which is substituted with one or more substituents selected from phenyl, which may be optionally substituted with one or more $R_{20}$'s;
$R_1$ is —C(O)$NR_2R_3$;
$R_2$ is:
  (a) H; or
  (b) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) ($C_2$-$C_6$)-alkenyl, 15) ($C_2$-$C_6$)-alkynyl, and 16) —$COOR_6$;
$R_3$ is:
  (a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$CONR_6R_6$, 13) ($C_2$-$C_6$)-alkenyl, 14) ($C_2$-$C_6$)-alkynyl, 15) —$COR_6$, and 16) —$COOR_6$;
  (b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;
  (c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;
  (d) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$; or
  (e) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;
$R_6$, at each occurrence, is independently:
  (a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —$NHC(CN)NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —$NHC(CN)NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$) alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$; or (f) hydrogen;

$R_9$ and $R_{10}$ are independently: (a) hydrogen; or (b) —$[(C=O)O_r]_s$($C_1$-$C_8$)alkyl, wherein the alkyl may be optionally substituted with one or more $R_{20}$'s;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) —($C_2$-$C_6$)-alkynyl; (q) —$COR_{26}$; (r) —$COOR_{26}$; (s) cycloalkyl, which may be optionally substituted with one or more $R_{21}$'s; (t) cycloalkylalkyl, which may be optionally substituted with one or more $R_{21}$'s; or (u) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o)—$CONR_{26}R_{26}$; (p) ($C_2$-$C_6$)-alkenyl; (q) ($C_2$-$C_6$)-alkynyl; (r) cycloalkyl; (s) cycloalkylalkyl; (t) —$COR_{26}$; or (u) —$COOR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —$NHC(CN)NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —CONR$_{36}$R$_{36}$, 18) =O, 19) ($C_2$-$C_6$)-alkynyl, 20) —COR$_{36}$, 21) —S(O)$_p$R$_{36}$, 22) —SO$_2$NHR$_{36}$, 23) —COOR$_{36}$, and 24) —NHC(CN)NHR$_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$; or (f) hydrogen;

$R_{29}$ and $R_{30}$ are independently hydrogen or —[(C=O)O$_r$]$_s$alkyl, wherein the alkyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —NR$_{49}$R$_{50}$, aryl, arylalkyl, heteroaryl, heteroarylalkyl, heterocyclyl, heterocyclylalkyl, haloalkyl, haloalkyloxy, —CONR$_{49}$R$_{50}$, alkenyl, arylalkyloxy, =O, alkynyl, cycloalkyl, cycloalkylalkyl, —COR$_{49}$ or —COOR$_{49}$;

$R_{49}$ and $R_{50}$, at each occurrence, are independently hydrogen, alkyl, aryl or heteroaryl;

r is 0 to 2;

s is 0 to 1; and p is 1 or 2.

7. A compound of claim 1, wherein:

A is phenyl, which is substituted with one or more substituents selected from the group consisting of: 1) halo, and 2) —OR$_6$;

B is phenyl, which is substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl;

C is alkyl, which is substituted with one or more substituents selected from the group consisting of [[: 1)]] phenyl, which may be optionally substituted with one or more $R_{20}$'s;

$R_1$ is —C(O)NHR$_3$;

$R_3$ is:

(a) alkyl, which may be optionally substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —CONR$_6$R$_6$, 13) ($C_2$-$C_6$)-alkenyl, 14) ($C_2$-$C_6$)-alkynyl, 15) —COR$_6$, and 16) —COOR$_6$;

(b) aryl, which may be optionally substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CONR$_6$R$_6$, 16) ($C_2$-$C_6$)-alkenyl, 17) =O, 18) ($C_2$-$C_6$)-alkynyl, 19) —COR$_6$, and 20) —COOR$_6$;
  (c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CONR$_6$R$_6$, 16) ($C_2$-$C_6$)-alkenyl, 17) =O, 18) ($C_2$-$C_6$)-alkynyl, 19) —COR$_6$, and 20) —COOR$_6$;
  (d) heteroaryl, which may be optionally substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CONR$_6$R$_6$, 16) ($C_2$-$C_6$)-alkenyl, 17) =O, 18) ($C_2$-$C_6$)-alkynyl, 19) —COR$_6$, and 20) —COOR$_6$; or
  (e) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —OR$_6$, 4) ($C_1$-$C_6$)-alkylthio, 5) cyano, 6) nitro, 7) —NR$_9$R$_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CONR$_6$R$_6$, 16) ($C_2$-$C_6$)-alkenyl, 17) =O, 18) ($C_2$-$C_6$)-alkynyl, 19) —COR$_6$, and 20) —COOR$_6$;

$R_6$, at each occurrence, is independently:
  (a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —CONR$_{36}$R$_{36}$, 16) =O, 17) ($C_2$-$C_6$)-alkynyl, 18) —COR$_{36}$, 19) —S(O)$_p$R$_{36}$, 20) —SO$_2$NHR$_{36}$, 21) —COOR$_{36}$, and 22) —NHC(CN)NHR$_{36}$;
  (b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —CONR$_{36}$R$_{36}$, 18) =O, 19) ($C_2$-$C_6$)-alkynyl, 20) —COR$_{36}$, 21) —S(O)$_p$R$_{36}$, 22) —SO$_2$NHR$_{36}$, 23) —COOR$_{36}$, and 24) —NHC(CN)NHR$_{36}$;
  (c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_6$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;
  (d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$) alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$; or (f) hydrogen;

$R_9$ and $R_{10}$ are independently: (a) hydrogen; or (b) —[(C=O)$O_r$]$_s$($C_1$-$C_8$)alkyl, wherein the alkyl may be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) —($C_2$-$C_6$)-alkynyl; (q) —$COR_{26}$; (r) —$COOR_{26}$; (s) cycloalkyl, which may be optionally substituted with one or more $R_{21}$'s; (t) cycloalkylalkyl, which may be optionally substituted with one or more $R_{21}$'s; or (u) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o)—$CONR_{26}R_{26}$; (p) ($C_2$-$C_6$)-alkenyl; (q) ($C_2$-$C_6$)-alkynyl; (r) cycloalkyl; (s) cycloalkylalkyl; (t) —$COR_{26}$; or (u) —$COOR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) (C1-C6)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$) alkyl, 16) ($C_2$-$C_6$)-alkenyl, 17) —COOH, 18)

—CONR$_{36}$R$_{36}$, 19) =O, 20) (C$_2$-C$_6$)-alkynyl, 21) —COR$_{36}$, 22) —S(O)$_p$R$_{36}$, 23) —SO$_2$NHR$_{36}$, 24) —COOR$_{36}$, and 25) —NHC(CN)NHR$_{36}$; or
(f) hydrogen;
R$_{29}$ and R$_{30}$ are independently hydrogen or —[(C=O)O$_r$]$_s$alkyl, wherein the alkyl may be optionally substituted with one or more R$_{40}$'s;
R$_{36}$, at each occurrence, is independently alkyl, aryl, heteroaryl or heterocyclyl, other than heteroaryl, wherein the alkyl, aryl, heteroaryl or heterocyclyl may be optionally substituted with one or more R$_{40}$'s;
R$_{40}$ is halo, —OH, alkyl, alkyloxy, alkylthio, cyano, nitro, aryl, arylalkyl, heteroaryl, heteroarylalkyl, heterocyclyl, heterocyclylalkyl, haloalkyl, haloalkyloxy, alkenyl, arylalkyloxy, =O, alkynyl, cycloalkyl or cycloalkylalkyl;
r is 0 to 2;
s is 0 to 1; and
p is 1 or 2.

8. A compound of claim 1, wherein:
A is phenyl, which is substituted with one or more substituents selected from the group consisting of: 1) halo, and 2) —OR$_6$;
B is phenyl, which is substituted with one or more substituents selected from the group consisting of: 1) halo, 2) (C$_1$-C$_6$)-alkyl, which may be optionally substituted with one or more R$_{20}$'s, 3) —OR$_6$, 4) (C$_1$-C$_6$)-alkylthio, 5) cyano, 6) nitro, 7) —NR$_9$R$_{10}$, 8) aryl, which may be optionally substituted with one or more R$_{20}$'s, 9) arylalkyl, which may be optionally substituted with one or more R$_{20}$'s, 10) heteroaryl, which may be optionally substituted with one or more R$_{20}$s, 11) heteroarylalkyl, which may be optionally substituted with one or more R$_{20}$'s, 12) heterocyclyl, which may be optionally substituted with one or more R$_{20}$'s, 13) heterocyclylalkyl, which may be optionally substituted with one or more R$_{20}$'s, and 14) halo(C$_1$-C$_6$)alkyl;
C is methyl, which is substituted with one or more substituents selected from phenyl, which may be optionally substituted with one or more R$_{20}$'s;
R$_1$ is —C(O)NHR$_3$;
R$_3$ is:
(a) alkyl, which may be optionally substituted with one or more substituents selected from the group consisting of: 1) halo, 2) (C$_1$-C$_6$)-alkyl, 3) —OR$_6$, 4) (C$_1$-C$_6$)-alkylthio, 5) cyano, 6) nitro, 7) —NR$_9$R$_{10}$, 8) aryl, which may be optionally substituted with one or more R$_{20}$'s, 9) heteroaryl, which may be optionally substituted with one or more R$_{20}$'s, 10) heterocyclyl, which may be optionally substituted with one or more R$_{20}$'s, 11) halo(C$_1$-C$_6$)alkyl, 12) —CONR$_6$R$_6$, 13) (C$_2$-C$_6$)-alkenyl, 14) (C$_2$-C$_6$)-alkynyl, 15) —COR$_6$, and 16) —COOR$_6$;
(b) aryl, which may be optionally substituted with one or more substituents selected from the group consisting of: 1) halo, 2) (C$_1$-C$_6$)-alkyl, 3) —OR$_6$, 4) (C$_1$-C$_6$)-alkylthio, 5) cyano, 6) nitro, 7) —NR$_9$R$_{10}$, 8) aryl, which may be optionally substituted with one or more R$_{20}$'s, 9) arylalkyl, which may be optionally substituted with one or more R$_{20}$'s, 10) heteroaryl, which may be optionally substituted with one or more R$_{20}$'s, 11) heteroarylalkyl, which may be optionally substituted with one or more R$_{20}$'s, 12) heterocyclyl, which may be optionally substituted with one or more R$_{20}$'s, 13) heterocyclylalkyl, which may be optionally substituted with one or more R$_{20}$'s, 14) halo(C$_1$-C$_6$)alkyl, 15) —CONR$_6$R$_6$, 16) (C$_2$-C$_6$)-alkenyl, 17) =O, 18) (C$_2$-C$_6$)-alkynyl, 19) —COR$_6$, and 20) —COOR$_6$;
(c) cycloalkyl, which may be optionally substituted with one or more substituents selected from the group consisting of: 1) halo, 2) (C$_1$-C$_6$)-alkyl, 3) —OR$_6$, 4) (C$_1$-C$_6$)-alkylthio, 5) cyano, 6) nitro, 7) —NR$_9$R$_{10}$, 8) aryl, which may be optionally substituted with one or more R$_{20}$'s, 9) arylalkyl, which may be optionally substituted with one or more R$_{20}$'s, 10) heteroaryl, which may be optionally substituted with one or more R$_{20}$'s, 11) heteroarylalkyl, which may be optionally substituted with one or more R$_{20}$'s, 12) heterocyclyl, which may be optionally substituted with one or more R$_{20}$'s, 13) heterocyclylalkyl, which may be optionally substituted with one or more R$_{20}$'s, 14) halo(C$_1$-C$_6$)alkyl, 15) —CONR$_6$R$_6$, 16) (C$_2$-C$_6$)-alkenyl, 17) =O, 18) (C$_2$-C$_6$)-alkynyl, 19) —COR$_6$, and 20) —COOR$_6$;
(d) heteroaryl, which may be optionally substituted with one or more substituents selected from the group consisting of: 1) halo, 2) (C$_1$-C$_6$)-alkyl, 3) —OR$_6$, 4) (C$_1$-C$_6$)-alkylthio, 5) cyano, 6) nitro, 7) —NR$_9$R$_{10}$, 8) aryl, which may be optionally substituted with one or more R$_{20}$'s, 9) arylalkyl, which may be optionally substituted with one or more R$_{20}$'s, 10) heteroaryl, which may be optionally substituted with one or more R$_{20}$'s, 11) heteroarylalkyl, which may be optionally substituted with one or more R$_{20}$'s, 12) heterocyclyl, which may be optionally substituted with one or more R$_{20}$'s, 13) heterocyclylalkyl, which may be optionally substituted with one or more R$_{20}$'s, 14) halo(C$_1$-C$_6$)alkyl, 15) —CONR$_6$R$_6$, 16) (C$_2$-C$_6$)-alkenyl, 17) =O, 18) (C$_2$-C$_6$)-alkynyl, 19) —COR$_6$, and 20) —COOR$_6$; or
(e) heterocyclyl, other than heteroaryl, which may be optionally substituted with one or more substituents selected from the group consisting of: 1) halo, 2) (C$_1$-C$_6$)-alkyl, 3) —OR$_6$, 4) (C$_1$-C$_6$)-alkylthio, 5) cyano, 6) nitro, 7) —NR$_9$R$_{10}$, 8) aryl, which may be optionally substituted with one or more R$_{20}$'s, 9) arylalkyl, which may be optionally substituted with one or more R$_{20}$'s, 10) heteroaryl, which may be optionally substituted with one or more R$_{20}$'s, 11) heteroarylalkyl, which may be optionally substituted with one or more R$_{20}$'s, 12) heterocyclyl, which may be optionally substituted with one or more R$_{20}$'s, 13) heterocyclylalkyl, which may be optionally substituted with one or more R$_{20}$'s, 14) halo(C$_1$-C$_6$)alkyl, 15) —CONR$_6$R$_6$, 16) (C$_2$-C$_6$)-alkenyl, 17) =O, 18) (C$_2$-C$_6$)-alkynyl, 19) —COR$_6$, and 20) —COOR$_6$;
R$_6$, at each occurrence, is independently:
(a) alkyl, which may be optionally substituted with one or more substituents selected from the group consisting of: 1) halo, 2) —OH, 3) (C$_1$-C$_6$)-alkyl, 4) —OR$_{36}$, 5) (C$_1$-C$_6$)-alkylthio, 6) cyano, 7) nitro, 8) —NR$_9$R$_{10}$, 9) aryl, which may be optionally substituted with one or more R$_{20}$'s, 10) heteroaryl, which may be optionally substituted with one or more R$_{20}$'s, 11) heterocyclyl, which may be optionally substituted with one or more R$_{20}$'s, 12) halo(C$_1$-C$_6$)alkyl, 13) (C$_2$-C$_6$)-alkenyl, 14) —COOH, 15) —CONR$_{36}$R$_{36}$, 16) =O, 17) (C$_2$-C$_6$)-alkynyl, 18) —COR$_{36}$, 19) —SO$_2$NHR$_{36}$, 20) —COOR$_{36}$, and 21) —NHC(CN)NHR$_{36}$;
(b) aryl, which may be optionally substituted with one or more substituents selected from the group consisting of: 1) halo, 2) —OH, 3) (C$_1$-C$_6$)-alkyl, 4) —OR$_{36}$, 5) (C$_1$-C$_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$) alkyl, 16) —COOH, 17) —CONR$_{36}$R$_{36}$, 18) =O, 19) ($C_2$-$C_6$)-alkynyl, 20) —COR$_{36}$, 21) —SO$_2$NHR$_{36}$, 22) —COOR$_{36}$, and 23) —NHC(CN)NHR$_{36}$;

(c) heteroaryl, which may be optionally substituted with one or more substituents selected from the group consisting of: 1) halo, 2) —OH, 3) ($C_1$-$C_6$)-alkyl, 4) —OR$_{36}$, 5) ($C_1$-$C_6$)-alkylthio, 6) cyano, 7) nitro, 8) —NR$_9$R$_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —SO$_2$NHR$_{36}$, 23) —COOR$_{36}$, and 24) —NHC(CN)NHR$_{36}$; or (d) hydrogen;

$R_9$ and $R_{10}$ are independently: (a) hydrogen; or (b) —[(C=O)O$_r$]$_s$($C_1$-$C_8$)alkyl, wherein the alkyl may be optionally substituted with one or more $R_{20}$'s;

$R_{20}$ is: (a) halo; (b) ($C_1$-$C_6$)-alkyl; (c) —OR$_{26}$; (d) ($C_1$-$C_6$)-alkylthio; (e) cyano; (f) nitro; (g) —NR$_{29}$R$_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p)-($C_2$-$C_6$)-alkynyl; (q) —COR$_{26}$; (r) —COOR$_{26}$; (s) cycloalkyl, which may be optionally substituted with one or more $R_{21}$'s; (t) cycloalkylalkyl, which may be optionally substituted with one or more $R_{21}$'s; or (u) —CONR$_{26}$R$_{26}$;

$R_{21}$ is: (a) halo; (b) ($C_1$-$C_6$)-alkyl; (c) —OR$_{26}$; (d) ($C_1$-$C_6$)-alkylthio; (e) cyano; (f) nitro; (g) —NR$_{29}$R$_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o)—CONR$_{26}$R$_{26}$; (p) ($C_2$-$C_6$)-alkenyl; (q) ($C_2$-$C_6$)-alkynyl; (r) cycloalkyl; (s) cycloalkylalkyl; (t) —COR$_{26}$; or (u) —COOR$_{26}$;

$R_{26}$, at each occurrence, is independently:
(a) alkyl, which may be optionally substituted with one or more substituents selected from the group consisting of: 1) halo, 2) —OH, 3) ($C_1$-$C_6$)-alkyl, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —CONR$_{36}$R$_{36}$, 16) =O, 17) ($C_2$-$C_6$)-alkynyl, 18) —COR$_{36}$, 19) —SO$_2$NHR$_{36}$, 20) —COOR$_{36}$, and 21) —NHC(CN)NHR$_{36}$;

(b) aryl, which may be optionally substituted with one or more substituents selected from the group consisting of: 1) halo, 2) —OH, 3) ($C_1$-$C_6$)-alkyl, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$) alkyl, 16) —COOH, 17) —CONR$_{36}$R$_{36}$, 18) =O, 19) ($C_2$-$C_6$)-alkynyl, 20) —COR$_{36}$, 21) —SO$_2$NHR$_{36}$, 22) —COOR$_{36}$, and 23) —NHC(CN)NHR$_{36}$;

(c) heteroaryl, which may be optionally substituted with one or more substituents selected from the group consisting of: 1) halo, 2) —OH, 3) ($C_1$-$C_6$)-alkyl, 4) —OR$_{36}$, 5) ($C_1$-$C_6$)-alkylthio, 6) cyano, 7) nitro, 8) —NR$_{29}$R$_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —CONR$_{36}$R$_{36}$, 19) =O, 20) ($C_2$-$C_6$)-alkynyl, 21) —COR$_{36}$, 22) —SO$_2$NHR$_{36}$, 23) —COOR$_{36}$, and 24) —NHC(CN)NHR$_{36}$; or (d) hydrogen;

$R_{29}$ and $R_{30}$ are independently hydrogen or —[(C=O)O$_r$]$_s$alkyl, wherein the alkyl may be optionally substituted with one or more $R_{40}$'s;

$R_{36}$, at each occurrence, is independently alkyl, aryl or heteroaryl, wherein the alkyl, aryl or heteroaryl may be optionally substituted with one or more $R_{40}$'s;

$R_{40}$ is halo, —OH, alkyl, alkyloxy, alkylthio, cyano, nitro, aryl, arylalkyl, heteroaryl, heteroarylalkyl, heterocyclyl, heterocyclylalkyl, haloalkyl, haloalkyloxy, alkenyl, arylalkyloxy, =O, alkynyl, cycloalkyl or cycloalkylalkyl;

r is 0 to 2; and s is 0 to 1.

9. A compound of claim 1, wherein:

A is:

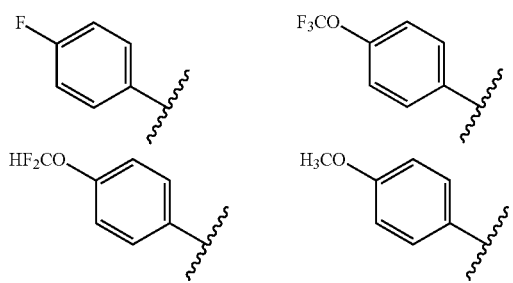

1103
-continued
1104
-continued
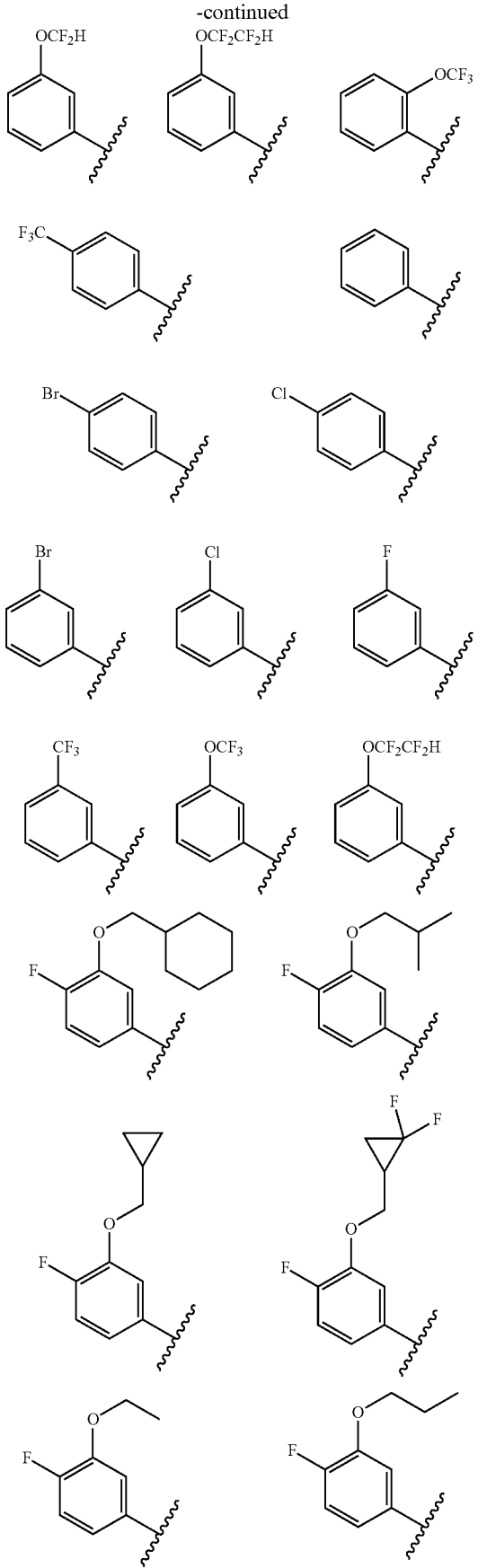
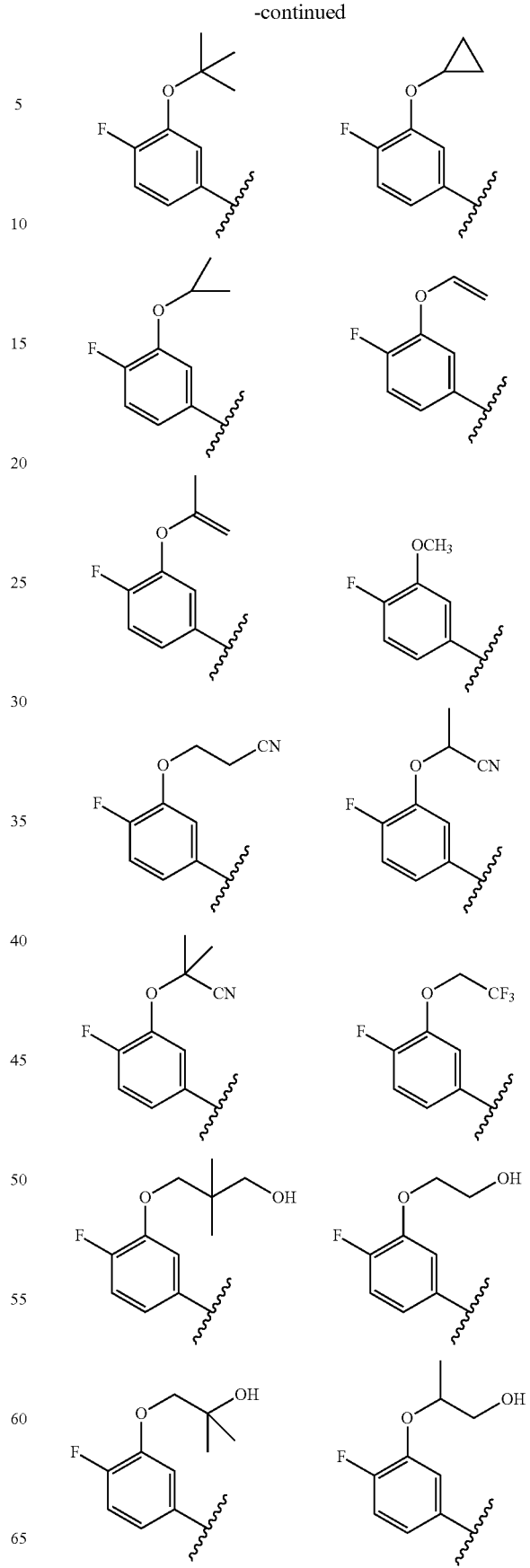

1105
-continued
1106
-continued
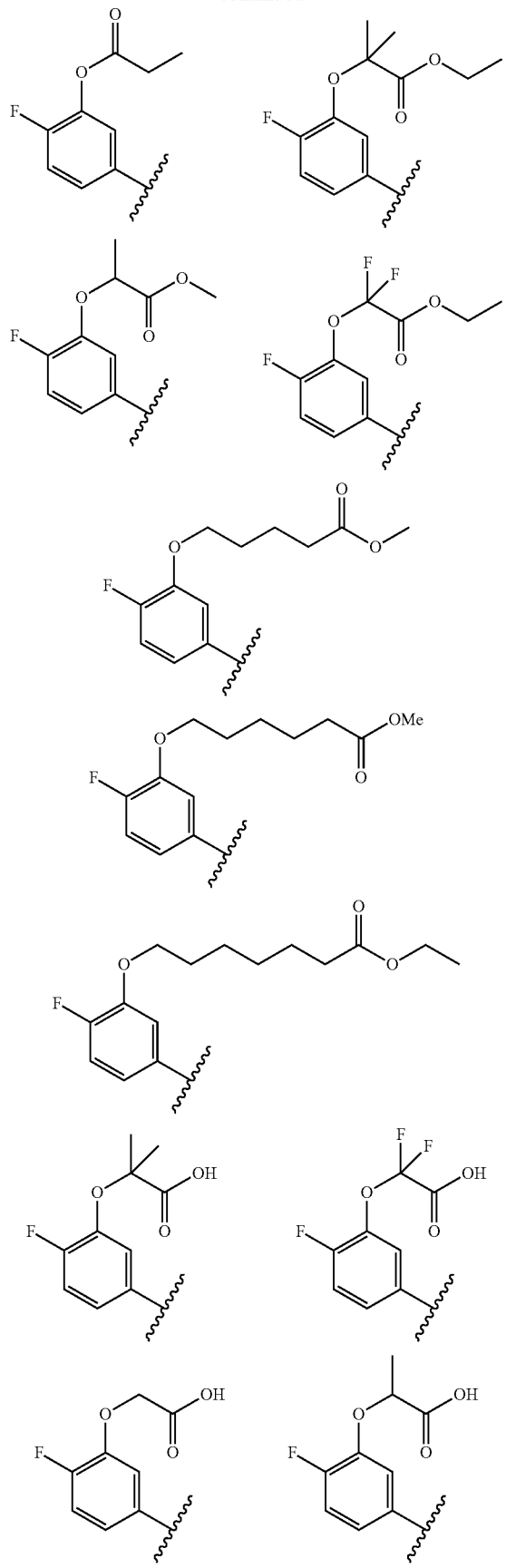
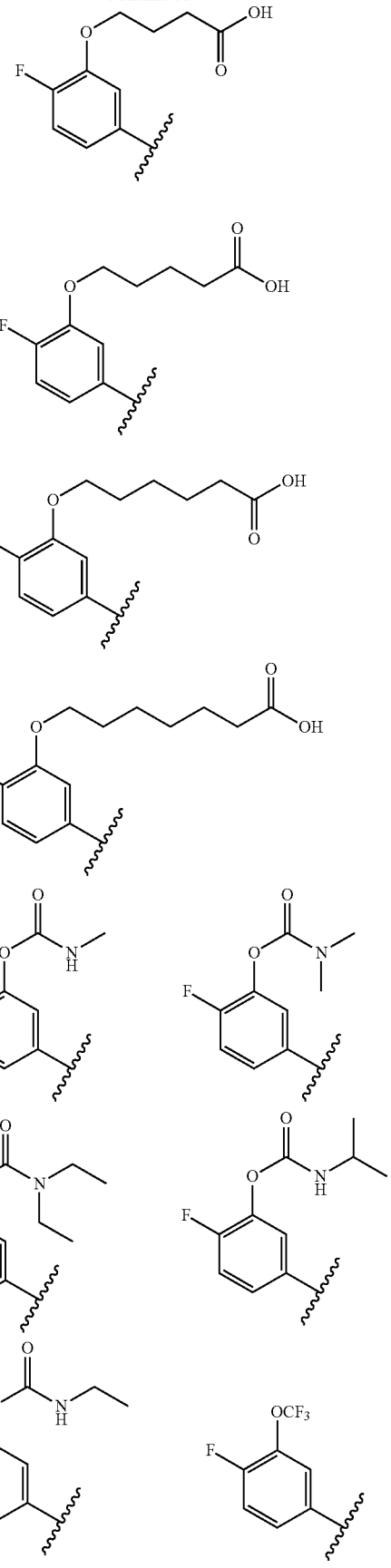

1107
-continued
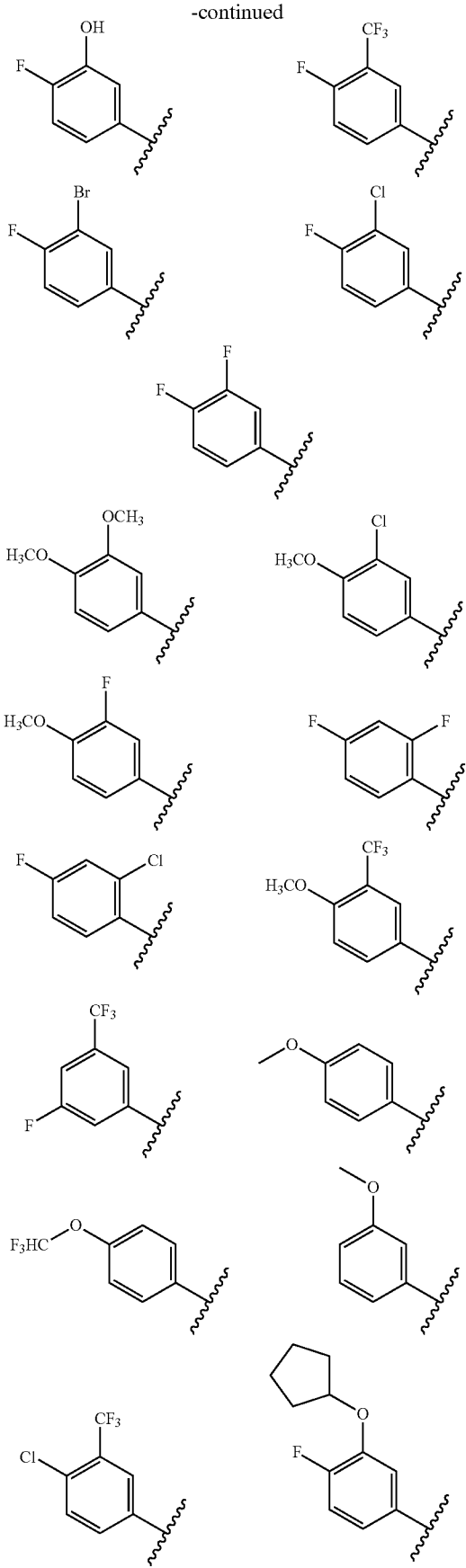
1108
-continued
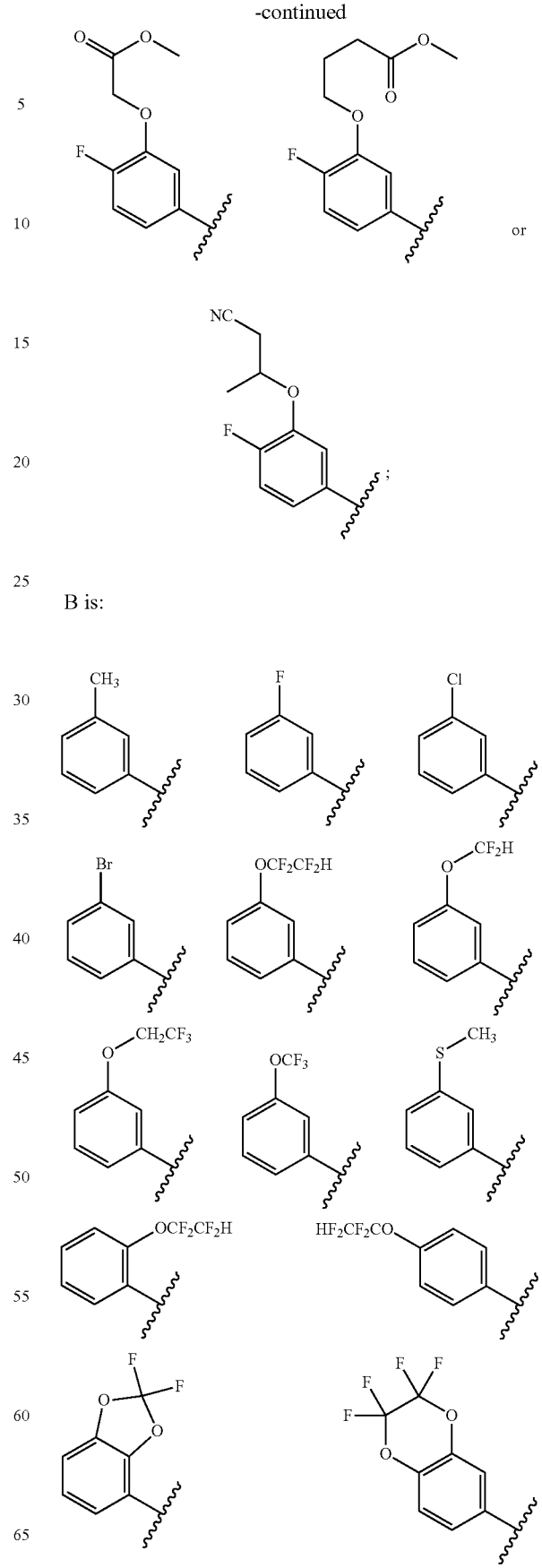
B is:

1109
-continued
1110
-continued
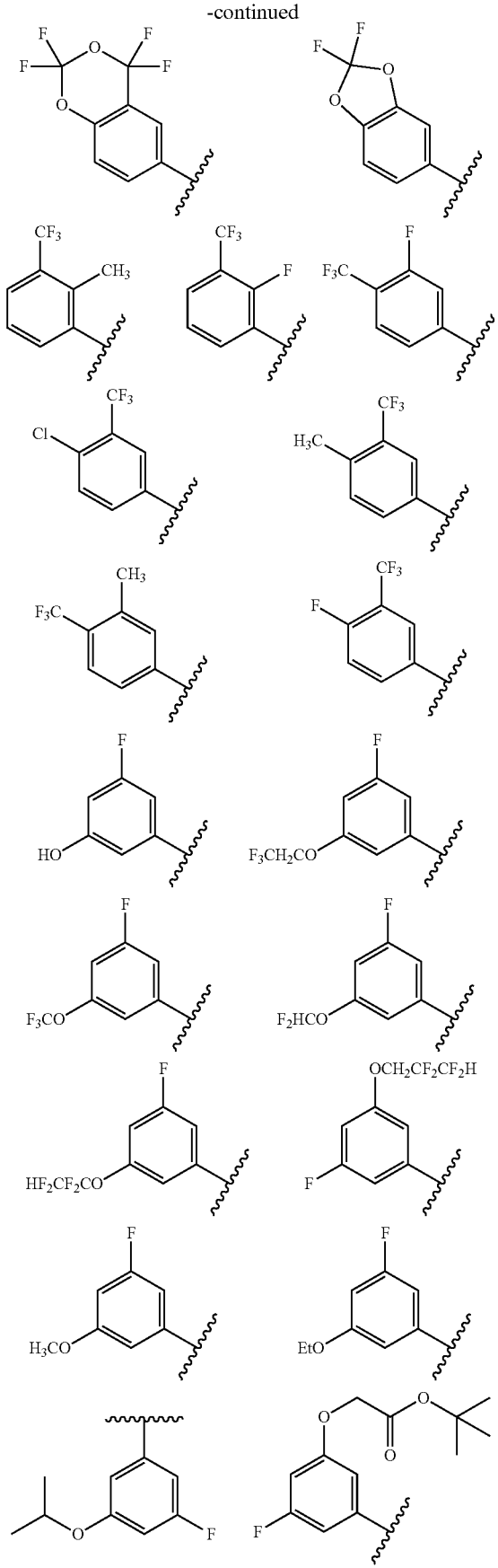
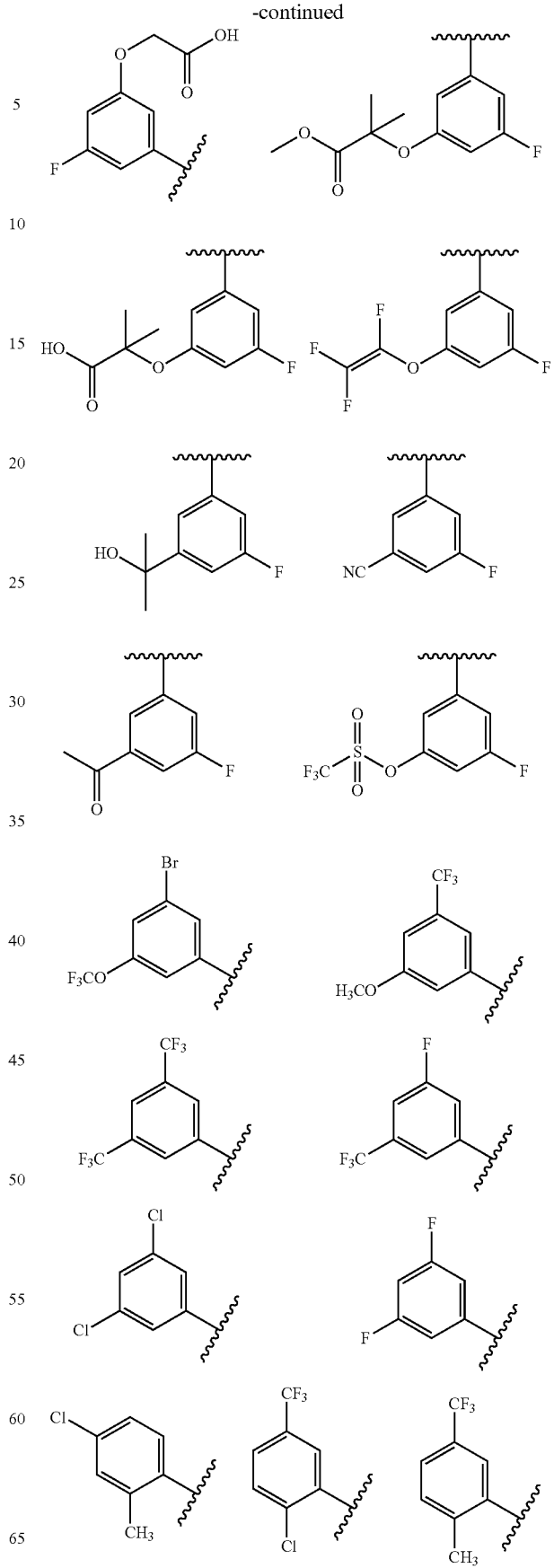

1111
-continued
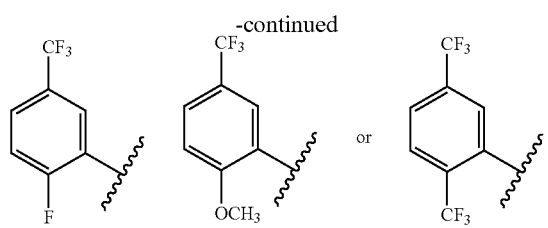
C is:
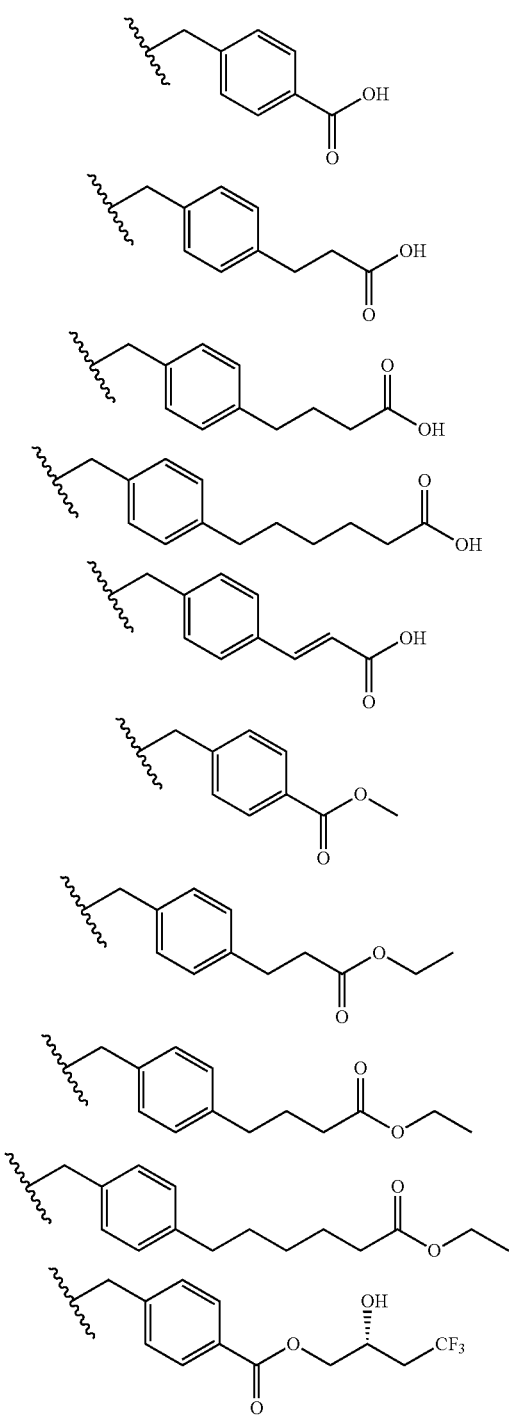
1112
-continued
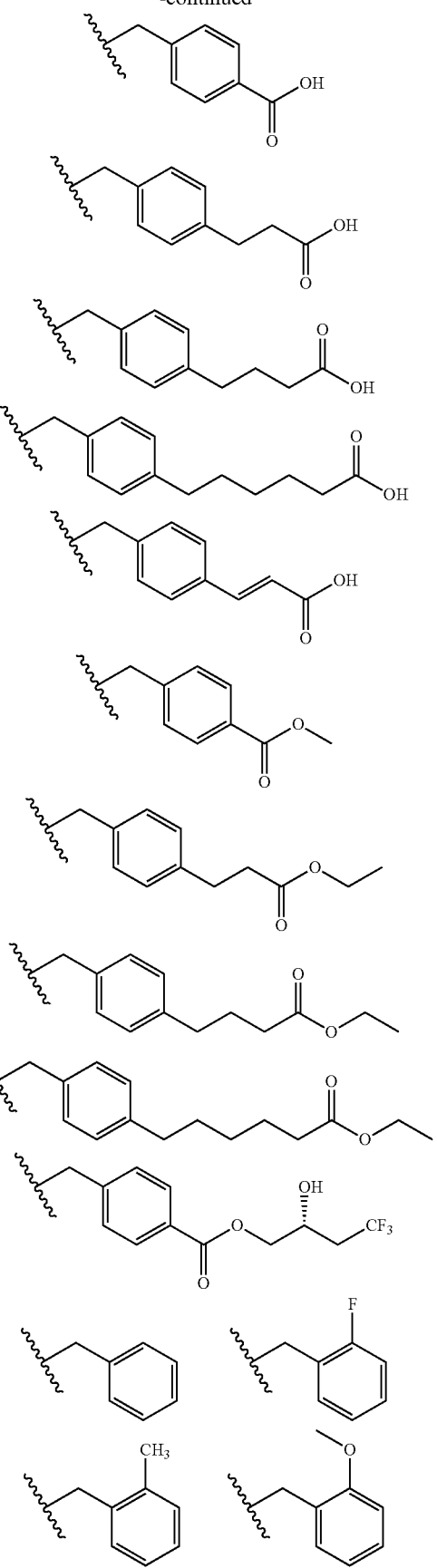

1113
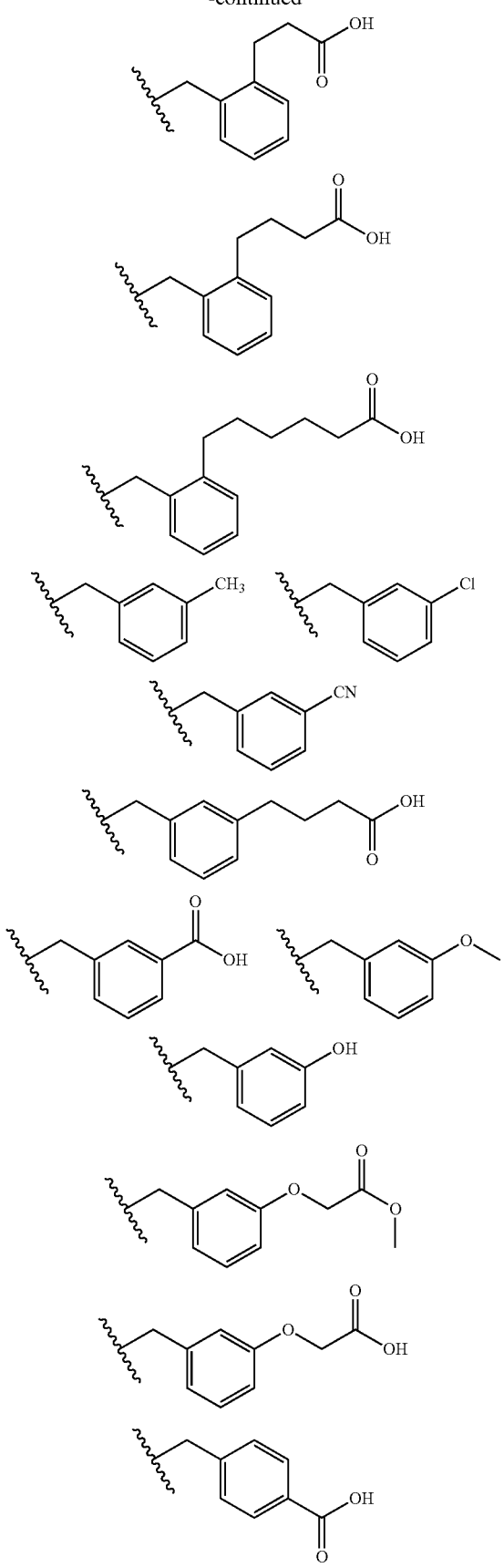
1114
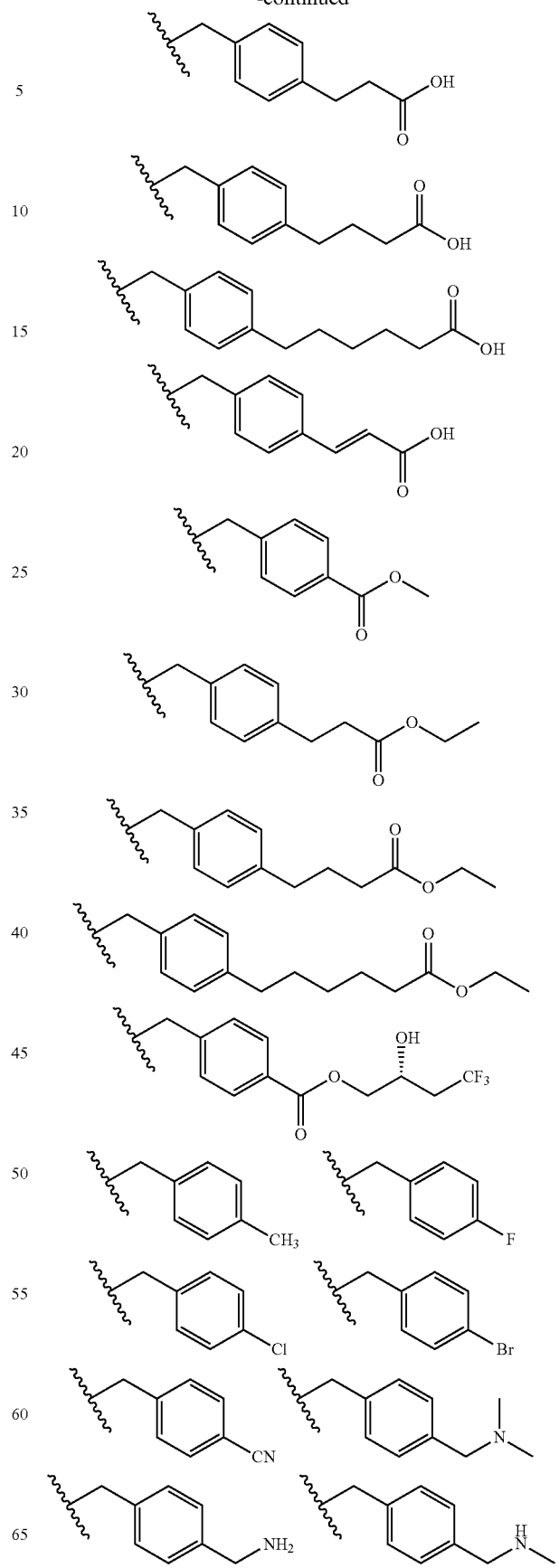

1115
-continued
1116
-continued
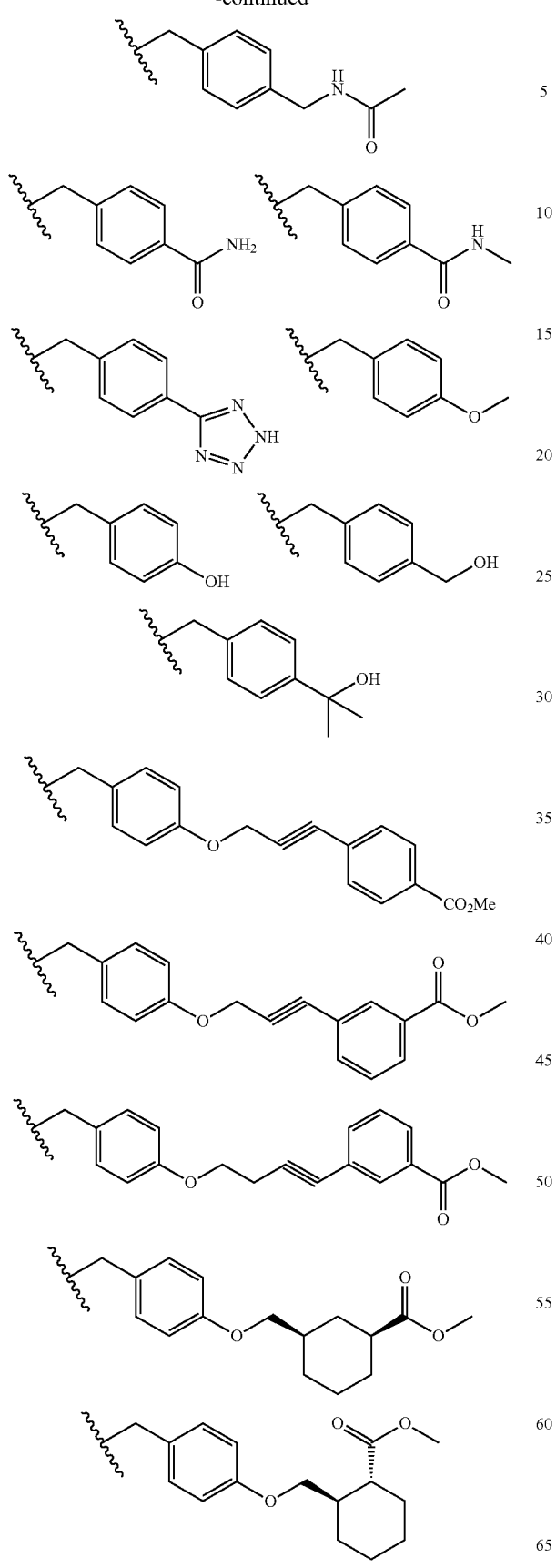
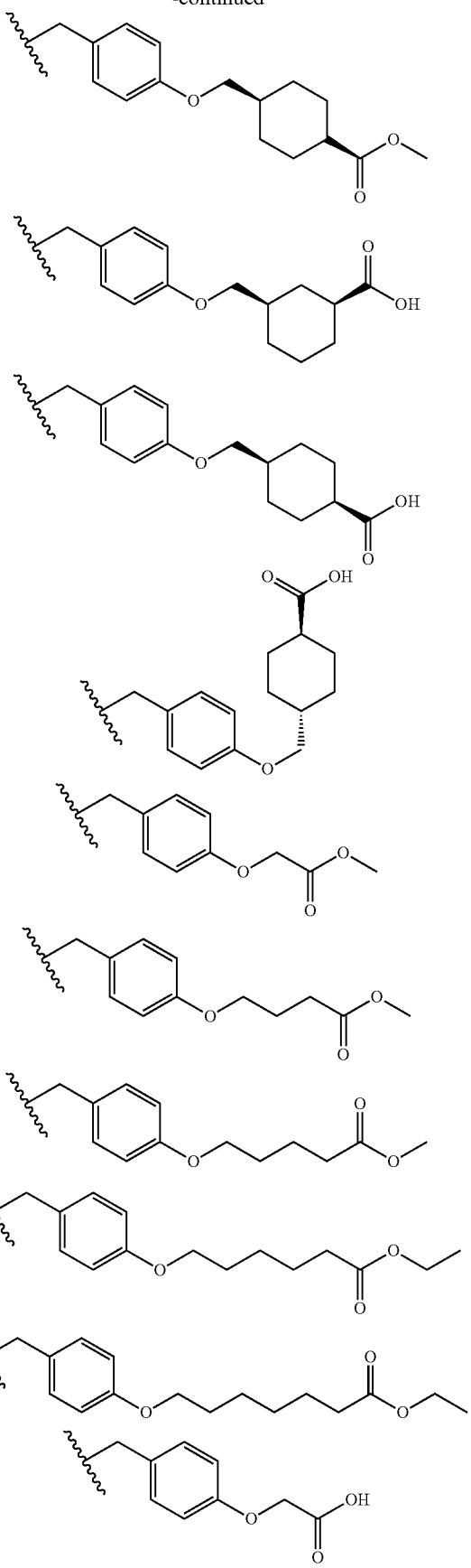

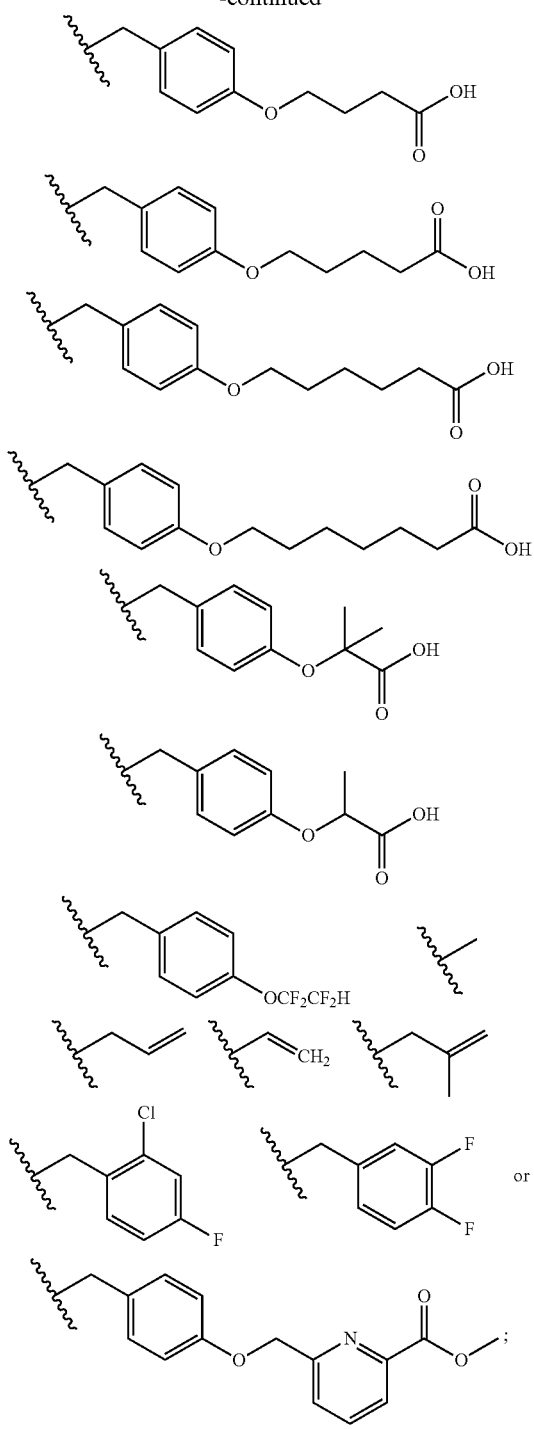
R₁ is:
(a) —C(O)NHR₃, wherein the R₃ is:
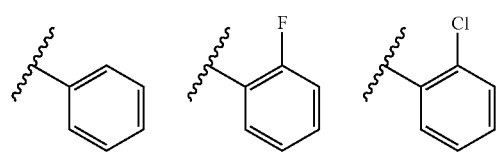
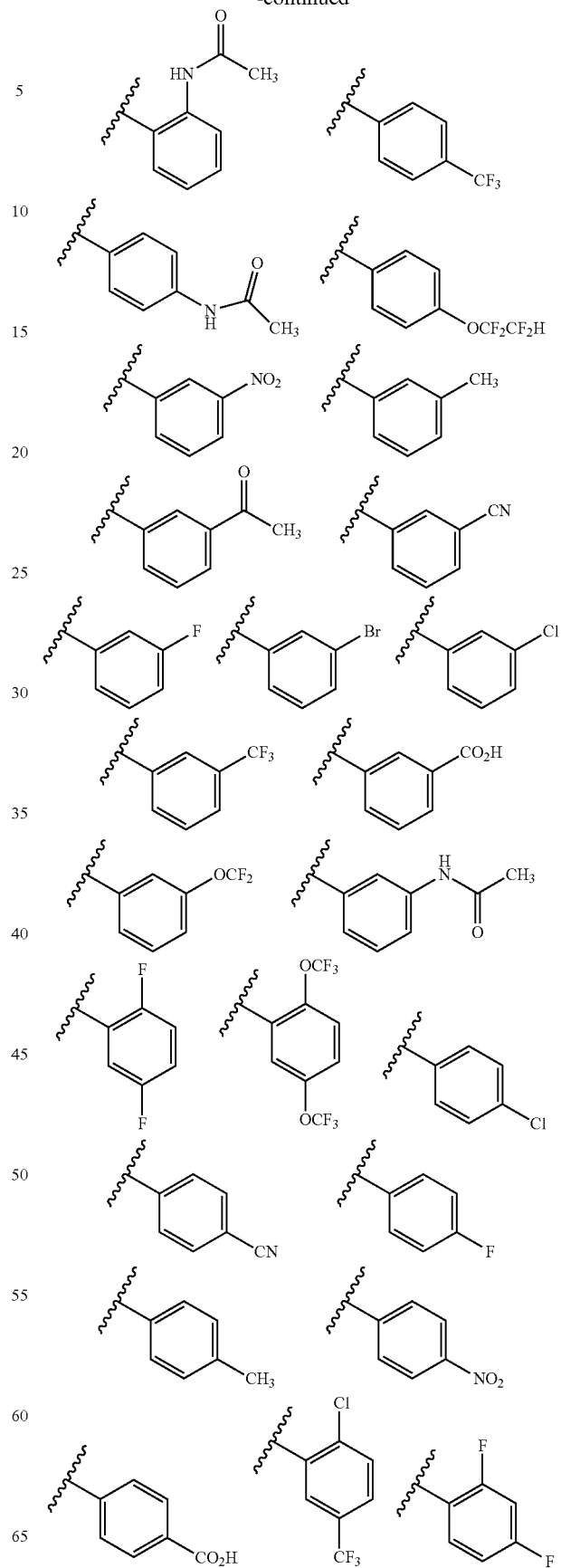

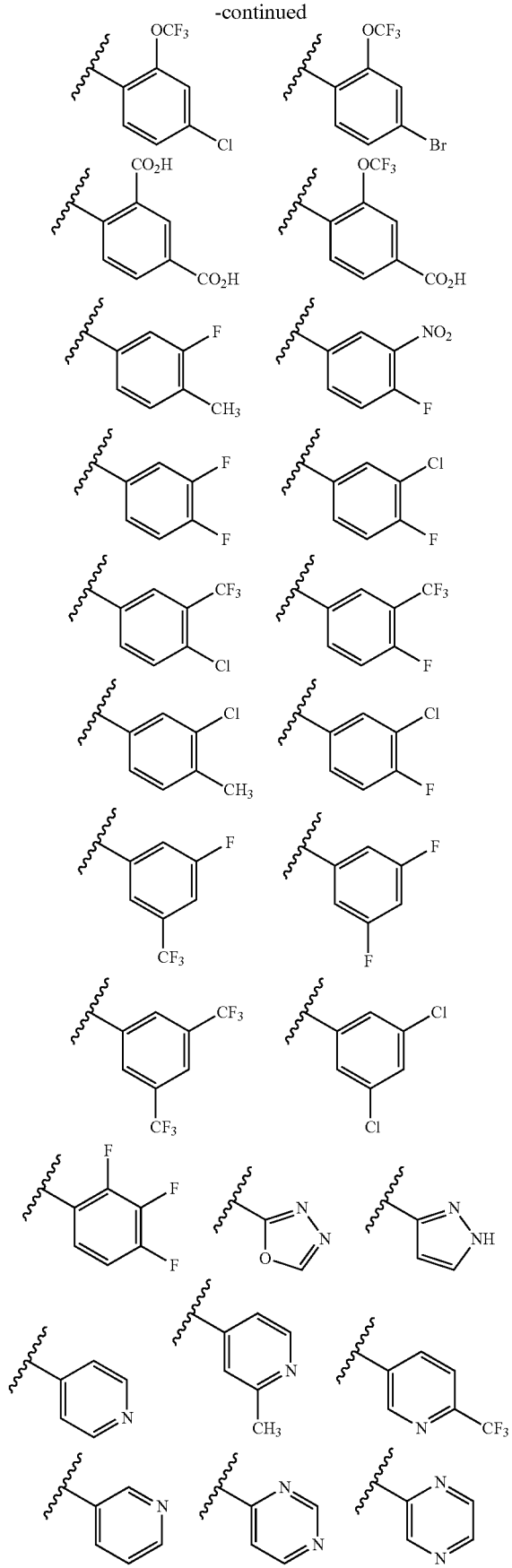
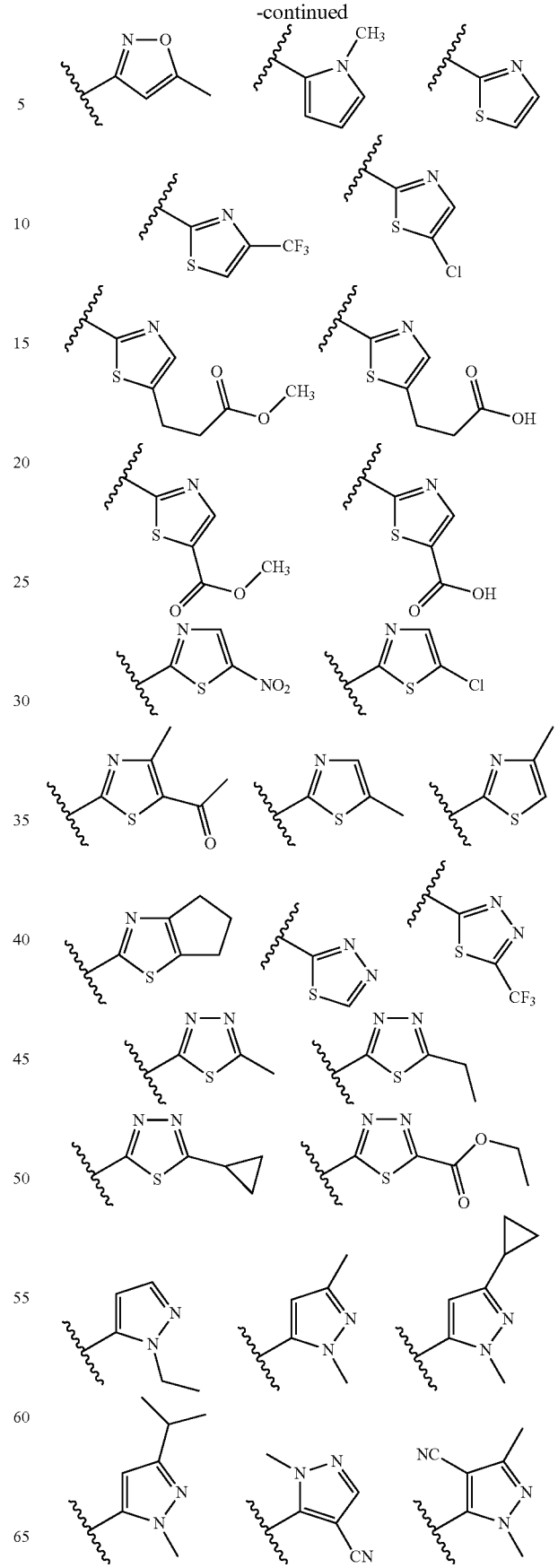

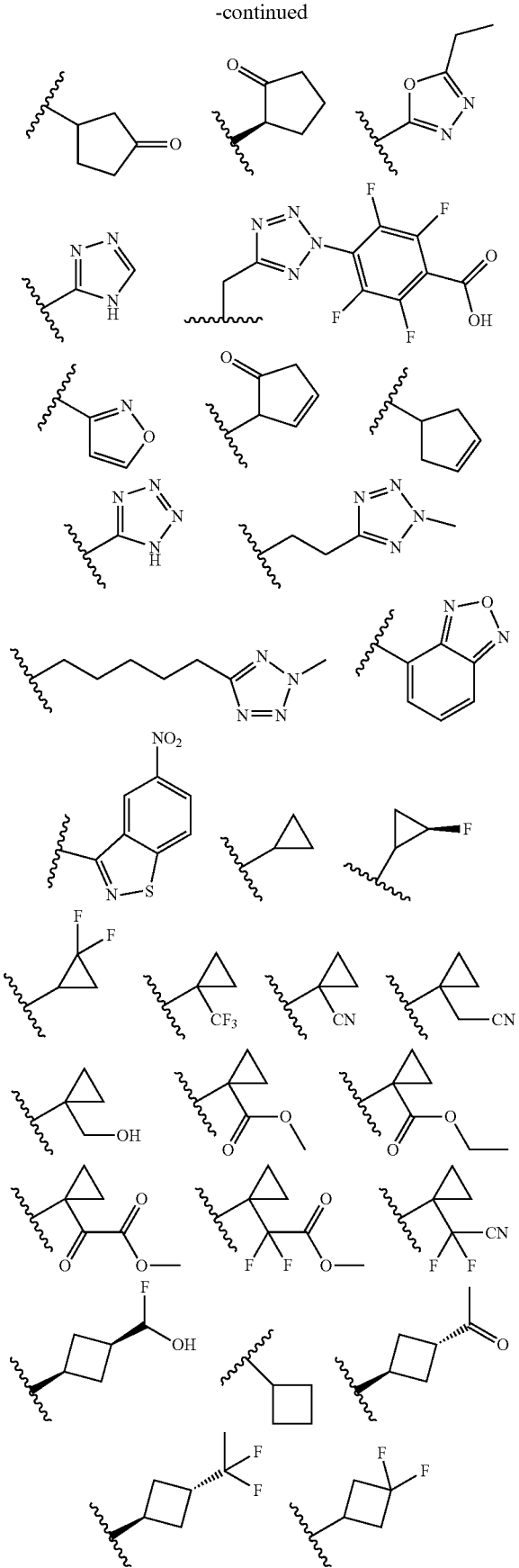
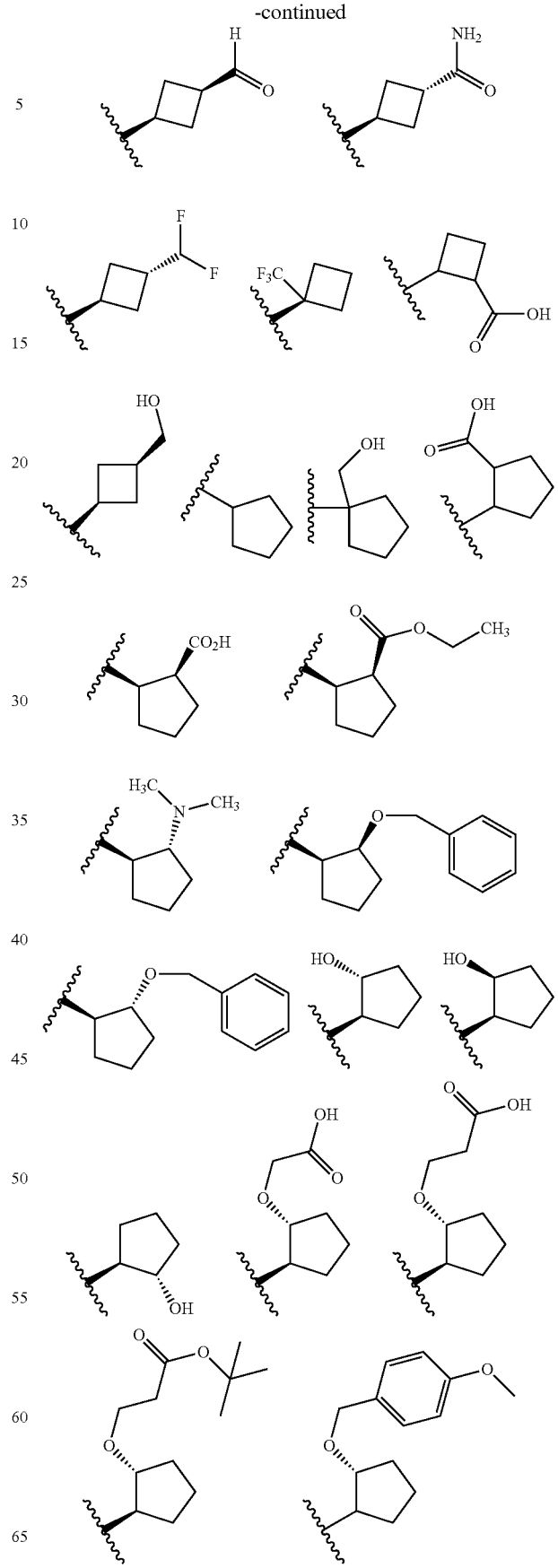

1123
-continued
1124
-continued
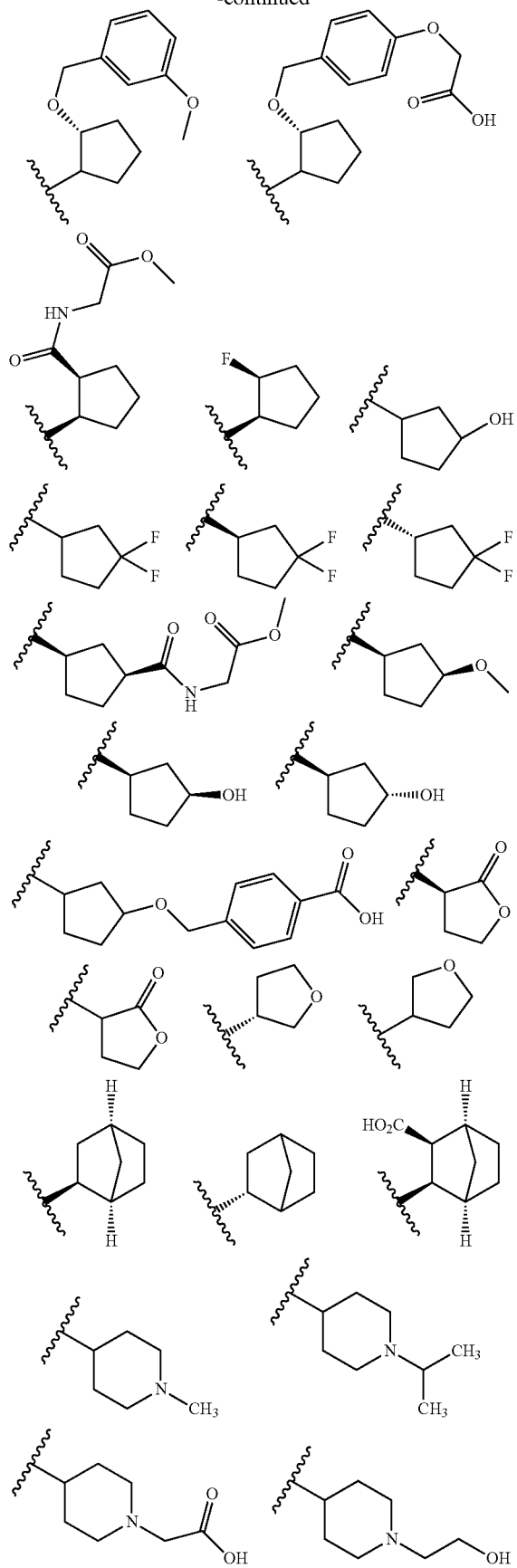
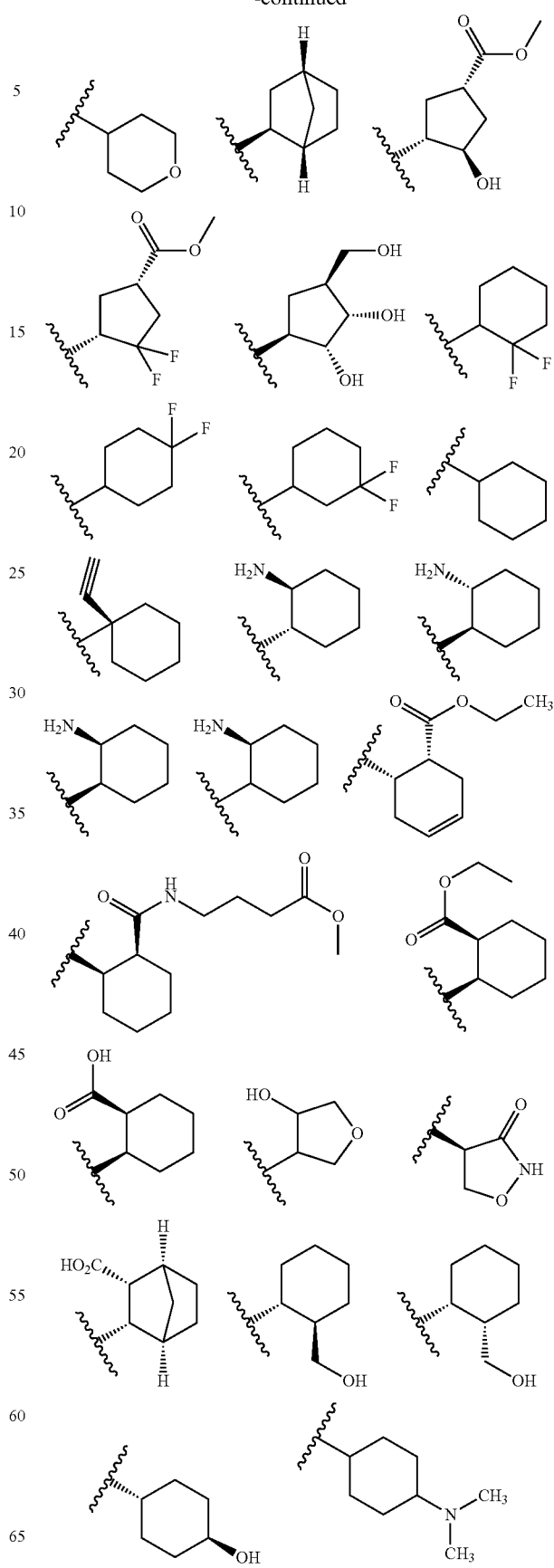

1125
-continued
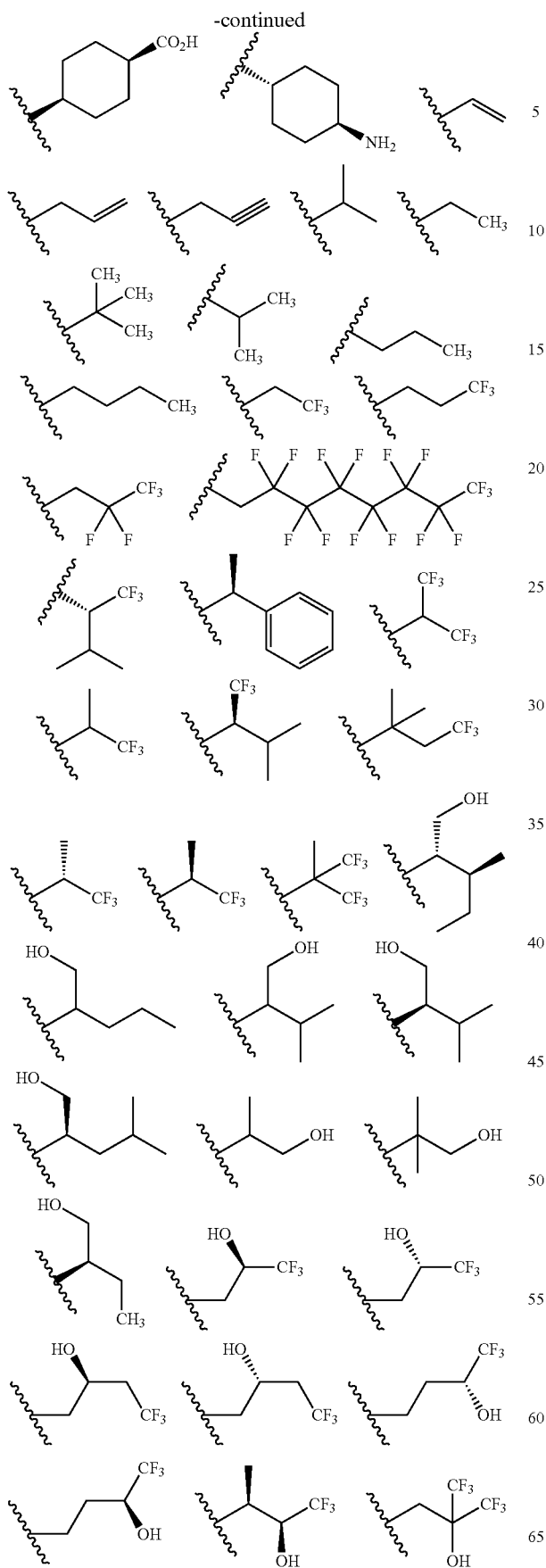
1126
-continued
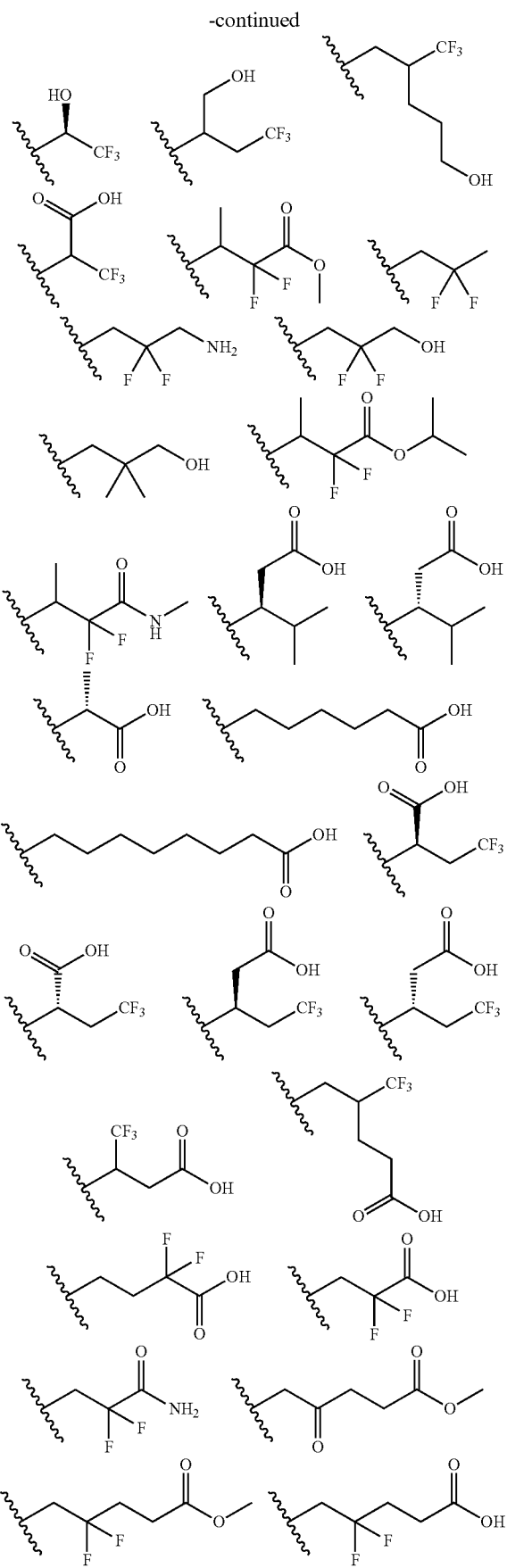

1127
-continued
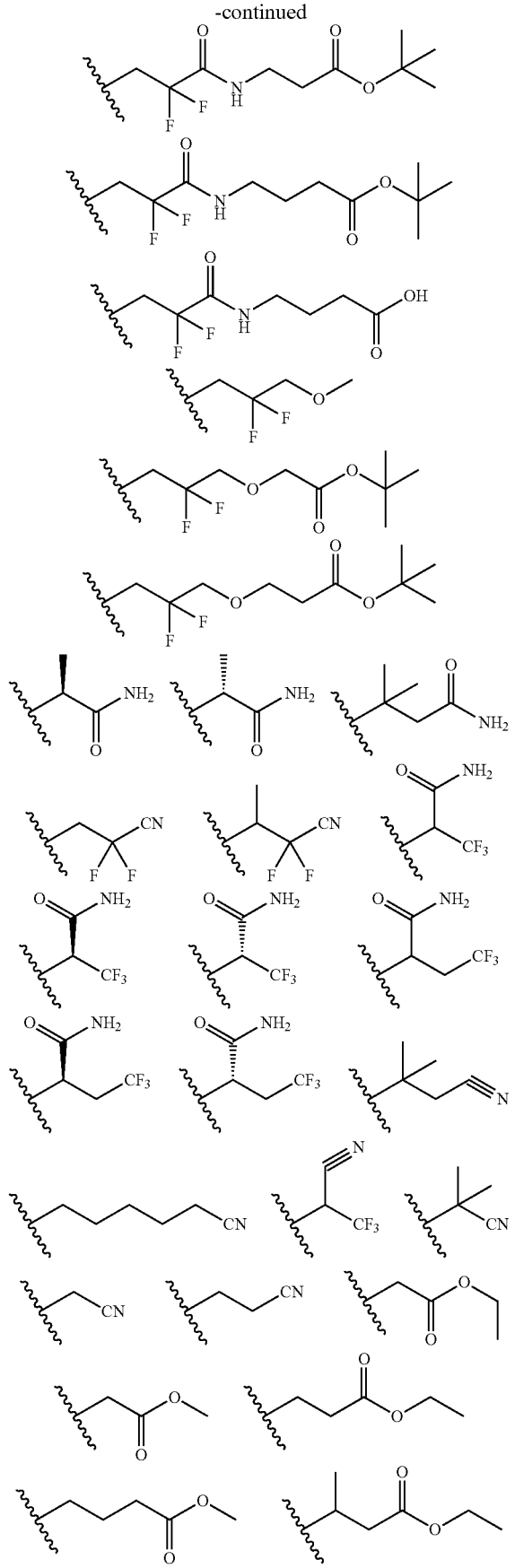
1128
-continued
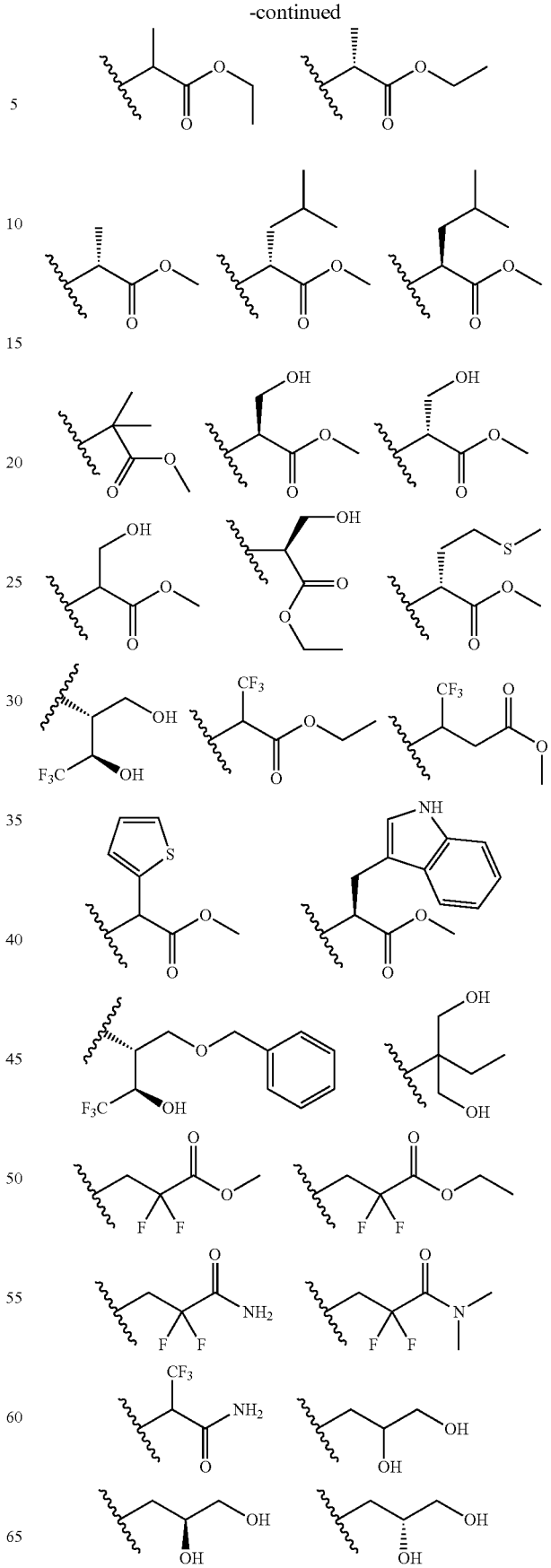

1129
-continued
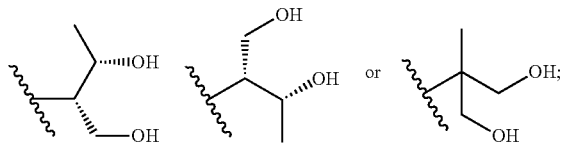
(b) —C(O)NR₂R₃, wherein the NR₂R₃ is:
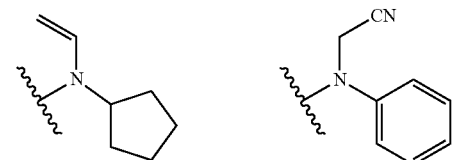
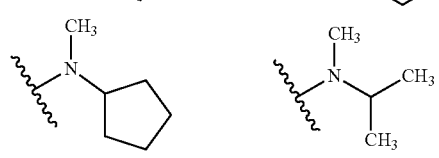
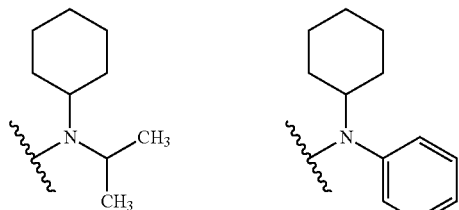
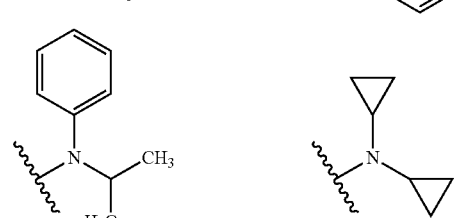
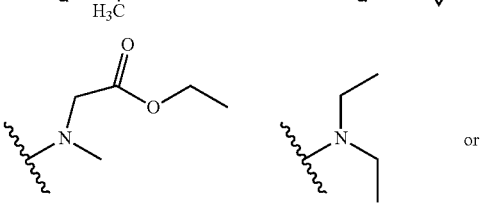
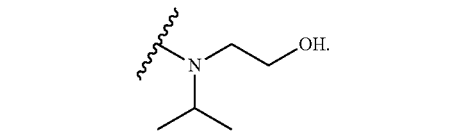 or
10. A compound of claim 2, wherein:
A is:
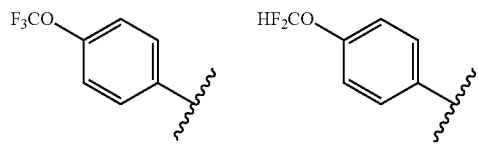
1130
-continued
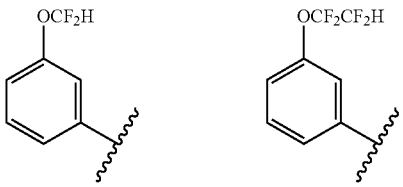

1131
-continued
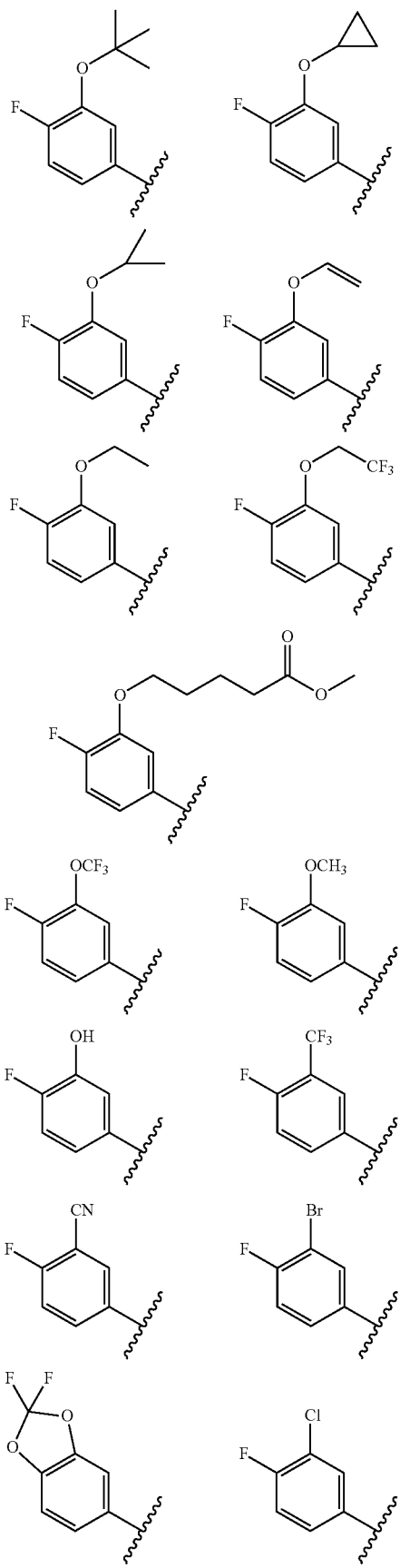
1132
-continued
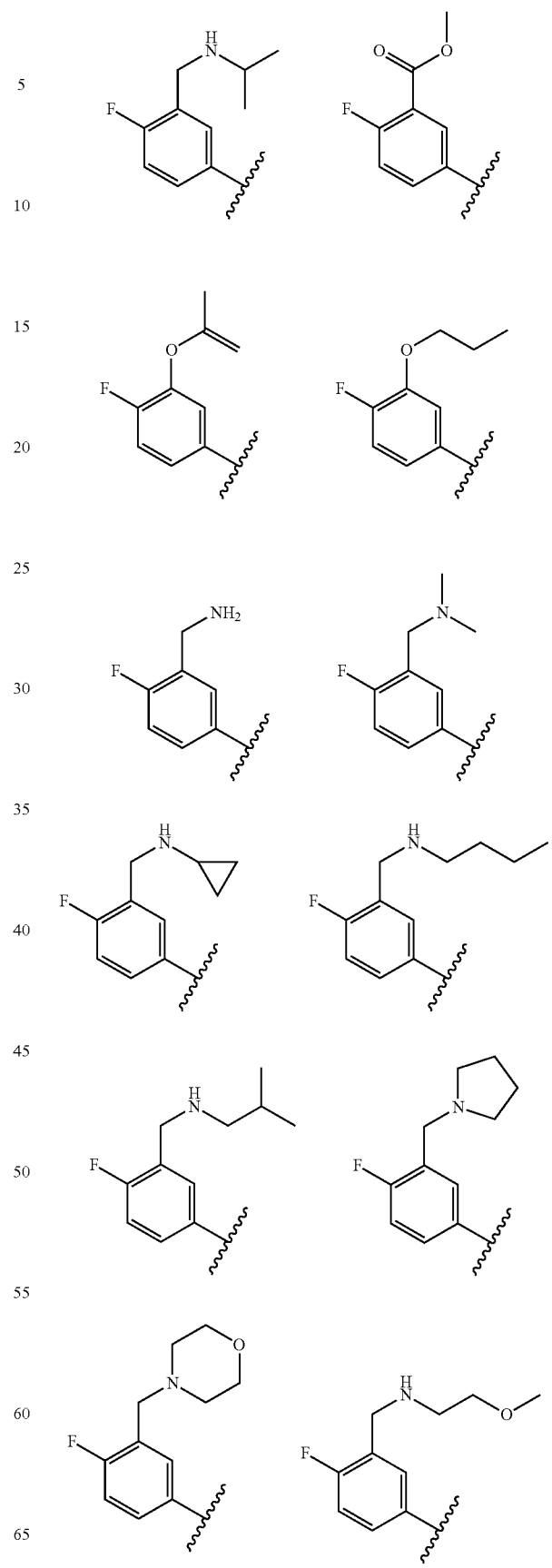

1133
-continued
1134
-continued
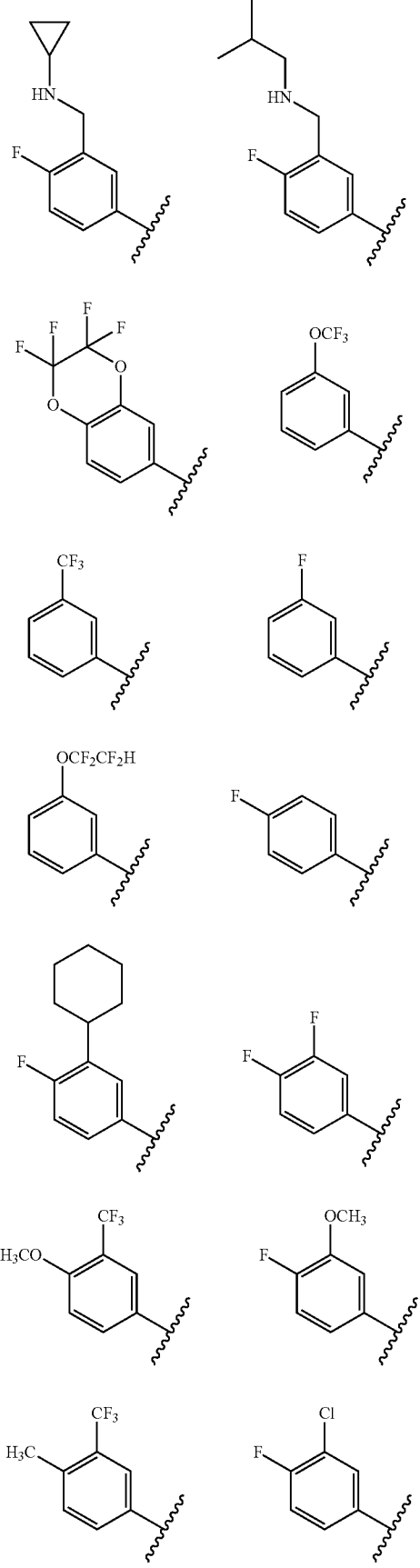
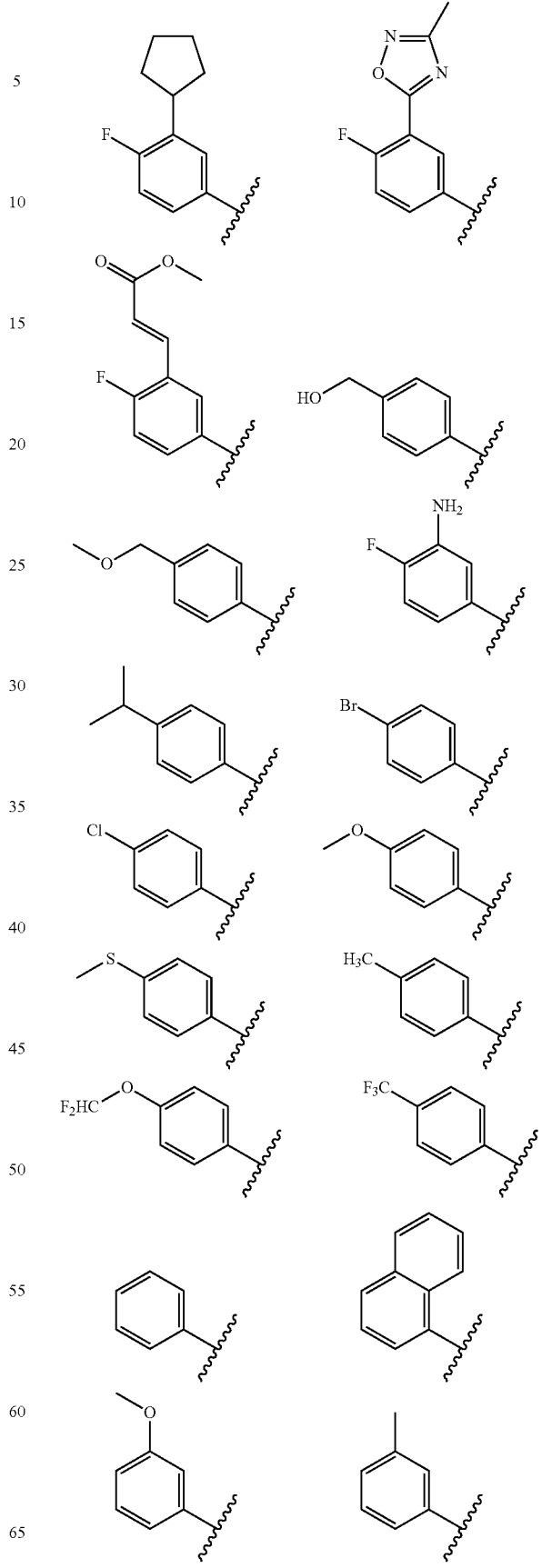

1135
-continued
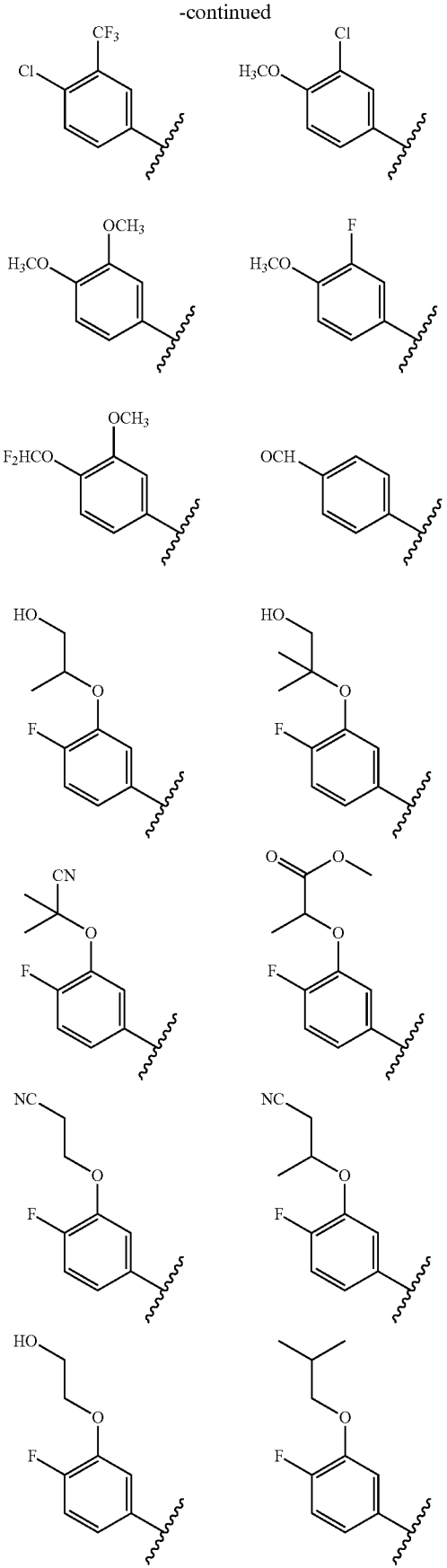
1136
-continued
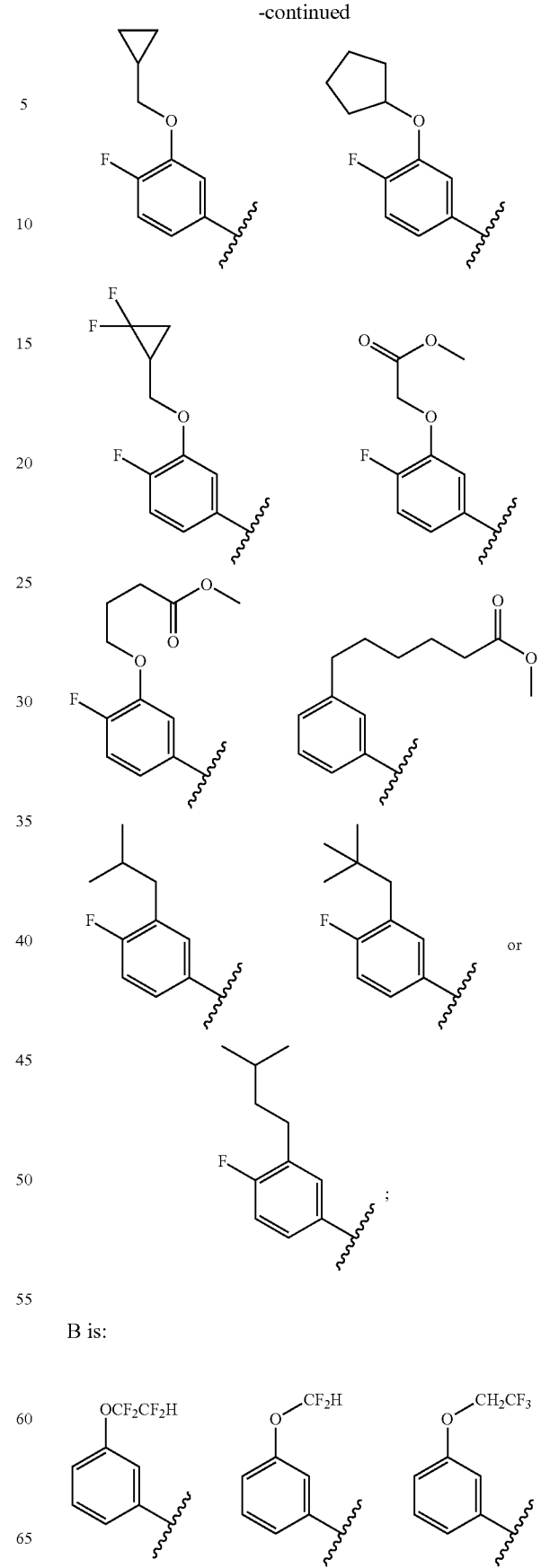
B is:

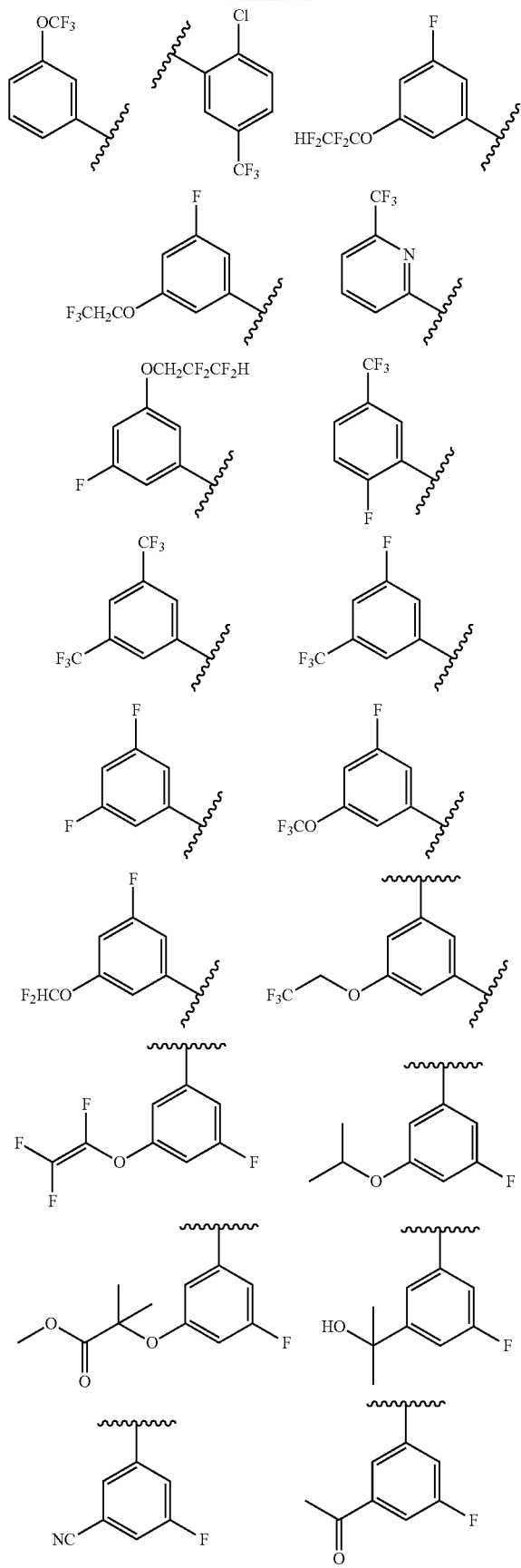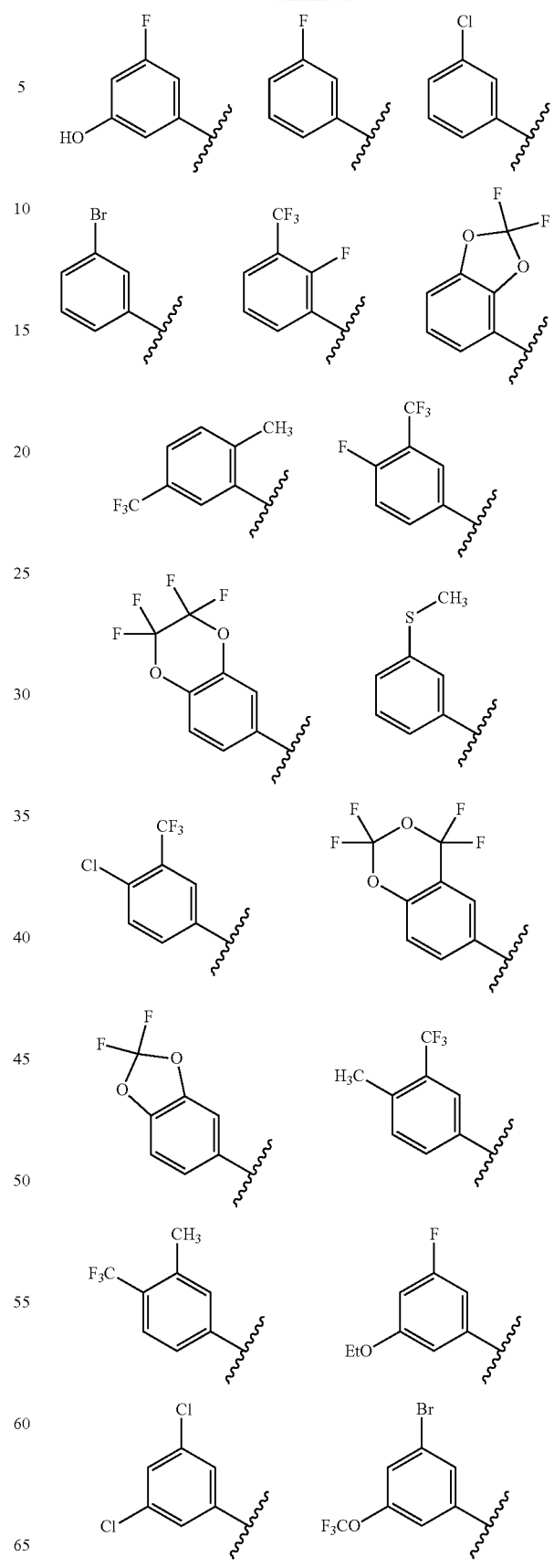

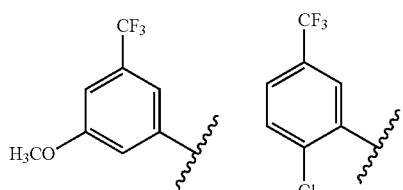
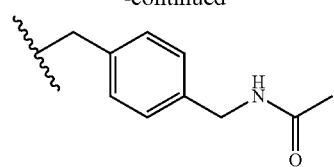
or
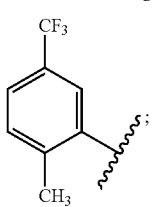
C is:
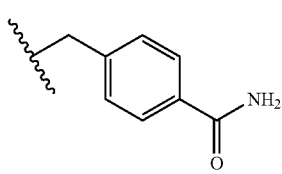
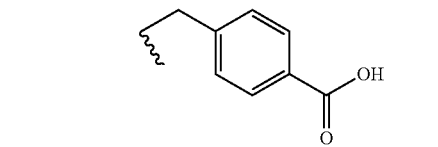
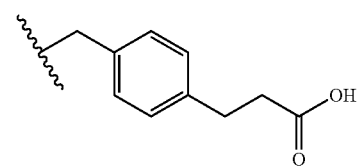
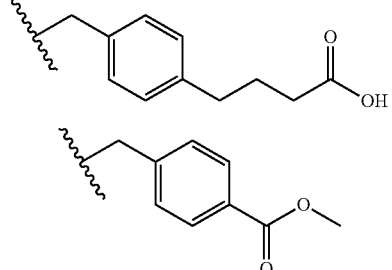
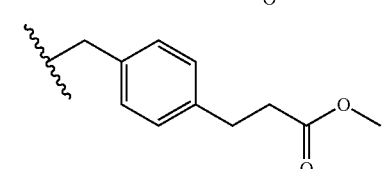
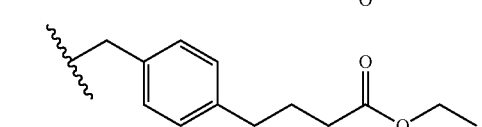
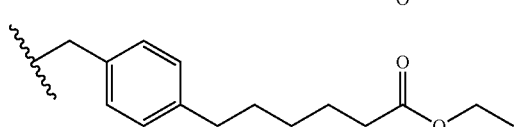
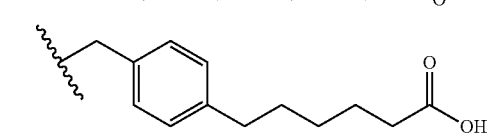

1141
-continued
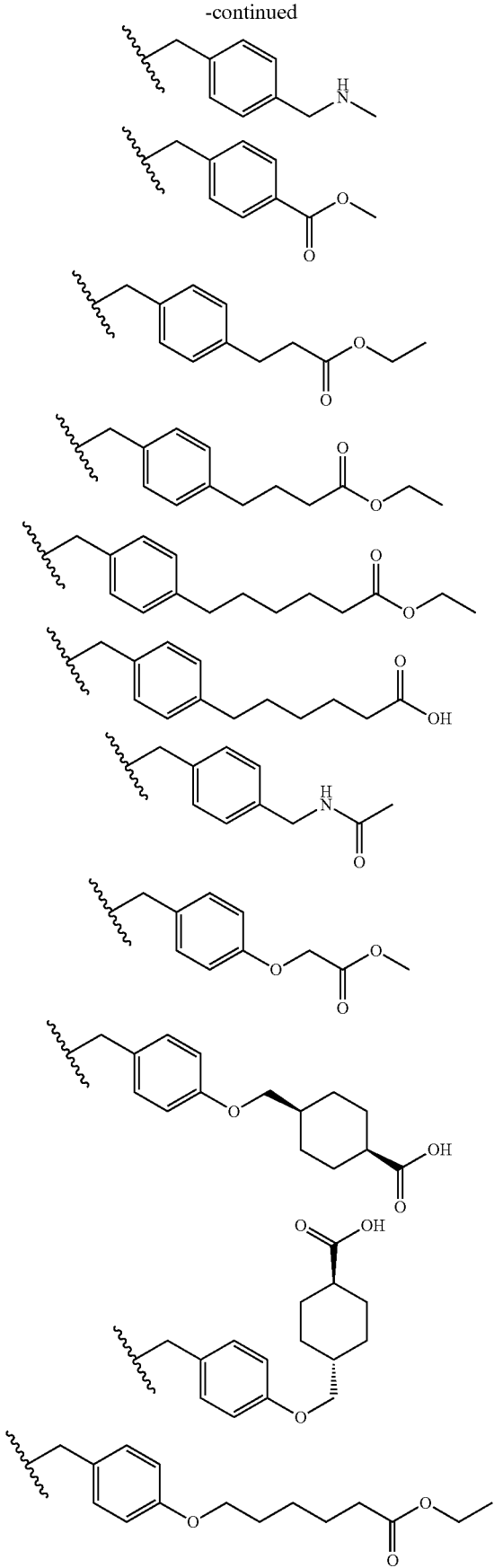
1142
-continued
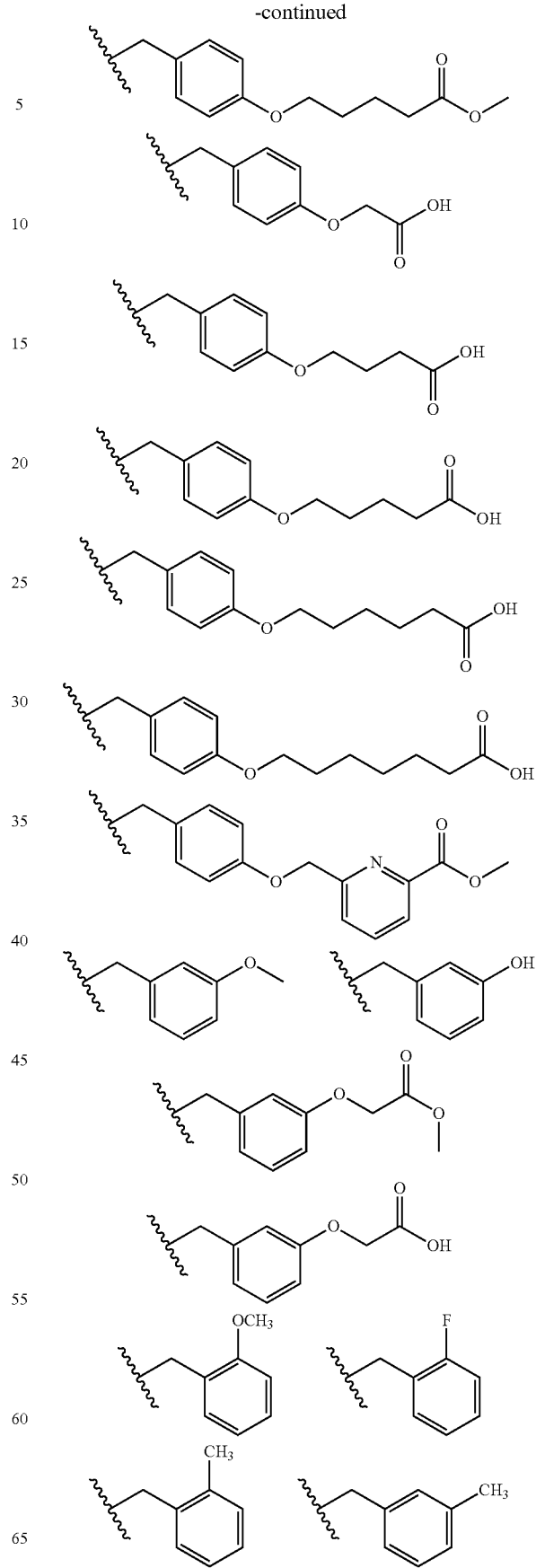

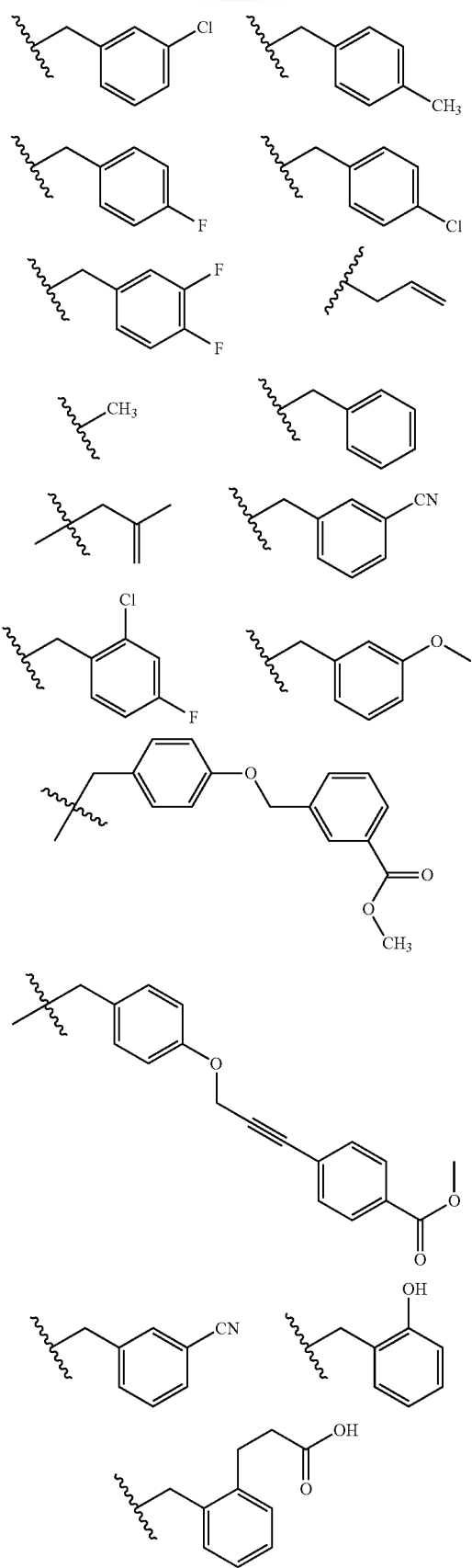
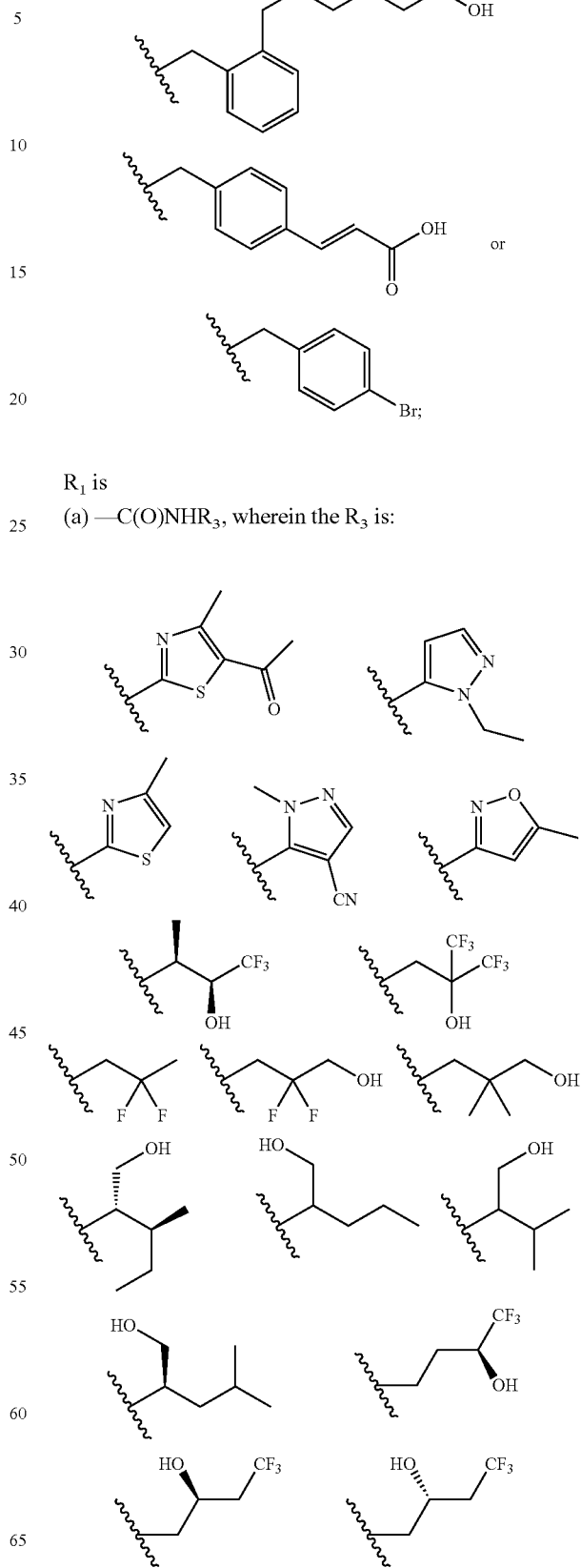
$R_1$ is
(a) —C(O)NHR$_3$, wherein the R$_3$ is:

1145
-continued
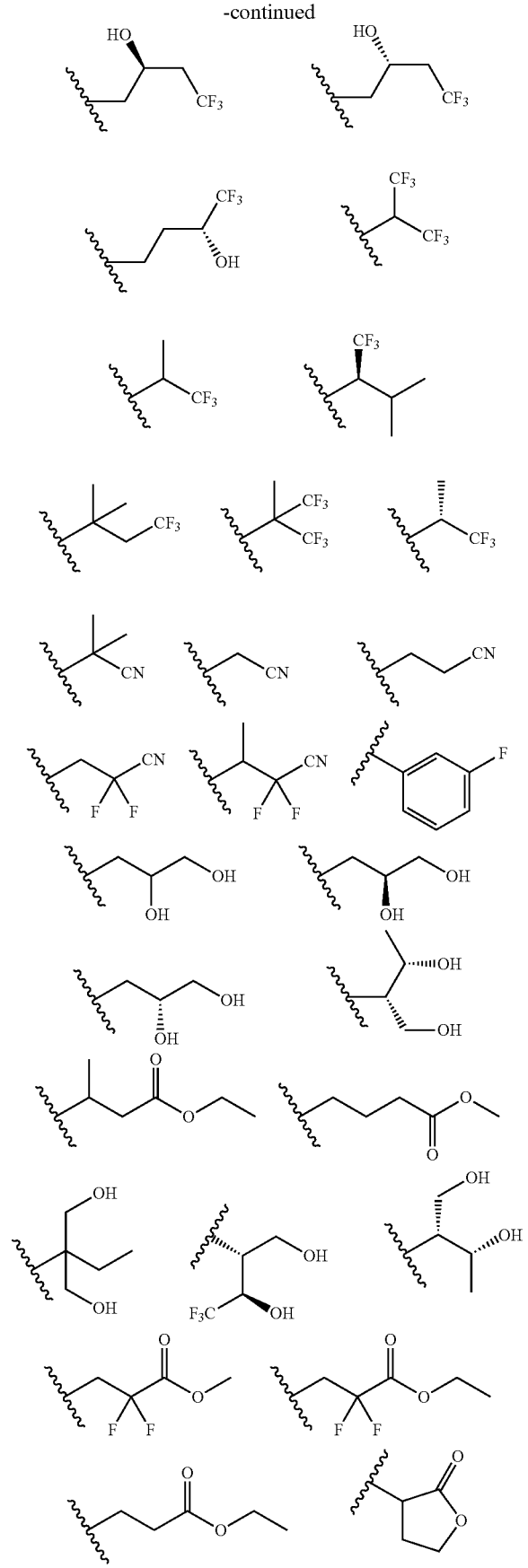
1146
-continued
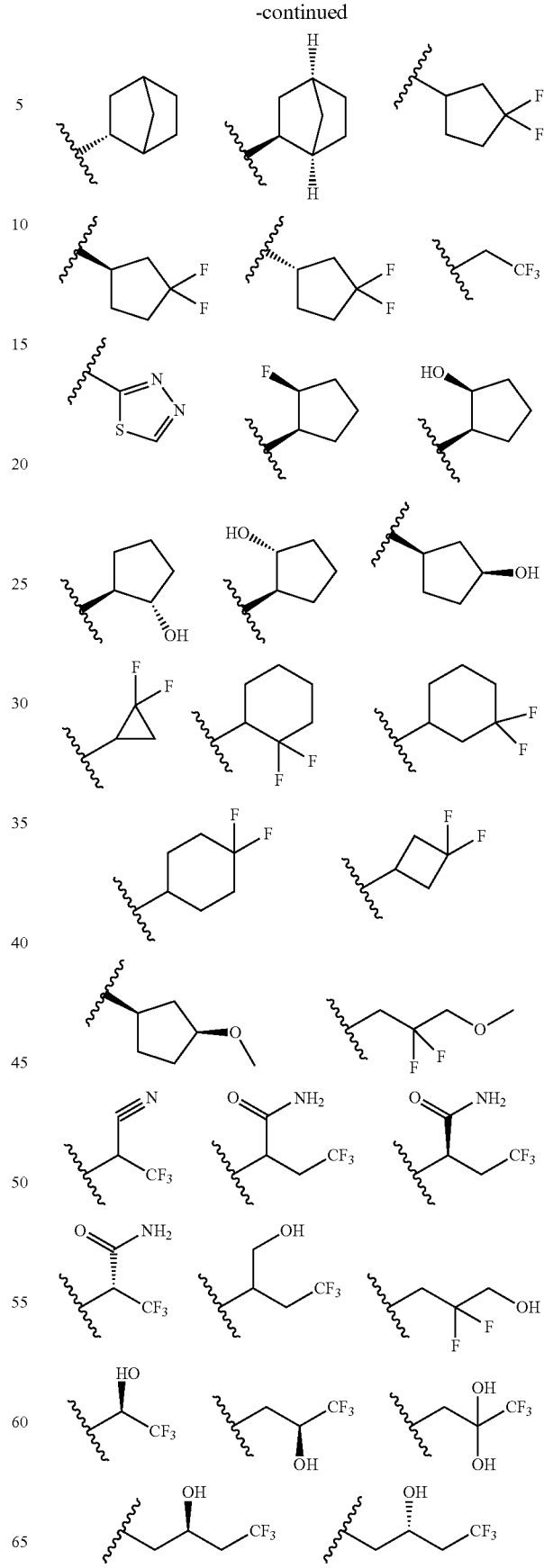

1147
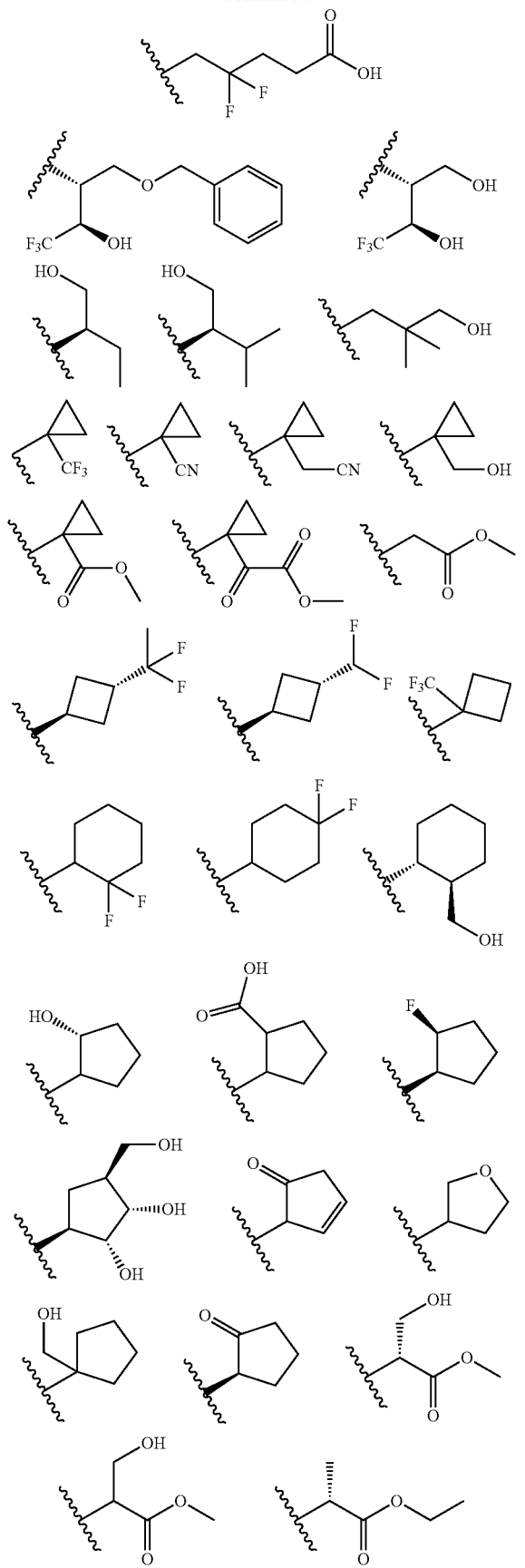
1148
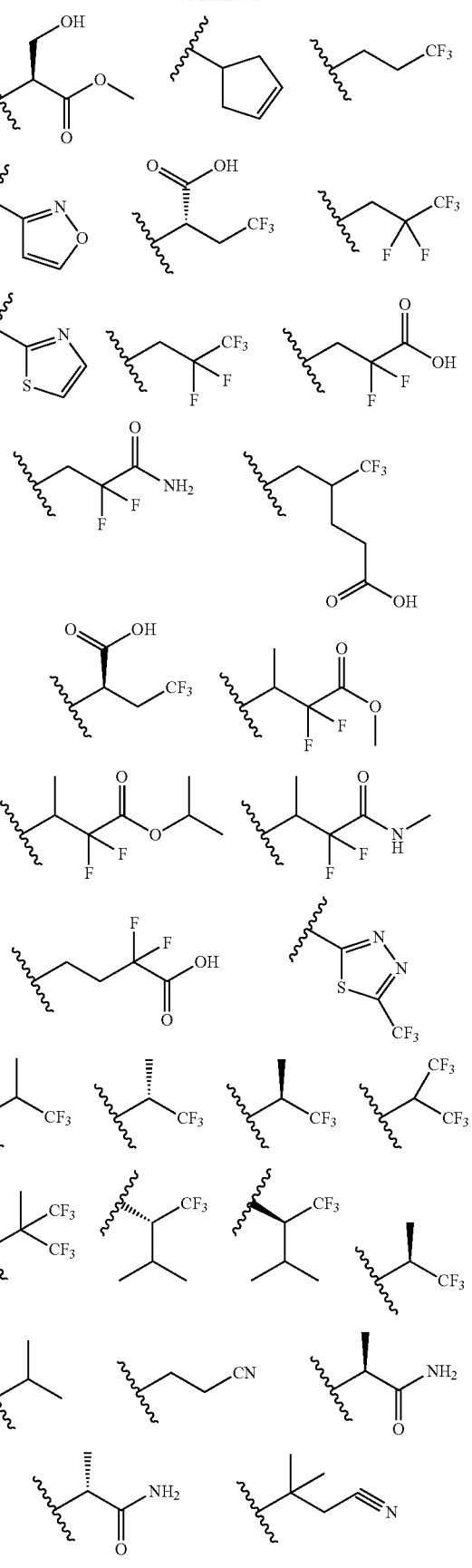

1149
-continued
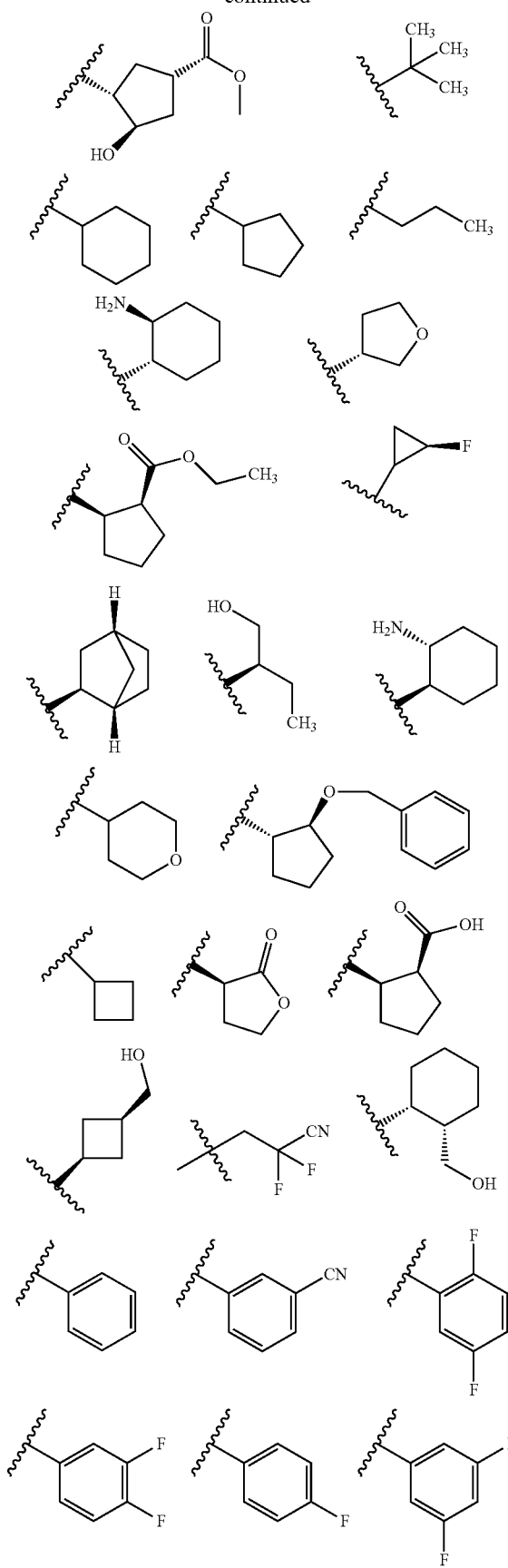
1150
-continued
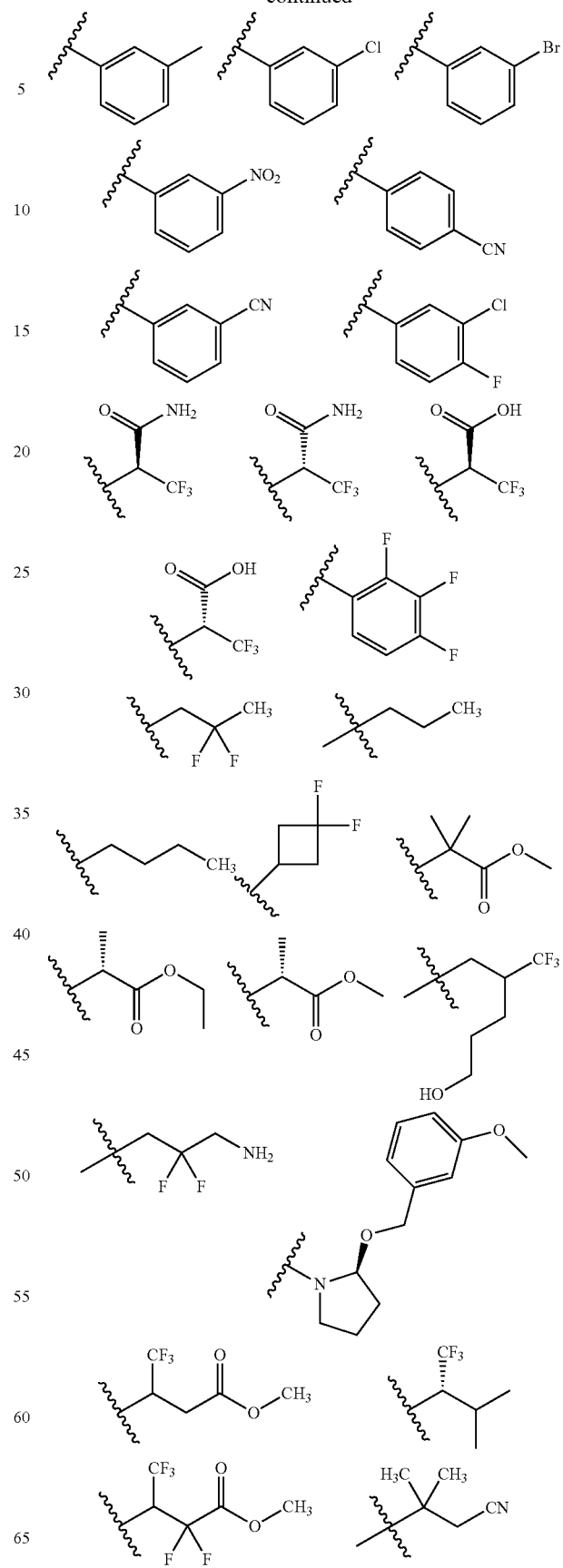

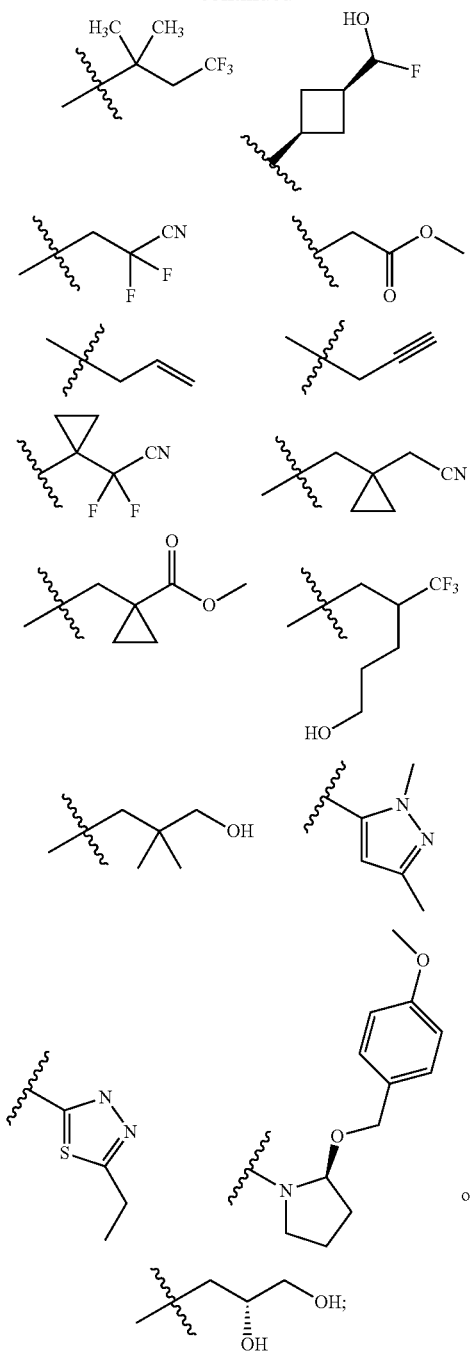

(b) —C(O)NR$_2$R$_3$, wherein the NR$_2$R$_3$ is:

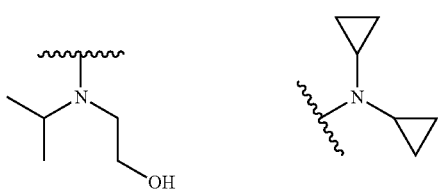

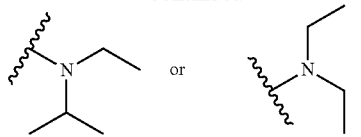

11. A compound of claim 1, wherein the compound is

| Example No. | Name |
|---|---|
| 1 | 1-cyclopentyl-3-(1-(4-fluoro-3-(trifluoromethyl)phenyl)-1-(3-fluoro-5-(trifluoromethyl)phenyl)-2-phenylethyl)urea |
| 4 | (R)-1-(1-(3-fluoro-5-(1,1,2,2-tetrafluoroethoxy)phenyl)-1-(4-fluorophenyl)-2-phenylethyl)-3-(3,3,3-trifluoropropyl)urea |
| 5 | (R)-1-(1-(3-fluoro-5-(1,1,2,2-tetrafluoroethoxy)phenyl)-1-(4-fluorophenyl)-2-phenylethyl)-3-(thiazol-2-yl)urea |
| 6 | 1-cyclopentyl-3-(1-(3-fluoro-5-(trifluoromethyl)phenyl)-1-(4-fluorophenyl)-2-phenylethyl)urea |
| 7 | 1-cyclopentyl-3-(1-(4-fluoro-3-(trifluoromethyl)phenyl)-1-(3-fluoro-5-(trifluoromethyl)phenyl)-2-phenylethyl)urea |
| 8 | 1-cyclopentyl-3-(1-(4-fluoro-3-(trifluoromethyl)phenyl)-1-(3-fluoro-5-(trifluoromethyl)phenyl)-2-phenylethyl)urea |
| 9 | (S)-1-cyclopentyl-3-(1-(3-fluoro-5-(trifluoromethyl)phenyl)-1-(4-fluorophenyl)-2-phenylethyl)urea |
| 10 | (R)-1-cyclopentyl-3-(1-(3-fluoro-5-(trifluoromethyl)phenyl)-1-(4-fluorophenyl)-2-phenylethyl)urea |
| 11 | 1-(1,1-bis(3-fluoro-5-(trifluoromethyl)phenyl)-2-phenylethyl)-3-cyclopentylurea |
| 12 | (R)-1-cyclopentyl-3-(1-(3-fluoro-5-(trifluoromethyl)phenyl)-2-phenyl-1-(3-(trifluoromethyl)phenyl)ethyl)urea |
| 13 | (R)-1-cyclopentyl-3-(1-(3,4-difluorophenyl)-1-(3-fluoro-5-(trifluoromethyl)phenyl)-2-phenylethyl)urea |
| 14 | (S)-1-cyclopentyl-3-(1-(3,4-difluorophenyl)-1-(3-fluoro-5-(trifluoromethyl)phenyl)-2-phenylethyl)urea |
| 15 | 2-(4-(3-(1-(3-fluoro-5-(trifluoromethyl)phenyl)-2-phenyl-1-(3-(trifluoromethyl)phenyl)ethyl)ureido)piperidin-1-yl)acetic acid |
| 16 | 1-(1-(3-fluoro-5-(trifluoromethyl)phenyl)-2-phenyl-1-(3-(trifluoromethyl)phenyl)ethyl)-3-(1-(2-hydroxyethyl)piperidin-4-yl)urea |
| 17 | (R)-1-cyclopentyl-3-(1-(3-fluoro-5-(trifluoromethyl)phenyl)-1-(4-methoxy-3-(trifluoromethyl)phenyl)-2-phenylethyl)urea |
| 18 | (R)-1-cyclopentyl-3-(1-(3-fluoro-5-(trifluoromethyl)phenyl)-1-(4-methyl-3-(trifluoromethyl)phenyl)-2-phenylethyl)urea |
| 19 | 1-cyclopentyl-3-(2-phenyl-1,1-bis(3-(1,1,2,2-tetrafluoroethoxy)phenyl)ethyl)urea |
| 20 | (R)-1-cyclopentyl-3-(1-(4-fluoro-3-(trifluoromethyl)phenyl)-1-(3-fluoro-5-(1,1,2,2-tetrafluoroethoxy)phenyl)-2-phenylethyl)urea |
| 21 | (R)-1-cyclopentyl-3-(1-(4-fluoro-3-methoxyphenyl)-1-(3-fluoro-5-(trifluoromethyl)phenyl)-2-phenylethyl)urea |
| 22 | (R)-1-cyclopentyl-3-(1-(3-fluoro-5-(trifluoromethyl)phenyl)-2-phenyl-1-(3-(trifluoromethoxy)phenyl)ethyl)urea |
| 23 | (R)-1-cyclobutyl-3-(1-(4-fluoro-3-(trifluoromethyl)phenyl)-1-(3-fluoro-5-(1,1,2,2-tetrafluoroethoxy)phenyl)-2-phenylethyl)urea |
| 24 | (R)-1-(1-(4-fluoro-3-(trifluoromethyl)phenyl)-1-(3-fluoro-5-(1,1,2,2-tetrafluoroethoxy)phenyl)-2-phenylethyl)-3-(2-methylpyridin-4-yl)urea |
| 25 | 1-((R)-1-(4-fluoro-3-(trifluoromethyl)phenyl)-1-(3-fluoro-5-(1,1,2,2-tetrafluoroethoxy)phenyl)-2-phenylethyl)-3-(2-oxo-tetrahydrofuran-3-yl)urea |
| 26 | (R)-1-(1-(4-fluoro-3-(trifluoromethyl)phenyl)-1-(3-fluoro-5-(1,1,2,2-tetrafluoroethoxy)phenyl)-2-phenylethyl)-3-(3,3,3-trifluoropropyl)urea |
| 27 | (R)-1-(1-(4-fluoro-3-(trifluoromethyl)phenyl)-1-(3-fluoro-5-(1,1,2,2-tetrafluoroethoxy)phenyl)-2-phenylethyl)-3-isopropylurea |
| 28 | 1-cyclopentyl-3-(1-(3-fluoro-5-(trifluoromethyl)phenyl)-1-(4-methoxyphenyl)-2-phenylethyl)urea |
| 29 | 1-cyclopentyl-3-(1-(3-fluoro-5-(trifluoromethyl)phenyl)-1-(4-(methylthio)phenyl)-2-phenylethyl)urea |
| 30 | 1-cyclopentyl-3-(1-(4-(difluoromethoxy)phenyl)-1-(3-fluoro-5-(trifluoromethyl)phenyl)-2-phenylethyl)urea |

| Example No. | Name |
|---|---|
| 31 | 1-cyclopentyl-3-(1-(3-fluoro-5-(trifluoromethyl)phenyl)-2-phenyl-1-p-tolylethyl)urea |
| 32 | 1-(1-(4-chloro-3-(trifluoromethyl)phenyl)-1-(3-fluoro-5-(trifluoromethyl)phenyl)-2-phenylethyl)-3-cyclopentylurea |
| 33 | 1-cyclopentyl-3-(1-(3-fluoro-5-(trifluoromethyl)phenyl)-1-(4-phenoxyphenyl)-2-phenylethyl)urea |
| 34 | 1-cyclopentyl-3-(1-(3-fluoro-5-(trifluoromethyl)phenyl)-1-(3-methoxyphenyl)-2-phenylethyl)urea |
| 35 | 1-cyclopentyl-3-(1-(3-fluoro-5-(trifluoromethyl)phenyl)-1-(2-fluorophenyl)-2-phenylethyl)urea |
| 36 | 1-cyclopentyl-3-(1-(2-fluoro-3-(trifluoromethyl)phenyl)-1-(3-fluoro-5-(trifluoromethyl)phenyl)-2-phenylethyl)urea |
| 37 | 1-(1-(4-tert-butylphenyl)-1-(3-fluoro-5-(trifluoromethyl)phenyl)-2-phenylethyl)-3-cyclopentylurea |
| 38 | (R)-1-(1-(4-fluoro-3-(trifluoromethyl)phenyl)-1-(3-fluoro-5-(1,1,2,2-tetrafluoroethoxy)phenyl)-2-phenylethyl)-3-(2,2,2-trifluoroethyl)urea |
| 39 | (R)-1-(1-(3-fluoro-5-(1,1,2,2-tetrafluoroethoxy)phenyl)-1-(4-fluorophenyl)-2-phenylethyl)-3-(2,2,2-trifluoroethyl)urea |
| 40 | (R)-1-(1-(3-fluoro-5-(trifluoromethyl)phenyl)-1-(4-methyl-3-(trifluoromethyl)phenyl)-2-phenylethyl)-3-(3,3,3-trifluoropropyl)urea |
| 41 | (R)-1-(1-(3-fluoro-5-(trifluoromethyl)phenyl)-1-(4-methyl-3-(trifluoromethyl)phenyl)-2-phenylethyl)-3-isopropylurea |
| 42 | (R)-1-(1-(3-fluoro-5-(trifluoromethyl)phenyl)-1-(4-methyl-3-(trifluoromethyl)phenyl)-2-phenylethyl)-3-(2,2,2-trifluoroethyl)urea |
| 43 | 1-((R)-1-(3-fluoro-5-(trifluoromethyl)phenyl)-1-(4-methyl-3-trifluoromethyl)phenyl)-2-phenylethyl)-3-(1-hydroxy-4-methylpentan-2-yl)urea |
| 44 | 1-((R)-1-(3-fluoro-5-(trifluoromethyl)phenyl)-1-(4-methyl-3-(trifluoromethyl)phenyl)-2-phenylethyl)-3-(1-hydroxy-4-methylpentan-2-yl)urea |
| 45 | (R)-1-(1-(3-fluoro-5-(1,1,2,2-tetrafluoroethoxy)phenyl)-1-(4-fluorophenyl)-2-phenylethyl)-3-isopropylurea |
| 46 | (R)-1,1-dicyclopropyl-3-(1-(3-fluoro-5-(1,1,2,2-tetrafluoroethoxy)phenyl)-1-(4-fluorophenyl)-2-phenylethyl)urea |
| 47 | (1S)-2-(1-((R)-1-(3-fluoro-5-(1,1,2,2-tetrafluoroethoxy)phenyl)-1-(4-fluorophenyl)-2-phenylethyl)ureido)cyclopentanecarboxylic acid |
| 48 | (S)-1-(1-(3-chloro-4-fluorophenyl)-1-(3-fluoro-5-(1,1,2,2-tetrafluoroethoxy)phenyl)-2-phenylethyl)-3-cyclopentylurea |
| 49 | 1-((R)-3,3-difluorocyclopentyl)-3-((R)-1-(4-fluoro-3-(trifluoromethyl)phenyl)-1-(3-fluoro-5-(1,1,2,2-tetrafluoroethoxy)phenyl)-2-phenylethyl)urea |
| 50 | (R)-1-(1-(4-fluoro-3-methoxyphenyl)-1-(3-fluoro-5-(trifluoromethyl)phenyl)-2-phenylethyl)-3-(2,2,2-trifluoroethyl)urea |
| 51 | (R)-3-(1-(4-fluoro-3-(trifluoromethyl)phenyl)-1-(3-fluoro-5-(1,1,2,2-tetrafluoroethoxy)phenyl)-2-phenylethyl)-1-(2-hydroxyethyl)-1-isopropylurea |
| 52 | (R)-1-(1-(4-fluoro-3-methoxyphenyl)-1-(3-fluoro-5-(trifluoromethyl)phenyl)-2-phenylethyl)-3-(3,3,3-trifluoropropyl)urea |
| 53 | (S)-1-(1-(3,5-bis(trifluoromethyl)phenyl)-1-(4-fluorophenyl)-2-phenylethyl)-3-cyclopentylurea |
| 54 | (R)-1-(1-(3,5-bis(trifluoromethyl)phenyl)-1-(4-fluorophenyl)-2-phenylethyl)-3-cyclopentylurea |
| 55 | (R)-1-(1-(3-fluoro-5-(1,1,2,2-tetrafluoroethoxy)phenyl)-1-(4-fluorophenyl)-2-phenylethyl)-3-(3,3,3-trifluoropropyl)urea |
| 82 | 1-(1,1-bis(3-(trifluoromethoxy)phenyl)but-3-enyl)-3-cyclopentylurea |
| 83 | (R)-1-(3,3-difluorocyclopentyl)-3-(2-phenyl-1,1-bis(3-(trifluoromethoxy)phenyl)ethyl)urea |
| 85 | 1-(2,2,3,3,3-pentafluoropropyl)-3-(2-phenyl-1,1-bis(3-(trifluoromethoxy)phenyl)ethyl)urea |
| 86 | 1-cyclopentyl-3-(2-(2-methoxyphenyl)-1,1-bis(3-(trifluoromethoxy)phenyl)ethyl)urea |
| 234 | 7-(3-(1-(3-cyclopentylureido)-1-(3-fluoro-5-(trifluoromethyl)phenyl)-2-phenylethyl)phenyl)heptanoic acid |
| 235 | (R)-6-(3-(1-(3-fluoro-5-(1,1,2,2-tetrafluoroethoxy)phenyl)-2-phenyl-1-(3-(2,2,2-trifluoroethyl)ureido)ethyl)phenyl)-hexanoic acid |
| 236 | 1-((2R,3R)-1-(benzyloxy)-4,4,4-trifluoro-3-hydroxybutan-2-yl)-3-((R)-1-(3-fluoro-5-(1,1,2,2-tetrafluoroethoxy)phenyl)-1-(4-fluorophenyl)-2-phenylethyl)urea |
| 237 | 1-((R)-1-(3-fluoro-5-(1,1,2,2-tetrafluoroethoxy)phenyl)-1-(4-fluorophenyl)-2-phenylethyl)-3-((2R,3R)-4,4,4-trifluoro-1,3-dihydroxybutan-2-yl)urea |
| 238 | 1-((R)-1-(3-fluoro-5-(1,1,2,2-tetrafluoroethoxy)phenyl)-1-(4-fluorophenyl)-2-phenylethyl)-3-((S)-4,4,4-trifluoro-2-hydroxybutyl)urea |
| 239 | (R)-1-(1-(3-fluoro-5-(1,1,2,2-tetrafluoroethoxy)phenyl)-1-(4-fluorophenyl)-2-phenylethyl)-3-(3,3,3-trifluoro-2-hydroxy-2-(trifluoromethyl)propyl)urea |
| 240 | (R)-1-(1-(3-fluoro-5-(1,1,2,2-tetrafluoroethoxy)phenyl)-1-(4-fluorophenyl)-2-phenylethyl)-3-(1-(trifluoromethyl)-cyclobutyl)urea |
| 241 | (R)-1-(1-(3-fluoro-5-(1,1,2,2-tetrafluoroethoxy)phenyl)-1-(4-fluorophenyl)-2-phenylethyl)-3-(1-(hydroxymethyl)-cyclopropyl)urea |
| 242 | (R)-1-(1-(cyanomethyl)cyclopropyl)-3-(1-(3-fluoro-5-(1,1,2,2-tetrafluoroethoxy)phenyl)-1-(4-fluorophenyl)-2-phenylethyl)urea |
| 243 | (R)-methyl 2-(1-(3-(1-(3-fluoro-5-(1,1,2,2-tetrafluoroethoxy)phenyl)-1-(4-fluorophenyl)-2-phenylethyl)ureido)cyclopropyl)-2-oxoacetate |
| 244 | (R)-methyl 2,2-difluoro-2-(1-(3-(1-(3-fluoro-5-(1,1,2,2-tetrafluoroethoxy)phenyl)-1-(4-fluorophenyl)-2-phenylethyl)ureido)cyclopropyl)acetate |
| 245 | (R)-1-cyclopentyl-3-(1-(4-fluoro-3-(trifluoromethyl)phenyl)-1-(3-fluoro-5-(1,1,2,2-tetrafluoroethoxy)phenyl)-2-phenylethyl)-1-methylurea |
| 246 | 1-((R)-1-(3-fluoro-5-(1,1,2,2-tetrafluoroethoxy)phenyl)-1-(4-fluorophenyl)-2-phenylethyl)-3-((1R,2R)-2-hydroxycyclopentyl)urea |
| 247 | 1-((R)-1-(3-fluoro-5-(1,1,2,2-tetrafluoroethoxy)phenyl)-1-(4-fluorophenyl)-2-phenylethyl)-3-((1R,2S)-2-fluorocyclopentyl)urea |
| 248 | 1-((R)-1-(3-fluoro-5-(1,1,2,2-tetrafluoroethoxy)phenyl)-1-(4-fluorophenyl)-2-phenylethyl)-3-((1r,3R)-3-formylcyclobutyl)urea |
| 249 | 1-((1r,3R)-3-(difluoromethyl)cyclobutyl)-3-((R)-1-(3-fluoro-5-(1,1,2,2-tetrafluoroethoxy)phenyl)-1-(4-fluorophenyl)-2-phenylethyl)urea |
| 250 | 1-((1r,3R)-3-acetylcyclobutyl)-3-((R)-1-(3-fluoro-5-(1,1,2,2-tetrafluoroethoxy)phenyl)-1-(4-fluorophenyl)-2-phenylethyl)urea |
| 252 | 1-((1R,3S)-3-((S)-fluoro(hydroxy)methyl)cyclobutyl)-3-((R)-1-(3-fluoro-5-(1,1,2,2-tetrafluoroethoxy)phenyl)-1-(4-fluorophenyl)-2-phenylethyl)urea |
| 253 | (R)-1-(2-cyano-2,2-difluoroethyl)-3-(1-(3-fluoro-5-(1,1,2,2-tetrafluoroethoxy)phenyl)-1-(4-fluorophenyl)-2-phenylethyl)urea |
| 254 | (R)-1-(1-(4-fluoro-3-(trifluoromethyl)phenyl)-1-(3-fluoro-5-hydroxyphenyl)-2-phenylethyl)-3-(2,2,2-trifluoroethyl)urea |
| 255 | (R)-1-(1-(4-fluoro-3-(trifluoromethyl)phenyl)-1-(3-fluoro-5-(2,2,2-trifluoroethoxy)phenyl)-2-phenylethyl)-3-(2,2,2-trifluoroethyl)urea |
| 256 | (R)-1-(1-(3-cyano-5-fluorophenyl)-1-(4-fluoro-3-(trifluoromethyl)phenyl)-2-phenylethyl)-3-(2,2,2-trifluoroethyl)urea |
| 257 | (R)-1-(1-(3-acetyl-5-fluorophenyl)-1-(4-fluoro-3-(trifluoromethyl)phenyl)-2-phenylethyl)-3-(2,2,2-trifluoroethyl)urea |
| 258 | (R)-1-(1-(4-fluoro-3-(trifluoromethyl)phenyl)-1-(3-fluoro-5-(2-hydroxypropan-2-yl)phenyl)-2-phenylethyl)-3-(2,2,2-trifluoroethyl)urea |
| 259 | (1S,4R)-methyl 3,3-difluoro-4-(3-((R)-1-(3-fluoro-5-(1,1,2,2-tetra-fluoroethoxy)phenyl)-1-(4-fluorophenyl)-2-)ureido)cyclopentanecarboxylate |
| 260 | (R)-1-(1-(3-fluoro-5-(1,1,2,2-tetrafluoroethoxy)phenyl)-1-(4-fluorophenyl)-2-phenylethyl)-3-(5-(2-methyl-2H-tetrazol-5-yl)pentyl)urea |
| 278 | 1-(2-(4-bromophenyl)-1,1-bis(3-(trifluoromethoxy)phenyl)ethyl)-3-(2,2,2-trifluoroethyl)urea |
| 304 | (R)-1-cyclopentyl-3-(1-(4-fluoro-3-(2-hydroxy-2-methylpropoxy)phenyl)-1-(3-fluoro-5-(trifluoromethyl)phenyl)-2-phenylethyl)urea |

| Example No. | Name |
|---|---|
| 308 | (R)-1-(3,3-difluorocyclobutyl)-3-(1-(4-fluoro-3-methoxyphenyl)-1-(3-fluoro-5-(trifluoromethyl)phenyl)-2-phenylethyl)urea |
| 313 | Ethyl 6-(4-(2-(3-cyclopentylureido)-2,2-bis(3-(trifluoromethoxy)phenyl)ethyl)phenoxy)hexanoate |
| 314 | 1-(2,2-difluorocyclohexyl)-3-((R)-1-(3-fluoro-5-(1,1,2,2-tetrafluoroethoxy)phenyl)-1-(4-fluorophenyl)-2-phenylethyl)urea |
| 319 | (R)-2,3,5,6-tetrafluoro-4-(4-((3-(1-(3-fluoro-5-(1,1,2,2-tetrafluoroethoxy)phenyl)-1-(4-fluorophenyl)-2-phenylethyl)ureido)methyl)-1H-1,2,3-triazol-1-yl)benzoic acid |
| 328 | (R)-1-(3,3-difluorocyclobutyl)-3-(1-(3-((dimethylamino)methyl)-4-fluorophenyl)-1-(3-fluoro-5-(1,1,2,2-tetrafluoroethoxy)phenyl)-2-phenylethyl)urea |
| 333 | 1-((R)-1-(3-fluoro-5-(1,1,2,2-tetrafluoroethoxy)phenyl)-1-(4-fluorophenyl)-2-phenylethyl)-3-((R)-2-oxocyclopentyl)urea |
| 334 | (R)-1-(1-(3-fluoro-5-(1,1,2,2-tetrafluoroethoxy)phenyl)-1-(4-fluorophenyl)-2-phenylethyl)-3-(5-oxocyclopent-1-enyl)urea |
| 346 | (R)-1-(1-(3-fluoro-5-(1,1,2,2-tetrafluoroethoxy)phenyl)-1-(4-formylphenyl)-2-phenylethyl)-3-(2,2,2-trifluoroethyl)urea |
| 349B | (R)-1-(1-(3-fluoro-5-(1,1,2,2-tetrafluoroethoxy)phenyl)-1-(4-fluorophenyl)-2-phenylethyl)-3-(1,3,4-thiadiazol-2-yl)urea |
| 350 | (R)-1-(1-(3-fluoro-5-(1,1,2,2-tetrafluoroethoxy)phenyl)-1-(4-fluorophenyl)-2-phenylethyl)-3-(thiazol-2-yl)urea |
| 351 | (R)-1-cyclopentyl-3-(1-(4-fluoro-3-methoxyphenyl)-1-(3-fluoro-5-(1,1,2,2-tetrafluoroethoxy)phenyl)-2-phenylethyl)urea |
| 352 | (R)-1-(1-(4-chlorophenyl)-1-(3-fluoro-5-(trifluoromethyl)phenyl)-2-phenylethyl)-3-cyclopentylurea |
| 353 | 1-cyclopentyl-3-(1-(3-fluoro-5-(1,1,2,2-tetrafluoroethoxy)phenyl)-2-phenyl-1-(4-(trifluoromethyl)phenyl)ethyl)urea |
| 354 | (R)-1-(1-(3-fluoro-5-(1,1,2,2-tetrafluoroethoxy)phenyl)-1-(4-fluorophenyl)-2-phenylethyl)-3-(isoxazol-3-yl)urea |
| 355 | (R)-1-cyclopentyl-3-(1-(4-fluoro-3-hydroxyphenyl)-1-(3-fluoro-5-(trifluoromethyl)phenyl)-2-phenylethyl)urea |
| 356 | 1-(1-(3-bromophenyl)-1-(3-fluoro-5-(trifluoromethyl)phenyl)-2-phenylethyl)-3-cyclopentylurea |
| 357 | 1-(1-(3-chlorophenyl)-1-(3-fluoro-5-(trifluoromethyl)phenyl)-2-phenylethyl)-3-clopentylurea |
| 358 | 1-(1-(4-bromophenyl)-1-(3-fluoro-5-(trifluoromethyl)phenyl)-2-phenylethyl)-3-cyclopentylurea |
| 359 | 1-cyclopentyl-3-(1-(3-fluoro-5-(trifluoromethyl)phenyl)-2-phenyl-1-(2-(trifluoromethoxy)phenyl)ethyl)urea |
| 360 | 1-cyclopentyl-3-(1-(3-fluoro-5-(trifluoromethyl)phenyl)-1-(4-isopropylphenyl)-2-phenylethyl)urea |
| 361 | 1-(1-(3-(1H-pyrrol-1-yl)phenyl)-1-(3-fluoro-5-(trifluoromethyl)phenyl)-2-phenylethyl)-3-cyclopentylurea |
| 362 | 1-cyclopentyl-3-(1-(biphenyl-3-yl)-1-(3-fluoro-5-(trifluoromethyl)phenyl)-2-phenylethyl)urea |
| 363 | 1-cyclopentyl-3-(1-(3-fluoro-5-(trifluoromethyl)phenyl)-2-phenyl-1-(4-(thiophen-3-yl)phenyl)ethyl)urea |
| 364 | 1-cyclopentyl-3-(1-(3-fluoro-5-(trifluoromethyl)phenyl)-2-phenyl-1-(3-(thiophen-3-yl)phenyl)ethyl)urea |
| 365 | 1-cyclopentyl-3-(1-(3-fluoro-5-(trifluoromethyl)phenyl)-1-(4-fluoronaphthalen-1-yl)-2-phenylethyl)urea |
| 366 | (R)-1-cyclopentyl-3-(1-(3-ethoxy-4-fluorophenyl)-1-(3-fluoro-5-(trifluoromethyl)phenyl)-2-phenylethyl)urea |
| 367 | 1-cyclopentyl-3-(1-(4-fluoro-3-methylphenyl)-1-(3-fluoro-5-(trifluoromethyl)phenyl)-2-phenylethyl)urea |
| 368 | 1-cyclopentyl-3-(1-(3-fluoro-5-(trifluoromethyl)phenyl)-2-phenyl-1-(4-(2-phenylethynyl)phenyl)ethyl)urea |
| 369 | 1-(1-(4-tert-butoxyphenyl)-1-(3-fluoro-5-(trifluoromethyl)phenyl)-2-phenylethyl)-3-cyclopentylurea |
| 370 | (R)-1-(cyclopent-3-enyl)-3-(1-(4-fluoro-3-(trifluoromethyl)phenyl)-1-(3-fluoro-5-(trifluoromethyl)phenyl)-2-phenylethyl)urea |
| 371 | (R)-1-(1-(4-fluoro-3-methoxyphenyl)-1-(3-fluoro-5-(1,1,2,2-tetrafluoroethoxy)phenyl)-2-phenylethyl)-3-(3,3,3-trifluoropropyl)urea |
| 372 | (R)-1-(1-(4-fluoro-3-methoxyphenyl)-1-(3-fluoro-5-(1,1,2,2-tetrafluoroethoxy)phenyl)-2-phenylethyl)-3-(2,2,2-trifluoroethyl)urea |
| 373 | (R)-2-(5-(1-(3-cyclopentylureido)-1-(3-fluoro-5-(trifluoromethyl)phenyl)-2-phenylethyl)-2-fluorophenoxy)acetic acid |
| 374 | (R)-2-(5-(1-(3-cyclopentylureido)-1-(3-fluoro-5-(trifluoromethyl)phenyl)-2-phenylethyl)-2-fluorophenoxy)-2,2-difluoroacetic acid |
| 375 | (R)-4-(5-(1-(3-cyclopentylureido)-1-(3-fluoro-5-(trifluoromethyl)phenyl)-2-phenylethyl)-2-fluorophenoxy)butanoic acid |
| 376 | (R)-methyl 5-(5-(1-(3-cyclopentylureido)-1-(3-fluoro-5-(trifluoromethyl)phenyl)-2-phenylethyl)-2-fluorophenoxy)pentanoate |
| 377 | 4-(1-(3-cyclopentylureido)-1-(3-fluoro-5-(trifluoromethyl)phenyl)-2-phenylethyl)-2-fluorobenzoic acid |
| 378 | 1-cyclopentyl-3-(1-(3-fluoro-4-methoxyphenyl)-1-(3-fluoro-5-(trifluoromethyl)phenyl)-2-phenylethyl)urea |
| 379 | 1-(1-(3-chloro-4-methoxyphenyl)-1-(3-fluoro-5-(trifluoromethyl)phenyl)-2-phenylethyl)-3-cyclopentylurea |
| 380 | 1-cyclopentyl-3-(1-(3,4-dimethoxyphenyl)-1-(3-fluoro-5-(trifluoromethyl)phenyl)-2-phenylethyl)urea |
| 381 | 1-cyclopentyl-3-(1-(3-(difluoromethoxy)phenyl)-1-(3-fluoro-5-(trifluoromethyl)phenyl)-2-phenylethyl)urea |
| 382 | 1-cyclopentyl-3-(1-(3-fluoro-5-(trifluoromethyl)phenyl)-2-phenyl-1-(3-(1,1,2,2-tetrafluoroethoxy)phenyl)ethyl)urea |
| 383 | 3-(3-(1-(3-cyclopentylureido)-1-(3-fluoro-5-(trifluoromethyl)phenyl)-2-phenylethyl)phenyl)propanoic acid |
| 384 | ethyl 3-(3-(1-(3-cyclopentylureido)-1-(3-fluoro-5-(trifluoromethyl)phenyl)-2-phenylethyl)phenyl)propanoate |
| 385 | ethyl 4-(3-(1-(3-cyclopentylureido)-1-(3-fluoro-5-(trifluoromethyl)phenyl)-2-phenylethyl)phenyl)butanoate |
| 386 | ethyl 6-(3-(1-(3-cyclopentylureido)-1-(3-fluoro-5-(trifluoromethyl)phenyl)-2-phenylethyl)phenyl)hexanoate |
| 387 | 4-(3-(1-(3-cyclopentylureido)-1-(3-fluoro-5-(trifluoromethyl)phenyl)-2-phenylethyl)phenyl)butanoic acid |
| 388 | 6-(3-(1-(3-cyclopentylureido)-1-(3-fluoro-5-(trifluoromethyl)phenyl)-2-phenylethyl)phenyl)hexanoic acid |
| 389 | ethyl 3-(4-(1-(3-cyclopentylureido)-1-(3-fluoro-5-(trifluoromethyl)phenyl)-2-phenylethyl)phenyl)propanoate |
| 390 | ethyl 4-(4-(1-(3-cyclopentylureido)-1-(3-fluoro-5-(trifluoromethyl)phenyl)-2-phenylethyl)phenyl)butanoate |
| 391 | ethyl 6-(4-(1-(3-cyclopentylureido)-1-(3-fluoro-5-(trifluoromethyl)phenyl)-2-phenylethyl)phenyl)hexanoate |
| 392 | 1-((S)-3,3-difluorocyclopentyl)-3-((R)-1-(4-fluoro-3-methoxyphenyl)-1-(3-fluoro-5-(trifluoromethyl)phenyl)-2-phenylethyl)urea |
| 393 | (R)-5-(5-(1-(3-cyclopentylureido)-1-(3-fluoro-5-(trifluoromethyl)phenyl)-2-phenylethyl)-2-fluorophenoxy)pentanoic acid |
| 394 | 3-(4-(1-(3-cyclopentylureido)-1-(3-fluoro-5-(trifluoromethyl)phenyl)-2-phenylethyl)phenyl)propanoic acid |
| 395 | 4-(4-(1-(3-cyclopentylureido)-1-(3-fluoro-5-(trifluoromethyl)phenyl)-2-phenylethyl)phenyl)butanoic acid |
| 396 | 6-(4-(1-(3-cyclopentylureido)-1-(3-fluoro-5-(trifluoromethyl)phenyl)-2-phenylethyl)phenyl)hexanoic acid |
| 397 | (R)-methyl 6-(5-(1-(3-cyclopentylureido)-1-(3-fluoro-5-(trifluoromethyl)phenyl)-2-phenylethyl)-2-fluorophenoxy)hexanoate |
| 398 | (R)-1-(1-(4-fluoro-3-(trifluoromethyl)phenyl)-1-(3-fluoro-5-(1,1,2,2-tetrafluoroethoxy)phenyl)-2-phenylethyl)-3-(3,3,3-trifluoropropyl)urea |
| 399 | (R)-1-(1-(4-fluoro-3-(trifluoromethyl)phenyl)-1-(3-fluoro-5-(1,1,2,2-tetrafluoroethoxy)phenyl)-2-phenylethyl)-3-isopropylurea |
| 400 | (R)-1-(1-(4-fluoro-3-(trifluoromethyl)phenyl)-1-(3-fluoro-5-(1,1,2,2-tetrafluoroethoxy)phenyl)-2-phenylethyl)-3-(2,2,2-trifluoroethyl)urea |
| 401 | (R)-1-(1-(4-fluoro-3-methoxyphenyl)-1-(3-fluoro-5-(1,1,2,2-tetrafluoroethoxy)phenyl)-2-phenylethyl)-3-(3,3,3-trifluoropropyl)urea |
| 402 | (R)-1-(1-(4-fluoro-3-methoxyphenyl)-1-(3-fluoro-5-(1,1,2,2-tetrafluoroethoxy)phenyl)-2-phenylethyl)-3-(2,2,2-trifluoroethyl)urea |
| 403 | (R)-6-(5-(1-(3-cyclopentylureido)-1-(3-fluoro-5-(trifluoromethyl)phenyl)-2-phenylethyl)-2-fluorophenoxy)hexanoic acid |

| Example No. | Name |
|---|---|
| 404 | (R)-1-(2,2-difluoro-3-hydroxypropyl)-3-(1-(3-fluoro-5-(1,1,2,2-tetrafluoroethoxy)phenyl)-1-(4-fluorophenyl)-2-phenylethyl)urea |
| 405 | (R)-1-(1-(4-fluoro-3-hydroxyphenyl)-1-(3-fluoro-5-(trifluoromethyl)phenyl)-2-phenylethyl)-3-(2,2,2-trifluoroethyl)urea |
| 406 | (R)-ethyl 7-(5-(1-(3-cyclopentylureido)-1-(3-fluoro-5-(trifluoromethyl)phenyl)-2-phenylethyl)-2-fluorophenoxy)heptanoate |
| 407 | (R)-7-(5-(1-(3-cyclopentylureido)-1-(3-fluoro-5-(trifluoromethyl)phenyl)-2-phenylethyl)-2-fluorophenoxy)heptanoic acid |
| 408 | 1-((R)-3,3-difluorocyclopentyl)-3-((R)-1-(3-fluoro-5-(1,1,2,2-tetrafluoroethoxy)phenyl)-1-(4-fluorophenyl)-2-phenylethyl)urea |
| 409 | 1-((S)-3,3-difluorocyclopentyl)-3-((R)-1-(3-fluoro-5-(1,1,2,2-tetrafluoroethoxy)phenyl)-1-(4-fluorophenyl)-2-phenylethyl)urea |
| 410 | 1-((1S,2R,3S,4S)-2,3-dihydroxy-4-(hydroxymethyl)cyclopentyl)-3-((R)-1-(3-fluoro-5-(1,1,2,2-tetrafluoroethoxy)phenyl)-1-(4-fluorophenyl)-2-phenylethyl)urea |
| 411 | (R)-1-(4,4-difluorocyclohexyl)-3-(1-(3-fluoro-5-(1,1,2,2-tetrafluoroethoxy)phenyl)-1-(4-fluorophenyl)-2-phenylethyl)urea |
| 412 | (R)-methyl 6-(2-fluoro-5-(1-(3-fluoro-5-(trifluoromethyl)phenyl)-2-phenyl-1-(3-(2,2,2-trifluoroethyl)ureido)ethyl)phenoxy)hexanoate |
| 413 | (R)-1-(1-(4-fluoro-3-(2-hydroxyethoxy)phenyl)-1-(3-fluoro-5-(trifluoromethyl)phenyl)-2-phenylethyl)-3-(2,2,2-trifluoroethyl)urea |
| 414 | (R)-6-(2-fluoro-5-(1-(3-fluoro-5-(trifluoromethyl)phenyl)-2-phenyl-1-(3-(2,2,2-trifluoroethyl)ureido)ethyl)phenoxy)hexanoic acid |
| 415 | 1-((R)-1-(3-fluoro-5-(1,1,2,2-tetrafluoroethoxy)phenyl)-1-(4-fluorophenyl)-2-phenylethyl)-3-((R)-2-oxotetrahydrofuran-3-yl)urea |
| 416 | (R)-1-(1-(3-fluoro-5-(1,1,2,2-tetrafluoroethoxy)phenyl)-1-(4-fluorophenyl)-2-phenylethyl)-3-(3-hydroxy-2,2-dimethylpropyl)urea |
| 417 | (R)-1-(1-(3-fluoro-5-(trifluoromethyl)phenyl)-1-(4-methoxyphenyl)-2-phenylethyl)-3-(2,2,2-trifluoroethyl)urea |
| 418 | (S)-1-(1-(3-fluoro-5-(trifluoromethyl)phenyl)-1-(4-methoxyphenyl)-2-phenylethyl)-3-(2,2,2-trifluoroethyl)urea |
| 419 | 1-((S)-3,3-difluorocyclopentyl)-3-((R)-1-(4-fluoro-3-(trifluoromethyl)phenyl)-1-(3-fluoro-5-(1,1,2,2-tetrafluoroethoxy)phenyl)-2-phenylethyl)urea |
| 420 | (R)-1-(1-(3-fluoro-5-(1,1,2,2-tetrafluoroethoxy)phenyl)-1-(4-fluorophenyl)-2-phenylethyl)-3-(2,2,3,3,3-pentafluoropropyl)urea |
| 421 | (1S,3R,4R)-methyl 3-((R)-1-(3-fluoro-5-(1,1,2,2-tetrafluoroethoxy)phenyl)-1-(4-fluorophenyl)-2-phenylethyl)ureido)-4-hydroxycyclopentanecarboxylate |
| 422 | 1-((R)-1-(3-fluoro-5-(1,1,2,2-tetrafluoroethoxy)phenyl)-1-(4-fluorophenyl)-2-phenylethyl)-3-((2S,3S)-4,4,4-trifluoro-3-hydroxybutan-2-yl)urea |
| 423 | 1-((R)-1-(3-fluoro-5-(1,1,2,2-tetrafluoroethoxy)phenyl)-1-(4-fluorophenyl)-2-phenylethyl)-3-(1,1,1-trifluoropropan-2-yl)urea |
| 424 | (R)-1-cyclopropyl-3-(1-(4-fluoro-3-(trifluoromethyl)phenyl)-1-(3-fluoro-5-(1,1,2,2-tetrafluoroethoxy)phenyl)-2-phenylethyl)urea |
| 425 | (R)-1-(1-(3-fluoro-5-(1,1,2,2-tetrafluoroethoxy)phenyl)-2-phenyl-1-(4-(trifluoromethyl)phenyl)ethyl)-3-(2,2,2-trifluoroethyl)urea |
| 426 | (R)-1-(1-(3-fluoro-5-(1,1,2,2-tetrafluoroethoxy)phenyl)-2-phenyl-1-(4-(trifluoromethyl)phenyl)ethyl)-3-(3,3,3-trifluoropropyl)urea |
| 427 | (S)-1-(1-(3-bromophenyl)-1-(3-fluoro-5-(trifluoromethyl)phenyl)-2-phenylethyl)-3-cyclopentylurea |
| 428 | (S)-1-(1-(3-bromophenyl)-1-(3-fluoro-5-(1,1,2,2-tetrafluoroethoxy)phenyl)-2-phenylethyl)-3-cyclopentylurea |
| 429 | (S)-1-(1-(3-bromo-4-fluorophenyl)-1-(3-fluoro-5-(trifluoromethyl)phenyl)-2-phenylethyl)-3-cyclopentylurea |
| 430 | (R)-1-cyclopentyl-3-(1-(4-(difluoromethoxy)phenyl)-1-(3-fluoro-5-(1,1,2,2-tetrafluoroethoxy)phenyl)-2-phenylethyl)urea |
| 431 | (S)-1-(1-(3-bromophenyl)-1-(3-fluoro-5-(trifluoromethyl)phenyl)-2-phenylethyl)-3-(2,2,2-trifluoroethyl)urea |
| 432 | (S)-1-(1-(3-bromophenyl)-1-(3-fluoro-5-(1,1,2,2-tetrafluoroethoxy)phenyl)-2-phenylethyl)-3-(2,2,2-trifluoroethyl)urea |
| 433 | (S)-1-(1-(3-bromo-4-fluorophenyl)-1-(3-fluoro-5-(trifluoromethyl)phenyl)-2-phenylethyl)-3-(2,2,2-trifluoroethyl)urea |
| 434 | (R)-1-(1-(4-(difluoromethoxy)phenyl)-1-(3-fluoro-5-(1,1,2,2-tetrafluoroethoxy)phenyl)-2-phenylethyl)-3-(2,2,2-trifluoroethyl)urea |
| 435 | (R)-1-(1-(3-fluoro-5-(1,1,2,2-tetrafluoroethoxy)phenyl)-1-(4-isopropylphenyl)-2-phenylethyl)-3-(2,2,2-trifluoroethyl)urea |
| 436 | (R)-1-(1-(3-bromophenyl)-1-(3-fluoro-5-(trifluoromethyl)phenyl)-2-phenylethyl)-3-cyclopentylurea |
| 437 | (R)-1-(1-(3-bromophenyl)-1-(3-fluoro-5-(1,1,2,2-tetrafluoroethoxy)phenyl)-2-phenylethyl)-3-cyclopentylurea |
| 438 | (R)-1-(1-(3-bromo-4-fluorophenyl)-1-(3-fluoro-5-(trifluoromethyl)phenyl)-2-phenylethyl)-3-cyclopentylurea |
| 439 | (R)-1-(4-cyano-1-methyl-1H-pyrazol-5-yl)-3-(1-(3-fluoro-5-(1,1,2,2-tetrafluoroethoxy)phenyl)-1-(4-fluorophenyl)-2-phenylethyl)urea |
| 440 | 1-(3,3-difluorocyclohexyl)-3-((R)-1-(3-fluoro-5-(1,1,2,2-tetrafluoroethoxy)phenyl)-1-(4-fluorophenyl)-2-phenylethyl)urea |
| 441 | (R)-1-(1-(3-ethoxy-4-fluorophenyl)-1-(3-fluoro-5-(trifluoromethyl)phenyl)-2-phenylethyl)-3-(2,2,2-trifluoroethyl)urea |
| 442 | (R)-1-(1-(4-fluoro-3-isopropoxyphenyl)-1-(3-fluoro-5-(trifluoromethyl)phenyl)-2-phenylethyl)-3-(2,2,2-trifluoroethyl)urea |
| 443 | 1-((R)-1-(4-fluoro-3-(trifluoromethyl)phenyl)-1-(3-fluoro-5-(1,1,2,2-tetrafluoroethoxy)phenyl)-2-phenylethyl)-3-((R)-3,3,3-trifluoro-2-hydroxypropyl)urea |
| 444 | 1-(((1r,3R)-3-(1,1-difluoroethoxy)cyclobutyl)-3-((R)-1-(3-fluoro-5-(1,1,2,2-tetrafluoroethoxy)phenyl)-1-(4-fluorophenyl)-2-phenylethyl)urea |
| 445 | (S)-1-(1-(3-chloro-4-fluorophenyl)-1-(3-fluoro-5-(1,1,2,2-tetrafluoroethoxy)phenyl)-2-phenylethyl)-3-(2,2,2-trifluoroethyl)urea |
| 446 | (S)-1-(1-(3-chloro-4-fluorophenyl)-1-(3-fluoro-5-(1,1,2,2-tetrafluoroethoxy)phenyl)-2-phenylethyl)-3-(3,3,3-trifluoropropyl)urea |
| 447 | 1-((R)-1-(4-fluoro-3-(trifluoromethyl)phenyl)-1-(3-fluoro-5-(1,1,2,2-tetrafluoroethoxy)phenyl)-2-phenylethyl)-3-((S)-3,3,3-trifluoro-2-hydroxypropyl)urea |
| 448 | (R)-1-cyclopentyl-3-(1-(3-fluoro-5-(1,1,2,2-tetrafluoroethoxy)phenyl)-1-(4-isopropylphenyl)-2-phenylethyl)urea |
| 449 | (S)-1-(1-(4-bromophenyl)-1-(3-fluoro-5-(trifluoromethyl)phenyl)-2-phenylethyl)-3-cyclopentylurea |
| 450 | (S)-1-(1-(3-bromo-4-fluorophenyl)-1-(3-fluoro-5-(1,1,2,2-tetrafluoroethoxy)phenyl)-2-phenylethyl)-3-cyclopentylurea |
| 451 | (R)-ethyl 6-(3-(1-(3-cyclopentylureido)-1-(3-fluoro-5-(trifluoromethyl)phenyl)-2-phenylethyl)phenyl)hexanoate |
| 452 | (R)-1-(1-(4-bromophenyl)-1-(3-fluoro-5-(trifluoromethyl)phenyl)-2-phenylethyl)-3-cyclopentylurea |
| 453 | (R)-1-(1-(3-bromo-4-fluorophenyl)-1-(3-fluoro-5-(1,1,2,2-tetrafluoroethoxy)phenyl)-2-phenylethyl)-3-cyclopentylurea |
| 454 | (S)-1-(1-(4-bromophenyl)-1-(3-fluoro-5-(trifluoromethyl)phenyl)-2-phenylethyl)-3-(2,2,2-trifluoroethyl)urea |
| 455 | (S)-1-(1-(3-bromo-4-fluorophenyl)-1-(3-fluoro-5-(1,1,2,2-tetrafluoroethoxy)phenyl)-2-phenylethyl)-3-(2,2,2-trifluoroethyl)urea |
| 456 | (R)-ethyl 6-(3-(1-(3-fluoro-5-(trifluoromethyl)phenyl)-2-phenyl-1-(3-(2,2,2-trifluoroethyl)ureido)ethyl)phenyl)hexanoate |
| 457 | (R)-ethyl 7-(3-(1-(3-fluoro-5-(1,1,2,2-tetrafluoroethoxy)phenyl)-2-phenyl-1-(3-(2,2,2-trifluoroethyl)ureido)ethyl)phenyl)heptanoate |
| 458 | (R)-ethyl 6-(3-(1-(3-fluoro-5-(1,1,2,2-tetrafluoroethoxy)phenyl)-2-phenyl-1-(3-(2,2,2-trifluoroethyl)ureido)ethyl)phenyl)hexanoate |
| 459 | (R)-7-(3-(1-(3-fluoro-5-(1,1,2,2-tetrafluoroethoxy)phenyl)-2-phenyl-1-(3-(2,2,2-trifluoroethyl)ureido)ethyl)phenyl)heptanoic acid |

| Example No. | Name |
|---|---|
| 460 | (R)-1-(1-(3-fluoro-5-(1,1,2,2-tetrafluoroethoxy)phenyl)-1-(4-fluorophenyl)-2-phenylethyl)-3-(1,1,1,3,3,3-hexafluoropropan-2-yl)urea |
| 461 | (R)-1-(3,3-difluorocyclobutyl)-3-(1-(3-fluoro-5-(1,1,2,2-tetrafluoroethoxy)phenyl)-1-(4-fluorophenyl)-2-phenylethyl)urea |
| 462 | (R)-1-(3,3-difluorocyclobutyl)-3-(1-(4-fluoro-3-(trifluoromethyl)phenyl)-1-(3-fluoro-5-(1,1,2,2-tetrafluoroethoxy)phenyl)-2-phenylethyl)urea |
| 463 | 1-((R)-1-(4-fluoro-3-(trifluoromethyl)phenyl)-1-(3-fluoro-5-(1,1,2,2-tetrafluoroethoxy)phenyl)-2-phenylethyl)-3-((S)-1,1,1-trifluoro-3-methylbutan-2-yl)urea |
| 464 | 1-((R)-1-(4-fluoro-3-(trifluoromethyl)phenyl)-1-(3-fluoro-5-(1,1,2,2-tetrafluoroethoxy)phenyl)-2-phenylethyl)-3((R)-1,1,1-trifluoro-3-methylbutan-2-yl)urea |
| 465 | 1-((R)-1-(3-fluoro-5-(1,1,2,2-tetrafluoroethoxy)phenyl)-1-(4-fluorophenyl)-2-phenylethyl)-3-(tetrahydrofuran-3-yl)urea |
| 466 | (R)-ethyl 7-(2-fluoro-5-(1-(3-fluoro-5-(trifluoromethyl)phenyl)-2-phenyl-1-(3-(2,2,2-trifluoroethyl)ureido)ethyl)phenyl)heptanoate |
| 467 | (R)-methyl 6-(2-fluoro-5-(1-(3-fluoro-5-(1,1,2,2-tetrafluoroethoxy)phenyl)-2-phenyl-1-(3-(2,2,2-trifluoroethyl)ureido)ethyl)phenyl)hexanoate |
| 468 | (R)-methyl 6-(2-fluoro-5-(1-(3-fluoro-5-(trifluoromethyl)phenyl)-2-phenyl-1-(3-(2,2,2-trifluoroethyl)ureido)ethyl)phenyl)hexanoate |
| 469 | (R)-7-(2-fluoro-5-(1-(3-fluoro-5-(1,1,2,2-tetrafluoroethoxy)phenyl)-2-phenyl-1-(3-(2,2,2-trifluoroethyl)ureido)ethyl)phenyl)heptanoic acid |
| 470 | (R)-7-(2-fluoro-5-(1-(3-fluoro-5-(trifluoromethyl)phenyl)-2-phenyl-1-(3-(2,2,2-trifluoroethyl)ureido)ethyl)phenyl)-heptanoic acid |
| 471 | (R)-6-(2-fluoro-5-(1-(3-fluoro-5-(1,1,2,2-tetrafluoroethoxy)phenyl)-2-phenyl-1-(3-(2,2,2-trifluoroethyl)ureido)-ethyl)phenyl)hexanoic acid |
| 472 | (R)-6-(2-fluoro-5-(1-(3-fluoro-5-(trifluoromethyl)phenyl)-2-phenyl-1-(3-(2,2,2-trifluoroethyl)ureido)-ethyl)phenyl)hexanoic acid |
| 473 | 1-((R)-1-(3-fluoro-5-(1,1,2,2-tetrafluoroethoxy)phenyl)-1-(4-fluorophenyl)-2-phenylethyl)-3-((1s,3S)-3-formylcyclobutyl)urea |
| 474 | (R)-1-(1-(4-fluoro-3-(trifluoromethyl)phenyl)-2-phenyl-1-(3-(1,1,2,2-tetrafluoroethoxy)phenyl)ethyl)-3-(2,2,2-trifluoroethyl)urea |
| 475 | (R)-1-(1-(4-fluoro-3-(trifluoromethyl)phenyl)-1-(3-fluoro-5-(trifluoromethyl)phenyl)-2-phenylethyl)-3-(2,2,2-trifluoroethyl)urea |
| 476 | 1-((R)-1-(4-fluoro-3-(trifluoromethyl)phenyl)-1-(3-fluoro-5-(1,1,2,2-tetrafluoroethoxy)phenyl)-2-phenylethyl)-3-((R)-4,4,4-trifluoro-3-hydroxybutyl)urea |
| 477 | 1-((R)-1-(4-fluoro-3-(trifluoromethyl)phenyl)-1-(3-fluoro-5-(1,1,2,2-tetrafluoroethoxy)phenyl)-2-phenylethyl)-3-((S)-4,4,4-trifluoro-3-hydroxybutyl)urea |
| 478 | (R)-1-(3-amino-2,2-difluoropropyl)-3-(1-(3-fluoro-5-(1,1,2,2-tetrafluoroethoxy)phenyl)-1-(4-fluorophenyl)-2-phenylethyl)urea |
| 479 | 1-(2,2-difluorocyclopropyl)-3-((R)-1-(3-fluoro-5-(1,1,2,2-tetrafluoroethoxy)phenyl)-1-(4-fluorophenyl)-2-phenylethyl)urea |
| 480 | (R)-1-(2-cyanopropan-2-yl)-3-(1-(3-fluoro-5-(1,1,2,2-tetrafluoroethoxy)phenyl)-1-(4-fluorophenyl)-2-phenylethyl)urea |
| 481 | (R)-1-(1-(3-fluoro-5-(1,1,2,2-tetrafluoroethoxy)phenyl)-1-(4-fluorophenyl)-2-phenylethyl)-3-(1-(trifluoromethyl)cyclopropyl)urea |
| 482 | (R)-1-(1-(3-fluoro-5-(1,1,2,2-tetrafluoroethoxy)phenyl)-1-(4-fluorophenyl)-2-phenylethyl)-3-(4,4,4-trifluoro-2-methylbutan-2-yl)urea |
| 483 | (R)-1-(1-cyanocyclopropyl)-3-(1-(3-fluoro-5-(1,1,2,2-tetrafluoroethoxy)phenyl)-1-(4-fluorophenyl)-2-phenylethyl)urea |
| 484 | (R)-1-(1-(4-bromophenyl)-1-(3-fluoro-5-(trifluoromethyl)phenyl)-2-phenylethyl)-3-(2,2,2-trifluoroethyl)urea |
| 485 | (S)-1-(1-(4-fluoro-3-(trifluoromethyl)phenyl)-1-(3-fluoro-5-(1,1,2,2-tetrafluoroethoxy)phenyl)-2-phenylethyl)-3-(2,2,2-trifluoroethyl)urea |
| 486 | (S)-1-(1-(4-fluoro-3-(trifluoromethyl)phenyl)-1-(3-fluoro-5-hydroxyphenyl)-2-phenylethyl)-3-(2,2,2-trifluoroethyl)urea |
| 487 | (R)-1-(1-(4-fluoro-3-(trifluoromethyl)phenyl)-1-(3-fluoro-5-isopropoxyphenyl)-2-phenylethyl)-3-(2,2,2-trifluoroethyl)urea |
| 488 | (R)-methyl 2,2-difluoro-3-(3-(1-(3-fluoro-5-(1,1,2,2-tetrafluoroethoxy)phenyl)-1-(4-fluorophenyl)-2-phenylethyl)ureido)propanoate |
| 489 | (R)-ethyl 2,2-difluoro-3-(3-(1-(3-fluoro-5-(1,1,2,2-tetrafluoroethoxy)phenyl)-1-(4-fluorophenyl)-2-phenylethyl)ureido)propanoate |
| 490 | (R)-1-(1-(3-fluoro-5-(1,1,2,2-tetrafluoroethoxy)phenyl)-1-(4-fluorophenyl)-2-phenylethyl)-3-(1,1,1,3,3,3-hexafluoro-2-methylpropan-2-yl)urea |
| 491 | (R)-1-(1-(3-fluoro-5-(trifluoromethyl)phenyl)-1-(4-fluorophenyl)-2-phenylethyl)-3-(1-(trifluoromethyl)cyclopropyl)urea |
| 492 | 1-((R)-3,3-difluorocyclopentyl)-3-((R)-1-(3-fluoro-4-methoxyphenyl)-1-(3-fluoro-5-(1,1,2,2-tetrafluoroethoxy)-phenyl)-2-phenylethyl)urea |
| 493 | (R)-1-(2-cyanoethyl)-3-(1-(3-fluoro-5-(1,1,2,2-tetrafluoroethoxy)phenyl)-1-(4-fluorophenyl)-2-phenylethyl)urea |
| 495 | 1-((R)-1-(3-fluoro-5-(1,1,2,2-tetrafluoroethoxy)phenyl)-1-(4-fluorophenyl)-2-phenylethyl)-3-((R)-1,1,1-trifluoropropan-2-yl)urea |
| 496 | (R)-1-(1-(4-fluoro-3-methoxyphenyl)-1-(3-fluoro-5-(trifluoromethyl)phenyl)-2-phenylethyl)-3-(1-(trifluoromethyl)cyclopropyl)urea |
| 497 | 1-((R)-1-(3-fluoro-5-(1,1,2,2-tetrafluoroethoxy)phenyl)-1-(4-fluorophenyl)-2-phenylethyl)-3-((R)-4,4,4-trifluoro-2-hydroxybutyl)urea |
| 498 | (R)-1-(3,3-difluorocyclobutyl)-3-(1-(3-fluoro-4-methoxyphenyl)-1-(3-fluoro-5-(1,1,2,2-tetrafluoroethoxy)phenyl)-2-phenylethyl)urea |
| 499 | 1-((R)-1-(4-fluoro-3-methoxyphenyl)-1-(3-fluoro-5-(trifluoromethyl)phenyl)-2-phenylethyl)-3-((R)-1,1,1-trifluoropropan-2-yl)urea |
| 500 | 2,2-difluoro-3-(3-((R)-1-(3-fluoro-5-(1,1,2,2-tetrafluoroethoxy)phenyl)-1-(4-fluorophenyl)-2-phenylethyl)ureido)butanamide |
| 501 | 1-(1-cyano-1,1-difluoropropan-2-yl)-3-((R)-1-(3-fluoro-5-(1,1,2,2-tetrafluoroethoxy)phenyl)-1-(4-fluorophenyl)-2-phenylethyl)urea |
| 502 | (R)-1-(3,3-difluorocyclobutyl)-3-(1-(4-fluoro-3-isopropoxyphenyl)-1-(3-fluoro-5-(1,1,2,2-tetrafluoroethoxy)phenyl)-2-phenylethyl)urea |
| 503 | (R)-1-(1-(4-fluoro-3-isopropoxyphenyl)-1-(3-fluoro-5-(1,1,2,2-tetrafluoroethoxy)phenyl)-2-phenylethyl)-3-(1-(trifluoromethyl)cyclopropyl)urea |
| 504 | (R)-1-(1-(4-fluoro-3-isopropoxyphenyl)-1-(3-fluoro-5-(trifluoromethyl)phenyl)-2-phenylethyl)-3-(1-(trifluoromethyl)cyclopropyl)urea |
| 505 | 1-((R)-1-(4-fluoro-3-isopropoxyphenyl)-1-(3-fluoro-5-(trifluoromethyl)phenyl)-2-phenylethyl)-3-((R)-1,1,1-trifluoropropan-2-yl)urea |
| 506 | (R)-1-(2-cyano-2,2-difluoroethyl)-3-(1-(4-fluoro-3-methoxyphenyl)-1-(3-fluoro-5-(1,1,2,2-tetrafluoroethoxy)phenyl)-2-phenylethyl)urea |
| 507 | (R)-3,3,4,4-tetrafluoro-N-(1-(4-fluoro-3-methoxyphenyl)-1-(3-fluoro-5-(trifluoromethyl)phenyl)-2-phenylethyl)pyrrolidine-1-carboxamide |
| 508 | (S)-3-fluoro-N-((R)-1-(4-fluoro-3-methoxyphenyl)-1-(3-fluoro-5-(trifluoromethyl)phenyl)-2-phenylethyl)pyrrolidine-1-carboxamide |
| 510 | (R)-2,2-difluoro-3-(3-(1-(3-fluoro-5-(1,1,2,2-tetrafluoroethoxy)phenyl)-1-(4-fluorophenyl)-2-phenylethyl)ureido)-N,N-dimethylpropanamide |
| 511 | 1-((R)-1-(4-fluoro-3-isopropoxyphenyl)-1-(3-fluoro-5-(1,1,2,2-tetrafluoroethoxy)phenyl)-2-phenylethyl)-3-((R)-1,1,1-trifluoropropan-2-yl)urea |
| 512 | (R)-1-(2-cyano-2,2-difluoroethyl)-3-(1-(4-fluoro-3-isopropoxyphenyl)-1-(3-fluoro-5-(1,1,2,2-tetrafluoroethoxy)phenyl)-2-phenylethyl)urea |
| 513 | 1-((S)-1-(3-chloro-4-methoxyphenyl)-1-(3-fluoro-5-(1,1,2,2-tetrafluoroethoxy)phenyl)-2-phenylethyl)-3-((R)-3,3-difluorocyclopentyl)urea |

| Example No. | Name |
|---|---|
| 514 | (R)-methyl 1-(3-(1-(3-fluoro-5-(1,1,2,2-tetrafluoroethoxy)phenyl)-1-(4-fluorophenyl)-2-phenylethyl)ureido)cyclopropanecarboxylate |
| 515 | (R)-1-(1-(3-fluoro-5-(1,1,2,2-tetrafluoroethoxy)phenyl)-1-(4-fluorophenyl)-2-phenylethyl)-3-(2-(2-methyl-2H-tetrazol-5-yl)ethyl)urea |
| 516 | (S)-1-(1-(3-chloro-4-methoxyphenyl)-1-(3-fluoro-5-(1,1,2,2-tetrafluoroethoxy)phenyl)-2-phenylethyl)-3-(3,3-difluorocyclobutyl)urea |
| 517 | (R)-3-fluoro-5-(1-(4-fluoro-3-(trifluoromethyl)phenyl)-2-phenyl-1-(3-(2,2,2-trifluoroethyl)ureido)ethyl) phenyltrifluoromethanesulfonate |
| 518 | (R)-1-(1-(4-bromophenyl)-1-(3-fluoro-5-(1,1,2,2-tetrafluoroethoxy)phenyl)-2-phenylethyl)-3-(2,2,2-trifluoroethyl)urea |
| 519 | (R)-1-(1-(3-fluoro-5-(1,1,2,2-tetrafluoroethoxy)phenyl)-2-phenyl-1-(4-(trifluoromethoxy)phenyl)ethyl)-3-(2,2,2-trifluoroethyl)urea |
| 520 | (R)-1-(1-(3-fluoro-5-(1,1,2,2-tetrafluoroethoxy)phenyl)-2-phenyl-1-(2,2,3,3-tetrafluoro-2,3-dihydrobenzo[b][1,4]dioxin-6-yl)ethyl)-3-2,2,2-trifluoroethyl)urea |
| 521 | (R)-1-(1-(4-bromophenyl)-1-(3-fluoro-5-(1,1,2,2-tetrafluoroethoxy)phenyl)-2-phenylethyl)-3-cyclopentylurea |
| 522 | (R)-1-cyclopentyl-3-(1-(3-fluoro-5-(1,1,2,2-tetrafluoroethoxy)phenyl)-2-phenyl-1-(4-(trifluoromethoxy)phenyl)ethyl)urea |
| 523 | (R)-1-cyclopentyl-3-(1-(3-fluoro-5-(1,1,2,2-tetrafluoroethoxy)phenyl)-2-phenyl-1-(2,2,3,3-tetrafluoro-2,3-dihydrobenzo[b][1,4]dioxin-6-yl)ethyl)urea |
| 524 | (R)-cyclopentyl-3-(1-(4-(difluoromethoxy)-3-methoxyphenyl)-1-(3-fluoro-5-(1,1,2,2-tetrafluoroethoxy)phenyl)-2-phenylethyl)urea |
| 525 | (S)-1-(1-(4-bromophenyl)-1-(3-fluoro-5-(1,1,2,2-tetrafluoroethoxy)phenyl)-2-phenylethyl)-3-cyclopentylurea |
| 526 | (S)-1-cyclopentyl-3-(1-(3-fluoro-5-(1,1,2,2-tetrafluoroethoxy)phenyl)-2-phenyl-1-(4-(trifluoromethoxy)phenyl)ethyl)urea |
| 527 | (S)-1-cyclopentyl-3-(1-(3-fluoro-5-(1,1,2,2-tetrafluoroethoxy)phenyl)-2-phenyl-1-(2,2,3,3-tetrafluoro-2,3-dihydrobenzo[b][1,4]dioxin-6-yl)ethyl)urea |
| 528 | (S)-1-cyclopentyl-3-(1-(4-(difluoromethoxy)-3-methoxyphenyl)-1-(3-fluoro-5-(1,1,2,2-tetrafluoroethoxy)phenyl)-2-phenylethyl)urea |
| 529 | (R)-1-(1-(2,2-difluorobenzo[d]dioxol-5-yl)-1-(3-fluoro-5-(1,1,2,2-tetrafluoroethoxy)phenyl)-2-phenylethyl)-3-(2,2,2-trifluoroethyl)urea |
| 530 | (R)-1-cyclopentyl-3-(1-(2,2-difluorobenzo[d][1,3]dioxol-5-yl)-1-(3-fluoro-5-(1,1,2,2-tetrafluoroethoxy)phenyl)-2-phenylethyl)urea |
| 531 | (S)-1-cyclopentyl-3-(1-(2,2-difluorobenzo[d][1,3]dioxol-5-yl)-1-(3-fluoro-5-(1,1,2,2-tetrafluoroethoxy)phenyl)-2-phenylethyl)urea |
| 532 | (R)-1-(1-(4-(difluoromethoxy)-3-methoxyphenyl)-1-(3-fluoro-5-(1,1,2,2-tetrafluoroethoxy)phenyl)-2-phenylethyl)-3-(2,2,2-trifluoroethyl)urea |
| 533 | (R)-1-(2,2-difluoropropyl)-3-(1-(3-fluoro-5-(1,1,2,2-tetrafluoroethoxy)phenyl)-1-(4-fluorophenyl)-2-phenylethyl)urea |
| 534 | (R)-1-(1-(3-fluoro-5-(1,1,2,2-tetrafluoroethoxy)phenyl)-1-(4-fluorophenyl)-2-phenylethyl)-3-propylurea |
| 535 | (R)-1-butyl-3-(1-(3-fluoro-5-(1,1,2,2-tetrafluoroethoxy)phenyl)-1-(4-fluorophenyl)-2-phenylethyl)urea |
| 536 | (R)-1-allyl-3-(1-(3-fluoro-5-(1,1,2,2-tetrafluoroethoxy)phenyl)-1-(4-fluorophenyl)-2-phenylethyl)urea |
| 537 | (R)-1-(1-(3-fluoro-5-(1,1,2,2-tetrafluoroethoxy)phenyl)-1-(4-fluorophenyl)-2-phenylethyl)-3-(prop-2-ynyl)urea |
| 538 | ethyl 3,3,3-trifluoro-2-(3-((R)-1-(3-fluoro-5-(1,1,2,2-tetrafluoroethoxy)phenyl)-1-(4-fluorophenyl)-2-phenylethyl)ureido)propanoate |
| 539 | 3,3,3-trifluoro-2-(3-((R)-1-(3-fluoro-5-(1,1,2,2-tetrafluoroethoxy)phenyl)-1-(4-fluorophenyl)-2-phenylethyl)ureido)propanamide |
| 543 | methyl 4,4,4-trifluoro-3-(3-((R)-1-(3-fluoro-5-(1,1,2,2-tetrafluoroethoxy)phenyl)-1-(4-fluorophenyl)-2-phenylethyl)ureido)butanoate |
| 544 | (R)-1-(1-(4-cyanophenyl)-1-(3-fluoro-5-(1,1,2,2-tetrafluoroethoxy)phenyl)-2-phenylethyl)-3-(2,2,2-trifluoroethyl)urea |
| 545 | (R)-1-(1-(cyanodifluoromethyl)cyclopropyl)-3-(1-(3-fluoro-5-(1,1,2,2-tetrafluoroethoxy)phenyl)-1-(4-fluorophenyl)-2-phenylethyl)urea |
| 548 | (R)-1-(1-(4-fluoro-3-isopropoxyphenyl)-1-(3-fluoro-5-(1,1,2,2-tetrafluoroethoxy)phenyl)-2-phenylethyl)-3-(2,2,2-trifluoroethyl)urea |
| 549 | (R)-1-(1-(3-tert-butoxy-4-fluorophenyl)-1-(3-fluoro-5-(1,1,2,2-tetrafluoroethoxy)phenyl)-2-phenylethyl)-3-(1-(trifluoromethyl)cyclopropyl)urea |
| 550 | (R)-1-(1-(4-fluoro-3-methoxyphenyl)-1-(3-fluoro-5-(1,1,2,2-tetrafluoroethoxy)phenyl)-2-phenylethyl)-3-(1-(trifluoromethyl)cyclopropyl)urea |
| 551 | (R)-methyl 4-(1-(3-fluoro-5-(1,1,2,2-tetrafluoroethoxy)phenyl)-2-phenyl-1-(3-(2,2,2-trifluoroethyl)ureido)ethyl)benzoate |
| 552 | (R)-1-(1-(3-((cyclopropylamino)methyl)-4-fluorophenyl)-1-(3-fluoro-5-(1,1,2,2-tetrafluoroethoxy)phenyl)-2-phenylethyl)-3-(3,3-difluorocyclobutyl)urea |
| 553 | (R)-1-(1-(3-((butylamino)methyl)-4-fluorophenyl)-1-(3-fluoro-5-(1,1,2,2-tetrafluoroethoxy)phenyl)-2-phenylethyl)-3-(3,3-difluorocyclobutyl)urea |
| 554 | (R)-1-(3,3-difluorocyclobutyl)-3-(1-(4-fluoro-3-((isobutylamino)methyl)phenyl)-1-(3-fluoro-5-(1,1,2,2-tetrafluoroethoxy)phenyl)-2-phenylethyl)urea |
| 555 | (R)-1-(3,3-difluorocyclobutyl)-3-(1-(4-fluoro-3-(morpholinomethyl)phenyl)-1-(3-fluoro-5-(1,1,2,2-tetrafluoroethoxy)phenyl)-2-phenylethyl)urea |
| 556 | (R)-1-(cyclopent-3-enyl)-3-(1-(4-fluoro-3-methoxyphenyl)-1-(3-fluoro-5-(trifluoromethyl)phenyl)-2-phenylethyl)urea |
| 559 | (R)-1-(1-(3-fluoro-5-(1,1,2,2-tetrafluoroethoxy)phenyl)-1-(4-(hydroxymethyl)phenyl)-2-phenylethyl)-3-(2,2,2-trifluoroethyl)urea |
| 560 | 1-((S)-3,3-difluorocyclopentyl)-3-((R)-1-(4-fluoro-3-isopropoxyphenyl)-1-(3-fluoro-5-(1,1,2,2-tetrafluoroethoxy)phenyl)-2-phenylethyl)urea |
| 758 | 1-(3,3-difluorocyclopentyl)-3-(2-phenyl-1,1-bis(3-(trifluoromethoxy)phenyl)ethyl)urea |
| 759 | (R)-1-(1,1-bis(4-fluoro-3-(trifluoromethyl)phenyl)-2-phenylethyl)-3-(3,3-difluorocyclopentyl)urea |
| 760 | 2-(3-(2-phenyl-1,1-bis(3-(trifluoromethoxy)phenyl)-ethyl)ureido)cyclopentanecarboxylic acid |
| 761 | (R)-1-(3,3-difluorocyclopentyl)-3-(2-phenyl-1,1-bis(3-(trifluoromethoxy)phenyl)ethyl)urea |
| 762 | (S)-1-(3,3-difluorocyclopentyl)-3-(2-phenyl-1,1-bis(3-(trifluoromethoxy)phenyl)ethyl)urea |
| 763 | 1-cyclobutyl-3-(2-phenyl-1,1-bis(3-(trifluoromethoxy)phenyl)ethyl)urea |
| 764 | 1-phenyl-3-(2-phenyl-1,1-bis(3-(trifluoromethoxy)phenyl)ethyl)urea |
| 765 | 4,4,4-trifluoro-3-(3-(2-phenyl-1,1-bis(3-(trifluoromethoxy)phenyl)ethyl)ureido)butanoic acid |
| 766 | 1-(5-cyclopropyl-1,3,4-thiadiazol-2-yl)-3-(2-phenyl-1,1-bis(3-(trifluoromethoxy)phenyl)ethyl)urea |
| 767 | 1-(2-phenyl-1,1-bis(3-(trifluoromethoxy)phenyl)ethyl)-3-(4-(trifluoromethyl)thiazol-2-yl)urea |
| 768 | ethyl 5-(3-(2-phenyl-1,1-bis(3-(trifluoromethoxy)-phenyl)ethyl)ureido)-1,3,4-thiadiazole-2-carboxylate |
| 769 | (R)-1-(1-hydroxy-4-methylpentan-2-yl)-3-(2-phenyl-1,1-bis(3-(trifluoromethoxy)phenyl)ethyl)urea |
| 770 | 1-(1-hydroxypropan-2-yl)-3-(2-phenyl-1,1-bis(3-(trifluoromethoxy)phenyl)ethyl)urea |
| 771 | 1-(5-nitrothiazol-2-yl)-3-(2-phenyl-1,1-bis(3-(trifluoromethoxy)phenyl)ethyl)urea |
| 772 | 1-(2,3-dihydroxypropyl)-3-(2-phenyl-1,1-bis(3-(trifluoromethoxy)phenyl)ethyl)urea |
| 773 | 1-(5-chlorothiazol-2-yl)-3-(2-phenyl-1,1-bis(3-(trifluoromethoxy)phenyl)ethyl)urea |
| 774 | 6-(3-(2-phenyl-1,1-bis(3-(trifluoromethoxy)phenyl)ethyl)ureido)hexanoic acid |
| 775 | 1-(2-phenyl-1,1-bis(3-(trifluoromethoxy)phenyl)ethyl)-3-(1H-tetrazol-5-yl)urea |
| 776 | 1-(2-phenyl-1,1-bis(3-(trifluoromethoxy)phenyl)ethyl)-3-(4H-1,2,4-triazol-3-yl)urea |
| 777 | 1-(1-hydroxy-2-(hydroxymethyl)butan-2-yl)-3-(2-phenyl-1,1-bis(3-(trifluoromethoxy)phenyl)ethyl)urea |
| 778 | methyl 3-hydroxy-2-(3-(2-phenyl-1,1-bis(3-(trifluoromethoxy)phenyl)ethyl)ureido)propanoate |

| Example No. | Name |
|---|---|
| 779 | 1-(5-ethyl-1,3,4-oxadiazol-2-yl)-3-(2-phenyl-1,1-bis(3-(trifluoromethoxy)phenyl)ethyl)urea |
| 780 | 1-(1-hydroxy-2-methylpropan-2-yl)-3-(2-phenyl-1,1-bis(3-(trifluoromethoxy)phenyl)ethyl)urea |
| 781 | 1-(5-acetyl-4-methylthiazol-2-yl)-3-(2-phenyl-1,1-bis(3-(trifluoromethoxy)phenyl)ethyl)urea |
| 782 | (R)-1-(2,3-dihydroxypropyl)-3-(2-phenyl-1,1-bis(3-(trifluoromethoxy)phenyl)ethyl)urea |
| 783 | (S)-ethyl 3-hydroxy-2-(3-(2-phenyl-1,1-bis(3-(trifluoromethoxy)phenyl)ethyl)ureido)propanoate |
| 784 | 1-((2S,3S)-1,3-dihydroxybutan-2-yl)-3-(2-phenyl-1,1-bis(3-(trifluoromethoxy)phenyl)ethyl)urea |
| 785 | (S)-1-(2,3-dihydroxypropyl)-3-(2-phenyl-1,1-bis(3-(trifluoromethoxy)phenyl)ethyl)urea |
| 786 | 8-(3-(2-phenyl-1,1-bis(3-(trifluoromethoxy)phenyl)ethyl)ureido)octanoic acid |
| 787 | 1-(1-ethyl-1H-pyrazol-5-yl)-3-(2-phenyl-1,1-bis(3-(trifluoromethoxy)phenyl)ethyl)urea |
| 788 | 1-(5-ethyl-1,3,4-thiadiazol-2-yl)-3-(2-phenyl-1,1-bis(3-(trifluoromethoxy)phenyl)ethyl)urea |
| 789 | 1-(isoxazol-3-yl)-3-(2-phenyl-1,1-bis(3-(trifluoromethoxy)phenyl)ethyl)urea |
| 790 | 1-(1,3-dimethyl-1H-pyrazol-5-yl)-3-(2-phenyl-1,1-bis(3-(trifluoromethoxy)phenyl)ethyl)urea |
| 791 | 1-(4-methylthiazol-2-yl)-3-(2-phenyl-1,1-bis(3-(trifluoromethoxy)phenyl)ethyl)urea |
| 792 | 1-(5-methylisoxazol-3-yl)-3-(2-phenyl-1,1-bis(3-(trifluoromethoxy)phenyl)ethyl)urea |
| 793 | 1-(5-methyl-1,3,4-thiadiazol-2-yl)-3-(2-phenyl-1,1-bis(3-(trifluoromethoxy)phenyl)ethyl)urea |
| 794 | 1-(2-phenyl-1,1-bis(3-(trifluoromethoxy)phenyl)ethyl)-3-(1,3,4-thiadiazol-2-yl)urea |
| 795 | 1-(2-phenyl-1,1-bis(3-(trifluoromethoxy)phenyl)ethyl)-3-(5-(trifluoromethyl)-1,3,4-thiadiazol-2-yl)urea |
| 796 | 1-(1-(hydroxymethyl)cyclopentyl)-3-(2-phenyl-1,1-bis(3-(trifluoromethoxy)phenyl)ethyl)urea |
| 797 | 1-(4-cyano-1,3-dimethyl-1H-pyrazol-5-yl)-3-(2-phenyl-1,1-bis(3-(trifluoromethoxy)phenyl)ethyl)urea |
| 798 | 1-((2R,3R)-1,3-dihydroxybutan-2-yl)-3-(2-phenyl-1,1-bis(3-(trifluoromethoxy)phenyl)ethyl)urea |
| 799 | 1-(3-isopropyl-1-methyl-1H-pyrazol-5-yl)-3-(2-phenyl-1,1-bis(3-(trifluoromethoxy)phenyl)ethyl)urea |
| 800 | 1-((1R,2R)-2-(hydroxymethyl)cyclohexyl)-3-(2-phenyl-1,1-bis(3-(trifluoromethoxy)phenyl)ethyl)urea |
| 801 | 1-(3-cyclopropyl-1-methyl-1H-pyrazol-5-yl)-3-(2-phenyl-1,1-bis(3-(trifluoromethoxy)phenyl)ethyl)urea |
| 802 | 1-(5-methylthiazol-2-yl)-3-(2-phenyl-1,1-bis(3-(trifluoromethoxy)phenyl)ethyl)urea |
| 803 | 1-(4-cyano-1-methyl-1H-pyrazol-5-yl)-3-(2-phenyl-1,1-bis(3-(trifluoromethoxy)phenyl)ethyl)urea |
| 804 | 1-(5,6-dihydro-4H-cyclopenta[d]thiazol-2-yl)-3-(2-phenyl-1,1-bis(3-(trifluoromethoxy)phenyl)ethyl)urea |
| 805 | 1-(1,3-dihydroxy-2-methylpropan-2-yl)-3-(2-phenyl-1,1-bis(3-(trifluoromethoxy)phenyl)ethyl)urea |
| 806 | 1-(1-hydroxy-3-methylbutan-2-yl)-3-(2-phenyl-1,1-bis(3-(trifluoromethoxy)phenyl)ethyl)urea |
| 807 | 1-((1R,2S)-2-(hydroxymethyl)cyclohexyl)-3-(2-phenyl-1,1-bis(3-(trifluoromethoxy)phenyl)ethyl)urea |
| 808 | 1-((2S,3S)-1-hydroxy-3-methylpentan-2-yl)-3-(2-phenyl-1,1-bis(3-(trifluoromethoxy)phenyl)ethyl)urea |
| 809 | 1-(1-hydroxypentan-2-yl)-3-(2-phenyl-1,1-bis(3-(trifluoromethoxy)phenyl)ethyl)urea |
| 811 | ethyl 3-(3-(2-phenyl-1,1-bis(3-(trifluoromethoxy)phenyl)ethyl)ureido)butanoate |
| 812 | ethyl 2-(1-methyl-3-(2-phenyl-1,1-bis(3-(trifluoromethoxy)phenyl)ethyl)ureido)acetate |
| 813 | methyl 2-(3-(2-phenyl-1,1-bis(3-(trifluoromethoxy)phenyl)ethyl)ureido)acetate |
| 814 | ethyl 3-(3-(2-phenyl-1,1-bis(3-(trifluoromethoxy)phenyl)ethyl)ureido)propanoate |
| 815 | ethyl 2-(3-(2-phenyl-1,1-bis(3-(trifluoromethoxy)phenyl)ethyl)ureido)propanoate |
| 816 | methyl 4-(3-(2-phenyl-1,1-bis(3-(trifluoromethoxy)phenyl)ethyl)ureido)butanoate |
| 817 | (R)-methyl 3-hydroxy-2-(3-(2-phenyl-1,1-bis(3-(trifluoromethoxy)phenyl)ethyl)ureido)propanoate |
| 818 | (S)-methyl 3-(1H-indol-3-yl)-2-(3-(2-phenyl-1,1-bis(3-(trifluoromethoxy)phenyl)ethyl)ureido)propanoate |
| 819 | methyl 1-(3-(2-phenyl-1,1-bis(3-(trifluoromethoxy)phenyl)ethyl)ureido)cyclopropanecarboxylate |
| 821 | (R)-ethyl 2-(3-(2-phenyl-1,1-bis(3-(trifluoromethoxy)phenyl)ethyl)ureido)propanoate |
| 822 | (S)-methyl 4-methyl-2-(3-(2-phenyl-1,1-bis(3-(trifluoromethoxy)phenyl)ethyl)ureido)pentanoate |
| 823 | ethyl 2-(3-(2-phenyl-1,1-bis(3-(trifluoromethoxy)phenyl)ethyl)ureido)acetate |
| 824 | (S)-methyl 3-hydroxy-2-(3-(2-phenyl-1,1-bis(3-(trifluoromethoxy)phenyl)ethyl)ureido)propanoate |
| 825 | (R)-methyl 4-methyl-2-(3-(2-phenyl-1,1-bis(3-(trifluoromethoxy)phenyl)ethyl)ureido)pentanoate |
| 826 | (R)-methyl 2-(3-(2-phenyl-1,1-bis(3-(trifluoromethoxy)phenyl)ethyl)ureido)propanoate |
| 827 | (R)-methyl 4-(methylthio)-2-(3-(2-phenyl-1,1-bis(3-(trifluoromethoxy)phenyl)ethyl)ureido)butanoate |
| 828 | ethyl 1-(3-(2-phenyl-1,1-bis(3-(trifluoromethoxy)phenyl)ethyl)ureido)cyclopropanecarboxylate |
| 829 | methyl 2-methyl-2-(3-(2-phenyl-1,1-bis(3-(trifluoromethoxy)phenyl)ethyl)ureido)propanoate |
| 830 | methyl 2-(3-(2-phenyl-1,1-bis(3-(trifluoromethoxy)phenyl)ethyl)ureido)-2-(thiophen-2-yl)acetate |
| 835 | (R)-2-(3-(2-phenyl-1,1-bis(3-(trifluoromethoxy)phenyl)ethyl)ureido)propanoic acid |
| 836 | 1-(3-(2-phenyl-1,1-bis(3-(trifluoromethoxy)phenyl)ethyl)ureido)cyclobutanecarboxylic acid |
| 841 | 1-(1,1-bis(3-(trifluoromethoxy)phenyl)ethyl)-3-cyclopentylurea |
| 845 | 1-(1,1-bis(3-(trifluoromethoxy)phenyl)but-3-enyl)-3-cyclopentylurea |
| 847 | 1-cyclopentyl-3-(2-(2-fluorophenyl)-1,1-bis(3-(trifluoromethoxy)phenyl)ethyl)urea |
| 848 | 1-cyclopentyl-3-(2-(4-methoxyphenyl)-1,1-bis(3-(trifluoromethoxy)phenyl)ethyl)urea |
| 850 | 1-cyclopentyl-3-(2-(4-hydroxyphenyl)-1,1-bis(3-(trifluoromethoxy)phenyl)ethyl)urea |
| 852 | 1-(2-(biphenyl-4-yl)-1,1-bis(3-(trifluoromethoxy)phenyl)ethyl)-3-cyclopentylurea |
| 853 | 1-cyclopentyl-3-(3-phenyl-1,1-bis(3-(trifluoromethoxy)phenyl)propyl)urea |
| 857 | 1-cyclopentyl-3-(2-(3-methoxyphenyl)-1,1-bis(3-(trifluoromethoxy)phenyl)ethyl)urea |
| 858 | 1-cyclopentyl-3-(2-(3-hydroxyphenyl)-1,1-bis(3-(trifluoromethoxy)phenyl)ethyl)urea |
| 877 | methyl 2-(4-(2-(3-cyclopentylureido)-2,2-bis(3-(trifluoromethoxy)phenyl)ethyl)phenoxy)acetate |
| 879 | 6-(4-(2-(3-cyclopentylureido)-2,2-bis(3-(trifluoromethoxy)phenyl)ethyl)phenoxy)hexanoic acid |
| 880 | methyl 2-(2-(3-cyclopentylureido)-2,2-bis(3-(trifluoromethoxy)phenyl)ethyl)phenoxy)acetate |
| 881 | 2-(4-(2-(3-cyclopentylureido)-2,2-bis(3-(trifluoromethoxy)phenyl)ethyl)phenoxy)acetic acid |
| 882 | 2-(3-(2-(3-cyclopentylureido)-2,2-bis(3-(trifluoromethoxy)phenyl)ethyl)phenoxy)acetic acid |
| 887 | 1-(2-(3-methylisoxazol-5-yl)-1,1-bis(3-(trifluoromethoxy)phenyl)ethyl)-3-(2,2,2-trifluoroethyl)urea |
| 888 | 1-(2-(4-methoxyphenyl)-1,1-bis(3-(trifluoromethoxy)phenyl)ethyl)-3-(2,2,2-trifluoroethyl)urea |
| 889 | methyl 4-(2-(3-cyclopentylureido)-2,2-bis(3-(trifluoromethoxy)phenyl)ethyl)benzoate |
| 893 | 4-(2-(3-cyclopentylureido)-2,2-bis(3-(trifluoromethoxy)phenyl)ethyl)benzoic acid |
| 897 | methyl 3-(2-(3-(2,2,2-trifluoroethyl)ureido)-2,2-bis(3-(trifluoromethoxy)phenyl)ethyl)benzoate |
| 898 | methyl 2-(4-(2-(3-(2,2,2-trifluoroethyl)ureido)-2,2-bis(3-(trifluoromethoxy)phenyl)ethyl)phenoxy)acetate |
| 899 | methyl 4-(4-(2-(3-(2,2,2-trifluoroethyl)ureido)-2,2-bis(3-(trifluoromethoxy)phenyl)ethyl)phenoxy)butanoate |
| 900 | methyl 5-(4-(2-(3-(2,2,2-trifluoroethyl)ureido)-2,2-bis(3-(trifluoromethoxy)phenyl)ethyl)phenoxy)pentanoate |
| 902 | (1r,4r)-4-((44-(2-(3-(2,2,2-trifluoroethyl)ureido)-2,2-bis(3-(trifluoromethoxy)phenyl)ethyl)phenoxy)methyl)-cyclohexanecarboxylic acid |
| 903 | 3-(2-(3-(2,2,2-trifluoroethyl)ureido)-2,2-bis(3-(trifluoromethoxy)phenyl)ethyl)benzoic acid |

-continued

| Example No. | Name |
|---|---|
| 904 | 2-(4-(2-(3-(2,2,2-trifluoroethyl)ureido)-2,2-bis(3-(trifluoromethoxy)phenyl)ethyl)phenoxy)acetic acid |
| 905 | 4-(4-(2-(3-(2,2,2-trifluoroethyl)ureido)-2,2-bis(3-(trifluoromethoxy)phenyl)ethyl)phenoxy)butanoic acid |
| 906 | 5-(4-(2-(3-(2,2,2-trifluoroethyl)ureido)-2,2-bis(3-(trifluoromethoxy)phenyl)ethyl)phenoxy)pentanoic acid |
| 907 | (1s,4s)-methyl 4-((4-(2-(3-(2,2,2-trifluoroethyl)ureido)-2,2-bis(3-(trifluoromethoxy)phenyl)ethyl)phenoxy)methyl)cyclohexanecarboxylate |
| 908 | (1s,4s)-methyl 4-((4-(2-(4-fluoro-3-(trifluoromethyl)benzamido)-2,2-bis(3-(trifluoromethoxy)phenyl)ethyl)phenoxy)methyl)cyclohexanecarboxylate |
| 909 | (1S,3R)-methyl 3-((4-(2-(3-(2,2,2-trifluoroethyl)ureido)-2,2-bis(3-(trifluoromethoxy)phenyl)ethyl)phenoxy)methyl)cyclohexanecarboxylate |
| 910 | ethyl 6-(4-(2-(3-(2,2,2-trifluoroethyl)ureido)-2,2-bis(3-(trifluoromethoxy)phenyl)ethyl)phenoxy)hexanoate |
| 912 | (1s,4s)-4-((4-(2-(3-(2,2,2-trifluoroethyl)ureido)-2,2-bis(3-(trifluoromethoxy)phenyl)ethyl)phenoxy)-(methyl)cyclohexanecarboxylic acid |
| 915 | (1S,3R)-3-((4-(2-(3-(2,2,2-trifluoroethyl)ureido)-2,2-bis(3-(trifluoromethoxy)phenyl)ethyl)phenoxy)methyl)-cyclohexanecarboxylic acid |
| 916 | 6-(4-(2-(3-(2,2,2-trifluoroethyl)ureido)-2,2-bis(3-(trifluoromethoxy)phenyl)ethyl)phenoxy)hexanoic acid |
| 917 | (1R,2R)-methyl 2-((4-(2-(3-(2,2,2-trifluoroethyl)ureido)-2,2-bis(3-(trifluoromethoxy)phenyl)ethyl)phenoxy)methyl)cyclohexanecarboxylate |
| 918 | 6-(4-(2-(3-(2,2,2-trifluoroethyl)ureido)-2,2-bis(3-(trifluoromethoxy)phenyl)ethyl)phenyl)hexanoic acid |
| 919 | ethyl 4-(4-(2-(3-(2,2,2-trifluoroethyl)ureido)-2,2-bis(3-(trifluoromethoxy)phenyl)ethyl)phenyl)butanoate |
| 923 | 4-(4-(2-(3-(2,2,2-trifluoroethyl)ureido)-2,2-bis(3-(trifluoromethoxy)phenyl)ethyl)phenyl)butanoic acid |
| 936 | 1-(3-chlorophenyl)-3-(2-phenyl-1,1-bis(3-(trifluoromethoxy)phenyl)ethyl)thiourea |
| 974 | (R)-1-(1-(3-fluoro-5-(1,1,2,2-tetrafluoroethoxy)phenyl)-1-(4-fluorophenyl)-2-(4-methoxyphenyl)ethyl)-3-(2,2,2-trifluoroethyl)urea |
| 976 | (R)-1-(1-(3-fluoro-5-(1,1,2,2-tetrafluoroethoxy)phenyl)-1-(4-fluorophenyl)-2-(4-hydroxyphenyl)ethyl)-3-(2,2,2-trifluoroethyl)urea |
| 979 | (R)-methyl 5-(4-(2-(3-fluoro-5-(1,1,2,2-tetrafluoroethoxy)phenyl)-2-(4-fluorophenyl)-2-(3-(2,2,2-trifluoroethyl)ureido)ethyl)phenoxy)pentanoate |
| 980 | (R)-5-(4-(2-(3-fluoro-5-(1,1,2,2-tetrafluoroethoxy)phenyl)-2-(4-fluorophenyl)-2-(3-(2,2,2-trifluoroethyl)-ureido)ethyl)phenoxy)pentanoic acid |
| 981 | (R)-ethyl 6-(4-(2-(3-fluoro-5-(1,1,2,2-tetrafluoroethoxy)phenyl)-2-(4-fluorophenyl)-2-(3-(2,2,2-trifluoroethyl)ureido)ethyl)phenoxy)hexanoate |
| 982 | (R)-6-(4-(2-(3-fluoro-5-(1,1,2,2-tetrafluoroethoxy)phenyl)-2-(4-fluorophenyl)-2-(3-(2,2,2-trifluoroethyl)-ureido)ethyl)phenoxy)hexanoic acid |
| 984 | (R)-ethyl 7-(4-(2-(3-fluoro-5-(1,1,2,2-tetrafluoroethoxy)phenyl)-2-(4-fluorophenyl)-2-(3-(2,2,2-trifluoroethyl)-ureido)ethyl)phenoxy)heptanoate |

-continued

| Example No. | Name |
|---|---|
| 986 | (R)-7-(4-(2-(3-fluoro-5-(1,1,2,2-tetrafluoroethoxy)phenyl)-2-(4-fluorophenyl)-2-(3-(2,2,2-trifluoroethyl)ureido)-ethyl)phenoxy)heptanoic acid |
| 988 | (R)-1-(2-(4-bromophenyl)-1-(4-fluoro-3-(trifluoromethyl)phenyl)-1-(3-fluoro-5-(1,1,2,2-tetrafluoroethoxy)-phenyl)ethyl)-3-(2,2,2-trifluoroethyl)urea |
| 989 | (S)-1-(2-(4-bromophenyl)-1-(4-fluoro-3-(trifluoromethyl)phenyl)-1-(3-fluoro-5-(1,1,2,2-tetrafluoroethoxy)-phenyl)ethyl)-3-(2,2,2-trifluoroethyl)urea |
| 1002 | (S)-ethyl 3-(4-(2-(4-fluoro-3-(trifluoromethyl)phenyl)-2-(3-fluoro-5-(1,1,2,2-tetrafluoroethoxy)phenyl)-2-(3-(2,2,2-trifluoroethyl)ureido)ethyl)phenyl)propanoate |
| 1003 | (R)-ethyl 3-(4-(2-(4-fluoro-3-(trifluoromethyl)phenyl)-2-(3-fluoro-5-(1,1,2,2-tetrafluoroethoxy)phenyl)-2-(3-(2,2,2-trifluoroethyl)ureido)ethyl)phenyl)propanoate |
| 1004 | (R)-ethyl 4-(4-(2-(4-fluoro-3-(trifluoromethyl)phenyl)-2-(3-fluoro-5-(1,1,2,2-tetrafluoroethoxy)phenyl)-2-(3-(2,2,2-trifluoroethyl)ureido)ethyl)phenyl)butanoate |
| 1005 | (R)-ethyl 6-(4-(2-(4-fluoro-3-(trifluoromethyl)phenyl)-2-(3-fluoro-5-(1,1,2,2-tetrafluoroethoxy)phenyl)-2-(3-(2,2,2-trifluoroethyl)ureido)ethyl)phenyl)hexanoate |
| 1006 | (S)-3-(4-(2-(4-fluoro-3-(trifluoromethyl)phenyl)-2-(3-fluoro-5-(1,1,2,2-tetrafluoroethoxy)phenyl)-2-(3-(2,2,2-trifluoroethyl)ureido)ethyl)phenyl)propanoic acid |
| 1009 | (R)-3-(4-(2-(4-fluoro-3-(trifluoromethyl)phenyl)-2-(3-fluoro-5-(1,1,2,2-tetrafluoroethoxy)phenyl)-2-(3-(2,2,2-trifluoroethyl)ureido)ethyl)phenyl)propanoic acid |
| 1010 | (R)-4-(4-(2-(4-fluoro-3-(trifluoromethyl)phenyl)-2-(3-fluoro-5-(1,1,2,2-tetrafluoroethoxy)phenyl)-2-(3-(2,2,2-trifluoroethyl)ureido)ethyl)phenyl)butanoic acid |
| 1011 | (R)-6-(4-(2-(4-fluoro-3-(trifluoromethyl)phenyl)-2-(3-fluoro-5-(1,1,2,2-tetrafluoroethoxy)phenyl)-2-(3-(2,2,2-trifluoroethyl)ureido)ethyl)phenyl)hexanoic acid |
| 1014 | (R)-1-(1-(4-fluoro-3-(trifluoromethyl)phenyl)-1-(3-fluoro-5-(1,1,2,2-tetrafluoroethoxy)phenyl)but-3-enyl)-3-(2,2,2-trifluoroethyl)urea |
| 1022 | (R)-1-(1-(4-fluoro-3-(trifluoromethyl)phenyl)-1-(3-fluoro-5-(1,1,2,2-tetrafluoroethoxy)phenyl)-2-(4-(hydroxymethyl)phenyl)ethyl)-3-(2,2,2-trifluoroethyl)urea |
| 1026 | (R)-4-(2-(4-fluoro-3-(trifluoromethyl)phenyl)-2-(3-fluoro-5-(1,1,2,2-tetrafluoroethoxy)phenyl)-2-(3-(2,2,2-trifluoroethyl)ureido)ethyl)benzamide. |

12. A pharmaceutical composition comprising a compound of claim 1 and a pharmaceutically acceptable carrier.

13. The pharmaceutical composition of claim 12 further comprising at least one additional therapeutic agent.

14. A compound of claim 1 having the name:
(R)-1-(4-fluoro-3-isopropoxyphenyl)-1-(3-fluoro-5-(1,1,2,2-tetrafluoroethoxy)phenyl)-2-phenylethanamine;
(R)-5-(1-amino-1-(3-fluoro-5-(1, 1,2,2-tetrafluoroethoxy)phenyl)-2-phenylethyl)-2-fluorophenol;
(R)-4-(1-amino-1-(3-fluoro-5-(1, 1,2,2-tetrafluoroethoxy)phenyl)-2-phenylethyl)benzonitrile; or
5-(1-amino-1-(3-fluoro-5-(1,1,2,2-tetrafluoroethoxy)phenyl)-2-phenylethyl)-2-fluorobenzonitrile;
or a pharmaceutically acceptable salt thereof.

* * * * *

UNITED STATES PATENT AND TRADEMARK OFFICE
CERTIFICATE OF CORRECTION

PATENT NO. : 8,642,576 B2
APPLICATION NO. : 13/597364
DATED : February 4, 2014
INVENTOR(S) : Mark E. Salvati et al.

It is certified that error appears in the above-identified patent and that said Letters Patent is hereby corrected as shown below:

In the Claims:

Claim 1:

Column 1043, line 64, change "(C2-C6)-alkynyl" to -- $(C_2-C_6)$-alkynyl --.

Column 1045, line 25, change "(C2-C6)-alkynyl" to -- $(C_2-C_6)$-alkynyl --.

Column 1046, line 22, change "$R_{10}$'s," to -- $R_{40}$'s, --.

Claim 3:

Column 1069, line 12, change "-$COR_E$," to -- -$COR_6$, --.

Column 1073, line 31, change "(C2-C6)-alkenyl," to $(C_2-C_6)$-alkenyl, --.

Column 1073, line 46, change "(C2-C6)-alkenyl," to -- $(C_2-C_6)$-alkenyl, --.

Column 1075, line 9, change "$R_{10}$'s," to -- $R_{40}$'s, --.

Column 1076, line 23, change "-$[(C-O)O_r]_s$alkyl," to -- -$[(C=O)O_r]_s$alkyl, --.

Claim 4:

Column 1081, line 24, change "$R_{40}$ s," to -- $R_{40}$'s, --.

Claim 7:

Column 1094, line 45, after "consisting of", delete "[[:1)]]".

Column 1096, line 35, change "-$NR_6R_{10}$," to -- -$NR_9R_{10}$, --.

Claim 8:

Column 1099, line 31, change "$R_{20}$ s," to -- $R_{20}$'s, --.

Signed and Sealed this
Thirty-first Day of March, 2015

Michelle K. Lee
*Director of the United States Patent and Trademark Office*

CERTIFICATE OF CORRECTION (continued)
U.S. Pat. No. 8,642,576 B2

In the Claims:

Claim 10:

Column 1107, lines 52 to 56, change " 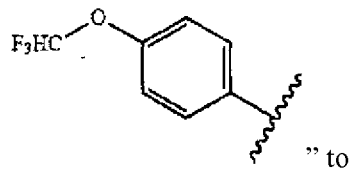 " to 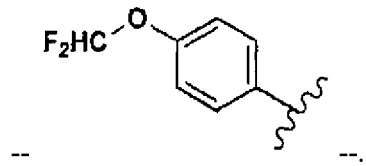 --.

Column 1118, lines 36 to 40, change " 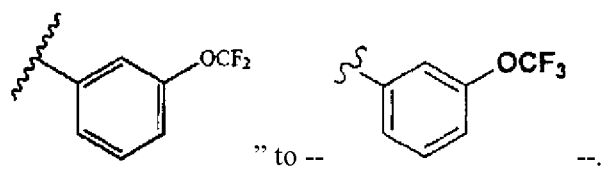 " to -- 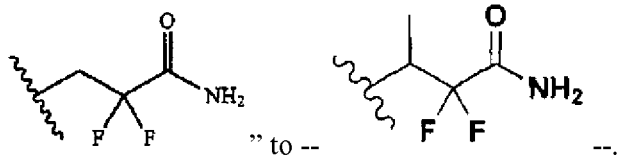 --.

Column 1128, lines 53 to 57, change " 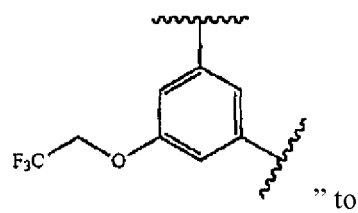 " to -- 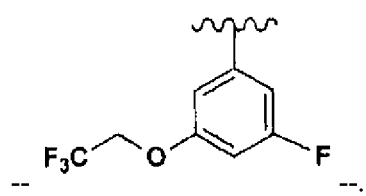 --.

Column 1137, lines 38 to 44, change " 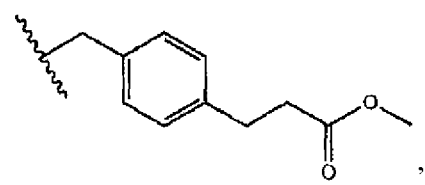 " to 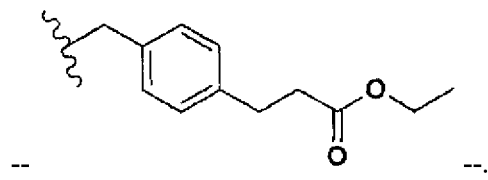 --.

Column 1139, lines 46 to 51, change "

CERTIFICATE OF CORRECTION (continued)
U.S. Pat. No. 8,642,576 B2

In the Claims:

Claim 10 (continued):

Column 1143, lines 32 to 40, change " 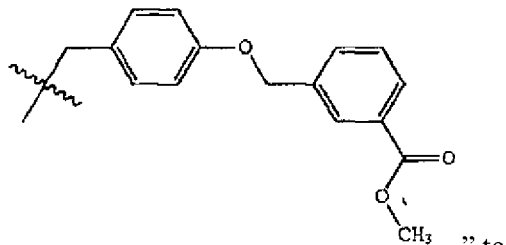 " to 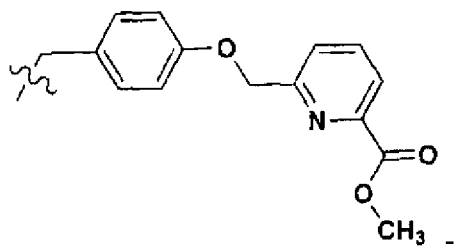 --.

Column 1146, lines 59 to 62, change " 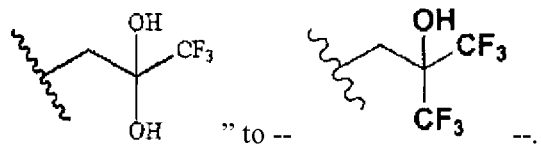 " to -- --.

Claim 11:

Column 1155, line 38, change "-3-clopentylurea" to -- -3-cyclopentylurea --.

Column 1161, line 21, change "-3-2,2,2-trifluoroethyl)urea" to -- -3-(2,2,2-trifluoroethyl)urea --.

Column 1161, line 39, change "(2,2-difluorobenzo[d]dioxol-5-yl)" to -- (2,2-difluorobenzo[d][1,3]dioxol-5-yl) --.

Column 1164, line 63, change "(1r,4r)-4-((44-" to -- (1r,4r)-4-((4- --.

Claim 14:

Column 1166, line 47, change "(3-fluoro-5-(1, 1,2,2-tetrafluoroethoxy)" to -- (3-fluoro-5-(1,1,2,2-tetrafluoroethoxy) --.

Column 1166, line 49, change "(3-fluoro-5-(1, 1,2,2-tetrafluoroethoxy)" to -- (3-fluoro-5-(1,1,2,2-tetrafluoroethoxy) --.